US012465641B2

(12) United States Patent
Schneider et al.

(10) Patent No.: US 12,465,641 B2
(45) Date of Patent: Nov. 11, 2025

(54) CHIMERIC ANTIGEN RECEPTOR THERAPIES FOR TREATING SOLID TUMORS

(71) Applicant: LENTIGEN TECHNOLOGY, INC., Gaithersburg, MD (US)

(72) Inventors: Dina Schneider, Potomac, MD (US); Peirong Hu, Ijamsville, MD (US); Tri Minh Tran, Frederick, MD (US); Brittany Steimle, Gaithersburg, MD (US); Aldo Sotelo, Sandy, UT (US)

(73) Assignee: LENTIGEN TECHNOLOGY, INC., Gaithersburg, MD (US)

( * ) Notice: Subject to any disclaimer, the term of this patent is extended or adjusted under 35 U.S.C. 154(b) by 0 days.

(21) Appl. No.: 18/228,770

(22) Filed: Aug. 1, 2023

(65) Prior Publication Data

US 2024/0091360 A1 Mar. 21, 2024

Related U.S. Application Data

(63) Continuation of application No. PCT/US2023/029008, filed on Jul. 28, 2023.

(60) Provisional application No. 63/433,632, filed on Dec. 19, 2022, provisional application No. 63/393,088, filed on Jul. 28, 2022.

(51) Int. Cl.

| | |
|---|---|
| ***A61P 35/00*** | (2006.01) |
| ***A61K 40/11*** | (2025.01) |
| ***A61K 40/31*** | (2025.01) |
| ***A61K 40/42*** | (2025.01) |
| ***C07K 14/725*** | (2006.01) |
| ***C07K 16/28*** | (2006.01) |
| ***C07K 16/30*** | (2006.01) |
| ***C12N 15/86*** | (2006.01) |

(52) U.S. Cl.

CPC ............ *A61K 40/421* (2025.01); *A61K 40/11* (2025.01); *A61K 40/31* (2025.01); *A61K 40/4202* (2025.01); *A61K 40/4255* (2025.01); *A61P 35/00* (2018.01); *C07K 14/7051* (2013.01); *C07K 16/28* (2013.01); *C07K 16/2803* (2013.01); *C07K 16/2827* (2013.01); *C07K 16/30* (2013.01); *C12N 15/86* (2013.01); *C07K 2319/03* (2013.01); *C12N 2740/15043* (2013.01)

(58) Field of Classification Search

None

See application file for complete search history.

(56) References Cited

U.S. PATENT DOCUMENTS

| | | | |
|---|---|---|---|
| 3,060,165 | A | 10/1962 | Craigl. et al. |
| 3,896,111 | A | 7/1975 | Kupchan et al. |
| 4,137,230 | A | 1/1979 | Hashimoto et al. |
| 4,235,871 | A | 11/1980 | Papahadjopoulo et al. |
| 4,248,870 | A | 2/1981 | Miyashita et al. |
| 4,256,746 | A | 3/1981 | Miyashita et al. |
| 4,260,608 | A | 4/1981 | Miyashita et al. |
| 4,265,814 | A | 5/1981 | Hashimoto et al. |
| 4,294,757 | A | 10/1981 | Asai |
| 4,307,016 | A | 12/1981 | Asai |
| 4,308,268 | A | 12/1981 | Miyashita et al. |
| 4,308,269 | A | 12/1981 | Miyashita et al. |
| 4,309,428 | A | 1/1982 | Miyashita et al. |
| 4,313,946 | A | 2/1982 | Powell et al. |
| 4,315,929 | A | 2/1982 | Freedman et al. |
| 4,317,821 | A | 3/1982 | Miyashita et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,450,254 | A | 5/1984 | Isely et al. |
| 4,486,414 | A | 12/1984 | Pettit |
| 4,501,728 | A | 2/1985 | Geho et al. |
| 4,689,401 | A | 8/1987 | Ferris |
| 4,816,444 | A | 3/1989 | Pettit et al. |
| 4,837,028 | A | 6/1989 | Allen |
| 4,879,278 | A | 11/1989 | Pettit et al. |
| 4,880,935 | A | 11/1989 | Thorpe |
| 4,902,505 | A | 2/1990 | Pardridge et al. |
| 4,957,735 | A | 9/1990 | Huang |
| 4,978,744 | A | 12/1990 | Pettit et al. |

(Continued)

FOREIGN PATENT DOCUMENTS

| | | |
|---|---|---|
| EP | 0425235 B1 | 9/1996 |
| EP | 3730612 | 10/2020 |

(Continued)

OTHER PUBLICATIONS

Ramaekers et al., Clin Chem Lab Med 2013. (Year: 2013).*

(Continued)

*Primary Examiner* — Zachary S Skelding

(74) *Attorney, Agent, or Firm* — Serge Sira, Esq.; Gergory J. Hwa, Esq.; Fish & Richardson P.C.

(57) ABSTRACT

Novel anti-effector moiety antibodies or antigen binding domains thereof and CARs that contain such effector moiety antigen binding domains, either with or without one or more booster elements, and host cells expressing the receptors, and nucleic acid molecules encoding the receptors are provided herein, as well as methods of use of same in a patient-specific immunotherapy that can be used to treat solid tumor cancers and other diseases and conditions.

10 Claims, 64 Drawing Sheets

Specification includes a Sequence Listing.

(56) References Cited

U.S. PATENT DOCUMENTS

| | | | | |
|---|---|---|---|---|
| 4,986,988 | A | 1/1991 | Pettit et al. | |
| 5,004,697 | A | 4/1991 | Pardridge | |
| 5,019,369 | A | 5/1991 | Presant et al. | |
| 5,055,303 | A | 10/1991 | Riley | |
| 5,076,973 | A | 12/1991 | Pettit et al. | |
| 5,079,163 | A | 1/1992 | Piatak et al. | |
| 5,122,368 | A | 6/1992 | Greenfield et al. | |
| 5,138,036 | A | 8/1992 | Pettit et al. | |
| 5,188,837 | A | 2/1993 | Domb | |
| 5,208,021 | A | 5/1993 | Johnson et al. | |
| 5,254,342 | A | 10/1993 | Shen et al. | |
| 5,268,164 | A | 12/1993 | Kozarich et al. | |
| 5,271,961 | A | 12/1993 | Mathiowitz et al. | |
| 5,410,024 | A | 4/1995 | Pettit et al. | |
| 5,413,797 | A | 5/1995 | Khan et al. | |
| 5,416,064 | A | 5/1995 | Chari et al. | |
| 5,449,752 | A | 9/1995 | Fujii et al. | |
| 5,504,191 | A | 4/1996 | Pettit et al. | |
| 5,506,206 | A | 4/1996 | Kozarich et al. | |
| 5,514,670 | A | 5/1996 | Friedman et al. | |
| 5,521,284 | A | 5/1996 | Pettit et al. | |
| 5,530,097 | A | 6/1996 | Pettit et al. | |
| 5,534,496 | A | 7/1996 | Lee et al. | |
| 5,554,725 | A | 9/1996 | Pettit | |
| 5,599,902 | A | 2/1997 | Pettit et al. | |
| 5,622,929 | A | 4/1997 | Willner et al. | |
| 5,635,483 | A | 6/1997 | Pettit et al. | |
| 5,663,149 | A | 9/1997 | Pettit et al. | |
| 5,665,860 | A | 9/1997 | Pettit et al. | |
| 5,780,588 | A | 7/1998 | Pettit et al. | |
| 5,792,458 | A | 8/1998 | Johnson et al. | |
| 5,824,805 | A | 10/1998 | King et al. | |
| 6,034,065 | A | 3/2000 | Pettit et al. | |
| 6,214,345 | B1 | 4/2001 | Firestone et al. | |
| 6,239,104 | B1 | 5/2001 | Pettit et al. | |
| 6,323,315 | B1 | 11/2001 | Pettit et al. | |
| 6,441,163 | B1 | 8/2002 | Chari et al. | |
| 6,884,869 | B2 | 4/2005 | Senter et al. | |
| 7,338,929 | B2 | 3/2008 | Debinski et al. | |
| 7,498,298 | B2 | 3/2009 | Doronina et al. | |
| 7,964,566 | B2 | 6/2011 | Doronina et al. | |
| 10,183,993 | B2 | 1/2019 | Orentas et al. | |
| 10,426,797 | B2 | 10/2019 | Orentas et al. | |
| 10,428,141 | B2 * | 10/2019 | Orentas | C12N 15/62 |
| 10,844,128 | B2 | 11/2020 | Orentas et al. | |
| 11,052,112 | B2 | 7/2021 | Orentas et al. | |
| 11,103,533 | B2 | 8/2021 | Schneider et al. | |
| 11,590,169 | B1 | 2/2023 | Schneider et al. | |
| 2002/0197266 | A1 | 12/2002 | Debinski et al. | |
| 2005/0238649 | A1 | 10/2005 | Doronina et al. | |
| 2006/0024317 | A1 | 2/2006 | Boyd et al. | |
| 2006/0074008 | A1 | 4/2006 | Senter et al. | |
| 2011/0070248 | A1 | 3/2011 | Ichikawa et al. | |
| 2011/0212088 | A1 | 9/2011 | Sabbadini et al. | |
| 2012/0213783 | A1 | 8/2012 | Rosenberg et al. | |

FOREIGN PATENT DOCUMENTS

| | | | |
|---|---|---|---|
| WO | WO 2004/010957 | 2/2004 | |
| WO | WO 2012/079000 | 6/2012 | |
| WO | WO 2013/126726 | 8/2013 | |
| WO | WO 2015/105522 | 7/2015 | |
| WO | WO 2018/045325 | 3/2018 | |
| WO | WO 2019/090110 | 5/2019 | |
| WO | WO-2020181164 A1 * | 9/2020 | A61K 35/17 |
| WO | WO 2021/102337 | 5/2021 | |
| WO | WO 2021/214270 | 10/2021 | |
| WO | WO 2022/150831 | 7/2022 | |

OTHER PUBLICATIONS

Struber et al. (Journal for ImmunoTherapy of Cancer 2020;8:e000676). (Year: 2020).*

Zhu et al. (Cancer Biology & Therapy 2019, vol. 20, No. 8, 1105-1112). (Year: 2019).*

Hudecek et al. (Cancer Immunol Res; 3(2); 125-35 (2014)). (Year: 2014).*

Melisi et al. (Cancer Chemotherapy and Pharmacology (2019) 83:975-991). (Year: 2019).*

Yang et al. (Molecular Therapy: Oncolytics vol. 17, pp. 571-585 (2020)). (Year: 2020).*

Carbone et al. (Seminars in Cancer Biology, 2004, 14: 399-405). (Year: 2004).*

Kean et al., (2018; Blood, pp. 2630-2639). (Year: 2018).*

Wang et al.(2015, Molecular Therapy pp. 184-191). (Year: 2015).*

Voskoglou-Nomikos et al., (Clinical Cancer Research, 2003, 9, 4227-4239). (Year: 2003).*

Assis-Mendonça et al. (BMC Cancer. Mar. 1, 2021;21(1):209, and supplemental Fig. 3). (Year: 2021).*

Wang et al. (Cellular Immunology 363 (2021) 104342). (Year: 2021).*

Srivastava et al., Cancer Cell 35, 489-503, (2019) with additional pp. e1-e8 and further pp. 1-12. (Year: 2019).*

Labanieh et al. (2022, Cell 185, 1745-1763, and additional pp. e1-e9; pp. 1-13). (Year: 2022).*

Tristan-Manzano et al. (Mol Ther Oncolytics. May 18, 2022;25:335-349 and Supplemental pp. 1-7). (Year: 2022).*

Weber et al. (Science. Apr. 2, 2021;372(6537):eaba1786 and supplemental pp. 1-40). (Year: 2021).*

Eyquem et al. (Nature. Mar. 2, 2017;543(7643):113-117, Methods and Extended Data pp. 1-14). (Year: 2017).*

Mary Gearing, Jan. 18, 2018, "Plasmids 101: Inducible Promoters," Addgene blog, retrieved from the internet Apr. 5, 2025, pp. 1-5. (Year: 2018).*

Qin et al., PLoS ONE 5(5): e10611 (2010). (Year: 2010).*

Ahmad et al., "scFv antibody: principles and clinical application," Journal of Immunology Research, Mar. 2012, 16 pages.

Alabanza et al., "Armored BCMA CAR T cells eliminate multiple myeloma and are resistant to the suppressive effects of TGF-ß," Frontiers in Immunology, Feb. 2022, 13:832645, 17 pages.

Al-Lazikani et al., "Standard conformations for the canonical structures of immunoglobulins," Journal of Molecular Biology, Nov. 1997, 273(4):927-48.

Anderson et al., "The tumor microenvironment," Current Biology, Aug. 2020, 30(16):R921-5.

Baskar et al., "Unique cell surface expression of receptor tyrosine kinase RORI in human B-cell chronic lymphocytic leukemia," Clinical Cancer Research, Jan. 2008, 14(2):396-404.

Batlle et al., "Transforming growth factor-ß signaling in immunity and cancer," Immunity, Apr. 2019, 50(4):924-40.

Bielamowicz et al., "Trivalent CAR T cells overcome interpatient antigenic variability in glioblastoma, " Neuro-oncology, Mar. 2018, 20(4):506-18.

Bierer et al., "Cyclosporin A and FK506: molecular mechanisms of immunosuppression and probes for transplantation biology," Current Opinion in Immunology, Oct. 1993, 5(5):763-73.

Bird et al., "Single-chain antigen-binding proteins," Science, Oct. 1988, 242(4877):423-6.

Blazar et al., "Strategies to inhibit alloantibody production in alloprimed murine recipients of hematopoietic stem cell grafts," American Journal of Transplantation, Apr. 2015, 15(4):931-41.

Brentjens et al., "Treatment of chronic lymphocytic leukemia with genetically targeted autologous T cells: case report of an unforeseen adverse event in a phase I clinical trial," Molecular Therapy, Apr. 2010, 18(4):666-8.

Brown et al., "Stem-like tumor-initiating cells isolated from IL 13Rα2 expressing gliomas are targeted and killed by IL13-zetakine-redirected T cells, " Clinical Cancer Research, Apr. 2012, 18(8):2199, 22 pages.

Capecchi, "High efficiency transformation by direct microinjection of DNA into cultured mammalian cells," Cell, Nov. 1980, 22(2):479-88.

Caruana et al., "Heparanase promotes tumor infiltration and antitumor activity of CAR-redirected T lymphocytes," Nature Medicine, May 2015, 21(5):524, 18 pages.

(56) References Cited

OTHER PUBLICATIONS

Clay et al., “Efficient transfer of a tumor antigen-reactive TCR to human peripheral blood lymphocytes confers anti-tumor reactivity,” The Journal of Immunology, Jul. 1, 1999, 163(1):507-13.
Daneshmanesh et al., “Orphan receptor tyrosine kinases RORI and ROR2 in hematological malignancies,” Leukemia & Lymphoma, Apr. 2013, 54(4):843-50.
Derynck et al., “TGF-ß biology in cancer progression and tumor immunotherapy,” Nature Reviews Clinical Oncology, Jan. 2021, 18(1), 51 pages.
Dubowchik et al., “Receptor-mediated and enzyme-dependent targeting of cytotoxic anticancer drugs,” Pharmacology & Therapeutics, Aug. 1999, 83(2):67-123.
Ellebrecht et al., “Reengineering chimeric antigen receptor T cells for targeted therapy of autoimmune disease. ” Science, Jul. 2016, 353(6295):179-84.
Felgner et al., “Lipofection: a highly efficient, lipid-mediated DNA-transfection procedure,” Proceedings of the National Academy of Sciences, Nov. 1987, 84(21):7413-7.
Fults et al., “Sustained-release of urease from a poloxamer gel matrix,” PDA Journal of Pharmaceutical Science and Technology, Mar. 1990, 44(2):58-65.
Funatsu et al., “The complete amino acid sequence of the A-chain of abrin-a, a toxic protein from the seeds of Abrus precatorius,” Agricultural and Biological Chemistry, Apr. 1988, 52(4):1095-7.
GenBank Acession No. AAA35664.1, “T lymphocyte surface glycoprotein (CD8-beta) precursor [Homo sapiens],” Apr. 27, 1993, 2 pages.
Gill et al., “Chimeric antigen receptor T cell therapy: 25 years in the making, ” Blood Reviews, May 2016, 30(3):157-67.
Gillespie et al., “Phase I open study of the effects of ascending doses of the cytotoxic immunoconjugate CMB-401 (hCTMO1-calicheamicin) in patients with epithelial ovarian cancer,” Annals of Oncology, Jun. 2000, 11(6):735-41.
Goyal et al., “Inclusion of a furin-sensitive spacer enhances the cytotoxicity of ribotoxin restrictocin containing recombinant single-chain immunotoxins,” Biochemical Journal, Jan. 2000, 345(2):247-54.
Graham et al., “A new technique for the assay of infectivity of human adenovirus 5 DNA,” Virology, Apr. 1973, 52(2):456-67.
Grupp et al., “Chimeric antigen receptor-modified T cells for acute lymphoid leukemia, ” New England Journal of Medicine, Apr. 2013, 368(16):1509-18.
Guedan et al., “Engineering and design of chimeric antigen receptors, ” Molecular Therapy-Methods & Clinical Development, Mar. 2019, 12:145-56.
Hamers-Casterman et al., “Naturally occurring antibodies devoid of light chains,” Nature, Jun. 1993, 363(6428):446-8.
Han et al., “Chimeric antigen receptor-engineered T cells for cancer immunotherapy: progress and challenges,” Journal of Hematology & Oncology, Dec. 2013, 6(1):1-7.
Han et al., “Multi-antigen-targeted chimeric antigen receptor T cells for cancer therapy,” Journal of Hematology & Oncology, Dec. 2019, 12:1-0.
Haso et al., “Anti-CD22-chimeric antigen receptors targeting B-cell precursor acute lymphoblastic leukemia,” Blood, The Journal of the American Society of Hematology, Feb. 2013, 121(7):1165-74.
Hay et al., “Kinetics and biomarkers of severe cytokine release syndrome after CD19 chimeric antigen receptor-modified T-cell therapy,” Blood, The Journal of the American Society of Hematology, Nov. 23, 2017, 130(21):2295-306.
He et al., “Co-expression of IL-7 improves NKG2D-based CAR T cell therapy on prostate cancer by enhancing the expansion and inhibiting the apoptosis and exhaustion,” Cancers, Jul. 2020, 12(7):1969, 17 pages.
Henderson et al., “Comparison of the effects of FK-506, cyclosporin A and rapamycin on IL-2 production,” Immunology, Jul. 1991, 73(3):316, 16 pages.
Holliger et al., “Diabodies: small bivalent and bispecific antibody fragments,” Proceedings of the National Academy of Sciences, Jul. 1993, 90(14):6444-8.
Hudecek et al. “Receptor affinity and extracellular domain modifications affect tumor recognition by RORI-specific chimeric antigen receptor T cells,” Clinical Cancer Research, Jun. 2013, 19(12):3153-64.
Huse et al., “Generation of a large combinatorial library of the immunoglobulin repertoire in phage lambda,” Science, Dec. 1989, 246(4935):1275-81.
Huston et al., “Protein engineering of antibody binding sites: recovery of specific activity in an anti-digoxin single-chain Fv analogue produced in *Escherichia coli*,” Proceedings of the National Academy of Sciences, Aug. 1988, 85(16):5879-83.
Ijntema et al., “Hydroxyapatite microcarriers for biocontrolled release of protein drugs,” International Journal of Pharmaceutics, Dec. 1994, 112(3):215-24.
Johnson et al., “Anti-tumor activity of CC49-doxorubicin immunoconjugates,” Anticancer Research, Jul. 1995, 15(4):1387-93.
Johnston et al., “Sustained delivery of interleukin-2 from a poloxamer 407 gel matrix following intraperitoneal injection in mice,” Pharmaceutical Research, Mar. 1992, 9:425-34.
Jones et al., “Improving the safety of cell therapy products by suicide gene transfer,” Frontiers in Pharmacology, Nov. 2014, 5:254, 8 pages.
Kao et al., “A cetuximab-mediated suicide system in chimeric antigen receptor-modified hematopoietic stem cells for cancer therapy,” Human Gene Therapy, Apr. 2019, 30(4):413-28.
Katsarou et al., “Combining a CAR and a chimeric costimulatory receptor enhances T cell sensitivity to low antigen density and promotes persistence,” Science Translational Medicine, Dec. 2021, 13(623):eabh1962, 18 pages.
Kindt et al. “Antibodies: Structure and Function, ” Kuby Immunology, 6th edition, W.H. Freeman and Co., Aug. 2006, p. 91.
Kipps, “RORI: An orphan becomes apparent,” Blood, The Journal of the American Society of Hematology, Oct. 2022, 140(14):1583-91.
Klein et al., “High-velocity microprojectiles for delivering nucleic acids into living cells, ” Nature, May 1987, 327(6117):70-3.
Kloss et al., “Dominant-negative TGF-ß receptor enhances PSMA-targeted human CAR T cell proliferation and augments prostate cancer eradication,” Molecular Therapy, Jul. 2018, 26(7):1855, 13 pages.
Kochenderfer et al., “B-cell depletion and remissions of malignancy along with cytokine-associated toxicity in a clinical trial of anti-CD19 chimeric-antigen-receptor-transduced T cells,” Blood, The Journal of the American Society of Hematology, Mar. 2012, 119(12):2709, 13 pages.
Kumaresan et al., “Bioengineering T cells to target carbohydrate to treat opportunistic fungal infection,” Proceedings of the National Academy of Sciences, Jul. 2014, 111(29):10660-5.
Laird et al., “Isolation and characterization of tox mutants of corynebacteriophage beta, ” Journal of Virology, Jul. 1976, 19(1):220-7.
Lau et al., “Conjugation of doxorubicin to monoclonal anti-carcinoembryonic antigen antibody via novel thiol-directed cross-linking reagents,” Bioorganic & Medicinal Chemistry, Oct. 1995, 3(10):1299-304.
Lau et al., “Novel doxorubicin-monoclonal anti-carcinoembryonic antigen antibody immunoconjugate activity in vitro,” Bioorganic & Medicinal Chemistry, Oct. 1995, 3(10):1305-12.
Lee et al., “Calicheamicins, a novel family of antitumor antibiotics, 3. Isolation, purification and characterization of calicheamicins beta 1Br, gamma 1Br, alpha 2I, alpha 3I, beta 1I, gamma 1I and delta 1I,” The Journal of Antibiotics, Jul. 1989, 42(7):1070-87.
Lee et al., “Clinical signs and symptoms in non-transfused patients with paroxysmal nocturnal hemoglobinuria from a Korean prospective PNH registry, ” Blood, Nov. 2013, 122(21):3720, presented at the American Society of Hematology 55th Annual Meeting, New Orleans, LA, Dec. 7-10, 2013, 4 pages.

(56) References Cited

OTHER PUBLICATIONS

Lefranc et al., "IMGT unique numbering for immunoglobulin and T cell receptor variable domains and Ig superfamily V-like domains," Developmental & Comparative Immunology, Jan. 2003, 27(1):55-77.
Lehner et al., "Redirecting T cells to Ewing's sarcoma family of tumors by a chimeric NKG2D receptor expressed by lentiviral transduction or mRNA transfection," PloS one, Feb. 2012, 7(2):e31210, 12 pages.
Li et al., "IL-7 and CCR2b co-expression-mediated enhanced CAR-T survival and infiltration in solid tumors," Frontiers in Oncology, Oct. 2021, 11:734593, 9 pages.
Lindo et al., "Befriending the hostile tumor microenvironment in CAR T-cell therapy," Frontiers in Immunology, Feb. 2021, 11:618387.
Liu et al., "Calcineurin is a common target of cyclophilin-cyclosporin A and Fkbp-FK506 complexes," Cell, Aug. 1991, 66(4): 807-15.
Lonberg et al., "Human antibodies from transgenic animals," Nature Biotechnology, Sep. 2005, 23(9):1117-25.
Lonberg, "Fully human antibodies from transgenic mouse and phage display platforms," Current Opinion in Immunology, Aug. 2008, 20(4):450-9.
Long et al., "Lessons learned from a highly-active CD22-specific chimeric antigen receptor," Oncoimmunology, Apr. 2013, 2(4):e23621, 3 pages.
Mabry et al., "Therapeutic bispecific antibodies: The selection of stable single-chain fragments to overcome engineering obstacles," Idrugs: the Investigational Drugs Journal, Aug. 1, 2010, 13(8):543-9.
Majzner et al., "Tumor antigen escape from CAR T-cell therapy," Cancer Discovery, Oct. 2018, 8(10):1219, 9 pages.
Milone et al., "Chimeric receptors containing CD137 signal transduction domains mediate enhanced survival of T cells and increased antileukemic efficacy in vivo," Molecular Therapy, Aug. 1, 2009, 17(8):1453, 13 pages.
Morgan et al., "Case report of a serious adverse event following the administration of T cells transduced with a chimeric antigen receptor recognizing ERBB2," Molecular Therapy, Apr. 2010, 18(4):843, 10 pages.
Narayan et al., "PSMA-targeting TGFß-insensitive armored CAR T cells in metastatic castration-resistant prostate cancer: a phase 1 trial," Nature Medicine, Apr. 2022, 28(4):724-34.
NCBI ID No. NP_000130.1, "high affinity immunoglobulin epsilon receptor subunit beta isoform 1 [Homo sapiens]," Sep. 9, 2021, 4 pages.
NCBI ID No. NP_000607.1, "T-cell surface glycoprotein CD4 isoform 1 precursor [Homo sapiens]," Jun. 12, 2022.
NCBI ID No. NP_000617.1, "B-cell antigen receptor complex-associated protein beta chain isoform 1 precursor [Homo sapiens]," Apr. 16, 2022, 5 pages.
NCBI ID No. NP_000723.1, T-cell surface glycoprotein CD3 delta chain isoform A precursor [Homo sapiens], Jun. 9, 2022, 4 pages.
NCBI ID No. NP_000724.1, "T-cell surface glycoprotein CD3 epsilon chain precursor [Homo sapiens]," Jun. 8, 2022, 4 pages.
NCBI ID No. NP_001552.2, "tumor necrosis factor receptor superfamily member 9 precursor [Homo sapiens]," Jun. 7, 2022, 4 pages.
NCBI ID No. NP_001758.2, "T-cell surface antigen CD2 isoform 2 precursor [Homo sapiens]," Jun. 3, 2022, 5 pages.
NCBI ID No. NP_001759.3, T-cell surface glycoprotein CD8 alpha chain isoform 1 precursor [Homo sapiens], Jun. 12, 2022, 4 pages.
NCBI ID No. NP_001762.2, "B-cell receptor CD22 isoform 1 precursor [Homo sapiens]," Apr. 17, 2022, 7 pages.
NCBI ID No. NP_001774.1, "B-cell antigen receptor complex-associated protein alpha chain isoform 1 precursor [Homo sapiens]," Jun. 8, 2022, 4 pages.
NCBI ID No. NP_001806.2, "carcinoembryonic antigen-related cell adhesion molecule 3 isoform 1 precursor [Homo sapiens]," Feb. 27, 2022, 4 pages.
NCBI ID No. NP_003318.1, "tumor necrosis factor receptor superfamily member 4 isoform 1 precursor [Homo sapiens]," Aug. 16, 2022, 4 pages.
NCBI ID No. NP_004097.1, "high affinity immunoglobulin epsilon receptor subunit gamma precursor [Homo sapiens]," May 15, 2022, 3 pages.
NCBI ID No. NP_006130.1, "T-cell-specific surface glycoprotein CD28 isoform 1 precursor [Homo sapiens]," May 22, 2022, 5 pages.
NCBI ID No. NP_036224.1, "inducible T-cell costimulator precursor [Homo sapiens]," Apr. 17, 2022, 3 pages.
NCBI ID No. NP_055022.2, "T-cell surface glycoprotein CD5 isoform 1 precursor [Homo sapiens]," Apr. 24, 2022, 4 pages.
NCBI ID No. NP_932170.1, "T-cell surface glycoprotein CD3 zeta chain isoform 1 precursor [Homo sapiens]," Jun. 12, 2022, 4 pages.
NCBI ID No. NP_000064.1, Mycolicibacterium smegmatis MC2 155, complete sequence, Apr. 11, 2022, 2 pages, 6 pages.
Neville et al., "Enhancement of immunotoxin efficacy by acid-cleavable cross-linking agents utilizing diphtheria toxin and toxin mutants," Journal of Biological Chemistry, Sep. 1989, 264(25):14653-61.
Nicolson et al., "The interaction of Ricinus communis agglutinin with normal and tumor cell surfaces," Biochimica et Biophysica Acta (BBA)-Biomembranes, May 1972, 266(2):543-7.
Olsnes et al., "Mechanism of action of the toxic lectins abrin and ricin, " Nature, Jun. 1974, 249(5458):627-31.
Olsnes, "[35] Ricin and ricinus agglutinin, toxic lectins from castor bean," Methods in Enzymology, Jan. 1978, (50):330-5.
Park et al., "Treating cancer with genetically engineered T cells, " Trends in Biotechnology, Nov. 2011, 29(11):550-7.
Phillips et al., "Targeting HER2-positive breast cancer with trastuzumab-DM1, an antibody-cytotoxic drug conjugate," Cancer Research, Nov. 2008, 68(22):9280-90.
Pietrobon et al., "Improving CAR T-cell persistence," International Journal of Molecular Sciences, Oct. 2021, 22(19):10828, 27 pages.
Poljak, "Production and structure of diabodies," Structure, Dec. 1994, 2(12):1121-3.
Porter et al., "Chimeric antigen receptor-modified T cells in chronic lymphoid leukemia, " New England Journal of Medicine, Aug. 2011, 365(8):725-33.
Rathore et al., "Overproduction of fungal ribotoxin a-sarcin in *Escherichia coli*: generation of an active immunotoxin," Gene, Jan. 1997, 190(1):31-5.
Sadelain et al., "The basic principles of chimeric antigen receptor design," Cancer Discovery, Apr. 2013, 3(4):388-98.
Schneider et al., "A tandem CD19/CD20 CAR lentiviral vector drives on-target and off-target antigen modulation in leukemia cell lines," Journal for Immunotherapy of Cancer, Dec. 2017, 5(1):1-7.
Schneider et al., "Trispecific CD19-CD20-CD22-targeting duoCAR-T cells eliminate antigen-heterogeneous B cell tumors in preclinical models," Science Translational Medicine, Mar. 2021, 13(586):eabc6401, 14 pages.
Schubert et al., "Third-generation CAR T cells targeting CD19 are associated with an excellent safety profile and might improve persistence of CAR T cells in treated patients, " Blood, Nov. 2019, 134(supp 1):51, 3 pages.
Shalabi et al., "Sequential loss of tumor surface antigens following chimeric antigen receptor T-cell therapies in diffuse large B-cell lymphoma," Haematologica, May 2018, 103(5):e215, 4 pages.
Sheriff et al., "Redefining the minimal antigen-binding fragment," Nature Structural Biology, Sep. 1996, 3(9):733-6.
Srivastava et al., "Immunogenic chemotherapy enhances recruitment of CAR-T cells to lung tumors and improves antitumor efficacy when combined with checkpoint blockade," Cancer Cell, Feb. 2021, 39(2):193, 27 pages.
Sterner et al., "CAR-T cell therapy: current limitations and potential strategies," Blood Cancer Journal, Apr. 2021, 11(4):69, 11 pages.
Stirpe et al., "Ribosome-inactivating proteins from plants: Present status and future prospects," Bio/technology, Apr. 1992, 10(4):405-12.
Subklewe et al., "Chimeric antigen receptor T cells: a race to revolutionize cancer therapy," Transfusion Medicine and Hemotherapy, Feb. 2019, 46(1):15-24.

(56) References Cited

OTHER PUBLICATIONS

Suzuki et al., "Engineering receptor-mediated cytotoxicity into human ribonucleases by steric blockade of inhibitor interaction," Nature Biotechnology, Mar. 1999, 17(3):265-70.
Tang et al., "TGF-ßinhibition via CRISPR promotes the long-term efficacy of CAR T cells against solid tumors," JCI Insight, Feb. 2020, 5(4), 40 pages.
Tedesco et al., "Biomarkers for predicting cytokine release syndrome following CD19-targeted CAR T cell therapy," The Journal of Immunology, Apr. 2021, 206(7):1561, 13 pages.
Thorpe et al., "New coupling agents for the synthesis of immunotoxins containing a hindered disulfide bond with improved stability in vivo," Cancer Research, Nov. 1987, 47(22):5924-31.
Till et al., "Adoptive immunotherapy for indolent non-Hodgkin lymphoma and mantle cell lymphoma using genetically modified autologous CD20-specific T cells," Blood, The Journal of the American Society of Hematology, Sep. 2008, 112(6):2261-71.
Tumaini et al., "Simplified process for the production of anti-CD19-CAR-engineered T cells," Cytotherapy, Nov. 2013, 15(11):1406-15.
Tzavlaki et al., "TGF-ß Signaling," Biomolecules, Mar. 2020, 10(3):487, 38 pages.
Wagner et al., "CAR T cell therapy for solid tumors: bright future or dark reality?," Molecular Therapy, Nov. 2020, 28(11):2320-39.
Walsh et al., "Multi-specific CAR targeting to prevent antigen escape," Current Hematologic Malignancy Reports, Oct. 2019, 14:451-9.
Ward et al., "Binding activities of a repertoire of single immunoglobulin variable domains secreted from *Escherichia coli*," Nature, Oct. 1989, 341(6242):544-6.
Winter et al., "Humanized antibodies," Immunology Today, Jun. 1993, 14(6):243-6.
Yeku et al., "Armored CAR T cells enhance antitumor efficacy and overcome the tumor microenvironment," Scientific Reports, Sep. 2017, 7(1):10541.
Yu et al., "The biosynthetic gene cluster of the maytansinoid antitumor agent ansamitocin from Actinosynnema pretiosum," Proceedings of the National Academy of Sciences, Jun. 2002, 99(12):7968-73.
Yvon et al., "Immunotherapy of metastatic melanoma using genetically engineered GD2-specific T cells," Clinical Cancer Research, Sep. 15, 2009, 15(18):5852-60.
Zhang et al., "Hurdles of CAR-T cell-based cancer immunotherapy directed against solid tumors," Science China Life Sciences, Apr. 2016, 59:340-8.
Zhang et al., "RORI is expressed in human breast cancer and associated with enhanced tumor-cell growth," PloS one, Mar. 2012, 7(3):e31127, 12 pages.
Zhang et al., "The onco-embryonic antigen RORI is expressed by a variety of human cancers," The American Journal of Pathology, Dec. 2012, 181(6):1903-10.
Zhao et al., "A herceptin-based chimeric antigen receptor with modified signaling domains leads to enhanced survival of transduced T lymphocytes and antitumor activity," The Journal of Immunology, Nov. 2009, 183(9):5563-74.
Zhao et al., "Bioorthogonal equipping CAR-T cells with hyaluronidase and checkpoint blocking antibody for enhanced solid tumor immunotherapy," ACS Central Science, Apr. 2022, 8(5):603-14.
Zhao et al., "Primary human lymphocytes transduced with NY-ESO-1 antigen-specific TCR genes recognize and kill diverse human tumor cell lines, " The Journal of Immunology, Apr. 2005, 174(7):4415-23.
International Search Report and Written Opinion in International Appln. No. PCT/US2023/029008, mailed on Mar. 21, 2024, 26 pages.
PCT International Preliminary Report on Patentability in International Appln. No. PCT/US2023/029008, mailed on Jan. 28, 2025, 14 pages.

* cited by examiner

A

B

C

A

B

C

A

B

A

B

A

B

OVCAR-3 Xenografts

B

C

D

C

A

B

C

C

A

B

F

G

H

I

J

C

D

E

F

G

SEQUENCE LISTING

Sequence total quantity: 256
SEQ ID NO: 1 moltype = DNA length = 728
FEATURE Location/Qualifiers
source 1..728
mol_type = other DNA
organism = Synthetic construct
SEQUENCE: 1
gaggtgcagt gcaacagtca ggagctgaac tggtcaagcc aggagccagc gtgaagatga 60
gctgcaaggc ctccggttac accttcacct cctacaacat gcactgggtg aaacagaccc 120
cgggacaagg gctcgaatgg attggcgcca tctaccccgg gaatggcgat acttcgtaca 180
accagaagtt caagggaaag gccaccctga ccgccgacaa gagctcctcc accgcgtata 240
tgcagttgag ctccctgacc tccgaggact ccgccgacta ctactgcgca cggtccaact 300
actatggaag ctcgtactgg ttcttcgatg tctgggggc cggcaccact gtgaccgtca 360
gctccggggg cggaggatcc ggtggaggcg gaagcggggg tggaggatcc gacattgtgc 420
tgactcagtc cccggcaatc ctgtcggcct caccgggcga aaaggtcacg atgacttgta 480
gagcgtcgtc cagcgtgaac tacatggatt ggtaccaaaa gaagcctgga tcgtcaccca 540
agccttggat ctacgctaca tctaacctgg cctccggcgt gccagcgcgg ttcagcgggt 600
ccggctcggg cacctcatac tcgctgacca tctcccgcgt ggaggctgag gacgccgcga 660
cctactactg ccagcagtgg tccttcaacc cgccgacttt tggaggcggt actaagctgg 720
agatcaaa 728

```
SEQ ID NO: 2            moltype = AA  length = 243
FEATURE                 Location/Qualifiers
source                  1..243
                        mol_type = protein
                        organism = Synthetic construct
SEQUENCE: 2
EVQLQQSGAE LVKPGASVKM SCKASGYTFT SYNMHWVKQT PGQGLEWIGA IYPGNGDTSY  60
NQKFKGKATL TADKSSSTAY MQLSSLTSED SADYYCARSN YYGSSYWFFD VWGAGTTVTV  120
SSGGGGSGGG GSGGGGSDIV LTQSPAILSA SPGEKVTMTC RASSSVNYMD WYQKKPGSSP  180
KPWIYATSNL ASGVPARFSG SGSGTSYSLT ISRVEAEDAA TYYCQQWSFN PPTFGGGTKL  240
EIK                                                               243

SEQ ID NO: 3            moltype = DNA  length = 1473
FEATURE                 Location/Qualifiers
source                  1..1473
                        mol_type = other DNA
                        organism = Synthetic construct
SEQUENCE: 3
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct gggggggccgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaagcggc cgcaactacc accccctgccc ctcggccgcc gactccggcc  840
ccaaccatcg caagccaacc cctctccttg cgccccgaag cttgccgccc ggccgcgggt  900
ggagccgtgc atacccgggg gctggacttt gcctgcgata tctacatttg ggccccgctg  960
gccggcactt gcggcgtgct cctgctgtcg ctggtcatca ccctttactg caagaggggc  1020
cggaagaagc tgctttacat cttcaagcag ccgttcatgc ggcccgtgca gacgactcag  1080
gaagaggacg gatgctcgtg cagattccct gaggaggaag aggggggatg cgaactgcgc  1140
gtcaagttct cacggtccgc cgacgccccc gcatatcaac agggccagaa tcagctctac  1200
aacgagctga acctgggaag gagagaggag tacgacgtgc tggacaagcg acgcggacgc  1260
gacccggaga tgggggggaa accacggcgg aaaaaccctc aggaaggact gtacaacgaa  1320
ctccagaaag acaagatggc ggaagcctac tcagaaatcg ggatgaaggg agagcggagg  1380
aggggaaagg gtcacgacgg gctgtaccag ggactgagca ccgccactaa ggatacctac  1440
gatgccttgc atatgcaagc actcccaccc cgg                              1473

SEQ ID NO: 4            moltype = AA  length = 491
FEATURE                 Location/Qualifiers
source                  1..491
                        mol_type = protein
                        organism = Synthetic construct
SEQUENCE: 4
MLLLVTSLLL CELPHPAFLL IPEVQLQQSG AELVKPGASV KMSCKASGYT FTSYNMHWVK  60
QTPGQGLEWI GAIYPGNGDT SYNQKFKGKA TLTADKSSST AYMQLSSLTS EDSADYYCAR  120
SNYYGSSYWF FDVWGAGTTV TVSSGGGGSG GGGSGGGGSD IVLTQSPAIL SASPGEKVTM  180
TCRASSSVNY MDWYQKKPGS SPKPWIYATS NLASGVPARF SGSGSGTSYS LTISRVEAED  240
AATYYCQQWS FNPPTFGGGT KLEIKAAATT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYQQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                      491

SEQ ID NO: 5            moltype = DNA  length = 66
FEATURE                 Location/Qualifiers
source                  1..66
                        mol_type = other DNA
                        organism = Synthetic construct
SEQUENCE: 5
atgctgctgc tggtgaccag cctgctgctg tgcgaactgc cgcatccggc gtttctgctg  60
attccg                                                            66

SEQ ID NO: 6            moltype = AA  length = 22
FEATURE                 Location/Qualifiers
source                  1..22
                        mol_type = protein
                        organism = Synthetic construct
SEQUENCE: 6
MLLLVTSLLL CELPHPAFLL IP                                          22

SEQ ID NO: 7            moltype = DNA  length = 747
```

```
FEATURE               Location/Qualifiers
source                1..747
                      mol_type = other DNA
                      organism = Synthetic construct
SEQUENCE: 7
caggtacagc tccagcagag tggcccaggg ctcgtgaagc caagccagac gctgtccctg  60
acttgtgcaa tttcagggga ttcagtttca tcaaatagcg cggcgtggaa ttggattcga  120
caatctcctt cccgagggtt ggaatggctt ggacgaacat attacagatc caaatggtat  180
aacgactatg cggtatcagt aaagtcaaga ataaccatta accccgacac aagcaagaac  240
caattctctt tgcagcttaa ctctgtcacg ccagaagaca cggcagtcta ttattgcgct  300
cgcgaggtaa cgggtgacct ggaagacgct tttgacattt gggggcaggg tacgatggtg  360
acagtcagtt cagggggcgg tgggagtggg ggagggggta gcgggggggg agggtcagac  420
attcagatga cccagtcccc ttcatccttg tctgcctccg tcggtgacag ggtgacaata  480
acatgcagag caagccaaac aatctggagc tatctcaact ggtaccagca gcgaccagga  540
aaagcgccaa acctgctgat ttacgctgct tcctccctcc aatcaggcgt gcctagtaga  600
tttagcggta ggggctccgg caccgatttt acgctcacta taagctctct tcaagcagaa  660
gattttgcga cttattactg ccagcagtcc tatagtatac ctcagacttt cggacagggt  720
accaagttgg agattaaggc ggccgca                                      747

SEQ ID NO: 8          moltype = AA  length = 249
FEATURE               Location/Qualifiers
source                1..249
                      mol_type = protein
                      organism = Synthetic construct
SEQUENCE: 8
QVQLQQSGPG LVKPSQTLSL TCAISGDSVS SNSAAWNWIR QSPSRGLEWL GRTYYRSKWY  60
NDYAVSVKSR ITINPDTSKN QFSLQLNSVT PEDTAVYYCA REVTGDLEDA FDIWGQGTMV  120
TVSSGGGGSG GGGSGGGGSD IQMTQSPSSL SASVGDRVTI TCRASQTIWS YLNWYQQRPG  180
KAPNLLIYAA SSLQSGVPSR FSGRGSGTDF TLTISSLQAE DFATYYCQQS YSIPQTFGQG  240
TKLEIKAAA                                                          249

SEQ ID NO: 9          moltype = DNA  length = 1482
FEATURE               Location/Qualifiers
source                1..1482
                      mol_type = other DNA
                      organism = Synthetic construct
SEQUENCE: 9
atgcttcttt tggtgacttc ccttttgctg tgcgagttgc cacaccccgc cttcctgctt  60
attccccagg tacagctcca gcagagtggc ccagggctcg tgaagccaag ccagacgctg  120
tccctgactt gtgcaatttc aggggattca gtttcatcaa atagcgcggc gtggaattgg  180
attcgacaat ctccttcccg agggttggaa tggcttggac gaacatatta cagatccaaa  240
tggtataacg actatgcggt atcagtaaag tcaagaataa ccattaaccc cgacacaagc  300
aagaaccaat tctctttgca gcttaactct gtcacgccag aagacacggc agtctattat  360
tgcgctcgcg aggtaacggg tgacctggaa gacgcttttg acatttgggg gcagggtacg  420
atggtgacag tcagttcagg gggcggtggg agtgggggag gggtagcgg gggggggaggg  480
tcagacattc agatgaccca gtccccttca tccttgtctg cctccgtcgg tgacagggtg  540
acaataacat gcagagcaag ccaaacaatc tggagctatc tcaactggta ccagcagcga  600
ccaggaaaag cgccaaacct gctgatttac gctgcttcct ccctccaatc aggcgtgcct  660
agtagattta gcggtagggg ctccggcacc gattttacgc tcactataag ctctcttcaa  720
gcagaagatt ttgcgactta ttactgccag cagtcctata gtatacctca gactttcgga  780
cagggtacca agttggagat taaggcggcc gcaactacca cccctgcccc tcggccgccg  840
actccggccc caaccatcgc aagccaaccc ctctccttgc gccccgaagc ttgccgcccg  900
gccgcgggtg gagccgtgca tacccggggg ctggactttg cctgcgatat ctacatttgg  960
gccccgctgg ccggcacttg cggcgtgctc ctgctgtcgc tggtcatcac cctttactgc  1020
aagaggggcc ggaagaagct gctttacatc ttcaagcagc cgttcatgcg gcccgtgcag  1080
acgactcagg aagaggacgg atgctcgtgc agattccctg aggaggaaga gggggggatgc  1140
gaactgcgcg tcaagttctc acggtccgcc gacgcccccg catatcaaca gggccagaat  1200
cagctctaca acgagctgaa cctgggaagg agagaggagt acgacgtgct ggacaagcga  1260
cgcggacgcg acccggagat ggggggggaaa ccacggcgga aaaaccctca ggaaggactg  1320
tacaacgaac tccagaaaga caagatggcg gaagcctact cagaaatcgg gatgaaggga  1380
gagcggagga ggggaaaggg tcacgacggg ctgtaccagg gactgagcac cgccactaag  1440
gatacctacg atgccttgca tatgcaagca ctcccacccc gg                     1482

SEQ ID NO: 10         moltype = AA  length = 494
FEATURE               Location/Qualifiers
source                1..494
                      mol_type = protein
                      organism = Synthetic construct
SEQUENCE: 10
MLLLVTSLLL CELPHPAFLL IPQVQLQQSG PGLVKPSQTL SLTCAISGDS VSSNSAAWNW  60
IRQSPSRGLE WLGRTYYRSK WYNDYAVSVK SRITINPDTS KNQFSLQLNS VTPEDTAVYY  120
CAREVTGDLE DAFDIWGQGT MVTVSSGGGG SGGGGSGGGG SDIQMTQSPS SLSASVGDRV  180
TITCRASQTI WSYLNWYQQR PGKAPNLLIY AASSLQSGVP SRFSGRGSGT DFTLTISSLQ  240
AEDFATYYCQ QSYSIPQTFG QGTKLEIKAA ATTTPAPRPP TPAPTIASQP LSLRPEACRP  300
AAGGAVHTRG LDFACDIYIW APLAGTCGVL LLSLVITLYC KRGRKKLLYI FKQPFMRPVQ  360
TTQEEDGCSC RFPEEEEGGC ELRVKFSRSA DAPAYQQGQN QLYNELNLGR REEYDVLDKR  420
RGRDPEMGGK PRRKNPQEGL YNELQKDKMA EAYSEIGMKG ERRRGKGHDG LYQGLSTATK  480
DTYDALHMQA LPPR                                                    494
```

```
SEQ ID NO: 11          moltype = DNA  length = 72
FEATURE                Location/Qualifiers
source                 1..72
                       mol_type = other DNA
                       organism = Synthetic construct
SEQUENCE: 11
atctacatct gggcgccctt ggccgggact tgtggggtcc ttctcctgtc actggttatc  60
accctttact gc                                                      72

SEQ ID NO: 12          moltype = AA  length = 22
FEATURE                Location/Qualifiers
source                 1..22
                       mol_type = protein
                       organism = Synthetic construct
SEQUENCE: 12
IWAPLAGTCG VLLLSLVITL YC                                           22

SEQ ID NO: 13          moltype = DNA  length = 141
FEATURE                Location/Qualifiers
source                 1..141
                       mol_type = other DNA
                       organism = Synthetic construct
SEQUENCE: 13
accacgacgc cagcgccgcg accaccaaca ccggcgccca ccatcgcgtc gcagcccctg  60
tccctgcgcc cagaggcgtg ccggccagcg gcggggggcg cagtgcacac gagggggctg  120
gactttgcct gcgatatcta c                                            141

SEQ ID NO: 14          moltype = AA  length = 47
FEATURE                Location/Qualifiers
source                 1..47
                       mol_type = protein
                       organism = Synthetic construct
SEQUENCE: 14
TTTPAPRPPT PAPTIASQPL SLRPEACRPA AGGAVHTRGL DFACDIY                47

SEQ ID NO: 15          moltype = AA  length = 69
FEATURE                Location/Qualifiers
source                 1..69
                       mol_type = protein
                       organism = Synthetic construct
SEQUENCE: 15
TTTPAPRPPT PAPTIASQPL SLRPEACRPA AGGAVHTRGL DFACDIYIWA PLAGTCGVLL  60
LSLVITLYC                                                          69

SEQ ID NO: 16          moltype = AA  length = 106
FEATURE                Location/Qualifiers
source                 1..106
                       mol_type = protein
                       organism = Synthetic construct
SEQUENCE: 16
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECS                 106

SEQ ID NO: 17          moltype = DNA  length = 126
FEATURE                Location/Qualifiers
source                 1..126
                       mol_type = other DNA
                       organism = Synthetic construct
SEQUENCE: 17
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                             126

SEQ ID NO: 18          moltype = AA  length = 42
FEATURE                Location/Qualifiers
source                 1..42
                       mol_type = protein
                       organism = Synthetic construct
SEQUENCE: 18
KRGRKKLLYI FKQPFMRPVQ TTQEEDGCSC RFPEEEEGGC EL                     42

SEQ ID NO: 19          moltype = DNA  length = 336
FEATURE                Location/Qualifiers
source                 1..336
                       mol_type = other DNA
                       organism = Synthetic construct
SEQUENCE: 19
agagtgaagt tcagcaggag cgcagacgcc cccgcgtaca agcagggcca gaaccagctc  60
tataacgagc tcaatctagg acgaagagag gagtacgatg ttttggacaa gagacgtggc  120
```

```
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgc                            336

SEQ ID NO: 20          moltype = AA  length = 112
FEATURE                Location/Qualifiers
source                 1..112
                       mol_type = protein
                       organism = Synthetic construct
SEQUENCE: 20
RVKFSRSADA PAYKQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 21          moltype = DNA  length = 1467
FEATURE                Location/Qualifiers
source                 1..1467
                       mol_type = other DNA
                       organism = Synthetic construct
SEQUENCE: 21
atgctgctgc tggtgaccag cctgctgctg tgcgaactgc cgcatccggc gtttctgctg  60
attccggata ttcagatgac ccagaccacc agcagcctga gcgcgagcct gggcgatcgc  120
gtgaccatta gctgccgcgc gagccaggat attagcaaat atctgaactg gtatcagcag  180
aaaccggatg gcaccgtgaa actgctgatt tatcatacca gccgcctgca tagcggcgtg  240
ccgagccgct ttagcggcag cggcagcggc accgattata gcctgaccat tagcaacctg  300
gaacaggaag atattgcgac ctatttttgc cagcagggca acaccctgcc gtataccttt  360
ggcggcggca ccaaactgga aattaccggc ggcggcggca gcggcggcgg cggcagcggc  420
ggcggcggca gcgaagtgaa actgcaggaa agcggcccgg gcctggtggc gccgagccag  480
agcctgagcg tgacctgcac cgtgagcggc gtgagcctgc cggattatgg cgtgagctgg  540
attcgccagc cgccgcgcaa aggcctggaa tggctgggcg tgatttgggg cagcgaaacc  600
acctattata acagcgcgct gaaaagccgc ctgaccatta ttaaagataa cagcaaaagc  660
caggtgtttc tgaaaatgaa cagcctgcag accgatgata ccgcgattta ttattgcgcg  720
aaacattatt attatggcgg cagctatgcg atggattatt ggggccaggg caccagcgtg  780
accgtgagca gcgcggcggc gccggcgccg cgcccgccga ccccggcgcc gaccattgcg  840
agccagccgc tgagcctgcg cccggaagcg tgccgcccgg cggcgggcgg cgcggtgcat  900
acccgcggcc tggattttgt gcagccgatg gcgctgattg tgctgggcgg cgtggcgggc  960
ctgctgctgt ttattggcct gggcattttt ttttgcgtgc gctgccgccc gcgccgcaaa  1020
aaactgctgt atatttttaa acagccgttt atgcgcccgg tgcagaccac ccaggaagaa  1080
gatggctgca gctgccgctt tccggaagaa gaagaaggcg gctgcgaact gcgcgtgaaa  1140
tttagccgca gcgcggatgc gccggcgtat cagcagggcc agaaccagct gtataacgaa  1200
ctgaacctgg gccgccgcga agaatatgat gtgctggata aacgccgcgg ccgcgatccg  1260
gaaatgggcg gcaaaccgcg ccgcaaaaac ccgcaggaag gcctgtataa cgaactgcag  1320
aaagataaaa tggcggaagc gtatagcgaa attggcatga aaggcgaacg ccgccgcggc  1380
aaaggccatg atggcctgta tcagggcctg agcaccgcga ccaaagatac ctatgatgcg  1440
ctgcatatgc aggcgctgcc gccgcgc                                      1467

SEQ ID NO: 22          moltype = AA  length = 489
FEATURE                Location/Qualifiers
source                 1..489
                       mol_type = protein
                       organism = Synthetic construct
SEQUENCE: 22
MLLLVTSLLL CELPHPAFLL IPDIQMTQTT SSLSASLGDR VTISCRASQD ISKYLNWYQQ  60
KPDGTVKLLI YHTSRLHSGV PSRFSGSGSG TDYSLTISNL EQEDIATYFC QQGNTLPYTF  120
GGGTKLEITG GGGSGGGGSG GGGSEVKLQE SGPGLVAPSQ SLSVTCTVSG VSLPDYGVSW  180
IRQPPRKGLE WLGVIWGSET TYYNSALKSR LTIIKDNSKS QVFLKMNSLQ TDDTAIYYCA  240
KHYYYGGSYA MDYWGQGTSV TVSSAAAPAP RPPTPAPTIA SQPLSLRPEA CRPAAGGAVH  300
TRGLDFVQPM ALIVLGGVAG LLLFIGLGIF FCVRCRPRRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                          489

SEQ ID NO: 23          moltype = DNA  length = 1548
FEATURE                Location/Qualifiers
source                 1..1548
                       mol_type = other DNA
                       organism = Synthetic construct
SEQUENCE: 23
gaggtgcagt tgcaacagtc aggagctgaa ctggtcaagc caggagccag cgtgaagatg  60
agctgcaagg cctccggtta caccttcacc tcctacaaca tgcactgggt gaaacagacc  120
ccgggacaag ggctcgaatg gattggcgcc atctaccccg ggaatggcga tacttcgtac  180
aaccagaagt tcaagggaaa ggccaccctg accgccgaca agagctcctc caccgcgtat  240
atgcagttga gctccctgac ctccgaggac tccgccgact actactgcgc acggtccaac  300
tactatggaa gctcgtactg gttcttcgat gtctgggggg ccggcaccac tgtgaccgtc  360
agctccgggg gcggaggatc cggtggaggc ggaagcgggg gtggaggatc cgacattgtg  420
ctgactcagt ccccggcaat cctgtcggcc tcaccgggcg aaaaggtcac gatgacttgt  480
agagcgtcgt ccagcgtgaa ctacatggat tggtaccaaa agaagcctgg atcgtcaccc  540
aagccttgga tctacgctac atctaacctg gcctccggcg tgccagcgcg gttcagcggg  600
tccggctcgg gcacctcata ctcgctgacc atctcccgcg tggaggctga ggacgccgcg  660
```

```
acctactact gccagcagtg gtccttcaac ccgccgactt ttggaggcgg tactaagctg  720
gagatcaaag gaggcggcgg cagcggcggg ggagggtccg gagggggtgg ttctggtgga  780
ggaggatcgg gaggcggtgg cagcgacatt cagatgactc agaccacctc ctccctgtcc  840
gcctccctgg gcgaccgcgt gaccatctca tgccgcgcca gccaggacat ctcgaagtac  900
ctcaactggt accagcagaa gcccgacgga accgtgaagc tcctgatcta ccacacctcc  960
cggctgcaca gcggagtgcc gtctagattc tcgggttcgg ggtcgggaac tgactactcc  1020
cttactattt ccaacctgga gcaggaggat attgccacct acttctgcca acaaggaaac  1080
accctgccgt acacttttgg cgggggaacc aagctggaaa tcactggcag cacatccggt  1140
tccgggaagc ccggctccgg agagggcagc accaaggggg aagtcaagct gcaggaatca  1200
ggacctggcc tggtggcccc gagccagtca ctgtccgtga cttgtactgt gtccggagtg  1260
tcgctcccgg attacggagt gtcctggatc aggcagccac ctcggaaagg attggaatgg  1320
ctcggagtca tctggggttc cgaaaccacc tattacaact cggcactgaa atccaggctc  1380
accattatca aggataactc caagtcacaa gtgttcctga agatgaatag cctgcagact  1440
gacgacacgg cgatctacta ttgcgccaag cactactact acggcggatc ctacgctatg  1500
gactactggg gccaggggac cagcgtgacc gtgtcatccg cggccgca              1548

SEQ ID NO: 24          moltype = AA  length = 516
FEATURE                Location/Qualifiers
source                 1..516
                       mol_type = protein
                       organism = Synthetic construct
SEQUENCE: 24
EVQLQQSGAE LVKPGASVKM SCKASGYTFT SYNMHWVKQT PGQGLEWIGA IYPGNGDTSY  60
NQKFKGKATL TADKSSSTAY MQLSSLTSED SADYYCARSN YYGSSYWFFD VWGAGTTVTV  120
SSGGGGSGGG GSGGGGSDIV LTQSPAILSA SPGEKVTMTC RASSSVNYMD WYQKKPGSSP  180
KPWIYATSNL ASGVPARFSG SGSGTSYSLT ISRVEAEDAA TYYCQQWSFN PPTFGGGTKL  240
EIKGGGGSGG GGSGGGGSGG GGSGGGGSDI QMTQTTSSLS ASLGDRVTIS CRASQDISKY  300
LNWYQQKPDG TVKLLIYHTS RLHSGVPSRF SGSGSGTDYS LTISNLEQED IATYFCQQGN  360
TLPYTFGGGT KLEITGSTSG SGKPGSGEGS TKGEVKLQES GPGLVAPSQS LSVTCTVSGV  420
SLPDYGVSWI RQPPRKGLEW LGVIWGSETT YYNSALKSRL TIIKDNSKSQ VFLKMNSLQT  480
DDTAIYYCAK HYYYGGSYAM DYWGQGTSVT VSSAAA                            516

SEQ ID NO: 25          moltype = DNA  length = 2283
FEATURE                Location/Qualifiers
source                 1..2283
                       mol_type = other DNA
                       organism = Synthetic construct
SEQUENCE: 25
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct ggggggccgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaaggagg cggcggcagc ggcgggggag ggtccggagg gggtggttct  840
ggtggaggag gatcgggagg cggtggcagc gacattcaga tgactcagac cacctcctcc  900
ctgtccgcct ccctgggcga ccgcgtgacc atctcatgcc gcgccagcca ggacatctcg  960
aagtacctca actggtacca gcagaagccc gacggaaccg tgaagctcct gatctaccac  1020
acctcccggc tgcacagcgg agtgccgtct agattctcgg gttcggggtc gggaactgac  1080
tactccctta ctatttccaa cctggagcag gaggatattg ccacctactt ctgccaacaa  1140
ggaaacaccc tgccgtacac ttttggcggg ggaaccaagc tggaaatcac tggcagcaca  1200
tccggttccg ggaagcccgg ctccggagag ggcagcacca agggggaagt caagctgcag  1260
gaatcaggac ctggcctggt ggccccgagc cagtcactgt ccgtgacttg tactgtgtcc  1320
ggagtgtcgc tcccggatta cggagtgtcc tggatcaggc agccacctcg gaaaggattg  1380
gaatggctcg gagtcatctg gggttccgaa accacctatt acaactcggc actgaaatcc  1440
aggctcacca ttatcaagga taactccaag tcacaagtgt tcctgaagat gaatagcctg  1500
cagactgacg acacggcgat ctactattgc gccaagcact actactacgg cggatcctac  1560
gctatggact actggggcca ggggaccagc gtgaccgtgt catccgcggc cgcaactacc  1620
acccctgccc ctcggccgcc gactccggcc ccaaccatcg caagccaacc cctctccttg  1680
cgccccgaag cttgccgccc ggccgcgggt ggagccgtgc atacccgggg gctggacttt  1740
gcctgcgata tctacatttg ggccccgctg gccggcactt gcggcgtgct cctgctgtcg  1800
ctggtcatca ccctttactg caagaggggc cggaagaagc tgctttacat cttcaagcag  1860
ccgttcatgc ggcccgtgca gacgactcag gaagaggacg gatgctcgtg cagattccct  1920
gaggaggaag aggggggatg cgaactgcgc gtcaagttct cacggtccgc cgacgccccc  1980
gcatatcaac agggccagaa tcagctctac aacgagctga acctgggaag gagagaggag  2040
tacgacgtgc tggacaagcg acgcggacgc gacccggaga tgggggggaa accacggcgg  2100
aaaaaccctc aggaaggact gtacaacgaa ctccagaaag acaagatggc ggaagcctac  2160
tcagaaatcg ggatgaaggg agagcggagg aggggaaagg gtcacgacgg gctgtaccag  2220
ggactgagca ccgccactaa ggatacctac gatgccttgc atatgcaagc actcccaccc  2280
cgg                                                                2283

SEQ ID NO: 26          moltype = AA  length = 761
```

```
FEATURE                Location/Qualifiers
source                 1..761
                       mol_type = protein
                       organism = Synthetic construct
SEQUENCE: 26
MLLLVTSLLL CELPHPAFLL IPEVQLQQSG AELVKPGASV KMSCKASGYT FTSYNMHWVK  60
QTPGQGLEWI GAIYPGNGDT SYNQKFKGKA TLTADKSSST AYMQLSSLTS EDSADYYCAR  120
SNYYGSSYWF FDVWGAGTTV TVSSGGGGSG GGGSGGGGSD IVLTQSPAIL SASPGEKVTM  180
TCRASSSVNY MDWYQKKPGS SPKPWIYATS NLASGVPARF SGSGSGTSYS LTISRVEAED  240
AATYYCQQWS FNPPTFGGGT KLEIKGGGGS GGGGSGGGGS GGGGSGGGGS DIQMTQTTSS  300
LSASLGDRVT ISCRASQDIS KYLNWYQQKP DGTVKLLIYH TSRLHSGVPS RFSGSGSGTD  360
YSLTISNLEQ EDIATYFCQQ GNTLPYTFGG GTKLEITGST SGSGKPGSGE GSTKGEVKLQ  420
ESGPGLVAPS QSLSVTCTVS GVSLPDYGVS WIRQPPRKGL EWLGVIWGSE TTYYNSALKS  480
RLTIIKDNSK SQVFLKMNSL QTDDTAIYYC AKHYYYGGSY AMDYWGQGTS VTVSSAAATT  540
TPAPRPPTPA PTIASQPLSL RPEACRPAAG GAVHTRGLDF ACDIYIWAPL AGTCGVLLLS  600
LVITLYCKRG RKKLLYIFKQ PFMRPVQTTQ EEDGCSCRFP EEEEGGCELR VKFSRSADAP  660
AYQQGQNQLY NELNLGRREE YDVLDKRRGR DPEMGGKPRR KNPQEGLYNE LQKDKMAEAY  720
SEIGMKGERR RGKGHDGLYQ GLSTATKDTY DALHMQALPP R                     761

SEQ ID NO: 27          moltype = DNA  length = 726
FEATURE                Location/Qualifiers
source                 1..726
                       mol_type = other DNA
                       organism = Synthetic construct
SEQUENCE: 27
gacatccaga tgacacagac tacatcctcc ctgtctgcct ctctgggaga cagagtcacc  60
atcagttgca gggcaagtca ggacattagt aaatatttaa attggtatca gcagaaacca  120
gatggaactg ttaaactcct gatctaccat acatcaagat tacactcagg agtcccatca  180
aggttcagtg gcagtgggtc tggaacagat tattctctca ccattagcaa cctggagcaa  240
gaagatattg ccacttactt ttgccaacag ggtaatacgc ttccgtacac gttcggaggg  300
gggaccaagc tggagatcac aggtggcggt ggctcgggcg gtggtgggtc gggtggcggc  360
ggatctgagg tgaaactgca ggagtcagga cctggcctgg tggcgccctc acagagcctg  420
tccgtcacat gcactgtctc aggggtctca ttacccgact atggtgtaag ctggattcgc  480
cagcctccac gaaagggtct ggagtggctg ggagtaatat ggggtagtga aaccacatac  540
tataattcag ctctcaaatc cagactgacc atcatcaagg acaactccaa gagccaagtt  600
ttcttaaaaa tgaacagtct gcaaactgat gacacagcca tttactactg tgccaaacat  660
tattactacg gtggtagcta tgctatggac tactggggcc aaggaacctc agtcaccgtc  720
tcctca                                                            726

SEQ ID NO: 28          moltype = AA  length = 242
FEATURE                Location/Qualifiers
source                 1..242
                       mol_type = protein
                       organism = Synthetic construct
SEQUENCE: 28
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGGG GSGGGGSGGG  120
GSEVKLQESG PGLVAPSQSL SVTCTVSGVS LPDYGVSWIR QPPRKGLEWL GVIWGSETTY  180
YNSALKSRLT IIKDNSKSQV FLKMNSLQTD DTAIYYCAKH YYYGGSYAMD YWGQGTSVTV  240
SS                                                                242

SEQ ID NO: 29          moltype = DNA  length = 1485
FEATURE                Location/Qualifiers
source                 1..1485
                       mol_type = other DNA
                       organism = Synthetic construct
SEQUENCE: 29
atgcttctcc tggtcacctc cctgctcctc tgcgaactgc ctcaccctgc cttccttctg  60
attcctgaca ctgacattca gatgactcag accacctctt ccttgtccgc gtcactggga  120
gacagagtga ccatctcgtg tcgcgcaagc caggatatct ccaagtacct gaactggtac  180
caacagaagc ccgacgggac tgtgaagctg ctgatctacc acacctcacg cctgcacagc  240
ggagtgccaa gcagattctc cggctccggc tcgggaaccg attactcgct taccattagc  300
aacctcgagc aggaggacat cgctacctac ttctgccagc aaggaaatac cctgccctac  360
accttcggcg gaggaaccaa attggaaatc accggctcca cgagcggctc cgggaagcct  420
ggttccgggg aaggctccac taagggtgaa gtgaagctcc aggagtccgg ccccggcctg  480
gtggcgccgt cgcaatcact ctctgtgacc tgtaccgtgt cgggagtgtc cctgcctgat  540
tacggcgtga gctggattcg gcagccgccg cggaagggcc tggaatggct gggtgtcatc  600
tggggatccg agactaccta ctacaactcg gccctgaagt cccgcctgac tatcatcaaa  660
gacaactcga agtcccaggt ctttctgaag atgaactccc tgcaaactga cgacaccgcc  720
atctattact gtgctaagca ctactactac ggtggaagct atgctatgga ctactggggc  780
caggggacat ccgtgacagt cagctccgcg gccgcaacta ccacccctgc ccctcggccg  840
ccgactccgg ccccaaccat cgcaagccaa cccctctcct tgcgccccga agcttgccgc  900
ccggccgcgg gtggagccgt gcatacccgg gggctggact ttgcctgcga tatctacatt  960
tgggccccgc tggccggcac ttgcggcgtg ctcctgctgt cgctggtcat caccctttac  1020
tgcaagaggg gccggaagaa gctgctttac atcttcaagc agccgttcat gcggcccgtg  1080
cagacgactc aggaagagga cggatgctcg tgcagattcc ctgaggagga agagggggga  1140
tgcgaactgc gcgtcaagtt ctcacggtcc gccgacgccc ccgcatatca acagggccag  1200
aatcagctct acaacgagct gaacctggga aggagagagg agtacgacgt gctggacaag  1260
cgacgcggac gcgacccgga gatggggggg aaaccacggc ggaaaaaccc tcaggaagga  1320
```

```
ctgtacaacg aactccagaa agacaagatg gcggaagcct actcagaaat cgggatgaag  1380
ggagagcgga ggaggggaaa gggtcacgac gggctgtacc agggactgag caccgccact  1440
aaggatacct acgatgcctt gcatatgcaa gcactcccac cccgg                  1485

SEQ ID NO: 30          moltype = AA  length = 495
FEATURE                Location/Qualifiers
source                 1..495
                       mol_type = protein
                       organism = Synthetic construct
SEQUENCE: 30
MLLLVTSLLL CELPHPAFLL IPDTDIQMTQ TTSSLSASLG DRVTISCRAS QDISKYLNWY  60
QQKPDGTVKL LIYHTSRLHS GVPSRFSGSG SGTDYSLTIS NLEQEDIATY FCQQGNTLPY  120
TFGGGTKLEI TGSTSGSGKP GSGEGSTKGE VKLQESGPGL VAPSQSLSVT CTVSGVSLPD  180
YGVSWIRQPP RKGLEWLGVI WGSETTYYNS ALKSRLTIIK DNSKSQVFLK MNSLQTDDTA  240
IYYCAKHYYY GGSYAMDYWG QGTSVTVSSA AATTTPAPRP PTPAPTIASQ PLSLRPEACR  300
PAAGGAVHTR GLDFACDIYI WAPLAGTCGV LLLSLVITLY CKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                   495

SEQ ID NO: 31          moltype = DNA  length = 1470
FEATURE                Location/Qualifiers
source                 1..1470
                       mol_type = other DNA
                       organism = Synthetic construct
SEQUENCE: 31
atgcttctcc tggtcacctc cctgctcctc tgcgaactgc ctcaccctgc cttccttctg  60
attcctgaca ttcagatgac tcagaccacc tcttccttgt ccgcgtcact gggagacaga  120
gtgaccatct cgtgtcgcgc aagccaggat atctccaagt acctgaactg gtaccaacag  180
aagcccgacg ggactgtgaa gctgctgatc taccacacct cacgcctgca cagcggagtg  240
ccaagcagat tctccggctc cggctcggga accgattact cgcttaccat tagcaacctc  300
gagcaggagg acatcgctac ctacttctgc cagcaaggaa ataccctgcc ctacaccttc  360
ggcggaggaa ccaaattgga aatcaccggc ggaggaggct ccgggggagg aggttccggg  420
ggcgggggtt ccgaagtgaa gctccaggag tccggccccg gcctggtggc gccgtcgcaa  480
tcactctctg tgacctgtac cgtgtcggga gtgtccctgc ctgattacgg cgtgagctgg  540
attcggcagc cgccgcggaa gggcctggaa tggctgggtg tcatctgggg atccgagact  600
acctactaca actcggccct gaagtcccgc ctgactatca tcaaagacaa ctcgaagtcc  660
caggtctttc tgaagatgaa ctccctgcaa actgacgaca ccgccatcta ttactgtgct  720
aagcactact actacggtgg aagctatgct atggactact gggggcaagg cacttcggtg  780
actgtgtcaa gcgcggccgc aactaccacc cctgcccctc ggccgccgac tccggcccca  840
accatcgcaa gccaacccct ctccttgcgc cccgaagctt gccgcccggc cgcgggtgga  900
gccgtgcata cccgggggct ggactttgcc tgcgatatct acatttgggc cccgctggcc  960
ggcacttgcg gcgtgctcct gctgtcgctg gtcatcaccc tttactgcaa gaggggccgg  1020
aagaagctgc tttacatctt caagcagccg ttcatgcggc ccgtgcagac gactcaggaa  1080
gaggacggat gctcgtgcag attccctgag gaggaagagg ggggatgcga actgcgcgtc  1140
aagttctcac ggtccgccga cgcccccgca tatcaacagg gccagaatca gctctacaac  1200
gagctgaacc tgggaaggag agaggagtac gacgtgctgg acaagcgacg cggacgcgac  1260
ccggagatgg gggggaaacc acggcggaaa aaccctcagg aaggactgta caacgaactc  1320
cagaaagaca agatggcgga agcctactca gaaatcggga tgaagggaga gcggaggagg  1380
ggaaagggtc acgacgggct gtaccaggga ctgagcaccg ccactaagga tacctacgat  1440
gccttgcata tgcaagcact cccaccccgg                                   1470

SEQ ID NO: 32          moltype = AA  length = 490
FEATURE                Location/Qualifiers
source                 1..490
                       mol_type = protein
                       organism = Synthetic construct
SEQUENCE: 32
MLLLVTSLLL CELPHPAFLL IPDIQMTQTT SSLSASLGDR VTISCRASQD ISKYLNWYQQ  60
KPDGTVKLLI YHTSRLHSGV PSRFSGSGSG TDYSLTISNL EQEDIATYFC QQGNTLPYTF  120
GGGTKLEITG GGGSGGGGSG GGGSEVKLQE SGPGLVAPSQ SLSVTCTVSG VSLPDYGVSW  180
IRQPPRKGLE WLGVIWGSET TYYNSALKSR LTIIKDNSKS QVFLKMNSLQ TDDTAIYYCA  240
KHYYYGGSYA MDYWGQGTSV TVSSAAATTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                         490

SEQ ID NO: 33          moltype = DNA  length = 1548
FEATURE                Location/Qualifiers
source                 1..1548
                       mol_type = other DNA
                       organism = Synthetic construct
SEQUENCE: 33
gacattcaga tgactcagac cacctcctcc ctgtccgcct ccctgggcga ccgcgtgacc  60
atctcatgcc gcgccagcca ggacatctcg aagtacctca actggtacca gcagaagccc  120
gacggaaccg tgaagctcct gatctaccac acctcccggc tgcacagcgg agtgccgtct  180
agattctcgg gttcggggtc gggaactgac tactccctta ctatttccaa cctggagcag  240
gaggatattg ccacctactt ctgccaacaa ggaaacaccc tgccgtacac ttttggcggg  300
```

```
ggaaccaagc tggaaatcac tggcagcaca tccggttccg ggaagcccgg ctccggagag  360
ggcagcacca agggggaagt caagctgcag gaatcaggac ctggcctggt ggccccgagc  420
cagtcactgt ccgtgacttg tactgtgtcc ggagtgtcgc tcccggatta cggagtgtcc  480
tggatcaggc agccacctcg gaaaggattg gaatggctcg gagtcatctg gggttccgaa  540
accacctatt acaactcggc actgaaatcc aggctcacca ttatcaagga taactccaag  600
tcacaagtgt tcctgaagat gaatagcctg cagactgacg acacggcgat ctactattgc  660
gccaagcact actactacgg cggatcctac gctatggact actggggcca ggggaccagc  720
gtgaccgtgt catccggagg cggcggcagc ggcgggggag ggtccggagg gggtggttct  780
ggtggaggag gatcgggagg cggtggcagc gaggtgcagt tgcaacagtc aggagctgaa  840
ctggtcaagc caggagccag cgtgaagatg agctgcaagg cctccggtta caccttcacc  900
tcctacaaca tgcactgggt gaaacagacc ccgggacaag ggctcgaatg gattggcgcc  960
atctaccccg ggaatggcga tacttcgtac aaccagaagt tcaagggaaa ggccaccctg  1020
accgccgaca agagctcctc caccgcgtat atgcagttga gctccctgac ctccgaggac  1080
tccgccgact actactgcgc acggtccaac tactatggaa gctcgtactg gttcttcgat  1140
gtctgggggg ccggcaccac tgtgaccgtc agctccgggg gcggaggatc cggtggaggc  1200
ggaagcgggg gtggaggatc cgacattgtg ctgactcagt ccccggcaat cctgtcggcc  1260
tcaccgggcg aaaaggtcac gatgacttgt agagcgtcgt ccagcgtgaa ctacatggat  1320
tggtaccaaa agaagcctgg atcgtcaccc aagccttgga tctacgctac atctaacctg  1380
gcctccggcg tgccagcgcg gttcagcggg tccggctcgg gcacctcata ctcgctgacc  1440
atctcccgcg tggaggctga ggacgccgcg acctactact gccagcagtg gtccttcaac  1500
ccgccgactt ttggaggcgg tactaagctg gagatcaaag cggccgca              1548

SEQ ID NO: 34          moltype = AA  length = 516
FEATURE                Location/Qualifiers
source                 1..516
                       mol_type = protein
                       organism = Synthetic construct
SEQUENCE: 34
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSSGGGGS GGGGSGGGGS GGGGSGGGGS EVQLQQSGAE LVKPGASVKM SCKASGYTFT  300
SYNMHWVKQT PGQGLEWIGA IYPGNGDTSY NQKFKGKATL TADKSSSTAY MQLSSLTSED  360
SADYYCARSN YYGSSYWFFD VWGAGTTVTV SSGGGGSGGG GSGGGGSDIV LTQSPAILSA  420
SPGEKVTMTC RASSSVNYMD WYQKKPGSSP KPWIYATSNL ASGVPARFSG SGSGTSYSLT  480
ISRVEAEDAA TYYCQQWSFN PPTFGGGTKL EIKAAA                          516

SEQ ID NO: 35          moltype = DNA  length = 2283
FEATURE                Location/Qualifiers
source                 1..2283
                       mol_type = other DNA
                       organism = Synthetic construct
SEQUENCE: 35
atgctccttc tcgtgacctc cctgcttctc tgcgaactgc cccatcctgc cttcctgctg  60
attcccgaca ttcagatgac tcagaccacc tcctccctgt ccgcctccct gggcgaccgc  120
gtgaccatct catgccgcgc cagccaggac atctcgaagt acctcaactg gtaccagcag  180
aagcccgacg gaaccgtgaa gctcctgatc taccacacct cccggctgca cagcggagtg  240
ccgtctagat tctcgggttc ggggtcggga actgactact cccttactat ttccaacctg  300
gagcaggagg atattgccac ctacttctgc caacaaggaa acaccctgcc gtacactttt  360
ggcgggggaa ccaagctgga aatcactggc agcacatccg gttccgggaa gcccggctcc  420
ggagagggca gcaccaaggg ggaagtcaag ctgcaggaat caggacctgg cctggtggcc  480
ccgagccagt cactgtccgt gacttgtact gtgtccggag tgtcgctccc ggattacgga  540
gtgtcctgga tcaggcagcc acctcggaaa ggattggaat ggctcggagt catctggggt  600
tccgaaacca cctattacaa ctcggcactg aaatccaggc tcaccattat caaggataac  660
tccaagtcac aagtgttcct gaagatgaat agcctgcaga ctgacgacac ggcgatctac  720
tattgcgcca agcactacta ctacggcgga tcctacgcta tggactactg gggccagggg  780
accagcgtga ccgtgtcatc cggaggcggc ggcagcggcg ggggagggtc cggagggggt  840
ggttctggtg gaggaggatc gggaggcggt ggcagcgagg tgcagttgca acagtcagga  900
gctgaactgg tcaagccagg agccagcgtg aagatgagct gcaaggcctc cggttacacc  960
ttcacctcct acaacatgca ctgggtgaaa cagaccccgg gacaagggct cgaatggatt  1020
ggcgccatct accccgggaa tggcgatact tcgtacaacc agaagttcaa gggaaaggcc  1080
accctgaccg ccgacaagag ctcctccacc gcgtatatgc agttgagctc cctgacctcc  1140
gaggactccg ccgactacta ctgcgcacgg tccaactact atggaagctc gtactggttc  1200
ttcgatgtct ggggggccgg caccactgtg accgtcagct ccgggggcgg aggatccggt  1260
ggaggcggaa gcgggggtgg aggatccgac attgtgctga ctcagtcccc ggcaatcctg  1320
tcggcctcac cgggcgaaaa ggtcacgatg acttgtagag cgtcgtccag cgtgaactac  1380
atggattggt accaaaagaa gcctggatcg tcacccaagc cttggatcta cgctacatct  1440
aacctggcct ccggcgtgcc agcgcggttc agcgggtccg gctcgggcac ctcatactcg  1500
ctgaccatct cccgcgtgga ggctgaggac gccgcgacct actactgcca gcagtggtcc  1560
ttcaacccgc cgacttttgg aggcggtact aagctggaga tcaaagcggc cgcaactacc  1620
acccctgccc ctcggccgcc gactccggcc ccaaccatcg caagccaacc cctctccttg  1680
cgccccgaag cttgccgccc ggccgcgggt ggagccgtgc atacccgggg gctggacttt  1740
gcctgcgata tctacatttg ggccccgctg gccggcactt gcggcgtgct cctgctgtcg  1800
ctggtcatca ccctttactg caagaggggc cggaagaagc tgctttacat cttcaagcag  1860
ccgttcatgc ggcccgtgca gacgactcag gaagaggacg gatgctcgtg cagattccct  1920
gaggaggaag aggggggatg cgaactgcgc gtcaagttct cacggtccgc cgacgccccc  1980
gcatatcaac agggccagaa tcagctctac aacgagctga acctgggaag gagagaggag  2040
tacgacgtgc tggacaagcg acgcggacgc gacccggaga tggggggcaa accacggcgg  2100
```

```
aaaaaccctc aggaaggact gtacaacgaa ctccagaaag acaagatggc ggaagcctac  2160
tcagaaatcg ggatgaaggg agagcggagg aggggaaagg gtcacgacgg gctgtaccag  2220
ggactgagca ccgccactaa ggatacctac gatgccttgc atatgcaagc actcccaccc  2280
cgg                                                                2283

SEQ ID NO: 36           moltype = AA  length = 761
FEATURE                 Location/Qualifiers
source                  1..761
                        mol_type = protein
                        organism = Synthetic construct
SEQUENCE: 36
MLLLVTSLLL CELPHPAFLL IPDIQMTQTT SSLSASLGDR VTISCRASQD ISKYLNWYQQ  60
KPDGTVKLLI YHTSRLHSGV PSRFSGSGSG TDYSLTISNL EQEDIATYFC QQGNTLPYTF  120
GGGTKLEITG STSGSGKPGS GEGSTKGEVK LQESGPGLVA PSQSLSVTCT VSGVSLPDYG  180
VSWIRQPPRK GLEWLGVIWG SETTYYNSAL KSRLTIIKDN SKSQVFLKMN SLQTDDTAIY  240
YCAKHYYYGG SYAMDYWGQG TSVTVSSGGG GSGGGGSGGG GSGGGGSGGG GSEVQLQQSG  300
AELVKPGASV KMSCKASGYT FTSYNMHWVK QTPGQGLEWI GAIYPGNGDT SYNQKFKGKA  360
TLTADKSSST AYMQLSSLTS EDSADYYCAR SNYYGSSYWF FDVWGAGTTV TVSSGGGGSG  420
GGGSGGGGSD IVLTQSPAIL SASPGEKVTM TCRASSSVNY MDWYQKKPGS SPKPWIYATS  480
NLASGVPARF SGSGSGTSYS LTISRVEAED AATYYCQQWS FNPPTFGGGT KLEIKAAATT  540
TPAPRPPTPA PTIASQPLSL RPEACRPAAG GAVHTRGLDF ACDIYIWAPL AGTCGVLLLS  600
LVITLYCKRG RKKLLYIFKQ PFMRPVQTTQ EEDGCSCRFP EEEEGGCELR VKFSRSADAP  660
AYQQGQNQLY NELNLGRREE YDVLDKRRGR DPEMGGKPRR KNPQEGLYNE LQKDKMAEAY  720
SEIGMKGERR RGKGHDGLYQ GLSTATKDTY DALHMQALPP R                      761

SEQ ID NO: 37           moltype = DNA  length = 732
FEATURE                 Location/Qualifiers
source                  1..732
                        mol_type = other DNA
                        organism = Synthetic construct
SEQUENCE: 37
gaggtccagc tggtacagtc tgggggaggc ttggtacagc ctggggggtc cctgagactc  60
tcctgtgcag cctctggatt cacctttgat gattatgcca tgcactgggt ccggcaagct  120
ccagggaagg gcctggagtg ggtctcaggt attagttgga atagtggtag cataggctat  180
gcggactctg tgaagggccg attcaccatc tccagagaca acgccaagaa ctccctgtat  240
ctgcaaatga acagtctgag agctgaggac acggccttgt attactgtgc aaaagattta  300
tcgtcagtgg ctggaccctt taactactgg ggccagggca ccctggtcac cgtctcctca  360
ggaggtggcg ggtctggtgg aggcggtagc ggcggtggcg gatcctcttc tgagctgact  420
caggaccctg ctgtgtctgt ggccttggga cagacagtca ggatcacatg ccaaggagac  480
agcctcagaa gctattatgc aagctggtac cagcagaagc caggacaggc ccctgtactt  540
gtcatctatg gtaaaaacaa ccggccctca gggatcccag accgattctc tggctccagc  600
tcaggaaaca cagcttcctt gaccatcact ggggctcagg cggaggatga ggctgactat  660
tactgtaact cccgggacag cagtggtaac catctggtat tcggcggagg cacccagctg  720
accgtcctcg gt                                                      732

SEQ ID NO: 38           moltype = AA  length = 244
FEATURE                 Location/Qualifiers
source                  1..244
                        mol_type = protein
                        organism = Synthetic construct
SEQUENCE: 38
EVQLVQSGGG LVQPGGSLRL SCAASGFTFD DYAMHWVRQA PGKGLEWVSG ISWNSGSIGY  60
ADSVKGRFTI SRDNAKNSLY LQMNSLRAED TALYYCAKDL SSVAGPFNYW GQGTLVTVSS  120
GGGGSGGGGS GGGGSSSELT QDPAVSVALG QTVRITCQGD SLRSYYASWY QQKPGQAPVL  180
VIYGKNNRPS GIPDRFSGSS SGNTASLTIT GAQAEDEADY YCNSRDSSGN HLVFGGGTQL  240
TVLG                                                               244

SEQ ID NO: 39           moltype = DNA  length = 1476
FEATURE                 Location/Qualifiers
source                  1..1476
                        mol_type = other DNA
                        organism = Synthetic construct
SEQUENCE: 39
atgctgctgc tggtgaccag cctgctgctg tgcgaactgc cgcatccggc gtttctgctg  60
attccggagg tccagctggt acagtctggg ggaggcttgg tacagcctgg ggggtccctg  120
agactctcct gtgcagcctc tggattcacc tttgatgatt atgccatgca ctgggtccgg  180
caagctccag ggaagggcct ggagtgggtc tcaggtatta gttggaatag tggtagcata  240
ggctatgcgg actctgtgaa gggccgattc accatctcca gagacaacgc caagaactcc  300
ctgtatctgc aaatgaacag tctgagagct gaggacacgg ccttgtatta ctgtgcaaaa  360
gatttatcgt cagtggctgg accctttaac tactggggcc agggcaccct ggtcaccgtc  420
tcctcaggag gtggcgggtc tggtggaggc ggtagcggcg gtggcggatc ctcttctgag  480
ctgactcagg accctgctgt gtctgtggcc ttgggacaga cagtcaggat cacatgccaa  540
ggagacagcc tcagaagcta ttatgcaagc tggtaccagc agaagccagg acaggcccct  600
gtacttgtca tctatggtaa aaacaaccgg ccctcaggga tcccagaccg attctctggc  660
tccagctcag gaaacacagc ttccttgacc atcactgggg ctcaggcgga ggatgaggct  720
gactattact gtaactcccg ggacagcagt ggtaaccatc tggtattcgg cggaggcacc  780
cagctgaccg tcctcggtgc ggccgcaact accacccctg cccctcggcc gccgactccg  840
gccccaacca tcgcaagcca acccctctcc ttgcgccccg aagcttgccg cccggccgcg  900
ggtggagccg tgcatacccg gggctggac tttgcctgcg atatctacat ttgggccccg  960
```

```
ctggccggca cttgcggcgt gctcctgctg tcgctggtca tcacccttta ctgcaagagg  1020
ggccggaaga agctgcttta catcttcaag cagccgttca tgcggcccgt gcagacgact  1080
caggaagagg acggatgctc gtgcagattc cctgaggagg aagagggggg atgcgaactg  1140
cgcgtcaagt tctcacggtc cgccgacgcc cccgcatatc aacagggcca gaatcagctc  1200
tacaacgagc tgaacctggg aaggagagag gagtacgacg tgctggacaa gcgacgcgga  1260
cgcgacccgg agatgggggg gaaaccacgg cggaaaaacc ctcaggaagg actgtacaac  1320
gaactccaga aagacaagat ggcggaagcc tactcagaaa tcgggatgaa gggagagcgg  1380
aggaggggaa agggtcacga cgggctgtac cagggactga gcaccgccac taaggatacc  1440
tacgatgcct tgcatatgca agcactccca ccccgg                             1476

SEQ ID NO: 40          moltype = AA  length = 492
FEATURE                Location/Qualifiers
source                 1..492
                       mol_type = protein
                       organism = Synthetic construct
SEQUENCE: 40
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGAAAT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                       492

SEQ ID NO: 41          moltype = DNA  length = 339
FEATURE                Location/Qualifiers
source                 1..339
                       mol_type = other DNA
                       organism = Synthetic construct
SEQUENCE: 41
gaggtgcagc tggtggagtc tgggggaggc ttggtacagc ctggagggtc cctgagactc  60
tcctgtgcag cctctggatt caccttcagt agctatggca tgagctgggt ccgccaggct  120
ccaagacaag ggcttgagtg ggtggccaac ataaagcaag atggaagtga gaaatactat  180
gcggactcag tgaagggccg attcaccatc tccagagaca attccaagaa cacgctgtat  240
ctgcaaatga acagcctgag agccgaggac acagccacgt attactgtgc gaaagaaaat  300
gtggactggg gccagggcac cctggtcacc gtctcctca                          339

SEQ ID NO: 42          moltype = AA  length = 113
FEATURE                Location/Qualifiers
source                 1..113
                       mol_type = protein
                       organism = Synthetic construct
SEQUENCE: 42
EVQLVESGGG LVQPGGSLRL SCAASGFTFS SYGMSWVRQA PRQGLEWVAN IKQDGSEKYY  60
ADSVKGRFTI SRDNSKNTLY LQMNSLRAED TATYYCAKEN VDWGQGTLVT VSS         113

SEQ ID NO: 43          moltype = DNA  length = 1083
FEATURE                Location/Qualifiers
source                 1..1083
                       mol_type = other DNA
                       organism = Synthetic construct
SEQUENCE: 43
atgctgctgc tggtgaccag cctgctgctg tgcgaactgc cgcatccggc gtttctgctg  60
attccggagg tgcagctggt ggagtctggg ggaggcttgg tacagcctgg agggtccctg  120
agactctcct gtgcagcctc tggattcacc ttcagtagct atggcatgag ctgggtccgc  180
caggctccaa gacaagggct tgagtgggtg gccaacataa agcaagatgg aagtgagaaa  240
tactatgcgg actcagtgaa gggccgattc accatctcca gagacaattc caagaacacg  300
ctgtatctgc aaatgaacag cctgagagcc gaggacacag ccacgtatta ctgtgcgaaa  360
gaaaatgtgg actggggcca gggcaccctg gtcaccgtct cctcagcggc cgcaactacc  420
acccctgccc ctcggccgcc gactccggcc ccaaccatcg caagccaacc cctctccttg  480
cgccccgaag cttgccgccc ggccgcgggt ggagccgtgc atacccgggg gctggacttt  540
gcctgcgata tctacatttg ggccccgctg gccggcactt gcggcgtgct cctgctgtcg  600
ctggtcatca ccctttactg caagaggggc cggaagaagc tgctttacat cttcaagcag  660
ccgttcatgc ggcccgtgca gacgactcag gaagaggacg gatgctcgtg cagattccct  720
gaggaggaag aggggggatg cgaactgcgc gtcaagttct cacggtccgc cgacgccccc  780
gcatatcaac agggccagaa tcagctctac aacgagctga acctgggaag gagagaggag  840
tacgacgtgc tggacaagcg acgcggacgc gacccggaga tgggggggaa accacggcgg  900
aaaaaccctc aggaaggact gtacaacgaa ctccagaaag acaagatggc ggaagcctac  960
tcagaaatcg ggatgaaggg agagcggagg aggggaaagg gtcacgacgg gctgtaccag  1020
ggactgagca ccgccactaa ggatacctac gatgccttgc atatgcaagc actcccaccc  1080
cgg                                                                 1083

SEQ ID NO: 44          moltype = AA  length = 361
FEATURE                Location/Qualifiers
source                 1..361
                       mol_type = protein
                       organism = Synthetic construct
```

```
SEQUENCE: 44
MLLLVTSLLL CELPHPAFLL IPEVQLVESG GGLVQPGGSL RLSCAASGFT FSSYGMSWVR  60
QAPRQGLEWV ANIKQDGSEK YYADSVKGRF TISRDNSKNT LYLQMNSLRA EDTATYYCAK  120
ENVDWGQGTL VTVSSAAATT TPAPRPPTPA PTIASQPLSL RPEACRPAAG GAVHTRGLDF  180
ACDIYIWAPL AGTCGVLLLS LVITLYCKRG RKKLLYIFKQ PFMRPVQTTQ EEDGCSCRFP  240
EEEEGGCELR VKFSRSADAP AYQQGQNQLY NELNLGRREE YDVLDKRRGR DPEMGGKPRR  300
KNPQEGLYNE LQKDKMAEAY SEIGMKGERR RGKGHDGLYQ GLSTATKDTY DALHMQALPP  360
R                                                                 361

SEQ ID NO: 45          moltype = DNA  length = 797
FEATURE                Location/Qualifiers
source                 1..797
                       mol_type = other DNA
                       organism = Synthetic construct
SEQUENCE: 45
atggcactgc ccgtgaccgc cctgcttctg ccgcttgcac ttctgctgca cgccgctagg  60
ccccaagtca ccctcaaaga gtcagggcca ggaatcctca agccctcaca gactctgtct  120
cttacttgct cattcagcgg attcagcctt tccacctctg gtatgggcgt ggggtggatt  180
aggcaaccta gcggaaaggg gcttgaatgg ctggcccaca tctggtggga cgacgacaag  240
tactacaacc cctcactgaa gtcccagctc actatttcca aagatacttc ccggaatcag  300
gtgttcctca agattacctc tgtcgacacc gctgataccg ccacttacta ttgttcacgc  360
agaccgagag gtaccatgga cgcaatggac tactggggac agggcaccag cgtgaccgtg  420
tcatctggcg gtggagggtc aggaggtgga ggtagcggag gcggtgggtc cgacattgtc  480
atgacccagg ccgccagcag cctgagcgct tcactgggcg acagggtgac catcagctgt  540
cgcgcatcac aagatatctc taagtatctt aattggtacc agcaaaagcc ggatggaacc  600
gtgaagctgc tgatctacta cacctcacgg ctgcattctg gagtgcctag ccgctttagc  660
ggatctgggt ccggtactga ctacagcctc accattagaa accttgaaca ggaggacatc  720
gcaacttatt tctgccaaca ggtctatact ctgccgtgga ccttcggcgg aggtaccaaa  780
ctggagatta agtccgg                                                797

SEQ ID NO: 46          moltype = AA  length = 265
FEATURE                Location/Qualifiers
source                 1..265
                       mol_type = protein
                       organism = Synthetic construct
SEQUENCE: 46
MALPVTALLL PLALLLHAAR PQVTLKESGP GILKPSQTLS LTCSFSGFSL STSGMGVGWI  60
RQPSGKGLEW LAHIWWDDDK YYNPSLKSQL TISKDTSRNQ VFLKITSVDT ADTATYYCSR  120
RPRGTMDAMD YWGQGTSVTV SSGGGGSGGG GSGGGGSDIV MTQAASSLSA SLGDRVTISC  180
RASQDISKYL NWYQQKPDGT VKLLIYYTSR LHSGVPSRFS GSGSGTDYSL TIRNLEQEDI  240
ATYFCQQVYT LPWTFGGGTK LEIKS                                       265

SEQ ID NO: 47          moltype = DNA  length = 1170
FEATURE                Location/Qualifiers
source                 1..1170
                       mol_type = other DNA
                       organism = Synthetic construct
SEQUENCE: 47
atggcactgc ccgtgaccgc cctgcttctg ccgcttgcac ttctgctgca cgccgctagg  60
ccccaagtca ccctcaaaga gtcagggcca ggaatcctca agccctcaca gactctgtct  120
cttacttgct cattcagcgg attcagcctt tccacctctg gtatgggcgt ggggtggatt  180
aggcaaccta gcggaaaggg gcttgaatgg ctggcccaca tctggtggga cgacgacaag  240
tactacaacc cctcactgaa gtcccagctc actatttcca aagatacttc ccggaatcag  300
gtgttcctca agattacctc tgtcgacacc gctgataccg ccacttacta ttgttcacgc  360
agaccgagag gtaccatgga cgcaatggac tactggggac agggcaccag cgtgaccgtg  420
tcatctggcg gtggagggtc aggaggtgga ggtagcggag gcggtgggtc cgacattgtc  480
atgacccagg ccgccagcag cctgagcgct tcactgggcg acagggtgac catcagctgt  540
cgcgcatcac aagatatctc taagtatctt aattggtacc agcaaaagcc ggatggaacc  600
gtgaagctgc tgatctacta cacctcacgg ctgcattctg gagtgcctag ccgctttagc  660
ggcacttgcg gcgtgctcct gctgtcgctg gtcatcaccc tttactgcaa gaggggccgg  720
aagaagctgc tttacatctt caagcagccg ttcatgcggc ccgtgcagac gactcaggaa  780
gaggacggat gctcgtgcag attccctgag gaggaagagg ggggatgcga actgcgcgtc  840
aagttctcac ggtccgccga cgcccccgca tatcaacagg gccagaatca gctctacaac  900
gagctgaacc tgggaaggag agaggagtac gacgtgctgg acaagcgacg cggacgcgac  960
ccggagatgg gggggaaacc acggcggaaa aaccctcagg aaggactgta caacgaactc  1020
cagaaagaca agatggcgga agcctactca gaaatcggga tgaagggaga gcggaggagg  1080
ggaaagggtc acgacgggct gtaccaggga ctgagcaccg ccactaagga tacctacgat  1140
gccttgcata tgcaagcact cccaccccgg                                  1170

SEQ ID NO: 48          moltype = AA  length = 490
FEATURE                Location/Qualifiers
source                 1..490
                       mol_type = protein
                       organism = Synthetic construct
SEQUENCE: 48
MALPVTALLL PLALLLHAAR PQVTLKESGP GILKPSQTLS LTCSFSGFSL STSGMGVGWI  60
RQPSGKGLEW LAHIWWDDDK YYNPSLKSQL TISKDTSRNQ VFLKITSVDT ADTATYYCSR  120
RPRGTMDAMD YWGQGTSVTV SSGGGGSGGG GSGGGGSDIV MTQAASSLSA SLGDRVTISC  180
RASQDISKYL NWYQQKPDGT VKLLIYYTSR LHSGVPSRFS GSGSGTDYSL TIRNLEQEDI  240
```

```
ATYFCQQVYT LPWTFGGGTK LEIKAAATTT PAPRPPTPAP TIASQPLSLR PEACRPAAGG  300
AVHTRGLDFA CDIYIWAPLA GTCGVLLLSL VITLYCKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                         490

SEQ ID NO: 49          moltype = DNA  length = 1467
FEATURE                Location/Qualifiers
source                 1..1467
                       mol_type = other DNA
                       organism = Synthetic construct
SEQUENCE: 49
atgctgctgc tggtcaccag cctgctgctg tgcgagctcc ctcaccccgc ctttctgctt  60
atcccggaca ttcagatgac acagaccacc tcgagcttgt ccgcgtcgct gggcgatcgc  120
gtgaccatct cctgccgggc ctcccaagac atttcaaagt atctcaactg gtaccagcag  180
aagccggacg gaaccgtgaa actgctgatc taccatacca gccgcctgca ctccggcgtg  240
ccgtcccgct tctccggatc gggttccgga actgactact cactgactat ctccaacttg  300
gaacaagagg acatcgccac ttacttctgt caacaaggaa atacccttcc ctacaccttc  360
gggggggggta ccaagctgga gatcactggg ggcggaggct ccggtggagg cggatccggc  420
ggtggaggga gcgaagtcaa gctgcaggaa tcaggaccag gactcgtggc gccatcccag  480
tccctgtcgg tgacctgtac tgtctccgga gtcagcctcc ccgattacgg agtgtcatgg  540
attaggcaac cccaagaaa agggctggaa tggctcggag tgatctgggg ctccgaaacc  600
acctactaca actcggcgct gaagtcccgg ctgaccatca tcaaggacaa ctccaagagc  660
caagtgttct tgaagatgaa cagcttgcag accgacgata ccgcaatcta ctactgtgcc  720
aagcactatt actacggggg gtcttacgcc atggactact ggggacaggg cacctccgtg  780
actgtgtcgt ccgcggccgc gcccgcccct cggcccccga ctcctgcccc gacgatcgct  840
tcccaacctc tctcgctgcg cccggaagca tgccggcccg ccgccggtgg cgctgtccac  900
actcgcggac tggactttga taccgcactg gcggccgtga tctgtagcgc cctggccacc  960
gtgctgctgg cgctgctcat cctttgcgtg atctactgca agcggcagcc taggcgaaag  1020
aagctcctct acattttcaa gcaacccttc atgcgccccg tgcaaaccac ccaggaggag  1080
gatggatgct catgccggtt ccctgaggaa gaagagggcg gttgcgagct cagagtgaaa  1140
ttcagccggt cggctgacgc cccggcgtac cagcagggcc agaaccagct gtacaatgag  1200
ctcaacctgg ggcgccgcga agagtacgac gtgctggaca agaggagagg cagagatccg  1260
gaaatgggcg gaaagccaag gcggaagaac ccgcaggaag gtctttacaa cgaactgcag  1320
aaggacaaga tggccgaggc ctactccgag attgggatga agggagaaag acggagggga  1380
aagggacatg acggacttta ccagggcctg agcactgcca cgaaggacac ctatgatgcc  1440
ctgcacatgc aggcgctgcc gcctcgg                                      1467

SEQ ID NO: 50          moltype = AA  length = 489
FEATURE                Location/Qualifiers
source                 1..489
                       mol_type = protein
                       organism = Synthetic construct
SEQUENCE: 50
MLLLVTSLLL CELPHPAFLL IPDIQMTQTT SSLSASLGDR VTISCRASQD ISKYLNWYQQ  60
KPDGTVKLLI YHTSRLHSGV PSRFSGSGSG TDYSLTISNL EQEDIATYFC QQGNTLPYTF  120
GGGTKLEITG GGGSGGGGSG GGGSEVKLQE SGPGLVAPSQ SLSVTCTVSG VSLPDYGVSW  180
IRQPPRKGLE WLGVIWGSET TYYNSALKSR LTIIKDNSKS QVFLKMNSLQ TDDTAIYYCA  240
KHYYYGGSYA MDYWGQGTSV TVSSAAAPAP RPPTPAPTIA SQPLSLRPEA CRPAAGGAVH  300
TRGLDFDTAL AAVICSALAT VLLALLILCV IYCKRQPRRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                          489

SEQ ID NO: 51          moltype = DNA  length = 2280
FEATURE                Location/Qualifiers
source                 1..2280
                       mol_type = other DNA
                       organism = Synthetic construct
SEQUENCE: 51
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct gggggggccgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaaggagg cggcggcagc ggcgggggag ggtccggagg gggtggttct  840
ggtggaggag gatcgggagg cggtggcagc gacattcaga tgactcagac cacctcctcc  900
ctgtccgcct ccctgggcga ccgcgtgacc atctcatgcc gcgccagcca ggacatctcg  960
aagtacctca actggtacca gcagaagccc gacggaaccg tgaagctcct gatctaccac  1020
acctcccggc tgcacagcgg agtgccgtct agattctcgg gttcggggtc gggaactgac  1080
tactccctta ctatttccaa cctggagcag gaggatattg ccacctactt ctgccaacaa  1140
```

```
ggaaacaccc tgccgtacac ttttggcggg ggaaccaagc tggaaatcac tggcagcaca  1200
tccggttccg ggaagcccgg ctccggagag ggcagcacca agggggaagt caagctgcag  1260
gaatcaggac ctggcctggt ggccccgagc cagtcactgt ccgtgacttg tactgtgtcc  1320
ggagtgtcgc tcccggatta cggagtgtcc tggatcaggc agccacctcg gaaaggattg  1380
gaatggctcg gagtcatctg gggttccgaa accacctatt acaactcggc actgaaatcc  1440
aggctcacca ttatcaagga taactccaag tcacaagtgt tcctgaagat gaatagcctg  1500
cagactgacg acacggcgat ctactattgc gccaagcact actactacgg cggatcctac  1560
gctatggact actggggcca ggggaccagc gtgaccgtgt catccgcggc cgcgactacc  1620
actcctgcac cacggccacc taccccagcc cccaccattg caagccagcc actttcactg  1680
cgccccgaag cgtgtagacc agctgctgga ggagccgtgc atacccgagg gctggacttc  1740
gcctgtgaca tctacatctg ggccccattg gctggaactt gcggcgtgct gctcttgtct  1800
ctggtcatta ccctgtactg ccggtcgaag aggtccagac tcttgcactc cgactacatg  1860
aacatgactc ctagaaggcc cggacccact agaaagcact accagccgta cgcccctcct  1920
cgggatttcg ccgcataccg gtccagagtg aagttcagcc gctcagccga tgcaccggcc  1980
taccagcagg gacagaacca gctctacaac gagctcaacc tgggtcggcg ggaagaatat  2040
gacgtgctgg acaaacggcg cggcagagat ccggagatgg ggggaaagcc gaggaggaag  2100
aaccctcaag agggcctgta caacgaactg cagaaggaca agatggcgga agcctactcc  2160
gagatcggca tgaagggaga acgccggaga gggaagggtc atgacggact gtaccagggc  2220
ctgtcaactg ccactaagga cacttacgat gcgctccata tgcaagcttt gcccccgcgg  2280

SEQ ID NO: 52           moltype = AA  length = 760
FEATURE                 Location/Qualifiers
source                  1..760
                        mol_type = protein
                        organism = Synthetic construct
SEQUENCE: 52
MLLLVTSLLL CELPHPAFLL IPEVQLQQSG AELVKPGASV KMSCKASGYT FTSYNMHWVK  60
QTPGQGLEWI GAIYPGNGDT SYNQKFKGKA TLTADKSSST AYMQLSSLTS EDSADYYCAR  120
SNYYGSSYWF FDVWGAGTTV TVSSGGGGSG GGGSGGGGSD IVLTQSPAIL SASPGEKVTM  180
TCRASSSVNY MDWYQKKPGS SPKPWIYATS NLASGVPARF SGSGSGTSYS LTISRVEAED  240
AATYYCQQWS FNPPTFGGGT KLEIKGGGGS GGGGSGGGGS GGGGSGGGGS DIQMTQTTSS  300
LSASLGDRVT ISCRASQDIS KYLNWYQQKP DGTVKLLIYH TSRLHSGVPS RFSGSGSGTD  360
YSLTISNLEQ EDIATYFCQQ GNTLPYTFGG GTKLEITGST SGSGKPGSGE GSTKGEVKLQ  420
ESGPGLVAPS QSLSVTCTVS GVSLPDYGVS WIRQPPRKGL EWLGVIWGSE TTYYNSALKS  480
RLTIIKDNSK SQVFLKMNSL QTDDTAIYYC AKHYYYGGSY AMDYWGQGTS VTVSSAAATT  540
TPAPRPPTPA PTIASQPLSL RPEACRPAAG GAVHTRGLDF ACDIYIWAPL AGTCGVLLLS  600
LVITLYCRSK RSRLLHSDYM NMTPRRPGPT RKHYQPYAPP RDFAAYRSRV KFSRSADAPA  660
YQQGQNQLYN ELNLGRREEY DVLDKRRGRD PEMGGKPRRK NPQEGLYNEL QKDKMAEAYS  720
EIGMKGERRR GKGHDGLYQG LSTATKDTYD ALHMQALPPR                        760

SEQ ID NO: 53           moltype = DNA  length = 3858
FEATURE                 Location/Qualifiers
source                  1..3858
                        mol_type = other DNA
                        organism = Synthetic construct
SEQUENCE: 53
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct gggggggccgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaaggagg cggcggcagc ggcgggggag ggtccggagg gggtggttct  840
ggtggaggag gatcgggagg cggtggcagc gacattcaga tgactcagac cacctcctcc  900
ctgtccgcct ccctgggcga ccgcgtgacc atctcatgcc gcgccagcca ggacatctcg  960
aagtacctca actggtacca gcagaagccc gacggaaccg tgaagctcct gatctaccac  1020
acctcccggc tgcacagcgg agtgccgtct agattctcgg gttcggggtc gggaactgac  1080
tactccctta ctatttccaa cctggagcag gaggatattg ccacctactt ctgccaacaa  1140
ggaaacaccc tgccgtacac ttttggcggg ggaaccaagc tggaaatcac tggcagcaca  1200
tccggttccg ggaagcccgg ctccggagag ggcagcacca agggggaagt caagctgcag  1260
gaatcaggac ctggcctggt ggccccgagc cagtcactgt ccgtgacttg tactgtgtcc  1320
ggagtgtcgc tcccggatta cggagtgtcc tggatcaggc agccacctcg gaaaggattg  1380
gaatggctcg gagtcatctg gggttccgaa accacctatt acaactcggc actgaaatcc  1440
aggctcacca ttatcaagga taactccaag tcacaagtgt tcctgaagat gaatagcctg  1500
cagactgacg acacggcgat ctactattgc gccaagcact actactacgg cggatcctac  1560
gctatggact actggggcca ggggaccagc gtgaccgtgt catccgcggc cgcgactacc  1620
actcctgcac cacggccacc taccccagcc cccaccattg caagccagcc actttcactg  1680
cgccccgaag cgtgtagacc agctgctgga ggagccgtgc atacccgagg gctggacttc  1740
gcctgtgaca tctacatctg ggccccattg gctggaactt gcggcgtgct gctcttgtct  1800
ctggtcatta ccctgtactg ccggtcgaag aggtccagac tcttgcactc cgactacatg  1860
aacatgactc ctagaaggcc cggacccact agaaagcact accagccgta cgcccctcct  1920
cgggatttcg ccgcataccg gtccagagtg aagttcagcc gctcagccga tgcaccggcc  1980
```

```
taccagcagg gacagaacca gctctacaac gagctcaacc tgggtcggcg ggaagaatat  2040
gacgtgctgg acaaacggcg cggcagagat ccggagatgg ggggaaagcc gaggaggaag  2100
aaccctcaag agggcctgta caacgaactg cagaaggaca agatggcgga agcctactcc  2160
gagatcggca tgaagggaga acgccggaga gggaagggtc atgacggact gtaccagggc  2220
ctgtcaactg ccactaagga cacttacgat gcgctccata tgcaagcttt gcccccgcgg  2280
cgcgcgaaac gcggcagcgg cgcgaccaac tttagcctgc tgaaacaggc gggcgatgtg  2340
gaagaaaacc cgggcccgcg agcaaagagg aatattatgc ttctattagt gacttccctt  2400
ttgctgtgcg agttgccaca ccccgccttc ctgcttattc cccaggtaca gctccagcag  2460
agtggcccag ggctcgtgaa gccaagccag acgctgtccc tgacttgtgc aatttcaggg  2520
gattcagttt catcaaatag cgcggcgtgg aattggattc gacaatctcc ttcccgaggg  2580
ttggaatggc ttggacgaac atattacaga tccaaatggt ataacgacta tgcggtatca  2640
gtaaagtcaa gaataaccat taaccccgac acaagcaaga accaattctc tttgcagctt  2700
aactctgtca cgccagaaga cacggcagtc tattattgcg ctcgcgaggt aacgggtgac  2760
ctggaagacg cttttgacat ttgggggcag ggtacgatgg tgacagtcag ttcagggggc  2820
ggtgggagtg ggggaggggg tagcgggggg ggagggtcag acattcagat gacccagtcc  2880
ccttcatcct tgtctgcctc cgtcggtgac agggtgacaa taacatgcag agcaagccaa  2940
acaatctgga gctatctcaa ctggtaccag cagcgaccag gaaaagcgcc aaacctgctg  3000
atttacgctg cttcctccct ccaatcaggc gtgcctagta gatttagcgg taggggctcc  3060
ggcaccgatt ttacgctcac tataagctct cttcaagcag aagattttgc gacttattac  3120
tgccagcagt cctatagtat acctcagact ttcggacagg gtaccaagtt ggagattaag  3180
gctagcgcaa ccactacgcc tgctccgcgg cctccaacgc ccgcgcccac gatagctagt  3240
cagccgttgt ctctccgacc agaggcgtgt agaccggccg ctggcggagc cgtacatact  3300
cgcggactcg acttcgcttg cgacatctac atttgggcac ccttggctgg gacctgtggg  3360
gtgctgttgc tgtccttggt tattacgttg tactgcaaga ggggccggaa gaagctgctt  3420
tacatcttca agcagccgtt catgcggccc gtgcagacga ctcaggaaga ggacggatgc  3480
tcgtgcagat tccctgagga ggaagagggg ggatgcgaac tgagagtcaa attttccagg  3540
tccgcagatg cccccgcgta ccagcaaggc cagaaccaac tttacaacga actgaacctg  3600
ggtcgccggg aggaatatga tgtgctggat aaacgaaggg ggagggaccc tgagatggga  3660
gggaaacctc gcaggaaaaa cccgcaggaa ggtttgtaca acgagttgca gaaggataag  3720
atggctgagg cttactctga aatagggatg aagggagaga gacggagagg aaaaggccat  3780
gatggccttt accagggctt gagcacagca acaaaggata cttacgacgc tcttcacatg  3840
caagctctgc caccacgg                                               3858

SEQ ID NO: 54          moltype = AA  length = 1287
FEATURE                Location/Qualifiers
source                 1..1287
                       mol_type = protein
                       organism = Synthetic construct
SEQUENCE: 54
IMLLLVTSLL LCELPHPAFL LIPEVQLQQS GAELVKPGAS VKMSCKASGY TFTSYNMHWV  60
KQTPGQGLEW IGAIYPGNGD TSYNQKFKGK ATLTADKSSS TAYMQLSSLT SEDSADYYCA  120
RSNYYGSSYW FFDVWGAGTT VTVSSGGGGS GGGGSGGGGS DIVLTQSPAI LSASPGEKVT  180
MTCRASSSVN YMDWYQKKPG SSPKPWIYAT SNLASGVPAR FSGSGSGTSY SLTISRVEAE  240
DAATYYCQQW SFNPPTFGGG TKLEIKGGGG SGGGGSGGGG SGGGGSGGGG SDIQMTQTTS  300
SLSASLGDRV TISCRASQDI SKYLNWYQQK PDGTVKLLIY HTSRLHSGVP SRFSGSGSGT  360
DYSLTISNLE QEDIATYFCQ QGNTLPYTFG GGTKLEITGS TSGSGKPGSG EGSTKGEVKL  420
QESGPGLVAP SQSLSVTCTV SGVSLPDYGV SWIRQPPRKG LEWLGVIWGS ETTYYNSALK  480
SRLTIIKDNS KSQVFLKMNS LQTDDTAIYY CAKHYYYGGS YAMDYWGQGT SVTVSSAAAT  540
TTPAPRPPTP APTIASQPLS LRPEACRPAA GGAVHTRGLD FACDIYIWAP LAGTCGVLLL  600
SLVITLYCRS KRSRLLHSDY MNMTPRRPGP TRKHYQPYAP PRDFAAYRSR VKFSRSADAP  660
AYQQGQNQLY NELNLGRREE YDVLDKRRGR DPEMGGKPRR KNPQEGLYNE LQKDKMAEAY  720
SEIGMKGERR RGKGHDGLYQ GLSTATKDTY DALHMQALPP RRAKRGSGAT NFSLLKQAGD  780
VEENPGPRAK RNIMLLLVTS LLLCELPHPA FLLIPQVQLQ QSGPGLVKPS QTLSLTCAIS  840
GDSVSSNSAA WNWIRQSPSR GLEWLGRTYY RSKWYNDYAV SVKSRITINP DTSKNQFSLQ  900
LNSVTPEDTA VYYCAREVTG DLEDAFDIWG QGTMVTVSSG GGGSGGGGSG GGGSDIQMTQ  960
SPSSLSASVG DRVTITCRAS QTIWSYLNWY QQRPGKAPNL LIYAASSLQS GVPSRFSGRG  1020
SGTDFTLTIS SLQAEDFATY YCQQSYSIPQ TFGQGTKLEI KASATTTPAP RPPTPAPTIA  1080
SQPLSLRPEA CRPAAGGAVH TRGLDFACDI YIWAPLAGTC GVLLLSLVIT LYCKRGRKKL  1140
LYIFKQPFMR PVQTTQEEDG CSCRFPEEEE GGCELRVKFS RSADAPAYQQ GQNQLYNELN  1200
LGRREEYDVL DKRRGRDPEM GGKPRRKNPQ EGLYNELQKD KMAEAYSEIG MKGERRRGKG  1260
HDGLYQGLST ATKDTYDALH MQALPPR                                     1287

SEQ ID NO: 55          moltype = DNA  length = 3852
FEATURE                Location/Qualifiers
source                 1..3852
                       mol_type = other DNA
                       organism = Synthetic construct
SEQUENCE: 55
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct gggggggccgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
```

```
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaaggagg cggcggcagc ggcgggggag ggtccggagg gggtggttct  840
ggtggaggag gatcgggagg cggtggcagc gacattcaga tgactcagac cacctcctcc  900
ctgtccgcct ccctgggcga ccgcgtgacc atctcatgcc gcgccagcca ggacatctcg  960
aagtacctca actggtacca gcagaagccc gacggaaccg tgaagctcct gatctaccac  1020
acctcccggc tgcacagcgg agtgccgtct agattctcgg gttcggggtc gggaactgac  1080
tactccctta ctatttccaa cctggagcag gaggatattg ccacctactt ctgccaacaa  1140
ggaaacaccc tgccgtacac ttttggcggg ggaaccaagc tggaaatcac tggcagcaca  1200
tccggttccg ggaagcccgg ctccggagag ggcagcacca aggggggaagt caagctgcag  1260
gaatcaggac ctggcctggt ggccccgagc cagtcactgt ccgtgacttg tactgtgtcc  1320
ggagtgtcgc tcccggatta cggagtgtcc tggatcaggc agccacctcg gaaaggattg  1380
gaatggctcg gagtcatctg gggttccgaa accacctatt acaactcggc actgaaatcc  1440
aggctcacca ttatcaagga taactccaag tcacaagtgt tcctgaagat gaatagcctg  1500
cagactgacg acacggcgat ctactattgc gccaagcact actactacgg cggatcctac  1560
gctatggact actggggcca ggggaccagc gtgaccgtgt catccgcggc cgcgactacc  1620
actcctgcac cacggccacc taccccagcc cccaccattg caagccagcc actttcactg  1680
cgccccgaag cgtgtagacc agctgctgga ggagccgtgc atacccgagg gctggacttc  1740
gcctgtgaca tctacatctg ggccccattg gctggaactt gcggcgtgct gctcttgtct  1800
ctggtcatta ccctgtactg ccggtcgaag aggtccagac tcttgcactc cgactacatg  1860
aacatgactc ctagaaggcc cggacccact agaaagcact accagccgta cgcccctcct  1920
cgggatttcg ccgcataccg gtccagagtg aagttcagcc gctcagccga tgcaccggcc  1980
taccagcagg gacagaacca gctctacaac gagctcaacc tgggtcggcg ggaagaatat  2040
gacgtgctgg acaaacggcg cggcagagat ccggagatgg ggggaaagcc gaggaggaag  2100
aaccctcaag agggcctgta caacgaactg cagaaggaca agatggcgga agcctactcc  2160
gagatcggca tgaagggaga acgccggaga gggaagggtc atgacggact gtaccagggc  2220
ctgtcaactg ccactaagga cacttacgat gcgctccata tgcaagcttt gcccccgcgg  2280
cgcgcgaaac gcggcagcgg cgcgaccaac tttagcctgc tgaaacaggc gggcgatgtg  2340
gaagaaaacc cgggcccgcg agcaaagagg aatattatgt tgctgctcgt gacctcgctc  2400
cttctgtgcg agctgcccca tccggctttt ctgctcatcc ctcaagtgca gctgcagcag  2460
tccggtcctg gactggtcaa gccgtcccag actctgagcc tgacttgcgc aattagcggg  2520
gactcagtct cgtccaattc ggcggcctgg aactggatcc ggcagtcacc atcaaggggc  2580
ctggaatggc tcgggcgcac ttactaccgg tccaaatggt ataccgacta cgccgtgtcc  2640
gtgaagaatc ggatcaccat taaccccgac acctcgaaga accagttctc actccaactg  2700
aacagcgtga cccccgagga taccgcggtg tactactgcg cacaagaagt ggaaccgcag  2760
gacgccttcg acatttgggg acagggaacg atggtcacag tgtcgtccgg tggaggaggt  2820
tccggaggcg gtggatctgg aggcggaggt tcggatatcc agatgaccca gagcccctcc  2880
tcggtgtccg catccgtggg cgataaggtc accattacct gtagagcgtc ccaggacgtg  2940
tccggatggc tggcctggta ccagcagaag ccaggcttgg ctcctcaact gctgatcttc  3000
ggcgccagca ctcttcaggg ggaagtgcca tcacgcttct ccggatccgg ttccggcacc  3060
gacttcaccc tgaccatcag cagcctccag cctgaggact tcgccactta ctactgccaa  3120
caggccaagt acttccccta taccttcgga agaggcacta agctggaaat caaggctagc  3180
gcaaccacta cgcctgctcc gcggcctcca acgcccgcgc ccacgatagc tagtcagccg  3240
ttgtctctcc gaccagaggc gtgtagaccg gccgctggcg gagccgtaca tactcgcgga  3300
ctcgacttcg cttgcgacat ctacatttgg gcacccttgg ctgggacctg tggggtgctg  3360
ttgctgtcct tggttattac gttgtactgc aagaggggcc ggaagaagct gctttacatc  3420
ttcaagcagc cgttcatgcg gcccgtgcag acgactcagg aagaggacgg atgctcgtgc  3480
agattccctg aggaggaaga gggggggatgc gaactgagag tcaaattttc caggtccgca  3540
gatgcccccg cgtaccagca aggccagaac caactttaca acgaactgaa cctgggtcgc  3600
cgggaggaat atgatgtgct ggataaacga agggggaggg accctgagat gggagggaaa  3660
cctcgcagga aaaacccgca ggaaggtttg tacaacgagt tgcagaagga taagatggct  3720
gaggcttact ctgaaatagg gatgaaggga gagagacgga gaggaaaagg ccatgatggc  3780
ctttaccagg gcttgagcac agcaacaaag gatacttacg acgctcttca catgcaagct  3840
ctgccaccac gg                                                     3852

SEQ ID NO: 56          moltype = AA  length = 1284
FEATURE                Location/Qualifiers
source                 1..1284
                       mol_type = protein
                       organism = Synthetic construct
SEQUENCE: 56
MLLLVTSLLL CELPHPAFLL IPEVQLQQSG AELVKPGASV KMSCKASGYT FTSYNMHWVK  60
QTPGQGLEWI GAIYPGNGDT SYNQKFKGKA TLTADKSSST AYMQLSSLTS EDSADYYCAR  120
SNYYGSSYWF FDVWGAGTTV TVSSGGGGSG GGGSGGGGSD IVLTQSPAIL SASPGEKVTM  180
TCRASSSVNY MDWYQKKPGS SPKPWIYATS NLASGVPARF SGSGSGTSYS LTISRVEAED  240
AATYYCQQWS FNPPTFGGGT KLEIKGGGGS GGGGSGGGGS GGGGSGGGGS DIQMTQTTSS  300
LSASLGDRVT ISCRASQDIS KYLNWYQQKP DGTVKLLIYH TSRLHSGVPS RFSGSGSGTD  360
YSLTISNLEQ EDIATYFCQQ GNTLPYTFGG GTKLEITGST SGSGKPGSGE GSTKGEVKLQ  420
ESGPGLVAPS QSLSVTCTVS GVSLPDYGVS WIRQPPRKGL EWLGVIWGSE TTYYNSALKS  480
RLTIIKDNSK SQVFLKMNSL QTDDTAIYYC AKHYYYGGSY AMDYWGQGTS VTVSSAAATT  540
TPAPRPPTPA PTIASQPLSL RPEACRPAAG GAVHTRGLDF ACDIYIWAPL AGTCGVLLLS  600
LVITLYCRSK RSRLLHSDYM NMTPRRPGPT RKHYQPYAPP RDFAAYRSRV KFSRSADAPA  660
YQQGQNQLYN ELNLGRREEY DVLDKRRGRD PEMGGKPRRK NPQEGLYNEL QKDKMAEAYS  720
EIGMKGERRR GKGHDGLYQG LSTATKDTYD ALHMQALPPR RAKRGSGATN FSLLKQAGDV  780
EENPGPRAKR NIMLLLVTSL LLCELPHPAF LLIPQVQLQQ SGPGLVKPSQ TLSLTCAISG  840
DSVSSNSAAW NWIRQSPSRG LEWLGRTYYR SKWYTDYAVS VKNRITINPD TSKNQFSLQL  900
NSVTPEDTAV YYCAQEVEPQ DAFDIWGQGT MVTVSSGGGG SGGGGSGGGG SDIQMTQSPS  960
SVSASVGDKV TITCRASQDV SGWLAWYQQK PGLAPQLLIF GASTLQGEVP SRFSGSGSGT  1020
DFTLTISSLQ PEDFATYYCQ QAKYFPYTFG RGTKLEIKAS ATTTPAPRPP TPAPTIASQP  1080
```

```
LSLRPEACRP AAGGAVHTRG LDFACDIYIW APLAGTCGVL LLSLVITLYC KRGRKKLLYI  1140
FKQPFMRPVQ TTQEEDGCSC RFPEEEEGGC ELRVKFSRSA DAPAYQQGQN QLYNELNLGR  1200
REEYDVLDKR RGRDPEMGGK PRRKNPQEGL YNELQKDKMA EAYSEIGMKG ERRRGKGHDG  1260
LYQGLSTATK DTYDALHMQA LPPR                                         1284

SEQ ID NO: 57          moltype =   length =
SEQUENCE: 57
000

SEQ ID NO: 58          moltype =   length =
SEQUENCE: 58
000

SEQ ID NO: 59          moltype = DNA  length = 3855
FEATURE                Location/Qualifiers
source                 1..3855
                       mol_type = other DNA
                       organism = Synthetic construct
SEQUENCE: 59
atgcttcttt tggtgacttc ccttttgctg tgcgagttgc cacaccccgc cttcctgctt  60
attccccagg tacagctcca gcagagtggc ccagggctcg tgaagccaag ccagacgctg  120
tccctgactt gtgcaatttc aggggattca gtttcatcaa atagcgcggc gtggaattgg  180
attcgacaat ctccttcccg agggttggaa tggcttggac gaacatatta cagatccaaa  240
tggtataacg actatgcggt atcagtaaag tcaagaataa ccattaaccc cgacacaagc  300
aagaaccaat tctctttgca gcttaactct gtcacgccag aagacacggc agtctattat  360
tgcgctcgcg aggtaacggg tgacctggaa gacgcttttg acatttgggg gcagggtacg  420
atggtgacag tcagttcagg gggcggtggg agtgggggag ggggtagcgg ggggggaggg  480
tcagacattc agatgaccca gtccccttca tccttgtctg cctccgtcgg tgacagggtg  540
acaataacat gcagagcaag ccaaacaatc tggagctatc tcaactggta ccagcagcga  600
ccaggaaaag cgccaaacct gctgatttac gctgcttcct ccctccaatc aggcgtgcct  660
agtagattta gcggtagggg ctccggcacc gattttacgc tcactataag ctctcttcaa  720
gcagaagatt ttgcgactta ttactgccag cagtcctata gtatacctca gactttcgga  780
cagggtacca agttggagat taaggcggcc gctaccacaa cccctgcgcc ccggcctcct  840
accccccgcac ccacgattgc ttctcaacct ctttcactcc gacctgaggc ttgtagacct  900
gcagccgggg gtgccgtcca cacacgggga ctcgacttcg cttgtgatat atatatttgg  960
gcgcccctgg ccggcacttg tggagttctt ttgctctctc ttgttatcac attgtactgc  1020
aagcgaggta ggaagaaatt gctttacatt tttaagcagc cgttcatgcg accagtacag  1080
actactcaag aagaagatgg gtgctcttgt cggttcccgg aagaagaaga gggtggttgc  1140
gagttgaggg tgaagttctc ccgctctgcc gacgcaccgg catatcagca gggacaaaac  1200
cagctctaca acgaattgaa cctgggtcgg cgggaagaat atgacgtgct cgataagcgg  1260
cggggtcgcg acccagaaat gggaggcaaa ccgcgcagga aaaatccaca ggagggactt  1320
tataacgaac ttcaaaagga taagatggca gaggcataca gcgaaatcgg gatgaaaggc  1380
gagagaagaa gggggaaagg gcacgatggt ctttaccagg ggctttctac cgcgacgaag  1440
gatacctacg atgctctcca tatgcaagca cttcctccta gacgggcaaa gcggggctca  1500
ggggcgacta acttttcact gttgaagcag gccggggatg tggaggagaa tcctggtcct  1560
agagctaagc gagtagacat ggccctgccc gtcactgcgc tgcttcttcc acttgcgctt  1620
ctgctgcacg cagcgcgccc ggaagtccag ctccagcaaa gcggagccga actcgtgaag  1680
ccgggggcct ccgtgaagat gagctgcaag gcatccggct acaccttcac tagctacaac  1740
atgcactggg tgaagcagac tccgggtcaa gggctggagt ggattggggc gatctacccg  1800
ggcaacggcg acacctccta caaccaaaag ttcaagggga aggctactct tacggcggac  1860
aagtcgtcca gcaccgcata catgcaactc tcctccctga cctccgagga ctcggcggac  1920
tactactgcg cccggagcaa ctactacggt tcctcctact ggttcttcga cgtgtggggt  1980
gccggaacta ctgtgactgt gtcctccggt ggtggcggat caggcggcgg gggatccggc  2040
ggtggaggat ccgacattgt gctgactcag tcccccgcaa tcctttcggc ctcccccgga  2100
gagaaggtca cgatgacttg cagggcttcg tcctccgtga actacatgga ttggtaccaa  2160
aagaagcccg ggtcgtcgcc taagccgtgg atctacgcta cctcaaacct ggcttccggc  2220
gtccctgcgc ggttcagcgg ctcggggagc ggtacctcat actcactcac catctcccgg  2280
gtggaggccg aagatgcggc cacctattat tgccaacagt ggtccttcaa tccgcccacc  2340
ttcgggggggg gaaccaagct cgagatcaag gggggtggcg gctcaggggg aggcggaagc  2400
ggagggggtg gctcgggcgg cggcggttcc ggcggcggag ggtccgatat ccaaatgacc  2460
cagactacta gctcgttgag cgcctcgctc ggcgacagag tgaccattag ctgcagggca  2520
tcccaggaca tttcaaagta cctgaactgg taccaacaga agcccgacgg aactgtgaag  2580
ctcctgatct accacacctc ccggctgcac tccggagtcc cgtcgagatt ttccggctcc  2640
ggaagcggaa ccgattattc gctcaccatt tctaacctgg aacaggagga cattgccact  2700
tacttctgtc aacaaggaaa cactctgcct tacacctttg gtggcggaac caagttggaa  2760
attaccggct ccacctccgg atccggaaag cctggatccg gagagggatc aaccaaggga  2820
gaagtgaagc tgcaggagag cgggcccggc cttgtcgccc cgagccagtc cttgtccgtg  2880
acctgtactg tctccggagt cagcctgccg gactacgggg tgtcctggat ccgccagccg  2940
cctcgcaagg gcctggagtg gctcggcgtg atctggggat ccgaaacgac ttactacaac  3000
tcggccctca agtcgaggct cactattatc aaggacaact cgaagtccca ggtgttcctc  3060
aagatgaact cgctgcaaac cgacgacaca gcgatctact actgtgcaaa gcattactac  3120
tacggaggca gctacgcaat ggactactgg ggacagggaa cctccgtgac tgtctctagc  3180
gctagcgcga ccactacgcc cgcccccccgc ccacctaccc ccgcccccgac cattgcgagc  3240
caaccgttgt cactccgccc ggaagcctgc cgccccgccg ctggcggagc cgtgcacacc  3300
cggggactgg acttcgcatg cgacatctac atttgggccc cgctggctgg aacctgtgga  3360
gtcctgctgc tctccctcgt gatcactctg tactgccggt cgaagcgctc aagactgctg  3420
cactcagact acatgaacat gactcctcgg cggccggggc cgactcggaa gcactaccag  3480
ccttacgcac ccccgagaga tttcgcggcc taccgctccc gggtcaagtt ttcccggtct  3540
gccgacgctc cggcgtacca gcaggggcag aaccagctct acaatgagct gaatctgggt  3600
```

```
cggagagaag agtacgatgt gctggataag cggagaggca gagatccaga aatgggagga  3660
aagcctcgga gaaagaaccc acaggaggga ctgtataatg agctgcagaa ggacaaaatg  3720
gccgaagcct acagcgagat cggcatgaag ggagagcggc gcagagggaa gggacatgac  3780
ggcctgtacc agggtctgag caccgcgact aaggacacct acgatgccct tcatatgcaa  3840
gcactccctc cgcgc                                                   3855

SEQ ID NO: 60          moltype = AA  length = 1286
FEATURE                Location/Qualifiers
source                 1..1286
                       mol_type = protein
                       organism = Synthetic construct
SEQUENCE: 60
IMLLLVTSLL LCELPHPAFL LIPQVQLQQS GPGLVKPSQT LSLTCAISGD SVSSNSAAWN  60
WIRQSPSRGL EWLGRTYYRS KWYNDYAVSV KSRITINPDT SKNQFSLQLN SVTPEDTAVY  120
YCAREVTGDL EDAFDIWGQG TMVTVSSGGG GSGGGGSGGG GSDIQMTQSP SSLSASVGDR  180
VTITCRASQT IWSYLNWYQQ RPGKAPNLLI YAASSLQSGV PSRFSGRGSG TDFTLTISSL  240
QAEDFATYYC QQSYSIPQTF GQGTKLEIKA AATTTPAPRP PTPAPTIASQ PLSLRPEACR  300
PAAGGAVHTR GLDFACDIYI WAPLAGTCGV LLLSLVITLY CKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPRRAKRG SGATNFSLLK QAGDVEENPG PRAKRVDMAL PVTALLLPLA  540
LLLHAARPEV QLQQSGAELV KPGASVKMSC KASGYTFTSY NMHWVKQTPG QGLEWIGAIY  600
PGNGDTSYNQ KFKGKATLTA DKSSSTAYMQ LSSLTSEDSA DYYCARSNYY GSSYWFFDVW  660
GAGTTVTVSS GGGGSGGGGS GGGGSDIVLT QSPAILSASP GEKVTMTCRA SSSVNYMDWY  720
QKKPGSSPKP WIYATSNLAS GVPARFSGSG SGTSYSLTIS RVEAEDAATY YCQQWSFNPP  780
TFGGGTKLEI KGGGGSGGGG SGGGGSGGGG SGGGGSDIQM TQTTSSLSAS LGDRVTISCR  840
ASQDISKYLN WYQQKPDGTV KLLIYHTSRL HSGVPSRFSG SGSGTDYSLT ISNLEQEDIA  900
TYFCQQGNTL PYTFGGGTKL EITGSTSGSG KPGSGEGSTK GEVKLQESGP GLVAPSQSLS  960
VTCTVSGVSL PDYGVSWIRQ PPRKGLEWLG VIWGSETTYY NSALKSRLTI IKDNSKSQVF  1020
LKMNSLQTDD TAIYYCAKHY YYGGSYAMDY WGQGTSVTVS SASATTTPAP RPPTPAPTIA  1080
SQPLSLRPEA CRPAAGGAVH TRGLDFACDI YIWAPLAGTC GVLLLSLVIT LYCRSKRSRL  1140
LHSDYMNMTP RRPGPTRKHY QPYAPPRDFA AYRSRVKFSR SADAPAYQQG QNQLYNELNL  1200
GRREEYDVLD KRRGRDPEMG GKPRRKNPQE GLYNELQKDK MAEAYSEIGM KGERRRGKGH  1260
DGLYQGLSTA TKDTYDALHM QALPPR                                       1286

SEQ ID NO: 61          moltype = DNA  length = 3849
FEATURE                Location/Qualifiers
source                 1..3849
                       mol_type = other DNA
                       organism = Synthetic construct
SEQUENCE: 61
atgttgctgc tcgtgacctc gctccttctg tgcgagctgc cccatccggc ttttctgctc  60
atccctcaag tgcagctgca gcagtccggt cctggactgg tcaagccgtc ccagactctg  120
agcctgactt gcgcaattag cggggactca gtctcgtcca attcggcggc ctggaactgg  180
atccggcagt caccatcaag gggcctggaa tggctcgggc gcacttacta ccggtccaaa  240
tggtataccg actacgccgt gtccgtgaag aatcggatca ccattaaccc cgacacctcg  300
aagaaccagt tctcactcca actgaacagc gtgacccccg aggataccgc ggtgtactac  360
tgcgcacaag aagtggaacc gcaggacgcc ttcgacattt ggggacaggg aacgatggtc  420
acagtgtcgt ccggtggagg aggttccgga ggcggtggat ctggaggcgg aggttcggat  480
atccagatga cccagagccc ctcctcggtg tccgcatccg tgggcgataa ggtcaccatt  540
acctgtagag cgtcccagga cgtgtccgga tggctggcct ggtaccagca gaagccaggc  600
ttggctcctc aactgctgat cttcggcgcc agcactcttc aggggggaagt gccatcacgc  660
ttctccggat ccggttccgg caccgacttc accctgacca tcagcagcct ccagcctgag  720
gacttcgcca cttactactg ccaacaggcc aagtacttcc cctatacctt cggaagaggc  780
actaagctgg aaatcaaggc ggccgctacc acaacccctg cgccccggcc tcctaccccc  840
gcacccacga ttgcttctca acctctttca ctccgacctg aggcttgtag acctgcagcc  900
gggggtgccg tccacacacg ggactcgac ttcgcttgtg atatatatat ttgggcgccc  960
ctggccggca cttgtggagt tcttttgctc tctcttgtta tcacattgta ctgcaagcga  1020
ggtaggaaga aattgcttta catttttaag cagccgttca tgcgaccagt acagactact  1080
caagaagaag atgggtgctc ttgtcggttc ccggaagaag aagagggtgg ttgcgagttg  1140
agggtgaagt tctcccgctc tgccgacgca ccggcatatc agcagggaca aaaccagctc  1200
tacaacgaat tgaacctggg tcggcgggaa gaatatgacg tgctcgataa gcggcggggt  1260
cgcgacccag aaatgggagg caaaccgcgc aggaaaaatc cacaggaggg actttataac  1320
gaacttcaaa aggataagat ggcagaggca tacagcgaaa tcgggatgaa aggcgagaga  1380
agaaggggga aagggcacga tggtctttac caggggcttt ctaccgcgac gaaggatacc  1440
tacgatgctc tccatatgca agcacttcct cctagacggg caaagcgggg ctcaggggcg  1500
actaactttt cactgttgaa gcaggccggg gatgtggagg agaatcctgg tcctagagct  1560
aagcgagtag acatggccct gcccgtcact gcgctgcttc ttccacttgc gcttctgctg  1620
cacgcagcgc gcccggaagt ccagctccag caaagcggag ccgaactcgt gaagccgggg  1680
gcctccgtga agatgagctg caaggcatcc ggctacacct tcactagcta caacatgcac  1740
tgggtgaagc agactccggg tcaagggctg gagtggattg gggcgatcta cccgggcaac  1800
ggcgacacct cctacaacca aaagttcaag gggaaggcta ctcttacggc ggacaagtcg  1860
tccagcaccg catacatgca actctcctcc ctgacctccg aggactcggc ggactactac  1920
tgcgcccgga gcaactacta cggttcctcc tactggttct tcgacgtgtg gggtgccgga  1980
actactgtga ctgtgtcctc cggtggtggc ggatcaggcg gcgggggatc cggcggtgga  2040
ggatccgaca ttgtgctgac tcagtccccc gcaatccttt cggcctcccc cggagagaag  2100
gtcacgatga cttgcagggc ttcgtcctcc gtgaactaca tggattggta ccaaaagaag  2160
cccgggtcgt cgcctaagcc gtggatctac gctacctcaa acctggcttc cggcgtccct  2220
gcgcggttca gcggctcggg gagcggtacc tcatactcac tcaccatctc ccgggtggag  2280
```

```
gccgaagatg cggccaccta ttattgccaa cagtggtcct tcaatccgcc caccttcggg  2340
gggggaacca agctcgagat caagggggt ggcggctcag ggggaggcgg aagcggaggg  2400
ggtggctcgg gcggcggcgg ttccggcggc ggaggtccg atatccaaat gacccagact  2460
actagctcgt tgagcgcctc gctcggcgac agagtgacca ttagctgcag ggcatcccag  2520
gacatttcaa agtacctgaa ctggtaccaa cagaagcccg acggaactgt gaagctcctg  2580
atctaccaca cctcccggct gcactccgga gtcccgtcga gattttccgg ctccggaagc  2640
ggaaccgatt attcgctcac catttctaac ctggaacagg aggacattgc cacttacttc  2700
tgtcaacaag gaaacactct gccttacacc tttggtggcg gaaccaagtt ggaaattacc  2760
ggctccacct ccggatccgg aaagcctgga tccggagagg gatcaaccaa gggagaagtg  2820
aagctgcagg agagcgggcc cggccttgtc gccccgagcc agtccttgtc cgtgacctgt  2880
actgtctccg gagtcagcct gccggactac ggggtgtcct ggatccgcca gccgcctcgc  2940
aagggcctgg agtggctcgg cgtgatctgg ggatccgaaa cgacttacta caactcggcc  3000
ctcaagtcga ggctcactat tatcaaggac aactcgaagt cccaggtgtt cctcaagatg  3060
aactcgctgc aaaccgacga cacagcgatc tactactgtg caaagcatta ctactacgga  3120
ggcagctacg caatggacta ctggggacag ggaacctccg tgactgtctc tagcgctagc  3180
gcgaccacta cgcccgcccc ccgcccacct accccccgccc cgaccattgc gagccaaccg  3240
ttgtcactcc gcccggaagc ctgccgcccc gccgctggcg gagccgtgca cacccgggga  3300
ctggacttcg catgcgacat ctacatttgg gccccgctgg ctggaacctg tggagtcctg  3360
ctgctctccc tcgtgatcac tctgtactgc cggtcgaagc gctcaagact gctgcactca  3420
gactacatga acatgactcc tcggcggccg gggccgactc ggaagcacta ccagccttac  3480
gcacccccga gagatttcgc ggcctaccgc tcccgggtca agttttcccg gtctgccgac  3540
gctccggcgt accagcaggg gcagaaccag ctctacaatg agctgaatct gggtcggaga  3600
gaagagtacg atgtgctgga taagcggaga ggcagagatc cagaaatggg aggaaagcct  3660
cggagaaaga acccacagga gggactgtat aatgagctgc agaaggacaa aatggccgaa  3720
gcctacagcg agatcggcat gaagggagag cggcgcagag ggaagggaca tgacggcctg  3780
taccagggtc tgagcaccgc gactaaggac acctacgatg cccttcatat gcaagcactc  3840
cctccgcgc                                                           3849
```

```
SEQ ID NO: 62          moltype = AA  length = 1283
FEATURE                Location/Qualifiers
source                 1..1283
                       mol_type = protein
                       organism = Synthetic construct
SEQUENCE: 62
MLLLVTSLLL CELPHPAFLL IPQVQLQQSG PGLVKPSQTL SLTCAISGDS VSSNSAAWNW  60
IRQSPSRGLE WLGRTYYRSK WYTDYAVSVK NRITINPDTS KNQFSLQLNS VTPEDTAVYY  120
CAQEVEPQDA FDIWGQGTMV TVSSGGGGSG GGGSGGGGSD IQMTQSPSSV SASVGDKVTI  180
TCRASQDVSG WLAWYQQKPG LAPQLLIFGA STLQGEVPSR FSGSGSGTDF TLTISSLQPE  240
DFATYYCQQA KYFPYTFGRG TKLEIKAAAT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PRRAKRGSGA TNFSLLKQAG DVEENPGPRA KRVDMALPVT ALLLPLALLL  540
HAARPEVQLQ QSGAELVKPG ASVKMSCKAS GYTFTSYNMH WVKQTPGQGL EWIGAIYPGN  600
GDTSYNQKFK GKATLTADKS SSTAYMQLSS LTSEDSADYY CARSNYYGSS YWFFDVWGAG  660
TTVTVSSGGG GSGGGGSGGG GSDIVLTQSP AILSASPGEK VTMTCRASSS VNYMDWYQKK  720
PGSSPKPWIY ATSNLASGVP ARFSGSGSGT SYSLTISRVE AEDAATYYCQ QWSFNPPTFG  780
GGTKLEIKGG GGSGGGGSGG GGSGGGGSGG GGSDIQMTQT TSSLSASLGD RVTISCRASQ  840
DISKYLNWYQ QKPDGTVKLL IYHTSRLHSG VPSRFSGSGS GTDYSLTISN LEQEDIATYF  900
CQQGNTLPYT FGGGTKLEIT GSTSGSGKPG SGEGSTKGEV KLQESGPGLV APSQSLSVTC  960
TVSGVSLPDY GVSWIRQPPR KGLEWLGVIW GSETTYYNSA LKSRLTIIKD NSKSQVFLKM  1020
NSLQTDDTAI YYCAKHYYYG GSYAMDYWGQ GTSVTVSSAS ATTTPAPRPP TPAPTIASQP  1080
LSLRPEACRP AAGGAVHTRG LDFACDIYIW APLAGTCGVL LLSLVITLYC RSKRSRLLHS  1140
DYMNMTPRRP GPTRKHYQPY APPRDFAAYR SRVKFSRSAD APAYQQGQNQ LYNELNLGRR  1200
EEYDVLDKRR GRDPEMGGKP RRKNPQEGLY NELQKDKMAE AYSEIGMKGE RRRGKGHDGL  1260
YQGLSTATKD TYDALHMQAL PPR                                           1283

SEQ ID NO: 63          moltype =   length =
SEQUENCE: 63
000

SEQ ID NO: 64          moltype =   length =
SEQUENCE: 64
000

SEQ ID NO: 65          moltype = DNA  length = 1476
FEATURE                Location/Qualifiers
source                 1..1476
                       mol_type = other DNA
                       organism = Synthetic construct
SEQUENCE: 65
atgcttcttt tggtgacttc ccttttgctg tgcgagttgc cacaccccgc cttcctgctt  60
attccccagg tacagcttca acagagtggg ccgggactgg tgaaacactc ccaaacactt  120
tctctgacgt gcgctatatc aggtgactct gtttcatcta attctgctgc gtggaactgg  180
attcgacaat ctcccagtcg cgggttggaa tggctgggac gaacatatta tcggtctaag  240
tggtataacg attatgctgt atctgttaaa tctcgaatta cgattaatcc tgacacctcc  300
aagaaccagt tctccctcca gttgaactca gtcacaccgg aagacactgc ggtctactat  360
tgcgctcaag aagtcgagcc acatgatgca ttcgacatct ggggccaggg aacgatggtc  420
accgtcagca gtggcggcgg cggatctggg ggtggcggtt ctggcggtgg aggatcagac  480
```

```
atacaaatga cgcagagtcc ctcaagtgtg tacgcgagtg tgggggataa ggtaactatt  540
acgtgcagag cgtcacagga tgttagtgga tggcttgcct ggtatcagca gaagccaggc  600
cttgctccac agctccttat cagtggtgct tctacacttc agggcgaggt tccgagtaga  660
ttctctggtt ctggatctgg tactgacttc actcttacaa tttcttcttt gcaaccagaa  720
gactttgcga cttattactg ccaacaggcc aaatacttcc cttatacatt tggccaaggt  780
accaagttgg agataaaggc ggccgcaact accacccctg cccctcggcc gccgactccg  840
gccccaacca tcgcaagcca acccctctcc ttgcgccccg aagcttgccg cccggccgcg  900
ggtggagccg tgcatacccg ggggctggac tttgcctgcg atatctacat ttgggccccg  960
ctggccggca cttgcggcgt gctcctgctg tcgctggtca tcacccttta ctgcaagagg  1020
ggccggaaga agctgcttta catcttcaag cagccgttca tgcggcccgt gcagacgact  1080
caggaagagg acggatgctc gtgcagattc cctgaggagg aagagggggg atgcgaactg  1140
cgcgtcaagt tctcacggtc cgccgacgcc cccgcatatc aacagggcca gaatcagctc  1200
tacaacgagc tgaacctggg aaggagagag gagtacgacg tgctggacaa gcgacgcgga  1260
cgcgacccgg agatgggggg gaaaccacgg cggaaaaacc ctcaggaagg actgtacaac  1320
gaactccaga aagacaagat ggcggaagcc tactcagaaa tcgggatgaa gggagagcgg  1380
aggaggggaa agggtcacga cgggctgtac cagggactga gcaccgccac taaggatacc  1440
tacgatgcct tgcatatgca agcactccca ccccgg                            1476

SEQ ID NO: 66          moltype = AA  length = 492
FEATURE                Location/Qualifiers
source                 1..492
                       mol_type = protein
                       organism = Synthetic construct
SEQUENCE: 66
MLLLVTSLLL CELPHPAFLL IPQVQLQQSG PGLVKHSQTL SLTCAISGDS VSSNSAAWNW  60
IRQSPSRGLE WLGRTYYRSK WYNDYAVSVK SRITINPDTS KNQFSLQLNS VTPEDTAVYY  120
CAQEVEPHDA FDIWGQGTMV TVSSGGGGSG GGGSGGGGSD IQMTQSPSSV YASVGDKVTI  180
TCRASQDVSG WLAWYQQKPG LAPQLLISGA STLQGEVPSR FSGSGSGTDF TLTISSLQPE  240
DFATYYCQQA KYFPYTFGQG TKLEIKAAAT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                   492

SEQ ID NO: 67          moltype = DNA  length = 1476
FEATURE                Location/Qualifiers
source                 1..1476
                       mol_type = other DNA
                       organism = Synthetic construct
SEQUENCE: 67
atgttgctgc tcgtgacctc gctccttctg tgcgagctgc cccatccggc ttttctgctc  60
atccctcaag tgcagctgca gcagtccggt cctggactgg tcaagccgtc ccagactctg  120
agcctgactt gcgcaattag cggggactca gtctcgtcca attcggcggc ctggaactgg  180
atccggcagt caccatcaag ggcctggaa tggctcgggc gcacttacta ccggtccaaa  240
tggtataccg actacgccgt gtccgtgaag aatcggatca ccattaaccc cgacacctcg  300
aagaaccagt tctcactcca actgaacagc gtgacccccg aggataccgc ggtgtactac  360
tgcgcacaag aagtggaacc gcaggacgcc ttcgacattt ggggacaggg aacgatggtc  420
acagtgtcgt ccggtggagg aggttccgga ggcggtggat ctggaggcgg aggttcggat  480
atccagatga cccagagccc ctcctcggtg tccgcatccg tgggcgataa ggtcaccatt  540
acctgtagag cgtcccagga cgtgtccgga tggctggcct ggtaccagca gaagccaggc  600
ttggctcctc aactgctgat cttcggcgcc agcactcttc agggggaagt gccatcacgc  660
ttctccggat ccggttccgg caccgacttc accctgacca tcagcagcct ccagcctgag  720
gacttcgcca cttactactg ccaacaggcc aagtacttcc cctatacctt cggaagaggc  780
actaagctgg aaatcaaggc ggccgcaact accacccctg cccctcggcc gccgactccg  840
gccccaacca tcgcaagcca acccctctcc ttgcgccccg aagcttgccg cccggccgcg  900
ggtggagccg tgcatacccg ggggctggac tttgcctgcg atatctacat ttgggccccg  960
ctggccggca cttgcggcgt gctcctgctg tcgctggtca tcacccttta ctgcaagagg  1020
ggccggaaga agctgcttta catcttcaag cagccgttca tgcggcccgt gcagacgact  1080
caggaagagg acggatgctc gtgcagattc cctgaggagg aagagggggg atgcgaactg  1140
cgcgtcaagt tctcacggtc cgccgacgcc cccgcatatc aacagggcca gaatcagctc  1200
tacaacgagc tgaacctggg aaggagagag gagtacgacg tgctggacaa gcgacgcgga  1260
cgcgacccgg agatgggggg gaaaccacgg cggaaaaacc ctcaggaagg actgtacaac  1320
gaactccaga aagacaagat ggcggaagcc tactcagaaa tcgggatgaa gggagagcgg  1380
aggaggggaa agggtcacga cgggctgtac cagggactga gcaccgccac taaggatacc  1440
tacgatgcct tgcatatgca agcactccca ccccgg                            1476

SEQ ID NO: 68          moltype = AA  length = 492
FEATURE                Location/Qualifiers
source                 1..492
                       mol_type = protein
                       organism = Synthetic construct
SEQUENCE: 68
MLLLVTSLLL CELPHPAFLL IPQVQLQQSG PGLVKPSQTL SLTCAISGDS VSSNSAAWNW  60
IRQSPSRGLE WLGRTYYRSK WYTDYAVSVK NRITINPDTS KNQFSLQLNS VTPEDTAVYY  120
CAQEVEPQDA FDIWGQGTMV TVSSGGGGSG GGGSGGGGSD IQMTQSPSSV SASVGDKVTI  180
TCRASQDVSG WLAWYQQKPG LAPQLLIFGA STLQGEVPSR FSGSGSGTDF TLTISSLQPE  240
DFATYYCQQA KYFPYTFGRG TKLEIKAAAT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYQQGQNQL YNELNLGRRE EYDVLDKRRG  420
```

```
RDPEMGGKPR RKNPQEGLYN ELQKDKMAEA YSEIGMKGER RRGKGHDGLY QGLSTATKDT  480
YDALHMQALP PR                                                      492

SEQ ID NO: 69           moltype = DNA  length = 1476
FEATURE                 Location/Qualifiers
source                  1..1476
                        mol_type = other DNA
                        organism = Synthetic construct
SEQUENCE: 69
atgttgctgc tcgtgacctc gctccttctg tgcgagctgc cccatccggc ttttctgctc  60
atccctcaag tgcagctgca gcagtccggt cctggactgg tcaagccgtc ccagactctg  120
agcctgactt gcgccattag cgggaactca gtctcgtcca attcggcggc ctggaactgg  180
atccggcagt caccatcaag ggcctggaa tggctcgggc gcacttacta ccggtccaaa  240
tggtataacg actacgccgt gtccgtgaag tcccggatca ccattaaccc cgacacctcg  300
aagaaccagt tctcactcca actgaacagc gtgacccccg aggataccgc ggtgtactac  360
tgcgcacaag aagtggaacc gcaggacgcc ttcgacattt ggggacaggg aacgatggtc  420
acagtgtcgt ccggtggagg aggttccgga ggcggtggat ctggaggcgg aggttcggat  480
atccagatga cccagagccc ctcctcggtg tccgcatccg tgggcgataa ggtcaccatt  540
acctgtagag cgtcccagga cgtgtccgga tggctggcct ggtaccagca gaagccaggc  600
ttggctcctc aactgctgat ctttggcgcc agcactcttc agggggaggt gccatcacgc  660
ttctccggag gtggttccgg caccgacttc accctgacca tcagcagcct ccagcctgag  720
gacttcgcca cttactactg ccaacaggcc aagtacttcc cctatacctt cggacaaggc  780
actaagctgg aaatcaaggc ggccgcaact accacccctg cccctcggcc gccgactccg  840
gccccaacca tcgcaagcca acccctctcc ttgcgccccg aagcttgccg cccggccgcg  900
ggtggagccg tgcatacccg ggggctggac tttgcctgcg atatctacat ttgggccccg  960
ctggccggca cttgcggcgt gctcctgctg tcgctggtca tcacccttta ctgcaagagg  1020
ggccggaaga agctgcttta catcttcaag cagccgttca tgcggcccgt gcagacgact  1080
caggaagagg acggatgctc gtgcagattc cctgaggagg aagagggggg atgcgaactg  1140
cgcgtcaagt tctcacggtc cgccgacgcc cccgcatatc aacagggcca gaatcagctc  1200
tacaacgagc tgaacctggg aaggagagag gagtacgacg tgctggacaa gcgacgcgga  1260
cgcgacccgg agatgggggg gaaaccacgg cggaaaaacc ctcaggaagg actgtacaac  1320
gaactccaga aagacaagat ggcggaagcc tactcagaaa tcgggatgaa gggagagcgg  1380
aggaggggaa agggtcacga cggctgtac cagggactga gcaccgccac taaggatacc  1440
tacgatgcct tgcatatgca agcactccca ccccgg                            1476

SEQ ID NO: 70           moltype = AA  length = 492
FEATURE                 Location/Qualifiers
source                  1..492
                        mol_type = protein
                        organism = Synthetic construct
SEQUENCE: 70
MLLLVTSLLL CELPHPAFLL IPQVQLQQSG PGLVKPSQTL SLTCAISGNS VSSNSAAWNW  60
IRQSPSRGLE WLGRTYYRSK WYNDYAVSVK SRITINPDTS KNQFSLQLNS VTPEDTAVYY  120
CAQEVEPQDA FDIWGQGTMV TVSSGGGGSG GGGSGGGGSD IQMTQSPSSV SASVGDKVTI  180
TCRASQDVSG WLAWYQQKPG LAPQLLIFGA STLQGEVPSR FSGGGSGTDF TLTISSLQPE  240
DFATYYCQQA KYFPYTFGQG TKLEIKAAAT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                      492

SEQ ID NO: 71           moltype =   length =
SEQUENCE: 71
000

SEQ ID NO: 72           moltype =   length =
SEQUENCE: 72
000

SEQ ID NO: 73           moltype = DNA  length = 2280
FEATURE                 Location/Qualifiers
source                  1..2280
                        mol_type = other DNA
                        organism = Synthetic construct
SEQUENCE: 73
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct ggggggccgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaaggagg cggcggcagc ggcgggggag ggtccggagg gggtggttct  840
```

ggtggaggag gatcgggagg cggtggcagc gacattcaga tgactcagac cacctcctcc 900
ctgtccgcct ccctgggcga ccgcgtgacc atctcatgcc gcgccagcca ggacatctcg 960
aagtacctca actggtacca gcagaagccc gacggaaccg tgaagctcct gatctaccac 1020
acctcccggc tgcacagcgg agtgccgtct agattctcgg gttcggggtc gggaactgac 1080
tactccctta ctatttccaa cctggagcag gaggatattg ccacctactt ctgccaacaa 1140
ggaaacaccc tgccgtacac ttttggcggg ggaaccaagc tggaaatcac tggcagcaca 1200
tccggttccg ggaagcccgg ctccggagag ggcagcacca agggggaagt caagctgcag 1260
gaatcaggac ctggcctggt ggccccgagc cagtcactgt ccgtgacttg tactgtgtcc 1320
ggagtgtcgc tcccggatta cggagtgtcc tggatcaggc agccacctcg gaaaggattg 1380
gaatggctcg gagtcatctg gggttccgaa accacctatt acaactcggc actgaaatcc 1440
aggctcacca ttatcaagga taactccaag tcacaagtgt tcctgaagat gaatagcctg 1500
cagactgacg acacggcgat ctactattgc gccaagcact actactacgg cggatcctac 1560
gctatggact actggggcca ggggaccagc gtgaccgtgt catccgcggc cgcgactacc 1620
actcctgcac cacggccacc taccccagcc cccaccattg caagccagcc actttcactg 1680
cgccccgaag cgtgtagacc agctgctgga ggagccgtgc atacccgagg gctggacttc 1740
gcctgtgaca tctacatctg ggccccattg gctggaactt gcggcgtgct gctcttgtct 1800
ctggtcatta ccctgtactg ccggtcgaag aggtccagac tcttgcactc cgactacatg 1860
aacatgactc ctagaaggcc cggacccact agaaagcact accagccgta cgcccctcct 1920
cgggatttcg ccgcataccg gtccagagtg aagttcagcc gctcagccga tgcaccggcc 1980
taccagcagg gacagaacca gctctacaac gagctcaacc tgggtcggcg ggaagaatat 2040
gacgtgctgg acaaacggcg cggcagagat ccggagatgg ggggaaagcc gaggaggaag 2100
aaccctcaag agggcctgta caacgaactg cagaaggaca agatggcgga agcctactcc 2160
gagatcggca tgaagggaga acgccggaga gggaagggtc atgacggact gtaccagggc 2220
ctgtcaactg ccactaagga cacttacgat gcgctccata tgcaagcttt gcccccgcgg 2280

SEQ ID NO: 74 moltype = AA length = 760
FEATURE Location/Qualifiers
source 1..760
mol_type = protein
organism = Synthetic construct
SEQUENCE: 74
MLLLVTSLLL CELPHPAFLL IPEVQLQQSG AELVKPGASV KMSCKASGYT FTSYNMHWVK 60
QTPGQGLEWI GAIYPGNGDT SYNQKFKGKA TLTADKSSST AYMQLSSLTS EDSADYYCAR 120
SNYYGSSYWF FDVWGAGTTV TVSSGGGGSG GGGSGGGGSD IVLTQSPAIL SASPGEKVTM 180
TCRASSSVNY MDWYQKKPGS SPKPWIYATS NLASGVPARF SGSGSGTSYS LTISRVEAED 240
AATYYCQQWS FNPPTFGGGT KLEIKGGGGS GGGGSGGGGS GGGGSGGGGS DIQMTQTTSS 300
LSASLGDRVT ISCRASQDIS KYLNWYQQKP DGTVKLLIYH TSRLHSGVPS RFSGSGSGTD 360
YSLTISNLEQ EDIATYFCQQ GNTLPYTFGG GTKLEITGST SGSGKPGSGE GSTKGEVKLQ 420
ESGPGLVAPS QSLSVTCTVS GVSLPDYGVS WIRQPPRKGL EWLGVIWGSE TTYYNSALKS 480
RLTIIKDNSK SQVFLKMNSL QTDDTAIYYC AKHYYYGGSY AMDYWGQGTS VTVSSAAATT 540
TPAPRPPTPA PTIASQPLSL RPEACRPAAG GAVHTRGLDF ACDIYIWAPL AGTCGVLLLS 600
LVITLYCRSK RSRLLHSDYM NMTPRRPGPT RKHYQPYAPP RDFAAYRSRV KFSRSADAPA 660
YQQGQNQLYN ELNLGRREEY DVLDKRRGRD PEMGGKPRRK NPQEGLYNEL QKDKMAEAYS 720
EIGMKGERRR GKGHDGLYQG LSTATKDTYD ALHMQALPPR 760

SEQ ID NO: 75 moltype = DNA length = 1482
FEATURE Location/Qualifiers
source 1..1482
mol_type = other DNA
organism = Synthetic construct
SEQUENCE: 75
atgcttcttt tggtgacttc ccttttgctg tgcgagttgc cacaccccgc cttcctgctt 60
attccccagg tacagctcca gcagagtggc ccagggctcg tgaagccaag ccagacgctg 120
tccctgactt gtgcaatttc aggggattca gtttcatcaa atagcgcggc gtggaattgg 180
attcgacaat ctccttcccg agggttggaa tggcttggac gaacatatta cagatccaaa 240
tggtataacg actatgcggt atcagtaaag tcaagaataa ccattaaccc cgacacaagc 300
aagaaccaat tctctttgca gcttaactct gtcacgccag aagacacggc agtctattat 360
tgcgctcgcg aggtaacggg tgacctggaa gacgcttttg acatttgggg gcagggtacg 420
atggtgacag tcagttcagg gggcggtggg agtgggggag ggggtagcgg gggggggggg 480
tcagacattc agatgaccca gtccccttca tccttgtctg cctccgtcgg tgacagggtg 540
acaataacat gcagagcaag ccaaacaatc tggagctatc tcaactggta ccagcagcga 600
ccaggaaaag cgccaaacct gctgatttac gctgcttcct ccctccaatc aggcgtgcct 660
agtagattta gcggtagggg ctccggcacc gattttacgc tcactataag ctctcttcaa 720
gcagaagatt ttgcgactta ttactgccag cagtcctata gtatacctca gactttcgga 780
cagggtacca agttggagat taaggcggcc gcaactacca cccctgcccc tcggccgccg 840
actccggccc caaccatcgc aagccaaccc ctctccttgc gccccgaagc ttgccgcccg 900
gccgcgggtg gagccgtgca tacccggggg ctggactttg cctgcgatat ctacatttgg 960
gccccgctgg ccggcacttg cggcgtgctc ctgctgtcgc tggtcatcac cctttactgc 1020
aagaggggcc ggaagaagct gctttacatc ttcaagcagc cgttcatgcg gcccgtgcag 1080
acgactcagg aagaggacgg atgctcgtgc agattccctg aggaggaaga ggggggatgc 1140
gaactgcgcg tcaagttctc acggtccgcc gacgccccg catatcaaca gggccagaat 1200
cagctctaca acgagctgaa cctgggaagg agagaggagt acgacgtgct ggacaagcga 1260
cgcggacgcg acccggagat gggggggaaa ccacggcgga aaaaccctca ggaaggactg 1320
tacaacgaac tccagaaaga caagatggcg gaagcctact cagaaatcgg gatgaaggga 1380
gagcggagga ggggaaaggg tcacgacggg ctgtaccagg gactgagcac cgccactaag 1440
gatacctacg atgccttgca tatgcaagca ctcccacccc gg 1482

SEQ ID NO: 76 moltype = AA length = 494
FEATURE Location/Qualifiers

```
source                  1..494
                        mol_type = protein
                        organism = Synthetic construct
SEQUENCE: 76
MLLLVTSLLL CELPHPAFLL IPQVQLQQSG PGLVKPSQTL SLTCAISGDS VSSNSAAWNW  60
IRQSPSRGLE WLGRTYYRSK WYNDYAVSVK SRITINPDTS KNQFSLQLNS VTPEDTAVYY  120
CAREVTGDLE DAFDIWGQGT MVTVSSGGGG SGGGGSGGGG SDIQMTQSPS SLSASVGDRV  180
TITCRASQTI WSYLNWYQQR PGKAPNLLIY AASSLQSGVP SRFSGRGSGT DFTLTISSLQ  240
AEDFATYYCQ QSYSIPQTFG QGTKLEIKAA ATTTPAPRPP TPAPTIASQP LSLRPEACRP  300
AAGGAVHTRG LDFACDIYIW APLAGTCGVL LLSLVITLYC KRGRKKLLYI FKQPFMRPVQ  360
TTQEEDGCSC RFPEEEEGGC ELRVKFSRSA DAPAYQQGQN QLYNELNLGR REEYDVLDKR  420
RGRDPEMGGK PRRKNPQEGL YNELQKDKMA EAYSEIGMKG ERRRGKGHDG LYQGLSTATK  480
DTYDALHMQA LPPR                                                   494

SEQ ID NO: 77           moltype = DNA  length = 66
FEATURE                 Location/Qualifiers
source                  1..66
                        mol_type = other DNA
                        organism = Synthetic construct
SEQUENCE: 77
atgcttcttt tggtgacttc ccttttgctg tgcgagttgc cacaccccgc cttcctgctt  60
attccc                                                            66

SEQ ID NO: 78           moltype = AA  length = 22
FEATURE                 Location/Qualifiers
source                  1..22
                        mol_type = protein
                        organism = Synthetic construct
SEQUENCE: 78
MLLLVTSLLL CELPHPAFLL IP                                          22

SEQ ID NO: 79           moltype = DNA  length = 63
FEATURE                 Location/Qualifiers
source                  1..63
                        mol_type = other DNA
                        organism = Synthetic construct
SEQUENCE: 79
atggccctgc ccgtcactgc gctgcttctt ccacttgcgc ttctgctgca cgcagcgcgc  60
ccg                                                               63

SEQ ID NO: 80           moltype = AA  length = 21
FEATURE                 Location/Qualifiers
source                  1..21
                        mol_type = protein
                        organism = Synthetic construct
SEQUENCE: 80
MALPVTALLL PLALLLHAAR P                                           21

SEQ ID NO: 81           moltype = DNA  length = 216
FEATURE                 Location/Qualifiers
source                  1..216
                        mol_type = other DNA
                        organism = Synthetic construct
SEQUENCE: 81
gcggccgcta ccacaacccc tgcgccccgg cctcctaccc ccgcacccac gattgcttct  60
caacctcttt cactccgacc tgaggcttgt agacctgcag ccggggggtgc cgtccacaca  120
cggggactcg acttcgcttg tgatatatat atttgggcgc ccctggccgg cacttgtgga  180
gttcttttgc tctctcttgt tatcacattg tactgc                           216

SEQ ID NO: 82           moltype = AA  length = 72
FEATURE                 Location/Qualifiers
source                  1..72
                        mol_type = protein
                        organism = Synthetic construct
SEQUENCE: 82
AAATTTPAPR PPTPAPTIAS QPLSLRPEAC RPAAGGAVHT RGLDFACDIY IWAPLAGTCG  60
VLLLSLVITL YC                                                     72

SEQ ID NO: 83           moltype = DNA  length = 126
FEATURE                 Location/Qualifiers
source                  1..126
                        mol_type = other DNA
                        organism = Synthetic construct
SEQUENCE: 83
aagcgaggta ggaagaaatt gctttacatt tttaagcagc cgttcatgcg accagtacag  60
actactcaag aagaagatgg gtgctcttgt cggttcccgg aagaagaaga gggtggttgc  120
gagttg                                                            126

SEQ ID NO: 84           moltype = AA  length = 42
```

```
FEATURE                Location/Qualifiers
source                 1..42
                       mol_type = protein
                       organism = Synthetic construct
SEQUENCE: 84
KRGRKKLLYI FKQPFMRPVQ TTQEEDGCSC RFPEEEEGGC EL                    42

SEQ ID NO: 85          moltype = DNA  length = 123
FEATURE                Location/Qualifiers
source                 1..123
                       mol_type = other DNA
                       organism = Synthetic construct
SEQUENCE: 85
cggtcgaagc gctcaagact gctgcactca gactacatga acatgactcc tcggcggccg  60
gggccgactc ggaagcacta ccagccttac gcacccccga gagatttcgc ggcctaccgc  120
tcc                                                                123

SEQ ID NO: 86          moltype = AA  length = 41
FEATURE                Location/Qualifiers
source                 1..41
                       mol_type = protein
                       organism = Synthetic construct
SEQUENCE: 86
RSKRSRLLHS DYMNMTPRRP GPTRKHYQPY APPRDFAAYR S                     41

SEQ ID NO: 87          moltype = DNA  length = 336
FEATURE                Location/Qualifiers
source                 1..336
                       mol_type = other DNA
                       organism = Synthetic construct
SEQUENCE: 87
agggtgaagt tctcccgctc tgccgacgca ccggcatatc agcagggaca aaaccagctc  60
tacaacgaat tgaacctggg tcggcgggaa gaatatgacg tgctcgataa gcggcggggt  120
cgcgacccag aaatgggagg caaaccgcgc aggaaaaatc cacaggaggg actttataac  180
gaacttcaaa aggataagat ggcagaggca tacagcgaaa tcgggatgaa aggcgagaga  240
agaagggggga aagggcacga tggtctttac caggggcttt ctaccgcgac gaaggatacc  300
tacgatgctc tccatatgca agcacttcct cctaga                            336

SEQ ID NO: 88          moltype = AA  length = 112
FEATURE                Location/Qualifiers
source                 1..112
                       mol_type = protein
                       organism = Synthetic construct
SEQUENCE: 88
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 89          moltype = DNA  length = 91
FEATURE                Location/Qualifiers
source                 1..91
                       mol_type = other DNA
                       organism = Synthetic construct
SEQUENCE: 89
cgggcaaagc ggggctcagg ggcgactaac ttttcactgt tgaagcaggc cggggatgtg  60
gaggagaatc ctggtcctag agctaagcga g                                 91

SEQ ID NO: 90          moltype = AA  length = 30
FEATURE                Location/Qualifiers
source                 1..30
                       mol_type = protein
                       organism = Synthetic construct
SEQUENCE: 90
RAKRGSGATN FSLLKQAGDV EENPGPRAKR                                  30

SEQ ID NO: 91          moltype =   length =
SEQUENCE: 91
000

SEQ ID NO: 92          moltype =   length =
SEQUENCE: 92
000

SEQ ID NO: 93          moltype =   length =
SEQUENCE: 93
000

SEQ ID NO: 94          moltype =   length =
SEQUENCE: 94
000
```

```
SEQ ID NO: 95          moltype = DNA  length = 366
FEATURE                Location/Qualifiers
source                 1..366
                       mol_type = other DNA
                       organism = Synthetic construct
SEQUENCE: 95
caggtacagc ttcaacagag tgggccggga ctggtgaaac actcccaaac actttctctg  60
acgtgcgcta tatcaggtga ctctgtttca tctaattctg ctgcgtggaa ctggattcga  120
caatctccca gtcgcgggtt ggaatggctg ggacgaacat attatcggtc taagtggtat  180
aacgattatg ctgtatctgt taaatctcga attacgatta atcctgacac ctccaagaac  240
cagttctccc tccagttgaa ctcagtcaca ccggaagaca ctgcggtcta ctattgcgct  300
caagaagtcg agccacatga tgcattcgac atctggggcc agggaacgat ggtcaccgtc  360
agcagt                                                             366

SEQ ID NO: 96          moltype = AA  length = 122
FEATURE                Location/Qualifiers
source                 1..122
                       mol_type = protein
                       organism = Synthetic construct
SEQUENCE: 96
QVQLQQSGPG LVKHSQTLSL TCAISGDSVS SNSAAWNWIR QSPSRGLEWL GRTYYRSKWY  60
NDYAVSVKSR ITINPDTSKN QFSLQLNSVT PEDTAVYYCA QEVEPHDAFD IWGQGTMVTV  120
SS                                                                 122

SEQ ID NO: 97          moltype = DNA  length = 321
FEATURE                Location/Qualifiers
source                 1..321
                       mol_type = other DNA
                       organism = Synthetic construct
SEQUENCE: 97
gacatacaaa tgacgcagag tccctcaagt gtgtacgcga gtgtgggga taaggtaact  60
attacgtgca gagcgtcaca ggatgttagt ggatggcttg cctggtatca gcagaagcca  120
ggccttgctc cacagctcct tatcagtggt gcttctacac ttcagggcga ggttccgagt  180
agattctctg gttctggatc tggtactgac ttcactctta caatttcttc tttgcaacca  240
gaagactttg cgacttatta ctgccaacag gccaaatact tcccttatac atttggccaa  300
ggtaccaagt tggagataaa g                                            321

SEQ ID NO: 98          moltype = AA  length = 107
FEATURE                Location/Qualifiers
source                 1..107
                       mol_type = protein
                       organism = Synthetic construct
SEQUENCE: 98
DIQMTQSPSS VYASVGDKVT ITCRASQDVS GWLAWYQQKP GLAPQLLISG ASTLQGEVPS  60
RFSGSGSGTD FTLTISSLQP EDFATYYCQQ AKYFPYTFGQ GTKLEIK                107

SEQ ID NO: 99          moltype = DNA  length = 366
FEATURE                Location/Qualifiers
source                 1..366
                       mol_type = other DNA
                       organism = Synthetic construct
SEQUENCE: 99
caagtgcagc tgcagcagtc cggtcctgga ctggtcaagc cgtcccagac tctgagcctg  60
acttgcgcaa ttagcgggga ctcagtctcg tccaattcgg cggcctggaa ctggatccgg  120
cagtcaccat caaggggcct ggaatggctc gggcgcactt actaccggtc caaatggtat  180
accgactacg ccgtgtccgt gaagaatcgg atcaccatta accccgacac ctcgaagaac  240
cagttctcac tccaactgaa cagcgtgacc cccgaggata ccgcggtgta ctactgcgca  300
caagaagtgg aaccgcagga cgccttcgac atttggggac agggaacgat ggtcacagtg  360
tcgtcc                                                             366

SEQ ID NO: 100         moltype = AA  length = 122
FEATURE                Location/Qualifiers
source                 1..122
                       mol_type = protein
                       organism = Synthetic construct
SEQUENCE: 100
QVQLQQSGPG LVKPSQTLSL TCAISGDSVS SNSAAWNWIR QSPSRGLEWL GRTYYRSKWY  60
TDYAVSVKNR ITINPDTSKN QFSLQLNSVT PEDTAVYYCA QEVEPQDAFD IWGQGTMVTV  120
SS                                                                 122

SEQ ID NO: 101         moltype = DNA  length = 321
FEATURE                Location/Qualifiers
source                 1..321
                       mol_type = other DNA
                       organism = Synthetic construct
SEQUENCE: 101
gatatccaga tgacccagag cccctcctcg gtgtccgcat ccgtgggcga taaggtcacc  60
attacctgta gagcgtccca ggacgtgtcc ggatggctgg cctggtacca gcagaagcca  120
```

```
ggcttggctc ctcaactgct gatcttcggc gccagcactc ttcaggggga agtgccatca  180
cgcttctccg gatccggttc cggcaccgac ttcaccctga ccatcagcag cctccagcct  240
gaggacttcg ccacttacta ctgccaacag gccaagtact tcccctatac cttcggaaga  300
ggcactaagc tggaaatcaa g                                            321

SEQ ID NO: 102         moltype = AA  length = 107
FEATURE                Location/Qualifiers
source                 1..107
                       mol_type = protein
                       organism = Synthetic construct
SEQUENCE: 102
DIQMTQSPSS VSASVGDKVT ITCRASQDVS GWLAWYQQKP GLAPQLLIFG ASTLQGEVPS  60
RFSGSGSGTD FTLTISSLQP EDFATYYCQQ AKYFPYTFGR GTKLEIK                107

SEQ ID NO: 103         moltype = DNA  length = 366
FEATURE                Location/Qualifiers
source                 1..366
                       mol_type = other DNA
                       organism = Synthetic construct
SEQUENCE: 103
caagtgcagc tgcagcagtc cggtcctgga ctggtcaagc cgtcccagac tctgagcctg  60
acttgcgcca ttagcgggaa ctcagtctcg tccaattcgg cggcctggaa ctggatccgg  120
cagtcaccat caaggggcct ggaatggctc gggcgcactt actaccggtc caaatggtat  180
aacgactacg ccgtgtccgt gaagtcccgg atcaccatta accccgacac ctcgaagaac  240
cagttctcac tccaactgaa cagcgtgacc cccgaggata ccgcggtgta ctactgcgca  300
caagaagtgg aaccgcagga cgccttcgac atttggggac agggaacgat ggtcacagtg  360
tcgtcc                                                             366

SEQ ID NO: 104         moltype = AA  length = 122
FEATURE                Location/Qualifiers
source                 1..122
                       mol_type = protein
                       organism = Synthetic construct
SEQUENCE: 104
QVQLQQSGPG LVKPSQTLSL TCAISGNSVS SNSAAWNWIR QSPSRGLEWL GRTYYRSKWY  60
NDYAVSVKSR ITINPDTSKN QFSLQLNSVT PEDTAVYYCA QEVEPQDAFD IWGQGTMVTV  120
SS                                                                 122

SEQ ID NO: 105         moltype = DNA  length = 321
FEATURE                Location/Qualifiers
source                 1..321
                       mol_type = other DNA
                       organism = Synthetic construct
SEQUENCE: 105
gatatccaga tgacccagag cccctcctcg gtgtccgcat ccgtgggcga taaggtcacc  60
attacctgta gagcgtccca ggacgtgtcc ggatggctgg cctggtacca gcagaagcca  120
ggcttggctc ctcaactgct gatctttggc gccagcactc ttcaggggga ggtgccatca  180
cgcttctccg gaggtggttc cggcaccgac ttcaccctga ccatcagcag cctccagcct  240
gaggacttcg ccacttacta ctgccaacag gccaagtact tcccctatac cttcggacaa  300
ggcactaagc tggaaatcaa g                                            321

SEQ ID NO: 106         moltype = AA  length = 107
FEATURE                Location/Qualifiers
source                 1..107
                       mol_type = protein
                       organism = Synthetic construct
SEQUENCE: 106
DIQMTQSPSS VSASVGDKVT ITCRASQDVS GWLAWYQQKP GLAPQLLIFG ASTLQGEVPS  60
RFSGGGSGTD FTLTISSLQP EDFATYYCQQ AKYFPYTFGQ GTKLEIK                107

SEQ ID NO: 107         moltype = AA  length = 18
FEATURE                Location/Qualifiers
source                 1..18
                       mol_type = protein
                       organism = Synthetic construct
SEQUENCE: 107
GSTSGSGKPG SGEGSTKG                                                18

SEQ ID NO: 108         moltype = AA  length = 25
FEATURE                Location/Qualifiers
source                 1..25
                       mol_type = protein
                       organism = Synthetic construct
SEQUENCE: 108
GGGGSGGGGS GGGGSGGGGS GGGGS                                        25

SEQ ID NO: 109         moltype = DNA  length = 3711
FEATURE                Location/Qualifiers
source                 1..3711
```

```
                        mol_type = other DNA
                        organism = Synthetic construct
SEQUENCE: 109
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct ggggggccgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaaggagg cggcggcagc ggcgggggag ggtccggagg gggtggttct  840
ggtggaggag gatcgggagg cggtggcagc gacattcaga tgactcagac cacctcctcc  900
ctgtccgcct ccctgggcga ccgcgtgacc atctcatgcc gcgccagcca ggacatctcg  960
aagtacctca actggtacca gcagaagccc gacggaaccg tgaagctcct gatctaccac  1020
acctcccggc tgcacagcgg agtgccgtct agattctcgg gttcggggtc gggaactgac  1080
tactccctta ctatttccaa cctggagcag gaggatattg ccacctactt ctgccaacaa  1140
ggaaacaccc tgccgtacac ttttggcggg ggaaccaagc tggaaatcac tggcagcaca  1200
tccggttccg ggaagcccgg ctccggagag ggcagcacca aggggggaagt caagctgcag  1260
gaatcaggac ctggcctggt ggccccgagc cagtcactgt ccgtgacttg tactgtgtcc  1320
ggagtgtcgc tcccggatta cggagtgtcc tggatcaggc agccacctcg gaaaggattg  1380
gaatggctcg gagtcatctg gggttccgaa accacctatt acaactcggc actgaaatcc  1440
aggctcacca ttatcaagga taactccaag tcacaagtgt tcctgaagat gaatagcctg  1500
cagactgacg acacggcgat ctactattgc gccaagcact actactacgg cggatcctac  1560
gctatggact actggggcca ggggaccagc gtgaccgtgt catccgcggc cgcaacgacc  1620
actcctgcac cacggccacc taccccagcc cccaccattg caagccagcc actttcactg  1680
cgccccgaag cgtgtagacc agctgctgga ggagccgtgc atacccgagg gctggacttc  1740
gcctgtgaca tctacatctg ggccccattg gctggaactt gcggcgtgct gctcttgtct  1800
ctggtcatta ccctgtactg ctggctgaca aaaaagaagt attcatctag tgtacatgat  1860
ccgaacggtg aatacatgtt catgcgcgcg gtgaacacgg ccaagaagag cagactgacc  1920
gacgtaaccc ttagagtgaa gtttagccgc tcagccgatg caccggccta ccagcaggga  1980
cagaaccagc tctacaacga gctcaacctg ggtcggcggg aagaatatga cgtgctggac  2040
aaacggcgcg gcagagatcc ggagatgggg ggaaagccga ggaggaagaa ccctcaagag  2100
ggcctgtaca acgaactgca gaaggacaag atggcggaag cctactccga gatcggcatg  2160
aagggagaac gccggagagg gaagggtcat gacggactgt accagggcct gtcaactgcc  2220
actaaggaca cttacgatgc gctccatatg caagctttgc ccccgcggcg cgcgaaacgc  2280
ggcagcggcg cgaccaactt tagcctgctg aaacaggcgg gcgatgtgga agaaaacccg  2340
ggcccgcgag caaagaggaa tattatggct ctgcctgtta cggcactgct ccttccgctt  2400
gcattgttgt tgcacgcagc gcggccccaa gtgcagctgc agcagtccgg tcctggactg  2460
gtcaagccgt cccagactct gagcctgact tgcgcaatta gcggggactc agtctcgtcc  2520
aattcggcgg cctggaactg gatccggcag tcaccatcaa ggggcctgga atggctcggg  2580
cgcacttact accggtccaa atggtatacc gactacgccg tgtccgtgaa gaatcggatc  2640
accattaacc ccgacacctc gaagaaccag ttctcactcc aactgaacag cgtgaccccc  2700
gaggataccg cggtgtacta ctgcgcacaa gaagtggaac cgcaggacgc cttcgacatt  2760
tggggacagg gaacgatggt cacagtgtcg tccggtggag gaggttccgg aggcggtgga  2820
tctggaggcg gaggttcgga tatccagatg acccagagcc cctcctcggt gtccgcatcc  2880
gtgggcgata aggtcaccat tacctgtaga gcgtcccagg acgtgtccgg atggctggcc  2940
tggtaccagc agaagccagg cttggctcct caactgctga tcttcggcgc cagcactctt  3000
caggggggaag tgccatcacg cttctccgga tccggttccg gcaccgactt caccctgacc  3060
atcagcagcc tccagcctga ggacttcgcc acttactact gccaacaggc caagtacttc  3120
ccctatacct tcggaagagg cactaagctg gaaatcaagg ctagcgcaac cactacgcct  3180
gctccgcggc ctccaacgcc cgcgcccacg atagctagtc agccgttgtc tctccgacca  3240
gaggcgtgta gaccggccgc tggcggagcc gtacatactc gcggactcga cttcgcttgc  3300
gacatctaca tttgggcacc cttggctggg acctgtgggg tgctgttgct gtccttggtt  3360
attacgttgt actgcagagt caaattttcc aggtccgcag atgcccccgc gtaccagcaa  3420
ggccagaacc aactttacaa cgaactgaac ctgggtcgcc gggaggaata tgatgtgctg  3480
gataaacgaa gggggaggga ccctgagatg ggagggaaac ctcgcaggaa aaacccgcag  3540
gaaggtttgt acaacgagtt gcagaaggat aagatggctg aggcttactc tgaaataggg  3600
atgaagggag agagacggag aggaaaaggc catgatggcc tttaccaggg cttaagcaca  3660
gcaacaaagg atacttacga cgctcttcac atgcaagctc tgccaccacg g           3711

SEQ ID NO: 110          moltype = AA  length = 1237
FEATURE                 Location/Qualifiers
source                  1..1237
                        mol_type = protein
                        organism = Synthetic construct
SEQUENCE: 110
MLLLVTSLLL CELPHPAFLL IPEVQLQQSG AELVKPGASV KMSCKASGYT FTSYNMHWVK  60
QTPGQGLEWI GAIYPGNGDT SYNQKFKGKA TLTADKSSST AYMQLSSLTS EDSADYYCAR  120
SNYYGSSYWF FDVWGAGTTV TVSSGGGGSG GGGSGGGGSD IVLTQSPAIL SASPGEKVTM  180
TCRASSSVNY MDWYQKKPGS SPKPWIYATS NLASGVPARF SGSGSGTSYS LTISRVEAED  240
AATYYCQQWS FNPPTFGGGT KLEIKGGGGS GGGGSGGGGS GGGGSGGGGS DIQMTQTTSS  300
LSASLGDRVT ISCRASQDIS KYLNWYQQKP DGTVKLLIYH TSRLHSGVPS RFSGSGSGTD  360
YSLTISNLEQ EDIATYFCQQ GNTLPYTFGG GTKLEITGST SGSGKPGSGE GSTKGEVKLQ  420
```

-continued

```
ESGPGLVAPS QSLSVTCTVS GVSLPDYGVS WIRQPPRKGL EWLGVIWGSE TTYYNSALKS  480
RLTIIKDNSK SQVFLKMNSL QTDDTAIYYC AKHYYYGGSY AMDYWGQGTS VTVSSAAATT  540
TPAPRPPTPA PTIASQPLSL RPEACRPAAG GAVHTRGLDF ACDIYIWAPL AGTCGVLLLS  600
LVITLYCWLT KKKYSSSVHD PNGEYMFMRA VNTAKKSRLT DVTLRVKFSR SADAPAYQQG  660
QNQLYNELNL GRREEYDVLD KRRGRDPEMG GKPRRKNPQE GLYNELQKDK MAEAYSEIGM  720
KGERRRGKGH DGLYQGLSTA TKDTYDALHM QALPPRRAKR GSGATNFSLL KQAGDVEENP  780
GPRAKRNIMA LPVTALLLPL ALLLHAARPQ VQLQQSGPGL VKPSQTLSLT CAISGDSVSS  840
NSAAWNWIRQ SPSRGLEWLG RTYYRSKWYT DYAVSVKNRI TINPDTSKNQ FSLQLNSVTP  900
EDTAVYYCAQ EVEPQDAFDI WGQGTMVTVS SGGGGSGGGG SGGGGSDIQM TQSPSSVSAS  960
VGDKVTITCR ASQDVSGWLA WYQQKPGLAP QLLIFGASTL QGEVPSRFSG SGSGTDFTLT  1020
ISSLQPEDFA TYYCQQAKYF PYTFGRGTKL EIKASATTTP APRPPTPAPT IASQPLSLRP  1080
EACRPAAGGA VHTRGLDFAC DIYIWAPLAG TCGVLLLSLV ITLYCRVKFS RSADAPAYQQ  1140
GQNQLYNELN LGRREEYDVL DKRRGRDPEM GGKPRRKNPQ EGLYNELQKD KMAEAYSEIG  1200
MKGERRRGKG HDGLYQGLST ATKDTYDALH MQALPPR                          1237

SEQ ID NO: 111          moltype = DNA  length = 3717
FEATURE                 Location/Qualifiers
source                  1..3717
                        mol_type = other DNA
                        organism = Synthetic construct
SEQUENCE: 111
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct gggggggcgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaaggagg cggcggcagc ggcgggggag ggtccggagg gggtggttct  840
ggtggaggag gatcgggagg cggtggcagc gacattcaga tgactcagac cacctcctcc  900
ctgtccgcct ccctgggcga ccgcgtgacc atctcatgcc gcgccagcca ggacatctcg  960
aagtacctca actggtacca gcagaagccc gacggaaccg tgaagctcct gatctaccac  1020
acctccccggc tgcacagcgg agtgccgtct agattctcgg gttcggggtc gggaactgac  1080
tactccctta ctatttccaa cctggagcag gaggatattg ccacctactt ctgccaacaa  1140
ggaaacaccc tgccgtacac ttttggcggg ggaaccaagc tggaaatcac tggcagcaca  1200
tccggttccg ggaagcccgg ctccggagag ggcagcacca agggggaagt caagctgcag  1260
gaatcaggac ctggcctggt ggccccgagc cagtcactgt ccgtgacttg tactgtgtcc  1320
ggagtgtcgc tcccggatta cggagtgtcc tggatcaggc agccacctcg gaaaggattg  1380
gaatggctcg gagtcatctg gggttccgaa accacctatt acaactcggc actgaaatcc  1440
aggctcacca ttatcaagga taactccaag tcacaagtgt tcctgaagat gaatagcctg  1500
cagactgacg acacggcgat ctactattgc gccaagcact actactacgg cggatcctac  1560
gctatggact actggggcca ggggaccagc gtgaccgtgt catccgcggc cgcaacgacc  1620
actccagcac cgagaccgcc aacccccgcg cctaccatcg caagtcaacc actttctctc  1680
aggcctgaag cgtgccgacc tgcagctggt ggggcagtac ataccagggg tttggacttc  1740
gcatgtgacg tggcggcaat tctcggcctg ggacttgtcc ttggtctgct tggtccgctc  1800
gcaatacttc tggccttgta cctgctccgc agagaccaaa gacttccgcc cgacgcccac  1860
aagcccccag gaggaggttc cttcagaacg cctatacaag aagaacaagc agatgcccac  1920
tctaccctgg ctaaaatcag ggtgaagttt agccgctcag ccgatgcacc ggcctaccag  1980
cagggacaga accagctcta caacgagctc aacctgggtc ggcgggaaga atatgacgtg  2040
ctggacaaac ggcgcggcag agatccggag atgggggggaa agccgaggag gaagaaccct  2100
caagagggcc tgtacaacga actgcagaag gacaagatgg cggaagccta ctccgagatc  2160
ggcatgaagg gagaacgccg gagagggaag ggtcatgacg gactgtacca gggcctgtca  2220
actgccacta aggacactta cgatgcgctc catatgcaag ctttgccccc gcggcgcgcg  2280
aaacgcggca gcggcgcgac caactttagc ctgctgaaac aggcgggcga tgtggaagaa  2340
aacccgggcc cgcgagcaaa gaggaatatt atggctctgc ctgttacggc actgctcctt  2400
ccgcttgcat tgttgttgca cgcagcgcgg ccccaagtgc agctgcagca gtccggtcct  2460
ggactggtca agccgtccca gactctgagc ctgacttgcg caattagcgg ggactcagtc  2520
tcgtccaatt cggcggcctg gaactggatc cggcagtcac catcaagggg cctggaatgg  2580
ctcgggcgca cttactaccg gtccaaatgg tataccgact acgccgtgtc cgtgaagaat  2640
cggatcacca ttaaccccga cacctcgaag aaccagttct cactccaact gaacagcgtg  2700
acccccgagg ataccgcggt gtactactgc gcacaagaag tggaaccgca ggacgccttc  2760
gacatttggg gacagggaac gatggtcaca gtgtcgtccg gtggaggagg ttccggaggc  2820
ggtggatctg gaggcggagg ttcggatatc cagatgaccc agagcccctc ctcggtgtcc  2880
gcatccgtgg gcgataaggt caccattacc tgtagagcgt cccaggacgt gtccggatgg  2940
ctggcctggt accagcagaa gccaggcttg gctcctcaac tgctgatctt cggcgccagc  3000
actcttcagg gggaagtgcc atcacgcttc tccggatccg gttccggcac cgacttcacc  3060
ctgaccatca gcagcctcca gcctgaggac ttcgccactt actactgcca acaggccaag  3120
tacttcccct ataccttcgg aagaggcact aagctggaaa tcaaggctag cgcaaccact  3180
acgcctgctc cgcggcctcc aacgcccgcg cccacgatag ctagtcagcc gttgtctctc  3240
cgaccagagg cgtgtagacc ggccgctggc ggagccgtac atactcgcgg actcgacttc  3300
gcttgcgaca tctacatttg ggcacccttg gctgggacct gtggggtgct gttgctgtcc  3360
ttggttatta cgttgtactg cagagtcaaa ttttccaggt ccgcagatgc cccccgcgtac  3420
cagcaaggcc agaaccaact ttacaacgaa ctgaacctgg gtcgccggga ggaatatgat  3480
```

```
gtgctggata aacgaagggg gagggaccct gagatgggag ggaaacctcg caggaaaaac  3540
ccgcaggaag gtttgtacaa cgagttgcag aaggataaga tggctgaggc ttactctgaa  3600
atagggatga agggagagag acggagagga aaaggccatg atggccttta ccagggctta  3660
agcacagcaa caaaggatac ttacgacgct cttcacatgc aagctctgcc accacgg     3717

SEQ ID NO: 112          moltype = AA  length = 1239
FEATURE                 Location/Qualifiers
source                  1..1239
                        mol_type = protein
                        organism = Synthetic construct
SEQUENCE: 112
MLLLVTSLLL CELPHPAFLL IPEVQLQQSG AELVKPGASV KMSCKASGYT FTSYNMHWVK  60
QTPGQGLEWI GAIYPGNGDT SYNQKFKGKA TLTADKSSST AYMQLSSLTS EDSADYYCAR  120
SNYYGSSYWF FDVWGAGTTV TVSSGGGGSG GGGSGGGGSD IVLTQSPAIL SASPGEKVTM  180
TCRASSSVNY MDWYQKKPGS SPKPWIYATS NLASGVPARF SGSGSGTSYS LTISRVEAED  240
AATYYCQQWS FNPPTFGGGT KLEIKGGGGS GGGGSGGGGS GGGGSGGGGS DIQMTQTTSS  300
LSASLGDRVT ISCRASQDIS KYLNWYQQKP DGTVKLLIYH TSRLHSGVPS RFSGSGSGTD  360
YSLTISNLEQ EDIATYFCQQ GNTLPYTFGG GTKLEITGST SGSGKPGSGE GSTKGEVKLQ  420
ESGPGLVAPS QSLSVTCTVS GVSLPDYGVS WIRQPPRKGL EWLGVIWGSE TTYYNSALKS  480
RLTIIKDNSK SQVFLKMNSL QTDDTAIYYC AKHYYYGGSY AMDYWGQGTS VTVSSAAATT  540
TPAPRPPTPA PTIASQPLSL RPEACRPAAG GAVHTRGLDF ACDVAAILGL GLVLGLLGPL  600
AILLALYLLR RDQRLPPDAH KPPGGGSFRT PIQEEQADAH STLAKIRVKF SRSADAPAYQ  660
QGQNQLYNEL NLGRREEYDV LDKRRGRDPE MGGKPRRKNP QEGLYNELQK DKMAEAYSEI  720
GMKGERRRGK GHDGLYQGLS TATKDTYDAL HMQALPPRRA KRGSGATNFS LLKQAGDVEE  780
NPGPRAKRNI MALPVTALLL PLALLLHAAR PQVQLQQSGP GLVKPSQTLS LTCAISGDSV  840
SSNSAAWNWI RQSPSRGLEW LGRTYYRSKW YTDYAVSVKN RITINPDTSK NQFSLQLNSV  900
TPEDTAVYYC AQEVEPQDAF DIWGQGTMVT VSSGGGGSGG GGSGGGGSDI QMTQSPSSVS  960
ASVGDKVTIT CRASQDVSGW LAWYQQKPGL APQLLIFGAS TLQGEVPSRF SGSGSGTDFT  1020
LTISSLQPED FATYYCQQAK YFPYTFGRGT KLEIKASATT TPAPRPPTPA PTIASQPLSL  1080
RPEACRPAAG GAVHTRGLDF ACDIYIWAPL AGTCGVLLLS LVITLYCRVK FSRSADAPAY  1140
QQGQNQLYNE LNLGRREEYD VLDKRRGRDP EMGGKPRRKN PQEGLYNELQ KDKMAEAYSE  1200
IGMKGERRRG KGHDGLYQGL STATKDTYDA LHMQALPPR                         1239

SEQ ID NO: 113          moltype = DNA  length = 3828
FEATURE                 Location/Qualifiers
source                  1..3828
                        mol_type = other DNA
                        organism = Synthetic construct
SEQUENCE: 113
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct gggggggccgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaaggagg cggcggcagc ggcgggggag ggtccggagg gggtggttct  840
ggtggaggag gatcgggagg cggtggcagc gacattcaga tgactcagac cacctcctcc  900
ctgtccgcct ccctgggcga ccgcgtgacc atctcatgcc gcgccagcca ggacatctcg  960
aagtacctca actggtacca gcagaagccc gacggaaccg tgaagctcct gatctaccac  1020
acctccccggc tgcacagcgg agtgccgtct agattctcgg gttcggggtc gggaactgac  1080
tactccctta ctatttccaa cctggagcag gaggatattg ccacctactt ctgccaacaa  1140
ggaaacaccc tgccgtacac ttttggcggg ggaaccaagc tggaaatcac tggcagcaca  1200
tccggttccg ggaagcccgg ctccggagag ggcagcacca agggggaagt caagctgcag  1260
gaatcaggac ctggcctggt ggccccgagc cagtcactgt ccgtgacttg tactgtgtcc  1320
ggagtgtcgc tcccggatta cggagtgtcc tggatcaggc agccacctcg gaaaggattg  1380
gaatggctcg gagtcatctg gggttccgaa accacctatt acaactcggc actgaaatcc  1440
aggctcacca ttatcaagga taactccaag tcacaagtgt tcctgaagat gaatagcctg  1500
cagactgacg acacggcgat ctactattgc gccaagcact actactacgg cggatcctac  1560
gctatggact actggggcca ggggaccagc gtgaccgtgt catccgcggc cgcaacgacc  1620
actccagcac cgagaccgcc aaccccccgcg cctaccatcg caagtcaacc actttctctc  1680
aggcctgaag cgtgccgacc tgcagctggt ggggcagtac ataccagggg tttggacttc  1740
gcatgtgacg tggcggcaat tctcggcctg ggacttgtcc ttggtctgct tggtccgctc  1800
gcaatacttc tggccttgta cctgctccgc agagaccaaa gacttccgcc cgacgcccac  1860
aagcccccag gaggaggttc cttcagaacg cctatacaag aagaacaagc agatgcccac  1920
tctaccctgg ctaaaatcag ggtgaagttt agccgctcag ccgatgcacc ggcctaccag  1980
cagggacaga accagctcta caacgagctc aacctgggtc ggcgggaaga atatgacgtg  2040
ctggacaaac ggcgcggcag agatccggag atgggggggaa agccgaggag gaagaaccct  2100
caagagggcc tgtacaacga actgcagaag gacaagatgg cggaagccta ctccgagatc  2160
ggcatgaagg gagaacgccg gagagggaag ggtcatgacg gactgtacca gggcctgtca  2220
actgccacta aggacactta cgatgcgctc catatgcaag ctttgccccc gcggcgcgcg  2280
aaacgcggca gcggcgcgac caactttagc ctgctgaaac aggcgggcga tgtggaagaa  2340
aacccgggcc cgcgagcaaa gaggaatatt atggctctgc ctgttacggc actgctcctt  2400
```

```
ccgcttgcat tgttgttgca cgcagcgcgg ccccaagtgc agctgcagca gtccggtcct  2460
ggactggtca agccgtccca gactctgagc ctgacttgcg caattagcgg ggactcagtc  2520
tcgtccaatt cggcggcctg gaactggatc cggcagtcac catcaagggg cctggaatgg  2580
ctcgggcgca cttactaccg gtccaaatgg tataccgact acgccgtgtc cgtgaagaat  2640
cggatcacca ttaaccccga cacctcgaag aaccagttct cactccaact gaacagcgtg  2700
acccccgagg ataccgcggt gtactactgc gcacaagaag tggaaccgca ggacgccttc  2760
gacatttggg gacagggaac gatggtcaca gtgtcgtccg gtggaggagg ttccggaggc  2820
ggtggatctg gaggcggagg ttcggatatc cagatgaccc agagcccctc ctcggtgtcc  2880
gcatccgtgg gcgataaggt caccattacc tgtagagcgt cccaggacgt gtccggatgg  2940
ctggcctggt accagcagaa gccaggcttg gctcctcaac tgctgatctt cggcgccagc  3000
actcttcagg gggaagtgcc atcacgcttc tccggatccg gttccggcac cgacttcacc  3060
ctgaccatca gcagcctcca gcctgaggac ttcgccactt actactgcca acaggccaag  3120
tacttcccct ataccttcgg aagaggcact aagctggaaa tcaaggctag cgcaaccact  3180
acgcctgctc cgcggcctcc aacgcccgcg cccacgatag ctagtcagcc gttgtctctc  3240
cgaccagagg cgtgtagacc ggccgctggc ggagccgtac atactcgcgg actcgacttc  3300
gcttgcgaca tctacatttg ggcacccttg gctgggacct gtggggtgct gttgctgtcc  3360
ttggttatta cgttgtactg ctggctgaca aaaaagaagt attcatctag tgtacatgat  3420
ccgaacggtg aatacatgtt catgcgcgcg gtgaacacgg ccaagaagag cagactgacc  3480
gacgtaaccc ttagagtcaa attttccagg tccgcagatg cccccgcgta ccagcaaggc  3540
cagaaccaac tttacaacga actgaacctg ggtcgccggg aggaatatga tgtgctggat  3600
aaacgaaggg ggagggaccc tgagatggga gggaaacctc gcaggaaaaa cccgcaggaa  3660
ggtttgtaca acgagttgca gaaggataag atggctgagg cttactctga aatagggatg  3720
aagggagaga gacggagagg aaaaggccat gatggccttt accagggctt gagcacagca  3780
acaaaggata cttacgacgc tcttcacatg caagctctgc caccacgg               3828
```

```
SEQ ID NO: 114          moltype = AA  length = 1276
FEATURE                 Location/Qualifiers
source                  1..1276
                        mol_type = protein
                        organism = Synthetic construct
SEQUENCE: 114
MLLLVTSLLL CELPHPAFLL IPEVQLQQSG AELVKPGASV KMSCKASGYT FTSYNMHWVK  60
QTPGQGLEWI GAIYPGNGDT SYNQKFKGKA TLTADKSSST AYMQLSSLTS EDSADYYCAR  120
SNYYGSSYWF FDVWGAGTTV TVSSGGGGSG GGGSGGGGSD IVLTQSPAIL SASPGEKVTM  180
TCRASSSVNY MDWYQKKPGS SPKPWIYATS NLASGVPARF SGSGSGTSYS LTISRVEAED  240
AATYYCQQWS FNPPTFGGGT KLEIKGGGGS GGGGSGGGGS GGGGSGGGGS DIQMTQTTSS  300
LSASLGDRVT ISCRASQDIS KYLNWYQQKP DGTVKLLIYH TSRLHSGVPS RFSGSGSGTD  360
YSLTISNLEQ EDIATYFCQQ GNTLPYTFGG GTKLEITGST SGSGKPGSGE GSTKGEVKLQ  420
ESGPGLVAPS QSLSVTCTVS GVSLPDYGVS WIRQPPRKGL EWLGVIWGSE TTYYNSALKS  480
RLTIIKDNSK SQVFLKMNSL QTDDTAIYYC AKHYYYGGSY AMDYWGQGTS VTVSSAAATT  540
TPAPRPPTPA PTIASQPLSL RPEACRPAAG GAVHTRGLDF ACDVAAILGL GLVLGLLGPL  600
AILLALYLLR RDQRLPPDAH KPPGGGSFRT PIQEEQADAH STLAKIRVKF SRSADAPAYQ  660
QGQNQLYNEL NLGRREEYDV LDKRRGRDPE MGGKPRRKNP QEGLYNELQK DKMAEAYSEI  720
GMKGERRRGK GHDGLYQGLS TATKDTYDAL HMQALPPRRA KRGSGATNFS LLKQAGDVEE  780
NPGPRAKRNI MALPVTALLL PLALLLHAAR PQVQLQQSGP GLVKPSQTLS LTCAISGDSV  840
SSNSAAWNWI RQSPSRGLEW LGRTYYRSKW YTDYAVSVKN RITINPDTSK NQFSLQLNSV  900
TPEDTAVYYC AQEVEPQDAF DIWGQGTMVT VSSGGGGSGG GGSGGGGSDI QMTQSPSSVS  960
ASVGDKVTIT CRASQDVSGW LAWYQQKPGL APQLLIFGAS TLQGEVPSRF SGSGSGTDFT  1020
LTISSLQPED FATYYCQQAK YFPYTFGRGT KLEIKASATT TPAPRPPTPA PTIASQPLSL  1080
RPEACRPAAG GAVHTRGLDF ACDIYIWAPL AGTCGVLLLS LVITLYCWLT KKKYSSSVHD  1140
PNGEYMFMRA VNTAKKSRLT DVTLRVKFSR SADAPAYQQG QNQLYNELNL GRREEYDVLD  1200
KRRGRDPEMG GKPRRKNPQE GLYNELQKDK MAEAYSEIGM KGERRRGKGH DGLYQGLSTA  1260
TKDTYDALHM QALPPR                                                  1276
```

```
SEQ ID NO: 115          moltype = DNA  length = 3855
FEATURE                 Location/Qualifiers
source                  1..3855
                        mol_type = other DNA
                        organism = Synthetic construct
SEQUENCE: 115
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct gggggggccgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaaggagg cggcggcagc ggcgggggag ggtccggagg gggtggttct  840
ggtggaggag gatcgggagg cggtggcagc gacattcaga tgactcagac cacctcctcc  900
ctgtccgcct ccctgggcga ccgcgtgacc atctcatgcc gcgccagcca ggacatctcg  960
aagtacctca actggtacca gcagaagccc gacggaaccg tgaagctcct gatctaccac  1020
acctcccggc tgcacagcgg agtgccgtct agattctcgg gttcggggtc gggaactgac  1080
tactccctta ctatttccaa cctggagcag gaggatattg ccacctactt ctgccaacaa  1140
```

```
ggaaacaccc tgccgtacac ttttggcggg ggaaccaagc tggaaatcac tggcagcaca  1200
tccggttccg ggaagcccgg ctccggagag ggcagcacca agggggaagt caagctgcag  1260
gaatcaggac ctggcctggt ggccccgagc cagtcactgt ccgtgacttg tactgtgtcc  1320
ggagtgtcgc tcccggatta cggagtgtcc tggatcaggc agccacctcg gaaaggattg  1380
gaatggctcg gagtcatctg gggttccgaa accacctatt acaactcggc actgaaatcc  1440
aggctcacca ttatcaagga taactccaag tcacaagtgt tcctgaagat gaatagcctg  1500
cagactgacg acacggcgat ctactattgc gccaagcact actactacgg cggatcctac  1560
gctatggact actggggcca ggggaccagc gtgaccgtgt catccgcggc cgcgactacc  1620
actcctgcac cacggccacc taccccagcc cccaccattg caagccagcc actttcactg  1680
cgccccgaag cgtgtagacc agctgctgga ggagccgtgc atacccgagg gctggacttc  1740
gcctgtgaca tctacatctg ggccccattg gctggaactt gcggcgtgct gctcttgtct  1800
ctggtcatta ccctgtactg ccaacggcgc aaataccgct ccaataaagg cgaaagtccg  1860
gtagaacccg cagaaccttg ccactacagt tgtcccagag aagaagaggg ttctacaata  1920
cctattcaag aggactatag gaaaccagag cccgcatgta gtcccagagt gaagttcagc  1980
cgctcagccg atgcaccggc ctaccagcag ggacagaacc agctctacaa cgagctcaac  2040
ctgggtcggc gggaagaata tgacgtgctg gacaaacggc gcggcagaga tccggagatg  2100
gggggaaagc cgaggaggaa gaaccctcaa gagggcctgt acaacgaact gcagaaggac  2160
aagatggcgg aagcctactc cgagatcggc atgaagggag aacgccggag agggaagggt  2220
catgacggac tgtaccaggg cctgtcaact gccactaagg acacttacga tgcgctccat  2280
atgcaagctt tgcccccgcg gcgcgcgaaa cgcggcagcg gcgcgaccaa ctttagcctg  2340
ctgaaacagg cgggcgatgt ggaagaaaac ccgggcccgc gagcaaagag gaatattatg  2400
gctctgcctg ttacggcact gctccttccg cttgcattgt tgttgcacgc agcgcggccc  2460
caagtgcagc tgcagcagtc cggtcctgga ctggtcaagc cgtcccagac tctgagcctg  2520
acttgcgcaa ttagcgggga ctcagtctcg tccaattcgg cggcctggaa ctggatccgg  2580
cagtcaccat caaggggcct ggaatggctc gggcgcactt actaccggtc caaatggtat  2640
accgactacg ccgtgtccgt gaagaatcgg atcaccatta accccgacac ctcgaagaac  2700
cagttctcac tccaactgaa cagcgtgacc cccgaggata ccgcggtgta ctactgcgca  2760
caagaagtgg aaccgcagga cgccttcgac atttggggac agggaacgat ggtcacagtg  2820
tcgtccggtg gaggaggttc cggaggcggt ggatctggag gcggaggttc ggatatccag  2880
atgacccaga gcccctcctc ggtgtccgca tccgtgggcg ataaggtcac cattacctgt  2940
agagcgtccc aggacgtgtc cggatggctg gcctggtacc agcagaagcc aggcttggct  3000
cctcaactgc tgatcttcgg cgccagcact cttcaggggg aagtgccatc acgcttctcc  3060
ggatccggtt ccggcaccga cttcaccctg accatcagca gcctccagcc tgaggacttc  3120
gccacttact actgccaaca ggccaagtac ttcccctata ccttcggaag aggcactaag  3180
ctggaaatca aggctagcgc aaccactacg cctgctccgc ggcctccaac gcccgcgccc  3240
acgatagcta gtcagccgtt gtctctccga ccagaggcgt gtagaccggc cgctggcgga  3300
gccgtacata ctcgcggact cgacttcgct tgcgacatct acatttgggc acccttggct  3360
gggacctgtg gggtgctgtt gctgtccttg gttattacgt tgtactgctg gctgacaaaa  3420
aagaagtatt catctagtgt acatgatccg aacggtgaat acatgttcat gcgcgcggtg  3480
aacacggcca agaagagcag actgaccgac gtaaccctta gagtcaaatt ttccaggtcc  3540
gcagatgccc ccgcgtacca gcaaggccag aaccaacttt acaacgaact gaacctgggt  3600
cgccgggagg aatatgatgt gctggataaa cgaaggggga gggaccctga gatgggaggg  3660
aaacctcgca ggaaaaaccc gcaggaaggt ttgtacaacg agttgcagaa ggataagatg  3720
gctgaggctt actctgaaat agggatgaag ggagagagac ggagaggaaa aggccatgat  3780
ggcctttacc agggcttgag cacagcaaca aaggatactt acgacgctct tcacatgcaa  3840
gctctgccac cacgg                                                   3855
```

```
SEQ ID NO: 116          moltype = AA  length = 1285
FEATURE                 Location/Qualifiers
source                  1..1285
                        mol_type = protein
                        organism = Synthetic construct
SEQUENCE: 116
MLLLVTSLLL CELPHPAFLL IPEVQLQQSG AELVKPGASV KMSCKASGYT FTSYNMHWVK  60
QTPGQGLEWI GAIYPGNGDT SYNQKFKGKA TLTADKSSST AYMQLSSLTS EDSADYYCAR  120
SNYYGSSYWF FDVWGAGTTV TVSSGGGGSG GGGSGGGGSD IVLTQSPAIL SASPGEKVTM  180
TCRASSSVNY MDWYQKKPGS SPKPWIYATS NLASGVPARF SGSGSGTSYS LTISRVEAED  240
AATYYCQQWS FNPPTFGGGT KLEIKGGGGS GGGGSGGGGS GGGGSGGGGS DIQMTQTTSS  300
LSASLGDRVT ISCRASQDIS KYLNWYQQKP DGTVKLLIYH TSRLHSGVPS RFSGSGSGTD  360
YSLTISNLEQ EDIATYFCQQ GNTLPYTFGG GTKLEITGST SGSGKPGSGE GSTKGEVKLQ  420
ESGPGLVAPS QSLSVTCTVS GVSLPDYGVS WIRQPPRKGL EWLGVIWGSE TTYYNSALKS  480
RLTIIKDNSK SQVFLKMNSL QTDDTAIYYC AKHYYYGGSY AMDYWGQGTS VTVSSAAATT  540
TPAPRPPTPA PTIASQPLSL RPEACRPAAG GAVHTRGLDF ACDIYIWAPL AGTCGVLLLS  600
LVITLYCQRR KYRSNKGESP VEPAEPCHYS CPREEEGSTI PIQEDYRKPE PACSPRVKFS  660
RSADAPAYQQ GQNQLYNELN LGRREEYDVL DKRRGRDPEM GGKPRRKNPQ EGLYNELQKD  720
KMAEAYSEIG MKGERRRGKG HDGLYQGLST ATKDTYDALH MQALPPRRAK RGSGATNFSL  780
LKQAGDVEEN PGPRAKRNIM ALPVTALLLP LALLLHAARP QVQLQQSGPG LVKPSQTLSL  840
TCAISGDSVS SNSAAWNWIR QSPSRGLEWL GRTYYRSKWY TDYAVSVKNR ITINPDTSKN  900
QFSLQLNSVT PEDTAVYYCA QEVEPQDAFD IWGQGTMVTV SSGGGGSGGG GSGGGGSDIQ  960
MTQSPSSVSA SVGDKVTITC RASQDVSGWL AWYQQKPGLA PQLLIFGAST LQGEVPSRFS  1020
GSGSGTDFTL TISSLQPEDF ATYYCQQAKY FPYTFGRGTK LEIKASATTT PAPRPPTPAP  1080
TIASQPLSLR PEACRPAAGG AVHTRGLDFA CDIYIWAPLA GTCGVLLLSL VITLYCWLTK  1140
KKYSSSVHDP NGEYMFMRAV NTAKKSRLTD VTLRVKFSRS ADAPAYQQGQ NQLYNELNLG  1200
RREEYDVLDK RRGRDPEMGG KPRRKNPQEG LYNELQKDKM AEAYSEIGMK GERRRGKGHD  1260
GLYQGLSTAT KDTYDALHMQ ALPPR                                        1285
```

```
SEQ ID NO: 117          moltype = DNA  length = 2268
FEATURE                 Location/Qualifiers
source                  1..2268
```

```
                         mol_type = other DNA
                         organism = Synthetic construct
SEQUENCE: 117
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct ggggggccgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaaggagg cggcggcagc ggcgggggag ggtccggagg gggtggttct  840
ggtggaggag gatcgggagg cggtggcagc gacattcaga tgactcagac cacctcctcc  900
ctgtccgcct ccctgggcga ccgcgtgacc atctcatgcc gcgccagcca ggacatctcg  960
aagtacctca actggtacca gcagaagccc gacggaaccg tgaagctcct gatctaccac  1020
acctcccggc tgcacagcgg agtgccgtct agattctcgg gttcggggtc gggaactgac  1080
tactccctta ctatttccaa cctggagcag gaggatattg ccacctactt ctgccaacaa  1140
ggaaacaccc tgccgtacac ttttggcggg ggaaccaagc tggaaatcac tggcagcaca  1200
tccggttccg ggaagcccgg ctccggagag ggcagcacca agggggaagt caagctgcag  1260
gaatcaggac ctggcctggt ggccccgagc cagtcactgt ccgtgacttg tactgtgtcc  1320
ggagtgtcgc tcccggatta cggagtgtcc tggatcaggc agccacctcg gaaaggattg  1380
gaatggctcg gagtcatctg ggttccgaa accacctatt acaactcggc actgaaatcc  1440
aggctcacca ttatcaagga taactccaag tcacaagtgt tcctgaagat gaatagcctg  1500
cagactgacg acacggcgat ctactattgc gccaagcact actactacgg cggatcctac  1560
gctatggact actggggcca ggggaccagc gtgaccgtgt catccgcggc cgcgactacc  1620
actcctgcac cacggccacc taccccagcc cccaccattg caagccagcc actttcactg  1680
cgccccgaag cgtgtagacc agctgctgga ggagccgtgc atacccgagg gctggacttc  1740
gcctgtgaca tctacatctg ggccccattg gctggaactt gcggcgtgct gctcttgtct  1800
ctggtcatta ccctgtactg ctggctgaca aaaaagaagt attcatctag tgtacatgat  1860
ccgaacggtg aatacatgtt catgcgcgcg gtgaacacgg ccaagaagag cagactgacc  1920
gacgtaaccc ttagagtgaa gttcagccgc tcagccgatg caccggccta ccagcaggga  1980
cagaaccagc tctacaacga gctcaacctg ggtcggcggg aagaatatga cgtgctggac  2040
aaacggcgcg gcagagatcc ggagatgggg ggaaagccga ggaggaagaa ccctcaagag  2100
ggcctgtaca acgaactgca gaaggacaag atggcggaag cctactccga gatcggcatg  2160
aagggagaac gccggagagg gaagggtcat gacggactgt accagggcct gtcaactgcc  2220
actaaggaca cttacgatgc gctccatatg caagctttgc cccgcgg                2268

SEQ ID NO: 118           moltype = AA  length = 756
FEATURE                  Location/Qualifiers
source                   1..756
                         mol_type = protein
                         organism = Synthetic construct
SEQUENCE: 118
MLLLVTSLLL CELPHPAFLL IPEVQLQQSG AELVKPGASV KMSCKASGYT FTSYNMHWVK  60
QTPGQGLEWI GAIYPGNGDT SYNQKFKGKA TLTADKSSST AYMQLSSLTS EDSADYYCAR  120
SNYYGSSYWF FDVWGAGTTV TVSSGGGGSG GGGSGGGGSD IVLTQSPAIL SASPGEKVTM  180
TCRASSSVNY MDWYQKKPGS SPKPWIYATS NLASGVPARF SGSGSGTSYS LTISRVEAED  240
AATYYCQQWS FNPPTFGGGT KLEIKGGGGS GGGGSGGGGS GGGGSGGGGS DIQMTQTTSS  300
LSASLGDRVT ISCRASQDIS KYLNWYQQKP DGTVKLLIYH TSRLHSGVPS RFSGSGSGTD  360
YSLTISNLEQ EDIATYFCQQ GNTLPYTFGG GTKLEITGST SGSGKPGSGE GSTKGEVKLQ  420
ESGPGLVAPS QSLSVTCTVS GVSLPDYGVS WIRQPPRKGL EWLGVIWGSE TTYYNSALKS  480
RLTIIKDNSK SQVFLKMNSL QTDDTAIYYC AKHYYYGGSY AMDYWGQGTS VTVSSAAATT  540
TPAPRPPTPA PTIASQPLSL RPEACRPAAG GAVHTRGLDF ACDIYIWAPL AGTCGVLLLS  600
LVITLYCWLT KKKYSSSVHD PNGEYMFMRA VNTAKKSRLT DVTLRVKFSR SADAPAYQQG  660
QNQLYNELNL GRREEYDVLD KRRGRDPEMG GKPRRKNPQE GLYNELQKDK MAEAYSEIGM  720
KGERRRGKGH DGLYQGLSTA TKDTYDALHM QALPPR                            756

SEQ ID NO: 119           moltype = DNA  length = 1461
FEATURE                  Location/Qualifiers
source                   1..1461
                         mol_type = other DNA
                         organism = Synthetic construct
SEQUENCE: 119
atgttgctgc tcgtgacctc gctccttctg tgcgagctgc cccatccggc ttttctgctc  60
atccctcaag tgcagctgca gcagtccggt cctggactgg tcaagccgtc ccagactctg  120
agcctgactt gcgcaattag cggggactca gtctcgtcca attcggcggc ctggaactgg  180
atccggcagt caccatcaag gggcctggaa tggctcgggc gcacttacta ccggtccaaa  240
tggtataccg actacgccgt gtccgtgaag aatcggatca ccattaaccc cgacacctcg  300
aagaaccagt tctcactcca actgaacagc gtgacccccg aggataccgc ggtgtactac  360
tgcgcacaag aagtggaacc gcaggacgcc ttcgacattt ggggacaggg aacgatggtc  420
acagtgtcgt ccggtggagg aggttccgga ggcggtggat ctggaggcgg aggttcggat  480
atccagatga cccagagccc ctcctcggtg tccgcatccg tgggcgataa ggtcaccatt  540
acctgtagag cgtcccagga cgtgtccgga tggctggcct ggtaccagca gaagccaggc  600
ttggctcctc aactgctgat cttcggcgcc agcactcttc agggggaagt gccatcacgc  660
```

```
ttctccggat ccggttccgg caccgacttc accctgacca tcagcagcct ccagcctgag  720
gacttcgcca cttactactg ccaacaggcc aagtacttcc cctatacctt cggaagaggc  780
actaagctgg aaatcaaggc ggccgcgact accactcctg caccacggcc acctacccca  840
gcccccacca ttgcaagcca gccactttca ctgcgccccg aagcgtgtag accagctgct  900
ggaggagccg tgcatacccg agggctggac ttcgcctgtg acatctacat ctgggcccca  960
ttggctggaa cttgcggcgt gctgctcttg tctctggtca ttaccctgta ctgctggctg  1020
acaaaaaaga agtattcatc tagtgtacat gatccgaacg gtgaatacat gttcatgcgc  1080
gcggtgaaca cggccaagaa gagcagactg accgacgtaa cccttagagt gaagttcagc  1140
cgctcagccg atgcaccggc ctaccagcag ggacagaacc agctctacaa cgagctcaac  1200
ctgggtcggc gggaagaata tgacgtgctg gacaaacggc gcggcagaga tccggagatg  1260
gggggaaagc cgaggaggaa gaaccctcaa gagggcctgt acaacgaact gcagaaggac  1320
aagatggcgg aagcctactc cgagatcggc atgaagggag aacgccggag agggaagggt  1380
catgacggac tgtaccaggg cctgtcaact gccactaagg acacttacga tgcgctccat  1440
atgcaagctt tgcccccgcg g                                            1461
```

```
SEQ ID NO: 120          moltype = AA  length = 487
FEATURE                 Location/Qualifiers
source                  1..487
                        mol_type = protein
                        organism = Synthetic construct
SEQUENCE: 120
MLLLVTSLLL CELPHPAFLL IPQVQLQQSG PGLVKPSQTL SLTCAISGDS VSSNSAAWNW  60
IRQSPSRGLE WLGRTYYRSK WYTDYAVSVK NRITINPDTS KNQFSLQLNS VTPEDTAVYY  120
CAQEVEPQDA FDIWGQGTMV TVSSGGGGSG GGGSGGGGSD IQMTQSPSSV SASVGDKVTI  180
TCRASQDVSG WLAWYQQKPG LAPQLLIFGA STLQGEVPSR FSGSGSGTDF TLTISSLQPE  240
DFATYYCQQA KYFPYTFGRG TKLEIKAAAT TTPAPRPPTP APTIASQPLS LRPEACRPAA  300
GGAVHTRGLD FACDIYIWAP LAGTCGVLLL SLVITLYCWL TKKKYSSSVH DPNGEYMFMR  360
AVNTAKKSRL TDVTLRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
MQALPPR                                                            487
```

```
SEQ ID NO: 121          moltype = DNA  length = 2274
FEATURE                 Location/Qualifiers
source                  1..2274
                        mol_type = other DNA
                        organism = Synthetic construct
SEQUENCE: 121
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct gggggggcgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaaggagg cggcggcagc ggcgggggag ggtccggagg gggtggttct  840
ggtggaggag gatcgggagg cggtggcagc gacattcaga tgactcagac cacctcctcc  900
ctgtccgcct ccctgggcga ccgcgtgacc atctcatgcc gcgccagcca ggacatctcg  960
aagtacctca actggtacca gcagaagccc gacggaaccg tgaagctcct gatctaccac  1020
acctcccggc tgcacagcgg agtgccgtct agattctcgg gttcggggtc gggaactgac  1080
tactccctta ctatttccaa cctggagcag gaggatattg ccacctactt ctgccaacaa  1140
ggaaacaccc tgccgtacac ttttggcggg ggaaccaagc tggaaatcac tggcagcaca  1200
tccggttccg ggaagcccgg ctccggagag ggcagcacca agggggaagt caagctgcag  1260
gaatcaggac ctggcctggt ggccccgagc cagtcactgt ccgtgacttg tactgtgtcc  1320
ggagtgtcgc tcccggatta cggagtgtcc tggatcaggc agccacctcg gaaaggattg  1380
gaatggctcg gagtcatctg gggttccgaa accacctatt acaactcggc actgaaatcc  1440
aggctcacca ttatcaagga taactccaag tcacaagtgt tcctgaagat gaatagcctg  1500
cagactgacg acacggcgat ctactattgc gccaagcact actactacgg cggatcctac  1560
gctatggact actggggcca ggggaccagc gtgaccgtgt catccgcggc cgcaacgacc  1620
actccagcac cgagaccgcc aacccccgcg cctaccatcg caagtcaacc actttctctc  1680
aggcctgaag cgtgccgacc tgcagctggt ggggcagtac ataccagggg tttggacttc  1740
gcatgtgacg tggcggcaat tctcggcctg ggacttgtcc ttggtctgct tggtccgctc  1800
gcaatacttc tggccttgta cctgctccgc agagaccaaa gacttccgcc cgacgcccac  1860
aagcccccag gaggaggttc cttcagaacg cctatacaag aagaacaagc agatgcccac  1920
tctaccctgg ctaaaatcag ggtgaagttt agccggtcag ctgatgcacc tgcatatcag  1980
cagggacaga accagctgta caatgagctg aacctcggac gaagagagga gtacgacgtg  2040
ttggacaaaa gacgaggtag agaccccgag atgggcggca agccgagaag aaaaaaccca  2100
caagaagggc tttataatga gcttcagaaa gataagatgg cagaggccta cagtgagatt  2160
ggcatgaagg gcgaaagaag gaggggcaaa ggacacgacg gtctctacca aggcctcagc  2220
acggctacca aagatacgta tgacgcattg catatgcagg cattgccgcc ccgc        2274
```

```
SEQ ID NO: 122          moltype = AA  length = 758
FEATURE                 Location/Qualifiers
source                  1..758
```

```
                         mol_type = protein
                         organism = Synthetic construct
SEQUENCE: 122
MLLLVTSLLL CELPHPAFLL IPEVQLQQSG AELVKPGASV KMSCKASGYT FTSYNMHWVK  60
QTPGQGLEWI GAIYPGNGDT SYNQKFKGKA TLTADKSSST AYMQLSSLTS EDSADYYCAR  120
SNYYGSSYWF FDVWGAGTTV TVSSGGGGSG GGGSGGGGSD IVLTQSPAIL SASPGEKVTM  180
TCRASSSVNY MDWYQKKPGS SPKPWIYATS NLASGVPARF SGSGSGTSYS LTISRVEAED  240
AATYYCQQWS FNPPTFGGGT KLEIKGGGGS GGGGSGGGGS GGGGSGGGGS DIQMTQTTSS  300
LSASLGDRVT ISCRASQDIS KYLNWYQQKP DGTVKLLIYH TSRLHSGVPS RFSGSGSGTD  360
YSLTISNLEQ EDIATYFCQQ GNTLPYTFGG GTKLEITGST SGSGKPGSGE GSTKGEVKLQ  420
ESGPGLVAPS QSLSVTCTVS GVSLPDYGVS WIRQPPRKGL EWLGVIWGSE TTYYNSALKS  480
RLTIIKDNSK SQVFLKMNSL QTDDTAIYYC AKHYYYGGSY AMDYWGQGTS VTVSSAAATT  540
TPAPRPPTPA PTIASQPLSL RPEACRPAAG GAVHTRGLDF ACDVAAILGL GLVLGLLGPL  600
AILLALYLLR RDQRLPPDAH KPPGGGSFRT PIQEEQADAH STLAKIRVKF SRSADAPAYQ  660
QGQNQLYNEL NLGRREEYDV LDKRRGRDPE MGGKPRRKNP QEGLYNELQK DKMAEAYSEI  720
GMKGERRRGK GHDGLYQGLS TATKDTYDAL HMQALPPR                         758

SEQ ID NO: 123           moltype = DNA  length = 2301
FEATURE                  Location/Qualifiers
source                   1..2301
                         mol_type = other DNA
                         organism = Synthetic construct
SEQUENCE: 123
atgctccttc tcgtgacctc cctgcttctc tgcgaactgc cccatcctgc cttcctgctg  60
attcccgagg tgcagttgca acagtcagga gctgaactgg tcaagccagg agccagcgtg  120
aagatgagct gcaaggcctc cggttacacc ttcacctcct acaacatgca ctgggtgaaa  180
cagaccccgg gacaagggct cgaatggatt ggcgccatct accccgggaa tggcgatact  240
tcgtacaacc agaagttcaa gggaaaggcc accctgaccg ccgacaagag ctcctccacc  300
gcgtatatgc agttgagctc cctgacctcc gaggactccg ccgactacta ctgcgcacgg  360
tccaactact atggaagctc gtactggttc ttcgatgtct gggggcccgg caccactgtg  420
accgtcagct ccgggggcgg aggatccggt ggaggcggaa gcgggggtgg aggatccgac  480
attgtgctga ctcagtcccc ggcaatcctg tcggcctcac cgggcgaaaa ggtcacgatg  540
acttgtagag cgtcgtccag cgtgaactac atggattggt accaaaagaa gcctggatcg  600
tcacccaagc cttggatcta cgctacatct aacctggcct ccggcgtgcc agcgcggttc  660
agcgggtccg gctcgggcac ctcatactcg ctgaccatct cccgcgtgga ggctgaggac  720
gccgcgacct actactgcca gcagtggtcc ttcaacccgc cgacttttgg aggcggtact  780
aagctggaga tcaaaggagg cggcggcagc ggcgggggag ggtccggagg gggtggttct  840
ggtggaggag gatcgggagg cggtggcagc gacattcaga tgactcagac cacctcctcc  900
ctgtccgcct ccctgggcga ccgcgtgacc atctcatgcc gcgccagcca ggacatctcg  960
aagtacctca actggtacca gcagaagccc gacggaaccg tgaagctcct gatctaccac  1020
acctcccggc tgcacagcgg agtgccgtct agattctcgg gttcggggtc gggaactgac  1080
tactccctta ctatttccaa cctggagcag gaggatattg ccacctactt ctgccaacaa  1140
ggaaacaccc tgccgtacac ttttggcggg ggaaccaagc tggaaatcac tggcagcaca  1200
tccggttccg ggaagcccgg ctccggagag ggcagcacca agggggaagt caagctgcag  1260
gaatcaggac ctggcctggt ggccccgagc cagtcactgt ccgtgacttg tactgtgtcc  1320
ggagtgtcgc tcccggatta cggagtgtcc tggatcaggc agccacctcg gaaaggattg  1380
gaatggctcg gagtcatctg gggttccgaa accacctatt acaactcggc actgaaatcc  1440
aggctcacca ttatcaagga taactccaag tcacaagtgt tcctgaagat gaatagcctg  1500
cagactgacg acacggcgat ctactattgc gccaagcact actactacgg cggatcctac  1560
gctatggact actggggcca ggggaccagc gtgaccgtgt catccgcggc cgcgactacc  1620
actcctgcac cacggccacc taccccagcc cccaccattg caagccagcc actttcactg  1680
cgccccgaag cgtgtagacc agctgctgga ggagccgtgc atacccgagg gctggacttc  1740
gcctgtgaca tctacatctg ggccccattg gctggaactt gcggcgtgct gctcttgtct  1800
ctggtcatta ccctgtactg ccaacggcgc aaataccgct ccaataaagg cgaaagtccg  1860
gtagaacccg cagaaccttg ccactacagt tgtcccagag aagaagaggg ttctacaata  1920
cctattcaag aggactatag gaaaccagag cccgcatgta gtcccagagt gaagttcagc  1980
cgctcagccg atgcaccggc ctaccagcag ggacagaacc agctctacaa cgagctcaac  2040
ctgggtcggc gggaagaata tgacgtgctg gacaaacggc gcggcagaga tccggagatg  2100
gggggaaagc cgaggaggaa gaaccctcaa gagggcctgt acaacgaact gcagaaggac  2160
aagatggcgg aagcctactc cgagatcggc atgaagggag aacgccggag agggaagggt  2220
catgacggac tgtaccaggg cctgtcaact gccactaagg acacttacga tgcgctccat  2280
atgcaagctt tgcccccgcg g                                           2301

SEQ ID NO: 124           moltype = AA  length = 767
FEATURE                  Location/Qualifiers
source                   1..767
                         mol_type = protein
                         organism = Synthetic construct
SEQUENCE: 124
MLLLVTSLLL CELPHPAFLL IPEVQLQQSG AELVKPGASV KMSCKASGYT FTSYNMHWVK  60
QTPGQGLEWI GAIYPGNGDT SYNQKFKGKA TLTADKSSST AYMQLSSLTS EDSADYYCAR  120
SNYYGSSYWF FDVWGAGTTV TVSSGGGGSG GGGSGGGGSD IVLTQSPAIL SASPGEKVTM  180
TCRASSSVNY MDWYQKKPGS SPKPWIYATS NLASGVPARF SGSGSGTSYS LTISRVEAED  240
AATYYCQQWS FNPPTFGGGT KLEIKGGGGS GGGGSGGGGS GGGGSGGGGS DIQMTQTTSS  300
LSASLGDRVT ISCRASQDIS KYLNWYQQKP DGTVKLLIYH TSRLHSGVPS RFSGSGSGTD  360
YSLTISNLEQ EDIATYFCQQ GNTLPYTFGG GTKLEITGST SGSGKPGSGE GSTKGEVKLQ  420
ESGPGLVAPS QSLSVTCTVS GVSLPDYGVS WIRQPPRKGL EWLGVIWGSE TTYYNSALKS  480
RLTIIKDNSK SQVFLKMNSL QTDDTAIYYC AKHYYYGGSY AMDYWGQGTS VTVSSAAATT  540
TPAPRPPTPA PTIASQPLSL RPEACRPAAG GAVHTRGLDF ACDIYIWAPL AGTCGVLLLS  600
```

```
LVITLYCQRR KYRSNKGESP VEPAEPCHYS CPREEEGSTI PIQEDYRKPE PACSPRVKFS  660
RSADAPAYQQ GQNQLYNELN LGRREEYDVL DKRRGRDPEM GGKPRRKNPQ EGLYNELQKD  720
KMAEAYSEIG MKGERRRGKG HDGLYQGLST ATKDTYDALH MQALPPR                767

SEQ ID NO: 125         moltype = DNA  length = 1350
FEATURE                Location/Qualifiers
source                 1..1350
                       mol_type = other DNA
                       organism = Synthetic construct
SEQUENCE: 125
atgttgctgc tcgtgacctc gctccttctg tgcgagctgc cccatccggc ttttctgctc  60
atccctcaag tgcagctgca gcagtccggt cctggactgg tcaagccgtc ccagactctg  120
agcctgactt gcgcaattag cggggactca gtctcgtcca attcggcggc ctggaactgg  180
atccggcagt caccatcaag gggcctggaa tggctcgggc gcacttacta ccggtccaaa  240
tggtataccg actacgccgt gtccgtgaag aatcggatca ccattaaccc cgacacctcg  300
aagaaccagt tctcactcca actgaacagc gtgacccccg aggataccgc ggtgtactac  360
tgcgcacaag aagtggaacc gcaggacgcc ttcgacattt ggggacaggg aacgatggtc  420
acagtgtcgt ccggtggagg aggttccgga ggcggtggat ctggaggcgg aggttcggat  480
atccagatga cccagagccc ctcctcggtg tccgcatccg tgggcgataa ggtcaccatt  540
acctgtagag cgtcccagga cgtgtccgga tggctggcct ggtaccagca gaagccaggc  600
ttggctcctc aactgctgat cttcggcgcc agcactcttc aggggggaagt gccatcacgc  660
ttctccggat ccggttccgg caccgacttc accctgacca tcagcagcct ccagcctgag  720
gacttcgcca cttactactg ccaacaggcc aagtacttcc cctatacctt cggaagaggc  780
actaagctgg aaatcaaggc ggccgcaacc actacaccag ctccgcggcc acccacccca  840
gcaccaacaa tagccagtca gcctttgtct ctgagacctg aggcttgtcg acccgctgca  900
ggtggggcag ttcatactcg gggtcttgat ttcgcctgcg atatatatat ttgggccccc  960
ctggcgggca cgtgtggggt gctccttctt tcactcgtaa ttactcttta ctgtagggtt  1020
aagttctcac gatccgccga tgcgccagca taccaacagg gacagaacca actttataat  1080
gagctgaatc ttggtcgcag ggaagaatat gatgtacttg ataaacgcag aggccgggat  1140
cccgagatgg gagggaaacc tcggagaaag aacccccagg agggcctgta taatgaattg  1200
caaaaagata aaatggctga agcttattca gagattggaa tgaaaggcga gcggagaaga  1260
ggaaaagggc acgacgggct ttaccaagga ctgtccaccg cgacaaagga cacgtacgac  1320
gcccttcata tgcaggcgct tcctccacga                                  1350

SEQ ID NO: 126         moltype = AA  length = 450
FEATURE                Location/Qualifiers
source                 1..450
                       mol_type = protein
                       organism = Synthetic construct
SEQUENCE: 126
MLLLVTSLLL CELPHPAFLL IPQVQLQQSG PGLVKPSQTL SLTCAISGDS VSSNSAAWNW  60
IRQSPSRGLE WLGRTYYRSK WYTDYAVSVK NRITINPDTS KNQFSLQLNS VTPEDTAVYY  120
CAQEVEPQDA FDIWGQGTMV TVSSGGGGSG GGGSGGGGSD IQMTQSPSSV SASVGDKVTI  180
TCRASQDVSG WLAWYQQKPG LAPQLLIFGA STLQGEVPSR FSGSGSGTDF TLTISSLQPE  240
DFATYYCQQA KYFPYTFGRG TKLEIKAAAT TTPAPRPPTP APTIASQPLS LRPEACRPAA  300
GGAVHTRGLD FACDIYIWAP LAGTCGVLLL SLVITLYCRV KFSRSADAPA YQQGQNQLYN  360
ELNLGRREEY DVLDKRRGRD PEMGGKPRRK NPQEGLYNEL QKDKMAEAYS EIGMKGERRR  420
GKGHDGLYQG LSTATKDTYD ALHMQALPPR                                  450

SEQ ID NO: 127         moltype = DNA  length = 726
FEATURE                Location/Qualifiers
source                 1..726
                       mol_type = other DNA
                       organism = Synthetic construct
SEQUENCE: 127
gaagtgcagc tggtggaaag cggcggcggc ctggtgcagc cgggcggcag cctgcgcctg  60
agctgcgcgg cgagcggctt taacattaaa gatacctata ttcattgggt gcgccaggcg  120
ccgggcaaag gcctggaatg ggtggcgcgc atttatccga ccaacggcta tacccgctat  180
gcggatagcg tgaaaggccg ctttaccatt agcgcggata ccagcaaaaa caccgcgtat  240
ctgcagatga acagcctgcg cgcggaagat accgcggtgt attattgcag ccgctggggc  300
ggcgatggct tttatgcgat ggattattgg ggccagggca ccctggtgac cgtgagcagc  360
ggcggcggcg gcagcggcgg cggcggcagc ggcggcggcg gcagcgatat tcagatgacc  420
cagagcccga gcagcctgag cgcgagcgtg ggcgatcgcg tgaccattac ctgccgcgcg  480
agccaggatg tgaacaccgc ggtggcgtgg tatcagcaga aaccgggcaa agcgccgaaa  540
ctgctgattt atagcgcgag ctttctgtat agcggcgtgc cgagccgctt tagcggcagc  600
cgcagcggca ccgattttac cctgaccatt agcagcctgc agccggaaga ttttgcgacc  660
tattattgcc agcagcatta taccaccccg ccgacctttg gccagggcac caaagtggaa  720
attaaa                                                            726

SEQ ID NO: 128         moltype = AA  length = 242
FEATURE                Location/Qualifiers
source                 1..242
                       mol_type = protein
                       organism = Synthetic construct
SEQUENCE: 128
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
GGGGSGGGGS GGGGSDIQMT QSPSSLSASV GDRVTITCRA SQDVNTAVAW YQQKPGKAPK  180
LLIYSASFLY SGVPSRFSGS RSGTDFTLTI SSLQPEDFAT YYCQQHYTTP PTFGQGTKVE  240
```

```
IK                                                          242

SEQ ID NO: 129         moltype = AA  length = 750
FEATURE                Location/Qualifiers
source                 1..750
                       mol_type = protein
                       organism = Synthetic construct
SEQUENCE: 129
ATGGAAGTGC AGCTCGTGGA GTCCGGAGGC GGAGTCGTGC AGCCGGGCAG ATCCCTGCGC  60
CTTTCCTGCT CGGCATCCGG GTTTACCTTC TCTGGCTACG GTCTGTCGTG GGTCAGACAG  120
GCTCCAGGGA AGGGCCTGGA ATGGGTGGCC ATGATCTCCT CGGGGGGTTC GTACACCTAC  180
TACGCCGACT CAGTGAAGGG CCGGTTCGCC ATCTCCCGCG ACAACGCCAA GAACACCCTG  240
TTCCTGCAAA TGGACTCGCT CCGGCCTGAG GACACTGGGG TGTACTTCTG CGCGAGACAC  300
GGAGATGACC CAGCTTGGTT CGCCTACTGG GGACAAGGCA CCCCTGTGAC CGTGTCCTCC  360
GCGAGCACCA AGGGAGGCGG AGGAGGTTCC GGTGGAGGGG GATCAGGGGG TGGAGGATCG  420
GACATTCAGC TGACCCAGAG CCCCTCAAGC CTGTCCGCGA GCGTTGGGGA CCGCGTGACC  480
ATCACCTGTT CGGTGTCCTC CTCCATCTCC TCCAACAATC TCCATTGGTA CCAGCAGAAA  540
CCGGGGAAAG CCCCCAAGCC GTGGATCTAC GGAACCTCCA ACCTGGCTAG CGGAGTGCCG  600
TCGAGGTTCT CGGGCTCCGG ATCAGGGACT GACTACACTT TCACTATTTC CTCCCTGCAA  660
CCGGAGGACA TTGCCACCTA CTACTGTCAG CAGTGGTCGT CCTACCCCTA CATGTATACC  720
TTCGGTCAAG GAACCAAGGT CGAGATCAAG                              750

SEQ ID NO: 130         moltype = AA  length = 246
FEATURE                Location/Qualifiers
source                 1..246
                       mol_type = protein
                       organism = Synthetic construct
SEQUENCE: 130
MEVQLVESGG GVVQPGRSLR LSCSASGFTF SGYGLSWVRQ APGKGLEWVA MISSGGSYTY  60
YADSVKGRFA ISRDNAKNTL FLQMDSLRPE DTGVYFCARH GDDPAWFAYW GQGTPVTVSS  120
GGGGGSGGGG SGGGGSDIQL TQSPSSLSAS VGDRVTITCS VSSSISSNNL HWYQQKPGKA  180
PKPWIYGTSN LASGVPSRFS GSGSGTDYTF TISSLQPEDI ATYYCQQWSS YPYMYTFGQG  240
TKVEIK                                                      246

SEQ ID NO: 131         moltype = DNA  length = 714
FEATURE                Location/Qualifiers
source                 1..714
                       mol_type = other DNA
                       organism = Synthetic construct
SEQUENCE: 131
gaagtacagc tcgtagagtc tgggggtggt ctcgttcaac caggtggctc tttgagactg  60
tcatgcgccg cgtctgggta cagcattaca aacgattacg catggaattg ggtgagacag  120
gctcccggaa agggcctcga atgggtagga tacatctcat atagcggtta tacaacgtac  180
aatcctagct tgaaatcaag gtttacaatc tccagggaca cgtcaaaaaa tacgctttac  240
cttcagatga actccctgcg agcagaagac acggctgtgt actactgtgc ccgatggaca  300
agtggcctcg attactgggg tcaaggtaca ctggtgacag tatcctctgg aggtggcgga  360
tcagggggcg gcggcagtgg tggaggtggt tcagatatcc agatgactca gtccccctct  420
tccctcagtg cctccgttgg tgaccgagtt actatcacgt gcaaagccag tgacttgatc  480
cataattggc tggcgtggta tcagcaaaaa cctggcaaag cacccaagct tctgatatat  540
ggtgcaacat ccctggaaac gggcgttccc agtcgctttt cagggtcagg gtcaggaact  600
gattttacgc tcaccatttc cagcctgcag cctgaagatt tcgctacata ctactgtcag  660
caatattgga ctactccatt taccttcggg caaggcacga aggttgagat aaag        714

SEQ ID NO: 132         moltype = AA  length = 238
FEATURE                Location/Qualifiers
source                 1..238
                       mol_type = protein
                       organism = Synthetic construct
SEQUENCE: 132
EVQLVESGGG LVQPGGSLRL SCAASGYSIT NDYAWNWVRQ APGKGLEWVG YISYSGYTTY  60
NPSLKSRFTI SRDTSKNTLY LQMNSLRAED TAVYYCARWT SGLDYWGQGT LVTVSSGGGG  120
SGGGGSGGGG SDIQMTQSPS SLSASVGDRV TITCKASDLI HNWLAWYQQK PGKAPKLLIY  180
GATSLETGVP SRFSGSGSGT DFTLTISSLQ PEDFATYYCQ QYWTTPFTFG QGTKVEIK    238

SEQ ID NO: 133         moltype = DNA  length = 732
FEATURE                Location/Qualifiers
source                 1..732
                       mol_type = other DNA
                       organism = Synthetic construct
SEQUENCE: 133
gaagtccagt tggttgagtc aggaggggga ctcgtgcaac ctggtggtag cttgcgcttg  60
tcatgtgctg cctccgggtt tacattctca tctttcggta tgcactgggt tagacaagca  120
cctgggaagg gcttggaatg ggttgcttac attagcagtg attctagcgc gatctactac  180
gctgacaccg taaagggcag atttaccatc agcagagata acgctaagaa ctccctctac  240
ctccagatga acagcctcag ggatgaagac actgctgttt attactgtgg gaggggccgc  300
gaaaatattt actacgggag ccgattggat tattggggtc aggggacaac agtgactgtt  360
tcaagcggtg gtgggggtc cggcggtggg ggaagcggcg gtgggggtc agatatacaa  420
ctgacacaga gccctagctt tttgagtgcg tctgtcgggg atagagttac gattacttgt  480
aaggcgagcc agaacgttga tacgaacgtg gcatggtacc agcagaagcc agggaaagct  540
```

```
ccgaaagccc ttatctattc tgctagttac cgatacagcg gcgtcccctc tcggttcagt  600
gggagtggaa gtggaacgga ctttaccctt acgatcagtt ccttgcaacc ggaggatttc  660
gccacctact actgccagca atacaataac tatcccttta cttttggcca gggcacaaag  720
cttgaaatca aa                                                      732

SEQ ID NO: 134         moltype = AA  length = 244
FEATURE                Location/Qualifiers
source                 1..244
                       mol_type = protein
                       organism = Synthetic construct
SEQUENCE: 134
EVQLVESGGG LVQPGGSLRL SCAASGFTFS SFGMHWVRQA PGKGLEWVAY ISSDSSAIYY  60
ADTVKGRFTI SRDNAKNSLY LQMNSLRDED TAVYYCGRGR ENIYYGSRLD YWGQGTTVTV  120
SSGGGGSGGG GSGGGGSDIQ LTQSPSFLSA SVGDRVTITC KASQNVDTNV AWYQQKPGKA  180
PKALIYSASY RYSGVPSRFS GSGSGTDFTL TISSLQPEDF ATYYCQQYNN YPFTFGQGTK  240
LEIK                                                               244

SEQ ID NO: 135         moltype = DNA  length = 720
FEATURE                Location/Qualifiers
source                 1..720
                       mol_type = other DNA
                       organism = Synthetic construct
SEQUENCE: 135
caagttcagt tgcagcagtc aggcgcggag ctggtgaaac caggtgcttc agtcaagttg  60
tcttgtaaag caagtggcta tacattcaca aattatgata tcaactgggt gcggcagagg  120
cccgaacagg gactggaatg gatcgggtgg atctttcctg gcgacggtag tactcaatac  180
aacgagaaat tcaagggaaa ggctactctt acaaccgaca cgtcatcatc tacagcttat  240
atgcaactta gtagactcac atcagaagac tccgctgtat acttttgtgc tcgacagacg  300
acggcaacat ggttcgccta ctgggggcaa ggaacactcg taaccgtatc tgcaggcggt  360
ggtggatctg gaggaggtgg aagcggtggt ggagggtccg acatcgttat gacgcaaagc  420
cccgcgaccc tcagtgtgac ccccggtgac agagtttcac tcagttgcag agcctctcag  480
agtatctcag attaccttca ctggtatcaa caaaaaagcc acgaaagccc cagattgctc  540
ataaagtacg cgagtcaatc aatctctggt attccctcta ggttctcagg ctcaggcagc  600
ggtagcgatt tcacattgtc tataaatagt gtggaacctg aggatgttgg cgtatattac  660
tgtcagaacg gtcactcctt cccgcttacg tttggggcgg ggacaaaatt ggaactcaag  720

SEQ ID NO: 136         moltype = AA  length = 240
FEATURE                Location/Qualifiers
source                 1..240
                       mol_type = protein
                       organism = Synthetic construct
SEQUENCE: 136
QVQLQQSGAE LVKPGASVKL SCKASGYTFT NYDINWVRQR PEQGLEWIGW IFPGDGSTQY  60
NEKFKGKATL TTDTSSSTAY MQLSRLTSED SAVYFCARQT TATWFAYWGQ GTLVTVSAGG  120
GGSGGGGSGG GGSDIVMTQS PATLSVTPGD RVSLSCRASQ SISDYLHWYQ QKSHESPRLL  180
IKYASQSISG IPSRFSGSGS GSDFTLSINS VEPEDVGVYY CQNGHSFPLT FGAGTKLELK  240

SEQ ID NO: 137         moltype = DNA  length = 723
FEATURE                Location/Qualifiers
source                 1..723
                       mol_type = other DNA
                       organism = Synthetic construct
SEQUENCE: 137
caagttcaat tgaaacagag tggtccgggt cttgttcagc caagtcagag tttgagcatc  60
acctgtactg tctccggatt tagtcttaca aattacggcg tacattgggt cagacaatcc  120
cctgggaagg gtttggaatg gctgggggtg atttggtcag gtggaaacac ggactacaat  180
actcccttta catcccgatt gtccataaac aaagataata gtaaatctca agtatttttt  240
aagatgaaca gtcttcaatc taacgataca gcgatctatt actgcgctcg cgcattgacg  300
tactatgact atgagtttgc ctattggggt caaggcacac ttgtcacagt aagcgcaggg  360
ggaggcgggt ctggaggggg cggatctggc ggtggcggaa gcgatatcct gttgactcag  420
tccccagtga tactttcagt atcaccgggc gaacgggtga gtttcagttg ccgcgcctct  480
caaagtatcg gaacgaatat acactggtac cagcagcgga caaacgggag cccgcgcttg  540
cttattaagt acgcttccga gtctatatca ggtattccat cccggttttc tggtagtgga  600
agtgggacag atttcacact gtctattaat tcagttgagt ctgaagacat cgcggattat  660
tactgccaac aaaacaataa ttggccgacg accttcggcg ctgggaccaa gcttgagctt  720
aag                                                                723

SEQ ID NO: 138         moltype = AA  length = 241
FEATURE                Location/Qualifiers
source                 1..241
                       mol_type = protein
                       organism = Synthetic construct
SEQUENCE: 138
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSNDT AIYYCARALT YYDYEFAYWG QGTLVTVSAG  120
GGGSGGGGSG GGGSDILLTQ SPVILSVSPG ERVSFSCRAS QSIGTNIHWY QQRTNGSPRL  180
LIKYASESIS GIPSRFSGSG SGTDFTLSIN SVESEDIADY YCQQNNNWPT TFGAGTKLEL  240
K                                                                  241
```

```
SEQ ID NO: 139          moltype = DNA  length = 723
FEATURE                 Location/Qualifiers
source                  1..723
                        mol_type = other DNA
                        organism = Synthetic construct
SEQUENCE: 139
gaggttcagt tgctccagtc tggacctgag ttggagaaac ccggtgctag tgtaatgatc  60
agctgcaagg catcaggttc cagtttcacc ggctataata tgaattgggt tcggcagaac  120
ataggcaaaa gtctcgagtg gataggtgcg attgacccgt actatggcgg cacttcatat  180
aaccaaaagt tcaagggtcg agctacactc actgtcgata aaagcagctc cacagcctat  240
atgcacctta agtcacttac tagcgaagat tctgccgtat attactgcgt atcaggtatg  300
gagtactggg ggcagggcac gtccgtcaca gtatcatccg gcggcggtgg tagcgggggga  360
ggaggttctg gtggtggggg gagtgaaata gtcatgactc aatcccctgc gaccctgtcc  420
gtatccccgg gagaacgcgc aactttgtcc tgtcgcagct ctcagtcttt ggttcatcgg  480
aatggtaata catacctgca ctggtatttg caaaaacccg gccagagtcc gaagctgctc  540
atccataagg tctccaatcg cttctctggg gtacctgatc ggtttagcgg gtctggatca  600
gggacggatt ttacactgaa aataagtaga gttgaggcag aggaccttgg agtctacttc  660
tgcagtcagt ccacgcacgt acctccactc acatttgggg ctgggaccaa gttggaactc  720
aaa                                                                723

SEQ ID NO: 140          moltype = AA  length = 241
FEATURE                 Location/Qualifiers
source                  1..241
                        mol_type = protein
                        organism = Synthetic construct
SEQUENCE: 140
EVQLLQSGPE LEKPGASVMI SCKASGSSFT GYNMNWVRQN IGKSLEWIGA IDPYYGGTSY  60
NQKFKGRATL TVDKSSSTAY MHLKSLTSED SAVYYCVSGM EYWGQGTSVT VSSGGGGSGG  120
GGSGGGGSEI VMTQSPATLS VSPGERATLS CRSSQSLVHR NGNTYLHWYL QKPGQSPKLL  180
IHKVSNRFSG VPDRFSGSGS GTDFTLKISR VEAEDLGVYF CSQSTHVPPL TFGAGTKLEL  240
K                                                                  241

SEQ ID NO: 141          moltype = DNA  length = 714
FEATURE                 Location/Qualifiers
source                  1..714
                        mol_type = other DNA
                        organism = Synthetic construct
SEQUENCE: 141
caagttcatt tgcaagagtc aggccctggc ctcgttaagc cctccgagac gctctctttg  60
acctgcacag tttcagatga ttccatttca tcatactact ggtcatggat tcggcagccg  120
ccagggaagg gcctcgaatg gattggacat atcagctact ccggaagtgc taactataac  180
ccatccttga aatccagagt cacaatttcc gtagacacat ctaagaacca attcagcctg  240
aaacttagtt ctgttactgc ggcggatact gcagtgtatt attgcgctaa ttgggatgac  300
gccttcaaca tctggggtca aggtacaatg gtgaccgtga gtagcggggg aggaggctca  360
ggcgggggtg gttcaggtgg tggaggctca gaaatcgtct tgacgcaaag tccaggaact  420
ttgagtttgt ctccaggaga acgcgcgacg ctttcttgcc gagcttcaca atccgtctcc  480
agctcttatt tggcttggta tcagcagaaa ccaggtcaag ctcccaggct tctgatctac  540
ggtgcgtctt cccgagccac tgggattccc gatcggttca gcgggtccgg cagcggaaca  600
gatttcactc tcaccatatc tagacttgaa ccggaggact tcgcagtgta ttactgtcag  660
cagtacggca gttcaccctg gacgtttggt cagggtacga aagttgagat caag        714

SEQ ID NO: 142          moltype = AA  length = 238
FEATURE                 Location/Qualifiers
source                  1..238
                        mol_type = protein
                        organism = Synthetic construct
SEQUENCE: 142
QVHLQESGPG LVKPSETLSL TCTVSDDSIS SYYWSWIRQP PGKGLEWIGH ISYSGSANYN  60
PSLKSRVTIS VDTSKNQFSL KLSSVTAADT AVYYCANWDD AFNIWGQGTM VTVSSGGGGS  120
GGGGSGGGGS EIVLTQSPGT LSLSPGERAT LSCRASQSVS SSYLAWYQQK PGQAPRLLIY  180
GASSRATGIP DRFSGSGSGT DFTLTISRLE PEDFAVYYCQ QYGSSPWTFG QGTKVEIK    238

SEQ ID NO: 143          moltype = DNA  length = 723
FEATURE                 Location/Qualifiers
source                  1..723
                        mol_type = other DNA
                        organism = Synthetic construct
SEQUENCE: 143
caagttcagc tgcaagaatc aggacctggg cttgtcaaac catctgaaac cctcagcttg  60
acttgtaccg tatcaggagg gtcaatttca agctcatcct actattgggg atggatcaga  120
caaccacccg ggaaagggct cgagtggata gggtccatat attacagcgg atctacatac  180
tacaacccgt cattgaagtc cagggtaacg attccggtgg acactagcaa gaatcagttt  240
agcctcaagt tgagcagtgt aactgctgcg gacacggcgg tatattattg tgctcgacac  300
ctcggtggag atgcttttga catatggggt caagggacaa cagtcaccgt tagctcaggt  360
ggagggggta gcgggggggg cggatctggg ggaggcggtt cattgcccgt acttacacag  420
ccaccctctg tcagcgtcgc acctggacaa accgctcgca tcacctgtgg cggaaataat  480
ataggttcca agtctgttca ttggtatcag cagaaaccgg gacaggcccc cgtccttgtg  540
gtgtatgatg attctgatag gccatctggt atcccagaac ggttttcagg tagcaattca  600
gggaatactg ccactctcac tattagcggt actcaagcta tggatgaggc cgactatttt  660
```

```
tgccagagct acgactctag taacccagtc gtgttcgggg gagggaccca gttgaccgtg  720
ctg                                                                723

SEQ ID NO: 144          moltype = AA  length = 241
FEATURE                 Location/Qualifiers
source                  1..241
                        mol_type = protein
                        organism = Synthetic construct
SEQUENCE: 144
QVQLQESGPG LVKPSETLSL TCTVSGGSIS SSSYYWGWIR QPPGKGLEWI GSIYYSGSTY  60
YNPSLKSRVT IPVDTSKNQF SLKLSSVTAA DTAVYYCARH LGGDAFDIWG QGTTVTVSSG  120
GGGSGGGGSG GGGSLPVLTQ PPSVSVAPGQ TARITCGGNN IGSKSVHWYQ QKPGQAPVLV  180
VYDDSDRPSG IPERFSGSNS GNTATLTISG TQAMDEADYF CQSYDSSNPV VFGGGTQLTV  240
L                                                                  241

SEQ ID NO: 145          moltype = DNA  length = 732
FEATURE                 Location/Qualifiers
source                  1..732
                        mol_type = other DNA
                        organism = Synthetic construct
SEQUENCE: 145
caggcggccc aggtacagct gcagcagtca ggggctgagg tgaagaagcc tgggtcctcg  60
gtgaaggtct cctgcaaggc ttctggaggc accttcagca gctatgctat cagctgggtg  120
cgacaggccc ctggacaagg gcttgagtgg atgggatgga tcaaccctaa cagtggtggc  180
acaaactatg cacagaggtt tcagggcagg gtcaccatga ccagggacac gtccatcagc  240
acagcctaca tggagctgag caggctgaga tctgacgaca cggccgtgta ttactgtgcg  300
agttataatg atgcttttga tatctggggc caaggcaccc tggtcaccgt ctcctcagga  360
ggtggcgggt ctggtggtgg cggtagcggt ggtggcggat ccaattttat gctgactcag  420
ccccactctg tgtcggagtc tccggggaag acggtaacca tctcctgcac ccgcagcagt  480
ggcagcattg ccagcaacta tgtgcagtgg taccagcagc gcccgggcag tgccccccacc  540
attgtgatct atgaggatga tcaaagaccc tctggggtcc ctgatcggtt ctctggctcc  600
atcgacacct cctccaactc tgcctccctc accatctctg gactgcagag tgaggacgag  660
gctgactact actgtcagtc ttatgagccc ggcaatgggg tattcggcgg agggaccaag  720
gtcaccgtcc ta                                                      732

SEQ ID NO: 146          moltype = AA  length = 244
FEATURE                 Location/Qualifiers
source                  1..244
                        mol_type = protein
                        organism = Synthetic construct
SEQUENCE: 146
QAAQVQLQQS GAEVKKPGSS VKVSCKASGG TFSSYAISWV RQAPGQGLEW MGWINPNSGG  60
TNYAQRFQGR VTMTRDTSIS TAYMELSRLR SDDTAVYYCA SYNDAFDIWG QGTLVTVSSG  120
GGGSGGGGSG GGGSNFMLTQ PHSVSESPGK TVTISCTRSS GSIASNYVQW YQQRPGSAPT  180
IVIYEDDQRP SGVPDRFSGS IDTSSNSASL TISGLQSEDE ADYYCQSYEP GNGVFGGGTK  240
VTVL                                                               244

SEQ ID NO: 147          moltype = DNA  length = 744
FEATURE                 Location/Qualifiers
source                  1..744
                        mol_type = other DNA
                        organism = Synthetic construct
SEQUENCE: 147
caagaacagc ttgtagagtc cggcggtaga ttggtgacac cgggggggag ccttaccctg  60
tcttgtaagg catctgggtt cgatttcagt gcgtattata tgagctgggt tcggcaggcg  120
cccgggaagg ggctggaatg gatagccact atatacccgt catccggcaa gacttactac  180
gcgacttggg taaacgggag gtttacgata agctcagata acgcccaaaa cacggttgat  240
ctccaaatga atagcttgac cgccgctgat agggcgacct atttctgtgc gcgggactct  300
tacgctgatg acggggccct cttcaatata tggggaccgg gaacgctcgt aaccatatca  360
tctggaggag gtgggagcgg aggcggaggg tcaggtgggg gcgggagcga actcgtactt  420
acacaatctc caagcgtaag cgcagcgttg ggagtccag caaagatcac ctgcactttg  480
tcaagcgccc acaaaacgga tacgatagat tggtatcagc aactccaagg tgaagcgcca  540
cgatatctca tgcaggtaca gagcgacggg agttatacta agaggcccgg ggtcccagac  600
agattcagtg gcagcagttc aggtgccgac agatacctga taataccctc agttcaagcc  660
gatgatgaag ccgattacta ctgtggggct gactacatag gtgggtatgt tttcgggggc  720
ggcactcaat tgacagttac aggg                                         744

SEQ ID NO: 148          moltype = AA  length = 248
FEATURE                 Location/Qualifiers
source                  1..248
                        mol_type = protein
                        organism = Synthetic construct
SEQUENCE: 148
QEQLVESGGR LVTPGGSLTL SCKASGFDFS AYYMSWVRQA PGKGLEWIAT IYPSSGKTYY  60
ATWVNGRFTI SSDNAQNTVD LQMNSLTAAD RATYFCARDS YADDGALFNI WGPGTLVTIS  120
SGGGGSGGGG SGGGGSELVL TQSPSVSAAL GSPAKITCTL SSAHKTDTID WYQQLQGEAP  180
RYLMQVQSDG SYTKRPGVPD RFSGSSSGAD RYLIIPSVQA DDEADYYCGA DYIGGYVFGG  240
GTQLTVTG                                                           248
```

```
SEQ ID NO: 149          moltype = DNA  length = 732
FEATURE                 Location/Qualifiers
source                  1..732
                        mol_type = other DNA
                        organism = Synthetic construct
SEQUENCE: 149
gaggtccagc tggtacagtc tggggggaggc ttggtacagc ctggggggtc cctgagactc  60
tcctgtgcag cctctggatt cacctttgat gattatgcca tgcactgggt ccggcaagct  120
ccagggaagg gcctggagtg ggtctcaggt attagttgga atagtggtag cataggctat  180
gcggactctg tgaagggccg attcaccatc tccagagaca acgccaagaa ctccctgtat  240
ctgcaaatga acagtctgag agctgaggac acggccttgt attactgtgc aaaagattta  300
tcgtcagtgg ctggaccctt taactactgg ggccagggca ccctggtcac cgtctcctca  360
ggaggtggcg ggtctggtgg aggcggtagc ggcggtggcg gatcctcttc tgagctgact  420
caggaccctg ctgtgtctgt ggccttggga cagacagtca ggatcacatg ccaaggagac  480
agcctcagaa gctattatgc aagctggtac cagcagaagc caggacaggc ccctgtactt  540
gtcatctatg gtaaaaacaa ccggccctca gggatcccag accgattctc tggctccagc  600
tcaggaaaca cagcttcctt gaccatcact ggggctcagg cggaggatga ggctgactat  660
tactgtaact cccgggacag cagtggtaac catctggtat tcggcggagg cacccagctg  720
accgtcctcg gt                                                      732

SEQ ID NO: 150          moltype = AA  length = 244
FEATURE                 Location/Qualifiers
source                  1..244
                        mol_type = protein
                        organism = Synthetic construct
SEQUENCE: 150
EVQLVQSGGG LVQPGGSLRL SCAASGFTFD DYAMHWVRQA PGKGLEWVSG ISWNSGSIGY  60
ADSVKGRFTI SRDNAKNSLY LQMNSLRAED TALYYCAKDL SSVAGPFNYW GQGTLVTVSS  120
GGGGSGGGGS GGGGSSSELT QDPAVSVALG QTVRITCQGD SLRSYYASWY QQKPGQAPVL  180
VIYGKNNRPS GIPDRFSGSS SGNTASLTIT GAQAEDEADY YCNSRDSSGN HLVFGGGTQL  240
TVLG                                                               244

SEQ ID NO: 151          moltype = DNA  length = 1392
FEATURE                 Location/Qualifiers
source                  1..1392
                        mol_type = other DNA
                        organism = Synthetic construct
SEQUENCE: 151
atgctgctgc tggtgaccag cctgctgctg tgcgaactgc cgcatccggc gtttctgctg  60
attccgcaag aacagcttgt agagtccggc ggtagattgg tgacaccggg ggggagcctt  120
accctgtctt gtaaggcatc tgggttcgat ttcagtgcgt attatatgag ctgggttcgg  180
caggcgcccg ggaaggggct ggaatggata gccactatat acccgtcatc cggcaagact  240
tactacgcga cttgggtaaa cggaggttt acgataagct cagataacgc ccaaaacacg  300
gttgatctcc aaatgaatag cttgaccgcc gctgataggg cgacctattt ctgtgcgcgg  360
gactcttacg ctgatgacgg ggccctcttc aatatatggg gaccgggaac gctcgtaacc  420
atatcatctg gaggaggtgg gagcggaggc ggagggtcag gtgggggcgg gagcgaactc  480
gtacttacac aatctccaag cgtaagcgca gcgttgggga gtccagcaaa gatcacctgc  540
actttgtcaa gcgcccacaa aacggatacg atagattggt atcagcaact ccaaggtgaa  600
gcgccacgat atctcatgca ggtacagagc gacgggagtt atactaagag gcccggggtc  660
ccagacagat tcagtggcag cagttcaggt gccgacagat acctgataat accctcagtt  720
caagccgatg atgaagccga ttactactgt ggggctgact acataggtgg gtatgttttc  780
gggggcggca ctcaattgac agttacaggg gcggccgcag agtcaaaata cggtcctccg  840
tgccctccgt gtccgatcta catttgggcc ccgctggccg gcacttgcgg cgtgctcctg  900
ctgtcgctgg tcatcaccct ttactgcaag aggggccgga agaagctgct ttacatcttc  960
aagcagccgt tcatgcggcc cgtgcagacg actcaggaag aggacggatg ctcgtgcaga  1020
ttccctgagg aggaagaggg gggatgcgaa ctgcgcgtca agttctcacg gtccgccgac  1080
gcccccgcat atcaacaggg ccagaatcag ctctacaacg agctgaacct gggaaggaga  1140
gaggagtacg acgtgctgga caagcgacgc ggacgcgacc cggagatggg ggggaaacca  1200
cggcggaaaa accctcagga aggactgtac aacgaactcc agaaagacaa gatggcggaa  1260
gcctactcag aaatcgggat gaagggagag cggaggaggg gaaagggtca cgacgggctg  1320
taccagggac tgagcaccgc cactaaggat acctacgatg ccttgcatat gcaagcactc  1380
ccaccccggt ag                                                      1392

SEQ ID NO: 152          moltype = AA  length = 463
FEATURE                 Location/Qualifiers
source                  1..463
                        mol_type = protein
                        organism = Synthetic construct
SEQUENCE: 152
MLLLVTSLLL CELPHPAFLL IPQEQLVESG GRLVTPGGSL TLSCKASGFD FSAYYMSWVR  60
QAPGKGLEWI ATIYPSSGKT YYATWVNGRF TISSDNAQNT VDLQMNSLTA ADRATYFCAR  120
DSYADDGALF NIWGPGTLVT ISSGGGGSGG GGSGGGGSEL VLTQSPSVSA ALGSPAKITC  180
TLSSAHKTDT IDWYQQLQGE APRYLMQVQS DGSYTKRPGV PDRFSGSSSG ADRYLIIPSV  240
QADDEADYYC GADYIGGYVF GGGTQLTVTG AAAESKYGPP CPPCPIYIWA PLAGTCGVLL  300
LSLVITLYCK RGRKKLLYIF KQPFMRPVQT TQEEDGCSCR FPEEEEGGCE LRVKFSRSAD  360
APAYQQGQNQ LYNELNLGRR EEYDVLDKRR GRDPEMGGKP RRKNPQEGLY NELQKDKMAE  420
AYSEIGMKGE RRRGKGHDGL YQGLSTATKD TYDALHMQAL PPR                    463

SEQ ID NO: 153          moltype = DNA  length = 1371
```

```
FEATURE                 Location/Qualifiers
source                  1..1371
                        mol_type = other DNA
                        organism = Synthetic construct
SEQUENCE: 153
atgctgctgc tggtgaccag cctgctgctg tgcgaactgc cgcatccggc gtttctgctg  60
attccgcaag ttcagctgca agaatcagga cctgggcttg tcaaaccatc tgaaaccctc  120
agcttgactt gtaccgtatc aggagggtca atttcaagct catcctacta ttggggatgg  180
atcagacaac cacccgggaa agggctcgag tggatagggt ccatatatta cagcggatct  240
acatactaca acccgtcatt gaagtccagg gtaacgattc cggtggacac tagcaagaat  300
cagtttagcc tcaagttgag cagtgtaact gctgcggaca cggcggtata ttattgtgct  360
cgacacctcg gtggagatgc ttttgacata tggggtcaag ggacaacagt caccgttagc  420
tcaggtggag ggggtagcgg ggggggcgga tctgggggag gcggttcatt gcccgtactt  480
acacagccac cctctgtcag cgtcgcacct ggacaaaccg ctcgcatcac ctgtggcgga  540
aataatatag gttccaagtc tgttcattgg tatcagcaga aaccgggaca ggcccccgtc  600
cttgtggtgt atgatgattc tgataggcca tctggtatcc cagaacggtt ttcaggtagc  660
aattcaggga atactgccac tctcactatt agcggtactc aagctatgga tgaggccgac  720
tatttttgcc agagctacga ctctagtaac ccagtcgtgt tcgggggagg gacccagttg  780
accgtgctgg cggccgcaga gtcaaaatac ggtcctccgt gccctccgtg tccgatctac  840
atttgggccc cgctggccgg cacttgcggc gtgctcctgc tgtcgctggt catcaccctt  900
tactgcaaga ggggccggaa gaagctgctt tacatcttca agcagccgtt catgcggccc  960
gtgcagacga ctcaggaaga ggacggatgc tcgtgcagat tccctgagga ggaagagggg  1020
ggatgcgaac tgcgcgtcaa gttctcacgg tccgccgacg cccccgcata tcaacagggc  1080
cagaatcagc tctacaacga gctgaacctg ggaaggagag aggagtacga cgtgctggac  1140
aagcgacgcg gacgcgaccc ggagatgggg gggaaaccac ggcggaaaaa ccctcaggaa  1200
ggactgtaca acgaactcca gaaagacaag atggcggaag cctactcaga aatcgggatg  1260
aagggagagc ggaggagggg aaagggtcac gacgggctgt accagggact gagcaccgcc  1320
actaaggata cctacgatgc cttgcatatg caagcactcc caccccggta g           1371

SEQ ID NO: 154          moltype = AA  length = 456
FEATURE                 Location/Qualifiers
source                  1..456
                        mol_type = protein
                        organism = Synthetic construct
SEQUENCE: 154
MLLLVTSLLL CELPHPAFLL IPQVQLQESG PGLVKPSETL SLTCTVSGGS ISSSSYYWGW  60
IRQPPGKGLE WIGSIYYSGS TYYNPSLKSR VTIPVDTSKN QFSLKLSSVT AADTAVYYCA  120
RHLGGDAFDI WGQGTTVTVS SGGGGSGGGG SGGGGSLPVL TQPPSVSVAP GQTARITCGG  180
NNIGSKSVHW YQQKPGQAPV LVVYDDSDRP SGIPERFSGS NSGNTATLTI SGTQAMDEAD  240
YFCQSYDSSN PVVFGGGTQL TVLAAAESKY GPPCPPCPIY IWAPLAGTCG VLLLSLVITL  300
YCKRGRKKLL YIFKQPFMRP VQTTQEEDGC SCRFPEEEEG GCELRVKFSR SADAPAYQQG  360
QNQLYNELNL GRREEYDVLD KRRGRDPEMG GKPRRKNPQE GLYNELQKDK MAEAYSEIGM  420
KGERRRGKGH DGLYQGLSTA TKDTYDALHM QALPPR                            456

SEQ ID NO: 155          moltype = DNA  length = 1380
FEATURE                 Location/Qualifiers
source                  1..1380
                        mol_type = other DNA
                        organism = Synthetic construct
SEQUENCE: 155
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gctgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tttgggcccc gctggccggc acttgcggcg tgctcctgct gtcgctggtc  900
atcacccttt actgcaagag gggccggaag aagctgcttt acatcttcaa gcagccgttc  960
atgcggcccg tgcagacgac tcaggaagag gacggatgct cgtgcagatt ccctgaggag  1020
gaagaggggg gatgcgaact gcgcgtcaag ttctcacggt ccgccgacgc ccccgcatat  1080
caacagggcc agaatcagct ctacaacgag ctgaacctgg gaaggagaga ggagtacgac  1140
gtgctggaca agcgacgcgg acgcgacccg gagatggggg ggaaaccacg gcggaaaaac  1200
cctcaggaag gactgtacaa cgaactccag aaagacaaga tggcggaagc ctactcagaa  1260
atcgggatga agggagagcg gaggagggga aagggtcacg acgggctgta ccagggactg  1320
agcaccgcca ctaaggatac ctacgatgcc ttgcatatgc aagcactccc accccggtag  1380

SEQ ID NO: 156          moltype = AA  length = 459
FEATURE                 Location/Qualifiers
source                  1..459
                        mol_type = protein
                        organism = Synthetic construct
```

SEQUENCE: 156
MLLLVTSLLL CELPHPAFLL IPQAAQVQLQ QSGAEVKKPG SSVKVSCKAS GGTFSSYAIS 60
WVRQAPGQGL EWMGWINPNS GGTNYAQRFQ GRVTMTRDTS ISTAYMELSR LRSDDTAVYY 120
CASYNDAFDI WGQGTLVTVS SGGGGSGGGG SGGGGSNFML TQPHSVSESP GKTVTISCTR 180
SSGSIASNYV QWYQQRPGSA PTIVIYEDDQ RPSGVPDRFS GSIDTSSNSA SLTISGLQSE 240
DEADYYCQSY EPGNGVFGGG TKVTVLAAAE SKYGPPCPPC PIYIWAPLAG TCGVLLLSLV 300
ITLYCKRGRK KLLYIFKQPF MRPVQTTQEE DGCSCRFPEE EEGGCELRVK FSRSADAPAY 360
QQGQNQLYNE LNLGRREEYD VLDKRRGRDP EMGGKPRRKN PQEGLYNELQ KDKMAEAYSE 420
IGMKGERRRG KGHDGLYQGL STATKDTYDA LHMQALPPR 459

SEQ ID NO: 157 moltype = DNA length = 1479
FEATURE Location/Qualifiers
source 1..1479
mol_type = other DNA
organism = Synthetic construct
SEQUENCE: 157
atgctgctgc tggtgaccag cctgctgctg tgcgaactgc cgcatccggc gtttctgctg 60
attccggagg tccagctggt acagtctggg ggaggcttgg tacagcctgg ggggtccctg 120
agactctcct gtgcagcctc tggattcacc tttgatgatt atgccatgca ctgggtccgg 180
caagctccag ggaagggcct ggagtgggtc tcaggtatta gttggaatag tggtagcata 240
ggctatgcgg actctgtgaa gggccgattc accatctcca gagacaacgc caagaactcc 300
ctgtatctgc aaatgaacag tctgagagct gaggacacgg ccttgtatta ctgtgcaaaa 360
gatttatcgt cagtggctgg accctttaac tactggggcc agggcaccct ggtcaccgtc 420
tcctcaggag gtggcgggtc tggtggaggc ggtagcggcg gtggcggatc ctcttctgag 480
ctgactcagg accctgctgt gtctgtggcc ttgggacaga cagtcaggat cacatgccaa 540
ggagacagcc tcagaagcta ttatgcaagc tggtaccagc agaagccagg acaggcccct 600
gtacttgtca tctatggtaa aaacaaccgg ccctcaggga tcccagaccg attctctggc 660
tccagctcag gaaacacagc ttccttgacc atcactgggg ctcaggcgga ggatgaggct 720
gactattact gtaactcccg ggacagcagt ggtaaccatc tggtattcgg cggaggcacc 780
cagctgaccg tcctcggtgc ggccgcaact accacccctg cccctcggcc gccgactccg 840
gccccaacca tcgcaagcca acccctctcc ttgcgccccg aagcttgccg cccggccgcg 900
ggtggagccg tgcatacccg gggctggac tttgcctgcg atatctacat ttgggccccg 960
ctggccggca cttgcggcgt gctcctgctg tcgctggtca tcacccttta ctgcaagagg 1020
ggccggaaga agctgcttta catcttcaag cagccgttca tgcggcccgt gcagacgact 1080
caggaagagg acggatgctc gtgcagattc cctgaggagg aagagggggg atgcgaactg 1140
cgcgtcaagt tctcacggtc cgccgacgcc cccgcatatc aacagggcca gaatcagctc 1200
tacaacgagc tgaacctggg aaggagagag gagtacgacg tgctggacaa gcgacgcgga 1260
cgcgacccgg agatgggggg gaaaccacgg cggaaaaacc ctcaggaagg actgtacaac 1320
gaactccaga aagacaagat ggcggaagcc tactcagaaa tcgggatgaa gggagagcgg 1380
aggaggggaa agggtcacga cgggctgtac cagggactga gcaccgccac taaggatacc 1440
tacgatgcct tgcatatgca agcactccca ccccggtag 1479

SEQ ID NO: 158 moltype = AA length = 492
FEATURE Location/Qualifiers
source 1..492
mol_type = protein
organism = Synthetic construct
SEQUENCE: 158
MLLLVTSLLL CELPHPAFLL IPEVQLVQSG GGLVQPGGSL RLSCAASGFT FDDYAMHWVR 60
QAPGKGLEWV SGISWNSGSI GYADSVKGRF TISRDNAKNS LYLQMNSLRA EDTALYYCAK 120
DLSSVAGPFN YWGQGTLVTV SSGGGGSGGG GSGGGGSSSE LTQDPAVSVA LGQTVRITCQ 180
GDSLRSYYAS WYQQKPGQAP VLVIYGKNNR PSGIPDRFSG SSSGNTASLT ITGAQAEDEA 240
DYYCNSRDSS GNHLVFGGGT QLTVLGAAAT TTPAPRPPTP APTIASQPLS LRPEACRPAA 300
GGAVHTRGLD FACDIYIWAP LAGTCGVLLL SLVITLYCKR GRKKLLYIFK QPFMRPVQTT 360
QEEDGCSCRF PEEEEGGCEL RVKFSRSADA PAYQQGQNQL YNELNLGRRE EYDVLDKRRG 420
RDPEMGGKPR RKNPQEGLYN ELQKDKMAEA YSEIGMKGER RRGKGHDGLY QGLSTATKDT 480
YDALHMQALP PR 492

SEQ ID NO: 159 moltype = DNA length = 3357
FEATURE Location/Qualifiers
source 1..3357
mol_type = other DNA
organism = Synthetic construct
SEQUENCE: 159
atgctgctgc tggtgaccag cctgctgctg tgcgaactgc cgcatccggc gtttctgctg 60
attccgcagg cggcccaggt acagctgcag cagtcagggg ctgaggtgaa gaagcctggg 120
tcctcggtga aggtctcctg caaggcttct ggaggcacct tcagcagcta tgctatcagc 180
tgggtgcgac aggcccctgg acaagggctt gagtggatgg gatggatcaa ccctaacagt 240
ggtggcacaa actatgcaca gaggtttcag ggcagggtca ccatgaccag ggacacgtcc 300
atcagcacag cctacatgga gttgagcagg ctgagatctg acgacacggc cgtgtattac 360
tgtgcgagtt ataatgatgc ttttgatatc tggggccaag gcaccctggt caccgtctcc 420
tcaggaggtg gcgggtctgg tggtggcggt agcggtggtg gcggatccaa ttttatgctg 480
actcagcccc actctgtgtc ggagtctccg gggaagacgg taaccatctc ctgcacccgc 540
agcagtggca gcattgccag caactatgtg cagtggtacc agcagcgccc gggcagtgcc 600
cccaccattg tgatctatga ggatgatcaa agaccctctg gggtccctga tcggttctct 660
ggctccatcg acacctcctc caactctgcc tccctcacca tctctggact gcagagtgag 720
gacgaggctg actactactg tcagtcttat gagcccggca atggggtatt cggcggaggg 780
accaaggtca ccgtcctagc tgccgcagag tcaaaatacg gtcctccgtg ccctccgtgt 840
ccgatctaca tttgggcccc gctggccggc acttgcggcg tgctcctgct gtcgctggtc 900

```
atcacccttt actgcaagcg cggccgcaag aaattgcttt acatttttaa gcagccgttc  960
atgcgaccag tacagactac tcaagaagaa gatgggtgct cttgtcggtt cccggaagaa  1020
gaagagggtg gttgcgagtt gagggtgaag ttctcccgct ctgccgacgc accggcatat  1080
cagcagggac aaaaccagct ctacaacgaa ttgaacctgg gtcggcggga agaatatgac  1140
gtgctcgata agcggcgggg tcgcgaccca gaaatgggag gcaaaccgcg caggaaaaat  1200
ccacaggagg gactttataa cgaacttcaa aaggataaga tggcagaggc atacagcgaa  1260
atcgggatga aaggcgagag aagaaggggg aaagggcacg atggtcttta ccaggggctt  1320
tctaccgcga cgaaggatac ctacgatgct ctccatatgc aagcacttcc tcctagacgg  1380
gcaaagcggg gctcaggggc gactaacttt tcactgttga agcaggccgg ggatgtggag  1440
gagaatcctg gtcctagagc taagcgagta atgctcttgc tcgtgacttc tttgcttttg  1500
tgcgaacttc cgcacccagc cttccttttg atacctatgg attgtgatat tgaaggtaaa  1560
gatggcaaac aatatgagag tgttctaatg gtcagcatcg atcaattatt ggacagcatg  1620
aaagaaattg gtagcaattg cctgaataat gaatttaact tttttaaaag acatatctgt  1680
gatgctaata aggaaggtat gtttttattc cgtgctgctc gcaagttgag gcaatttctt  1740
aaaatgaata gcactggtga ttttgatctc cacttattaa aagtttcaga aggcacaaca  1800
atactgttga actgcactgg ccaggttaaa ggaagaaaac cagctgccct gggtgaagcc  1860
caaccaacaa agagtttgga agaaaataaa tctttaaagg aacagaaaaa actgaatgac  1920
ttgtgtttcc taaagagact attacaagag ataaaaactt gttggaataa aattttgatg  1980
ggcactaaag aacactccgg aggttccggt ggtggctcag gtggtggctc aggtgaaagt  2040
ggctatgctc aaaatggaga cttggaagat gcagaactgg atgactactc attctcatgc  2100
tatagccagt tggaagtgaa tggatcgcag cactcactga cctgtgcttt tgaggaccca  2160
gatgtcaaca tcaccaatct ggaatttgaa atatgtgggg ccctcgtgga ggtaaagtgc  2220
ctgaatttca ggaaactaca agagatatat ttcatcgaga caaagaaatt cttactgatt  2280
ggaaagagca atatatgtgt gaaggttgga gaaaagagtc taacctgcaa aaaaatagac  2340
ctaaccacta tagttaaacc tgaggctcct tttgacctga gtgtcgtcta tcgggaagga  2400
gccaatgact ttgtggtgac atttaataca tcacacttgc aaaagaagta tgtaaaagtt  2460
ttaatgcacg atgtagctta ccgccaggaa aaggatgaaa acaaatggac gcatgtgaat  2520
ttatccagca caaagctgac actcctgcag agaaagctcc aaccggcagc aatgtatgag  2580
attaaagttc gatccatccc tgatcactat tttaaaggct tctggagtga atggagtcca  2640
agttattact tcagaactcc agagatcaat aatagctcag gggagatgga tcctatctta  2700
ctaaccatca gcattttgag ttttttctct gtcgctctgt tggtcatctt ggcctgtgtg  2760
ttatggaaaa aaaggattaa gcctatcgta tggcccagtc tccccgatca taagaagact  2820
ctggaacatc tttgtaagaa accaagaaaa aatttaaatg tgagtttcaa tcctgaaagt  2880
ttcctggact gccagattca tagggtggat gacattcaag ctagagatga agtggaaggt  2940
tttctgcaag atacgtttcc tcagcaacta gaagaatctg agaagcagag gcttggaggg  3000
gatgtgcaga gccccaactg cccatctgag gatgtagtca tcactccaga aagctttgga  3060
agagattcat ccctcacatg cctggctggg aatgtcagtg catgtgacgc ccctattctc  3120
tcctcttcca ggtccctaga ctgcagggag agtggcaaga atgggcctca tgtgtaccag  3180
gacctccttc ttagccttgg gactacaaac agcacgctgc cccctccatt ttctctccaa  3240
tctggaatcc tgacattgaa cccagttgct cagggtcagc ccattcttac ttccctggga  3300
tcaaatcaag aagaagcata tgtcaccatg tccagcttct accaaaacca gccctag     3357
```

```
SEQ ID NO: 160          moltype = AA  length = 1118
FEATURE                 Location/Qualifiers
source                  1..1118
                        mol_type = protein
                        organism = Synthetic construct
SEQUENCE: 160
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRV MLLLVTSLLL CELPHPAFLL IPMDCDIEGK DGKQYESVLM VSIDQLLDSM  540
KEIGSNCLNN EFNFFKRHIC DANKEGMFLF RAARKLRQFL KMNSTGDFDL HLLKVSEGTT  600
ILLNCTGQVK GRKPAALGEA QPTKSLEENK SLKEQKKLND LCFLKRLLQE IKTCWNKILM  660
GTKEHSGGSG GGSGGGSGES GYAQNGDLED AELDDYSFSC YSQLEVNGSQ HSLTCAFEDP  720
DVNITNLEFE ICGALVEVKC LNFRKLQEIY FIETKKFLLI GKSNICVKVG EKSLTCKKID  780
LTTIVKPEAP FDLSVVYREG ANDFVVTFNT SHLQKKYVKV LMHDVAYRQE KDENKWTHVN  840
LSSTKLTLLQ RKLQPAAMYE IKVRSIPDHY FKGFWSEWSP SYYFRTPEIN NSSGEMDPIL  900
LTISILSFFS VALLVILACV LWKKRIKPIV WPSLPDHKKT LEHLCKKPRK NLNVSFNPES  960
FLDCQIHRVD DIQARDEVEG FLQDTFPQQL EESEKQRLGG DVQSPNCPSE DVVITPESFG  1020
RDSSLTCLAG NVSACDAPIL SSSRSLDCRE SGKNGPHVYQ DLLLSLGTTN STLPPPFSLQ  1080
SGILTLNPVA QGQPILTSLG SNQEEAYVTM SSFYQNQP                         1118
```

```
SEQ ID NO: 161          moltype = DNA  length = 2049
FEATURE                 Location/Qualifiers
source                  1..2049
                        mol_type = other DNA
                        organism = Synthetic construct
SEQUENCE: 161
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
```

```
atcagcacag cctacatgga gttgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg ggtccctga  tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc tgccgcagag tcaaaatacg gtcctccgtg ccctccgtgt  840
ccgatctaca tttgggcccc gctggccggc acttgcggcg tgctcctgct gtcgctggtc  900
atcacccttt actgcaagcg cggccgcaag aaattgcttt acatttttaa gcagccgttc  960
atgcgaccag tacagactac tcaagaagaa gatgggtgct cttgtcggtt cccggaagaa  1020
gaagagggtg gttgcgagtt gagggtgaag ttctcccgct ctgccgacgc accggcatat  1080
cagcagggac aaaaccagct ctacaacgaa ttgaacctgg gtcggcggga agaatatgac  1140
gtgctcgata agcggcgggg tcgcgaccca gaaatgggag gcaaaccgcg caggaaaaat  1200
ccacaggagg gactttataa cgaacttcaa aaggataaga tggcagaggc atacagcgaa  1260
atcgggatga aaggcgagag aagaaggggg aaagggcacg atggtcttta ccaggggctt  1320
tctaccgcga cgaaggatac ctacgatgct ctccatatgc aagcacttcc tcctagacgg  1380
gcaaagcggg gctcaggggc gactaacttt tcactgttga agcaggccgg ggatgtggag  1440
gagaatcctg gtcctagagc taagcgagta gacatgggaa gagggctgct ccgaggcttg  1500
tggccgttgc atattgtatt gtggacgcgg atagcgagta caatcccgcc tcacgtgcaa  1560
aaatcagtta ataacgacat gatcgttact gacaacaatg gcgcagttaa atttccgcag  1620
ctttgtaaat tctgtgatgt aagattttca acgtgcgata accagaaaag ctgtatgtcc  1680
aactgcagca tcacatcaat ctgtgaaaaa ccccaagagg tatgtgtggc cgtctggcga  1740
aagaatgacg aaaatatcac actggagacc gtttgtcacg atcctaaact cccttatcat  1800
gactttattc tggaagacgc agcgtcaccg aagtgtataa tgaaagagaa gaagaagcct  1860
ggagagacgt tttcatgtg cagttgctcc tcagatgagt gtaatgacaa catcattttt  1920
tccgaggagt acaatacgag taacccagac ctcctgctgg ttattttcca ggtaaccggc  1980
atcagtttgt tgcccccact gggtgttgca atcagtgtaa taatcatatt ttattgttac  2040
cgggtgtga                                                          2049
```

```
SEQ ID NO: 162          moltype = AA  length = 682
FEATURE                 Location/Qualifiers
source                  1..682
                        mol_type = protein
                        organism = Synthetic construct
SEQUENCE: 162
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRV DMGRGLLRGL WPLHIVLWTR IASTIPPHVQ KSVNNDMIVT DNNGAVKFPQ  540
LCKFCDVRFS TCDNQKSCMS NCSITSICEK PQEVCVAVWR KNDENITLET VCHDPKLPYH  600
DFILEDAASP KCIMKEKKKP GETFFMCSCS SDECNDNIIF SEEYNTSNPD LLLVIFQVTG  660
ISLLPPLGVA ISVIIIFYCY RV                                           682
```

```
SEQ ID NO: 163          moltype = DNA  length = 2550
FEATURE                 Location/Qualifiers
source                  1..2550
                        mol_type = other DNA
                        organism = Synthetic construct
SEQUENCE: 163
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gttgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg ggtccctga  tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc tgccgcagag tcaaaatacg gtcctccgtg ccctccgtgt  840
ccgatctaca tttgggcccc gctggccggc acttgcggcg tgctcctgct gtcgctggtc  900
atcacccttt actgcaagcg cggccgcaag aaattgcttt acatttttaa gcagccgttc  960
atgcgaccag tacagactac tcaagaagaa gatgggtgct cttgtcggtt cccggaagaa  1020
gaagagggtg gttgcgagtt gagggtgaag ttctcccgct ctgccgacgc accggcatat  1080
cagcagggac aaaaccagct ctacaacgaa ttgaacctgg gtcggcggga agaatatgac  1140
gtgctcgata agcggcgggg tcgcgaccca gaaatgggag gcaaaccgcg caggaaaaat  1200
ccacaggagg gactttataa cgaacttcaa aaggataaga tggcagaggc atacagcgaa  1260
atcgggatga aaggcgagag aagaaggggg aaagggcacg atggtcttta ccaggggctt  1320
tctaccgcga cgaaggatac ctacgatgct ctccatatgc aagcacttcc tcctagacgg  1380
```

```
gcaaagcggg gctcaggggc gactaacttt tcactgttga agcaggccgg ggatgtggag  1440
gagaatcctg gtcctagagc taagcgagct agcgtgtaca tggcactgcc cgtgaccgcc  1500
ctgcttctgc cgcttgcact tctgctgcac gccgctaggc ccaggaaggt ttgcaatgga  1560
atcggtatag ggagtttaa ggattcactt agcataaacg ctactaacat taaacacttc  1620
aaaaactgta cgagtataag tggagatctt cacattttgc cggttgcatt ccgaggcgat  1680
tcattcaccc acacgccacc gcttgaccca caagaattgg atattcttaa aaccgttaaa  1740
gaaataacgg ggtttttgct cattcaagcg tggccagaaa atcgcactga cctccatgct  1800
ttcgagaacc tggagattat aagaggacga actaagcagc atggtcaatt ctcccttgct  1860
gtggtcagcc tgaacatcac cagtcttggt ttgcggtccc tcaaggaaat ttcagatgga  1920
gatgtcatca taagcggcaa caagaatttg tgctatgcaa ataccataaa ctggaaaaaa  1980
ctgtttggca cttccggcca gaaaaccaag attatttcaa atcggggtga gaacagctgc  2040
aaagccaccg gccaggtttg tcatgccttg tgctctccgg aaggctgttg ggggccagaa  2100
cccagggact gcgtcagttg cagaaacgtc tcaagaggcc gcgaatgcgt tgacaagtgt  2160
aacctccttg agggtgagcc acgagagttt gttgagaaca gcgagtgtat acaatgtcac  2220
cctgaatgtt tgccccaggc tatgaatata acctgcacag gccgcgggcc tgataactgc  2280
atccagtgtg ctcattacat agatggacct cactgtgtga aaacctgccc ggccggagtt  2340
atgggagaaa acaacactct ggtgtggaaa tacgctgatg caggccacgt gtgccacctt  2400
tgtcacccga attgcacata tgggtgtacc ggtcctggac ttgaaggttg ccctaccaat  2460
ggccctaaaa tacccagtat cgcaactggc atggtaggcg ctcttctctt gctcttggta  2520
gttgctctcg gcataggtct ttttatgtga                                 2550

SEQ ID NO: 164          moltype = AA  length = 849
FEATURE                 Location/Qualifiers
source                  1..849
                        mol_type = protein
                        organism = Synthetic construct
SEQUENCE: 164
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRA SVYMALPVTA LLLPLALLLH AARPRKVCNG IGIGEFKDSL SINATNIKHF  540
KNCTSISGDL HILPVAFRGD SFTHTPPLDP QELDILKTVK EITGFLLIQA WPENRTDLHA  600
FENLEIIRGR TKQHGQFSLA VVSLNITSLG LRSLKEISDG DVIISGNKNL CYANTINWKK  660
LFGTSGQKTK IISNRGENSC KATGQVCHAL CSPEGCWGPE PRDCVSCRNV SRGRECVDKC  720
NLLEGEPREF VENSECIQCH PECLPQAMNI TCTGRGPDNC IQCAHYIDGP HCVKTCPAGV  780
MGENNTLVWK YADAGHVCHL CHPNCTYGCT GPGLEGCPTN GPKIPSIATG MVGALLLLLV  840
VALGIGLFM                                                        849

SEQ ID NO: 165          moltype = DNA  length = 3459
FEATURE                 Location/Qualifiers
source                  1..3459
                        mol_type = other DNA
                        organism = Synthetic construct
SEQUENCE: 165
atgctgctgc tggtgaccag cctgctgctg tgcgaactgc cgcatccggc gtttctgctg  60
attccggagg tccagctggt acagtctggg ggaggcttgg tacagcctgg ggggtccctg  120
agactctcct gtgcagcctc tggattcacc tttgatgatt atgccatgca ctgggtccgg  180
caagctccag ggaagggcct ggagtgggtc tcaggtatta gttggaatag tggtagcata  240
ggctatgcgg actctgtgaa gggccgattc accatctcca gagacaacgc caagaactcc  300
ctgtatctgc aaatgaacag tctgagagct gaggacacgg ccttgtatta ctgtgcaaaa  360
gatttatcgt cagtggctgg accctttaac tactggggcc agggcaccct ggtcaccgtc  420
tcctcaggag gtggcgggtc tggtggaggc ggtagcggcg gtggcggatc ctcttctgag  480
ctgactcagg accctgctgt gtctgtggcc ttgggacaga cagtcaggat cacatgccaa  540
ggagacagcc tcagaagcta ttatgcaagc tggtaccagc agaagccagg acaggcccct  600
gtacttgtca tctatggtaa aaacaaccgg ccctcaggga tcccagaccg attctctggc  660
tccagctcag gaaacacagc ttccttgacc atcactgggg ctcaggcgga ggatgaggct  720
gactattact gtaactcccg ggacagcagt ggtaaccatc tggtattcgg cggaggcacc  780
cagctgaccg tcctcggtgc ggccgctacc acaacccctg cgccccggcc tcctaccccc  840
gcacccacga ttgcttctca acctctttca ctccgacctg aggcttgtag acctgcagcc  900
gggggtgccg tccacacacg gggactcgac ttcgcttgtg atatatatat ttgggcgccc  960
ctggccggca cttgtggagt tcttttgctc tctcttgtta tcacattgta ctgcaagcga  1020
ggtaggaaga aattgcttta catttttaag cagccgttca tgcgaccagt acagactact  1080
caagaagaag atgggtgctc ttgtcggttc ccggaagaag aagagggtgg ttgcgagttg  1140
agggtgaagt tctcccgctc tgccgacgca ccggcatatc agcagggaca aaaccagctc  1200
tacaacgaat tgaacctggg tcggcgggaa gaatatgacg tgctcgataa gcggcggggt  1260
cgcgacccag aaatgggagg caaaccgcgc aggaaaaatc cacaggaggg actttataac  1320
gaacttcaaa aggataagat ggcagaggca tacagcgaaa tcgggatgaa aggcgagaga  1380
agaaggggga aagggcacga tggtctttac caggggcttt ctaccgcgac gaaggatacc  1440
tacgatgctc tccatatgca agcacttcct cctagacggg caaagcgggg ctcaggggcg  1500
actaactttt cactgttgaa gcaggccggg gatgtggagg agaatcctgg tcctagagct  1560
aagcgagtaa tgctcttgct cgtgacttct ttgcttttgt gcgaacttcc gcacccagcc  1620
ttccttttga tacctatgga ttgtgatatt gaaggtaaag atggcaaaca atatgagagt  1680
gttctaatgg tcagcatcga tcaattattg gacagcatga aagaaattgg tagcaattgc  1740
ctgaataatg aatttaactt ttttaaaaga catatctgtg atgctaataa ggaaggtatg  1800
```

```
tttttattcc gtgctgctcg caagttgagg caatttctta aaatgaatag cactggtgat  1860
tttgatctcc acttattaaa agtttcagaa ggcacaacaa tactgttgaa ctgcactggc  1920
caggttaaag gaagaaaacc agctgccctg ggtgaagccc aaccaacaaa gagtttggaa  1980
gaaaataaat ctttaaagga acagaaaaaa ctgaatgact tgtgtttcct aaagagacta  2040
ttacaagaga taaaaacttg ttggaataaa attttgatgg gcactaaaga acactccgga  2100
ggttccggtg gtggctcagg tggtggctca ggtgaaagtg gctatgctca aaatggagac  2160
ttggaagatg cagaactgga tgactactca ttctcatgct atagccagtt ggaagtgaat  2220
ggatcgcagc actcactgac ctgtgctttt gaggacccag atgtcaacat caccaatctg  2280
gaatttgaaa tatgtggggc cctcgtggag gtaaagtgcc tgaatttcag gaaactacaa  2340
gagatatatt tcatcgagac aaagaaattc ttactgattg gaaagagcaa tatatgtgtg  2400
aaggttggag aaaagagtct aacctgcaaa aaaatagacc taaccactat agttaaacct  2460
gaggctcctt ttgacctgag tgtcgtctat cgggaaggag ccaatgactt tgtggtgaca  2520
tttaatacat cacacttgca aaagaagtat gtaaaagttt taatgcacga tgtagcttac  2580
cgccaggaaa aggatgaaaa caaatggacg catgtgaatt tatccagcac aaagctgaca  2640
ctcctgcaga gaaagctcca accggcagca atgtatgaga ttaaagttcg atccatccct  2700
gatcactatt ttaaaggctt ctggagtgaa tggagtccaa gttattactt cagaactcca  2760
gagatcaata atagctcagg ggagatggat cctatcttac taaccatcag cattttgagt  2820
tttttctctg tcgctctgtt ggtcatcttg gcctgtgtgt tatggaaaaa aaggattaag  2880
cctatcgtat ggcccagtct ccccgatcat aagaagactc tggaacatct ttgtaagaaa  2940
ccaagaaaaa atttgaatgt gagtttcaat cctgaaagtt tcctggactg ccagattcat  3000
agggtggatg acattcaagc tagagatgaa gtggaaggtt ttctgcaaga tacgtttcct  3060
cagcaactag aagaatctga gaagcagagg cttggagggg atgtgcagag ccccaactgc  3120
ccatctgagg atgtagtcat cactccagaa agctttggaa gagattcatc cctcacatgc  3180
ctggctggga atgtcagtgc atgtgacgcc cctattctct cctcttccag gtccctagac  3240
tgcagggaga gtggcaagaa tgggcctcat gtgtaccagg acctccttct tagccttggg  3300
actacaaaca gcacgctgcc ccctccattt tctctccaat ctggaatcct gacattgaac  3360
ccagttgctc agggtcagcc cattcttact tccctgggat caaatcaaga agaagcatat  3420
gtcaccatgt ccagcttcta ccaaaaccag cctaggtaa                         3459

SEQ ID NO: 166         moltype = AA  length = 1152
FEATURE                Location/Qualifiers
source                 1..1152
                       mol_type = protein
                       organism = Synthetic construct
SEQUENCE: 166
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGAAAT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PRRAKRGSGA TNFSLLKQAG DVEENPGPRA KRVMLLLVTS LLLCELPHPA  540
FLLIPMDCDI EGKDGKQYES VLMVSIDQLL DSMKEIGSNC LNNEFNFFKR HICDANKEGM  600
FLFRAARKLR QFLKMNSTGD FDLHLLKVSE GTTILLNCTG QVKGRKPAAL GEAQPTKSLE  660
ENKSLKEQKK LNDLCFLKRL LQEIKTCWNK ILMGTKEHSG GSGGGSGGGS GESGYAQNGD  720
LEDAELDDYS FSCYSQLEVN GSQHSLTCAF EDPDVNITNL EFEICGALVE VKCLNFRKLQ  780
EIYFIETKKF LLIGKSNICV KVGEKSLTCK KIDLTTIVKP EAPFDLSVVY REGANDFVVT  840
FNTSHLQKKY VKVLMHDVAY RQEKDENKWT HVNLSSTKLT LLQRKLQPAA MYEIKVRSIP  900
DHYFKGFWSE WSPSYYFRTP EINNSSGEMD PILLTISILS FFSVALLVIL ACVLWKKRIK  960
PIVWPSLPDH KKTLEHLCKK PRKNLNVSFN PESFLDCQIH RVDDIQARDE VEGFLQDTFP  1020
QQLEESEKQR LGGDVQSPNC PSEDVVITPE SFGRDSSLTC LAGNVSACDA PILSSSRSLD  1080
CRESGKNGPH VYQDLLLSLG TTNSTLPPPF SLQSGILTLN PVAQGQPILT SLGSNQEEAY  1140
VTMSSFYQNQ PR                                                      1152

SEQ ID NO: 167         moltype = DNA  length = 3453
FEATURE                Location/Qualifiers
source                 1..3453
                       mol_type = other DNA
                       organism = Synthetic construct
SEQUENCE: 167
atgctgctgc tggtgaccag cctgctgctg tgcgaactgc cgcatccggc gtttctgctg  60
attccggagg tccagctggt acagtctggg ggaggcttgg tacagcctgg ggggtccctg  120
agactctcct gtgcagcctc tggattcacc tttgatgatt atgccatgca ctgggtccgg  180
caagctccag ggaagggcct ggagtgggtc tcaggtatta gttggaatag tggtagcata  240
ggctatgcgg actctgtgaa gggccgattc accatctcca gagacaacgc caagaactcc  300
ctgtatctgc aaatgaacag tctgagagct gaggacacgg ccttgtatta ctgtgcaaaa  360
gatttatcgt cagtggctgg acccttttaac tactggggcc agggcaccct ggtcaccgtc  420
tcctcaggag gtggcgggtc tggtggaggc ggtagcggcg gtggcggatc ctcttctgag  480
ctgactcagg accctgctgt gtctgtggcc ttgggacaga cagtcaggat cacatgccaa  540
ggagacagcc tcagaagcta ttatgcaagc tggtaccagc agaagccagg acaggcccct  600
gtacttgtca tctatggtaa aaacaaccgg ccctcaggga tcccagaccg attctctggc  660
tccagctcag gaaacacagc ttccttgacc atcactgggg ctcaggcgga ggatgaggct  720
gactattact gtaactcccg ggacagcagt ggtaaccatc tggtattcgg cggaggcacc  780
cagctgaccg tcctcggtgc ggccgcaacc actacgcctg ctccgcggcc tccaacgccc  840
gcgcccacga tagctagtca gccgttgtct ctccgaccag aggcgtgtag accggccgct  900
ggcggagccg tacatactcg cggactcgac ttcgcttgcg acatctacat ttgggcaccc  960
ttggctggga cctgtggggt gctgttgctg tccttggtta ttacgttgta ctgccggtcg  1020
```

```
aagaggtcca gactcttgca ctccgactac atgaacatga ctcctagaag gcccggaccc  1080
actagaaagc actaccagcc gtacgcccct cctcgggatt tcgccgcata ccggtccaga  1140
gtcaaatttt ccaggtccgc agatgccccc gcgtaccagc aaggccagaa ccaactttac  1200
aacgaactga acctgggtcg ccgggaggaa tatgatgtgc tggataaacg aagggggagg  1260
gaccctgaga tgggagggaa acctcgcagg aaaaacccgc aggaaggttt gtacaacgag  1320
ttgcagaagg ataagatggc tgaggcttac tctgaaatag ggatgaaggg agagagacgg  1380
agaggaaaag gccatgatgg cctttaccag ggcttaagca cagcaacaaa ggatacttac  1440
gacgctcttc acatgcaagc tctgccacca cggcgggcaa agcggggctc aggggcgact  1500
aacttttcac tgttgaagca ggccggggat gtggaggaga atcctggtcc tagagctaag  1560
cgagtaatgc tcttgctcgt gacttctttg cttttgtgcg aacttccgca cccagccttc  1620
cttttgatac ctatggattg tgatattgaa ggtaaagatg gcaaacaata tgagagtgtt  1680
ctaatggtca gcatcgatca attattggac agcatgaaag aaattggtag caattgcctg  1740
aataatgaat ttaacttttt taaaagacat atctgtgatg ctaataagga aggtatgttt  1800
ttattccgtg ctgctcgcaa gttgaggcaa tttcttaaaa tgaatagcac tggtgatttt  1860
gatctccact tattaaaagt ttcagaaggc acaacaatac tgttgaactg cactggccag  1920
gttaaaggaa gaaaaccagc tgccctgggt gaagcccaac caacaaagag tttggaagaa  1980
aataaatctt taaaggaaca gaaaaaactg aatgacttgt gtttcctaaa gagactatta  2040
caagagataa aaacttgttg gaataaaatt ttgatgggca ctaaagaaca ctccggaggt  2100
tccggtggtg gctcaggtgg tggctcaggt gaaagtggct atgctcaaaa tggagacttg  2160
gaagatgcag aactggatga ctactcattc tcatgctata gccagttgga agtgaatgga  2220
tcgcagcact cactgacctg tgcttttgag gacccagatg tcaacatcac caatctggaa  2280
tttgaaatat gtggggccct cgtggaggta aagtgcctga atttcaggaa actacaagag  2340
atatatttca tcgagacaaa gaaattctta ctgattggaa agagcaatat atgtgtgaag  2400
gttggagaaa agagtctaac ctgcaaaaaa atagacctaa ccactatagt taaacctgag  2460
gctccttttg acctgagtgt cgtctatcgg gaaggagcca atgactttgt ggtgacattt  2520
aatacatcac acttgcaaaa gaagtatgta aaagttttaa tgcacgatgt agcttaccgc  2580
caggaaaagg atgaaaacaa atggacgcat gtgaatttat ccagcacaaa gctgacactc  2640
ctgcagagaa agctccaacc ggcagcaatg tatgagatta aagttcgatc catccctgat  2700
cactatttta aaggcttctg gagtgaatgg agtccaagtt attacttcag aactccagag  2760
atcaataata gctcagggga gatggatcct atcttactaa ccatcagcat tttgagtttt  2820
ttctctgtcg ctctgttggt catcttggcc tgtgtgttat ggaaaaaaag gattaagcct  2880
atcgtatggc ccagtctccc cgatcataag aagactctgg aacatctttg taagaaacca  2940
agaaaaaatt taaatgtgag tttcaatcct gaaagtttcc tggactgcca gattcatagg  3000
gtggatgaca ttcaagctag agatgaagtg gaaggttttc tgcaagatac gtttcctcag  3060
caactagaag aatctgagaa gcagaggctt ggaggggatg tgcagagccc caactgccca  3120
tctgaggatg tagtcatcac tccagaaagc tttggaagag attcatccct cacatgcctg  3180
gctgggaatg tcagtgcatg tgacgcccct attctctcct cttccaggtc cctagactgc  3240
agggagagtg gcaagaatgg gcctcatgtg taccaggacc tccttcttag ccttgggact  3300
acaaacagca cgctgccccc tccattttct ctccaatctg gaatcctgac attgaaccca  3360
gttgctcagg gtcagcccat tcttacttcc ctgggatcaa atcaagaaga agcatatgtc  3420
accatgtcca gcttctacca aaaccagccc tag                               3453

SEQ ID NO: 168         moltype = AA  length = 1150
FEATURE                Location/Qualifiers
source                 1..1150
                       mol_type = protein
                       organism = Synthetic construct
SEQUENCE: 168
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGAAAT TTPAPRPPTP APTIASQPLS LRPEACRPAA  300
GGAVHTRGLD FACDIYIWAP LAGTCGVLLL SLVITLYCRS KRSRLLHSDY MNMTPRRPGP  360
TRKHYQPYAP PRDFAAYRSR VKFSRSADAP AYQQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP RRAKRGSGAT NFSLLKQAGD VEENPGPRAK RVMLLLVTSL LLCELPHPAF  540
LLIPMDCDIE GKDGKQYESV LMVSIDQLLD SMKEIGSNCL NNEFNFFKRH ICDANKEGMF  600
LFRAARKLRQ FLKMNSTGDF DLHLLKVSEG TTILLNCTGQ VKGRKPAALG EAQPTKSLEE  660
NKSLKEQKKL NDLCFLKRLL QEIKTCWNKI LMGTKEHSGG SGGGSGGGSG ESGYAQNGDL  720
EDAELDDYSF SCYSQLEVNG SQHSLTCAFE DPDVNITNLE FEICGALVEV KCLNFRKLQE  780
IYFIETKKFL LIGKSNICVK VGEKSLTCKK IDLTTIVKPE APFDLSVVYR EGANDFVVTF  840
NTSHLQKKYV KVLMHDVAYR QEKDENKWTH VNLSSTKLTL LQRKLQPAAM YEIKVRSIPD  900
HYFKGFWSEW SPSYYFRTPE INNSSGEMDP ILLTISILSF FSVALLVILA CVLWKKRIKP  960
IVWPSLPDHK KTLEHLCKKP RKNLNVSFNP ESFLDCQIHR VDDIQARDEV EGFLQDTFPQ  1020
QLEESEKQRL GGDVQSPNCP SEDVVITPES FGRDSSLTCL AGNVSACDAP ILSSSRSLDC  1080
RESGKNGPHV YQDLLLSLGT TNSTLPPPFS LQSGILTLNP VAQGQPILTS LGSNQEEAYV  1140
TMSSFYQNQP                                                         1150

SEQ ID NO: 169         moltype = DNA  length = 2148
FEATURE                Location/Qualifiers
source                 1..2148
                       mol_type = other DNA
                       organism = Synthetic construct
SEQUENCE: 169
atgctgctgc tggtgaccag cctgctgctg tgcgaactgc cgcatccggc gtttctgctg  60
attccggagg tccagctggt acagtctggg ggaggcttgg tacagcctgg ggggtccctg  120
agactctcct gtgcagcctc tggattcacc tttgatgatt atgccatgca ctgggtccgg  180
caagctccag ggaagggcct ggagtgggtc tcaggtatta gttggaatag tggtagcata  240
```

```
ggctatgcgg actctgtgaa gggccgattc accatctcca gagacaacgc caagaactcc  300
ctgtatctgc aaatgaacag tctgagagct gaggacacgg ccttgtatta ctgtgcaaaa  360
gatttatcgt cagtggctgg accctttaac tactggggcc agggcaccct ggtcaccgtc  420
tcctcaggag gtggcgggtc tggtggaggc ggtagcggcg gtggcggatc ctcttctgag  480
ctgactcagg accctgctgt gtctgtggcc ttgggacaga cagtcaggat cacatgccaa  540
ggagacagcc tcagaagcta ttatgcaagc tggtaccagc agaagccagg acaggcccct  600
gtacttgtca tctatggtaa aaacaaccgg ccctcaggga tcccagaccg attctctggc  660
tccagctcag gaaacacagc ttccttgacc atcactgggg ctcaggcgga ggatgaggct  720
gactattact gtaactcccg ggacagcagt ggtaaccatc tggtattcgg cggaggcacc  780
cagctgaccg tcctcggtgc ggccgctacc acaacccctg cgccccggcc tcctaccccc  840
gcacccacga ttgcttctca acctctttca ctccgacctg aggcttgtag acctgcagcc  900
gggggtgccg tccacacacg ggactcgac ttcgcttgtg atatatatat ttgggcgccc  960
ctggccggca cttgtggagt tcttttgctc tctcttgtta tcacattgta ctgcaagcga  1020
ggtaggaaga aattgcttta catttttaag cagccgttca tgcgaccagt acagactact  1080
caagaagaag atgggtgctc ttgtcggttc ccggaagaag aagagggtgg ttgcgagttg  1140
agggtgaagt tctcccgctc tgccgacgca ccggcatatc agcagggaca aaaccagctc  1200
tacaacgaat tgaacctggg tcggcgggaa gaatatgacg tgctcgataa gcggcggggt  1260
cgcgacccag aaatgggagg caaaccgcgc aggaaaaatc cacaggaggg actttataac  1320
gaacttcaaa aggataagat ggcagaggca tacagcgaaa tcgggatgaa aggcgagaga  1380
agaaggggga aagggcacga tggtctttac cagggggcttt ctaccgcgac gaaggatacc  1440
tacgatgctc tccatatgca agcacttcct cctagacggg caaagcgggg ctcaggggcg  1500
actaactttt cactgttgaa gcaggccggg gatgtggagg agaatcctgg tcctagagct  1560
aagcgagtag acatgggaag agggctgctc cgaggcttgt ggccgttgca tattgtattg  1620
tggacgcgga tagcgagtac aatcccgcct cacgtgcaaa aatcagttaa taacgacatg  1680
atcgttactg acaacaatgg cgcagttaaa tttccgcagc tttgtaaatt ctgtgatgta  1740
agattttcaa cgtgcgataa ccagaaaagc tgtatgtcca actgcagcat cacatcaatc  1800
tgtgaaaaac cccaagaggt atgtgtggcc gtctggcgaa agaatgacga aaatatcaca  1860
ctggagaccg tttgtcacga tcctaaactc ccttatcatg actttattct ggaagacgca  1920
gcgtcaccga agtgtataat gaaagagaag aagaagcctg gagagacgtt tttcatgtgc  1980
agttgctcct cagatgagtg taatgacaac atcatttttt ccgaggagta caatacgagt  2040
aacccagacc tcctgctggt tattttccag gtaaccggca tcagtttgtt gcccccactg  2100
ggtgttgcaa tcagtgtaat aatcatattt tattgttacc gggtgtga              2148

SEQ ID NO: 170         moltype = AA  length = 715
FEATURE                Location/Qualifiers
source                 1..715
                       mol_type = protein
                       organism = Synthetic construct
SEQUENCE: 170
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGAAAT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PRRAKRGSGA TNFSLLKQAG DVEENPGPRA KRVDMGRGLL RGLWPLHIVL  540
WTRIASTIPP HVQKSVNNDM IVTDNNGAVK FPQLCKFCDV RFSTCDNQKS CMSNCSITSI  600
CEKPQEVCVA VWRKNDENIT LETVCHDPKL PYHDFILEDA ASPKCIMKEK KKPGETFFMC  660
SCSSDECNDN IIFSEEYNTS NPDLLLVIFQ VTGISLLPPL GVAISVIIIF YCYRV       715

SEQ ID NO: 171         moltype = DNA  length = 4605
FEATURE                Location/Qualifiers
source                 1..4605
                       mol_type = other DNA
                       organism = Synthetic construct
SEQUENCE: 171
atgctgctgc tggtgaccag cctgctgctg tgcgaactgc cgcatccggc gtttctgctg  60
attccggagg tccagctggt acagtctggg ggaggcttgg tacagcctgg ggggtccctg  120
agactctcct gtgcagcctc tggattcacc tttgatgatt atgccatgca ctgggtccgg  180
caagctccag ggaagggcct ggagtgggtc tcaggtatta gttggaatag tggtagcata  240
ggctatgcgg actctgtgaa gggccgattc accatctcca gagacaacgc caagaactcc  300
ctgtatctgc aaatgaacag tctgagagct gaggacacgg ccttgtatta ctgtgcaaaa  360
gatttatcgt cagtggctgg accctttaac tactggggcc agggcaccct ggtcaccgtc  420
tcctcaggag gtggcgggtc tggtggaggc ggtagcggcg gtggcggatc ctcttctgag  480
ctgactcagg accctgctgt gtctgtggcc ttgggacaga cagtcaggat cacatgccaa  540
ggagacagcc tcagaagcta ttatgcaagc tggtaccagc agaagccagg acaggcccct  600
gtacttgtca tctatggtaa aaacaaccgg ccctcaggga tcccagaccg attctctggc  660
tccagctcag gaaacacagc ttccttgacc atcactgggg ctcaggcgga ggatgaggct  720
gactattact gtaactcccg ggacagcagt ggtaaccatc tggtattcgg cggaggcacc  780
cagctgaccg tcctcggtgc ggccgctacc acaacccctg cgccccggcc tcctaccccc  840
gcacccacga ttgcttctca acctctttca ctccgacctg aggcttgtag acctgcagcc  900
gggggtgccg tccacacacg ggactcgac ttcgcttgtg atatatatat ttgggcgccc  960
ctggccggca cttgtggagt tcttttgctc tctcttgtta tcacattgta ctgcaagcga  1020
ggtaggaaga aattgcttta catttttaag cagccgttca tgcgaccagt acagactact  1080
caagaagaag atgggtgctc ttgtcggttc ccggaagaag aagagggtgg ttgcgagttg  1140
agggtgaagt tctcccgctc tgccgacgca ccggcatatc agcagggaca aaaccagctc  1200
tacaacgaat tgaacctggg tcggcgggaa gaatatgacg tgctcgataa gcggcggggt  1260
```

```
cgcgacccag aaatgggagg caaaccgcgc aggaaaaatc cacaggaggg actttataac  1320
gaacttcaaa aggataagat ggcagaggca tacagcgaaa tcgggatgaa aggcgagaga  1380
agaaggggga aagggcacga tggtctttac caggggcttt ctaccgcgac gaaggatacc  1440
tacgatgctc tccatatgca agcacttcct cctagacggg caaagcgggg ctcaggggcg  1500
actaactttt cactgttgaa gcaggccggg gatgtggagg agaatcctgg tcctagagct  1560
aagcgagtaa tgctcttgct cgtgacttct ttgcttttgt gcgaacttcc gcacccagcc  1620
ttcctttttga tacctatgga ttgtgatatt gaaggtaaag atggcaaaca atatgagagt  1680
gttctaatgg tcagcatcga tcaattattg gacagcatga aagaaattgg tagcaattgc  1740
ctgaataatg aatttaactt ttttaaaaga catatctgtg atgctaataa ggaaggtatg  1800
tttttattcc gtgctgctcg caagttgagg caatttctta aaatgaatag cactggtgat  1860
tttgatctcc acttattaaa agtttcagaa ggcacaacaa tactgttgaa ctgcactggc  1920
caggttaaag gaagaaaacc agctgccctg ggtgaagccc aaccaacaaa gagtttggaa  1980
gaaaataaat ctttaaagga acagaaaaaa ctgaatgact tgtgtttcct aaagagacta  2040
ttacaagaga taaaaacttg ttggaataaa attttgatgg gcactaaaga acactccgga  2100
ggttccggtg gtggctcagg tggtggctca ggtgaaagtg gctatgctca aaatggagac  2160
ttggaagatg cagaactgga tgactactca ttctcatgct atagccagtt ggaagtgaat  2220
ggatcgcagc actcactgac ctgtgctttt gaggacccag atgtcaacat caccaatctg  2280
gaatttgaaa tatgtggggc cctcgtggag gtaaagtgcc tgaatttcag gaaactacaa  2340
gagatatatt tcatcgagac aaagaaattc ttactgattg gaaagagcaa tatatgtgtg  2400
aaggttggag aaaagagtct aacctgcaaa aaaatagacc taaccactat agttaaacct  2460
gaggctcctt ttgacctgag tgtcgtctat cgggaaggag ccaatgactt tgtggtgaca  2520
tttaatacat cacacttgca aaagaagtat gtaaaagttt taatgcacga tgtagcttac  2580
cgccaggaaa aggatgaaaa caaatggacg catgtgaatt tatccagcac aaagctgaca  2640
ctcctgcaga gaaagctcca accggcagca atgtatgaga ttaaagttcg atccatccct  2700
gatcactatt ttaaaggctt ctggagtgaa tggagtccaa gttattactt cagaactcca  2760
gagatcaata atagctcagg ggagatggat cctatcttac taaccatcag cattttgagt  2820
tttttctctg tcgctctgtt ggtcatcttg gcctgtgtgt tatggaaaaa aaggattaag  2880
cctatcgtat ggcccagtct ccccgatcat aagaagactc tggaacatct ttgtaagaaa  2940
ccaagaaaaa atttgaatgt gagtttcaat cctgaaagtt tcctggactg ccagattcat  3000
agggtggatg acattcaagc tagagatgaa gtggaaggtt ttctgcaaga tacgtttcct  3060
cagcaactag aagaatctga gaagcagagg cttggagggg atgtgcagag ccccaactgc  3120
ccatctgagg atgtagtcat cactccagaa agctttggaa gagattcatc cctcacatgc  3180
ctggctggga atgtcagtgc atgtgacgcc cctattctct cctcttccag gtccctagac  3240
tgcagggaga gtggcaagaa tgggcctcat gtgtaccagg acctccttct tagccttggg  3300
actacaaaca gcacgctgcc ccctccattt tctctccaat ctggaatcct gacattgaac  3360
ccagttgctc agggtcagcc cattcttact tccctgggat caaatcaaga agaagcatat  3420
gtcaccatgt ccagcttcta ccaaaaccag cctaggcgcg cgaaacgcgg cagcggcgaa  3480
ggccgcggca gcctgctgac ctgcggcgat gtggaagaaa acccaggccc gatgatggca  3540
ctgcccgtga ccgccctgct tctgccgctt gcacttctgc tgcacgccgc taggcccagg  3600
aaggtttgca atggaatcgg tataggggag tttaaggatt cacttagcat aaacgctact  3660
aacattaaac acttcaaaaa ctgtacgagt ataagtggag atcttcacat tttgccggtt  3720
gcattccgag gcgattcatt cacccacacg ccaccgcttg acccacaaga attggatatt  3780
cttaaaaccg ttaaagaaat aacggggttt ttgctcattc aagcgtggcc agaaaatcgc  3840
actgacctcc atgctttcga gaacctggag attataagag gacgaactaa gcagcatggt  3900
caattctccc ttgctgtggt cagcctgaac atcaccagtc ttggtttgcg gtccctcaag  3960
gaaatttcag atggagatgt catcataagc ggcaacaaga atttgtgcta tgcaaatacc  4020
ataaactgga aaaaactgtt tggcacttcc ggccagaaaa ccaagattat ttcaaatcgg  4080
ggtgagaaca gctgcaaagc caccggccag gtttgtcatg ccttgtgctc tccggaaggc  4140
tgttgggggc cagaacccag ggactgcgtc agttgcagaa acgtctcaag aggccgcgaa  4200
tgcgttgaca agtgtaacct ccttgagggt gagccacgag agtttgttga gaacagcgag  4260
tgtatacaat gtcaccctga atgtttgccc caggctatga atataacctg cacaggccgc  4320
gggcctgata actgcatcca gtgtgctcat tacatagatg gacctcactg tgtgaaaacc  4380
tgcccggccg gagttatggg agaaaacaac actctggtgt ggaaatacgc tgatgcaggc  4440
cacgtgtgcc acctttgtca cccgaattgc acatatgggt gtaccggtcc tggacttgaa  4500
ggttgcccta ccaatggccc taaaataccc agtatcgcaa ctggcatggt aggcgctctt  4560
ctcttgctct tggtagttgc tctcggcata ggtcttttta tgtga                 4605
```

```
SEQ ID NO: 172          moltype = AA  length = 1534
FEATURE                 Location/Qualifiers
source                  1..1534
                        mol_type = protein
                        organism = Synthetic construct
SEQUENCE: 172
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGAAAT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PRRAKRGSGA TNFSLLKQAG DVEENPGPRA KRVMLLLVTS LLLCELPHPA  540
FLLIPMDCDI EGKDGKQYES VLMVSIDQLL DSMKEIGSNC LNNEFNFFKR HICDANKEGM  600
FLFRAARKLR QFLKMNSTGD FDLHLLKVSE GTTILLNCTG QVKGRKPAAL GEAQPTKSLE  660
ENKSLKEQKK LNDLCFLKRL LQEIKTCWNK ILMGTKEHSG GSGGGSGGGS GESGYAQNGD  720
LEDAELDDYS FSCYSQLEVN GSQHSLTCAF EDPDVNITNL EFEICGALVE VKCLNFRKLQ  780
EIYFIETKKF LLIGKSNICV KVGEKSLTCK KIDLTTIVKP EAPFDLSVVY REGANDFVVT  840
FNTSHLQKKY VKVLMHDVAY RQEKDENKWT HVNLSSTKLT LLQRKLQPAA MYEIKVRSIP  900
DHYFKGFWSE WSPSYYFRTP EINNSSGEMD PILLTISILS FFSVALLVIL ACVLWKKRIK  960
```

```
PIVWPSLPDH KKTLEHLCKK PRKNLNVSFN PESFLDCQIH RVDDIQARDE VEGFLQDTFP  1020
QQLEESEKQR LGGDVQSPNC PSEDVVITPE SFGRDSSLTC LAGNVSACDA PILSSSRSLD  1080
CRESGKNGPH VYQDLLLSLG TTNSTLPPPF SLQSGILTLN PVAQGQPILT SLGSNQEEAY  1140
VTMSSFYQNQ PRRAKRGSGE GRGSLLTCGD VEENPGPMMA LPVTALLLPL ALLLHAARPR  1200
KVCNGIGIGE FKDSLSINAT NIKHFKNCTS ISGDLHILPV AFRGDSFTHT PPLDPQELDI  1260
LKTVKEITGF LLIQAWPENR TDLHAFENLE IIRGRTKQHG QFSLAVVSLN ITSLGLRSLK  1320
EISDGDVIIS GNKNLCYANT INWKKLFGTS GQKTKIISNR GENSCKATGQ VCHALCSPEG  1380
CWGPEPRDCV SCRNVSRGRE CVDKCNLLEG EPREFVENSE CIQCHPECLP QAMNITCTGR  1440
GPDNCIQCAH YIDGPHCVKT CPAGVMGENN TLVWKYADAG HVCHLCHPNC TYGCTGPGLE  1500
GCPTNGPKIP SIATGMVGAL LLLLVVALGI GLFM                             1534

SEQ ID NO: 173          moltype = DNA  length = 2187
FEATURE                 Location/Qualifiers
source                  1..2187
                        mol_type = other DNA
                        organism = Synthetic construct
SEQUENCE: 173
atgctgttac ttgtgacaag cttgcttcta tgtgaactgc cgcatccggc gtttctgctg  60
attccggaag tacagctggt acagtctgga gggggattgg ttcagccggg cgggtctttg  120
cgcctgtcct gcgcagctag tggcttcact tttgatgact atgctatgca ctgggtcaga  180
caagcgcctg gcaaaggcct tgaatgggtg tccggaatta gctggaatag tggatccatc  240
ggctatgccg atagtgtaaa gggcaggttc acgatcagcc gggataatgc aaagaactct  300
ctctatttgc aaatgaacag tctgcgggct gaagatactg ctctttacta ttgtgctaaa  360
gatttgtcaa gcgtcgccgg acccttcaac tactggggtc aagggacact ggtgacagtt  420
agcagcggtg gtggaggctc cggtggaggt ggtagtggtg gaggaggtag ttcttctgag  480
cttacgcaag atccggcggt tagtgttgct ctggggcaga ctgtacgaat cacgtgccag  540
ggtgactctt tgcgctctta ctacgctagt tggtatcaac aaaaacccgg acaagcgccc  600
gtcctcgtca tctatggcaa gaacaatcgc ccaagcggca tccctgatag gttctccgga  660
tcatcttcag ggaacacagc ctccctgact attacaggtg ctcaagctga ggacgaggct  720
gactattatt gcaacagccg ggactctagc ggtaaccact tggtctttgg tgggggtacc  780
cagctgacgg tacttggagg tggtggaggt tcaggtggtg gcggatcagg tggaggtggt  840
tctggagggg gtggaagtgg cggaggtggt tcacaggcgg cccaggtaca gctgcagcag  900
tcaggggctg aggtgaagaa gcctgggtcc tcggtgaagg tctcctgcaa ggcttctgga  960
ggcaccttca gcagctatgc tatcagctgg gtgcgacagg cccctggaca agggcttgag  1020
tggatgggat ggatcaaccc taacagtggt ggcacaaact atgcacagag gtttcagggc  1080
agggtcacca tgaccaggga cacgtccatc agcacagcct acatggagtt gagcaggctg  1140
agatctgacg acacggccgt gtattactgt gcgagttata atgatgcttt tgatatctgg  1200
ggccaaggca ccctggtcac cgtctcctca ggaggtggcg ggtctggtgg tggcggtagc  1260
ggaggtggtg gatctaattt tatgctgact cagccccact ctgtgtcgga gtctccgggg  1320
aagacggtaa ccatctcctg cacccgcagc agtggcagca ttgccagcaa ctatgtgcag  1380
tggtaccagc agcgaccggg cagtgccccc accattgtga tctatgagga tgatcaaaga  1440
ccctctgggg tccctgatcg gttctctggc tccatcgaca cctcctccaa ctctgcctcc  1500
ctcaccatct ctggactgca gagtgaggac gaggctgact actactgtca gtcttatgag  1560
cccggcaatg gggtattcgg cggagggacc aaggtcaccg tcctagcggc cgcagagtca  1620
aaatacggtc ctccgtgccc tccgtgtccg atctacattt gggcccccgct ggccggcact  1680
tgcggcgtgc tcctgctgtc gctggtcatc accctttact gcaagagggg ccggaagaag  1740
ctgctttaca tcttcaagca gccgttcatg cggcccgtgc agacgactca ggaagaggac  1800
ggatgctcgt gcagattccc tgaggaggaa gagggggggat gcgaactgcg cgtcaagttc  1860
tcacggtccg ccgacgcccc cgcatatcaa cagggccaga atcagctcta caacgagctg  1920
aacctgggaa ggagagagga gtacgacgtg ctggacaagc gacgcggacg cgacccggag  1980
atgggggggga aaccacggcg gaaaaaccct caggaaggac tgtacaacga actccagaaa  2040
gacaagatgg cggaagccta ctcagaaatc gggatgaagg gagagcggag gaggggaaag  2100
ggtcacgacg ggctgtacca gggactgagc accgccacta aggataccta cgatgccttg  2160
catatgcaag cactcccacc ccggtag                                     2187

SEQ ID NO: 174          moltype = AA  length = 728
FEATURE                 Location/Qualifiers
source                  1..728
                        mol_type = protein
                        organism = Synthetic construct
SEQUENCE: 174
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGGGGG SGGGGSGGGG SGGGGSGGGG SQAAQVQLQQ  300
SGAEVKKPGS SVKVSCKASG GTFSSYAISW VRQAPGQGLE WMGWINPNSG GTNYAQRFQG  360
RVTMTRDTSI STAYMELSRL RSDDTAVYYC ASYNDAFDIW GQGTLVTVSS GGGGSGGGGS  420
GGGGSNFMLT QPHSVSESPG KTVTISCTRS SGSIASNYVQ WYQQRPGSAP TIVIYEDDQR  480
PSGVPDRFSG SIDTSSNSAS LTISGLQSED EADYYCQSYE PGNGVFGGGT KVTVLAAAES  540
KYGPPCPPCP IYIWAPLAGT CGVLLLSLVI TLYCKRGRKK LLYIFKQPFM RPVQTTQEED  600
GCSCRFPEEE EGGCELRVKF SRSADAPAYQ QGQNQLYNEL NLGRREEYDV LDKRRGRDPE  660
MGGKPRRKNP QEGLYNELQK DKMAEAYSEI GMKGERRRGK GHDGLYQGLS TATKDTYDAL  720
HMQALPPR                                                          728

SEQ ID NO: 175          moltype = DNA  length = 4164
FEATURE                 Location/Qualifiers
source                  1..4164
                        mol_type = other DNA
```

organism = Synthetic construct
SEQUENCE: 175
atgctgttac ttgtgacaag cttgcttcta tgtgaactgc cgcatccggc gtttctgctg 60
attccggaag tacagctggt acagtctgga gggggattgg ttcagccggg cgggtctttg 120
cgcctgtcct gcgcagctag tggcttcact tttgatgact atgctatgca ctgggtcaga 180
caagcgcctg gcaaaggcct tgaatgggtg tccggaatta gctggaatag tggatccatc 240
ggctatgccg atagtgtaaa gggcaggttc acgatcagcc gggataatgc aaagaactct 300
ctctatttgc aaatgaacag tctgcgggct gaagatactg ctctttacta ttgtgctaaa 360
gatttgtcaa gcgtcgccgg acccttcaac tactggggtc aagggacact ggtgacagtt 420
agcagcggtg gtggaggctc cggtggaggt ggtagtggtg gaggaggtag ttcttctgag 480
cttacgcaag atccggcggt tagtgttgct ctggggcaga ctgtacgaat cacgtgccag 540
ggtgactctt tgcgctctta ctacgctagt tggtatcaac aaaaacccgg acaagcgccc 600
gtcctcgtca tctatggcaa gaacaatcgc ccaagcggca tccctgatag gttctccgga 660
tcatcttcag ggaacacagc ctccctgact attacaggtg ctcaagctga ggacgaggct 720
gactattatt gcaacagccg ggactctagc ggtaaccact tggtctttgg tgggggtacc 780
cagctgacgg tacttggagg tggtggaggt tcaggtggtg gcggatcagg tggaggtggt 840
tctggagggg gtggaagtgg cggaggtggt tcacaggcgg cccaggtaca gctgcagcag 900
tcaggggctg aggtgaagaa gcctgggtcc tcggtgaagg tctcctgcaa ggcttctgga 960
ggcaccttca gcagctatgc tatcagctgg gtgcgacagg cccctggaca agggcttgag 1020
tggatgggat ggatcaaccc taacagtggt ggcacaaact atgcacagag gtttcagggc 1080
agggtcacca tgaccaggga cacgtccatc agcacagcct acatggagtt gagcaggctg 1140
agatctgacg acacggccgt gtattactgt gcgagttata atgatgcttt tgatatctgg 1200
ggccaaggca ccctggtcac cgtctcctca ggaggtggcg ggtctggtgg tggcggtagc 1260
ggtggtggcg gatccaattt tatgctgact cagccccact ctgtgtcgga gtctccgggg 1320
aagacggtaa ccatctcctg cacccgcagc agtggcagca ttgccagcaa ctatgtgcag 1380
tggtaccagc agcgcccggg cagtgccccc accattgtga tctatgagga tgatcaaaga 1440
ccctctgggg tccctgatcg gttctctggc tccatcgaca cctcctccaa ctctgcctcc 1500
ctcaccatct ctggactgca gagtgaggac gaggctgact actactgtca gtcttatgag 1560
cccggcaatg ggggtattcgg cggagggacc aaggtcaccg tcctagctgc cgcagagtca 1620
aaatacggtc ctccgtgccc tccgtgtccg atctacattt gggccccgct ggccggcact 1680
tgcggcgtgc tcctgctgtc gctggtcatc accctttact gcaagcgcgg ccgcaagaaa 1740
ttgctttaca tttttaagca gccgttcatg cgaccagtac agactactca agaagaagat 1800
gggtgctctt gtcggttccc ggaagaagaa gagggtggtt gcgagttgag ggtgaagttc 1860
tcccgctctg ccgacgcacc ggcatatcag cagggacaaa accagctcta caacgaattg 1920
aacctgggtc ggcgggaaga atatgacgtg ctcgataagc ggcggggtcg cgacccagaa 1980
atgggaggca aaccgcgcag gaaaaatcca caggagggac tttataacga acttcaaaag 2040
gataagatgg cagaggcata cagcgaaatc gggatgaaag gcgagagaag aaggggggaaa 2100
gggcacgatg gtctttacca ggggctttct accgcgacga aggataccta cgatgctctc 2160
catatgcaag cacttcctcc tagacgggca aagcggggct caggggcgac taacttttca 2220
ctgttgaagc aggccgggga tgtggaggag aatcctggtc ctagagctaa gcgagtaatg 2280
ctcttgctcg tgacttcttt gcttttgtgc gaacttccgc acccagcctt ccttttgata 2340
cctatggatt gtgatattga aggtaaagat ggcaaacaat atgagagtgt tctaatggtc 2400
agcatcgatc aattattgga cagcatgaaa gaaattggta gcaattgcct gaataatgaa 2460
tttaactttt ttaaaagaca tatctgtgat gctaataagg aaggtatgtt tttattccgt 2520
gctgctcgca agttgaggca atttcttaaa atgaatagca ctggtgattt tgatctccac 2580
ttattaaaag tttcagaagg cacaacaata ctgttgaact gcactggcca ggttaaagga 2640
agaaaaccag ctgccctggg tgaagcccaa ccaacaaaga gtttggaaga aaataaatct 2700
ttaaaggaac agaaaaaact gaatgacttg tgtttcctaa agagactatt acaagagata 2760
aaaacttgtt ggaataaaat tttgatgggc actaaagaac actccggagg ttccggtggt 2820
ggctcaggtg gtggctcagg tgaaagtggc tatgctcaaa atggagactt ggaagatgca 2880
gaactggatg actactcatt ctcatgctat agccagttgg aagtgaatgg atcgcagcac 2940
tcactgacct gtgcttttga ggacccagat gtcaacatca ccaatctgga atttgaaata 3000
tgtggggccc tcgtggaggt aaagtgcctg aatttcagga aactacaaga gatatatttc 3060
atcgagacaa agaaattctt actgattgga aagagcaata tatgtgtgaa ggttggagaa 3120
aagagtctaa cctgcaaaaa aatagaccta accactatag ttaaacctga ggctcctttt 3180
gacctgagtg tcgtctatcg ggaaggagcc aatgactttg tggtgacatt taatacatca 3240
cacttgcaaa agaagtatgt aaaagtttta atgcacgatg tagcttaccg ccaggaaaag 3300
gatgaaaaca aatggacgca tgtgaattta tccagcacaa agctgacact cctgcagaga 3360
aagctccaac cggcagcaat gtatgagatt aaagttcgat ccatccctga tcactatttt 3420
aaaggcttct ggagtgaatg gagtccaagt tattacttca gaactccaga gatcaataat 3480
agctcagggg agatggatcc tatcttacta accatcagca ttttgagttt tttctctgtc 3540
gctctgttgg tcatcttggc ctgtgtgtta tggaaaaaaa ggattaagcc tatcgtatgg 3600
cccagtctcc ccgatcataa gaagactctg gaacatcttt gtaagaaacc aagaaaaaat 3660
ttaaatgtga gtttcaatcc tgaaagtttc ctggactgcc agattcatag ggtggatgac 3720
attcaagcta gagatgaagt ggaaggtttt ctgcaagata cgtttcctca gcaactagaa 3780
gaatctgaga agcagaggct tggaggggat gtgcagagcc ccaactgccc atctgaggat 3840
gtagtcatca ctccagaaag ctttggaaga gattcatccc tcacatgcct ggctgggaat 3900
gtcagtgcat gtgacgcccc tattctctcc tcttccaggt ccctagactg cagggagagt 3960
ggcaagaatg ggcctcatgt gtaccaggac ctccttctta gccttgggac tacaaacagc 4020
acgctgcccc ctccatttc tctccaatct ggaatcctga cattgaaccc agttgctcag 4080
ggtcagccca ttcttacttc cctgggatca aatcaagaag aagcatatgt caccatgtcc 4140
agcttctacc aaaaccagcc ctag 4164

SEQ ID NO: 176 moltype = AA length = 1387
FEATURE Location/Qualifiers
source 1..1387
mol_type = protein
organism = Synthetic construct
SEQUENCE: 176

```
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGGGGG SGGGGSGGGG SGGGGSGGGG SQAAQVQLQQ  300
SGAEVKKPGS SVKVSCKASG GTFSSYAISW VRQAPGQGLE WMGWINPNSG GTNYAQRFQG  360
RVTMTRDTSI STAYMELSRL RSDDTAVYYC ASYNDAPDIW GQGTLVTVSS GGGGSGGGGS  420
GGGGSNFMLT QPHSVSESPG KTVTISCTRS SGSIASNYVQ WYQQRPGSAP TIVIYEDDQR  480
PSGVPDRFSG SIDTSSNSAS LTISGLQSED EADYYCQSYE PGNGVFGGGT KVTVLAAAES  540
KYGPPCPPCP IYIWAPLAGT CGVLLLSLVI TLYCKRGRKK LLYIFKQPFM RPVQTTQEED  600
GCSCRFPEEE EGGCELRVKF SRSADAPAYQ QGQNQLYNEL NLGRREEYDV LDKRRGRDPE  660
MGGKPRRKNP QEGLYNELQK DKMAEAYSEI GMKGERRRGK GHDGLYQGLS TATKDTYDAL  720
HMQALPPRRA KRGSGATNFS LLKQAGDVEE NPGPRAKRVM LLLVTSLLLC ELPHPAFLLI  780
PMDCDIEGKD GKQYESVLMV SIDQLLDSMK EIGSNCLNNE FNFFKRHICD ANKEGMFLFR  840
AARKLRQFLK MNSTGDFDLH LLKVSEGTTI LLNCTGQVKG RKPAALGEAQ PTKSLEENKS  900
LKEQKKLNDL CFLKRLLQEI KTCWNKILMG TKEHSGGSGG GSGGGSGESG YAQNGDLEDA  960
ELDDYSFSCY SQLEVNGSQH SLTCAFEDPD VNITNLEFEI CGALVEVKCL NFRKLQEIYF  1020
IETKKFLLIG KSNICVKVGE KSLTCKKIDL TTIVKPEAPF DLSVVYREGA NDFVVTFNTS  1080
HLQKKYVKVL MHDVAYRQEK DENKWTHVNL SSTKLTLLQR KLQPAAMYEI KVRSIPDHYF  1140
KGFWSEWSPS YYFRTPEINN SSGEMDPILL TISILSFFSV ALLVILACVL WKKRIKPIVW  1200
PSLPDHKKTL EHLCKKPRKN LNVSFNPESF LDCQIHRVDD IQARDEVEGF LQDTFPQQLE  1260
ESEKQRLGGD VQSPNCPSED VVITPESFGR DSSLTCLAGN VSACDAPILS SSRSLDCRES  1320
GKNGPHVYQD LLLSLGTTNS TLPPPFSLQS GILTLNPVAQ GQPILTSLGS NQEEAYVTMS  1380
SFYQNQP                                                            1387

SEQ ID NO: 177          moltype = DNA  length = 4296
FEATURE                 Location/Qualifiers
source                  1..4296
                        mol_type = other DNA
                        organism = Synthetic construct
SEQUENCE: 177
atgctgttac ttgtgacaag cttgcttcta tgtgaactgc cgcatccggc gtttctgctg  60
attccggaag tacagctggt acagtctgga gggggattgg ttcagccggg cgggtctttg  120
cgcctgtcct gcgcagctag tggcttcact tttgatgact atgctatgca ctgggtcaga  180
caagcgcctg gcaaaggcct tgaatgggtg tccggaatta gctggaatag tggatccatc  240
ggctatgccg atagtgtaaa gggcaggttc acgatcagcc gggataatgc aaagaactct  300
ctctatttgc aaatgaacag tctgcgggct gaagatactg ctctttacta ttgtgctaaa  360
gatttgtcaa gcgtcgccgg acccttcaac tactggggtc aagggacact ggtgacagtt  420
agcagcggtg gtggaggctc cggtggaggt ggtagtggtg gaggaggtag ttcttctgag  480
cttacgcaag atccggcggt tagtgttgct ctggggcaga ctgtacgaat cacgtgccag  540
ggtgactctt tgcgctctta ctacgctagt tggtatcaac aaaaacccgg acaagcgccc  600
gtcctcgtca tctatggcaa gaacaatcgc ccaagcggca tccctgatag gttctccgga  660
tcatcttcag ggaacacagc ctccctgact attacaggtg ctcaagctga ggacgaggct  720
gactattatt gcaacagccg ggactctagc ggtaaccact tggtctttgg tgggggtacc  780
cagctgacgg tacttggagg tggtggaggt tcaggtggtg gcggatcagg tggaggtggt  840
tctggagggg gtggaagtgg cggaggtggt tcacaggcgg cccaggtaca gctgcagcag  900
tcaggggctg aggtgaagaa gcctgggtcc tcggtgaagg tctcctgcaa ggcttctgga  960
ggcaccttca gcagctatgc tatcagctgg gtgcgacagg cccctggaca agggcttgag  1020
tggatgggat ggatcaaccc taacagtggt ggcacaaact atgcacagag gtttcagggc  1080
agggtcacca tgaccaggga cacgtccatc agcacagcct acatggagtt gagcaggctg  1140
agatctgacg acacggccgt gtattactgt gcgagttata atgatgcttt tgatatctgg  1200
ggccaaggca ccctggtcac cgtctcctca ggaggtggcg ggtctggtgg tggcggtagc  1260
ggtggtggcg gatccaattt tatgctgact cagccccact ctgtgtcgga gtctccgggg  1320
aagacggtaa ccatctcctg cacccgcagc agtggcagca ttgccagcaa ctatgtgcag  1380
tggtaccagc agcgcccggg cagtgccccc accattgtga tctatgagga tgatcaaaga  1440
ccctctgggg tccctgatcg gttctctggc tccatcgaca cctcctccaa ctctgcctcc  1500
ctcaccatct ctggactgca gagtgaggac gaggctgact actactgtca gtcttatgag  1560
cccggcaatg ggggtattcgg cggagggacc aaggtcaccg tcctagcggc cgcagagtca  1620
aaatacggtc ctccgtgccc tccgtgtccg ttctgggtgc ttgtcgttgt tgggggtgta  1680
ctcgcatgtt attctttgct ggtgactgtg gcgtttatca tcttctgggt aaggagtaaa  1740
cgcagccgcc tgctgcattc agactacatg aacatgaccc cacggcggcc cggcccaacg  1800
cgcaaacact accaacctta cgccccaccg cgagactttg ccgcctacag atccaagcgc  1860
ggacggaaga aactcttgta catcttcaag cagccgttca tgcgccctgt gcaaaccacc  1920
caagaagagg acgggtgctc ctgccggttc ccggaagagg aagagggcgg ctgcgaactg  1980
cgcgtgaagt tttcccggtc cgccgacgct ccggcgtacc agcaggggca aaaccagctg  2040
tacaacgaac ttaacctcgg tcgccgggaa gaatatgacg tgctggacaa gcggcgggga  2100
agagatcccg agatgggtgg aaagccgcgg cggaagaacc ctcaggaggg cttgtacaac  2160
gagctgcaaa aggacaaaat ggccgaagcc tactccgaga ttggcatgaa gggagagcgc  2220
agacgcggga agggacacga tggactgtac cagggactgt caaccgcgac taaggacact  2280
tacgacgccc tgcacatgca ggccctgccc ccgcgccggg caaagcgggg ctcaggggcg  2340
actaactttt cactgttgaa gcaggccggg gatgtggagg agaatcctgg tcctagagct  2400
aagcgagtaa tgctcttgct cgtgacttct ttgcttttgt gcgaacttcc gcacccagcc  2460
ttccttttga tacctatgga ttgtgatatt gaaggtaaag atggcaaaca atatgagagt  2520
gttctaatgg tcagcatcga tcaattattg gacagcatga aagaaattgg tagcaattgc  2580
ctgaataatg aatttaactt ttttaaaaga catatctgtg atgctaataa ggaaggtatg  2640
tttttattcc gtgctgctcg caagttgagg caatttctta aaatgaatag cactggtgat  2700
tttgatctcc acttattaaa agtttcagaa ggcacaacaa tactgttgaa ctgcactggc  2760
caggttaaag gaagaaaacc agctgccctg ggtgaagccc aaccaacaaa gagtttggaa  2820
gaaaataaat ctttaaagga acagaaaaaa ctgaatgact tgtgtttcct aaagagacta  2880
```

```
ttacaagaga taaaaacttg ttggaataaa attttgatgg gcactaaaga acactccgga  2940
ggttccggtg gtggctcagg tggtggctca ggtgaaagtg gctatgctca aaatggagac  3000
ttggaagatg cagaactgga tgactactca ttctcatgct atagccagtt ggaagtgaat  3060
ggatcgcagc actcactgac ctgtgctttt gaggacccag atgtcaacat caccaatctg  3120
gaatttgaaa tatgtggggc cctcgtggag gtaaagtgcc tgaatttcag gaaactacaa  3180
gagatatatt tcatcgagac aaagaaattc ttactgattg gaaagagcaa tatatgtgtg  3240
aaggttggag aaaagagtct aacctgcaaa aaaatagacc taaccactat agttaaacct  3300
gaggctcctt ttgacctgag tgtcgtctat cgggaaggag ccaatgactt tgtggtgaca  3360
tttaatacat cacacttgca aaagaagtat gtaaaagttt taatgcacga tgtagcttac  3420
cgccaggaaa aggatgaaaa caaatggacg catgtgaatt tatccagcac aaagctgaca  3480
ctcctgcaga gaaagctcca accggcagca atgtatgaga ttaaagttcg atccatccct  3540
gatcactatt ttaaaggctt ctggagtgaa tggagtccaa gttattactt cagaactcca  3600
gagatcaata atagctcagg ggagatggat cctatcttac taaccatcag cattttgagt  3660
tttttctctg tcgctctgtt ggtcatcttg gcctgtgtgt tatggaaaaa aaggattaag  3720
cctatcgtat ggcccagtct ccccgatcat aagaagactc tggaacatct ttgtaagaaa  3780
ccaagaaaaa atttaaatgt gagtttcaat cctgaaagtt tcctggactg ccagattcat  3840
agggtggatg acattcaagc tagagatgaa gtggaaggtt ttctgcaaga tacgtttcct  3900
cagcaactag aagaatctga gaagcagagg cttggagggg atgtgcagag ccccaactgc  3960
ccatctgagg atgtagtcat cactccagaa agctttggaa gagattcatc cctcacatgc  4020
ctggctggga atgtcagtgc atgtgacgcc cctattctct cctcttccag gtccctagac  4080
tgcagggaga gtggcaagaa tgggcctcat gtgtaccagg acctccttct tagccttggg  4140
actacaaaca gcacgctgcc ccctcccatt tctctccaat ctggaatcct gacattgaac  4200
ccagttgctc agggtcagcc cattcttact tccctgggat caaatcaaga agaagcatat  4260
gtcaccatgt ccagcttcta ccaaaaccag ccctag                            4296

SEQ ID NO: 178         moltype = AA  length = 1431
FEATURE                Location/Qualifiers
source                 1..1431
                       mol_type = protein
                       organism = Synthetic construct
SEQUENCE: 178
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGGGGG SGGGGSGGGG SGGGGSGGGG SQAAQVQLQQ  300
SGAEVKKPGS SVKVSCKASG GTFSSYAISW VRQAPGQGLE WMGWINPNSG GTNYAQRFQG  360
RVTMTRDTSI STAYMELSRL RSDDTAVYYC ASYNDAFDIW GQGTLVTVSS GGGGSGGGGS  420
GGGGSNFMLT QPHSVSESPG KTVTISCTRS SGSIASNYVQ WYQQRPGSAP TIVIYEDDQR  480
PSGVPDRFSG SIDTSSNSAS LTISGLQSED EADYYCQSYE PGNGVFGGGT KVTVLAAAES  540
KYGPPCPPCP FWVLVVVGGV LACYSLLVTV AFIIFWVRSK RSRLLHSDYM NMTPRRPGPT  600
RKHYQPYAPP RDFAAYRSKR GRKKLLYIFK QPFMRPVQTT QEEDGCSCRF PEEEEGGCEL  660
RVKFSRSADA PAYQQGQNQL YNELNLGRRE EYDVLDKRRG RDPEMGGKPR RKNPQEGLYN  720
ELQKDKMAEA YSEIGMKGER RRGKGHDGLY QGLSTATKDT YDALHMQALP PRRAKRGSGA  780
TNFSLLKQAG DVEENPGPRA KRVMLLLVTS LLLCELPHPA FLLIPMDCDI EGKDGKQYES  840
VLMVSIDQLL DSMKEIGSNC LNNEFNFFKR HICDANKEGM FLFRAARKLR QFLKMNSTGD  900
FDLHLLKVSE GTTILLNCTG QVKGRKPAAL GEAQPTKSLE ENKSLKEQKK LNDLCFLKRL  960
LQEIKTCWNK ILMGTKEHSG GSGGGSGGGS GESGYAQNGD LEDAELDDYS FSCYSQLEVN  1020
GSQHSLTCAF EDPDVNITNL EFEICGALVE VKCLNFRKLQ EIYFIETKKF LLIGKSNICV  1080
KVGEKSLTCK KIDLTTIVKP EAPFDLSVVY REGANDFVVT FNTSHLQKKY VKVLMHDVAY  1140
RQEKDENKWT HVNLSSTKLT LLQRKLQPAA MYEIKVRSIP DHYFKGFWSE WSPSYYFRTP  1200
EINNSSGEMD PILLTISILS FFSVALLVIL ACVLWKKRIK PIVWPSLPDH KKTLEHLCKK  1260
PRKNLNVSFN PESFLDCQIH RVDDIQARDE VEGFLQDTFP QQLEESEKQR LGGDVQSPNC  1320
PSEDVVITPE SFGRDSSLTC LAGNVSACDA PILSSSRSLD CRESGKNGPH VYQDLLLSLG  1380
TTNSTLPPPF SLQSGILTLN PVAQGQPILT SLGSNQEEAY VTMSSFYQNQ P           1431

SEQ ID NO: 179         moltype = DNA  length = 4287
FEATURE                Location/Qualifiers
source                 1..4287
                       mol_type = other DNA
                       organism = Synthetic construct
SEQUENCE: 179
atgctgttac ttgtgacaag cttgcttcta tgtgaactgc cgcatccggc gtttctgctg  60
attccggaag tacagctggt acagtctgga gggggattgg ttcagccggg cgggtctttg  120
cgcctgtcct gcgcagctag tggcttcact tttgatgact atgctatgca ctgggtcaga  180
caagcgcctg gcaaaggcct tgaatgggtg tccggaatta gctggaatag tggatccatc  240
ggctatgccg atagtgtaaa gggcaggttc acgatcagcc gggataatgc aaagaactct  300
ctctatttgc aaatgaacag tctgcgggct gaagatactg ctctttacta ttgtgctaaa  360
gatttgtcaa gcgtcgccgg acccttcaac tactggggtc aagggacact ggtgacagtt  420
agcagcggtg gtggaggctc cggtggaggt ggtagtggtg gaggaggtag ttcttctgag  480
cttacgcaag atccggcggt tagtgttgct ctggggcaga ctgtacgaat cacgtgccag  540
ggtgactctt tgcgctctta ctacgctagt tggtatcaac aaaaacccgg acaagcgccc  600
gtcctcgtca tctatggcaa gaacaatcgc ccaagcggca tccctgatag gttctccgga  660
tcatcttcag ggaacacagc ctccctgact attacaggtg ctcaagctga ggacgaggct  720
gactattatt gcaacagccg ggactctagc ggtaaccact tggtctttgg tgggggtacc  780
cagctgacgg tacttggagg tggtggaggt tcaggtggtg gcggatcagg tggaggtggt  840
tctggagggg gtggaagtgg cggaggtggt tcacaggcgg cccaggtaca gctgcagcag  900
tcaggggctg aggtgaagaa gcctgggtcc tcggtgaagg tctcctgcaa ggcttctgga  960
ggcaccttca gcagctatgc tatcagctgg gtgcgacagg cccctggaca agggcttgag  1020
```

```
tggatgggat ggatcaaccc taacagtggt ggcacaaact atgcacagag gtttcagggc  1080
agggtcacca tgaccaggga cacgtccatc agcacagcct acatggagtt gagcaggctg  1140
agatctgacg acacggccgt gtattactgt gcgagttata atgatgcttt tgatatctgg  1200
ggccaaggca ccctggtcac cgtctcctca ggaggtggcg ggtctggtgg tggcggtagc  1260
ggtggtggcg gatccaattt tatgctgact cagccccact ctgtgtcgga gtctccgggg  1320
aagacggtaa ccatctcctg cacccgcagc agtggcagca ttgccagcaa ctatgtgcag  1380
tggtaccagc agcgcccggg cagtgccccc accattgtga tctatgagga tgatcaaaga  1440
ccctctgggg tccctgatcg gttctctggc tccatcgaca cctcctccaa ctctgcctcc  1500
ctcaccatct ctggactgca gagtgaggac gaggctgact actactgtca gtcttatgag  1560
cccggcaatg ggtattcgg cggagggacc aaggtcaccg tcctagcggc cgcagagtca  1620
aaatacggtc ctccgtgccc tccgtgtccg atctacatct gggccccatt ggctggaact  1680
tgcggcgtgc tgctcttgtc tctggtcatt accctgtact gcaggagtaa acgcagccgc  1740
ctgctgcatt cagactacat gaacatgacc ccacggcggc ccggcccaac gcgcaaacac  1800
taccaacctt acgccccacc gcgagacttt gccgcctaca gatccaagcg cggacggaag  1860
aaactcttgt acatcttcaa gcagccgttc atgcgccctg tgcaaaccac ccaagaagag  1920
gacgggtgct cctgccggtt cccggaagag gaagagggcg gctgcgaact gcgcgtgaag  1980
ttttcccggt ccgccgacgc tccggcgtac cagcaggggc aaaaccagct gtacaacgaa  2040
cttaacctcg gtcgccggga agaatatgac gtgctggaca agcggcgggg aagagatccc  2100
gagatgggtg gaaagccgcg gcggaagaac cctcaggagg gcttgtacaa cgagctgcaa  2160
aaggacaaaa tggccgaagc ctactccgag attggcatga agggagagcg cagacgcggg  2220
aagggacacg atggactgta ccagggactg tcaaccgcga ctaaggacac ttacgacgcc  2280
ctgcacatgc aggccctgcc cccgcgccgg gcaaagcggg gctcaggggc gactaacttt  2340
tcactgttga agcaggccgg ggatgtggag gagaatcctg gtcctagagc taagcgagta  2400
atgctcttgc tcgtgacttc tttgcttttg tgcgaacttc cgcacccagc cttccttttg  2460
atacctatgg attgtgatat tgaaggtaaa gatggcaaac aatatgagag tgttctaatg  2520
gtcagcatcg atcaattatt ggacagcatg aaagaaattg gtagcaattg cctgaataat  2580
gaatttaact tttttaaaag acatatctgt gatgctaata aggaaggtat gtttttattc  2640
cgtgctgctc gcaagttgag gcaatttctt aaaatgaata gcactggtga ttttgatctc  2700
cacttattaa aagtttcaga aggcacaaca atactgttga actgcactgg ccaggttaaa  2760
ggaagaaaac cagctgccct gggtgaagcc caaccaacaa agagtttgga agaaaataaa  2820
tctttaaagg aacagaaaaa actgaatgac ttgtgtttcc taaagagact attacaagag  2880
ataaaaactt gttggaataa aattttgatg ggcactaaag aacactccgg aggttccggt  2940
ggtggctcag gtggtggctc aggtgaaagt ggctatgctc aaaatggaga cttggaagat  3000
gcagaactgg atgactactc attctcatgc tatagccagt tggaagtgaa tggatcgcag  3060
cactcactga cctgtgcttt tgaggaccca gatgtcaaca tcaccaatct ggaatttgaa  3120
atatgtgggg ccctcgtgga ggtaaagtgc ctgaatttca ggaaactaca agagatatat  3180
ttcatcgaga caaagaaatt cttactgatt ggaaagagca atatatgtgt gaaggttgga  3240
gaaaagagtc taacctgcaa aaaaatagac ctaaccacta tagttaaacc tgaggctcct  3300
tttgacctga gtgtcgtcta tcgggaagga gccaatgact ttgtggtgac atttaataca  3360
tcacacttgc aaaagaagta tgtaaaagtt ttaatgcacg atgtagctta ccgccaggaa  3420
aaggatgaaa acaaatggac gcatgtgaat ttatccagca caaagctgac actcctgcag  3480
agaaagctcc aaccggcagc aatgtatgag attaaagttc gatccatccc tgatcactat  3540
tttaaaggct tctggagtga atggagtcca agttattact tcagaactcc agagatcaat  3600
aatagctcag gggagatgga tcctatctta ctaaccatca gcattttgag tttttctct  3660
gtcgctctgt tggtcatctt ggcctgtgtg ttatggaaaa aaaggattaa gcctatcgta  3720
tggcccagtc tccccgatca taagaagact ctggaacatc tttgtaagaa accaagaaaa  3780
aatttaaatg tgagtttcaa tcctgaaagt ttcctggact gccagattca tagggtggat  3840
gacattcaag ctagagatga agtggaaggt tttctgcaag atacgtttcc tcagcaacta  3900
gaagaatctg agaagcagag gcttggaggg gatgtgcaga gccccaactg cccatctgag  3960
gatgtagtca tcactccaga aagctttgga agagattcat ccctcacatg cctggctggg  4020
aatgtcagtg catgtgacgc ccctattctc tcctcttcca ggtccctaga ctgcagggag  4080
agtggcaaga atgggcctca tgtgtaccag gacctccttc ttagccttgg gactacaaac  4140
agcacgctgc cccctccatt ttctctccaa tctggaatcc tgacattgaa cccagttgct  4200
cagggtcagc ccattcttac ttccctggga tcaaatcaag aagaagcata tgtcaccatg  4260
tccagcttct accaaaacca gccctag                                 4287

SEQ ID NO: 180          moltype = AA  length = 1428
FEATURE                 Location/Qualifiers
source                  1..1428
                        mol_type = protein
                        organism = Synthetic construct
SEQUENCE: 180
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGGGGG SGGGGSGGGG SGGGGSGGGG SQAAQVQLQQ  300
SGAEVKKPGS SVKVSCKASG GTFSSYAISW VRQAPGQGLE WMGWINPNSG GTNYAQRFQG  360
RVTMTRDTSI STAYMELSRL RSDDTAVYYC ASYNDAFDIW GQGTLVTVSS GGGGSGGGGS  420
GGGGSNFMLT QPHSVSESPG KTVTISCTRS SGSIASNYVQ WYQQRPGSAP TIVIYEDDQR  480
PSGVPDRFSG SIDTSSNSAS LTISGLQSED EADYYCQSYE PGNGVFGGGT KVTVLAAAES  540
KYGPPCPPCP IYIWAPLAGT CGVLLLSLVI TLYCRSKRSR LLHSDYMNMT PRRPGPTRKH  600
YQPYAPPRDF AAYRSKRGRK KLLYIFKQPF MRPVQTTQEE DGCSCRFPEE EEGGCELRVK  660
FSRSADAPAY QQGQNQLYNE LNLGRREEYD VLDKRRGRDP EMGGKPRRKN PQEGLYNELQ  720
KDKMAEAYSE IGMKGERRRG KGHDGLYQGL STATKDTYDA LHMQALPPRR AKRGSGATNF  780
SLLKQAGDVE ENPGPRAKRV MLLLVTSLLL CELPHPAFLL IPMDCDIEGK DGKQYESVLM  840
VSIDQLLDSM KEIGSNCLNN EFNFFKRHIC DANKEGMFLF RAARKLRQFL KMNSTGDFDL  900
HLLKVSEGTT ILLNCTGQVK GRKPAALGEA QPTKSLEENK SLKEQKKLND LCFLKRLLQE  960
IKTCWNKILM GTKEHSGGSG GGSGGGSGES GYAQNGDLED AELDDYSFSC YSQLEVNGSQ  1020
```

```
HSLTCAFEDP DVNITNLEFE ICGALVEVKC LNFRKLQEIY FIETKKFLLI GKSNICVKVG  1080
EKSLTCKKID LTTIVKPEAP FDLSVVYREG ANDFVVTFNT SHLQKKYVKV LMHDVAYRQE  1140
KDENKWTHVN LSSTKLTLLQ RKLQPAAMYE IKVRSIPDHY FKGFWSEWSP SYYFRTPEIN  1200
NSSGEMDPIL LTISILSFFS VALLVILACV LWKKRIKPIV WPSLPDHKKT LEHLCKKPRK  1260
NLNVSFNPES FLDCQIHRVD DIQARDEVEG FLQDTFPQQL EESEKQRLGG DVQSPNCPSE  1320
DVVITPESFG RDSSLTCLAG NVSACDAPIL SSSRSLDCRE SGKNGPHVYQ DLLLSLGTTN  1380
STLPPPFSLQ SGILTLNPVA QGQPILTSLG SNQEEAYVTM SSFYQNQP              1428

SEQ ID NO: 181         moltype = DNA  length = 4902
FEATURE                Location/Qualifiers
source                 1..4902
                       mol_type = other DNA
                       organism = Synthetic construct
SEQUENCE: 181
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gttgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccggtggcgg caattctcgg cctgggactt gtccttggtc tgcttggtcc gctcgcaata  900
cttctggcct tgtacctgct ccgcagagac caaagacttc cgcccgacgc ccacaagccc  960
ccaggaggag gttccttcag aacgcctata caagaagaac aagcagatgc ccactctacc  1020
ctggctaaaa tcagggtgaa gtttagccgc tcagccgatg caccggccta ccagcaggga  1080
cagaaccagc tctacaacga gctcaacctg ggtcggcggg aagaatatga cgtgctggac  1140
aaacggcgcg gcagagatcc ggagatgggg ggaaagccga ggaggaagaa ccctcaagag  1200
ggcctgtaca acgaactgca gaaggacaag atggcggaag cctactccga gatcggcatg  1260
aagggagaac gccggagagg gaagggtcat gacggactgt accagggcct gtcaactgcc  1320
actaaggaca cttacgatgc gctccatatg caagctttgc ccccgcggcg cgcgaaacgc  1380
ggcagcggcg cgaccaactt tagcctgctg aaacaggcgg gcgatgtgga agaaaacccg  1440
ggcccgcgag caaagaggaa tattatggct ctgcctgtta cggcactgct ccttccgctt  1500
gcattgttgt tgcacgcagc gcggcccgag gtccagctgg tacagtctgg gggaggcttg  1560
gtacagcctg gggggtccct gagactctcc tgtgcagcct ctggattcac ctttgatgat  1620
tatgccatgc actgggtccg gcaagctcca gggaagggcc tggagtgggt ctcaggtatt  1680
agttggaata gtggtagcat aggctatgcg gactctgtga agggccgatt caccatctcc  1740
agagacaacg ccaagaactc cctgtatctg caaatgaaca gtctgagagc tgaggacacg  1800
gccttgtatt actgtgcaaa agatttatcg tcagtggctg gaccctttaa ctactggggc  1860
cagggcaccc tggtcaccgt ctcctcagga ggtggcgggt ctggtggagg cggtagcggc  1920
ggtggcggat cctcttctga gctgactcag gaccctgctg tgtctgtggc cttgggacag  1980
acagtcagga tcacatgcca aggagacagc ctcagaagct attatgcaag ctggtaccag  2040
cagaagccag gacaggcccc tgtacttgtc atctatggta aaaacaaccg gccctcaggg  2100
atcccagacc gattctctgg ctccagctca ggaaacacag cttccttgac catcactggg  2160
gctcaggcgg aggatgaggc tgactattac tgtaactccc gggacagcag tggtaaccat  2220
ctggtattcg gcggaggcac ccagctgacc gtcctcggtg ctagcgcaac cactacgcct  2280
gctccgcggc ctccaacgcc cgcgcccacg atagctagtc agccgttgtc tctccgacca  2340
gaggcgtgta gaccggccgc tggcggagcc gtacatactc gcggactcga cttcgcttgc  2400
gacatctaca tttgggcacc cttggctggg acctgtgggg tgctgttgct gtccttggtt  2460
attacgttgt actgctggct gacaaaaaag aagtattcat ctagtgtaca tgatccgaac  2520
ggtgaataca tgttcatgcg cgcggtgaac acggccaaga agagcagact gaccgacgta  2580
acccttagag tcaaattttc caggtccgca gatgccccccg cgtaccagca aggccagaac  2640
caactttaca acgaactgaa cctgggtcgc cgggaggaat atgatgtgct ggataaacga  2700
agggggaggg accctgagat gggagggaaa cctcgcagga aaaacccgca ggaaggtttg  2760
tacaacgagt tgcagaagga taagatggct gaggcttact ctgaaatagg gatgaaggga  2820
gagagacgga gaggaaaagg ccatgatggc ctttaccagg gcttgagcac agcaacaaag  2880
gatacttacg acgctcttca catgcaagct ctgccaccac ggcgggcaaa gcggggctca  2940
ggggcgacta acttttcact gttgaagcag gccggggatg tggaggagaa tcctggtcct  3000
agagctaagc gagtaatgct cttgctcgtg acttctttgc ttttgtgcga acttccgcac  3060
ccagccttcc ttttgatacc tatggattgt gatattgaag gtaaagatgg caaacaatat  3120
gagagtgttc taatggtcag catcgatcaa ttattggaca gcatgaaaga aattggtagc  3180
aattgcctga ataatgaatt taacttttttt aaaagacata tctgtgatgc taataaggaa  3240
ggtatgtttt tattccgtgc tgctcgcaag ttgaggcaat ttcttaaaat gaatagcact  3300
ggtgattttg atctccactt attaaaagtt tcagaaggca caacaatact gttgaactgc  3360
actggccagg ttaaaggaag aaaaccagct gccctgggtg aagcccaacc aacacaaagagt  3420
ttggaagaaa ataaatcttt aaaggaacag aaaaaactga atgacttgtg tttcctaaag  3480
agactattac aagagataaa aacttgttgg aataaaattt tgatgggcac taaagaacac  3540
tccggaggtt ccggtggtgg ctcaggtggt ggctcaggtg aaagtggcta tgctcaaaat  3600
ggagacttgg aagatgcaga actggatgac tactcattct catgctatag ccagttggaa  3660
gtgaatggat cgcagcactc actgacctgt gcttttgagg acccagatgt caacatcacc  3720
aatctggaat ttgaaatatg tggggccctc gtggaggtaa agtgcctgaa tttcaggaaa  3780
ctacaagaga tatatttcat cgagacaaag aaattcttac tgattggaaa gagcaatata  3840
tgtgtgaagg ttggagaaaa gagtctaacc tgcaaaaaaa tagacctaac cactatagtt  3900
```

```
aaacctgagg ctccttttga cctgagtgtc gtctatcggg aaggagccaa tgactttgtg  3960
gtgacattta atacatcaca cttgcaaaag aagtatgtaa aagttttaat gcacgatgta  4020
gcttaccgcc aggaaaagga tgaaaacaaa tggacgcatg tgaatttatc cagcacaaag  4080
ctgacactcc tgcagagaaa gctccaaccg gcagcaatgt atgagattaa agttcgatcc  4140
atccctgatc actattttaa aggcttctgg agtgaatgga gtccaagtta ttacttcaga  4200
actccagaga tcaataatag ctcaggggag atggatccta tcttactaac catcagcatt  4260
ttgagttttt tctctgtcgc tctgttggtc atcttggcct gtgtgttatg gaaaaaaagg  4320
attaagccta tcgtatggcc cagtctcccc gatcataaga agactctgga acatctttgt  4380
aagaaaccaa gaaaaaattt aaatgtgagt ttcaatcctg aaagtttcct ggactgccag  4440
attcataggg tggatgacat tcaagctaga gatgaagtgg aaggttttct gcaagatacg  4500
tttcctcagc aactagaaga atctgagaag cagaggcttg gaggggatgt gcagagcccc  4560
aactgcccat ctgaggatgt agtcatcact ccagaaagct ttggaagaga ttcatccctc  4620
acatgcctgg ctgggaatgt cagtgcatgt gacgccccta ttctctcctc ttccaggtcc  4680
ctagactgca gggagagtgg caagaatggg cctcatgtgt accaggacct ccttcttagc  4740
cttgggacta caaacagcac gctgccccct ccattttctc tccaatctgg aatcctgaca  4800
ttgaacccag ttgctcaggg tcagcccatt cttacttccc tgggatcaaa tcaagaagaa  4860
gcatatgtca ccatgtccag cttctaccaa aaccagccct ag                    4902

SEQ ID NO: 182         moltype = AA  length = 1633
FEATURE                Location/Qualifiers
source                 1..1633
                       mol_type = protein
                       organism = Synthetic construct
SEQUENCE: 182
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PVAAILGLGL VLGLLGPLAI  300
LLALYLLRRD QRLPPDAHKP PGGGSFRTPI QEEQADAHST LAKIRVKFSR SADAPAYQQG  360
QNQLYNELNL GRREEYDVLD KRRGRDPEMG GKPRRKNPQE GLYNELQKDK MAEAYSEIGM  420
KGERRRGKGH DGLYQGLSTA TKDTYDALHM QALPPRRAKR GSGATNFSLL KQAGDVEENP  480
GPRAKRNIMA LPVTALLLPL ALLLHAARPE VQLVQSGGGL VQPGGSLRLS CAASGFTFDD  540
YAMHWVRQAP GKGLEWVSGI SWNSGSIGYA DSVKGRFTIS RDNAKNSLYL QMNSLRAEDT  600
ALYYCAKDLS SVAGPFNYWG QGTLVTVSSG GGGSGGGGSG GGGSSSELTQ DPAVSVALGQ  660
TVRITCQGDS LRSYYASWYQ QKPGQAPVLV IYGKNNRPSG IPDRFSGSSS GNTASLTITG  720
AQAEDEADYY CNSRDSSGNH LVFGGGTQLT VLGASATTTP APRPPTPAPT IASQPLSLRP  780
EACRPAAGGA VHTRGLDFAC DIYIWAPLAG TCGVLLLSLV ITLYCWLTKK KYSSSVHDPN  840
GEYMFMRAVN TAKKSRLTDV TLRVKFSRSA DAPAYQQGQN QLYNELNLGR REEYDVLDKR  900
RGRDPEMGGK PRRKNPQEGL YNELQKDKMA EAYSEIGMKG ERRRGKGHDG LYQGLSTATK  960
DTYDALHMQA LPPRRAKRGS GATNFSLLKQ AGDVEENPGP RAKRVMLLLV TSLLLCELPH  1020
PAFLLIPMDC DIEGKDGKQY ESVLMVSIDQ LLDSMKEIGS NCLNNEFNFF KRHICDANKE  1080
GMFLFRAARK LRQFLKMNST GDFDLHLLKV SEGTTILLNC TGQVKGRKPA ALGEAQPTKS  1140
LEENKSLKEQ KKLNDLCFLK RLLQEIKTCW NKILMGTKEH SGGSGGGSGG GSGESGYAQN  1200
GDLEDAELDD YSFSCYSQLE VNGSQHSLTC AFEDPDVNIT NLEFEICGAL VEVKCLNFRK  1260
LQEIYFIETK KFLLIGKSNI CVKVGEKSLT CKKIDLTTIV KPEAPFDLSV VYREGANDFV  1320
VTFNTSHLQK KYVKVLMHDV AYRQEKDENK WTHVNLSSTK LTLLQRKLQP AAMYEIKVRS  1380
IPDHYFKGFW SEWSPSYYFR TPEINNSSGE MDPILLTISI LSFFSVALLV ILACVLWKKR  1440
IKPIVWPSLP DHKKTLEHLC KKPRKNLNVS FNPESFLDCQ IHRVDDIQAR DEVEGFLQDT  1500
FPQQLEESEK QRLGGDVQSP NCPSEDVVIT PESFGRDSSL TCLAGNVSAC DAPILSSSRS  1560
LDCRESGKNG PHVYQDLLLS LGTTNSTLPP PFSLQSGILT LNPVAQGQPI LTSLGSNQEE  1620
AYVTMSSFYQ NQP                                                    1633

SEQ ID NO: 183         moltype = DNA  length = 4923
FEATURE                Location/Qualifiers
source                 1..4923
                       mol_type = other DNA
                       organism = Synthetic construct
SEQUENCE: 183
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gttgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tctgggcccc attggctgga acttgcggcg tgctgctctt gtctctggtc  900
attaccctgt actgcaagcg cggacggaag aaactcttgt acatcttcaa gcagccgttc  960
atgcgccctg tgcaaaccac ccaagaagag gacgggtgct cctgccggtt cccggaagag  1020
gaagagggcg gctgcgaact gagagtgaag tttagccgct cagccgatgc accggcctac  1080
cagcagggac agaaccagct ctacaacgag ctcaacctgg gtcggcggga agaatatgac  1140
gtgctggaca aacggcgcgg cagagatccg gagatggggg gaaagccgag gaggaagaac  1200
```

```
cctcaagagg gcctgtacaa cgaactgcag aaggacaaga tggcggaagc ctactccgag  1260
atcggcatga agggagaacg ccggagaggg aagggtcatg acggactgta ccagggcctg  1320
tcaactgcca ctaaggacac ttacgatgcg ctccatatgc aagctttgcc cccgcggcgc  1380
gcgaaacgcg gcagcggcgc gaccaacttt agcctgctga aacaggcggg cgatgtggaa  1440
gaaaacccgg gcccgcgagc aaagaggaat attatggctc tgcctgttac ggcactgctc  1500
cttccgcttg cattgttgtt gcacgcagcg cggcccgagg tccagctggt acagtctggg  1560
ggaggcttgg tacagcctgg ggggtccctg agactctcct gtgcagcctc tggattcacc  1620
tttgatgatt atgccatgca ctgggtccgg caagctccag ggaagggcct ggagtgggtc  1680
tcaggtatta gttggaatag tggtagcata ggctatgcgg actctgtgaa gggccgattc  1740
accatctcca gagacaacgc caagaactcc ctgtatctgc aaatgaacag tctgagagct  1800
gaggacacgg ccttgtatta ctgtgcaaaa gatttatcgt cagtggctgg accctttaac  1860
tactggggcc agggcaccct ggtcaccgtc tcctcaggag gtggcgggtc tggtggaggc  1920
ggtagcggcg gtggcggatc ctcttctgag ctgactcagg accctgctgt gtctgtggcc  1980
ttgggacaga cagtcaggat cacatgccaa ggagacagcc tcagaagcta ttatgcaagc  2040
tggtaccagc agaagccagg acaggcccct gtacttgtca tctatggtaa aaacaaccgg  2100
ccctcaggga tcccagaccg attctctggc tccagctcag gaaacacagc ttccttgacc  2160
atcactgggg ctcaggcgga ggatgaggct gactattact gtaactcccg ggacagcagt  2220
ggtaaccatc tggtattcgg cggaggcacc cagctgaccg tcctcggtgc tagcgcaacc  2280
actacgcctg ctccgcggcc tccaacgccc gcgcccacga tagctagtca gccgttgtct  2340
ctccgaccag aggcgtgtag accggccgct ggcggagccg tacatactcg cggactcgac  2400
ttcgcttgcg acatctacat ttgggcaccc ttggctggga cctgtggggt gctgttgctg  2460
tccttggtta ttacgttgta ctgccggtcg aagaggtcca gactcttgca ctccgactac  2520
atgaacatga ctcctagaag gcccggaccc actagaaagc actaccagcc gtacgcccct  2580
cctcgggatt tcgccgcata ccggtccaga gtcaaatttt ccaggtccgc agatgccccc  2640
gcgtaccagc aaggccagaa ccaactttac aacgaactga acctgggtcg ccgggaggaa  2700
tatgatgtgc tggataaacg aagggggagg gaccctgaga tgggagggaa acctcgcagg  2760
aaaaacccgc aggaaggttt gtacaacgag ttgcagaagg ataagatggc tgaggcttac  2820
tctgaaatag ggatgaaggg agagagacgg agaggaaaag gccatgatgg cctttaccag  2880
ggcttaagca cagcaacaaa ggatacttac gacgctcttc acatgcaagc tctgccacca  2940
cggcgggcaa agcggggctc agggggcgact aacttttcac tgttgaagca ggccggggat  3000
gtggaggaga atcctggtcc tagagctaag cgagtaatgc tcttgctcgt gacttctttg  3060
cttttgtgcg aacttccgca cccagccttc cttttgatac ctatggattg tgatattgaa  3120
ggtaaagatg gcaaacaata tgagagtgtt ctaatggtca gcatcgatca attattggac  3180
agcatgaaag aaattggtag caattgcctg aataatgaat ttaacttttt taaaagacat  3240
atctgtgatg ctaataagga aggtatgttt ttattccgtg ctgctcgcaa gttgaggcaa  3300
tttcttaaaa tgaatagcac tggtgatttt gatctccact tattaaaagt ttcagaaggc  3360
acaacaatac tgttgaactg cactggccag gttaaaggaa gaaaaccagc tgccctgggt  3420
gaagcccaac caacaaagag tttggaagaa aataaatctt taaaggaaca gaaaaaactg  3480
aatgacttgt gtttcctaaa gagactatta caagagataa aaacttgttg gaataaaatt  3540
ttgatgggca ctaaagaaca ctccggaggt tccggtggtg gctcaggtgg tggctcaggt  3600
gaaagtggct atgctcaaaa tggagacttg gaagatgcag aactggatga ctactcattc  3660
tcatgctata gccagttgga agtgaatgga tcgcagcact cactgacctg tgcttttgag  3720
gacccagatg tcaacatcac caatctggaa tttgaaatat gtggggccct cgtggaggta  3780
aagtgcctga atttcaggaa actacaagag atatatttca tcgagacaaa gaaattctta  3840
ctgattggaa agagcaatat atgtgtgaag gttggagaaa agagtctaac ctgcaaaaaa  3900
atagacctaa ccactatagt taaacctgag gctccttttg acctgagtgt cgtctatcgg  3960
gaaggagcca atgactttgt ggtgacattt aatacatcac acttgcaaaa gaagtatgta  4020
aaagttttaa tgcacgatgt agcttaccgc caggaaaagg atgaaaacaa atggacgcat  4080
gtgaatttat ccagcacaaa gctgacactc ctgcagagaa agctccaacc ggcagcaatg  4140
tatgagatta aagttcgatc catccctgat cactatttta aaggcttctg gagtgaatgg  4200
agtccaagtt attacttcag aactccagag atcaataata gctcagggga gatggatcct  4260
atcttactaa ccatcagcat tttgagtttt ttctctgtcg ctctgttggt catcttggcc  4320
tgtgtgttat ggaaaaaaag gattaagcct atcgtatggc ccagtctccc cgatcataag  4380
aagactctgg aacatctttg taagaaacca agaaaaaatt taaatgtgag tttcaatcct  4440
gaaagtttcc tggactgcca gattcatagg gtggatgaca ttcaagctag agatgaagtg  4500
gaaggttttc tgcaagatac gtttcctcag caactagaag aatctgagaa gcagaggctt  4560
ggaggggatg tgcagagccc caactgccca tctgaggatg tagtcatcac tccagaaagc  4620
tttggaagag attcatccct cacatgcctg gctgggaatg tcagtgcatg tgacgcccct  4680
attctctcct cttccaggtc cctagactgc agggagagtg gcaagaatgg gcctcatgtg  4740
taccaggacc tccttcttag ccttgggact acaaacagca cgctgccccc tccattttct  4800
ctccaatctg gaatcctgac attgaaccca gttgctcagg gtcagcccat tcttacttcc  4860
ctgggatcaa atcaagaaga agcatatgtc accatgtcca gcttctacca aaaccagccc  4920
tag                                                                 4923
```

```
SEQ ID NO: 184         moltype = AA  length = 1640
FEATURE                Location/Qualifiers
source                 1..1640
                       mol_type = protein
                       organism = Synthetic construct
SEQUENCE: 184
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRN IMALPVTALL LPLALLLHAA RPEVQLVQSG GGLVQPGGSL RLSCAASGFT  540
```

```
FDDYAMHWVR QAPGKGLEWV SGISWNSGSI GYADSVKGRF TISRDNAKNS LYLQMNSLRA  600
EDTALYYCAK DLSSVAGPFN YWGQGTLVTV SSGGGGSGGG GSGGGGSSSE LTQDPAVSVA  660
LGQTVRITCQ GDSLRSYYAS WYQQKPGQAP VLVIYGKNNR PSGIPDRFSG SSSGNTASLT  720
ITGAQAEDEA DYYCNSRDSS GNHLVFGGGT QLTVLGASAT TTPAPRPPTP APTIASQPLS  780
LRPEACRPAA GGAVHTRGLD FACDIYIWAP LAGTCGVLLL SLVITLYCRS KRSRLLHSDY  840
MNMTPRRPGP TRKHYQPYAP PRDFAAYRSR VKFSRSADAP AYQQGQNQLY NELNLGRREE  900
YDVLDKRRGR DPEMGGKPRR KNPQEGLYNE LQKDKMAEAY SEIGMKGERR RGKGHDGLYQ  960
GLSTATKDTY DALHMQALPP RRAKRGSGAT NFSLLKQAGD VEENPGPRAK RVMLLLVTSL  1020
LLCELPHPAF LLIPMDCDIE GKDGKQYESV LMVSIDQLLD SMKEIGSNCL NNEFNFFKRH  1080
ICDANKEGMF LFRAARKLRQ FLKMNSTGDF DLHLLKVSEG TTILLNCTGQ VKGRKPAALG  1140
EAQPTKSLEE NKSLKEQKKL NDLCFLKRLL QEIKTCWNKI LMGTKEHSGG SGGGSGGGSG  1200
ESGYAQNGDL EDAELDDYSF SCYSQLEVNG SQHSLTCAFE DPDVNITNLE FEICGALVEV  1260
KCLNFRKLQE IYFIETKKFL LIGKSNICVK VGEKSLTCKK IDLTTIVKPE APFDLSVVYR  1320
EGANDFVVTF NTSHLQKKYV KVLMHDVAYR QEKDENKWTH VNLSSTKLTL LQRKLQPAAM  1380
YEIKVRSIPD HYFKGFWSEW SPSYYFRTPE INNSSGEMDP ILLTISILSF FSVALLVILA  1440
CVLWKKRIKP IVWPSLPDHK KTLEHLCKKP RKNLNVSFNP ESFLDCQIHR VDDIQARDEV  1500
EGFLQDTFPQ QLEESEKQRL GGDVQSPNCP SEDVVITPES FGRDSSLTCL AGNVSACDAP  1560
ILSSSRSLDC RESGKNGPHV YQDLLLSLGT TNSTLPPPFS LQSGILTLNP VAQGQPILTS  1620
LGSNQEEAYV TMSSFYQNQP                                             1640

SEQ ID NO: 185          moltype = DNA  length = 3198
FEATURE                 Location/Qualifiers
source                  1..3198
                        mol_type = other DNA
                        organism = Synthetic construct
SEQUENCE: 185
atgctgctgc tggtgaccag cctgctgctg tgcgaactgc cgcatccggc gtttctgctg  60
attccggagg tccagctggt acagtctggg ggaggcttgg tacagcctgg ggggtccctg  120
agactctcct gtgcagcctc tggattcacc tttgatgatt atgccatgca ctgggtccgg  180
caagctccag ggaagggcct ggagtgggtc tcaggtatta gttggaatag tggtagcata  240
ggctatgcgg actctgtgaa gggccgattc accatctcca gagacaacgc caagaactcc  300
ctgtatctgc aaatgaacag tctgagagct gaggacacgg ccttgtatta ctgtgcaaaa  360
gatttatcgt cagtggctgg acccttttaac tactggggcc agggcaccct ggtcaccgtc  420
tcctcaggag gtggcgggtc tggtggaggc ggtagcggcg gtggcggatc ctcttctgag  480
ctgactcagg accctgctgt gtctgtggcc ttgggacaga cagtcaggat cacatgccaa  540
ggagacagcc tcagaagcta ttatgcaagc tggtaccagc agaagccagg acaggcccct  600
gtacttgtca tctatggtaa aaacaaccgg ccctcaggga tcccagaccg attctctggc  660
tccagctcag gaaacacagc ttccttgacc atcactgggg ctcaggcgga ggatgaggct  720
gactattact gtaactcccg ggacagcagt ggtaaccatc tggtattcgg cggaggcacc  780
cagctgaccg tcctcggtgc ggccgcaact accacccctg cccctcggcc gccgactccg  840
gccccaacca tcgcaagcca acccctctcc ttgcgccccg aagcttgccg cccggccgcg  900
ggtggagccg tgcatacccg ggggctggac tttgcctgcg atatctacat ttgggccccg  960
ctggccggca cttgcggcgt gctcctgctg tcgctggtca tcacccttta ctgcaagagg  1020
ggccggaaga agctgcttta catcttcaag cagccgttca tgcggcccgt gcagacgact  1080
caggaagagg acggatgctc gtgcagattc cctgaggagg aagagggggg atgcgaactg  1140
cgcgtcaagt tctcacggtc cgccgacgcc cccgcatatc aacagggcca gaatcagctc  1200
tacaacgagc tgaacctggg aaggagagag gagtacgacg tgctggacaa gcgacgcgga  1260
cgcgacccgg agatgggggg gaaaccacgg cggaaaaacc ctcaggaagg actgtacaac  1320
gaactccaga aagacaagat ggcggaagcc tactcagaaa tcgggatgaa gggagagcgg  1380
aggaggggaa agggtcacga cgggctgtac cagggactga gcaccgccac taaggatacc  1440
tacgatgcct tgcatatgca agcactccca ccccggcggg caaagcgggg ctcaggggcg  1500
actaactttt cactgttgaa gcaggccggg gatgtggagg agaatcctgg tcctagagca  1560
aagcgaatgc ttctacgttc taaacctgca cttcctccac cacttatgct acttcttcta  1620
ggacctcttg gtcctctatc acctggagct ctacctcgac ctgcacaagc acaggacgtc  1680
gtggacctgg acttcttcac ccaggagccg ctgcacctgg tgagcccctc gttcctgtcc  1740
gtcaccattg acgccaacct ggccacggac ccgcggttcc tcatcctcct gggttctcca  1800
aagcttcgta ccttggccag aggcttgtct cctgcgtacc tgaggtttgg tggcaccaag  1860
acagacttcc taattttcga tcccaagaag gaatcaacct ttgaagagag aagttactgg  1920
caatctcaag tcaaccagga tatttgcaaa tatggatcca tccctcctga tgtggaggag  1980
aagttacggt tggaatggcc ctaccaggag caattgctac tccgagaaca ctaccagaaa  2040
aagttcaaga acagcaccta ctcaagaagc tctgtagatg tgctatacac ttttgcaaac  2100
tgctcaggac tggacttgat ctttggccta aatgcgttat taagaacagc agatttgcag  2160
tggaacagtt ctaatgctca gttgctcctg gactactgct cttccaaggg gtataacatt  2220
tcttgggaac taggcaatga acctaacagt ttccttaaga aggctgatat tttcatcaat  2280
gggtcgcagt taggagaaga ttttattcaa ttgcataaac ttctaagaaa gtccaccttc  2340
aaaaatgcaa aactctatgg tcctgatgtt ggtcagcctc gaagaaagac ggctaagatg  2400
ctgaagagct tcctgaaggc tggtggagaa gtgattgatt cagttacatg gcatcactac  2460
tatttgaatg gacggactgc taccaaggaa gattttctaa accctgatgt attggacatt  2520
tttatttcat ctgtgcaaaa agttttccag gtggttgaga gcaccaggcc tggcaagaag  2580
gtctggttag gagaaacaag ctctgcatat ggaggcggag cgcccttgct atccgacacc  2640
tttgcagctg gctttatgtg gctggataaa ttgggcctgt cagcccgaat gggaatagaa  2700
gtggtgatga ggcaagtatt ctttggagca ggaaactacc atttagtgga tgaaaacttc  2760
gatcctttac ctgattattg gctatctctt ctgttcaaga aattggtggg caccaaggtg  2820
ttaatggcaa gcgtgcaagg ttcaaagaga aggaagcttc gagtatacct tcattgcaca  2880
aacactgaca atccaaggta taaagaagga gatttaactc tgtatgccat aaacctccat  2940
aatgtcacca agtacttgcg gttaccctat ccttttcta acaagcaagt ggataaatac  3000
cttctaagac ctttgggacc tcatggatta ctttccaaat ctgtccaact caatggtcta  3060
actctaaaga tggtggatga tcaaaccttg ccacctttaa tggaaaaacc tctccggcca  3120
ggaagttcac tgggcttgcc agctttctca tatagttttt ttgtgataag aaatgccaaa  3180
```

```
gttgctgctt gcatctaa                                              3198

SEQ ID NO: 186          moltype = AA  length = 1065
FEATURE                 Location/Qualifiers
source                  1..1065
                        mol_type = protein
                        organism = Synthetic construct
SEQUENCE: 186
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGAAAT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PRRAKRGSGA TNFSLLKQAG DVEENPGPRA KRMLLRSKPA LPPPLMLLLL  540
GPLGPLSPGA LPRPAQAQDV VDLDFFTQEP LHLVSPSFLS VTIDANLATD PRFLILLGSP  600
KLRTLARGLS PAYLRFGGTK TDFLIFDPKK ESTFEERSYW QSQVNQDICK YGSIPPDVEE  660
KLRLEWPYQE QLLLREHYQK KFKNSTYSRS SVDVLYTFAN CSGLDLIFGL NALLRTADLQ  720
WNSSNAQLLL DYCSSKGYNI SWELGNEPNS FLKKADIFIN GSQLGEDFIQ LHKLLRKSTF  780
KNAKLYGPDV GQPRRKTAKM LKSFLKAGGE VIDSVTWHHY YLNGRTATKE DFLNPDVLDI  840
FISSVQKVFQ VVESTRPGKK VWLGETSSAY GGGAPLLSDT FAAGFMWLDK LGLSARMGIE  900
VVMRQVFFGA GNYHLVDENF DPLPDYWLSL LFKKLVGTKV LMASVQGSKR RKLRVYLHCT  960
NTDNPRYKEG DLTLYAINLH NVTKYLRLPY PFSNKQVDKY LLRPLGPHGL LSKSVQLNGL  1020
TLKMVDDQTL PPLMEKPLRP GSSLGLPAFS YSFFVIRNAK VAACI                1065

SEQ ID NO: 187          moltype = DNA  length = 3549
FEATURE                 Location/Qualifiers
source                  1..3549
                        mol_type = other DNA
                        organism = Synthetic construct
SEQUENCE: 187
atgctgctgc tggtgaccag cctgctgctg tgcgaactgc cgcatccggc gtttctgctg  60
attccggagg tccagctggt acagtctggg ggaggcttgg tacagcctgg ggggtccctg  120
agactctcct gtgcagcctc tggattcacc tttgatgatt atgccatgca ctgggtccgg  180
caagctccag ggaagggcct ggagtgggtc tcaggtatta gttggaatag tggtagcata  240
ggctatgcgg actctgtgaa gggccgattc accatctcca gagacaacgc caagaactcc  300
ctgtatctgc aaatgaacag tctgagagct gaggacacgg ccttgtatta ctgtgcaaaa  360
gatttatcgt cagtggctgg accctttaac tactggggcc agggcaccct ggtcaccgtc  420
tcctcaggag gtggcgggtc tggtggaggc ggtagcggcg gtggcggatc ctcttctgag  480
ctgactcagg accctgctgt gtctgtggcc ttgggacaga cagtcaggat cacatgccaa  540
ggagacagcc tcagaagcta ttatgcaagc tggtaccagc agaagccagg acaggcccct  600
gtacttgtca tctatggtaa aaacaaccgg ccctcaggga tcccagaccg attctctggc  660
tccagctcag gaaacacagc ttccttgacc atcactgggg ctcaggcgga ggatgaggct  720
gactattact gtaactcccg ggacagcagt ggtaaccatc tggtattcgg cggaggcacc  780
cagctgaccg tcctcggtgc ggccgcaact accacccctg cccctcggcc gccgactccg  840
gccccaacca tcgcaagcca acccctctcc ttgcgccccg aagcttgccg cccggccgcg  900
ggtggagccg tgcatacccg ggggctggac tttgcctgcg atatctacat ttgggccccg  960
ctggccggca cttgcggcgt gctcctgctg tcgctggtca tcacccttta ctgcaagagg  1020
ggccggaaga agctgcttta catcttcaag cagccgttca tgcggcccgt gcagacgact  1080
caggaagagg acggatgctc gtgcagattc cctgaggagg aagagggggg atgcgaactg  1140
cgcgtcaagt tctcacggtc cgccgacgcc cccgcatatc aacagggcca gaatcagctc  1200
tacaacgagc tgaacctggg aaggagagag gagtacgacg tgctggacaa gcgacgcgga  1260
cgcgacccgg agatgggggg gaaaccacgg cggaaaaacc ctcaggaagg actgtacaac  1320
gaactccaga aagacaagat ggcggaagcc tactcagaaa tcgggatgaa gggagagcgg  1380
aggaggggaa agggtcacga cggcctgtac cagggactga gcaccgccac taaggatacc  1440
tacgatgcct tgcatatgca agcactccca ccccggcggg caaagcgggg ctcaggggcg  1500
actaactttt cactgttgaa gcaggccggg gatgtggagg agaatcctgg tcctagagca  1560
aagcgaatgg aagctcttat ggctagggga gcgctcacag gtccattgcg ggcactgtgc  1620
ctgttggggt gcctgttgtc tcatgcggct gcggctccgt caccaattat caaatttcct  1680
ggcgacgttg ccccgaagac agacaaggaa cttgccgtgc agtacctcaa tacgttctat  1740
ggatgtccta aagaatcatg caatctgttc gttttgaaag atacccttaa gaagatgcaa  1800
aagttctttg gcttgcccca gactggggac cttgaccaga atacaattga aactatgaga  1860
aaaccgagat gcggcaaccc cgatgtggct aactacaact tttttcccag aaagcctaaa  1920
tgggataaga accagattac ataccggata ataggatata cacccgacct ggacccggag  1980
acagttgacg acgcatttgc gcgcgccttt caggtttggt cagatgtaac tccgcttcgc  2040
ttttcacgaa tacatgacgg agaagctgac atcatgatta atttcggtcg gtgggagcat  2100
ggggatggtt atcctttcga cggcaaagac gggctgctcg cccatgcctt tgcgcctggg  2160
accggcgtcg gtggtgatag ccacttcgat gacgatgaac tctggaccct cggagaggga  2220
caagtggtga gagtaaaata cggaaacgcc gacggagaat attgcaagtt cccctttcta  2280
ttcaatggta aggaatataa tagctgtact gatacaggta gatcagacgg cttcctttgg  2340
tgctcaacca cctacaattt cgaaaaagat ggtaagtacg gcttctgccc tcatgaggcc  2400
ctgttcacta tgggaggcaa tgcagaggga cagccgtgca aatttccatt tcgctttcaa  2460
ggtacgagct acgattcttg tacgacggag gggagaacgg atgggtatag atggtgtggc  2520
acaacagagg attacgatag agacaagaaa tatgggttct gtcccgagac cgctatgagt  2580
acagttgggg gtaattccga gggagctccc tgcgtgttcc cgttcacatt cttgggtaac  2640
aagtacgagt cctgtaccag cgctgggcgg tctgatggta aaatgtggtg tgcaacgacg  2700
gcaaattacg acgacgatcg gaagtggggt tttgtcctg accagggtta ctctctgttt  2760
```

```
ctcgttgcag cgcatgaatt tggacacgca atgggtcttg agcactcaca ggaccccggc  2820
gcacttatgg cgccaatata cacttacacc aagaacttta gattgagtca ggacgatatt  2880
aagggcatcc aggagcttta tggagcctca ccagacatcg atctggggac tggtcccact  2940
cccactcttg gtcctgtcac accagaaatt tgtaaacagg atatagtctt tgatggtata  3000
gcccagattc gcggagagat ctttttcttt aaggacaggt tcatctggag gacagtgacg  3060
ccaagagata aacccatggg tcctctgttg gtagcaacct tctggcccga gctcccagag  3120
aagatagatg cagtgtatga ggccccacaa gaggagaaag cggtcttttt cgcggggaat  3180
gagtattgga tctactcagc ctccactctg gaaagagggt acccaaaacc actgacttct  3240
ctgggtttgc cccagatgt acagcgagta gatgctgcat ttaattggag caagaataag  3300
aagacctaca ttttcgcggg ggataagttc tggaggtaca atgaagtcaa gaagaaaatg  3360
gatcccggat ttccaaagct catagccgac gcatggaatg ccatcccgga caacctggat  3420
gccgtcgtag acttgcaggg tgggggacac tcctattttt tcaaaggagc gtattatttg  3480
aaattggaga atcaaagtct taagtcagtt aagtttggat caatcaagag cgactggctc  3540
gggtgttag                                                          3549

SEQ ID NO: 188         moltype = AA  length = 1182
FEATURE                Location/Qualifiers
source                 1..1182
                       mol_type = protein
                       organism = Synthetic construct
SEQUENCE: 188
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGAAAT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PRRAKRGSGA TNFSLLKQAG DVEENPGPRA KRMEALMARG ALTGPLRALC  540
LLGCLLSHAA AAPSPIIKFP GDVAPKTDKE LAVQYLNTFY GCPKESCNLF VLKDTLKKMQ  600
KFFGLPQTGD LDQNTIETMR KPRCGNPDVA NYNFFPRKPK WDKNQITYRI IGYTPDLDPE  660
TVDDAFARAF QVWSDVTPLR FSRIHDGEAD IMINFGRWEH GDGYPFDGKD GLLAHAFAPG  720
TGVGGDSHFD DDELWTLGEG QVVRVKYGNA DGEYCKFPFL FNGKEYNSCT DTGRSDGFLW  780
CSTTYNFEKD GKYGFCPHEA LFTMGGNAEG QPCKFPFRFQ GTSYDSCTTE GRTDGYRWCG  840
TTEDYDRDKK YGFCPETAMS TVGGNSEGAP CVFPFTFLGN KYESCTSAGR SDGKMWCATT  900
ANYDDDRKWG FCPDQGYSLF LVAAHEFGHA MGLEHSQDPG ALMAPIYTYT KNFRLSQDDI  960
KGIQELYGAS PDIDLGTGPT PTLGPVTPEI CKQDIVFDGI AQIRGEIFFF KDRFIWRTVT  1020
PRDKPMGPLL VATFWPELPE KIDAVYEAPQ EEKAVFFAGN EYWIYSASTL ERGYPKPLTS  1080
LGLPPDVQRV DAAFNWSKNK KTYIFAGDKF WRYNEVKKKM DPGFPKLIAD AWNAIPDNLD  1140
AVVDLQGGGH SYFFKGAYYL KLENQSLKSV KFGSIKSDWL GC                     1182

SEQ ID NO: 189         moltype = DNA  length = 3747
FEATURE                Location/Qualifiers
source                 1..3747
                       mol_type = other DNA
                       organism = Synthetic construct
SEQUENCE: 189
atgctgctgc tggtgaccag cctgctgctg tgcgaactgc cgcatccggc gtttctgctg  60
attccggagg tccagctggt acagtctggg ggaggcttgg tacagcctgg ggggtccctg  120
agactctcct gtgcagcctc tggattcacc tttgatgatt atgccatgca ctgggtccgg  180
caagctccag ggaagggcct ggagtgggtc tcaggtatta gttggaatag tggtagcata  240
ggctatgcgg actctgtgaa gggccgattc accatctcca gagacaacgc caagaactcc  300
ctgtatctgc aaatgaacag tctgagagct gaggacacgg ccttgtatta ctgtgcaaaa  360
gatttatcgt cagtggctgg accctttaac tactggggcc agggcaccct ggtcaccgtc  420
tcctcaggag gtggcgggtc tggtggaggc ggtagcggcg gtggcggatc ctcttctgag  480
ctgactcagg accctgctgt gtctgtggcc ttgggacaga cagtcaggat cacatgccaa  540
ggagacagcc tcagaagcta ttatgcaagc tggtaccagc agaagccagg acaggcccct  600
gtacttgtca tctatggtaa aaacaaccgg ccctcaggga tcccagaccg attctctggc  660
tccagctcag gaaacacagc ttccttgacc atcactgggg ctcaggcgga ggatgaggct  720
gactattact gtaactcccg ggacagcagt ggtaaccatc tggtattcgg cggaggcacc  780
cagctgaccg tcctcggtgc ggccgcaact accacccctg cccctcggcc gccgactccg  840
gccccaacca tcgcaagcca acccctctcc ttgcgccccg aagcttgccg cccggccgcg  900
ggtggagccg tgcatacccg ggggctggac tttgcctgcg atatctacat ttgggccccg  960
ctggccggca cttgcggcgt gctcctgctg tcgctggtca tcaccctta ctgcaagagg  1020
ggccggaaga agctgcttta catcttcaag cagccgttca tgcggcccgt gcagacgact  1080
caggaagagg acggatgctc gtgcagattc cctgaggagg aagagggggg atgcgaactg  1140
cgcgtcaagt tctcacggtc cgccgacgcc cccgcatatc aacagggcca gaatcagctc  1200
tacaacgagc tgaacctggg aaggagagag gagtacgacg tgctggacaa gcgacgcgga  1260
cgcgacccgg agatgggggg gaaaccacgg cggaaaaacc ctcaggaagg actgtacaac  1320
gaactccaga aagacaagat ggcggaagcc tactcagaaa tcgggatgaa gggagagcgg  1380
aggaggggaa agggtcacga cggctgtac cagggactga gcaccgccac taaggatacc  1440
tacgatgcct tgcatatgca agcactccca ccccggcggg caaagcgggg ctcaggggcg  1500
actaactttt cactgttgaa gcaggccggg gatgtggagg agaatcctgg tcctagagca  1560
aagcgaatgg atgcaatgaa gagagggctc tgctgtgtgc tgctgctgtg tggagcagtc  1620
ttcgtttcgc ccagcctgaa ctttcgcgcc ccaccagtga tccctaatgt gccattcctt  1680
tgggcttgga atgcgccttc tgaattctgc ttgggaaaat ttgatgagcc tctggatatg  1740
tctcttttca gttttattgg gtcaccaagg attaacgcga ctggacaagg agtgacgata  1800
ttttatgtcg ataggctcgg ctactacccc tacatagatt ccattaccgg cgtaaccgtg  1860
```

```
aatggtggta tccctcaaaa gatctctctt caagaccact tggacaaagc aaaaaaagac  1920
attacattct acatgccggt ggataacctg gggatggccg ttatcgattg ggaggagtgg  1980
agacccacgt gggctagaaa ctggaagccg aaggacgtct ataaaaacag gtctatcgaa  2040
ttggttcagc agcagaacgt gcaattgtcc ttgactgagg cgacagagaa ggccaagcaa  2100
gagtttgaga aggcgggaaa ggactttttg gttgagacca ttaagctcgg taaactgctg  2160
cgacctaatc atctgtgggg ttactacctc ttccctgact gctacaatca ccattacaag  2220
aaaccgggct acaatggctc ttgttttaat gtcgaaatca aacgaaacga cgacctgagc  2280
tggctttgga acgaatccac cgcactctac cccagcatct atctgaacac ccagcagagt  2340
cctgtagcag caacgctgta cgtccggaac cgggtacgag aggcaatcag agtatctaag  2400
atcccggatg ctaaatcccc actgccggta tttgcgtaca cccgaatcgt gttcactgac  2460
caggttctga agtttctctc ccaggacgaa cttgtctata cgtttggaga gacagtagca  2520
ctcggcgcat caggcattgt tatatgggga acccttagca tcatgcggtc aatgaagtcc  2580
tgcttgcttc ttgataacta tatggagaca atcttgaacc cctatatcat caatgtaaca  2640
cttgcagcaa aaatgtgctc ccaagtactc tgtcaagagc agggagtatg catacgaaaa  2700
aattggaaca gttccgacta cctgcacctt aaccccgata attttgctat acagcttgaa  2760
aagggcggaa aatttacagt ccgagggaag ccgacattgg aggatctcga gcaattctct  2820
gaaaagtttt attgctcatg ctacagtacc cttagctgta aagaaaaggc ggacgtcaag  2880
gatactgacg ccgtggacgt ctgcatcgcc gacggagttt gcatcgacgc atttcttaaa  2940
cctcccatgg aaaccgaaga gccacaaatc ttctataacg cttctccctc aacacttagt  3000
gctactatgt ttatagtttc tattttgttc cttattattt caagtgtagc tagtcttgct  3060
agcgacaaaa ctcacacatg cccaccgtgc ccagcacctg aagctgcggg gggaccgtca  3120
gtcttcctct tcccccaaa acccaaggac accctcatga tctcccggac ccctgaggtc  3180
acatgcgtgg tggtggacgt gagccacgaa gaccctgagg tcaagttcaa ctggtacgtg  3240
gacggcgtgg aggtgcataa tgccaagaca aagccgcggg aggagcagta caacagcacg  3300
taccgtgtgg tcagcgtcct caccgtcctg caccaggact ggctgaatgg caaggagtac  3360
aagtgcaagg tctccaacaa ggcacttggg gcccctatcg agaaaaccat ctccaaagcc  3420
aaagggcagc cccgagaacc acaggtgtac accctgcccc catctcggga ggagatgacc  3480
aagaaccagg tcagcctgac ctgcctggtc aaaggcttct atcccagcga catcgccgtg  3540
gagtgggaga gcaatgggca gccggagaac aactacaaga ccacgcctcc cgtgctggac  3600
tccgacggct ccttcttcct ctacagcaag ctcaccgtgg acaagagcag gtggcagcag  3660
gggaacgtct tctcatgctc cgtgatgcac gaggctctgc acaaccacta cacgcagaag  3720
agcctctccc tgtctccggg taaataa                                      3747
```

```
SEQ ID NO: 190          moltype = AA  length = 1248
FEATURE                 Location/Qualifiers
source                  1..1248
                        mol_type = protein
                        organism = Synthetic construct
SEQUENCE: 190
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGAAAT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PRRAKRGSGA TNFSLLKQAG DVEENPGPRA KRMDAMKRGL CCVLLLCGAV  540
FVSPSLNFRA PPVIPNVPFL WAWNAPSEFC LGKFDEPLDM SLFSFIGSPR INATGQGVTI  600
FYVDRLGYYP YIDSITGVTV NGGIPQKISL QDHLDKAKKD ITFYMPVDNL GMAVIDWEEW  660
RPTWARNWKP KDVYKNRSIE LVQQQNVQLS LTEATEKAKQ EFEKAGKDFL VETIKLGKLL  720
RPNHLWGYYL FPDCYNHHYK KPGYNGSCFN VEIKRNDDLS WLWNESTALY PSIYLNTQQS  780
PVAATLYVRN RVREAIRVSK IPDAKSPLPV FAYTRIVFTD QVLKFLSQDE LVYTFGETVA  840
LGASGIVIWG TLSIMRSMKS CLLLDNYMET ILNPYIINVT LAAKMCSQVL CQEQGVCIRK  900
NWNSSDYLHL NPDNFAIQLE KGGKFTVRGK PTLEDLEQFS EKFYCSCYST LSCKEKADVK  960
DTDAVDVCIA DGVCIDAFLK PPMETEEPQI FYNASPSTLS ATMFIVSILF LIISSVASLA  1020
SDKTHTCPPC PAPEAAGGPS VFLFPPKPKD TLMISRTPEV TCVVVDVSHE DPEVKFNWYV  1080
DGVEVHNAKT KPREEQYNST YRVVSVLTVL HQDWLNGKEY KCKVSNKALG APIEKTISKA  1140
KGQPREPQVY TLPPSREEMT KNQVSLTCLV KGFYPSDIAV EWESNGQPEN NYKTTPPVLD  1200
SDGSFFLYSK LTVDKSRWQQ GNVFSCSVMH EALHNHYTQK SLSLSPGK                1248
```

```
SEQ ID NO: 191          moltype = DNA  length = 3099
FEATURE                 Location/Qualifiers
source                  1..3099
                        mol_type = other DNA
                        organism = Synthetic construct
SEQUENCE: 191
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gctgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg ggtccctga tcggttctct  660
ggctccatcg acacctcctc caactctgcc tccctcacca tctctggact gcagagtgag  720
```

```
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tttgggcccc gctggccggc acttgcggcg tgctcctgct gtcgctggtc  900
atcacccttt actgcaagag gggccggaag aagctgcttt acatcttcaa gcagccgttc  960
atgcggcccg tgcagacgac tcaggaagag gacggatgct cgtgcagatt ccctgaggag  1020
gaagaggggg gatgcgaact gcgcgtcaag ttctcacggt ccgccgacgc ccccgcatat  1080
caacagggcc agaatcagct ctacaacgag ctgaacctgg gaaggagaga ggagtacgac  1140
gtgctggaca agcgacgcgg acgcgacccg gagatggggg ggaaaccacg gcggaaaaac  1200
cctcaggaag gactgtacaa cgaactccag aaagacaaga tggcggaagc ctactcagaa  1260
atcgggatga agggagagcg gaggagggga aagggtcacg acgggctgta ccagggactg  1320
agcaccgcca ctaaggatac ctacgatgcc ttgcatatgc aagcactccc accccggcgg  1380
gcaaagcggg gctcaggggc gactaacttt tcactgttga agcaggccgg ggatgtggag  1440
gagaatcctg gtcctagagc aaagcgaatg cttctacgtt ctaaacctgc acttcctcca  1500
ccacttatgc tacttcttct aggacctctt ggtcctctat cacctggagc tctacctcga  1560
cctgcacaag cacaggacgt cgtggacctg gacttcttca cccaggagcc gctgcacctg  1620
gtgagcccct cgttcctgtc cgtcaccatt gacgccaacc tggccacgga cccgcggttc  1680
ctcatcctcc tgggttctcc aaagcttcgt accttggcca gaggcttgtc tcctgcgtac  1740
ctgaggtttg gtggcaccaa gacagacttc ctaattttcg atcccaagaa ggaatcaacc  1800
tttgaagaga gaagttactg gcaatctcaa gtcaaccagg atatttgcaa atatggatcc  1860
atccctcctg atgtggagga gaagttacgg ttggaatggc cctaccagga gcaattgcta  1920
ctccgagaac actaccagaa aaagttcaag aacagcacct actcaagaag ctctgtagat  1980
gtgctataca cttttgcaaa ctgctcagga ctggacttga tctttggcct aaatgcgtta  2040
ttaagaacag cagatttgca gtggaacagt tctaatgctc agttgctcct ggactactgc  2100
tcttccaagg ggtataacat ttcttgggaa ctaggcaatg aacctaacag tttccttaag  2160
aaggctgata ttttcatcaa tgggtcgcag ttaggagaag attttattca attgcataaa  2220
cttctaagaa agtccacctt caaaaatgca aaactctatg gtcctgatgt tggtcagcct  2280
cgaagaaaga cggctaagat gctgaagagc ttcctgaagg ctggtggaga agtgattgat  2340
tcagttacat ggcatcacta ctatttgaat ggacggactg ctaccaagga agattttcta  2400
aaccctgatg tattggacat tttatttca tctgtgcaaa aagttttcca ggtggttgag  2460
agcaccaggc ctggcaagaa ggtctggtta ggagaaacaa gctctgcata tggaggcgga  2520
gcgcccttgc tatccgacac ctttgcagct ggctttatgt ggctggataa attgggcctg  2580
tcagcccgaa tgggaataga agtggtgatg aggcaagtat tctttggagc aggaaactac  2640
catttagtgg atgaaaactt cgatccttta cctgattatt ggctatctct tctgttcaag  2700
aaattggtgg gcaccaaggt gttaatggca agcgtgcaag gttcaaagag aaggaagctt  2760
cgagtatacc ttcattgcac aaacactgac aatccaaggt ataaagaagg agatttaact  2820
ctgtatgcca taaacctcca taatgtcacc aagtacttgc ggttacccta tccttttct  2880
aacaagcaag tggataaata ccttctaaga cctttgggac ctcatggatt actttccaaa  2940
tctgtccaac tcaatggtct aactctaaag atggtggatg atcaaacctt gccaccttta  3000
atggaaaaac ctctccggcc aggaagttca ctgggcttgc cagctttctc atatagtttt  3060
tttgtgataa gaaatgccaa agttgctgct tgcatctaa                        3099
```

```
SEQ ID NO: 192          moltype = AA  length = 1032
FEATURE                 Location/Qualifiers
source                  1..1032
                        mol_type = protein
                        organism = Synthetic construct
SEQUENCE: 192
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRM LLRSKPALPP PLMLLLLGPL GPLSPGALPR PAQAQDVVDL DFFTQEPLHL  540
VSPSFLSVTI DANLATDPRF LILLGSPKLR TLARGLSPAY LRFGGTKTDF LIFDPKKEST  600
FEERSYWQSQ VNQDICKYGS IPPDVEEKLR LEWPYQEQLL LREHYQKKFK NSTYSRSSVD  660
VLYTFANCSG LDLIFGLNAL LRTADLQWNS SNAQLLLDYC SSKGYNISWE LGNEPNSFLK  720
KADIFINGSQ LGEDFIQLHK LLRKSTFKNA KLYGPDVGQP RRKTAKMLKS FLKAGGEVID  780
SVTWHHYYLN GRTATKEDFL NPDVLDIFIS SVQKVFQVVE STRPGKKVWL GETSSAYGGG  840
APLLSDTFAA GFMWLDKLGL SARMGIEVVM RQVFFGAGNY HLVDENFDPL PDYWLSLLFK  900
KLVGTKVLMA SVQGSKRRKL RVYLHCTNTD NPRYKEGDLT LYAINLHNVT KYLRLPYPFS  960
NKQVDKYLLR PLGPHGLLSK SVQLNGLTLK MVDDQTLPPL MEKPLRPGSS LGLPAFSYSF  1020
FVIRNAKVAA CI                                                     1032
```

```
SEQ ID NO: 193          moltype = DNA  length = 3450
FEATURE                 Location/Qualifiers
source                  1..3450
                        mol_type = other DNA
                        organism = Synthetic construct
SEQUENCE: 193
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gctgagcagg ctgagatctg acgacacggc cgtgtattac  360
tgtgcgagtt ataatgatgc ttttgatatc tggggccaag gcaccctggt caccgtctcc  420
```

-continued

```
tcaggaggtg gcgggtctgg tggtggcggt agcggtggtg gcggatccaa ttttatgctg  480
actcagcccc actctgtgtc ggagtctccg ggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tttgggcccc gctggccggc acttgcggcg tgctcctgct gtcgctggtc  900
atcacccttt actgcaagag gggccggaag aagctgcttt acatcttcaa gcagccgttc  960
atgcggcccg tgcagacgac tcaggaagag gacggatgct cgtgcagatt ccctgaggag  1020
gaagaggggg gatgcgaact gcgcgtcaag ttctcacggt ccgccgacgc ccccgcatat  1080
caacagggcc agaatcagct ctacaacgag ctgaacctgg gaaggagaga ggagtacgac  1140
gtgctggaca agcgacgcgg acgcgacccg gagatggggg ggaaaccacg gcggaaaaac  1200
cctcaggaag gactgtacaa cgaactccag aaagacaaga tggcggaagc ctactcagaa  1260
atcgggatga agggagagcg gaggaggga aagggtcacg acgggctgta ccagggactg  1320
agcaccgcca ctaaggatac ctacgatgcc ttgcatatgc aagcactccc accccggcgg  1380
gcaaagcggg gctcagggc gactaacttt tcactgttga agcaggccgg ggatgtggag  1440
gagaatcctg gtcctagagc aaagcgaatg gaagctctta tggctagggg agcgctcaca  1500
ggtccattgc gggcactgtg cctgttgggg tgcctgttgt ctcatgcggc tgcggctccg  1560
tcaccaatta tcaaatttcc tggcgacgtt gccccgaaga cagacaagga acttgccgtg  1620
cagtacctca atacgttcta tggatgtcct aaagaatcat gcaatctgtt cgttttgaaa  1680
gataccctta agaagatgca aaagttcttt ggcttgccac agactgggga ccttgaccag  1740
aatacaattg aaactatgag aaaaccgaga tgcggcaacc ccgatgtggc taactacaac  1800
tttttcccca gaaagcctaa atgggataag aaccagatta cataccggat aataggatat  1860
acacccgacc tggacccgga gacagttgac gacgcatttg cgcgcgcctt tcaggtttgg  1920
tcagatgtaa ctccgcttcg cttttcacga atacatgacg gagaagctga catcatgatt  1980
aatttcggtc ggtgggagca tggggatggt tatcctttcg acggcaaaga cgggctgctc  2040
gcccatgcct ttgcgcctgg gaccggcgtc ggtggtgata gccacttcga tgacgatgaa  2100
ctctggaccc tcggagaggg acaagtggtg agagtaaaat acggaaacgc cgacggagaa  2160
tattgcaagt tccccttct attcaatggt aaggaatata atagctgtac tgatacaggt  2220
agatcagacg gcttcctttg gtgctcaacc acctacaatt tcgaaaaaga tggtaagtac  2280
ggcttctgcc ctcatgaggc cctgttcact atgggaggca atgcagaggg acagccgtgc  2340
aaatttccat ttcgctttca aggtacgagc tacgattctt gtacgacgga ggggagaacg  2400
gatgggtata gatggtgtgg cacaacagag gattacgata gagacaagaa atatgggttc  2460
tgtcccgaga ccgctatgag tacagttggg ggtaattccg agggagctcc ctgcgtgttc  2520
ccgttcacat tcttgggtaa caagtacgag tcctgtacca gcgctgggcg gtctgatggt  2580
aaaatgtggt gtgcaacgac ggcaaattac gacgacgatc ggaagtgggg tttttgtcct  2640
gaccagggtt actctctgtt tctcgttgca gcgcatgaat ttggacacgc aatgggtctt  2700
gagcactcac aggaccccgg cgcacttatg gcgccaatat acacttacac caagaacttt  2760
agattgagtc aggacgatat taagggcatc caggagcttt atggagcctc accagacatc  2820
gatctgggga ctggtcccac tcccactctt ggtcctgtca caccagaaat ttgtaaacag  2880
gatatagtct ttgatggtat agcccagatt cgcggagaga tctttttctt taaggacagg  2940
ttcatctgga ggacagtgac gccaagagat aaacccatgg gtcctctgtt ggtagcaacc  3000
ttctggcccg agctcccaga gaagatagat gcagtgtatg aggcccccaca agaggagaaa  3060
gcggtctttt tcgcggggaa tgagtattgg atctactcag cctccactct ggaaagaggg  3120
tacccaaaac cactgacttc tctgggtttg cccccagatg tacagcgagt agatgctgca  3180
tttaattgga gcaagaataa gaagacctac attttcgcgg gggataagtt ctggaggtac  3240
aatgaagtca agaagaaaat ggatcccgga tttccaaagc tcatagccga cgcatggaat  3300
gccatcccgg acaacctgga tgccgtcgta gacttgcagg gtgggggaca ctcctatttt  3360
ttcaaaggag cgtattattt gaaattggag aatcaaagtc ttaagtcagt taagtttgga  3420
tcaatcaaga gcgactggct cgggtgttag                                 3450
```

```
SEQ ID NO: 194          moltype = AA  length = 1149
FEATURE                 Location/Qualifiers
source                  1..1149
                        mol_type = protein
                        organism = Synthetic construct
SEQUENCE: 194
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRM EALMARGALT GPLRALCLLG CLLSHAAAAP SPIIKFPGDV APKTDKELAV  540
QYLNTFYGCP KESCNLFVLK DTLKKMQKFF GLPQTGDLDQ NTIETMRKPR CGNPDVANYN  600
FFPRKPKWDK NQITYRIIGY TPDLDPETVD DAFARAFQVW SDVTPLRFSR IHDGEADIMI  660
NFGRWEHGDG YPFDGKDGLL AHAFAPGTGV GGDSHFDDDE LWTLGEGQVV RVKYGNADGE  720
YCKFPFLFNG KEYNSCTDTG RSDGFLWCST TYNFEKDGKY GFCPHEALFT MGGNAEGQPC  780
KFPFRFQGTS YDSCTTEGRT DGYRWCGTTE DYDRDKKYGF CPETAMSTVG GNSEGAPCVF  840
PFTFLGNKYE SCTSAGRSDG KMWCATTANY DDDRKWGFCP DQGYSLFLVA AHEFGHAMGL  900
EHSQDPGALM APIYTYTKNF RLSQDDIKGI QELYGASPDI DLGTGPTPTL GPVTPEICKQ  960
DIVFDGIAQI RGEIFFFKDR FIWRTVTPRD KPMGPLLVAT FWPELPEKID AVYEAPQEEK  1020
AVFFAGNEYW IYSASTLERG YPKPLTSLGL PPDVQRVDAA FNWSKNKKTY IFAGDKFWRY  1080
NEVKKKMDPG FPKLIADAWN AIPDNLDAVV DLQGGGHSYF FKGAYYLKLE NQSLKSVKFG  1140
SIKSDWLGC                                                        1149
```

```
SEQ ID NO: 195          moltype = DNA  length = 3648
FEATURE                 Location/Qualifiers
source                  1..3648
                        mol_type = other DNA
                        organism = Synthetic construct
SEQUENCE: 195
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gctgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tttgggcccc gctggccggc acttgcggcg tgctcctgct gtcgctggtc  900
atcacccttt actgcaagag gggccggaag aagctgcttt acatcttcaa gcagccgttc  960
atgcggcccg tgcagacgac tcaggaagag gacggatgct cgtgcagatt ccctgaggag  1020
gaagaggggg gatgcgaact gcgcgtcaag ttctcacggt ccgccgacgc ccccgcatat  1080
caacagggcc agaatcagct ctacaacgag ctgaacctgg gaaggagaga ggagtacgac  1140
gtgctggaca agcgacgcgg acgcgacccg gagatggggg ggaaaccacg gcggaaaaac  1200
cctcaggaag gactgtacaa cgaactccag aaagacaaga tggcggaagc ctactcagaa  1260
atcgggatga agggagagcg gaggagggga aagggtcacg acgggctgta ccagggactg  1320
agcaccgcca ctaaggatac ctacgatgcc ttgcatatgc aagcactccc accccggcgg  1380
gcaaagcggg gctcaggggc gactaacttt tcactgttga agcaggccgg ggatgtggag  1440
gagaatcctg gtcctagagc aaagcgaatg gatgcaatga agagagggct ctgctgtgtg  1500
ctgctgctgt gtggagcagt cttcgtttcg cccagcctga actttcgcgc cccaccagtg  1560
atccctaatg tgccattcct ttgggcttgg aatgcgcctt ctgaattctg cttgggaaaa  1620
tttgatgagc ctctggatat gtctcttttc agttttattg ggtcaccaag gattaacgcg  1680
actggacaag gagtgacgat attttatgtc gataggctcg gctactaccc ctacatagat  1740
tccattaccg gcgtaaccgt gaatggtggt atccctcaaa agatctctct tcaagaccac  1800
ttggacaaag caaaaaaaga cattacattc tacatgccgg tggataacct ggggatggcc  1860
gttatcgatt gggaggagtg gagacccacg tgggctagaa actggaagcc gaaggacgtc  1920
tataaaaaca ggtctatcga attggttcag cagcagaacg tgcaattgtc cttgactgag  1980
gcgacagaga aggccaagca agagtttgag aaggcgggaa aggacttttt ggttgagacc  2040
attaagctcg gtaaactgct gcgacctaat catctgtggg gttactacct cttccctgac  2100
tgctacaatc accattacaa gaaaccgggc tacaatggct cttgttttaa tgtcgaaatc  2160
aaacgaaacg acgacctgag ctggctttgg aacgaatcca ccgcactcta ccccagcatc  2220
tatctgaaca cccagcagag tcctgtagca gcaacgctgt acgtccggaa ccgggtacga  2280
gaggcaatca gagtatctaa gatcccggat gctaaatccc cactgccggt atttgcgtac  2340
acccgaatcg tgttcactga ccaggttctg aagtttctct cccaggacga acttgtctat  2400
acgtttggag agacagtagc actcggcgca tcaggcattg ttatatgggg aacccttagc  2460
atcatgcggt caatgaagtc ctgcttgctt cttgataact atatggagac aatcttgaac  2520
ccctatatca tcaatgtaac acttgcagca aaaatgtgct cccaagtact ctgtcaagag  2580
cagggagtat gcatacgaaa aaattggaac agttccgact acctgcacct taaccccgat  2640
aattttgcta tacagcttga aaagggcgga aaatttacag tccgagggaa gccgacattg  2700
gaggatctcg agcaattctc tgaaaagttt tattgctcat gctacagtac ccttagctgt  2760
aaagaaaagg cggacgtcaa ggatactgac gccgtggacg tctgcatcgc cgacggagtt  2820
tgcatcgacg catttcttaa acctcccatg gaaaccgaag agccacaaat cttctataac  2880
gcttctccct caacacttag tgctactatg tttatagttt ctattttgtt ccttattatt  2940
tcaagtgtag ctagtcttgc tagcgacaaa actcacacat gcccaccgtg cccagcacct  3000
gaagctgcgg ggggaccgtc agtcttcctc ttccccccaa aacccaagga caccctcatg  3060
atctcccgga cccctgaggt cacatgcgtg gtggtggacg tgagccacga agaccctgag  3120
gtcaagttca actggtacgt ggacggcgtg gaggtgcata atgccaagac aaagccgcgg  3180
gaggagcagt acaacagcac gtaccgtgtg gtcagcgtcc tcaccgtcct gcaccaggac  3240
tggctgaatg gcaaggagta caagtgcaag gtctccaaca aggcacttgg ggcccctatc  3300
gagaaaacca tctccaaagc caaagggcag ccccgagaac cacaggtgta caccctgccc  3360
ccatctcggg aggagatgac caagaaccag gtcagcctga cctgcctggt caaaggcttc  3420
tatcccagcg acatcgccgt ggagtgggag agcaatgggc agccggagaa caactacaag  3480
accacgcctc ccgtgctgga ctccgacggc tccttcttcc tctacagcaa gctcaccgtg  3540
gacaagagca ggtggcagca ggggaacgtc ttctcatgct ccgtgatgca cgaggctctg  3600
cacaaccact acacgcagaa gagcctctcc ctgtctccgg gtaaataa             3648

SEQ ID NO: 196          moltype = AA  length = 1215
FEATURE                 Location/Qualifiers
source                  1..1215
                        mol_type = protein
                        organism = Synthetic construct
SEQUENCE: 196
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
```

```
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRM DAMKRGLCCV LLLCGAVFVS PSLNFRAPPV IPNVPFLWAW NAPSEFCLGK  540
FDEPLDMSLF SFIGSPRINA TGQGVTIFYV DRLGYYPYID SITGVTVNGG IPQKISLQDH  600
LDKAKKDITF YMPVDNLGMA VIDWEEWRPT WARNWKPKDV YKNRSIELVQ QQNVQLSLTE  660
ATEKAKQEFE KAGKDFLVET IKLGKLLRPN HLWGYYLFPD CYNHHYKKPG YNGSCFNVEI  720
KRNDDLSWLW NESTALYPSI YLNTQQSPVA ATLYVRNRVR EAIRVSKIPD AKSPLPVFAY  780
TRIVFTDQVL KFLSQDELVY TFGETVALGA SGIVIWGTLS IMRSMKSCLL LDNYMETILN  840
PYIINVTLAA KMCSQVLCQE QGVCIRKNWN SSDYLHLNPD NFAIQLEKGG KFTVRGKPTL  900
EDLEQFSEKF YCSCYSTLSC KEKADVKDTD AVDVCIADGV CIDAFLKPPM ETEEPQIFYN  960
ASPSTLSATM FIVSILFLII SSVASLASDK THTCPPCPAP EAAGGPSVFL FPPKPKDTLM  1020
ISRTPEVTCV VVDVSHEDPE VKFNWYVDGV EVHNAKTKPR EEQYNSTYRV VSVLTVLHQD  1080
WLNGKEYKCK VSNKALGAPI EKTISKAKGQ PREPQVYTLP PSREEMTKNQ VSLTCLVKGF  1140
YPSDIAVEWE SNGQPENNYK TTPPVLDSDG SFFLYSKLTV DKSRWQQGNV FSCSVMHEAL  1200
HNHYTQKSLS LSPGK                                                  1215

SEQ ID NO: 197          moltype = DNA  length = 2319
FEATURE                 Location/Qualifiers
source                  1..2319
                        mol_type = other DNA
                        organism = Synthetic construct
SEQUENCE: 197
atgctgttac ttgtgacaag cttgcttcta tgtgaactgc cgcatccggc gtttctgctg  60
attccggaag tacagctggt acagtctgga gggggattgg ttcagccggg cgggtctttg  120
cgcctgtcct gcgcagctag tggcttcact tttgatgact atgctatgca ctgggtcaga  180
caagcgcctg gcaaaggcct tgaatgggtg tccggaatta gctggaatag tggatccatc  240
ggctatgccg atagtgtaaa gggcaggttc acgatcagcc gggataatgc aaagaactct  300
ctctatttgc aaatgaacag tctgcgggct gaagatactg ctctttacta ttgtgctaaa  360
gatttgtcaa gcgtcgccgg acccttcaac tactggggtc aagggacact ggtgacagtt  420
agcagcggtg gtggaggctc cggtggaggt ggtagtggtg gaggaggtag ttcttctgag  480
cttacgcaag atccggcggt tagtgttgct ctggggcaga ctgtacgaat cacgtgccag  540
ggtgactctt tgcgctctta ctacgctagt tggtatcaac aaaaacccgg acaagcgccc  600
gtcctcgtca tctatggcaa gaacaatcgc ccaagcggca tccctgatag gttctccgga  660
tcatcttcag ggaacacagc ctccctgact attacaggtg ctcaagctga ggacgaggct  720
gactattatt gcaacagccg ggactctagc ggtaaccact tggtctttgg tgggggtacc  780
cagctgacgg tacttggagg tggtggaggt tcaggtggtg gcggatcagg tggaggtggt  840
tctggagggg gtggaagtgg cggaggtggt tcacaggcgg cccaggtaca gctgcagcag  900
tcaggggctg aggtgaagaa gcctgggtcc tcggtgaagg tctcctgcaa ggcttctgga  960
ggcaccttca gcagctatgc tatcagctgg gtgcgacagg cccctggaca agggcttgag  1020
tggatgggat ggatcaaccc taacagtggt ggcacaaact atgcacagag gtttcagggc  1080
agggtcacca tgaccaggga cacgtccatc agcacagcct acatggagtt gagcaggctg  1140
agatctgacg acacggccgt gtattactgt gcgagttata atgatgcttt tgatatctgg  1200
ggccaaggca ccctggtcac cgtctcctca ggaggtggcg ggtctggtgg tggcggtagc  1260
ggtggtggcg gatccaattt tatgctgact cagccccact ctgtgtcgga gtctccgggg  1320
aagacggtaa ccatctcctg cacccgcagc agtggcagca ttgccagcaa ctatgtgcag  1380
tggtaccagc agcgcccggg cagtgccccc accattgtga tctatgagga tgatcaaaga  1440
ccctctgggg tccctgatcg gttctctggc tccatcgaca cctcctccaa ctctgcctcc  1500
ctcaccatct ctggactgca gagtgaggac gaggctgact actactgtca gtcttatgag  1560
cccggcaatg gggtattcgg cggagggacc aaggtcaccg tcctagcggc cgcagagtca  1620
aaatacggtc ctccgtgccc tccgtgtccg ttctgggtgc ttgtcgttgt tgggggtgta  1680
ctcgcatgtt attctttgct ggtgactgtg gcgtttatca tcttctgggt aaggagtaaa  1740
cgcagccgcc tgctgcattc agactacatg aacatgaccc cacggcggcc cggcccaacg  1800
cgcaaacact accaacctta cgccccaccg cgagacttgg ccgcctacag atccaagcgc  1860
ggacggaaga aactcttgta catcttcaag cagccgttca tgcgccctgt gcaaaccacc  1920
caagaagagg acgggtgctc ctgccggttc ccggaagagg aagagggcgg ctgcgaactg  1980
cgcgtgaagt tttcccggtc cgccgacgct ccggcgtacc agcaggggca aaaccagctg  2040
tacaacgaac ttaacctcgg tcgccgggaa gaatatgacg tgctggacaa gcggcgggga  2100
agagatcccg agatgggtgg aaagccgcgg cggaagaacc ctcaggaggg cttgtacaac  2160
gagctgcaaa aggacaaaat ggccgaagcc tactccgaga ttggcatgaa gggagagcgc  2220
agacgcggga agggacacga tggactgtac cagggactgt caaccgcgac taaggacact  2280
tacgacgccc tgcacatgca ggccctgccc ccgcgctaa                        2319

SEQ ID NO: 198          moltype = AA  length = 772
FEATURE                 Location/Qualifiers
source                  1..772
                        mol_type = protein
                        organism = Synthetic construct
SEQUENCE: 198
MLLLVTSLLL CELPHPAFLL IPEVQLVQSG GGLVQPGGSL RLSCAASGFT FDDYAMHWVR  60
QAPGKGLEWV SGISWNSGSI GYADSVKGRF TISRDNAKNS LYLQMNSLRA EDTALYYCAK  120
DLSSVAGPFN YWGQGTLVTV SSGGGGSGGG GSGGGGSSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHLVFGGGT QLTVLGGGGG SGGGGSGGGG SGGGGSGGGG SQAAQVQLQQ  300
SGAEVKKPGS SVKVSCKASG GTFSSYAISW VRQAPGQGLE WMGWINPNSG GTNYAQRFQG  360
RVTMTRDTSI STAYMELSRL RSDDTAVYYC ASYNDAFDIW GQGTLVTVSS GGGGSGGGGS  420
GGGGSNFMLT QPHSVSESPG KTVTISCTRS SGSIASNYVQ WYQQRPGSAP TIVIYEDDQR  480
PSGVPDRFSG SIDTSSNSAS LTISGLQSED EADYYCQSYE PGNGVFGGGT KVTVLAAAES  540
KYGPPCPPCP FWVLVVVGGV LACYSLLVTV AFIIFWVRSK RSRLLHSDYM NMTPRRPGPT  600
```

```
RKHYQPYAPP RDFAAYRSKR GRKKLLYIFK QPFMRPVQTT QEEDGCSCRF PEEEEGGCEL  660
RVKFSRSADA PAYQQGQNQL YNELNLGRRE EYDVLDKRRG RDPEMGGKPR RKNPQEGLYN  720
ELQKDKMAEA YSEIGMKGER RRGKGHDGLY QGLSTATKDT YDALHMQALP PR          772

SEQ ID NO: 199          moltype = DNA  length = 1183
FEATURE                 Location/Qualifiers
source                  1..1183
                        mol_type = other DNA
                        organism = Synthetic construct
SEQUENCE: 199
cgtgaggctc cggtgcccgt cagtgggcag agcgcacatc gcccacagtc cccgagaagt  60
tggggggagg ggtcggcaat tgaaccggtg cctagagaag gtggcgcggg gtaaactggg  120
aaagtgatgt cgtgtactgg ctccgccttt ttcccgaggg tgggggagaa ccgtatataa  180
gtgcagtagt cgccgtgaac gttctttttc gcaacgggtt tgccgccaga acacaggtaa  240
gtgccgtgtg tggttcccgc gggcctggcc tctttacggg ttatggccct tgcgtgcctt  300
gaattacttc cacctggctg cagtacgtga ttcttgatcc cgagcttcgg gttggaagtg  360
ggtgggagag ttcgaggcct tgcgcttaag gagccccttc gcctcgtgct tgagttgagg  420
cctggcctgg gcgctggggc cgccgcgtgc gaatctggtg gcaccttcgc gcctgtctcg  480
ctgctttcga taagtctcta gccatttaaa atttttgatg acctgctgcg acgctttttt  540
tctggcaaga tagtcttgta aatgcgggcc aagatctgca cactggtatt tcggtttttg  600
gggccgcggg cggcgacggg gcccgtgcgt cccagcgcac atgttcggcg aggcggggcc  660
tgcgagcgcg gccaccgaga atcggacggg ggtagtctca agctggccgg cctgctctgg  720
tgcctggcct cgcgccgccg tgtatcgccc cgccctgggc ggcaaggctg gcccggtcgg  780
caccagttgc gtgagcggaa agatggccgc ttcccggccc tgctgcaggg agctcaaaat  840
ggaggacgcg gcgctcggga gagcgggcgg gtgagtcacc cacacaaagg aaaagggcct  900
ttccgtcctc agccgtcgct tcatgtgact ccacggagta ccgggcgccg tccaggcacc  960
tcgattagtt ctcgagcttt tggagtacgt cgtctttagg ttggggggag gggttttatg  1020
cgatggagtt tccccacact gagtgggtgg agactgaagt taggccagct tggcacttga  1080
tgtaattctc cttggaattt gccctttttg agtttggatc ttggttcatt ctcaagcctc  1140
agacagtggt tcaaagtttt tttcttccat ttcaggtgtc gtg                    1183

SEQ ID NO: 200          moltype = DNA  length = 497
FEATURE                 Location/Qualifiers
source                  1..497
                        mol_type = other DNA
                        organism = Synthetic construct
SEQUENCE: 200
agtggtccag gctctagttt tgactcaaca atatcaccag ctgaagccta tagagtacga  60
gccatagata gaataaaaga ttttatttag tctccagaaa aaggggggaa tgaaagaccc  120
cacctgtagg tttggcaagc taggatcaag gttaggaaca gagagacagc agaatatggg  180
ccaaacagga tatctgtggt aagcagttcc tgccccggct cagggccaag aacagttgga  240
acagcagaat atgggccaaa caggatatct gtggtaagca gttcctgccc cggctcaggg  300
ccaagaacag atggtcccca gatgcggtcc cgccctcagc agtttctaga gaaccatcag  360
atgtttccag ggtgccccaa ggacctgaaa tgaccctgtg ccttatttga actaaccaat  420
cagttcgctt ctcgcttctg ttcgcgcgct tctgctcccc gagctcaata aaagagccca  480
caacccctca ctcggcg                                                 497

SEQ ID NO: 201          moltype = DNA  length = 367
FEATURE                 Location/Qualifiers
source                  1..367
                        mol_type = other DNA
                        organism = Synthetic construct
SEQUENCE: 201
tgaaagaccc cacctgtagg tttggcaagc tagcttaagt aacgccattt tgcaaggcat  60
ggaaaataca taactgagaa tagagaagtt cagatcaagg ttaggaacag agagacagca  120
gaatatgggc caaacaggat atctgtggta agcagttcct gccccggctc agggccaaga  180
acagatggtc cccagatgcg gtcccgccct cagcagtttc tagagaacca tcagatgttt  240
ccagggtgcc ccaaggacct gaaaatgacc ctgtgcctta tttgaactaa ccaatcagtt  300
cgcttctcgc ttctgttcgc gcgtttctgc tccccgagct caataaaaga gcccacaacc  360
cctcact                                                            367

SEQ ID NO: 202          moltype = DNA  length = 515
FEATURE                 Location/Qualifiers
source                  1..515
                        mol_type = other DNA
                        organism = Synthetic construct
SEQUENCE: 202
tccacggggt tggggttgcg ccttttccaa ggcagccctg ggtttgcgca gggacgcggc  60
tgctctgggc gtggttccgg gaaacgcagc ggcgccgacc ctgggtctcg cacattcttc  120
acgtccgttc gcagcgtcac ccggatcttc gccgctaccc ttgtgggccc cccggcgacg  180
cttcctgctc cgcccctaag tcgggaaggt tccttgcggt tcgcggcgtg ccggacgtga  240
caaacggaag ccgcacgtct cactagtacc ctcgcagacg gacagcgcca gggagcaatg  300
gcagcgcgcc gaccgcgatg ggctgtggcc aatagcggct gctcagcggg gcgcgccgag  360
agcagcggcc gggaaggggc ggtgcgggag gcggggtgtg gggcggtagt gtgggccctg  420
ttcctgcccg cgcggtgttc cgcattctgc aagcctccgg agcgcacgtc ggcagtcggc  480
tccctcgttg accgaatcac cgacctctct ccccg                              515

SEQ ID NO: 203          moltype = DNA  length = 244
FEATURE                 Location/Qualifiers
```

```
source                  1..244
                        mol_type = other DNA
                        organism = Synthetic construct
SEQUENCE: 203
tggaggaaaa actgtttcat acagaaggcg tggaggaaaa actgtttcat acagaaggcg  60
tggaggaaaa actgtttcat acagaaggcg tggaggaaaa actgtttcat acagaaggcg  120
tggaggaaaa actgtttcat acagaaggcg tggaggaaaa actgtttcat acagaaggcg  180
tctgcaggag actctagagg gtatataatg gtttaaactt aagcttggta ccgggccccc  240
gaag                                                               244

SEQ ID NO: 204          moltype = DNA  length = 118
FEATURE                 Location/Qualifiers
source                  1..118
                        mol_type = other DNA
                        organism = Synthetic construct
SEQUENCE: 204
tgagtcagtg actcagtgag tcagtgactc agtgagtcag tgactcagct cgaggatctc  60
gctagcggga atttccgggg actttccggg aatttccggg gactttccgg gaatttcc    118

SEQ ID NO: 205          moltype = DNA  length = 432
FEATURE                 Location/Qualifiers
source                  1..432
                        mol_type = other DNA
                        organism = Synthetic construct
SEQUENCE: 205
atgaaaacgt ttgagatact taaacatctc caggccgacg ccattgtcct gttcatgaag  60
gttcataatt ttcattggaa cgtgaaagga actgatttct ttaatgtcca caaagccacc  120
gaggaaattt atgaggagtt tgcggatatg tttgacgatt tggctgaacg aatagtgcag  180
ttgggtcatc atccgttggt aactctgtcc gaggcaatca agcttacgag ggtgaaagag  240
gagacaaaga catcattcca ctctaaggac attttcaaag aaattttgga agattataaa  300
tacctggaaa aggagttcaa ggagctttcc aacacggccg aaaaggaggg agacaaagtt  360
acagtcacat atgcggacga tcaactggcc aagctccaga agagtatctg gatgctccaa  420
gcccatttgg cc                                                      432

SEQ ID NO: 206          moltype = AA  length = 144
FEATURE                 Location/Qualifiers
source                  1..144
                        mol_type = protein
                        organism = Synthetic construct
SEQUENCE: 206
MKTFEILKHL QADAIVLFMK VHNFHWNVKG TDFFNVHKAT EEIYEEFADM FDDLAERIVQ  60
LGHHPLVTLS EAIKLTRVKE ETKTSFHSKD IFKEILEDYK YLEKEFKELS NTAEKEGDKV  120
TVTYADDQLA KLQKSIWMLQ AHLA                                         144

SEQ ID NO: 207          moltype = AA  length = 660
FEATURE                 Location/Qualifiers
source                  1..660
                        mol_type = protein
                        organism = Synthetic construct
SEQUENCE: 207
MEALMARGAL TGPLRALCLL GCLLSHAAAA PSPIIKFPGD VAPKTDKELA VQYLNTFYGC  60
PKESCNLFVL KDTLKKMQKF FGLPQTGDLD QNTIETMRKP RCGNPDVANY NFFPRKPKWD  120
KNQITYRIIG YTPDLDPETV DDAFARAFQV WSDVTPLRFS RIHDGEADIM INFGRWEHGD  180
GYPFDGKDGL LAHAFAPGTG VGGDSHFDDD ELWTLGEGQV VRVKYGNADG EYCKFPFLFN  240
GKEYNSCTDT GRSDGFLWCS TTYNFEKDGK YGFCPHEALF TMGGNAEGQP CKFPFRFQGT  300
SYDSCTTEGR TDGYRWCGTT EDYDRDKKYG FCPETAMSTV GGNSEGAPCV FPFTFLGNKY  360
ESCTSAGRSD GKMWCATTAN YDDDRKWGFC PDQGYSLFLV AAHEFGHAMG LEHSQDPGAL  420
MAPIYTYTKN FRLSQDDIKG IQELYGASPD IDLGTGPTPT LGPVTPEICK QDIVFDGIAQ  480
IRGEIFFFKD RFIWRTVTPR DKPMGPLLVA TFWPELPEKI DAVYEAPQEE KAVFFAGNEY  540
WIYSASTLER GYPKPLTSLG LPPDVQRVDA AFNWSKNKKT YIFAGDKFWR YNEVKKKMDP  600
GFPKLIADAW NAIPDNLDAV VDLQGGGHSY FFKGAYYLKL ENQSLKSVKF GSIKSDWLGC  660

SEQ ID NO: 208          moltype = DNA  length = 1980
FEATURE                 Location/Qualifiers
source                  1..1980
                        mol_type = other DNA
                        organism = Synthetic construct
SEQUENCE: 208
atggaagctc ttatggctag gggagcgctc acaggtccat tgcgggcact gtgcctgttg  60
gggtgcctgt tgtctcatgc ggctgcggct ccgtcaccaa ttatcaaatt tcctggcgac  120
gttgccccga agacagacaa ggaacttgcc gtgcagtacc tcaatacgtt ctatggatgt  180
cctaaagaat catgcaatct gttcgttttg aaagataccc ttaagaagat gcaaaagttc  240
tttggcttgc cacagactgg ggaccttgac cagaatacaa ttgaaactat gagaaaaccg  300
agatgcggca accccgatgt ggctaactac aacttttttc ccagaaagcc taaatgggat  360
aagaaccaga ttacataccg gataatagga tatacacccg acctggaccc ggagacagtt  420
gacgacgcat ttgcgcgcgc ctttcaggtt tggtcagatg taactccgct tcgcttttca  480
cgaatacatg acggagaagc tgacatcatg attaatttcg gtcggtggga gcatggggat  540
ggttatcctt tcgacggcaa agacgggctg ctcgcccatg cctttgcgcc tgggaccggc  600
gtcggtggtg atagccactt cgatgacgat gaactctgga ccctcggaga gggacaagtg  660
```

```
gtgagagtaa aatacggaaa cgccgacgga gaatattgca agttcccctt tctattcaat  720
ggtaaggaat ataatagctg tactgataca ggtagatcag acggcttcct ttggtgctca  780
accacctaca atttcgaaaa agatggtaag tacggcttct gccctcatga ggccctgttc  840
actatgggag gcaatgcaga gggacagccg tgcaaatttc catttcgctt tcaaggtacg  900
agctacgatt cttgtacgac ggaggggaga acggatgggt atagatggtg tggcacaaca  960
gaggattacg atagagacaa gaaatatggg ttctgtcccg agaccgctat gagtacagtt  1020
gggggtaatt ccgagggagc tccctgcgtg ttcccgttca cattcttggg taacaagtac  1080
gagtcctgta ccagcgctgg gcggtctgat ggtaaaatgt ggtgtgcaac gacggcaaat  1140
tacgacgacg atcggaagtg gggtttttgt cctgaccagg gttactctct gtttctcgtt  1200
gcagcgcatg aatttggaca cgcaatgggt cttgagcact cacaggaccc cggcgcactt  1260
atggcgccaa tatacactta caccaagaac tttagattga gtcaggacga tattaagggc  1320
atccaggagc tttatggagc ctcaccagac atcgatctgg ggactggtcc cactccccact  1380
cttggtcctg tcacaccaga aatttgtaaa caggatatag tctttgatgg tatagcccag  1440
attcgcggag agatcttttt ctttaaggac aggttcatct ggaggacagt gacgccaaga  1500
gataaaccca tgggtcctct gttggtagca accttctggc ccgagctccc agagaagata  1560
gatgcagtgt atgaggcccc acaagaggag aaagcggtct ttttcgcggg gaatgagtat  1620
tggatctact cagcctccac tctggaaaga gggtacccaa aaccactgac ttctctgggt  1680
ttgcccccag atgtacagcg agtagatgct gcatttaatt ggagcaagaa taagaagacc  1740
tacattttcg cgggggataa gttctggagg tacaatgaag tcaagaagaa aatggatccc  1800
ggatttccaa agctcatagc cgacgcatgg aatgccatcc cggacaacct ggatgccgtc  1860
gtagacttgc agggtggggg acactcctat tttttcaaag gagcgtatta tttgaaattg  1920
gagaatcaaa gtcttaagtc agttaagttt ggatcaatca agagcgactg gctcgggtgt  1980

SEQ ID NO: 209         moltype = AA  length = 707
FEATURE                Location/Qualifiers
source                 1..707
                       mol_type = protein
                       organism = Synthetic construct
SEQUENCE: 209
MSLWQPLVLV LLVLGCCFAA PRQRQSTLVL FPGDLRTNLT DRQLAEEYLY RYGYTRVAEM  60
RGESKSLGPA LLLLQKQLSL PETGELDSAT LKAMRTPRCG VPDLGRFQTF EGDLKWHHHN  120
ITYWIQNYSE DLPRAVIDDA FARAFALWSA VTPLTFTRVY SRDADIVIQF GVAEHGDGYP  180
FDGKDGLLAH AFPPGPGIQG DAHFDDDELW SLGKGVVVPT RFGNADGAAC HFPFIFEGRS  240
YSACTTDGRS DGLPWCSTTA NYDTDDRFGF CPSERLYTQD GNADGKPCQF PFIFQGQSYS  300
ACTTDGRSDG YRWCATTANY DRDKLFGFCP TRADSTVMGG NSAGELCVFP FTFLGKEYST  360
CTSEGRGDGR LWCATTSNFD SDKKWGFCPD QGYSLFLVAA HEFGHALGLD HSSVPEALMY  420
PMYRFTEGPP LHKDDVNGIR HLYGPRPEPE PRPPTTTTPQ PTAPPTVCPT GPPTVHPSER  480
PTAGPTGPPS AGPTGPPTAG PSTATTVPLS PVDDACNVNI FDAIAEIGNQ LYLFKDGKYW  540
RFSEGRGSRP QGPFLIADKW PALPRKLDSV FEERLSKKLF FFSGRQVWVY TGASVLGPRR  600
LDKLGLGADV AQVTGALRSG RGKMLLFSGR RLWRFDVKAQ MVDPRSASEV DRMFPGVPLD  660
THDVFQYREK AYFCQDRFYW RVSSRSELNQ VDQVGYVTYD ILQCPED                707

SEQ ID NO: 210         moltype = DNA  length = 2121
FEATURE                Location/Qualifiers
source                 1..2121
                       mol_type = other DNA
                       organism = Synthetic construct
SEQUENCE: 210
atgagcctct ggcagcccct ggtcctggtg ctcctggtgc tgggctgctg ctttgctgcc  60
cccagacagc gccagtccac ccttgtgctc ttccctggag acctgagaac caatctcacc  120
gacaggcagc tggcagagga atacctgtac cgctatggtt acactcgggt ggcagagatg  180
cgtggagagt cgaaatctct ggggcctgcg ctgctgcttc tccagaagca actgtccctg  240
cccgagaccg gtgagctgga tagcgccacg ctgaaggcca tgcgaacccc acggtgcggg  300
gtcccagacc tgggcagatt ccaaaccttt gagggcgacc tcaagtggca ccaccacaac  360
atcacctatt ggatccaaaa ctactcggaa gacttgccgc gggcggtgat tgacgacgcc  420
tttgcccgcg ccttcgcact gtggagcgcg gtgacgccgc tcaccttcac tcgcgtgtac  480
agccgggacg cagacatcgt catccagttt ggtgtcgcgg agcacggaga cgggtatccc  540
ttcgacggga aggacgggct cctggcacac gcctttcctc ctggccccgg cattcaggga  600
gacgcccatt tcgacgatga cgagttgtgg tccctgggca agggcgtcgt ggttccaact  660
cggtttggaa acgcagatgg cgcggcctgc cacttcccct tcatcttcga gggccgctcc  720
tactctgcct gcaccaccga tggacggtcc gacggcttgc cctggtgcag taccacggcc  780
aactacgaca ccgacgaccg gtttggcttc tgccccagcg agagactcta cacccaggac  840
ggcaatgctg atgggaaacc ctgccagttt ccattcatct tccaaggcca atcctactcc  900
gcctgcacca cggacggtcg ctccgacggg taccgctggt gcgccaccac cgccaactac  960
gaccgggaca agctcttcgg cttctgcccg acccgagctg actcgacggt gatggggggc  1020
aactcggcgg gggagctgtg cgtcttcccc ttcactttcc tgggtaagga gtactcgacc  1080
tgtaccagcg agggccgcgg agatgggcgc ctctggtgcg ctaccacctc gaactttgac  1140
agcgacaaga agtggggctt ctgcccggac caaggataca gtttgttcct cgtggcggcg  1200
catgagttcg gccacgcgct gggcttagat cattcctcag tgccggaggc gctcatgtac  1260
cctatgtacc gcttcactga ggggcccccc ttgcataagg acgacgtgaa tggcatccgg  1320
cacctctatg gtcctcgccc tgaacctgag ccacgacctc caacaaccac cacaccgcag  1380
cccacggctc caccgacggt ctgccccacc ggaccccccca ctgtccaccc ctcagagcgc  1440
cccactgctg gcccaacagg acctccctca gctggcccca caggtccccc aactgctggc  1500
ccttctacgg ccactactgt gcctttgagt ccggtggacg atgcctgcaa cgtgaacatc  1560
ttcgacgcca tcgcggagat tgggaaccag ctgtatttgt tcaaggatgg gaagtactgg  1620
cgattctctg agggcagggg gagccggccg cagggcccct tccttatcgc cgacaagtgg  1680
cccgcgctgc cccgcaagct ggactcggtc tttgaggagc ggctctccaa gaagcttttc  1740
ttcttctctg gtcgccaggt gtgggtgtac acaggtgcgt cggtgctggg accgaggcgt  1800
ctagacaagc taggcctggg agcagacgtg gcccaggtga ccggggccct ccggagtggc  1860
```

```
agggggaaga tgctgctgtt cagcgggcgg cgcctctgga ggttcgacgt gaaggcgcag  1920
atggtggatc cccggagcgc cagcgaggtg gaccggatgt tccccggggt gcctttggac  1980
acgcacgacg tcttccagta ccgagagaaa gcctatttct gccaggaccg cttctactgg  2040
cgcgtgagtt cccggagtga gttgaaccag gtggaccaag tgggctacgt gacctatgac  2100
atcctgcagt gccctgagga c                                            2121

SEQ ID NO: 211         moltype = AA  length = 543
FEATURE                Location/Qualifiers
source                 1..543
                       mol_type = protein
                       organism = Synthetic construct
SEQUENCE: 211
MLLRSKPALP PPLMLLLLGP LGPLSPGALP RPAQAQDVVD LDFFTQEPLH LVSPSFLSVT  60
IDANLATDPR FLILLGSPKL RTLARGLSPA YLRFGGTKTD FLIFDPKKES TFEERSYWQS  120
QVNQDICKYG SIPPDVEEKL RLEWPYQEQL LLREHYQKKF KNSTYSRSSV DVLYTFANCS  180
GLDLIFGLNA LLRTADLQWN SSNAQLLLDY CSSKGYNISW ELGNEPNSFL KKADIFINGS  240
QLGEDFIQLH KLLRKSTFKN AKLYGPDVGQ PRRKTAKMLK SFLKAGGEVI DSVTWHHYYL  300
NGRTATKEDF LNPDVLDIFI SSVQKVFQVV ESTRPGKKVW LGETSSAYGG GAPLLSDTFA  360
AGFMWLDKLG LSARMGIEVV MRQVFFGAGN YHLVDENFDP LPDYWLSLLF KKLVGTKVLM  420
ASVQGSKRRK LRVYLHCTNT DNPRYKEGDL TLYAINLHNV TKYLRLPYPF SNKQVDKYLL  480
RPLGPHGLLS KSVQLNGLTL KMVDDQTLPP LMEKPLRPGS SLGLPAFSYS FFVIRNAKVA  540
ACI                                                                543

SEQ ID NO: 212         moltype = DNA  length = 1629
FEATURE                Location/Qualifiers
source                 1..1629
                       mol_type = other DNA
                       organism = Synthetic construct
SEQUENCE: 212
atgcttctac gttctaaacc tgcacttcct ccaccactta tgctacttct tctaggacct  60
cttggtcctc tatcacctgg agctctacct cgacctgcac aagcacagga cgtcgtggac  120
ctggacttct tcacccagga gccgctgcac ctggtgagcc cctcgttcct gtccgtcacc  180
attgacgcca acctggccac ggacccgcgg ttcctcatcc tcctgggttc tccaaagctt  240
cgtaccttgg ccagaggctt gtctcctgcg tacctgaggt ttggtggcac caagacagac  300
ttcctaattt tcgatcccaa gaaggaatca acctttgaag agagaagtta ctggcaatct  360
caagtcaacc aggatatttg caaatatgga tccatccctc ctgatgtgga ggagaagtta  420
cggttggaat ggccctacca ggagcaattg ctactccgag aacactacca gaaaaagttc  480
aagaacagca cctactcaag aagctctgta gatgtgctat acacttttgc aaactgctca  540
ggactggact tgatctttgg cctaaatgcg ttattaagaa cagcagattt gcagtggaac  600
agttctaatg ctcagttgct cctggactac tgctcttcca aggggtataa catttcttgg  660
gaactaggca atgaacctaa cagtttcctt aagaaggctg atattttcat caatgggtcg  720
cagttaggag aagattttat tcaattgcat aaacttctaa gaaagtccac cttcaaaaat  780
gcaaaactct atggtcctga tgttggtcag cctcgaagaa agacggctaa gatgctgaag  840
agcttcctga aggctggtgg agaagtgatt gattcagtta catggcatca ctactatttg  900
aatggacgga ctgctaccaa ggaagatttt ctaaaccctg atgtattgga cattttttatt  960
tcatctgtgc aaaaagtttt ccaggtggtt gagagcacca ggcctggcaa gaaggtctgg  1020
ttaggagaaa caagctctgc atatggaggc ggagcgccct tgctatccga cacctttgca  1080
gctggcttta tgtggctgga taaattgggc ctgtcagccc gaatgggaat agaagtggtg  1140
atgaggcaag tattctttgg agcaggaaac taccatttag tggatgaaaa cttcgatcct  1200
ttacctgatt attggctatc tcttctgttc aagaaattgg tgggcaccaa ggtgttaatg  1260
gcaagcgtgc aaggttcaaa gagaaggaag cttcgagtat accttcattg cacaaacact  1320
gacaatccaa ggtataaaga aggagattta actctgtatg ccataaacct ccataatgtc  1380
accaagtact tgcggttacc ctatcctttt tctaacaagc aagtggataa ataccttcta  1440
agacctttgg gacctcatgg attactttcc aaatctgtcc aactcaatgg tctaactcta  1500
aagatggtgg atgatcaaac cttgccacct ttaatggaaa aacctctccg gccaggaagt  1560
tcactgggct tgccagcttt ctcatatagt ttttttgtga taagaaatgc caaagttgct  1620
gcttgcatc                                                          1629

SEQ ID NO: 213         moltype = AA  length = 497
FEATURE                Location/Qualifiers
source                 1..497
                       mol_type = protein
                       organism = Synthetic construct
SEQUENCE: 213
MDAMKRGLCC VLLLCGAVFV SPSLNFRAPP VIPNVPFLWA WNAPSEFCLG KFDEPLDMSL  60
FSFIGSPRIN ATGQGVTIFY VDRLGYYPYI DSITGVTVNG GIPQKISLQD HLDKAKKDIT  120
FYMPVDNLGM AVIDWEEWRP TWARNWKPKD VYKNRSIELV QQQNVQLSLT EATEKAKQEF  180
EKAGKDFLVE TIKLGKLLRP NHLWGYYLFP DCYNHHYKKP GYNGSCFNVE IKRNDDLSWL  240
WNESTALYPS IYLNTQQSPV AATLYVRNRV REAIRVSKIP DAKSPLPVFA YTRIVFTDQV  300
LKFLSQDELV YTFGETVALG ASGIVIWGTL SIMRSMKSCL LLDNYMETIL NPYIINVTLA  360
AKMCSQVLCQ EQGVCIRKNW NSSDYLHLNP DNFAIQLEKG GKFTVRGKPT LEDLEQFSEK  420
FYCSCYSTLS CKEKADVKDT DAVDVCIADG VCIDAFLKPP METEEPQIFY NASPSTLSAT  480
MFIVSILFLI ISSVASL                                                 497

SEQ ID NO: 214         moltype = DNA  length = 1491
FEATURE                Location/Qualifiers
source                 1..1491
                       mol_type = other DNA
                       organism = Synthetic construct
```

SEQUENCE: 214
atggatgcaa tgaagagagg gctctgctgt gtgctgctgc tgtgtggagc agtcttcgtt 60
tcgcccagcc tgaactttcg cgccccacca gtgatcccta atgtgccatt cctttgggct 120
tggaatgcgc cttctgaatt ctgcttggga aaatttgatg agcctctgga tatgtctctt 180
ttcagtttta ttgggtcacc aaggattaac gcgactggac aaggagtgac gatattttat 240
gtcgataggc tcggctacta cccctacata gattccatta ccggcgtaac cgtgaatggt 300
ggtatccctc aaaagatctc tcttcaagac cacttggaca aagcaaaaaa agacattaca 360
ttctacatgc cggtggataa cctggggatg gccgttatcg attgggagga gtggagaccc 420
acgtgggcta gaaactggaa gccgaaggac gtctataaaa acaggtctat cgaattggtt 480
cagcagcaga acgtgcaatt gtccttgact gaggcgacag agaaggccaa gcaagagttt 540
gagaaggcgg gaaaggactt tttggttgag accattaagc tcggtaaact gctgcgacct 600
aatcatctgt ggggttacta cctcttccct gactgctaca atcaccatta caagaaaccg 660
ggctacaatg gctcttgttt taatgtcgaa atcaaacgaa acgacgacct gagctggctt 720
tggaacgaat ccaccgcact ctaccccagc atctatctga acacccagca gagtcctgta 780
gcagcaacgc tgtacgtccg gaaccgggta cgagaggcaa tcagagtatc taagatcccg 840
gatgctaaat ccccactgcc ggtatttgcg tacacccgaa tcgtgttcac tgaccaggtt 900
ctgaagtttc tctcccagga cgaacttgtc tatacgtttg gagagacagt agcactcggc 960
gcatcaggca ttgttatatg ggaaccctt agcatcatgc ggtcaatgaa gtcctgcttg 1020
cttcttgata actatatgga gacaatcttg aacccctata tcatcaatgt aacacttgca 1080
gcaaaaaatgt gctcccaagt actctgtcaa gagcagggag tatgcatacg aaaaaattgg 1140
aacagttccg actacctgca ccttaacccc gataattttg ctatacagct tgaaaagggc 1200
ggaaaattta cagtccgagg gaagccgaca ttggaggatc tcgagcaatt ctctgaaaag 1260
ttttattgct catgctacag tacccttagc tgtaaagaaa aggcggacgt caaggatact 1320
gacgccgtgg acgtctgcat cgccgacgga gtttgcatcg acgcatttct taaacctccc 1380
atggaaaccg aagagccaca aatcttctat aacgcttctc cctcaacact tagtgctact 1440
atgtttatag tttctatttt gttccttatt atttcaagtg tagctagtct t 1491

SEQ ID NO: 215 moltype = AA length = 478
FEATURE Location/Qualifiers
source 1..478
mol_type = protein
organism = Synthetic construct
SEQUENCE: 215
MDAMKRGLCC VLLLCGAVFV SPSLNFRAPP VIPNVPFLWA WNAPSEFCLG KFDEPLDMSL 60
FSFIGSPRIN ATGQGVTIFY VDRLGYYPYI DSITGVTVNG GIPQKISLQD HLDKAKKDIT 120
FYMPVDNLGM AVIDWEEWRP TWARNWKPKD VYKNRSIELV QQQNVQLSLT EATEKAKQEF 180
EKAGKDFLVE TIKLGKLLRP NHLWGYYLFP DCYNHHYKKP GYNGSCFNVE IKRNDDLSWL 240
WNESTALYPS IYLNTQQSPV AATLYVRNRV REAIRVSKIP DAKSPLPVFA YTRIVFTDQV 300
LKFLSQDELV YTFGETVALG ASGIVIWGTL SIMRSMKSCL LLDNYMETIL NPYIINVTLA 360
AKMCSQVLCQ EQGVCIRKNW NSSDYLHLNP DNFAIQLEKG GKFTVRGKPT LEDLEQFSEK 420
FYCSCYSTLS CKEKADVKDT DAVDVCIADG VCIDAFLKPP METEEPQIFY NASPSTLS 478

SEQ ID NO: 216 moltype = DNA length = 1434
FEATURE Location/Qualifiers
source 1..1434
mol_type = other DNA
organism = Synthetic construct
SEQUENCE: 216
atggatgcaa tgaagagagg gctctgctgt gtgctgctgc tgtgtggagc agtcttcgtt 60
tcgcccagcc tgaactttcg cgccccacca gtgatcccta atgtgccatt cctttgggct 120
tggaatgcgc cttctgaatt ctgcttggga aaatttgatg agcctctgga tatgtctctt 180
ttcagtttta ttgggtcacc aaggattaac gcgactggac aaggagtgac gatattttat 240
gtcgataggc tcggctacta cccctacata gattccatta ccggcgtaac cgtgaatggt 300
ggtatccctc aaaagatctc tcttcaagac cacttggaca aagcaaaaaa agacattaca 360
ttctacatgc cggtggataa cctggggatg gccgttatcg attgggagga gtggagaccc 420
acgtgggcta gaaactggaa gccgaaggac gtctataaaa acaggtctat cgaattggtt 480
cagcagcaga acgtgcaatt gtccttgact gaggcgacag agaaggccaa gcaagagttt 540
gagaaggcgg gaaaggactt tttggttgag accattaagc tcggtaaact gctgcgacct 600
aatcatctgt ggggttacta cctcttccct gactgctaca atcaccatta caagaaaccg 660
ggctacaatg gctcttgttt taatgtcgaa atcaaacgaa acgacgacct gagctggctt 720
tggaacgaat ccaccgcact ctaccccagc atctatctga acacccagca gagtcctgta 780
gcagcaacgc tgtacgtccg gaaccgggta cgagaggcaa tcagagtatc taagatcccg 840
gatgctaaat ccccactgcc ggtatttgcg tacacccgaa tcgtgttcac tgaccaggtt 900
ctgaagtttc tctcccagga cgaacttgtc tatacgtttg gagagacagt agcactcggc 960
gcatcaggca ttgttatatg ggaaccctt agcatcatgc ggtcaatgaa gtcctgcttg 1020
cttcttgata actatatgga gacaatcttg aacccctata tcatcaatgt aacacttgca 1080
gcaaaaaatgt gctcccaagt actctgtcaa gagcagggag tatgcatacg aaaaaattgg 1140
aacagttccg actacctgca ccttaacccc gataattttg ctatacagct tgaaaagggc 1200
ggaaaattta cagtccgagg gaagccgaca ttggaggatc tcgagcaatt ctctgaaaag 1260
ttttattgct catgctacag tacccttagc tgtaaagaaa aggcggacgt caaggatact 1320
gacgccgtgg acgtctgcat cgccgacgga gtttgcatcg acgcatttct taaacctccc 1380
atggaaaccg aagagccaca aatcttctat aacgcttctc cctcaacact tagt 1434

SEQ ID NO: 217 moltype = AA length = 471
FEATURE Location/Qualifiers
source 1..471
mol_type = protein
organism = Synthetic construct
SEQUENCE: 217

```
MDAMKRGLCC VLLLCGAVFV SPSLNFRAPP VIPNVPFLWA WNAPSEFCLG KFDEPLDMSL  60
FSFIGSPRIN ATGQGVTIFY VDRLGYYPYI DSITGVTVNG GIPQKISLQD HLDKAKKDIT  120
FYMPVDNLGM AVIDWEEWRP TWARNWKPKD VYKNRSIELV QQQNVQLSLT EATEKAKQEF  180
EKAGKDFLVE TIKLGKLLRP NHLWGYYLFP DCYNHHYKKP GYNGSCFNVE IKRNDDLSWL  240
WNESTALYPS IYLNTQQSPV AATLYVRNRV REAIRVSKIP DAKSPLPVFA YTRIVFTDQV  300
LKFLSQDELV YTFGETVALG ASGIVIWGTL SIMRSMKSCL LLDNYMETIL NPYIINVTLA  360
AKMCSQVLCQ EQGVCIRKNW NSSDYLHLNP DNFAIQLEKG GKFTVRGKPT LEDLEQFSEK  420
FYCSCYSTLS CKEKADVKDT DAVDVCIADG VCIDAFLKPP METEEPQIFY N           471

SEQ ID NO: 218         moltype = DNA  length = 1413
FEATURE                Location/Qualifiers
source                 1..1413
                       mol_type = other DNA
                       organism = Synthetic construct
SEQUENCE: 218
atggatgcaa tgaagagagg gctctgctgt gtgctgctgc tgtgtggagc agtcttcgtt  60
tcgcccagcc tgaactttcg cgcccccacca gtgatccccta atgtgccatt cctttgggct  120
tggaatgcgc cttctgaatt ctgcttggga aaatttgatg agcctctgga tatgtctctt  180
ttcagtttta ttgggtcacc aaggattaac gcgactggac aaggagtgac gatattttat  240
gtcgataggc tcggctacta cccctacata gattccatta ccggcgtaac cgtgaatggt  300
ggtatccctc aaaagatctc tcttcaagac cacttggaca aagcaaaaaa agacattaca  360
ttctacatgc cggtggataa cctggggatg gccgttatcg attgggagga gtggagaccc  420
acgtgggcta gaaactggaa gccgaaggac gtctataaaa acaggtctat cgaattggtt  480
cagcagcaga acgtgcaatt gtccttgact gaggcgacag agaaggccaa gcaagagttt  540
gagaaggcgg gaaaggactt tttggttgag accattaagc tcggtaaact gctgcgacct  600
aatcatctgt ggggttacta cctcttccct gactgctaca atcaccatta caagaaaccg  660
ggctacaatg gctcttgttt taatgtcgaa atcaaacgaa acgacgacct gagctggctt  720
tggaacgaat ccaccgcact ctaccccagc atctatctga acacccagca gagtcctgta  780
gcagcaacgc tgtacgtccg gaaccgggta cgagaggcaa tcagagtatc taagatcccg  840
gatgctaaat ccccactgcc ggtatttgcg tacacccgaa tcgtgttcac tgaccaggtt  900
ctgaagtttc tctcccagga cgaacttgtc tatacgtttg gagagacagt agcactcggc  960
gcatcaggca ttgttatatg ggaacccctt agcatcatgc ggtcaatgaa gtcctgcttg  1020
cttcttgata actatatgga gacaatcttg aacccctata tcatcaatgt aacacttgca  1080
gcaaaaatgt gctcccaagt actctgtcaa gagcagggag tatgcatacg aaaaaaattgg  1140
aacagttccg actacctgca ccttaacccc gataattttg ctatacagct tgaaaagggc  1200
ggaaaattta cagtccgagg gaagccgaca ttggaggatc tcgagcaatt ctctgaaaag  1260
ttttattgct catgctacag tacccttagc tgtaaagaaa aggcggacgt caaggatact  1320
gacgccgtgg acgtctgcat cgccgacgga gtttgcatcg acgcatttct taaacctccc  1380
atggaaaccg aagagccaca aatcttctat aac                                1413

SEQ ID NO: 219         moltype = AA  length = 509
FEATURE                Location/Qualifiers
source                 1..509
                       mol_type = protein
                       organism = Synthetic construct
SEQUENCE: 219
MGVLKFKHIF FRSFVKSSGV SQIVFTFLLI PCCLTLNFRA PPVIPNVPFL WAWNAPSEFC  60
LGKFDEPLDM SLFSFIGSPR INATGQGVTI FYVDRLGYYP YIDSITGVTV NGGIPQKISL  120
QDHLDKAKKD ITFYMPVDNL GMAVIDWEEW RPTWARNWKP KDVYKNRSIE LVQQQNVQLS  180
LTEATEKAKQ EFEKAGKDFL VETIKLGKLL RPNHLWGYYL FPDCYNHHYK KPGYNGSCFN  240
VEIKRNDDLS WLWNESTALY PSIYLNTQQS PVAATLYVRN RVREAIRVSK IPDAKSPLPV  300
FAYTRIVFTD QVLKFLSQDE LVYTFGETVA LGASGIVIWG TLSIMRSMKS CLLLDNYMET  360
ILNPYIINVT LAAKMCSQVL CQEQGVCIRK NWNSSDYLHL NPDNFAIQLE KGGKFTVRGK  420
PTLEDLEQFS EKFYCSCYST LSCKEKADVK DTDAVDVCIA DGVCIDAFLK PPMETEEPQI  480
FYNASPSTLS ATMFIVSILF LIISSVASL                                   509

SEQ ID NO: 220         moltype = DNA  length = 1527
FEATURE                Location/Qualifiers
source                 1..1527
                       mol_type = other DNA
                       organism = Synthetic construct
SEQUENCE: 220
atgggagtgc taaaattcaa gcacatcttt ttcagaagct ttgttaaatc aagtggagta  60
tcccagatag ttttcacctt ccttctgatt ccatgttgct tgactctgaa ctttcgcgcc  120
ccaccagtga tccctaatgt gccattcctt tgggcttgga atgcgccttc tgaattctgc  180
ttgggaaaat ttgatgagcc tctggatatg tctcttttca gttttattgg gtcaccaagg  240
attaacgcga ctggacaagg agtgacgata ttttatgtcg ataggctcgg ctactacccc  300
tacatagatt ccattaccgg cgtaaccgtg aatggtggta tccctcaaaa gatctctctt  360
caagaccact tggacaaagc aaaaaaagac attacattct acatgccggt ggataacctg  420
gggatggccg ttatcgattg ggaggagtgg agacccacgt gggctagaaa ctggaagccg  480
aaggacgtct ataaaaacag gtctatcgaa ttggttcagc agcagaacgt gcaattgtcc  540
ttgactgagg cgacagagaa ggccaagcaa gagtttgaga aggcgggaaa ggactttttg  600
gttgagacca ttaagctcgg taaactgctg cgacctaatc atctgtgggg ttactacctc  660
ttccctgact gctacaatca ccattacaag aaaccgggct acaatggctc ttgttttaat  720
gtcgaaatca aacgaaacga cgacctgagc tggctttgga acgaatccac cgcactctac  780
cccagcatct atctgaacac ccagcagagt cctgtagcag caacgctgta cgtccggaac  840
cgggtacgag aggcaatcag agtatctaag atcccggatg ctaaatcccc actgccggta  900
tttgcgtaca cccgaatcgt gttcactgac caggttctga agtttctctc ccaggacgaa  960
cttgtctata cgtttggaga gacagtagca ctcggcgcat caggcattgt tatatgggga  1020
```

```
acccttagca tcatgcggtc aatgaagtcc tgcttgcttc ttgataacta tatggagaca  1080
atcttgaacc cctatatcat caatgtaaca cttgcagcaa aaatgtgctc ccaagtactc  1140
tgtcaagagc agggagtatg catacgaaaa aattggaaca gttccgacta cctgcacctt  1200
aaccccgata attttgctat acagcttgaa aagggcggaa aatttacagt ccgagggaag  1260
ccgacattgg aggatctcga gcaattctct gaaaagtttt attgctcatg ctacagtacc  1320
cttagctgta aagaaaaggc ggacgtcaag gatactgacg ccgtggacgt ctgcatcgcc  1380
gacggagttt gcatcgacgc atttcttaaa cctcccatgg aaaccgaaga gccacaaatc  1440
ttctataacg cttctccctc aacacttagt gctactatgt ttatagtttc tattttgttc  1500
cttattattt caagtgtagc tagtctt                                      1527

SEQ ID NO: 221         moltype = AA  length = 490
FEATURE                Location/Qualifiers
source                 1..490
                       mol_type = protein
                       organism = Synthetic construct
SEQUENCE: 221
MGVLKFKHIF FRSFVKSSGV SQIVFTFLLI PCCLTLNFRA PPVIPNVPFL WAWNAPSEFC  60
LGKFDEPLDM SLFSFIGSPR INATGQGVTI FYVDRLGYYP YIDSITGVTV NGGIPQKISL  120
QDHLDKAKKD ITFYMPVDNL GMAVIDWEEW RPTWARNWKP KDVYKNRSIE LVQQQNVQLS  180
LTEATEKAKQ EFEKAGKDFL VETIKLGKLL RPNHLWGYYL FPDCYNHHYK KPGYNGSCFN  240
VEIKRNDDLS WLWNESTALY PSIYLNTQQS PVAATLYVRN RVREAIRVSK IPDAKSPLPV  300
FAYTRIVFTD QVLKFLSQDE LVYTFGETVA LGASGIVIWG TLSIMRSMKS CLLLDNYMET  360
ILNPYIINVT LAAKMCSQVL CQEQGVCIRK NWNSSDYLHL NPDNFAIQLE KGGKFTVRGK  420
PTLEDLEQFS EKFYCSCYST LSCKEKADVK DTDAVDVCIA DGVCIDAFLK PPMETEEPQI  480
FYNASPSTLS                                                         490

SEQ ID NO: 222         moltype = DNA  length = 1470
FEATURE                Location/Qualifiers
source                 1..1470
                       mol_type = other DNA
                       organism = Synthetic construct
SEQUENCE: 222
atgggagtgc taaaattcaa gcacatcttt ttcagaagct ttgttaaatc aagtggagta  60
tcccagatag ttttcacctt ccttctgatt ccatgttgct tgactctgaa ctttcgcgcc  120
ccaccagtga tccctaatgt gccattcctt tgggcttgga atgcgccttc tgaattctgc  180
ttgggaaaat ttgatgagcc tctggatatg tctcttttca gttttattgg gtcaccaagg  240
attaacgcga ctggacaagg agtgacgata ttttatgtcg ataggctcgg ctactacccc  300
tacatagatt ccattaccgg cgtaaccgtg aatggtggta tccctcaaaa gatctctctt  360
caagaccact tggacaaagc aaaaaaagac attacattct acatgccggt ggataacctg  420
gggatggccg ttatcgattg ggaggagtgg agacccacgt gggctagaaa ctggaagccg  480
aaggacgtct ataaaaacag gtctatcgaa ttggttcagc agcagaacgt gcaattgtcc  540
ttgactgagg cgacagagaa ggccaagcaa gagtttgaga aggcgggaaa ggacttttg  600
gttgagacca ttaagctcgg taaactgctg cgacctaatc atctgtgggg ttactacctc  660
ttccctgact gctacaatca ccattacaag aaaccgggct acaatggctc ttgttttaat  720
gtcgaaatca aacgaaacga cgacctgagc tggctttgga acgaatccac cgcactctac  780
cccagcatct atctgaacac ccagcagagt cctgtagcag caacgctgta cgtccggaac  840
cgggtacgag aggcaatcag agtatctaag atcccggatg ctaaatcccc actgccggta  900
tttgcgtaca cccgaatcgt gttcactgac caggttctga agtttctctc ccaggacgaa  960
cttgtctata cgtttggaga gacagtagca ctcggcgcat caggcattgt tatatgggga  1020
acccttagca tcatgcggtc aatgaagtcc tgcttgcttc ttgataacta tatggagaca  1080
atcttgaacc cctatatcat caatgtaaca cttgcagcaa aaatgtgctc ccaagtactc  1140
tgtcaagagc agggagtatg catacgaaaa aattggaaca gttccgacta cctgcacctt  1200
aaccccgata attttgctat acagcttgaa aagggcggaa aatttacagt ccgagggaag  1260
ccgacattgg aggatctcga gcaattctct gaaaagtttt attgctcatg ctacagtacc  1320
cttagctgta aagaaaaggc ggacgtcaag gatactgacg ccgtggacgt ctgcatcgcc  1380
gacggagttt gcatcgacgc atttcttaaa cctcccatgg aaaccgaaga gccacaaatc  1440
ttctataacg cttctccctc aacacttagt                                   1470

SEQ ID NO: 223         moltype = AA  length = 483
FEATURE                Location/Qualifiers
source                 1..483
                       mol_type = protein
                       organism = Synthetic construct
SEQUENCE: 223
MGVLKFKHIF FRSFVKSSGV SQIVFTFLLI PCCLTLNFRA PPVIPNVPFL WAWNAPSEFC  60
LGKFDEPLDM SLFSFIGSPR INATGQGVTI FYVDRLGYYP YIDSITGVTV NGGIPQKISL  120
QDHLDKAKKD ITFYMPVDNL GMAVIDWEEW RPTWARNWKP KDVYKNRSIE LVQQQNVQLS  180
LTEATEKAKQ EFEKAGKDFL VETIKLGKLL RPNHLWGYYL FPDCYNHHYK KPGYNGSCFN  240
VEIKRNDDLS WLWNESTALY PSIYLNTQQS PVAATLYVRN RVREAIRVSK IPDAKSPLPV  300
FAYTRIVFTD QVLKFLSQDE LVYTFGETVA LGASGIVIWG TLSIMRSMKS CLLLDNYMET  360
ILNPYIINVT LAAKMCSQVL CQEQGVCIRK NWNSSDYLHL NPDNFAIQLE KGGKFTVRGK  420
PTLEDLEQFS EKFYCSCYST LSCKEKADVK DTDAVDVCIA DGVCIDAFLK PPMETEEPQI  480
FYN                                                                483

SEQ ID NO: 224         moltype = DNA  length = 1449
FEATURE                Location/Qualifiers
source                 1..1449
                       mol_type = other DNA
                       organism = Synthetic construct
```

```
SEQUENCE: 224
atgggagtgc taaaattcaa gcacatcttt ttcagaagct ttgttaaatc aagtggagta  60
tcccagatag ttttcacctt ccttctgatt ccatgttgct tgactctgaa ctttcgcgcc  120
ccaccagtga tccctaatgt gccattcctt tgggcttgga atgcgccttc tgaattctgc  180
ttgggaaaat ttgatgagcc tctggatatg tctcttttca gttttattgg gtcaccaagg  240
attaacgcga ctggacaagg agtgacgata ttttatgtcg ataggctcgg ctactacccc  300
tacatagatt ccattaccgg cgtaaccgtg aatggtggta tccctcaaaa gatctctctt  360
caagaccact tggacaaagc aaaaaaagac attacattct acatgccggt ggataacctg  420
gggatggccg ttatcgattg ggaggagtgg agacccacgt gggctagaaa ctggaagccg  480
aaggacgtct ataaaaacag gtctatcgaa ttggttcagc agcagaacgt gcaattgtcc  540
ttgactgagg cgacagagaa ggccaagcaa gagtttgaga aggcgggaaa ggactttttg  600
gttgagacca ttaagctcgg taaactgctg cgacctaatc atctgtgggg ttactacctc  660
ttccctgact gctacaatca ccattacaag aaaccgggct acaatggctc ttgttttaat  720
gtcgaaatca aacgaaacga cgacctgagc tggctttgga acgaatccac cgcactctac  780
cccagcatct atctgaacac ccagcagagt cctgtagcag caacgctgta cgtccggaac  840
cgggtacgag aggcaatcag agtatctaag atcccggatg ctaaatcccc actgccggta  900
tttgcgtaca cccgaatcgt gttcactgac caggttctga agtttctctc ccaggacgaa  960
cttgtctata cgtttggaga gacagtagca ctcggcgcat caggcattgt tatatgggga  1020
acccttagca tcatgcggtc aatgaagtcc tgcttgcttc ttgataacta tatggagaca  1080
atcttgaacc cctatatcat caatgtaaca cttgcagcaa aaatgtgctc ccaagtactc  1140
tgtcaagagc agggagtatg catacgaaaa aattggaaca gttccgacta cctgcacctt  1200
aaccccgata attttgctat acagcttgaa aagggcggaa aatttacagt ccgagggaag  1260
ccgacattgg aggatctcga gcaattctct gaaaagtttt attgctcatg ctacagtacc  1320
cttagctgta aagaaaaggc ggacgtcaag gatactgacg ccgtggacgt ctgcatcgcc  1380
gacggagttt gcatcgacgc atttcttaaa cctcccatgg aaaccgaaga gccacaaatc  1440
ttctataac                                                          1449

SEQ ID NO: 225         moltype = AA  length = 500
FEATURE                Location/Qualifiers
source                 1..500
                       mol_type = protein
                       organism = Synthetic construct
SEQUENCE: 225
MLLLVTSLLL CELPHPAFLL IPMEVQLVES GGGVVQPGRS LRLSCSASGF TFSGYGLSWV  60
RQAPGKGLEW VAMISSGGSY TYYADSVKGR FAISRDNAKN TLFLQMDSLR PEDTGVYFCA  120
RHGDDPAWFA YWGQGTPVTV SSASTKGGGG GSGGGGSGGG GSDIQLTQSP SSLSASVGDR  180
VTITCSVSSS ISSNNLHWYQ QKPGKAPKPW IYGTSNLASG VPSRFSGSGS GTDYTFTISS  240
LQPEDIATYY CQQWSSYPYM YTFGQGTKVE IKRTAAATTT PAPRPPTPAP TIASQPLSLR  300
PEACRPAAGG AVHTRGLDFA CDIYIWAPLA GTCGVLLLSL VITLYCKRGR KKLLYIFKQP  360
FMRPVQTTQE EDGCSCRFPE EEEGGCELRV KFSRSADAPA YQQGQNQLYN ELNLGRREEY  420
DVLDKRRGRD PEMGGKPRRK NPQEGLYNEL QKDKMAEAYS EIGMKGERRR GKGHDGLYQG  480
LSTATKDTYD ALHMQALPPR                                              500

SEQ ID NO: 226         moltype = DNA  length = 1500
FEATURE                Location/Qualifiers
source                 1..1500
                       mol_type = other DNA
                       organism = Synthetic construct
SEQUENCE: 226
atgttgctgc tcgtgaccag cctccttctg tgcgaacttc cccaccccgc attcctgctg  60
attcctatgg aagtgcagct cgtggagtcc ggaggcggag tcgtgcagcc gggcagatcc  120
ctgcgccttt cctgctcggc atccgggttt accttctctg gctacggtct gtcgtgggtc  180
agacaggctc cagggaaggg cctggaatgg gtggccatga tctcctcggg gggttcgtac  240
acctactacg ccgactcagt gaagggccgg ttcgccatct cccgcgacaa cgccaagaac  300
accctgttcc tgcaaatgga ctcgctccgg cctgaggaca ctggggtgta cttctgcgcg  360
agacacggag atgacccagc ttggttcgcc tactggggac aaggcacccc tgtgaccgtg  420
tcctccgcga gcaccaaggg aggcggagga ggttccggtg gagggggatc agggggtgga  480
ggatcggaca ttcagctgac ccagagcccc tcaagcctgt ccgcgagcgt tggggaccgc  540
gtgaccatca cctgttcggt gtcctcctcc atctcctcca acaatctcca ttggtaccag  600
cagaaaccgg ggaaagcccc caagccgtgg atctacggaa cctccaacct ggctagcgga  660
gtgccgtcga ggttctcggg ctccggatca gggactgact acactttcac tatttcctcc  720
ctgcaaccgg aggacattgc cacctactac tgtcagcagt ggtcgtccta cccctacatg  780
tataccttcg gtcaaggaac caaggtcgag atcaagagga cagcggccgc aacgaccact  840
cctgcacccc gccctccgac tccggcccca accattgcca gccagcccct gtccctgcgg  900
ccggaagcct gcagaccggc tgccggcgga gccgtccata cccggggact ggatttcgcc  960
tgcgatatct atatctgggc accactcgcc ggaacctgtg gagtgctgct gctgtccctt  1020
gtgatcaccc tgtactgcaa gcgcggacgg aagaaactct tgtacatctt caagcagccg  1080
ttcatgcgcc ctgtgcaaac cacccaagaa gaggacgggt gctcctgccg gttcccggaa  1140
gaggaagagg gcggctgcga actgcgcgtg aagttttccc ggtccgccga cgctccggcg  1200
taccagcagg ggcaaaacca gctgtacaac gaacttaacc tcggtcgccg ggaagaatat  1260
gacgtgctgg acaagcggcg gggaagagat cccgagatgg gtggaaagcc gcggcggaag  1320
aaccctcagg agggcttgta caacgagctg caaaaggaca aaatggccga agcctactcc  1380
gagattggca tgaagggaga gcgcagacgc gggaagggac acgatggact gtaccaggga  1440
ctgtcaaccg cgactaagga cacttacgac gccctgcaca tgcaggccct gcccccgcgc  1500

SEQ ID NO: 227         moltype = AA  length = 1196
FEATURE                Location/Qualifiers
source                 1..1196
                       mol_type = protein
```

```
                         organism = Synthetic construct
SEQUENCE: 227
MSLWQPLVLV LLVLGCCFAA PRQRQSTLVL FPGDLRTNLT DRQLAEEYLY RYGYTRVAEM  60
RGESKSLGPA LLLLQKQLSL PETGELDSAT LKAMRTPRCG VPDLGRFQTF EGDLKWHHHN  120
ITYWIQNYSE DLPRAVIDDA FARAFALWSA VTPLTFTRVY SRDADIVIQF GVAEHGDGYP  180
FDGKDGLLAH AFPPGPGIQG DAHFDDDELW SLGKGVVVPT RFGNADGAAC HFPFIFEGRS  240
YSACTTDGRS DGLPWCSTTA NYDTDDRFGF CPSERLYTQD GNADGKPCQF PFIFQGQSYS  300
ACTTDGRSDG YRWCATTANY DRDKLFGFCP TRADSTVMGG NSAGELCVFP FTFLGKEYST  360
CTSEGRGDGR LWCATTSNFD SDKKWGFCPD QGYSLFLVAA HEFGHALGLD HSSVPEALMY  420
PMYRFTEGPP LHKDDVNGIR HLYGPRPEPE PRPPTTTTPQ PTAPPTVCPT GPPTVHPSER  480
PTAGPTGPPS AGPTGPPTAG PSTATTVPLS PVDDACNVNI FDAIAEIGNQ LYLFKDGKYW  540
RFSEGRGSRP QGPFLIADKW PALPRKLDSV FEERLSKKLF FFSGRQVWVY TGASVLGPRR  600
LDKLGLGADV AQVTGALRSG RGKMLLFSGR RLWRFDVKAQ MVDPRSASEV DRMFPGVPLD  660
THDVFQYREK AYFCQDRFYW RVSSRSELNQ VDQVGYVTYD ILQCPEDRAK RGSGATNFSL  720
LKQAGDVEEN PGPRAKRMLL LVTSLLLCEL PHPAFLLIPQ AAQVQLQQSG AEVKKPGSSV  780
KVSCKASGGT FSSYAISWVR QAPGQGLEWM GWINPNSGGT NYAQRFQGRV TMTRDTSIST  840
AYMELSRLRS DDTAVYYCAS YNDAFDIWGQ GTLVTVSSGG GGSGGGGSGG GGSNFMLTQP  900
HSVSESPGKT VTISCTRSSG SIASNYVQWY QQRPGSAPTI VIYEDDQRPS GVPDRFSGSI  960
DTSSNSASLT ISGLQSEDEA DYYCQSYEPG NGVFGGGTKV TVLAAAESKY GPPCPPCPIY  1020
IWAPLAGTCG VLLLSLVITL YCKRGRKKLL YIFKQPFMRP VQTTQEEDGC SCRFPEEEEG  1080
GCELRVKFSR SADAPAYQQG QNQLYNELNL GRREEYDVLD KRRGRDPEMG GKPRRKNPQE  1140
GLYNELQKDK MAEAYSEIGM KGERRRGKGH DGLYQGLSTA TKDTYDALHM QALPPR      1196

SEQ ID NO: 228           moltype = DNA  length = 3588
FEATURE                  Location/Qualifiers
source                   1..3588
                         mol_type = other DNA
                         organism = Synthetic construct
SEQUENCE: 228
atgagcctct ggcagcccct ggtcctggtg ctcctggtgc tgggctgctg ctttgctgcc  60
cccagacagc gccagtccac ccttgtgctc ttccctggag acctgagaac caatctcacc  120
gacaggcagc tggcagagga atacctgtac cgctatggtt acactcgggt ggcagagatg  180
cgtggagagt cgaaatctct ggggcctgcg ctgctgcttc tccagaagca actgtccctg  240
cccgagaccg gtgagctgga tagcgccacg ctgaaggcca tgcgaacccc acggtgcggg  300
gtcccagacc tgggcagatt ccaaaccttt gagggcgacc tcaagtggca ccaccacaac  360
atcacctatt ggatccaaaa ctactcggaa gacttgccgc gggcggtgat tgacgacgcc  420
tttgcccgcg ccttcgcact gtggagcgcg gtgacgccgc tcaccttcac tcgcgtgtac  480
agccgggacg cagacatcgt catccagttt ggtgtcgcgg agcacggaga cgggtatccc  540
ttcgacggga aggacgggct cctggcacac gcctttcctc ctggccccgg cattcaggga  600
gacgcccatt tcgacgatga cgagttgtgg tccctgggca agggcgtcgt ggttccaact  660
cggtttggaa acgcagatgg cgcggcctgc cacttcccct tcatcttcga gggccgctcc  720
tactctgcct gcaccaccga tggacggtcc gacggcttgc cctggtgcag taccacggcc  780
aactacgaca ccgacgaccg gtttggcttc tgccccagcg agagactcta cacccaggac  840
ggcaatgctg atgggaaacc ctgccagttt ccattcatct tccaaggcca atcctactcc  900
gcctgcacca cggacggtcg ctccgacggg taccgctggt gcgccaccac cgccaactac  960
gaccgggaca agctcttcgg cttctgcccg acccgagctg actcgacggt gatggggggc  1020
aactcggcgg gggagctgtg cgtcttcccc ttcactttcc tgggtaagga gtactcgacc  1080
tgtaccagcg agggccgcgg agatgggcgc ctctggtgcg ctaccacctc gaactttgac  1140
agcgacaaga agtggggctt ctgcccggac caaggataca gtttgttcct cgtggcggcg  1200
catgagttcg gccacgcgct gggcttagat cattcctcag tgccggaggc gctcatgtac  1260
cctatgtacc gcttcactga ggggcccccc ttgcataagg acgacgtgaa tggcatccgg  1320
cacctctatg gtcctcgccc tgaacctgag ccacgacctc caacaaccac cacaccgcag  1380
cccacggctc caccgacggt ctgccccacc ggacccccca ctgtccaccc ctcagagcgc  1440
cccactgctg gcccaacagg acctccctca gctggcccca caggtccccc aactgctggc  1500
ccttctacgg ccactactgt gcctttgagt ccggtggacg atgcctgcaa cgtgaacatc  1560
ttcgacgcca tcgcggagat tggaaccag ctgtatttgt tcaaggatgg gaagtactgg  1620
cgattctctg agggcagggg gagccggccg cagggcccct tccttatcgc cgacaagtgg  1680
cccgcgctgc cccgcaagct ggactcggtc tttgaggagc ggctctccaa gaagcttttc  1740
ttcttctctg gtcgccaggt gtgggtgtac acaggtgcgt cggtgctggg accgaggcgt  1800
ctagacaagc taggcctggg agcagacgtg gcccaggtga ccggggccct ccggagtggc  1860
agggggaaga tgctgctgtt cagcgggcgg cgcctctgga ggttcgacgt gaaggcgcag  1920
atggtggatc cccggagcgc cagcgaggtg gaccggatgt tccccggggt gcctttggac  1980
acgcacgacg tcttccagta ccgagagaaa gcctatttct gccaggaccg cttctactgg  2040
cgcgtgagtt cccggagtga gttgaaccag gtggaccaag tgggctacgt gacctatgac  2100
atcctgcagt gccctgagga ccgggcaaag cggggctcag ggcgactaa cttttcactg  2160
ttgaagcagg ccggggatgt ggaggagaat cctggtccta gagcaaagcg aatgctgctg  2220
ctggtgacca gcctgctgct gtgcgaactg ccgcatccgg cgtttctgct gattccgcag  2280
gcggcccagg tacagctgca gcagtcaggg gctgaggtga agaagcctgg gtcctcggtg  2340
aaggtctcct gcaaggcttc tggaggcacc ttcagcagct atgctatcag ctgggtgcga  2400
caggcccctg gacaagggct tgagtggatg ggatggatca accctaacag tggtggcaca  2460
aactatgcac agaggtttca gggcagggtc accatgacca gggacacgtc catcagcaca  2520
gcctacatgg agctgagcag gctgagatct gacgacacgg ccgtgtatta ctgtgcgagt  2580
tataatgatg cttttgatat ctggggccaa ggcaccctgg tcaccgtctc ctcaggaggt  2640
ggcgggtctg gtggtggcgg tagcggtggt ggcggatcca attttatgct gactcagccc  2700
cactctgtgt cggagtctcc ggggaagacg gtaaccatct cctgcacccg cagcagtggc  2760
agcattgcca gcaactatgt gcagtggtac cagcagcgcc cgggcagtgc ccccaccatt  2820
gtgatctatg aggatgatca aagaccctct ggggtccctg atcggttctc tggctccatc  2880
gacacctcct ccaactctgc ctccctcacc atctctggac tgcagagtga ggacgaggct  2940
gactactact gtcagtctta tgagcccggc aatggggtat tcggcggagg gaccaaggtc  3000
```

```
accgtcctag cggccgcaga gtcaaaatac ggtcctccgt gccctccgtg tccgatctac  3060
atttgggccc cgctggccgg cacttgcggc gtgctcctgc tgtcgctggt catcaccctt  3120
tactgcaaga ggggccggaa gaagctgctt tacatcttca agcagccgtt catgcggccc  3180
gtgcagacga ctcaggaaga ggacggatgc tcgtgcagat tccctgagga ggaagagggg  3240
ggatgcgaac tgcgcgtcaa gttctcacgg tccgccgacg cccccgcata tcaacagggc  3300
cagaatcagc tctacaacga gctgaacctg ggaaggagag aggagtacga cgtgctggac  3360
aagcgacgcg gacgcgaccc ggagatgggg gggaaaccac ggcggaaaaa ccctcaggaa  3420
ggactgtaca acgaactcca gaaagacaag atggcggaag cctactcaga aatcgggatg  3480
aagggagagc ggaggagggg aaagggtcac gacgggctgt accagggact gagcaccgcc  3540
actaaggata cctacgatgc cttgcatatg caagcactcc caccccgg               3588

SEQ ID NO: 229         moltype = AA  length = 1073
FEATURE                Location/Qualifiers
source                 1..1073
                       mol_type = protein
                       organism = Synthetic construct
SEQUENCE: 229
MLLLVTSLLL CELPHPAFLL IPMEVQLVES GGGVVQPGRS LRLSCSASGF TFSGYGLSWV  60
RQAPGKGLEW VAMISSGGSY TYYADSVKGR FAISRDNAKN TLFLQMDSLR PEDTGVYFCA  120
RHGDDPAWFA YWGQGTPVTV SSASTKGGGG GSGGGGSGGG GSDIQLTQSP SSLSASVGDR  180
VTITCSVSSS ISSNNLHWYQ QKPGKAPKPW IYGTSNLASG VPSRFSGSGS GTDYTFTISS  240
LQPEDIATYY CQQWSSYPYM YTFGQGTKVE IKRTAAATTT PAPRPPTPAP TIASQPLSLR  300
PEACRPAAGG AVHTRGLDFA CDIYIWAPLA GTCGVLLLSL VITLYCKRGR KKLLYIFKQP  360
FMRPVQTTQE EDGCSCRFPE EEEGGCELRV KFSRSADAPA YQQGQNQLYN ELNLGRREEY  420
DVLDKRRGRD PEMGGKPRRK NPQEGLYNEL QKDKMAEAYS EIGMKGERRR GKGHDGLYQG  480
LSTATKDTYD ALHMQALPPR RAKRGSGATN FSLLKQAGDV EENPGPRAKR MLLRSKPALP  540
PPLMLLLLGP LGPLSPGALP RPAQAQDVVD LDFFTQEPLH LVSPSFLSVT IDANLATDPR  600
FLILLGSPKL RTLARGLSPA YLRFGGTKTD FLIFDPKKES TFEERSYWQS QVNQDICKYG  660
SIPPDVEEKL RLEWPYQEQL LLREHYQKKF KNSTYSRSSV DVLYTFANCS GLDLIFGLNA  720
LLRTADLQWN SSNAQLLLDY CSSKGYNISW ELGNEPNSFL KKADIFINGS QLGEDFIQLH  780
KLLRKSTFKN AKLYGPDVGQ PRRKTAKMLK SFLKAGGEVI DSVTWHHYYL NGRTATKEDF  840
LNPDVLDIFI SSVQKVFQVV ESTRPGKKVW LGETSSAYGG GAPLLSDTFA AGFMWLDKLG  900
LSARMGIEVV MRQVFFGAGN YHLVDENFDP LPDYWLSLLF KKLVGTKVLM ASVQGSKRRK  960
LRVYLHCTNT DNPRYKEGDL TLYAINLHNV TKYLRLPYPF SNKQVDKYLL RPLGPHGLLS  1020
KSVQLNGLTL KMVDDQTLPP LMEKPLRPGS SLGLPAFSYS FFVIRNAKVA ACI         1073

SEQ ID NO: 230         moltype = DNA  length = 3219
FEATURE                Location/Qualifiers
source                 1..3219
                       mol_type = other DNA
                       organism = Synthetic construct
SEQUENCE: 230
atgttgctgc tcgtgaccag cctccttctg tgcgaacttc cccaccccgc attcctgctg  60
attcctatgg aagtgcagct cgtggagtcc ggaggcggag tcgtgcagcc gggcagatcc  120
ctgcgccttt cctgctcggc atccgggttt accttctctg gctacggtct gtcgtgggtc  180
agacaggctc cagggaaggg cctggaatgg gtggccatga tctcctcggg gggttcgtac  240
acctactacg ccgactcagt gaagggccgg ttcgccatct cccgcgacaa cgccaagaac  300
accctgttcc tgcaaatgga ctcgctccgg cctgaggaca ctggggtgta cttctgcgcg  360
agacacggag atgacccagc ttggttcgcc tactggggac aaggcacccc tgtgaccgtg  420
tcctccgcga gcaccaaggg aggcggagga ggttccggtg gaggggggatc agggggtgga  480
ggatcggaca ttcagctgac ccagagcccc tcaagcctgt ccgcgagcgt tggggaccgc  540
gtgaccatca cctgttcggt gtcctcctcc atctcctcca acaatctcca ttggtaccag  600
cagaaaccgg ggaaagcccc caagccgtgg atctacggaa cctccaacct ggctagcgga  660
gtgccgtcga ggttctcggg ctccggatca gggactgact acactttcac tatttcctcc  720
ctgcaaccgg aggacattgc cacctactac tgtcagcagt ggtcgtccta cccctacatg  780
tataccttcg gtcaaggaac caaggtcgag atcaagagga cagcggccgc aactaccacc  840
cctgcccctc ggccgccgac tccggcccca accatcgcaa gccaacccct ctccttgcgc  900
cccgaagctt gccgcccggc cgcgggtgga gccgtgcata cccgggggct ggactttgcc  960
tgcgatatct acatttgggc cccgctggcc ggcacttgcg gcgtgctcct gctgtcgctg  1020
gtcatcaccc tttactgcaa gaggggccgg aagaagctgc tttacatctt caagcagccg  1080
ttcatgcggc ccgtgcagac gactcaggaa gaggacggat gctcgtgcag attccctgag  1140
gaggaagagg ggggatgcga actgcgcgtc aagttctcac ggtccgccga cgcccccgca  1200
tatcaacagg gccagaatca gctctacaac gagctgaacc tgggaaggag agaggagtac  1260
gacgtgctgg acaagcgacg cggacgcgac ccggagatgg gggggaaacc acggcggaaa  1320
aaccctcagg aaggactgta caacgaactc cagaaagaca agatggcgga agcctactca  1380
gaaatcggga tgaagggaga gcggaggagg ggaaagggtc acgacgggct gtaccaggga  1440
ctgagcaccg ccactaagga tacctacgat gccttgcata tgcaagcact cccaccccgg  1500
cgggcaaagc ggggctcagg ggcgactaac ttttcactgt tgaagcaggc cggggatgtg  1560
gaggagaatc ctggtcctag agcaaagcga atgcttctac gttctaaacc tgcacttcct  1620
ccaccactta tgctacttct tctaggacct cttggtcctc tatcacctgg agctctacct  1680
cgacctgcac aagcacagga cgtcgtggac ctggacttct tcacccagga gccgctgcac  1740
ctggtgagcc cctcgttcct gtccgtcacc attgacgcca acctggccac ggacccgcgg  1800
ttcctcatcc tcctgggttc tccaaagctt cgtaccttgg ccagaggctt gtctcctgcg  1860
tacctgaggt ttggtggcac caagacagac ttcctaattt tcgatcccaa gaaggaatca  1920
acctttgaag agagaagtta ctggcaatct caagtcaacc aggatatttg caaatatgga  1980
tccatccctc ctgatgtgga ggagaagtta cggttggaat ggccctacca ggagcaattg  2040
ctactccgag aacactacca gaaaaagttc aagaacagca cctactcaag aagctctgta  2100
gatgtgctat acacttttgc aaactgctca ggactggact tgatctttgg cctaaatgcg  2160
ttattaagaa cagcagattt gcagtggaac agttctaatg ctcagttgct cctggactac  2220
```

```
tgctcttcca aggggtataa catttcttgg gaactaggca atgaacctaa cagtttcctt  2280
aagaaggctg atattttcat caatgggtcg cagttaggag aagattttat tcaattgcat  2340
aaacttctaa gaaagtccac cttcaaaaat gcaaaactct atggtcctga tgttggtcag  2400
cctcgaagaa agacggctaa gatgctgaag agcttcctga aggctggtgg agaagtgatt  2460
gattcagtta catggcatca ctactatttg aatggacgga ctgctaccaa ggaagatttt  2520
ctaaaccctg atgtattgga catttttatt tcatctgtgc aaaaagtttt ccaggtggtt  2580
gagagcacca ggcctggcaa gaaggtctgg ttaggagaaa caagctctgc atatggaggc  2640
ggagcgccct tgctatccga cacctttgca gctggcttta tgtggctgga taaattgggc  2700
ctgtcagccc gaatgggaat agaagtggtg atgaggcaag tattctttgg agcaggaaac  2760
taccatttag tggatgaaaa cttcgatcct ttacctgatt attggctatc tcttctgttc  2820
aagaaattgg tgggcaccaa ggtgttaatg gcaagcgtgc aaggttcaaa gagaaggaag  2880
cttcgagtat accttcattg cacaaacact gacaatccaa ggtataaaga aggagattta  2940
actctgtatg ccataaacct ccataatgtc accaagtact tgcggttacc ctatcctttt  3000
tctaacaagc aagtggataa ataccttcta agacctttgg gacctcatgg attactttcc  3060
aaatctgtcc aactcaatgg tctaactcta aagatggtgg atgatcaaac cttgccacct  3120
ttaatggaaa aacctctccg gccaggaagt tcactgggct tgccagcttt ctcatatagt  3180
tttttgtga taagaaatgc caaagttgct gcttgcatc                        3219

SEQ ID NO: 231         moltype = AA  length = 1027
FEATURE                Location/Qualifiers
source                 1..1027
                       mol_type = protein
                       organism = Synthetic construct
SEQUENCE: 231
MLLLVTSLLL CELPHPAFLL IPMEVQLVES GGGVVQPGRS LRLSCSASGF TFSGYGLSWV  60
RQAPGKGLEW VAMISSGGSY TYYADSVKGR FAISRDNAKN TLFLQMDSLR PEDTGVYFCA  120
RHGDDPAWFA YWGQGTPVTV SSASTKGGGG GSGGGGSGGG GSDIQLTQSP SSLSASVGDR  180
VTITCSVSSS ISSNNLHWYQ QKPGKAPKPW IYGTSNLASG VPSRFSGSGS GTDYTFTISS  240
LQPEDIATYY CQQWSSYPYM YTFGQGTKVE IKRTAAATTT PAPRPPTPAP TIASQPLSLR  300
PEACRPAAGG AVHTRGLDFA CDIYIWAPLA GTCGVLLLSL VITLYCKRGR KKLLYIFKQP  360
FMRPVQTTQE EDGCSCRFPE EEEGGCELRV KFSRSADAPA YQQGQNQLYN ELNLGRREEY  420
DVLDKRRGRD PEMGGKPRRK NPQEGLYNEL QKDKMAEAYS EIGMKGERRR GKGHDGLYQG  480
LSTATKDTYD ALHMQALPPR RAKRGSGATN FSLLKQAGDV EENPGPRAKR MDAMKRGLCC  540
VLLLCGAVFV SPSLNFRAPP VIPNVPFLWA WNAPSEFCLG KFDEPLDMSL FSFIGSPRIN  600
ATGQGVTIFY VDRLGYYPYI DSITGVTVNG GIPQKISLQD HLDKAKKDIT FYMPVDNLGM  660
AVIDWEEWRP TWARNWKPKD VYKNRSIELV QQQNVQLSLT EATEKAKQEF EKAGKDFLVE  720
TIKLGKLLRP NHLWGYYLFP DCYNHHYKKP GYNGSCFNVE IKRNDDLSWL WNESTALYPS  780
IYLNTQQSPV AATLYVRNRV REAIRVSKIP DAKSPLPVFA YTRIVFTDQV LKFLSQDELV  840
YTFGETVALG ASGIVIWGTL SIMRSMKSCL LLDNYMETIL NPYIINVTLA AKMCSQVLCQ  900
EQGVCIRKNW NSSDYLHLNP DNFAIQLEKG GKFTVRGKPT LEDLEQFSEK FYCSCYSTLS  960
CKEKADVKDT DAVDVCIADG VCIDAFLKPP METEEPQIFY NASPSTLSAT MFIVSILFLI  1020
ISSVASL                                                         1027

SEQ ID NO: 232         moltype = DNA  length = 3081
FEATURE                Location/Qualifiers
source                 1..3081
                       mol_type = other DNA
                       organism = Synthetic construct
SEQUENCE: 232
atgttgctgc tcgtgaccag cctccttctg tgcgaacttc cccaccccgc attcctgctg  60
attcctatgg aagtgcagct cgtggagtcc ggaggcggag tcgtgcagcc gggcagatcc  120
ctgcgccttt cctgctcggc atccgggttt accttctctg gctacggtct gtcgtgggtc  180
agacaggctc cagggaaggg cctggaatgg gtggccatga tctcctcggg gggttcgtac  240
acctactacg ccgactcagt gaagggccgg ttcgccatct cccgcgacaa cgccaagaac  300
accctgttcc tgcaaatgga ctcgctccgg cctgaggaca ctggggtgta cttctgcgcg  360
agacacggag atgacccagc ttggttcgcc tactggggac aaggcacccc tgtgaccgtg  420
tcctccgcga gcaccaaggg aggcggagga ggttccggtg gagggggatc agggggtgga  480
ggatcggaca ttcagctgac ccagagcccc tcaagcctgt ccgcgagcgt tggggaccgc  540
gtgaccatca cctgttcggt gtcctcctcc atctcctcca acaatctcca ttggtaccag  600
cagaaaccgg ggaaagcccc caagccgtgg atctacggaa cctccaacct ggctagcgga  660
gtgccgtcga ggttctcggg ctccggatca gggactgact acactttcac tatttcctcc  720
ctgcaaccgg aggacattgc cacctactac tgtcagcagt ggtcgtccta cccctacatg  780
tataccttcg gtcaaggaac caaggtcgag atcaagagga cagcggccgc aactaccacc  840
cctgcccctc ggccgccgac tccggcccca accatcgcaa gccaacccct ctccttgcgc  900
cccgaagctt gccgcccggc cgcgggtgga gccgtgcata cccgggggct ggactttgcc  960
tgcgatatct acatttgggc cccgctggcc ggcacttgcg gcgtgctcct gctgtcgctg  1020
gtcatcaccc tttactgcaa gaggggccgg aagaagctgc tttacatctt caagcagccg  1080
ttcatgcggc ccgtgcagac gactcaggaa gaggacggat gctcgtgcag attccctgag  1140
gaggaagagg ggggatgcga actgcgcgtc aagttctcac ggtccgccga cgccccccgca  1200
tatcaacagg gccagaatca gctctacaac gagctgaacc tgggaaggag agaggagtac  1260
gacgtgctgg acaagcgacg cggacgcgac ccggagatgg gggggaaacc acggcggaaa  1320
aaccctcagg aaggactgta caacgaactc cagaaagaca agatggcgga agcctactca  1380
gaaatcggga tgaagggaga gcggaggagg ggaaagggtc acgacgggct gtaccaggga  1440
ctgagcaccg ccactaagga tacctacgat gccttgcata tgcaagcact cccaccccgg  1500
cgggcaaagc ggggctcagg ggcgactaac ttttcactgt tgaagcaggc cggggatgtg  1560
gaggagaatc ctgggtcctag agcaaagcga atggatgcaa tgaagagagg gctctgctgt  1620
gtgctgctgc tgtgtggagc agtcttcgtt tcgcccagcc tgaactttcg cgccccacca  1680
gtgatcccta atgtgccatt cctttgggct tggaatgcgc cttctgaatt ctgcttggga  1740
aaatttgatg agcctctgga tatgtctctt ttcagtttta ttgggtcacc aaggattaac  1800
```

```
gcgactggac aaggagtgac gatattttat gtcgataggc tcggctacta cccctacata  1860
gattccatta ccggcgtaac cgtgaatggt ggtatccctc aaaagatctc tcttcaagac  1920
cacttggaca aagcaaaaaa agacattaca ttctacatgc cggtggataa cctggggatg  1980
gccgttatcg attgggagga gtggagaccc acgtgggcta gaaactggaa gccgaaggac  2040
gtctataaaa acaggtctat cgaattggtt cagcagcaga acgtgcaatt gtccttgact  2100
gaggcgacag agaaggccaa gcaagagttt gagaaggcgg gaaaggactt tttggttgag  2160
accattaagc tcggtaaact gctgcgacct aatcatctgt ggggttacta cctcttccct  2220
gactgctaca atcaccatta caagaaaccg ggctacaatg gctcttgttt taatgtcgaa  2280
atcaaacgaa acgacgacct gagctggctt tggaacgaat ccaccgcact ctaccccagc  2340
atctatctga acacccagca gagtcctgta gcagcaacgc tgtacgtccg gaaccgggta  2400
cgagaggcaa tcagagtatc taagatcccg gatgctaaat ccccactgcc ggtatttgcg  2460
tacacccgaa tcgtgttcac tgaccaggtt ctgaagtttc tctcccagga cgaacttgtc  2520
tatacgtttg gagagacagt agcactcggc gcatcaggca ttgttatatg ggaacccctt  2580
agcatcatgc ggtcaatgaa gtcctgcttg cttcttgata actatatgga gacaatcttg  2640
aacccctata tcatcaatgt aacacttgca gcaaaaatgt gctcccaagt actctgtcaa  2700
gagcagggag tatgcatacg aaaaaattgg aacagttccg actacctgca ccttaacccc  2760
gataattttg ctatacagct tgaaaagggc ggaaaattta cagtccgagg gaagccgaca  2820
ttggaggatc tcgagcaatt ctctgaaaag ttttattgct catgctacag taccettagc  2880
tgtaaagaaa aggcggacgt caaggatact gacgccgtgg acgtctgcat cgccgacgga  2940
gtttgcatcg acgcatttct taaacctccc atggaaaccg aagagccaca aatcttctat  3000
aacgcttctc cctcaacact tagtgctact atgtttatag tttctatttt gttccttatt  3060
atttcaagtg tagctagtct t                                            3081

SEQ ID NO: 233         moltype = AA  length = 986
FEATURE                Location/Qualifiers
source                 1..986
                       mol_type = protein
                       organism = Synthetic construct
SEQUENCE: 233
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRM DAMKRGLCCV LLLCGAVFVS PSLNFRAPPV IPNVPFLWAW NAPSEFCLGK  540
FDEPLDMSLF SFIGSPRINA TGQGVTIFYV DRLGYYPYID SITGVTVNGG IPQKISLQDH  600
LDKAKKDITF YMPVDNLGMA VIDWEEWRPT WARNWKPKDV YKNRSIELVQ QQNVQLSLTE  660
ATEKAKQEFE KAGKDFLVET IKLGKLLRPN HLWGYYLFPD CYNHHYKKPG YNGSCFNVEI  720
KRNDDLSWLW NESTALYPSI YLNTQQSPVA ATLYVRNRVR EAIRVSKIPD AKSPLPVFAY  780
TRIVFTDQVL KFLSQDELVY TFGETVALGA SGIVIWGTLS IMRSMKSCLL LDNYMETILN  840
PYIINVTLAA KMCSQVLCQE QGVCIRKNWN SSDYLHLNPD NFAIQLEKGG KFTVRGKPTL  900
EDLEQFSEKF YCSCYSTLSC KEKADVKDTD AVDVCIADGV CIDAFLKPPM ETEEPQIFYN  960
ASPSTLSATM FIVSILFLII SSVASL                                       986

SEQ ID NO: 234         moltype = DNA  length = 2958
FEATURE                Location/Qualifiers
source                 1..2958
                       mol_type = other DNA
                       organism = Synthetic construct
SEQUENCE: 234
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gctgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tttgggcccc gctggccggc acttgcggcg tgctcctgct gtcgctggtc  900
atcacccttt actgcaagag gggccggaag aagctgcttt acatcttcaa gcagccgttc  960
atgcggcccg tgcagacgac tcaggaagag gacggatgct cgtgcagatt ccctgaggag  1020
gaagaggggg gatgcgaact gcgcgtcaag ttctcacggt ccgccgacgc ccccgcatat  1080
caacagggcc agaatcagct ctacaacgag ctgaacctgg gaaggagaga ggagtacgac  1140
gtgctggaca agcgacgcgg acgcgacccg gagatggggg ggaaaccacg gcggaaaaac  1200
cctcaggaag gactgtacaa cgaactccag aaagacaaga tggcggaagc ctactcagaa  1260
atcgggatga agggagagcg gaggagggga aagggtcacg acgggctgta ccagggactg  1320
agcaccgcca ctaaggatac ctacgatgcc ttgcatatgc aagcactccc accccggcgg  1380
gcaaagcggg gctcaggggc gactaacttt tcactgttga agcaggccgg ggatgtggag  1440
gagaatcctg gtcctagagc aaagcgaatg gatgcaatga agagagggct ctgctgtgtg  1500
ctgctgctgt gtggagcagt cttcgtttcg cccagcctga actttcgcgc cccaccagtg  1560
```

```
atccctaatg tgccattcct ttgggcttgg aatgcgcctt ctgaattctg cttgggaaaa  1620
tttgatgagc ctctggatat gtctcttttc agttttattg ggtcaccaag gattaacgcg  1680
actggacaag gagtgacgat attttatgtc gataggctcg gctactaccc ctacatagat  1740
tccattaccg gcgtaaccgt gaatggtggt atccctcaaa agatctctct tcaagaccac  1800
ttggacaaag caaaaaaaga cattacattc tacatgccgg tggataacct ggggatggcc  1860
gttatcgatt gggaggagtg gagacccacg tgggctagaa actggaagcc gaaggacgtc  1920
tataaaaaca ggtctatcga attggttcag cagcagaacg tgcaattgtc cttgactgag  1980
gcgacagaga aggccaagca agagtttgag aaggcgggaa aggacttttt ggttgagacc  2040
attaagctcg gtaaactgct gcgacctaat catctgtggg gttactacct cttccctgac  2100
tgctacaatc accattacaa gaaaccgggc tacaatggct cttgttttaa tgtcgaaatc  2160
aaacgaaacg acgacctgag ctggctttgg aacgaatcca ccgcactcta ccccagcatc  2220
tatctgaaca cccagcagag tcctgtagca gcaacgctgt acgtccggaa ccgggtacga  2280
gaggcaatca gagtatctaa gatcccggat gctaaatccc cactgccggt atttgcgtac  2340
acccgaatcg tgttcactga ccaggttctg aagtttctct cccaggacga acttgtctat  2400
acgtttggag agacagtagc actcggcgca tcaggcattg ttatatgggg aacccttagc  2460
atcatgcggt caatgaagtc ctgcttgctt cttgataact atatggagac aatcttgaac  2520
ccctatatca tcaatgtaac acttgcagca aaaatgtgct cccaagtact ctgtcaagag  2580
cagggagtat gcatacgaaa aaattggaac agttccgact acctgcacct taaccccgat  2640
aattttgcta tacagcttga aaagggcgga aaatttacag tccgagggaa gccgacattg  2700
gaggatctcg agcaattctc tgaaaagttt tattgctcat gctacagtac ccttagctgt  2760
aaagaaaagg cggacgtcaa ggatactgac gccgtggacg tctgcatcgc cgacggagtt  2820
tgcatcgacg catttcttaa acctcccatg gaaaccgaag agccacaaat cttctataac  2880
gcttctccct caacacttag tgctactatg tttatagttt ctattttgtt ccttattatt  2940
tcaagtgtag ctagtctt                                                2958

SEQ ID NO: 235          moltype = AA  length = 967
FEATURE                 Location/Qualifiers
source                  1..967
                        mol_type = protein
                        organism = Synthetic construct
SEQUENCE: 235
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRM DAMKRGLCCV LLLCGAVFVS PSLNFRAPPV IPNVPFLWAW NAPSEFCLGK  540
FDEPLDMSLF SFIGSPRINA TGQGVTIFYV DRLGYYPYID SITGVTVNGG IPQKISLQDH  600
LDKAKKDITF YMPVDNLGMA VIDWEEWRPT WARNWKPKDV YKNRSIELVQ QQNVQLSLTE  660
ATEKAKQEFE KAGKDFLVET IKLGKLLRPN HLWGYYLFPD CYNHHYKKPG YNGSCFNVEI  720
KRNDDLSWLW NESTALYPSI YLNTQQSPVA ATLYVRNRVR EAIRVSKIPD AKSPLPVFAY  780
TRIVFTDQVL KFLSQDELVY TFGETVALGA SGIVIWGTLS IMRSMKSCLL LDNYMETILN  840
PYIINVTLAA KMCSQVLCQE QGVCIRKNWN SSDYLHLNPD NFAIQLEKGG KFTVRGKPTL  900
EDLEQFSEKF YCSCYSTLSC KEKADVKDTD AVDVCIADGV CIDAFLKPPM ETEEPQIFYN  960
ASPSTLS                                                            967

SEQ ID NO: 236          moltype = DNA  length = 2901
FEATURE                 Location/Qualifiers
source                  1..2901
                        mol_type = other DNA
                        organism = Synthetic construct
SEQUENCE: 236
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gctgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tttgggcccc gctggccggc acttgcggcg tgctcctgct gtcgctggtc  900
atcacccttt actgcaagag gggccggaag aagctgcttt acatcttcaa gcagccgttc  960
atgcggcccg tgcagacgac tcaggaagag gacggatgct cgtgcagatt ccctgaggag  1020
gaagaggggg gatgcgaact gcgcgtcaag ttctcacggt ccgccgacgc ccccgcatat  1080
caacagggcc agaatcagct ctacaacgag ctgaacctgg gaaggagaga ggagtacgac  1140
gtgctggaca agcgacgcgg acgcgacccg gagatggggg ggaaaccacg gcggaaaaac  1200
cctcaggaag gactgtacaa cgaactccag aaagacaaga tggcggaagc ctactcagaa  1260
atcgggatga agggagagcg gaggagggga aagggtcacg acgggctgta ccagggactg  1320
agcaccgcca ctaaggatac ctacgatgcc ttgcatatgc aagcactccc accccggcgg  1380
gcaaagcggg gctcaggggc gactaacttt tcactgttga agcaggccgg ggatgtggag  1440
```

```
gagaatcctg gtcctagagc aaagcgaatg gatgcaatga agagagggct ctgctgtgtg  1500
ctgctgctgt gtggagcagt cttcgtttcg cccagcctga actttcgcgc ccccaccagtg  1560
atccctaatg tgccattcct ttgggcttgg aatgcgcctt ctgaattctg cttgggaaaa  1620
tttgatgagc ctctggatat gtctcttttc agttttattg ggtcaccaag gattaacgcg  1680
actggacaag gagtgacgat attttatgtc gataggctcg gctactaccc ctacatagat  1740
tccattaccg gcgtaaccgt gaatggtggt atccctcaaa agatctctct tcaagaccac  1800
ttggacaaag caaaaaaaga cattacattc tacatgccgg tggataacct ggggatggcc  1860
gttatcgatt gggaggagtg gagacccacg tgggctagaa actggaagcc gaaggacgtc  1920
tataaaaaca ggtctatcga attggttcag cagcagaacg tgcaattgtc cttgactgag  1980
gcgacagaga aggccaagca agagtttgag aaggcgggaa aggacttttt ggttgagacc  2040
attaagctcg gtaaactgct gcgacctaat catctgtggg gttactacct cttccctgac  2100
tgctacaatc accattacaa gaaaccgggc tacaatggct cttgttttaa tgtcgaaatc  2160
aaacgaaacg acgacctgag ctggctttgg aacgaatcca ccgcactcta ccccagcatc  2220
tatctgaaca cccagcagag tcctgtagca gcaacgctgt acgtccggaa ccgggtacga  2280
gaggcaatca gagtatctaa gatcccggat gctaaatccc cactgccggt atttgcgtac  2340
acccgaatcg tgttcactga ccaggttctg aagtttctct cccaggacga acttgtctat  2400
acgtttggag agacagtagc actcggcgca tcaggcattg ttatatgggg aacccttagc  2460
atcatgcggt caatgaagtc ctgcttgctt cttgataact atatggagac aatcttgaac  2520
ccctatatca tcaatgtaac acttgcagca aaaatgtgct cccaagtact ctgtcaagag  2580
cagggagtat gcatacgaaa aaattggaac agttccgact acctgcacct taaccccgat  2640
aattttgcta tacagcttga aaagggcgga aaatttacag tccgagggaa gccgacattg  2700
gaggatctcg agcaattctc tgaaaagttt tattgctcat gctacagtac ccttagctgt  2760
aaagaaaagg cggacgtcaa ggatactgac gccgtggacg tctgcatcgc cgacggagtt  2820
tgcatcgacg catttcttaa acctcccatg gaaaccgaag agccacaaat cttctataac  2880
gcttctccct caacacttag t                                            2901

SEQ ID NO: 237          moltype = AA  length = 960
FEATURE                 Location/Qualifiers
source                  1..960
                        mol_type = protein
                        organism = Synthetic construct
SEQUENCE: 237
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRM DAMKRGLCCV LLLCGAVFVS PSLNFRAPPV IPNVPFLWAW NAPSEFCLGK  540
FDEPLDMSLF SFIGSPRINA TGQGVTIFYV DRLGYYPYID SITGVTVNGG IPQKISLQDH  600
LDKAKKDITF YMPVDNLGMA VIDWEEWRPT WARNWKPKDV YKNRSIELVQ QQNVQLSLTE  660
ATEKAKQEFE KAGKDFLVET IKLGKLLRPN HLWGYYLFPD CYNHHYKKPG YNGSCFNVEI  720
KRNDDLSWLW NESTALYPSI YLNTQQSPVA ATLYVRNRVR EAIRVSKIPD AKSPLPVFAY  780
TRIVFTDQVL KFLSQDELVY TFGETVALGA SGIVIWGTLS IMRSMKSCLL LDNYMETILN  840
PYIINVTLAA KMCSQVLCQE QGVCIRKNWN SSDYLHLNPD NFAIQLEKGG KFTVRGKPTL  900
EDLEQFSEKF YCSCYSTLSC KEKADVKDTD AVDVCIADGV CIDAFLKPPM ETEEPQIFYN  960

SEQ ID NO: 238          moltype = DNA  length = 2880
FEATURE                 Location/Qualifiers
source                  1..2880
                        mol_type = other DNA
                        organism = Synthetic construct
SEQUENCE: 238
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gctgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg ggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tttgggcccc gctggccggc acttgcggcg tgctcctgct gtcgctggtc  900
atcacccttt actgcaagag gggccggaag aagctgcttt acatcttcaa gcagccgttc  960
atgcggcccg tgcagacgac tcaggaagag gacggatgct cgtgcagatt ccctgaggag  1020
gaagaggggg gatgcgaact gcgcgtcaag ttctcacggt ccgccgacgc ccccgcatat  1080
caacagggcc agaatcagct ctacaacgag ctgaacctgg gaaggagaga ggagtacgac  1140
gtgctggaca agcgacgcgg acgcgacccg gagatggggg ggaaaccacg gcggaaaaac  1200
cctcaggaag gactgtacaa cgaactccag aaagacaaga tggcggaagc ctactcagaa  1260
atcgggatga agggagagcg gaggagggga aagggtcacg acgggctgta ccagggactg  1320
agcaccgcca ctaaggatac ctacgatgcc ttgcatatgc aagcactccc accccggcgg  1380
gcaaagcggg gctcaggggc gactaacttt tcactgttga agcaggccgg ggatgtggag  1440
```

```
gagaatcctg gtcctagagc aaagcgaatg gatgcaatga agagagggct ctgctgtgtg  1500
ctgctgctgt gtggagcagt cttcgtttcg cccagcctga actttcgcgc cccaccagtg  1560
atccctaatg tgccattcct ttgggcttgg aatgcgcctt ctgaattctg cttgggaaaa  1620
tttgatgagc ctctggatat gtctcttttc agttttattg ggtcaccaag gattaacgcg  1680
actggacaag gagtgacgat attttatgtc gataggctcg gctactaccc ctacatagat  1740
tccattaccg gcgtaaccgt gaatggtggt atccctcaaa agatctctct tcaagaccac  1800
ttggacaaag caaaaaaaga cattacattc tacatgccgg tggataacct ggggatggcc  1860
gttatcgatt gggaggagtg gagacccacg tgggctagaa actggaagcc gaaggacgtc  1920
tataaaaaca ggtctatcga attggttcag cagcagaacg tgcaattgtc cttgactgag  1980
gcgacagaga aggccaagca agagtttgag aaggcgggaa aggacttttt ggttgagacc  2040
attaagctcg gtaaactgct gcgacctaat catctgtggg gttactacct cttccctgac  2100
tgctacaatc accattacaa gaaaccgggc tacaatggct cttgttttaa tgtcgaaatc  2160
aaacgaaacg acgacctgag ctggctttgg aacgaatcca ccgcactcta ccccagcatc  2220
tatctgaaca cccagcagag tcctgtagca gcaacgctgt acgtccggaa ccgggtacga  2280
gaggcaatca gagtatctaa gatcccggat gctaaatccc cactgccggt atttgcgtac  2340
acccgaatcg tgttcactga ccaggttctg aagtttctct cccaggacga acttgtctat  2400
acgtttggag agacagtagc actcggcgca tcaggcattg ttatatgggg aaccccttagc  2460
atcatgcggt caatgaagtc ctgcttgctt cttgataact atatggagac aatcttgaac  2520
ccctatatca tcaatgtaac acttgcagca aaaatgtgct cccaagtact ctgtcaagag  2580
cagggagtat gcatacgaaa aaattggaac agttccgact acctgcacct taaccccgat  2640
aattttgcta tacagcttga aaagggcgga aaatttacag tccgagggaa gccgacattg  2700
gaggatctcg agcaattctc tgaaaagttt tattgctcat gctacagtac ccttagctgt  2760
aaagaaaagg cggacgtcaa ggatactgac gccgtggacg tctgcatcgc cgacggagtt  2820
tgcatcgacg catttcttaa acctcccatg gaaaccgaag agccacaaat cttctataac  2880

SEQ ID NO: 239          moltype = AA  length = 998
FEATURE                 Location/Qualifiers
source                  1..998
                        mol_type = protein
                        organism = Synthetic construct
SEQUENCE: 239
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRM GVLKFKHIFF RSFVKSSGVS QIVFTFLLIP CCLTLNFRAP PVIPNVPFLW  540
AWNAPSEFCL GKFDEPLDMS LFSFIGSPRI NATGQGVTIF YVDRLGYYPY IDSITGVTVN  600
GGIPQKISLQ DHLDKAKKDI TFYMPVDNLG MAVIDWEEWR PTWARNWKPK DVYKNRSIEL  660
VQQQNVQLSL TEATEKAKQE FEKAGKDFLV ETIKLGKLLR PNHLWGYYLF PDCYNHHYKK  720
PGYNGSCFNV EIKRNDDLSW LWNESTALYP SIYLNTQQSP VAATLYVRNR VREAIRVSKI  780
PDAKSPLPVF AYTRIVFTDQ VLKFLSQDEL VYTFGETVAL GASGIVIWGT LSIMRSMKSC  840
LLLDNYMETI LNPYIINVTL AAKMCSQVLC QEQGVCIRKN WNSSDYLHLN PDNFAIQLEK  900
GGKFTVRGKP TLEDLEQFSE KFYCSCYSTL SCKEKADVKD TDAVDVCIAD GVCIDAFLKP  960
PMETEEPQIF YNASPSTLSA TMFIVSILFL IISSVASL                         998

SEQ ID NO: 240          moltype = DNA  length = 2994
FEATURE                 Location/Qualifiers
source                  1..2994
                        mol_type = other DNA
                        organism = Synthetic construct
SEQUENCE: 240
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gctgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tttgggcccc gctggccggc acttgcggcg tgctcctgct gtcgctggtc  900
atcacccttt actgcaagag gggccggaag aagctgcttt acatcttcaa gcagccgttc  960
atgcggcccg tgcagacgac tcaggaagag gacggatgct cgtgcagatt ccctgaggag  1020
gaagaggggg gatgcgaact gcgcgtcaag ttctcacggt ccgccgacgc ccccgcatat  1080
caacagggcc agaatcagct ctacaacgag ctgaacctgg gaaggagaga ggagtacgac  1140
gtgctggaca agcgacgcgg acgcgacccg gagatggggg ggaaaccacg gcggaaaaac  1200
cctcaggaag gactgtacaa cgaactccag aaagacaaga tggcggaagc ctactcagaa  1260
atcgggatga agggagagcg gaggagggga aagggtcacg acgggctgta ccagggactg  1320
agcaccgcca ctaaggatac ctacgatgcc ttgcatatgc aagcactccc accccggcgg  1380
gcaaagcggg gctcaggggc gactaacttt tcactgttga agcaggccgg ggatgtggag  1440
```

```
gagaatcctg gtcctagagc aaagcgaatg ggagtgctaa aattcaagca catctttttc  1500
agaagctttg ttaaatcaag tggagtatcc cagatagttt tcaccttcct tctgattcca  1560
tgttgcttga ctctgaactt tcgcgcccca ccagtgatcc ctaatgtgcc attcctttgg  1620
gcttggaatg cgccttctga attctgcttg ggaaaatttg atgagcctct ggatatgtct  1680
cttttcagtt ttattgggtc accaaggatt aacgcgactg gacaaggagt gacgatattt  1740
tatgtcgata ggctcggcta ctacccctac atagattcca ttaccggcgt aaccgtgaat  1800
ggtggtatcc ctcaaaagat ctctcttcaa gaccacttgg acaaagcaaa aaaagacatt  1860
acattctaca tgccggtgga taacctgggg atggccgtta tcgattggga ggagtggaga  1920
cccacgtggg ctagaaactg gaagccgaag gacgtctata aaaacaggtc tatcgaattg  1980
gttcagcagc agaacgtgca attgtccttg actgaggcga cagagaaggc caagcaagag  2040
tttgagaagg cgggaaagga ctttttggtt gagaccatta agctcggtaa actgctgcga  2100
cctaatcatc tgtggggtta ctacctcttc cctgactgct acaatcacca ttacaagaaa  2160
ccgggctaca atggctcttg ttttaatgtc gaaatcaaac gaaacgacga cctgagctgg  2220
ctttggaacg aatccaccgc actctacccc agcatctatc tgaacaccca gcagagtcct  2280
gtagcagcaa cgctgtacgt ccggaaccgg gtacgagagg caatcagagt atctaagatc  2340
ccggatgcta aatccccact gccggtattt gcgtacaccc gaatcgtgtt cactgaccag  2400
gttctgaagt ttctctccca ggacgaactt gtctatacgt ttggagagac agtagcactc  2460
ggcgcatcag gcattgttat atggggaacc cttagcatca tgcggtcaat gaagtcctgc  2520
ttgcttcttg ataactatat ggagacaatc ttgaacccct atatcatcaa tgtaacactt  2580
gcagcaaaaa tgtgctccca agtactctgt caagagcagg gagtatgcat acgaaaaaat  2640
tggaacagtt ccgactacct gcaccttaac cccgataatt ttgctataca gcttgaaaag  2700
ggcggaaaat ttacagtccg agggaagccg acattggagg atctcgagca attctctgaa  2760
aagtttttatt gctcatgcta cagtaccctt agctgtaaag aaaaggcgga cgtcaaggat  2820
actgacgccg tggacgtctg catcgccgac ggagtttgca tcgacgcatt tcttaaacct  2880
cccatggaaa ccgaagagcc acaaatcttc tataacgctt ctccctcaac acttagtgct  2940
actatgttta tagtttctat tttgttcctt attatttcaa gtgtagctag tctt        2994
```

```
SEQ ID NO: 241         moltype = AA  length = 979
FEATURE                Location/Qualifiers
source                 1..979
                       mol_type = protein
                       organism = Synthetic construct
SEQUENCE: 241
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRM GVLKFKHIFF RSFVKSSGVS QIVFTFLLIP CCLTLNFRAP PVIPNVPFLW  540
AWNAPSEFCL GKFDEPLDMS LFSFIGSPRI NATGQGVTIF YVDRLGYYPY IDSITGVTVN  600
GGIPQKISLQ DHLDKAKKDI TFYMPVDNLG MAVIDWEEWR PTWARNWKPK DVYKNRSIEL  660
VQQQNVQLSL TEATEKAKQE FEKAGKDFLV ETIKLGKLLR PNHLWGYYLF PDCYNHHYKK  720
PGYNGSCFNV EIKRNDDLSW LWNESTALYP SIYLNTQQSP VAATLYVRNR VREAIRVSKI  780
PDAKSPLPVF AYTRIVFTDQ VLKFLSQDEL VYTFGETVAL GASGIVIWGT LSIMRSMKSC  840
LLLDNYMETI LNPYIINVTL AAKMCSQVLC QEQGVCIRKN WNSSDYLHLN PDNFAIQLEK  900
GGKFTVRGKP TLEDLEQFSE KFYCSCYSTL SCKEKADVKD TDAVDVCIAD GVCIDAFLKP  960
PMETEEPQIF YNASPSTLS                                               979
```

```
SEQ ID NO: 242         moltype = DNA  length = 2937
FEATURE                Location/Qualifiers
source                 1..2937
                       mol_type = other DNA
                       organism = Synthetic construct
SEQUENCE: 242
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gctgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tttgggcccc gctggccggc acttgcggcg tgctcctgct gtcgctggtc  900
atcacccttt actgcaagag gggccggaag aagctgcttt acatcttcaa gcagccgttc  960
atgcggcccg tgcagacgac tcaggaagag gacggatgct cgtgcagatt ccctgaggag  1020
gaagaggggg gatgcgaact gcgcgtcaag ttctcacggt ccgccgacgc ccccgcatat  1080
caacagggcc agaatcagct ctacaacgag ctgaacctgg gaaggagaga ggagtacgac  1140
gtgctggaca agcgacgcgg acgcgacccg gagatggggg ggaaaccacg gcggaaaaac  1200
cctcaggaag gactgtacaa cgaactccag aaagacaaga tggcggaagc ctactcagaa  1260
atcgggatga agggagagcg gaggagggga aagggtcacg acgggctgta ccagggactg  1320
```

```
agcaccgcca ctaaggatac ctacgatgcc ttgcatatgc aagcactccc accccggcgg  1380
gcaaagcggg gctcaggggc gactaacttt tcactgttga agcaggccgg ggatgtggag  1440
gagaatcctg gtcctagagc aaagcgaatg ggagtgctaa aattcaagca catcttttc   1500
agaagctttg ttaaatcaag tggagtatcc cagatagttt tcaccttcct tctgattcca  1560
tgttgcttga ctctgaactt tcgcgcccca ccagtgatcc ctaatgtgcc attcctttgg  1620
gcttggaatg cgccttctga attctgcttg ggaaaatttg atgagcctct ggatatgtct  1680
cttttcagtt ttattgggtc accaaggatt aacgcgactg gacaaggagt gacgatattt  1740
tatgtcgata ggctcggcta ctacccctac atagattcca ttaccggcgt aaccgtgaat  1800
ggtggtatcc ctcaaaagat ctctcttcaa gaccacttgg acaaagcaaa aaaagacatt  1860
acattctaca tgccggtgga taacctgggg atggccgtta tcgattggga ggagtggaga  1920
cccacgtggg ctagaaactg gaagccgaag gacgtctata aaaacaggtc tatcgaattg  1980
gttcagcagc agaacgtgca attgtccttg actgaggcga cagagaaggc caagcaagag  2040
tttgagaagg cgggaaagga ctttttggtt gagaccatta agctcggtaa actgctgcga  2100
cctaatcatc tgtggggtta ctacctcttc cctgactgct acaatcacca ttacaagaaa  2160
ccgggctaca atggctcttg ttttaatgtc gaaatcaaac gaaacgacga cctgagctgg  2220
ctttggaacg aatccaccgc actctacccc agcatctatc tgaacaccca gcagagtcct  2280
gtagcagcaa cgctgtacgt ccggaaccgg gtacgagagg caatcagagt atctaagatc  2340
ccggatgcta aatccccact gccggtattt gcgtacaccc gaatcgtgtt cactgaccag  2400
gttctgaagt ttctctccca ggacgaactt gtctatacgt ttggagagac agtagcactc  2460
ggcgcatcag gcattgttat atggggaacc cttagcatca tgcggtcaat gaagtcctgc  2520
ttgcttcttg ataactatat ggagacaatc ttgaacccct atatcatcaa tgtaacactt  2580
gcagcaaaaa tgtgctccca agtactctgt caagagcagg gagtatgcat acgaaaaaat  2640
tggaacagtt ccgactacct gcaccttaac cccgataatt ttgctataca gcttgaaaag  2700
ggcggaaaat ttacagtccg agggaagccg acattggagg atctcgagca attctctgaa  2760
aagttttatt gctcatgcta cagtaccctt agctgtaaag aaaaggcgga cgtcaaggat  2820
actgacgccg tggacgtctg catcgccgac ggagtttgca tcgacgcatt tcttaaacct  2880
cccatggaaa ccgaagagcc acaaatcttc tataacgctt ctccctcaac acttagt     2937
```

```
SEQ ID NO: 243          moltype = AA  length = 972
FEATURE                 Location/Qualifiers
source                  1..972
                        mol_type = protein
                        organism = Synthetic construct
SEQUENCE: 243
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRM GVLKFKHIFF RSFVKSSGVS QIVFTFLLIP CCLTLNFRAP PVIPNVPFLW  540
AWNAPSEFCL GKFDEPLDMS LFSFIGSPRI NATGQGVTIF YVDRLGYYPY IDSITGVTVN  600
GGIPQKISLQ DHLDKAKKDI TFYMPVDNLG MAVIDWEEWR PTWARNWKPK DVYKNRSIEL  660
VQQQNVQLSL TEATEKAKQE FEKAGKDFLV ETIKLGKLLR PNHLWGYYLF PDCYNHHYKK  720
PGYNGSCFNV EIKRNDDLSW LWNESTALYP SIYLNTQQSP VAATLYVRNR VREAIRVSKI  780
PDAKSPLPVF AYTRIVFTDQ VLKFLSQDEL VYTFGETVAL GASGIVIWGT LSIMRSMKSC  840
LLLDNYMETI LNPYIINVTL AAKMCSQVLC QEQGVCIRKN WNSSDYLHLN PDNFAIQLEK  900
GGKFTVRGKP TLEDLEQFSE KFYCSCYSTL SCKEKADVKD TDAVDVCIAD GVCIDAFLKP  960
PMETEEPQIF YN                                                      972
```

```
SEQ ID NO: 244          moltype = DNA  length = 2916
FEATURE                 Location/Qualifiers
source                  1..2916
                        mol_type = other DNA
                        organism = Synthetic construct
SEQUENCE: 244
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gctgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tttgggcccc gctggccggc acttgcggcg tgctcctgct gtcgctggtc  900
atcacccttt actgcaagag gggccggaag aagctgcttt acatcttcaa gcagccgttc  960
atgcggcccg tgcagacgac tcaggaagag gacggatgct cgtgcagatt ccctgaggag  1020
gaagaggggg gatgcgaact gcgcgtcaag ttctcacggt ccgccgacgc ccccgcatat  1080
caacagggcc agaatcagct ctacaacgag ctgaacctgg gaaggagaga ggagtacgac  1140
gtgctggaca agcgacgcgg acgcgacccg gagatggggg ggaaaccacg gcggaaaaac  1200
cctcaggaag gactgtacaa cgaactccag aaagacaaga tggcggaagc ctactcagaa  1260
```

```
atcgggatga agggagagcg gaggagggga aagggtcacg acgggctgta ccagggactg  1320
agcaccgcca ctaaggatac ctacgatgcc ttgcatatgc aagcactccc accccggcgg  1380
gcaaagcggg gctcaggggc gactaacttt tcactgttga agcaggccgg ggatgtggag  1440
gagaatcctg gtcctagagc aaagcgaatg ggagtgctaa aattcaagca catctttttc  1500
agaagctttg ttaaatcaag tggagtatcc cagatagttt tcaccttcct tctgattcca  1560
tgttgcttga ctctgaactt tcgcgcccca ccagtgatcc ctaatgtgcc attcctttgg  1620
gcttggaatg cgccttctga attctgcttg ggaaaatttg atgagcctct ggatatgtct  1680
cttttcagtt ttattgggtc accaaggatt aacgcgactg gacaaggagt gacgatattt  1740
tatgtcgata ggctcggcta ctacccctac atagattcca ttaccggcgt aaccgtgaat  1800
ggtggtatcc ctcaaaagat ctctcttcaa gaccacttgg acaaagcaaa aaaagacatt  1860
acattctaca tgccggtgga taacctgggg atggccgtta tcgattggga ggagtggaga  1920
cccacgtggg ctagaaactg gaagccgaag gacgtctata aaaacaggtc tatcgaattg  1980
gttcagcagc agaacgtgca attgtccttg actgaggcga cagagaaggc caagcaagag  2040
tttgagaagg cgggaaagga ctttttggtt gagaccatta agctcggtaa actgctgcga  2100
cctaatcatc tgtggggtta ctacctcttc cctgactgct acaatcacca ttacaagaaa  2160
ccgggctaca atggctcttg ttttaatgtc gaaatcaaac gaaacgacga cctgagctgg  2220
ctttggaacg aatccaccgc actctacccc agcatctatc tgaacaccca gcagagtcct  2280
gtagcagcaa cgctgtacgt ccggaaccgg gtacgagagg caatcagagt atctaagatc  2340
ccggatgcta aatccccact gccggtattt gcgtacaccc gaatcgtgtt cactgaccag  2400
gttctgaagt ttctctccca ggacgaactt gtctatacgt ttggagagac agtagcactc  2460
ggcgcatcag gcattgttat atggggaacc cttagcatca tgcggtcaat gaagtcctgc  2520
ttgcttcttg ataactatat ggagacaatc ttgaacccct atatcatcaa tgtaacactt  2580
gcagcaaaaa tgtgctccca agtactctgt caagagcagg gagtatgcat acgaaaaaat  2640
tggaacagtt ccgactacct gcaccttaac cccgataatt ttgctataca gcttgaaaag  2700
ggcggaaaat ttacagtccg agggaagccg acattggagg atctcgagca attctctgaa  2760
aagttttatt gctcatgcta cagtaccctt agctgtaaag aaaaggcgga cgtcaaggat  2820
actgacgccg tggacgtctg catcgccgac ggagtttgca tcgacgcatt tcttaaacct  2880
cccatggaaa ccgaagagcc acaaatcttc tataac                            2916
```

```
SEQ ID NO: 245         moltype = DNA  length = 1476
FEATURE                Location/Qualifiers
source                 1..1476
                       mol_type = other DNA
                       organism = Synthetic construct
SEQUENCE: 245
atgctcttgc tcgtgacttc tttgcttttg tgcgaacttc cgcacccagc cttccttttg  60
atacctcagg tacagctgca gcagtcaggg gctgaggtga agaagcctgg aagctcagtg  120
aaggtctcct gcaaggattc tggaggcacc ctcagcagcc atgctatcag ctgggtgcga  180
caggcccctg gacaagggct tgagtggatg ggaggaatca tccctatcct tggtatagca  240
aactacgcac agaagttcca gggcagagtc acgattacag cggacgaatc cacgagcaca  300
gcctacatgg agctgagcag cctgagatct gaggacacgg ccgtgtatta ctgtgcgaga  360
gggggtccag ggagttacca tatggacgtc tggggcaaag gcaccctggt caccgtctcc  420
tcaggaggtg gcgggtctgg tggaggcggc agcggtggtg gcggatccga aattgtgctg  480
actcagtctc cagccaccct gtctttgtct ccaggggaaa gagccaccct ctcctgcagg  540
gccagtcaga gtgttggcag ctccttaggc tggtaccaac agaaacctgg ccaggctccc  600
aggctcctca tctatgatgt atccaacagg gcctctggca tcccagccag gttcagtggc  660
agtgggtctg ggatagactt cactctcacc atcagcagcc tagagcctga agattttgca  720
gtttattact gtcagcagcg tagcaactgg ccccccatgt acacttttgg ccaggggacc  780
aagctggaga tcaaagcggc cgcaacgacc actcctgcac cccgccctcc gactccggcc  840
ccaaccattg ccagccagcc cctgtccctg cggccggaag cctgcagacc ggctgccggc  900
ggagccgtcc atacccgggg actggatttc gcctgcgata tctatatctg ggcaccactc  960
gccggaacct gtggagtgct gctgctgtcc cttgtgatca ccctgtactg caagcgcgga  1020
cggaagaaac tcttgtacat cttcaagcag ccgttcatgc gccctgtgca aaccacccaa  1080
gaagaggacg ggtgctcctg ccggttcccg gaagaggaag agggcggctg cgaactgcgc  1140
gtgaagtttt cccggtccgc cgacgctccg gcgtaccagc aggggcaaaa ccagctgtac  1200
aacgaactta acctcggtcg ccgggaagaa tatgacgtgc tggacaagcg gcggggaaga  1260
gatcccgaga tgggtggaaa gccgcggcgg aagaaccctc aggagggctt gtacaacgag  1320
ctgcaaaagg acaaaatggc cgaagcctac tccgagattg gcatgaaggg agagcgcaga  1380
cgcgggaagg gacacgatgg actgtaccag ggactgtcaa ccgcgactaa ggacacttac  1440
gacgccctgc acatgcaggc cctgcccccg cgctaa                            1476
```

```
SEQ ID NO: 246         moltype = AA  length = 491
FEATURE                Location/Qualifiers
source                 1..491
                       mol_type = protein
                       organism = Synthetic construct
SEQUENCE: 246
MLLLVTSLLL CELPHPAFLL IPQVQLQQSG AEVKKPGSSV KVSCKDSGGT LSSHAISWVR  60
QAPGQGLEWM GGIIPILGIA NYAQKFQGRV TITADESTST AYMELSSLRS EDTAVYYCAR  120
GGPGSYHMDV WGKGTLVTVS SGGGGSGGGG SGGGGSEIVL TQSPATLSLS PGERATLSCR  180
ASQSVGSSLG WYQQKPGQAP RLLIYDVSNR ASGIPARFSG SGSGIDFTLT ISSLEPEDFA  240
VYYCQQRSNW PPMYTFGQGT KLEIKAAATT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYQQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                      491
```

```
SEQ ID NO: 247         moltype = DNA  length = 1476
FEATURE                Location/Qualifiers
```

```
source                  1..1476
                        mol_type = other DNA
                        organism = Synthetic construct
SEQUENCE: 247
atgctcttgc tcgtgacttc tttgcttttg tgcgaacttc cgcacccagc cttccttttg  60
atacctcagc tgcagctgca ggagtccggc ccaggactgg tgaagccttc ggagaccctg  120
tccctcacct gcgctgtctc tggtggctcc gtcagcagta gtaactggtg gagttgggtc  180
cgccagcccc cagggaaggg gctggagtgg attggggaaa tctatcatag tgggagcacc  240
aactacaacc cgtccctcaa gagtcgagtc accatatcag tagacaagtc caagaatcaa  300
ttctccctgc acctgaactc tgtgactccc gaggacacgg ctgtgtacta ctgtgcgaga  360
gaggtggctg gttctgcggc ttttgacatc tggggccaag ggacaatggt caccgtctcc  420
tcaggaggtg gcgggtctgg tggaggcggc agcggtggtg gcggatccca gtctgtcgtg  480
acgcagccgc cctcagtgtc tgcggcccca ggacagaagg tcaccatctc ctgctctgga  540
agcagctcca acattgggaa taattatgta tcctggtacc agcagctccc aggaacagcc  600
cccaaactcc tcatctatgg aaataataag cgaccctcag ggattcctga ccgattctct  660
ggctccaagt ctggcacgtc agccaccctg ggcatcaccg gactccagac tggggacgag  720
gccgattatt actgcggaac atgggatagc agcctgagtg cggtattcgg cggaggcacc  780
cagctgaccg tcctcgcggc cgcaacgacc actcctgcac cccgccctcc gactccggcc  840
ccaaccattg ccagccagcc cctgtccctg cggccggaag cctgcagacc ggctgccggc  900
ggagccgtcc atacccgggg actggatttc gcctgcgata tctatatctg ggcaccactc  960
gccggaacct gtggagtgct gctgctgtcc cttgtgatca ccctgtactg caagcgcgga  1020
cggaagaaac tcttgtacat cttcaagcag ccgttcatgc gccctgtgca aaccacccaa  1080
gaagaggacg ggtgctcctg ccggttcccg gaagaggaag agggcggctg cgaactgcgc  1140
gtgaagtttt cccggtccgc cgacgctccg gcgtaccagc aggggcaaaa ccagctgtac  1200
aacgaactta acctcggtcg ccgggaagaa tatgacgtgc tggacaagcg gcggggaaga  1260
gatcccgaga tgggtggaaa gccgcggcgg aagaaccctc aggagggctt gtacaacgag  1320
ctgcaaaagg acaaaatggc cgaagcctac tccgagattg gcatgaaggg agagcgcaga  1380
cgcgggaagg gacacgatgg actgtaccag ggactgtcaa ccgcgactaa ggacacttac  1440
gacgccctgc acatgcaggc cctgcccccg cgctaa                            1476

SEQ ID NO: 248          moltype = AA  length = 491
FEATURE                 Location/Qualifiers
source                  1..491
                        mol_type = protein
                        organism = Synthetic construct
SEQUENCE: 248
MLLLVTSLLL CELPHPAFLL IPQLQLQESG PGLVKPSETL SLTCAVSGGS VSSSNWWSWV  60
RQPPGKGLEW IGEIYHSGST NYNPSLKSRV TISVDKSKNQ FSLHLNSVTP EDTAVYYCAR  120
EVAGSAAFDI WGQGTMVTVS SGGGGSGGGG SGGGGSQSVV TQPPSVSAAP GQKVTISCSG  180
SSSNIGNNYV SWYQQLPGTA PKLLIYGNNK RPSGIPDRFS GSKSGTSATL GITGLQTGDE  240
ADYYCGTWDS SLSAVFGGGT QLTVLAAATT TPAPRPPTPA PTIASQPLSL RPEACRPAAG  300
GAVHTRGLDF ACDIYIWAPL AGTCGVLLLS LVITLYCKRG RKKLLYIFKQ PFMRPVQTTQ  360
EEDGCSCRFP EEEEGGCELR VKFSRSADAP AYQQGQNQLY NELNLGRREE YDVLDKRRGR  420
DPEMGGKPRR KNPQEGLYNE LQKDKMAEAY SEIGMKGERR RGKGHDGLYQ GLSTATKDTY  480
DALHMQALPP R                                                       491

SEQ ID NO: 249          moltype = DNA  length = 1467
FEATURE                 Location/Qualifiers
source                  1..1467
                        mol_type = other DNA
                        organism = Synthetic construct
SEQUENCE: 249
atgctcttgc tcgtgacttc tttgcttttg tgcgaacttc cgcacccagc cttccttttg  60
atacctgaca ttgtgatgac ccagtctcac aaattcatgt ccacatcaat tggagccagg  120
gtcagcatca cctgcaaggc cagtcaggat gtgagaactg ctgtagcctg gtatcaacag  180
aaaccaggcc agtctcctaa acttcttatt tactcagcat cctaccggta cactggagtc  240
cctgatcgct tcactggcag tggatctggg acggatttca ctttcaccat cagcagtgtg  300
caggctgaag acctggcagt ttattactgt cagcaacatt atggtactcc tccgtggacg  360
ttcggtggag gcaccaagct ggaaatcaaa ggcggcggag gatctggcgg aggcggaagt  420
ggcggagggg gctctgaagt gcagctggtg gagtctgggg gaggcttggt gaagcctgga  480
gggtccctga aactctcctg tgaagcctcc agattcactt tcagtagcta tgccatgtct  540
tgggttcgcc agactccgga gaagaggctg gagtgggtcg cagccattag tggaggtggt  600
aggtacacct actatccaga cagtatgaag ggtcgattca ccatctccag agacaatgcc  660
aagaatttcc tgtacctgca aatgagcagt ctgaggtctg aggacacggc catgtattac  720
tgtgcaagac actatgatgg ttatcttgac tactggggcc aaggcaccac tctcacagtc  780
tcctcagcgg ccgcaacgac cactcctgca ccccgccctc cgactccggc cccaaccatt  840
gccagccagc ccctgtccct gcggccggaa gcctgcagac cggctgccgg cggagccgtc  900
catacccggg gactggattt cgcctgcgat atctatatct gggcaccact cgccggaacc  960
tgtggagtgc tgctgctgtc ccttgtgatc accctgtact gcaagcgcgg acggaagaaa  1020
ctcttgtaca tcttcaagca gccgttcatg cgccctgtgc aaaccaccca agaagaggac  1080
gggtgctcct gccggttccc ggaagaggaa gagggcggct gcgaactgcg cgtgaagttt  1140
tcccggtccg ccgacgctcc ggcgtaccag caggggcaaa accagctgta caacgaactt  1200
aacctcggtc gccgggaaga atatgacgtg ctggacaagc ggcggggaag agatcccgag  1260
atgggtggaa agccgcggcg gaagaaccct caggagggct tgtacaacga gctgcaaaag  1320
gacaaaatgg ccgaagccta ctccgagatt ggcatgaagg gagagcgcag acgcgggaag  1380
ggacacgatg gactgtacca gggactgtca accgcgacta aggacactta cgacgccctg  1440
cacatgcagg ccctgccccc gcgctaa                                      1467

SEQ ID NO: 250          moltype = AA  length = 488
```

```
FEATURE                Location/Qualifiers
source                 1..488
                       mol_type = protein
                       organism = Synthetic construct
SEQUENCE: 250
MLLLVTSLLL CELPHPAFLL IPDIVMTQSH KFMSTSIGAR VSITCKASQD VRTAVAWYQQ  60
KPGQSPKLLI YSASYRYTGV PDRFTGSGSG TDFTFTISSV QAEDLAVYYC QQHYGTPPWT  120
FGGGTKLEIK GGGGSGGGGS GGGGSEVQLV ESGGGLVKPG GSLKLSCEAS RFTFSSYAMS  180
WVRQTPEKRL EWVAAISGGG RYTYYPDSMK GRFTISRDNA KNFLYLQMSS LRSEDTAMYY  240
CARHYDGYLD YWGQGTTLTV SSAAATTTPA PRPPTPAPTI ASQPLSLRPE ACRPAAGGAV  300
HTRGLDFACD IYIWAPLAGT CGVLLLSLVI TLYCKRGRKK LLYIFKQPFM RPVQTTQEED  360
GCSCRFPEEE EGGCELRVKF SRSADAPAYQ QGQNQLYNEL NLGRREEYDV LDKRRGRDPE  420
MGGKPRRKNP QEGLYNELQK DKMAEAYSEI GMKGERRRGK GHDGLYQGLS TATKDTYDAL  480
HMQALPPR                                                        488

SEQ ID NO: 251         moltype = DNA  length = 2607
FEATURE                Location/Qualifiers
source                 1..2607
                       mol_type = other DNA
                       organism = Synthetic construct
SEQUENCE: 251
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gttgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tctgggcccc attggctgga acttgcggcg tgctgctctt gtctctggtc  900
attaccctgt actgcaagcg cggacggaag aaactcttgt acatcttcaa gcagccgttc  960
atgcgccctg tgcaaaccac ccaagaagag gacgggtgct cctgccggtt cccggaagag  1020
gaagagggcg gctgcgaact gagagtgaag tttagccgct cagccgatgc accggcctac  1080
cagcagggac agaaccagct ctacaacgag ctcaacctgg gtcggcggga agaatatgac  1140
gtgctggaca aacggcgcgg cagagatccg gagatggggg gaaagccgag gaggaagaac  1200
cctcaagagg gcctgtacaa cgaactgcag aaggacaaga tggcggaagc ctactccgag  1260
atcggcatga agggagaacg ccggagaggg aagggtcatg acggactgta ccagggcctg  1320
tcaactgcca ctaaggacac ttacgatgcg ctccatatgc aagctttgcc cccgcggcgc  1380
gcgaaacgcg gcagcggcgc gaccaacttt agcctgctga aacaggcggg cgatgtggaa  1440
gaaaacccgg gcccgcgagc aaagaggaat attatggctc tgcctgttac ggcactgctc  1500
cttccgcttg cattgttgtt gcacgcagcg cggccccaag tgcaactgca acaatccggt  1560
gctgaagtga agaaaccggg tagctccgtc aaggtgtctt gtaaagattc aggcggaact  1620
ttgtcttctc atgcgatttc atgggtacgc caagccccag ggcagggact tgaatggatg  1680
ggaggaatca tccctatcct tggtatagca aactacgcac agaagttcca gggcagagtc  1740
acgattacag cggacgaatc cacgagcact gcgtatatgg agctgagttc tctgaggagc  1800
gaagatactg ctgtctacta ctgtgcgaga gggggtccag ggagttacca tatggacgtc  1860
tggggaaagg gcactttggt cactgtttct agcggtggtg gaggcagtgg tggcggagga  1920
tcagggggcg gggggtccga aattgtgctg actcagtctc cagccaccct gtctttgtct  1980
ccaggggaaa gagccaccct ctcctgcagg gccagtcaga gtgttggcag ctccttaggc  2040
tggtaccaac agaaacctgg ccaggctccc aggctcctca tctatgatgt atccaacagg  2100
gcctctggca tcccagccag gttcagtggc agtgggtctg ggatagactt cactctcacc  2160
atcagcagcc tagagcctga agattttgca gtttattact gtcagcagcg tagcaactgg  2220
ccccccatgt acacttttgg ccaggggacc aagctggaga tcaaagctag cgcaactacc  2280
actcctgcac cacggccacc taccccagcc cccaccattg caagccagcc actttcactg  2340
cgccccgaag cgtgtagacc agctgctgga ggagccgtgc atacccgagg gctggacttc  2400
gcctgtgaca tctacatttg ggcacccttg gctgggacct gtggggtgct gttgctgtcc  2460
ttggttatta cgttgtactg ccggtcgaag aggtccagac tcttgcactc cgactacatg  2520
aacatgactc ctagaaggcc cggacccact agaaagcact accagccgta cgcccctcct  2580
cgggatttcg ccgcataccg gtcctga                                   2607

SEQ ID NO: 252         moltype = AA  length = 868
FEATURE                Location/Qualifiers
source                 1..868
                       mol_type = protein
                       organism = Synthetic construct
SEQUENCE: 252
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
```

```
IGMKGERRRG KGHDGLYQGL STATKDTYDA LHMQALPPRR AKRGSGATNF SLLKQAGDVE  480
ENPGPRAKRN IMALPVTALL LPLALLLHAA RPQVQLQQSG AEVKKPGSSV KVSCKDSGGT  540
LSSHAISWVR QAPGQGLEWM GGIIPILGIA NYAQKFQGRV TITADESTST AYMELSSLRS  600
EDTAVYYCAR GGPGSYHMDV WGKGTLVTVS SGGGGSGGGG SGGGGSEIVL TQSPATLSLS  660
PGERATLSCR ASQSVGSSLG WYQQKPGQAP RLLIYDVSNR ASGIPARFSG SGSGIDFTLT  720
ISSLEPEDFA VYYCQQRSNW PPMYTFGQGT KLEIKASATT TPAPRPPTPA PTIASQPLSL  780
RPEACRPAAG GAVHTRGLDF ACDIYIWAPL AGTCGVLLLS LVITLYCRSK RSRLLHSDYM  840
NMTPRRPGPT RKHYQPYAPP RDFAAYRS                                    868

SEQ ID NO: 253         moltype = DNA  length = 2607
FEATURE                Location/Qualifiers
source                 1..2607
                       mol_type = other DNA
                       organism = Synthetic construct
SEQUENCE: 253
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gttgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tctgggcccc attggctgga acttgcggcg tgctgctctt gtctctggtc  900
attaccctgt actgcaagcg cggacggaag aaactcttgt acatcttcaa gcagccgttc  960
atgcgccctg tgcaaaccac ccaagaagag gacgggtgct cctgccggtt cccggaagag  1020
gaagagggcg gctgcgaact gagagtgaag tttagccgct cagccgatgc accggcctac  1080
cagcagggac agaaccagct ctacaacgag ctcaacctgg gtcggcggga agaatatgac  1140
gtgctggaca aacggcgcgg cagagatccg gagatggggg gaaagccgag gaggaagaac  1200
cctcaagagg gcctgtacaa cgaactgcag aaggacaaga tggcggaagc ctactccgag  1260
atcggcatga agggagaacg ccggagaggg aagggtcatg acggactgta ccagggcctg  1320
tcaactgcca ctaaggacac ttacgatgcg ctccatatgc aagctttgcc cccgcggcgc  1380
gcgaaacgcg gcagcggcgc gaccaacttt agcctgctga aacaggcggg cgatgtggaa  1440
gaaaacccgg gcccgcgagc aaagaggaat attatggctc tgcctgttac ggcactgctc  1500
cttccgcttg cattgttgtt gcacgcagcg cggccccagc tgcagctgca ggagtccggc  1560
ccaggactgg tgaagccttc ggagaccctg tccctcacct gcgctgtctc tggtggctcc  1620
gtcagcagta gtaactggtg gagttgggtc cgccagcccc cagggaaggg gctggagtgg  1680
attggggaaa tctatcatag tgggagcacc aactacaacc cgtccctcaa gagtcgagtc  1740
accatatcag tagacaagtc caagaatcaa ttctccctgc acctgaactc tgtgactccc  1800
gaggacacgg ctgtgtacta ctgtgcgaga gaggtggctg gttctgcggc tttcgacatc  1860
tggggtcagg gaacgatggt gactgtctct tctggaggcg gagggtctgg tggcggaggc  1920
tcaggtgggg gcggaagcca aagtgtagtg acgcagccgc cctcagtgtc tgcggcccca  1980
ggacagaagg tcaccatctc ctgctctgga agcagctcca acattgggaa taattatgta  2040
tcctggtacc agcagctccc aggaacagcc cccaaactcc tcatctatgg aaataataag  2100
cgaccctcag ggattcctga ccgattctct ggctccaagt ctggcacgtc agccaccctg  2160
ggcatcaccg gactccagac tggggacgag gccgattatt actgcggaac atgggatagc  2220
agcctgagtg cggtattcgg cggaggcacc cagctgaccg tcctcgctag cgcaactacc  2280
actcctgcac cacggccacc taccccagcc cccaccattg caagccagcc actttcactg  2340
cgccccgaag cgtgtagacc agctgctgga ggagccgtgc atacccgagg gctggacttc  2400
gcctgtgaca tctacatttg ggcacccttg gctgggacct gtggggtgct gttgctgtcc  2460
ttggttatta cgttgtactg ccggtcgaag aggtccagac tcttgcactc cgactacatg  2520
aacatgactc ctagaaggcc cggacccact agaaagcact accagccgta cgcccctcct  2580
cgggatttcg ccgcataccg gtcctga                                     2607

SEQ ID NO: 254         moltype = AA  length = 868
FEATURE                Location/Qualifiers
source                 1..868
                       mol_type = protein
                       organism = Synthetic construct
SEQUENCE: 254
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRN IMALPVTALL LPLALLLHAA RPQLQLQESG PGLVKPSETL SLTCAVSGGS  540
VSSSNWWSWV RQPPGKGLEW IGEIYHSGST NYNPSLKSRV TISVDKSKNQ FSLHLNSVTP  600
EDTAVYYCAR EVAGSAAFDI WGQGTMVTVS SGGGGSGGGG SGGGGSQSVV TQPPSVSAAP  660
GQKVTISCSG SSSNIGNNYV SWYQQLPGTA PKLLIYGNNK RPSGIPDRFS GSKSGTSATL  720
GITGLQTGDE ADYYCGTWDS SLSAVFGGGT QLTVLASATT TPAPRPPTPA PTIASQPLSL  780
```

```
RPEACRPAAG GAVHTRGLDF ACDIYIWAPL AGTCGVLLLS LVITLYCRSK RSRLLHSDYM  840
NMTPRRPGPT RKHYQPYAPP RDFAAYRS                                     868

SEQ ID NO: 255          moltype = DNA  length = 2598
FEATURE                 Location/Qualifiers
source                  1..2598
                        mol_type = other DNA
                        organism = Synthetic construct
SEQUENCE: 255
atgctgctgc tggtgaccag cctgctgctg tgcgaactgc cgcatccggc gtttctgctg  60
attccgcagg cggcccaggt acagctgcag cagtcagggg ctgaggtgaa gaagcctggg  120
tcctcggtga aggtctcctg caaggcttct ggaggcacct tcagcagcta tgctatcagc  180
tgggtgcgac aggcccctgg acaagggctt gagtggatgg gatggatcaa ccctaacagt  240
ggtggcacaa actatgcaca gaggtttcag ggcagggtca ccatgaccag ggacacgtcc  300
atcagcacag cctacatgga gttgagcagg ctgagatctg acgacacggc cgtgtattac  360
tgtgcgagtt ataatgatgc ttttgatatc tggggccaag gcaccctggt caccgtctcc  420
tcaggaggtg gcgggtctgg tggtggcggt agcggtggtg gcggatccaa ttttatgctg  480
actcagcccc actctgtgtc ggagtctccg gggaagacgg taaccatctc ctgcacccgc  540
agcagtggca gcattgccag caactatgtg cagtggtacc agcagcgccc gggcagtgcc  600
cccaccattg tgatctatga ggatgatcaa agaccctctg gggtccctga tcggttctct  660
ggctccatcg acacctcctc caactctgcc tccctcacca tctctggact gcagagtgag  720
gacgaggctg actactactg tcagtcttat gagcccggca atggggtatt cggcggaggg  780
accaaggtca ccgtcctagc ggccgcagag tcaaaatacg gtcctccgtg ccctccgtgt  840
ccgatctaca tctgggcccc attggctgga acttgcggcg tgctgctctt gtctctggtc  900
attaccctgt actgcaagcg cggacggaag aaactcttgt acatcttcaa gcagccgttc  960
atgcgccctg tgcaaaccac ccaagaagag gacgggtgct cctgccggtt cccggaagag  1020
gaagagggcg gctgcgaact gagagtgaag tttagccgct cagccgatgc accggcctac  1080
cagcagggac agaaccagct ctacaacgag ctcaacctgg gtcggcggga agaatatgac  1140
gtgctggaca aacggcgcgg cagagatccg gagatggggg gaaagccgag gaggaagaac  1200
cctcaagagg gcctgtacaa cgaactgcag aaggacaaga tggcggaagc ctactccgag  1260
atcggcatga agggagaacg ccggagaggg aagggtcatg acggactgta ccagggcctg  1320
tcaactgcca ctaaggacac ttacgatgcg ctccatatgc aagctttgcc cccgcggcgc  1380
gcgaaacgcg gcagcggcgc gaccaacttt agcctgctga aacaggcggg cgatgtggaa  1440
gaaaacccgg gcccgcgagc aaagaggaat attatggctc tgcctgttac ggcactgctc  1500
cttccgcttg cattgttgtt gcacgcagcg cggcccgaca ttgtgatgac ccagtctcac  1560
aaattcatgt ccacatcaat tggagccagg gtcagcatca cctgcaaggc cagtcaggat  1620
gtgagaactg ctgtagcctg gtatcaacag aaaccaggcc agtctcctaa acttcttatt  1680
tactcagcat cctaccggta cactggagtc cctgatcgct tcactggcag tggatctggg  1740
acggatttca ctttcaccat cagcagtgtg caggctgaag acctggcagt ttattactgt  1800
cagcaacatt atggtactcc tccgtggacg ttcggtggag gcaccaagct ggaaatcaaa  1860
ggcggcggag gatctggcgg aggcggaagt ggcggagggg gctctgaagt gcagctggtg  1920
gagtctgggg gaggcttggt gaagcctgga gggtccctga aactctcctg tgaagcctcc  1980
agattcactt tcagtagcta tgccatgtct tgggttcgcc agactccgga gaagaggctg  2040
gagtgggtcg cagccattag tggaggtggt aggtacacct actatccaga cagtatgaag  2100
ggtcgattca ccatctccag agacaatgcc aagaatttcc tgtacctgca aatgagcagt  2160
ctgaggtctg aggacacggc catgtattac tgtgcaagac actatgatgg ttatcttgac  2220
tactggggcc aaggcaccac tctcacagtc tcctcagcta gcgcaactac cactcctgca  2280
ccacggccac ctaccccagc ccccaccatt gcaagccagc cactttcact gcgccccgaa  2340
gcgtgtagac cagctgctgg aggagccgtg catacccgag ggctggactt cgcctgtgac  2400
atctacattt gggcaccctt ggctgggacc tgtggggtgc tgttgctgtc cttggttatt  2460
acgttgtact gccggtcgaa gaggtccaga ctcttgcact ccgactacat gaacatgact  2520
cctagaaggc ccggacccac tagaaagcac taccagccgt acgcccctcc tcgggatttc  2580
gccgcatacc ggtcctga                                                2598

SEQ ID NO: 256          moltype = AA  length = 865
FEATURE                 Location/Qualifiers
source                  1..865
                        mol_type = protein
                        organism = Synthetic construct
SEQUENCE: 256
MLLLVTSLLL CELPHPAFLL IPQAAQVQLQ QSGAEVKKPG SSVKVSCKAS GGTFSSYAIS  60
WVRQAPGQGL EWMGWINPNS GGTNYAQRFQ GRVTMTRDTS ISTAYMELSR LRSDDTAVYY  120
CASYNDAFDI WGQGTLVTVS SGGGGSGGGG SGGGGSNFML TQPHSVSESP GKTVTISCTR  180
SSGSIASNYV QWYQQRPGSA PTIVIYEDDQ RPSGVPDRFS GSIDTSSNSA SLTISGLQSE  240
DEADYYCQSY EPGNGVFGGG TKVTVLAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPRRKN PQEGLYNELQ KDKMAEAYSE  420
IGMKGERRRG KGHDGLYQGL STATKDTYDA LHMQALPPRR AKRGSGATNF SLLKQAGDVE  480
ENPGPRAKRN IMALPVTALL LPLALLLHAA RPDIVMTQSH KFMSTSIGAR VSITCKASQD  540
VRTAVAWYQQ KPGQSPKLLI YSASYRYTGV PDRFTGSGSG TDFTFTISSV QAEDLAVYYC  600
QQHYGTPPWT FGGGTKLEIK GGGGSGGGGS GGGGSEVQLV ESGGGLVKPG GSLKLSCEAS  660
RFTFSSYAMS WVRQTPEKRL EWVAAISGGG RYTYYPDSMK GRFTISRDNA KNFLYLQMSS  720
LRSEDTAMYY CARHYDGYLD YWGQGTTLTV SSASATTTPA PRPPTPAPTI ASQPLSLRPE  780
ACRPAAGGAV HTRGLDFACD IYIWAPLAGT CGVLLLSLVI TLYCRSKRSR LLHSDYMNMT  840
PRRPGPTRKH YQPYAPPRDF AAYRS                                        865
```

CHIMERIC ANTIGEN RECEPTOR THERAPIES FOR TREATING SOLID TUMORS

CROSS-REFERENCE TO RELATED APPLICATIONS

This application is a continuation of and claims priority under 35 U.S.C. § 120 from PCT Application No. PCT/US2023/029008, filed on Jul. 28, 2023, which claims priority to U.S. Provisional Patent Application No. 63/393,088, filed on Jul. 28, 2022, and to the U.S. Provisional Patent Application No. 63/433,632, filed on Dec. 19, 2022. The entire contents of each of these priority applications are incorporated herein by reference in their entirety.

FIELD OF THE DISCLOSURE

This application relates to the field of cancer, particularly to a composition encoding functional chimeric antigen receptors and methods of use of same in patient-specific immunotherapy to treat solid tumors.

SEQUENCE LISTING

This application contains a Sequence Listing that has been submitted electronically as an XML file named 42449-0087002 SL ST26.xml. The XML file, created on Oct. 2, 2023, is 509,810 bytes in size. The material in the XML file is hereby incorporated by reference in its entirety.

BACKGROUND OF THE INVENTION

Cancer is one of the deadliest threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

Chimeric Antigen Receptors are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4): e23621). The antigen-binding motif of a CAR is commonly fashioned after a single chain Fragment variable (scFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Tandem, or even triple- or quadruple targeting domains may be constructed by linking multiple antigen-binding motifs sequentially, and attaching them to CAR hinge, transmembrane domain and intracellular sequences. Alternate cell types for CAR expression (such as NK, NKT, iNKT, or gamma-delta T cells) are also under development (Brown C E et al. Clin Cancer Res. 2012; 18(8):2199-209; Lehner M et al. PLoS One. 2012; 7 (2): e31210). There remains significant work with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the scFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al. J Immunol. 2009: 183 (9): 5563-74). With the advent of new technology, the activation of T cells with beads linked to anti-CD3 and anti-CD28 antibody, the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia. Blood. 2013; 121 (7):1165-74; Kochenderfer J N et al. Blood. 2012; 119 (12):2709-20). This is borne out by the clinical success of CD19-specific CARs that are in a second generation CD28/CD3-ζ(Lee D W et al. American Society of Hematology Annual Meeting. New Orleans, LA; Dec. 7-10, 2013) and a CD137/CD3-ζ signaling format (Porter D L et al. N Engl J Med. 2011, 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured.

Chimeric antigen receptor (CAR) T-cell therapy is a promising approach in treating both hematological and solid tumors, however the desired treatment benefits in solid tumors have not been achieved yet, whereas treatment of hematologic malignancies has proven highly effective, yielding several US Food and Drug Administration (FDA)-approvals for CAR T products for B cell malignancies and multiple myeloma (Gill S, et al., Blood Rev. 2016; 30(3): 157-1671; Victor E. et al., J Immunol Apr. 1, 2021, 206 (7) 1561-1568; Wagner J, et al., Mol Ther. 2020 Nov. 4; 28(11):2320-2339: He C, et al., Cancers. 2020; 12(7):196). CAR cells are recombinant receptors for antigens, which redirect the specificity and function of T lymphocytes and other immune cells toward intended tumor targets (Sadelain M, et al., Cancer Discov. 2013; 3:388-98). Engineered CAR T molecules redirect the immune activity towards desired antigens and depending on the quantity and quality of this interaction can have a lasting desired effect against tumor cells. Solid tumors present a challenge to current CAR T targeting approaches. Challenges to this therapeutic modality include tumor antigen escape, insufficient persistence of the engineered CAR molecules, and reduced effectiveness within the solid tumor environment. Additionally, CAR T cell—mediated toxicity resulting in cytokine release syndrome (CRS) and Immune Effector Cell Associated Neurotoxicity (ICANS), as well as off-target, and on-target off-tumor CAR reactivity, hamper further advancement of the CAR therapies in solid tumors. Optimization of CAR design remains largely empiric, and small modifications to the modular design can have a significant impact on a particular therapy (Guedan S, et al., Mol Ther Methods Clin Dev. 2018 Dec. 31; 12:145-156). Co-expression of multiple CAR molecules in the same effector cell, and optimization of CAR architecture and co-stimulatory domains is feasible, and may improve CAR T effector function an persistence (Schneider D, et al., Sci Transl Med. 2021 Mar. 24; 13(586)). In addition, third generation CAR T cells combining the signaling potential of two costimulatory domains may lead to improved CAR survival, expansion and effectiveness (Subklewe M, et al., Transfus Med Hemother. 2019; 46(1):15-24: Maria-Luisa Schubert, M D et al., Blood. 2019. 134 (Supplement_1)).

Tumor antigen escape and tumor target heterogeneity are common causes of CAR therapy failure, and recent studies suggest this may be an especially important factor in the treatment of solid tumors (Majzner R G, and Mackall C L., Cancer Discov. 2018 October; 8(10):1219-1226). Single targeting CAR therapies have shown effective in treating various cancers including B-ALL and multiple myeloma, but rates of relapse in some instances are as high as 60% (Walsh Z, et al., Curr Hematol Malig Rep 14, 451-459 (2019). By targeting multiple antigens simultaneously, risk of relapse and resistance are diminished (Schneider D, et al., Sci Transl Med. 2021 Mar. 24; 13(586)). Several options to avoid this outcome have been tested clinically, including sequential mono CAR treatment or co-infusions with CD19 and CD22 CARs, but proved ultimately ineffective (Shalabi H, et al., Haematologica Italy. 2018; 103:e215-8). Ongoing or completed studies with multi-targeting CARs focused on various combinations of CD19, CD20, CD22, HER2, TSLPR, IL-13Rα2 and more (Walsh, Z. et al., Curr Hematol Malig Rep 14, 451-459 (2019); Shalabi H, et al., Haematologica Italy. 2018; 103:e215-8; Bielamowicz K, et al., Neuro-Oncology. 2018; 20(4): 506-18; Han X, et al., J Hematol Oncol 12, 128 (2019). Further clinical evidence is needed to determine which of the multi-targeting CAR therapies will prove most effective.

As noted, the efficacy of CAR therapies may be curtailed by short CAR T cell persistence and eventually being overwhelmed by the rebounding tumor burden, and this is especially true of solid tumors. The use of Interleukin (IL)-7 and CCR2b in in-vivo experiments has proved efficacious, showing both improved persistence and improved anti-tumor activity in neuroblastoma and melanoma models (Guangchao Li, et al., Frontiers in Oncology. 2021; 11: 2021). In a study with hematologic cancer, multiplex targeting and co-stimulation through the combination of a CAR and a chimeric costimulatory receptors (CCRs) has shown to be an effective method of by enhancing cytotoxic efficacy and persistence, thus preventing relapses of tumor clones and ultimately to improving clinical outcomes of CAR T cell treatment (Katsarou A, et al., Sci Transl Med. 2021 Dec. 8; 13(623); Pietrobon, V., et al., Int. J. Mol. Sci. 2021, 22, 10828).

Thus, while it may be believed that CARs can trigger T-cell activation in a manner similar to an endogenous T-cell receptor, a major impediment to the clinical application of CAR-based technology to date has been limited by in vivo expansion of CAR+ T cells, rapid disappearance of the cells after infusion, disappointing clinical activity, relapse of the underlying medical disease or condition. Many of these issues arise due to tumor target heterogeneity and tumor-mediated resistance to therapy, including the impact of tumor microenvironment and tumor stromal factors, and may be addressed by CAR T cell engineering.

Solid tumors present a challenging environment for CARs including an immunosuppressive environment characterized by physical, functional, and dynamic barriers hindering T-cell function. The tumor micro environment (TME) can prove difficult for successful CAR function and targeting. Tumors can employ strategies to resist the targeted effects of the CARs by increasing the production of inhibitory cytokines (Lindo L, et al., Front Immunol. 2021 Feb. 10; 11:618387). To counteract this increasingly hostile environment, research of "armored" CARs has been developing. Alabanza et al. (Front Immunol. 2022 Feb. 9; 13:832645) used this approach by co-expressing a TGFβ Receptor II dominant-negative form ("armor") on BCMA—targeting CAR T cells, in order to resist the suppressive effects of TGFβ in the multiple myeloma bone marrow niche. This resulted in functional persistence despite sustained exposure to TGFβ in animal models of Multiple Myeloma. The TME comprises a varied cell population that proves difficult to target. Yeku et al. (2017) study of ovarian cancer showed previous CAR T cell therapy for ovarian cancer directed against the folate receptor were largely unsuccessful in clinical trials due in part to action of immunosuppressive cytokines such as IL-4, IL-6, LIF, IL-10, TGFβ, myeloid derived suppressor cells, tumor associated macrophages (TAMs) and regulatory T cells which suppress the effects of the targeting CARs. By creating an IL-12 armored CAR T cell they showed treatment could overcome the inhibitory microenvironment, alter the ascitic cytokine and TAM microenvironment, and overcome PD-L1-mediated inhibition (Yeku 00, et al., Sci Rep 7, 10541 (2017).

In addition to a challenging TME, the tumor stroma barrier presents challenges for effective CAR penetration. Solid tumors have a dense extracellular matrix (ECM) formed by cancer-associated fibroblasts (CAFs) which inhibits T cells from infiltrating the deep area of the tumor, thus negating continuous contact between tumor cells and CAR-T cells (Zhang, B. L et al., Sci. China Life Sci. 2016, 59 (4), 340-348). One approach is to facilitate the degradation of the ECM, thus allowing for effective CAR-T cell infiltration into the solid tumors' matrix. Engineering hyaluronidase (HAase) and the checkpoint blocking antibody α-PDL1 on the CAR-T cell surface has shown enhanced tumor infiltration and antitumor efficacy in solid tumors. (Yangyang Zhao, et al., ACS Central Science 2022 8 (5), 603-614). Similarly, an approach to engineer CARs to express the enzyme heparanase (HPSE), showed improve capacity to breakdown the ECM (Caruana I, et al., Nat Med. 2015 May; 21(5): 524-529).

Along with the various strategies discussed earlier that aim to improve the persistence and effectiveness of the CAR therapy, measures continue to be developed to improve the safety profile of CAR T therapies. Widespread adoption and application of CAR-T therapies has been limited because of the many challenges including tumor lysis syndrome, neurotoxicity syndrome, and cytokine release syndrome. Cytokine release syndrome (CRS) is a systemic inflammatory response triggered by T-cell activation. CRS is mainly caused by the activated CAR-T cell resulting in a notable increase in the secretion of proinflammatory factors (e.g., IL-6, IFN-γ, and TNF-α) by immune cells that disrupt the balance between proinflammatory and anti-inflammatory responses (Hay K A, et al., Blood. 2017; 130: 2295-306).

The use of suicide genes to prevent undue off target activity and improving the safety of CAR T cells is becoming increasingly important. Suicide genes, as a controlling gene, which are co-expressed with the CAR construct and are able to induce cell death when activated by an additional agent such as a drug or antibody. By design, the best possible agent for suicide gene activation will be biologically inert, have sufficient bio-availability and bio-distribution profiles, and be characterized by negligible or absent toxicity. (Jones B S, et al., Front Pharmacol. 2014; 5:254). Proof of concept of this was shown in a study by Kao et al., (2019) using truncated epidermal growth factor receptor (EGFRt) as a suicide gene system co-delivered with anti-CD19 CAR. Both in-vitro and in-vivo analysis showed positive results (Kao Roy L, et al. Human Gene Therapy. April 2019; 413-428). Clinical evaluation of these strategies is ongoing but holds promise to unlock a wide array of safer CAR T therapeutic strategies.

Accordingly, there is an urgent and long felt need in the art for discovering compositions and methods for treatment of cancer using a CAR-based therapy that can exhibit cancer-specific intended therapeutic attributes without the aforementioned short comings.

The present invention addresses these ongoing unmet needs by providing boosted CAR compositions that exhibit one or more of the following characteristics: i) a high surface expression on transduced T cells, ii) a high degree of cytolysis and transduced T cell in vivo expansion and persistence, iii) multi-targeting to overcome antigen escape, iv) armor so as to overcome immunosuppression in TME, v) cytokine stimulated element to promote autonomous T cell stimulation with cytokines, resulting in heightened anti-tumor cytotoxicity, expansion, memory formation, cytokine secretion, persistence, vi) digestive enzymes to overcome the physical barrier of tumor stroma/extracellular matrix (ECM) and enable CAR T tumor penetration, and vii) an on-switch or off-switch, to control the expression of the CAR, or the co-expressed functional "booster" element(s), as well as therapeutic methods of using such boosted CARs that can be used to treat solid tumors, including tumors expressing a targetable antigen, such as CD19, CD20, CD22, ROR1, mesothelin, CD33/IL3Ra, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, GD2, GD3, GM2, Ley, polysialic acid, fucosyl GM1, GM3, Tn, STn, sLe(animal), GloboH, CD5, CD7, CD19, CD20, CD22, CD25, CD37, CD30, CD33, CD38, CD123, CD45, CAMPATH-1, BCMA, CS-1, PD-L1, CD276/B7-H3, B7-H4, B7-DC, HLA-DR carcinoembryonic antigen (CEA), TAG-72, EpCAM, folate-binding protein, folate receptor alpha (FOLR1), folate receptor beta (FOLR2), A33, G250, pro state-specific membrane antigen (PSMA), ferritin, CA-125, CA19-9, CD44v6, epidermal growth factor, p185, IL-2 receptor, interleukin 1 receptor accessory protein (IL1RAP), EGFRvIII (de2-7), fibroblast activation protein, tenascin, a metalloproteinase, endosialin, vascular endothelial growth factor, $\alpha v\beta 3$, WT1, LMP2, HPV E6, HPV E7, Her-2/neu, p53 nonmutant, NY-ESO-1, MelanA/MART 1, Ras mutant, gp100, FGFR1, FGFR2, FGFR3, FGFR4, GPC1, GPC2, GPC3, p53 mutant, PR1, bcr-abl, tyrosinase, survivin, PSA, hTERT, a Sarcoma translocation breakpoint fusion protein, EphA2, PAP, ML-IAP, AFP, ERG, NA17, PAX3, ALK, androgen receptor, cyclin B1, MYCN, RhoC, TRP-2, mesothelin, PSCA, MAGE A1, MAGE A3, CYP1B 1, PLAV1, BORIS, ETV6-AML, NY-BR-1, RGS5, SART3, Carbonic anhydrase IX, PAX5, OY-TES 1, Sperm protein 17, LCK, HMWMAA, AKAP-4, SSX2, XAGE 1, B7H3, Legumain, Tie 3, PAGE4, VEGFR2, MAD-CT-1, PDGFR-B, MAD-CT-2, TRAIL 1, MUC1, MUC16/CA125, MAGE A4, MAGE C2, GAGE, EGFR, EGFR1, EGFR2/Her2, CMET, HER3, CA6, NAPI2B, TROP2, TEM1, TEM7, TEM8, FAP, LAP, CLDN3, CLDN6, CLDN8, CLDN16, CLDN18.2, RON, LY6E, DLL3, PTK7, UPK1B, STRA6, TMPRSS3, TMRRSS4, TMEM238, Clorf186, LIV1, ROR1, ROR2, Fos-related antigen 1, VEGFR1, endoglin, CD90, CD326, CD70, SSEA4, CD318, CLA, TSPAN8, GPRC5D, EpCAM, Thy1, IL13Ra2, BDCA1, BDCA2, BDCA3, GD2, PSMA, FAP, CLL1, SLAMF7/CS1, CD147, DPPA5, GRP78, CD66c, VISTA, LRRC5, LRRC15, or any combinations thereof or a fragment thereof is provided, wherein the antibody or a fragment thereof comprises a fragment selected from the group consisting of an Fab fragment, an F(ab')2 fragment, an Fv fragment, a nanobody, a VHH, a ligand peptide, and a single chain Fv (ScFv), or a fragment of any of the preceding, or a molecule that is at least 80%, 85%, 90%, 95%, 96%, 97%, 98% or 99% homologous to any of the preceding, or any combination thereof, or other antigens, or any combination thereof, as well as other diseases and/or conditions expressing CAR-relevant targets.

SUMMARY OF THE INVENTION

Novel anti-effector moiety antibodies or antigen binding domains thereof and chimeric antigen receptors (CARs) that contain such effector moiety antigen binding domains are provided herein, as well as host cells (e.g., T cells) expressing the receptors, and nucleic acid molecules encoding the receptors. CAR may consist either of a single molecule expressed on the effector cell surface, or a CAR comprised of an effector cell-expressed signaling module and a soluble targeting module, such as when the soluble targeting module binds to the cell-expressed signaling module, a complete functional CAR is formed. The CARs exhibit a high surface expression on transduced T cells, with a high degree of cytolysis and transduced T cell expansion and persistence in vivo. Methods of using the disclosed CARs, host cells, and nucleic acid molecules are also provided, for example, to treat a cancer in a subject.

In its broadest aspect, novel chimeric antigen receptors (CARs) are provided herein comprising a boosted CAR comprising a CAR construct with a main effector moiety molecule followed by one or more 2A sequences, in frame to one or more additional "booster" elements for improved function, including enhanced tumor penetration, to improve the therapeutic effect of CAR-T cells in solid tumors, hematologic tumors, autoimmune disease, hereditary disease, or other relevant indications.

In yet another broad aspect, novel chimeric antigen receptors (CARs) are provided herein comprising a boosted CAR wherein the functional co-expressed boosted CAR elements are expressed from a single multi-cistronic vector at high transduction efficiency, thereby simplifying the CAR manufacturing and release and reducing cost for market implementation. In one aspect, the boosted CAR compositions comprise one or more of the following characteristics: i) a high surface expression on transduced T cells, ii) multi-targeting to overcome antigen escape, iii) one or more armor elements so as to overcome immunosuppression in TME, iv) one or more cytokine stimulated elements (including, for example, and not by way of limitation, chemo attractive-receptors and/or secretion of chemotactic molecules) to promote autonomous T cell stimulation with cytokines, resulting in heightened anti-tumor cytotoxicity, expansion, memory formation, cytokine secretion, persistence, v) one or more digestive enzymes to overcome the physical barrier of tumor stroma/extracellular matrix (ECM) and enable CAR T tumor penetration, vi) one or more pro-inflammatory immune activators, and vii) one or more on-switches or off-switches, to control the expression of the CAR, wherein the boosted CARs achieve a high degree of cytolysis and transduced T cell in vivo expansion and persistence to promote in vivo expansion, persistence of patient-specific anti-tumor T-cells resulting in tumor stabilization, reduction, elimination, remission of cancer or autoimmune, alloimmune, or autoaggressive disease, or prevention or amelioration of relapse of cancer or autoimmune, alloimmune, or autoaggressive disease, or a combination thereof, in a patient-specific manner.

In yet another broad aspect, the novel chimeric antigen receptors (CARs) provided herein may comprise single, tandem, or multi-targeting CAR constructs (including those in a DuoCAR format), or any combination thereof.

In certain aspects, the novel boosted CARs are under the control of one or more constitutive promoters, tissue specific promoters, or inducible promoters, or any combination thereof.

In certain aspects, the one or more switches comprising a tag, a kill switch, an on switch, an off switch, and/or an adapter switch, or any combination thereof.

In certain embodiments, the single, tandem, multi-targeting CARs, and DuoCARs (either with or without one or more booster elements) novel chimeric antigen receptors (CARs) are provided are used to transduce effector cells for the treatment of solid and hematologic tumors and other diseases through targeted antigens (for example, and not by way of limitation, CD19, CD20, CD22, ROR1, mesothelin, CD33/IL3Ra, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, GD2, GD3, GM2, Ley, polysialic acid, fucosyl GM1, GM3, Tn, STn, sLe(animal), GloboH, CD5, CD7, CD19, CD20, CD22, CD25, CD37, CD30, CD33, CD38, CD123, CD45, CAMPATH-1, BCMA, CS-1, PD-L1, CD276/B7-H3, B7-H4, B7-DC, HLA-DR carcinoembryonic antigen (CEA), TAG-72, EpCAM, folate-binding protein, folate receptor alpha (FOLR1), folate receptor beta (FOLR2), A33, G250, pro state-specific membrane antigen (PSMA), ferritin, CA-125, CA19-9, CD44v6, epidermal growth factor, p185, IL-2 receptor, interleukin 1 receptor accessory protein (IL1RAP), EGFRvIII (de2-7), fibroblast activation protein, tenascin, a metalloproteinase, endosialin, vascular endothelial growth factor, $\alpha v\beta 3$, WT1, LMP2, HPV E6, HPV E7, Her-2/neu, p53 nonmutant, NY-ESO-1, MelanA/MART 1, Ras mutant, gp100, FGFR1, FGFR2, FGFR3, FGFR4, GPC1, GPC2, GPC3, p53 mutant, PR1, bcr-abl, tyrosinase, survivin, PSA, hTERT, a Sarcoma translocation breakpoint fusion protein, EphA2, PAP, ML-IAP, AFP, ERG, NA17, PAX3, ALK, androgen receptor, cyclin B 1, MYCN, RhoC, TRP-2, mesothelin, PSCA, MAGE A1, MAGE A3, CYP1B 1, PLAV1, BORIS, ETV6-AML, NY-BR-1, RGS5, SART3, Carbonic anhydrase IX, PAX5, OY-TES 1, Sperm protein 17, LCK, HMWMAA, AKAP-4, SSX2, XAGE 1, B7H3, Legumain, Tie 3, PAGE4, VEGFR2, MAD-CT-1, PDGFR-B, MAD-CT-2, TRAIL 1, MUC1, MUC16/CA125, MAGE A4, MAGE C2, GAGE, EGFR, EGFR1, EGFR2/Her2, CMET, HER3, CA6, NAPI2B, TROP2, TEM1, TEM7, TEM8, FAP, LAP, CLDN3, CLDN6, CLDN8, CLDN16, CLDN18.2, RON, LY6E, DLL3, PTK7, UPK1B, STRA6, TMPRSS3, TMRRSS4, TMEM238, Clorf186, LIV1, ROR1, ROR2, Fos-related antigen 1, VEGFR1, endoglin, CD90, CD326, CD70, SSEA4, CD318, CLA, TSPAN8, GPRCSD, EpCAM, Thy1, IL13Ra2, BDCA1, BDCA2, BDCA3, GD2, PSMA, FAP, CLL1, SLAMF7/CS1, CD147, DPPA5, GRP78, CD66c, VISTA, LRRC5, LRRC15, or any combinations thereof or a fragment thereof is provided, wherein the antibody or a fragment thereof comprises a fragment selected from the group consisting of an Fab fragment, an F(ab')2 fragment, an Fv fragment, a nanobody, a VHH, a ligand peptide, and a single chain Fv (ScFv), or a fragment of any of the preceding, or a molecule that is at least 80%, 85%, 90°/%, 95%, 96%, 97%, 98% or 99% homologous to any of the preceding, or any combination thereof.

In certain aspects, the effector cells comprise T cells, natural killer (NK) cells, natural killer T (NKT) cells, invariant natural killer T (iNKT) cells, dendritic cells (DCs), gamma delta T cells, monocytes, macrophages, stem cells, and induced pluripotent stem (iPS) cells.

In yet another broad aspect, one or more of the above-identified novel boosted chimeric antigen receptors (CARs) provided supra with respect to SEQ ID NOs: 151 to 256 may comprise either a single, tandem, or multi-targeting CAR construct (including those in a DuoCAR format), or any combination thereof.

For each of the various aspects and embodiments of the single, tandem, multi-targeting CARs, and DuoCARs, (either with or without one or more booster elements) CAR constructs specifically contemplated herein, the nucleotide sequences encoding the functional CAR (either with or without one or more booster elements) comprise the nucleotide sequence of SEQ ID NO: 151, 153, 155, 157, 159, 161, 163, 165, 167, 169, 171, 173, 175, 177, 179,181, 183, 185, 187,189, 191, 193, 195, 197, 226, 228, 230, 232, 234, 236, 238, 240, 242, 244, 245, 247, 249, 251, 253, or 255, or any combination thereof.

For each of the various aspects and embodiments of the single, tandem, multi-targeting CARs, and DuoCARs, (either with or without one or more booster elements) CAR constructs specifically contemplated herein, each vector encodes a functional CAR (either with or without one or more booster elements) comprising the amino acid sequence of SEQ ID NO: 152, 154, 156, 158, 160, 162, 164, 166, 168, 170, 172, 174, 176, 178, 180, 182, 184, 186, 188, 190, 192, 194, 196, 198, 225, 227, 229, 231, 233, 235, 237, 239, 241, 243, 246, 248, 250, 252, 254, or 256, or any combination thereof.

In yet another broad aspect, one or more of the above-identified novel boosted chimeric antigen receptors (CARs) provided supra with respect to SEQ ID NOs: 127 to 149 may comprise either a single, tandem, or multi-targeting CAR construct (including those in a DuoCAR format), or any combination thereof.

For each of the various aspects and embodiments, an isolated polynucleotide encoding a fully human anti-ROR1 and/or anti-MSLN antibody or a fragment thereof is provided comprising a nucleic acid sequence selected from the group consisting of SEQ ID NOs: 143, 145, 147, and 149.

For each of the various aspects and embodiments, an isolated polynucleotide encoding a fully human anti-HER2, FOLR1, MUC16, CD276, EGFR, GD2, NKGD2 antibody or a fragment thereof is provided comprising a nucleic acid sequence selected from the group consisting of SEQ ID NOs: 127, 129, 131, 133, 135, 137, 139, and 141.

For each of the various aspects and embodiments, novel single, tandem, DuoCARs, or multiple-targeting CARs (either with or without one or more booster elements) are provided herein comprising a single, tandem, DuoCAR, or multiple-targeting CAR molecule (either with or without one or more booster elements) comprising at least one extracellular antigen binding domain comprising an anti-ROR1 and/or anti-MSLN antigen binding domain comprising the nucleic acid sequence selected from the group consisting of SEQ ID NOs: 143, 145, 147, and 149; at least one linker domain; at least one transmembrane domain; and at least one intracellular signaling domain.

For each of the various aspects and embodiments, novel single, tandem, DuoCAR, or multiple-targeting CARs (either with or without one or more booster elements) are provided herein comprising a single, tandem, DuoCAR, or multiple-targeting CAR molecule (either with or without one or more booster elements) comprising at least one extracellular antigen binding domain comprising an anti-HER2, FOLR1, MUC16, CD276, EGFR, GD2, and/or NKGD2 antigen binding domain comprising the nucleic acid sequence selected from the group consisting of SEQ ID NOs: 127, 129, 131, 133, 135, 137, 139, and 141; at least one linker domain; at least one transmembrane domain; and at least one intracellular signaling domain. For each of the various aspects and embodiments, novel single, tandem, DuoCAR, or multiple-targeting CARs (either with or without one or more booster elements) are provided herein comprising a single, tandem, DuoCAR, or multiple-targeting CAR molecule (either with or without one or more booster elements) comprising at least one extracellular antigen binding domain comprising an anti-ROR1 and/or anti-MSLN antigen binding domain comprising the amino acid sequence selected from the group consisting of SEQ ID NOs: 144, 146, 148, and 150; at least one linker domain; at least one transmembrane domain; and at least one intracellular signaling domain.

For each of the various aspects and embodiments, novel single, tandem, DuoCAR, or multiple-targeting CARs (either with or without one or more booster elements) are provided herein comprising a single, tandem, DuoCAR, or multiple-targeting CAR molecule (either with or without one or more booster elements) comprising at least one extracellular antigen binding domain comprising an anti-HER2, FOLR1, MUC16, CD276, EGFR, GD2, and/or NKGD2 antigen binding domain comprising the amino acid sequence selected from the group consisting of SEQ ID NOs: 128, 130, 132, 134, 136, 138, 140, and 142; at least one linker domain; at least one transmembrane domain; and at least one intracellular signaling domain.

In one embodiment, an isolated polynucleotide encoding a fully human anti-ROR1 and/or anti-MSLN anti-ROR1 and/or anti-MSLN and/or anti FolR1, and/or anti HER2/ERBB2, and/or anti GPC3, and/or anti-FGFR4, and/or anti GD2 antibody or a fragment thereof is provided, wherein the antibody or a fragment thereof comprises a nucleic acid sequence selected from the group consisting of SEQ ID NOs: 127, 129, 131, 133, 135, 137, 139, 141, 143, 145, 147, and 149.

In one embodiment, an isolated polynucleotide encoding a fully human anti-ROR1 and/or anti-MSLN anti-ROR1 and/or anti-MSLN and/or anti FolR1, and/or anti HER2/ERBB2, and/or anti GPC3, and/or anti-FGFR4, and/or anti GD2 antibody or a fragment thereof is provided, wherein the antibody or a fragment thereof comprises an amino acid sequence selected from the group consisting of SEQ ID NOs: 128, 130, 132, 134, 136, 138, 140, 142, 144, 146, 148, and 150.

In one aspect, an isolated nucleic acid molecule encoding a single, tandem, DuoCAR, or multiple-targeting chimeric antigen receptor (CAR) (either with or without one or more boosting elements) is provided comprising, from N-terminus to C-terminus, at least one anti-ROR1 and/or anti-MSLN antigen binding domain encoded by a nucleotide sequence comprising a nucleic acid sequence selected from the group consisting of SEQ ID NOs: 143, 145, 147, and 149, at least one transmembrane domain, and at least one intracellular signaling domain.

In one aspect, an isolated nucleic acid molecule encoding a single, tandem, DuoCAR, or multiple-targeting chimeric antigen receptor (CAR) (either with or without one or more boosting elements) is provided comprising, from N-terminus to C-terminus, at least one anti-ROR1 and/or anti-MSLN antigen binding domain encoded by a nucleotide sequence comprising an amino acid sequence selected from the group consisting of SEQ ID NOs: 144, 146, 148, and 150, at least one transmembrane domain, and at least one intracellular signaling domain.

In one embodiment, the targeting domain of the single, tandem, DuoCAR, or multiple-targeting CAR (either with or without one or more boosting elements) is expressed separately in the form of monoclonal antibody, ScFv Fab, Fab'2 and is containing an antigen-targeting domain comprising a nucleic acid sequence selected from the group consisting of SEQ ID NOs: 143, 145, 147, and 149, coupled to an additional binding tag or epitope, whereas the effector-cell expressed component of the single, tandem, DuoCAR, or multiple-targeting CAR (either with or without one or more boosting elements) contains a binding domain specifically directed to bind the tag or epitope expressed on the soluble single, tandem, DuoCAR, or multiple-targeting CAR (either with or without one or more boosting elements) module, such as specific binding on the soluble component of the single, tandem, DuoCAR, or multiple-targeting CAR (either with or without one or more boosting elements) to the cell bound component of the single, tandem, DuoCAR, or multiple-targeting CAR (either with or without one or more boosting elements) forms the full functional single, tandem, DuoCAR, or multiple-targeting CAR (either with or without one or more boosting elements) structure.

In yet another embodiment, an isolated nucleic acid molecule encoding the single, tandem, Duo, or multiple-targeting CAR (either with or without one or more boosting elements) is provided wherein the encoded single, tandem, DuoCAR, or multiple-targeting CAR (either with or without one or more boosting elements) extracellular anti-ROR1 and/or anti-MSLN antigen binding domain further comprises at least one lipocalin-based antigen binding antigen (anticalins) that binds to ROR1 and/or MSLN.

In one embodiment, an isolated nucleic acid molecule is provided wherein the encoded extracellular anti-ROR1 and/or anti-MSLN antigen binding domain is connected to the transmembrane domain by a linker domain.

In another embodiment, an isolated nucleic acid molecule encoding the single, tandem, DuoCAR, or multiple-targeting CAR (either with or without one or more boosting elements) is provided wherein the encoded anti-ROR1 and/or anti-MSLN extracellular antigen binding domain is preceded by a sequence encoding a leader or signal peptide.

In one aspect, the single, tandem, DuoCAR, or multiple-targeting CARs (either with or without one or more boosting elements) provided herein further comprise a linker or spacer domain.

In one embodiment, an isolated nucleic acid molecule encoding the single, tandem, DuoCAR, or multiple-targeting CAR (either with or without one or more boosting elements) is provided wherein the extracellular anti-ROR1 and/or anti-MSLN antigen binding domain, the intracellular signaling domain, or both are connected to the transmembrane domain by a linker or spacer domain.

In one embodiment, an isolated nucleic acid molecule encoding the single, tandem, DuoCAR, or multiple-targeting CAR (either with or without one or more boosting elements) is provided wherein the encoded linker domain is derived from the extracellular domain of IgG1, IgG2, IgG3 or IgG4, CD8, TNFRSF19, or CD28, and is linked to a transmembrane domain.

In another embodiment, an isolated nucleic acid molecule encoding the single, tandem, DuoCAR, or multiple-targeting CAR (either with or without one or more boosting elements) is provided wherein the encoded single, tandem, DuoCAR, or multiple-targeting CAR (either with or without one or more boosting elements) further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or a combination thereof.

In yet another aspect, a pharmaceutical composition is provided comprising an anti-tumor effective amount of a population of human T cells, wherein the T cells comprise a nucleic acid sequence that encodes a single, tandem, or multi-targeting, chimeric antigen receptor (CAR) construct, wherein the CAR comprises at least one extracellular antigen binding domain comprising an anti-MSLN and/or anti-ROR1 antigen binding domain comprising the amino acid sequence selected from the group consisting of SEQ ID NOs: 144, 146, 148, and 150; at least one linker domain; at least one transmembrane domain; and at least one intracellular signaling domain, wherein the T cells are T cells of a human having a cancer or an autoimmune, alloimmune, or autoaggressive disease. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or a combination thereof.

In another aspect, methods of making single, tandem, DuoCAR, or multiple-targeting CAR construct-containing T cells (hereinafter "CAR-T cells") (either with or without one or more booster elements) are provided. The methods include transducing a T cell with a vector or nucleic acid molecule encoding a disclosed CAR that specifically binds MSLN and/or ROR1, thereby making the CAR-T cell.

In yet another aspect, a method of generating a population of RNA-engineered cells is provided that comprises introducing an in vitro transcribed RNA or synthetic RNA of a nucleic acid molecule encoding a disclosed single, tandem, DuoCAR, or multiple-targeting CAR (either with or without one or more booster elements) into a cell of a subject, thereby generating a single, tandem, DuoCAR, or multiple-targeting CAR cell (either with or without one or more booster elements).

In yet another aspect, a method for diagnosing a disease, disorder or condition associated with the expression of MLSN and/or ROR1 on a cell, is provided comprising a) contacting the cell with a human anti-MSLN and/or anti-ROR1 antibody or fragment thereof, wherein the antibody or a fragment thereof comprises an amino acid sequence selected from the group consisting of SEQ ID NOs: 144, 146, 148, and 150; and b) detecting the presence of MSLN and/or ROR1 wherein the presence of MSLN and/or ROR1 diagnoses for the disease, disorder or condition associated with the expression of MSLN and/or ROR1.

In another embodiment, a method of inhibiting MSLN and/or ROR1-dependent T cell inhibition, is provided comprising contacting a cell with a human anti-MSLN and/or anti-ROR1 antibody or fragment thereof, wherein the antibody or a fragment thereof comprises an amino acid sequence selected from the group consisting of SEQ ID NOs: 144, 146, 148, and 150. In one embodiment, the cell is selected from the group consisting of a MSLN and/or ROR1-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed single, tandem, or multiple-targeting CAR (either with or without one or more booster elements).

In another embodiment, a method of treating or preventing cancer in a mammal is provided comprising administering to the mammal one or more of the disclosed single, tandem, or multiple-targeting CARs (either with or without one or more booster elements), in an amount effective to treat or prevent cancer in the mammal. The method includes administering to the subject a therapeutically effective amount of host cells expressing a disclosed single, tandem, or multiple-targeting CAR (either with or without one or more booster elements) that specifically binds MSLN and/or ROR1 and/or one or more of the aforementioned antigens, under conditions sufficient to form an immune complex of the antigen binding domain on the single, tandem, or multiple-targeting CAR (either with or without one or more booster elements) and the extracellular domain of MSLN and/or ROR1 and/or one or more of the aforementioned antigens in the subject.

In yet another embodiment, a method is provided for generating a persisting population of genetically engineered T cells in a human diagnosed with cancer. In one embodiment, the method comprises administering to a human a T cell genetically engineered to express a single, tandem, or multiple-targeting CAR (either with or without one or more booster elements) wherein the single, tandem, or multiple-targeting CAR (either with or without one or more booster elements) comprises at least one MSLN and/or ROR1 antigen binding domain comprising the amino acid sequence of SEQ ID NOs: 144, 146, 148, and 150, or any combination thereof; at least one transmembrane domain; and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

In one aspect of the present invention, an immunotherapy composition is provided comprising a single, tandem, DuoCAR, or multiple-targeting CAR (either with or without one or more booster elements) which immunotherapy composition may be used to transduce autologous lymphocytes to generate active patient-specific anti-tumor lymphocyte cell populations that can be infused directly back into the patient to promote in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In one embodiment, a pharmaceutical composition is provided wherein the at least one transmembrane domain of the single, tandem, DuoCAR, or multi-targeting CAR (either with or without one or more boosting elements) contains a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

It will be understood that the single, tandem, DuoCAR, or multiple-targeting CARs (either with or without one or more booster elements), host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

(FIG. 2A) Mono CAR armed with membrane bound IL7 (mIL7) comprised a ROR1 or MSLN scFv binding domain, IgG4 or CD8 hinge domain, CD8 transmembrane domain, 41BB or CD28 co-stimulatory domain, a CD3 activation domain, followed by a 2A peptide, and in frame to membrane bound IL7. Tandem boosted CAR constructs comprised of a MSLN-ROR1 tandem scFv targeting domain, IgG4 short hinge, CD8 or CD28 transmembrane domain, a single 4-1BB or tandem CD28_4-1BB co-stimulatory domain, a CD3ζ activation domain, and a 2A sequence connected mIL7. DuoCAR constructs contained a mono ROR1 CAR, followed by 2A sequence, a mono MSLN CAR with different co-stimulatory domain or transmembrane domain, in frame to 2A peptide connected m IL7. Mono ROR or MSLN CARs and tandem CARs were included as control constructs. Primary T cells from healthy donor were activated with TransAct in the presence of IL-2, and transduced with lentiviral vectors encoding ROR1 and/or MSLN CAR constructs. Transduced T cells were assayed for CAR surface expression with ROR1 Fc and/or MSLN His staining followed by anti-Fc-AF647 or anti-His APC with flow cytometry. (FIG. 2B) Percentage of ROR1 CAR expression in T cells transduced with CAR constructed encoding ROR1 binders was plotted. (FIG. 2C) Percentage of MSLN CAR expression in T cells transduced with MSLN binder containing CAR was quantified. Mean fluoresce intensity of ROR1 binder expression (FIG. 2D) and MSLN binder expression (FIG. 2E) were presented as bar figures. Data represented one independent experiment from two different donors.

(FIG. 4A) OVCAR-3, (FIG. 4B) NCI-H226, (FIG. 4C) CAPAN-1 was plotted as bar figures. Data represented one independent experiment from one to two different donors.

(FIG. 6A) Expression of membrane bound IL7 was determined by western using IL7 antibody followed with goat anti mouse HPR conjugated secondary antibody. GAPDH measured by anti-GAPDH and goat anti-Rabbit secondary antibody was included as loading control. CAR T cells were transduced with lentivirus encoding ROR1 and/or MSLN CAR constructs with or without mIL7 at MOI 20. Transduced CAR T cells were washed and cultivated at 1e6/ml using TexMACS medium without IL-2 supplement. long term target cell stimulation. Cell expansion (FIG. 6B) and T cell size (FIG. 6C) were monitored weekly until no cell expansion observed for continuously 2-3 weeks. Data represented one independent experiment from two separate donors.

(FIG. 8A) MSLN CAR D0181 comprised of MSLN scFv binding domain, CD8 hinge domain and transmembrane domain, 41BB co-stimulatory domain and a CD3ζ activation domain. Boosted CAR D0211 comprised of a mono MSLN CAR, a 2A peptide linker and in frame to a dominant negative TGFβ receptor II (TGFβRIIdn). Primary T cells from healthy donors were activated with TransAct in the presence of IL-2, and transduced with lentiviral vectors encoding MSLN CAR D0181 and boosted MSLN CAR D0211 constructs. (FIG. 8B) CAR surface expression was assessed by flow cytometry using MSLN-His followed by anti-His-APC staining. The TGFβRIIdn expression of was determined by biotinylated TGFβR and streptavidin PE staining. Histogram overlay of UTD, CAR D0181 and D0211 was shown in right. (FIG. 8C) Luciferase-based cytotoxicity assays were performed using MSLN+ tumor line NCI-H226, A431-MSLN and a MSLN-A431. All target lines were stably transduced with firefly luciferase. CAR T cells and tumor cells were co-cultured overnight at the 10 series effector to target (E:T) ratios. Percentage specific target lysis was assessed by luminometry and normalized to percentage of CAR expression. Non-linear EC50 shift, x is log concentration was used for curve fit. (FIG. 8D) Culture supernatants of CAR T cells was evaluated after overnight incubation with MSLN+ NCI-H226 target cells at 10 different E:T ratios. Cytokine production of IFNγ, and TNFα, were analyzed by ELISA. Mean t SEM of two technical replicates. Data represented one independent experiment from four separate donors. (FIG. 8E) Kinetic killing assay testing the functionality of MSLN and ROR1 CAR T cells boosted with TGFβRIIdn-armor against AsPc-1 tumor cell line, in the presence or absence of TGFβ.

(FIG. 10A) MSLN targeting CAR comprised of a fully human MSLN scFv targeting domain, a CD8 hinge and transmembrane domain, a 4-1 BB co-stimulatory domain and a CD3ζ activation domain. ROR1 targeting CAR comprised of a fully human ROR1 scFv9 targeting domain, a IgG4 short hinge, CD8 transmembrane domain, a 4-1BB co-stimulatory domain and a CD3ζ activation domain. Booster CARs contained mono targeting CARs, followed by 2A peptide, in frame to an ECM molecule. Heparanase (HPSE), Metalloproteinase (MMP2), Hyaluronidase PH-20 were selected as booster molecules. (FIG. 10B) Primary T cells from healthy donor were activated with TransAct in the presence of IL-2, and transduced with lentiviral vectors encoding CAR constructs. Transduced T cells were assayed for CAR surface expression with ROR1 Fc or MSLN-His staining followed by anti-Fc-AF647 or anti-His APC respectively with flow cytometry. CD4 staining was included to identify CD4+ and CD8+ population. Percentage of CAR positivity was listed above the plot. UTD—untransduced control.

(FIG. 11A) MEC-1 ROR1$^{Hi}$ MSLN$^{Hi}$, (FIG. 11C) NCI H226 and ROR-MSLN-tumor line, (FIG. 11B) MEC-1, and (FIG. 11D) HL-60. All target lines were stably transduced with firefly luciferase. CAR T cells and tumor cells were co-cultured overnight at the indicated effector to target (E:T) ratios: 1.25:1, 5:1, or 10:1. Percentage specific target lysis was assessed by luminometry. Data represented one independent experiment from two different donors. Mean±SEM of three technical replicates. Representative experiment from one donor was shown in the panel.

(FIG. 12A) Secreted HPSE by CAR D0344 and CAR D0347 was measured by ELISA, mono CAR DO181, CAR D0290 and un-transduced T cell (UTD) from same donor were included as control. Culture supernatants of CAR T cells was evaluated after overnight incubation. (FIG. 12B) HPSE functionality was evaluated by migration assay using 0, 2.5 or 5 mg/ml Cultrex coated transwell. One million thawed CAR T cells were seed into precoated transwell. After 24 hr, the total CAR T cells migrated into bottom chamber was quantify using Absolute counting beads by flow cytometer.

(FIG. 13A) representative mouse bioluminescent images were shown at indicated time points. (FIG. 13B) Time course of tumor growth based on mouse whole body bioluminescence (radiance) were quantified as photons per second per cm$^2$ per steradian. TA-tumor alone, UTD—non-transduced T cell control. N=6, mean±SEM.

(FIG. 15A) Mouse bioluminescent images were shown at indicated time points. (FIG. 15B) Time course of tumor growth based on mouse whole body bioluminescence (radiance) were quantified as photons per second per $cm^2$ per steradian and plotted. TA-tumor alone, UTD—non-transduced T cell control. N=4~5, mean t SEM.

FIG. 17A) ROR1 targeting CAR comprised of a fully human ROR1 scFv9 targeting domain, a IgG4 short hinge, CD8 transmembrane domain, a 4-1BB co-stimulatory domain and a CD33 activation domain. FolR1 targeting CAR comprised of a fully human Farle scFv targeting domain, a CD8 hinge and transmembrane domain, a 4-1BB co-stimulatory domain and a CD3ζ activation domain under the PGK or EF1α promoter. Booster CARs contained mono targeting CARS, followed by 2A peptide, in frame to an ECM molecule. Matrix Metalloproteinase-2 (MMP-2), Matrix Metalloproteinase-9 (MMP-9), Hyaluronidase (PH-20), and Heparanase (HPSE), were selected as booster molecules. For the ROR1 CAR set expressing hyaluronidase, PH-20 is expressed under the native or tPA signaling peptide in the presence, absence or retains 7 amino acids of the GPI anchor. FIG. 17B) Primary T cells from a healthy donor were activated with TransAct in the presence of IL-2, and transduced with lentiviral vectors encoding CAR constructs. Transduced T cells were assayed for CAR surface expression with ROR1-Fc or FolR1-Fc staining followed by anti-Fc-AF647 with flow cytometry. CD4 staining was included to identify CD4+ and CD8+ population. Percentage of CAR positivity was listed above the plot. UTD—un-transduced control.

(FIG. 18A) Data represented one independent experiment from 3 different donors. Mean f SD of three technical replicates. Representative experiment from one donor was shown in the panel. (FIG. 18B) Data represented one independent experiment from 1 donor. Mean f SD of three technical replicates. (FIG. 18C) FolR1 CARs were tested against FolR1+ line OVCAR3 and HL-60 was used as a negative control for nonspecific killing. CAR-T cells and tumor cells were co-cultured overnight at the indicated effector to target (E:T) ratios: 10:1, 2.5:1, or 1.25:1. Percentage specific target lysis was assessed by luminometry. Data represented one independent experiment from 3 different donors. Mean t SD of three technical replicates. Representative experiment from one donor was shown in the panel. All target lines were stably transduced with firefly luciferase. (FIG. 18D, FIG. 18E) Cytokine production of IFNγ, and TNFα, were analyzed by ELISA. (FIG. 18D) Culture supernatants of CAR-T cells was evaluated after overnight incubation with ROR1+ NCI-H226 target cells at E:T ratios 10:1, 5:1, 1.25:1. Mean f SD of three technical replicates. Data represents 3 independent experiments from 3 separate donors. (FIG. 18E) Culture supernatants of CAR-T cells was evaluated after overnight incubation with FolR1+ OVCAR3 target cells at E:T ratios 10:1, 2.5:1, 1.25:1. Mean f SD of three technical replicates. Data represents 3 independent experiments from 3 separate donors.

(FIG. 19A) Left: Concentration of secreted MMP-9 by ROR1 co-expressing MMP-9 (D0373). Un-transduced and CAR D0290 were also measured by MMP-9 ELISA. Data represents one independent experiment out of 2 different donors tested. Right: HPSE by CAR D0368 and D0369 was measured by ELISA, CAR D0351 and un-transduced T cell (UTD) from same donor were included as controls. Culture supernatants of CAR-T cells was evaluated from final day of CAR-T production. (FIG. 19B) MMP-2, MMP-9 functionality was evaluated by migration assay using 0 or 5 mg/ml Cultrex™ coated transwell. Half a million thawed CAR-T cells were seeded into precoated transwells. After 24 hr, the total CAR-T cells migrated into bottom chamber was quantify using Absolute counting beads by flow cytometer. (FIG. 19C) HPSE and PH-20 functionality was evaluated by migration assay using 0 or 5 mg/ml Cultrex™ coated (FIG. 19C) or hyaluronan coated (FIG. 19D) transwell, respectively. Half a million thawed CAR-T cells were seeded into precoated transwells. After 24 hr, the total CAR-T cells migrated into bottom chamber was quantify using Absolute counting beads for Cultrex™ coated by flow cytometer.

(FIG. 20A) Representative mouse bioluminescent images were shown at indicated time points. (FIG. 20B) Time course of tumor growth based on mouse whole body bioluminescence (radiance, photons/sec/cm2/sr) were quantified and plotted as shown. TA-tumor alone, UTD—un-transduced T cell control. N=4, mean±SD. (FIG. 20C) Body weight changes of mice during OVCAR3 xenograft study. OVCAR3 bearing mice were treated with CAR-T cells weights were recorded three times/week. Body weight change was calculated as the percentage of change from study initiation. Mean±SEM. TA-tumor alone, UTD—non-transduced T cell control. N=4 mice/group.

(FIG. 21A) CAR-T infiltration, CAR expression (percent and gMFI), and CD4: CD8 ratios were measured in the bone marrow (top) and spleen (middle) at study end of life. All samples were normalized by volume and Absolute counting beads. Spleen weights were measured to have no significant difference between treatment groups. (FIG. 21B) Memory phenotype of CAR-T cells in the bone marrow (top) and spleen (bottom). Naïve, central memory, effector memory and effector cells were measured for CAR-T+ cells (left), CAR+CD4+ (middle) and CAR+CD8+ (right). Mean±SD. Statistical difference was calculated using One-Way ANOVA in Prism software. For B, the statistical difference of the effector population was measured between different treatment groups. TA-tumor alone, UTD—non-transduced T cell control. N=4 mice/group.

(FIG. 22A) ROR1 or CD276 CAR comprised a ROR1 or CD276 scFv binding domain, IgG4 or CD8 hinge domain, CD8 transmembrane domain, 41BB co-stimulatory domain, a CD3 activation domain. (FIG. 22B) Representative flow plots of CAR expression on transduced T cells. CAR and CAR/CCR T cells were stained with ROR1-Fc followed by anti Fc AF647 for ROR1 CAR detection, and with CD276-His for CD276 CCR detection. (FIG. 22C) Average CAR expression in T cells from three healthy donors. Error bars represented mean f SEM.

(FIG. 23B) AsPC-1; (FIG. 23C) NCI-H226. All target lines were stably transduced with firefly luciferase. CAR T cells and tumor cells were co-cultured overnight at the 10 series effector to target (E:T) ratios. Percentage specific target lysis was assessed by luminometry and normalized to percentage of CAR expression. Nonlinear EC50 shift, where x is log concentration was used for curve fit. Data represent one independent experiment out of three experiments in T cells from different donors. Error bars represent mean t SEM.

(FIG. 24A) CD276 CCR boosted ROR1 CAR comprises a ROR1 CAR in frame to a CD276 CCR, linked by P2A ribosomal skip element. (FIG. 24B) Transduced primary T cells were gated based on forward and side scatter, doublet exclusion, and viability dye negativity. Surface CAR expression of the ROR1-targeting or the CD276-targeting domains of each binder was detected by co-staining ROR1-Fc and CD276-His, followed by anti-Fc and anti-His FL conjugate. Representative flow plots of ROR1 CAR and CD276 CCR co-expression are shown. (FIG. 24C) CAR and CCR co-expression on T cell surface was quantified. Mean of results from transduction of T cells from three healthy donors are shown, error bars indicate±SEM.

(FIG. 25B) ROR1-CD276-tumor line RS4; 11; and single target positive cell line (FIG. 25C) ROR1+CD276-RS4; 11-ROR1; (FIG. 25D) ROR1-CD276+RS4:11-CD276. All target lines were stably transduced with firefly luciferase. CAR T cells and tumor cells were co-cultured overnight at a series of 10 effector to target ratios. Percentage specific target lysis was assessed by luminometry and normalized to percentage of CAR expression. Nonlinear EC50 shift, where x is log of concentration, was used for curve fit. Data represent one independent experiment from three experiments performed on T cells from 3 different donors. Error bar=Mean±SEM (FIG. 26A) OVCAR-3, (FIG. 26B) RS4; 11-ROR1 was plotted as bar figures. Data represent Mean f SEM of independent experiments using T cells from 3 different donors.

(FIG. 27A) Schematic diagram of CAR constructs. (FIG. 27B) Left: flow plot examples of percentage of $CAR^{+}$T-cells; Center: percentage of $CAR^{+}$T-cells (n=3 donors); right: CAR density (n=3 donors): all were at day 8 of transduction. (FIG. 27C) Quantification of ROR1 molecules per cell in different hematologic cell lines, the experiment was performed in duplicates employing anti-ROR1 Ab from BD Biociences; a separate experiment was also performed in duplicates using anti-ROR-1 Abs from Miltenyi Biotec and R&D systems with similar results. (FIG. 27D) In vitro cytotoxic activity of CAR-Ts when co-cultured for 18 hrs with MCL cell line Jeko-1; left: a representative Killing curve; right: relative potency of LTG2529 vs LTG2527 (n=3 donors). (FIG. 27E) Quantification of cytokines secreted in 18-hr co-culture of CAR Ts with Jeko-1 cell line by ELISA, a representative data from 3 donors was shown. (FIGS. 27F-27K): NSG mice were implanted with Jeko-1 cells (i.v., 0.5e6 cells/mouse; 6 mice/group) at day #-6, followed by staging at day #-1, CAR T cells were administered (i.v., 3e6 $CAR^{+}$T cells/mouse) at day #0 (FIG. 27F); tumor progression was quantified by Bioluminescence Imaging (FIG. 27G, FIG. 27H), body weight was monitored (FIG. 27I), blood was sampled at the indicated time points and the tumor cells (FIG. 27J) or T-cells (FIG. 27K) were quantified by Flow Cytometry. Notes: *: p<0.05: **: p<0.01; n/s: not significant.

Figure 1:
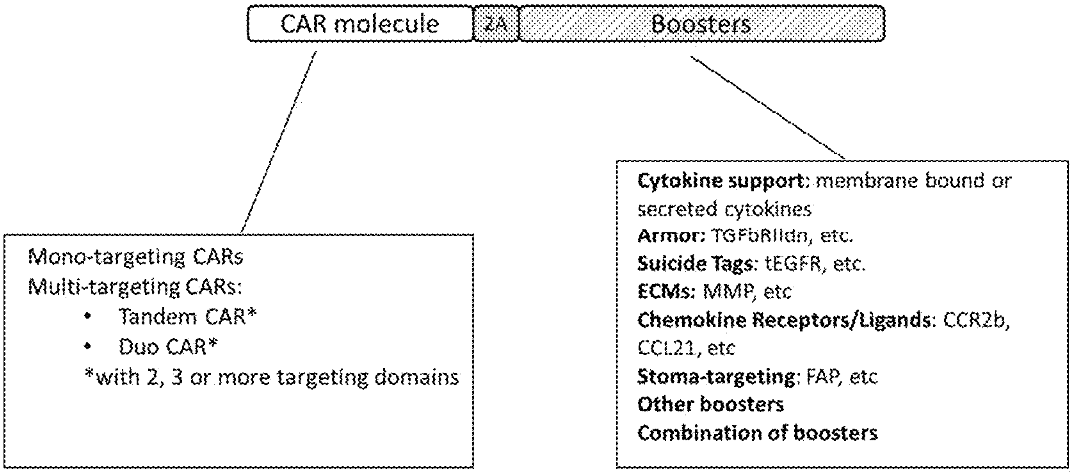
FIG. 1 depicts the structure of boosted CAR. Boosted CAR comprised of a CAR molecule followed by a 2A sequence, in frame to a boosting element. CAR molecule represented mono CARs and multi-targeting tandem or Dual CARs. Boosting elements various from cytokines (membrane bound IL7), armors (TGFβRIIdn), suicide tag (tEGFR), extracellular matrix enzymes (ECMs), chemokine receptors (CXCL8, CCL2), stroma targeting molecules (FAP), et al.

at day −7, followed by staging at day −1; CAR-Ts (5e6 $CAR^{+}$T-cells/mouse) were administered (i.v.) at day 0 (D): tumor progression was quantified by Bioluminescence imaging (E, F); body weight was monitored (G); blood was sampled at the indicated time points to quantify CAR+ T cells in both CD8 and CD4 subpopulations (H) as well as memory T cells (1).

FIGS. 29A-29K depict that Dominant negative TGFbRII (DN) obstructed TGFb1 signaling in T cells transduced with LTG2529 and reduced the inhibitory effect of TGFb1 on CAR-Ts' cytotoxic activity against pancreatic cancer cell line AsPC-1 in vitro. (FIG. 29A) schematic diagram of constructs of LTG2529 alone and LTG2529 armored with DN (namely D0228). (FIG. 29B) At day 8 of transduction, CAR expression (left: flow plots, center: graph from the flow plots) and memory phenotype (right) of both CD8' and CD4'T-cells transduced with LTG2529 or D0228 were analyzed by Flow cytometry; 3 independent experiments were performed, employing 3 donors, with similar results. (FIG. 29C) Expression of TGFbRII in T-cells transduced with LTG2529 or D0228 was assessed by Flow cytometry; 3 independent experiments were performed, employing 3 donors, with similar results. (FIG. 29D) CAR-Ts were IL-2 starved for 22 hrs to synchronize the cells followed by treatment with TGFb1 (10 ng/mL) for 0.5 or 2 hrs: cells were then stained with pSmad2/3 and subject to Flow analysis, upper panel: flow plots: lower panel: graph from the plots in the upper panel; the data is the representative of 3 independent experiments performed on 3 donors. (FIG. 29E) Expression of ROR1 on AsPC-1 cell line was assessed by flow cytometry. (FIG. 29F) AsPC-1 was co-cultured with CAR-Ts without or with TGFb1 (1 or 10 ng/mL); tumor cell lysis was measured by xCELLigence; left: % cytolysis; center: Time at which 50% tumor cells were killed ($KT_{50}$); right: cytotoxic relative potency of CAR-Ts treated with TGFb1 vs non-treatment; 2 independent experiments employing 2 donors were performed in triplicates with similar results. (FIG. 29G) Cytokine production from the experiments in (FIG. 29E) was quantified by ELISA; 2 independent experiments employing 2 donors were performed in triplicates with similar results. (FIG. 29H, FIG. 29I): Production of TGFb1 either in active or latent form by various solid tumor cell lines (FIG. 29H) or by AsPC-1 ectopically overexpressing TGF1 (FIG. 29I) was assessed by ELISA; data are representative of 2 independent experiments with similar results. (FIG. 29J) AsPC-1 overexpressing TGFb1 (AsPC-1/TGFb) or AspC-1 ctrl was co-cultured with CAR-Ts, % cytolysis of tumor cells was shown. (FIG. 29K) Cytokine production from the experiments in (FIG. 29E) was quantified by ELISA; 2 independent experiments employing 2 donors were performed in triplicates with similar results. Notes: *: $p<0.05$; : $P<0.01$; *: $P<0.001$.

Figures 30A, 30B:
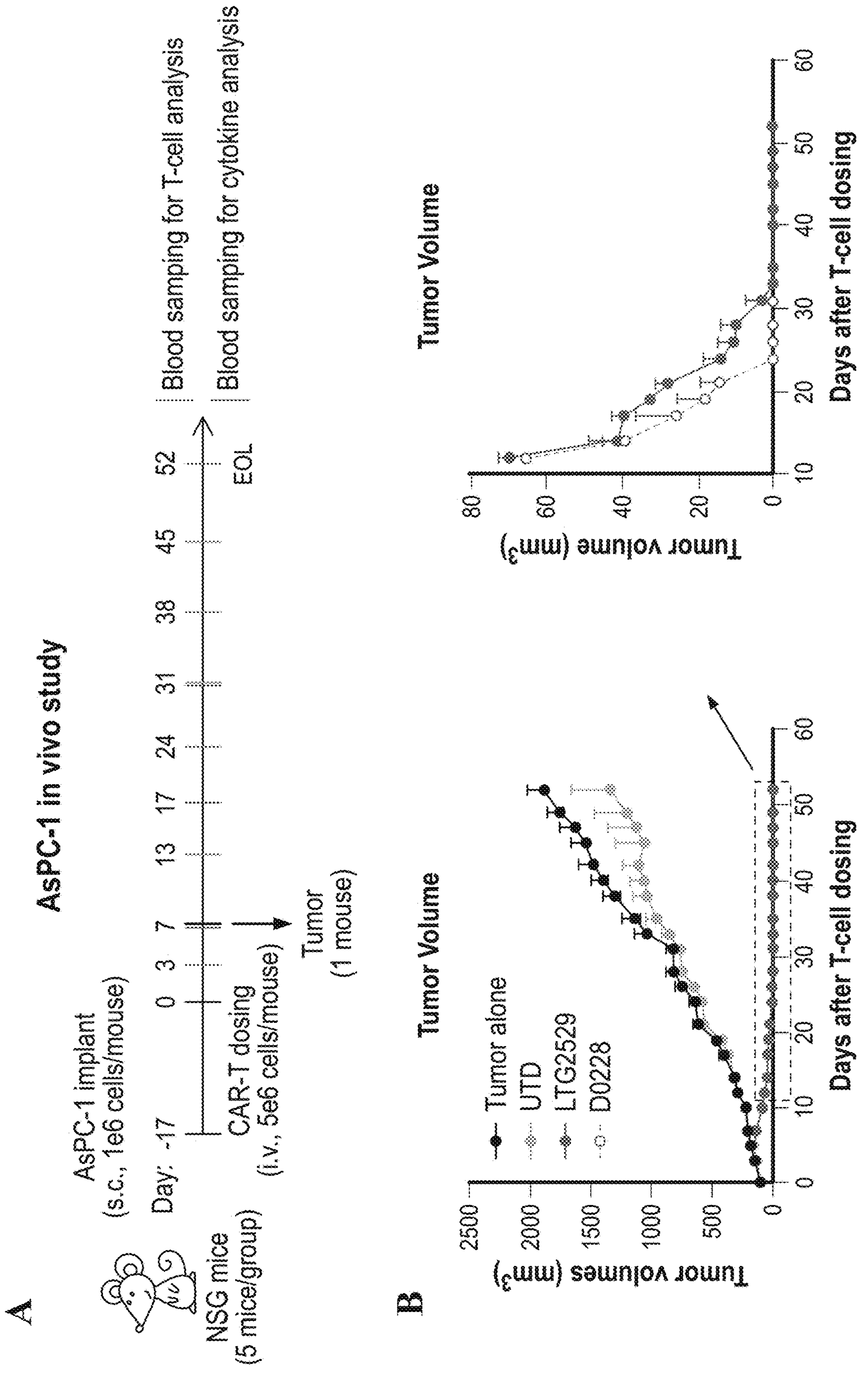
Figures 30C, 30D, 30E:
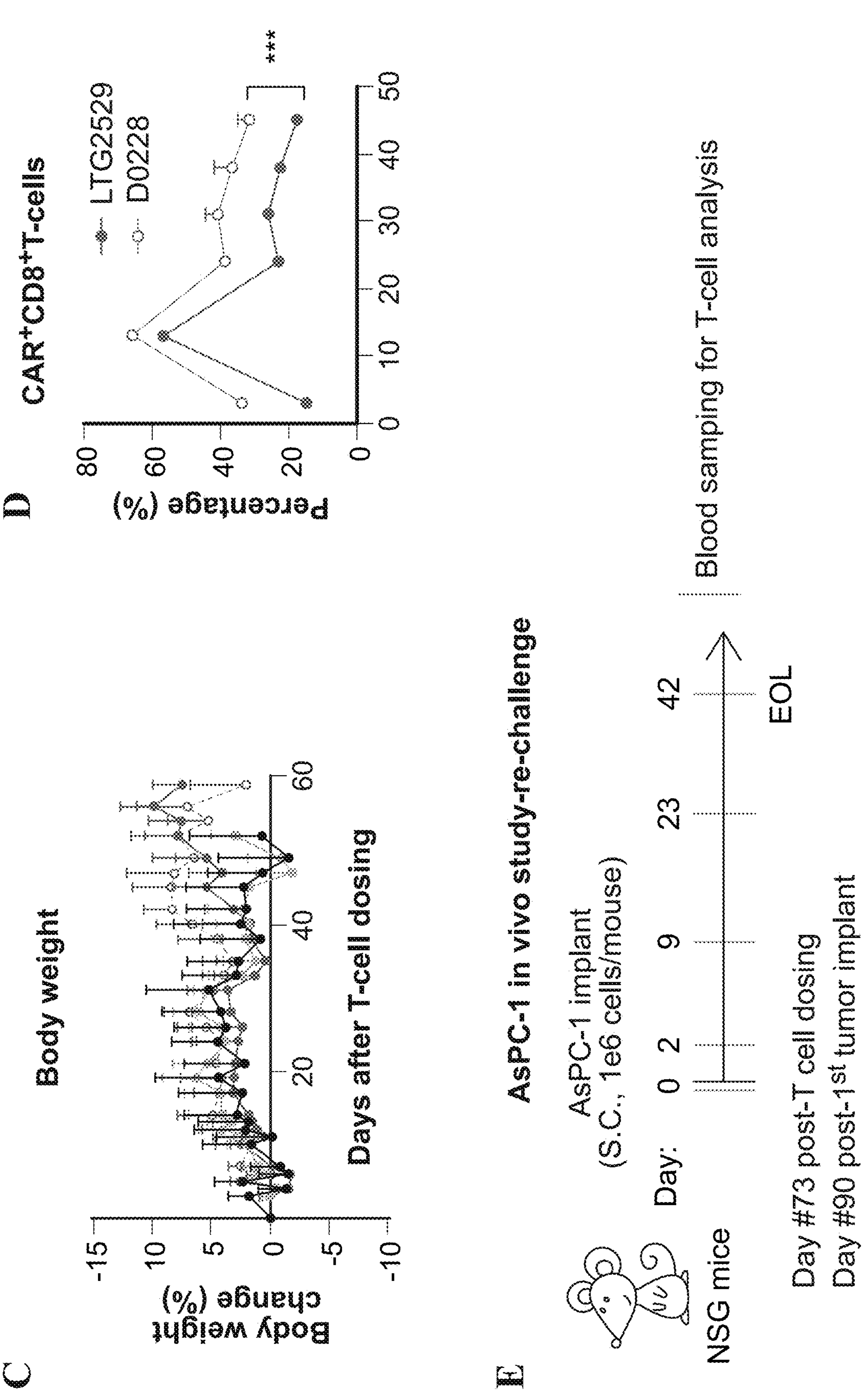
Figure 30F:
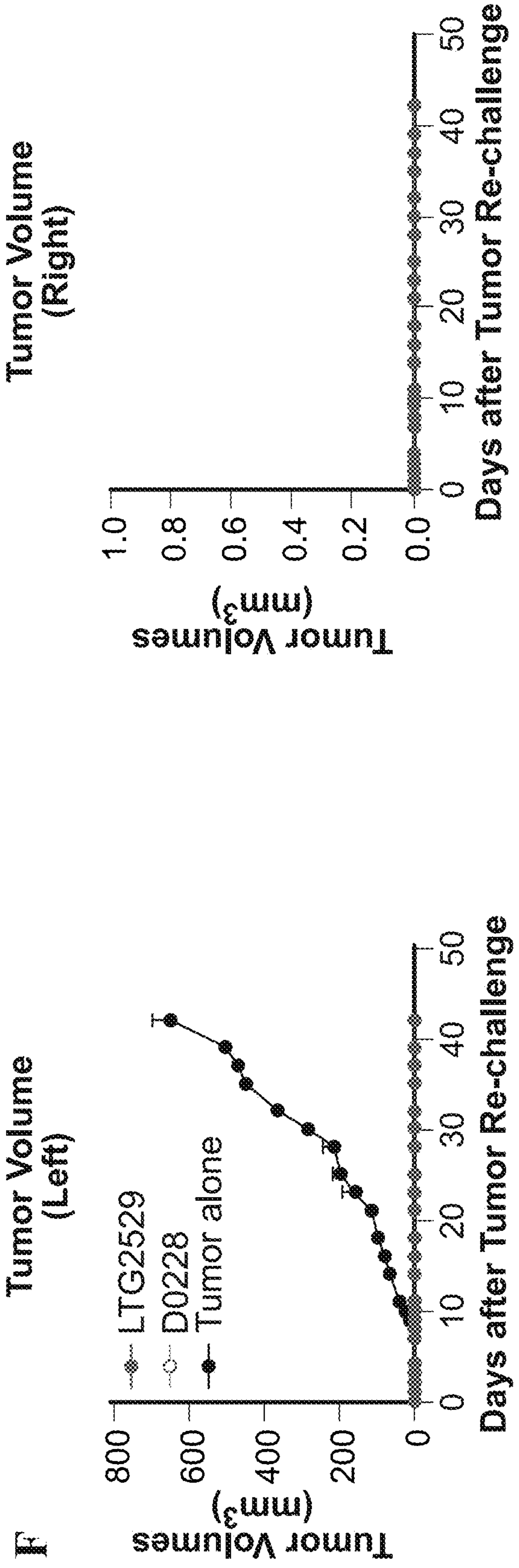
Figure 30G:
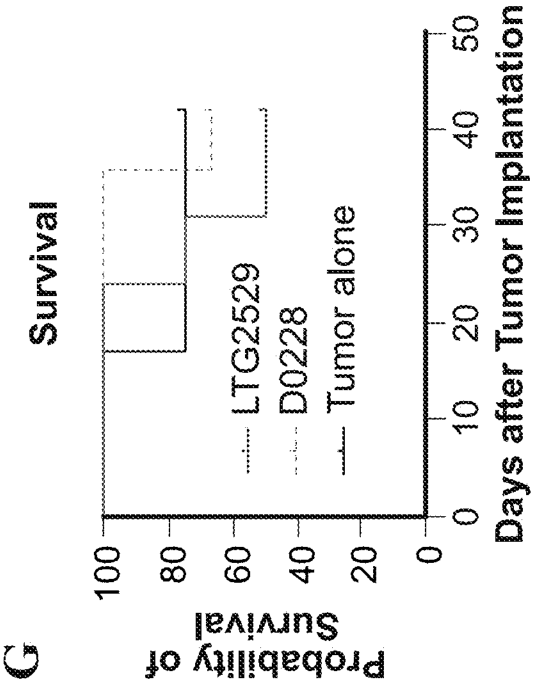
Figures 30H, 30I, 30J:
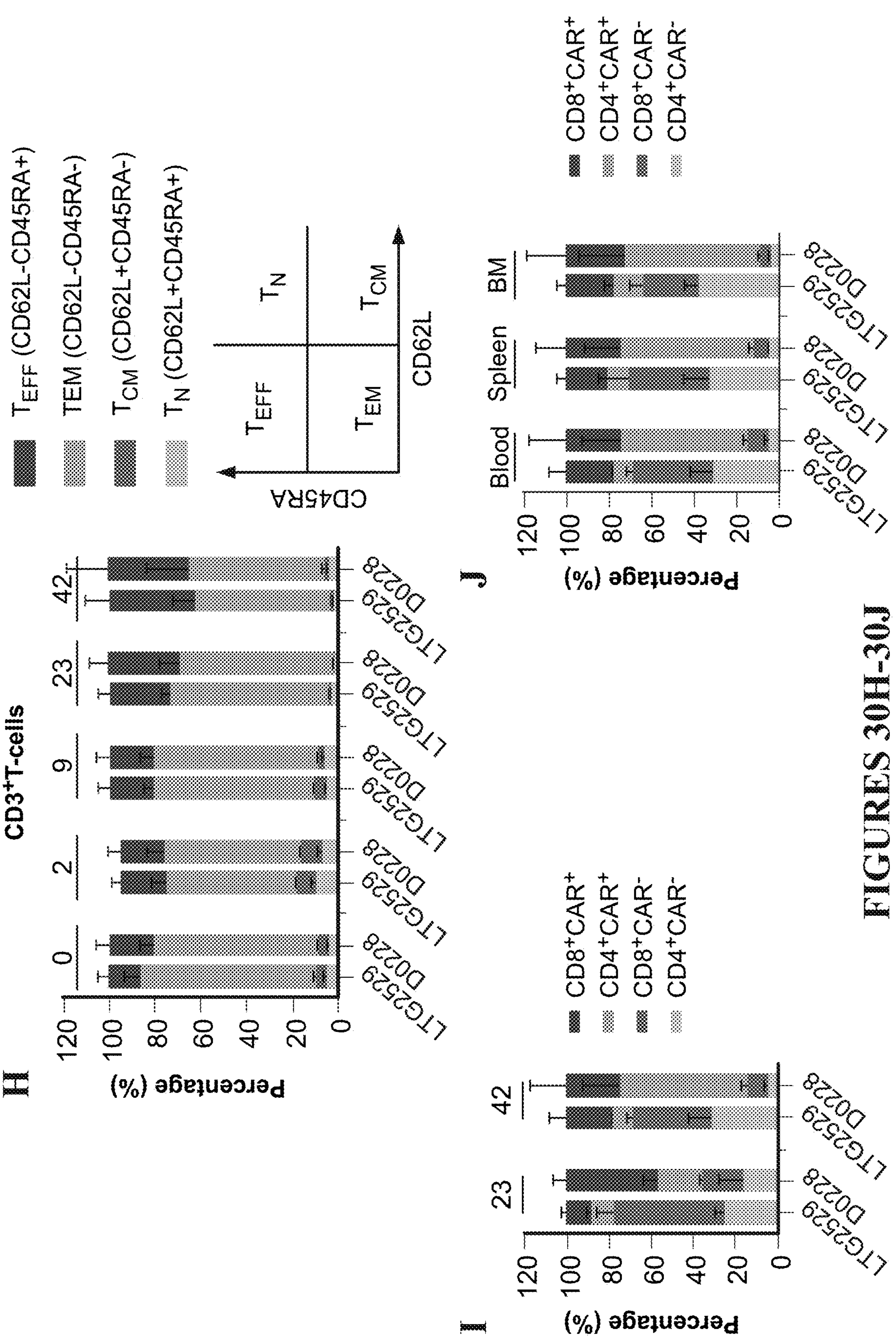

FIGS. 30A-30J depict that TGFbRIIDN showed higher frequency of CAR+ T cells in Pancreatic cancer xenograft model employing AsPC-1 which produced low level of TGFb1. (FIGS. 30A-30D): Efficacy of CAR-Ts in in vivo pancreatic cancer AsPC-1 xenograft model: NSG mice (5 mice/group) were implanted subcutaneously with AsPC-1 cells (1e6 cells/mouse) at day −17, followed by staging and CAR-T infusion (i.v., 5e6 $CAR^{+}$T-cells/mouse) at day 0 (FIG. 30A); tumor volume was measured (FIG. 30B)(left: tumor volume from mice across all groups; right: tumor volume from mice treated with armored and non-armored CARs started at day 10 post T cell dosing); body weight was monitored (FIG. 30C); blood from mice were sampled and quantified for CD8 subpopulation of CAR+ T cells (FIG. 30D). (FIGS. 30E-J): At day 73 post T cell dosing, mice (4 from the non-armored CAR-treated group, and 3 from the armored CAR-treated group; notes: 1 mouse from the armored group were euthanized due to excessive weight loss at day 60 post T cell infusion) were re-challenged with AsPC-1 cells (1e6 cells/mouse, on the left flank; as the first challenge was on the right flank)(FIG. 30E); tumor volume on both flank (FIG. 30F), and survival rate (FIG. 30G) were monitored; blood from mice were sampled at the indicated time points to quantify T cell memory phenotype (FIG. 30H), percentage of CAR+ cells (FIG. 30I); T-cells isolated from spleen and bone marrow at the terminated time point were also analyzed for CAR+ T-cell components by flow cytometry (FIG. 30J).

Figures 31A, 31B:
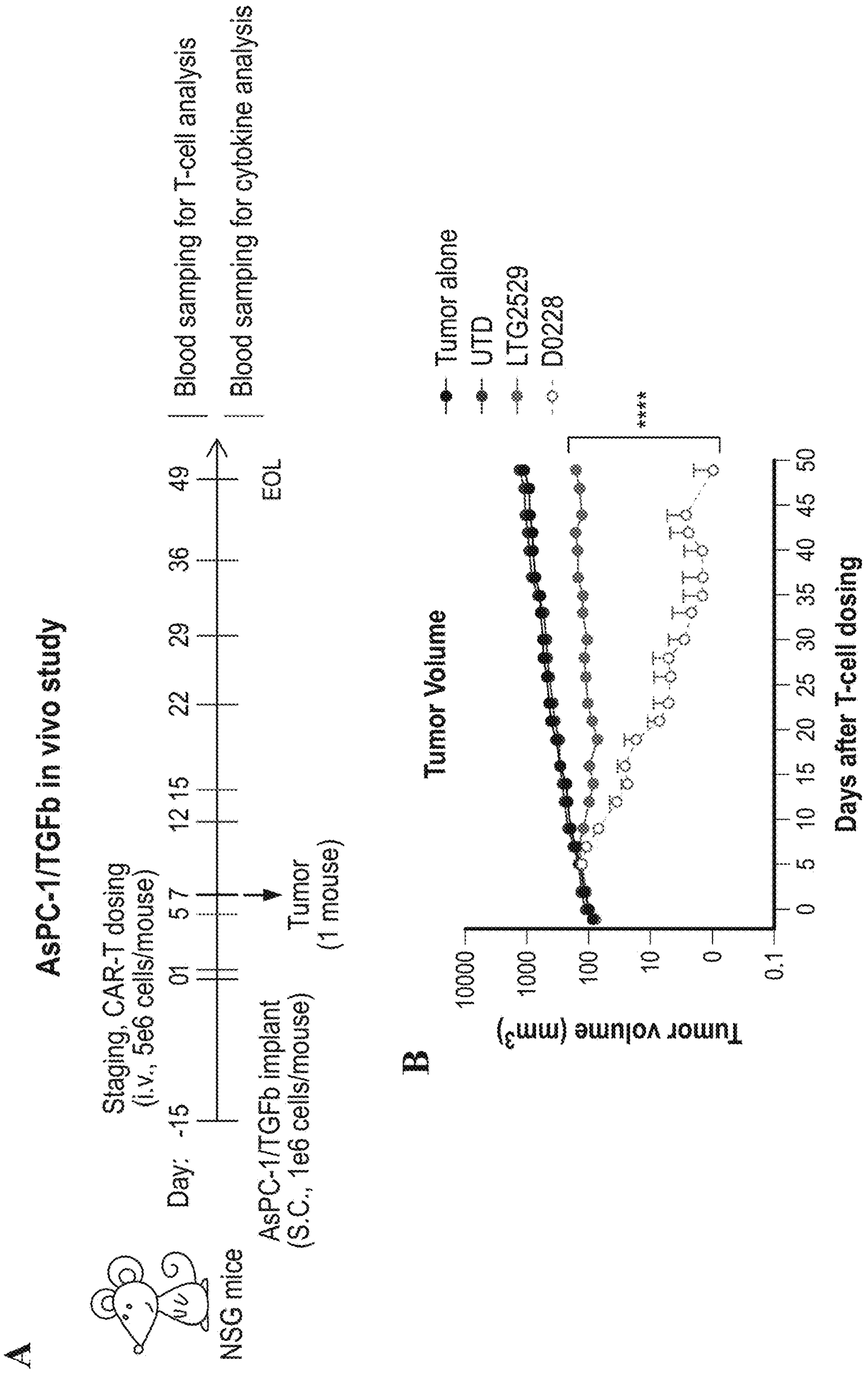
Figures 31C, 31D:
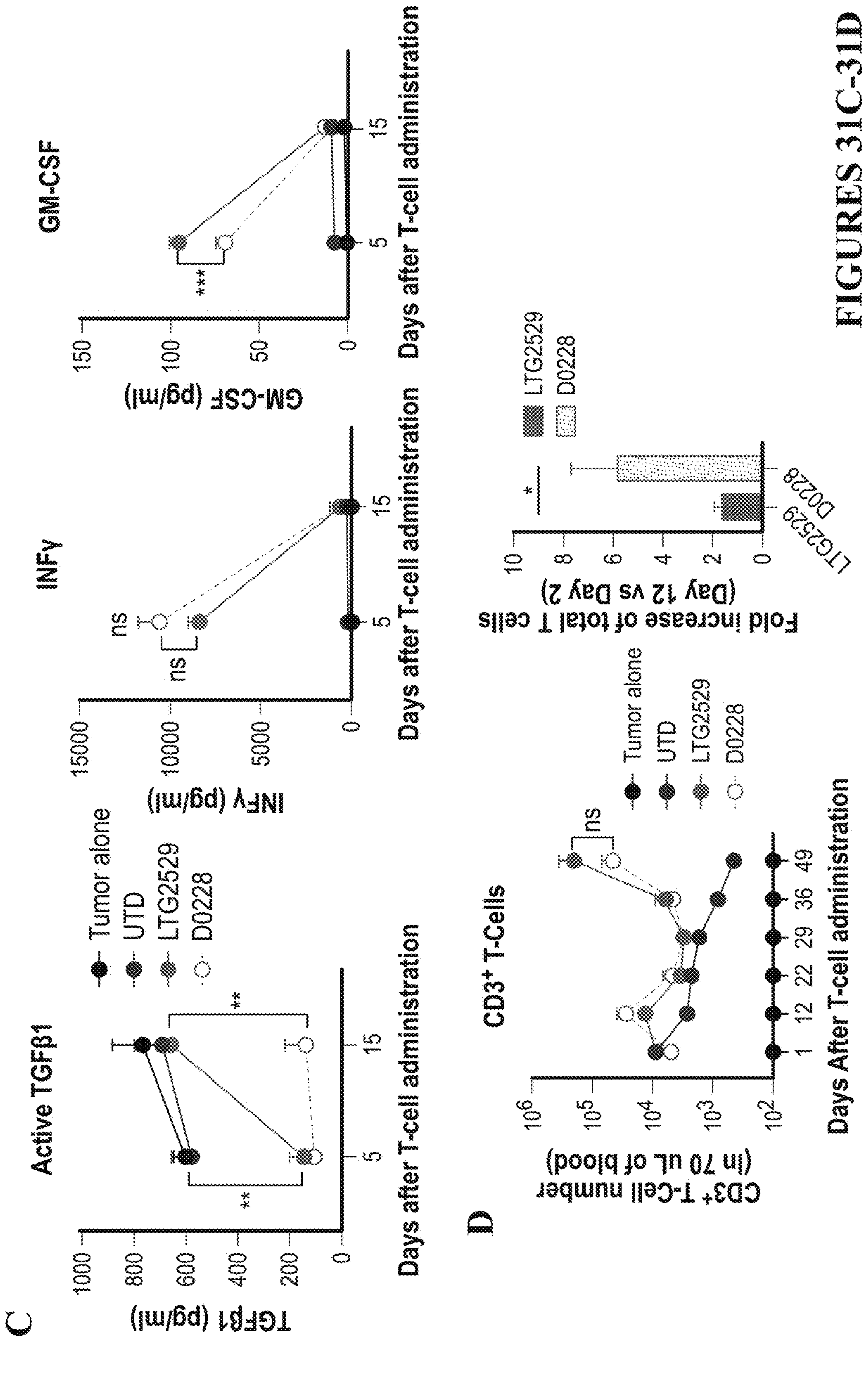
Figures 31E, 31F, 31G:
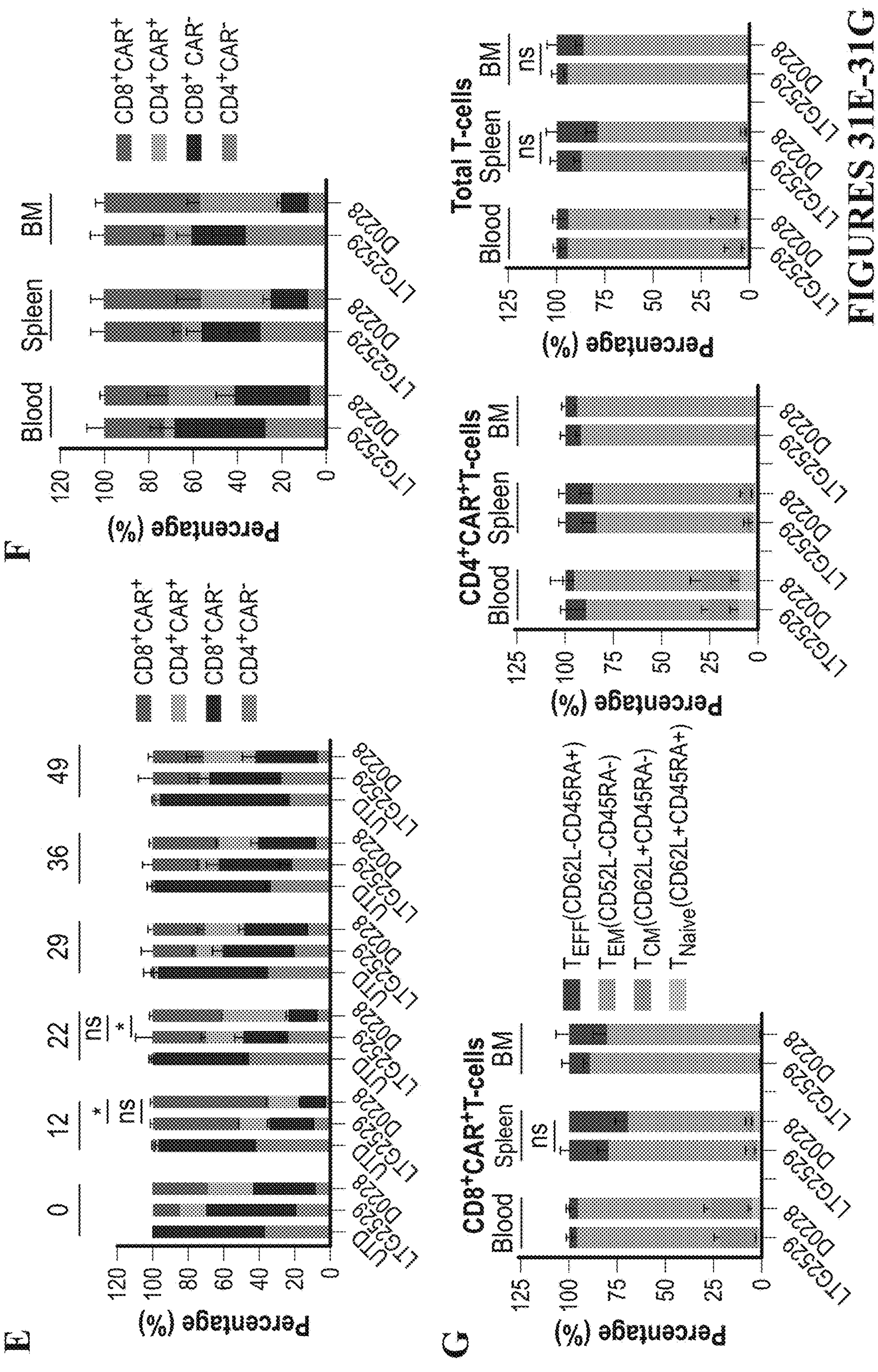

FIGS. 31A-31G depict the attenuation of the inhibitory effect of TGFb by TGFbRIIDN-armored ROR1 CAR T cells in Pancreatic cancer xenograft model employing AsPC-1 overexpressing TGFb. NSG mice (5 mice/group) were implanted subcutaneously with AsPC-1/TGFb cells (1e6 cells/mouse) at day −15, followed by staging and CAR-T infusion (i.v., 5e6 $CAR^{+}$T-cells/mouse) at day 0 (FIG. 31A); tumor volume was monitored (FIG. 31B); blood from mice was sampled at day 5 and day 15 post T cell infusion and was quantified for cytokines (FIG. 31C), including TGFb1 (left), IFNg (center), and GM-CSF (right): T-cells isolated from blood at the indicated time points were quantified for total cell number (FIG. 31D), CAR+components in both CD8 and CD4 subpopulations (FIG. 31E). At the terminated time point (day 49 post T cell infusion), T cells from blood, spleen, and bone marrow were harvested and quantified for CAR+components (FIG. 31F) and memory phenotype (FIG. 31G) in both CD4 and CD8 subpopulations.

DETAILED DESCRIPTION

Definitions

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided.

The term "about" when referring to a measurable value such as an amount, a temporal duration, and the like, is meant to encompass variations of +/−20%, +/−10%, or more preferably +/−5%, or +/−1%, or still more preferably +/−0.1% from the specified value, as such variations are appropriate to perform the disclosed methods.

Unless otherwise noted, the technical terms herein are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: A Comprehensive Desk Reference*, published by VCH Publishers, Inc., 1995; and other similar references.

Novel anti-effector moiety antibodies or antigen binding domains thereof and chimeric antigen receptors (CARs) that contain such effector moiety antigen binding domains are provided herein, as well as host cells (e.g., T cells) expressing the receptors, and nucleic acid molecules encoding the receptors. CAR may consist either of a single molecule expressed on the effector cell surface, or a CAR comprised of an effector cell-expressed signaling module and a soluble targeting module, such as when the soluble targeting module binds to the cell-expressed signaling module, a complete functional CAR is formed. The CARs exhibit a high surface expression on transduced T cells, with a high degree of cytolysis and transduced T cell expansion and persistence in vivo. Methods of using the disclosed CARs, host cells, and nucleic acid molecules are also provided, for example, to treat a cancer in a subject.

In its broadest aspect, novel chimeric antigen receptors (CARs) are provided herein comprising a boosted CAR comprising a CAR construct with a main effector moiety molecule followed by one or more 2A sequences, in frame to one or more additional "booster" elements for improved function, including enhanced tumor penetration, to improve the therapeutic effect of CAR-T cells in solid tumors, hematologic tumors, autoimmune disease, hereditary disease, or other relevant indications.

In yet another broad aspect, novel chimeric antigen receptors (CARs) are provided herein comprising a boosted CAR wherein the functional co-expressed boosted CAR elements are expressed from a single multi-cistronic vector at high transduction efficiency, thereby simplifying the CAR manufacturing and release and reducing cost for market implementation. In one aspect, the boosted CAR compositions comprise one or more of the following characteristics: i) a high surface expression on transduced T cells; ii) multi-targeting to overcome antigen escape; iii) one or more armor elements so as to overcome immunosuppression in TME; iv) one or more cytokine stimulated elements to promote autonomous T cell stimulation with cytokines, resulting in heightened anti-tumor cytotoxicity, expansion, memory formation, cytokine secretion, persistence; v) one or more digestive enzymes to overcome the physical barrier of tumor stroma/extracellular matrix (ECM) and enable CAR T tumor penetration; vi) one or more pro-inflammatory immune activators; and vii) one or more on-switches or off-switches, to control the expression of the CAR; or any combination thereof, wherein the boosted CARs achieve a high degree of cytolysis and transduced T cell in vivo expansion and persistence to promote in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In yet another broad aspect, the novel chimeric antigen receptors (CARs) provided herein may comprise single, tandem, or multi-targeting CAR constructs (including those in a DuoCAR format), or any combination thereof.

In certain aspects, the novel boosted CARs are under the control of one or more constitutive promoters, tissue specific promoters, or inducible promoters, or any combination thereof.

In certain aspects, the novel boosted CARs may comprise one or more pro-inflammatory immune activators.

In certain aspects, the one or more pro-inflammatory immune activators may comprise boosters that turn "cold" immune environment to "hot", such as neutrophil-activating protein (NAP) from bacteria such as *Helicobacter pylori*, bacterial lipopolysaccharide (LPS) components, or Polyinosine-polycytidylic acid (poly(I:C), or soluble inflammatory factors such as FLT3 Ligand, or oncolytic viruses, or TNF family cytokines, including CD40 ligand (CD40L), tumor necrosis factor (TNF) and receptor activator of nuclear factor-κB (RANKL)/TRANCE which can trigger or enhance exogenous bystander responses against solid cancers.

In one aspect, such elements when used as a booster to CAR T cell therapy may reduce or ablate tumor growth, and/or increase survival rates, regardless of target antigen, tumor type and host haplotype. Such boosters may act by supporting dendritic cell maturation and bystander responses, leading to epitope spreading and infiltration of CD8+ cells targeting tumor associated antigens other than CAR T-targeted antigen.

In certain aspects, the one or more switches comprises a tag, a kill switch, an on switch, an off switch, and/or an adapter switch, or any combination thereof.

In certain aspects, the novel boosted CARs switch may be a tag (CD19, CD34, CD22, EGFR), or a kill switch (iCAS9), or an [ON] switch, or an [OFF] switch, or adapter switch, or any combination thereof.

In certain embodiments, the single, tandem, multi-targeting, DuoCARs (either with or without one or more booster elements) novel chimeric antigen receptors (CARs) are provided are used to transduce effector cells for the treatment of solid and hematologic tumors and other diseases through targeted antigens (for example, and not by way of limitation, CD19, CD20, CD22, ROR1, mesothelin, CD33/IL3Ra, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, GD2, GD3, GM2, Ley, polysialic acid, fucosyl GM1, GM3, Tn, STn, sLe(animal), GloboH, CD5, CD7, CD19, CD20, CD22, CD25, CD37, CD30, CD33, CD38, CD123, CD45, CAMPATH-1, BCMA, CS-1, PD-L1, CD276/B7-H3, B7-H4, B7-DC, HLA-DR carcinoembryonic antigen (CEA), TAG-72, EpCAM, folate-binding protein, folate receptor alpha (FOLR1), folate receptor beta (FOLR2), A33, G250, pro state-specific membrane antigen (PSMA), ferritin, CA-125, CA19-9, CD44v6, epidermal growth factor, p185, IL-2 receptor, interleukin 1 receptor accessory protein (IL1RAP), EGFRvIII (de2-7), fibroblast activation protein, tenascin, a metalloproteinase, endosialin, vascular endothelial growth factor, αvβ3, WT1, LMP2, HPV E6, HPV E7, Her-2/neu, p53 nonmutant, NY-ESO-1, MelanA/MART 1, Ras mutant, gp100, FGFR1, FGFR2, FGFR3, FGFR4, GPC1, GPC2, GPC3, p53 mutant, PR1, bcr-abl, tyrosinase, survivin, PSA, hTERT, a Sarcoma translocation breakpoint fusion protein, EphA2, PAP, ML-IAP, AFP, ERG, NA17, PAX3, ALK, androgen receptor, cyclin B 1, MYCN, RhoC, TRP-2, mesothelin, PSCA, MAGE A1, MAGE A3, CYP1B 1, PLAV1, BORIS, ETV6-AML, NY-BR-1, RGS5, SART3, Carbonic anhydrase IX, PAX5, OY-TES 1, Sperm protein 17, LCK, HMWMAA, AKAP-4, SSX2, XAGE 1, B7H3, Legumain, Tie 3, PAGE4, VEGFR2, MAD-CT-1, PDGFR-B, MAD-CT-2, TRAIL 1, MUC1, MUC16/CA125, MAGE A4, MAGE C2, GAGE, EGFR, EGFR1, EGFR2/Her2, CMET, HER3, CA6, NAPI2B, TROP2, TEM1, TEM7, TEM8, FAP, LAP, CLDN3, CLDN6, CLDN8, CLDN16, CLDN18.2, RON, LY6E, DLL3, PTK7, UPK1B, STRA6, TMPRSS3, TMRRSS4, TMEM238, Clorf186, LIV1, ROR1, ROR2, Fos-related antigen 1, VEGFR1, endoglin, CD90, CD326, CD70, SSEA4, CD318, CLA, TSPAN8, GPRC5D, EpCAM, Thy1, IL13Ra2, BDCA1, BDCA2, BDCA3, GD2, PSMA, FAP, CLL1, SLAMF7/CS1, CD147, DPPA5, GRP78, CD66c, VISTA, LRRC5, LRRC15, or any combinations thereof or a fragment thereof is provided, wherein the antibody or a fragment thereof comprises a fragment selected from the group consisting of an Fab fragment, an F(ab')2 fragment, an Fv fragment, a nanobody, a VHH, a ligand peptide, and a single chain Fv (ScFv), or a fragment of any of the preceding, or a molecule that is at least 80%, 85%, 90%, 95%, 96%, 97%, 98% or 99% homologous to any of the preceding, or any combination thereof.

In one embodiment, an isolated polynucleotide encoding a fully human anti-ROR1 and/or anti-MSLN and/or anti FolR1, and/or anti HER2/ERBB2, and/or anti GPC3, and/or anti-FGFR4, and/or anti-GD2, and/or anti CD276, and/or anti GPC2, and/or anti FGFR2, and/or anti PSMA, and/or anti MUC1, and/or anti MUC16, and/or anti IL13R alpha antibody, or any combinations thereof or a fragment thereof is provided, wherein the antibody or a fragment thereof comprises a fragment selected from the group consisting of an Fab fragment, an F(ab')2 fragment, an Fv fragment, a nanobody, a VHH, a ligand peptide, and a single chain Fv (ScFv).

In one embodiment, an isolated polynucleotide encoding an anti-GD2, anti-GD3, anti-GM2, anti-Ley, anti-polysialic acid, anti-fucosyl GM1, anti-GM3, anti-Tn, anti-STn, anti-sLe(animal), anti-GloboH, anti-CD5, anti-CD7, anti-CD19, anti-CD20, anti-CD22, anti-CD25, anti-CD37, anti-CD30, anti-CD33, anti-CD38, anti-CD123, anti-CD45, anti-CAMPATH-1, anti-BCMA, anti-CS-1, anti-PD-L1, anti-CD276/B7-H3, anti-B7-H4, anti-B7-DC, anti-HLA-DR carcinoembryonic antigen (CEA), anti-TAG-72, anti-EpCAM, anti-folate-binding protein, anti-folate receptor alpha (FOLR1), anti-folate receptor beta (FOLR2), anti-A33, anti-G250, anti-prostate-specific membrane antigen (PSMA), anti-ferritin, anti-CA-125, anti-CA19-9, anti-CD44v6, anti-epidermal growth factor, anti-p185, anti-IL-2 receptor, anti-interleukin 1 receptor accessory protein (IL1RAP), anti-EGFRvIII (de2-7), anti-fibroblast activation protein, anti-tenascin, anti-a metalloproteinase, anti-endosialin, anti-vascular endothelial growth factor, anti-$\alpha v\beta 3$, anti-WT1, anti-LMP2, anti-HPV E6, anti-HPV E7, anti-Her-2/neu, anti-p53 nonmutant, anti-NY-ESO-1, anti-MelanA/MART 1, anti-Ras mutant, anti-gp100, anti-FGFR1, anti-FGFR2, anti-FGFR3, anti-FGFR4, anti-GPC1, anti-GPC2, anti-GPC3, anti-p53 mutant, anti-PR1, anti-bcr-abl, anti-tyrosinase, anti-survivin, anti-PSA, anti-hTERT, anti-Sarcoma translocation breakpoint fusion protein, anti-EphA2, anti-PAP, anti-ML-IAP, anti-AFP, anti-ERG, anti-NA17, anti-PAX3, anti-ALK, anti-androgen receptor, anti-cyclin B 1, anti-MYCN, anti-RhoC, anti-TRP-2, anti-mesothelin, anti-PSCA, anti-MAGE A1, anti-MAGE A3, anti-CYP1B 1, anti-PLAV1, anti-BORIS, anti-ETV6-AML, anti-NY-BR-1, anti-RGS5, anti-SART3, anti-Carbonic anhydrase IX, anti-PAX5, anti-OY-TES 1, anti-Sperm protein 17, anti-LCK, anti-HMWMAA, anti-AKAP-4, anti-SSX2, anti-XAGE 1, anti-B7H3, anti-Legumain, anti-Tie 3, anti-PAGE4, anti-VEGFR2, anti-MAD-CT-1, anti-PDGFR-B, anti-MAD-CT-2, anti-TRAIL 1, anti-MUC1, anti-MUC16/CA125, anti-MAGE A4, anti-MAGE C2, anti-GAGE, anti-EGFR, anti-EGFR1, anti-EGFR2/Her2, anti-CMET, anti-HER3, anti-CA6, anti-NAPI2B, anti-TROP2, anti-TEM1, anti-TEM7, anti-TEM8, anti-FAP, anti-LAP, anti-CLDN6, anti-CLDN8, anti-CLDN16, anti-CLDN18.2, anti-RON, anti-LY6E, anti-DLL3, anti-PTK7, anti-UPK1B, anti-STRA6, anti-TMPRSS3, anti-TMRRSS4, anti-TMEM238, anti-Clorf186, anti-LIV1, anti-ROR1, anti-ROR2, anti-Fos-related antigen 1, anti-VEGFR1, anti-endoglin, anti-CD90, anti-CD326, anti-CD70, anti-SSEA4, anti-CD318, anti-CLA, anti-TSPAN8, anti-GPRC5D, anti-EpCAM, anti-Thy1, anti-IL13Ra2, anti-BDCA1, anti-BDCA2, anti-BDCA3, anti-GD2, anti-PSMA, anti-FAP, anti-CLL1, anti-SLAMF7/CS1, anti-CD147, anti-DPPA5, anti-GRP78, anti-CD66c, VISTA, LRRC5, LRRC15 antibody, or any combinations thereof or a fragment thereof is provided, wherein the antibody or a fragment thereof comprises a fragment selected from the group consisting of an Fab fragment, an $F(ab')_2$ fragment, an Fv fragment, a nanobody, a VHH, a ligand peptide, and a single chain Fv (ScFv), or a fragment of any of the preceding, or a molecule that is at least 80%, 85%, 90%/o, 95%, 96%, 97%, 98% or 99% homologous to any of the preceding, or any combination thereof.

In one embodiment, an isolated nucleic acid molecule encoding the single, tandem, DuoCAR, or multiple-targeting CAR (either with or without one or more boosting elements) is provided wherein the encoded extracellular ROR1 and/or MSLN antigen binding domain comprises at least one single chain variable fragment of an antibody that binds to ROR1 and/or MSLN.

In another embodiment, an isolated nucleic acid molecule encoding the single, tandem, DuoCAR, or multiple-targeting CAR (either with or without one or more boosting elements) is provided wherein the encoded extracellular ROR1 and/or MSLN antigen binding domain comprises at least one heavy chain variable region of an antibody that binds to ROR1 and/or MSLN.

In another embodiment, an isolated nucleic acid molecule encoding the single, tandem, DuoCAR, or multiple-targeting CAR (either with or without one or more boosting elements) is provided wherein the encoded extracellular ROR1 and/or MSLN antigen binding domain comprises an ScFv.

In yet another broad aspect, one or more of the above-identified novel boosted chimeric antigen receptors (CARs) provided supra with respect to SEQ ID NOs: 151 to 256 may comprise either a single, tandem, or multi-targeting CAR construct (including those in a DuoCAR format), or any combination thereof.

For each of the various aspects and embodiments of the single, tandem, multi-targeting, DuoCARs, (either with or without one or more booster elements) CAR constructs specifically contemplated herein, the nucleotide sequences encoding the functional CAR (either with or without one or more booster elements) comprise the nucleotide sequence of SEQ ID NO: 151, 153, 155, 157, 159, 161, 163, 165, 167, 169, 171, 173, 175, 177, 179, 181, 183, 185, 187, 189, 191, 193, 195, 197, 226, 228, 230, 232, 234, 236, 238, 240, 242, 244, 245, 247, 249, 251, 253, or 255, or any combination thereof.

For each of the various aspects and embodiments of the single, tandem, multi-targeting, DuoCARs, (either with or without one or more booster elements) CAR constructs specifically contemplated herein, each vector encodes a functional CAR (either with or without one or more booster elements) comprising the amino acid sequence of SEQ ID NO: 152, 154, 156, 158, 160, 162, 164, 166, 168, 170, 172, 174, 176, 178, 180, 182, 184, 186, 188, 190, 192, 194, 196, 198, 225, 227, 229, 231, 233, 235, 237, 239, 241, 243, 246, 248, 250, 252, 254, or 256, or any combination thereof.

For each of the various aspects and embodiments, an isolated polynucleotide encoding a fully human anti-ROR1 and/or anti-MSLN and/or anti FolR1, and/or anti HER2/

ERBB2, and/or anti GPC3, and/or anti-FGFR4, and/or anti GD2 antibody or a fragment thereof is provided comprising a nucleic acid sequence selected from the group consisting of SEQ ID NOs: 143, 145, 147, 149.

For each of the various aspects and embodiments, novel single, tandem, DuoCARs, or multiple-targeting CARs (either with or without one or more booster elements) are provided herein comprising a single, tandem, DuoCAR, or multiple-targeting CAR molecule (either with or without one or more booster elements) comprising at least one extracellular antigen binding domain comprising an anti-ROR1 and/or anti-MSLN antigen binding domain comprising the nucleic acid sequence selected from the group consisting of SEQ ID NOs: 143, 145, 147, and 149; at least one linker domain; at least one transmembrane domain; and at least one intracellular signaling domain.

For each of the various aspects and embodiments, novel single, tandem, DuoCARs, or multiple-targeting CARs (either with or without one or more booster elements) are provided herein comprising a single, tandem, DuoCAR, or multiple-targeting CAR molecule (either with or without one or more booster elements) comprising at least one extracellular antigen binding domain comprising an anti-ROR1 and/or anti-MSLN antigen binding domain comprising the amino acid sequence selected from the group consisting of SEQ ID NOs: 144, 146, 148, and 150; at least one linker domain; at least one transmembrane domain; and at least one intracellular signaling domain.

In one embodiment, an isolated polynucleotide encoding a fully human anti-ROR1 and/or anti-MSLN anti-ROR1 and/or anti-MSLN and/or anti FolR1, and/or anti HER2/ERBB2, and/or anti GPC3, and/or anti-FGFR4, and/or anti GD2 antibody or a fragment thereof is provided, wherein the antibody or a fragment thereof comprises a nucleic acid sequence selected from the group consisting of SEQ ID NOs: 143, 145, 147, and 149.

In one embodiment, an isolated polynucleotide encoding a fully human anti-ROR1 and/or anti-MSLN anti-ROR1 and/or anti-MSLN and/or anti FolR1, and/or anti HER2/ERBB2, and/or anti GPC3, and/or anti-FGFR4, and/or anti GD2 antibody or a fragment thereof is provided, wherein the antibody or a fragment thereof comprises an amino acid sequence selected from the group consisting of SEQ ID NOs: 144, 146, 148, and 150.

In one aspect, an isolated nucleic acid molecule encoding a single, tandem, DuoCAR, or multiple-targeting chimeric antigen receptor (CAR) (either with or without one or more boosting elements) is provided comprising, from N-terminus to C-terminus, at least one ROR1 and/or MSLN antigen binding domain encoded by a nucleotide sequence comprising a nucleic acid sequence selected from the group consisting of SEQ ID NOs: 143, 145, 147, and 149, at least one transmembrane domain, and at least one intracellular signaling domain.

In one aspect, an isolated nucleic acid molecule encoding a single, tandem, DuoCAR, or multiple-targeting chimeric antigen receptor (CAR) (either with or without one or more boosting elements) is provided comprising, from N-terminus to C-terminus, at least one ROR1 and/or MSLN antigen binding domain encoded by a nucleotide sequence comprising an amino acid sequence selected from the group consisting of SEQ ID NOs: 144, 146, 148, and 150, at least one transmembrane domain, and at least one intracellular signaling domain.

In one embodiment, the targeting domain of the single, tandem, DuoCAR, or multiple-targeting CAR (either with or without one or more boosting elements) is expressed separately in the form of monoclonal antibody, ScFv Fab, Fab'2 and is containing an antigen-targeting domain comprising a nucleic acid sequence selected from the group consisting of SEQ ID NOs: 143, 145, 147, and 149, coupled to an additional binding tag or epitope, whereas the effector-cell expressed component of the single, tandem, DuoCAR, or multiple-targeting CAR (either with or without one or more boosting elements) contains a binding domain specifically directed to bind the tag or epitope expressed on the soluble single, tandem, DuoCAR, or multiple-targeting CAR (either with or without one or more boosting elements) module, such as specific binding on the soluble component of the single, tandem, DuoCAR, or multiple-targeting CAR (either with or without one or more boosting elements) to the cell bound component of the single, tandem, DuoCAR, or multiple-targeting CAR (either with or without one or more boosting elements) forms the full functional single, tandem, DuoCAR, or multiple-targeting CAR (either with or without one or more boosting elements) structure.

In another embodiment, the targeting domain of the single, tandem, DuoCAR, or multiple-targeting CAR (either with or without one or more boosting elements) is expressed separately in the form of a monoclonal antibody, ScFv Fab, Fab'2 and contains an antigen-targeting domain comprising a nucleic acid sequence selected from the group consisting of SEQ ID NOs: 143, 145, 147, and 149, and an additional ScFv, whereas the effector-cell expressed component of the single, tandem, DuoCAR, or multiple-targeting CAR (either with or without one or more boosting elements) contains a tag or epitope specifically reactive with the additional ScFv expressed on the soluble single, tandem, DuoCAR, or multiple-targeting CAR (either with or without one or more boosting elements) module, such as specific binding on the soluble component of the single, tandem, DuoCAR, or multiple-targeting CAR (either with or without one or more boosting elements) to the cell bound component of the single, tandem, DuoCAR, or multiple-targeting CAR (either with or without one or more boosting elements) forms the full functional single, tandem, DuoCAR, or multiple-targeting CAR (either with or without one or more boosting elements) structure.

In yet another embodiment, an isolated nucleic acid molecule encoding the single, tandem, DuoCAR, or multiple-targeting CAR (either with or without one or more boosting elements) is provided wherein the encoded single, tandem, DuoCAR, or multiple-targeting CAR (either with or without one or more boosting elements) extracellular ROR1 and/or MSLN antigen binding domain further comprises at least one lipocalin-based antigen binding antigen (anticalins) that binds to ROR1 and/or MSLN.

In one embodiment, an isolated nucleic acid molecule is provided wherein the encoded extracellular ROR1 and/or MSLN antigen binding domain is connected to the transmembrane domain by a linker domain.

In another embodiment, an isolated nucleic acid molecule encoding the single, tandem, DuoCAR, or multiple-targeting CAR (either with or without one or more boosting elements) is provided wherein the encoded ROR1 and/or MSLN extracellular antigen binding domain is preceded by a sequence encoding a leader or signal peptide.

In yet another embodiment, an isolated nucleic acid molecule encoding the single, tandem, DuoCAR, or multiple-targeting CAR (either with or without one or more boosting elements) is provided comprising at least one ROR1 and/or MSLN antigen binding domain encoded by a nucleotide sequence comprising a nucleic acid sequence selected from the group consisting of SEQ ID NOs: 143, 145, 147, and 149, and wherein the single, tandem, DuoCAR, or multiple-targeting CAR (either with or without one or more boosting elements) additionally encodes an extracellular antigen binding domain targets an antigen that includes, but is not limited to, CD19, CD20, CD22, ROR1, mesothelin, CD33/IL3Ra, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, GD2, GD3, GM2, Ley, polysialic acid, fucosyl GM1, GM3, Tn, STn, sLe(animal), GloboH, CD5, CD7, CD19, CD20, CD22, CD25, CD37, CD30, CD33, CD38, CD123, CD45, CAMPATH-1, BCMA, CS-1, PD-L1, CD276/B7-H3, B7-H4, B7-DC, HLA-DR carcinoembryonic antigen (CEA), TAG-72, EpCAM, folate-binding protein, folate receptor alpha (FOLR1), folate receptor beta (FOLR2), A33, G250, pro state-specific membrane antigen (PSMA), ferritin, CA-125, CA19-9, CD44v6, epidermal growth factor, p185, IL-2 receptor, interleukin 1 receptor accessory protein (IL1RAP), EGFRvIII (de2-7), fibroblast activation protein, tenascin, a metalloproteinase, endosialin, vascular endothelial growth factor, αvβ3, WT1, LMP2, HPV E6, HPV E7, Her-2/neu, p53 nonmutant, NY-ESO-1, MelanA/MART 1, Ras mutant, gp100, FGFR1, FGFR2, FGFR3, FGFR4, GPC1, GPC2, GPC3, p53 mutant, PR1, bcr-abl, tyrosinase, survivin, PSA, hTERT, a Sarcoma translocation breakpoint fusion protein, EphA2, PAP, ML-IAP, AFP, ERG, NA17, PAX3, ALK, androgen receptor, cyclin B 1, MYCN, RhoC, TRP-2, mesothelin, PSCA, MAGE A1, MAGE A3, CYP1B 1, PLAV1, BORIS, ETV6-AML, NY-BR-1, RGS5, SART3, Carbonic anhydrase IX, PAX5, OY-TES 1, Sperm protein 17, LCK, HMWMAA, AKAP-4, SSX2, XAGE 1, B7H3, Legumain, Tie 3, PAGE4, VEGFR2, MAD-CT-1, PDGFR-B, MAD-CT-2, TRAIL 1, MUC1, MUC16/CA125, MAGE A4, MAGE C2, GAGE, EGFR, EGFR1, EGFR2/Her2, CMET, HER3, CA6, NAPI2B, TROP2, TEM1, TEM7, TEM8, FAP, LAP, CLDN3, CLDN6, CLDN8, CLDN16, CLDN18.2, RON, LY6E, DLL3, PTK7, UPK1B, STRA6, TMPRSS3, TMRRSS4, TMEM238, Clorf186, LIV1, ROR1, ROR2, Fos-related antigen 1, VEGFR1, endoglin, CD90, CD326, CD70, SSEA4, CD318, CLA, TSPAN8, GPRC5D, EpCAM, Thy1, IL13Ra2, BDCA1, BDCA2, BDCA3, GD2, PSMA, FAP, CLL1, SLAMF7/CS1, CD147, DPPA5, GRP78, CD66c, VISTA, LRRC5, LRRC15, or any combinations thereof or a fragment thereof is provided, wherein the antibody or a fragment thereof comprises a fragment selected from the group consisting of an Fab fragment, an F(ab')2 fragment, an Fv fragment, a nanobody, a VHH, a ligand peptide, and a single chain Fv (ScFv), or a fragment of any of the preceding, or a molecule that is at least 80%, 85%, 90%, 95%, 96%, 97%, 98% or 99% homologous to any of the preceding, or any combination thereof.

In certain embodiments, an isolated nucleic acid molecule encoding the single, tandem, DuoCAR, or multiple-targeting CAR (either with or without one or more boosting elements) is provided wherein the additionally encoded extracellular antigen binding domain comprises an anti-CD19 ScFv antigen binding domain, an anti-CD20 ScFv antigen binding domain, an anti-CD22 ScFv antigen binding domain, anti-BCMA ScFv antigen binding domain, anti-CD5 ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PSMA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the single, tandem, DuoCAR, or multiple-targeting CARs (either with or without one or more boosting elements) provided herein further comprise a linker or spacer domain.

In one embodiment, an isolated nucleic acid molecule encoding the single, tandem, DuoCAR, or multiple-targeting CAR (either with or without one or more boosting elements) is provided wherein the extracellular ROR1 and/or MSLN antigen binding domain, the intracellular signaling domain, or both are connected to the transmembrane domain by a linker or spacer domain.

In one embodiment, an isolated nucleic acid molecule encoding the single, tandem, DuoCAR, or multiple-targeting CAR (either with or without one or more boosting elements) is provided wherein the encoded linker domain is derived from the extracellular domain of IgG1, IgG2, IgG3 or IgG4, CD8, TNFRSF19, or CD28, and is linked to a transmembrane domain.

In another embodiment, an isolated nucleic acid molecule encoding the single, tandem, DuoCAR, or multiple-targeting CAR (either with or without one or more boosting elements) is provided wherein the encoded single, tandem, DuoCAR, or multiple-targeting CAR (either with or without one or more boosting elements) further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, CD271, TNFRSF19, Fc epsilon R, or a combination thereof.

In yet another embodiment, an isolated nucleic acid molecule encoding the single, tandem, DuoCAR, or multiple-targeting CAR (either with or without one or more boosting elements) is provided wherein the encoded intracellular signaling domain further comprises a CD3 zeta intracellular domain.

In one embodiment, an isolated nucleic acid molecule encoding the single, tandem, DuoCAR, or multiple-targeting CAR (either with or without one or more boosting elements) is provided wherein the encoded intracellular signaling domain is arranged on a C-terminal side relative to the CD3 zeta intracellular domain.

In another embodiment, an isolated nucleic acid molecule encoding the single, tandem, DuoCAR, or multiple-targeting CAR (either with or without one or more boosting elements) is provided wherein the encoded at least one intracellular signaling domain comprises a costimulatory domain, a primary signaling domain, or a combination thereof.

In another embodiment, an immunotherapy composition is provided wherein the at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), PD-1, GITR, CTLA-4, or any combination thereof.

In one embodiment, an isolated nucleic acid molecule encoding the single, tandem, DuoCAR, or multiple-targeting CAR (either with or without one or more boosting elements) is provided that further contains a leader sequence or signal peptide wherein the leader or signal peptide nucleotide sequence comprises the nucleotide sequence of SEQ ID NO: 13, SEQ ID NO: 39, SEQ ID NO: 41, or SEQ ID NO: 43.

In yet another embodiment, an isolated nucleic acid molecule encoding the single, tandem, DuoCAR, or multiple-targeting CAR (either with or without one or more boosting elements) is provided wherein the encoded leader sequence comprises the amino acid sequence of SEQ ID NO: 14, SEQ ID NO: 40, SEQ ID NO: 42, or SEQ ID NO: 44.

In one aspect, a single, tandem, DuoCAR, or multiple-targeting chimeric antigen receptor (CAR)(either with or without one or more boosting elements) is provided herein comprising, from N-terminus to C-terminus, at least one ROR1 and/or MSLN antigen binding domain, at least one transmembrane domain, and at least one intracellular signaling domain.

In one embodiment, a single, tandem, DuoCAR, or multiple-targeting CAR (either with or without one or more boosting elements) is provided wherein the extracellular ROR1 and/or MSLN antigen binding domain comprises at least one single chain variable fragment of an antibody that binds to the antigen, or at least one heavy chain variable region of an antibody that binds to the antigen, or a combination thereof.

In another embodiment, a single, tandem, DuoCAR, or multiple-targeting CAR (either with or without one or more boosting elements) is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In some embodiments, the single, tandem, DuoCAR, or multiple-targeting CAR (either with or without one or more boosting elements) is provided wherein single, tandem, DuoCAR, or multiple-targeting CAR (either with or without one or more boosting elements) additionally encodes an extracellular antigen binding domain comprising anti-CD19, anti-CD20, anti-CD22, anti-CD33, anti-CD38, anti-CD123 (IL3RA), anti-CD138, anti-GPC2, anti-GPC3, anti-FGFR4, anti-c-Met, anti-PSMA, anti-Glycolipid F77, anti-EGFRvIII, anti-GD-2, anti-NY-ESO-1 TCR, anti-MAGE A3 TCR, anti-GD2, anti-GD3, anti-GM2, anti-Ley, anti-polysialic acid, anti-fucosyl GM1, anti-GM3, anti-Tn, anti-STn, anti-sLe(animal), anti-GloboH, anti-CD5, anti-CD7, anti-CD19, anti-CD20, anti-CD22, anti-CD25, anti-CD37, anti-CD30, anti-CD33, anti-CD38, anti-CD123, anti-CD45, anti-CAMPATH-1, anti-BCMA, anti-CS-1, anti-PD-L1, anti-CD276/B7-H3, anti-B7-H4, anti-B7-DC, anti-HLA-DR carcinoembryonic antigen (CEA), anti-TAG-72, anti-Ep-CAM, anti-folate-binding protein, anti-folate receptor alpha (FOLR1), anti-folate receptor beta (FOLR2), anti-A33, anti-G250, anti-prostate-specific membrane antigen (PSMA), anti-ferritin, anti-CA-125, anti-CA19-9, anti-CD44v6, anti-epidermal growth factor, anti-p185, anti-IL-2 receptor, anti-interleukin 1 receptor accessory protein (IL1RAP), anti-EGFRvIII (de2-7), anti-fibroblast activation protein, anti-tenascin, anti-a metalloproteinase, anti-endosialin, anti-vascular endothelial growth factor, anti-$\alpha v\beta 3$, anti-WT1, anti-LMP2, anti-HPV E6, anti-HPV E7, anti-Her-2/neu, anti-p53 nonmutant, anti-NY-ESO-1, anti-MelanA/MART 1, anti-Ras mutant, anti-gp100, anti-GPRC5D, anti-FGFR1, anti-FGFR2, anti-FGFR3, anti-FGFR4, anti-GPC1, anti-GPC2, anti-GPC3, anti-p53 mutant, anti-PR1, anti-bcr-abl, anti-tyrosinase, anti-survivin, anti-PSA, anti-hTERT, anti-a Sarcoma translocation breakpoint fusion protein, anti-EphA2, anti-PAP, anti-ML-IAP, anti-AFP, anti-ERG, anti-NA17, anti-PAX3, anti-ALK, anti-androgen receptor, anti-cyclin B 1, anti-MYCN, anti-RhoC, anti-TRP-2, anti-mesothelin, anti-PSCA, anti-MAGE A1, anti-MAGE A3, anti-CYP1B 1, anti-PLAV1, anti-BORIS, anti-ETV6-AML, anti-NY-BR-1, anti-RGS5, anti-SART3, anti-Carbonic anhydrase IX, anti-PAX5, anti-OY-TES 1, anti-Sperm protein 17, anti-LCK, anti-HMWMAA, anti-AKAP-4, anti-SSX2, anti-XAGE 1, anti-B7H3, anti-Legumain, anti-Tie 3, anti-PAGE4, anti-VEGFR2, anti-MAD-CT-1, anti-PDGFR-B, anti-MAD-CT-2, anti-TRAIL 1, anti-MUC1, anti-MUC16/CA125, anti-MAGE A4, anti-MAGE anti-C2, anti-GAGE, anti-EGFR, anti-EGFR1, anti-EGFR2/Her2, anti-CMET, anti-HER3, anti-CA6, anti-NAPI2B, anti-TROP2, anti-TEM1, anti-TEM7, anti-TEM8, anti-FAP, anti-LAP, anti-CLDN6, anti-CLDN8, anti-CLDN16, anti-CLDN18.2, anti-RON, anti-LY6E, anti-DLL3, anti-PTK7, anti-UPK1B, anti-STRA6, anti-TMPRSS3, anti-TMRRSS4, anti-TMEM238, anti-Clorfl86, anti-LIV1, anti-ROR1, anti-ROR2, anti-Fos-related antigen 1, anti-VEGFR1, anti-endoglin, anti-CD90, anti-CD326, anti-CD70, anti-SSEA4, anti-CD318, anti-CLA, anti-TSPAN8, GPRC5D, EpCAM, Thy1, IL13Ra2, BDCA1, BDCA2, BDCA3, GD2, PSMA, FAP, CLL1, SLAMF7/CS1, anti-CD147, anti-DPPA5, anti-GRP78, anti-CD66c, anti-VISTA, anti-LRRC5, anti-LRRC15 antibody, or any combinations thereof or a fragment thereof is provided, wherein the antibody or a fragment thereof comprises a fragment selected from the group consisting of an Fab fragment, an F(ab')2 fragment, an Fv fragment, a nanobody, a VHH, a ligand peptide, and a single chain Fv (ScFv), or a fragment of any of the preceding, or a molecule that is at least 80% 85%, 90%, 95%, 96%, 97%, 98% or 99% homologous to any of the preceding, or any combination thereof or an amino acid sequence with 85%, 90%, 95%, 96%, 97%, 98% or 99% identity thereof, or any combination thereof.

In one embodiment, the single, tandem, DuoCAR, or multiple-targeting CAR (either with or without one or more boosting elements) is provided wherein the extracellular antigen binding domain additionally comprises an anti-CD19 ScFv antigen binding domain, an anti-CD20 ScFv antigen binding domain, an anti-CD22 ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one embodiment, the single, tandem, DuoCAR, or multiple-targeting CAR (either with or without one or more boosting elements) is provided wherein the extracellular antigen binding domain alternatively comprises an anti-CD19 ScFv antigen binding domain, an anti-CD20 ScFv antigen binding domain, an anti-CD22 ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, the single, tandem, DuoCAR, or multiple-targeting CAR (either with or without one or more boosting elements) is provided wherein the extracellular antigen binding domain additionally comprises an immunoglobulin variable heavy chain only (VH) anti-CD19 antigen binding domain, an anti-CD20 VH antigen binding domain, an anti-CD22 VH antigen binding domain, an anti-CD33 VH antigen binding domain, an anti-CD38 VH antigen binding domain, an anti-CD123 (IL3RA) VH antigen binding domain, an anti-CD138 VH antigen binding domain, an anti-GPC2 VH antigen binding domain, an anti-GPC3 VH antigen binding domain, an anti-FGFR4 VH antigen binding domain, an anti-c-Met VH antigen binding domain, an anti-PMSA VH antigen binding domain, an anti-glycolipid F77 VH antigen binding domain, an anti-EGFRvIII VH antigen binding domain, an anti-GD-2 VH antigen binding domain, an anti-NY-ESO-1 TCR VH antigen binding domain, an anti-MAGE A3 TCR VH antigen binding domain, or an amino acid sequence with 85%, 90%, 95%, 96%, 97%, 98% or 99% identity thereof, or any combination thereof.

In another embodiment, the single, tandem, DuoCAR, or multiple-targeting CAR (either with or without one or more boosting elements) is provided wherein the extracellular antigen binding domain alternatively comprises an immunoglobulin variable heavy chain only (VH) anti-CD19 antigen binding domain, an anti-CD20 VH antigen binding domain, an anti-CD22 VH antigen binding domain, an anti-CD33 VH antigen binding domain, an anti-CD38 VH antigen binding domain, an anti-CD123 (IL3RA) VH antigen binding domain, an anti-CD138 VH antigen binding domain, an anti-GPC2 VH antigen binding domain, an anti-GPC3 VH antigen binding domain, an anti-FGFR4 VH antigen binding domain, an anti-c-Met VH antigen binding domain, an anti-PMSA VH antigen binding domain, an anti-glycolipid F77 VH antigen binding domain, an anti-EGFRvIII VH antigen binding domain, an anti-GD-2 VH antigen binding domain, an anti-NY-ESO-1 TCR VH antigen binding domain, an anti-MAGE A3 TCR VH antigen binding domain, or an amino acid sequence with 85%, 90%, 95%, 96%, 97%, 98% or 99% identity thereof, or any combination thereof.

In another embodiment, the single, tandem, DuoCAR, or multiple-targeting CAR (either with or without one or more boosting elements) is provided wherein the extracellular antigen binding domain additionally comprises a protein or a peptide (P) sequence capable of specifically binding target antigen, which may be derived from a natural or a synthetic sequence comprising anti-CD19 P antigen binding domain, an anti-CD20 P antigen binding domain, an anti-CD22 P antigen binding domain, an anti-CD33 P antigen binding domain, an anti-CD38 P antigen binding domain, an anti-CD123 (IL3RA) P antigen binding domain, an anti-CD138 P antigen binding domain, an anti-BCMA (CD269) P antigen binding domain, an anti-GPC2 P antigen binding domain, an anti-GPC3 P antigen binding domain, an anti-FGFR4 P antigen binding domain, an anti-c-Met P antigen binding domain, an anti-PMSA P antigen binding domain, an anti-glycolipid F77 P antigen binding domain, an anti-EGFRvIII P antigen binding domain, an anti-GD-2 P antigen binding domain, an anti-NY-ESO-1 TCR P antigen binding domain, an anti-MAGE A3 TCR P antigen binding domain, or an amino acid sequence with 85%, 90%, 95%, 96%, 97%, 98% or 99% identity thereof, or any combination thereof. In another embodiment, a single, tandem, DuoCAR, or multiple-targeting CAR (either with or without one or more boosting elements) is provided wherein the at least one intracellular signaling domain comprises a costimulatory domain and a primary signaling domain.

In another embodiment, the single, tandem, DuoCAR, or multiple-targeting CAR (either with or without one or more boosting elements) is provided wherein the extracellular antigen binding domain alternatively comprises a protein or a peptide (P) sequence capable of specifically binding target antigen, which may be derived from a natural or a synthetic sequence comprising anti-CD19 P antigen binding domain, an anti-CD20 P antigen binding domain, an anti-CD22 P antigen binding domain, an anti-CD33 P antigen binding domain, an anti-CD38 P antigen binding domain, an anti-CD123 (IL3RA) P antigen binding domain, an anti-CD138 P antigen binding domain, an anti-BCMA (CD269) P antigen binding domain, an anti-GPC2 P antigen binding domain, an anti-GPC3 P antigen binding domain, an anti-FGFR4 P antigen binding domain, an anti-c-Met P antigen binding domain, an anti-PMSA P antigen binding domain, an anti-glycolipid F77 P antigen binding domain, an anti-EGFRvIII P antigen binding domain, an anti-GD-2 P antigen binding domain, an anti-NY-ESO-1 TCR P antigen binding domain, an anti-MAGE A3 TCR P antigen binding domain, or an amino acid sequence with 85%, 90%, 95%, 96%, 97%, 98% or 99% identity thereof, or any combination thereof. In another embodiment, a single, tandem, DuoCAR, or multiple-targeting CAR (either with or without one or more boosting elements) is provided wherein the at least one intracellular signaling domain comprises a costimulatory domain and a primary signaling domain.

In yet another embodiment, a single, tandem, DuoCAR, or multiple-targeting CAR (either with or without one or more boosting elements) is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a boosted CAR comprises the nucleic acid sequence of SEQ ID NO: 151. In one embodiment, the nucleic acid sequence encodes a boosted CAR comprising the amino acid sequence of SEQ ID NO: 152.

In another embodiment, the nucleic acid sequence encoding a boosted CAR comprises the nucleic acid sequence of SEQ ID NO: 153. In one embodiment, the nucleic acid sequence encodes a CAR comprising the amino acid sequence of SEQ ID NO: 154.

In another embodiment, the nucleic acid sequence encoding a boosted CAR comprises the nucleic acid sequence of SEQ ID NO: 155. In one embodiment, the nucleic acid sequence encodes a CAR comprising the amino acid sequence of SEQ ID NO: 156.

In another embodiment, the nucleic acid sequence encoding a boosted CAR comprises the nucleic acid sequence of SEQ ID NO: 157. In one embodiment, the nucleic acid sequence encodes a CAR comprising the amino acid sequence of SEQ ID NO: 158.

In another embodiment, the nucleic acid sequence encoding a boosted CAR comprises the nucleic acid sequence of SEQ ID NO: 159. In one embodiment, the nucleic acid sequence encodes a CAR comprising the amino acid sequence of SEQ ID NO: 160.

In another embodiment, the nucleic acid sequence encoding a boosted CAR comprises the nucleic acid sequence of SEQ ID NO; 161. In one embodiment, the nucleic acid sequence encodes a CAR comprising the amino acid sequence of SEQ ID NO: 162.

In another embodiment, the nucleic acid sequence encoding a CAR comprises the nucleic acid sequence of SEQ ID NO; 163. In one embodiment, the nucleic acid sequence encodes a CAR comprising the amino acid sequence of SEQ ID NO: 164.

In another embodiment, the nucleic acid sequence encoding a CAR comprises the nucleic acid sequence of SEQ ID NO: 165. In one embodiment, the nucleic acid sequence encodes a CAR comprising the amino acid sequence of SEQ ID NO. 166.

In another embodiment, the nucleic acid sequence encoding a CAR comprises the nucleic acid sequence of SEQ ID NO: 167. In one embodiment, the nucleic acid sequence encodes a CAR comprising the amino acid sequence of SEQ ID NO: 168.

In another embodiment, the nucleic acid sequence encoding a CAR comprises the nucleic acid sequence of SEQ ID NO. 179. In one embodiment, the nucleic acid sequence encodes a CAR comprising the amino acid sequence of SEQ ID NO: 180.

In another embodiment, the nucleic acid sequence encoding a CAR comprises the nucleic acid sequence of SEQ ID NO: 181. In one embodiment, the nucleic acid sequence encodes a CAR comprising the amino acid sequence of SEQ ID NO; 182.

In another embodiment, the nucleic acid sequence encoding a CAR comprises the nucleic acid sequence of SEQ ID NO: 183. In one embodiment, the nucleic acid sequence encodes a CAR comprising the amino acid sequence of SEQ ID NO: 184.

In another embodiment, the nucleic acid sequence encoding a CAR comprises the nucleic acid sequence of SEQ ID NO: 185. In one embodiment, the nucleic acid sequence encodes a CAR comprising the amino acid sequence of SEQ ID NO: 186.

In another embodiment, the nucleic acid sequence encoding a CAR comprises the nucleic acid sequence of SEQ ID NO: 187. In one embodiment, the nucleic acid sequence encodes a CAR comprising the amino acid sequence of SEQ ID NO: 188.

In another embodiment, the nucleic acid sequence encoding a CAR comprises the nucleic acid sequence of SEQ ID NO: 189. In one embodiment, the nucleic acid sequence encodes a CAR comprising the amino acid sequence of SEQ ID NO: 190.

In another embodiment, the nucleic acid sequence encoding a CAR comprises the nucleic acid sequence of SEQ ID NO: 191. In one embodiment, the nucleic acid sequence encodes a CAR comprising the amino acid sequence of SEQ ID NO: 192.

In another embodiment, the nucleic acid sequence encoding a CAR comprises the nucleic acid sequence of SEQ ID NO: 193. In one embodiment, the nucleic acid sequence encodes a CAR comprising the amino acid sequence of SEQ ID NO: 194.

In another embodiment, the nucleic acid sequence encoding a CAR comprises the nucleic acid sequence of SEQ ID NO: 195. In one embodiment, the nucleic acid sequence encodes a CAR comprising the amino acid sequence of SEQ ID NO: 196.

In another embodiment, the nucleic acid sequence encoding a CAR comprises the nucleic acid sequence of SEQ ID NO: 197. In one embodiment, the nucleic acid sequence encodes a CAR comprising the amino acid sequence of SEQ ID NO: 198.

In another embodiment, the nucleic acid sequence encoding a CAR comprises the nucleic acid sequence of SEQ ID NO: 226. In one embodiment, the nucleic acid sequence encodes a CAR comprising the amino acid sequence of SEQ ID NO: 225.

In another embodiment, the nucleic acid sequence encoding a CAR comprises the nucleic acid sequence of SEQ ID NO: 228. In one embodiment, the nucleic acid sequence encodes a CAR comprising the amino acid sequence of SEQ ID NO: 227.

In another embodiment, the nucleic acid sequence encoding a CAR comprises the nucleic acid sequence of SEQ ID NO: 230. In one embodiment, the nucleic acid sequence encodes a CAR comprising the amino acid sequence of SEQ ID NO: 229.

In another embodiment, the nucleic acid sequence encoding a CAR comprises the nucleic acid sequence of SEQ ID NO: 232. In one embodiment, the nucleic acid sequence encodes a CAR comprising the amino acid sequence of SEQ ID NO: 231.

In another embodiment, the nucleic acid sequence encoding a CAR comprises the nucleic acid sequence of SEQ ID NO: 234. In one embodiment, the nucleic acid sequence encodes a CAR comprising the amino acid sequence of SEQ ID NO: 233.

In another embodiment, the nucleic acid sequence encoding a CAR comprises the nucleic acid sequence of SEQ ID NO: 236. In one embodiment, the nucleic acid sequence encodes a CAR comprising the amino acid sequence of SEQ ID NO: 235.

In another embodiment, the nucleic acid sequence encoding a CAR comprises the nucleic acid sequence of SEQ ID NO: 238. In one embodiment, the nucleic acid sequence encodes a CAR comprising the amino acid sequence of SEQ ID NO: 237.

In another embodiment, the nucleic acid sequence encoding a CAR comprises the nucleic acid sequence of SEQ ID NO: 240. In one embodiment, the nucleic acid sequence encodes a CAR comprising the amino acid sequence of SEQ ID NO: 239.

In another embodiment, the nucleic acid sequence encoding a CAR comprises the nucleic acid sequence of SEQ ID NO: 242. In one embodiment, the nucleic acid sequence encodes a CAR comprising the amino acid sequence of SEQ ID NO: 241.

In another embodiment, the nucleic acid sequence encoding a CAR comprises the nucleic acid sequence of SEQ ID NO: 244. In one embodiment, the nucleic acid sequence encodes a CAR comprising the amino acid sequence of SEQ ID NO: 243.

In another embodiment, the nucleic acid sequence encoding a CAR comprises the nucleic acid sequence of SEQ ID NO: 245. In one embodiment, the nucleic acid sequence encodes a CAR comprising the amino acid sequence of SEQ ID NO: 246.

In another embodiment, the nucleic acid sequence encoding a CAR comprises the nucleic acid sequence of SEQ ID NO: 247. In one embodiment, the nucleic acid sequence encodes a CAR comprising the amino acid sequence of SEQ ID NO: 248.

In another embodiment, the nucleic acid sequence encoding a CAR comprises the nucleic acid sequence of SEQ ID NO: 249. In one embodiment, the nucleic acid sequence encodes a CAR comprising the amino acid sequence of SEQ ID NO: 250.

In another embodiment, the nucleic acid sequence encoding a CAR comprises the nucleic acid sequence of SEQ ID NO: 251. In one embodiment, the nucleic acid sequence encodes a CAR comprising the amino acid sequence of SEQ ID NO: 252.

In another embodiment, the nucleic acid sequence encoding a CAR comprises the nucleic acid sequence of SEQ ID NO: 253. In one embodiment, the nucleic acid sequence encodes a CAR comprising the amino acid sequence of SEQ ID NO: 254.

In another embodiment, the nucleic acid sequence encoding a CAR comprises the nucleic acid sequence of SEQ ID NO: 255. In one embodiment, the nucleic acid sequence encodes a CAR comprising the amino acid sequence of SEQ ID NO: 256.

In one aspect, the single, tandem, DuoCARs, or multi-targeting CARs (either with or without one or more boosting elements) disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the disclosed single, tandem, DuoCARs, or multi-targeting CARs (either with or without one or more boosting elements) can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter or any combination thereof.

In yet another embodiment, the vector expressing the single, tandem, DuoCAR, or multi-targeting CAR (either with or without one or more boosting elements) can be further modified to include one or more operative elements to control the expression of single, tandem, DuoCAR, or multi-targeting CAR T cells (either with or without one or more boosting elements), or to eliminate single, tandem, DuoCAR, or multi-targeting CAR T cells (either with or without one or more boosting elements) cells by virtue of a suicide switch. The suicide switch can include, for example, an apoptosis inducing signaling cascade or a drug that induces cell death. In a preferred embodiment, the vector expressing the single, tandem, DuoCAR, or multi-targeting CAR (either with or without one or more boosting elements) can be further modified to express an enzyme such thymidine kinase (TK) or cytosine deaminase (CD).

In another aspect, host cells including the nucleic acid molecule encoding the single, tandem, DuoCAR, or multi-targeting CAR (either with or without one or more boosting elements) are also provided. In some embodiments, the host cell is a T cell, such as a primary T cell obtained from a subject. In one embodiment, the host cell is a CD8+ T cell.

In yet another aspect, a pharmaceutical composition is provided comprising an anti-tumor effective amount of a population of human T cells, wherein the T cells comprise a nucleic acid sequence that encodes a single, tandem, or multi-targeting, chimeric antigen receptor (CAR) construct, wherein the CAR comprises at least one extracellular antigen binding domain comprising a MSLN and/or ROR1 antigen binding domain comprising the amino acid sequence selected from the group consisting of SEQ ID NOs: 144, 146, 148, and 150; at least one linker domain; at least one transmembrane domain; and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or a combination thereof.

In yet another aspect, a pharmaceutical composition is provided comprising an anti-tumor effective amount of a population of human T cells, wherein the T cells comprise a nucleic acid sequence that encodes a single, tandem, or multi-targeting, boosted chimeric antigen receptor (CAR) construct, wherein the boosted CAR comprises at least one extracellular antigen binding domain comprising a MSLN and/or ROR1 antigen binding domain comprising the amino acid sequence selected from the group consisting of SEQ ID NOs: 144, 146, 148, and 150; at least one linker domain; at least one transmembrane domain; and at least one intracellular signaling domain followed by one or more 2A sequences, in frame to one or more armor molecules, one or more extracellular matrix enzymes, one or more chemokine receptors, one or more stroma-targeting molecules, one or more tumor microenvironment (TME)-digestive elements, one or more switch tag elements, one or more chemo attractive-receptors, one or more chemotactic molecule secretors, one or more switches, and/or one or more cytokines, or any combination thereof; and a pharmaceutically acceptable excipient, wherein the boosted CARs are used to genetically modify one or more human T cell lymphocyte populations, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or a combination thereof.

In one embodiment, a pharmaceutical composition is provided wherein the at least one transmembrane domain of the CAR (either with or without one or more booster elements) contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In another embodiment, a pharmaceutical composition is provided wherein the human cancer includes an adult carcinoma comprising oral and pharynx cancer (tongue, mouth, pharynx, head and neck), digestive system cancers (esophagus, stomach, small intestine, colon, rectum, anus, liver, intrahepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in multiple myeloma (MM), smoldering multiple myeloma (SMM), monoclonal gammopathy of undetermined significance (MGUS), adult and pediatric hematologic malignancies, including acute lymphoblastic leukemia (ALL), CLL (Chronic lymphocytic leukemia), non-Hodgkin's lymphoma (NHL), including follicular lymphoma (FL), diffuse large B cell lymphoma (DLBCL), mantle cell lymphoma (MCL), Hodgkin's lymphoma (HL). chronic myelogenous leukemia (CML), lung cancer, breast cancer, ovarian cancer, prostate cancer, colon cancer, melanoma or other hematological cancer and solid tumors, or any combination thereof.

In another aspect, methods of making single, tandem, DuoCAR, or multiple-targeting CAR construct-containing T cells (hereinafter "CAR-T cells") (either with or without one or more booster elements) are provided. The methods include transducing a T cell with a vector or nucleic acid molecule encoding a disclosed CAR that specifically binds MSLN and/or ROR1, thereby making the CAR-T cell.

In yet another aspect, a method of generating a population of RNA-engineered cells is provided that comprises introducing an in vitro transcribed RNA or synthetic RNA of a nucleic acid molecule encoding a disclosed single, tandem, DuoCAR, or multiple-targeting CAR (either with or without one or more booster elements) into a cell of a subject, thereby generating a single, tandem, DuoCAR, or multiple-targeting CAR cell (either with or without one or more booster elements).

In yet another aspect, a method for diagnosing a disease, disorder or condition associated with the expression of MLSN and/or ROR1 on a cell, is provided comprising a) contacting the cell with a human anti-MLSN and/or ROR1 antibody or fragment thereof, wherein the antibody or a fragment thereof comprises an amino acid sequence selected from the group consisting of SEQ ID NOs: 144, 146, 148, and 150; and b) detecting the presence of MSLN and/or ROR1 wherein the presence of MSLN and/or ROR1 diagnoses for the disease, disorder or condition associated with the expression of MSLN and/or ROR1.

In one embodiment, the disease, disorder or condition associated with the expression of MSLN and/or ROR1 is cancer including hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another embodiment, a method of diagnosing, prognosing, or determining risk of a MSLN and/or ROR1-related disease in a mammal, is provided comprising detecting the expression of MSLN and/or ROR1 in a sample derived from the mammal comprising: a) contacting the sample with a human anti-MSLN and/or anti-ROR1 antibody or fragment thereof, wherein the antibody or a fragment thereof comprises an amino acid sequence selected from the group consisting of SEQ ID NOs: 144, 146, 148, and 150; and b) detecting the presence of MSLN and/or ROR1 wherein the presence of MSLN and/or ROR1 diagnoses for a MSLN and/or ROR1-related disease in the mammal.

In another embodiment, a method of inhibiting MSLN and/or ROR1-dependent T cell inhibition, is provided comprising contacting a cell with a human anti-MSLN and/or ROR1 antibody or fragment thereof, wherein the antibody or a fragment thereof comprises an amino acid sequence selected from the group consisting of SEQ ID NOs: 144, 146, 148, and 150. In one embodiment, the cell is selected from the group consisting of a MSLN and/or ROR1-expressing tumor cell, a tumor-associated macrophage, and any combination thereof.

In another embodiment, a method of blocking T-cell inhibition mediated by a MSLN and/or ROR1-expressing cell and altering the tumor microenvironment to inhibit tumor growth in a mammal, is provided comprising administering to the mammal an effective amount of a composition comprising an isolated anti-MSLN and/or anti-ROR1 antibody or fragment thereof, wherein the antibody or a fragment thereof comprises an amino acid sequence selected from the group consisting of SEQ ID NOs: 144, 146, 148, and 150. In one embodiment, the cell is selected from the group consisting of a MSLN and/or ROR1-expressing tumor cell, a tumor-associated macrophage, and any combination thereof.

In another embodiment, a method of inhibiting, suppressing or preventing immunosuppression of an anti-tumor or anti-cancer immune response in a mammal, is provided comprising administering to the mammal an effective amount of a composition comprising an isolated anti-MSLN and/or anti-ROR1 antibody or fragment thereof, wherein the antibody or a fragment thereof comprises an amino acid sequence selected from the group consisting of SEQ ID NOs: 144, 146, 148, and 150. In one embodiment, the antibody or fragment thereof inhibits the interaction between a first cell with a T cell, wherein the first cell is selected from the group consisting of a MSLN and/or ROR1-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed single, tandem, or multiple-targeting CAR (either with or without one or more booster elements).

In another embodiment, a method of treating or preventing cancer in a mammal is provided comprising administering to the mammal one or more of the disclosed single, tandem, or multiple-targeting CARs (either with or without one or more booster elements), in an amount effective to treat or prevent cancer in the mammal. The method includes administering to the subject a therapeutically effective amount of host cells expressing a disclosed single, tandem, or multiple-targeting CAR (either with or without one or more booster elements) that specifically binds MSLN and/or ROR1 and/or one or more of the aforementioned antigens, under conditions sufficient to form an immune complex of the antigen binding domain on the single, tandem, or multiple-targeting CAR (either with or without one or more booster elements) and the extracellular domain of MSLN and/or ROR1 and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a single, tandem, or multiple-targeting chimeric antigen receptor (CAR) (either with or without one or more booster elements), wherein the single, tandem, or multiple-targeting CAR (either with or without one or more booster elements) includes at least one extracellular MSLN and/or ROR1 antigen binding domain comprising the amino acid sequence of SEQ ID NOs: 144, 146, 148, and 150, or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a single, tandem, or multiple-targeting chimeric antigen receptor (CAR) (either with or without one or more booster elements), wherein the single, tandem, or multiple-targeting CAR (either with or without one or more booster elements) comprises at least one MSLN and/or ROR1 antigen binding domain comprising the amino acid sequence of SEQ ID NOs: 144, 146, 148, and 150, or any combination thereof, at least one linker or spacer domain, at least one transmembrane domain, at least one intracellular signaling domain, wherein the T cells are T cells of the subject having cancer. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In yet another embodiment, a method is provided for treating a mammal having an autoimmune, alloimmune, or autoaggressive disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a single, tandem, or multiple-targeting chimeric antigen receptor (CAR) (either with or without one or more booster elements), wherein the single, tandem, or multiple-targeting CAR (either with or without one or more booster elements) includes at least one extracellular MSLN and/or ROR1 antigen binding domain comprising the amino acid sequence of SEQ ID NOs: 144, 146, 148, and 150, or any combination thereof, at least one linker or spacer domain, at least one transmembrane domain, at least one intracellular signaling domain, and wherein the T cells are T cells of the subject having an autoimmune, alloimmune, or autoaggressive disease, disorder or condition.

In yet another embodiment, a method is provided for treating autoimmune, alloimmune, or autoaggressive diseases in a subject in need thereof comprising administering to the subject a pharmaceutical composition comprising an anti-tumor effective amount of a population of T cells, wherein the T cells comprise a nucleic acid sequence that encodes a single, tandem, or multiple-targeting chimeric antigen receptor (CAR) (either with or without one or more booster elements), wherein the single, tandem, or multiple-targeting CAR (either with or without one or more booster elements) comprises at least one MSLN and/or ROR1 antigen binding domain comprising the amino acid sequence of SEQ ID NOs: 144, 146, 148, and 150, or any combination thereof, at least one linker or spacer domain, at least one transmembrane domain, at least one intracellular signaling domain, wherein the T cells are T cells of the subject having an autoimmune, alloimmune, or autoaggressive disease, disorder or condition. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In yet another embodiment, a method is provided for treating a mammal having an autoimmune, alloimmune, or autoaggressive disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a single, tandem, or multiple-targeting chimeric antigen receptor (CAR) (either with or without one or more booster elements), wherein the single, tandem, or multiple-targeting CAR (either with or without one or more booster elements) includes at least one extracellular MSLN and/or ROR1 antigen binding domain comprising the amino acid sequence of SEQ ID NOs: 152, 154, 156, 158, 160, 162, 164, 166, 168, 170, 172, 174, 176, 178, 180, 182, 184, 186, 188, 190, 192, 194, 196, 198, 225, 227, 229, 231, 233, 235, 237, 239, 241, 243, 246, 248, 250, 252, 254, or 256, or any combination thereof, at least one linker or spacer domain, at least one transmembrane domain, at least one intracellular signaling domain, and wherein the T cells are T cells of the subject having an autoimmune, alloimmune, or autoaggressive disease, disorder or condition.

In yet another embodiment, a method is provided for treating autoimmune, alloimmune, or autoaggressive diseases in a subject in need thereof comprising administering to the subject a pharmaceutical composition comprising an anti-tumor effective amount of a population of T cells, wherein the T cells comprise a nucleic acid sequence that encodes a single, tandem, or multiple-targeting chimeric antigen receptor (CAR) (either with or without one or more booster elements), wherein the single, tandem, or multiple-targeting CAR (either with or without one or more booster elements) comprises at least one MSLN and/or ROR1 antigen binding domain comprising the amino acid sequence of SEQ ID NOs: 152, 154, 156, 158, 160, 162, 164, 166, 168, 170, 172, 174, 176, 178, 180, 182, 184, 186, 188, 190, 192, 194, 196, 198, 225, 227, 229, 231, 233, 235, 237, 239, 241, 243, 246, 248, 250, 252, 254, or 256, or any combination thereof, at least one linker or spacer domain, at least one transmembrane domain, at least one intracellular signaling domain, wherein the T cells are T cells of the subject having an autoimmune, alloimmune, or autoaggressive disease, disorder or condition. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

For each of the various aspects and embodiments of the methods for treating autoimmune, alloimmune, or autoaggressive diseases in a subject in need thereof, the single, tandem, multi-targeting, DuoCAR, (either with or without one or more booster elements) CAR constructs specifically contemplated supra and/or infra, the nucleotide sequences encoding any of the aforementioned functional CARs (either with or without one or more booster elements) referenced supra and/or infra, may be used to treat an autoimmune, alloimmune, or autoaggressive disease, disorder or condition.

For each of the various aspects and embodiments of the methods for treating autoimmune, alloimmune, or autoaggressive diseases in a subject in need thereof, the single, tandem, multi-targeting, DuoCAR, (either with or without one or more booster elements) CAR constructs specifically contemplated supra and/or infra, the amino acid sequences encoding any of the aforementioned functional CARs (either with or without one or more booster elements) referenced supra and/or infra, may be used to treat an autoimmune, alloimmune, or autoaggressive disease, disorder or condition.

For the various aspects and embodiments of the methods for treating autoimmune, alloimmune, or autoaggressive diseases described herein, exemplary non-limiting examples of autoimmune diseases include chronic graft-vs-host disease (GVHD), lupus, arthritis, immune complex glomerulonephritis, Goodpasture's, uveitis, hepatitis, systemic sclerosis or scleroderma, type I diabetes, multiple sclerosis, cold agglutinin disease, Pemphigus vulgaris, Grave's disease, autoimmune hemolytic anemia, Hemophilia A, Primary Sjogren's Syndrome, thrombotic thrombocytopenia purpura, neuromyelits optica, Evan's syndrome, IgM mediated neuropathy, cyroglobulinemia, dermatomyositis, idiopathic thrombocytopenia, ankylosing spondylitis, bullous pemphigoid, acquired angioedema, chronic urticarial, antiphospholipid demyelinating polyneuropathy, and autoimmune thrombocytopenia or neutropenia or pure red cell aplasias, while exemplary non-limiting examples of alloimmune diseases include allosensitization (see, for example, Blazar et al., 2015, Am. J. Transplant., 15(4):931-41) or xenosensitization from hematopoietic or solid organ transplantation, blood transfusions, pregnancy with fetal allosensitization, neonatal alloimmune thrombocytopenia, hemolytic disease of the newborn, sensitization to foreign antigens such as can occur with replacement of inherited or acquired deficiency disorders treated with enzyme or protein replacement therapy, blood products, and gene therapy.

Antigen binding domains that are specific for a ligand on B cells, plasma cells or plasmablasts are useful in the methods of treating autoimmune diseases, alloimmune diseases, or autoaggressive diseases as described herein. For example, a CAR construct can contain an antigen binding domain that is specific for, without limitation, CD19, CD20, CD22, CD138, BCMA, CD319, CD10, CD24, CD27, CD38, or CD45R. In addition, a CAR construct can contain an antigen binding domain that is specific for, without limitation, an autoimmune specific antigen. Autoimmune specific antigens include, for example, the antigen that results in systemic lupus erythematosus (SLE), Graves' disease, celiac disease, diabetes mellitus type 1, rheumatoid arthritis (RA), sarcoidosis, Sjogren's syndrome, polymyositis (PM), and dermatomyositis (DM), mucocutaneous pemphigus vulgaris, myasthenia gravis. See, for example, Ellebrecht et al., 2016, Science, 353:179-84.

In yet another embodiment, a method is provided for generating a persisting population of genetically engineered T cells in a human diagnosed with cancer. In one embodiment, the method comprises administering to a human a T cell genetically engineered to express a single, tandem, or multiple-targeting CAR (either with or without one or more booster elements) wherein the single, tandem, or multiple-targeting CAR (either with or without one or more booster elements) comprises at least one MSLN and/or ROR1 antigen binding domain comprising the amino acid sequence of SEQ ID NOs: 144, 146, 148, and 150, or any combination thereof; at least one transmembrane domain; and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the single, tandem, or multiple-targeting CARs (either with or without one or more booster elements) disclosed herein, In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

In one aspect of the present invention, an immunotherapy composition is provided comprising a single, tandem, DuoCAR, or multiple-targeting CAR (either with or without one or more booster elements) which immunotherapy composition may be used to transduce autologous lymphocytes to generate active patient-specific anti-tumor lymphocyte cell populations that can be infused directly back into the patient to promote in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In yet another aspect, a pharmaceutical composition is provided comprising an anti-tumor effective amount of a population of human T cells, wherein the T cells comprise a nucleic acid sequence that encodes a chimeric antigen receptor (CAR), wherein the CAR comprises at least one extracellular antigen binding domain comprising an anti-ROR1 and/or anti-MSLN antigen binding domain comprising the amino acid sequence selected from the group consisting of SEQ ID NOs: 144, 146, 148, and 150; at least one linker domain; at least one transmembrane domain; and at least one intracellular signaling domain; and at least one boosting element comprising one or more armor molecules (TGFβRIIdn, truncated PD-1 (decoy), PD-1 dominant-negative (PD-1dn), synthetic PD-1 activating receptor, truncated CTLA-4, truncated Tim-3, truncated TIGIT, TIGIT neutralizing antibody, TIGIT intrabody, TIGIT shRNA), one or more extracellular matrix enzymes (ECMs), one or more chemokine receptors (CXCL8, CCL2) one or more stroma-targeting molecules (FAP, LRRC15, CD276/B7-H3, TEM7, TEM8, TEM1), one or more TME-digestive element (heparanase (HPSE), MMP (MMP-1, MMP-2, MMP-9, MMP-12, MMP-13) and hyaluronidase 1, hyaluronidase 2, hyaluronidase 3, hyaluronidase 4, PH-20, and hyaluronoglucosaminidase pseudogene 1 (HYALP1), tissue inhibitors of metalloproteinases (TIMPs) (TIMP-1, TIMP-2, TIMP-3, TIMP-4), hyaluronidase), one or more switches (tag, kill switch, on switch, off switch, adapter switch, truncated EGF receptor, truncated CD19, truncated CD20, CD20 mimotope, truncated CD34, truncated LNGF receptor), chimeric costimulatory receptor (CCR), and/or one or more cytokines (membrane-bound or soluble IL-2, IL-4, IL-6, IL-7, IL-8, IL-9, IL-10, IL-11, IL-12, IL-15, IL-18, IL-21, TNFα, IFNγ (each of the aforementioned may be with or without FC (antibody fragment crystallizable) element)), or a combination of membrane bound receptor and tethered cytokine ligand (mbIL15, mbIL7, mbIL-21), innate system-inducting ligands (TLR ligands, LPS, bacterial products), or any combination thereof, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or a combination thereof.

In one embodiment, a pharmaceutical composition is provided wherein the at least one transmembrane domain of the single, tandem, DuoCAR, or multi-targeting CAR (either with or without one or more boosting elements) contains a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

It will be understood that the single, tandem, DuoCAR, or multiple-targeting CARs (either with or without one or more booster elements), host cells, nucleic acids, and methods are useful beyond the specific aspects and embodiments that are described in detail herein. The foregoing features and advantages of the disclosure will become more apparent from the following detailed description, which proceeds with reference to the accompanying figures.

In one aspect of the above-identified invention, the DuoCARs (either with or without one or more boosters) disclosed herein comprise at least two vectors, each vector encoding a functional CAR (either with or without one or more boosters), whereby the combination of vectors results in the expression of two or more non-identical binding domains, herein each vector encoded binding domain(s) are covalently linked to a transmembrane domain and one or more non-identical intracellular signaling motifs, at least one extracellular domain capable of binding to an antigen, at least one transmembrane domain, and at least one intracellular domain.

In certain aspects of the boosted CARs of the present invention, an immunotherapy composition is provided comprising one or more isolated nucleic acid molecules encoding at least two vectors, each vector encoding a functional DuoCAR (either with or without one or more booster elements), whereby the combination of vectors results in the expression of two or more non-identical binding domains, wherein each vector encoded binding domain(s) are covalently linked to a transmembrane domain and one or more non-identical intracellular signaling motifs, which immunotherapy composition may be used to transduce autologous lymphocytes to generate active patient-specific anti-tumor lymphocyte cell populations that can be infused directly back into the patient to promote in vivo expansion, persistence of patient-specific anti-tumor T-cells resulting in tumor stabilization, reduction, elimination, remission of cancer, or prevention or amelioration of relapse of cancer, or a combination thereof, in a patient-specific manner. Novel adoptive immunotherapy compositions comprising such two or more vector-transduced lymphocytes are provided herein as well as are methods of use of same in a patient-specific combination immunotherapy that can be used to treat cancers and other diseases and conditions.

Thus, in one aspect, lentiviral vectors expressing Duo chimeric antigen receptors (DuoCARs) (either with or without one or more booster elements) are provided herein, as well as nucleic acid molecules encoding the lentiviral vectors expressing DuoCARs (either with or without one or more booster elements). Methods of using the disclosed lentiviral vectors expressing DuoCARs (either with or without one or more booster elements), host cells, and nucleic acid molecules are also provided, for example, to treat a cancer in a subject.

In one aspect, an immunotherapy composition is provided comprising one or more isolated nucleic acid molecules encoding at least two vectors (DuoCARs) (either with or without one or more booster elements), each vector encoding a functional CAR (either with or without one or more booster elements), wherein at least one binding domain(s) in one of the vectors are non-identical, and whereby the combination of vectors results in the expression of two or more non-identical binding domains, wherein each vector encoded binding domain(s) are covalently linked to a transmembrane domain and one or more non-identical intracellular signaling motifs.

In one embodiment, an immunotherapy composition is provided comprising one or more isolated nucleic acid molecules encoding at least three vectors (TrioCARs) (either with or without one or more booster elements), each vector encoding a functional CAR (either with or without one or more booster elements), whereby the combination of vectors results in the expression of two or more non-identical binding domains, wherein each vector encoded binding domain(s) are covalently linked to a transmembrane domain and one or more non-identical intracellular signaling motifs.

In one embodiment, an immunotherapy composition is provided comprising one or more isolated nucleic acid molecules encoding at least four vectors (QuatroCARs) (either with or without one or more booster elements), each vector encoding a functional CAR (either with or without one or more booster elements), whereby the combination of vectors results in the expression of two or more non-identical binding domains, wherein each vector encoded binding domain(s) are covalently linked to a transmembrane domain and one or more non-identical intracellular signaling motifs.

In yet another embodiment, an immunotherapy composition is provided comprising one or more isolated nucleic acid molecules encoding at least two, three, four, five, six, seven, eight, nine, or ten vectors (e.g., an "nCAR") (either with or without one or more booster elements), each vector encoding a functional CAR (either with or without one or more booster elements), whereby the combination of vectors results in the expression of two or more non-identical binding domains, wherein each vector encoded binding domain(s) are covalently linked to a transmembrane domain and one or more non-identical intracellular signaling motifs, wherein each unique member of the nCAR set when assembled into a CAR product constitutes a unique CAR composition referred to herein as "nCAR" (either with or without one or more booster elements) (e.g., DuoCAR, TrioCAR, QuatroCAR, PentaCAR, HexaCAR, HeptaCAR, OctaCAR, NonaCAR, and DecaCAR, etc.).

In another aspect, the DuoCARs (either with or without one or more boosters) are used to enhance the immune response to tumor mediated by the therapeutic T cell population. The immune response is enhanced in multiple ways.

First, DuoCARs enable multi-targeting of tumor cells, reducing the risk of tumor antigen escape and enabling efficient elimination of antigen-heterogeneous tumors. This feature is especially important in targeting solid tumors, which often display antigen heterogeneity and antigen loss. Table 1, infra, exemplifies CARs with dual targeting capacity of solid tumor antigens mesothelin and ROR1.

In addition, the DuoCAR format, allows for introduction of multiple co-stimulatory domains in CAR architecture, so that stronger overall stimulation can be provided for CAR T cell effector functions, differentiation and memory formation, and persistence. For example, same CAR T cell can benefit form CD28-stimulation required for potent CAR T cell activation, expansion and cytokine production, and 4-1BB stimulation to extend CAR T cell survival and persistence in the patient. Each DuoCAR chain may be a $2^{nd}$ or a $3^{rd}$ generation DuoCAR, and may incorporate one or two co-stimulatory domains. By providing a third T cell activating sequence on a separate vector CAR construct (either with or without one or more boosters), the inventors are able to regain the advantage of expressing two or more targeting domains, improved co-stimulation, and a booster payload, without incurring the disadvantage of the decreased expression of the CAR at the T cell surface at the CAR % level.

In a second aspect, the DuoCARs (either with or without one or more boosters) of the present invention may target cell-types other than the tumor that mediate immunosuppressive effects. For example, if immunosuppressive cells expressing one of the targeted antigens are present in the tumor lesion and also inhibit an anti-tumor immunity, as by the production of IL-10 or other mediators, the second benefit to the use of the DuoCAR-expressing (either with or without one or more boosters) tumor-specific T cell population is that the immunosuppressive cell population is also removed.

For example, if immunosuppressive B cells are present within a solid tumor lesion, these could be eliminated by the use of a B cell-specific DuoCAR (such as CD19-specific DuoCARs, either with or without one or more boosters). If immunosuppressive fibroblast-like cells are present, these could be removed by stromal-specific DuoCARs (either with or without one or more boosters) (for example by targeting fibroblast activating protein-alpha (FAP)). If malformed vasculature is responsible for the lack of an efficacious immune response a DuoCAR specific for these types of vascular or lymph vessel specific targets (such as anti-VEGFR) may also improve therapeutic outcome.

In a third aspect, the DuoCARs (either with or without one or more boosters) of the present invention target an immunosuppressive population that is distal to the tumor, i.e. present in another compartment in the body. For example, using a DuoCAR (either with or without one or more boosters) to target myeloid derived suppressor cells (MDSCs), that may be present either in the tumor lesion itself or in the regional lymph nodes or bone marrow. It is well established that tumor-draining lymph nodes can either be loci of immune activation or immune suppression. This depends upon the overall inflammatory tone of the lymph node as well as distal dendritic cell differentiation prior to migration to the lymph node. If a tumor-draining lymph node is populated with myeloid-derived suppressor cells (MDSC) or miss-differentiated antigen presenting cells such as dendritic cells, a DuoCAR (either with or without one or more boosters) that targets these cell types, although distal to the tumor itself, may also improve therapeutic outcome. Beyond the cancer-specific DuoCAR (either with or without one or more boosters) immunotherapeutic applications, a second application of DuoCARs (either with or without one or more boosters) would be the prevention or treatment of autoimmune, alloimmune, autoaggressive and/or inflammatory diseases. The difference from oncologic-based applications is that T-regulatory cells (Treg), or induced T-regulatory cells (iTreg), or other cells cultured in conditions that promote Th-2-like immune responses, would be the cellular substrate. For oncologic application Th-1 like cells are the cellular substrate. In therapeutic applications as diverse as graft-versus-host disease (GvHD) following hematopoietic stem cell transplantation (HSCT), allergic airway, gut, or other mucosal inflammation, or skin allergies, the presence of CAR-modified lymphocytes that produce immune-inhibitory cytokines, such as transforming growth factor-beta (TFG-beta), would serve to exert a broad tolerogenic signal that ameliorates the autoimmune-, alloimmune-, autoaggressive- or inflammation-driven disease. This approach includes neurological inflammatory conditions of the periphery or central nervous system (CNS) such as Alzheimer's disease, multiple sclerosis, traumatic brain injury, Parkinson's disease, and CTE (chronic traumatic encephalopathy due to repeated concussions or micro-concussions), or connective tissue diseases such as Rheumatoid arthritis, Scleroderma, Granulomatosis with polyangiitis, Churg-Strauss syndrome, Lupus, Microscopic polyangiitis, Polymyositis/dermatomyositis, Marfan syndrome, or Epidermolysis bullosa acquisita. This approach also includes progressive scarring diseases such as COPD (chronic obstructive pulmonary disease) or fibrotic diseases of the lung, heart, kidney, or liver. For example, systemic scleroderma is a progressive, rare disease that causes fibrosis not only in the skin but also in tissues throughout the body, including the heart, lungs and kidneys.

In the treatment of inflammatory diseases, lymphocytes specific for tissue antigens, distress markers on the surface of inflamed cells, or misfolded proteins (such as tau protein or beta-amyloid) would be created by generating DuoCAR (either with or without one or more boosters) expression vectors that are specific for these targets. Single antibody-based therapy for Alzheimer's is already in clinical development (i.e., Solanezumab by Eli Lilly and Company and Aducanumab by Biogen, Inc.). In Alzheimer's disease, antibody to monomeric or aggregated beta-amyloid could be used in a CAR (either with or without one or more boosters) format in lieu of binders to cell surface proteins. Binders to tau protein or tau-peptides bound by MHC molecules could also be used as binding motifs for CARs (either with or without one or more boosters). Receptors that mediate the homing of lymphocytes to specific peripheral tissues can also be included in a CAR (either with or without one or more boosters) format, in order to render regional specificity to the CAR-expressing (either with or without one or more boosters) Treg population. Adhesion receptor domains known to drive lymphocyte infiltration into specific tissues and cytokine sequences or cytokine or chemokine receptors or binders could be used as part of the CAR (either with or without one or more boosters) domain. Adhesion molecules such as CD44 and integrin alpha-4 are known to target lymphocytes to the CNS, thus including domains from adhesion molecules know to mediate CNS migratory behavior of lymphocyte populations could also be used to target CAR-expressing (either with or without one or more boosters) lymphocytes to regions of disease. The same would hold true for the gut (i.e. binders to MAdCAm-1, expression of a CCR9, or anti-CCL25, etc.), lung (i.e. P-selectin or mesothelin), skin (i.e. binders to E-selectin), or other mucosal surfaces.

To use this approach, a patient with an inflammatory condition or whose disease could be treated by mitigation of inflammatory pathology, such as Alzheimer's disease, would be admitted to the clinic and peripheral blood harvested. Treg cells could be selected directly by immunomagnetic beads (Regulatory T cell isolation kit, Miltenyi Biotec), or induced by culture in the appropriate cytokine milieu. These Treg or iTreg would then be transduced with a DuoCAR (either with or without one or more boosters) vector and if required expanded in vitro (Treg expansion kit, Miltenyi Biotec). The DuoCAR (either with or without one or more boosters) binding domains would be derived from antibodies or receptors that mediate tissue specific homing and disease-associated binders, such as anti-beta amyloid. The engineered immune effector cells thus generated would be targeted to the appropriate site, and produce cytokines consistent with their Th2 or Treg differentiation pattern. It is also known that CAR-T cells can be engineered to secrete specific genetic payloads upon activation of the CAR receptor (either with or without one or more boosters). In addition to the DuoCAR (either with or without one or more boosters) payload expressed from the vector, additional therapeutic proteins or peptides could be expressed or secreted by the engineered T cell populations such as: i) one or more A-beta DPs (amyloid beta degrading proteases), ii) one or more matrix proteases (such as MMP-9 and MMP9), iii) one or more peptides or soluble antibody-like binders that interfere with plaque formation, iv) one or more cytokines (such as TGF-beta, IL-2, IL-4, IL-6, IL-7, IL-8, IL-9, IL-10, IL-11, IL-12, IL-15, IL-18, IL-21), v) one or more armor elements so as to overcome immunosuppression in TME, vi) one or more digestive enzymes to overcome the physical barrier of tumor stroma/extracellular matrix (ECM) and enable CAR T tumor penetration, vii) one or more pro-inflammatory immune activators, and viii) one or more on-switches or off-switches, or any combination thereof, to control the expression of the CAR, wherein the boosted CARs achieve a high surface expression on transduced T cells, a multi-targeting activity to overcome antigen escape, a high degree of cytolysis and transduced T cell in vivo expansion and persistence to promote in vivo expansion, persistence of patient-specific anti-tumor T-cells resulting in tumor stabilization, reduction, elimination, remission of cancer or autoimmune, alloimmune, or autoaggressive disease, or prevention or amelioration of relapse of cancer or autoimmune, alloimmune, or autoaggressive disease, or a combination thereof, in a patient-specific manner. In reference to the parent one or more boosting elements of the single, tandem, DuoCARs, or multiple-targeting CARs, the functional boosting element portion can comprise, for instance, about 10%, 25%, 30%, 50%, 68%, 80%, 90%, 95%, or more, of the parent one or more boosting elements of the single, tandem, DuoCARs, or multiple-targeting CARs.

MiRNAs could also be expressed within cells to modulate T cell function. Examples of miRNAs are miR-92a, miR-21, miR-155, miR-146a, miR-3162, miR-1202, miR-1246 and miR-4281, miR-142, miR-17-92. Also shRNAs to miRNAs could be developed. Examples are shRNAs targeted to miR-28, miR-150 and miR-107, which normally bind to PD1 and increase its expression.

Beyond oncology-based and inflammatory and autoimmune, alloimmune, or autoaggressive disease-based applications, a third application of the DuoCAR (either with or without one or more boosters) technology is the generation of therapeutic lymphocyte populations specific for viral, bacterial, or fungal antigens. Thus, as for oncology applications described for B cell malignancies, the targeting of infectious disease would allow the DuoCAR (either with or without one or more boosters) products to mediate immunoprotective or immunotherapeutic activity against the infective agents or the diseased tissues where they reside based upon recognition of microbial antigens. Unlike T cell receptor (TCR)-based approaches, where the T cell receptor itself mediates the recognition of pathogen encoded peptides, the DuoCAR (either with or without one or more boosters) approach would utilize binding proteins expressed in a CAR (either with or without one or more boosters) vector format that would give antibody-like recognition (that is, not requiring antigen processing) to the transduced T cell population. The activation of the therapeutic T cell population would result in an immune activating locus able to eliminate the infected cells, and if the microbial antigen is not cell associated, to release soluble mediators like interferon-gamma that would enable an effective immune response to be mounted against the infectious agent.

For example, HIV is known to be highly variable, and yet specific clades or families can be categorized and antibody to clade-specific viral envelope protein (env, gp120) created. Using the DuoCAR (either with or without one or more boosters) approach, three or more clade-specific antibody-like binders are included in the CAR (either with or without one or more boosters) constructs resulting in broad anti-HIV immune activity. In addition to viral proteins, bacterial protein can be targeted. A current medical challenge is the treatment of antibiotic resistant bacterial strains that often arise in healthcare settings. These include VRE (vancomycin resistant enterococci), MRSA (methicillin-resistant *Staphylococcus aureus*), KPC (*Klebsiella pneumoniae* carbapenemase producing gram-negative bacteria, also CRKP), and others. *Klebsiella* cell surface antigens include the O antigen (9 variants) and the K antigen (appx. 80 variants). The O antigen spectrum could readily be covered with a small DuoCAR (either with or without one or more boosters) library, as could a number of the K antigens. For use, CAR constructs (either with or without one or more boosters) would be created that feature antibodies that bind to different K or O serotypes, and these CAR vectors (either with or without one or more boosters) used to transduce a Th1-like effector cell population, isolated and activated as for oncology applications. In fungal diseases, the work of L. Cooper et al. (Kumasesan, P. R., 2014, PNAS USA, 111:10660) demonstrated that a fungal binding protein normally expressed on human cells, dectin-1, can be reconfigured as a CAR (either with or without one or more boosters), and used to control fungal growth in vitro. The human disease aspergillosis occurs in severely immunosuppressed individuals and is caused by the fungus *A. fumigatus*. Multiple groups have produced monoclonal antibodies specific for the antigenic components of the *aspergillus* cell surface, thus opening the door to adoptive immunotherapy with Duo- CARs (either with or without one or more boosters) that target three or more *aspergillus* antigens on the fungal surface. Thus, in all of these infectious disease applications, the ability to create immunoglobulin-like binders to microbial antigens allows a plurality of antigens to be targeted by CAR-expressing (either with or without one or more boosters) effector lymphocyte populations.

What follows is a detailed description of the DuoCARs (either with or without one or more boosters) that may be used in the patient-specific autologous anti-tumor lymphocyte cell population(s) disclosed herein, including a description of their extracellular domain, the transmembrane domain and the intracellular domain, along with additional description of the DuoCARs (either with or without one or more boosters), antibodies and antigen binding fragments thereof, conjugates, nucleotides, expression, vectors, and host cells, methods of treatment, compositions, and kits employing the disclosed DuoCARs (either with or without one or more boosters). While the compositions and methods of the present invention have been illustrated with reference to the generation and utilization of DuoCARs (either with or without one or more boosters), it is contemplated herein that the compositions and methods are specifically intended to include the generation and utilization of TrioCARs (either with or without one or more boosters) and QuatroCARs (either with or without one or more boosters).

In one embodiment, an immunotherapy composition is provided comprising: (a) at least two vectors, each comprising nucleic acid sequences that are functional in cells; (b) wherein each vector encodes a functional CAR (either with or without one or more booster elements); (c) wherein each CAR (either with or without one or more booster elements) comprises of at least one binding domain, a single transmembrane domain, and at least one intracellular signaling motif; (d) wherein the at least one binding domains in one of the vectors are non-identical; and (e) wherein the at least one binding domain, a single transmembrane domain, at least one linker domain, and at least one intracellular signaling motif are covalently linked in each said vector, wherein the combination of vectors are used to genetically modify one or more lymphocyte populations.

In another embodiment, an immunotherapy composition is provided comprising: (a) at least two vectors, each comprising nucleic acid sequences that are functional in cells; (b) wherein each vector encodes a functional CAR (either with or without one or more booster elements); (c) wherein each CAR (either with or without one or more booster elements) comprises at least one binding domain, a single transmembrane domain, and at least one intracellular signaling motif; (d) wherein the at least one binding domain(s) in each vector are non-identical; (e) wherein the at least one signaling motif combinations are non-identical between each of the vectors; and (f) wherein the at least one binding domain, a single transmembrane domain, and at least one intracellular signaling motif are covalently linked in each said vector, wherein the combination of two or more vectors are used to genetically modify one or more lymphocyte populations.

In another embodiment, an immunotherapy composition is provided wherein the linker or spacer domain of the CAR (either with or without one or more booster elements) is derived from the extracellular domain of IgG1, IgG2, IgG3 or IgG4, CD8, TNFRSF19, or CD28, and is linked to the transmembrane domain.

In another embodiment, an immunotherapy composition is provided wherein the CAR (either with or without one or more booster elements) further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, CD271, TNFRSF19, Fc epsilon R, or any combination thereof.

In another embodiment, an immunotherapy composition is provided wherein the at least one intracellular signaling domain comprises a costimulatory domain, a primary signaling domain, or any combination thereof.

In another embodiment, an immunotherapy composition is provided wherein the at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), PD-1, GITR, CTLA-4, or any combination thereof.

In another embodiment, an immunotherapy composition is provided wherein a single vector is used to encode all chimeric antigen receptors (e.g., retroviral, adenoviral, SV40, herpes vector, POX vector, RNA, plasmid, cosmid, or any viral vector or non-viral vector), in combination with a CRISPR system for integration.

In another embodiment, an immunotherapy composition is provided wherein each vector is an RNA or DNA vector, alone or in combination with a transfection reagent or a method to deliver the RNA or DNA into the cell, a non-limiting example being electroporation.

In another embodiment, an immunotherapy composition is provided wherein at least one vector expresses a nucleic acid molecule that modulates the expression of a nucleic acid in the cell.

In another embodiment, an immunotherapy composition is provided wherein the nucleic acid molecule inhibits or deletes the expression of an endogenous gene.

In certain embodiments, an immunotherapy composition is provided wherein the active patient-specific autologous anti-tumor lymphocyte cell population is generated within one day, two days, three days, four days, five days, seven days, ten days, twelve days, fourteen days, twenty-one days, or one month of lymphocyte harvest or tumor biopsy and wherein the active patient-specific autologous anti-tumor lymphocyte cell population that can be infused back into a patient suffering from cancer and is capable of promoting in vivo expansion, persistence of patient-specific anti-tumor lymphocyte cells resulting in tumor stabilization, reduction, elimination, remission of cancer, or prevention or amelioration of relapse of cancer, or a combination thereof, in a patient-specific manner.

In one aspect, isolated nucleic acid molecules encoding the aforementioned chimeric antigen receptors (including the DuoCARs recited, supra) are provided herein.

In one aspect, the CARs (either with or without one or more booster elements) used in the patient-specific autologous lymphocyte population(s) of the immunotherapy composition of the present invention, the CARs (either with or without one or more booster elements) are modified to express or contain a detectable marker for use in diagnosis, monitoring, and/or predicting the treatment outcome such as progression free survival of cancer patients or for monitoring the progress of such treatment. In one embodiment of the CARs (either with or without one or more booster elements) used in the patient-specific autologous anti-tumor lymphocyte cell population(s), the nucleic acid molecules encoding the disclosed CARs (either with or without one or more booster elements) can be contained in a vector, such as a viral or non-viral vector. The vector is a DNA vector, an RNA vector, a plasmid vector, a cosmid vector, a herpes virus vector, a measles virus vector, a lentiviral vector, adenoviral vector, or a retrovirus vector, or a combination thereof.

In certain embodiments of the CARs (either with or without one or more booster elements) used in the patient-specific autologous anti-tumor lymphocyte cell population (s), the two or more lentiviral vectors are pseudotyped with different viral glycoproteins (GPs) including for example, and not by way of limitation, amphotropic murine leukemia virus [MLV-A], a baboon endogenous virus (BaEV), GP164, gibbon ape leukemia virus [GALV], RD114, feline endogenous virus retroviral-derived GPs, and vesicular stomatitis virus [VSV], measles virus, fowl plague virus [FPV], Ebola virus [EboV], lymphocytic choriomeningitis virus [LCMV]) non retroviral-derived GPs, as well as chimeric variants thereof including, for example, and not by way of limitation, chimeric GPs encoding the extracellular and transmembrane domains of GALV or RD114 GPs fused to the cytoplasmic tail (designated TR) of MLV-A GP.

In certain embodiments of the CARs (either with or without one or more booster elements) used in the patient-specific autologous anti-tumor lymphocyte cell population (s), the vector further comprises a promoter wherein the promoter is an inducible promoter, a tissue specific promoter, a constitutive promoter, a suicide promoter or any combination thereof.

In yet another embodiment of the CARs (either with or without one or more booster elements) used in the patient-specific autologous anti-tumor lymphocyte cell population (s), the vector expressing the CAR (either with or without one or more booster elements) can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR (either with or without one or more booster elements) can be further modified to express an enzyme such thymidine kinase (TK) or cytosine deaminase (CD).

In another aspect of the CARs (either with or without one or more booster elements) used in the patient-specific autologous anti-tumor lymphocyte cell population(s), host cells including the nucleic acid molecule(s) encoding the CARs (either with or without one or more booster elements) are also provided. In some embodiments, the host cell is a T cell, such as a primary T cell obtained from a subject. In one embodiment, the host cell is a CD8+ T cell. In one embodiment the host cell is a CD4+ T cell. In one embodiment the host cells are selected CD4+ and CD8+ lymphocytes purified directly from a patient product without regard to proportionality. In another embodiment the number of CD4+ and CD8+ T cells in the product are specific. In another embodiment specific subsets of T cells are utilized as identified by phenotypic markers including T naïve cells (Tn), T effector memory cells (Tem), T central memory cells (Tcm), T regulatory cells (Treg), induced T regulatory cells (iTreg), T suppressor cells (Ts), T stem cell memory cells (Tscm), Natural Killer (NK) cells, invariant Natural Killer T (iNKT) cells, and lymphokine activated killer (LAK) cells.

In one embodiment, as used herein, invariant Natural Killer T cells are a small population of αβ T lymphocytes highly conserved from mice to humans. iNKT cells have been suggested to play important roles in regulating many diseases, including cancer, infections, allergies, and autoimmunity. When stimulated, iNKT cells rapidly release a large amount of effector cytokines like IFN-γ and IL-4, both as a cell population and at the single-cell level. These cytokines then activate various immune effector cells, such as natural killer (NK) cells and dendritic cells (DCs) of the innate immune system, as well as CD4 helper and CD8 cytotoxic conventional as T cells of the adaptive immune system via activated DCs. Because of their unique activation mechanism, iNKT cells can attack multiple diseases independent of antigen- and MHC-restrictions, making them attractive universal therapeutic agents. Notably, because of the capacity of effector NK cells and conventional αβ T cells to specifically recognize diseased tissue cells, iNKT cell-induced immune reactions result in limited off-target side effects.

In one aspect, a pharmaceutical composition is provided comprising an anti-tumor effective amount of a population of human T cells comprising novel single, tandem, or multi-targeting CAR constructs, or any combination thereof, comprising a CAR molecule followed by one or more 2A sequences, in frame to one or more armor molecules, one or more extracellular matrix enzymes, one or more chemokine receptors, one or more stroma-targeting molecules, one or more tumor microenvironment (TME)-digestive elements, one or more switch tag elements, one or more chemo attractive-receptors, one or more chemotactic molecule secretors, one or more switches, and/or one or more cytokines, or any combination thereof: and a pharmaceutically acceptable excipient, wherein the boosted CARs are used to genetically modify one or more human T cell lymphocyte populations.

In yet another embodiment, a pharmaceutical composition is provided comprising an anti-tumor effective amount of an immunotherapy composition comprising a population of patient-specific autologous anti-tumor lymphocyte cell population(s) of a human having a cancer, wherein the cells of the population include cells comprising nucleic acid molecules encoding at least two vectors, each vector encoding a functional CAR (either with or without one or more booster elements), whereby the combination of vectors results in the expression of two or more non-identical binding domains, wherein each vector encoded binding domain(s) are covalently linked to a transmembrane domain and one or more non-identical intracellular signaling motifs.

In yet another embodiment, a pharmaceutical composition is provided comprising an anti-tumor effective amount of an immunotherapy composition comprising a population of patient-specific autologous anti-tumor lymphocyte cell population(s) of a human having a cancer, wherein the cells of the population include cells comprising (a) nucleic acid molecules encoding two or more vectors; (b) wherein each vector encodes a functional CAR (either with or without one or more booster elements); (c) wherein each CAR (either with or without one or more booster elements) comprises of at least one binding domain, at least one transmembrane domain, at least one linker domain, and at least one intracellular signaling motif; (d) wherein the at least one binding domains in one of the vectors are non-identical; and (e) wherein the at least one binding domain, a single transmembrane domain, at least one linker domain, and at least one intracellular signaling motif are covalently linked in each said vector, wherein the combination of vectors are used to genetically modify one or more lymphocyte populations.

In yet another embodiment, a pharmaceutical composition is provided comprising an anti-tumor effective amount of an immunotherapy composition comprising a population of patient-specific autologous anti-tumor lymphocyte cell population(s) of a human having a cancer, wherein the cells of the population include cells comprising (a) nucleic acid molecules encoding two or more vectors; (b) wherein each vector encodes a functional CAR (either with or without one or more booster elements); (c) wherein each CAR (either with or without one or more booster elements) comprises at least one binding domain, at least one transmembrane domain, at least one linker domain, and at least one intracellular signaling motif, (d) wherein the at least one binding domain(s) in each vector are non-identical; (e) wherein the at least one signaling motif combinations are non-identical between each of the vectors; and (f) wherein the at least one binding domain, a single transmembrane domain, at least one linker domain, and at least one intracellular signaling motif are covalently linked in each said vector, wherein the combination of two or more vectors are used to genetically modify one or more lymphocyte populations.

In one embodiment, the cancer is a refractory cancer non-responsive to one or more chemotherapeutic agents. The cancer includes hematopoietic cancer, myelodysplastic syndrome, pancreatic cancer, head and neck cancer, cutaneous tumors, minimal residual disease (MRD) in acute lymphoblastic leukemia (ALL), acute myeloid leukemia (AML), lung cancer, breast cancer, ovarian cancer, prostate cancer, colon cancer, melanoma or other hematological cancer and solid tumors, or any combination thereof. In another embodiment, the cancer includes a hematological cancer such as leukemia (e.g., chronic lymphocytic leukemia (CLL), acute lymphocytic leukemia (ALL), acute myeloid leukemia (AML), or chronic myelogenous leukemia (CML), lymphoma (e.g., mantle cell lymphoma, non-Hodgkin's lymphoma or Hodgkin's lymphoma) or multiple myeloma, or any combination thereof.

In yet another embodiment, the cancer includes an adult carcinoma comprising coral and pharynx cancer (tongue, mouth, pharynx, head and neck), digestive system cancers (esophagus, stomach, small intestine, colon, rectum, anus, liver, intrahepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In another aspect, a pharmaceutical composition is provided comprising an autologous lymphocyte cell population transduced with two or more lentiviral vectors encoding single or multiple chimeric antigen receptors (DuoCARs) (either with or without one or more booster elements), thereby generating a patient-specific autologous anti-tumor lymphocyte cell population capable of promoting in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In another aspect, a pharmaceutical composition is provided comprising an autologous T cell population transduced with one or more lentiviral vectors encoding single or multiple chimeric antigen receptors (DuoCARs) (either with or without one or more booster elements) to generate an patient-specific autologous anti-tumor lymphocyte cell population capable of promoting in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In another aspect, methods of making active patient-specific autologous anti-tumor Duo (either with or without one or more booster elements) CAR-containing lymphocyte cells are provided. The methods include transducing a lymphocyte cell with two or more vectors or nucleic acid molecule encoding two or more chimeric antigen receptors (DuoCARs) (either with or without one or more booster elements) that specifically bind an antigen, thereby making active patient-specific autologous anti-tumor DuoCAR-containing lymphocyte cells.

In yet another aspect, a method of generating a population of RNA-engineered lymphocyte cells is provided that comprises introducing an in vitro transcribed RNA or synthetic RNA of a nucleic acid molecule encoding a two or more chimeric antigen receptors (DuoCARs) (either with or without one or more booster elements) into a cell population of a subject, thereby generating an patient-specific autologous anti-tumor lymphocyte cell population capable of promoting in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In another aspect, a method is provided for treating a mammal having a disease, disorder or condition associated with an elevated expression of a tumor antigen, the method comprising administering to the subject a pharmaceutical composition comprising an anti-tumor effective amount of an autologous lymphocyte cell population transduced with one or more lentiviral vectors encoding single or multiple chimeric antigen receptors (DuoCARs) (either with or without one or more booster elements) thereby generating an patient-specific autologous anti-tumor lymphocyte cell population capable of promoting in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In another aspect, a method is provided for treating a mammal having a disease, disorder or condition associated with an elevated expression of a tumor antigen, the method comprising administering to the subject a pharmaceutical composition comprising an anti-tumor effective amount of an autologous lymphocyte cell population transduced with two or more lentiviral vectors encoding single or multiple chimeric antigen receptors (DuoCARs) (either with or without one or more booster elements) to generate an patient-specific autologous anti-tumor lymphocyte cell population which can be infused directly back into the patient to promote in vivo expansion, persistence of patient-specific anti-tumor T-cells resulting in tumor stabilization, reduction, elimination, or remission of cancer, or prevention or amelioration of relapse of cancer, or any combination thereof, in a patient-specific manner.

In one embodiment, a method is provided for treating a mammal having a disease, disorder or condition associated with an elevated expression of a tumor antigen, the method comprising administering to the subject a pharmaceutical composition comprising at least two vectors, each vector encoding a functional CAR (DuoCARs) (either with or without one or more booster elements), whereby the combination of vectors results in the expression of two or more non-identical binding domains, wherein each vector encoded binding domain(s) are covalently linked to a transmembrane domain and one or more non-identical intracellular signaling motifs, and a pharmaceutically acceptable excipient, wherein the combination of vectors are used to genetically modify one or more lymphocyte populations.

In another embodiment, a method is provided for treating a mammal having a disease, disorder or condition associated with an elevated expression of a tumor antigen, the method comprising administering to the subject a pharmaceutical composition comprising (a) nucleic acid molecules encoding two or more vectors; (b) wherein each vector encodes a functional DuoCAR (either with or without one or more booster elements); (c) wherein each CAR (either with or without one or more booster elements) comprises of at least one binding domain, at least one transmembrane domain, and at least one intracellular signaling motif; (d) wherein the at least one binding domains in one of the vectors are non-identical; and (e) wherein the at least one binding domain, a single transmembrane domain, and at least one intracellular signaling motif are covalently linked in each said vector, wherein the combination of vectors are used to genetically modify one or more lymphocyte populations.

In yet another embodiment, a method is provided for treating a mammal having a disease, disorder or condition associated with an elevated expression of a tumor antigen, the method comprising administering to the subject a pharmaceutical composition comprising (a) nucleic acid molecules encoding two or more vectors; (b) wherein each vector encodes a functional DuoCAR (either with or without one or more booster elements); (c) wherein each CAR (either with or without one or more booster elements) comprises at least one binding domain, at least one transmembrane domain, and at least one intracellular signaling motif; (d) wherein the at least one binding domain(s) in each vector are non-identical; (e) wherein the at least one signaling motif combinations are non-identical between each of the vectors; and (f) wherein the at least one binding domain, a single transmembrane domain, and at least one intracellular signaling motif are covalently linked in each said vector, wherein the combination of two or more vectors are used to genetically modify one or more lymphocyte populations.

In certain embodiments, the genetically modified lymphocytes are autologous T cell lymphocytes, and wherein the autologous or allogeneic T cell lymphocytes are infused directly back into the patient so as to prevent or ameliorate relapse of malignant disease.

In certain other embodiments, the genetically modified lymphocytes are autologous T cell lymphocytes, and wherein the autologous lymphocytes are infused directly back into the patient to promote in vivo expansion, persistence of patient-specific anti-tumor T-cell lymphocytes resulting in tumor stabilization, reduction, elimination, or remission of cancer, or prevention or amelioration of relapse of cancer, or any combination thereof, in a patient-specific manner.

In yet another embodiment, the T cell has been preselected by virtue of expressing specific activation or memory-associated surface markers.

In yet another embodiment, the T cell is derived from a hematopoietic stem cell donor, and wherein the procedure is carried out in the context of hematopoietic stem cell transplantation.

In certain embodiments, a method is provided wherein the lymphocyte cell has been preselected by virtue of expressing specific activation or memory-associated surface markers.

In certain embodiments, a method is provided herein wherein the lymphocyte cell is a T cell and is derived from a hematopoietic stem cell donor, and wherein the procedure is carried out in the context of hematopoietic stem cell transplantation.

In yet another aspect, a method is provided for generating a persisting population of genetically engineered patient-specific autologous anti-tumor lymphocyte cell population (s) in a human diagnosed with cancer. In one embodiment, the method comprises administering to a human patient in need thereof one or more patient-specific autologous anti-tumor lymphocyte cell population(s) described herein, wherein the persisting population of patient-specific autologous anti-tumor lymphocyte cell population(s), or the population of progeny of the lymphocyte cells, persists in the human for at least one month, two months, three months, four months, five months, six months, seven months, eight months, nine months, ten months, eleven months, twelve months, two years, or three years after administration.

In one embodiment, the progeny lymphocyte cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using a patient-specific autologous anti-tumor lymphocyte cell population(s) comprising one or more of the DuoCAR (either with or without one or more booster elements) immunotherapeutic compositions as disclosed herein.

In yet another aspect, a kit is provided for making a DuoCAR immunotherapeutic composition (either with or without one or more booster elements) comprising a patient-specific autologous anti-tumor lymphocyte cell population (s) as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

While the compositions and methods of the present invention have been illustrated with reference to the generation and utilization of DuoCARs (either with or without one or more booster elements), it is contemplated herein that the compositions and methods are specifically intended to include the generation and utilization of TrioCARs and QuatroCARs (either with or without one or more booster elements).

In yet another aspect, an immunotherapy composition comprising one or more isolated nucleic acids encoding at least one vector, wherein said vector contains a nucleic acid sequence that results in at least one messenger RNA (i.e., a multi-cistronic nucleic acid or a nucleic acid resulting in more than one transcript) encoding a DuoCAR (either with or without one or more booster elements), resulting in the ability to bind two or more non-identical antigen targets, thereby generating multiple antigen specificities residing in a single cell expressing said vector.

In yet another aspect, an immunotherapy composition comprising one or more isolated nucleic acids encoding at least two vectors, as described supra, wherein each vector further encodes a functional tag or anti-tag binding moiety (AT-CAR) (either with or without one or more booster elements) that reconstitutes a functional chimeric antigen receptor upon co-incubation or co-administration of a soluble binder (such as a tagged scFv, or a scFv linked to an anti-tag binder), whereby the combination of the two vectors results in the ability to bind two or more non-identical antigen binding domains, resulting in multiple antigen specificities residing in a cell expressing these two vectors.

In yet another aspect, an immunotherapy composition comprising one or more isolated nucleic acids encoding at least two vectors, as described supra, wherein each vector encoding a functional tag or anti-tag binding moiety (AT-CAR) (either with or without one or more booster elements) that reconstitutes a functional chimeric antigen receptor upon co-incubation or co-administration of a soluble binder (such as a tagged scFv, or a scFv linked to an anti-tag binder), wherein each vector expresses a unique tag (or anti-tag) that can bind soluble protein or protein modified structures resulting in multiple antigen specificities, or wherein each vector expresses a unique tag (or anti-tag) that binds only one of the soluble binding domains resulting in a specific linkage of the AT-CAR (either with or without one or more booster elements) encoded intracellular signaling motifs to the antigen-binding domains of the tagged (or anti-tagged) binder.

In a non-limiting embodiment for the manufacture of DuoCAR vectors (either with or without one or more booster elements), each of the compositions and methods disclosed in the embodiments and aspects referred to supra, the two vectors can be made separately and then added to the T cells sequentially or at the same time. In another non limiting embodiment, the plasmid DNA of the two or more vectors can be combined before or during transfection of production cells, or integrated in the production cells genome, to produce a mixture of viral vectors that contain the multiple DuoCAR (either with or without one or more booster elements) vector particles, subsequently used for the transduction and genetic modification of patient T Cells.

In each of the aforementioned aspects and embodiments described supra, for example, scFv binders have been created for mesothelin, as disclosed in Applicant's issued U.S. Pat. No. 10,183,993, entitled Compositions and Methods for Treating Cancer with Anti-Mesothelin Immunotherapy, and assigned Lentigen Technology, Inc. matter number LEN_017, nucleotide sequence ScFv antigen SEQ ID NO: 149 and amino acid sequence SEQ ID NO: 150, respectively, that can be incorporated into functional CARs, nucleotide sequence SEQ ID NO: 39 and amino acid sequence SEQ ID NO: 40, respectively, and that can thereby be incorporated into a DuoCAR therapy.

In each of the aforementioned aspects and embodiments described supra, in addition to scFv sequences, single chain antigen binders (as opposed to scFv) can be incorporated into a single, tandem, DuoCAR, or multi-targeting CAR application. For example, the CD33-specific heavy chain only binder, as disclosed in Applicant's issued U.S. Pat. No. 10,426,797, entitled Compositions and Methods For Treating Cancer With Anti-CD33 Immunotherapy, and assigned Lentigen Technology, Inc. matter number LEN_018, nucleotide sequence SEQ ID NO: 41 and amino acid sequence SEQ ID NO: 42, respectively, can be incorporated into a functional CAR, LTG1906, nucleotide sequence SEQ ID NO: 43 and amino acid sequence SEQ ID NO: 44, respectively, that targets CD33-expressing malignancies.

In each of the aforementioned aspects and embodiments described supra, one example of a single, tandem, DuoCAR, or multi-targeting CAR therapeutic application would be the treatment of leukemia that expresses the CD19, CD20, and TSLPR antigens. In this case, LTG1496 or LTG1497 (SEQ ID NOs: 35, 26, respectively) could be combined with a TSLPR-specific CAR (LTG1789), SEQ ID NO: 47 and amino acid sequence SEQ ID NO: 48, respectively, that had been created from TSLPR-specific scFV domains, nucleotide sequence SEQ ID NO: 45 and amino acid sequence SEQ ID NO: 46.

In each of the aforementioned aspects and embodiments described supra, another example of a single, tandem, DuoCAR, or multi-targeting CAR therapeutic application would be the treatment of cancer that expresses the CD38 antigen. For instance, the CD38-specific binders, as disclosed in Applicant's issued U.S. Pat. No. 11,103,533; entitled Compositions and Methods For Treating Cancer With Anti-CD38 Immunotherapy; as filed on Nov. 30, 2018; and assigned Lentigen Technology, Inc. matter number LEN_026; can be incorporated into one or more functional CARs that target CD38-expressing malignancies, as disclosed in Applicant's issued U.S. Pat. No. 11,103,533, the entirety of which is incorporated by reference herein.

In each of the aforementioned aspects and embodiments described supra, another example of a single, tandem, DuoCAR, or multi-targeting CAR therapeutic application would be the treatment of cancer that expresses the CD123 antigen. For instance, the CD123-specific binders, as disclosed in Applicant's issued U.S. Pat. No. 10,844,128; entitled Compositions and Methods For Treating Cancer With Anti-CD123 Immunotherapy; as filed on Sep. 20, 2019; and assigned Lentigen Technology, Inc. matter number LEN_024; and claiming priority to Provisional Patent Application No. 62/734,106; as filed on Sep. 20, 2018; can be incorporated into one or more functional CARs that target CD123-expressing malignancies, as disclosed in Applicant's issued U.S. Pat. No. 10,844,128, the entirety of which is incorporated by reference herein.

In each of the aforementioned aspects and embodiments described supra, another example of a single, tandem, DuoCAR, or multi-targeting CAR therapeutic application would be the treatment of cancer that expresses the CD123 antigen. For instance, the CD123-specific binders, as disclosed in Applicant's U.S. co-pending patent application Ser. No. 17/685,132; entitled Compositions and Methods For Treating Cancer With Anti-CD123 Immunotherapy; as filed on Mar. 2, 2022; and assigned Lentigen Technology, Inc. matter number MBG_99; can be incorporated into one or more functional CARs that target CD123-expressing malignancies, as disclosed in Applicant's co-pending U.S. patent application Ser. No. 17/685,132, the entirety of which is incorporated by reference herein.

In each of the aforementioned aspects and embodiments described supra, another example of a single, tandem, DuoCAR, or multi-targeting CAR therapeutic application would be the treatment of cancer that expresses the BCMA antigen. For instance, the BCMA-specific binders, as disclosed in Applicant's issued U.S. Pat. No. 11,052,112; entitled Fully Human BCMA CART Cells for the Treatment of Multiple Myeloma and Other BCMA-Positive Malignancies; as filed on May 30, 2019; and assigned Lentigen Technology, Inc. matter number MBG_13; can be incorporated into one or more functional CARs that target BCMA-expressing malignancies, as disclosed in Applicant's issued U.S. Pat. No. 11,052,112, the entirety of which is incorporated by reference herein.

In each of the aforementioned aspects and embodiments described supra, examples of tandem-CARs (containing 2 scFv domains, as described in nucleotide sequence SEQ ID: 23 and amino acid sequence SEQ ID:24) on which this technology is based include the CD20_CD19 CAR LTG1497, nucleotide sequence SEQ ID NO: 25 and amino acid sequence SEQ ID NO: 26. In some cases reversing the order of the two binders may provide a better DuoCAR expression in target cells. Thus, LTG1497, where the CD19 scFv is more proximal, as shown in nucleotide sequence SEQ ID NO: 25 and amino acid sequence SEQ ID NO: 26; and LTG1496 where the CD19 scFV is more distal to the membrane, as shown in nucleotide sequence SEQ ID NO: 33 and amino acid sequence SEQ ID NO: 34, can both be used as one of the members of a DuoSet comprising a DuoCAR.

In each of the aforementioned aspects and embodiments described supra, one or more of the above-identified novel boosted chimeric antigen receptors (CARs) provided supra with respect to each of the aforementioned of applicant's co-pending patent applications or issued patents SEQ ID NOs: 23, 24, 25, 26, 33, 34, 35, 41, 42, 43, 44, 45, 46, 47, and 48 may comprise either a single, tandem, or multi-targeting CAR construct (including those in a DuoCARformal), or any combination thereof.

In each of the aforementioned aspects and embodiments described supra, Applicant's co-pending patent applications and/or issued patents demonstrate one or more additional characteristics of the DuoCAR constructs, including, for example, i) despite the reduction in MFI of the larger payload constructs, multi-targeting in the DuoCAR format was superior in tumor cell killing as compared to monoCAR targeting; ii) mesothelin boosted CARs with mbIL7 showed superior, antigen-dependent target cell killing as compared to the non-boosted mesothelin CARs; iii) in addition, the mIL7 boosted DuoCARs and tandem CARs demonstrated superior target killing as compared to the non-boosted CARs counterparts; iv) in addition mIL7-boosted DuoCARs and Tandem CARs demonstrated superior cytokine elaboration in response to tumor antigen, greater long-term persistence and expansion under cytokine-poor conditions, and better preservation of effector function; v) mesothelin CARs boosted with TGFBRIIdn armor demonstrated robust transduction an expansion in culture, and robust killing of tumor lines expressing high, medium or low levels of mesothelin, despite the armor payload; and/or vi) mesothelin and ROR1 CARs with HPSE booster effectively digested the ECM in a transwell migration assay, and/or any combination thereof.

A. Chimeric Antigen Receptors (as Present in Single, Tandem, DuoCARs, Multiple-Targeting CARs, Either with or without One or More Boosters)

A CAR is an artificially constructed hybrid protein or polypeptide containing the antigen binding domains of an antibody (e.g., single chain variable fragment (scFv)) linked to T-cell signaling domains via a transmembrane domain. Characteristics of DuoCARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing DuoCARs the ability to recognize antigen independent of antigen processing, thus bypassing a major mechanism of tumor escape. Moreover, when expressed in T-cells, DuoCARs advantageously do not dimerize with endogenous T cell receptor (TCR) alpha and beta chains.

As disclosed herein, the intracellular T cell signaling domains of the DuoCARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen. In some instances, the activation domains can be attenuated by the mutation of specific sites of phosphorylation, i.e. the ITAM motifs in the CD3 zeta chain, thus carefully modulating the degree of signal transduction mediated by that domain.

1. Extracellular Domain

In one embodiment, the single, tandem, DuoCAR, or multiple-targeting CAR (with or without one or more boosting elements) used in the patient-specific autologous anti-tumor lymphocyte cell population(s) as disclosed herein, comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in the single, tandem, DuoCAR, or multiple-targeting CAR (with or without one or more boosting elements) include those associated with viral, bacterial and parasitic infections, autoimmune disease, alloimmune disease, autoaggressive disease and cancer cells.

In one embodiment, the single, tandem, DuoCAR, or multiple-targeting CAR (with or without one or more boosting elements) can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens are well known in the art and include, for example, a glioma-associated antigen, carcinoembryonic antigen (CEA), beta-human chorionic gonadotropin, alpha-fetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I receptor, IGF-II receptor, IGF-I receptor, CD19, CD20, CD22, ROR1, mesothelin, CD33/IL3Ra, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, GD2, GD3, GM2, Ley, polysialic acid, fucosyl GM1, GM3, Tn, STn, sLe(animal), GloboH, CD5, CD7, CD19, CD20, CD22, CD25, CD37, CD30, CD33, CD38, CD123, CD45, CAMPATH-1, BCMA, CS-1, PD-L1, CD276/B7-H3, B7-H4, B7-DC, HLA-DR carcinoembryonic antigen (CEA), TAG-72, EpCAM, folate-binding protein, folate receptor alpha (FOLR1), folate receptor beta (FOLR2), A33, G250, pro state-specific membrane antigen (PSMA), ferritin, CA-125, CA19-9, CD44v6, epidermal growth factor, p185, IL-2 receptor, interleukin 1 receptor accessory protein (IL1RAP), EGFRvIII (de2-7), fibroblast activation protein, tenascin, a metalloproteinase, endosialin, vascular endothelial growth factor, αvβ3, WT1, LMP2, HPV E6, HPV E7, Her-2/neu, p53 nonmutant, NY-ESO-1, MelanA/MART 1, Ras mutant, gp100, FGFR1, FGFR2, FGFR3, FGFR4, GPC1, GPC2, GPC3, p53 mutant, PR1, bcr-abl, tyrosinase, survivin, PSA, hTERT, a Sarcoma translocation breakpoint fusion protein, EphA2, PAP, ML- IAP, AFP, ERG, NA17, PAX3, ALK, androgen receptor, cyclin B 1, MYCN, RhoC, TRP-2, mesothelin, PSCA, MAGE A1, MAGE A3, CYP1B 1, PLAV1, BORIS, ETV6-AML, NY-BR-1, RGS5, SART3, Carbonic anhydrase IX, PAX5, OY-TES 1, Sperm protein 17, LCK, HMWMAA, AKAP-4, SSX2, XAGE 1, B7H3, Legumain, Tie 3, PAGE4, VEGFR2, MAD-CT-1, PDGFR-B, MAD-CT-2, TRAIL 1, MUC1, MUC16/CA125, MAGE A4, MAGE C2, GAGE, EGFR, EGFR1, EGFR2/Her2, CMET, HER3, CA6, NAPI2B, TROP2, TEM1, TEM7, TEM8, FAP, LAP, CLDN3, CLDN6, CLDN8, CLDN16, CLDN18.2, RON, LY6E, DLL3, PTK7, UPK1B, STRA6, TMPRSS3, TMRRSS4, TMEM238, Clorfl86, LIV1, ROR1, ROR2, Fos-related antigen 1, VEGFR1, endoglin, CD90, CD326, CD70, SSEA4, CD318, CLA, TSPAN8, GPRC5D, EpCAM, Thy1, IL13Ra2, BDCA1, BDCA2, BDCA3, GD2, PSMA, FAP, CLL1, SLAMF7/CS1, CD147, DPPA5, GRP78, CD66c, VISTA, LRRC5, LRRC15, or any combinations thereof or a fragment thereof is provided, wherein the antibody or a fragment thereof comprises a fragment selected from the group consisting of an Fab fragment, an F(ab')2 fragment, an Fv fragment, a nanobody, a VHH, a ligand peptide, and a single chain Fv (ScFv), or a fragment of any of the preceding, or a molecule that is at least 80%, 85%, 90%, 95%, 96%, 97%, 98% or 99% homologous to any of the preceding, or any combination thereof. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20, CD22, and CD37 are other candidates for target antigens in B-cell lymphoma. Some of these antigens (CEA, HER-2, CD19, CD20, CD22, idiotype) have been used as targets for passive immunotherapy with monoclonal antibodies with limited success.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells, but which are expressed at much higher levels on tumor cells.

Non-limiting examples of TSAs or TAAs include the following: Differentiation antigens such as MART-1/MelanA (MART-1), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3CA 27.29BCAA, CA 195, CA 242, CA-50, CAM43, CD68\P1, CO-029, FGF-5, G250, Ga733EpCAM, HTgp-175, M344, MA-50, MG7-Ag, MOV18, NB/70K, NY-CO-1, RCAS1, SDCCAG16, TA-90Mac-2 binding proteincyclophilin C-associated protein, TAAL6, TAG72, TLP, and TPS.

In a preferred embodiment, the antigen binding domain portion of the single, tandem, DuoCAR, or multiple-targeting CAR (with or without one or more boosting elements) targets an antigen that includes but is not limited to CD19, CD20, CD22, ROR1, mesothelin, CD33/IL3Ra, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, GD2, GD3, GM2, Ley, polysialic acid, fucosyl GM1, GM3, Tn, STn, sLe(animal), GloboH, CD5, CD7, CD19, CD20, CD22, CD25, CD37, CD30, CD33, CD38, CD123, CD45, CAMPATH-1, BCMA, CS-1, PD-L1, CD276/B7-H3, B7-H4, B7-DC, HLA-DR carcinoembryonic antigen (CEA), TAG-72, EpCAM, folate-binding protein, folate receptor alpha (FOLR1), folate receptor beta (FOLR2), A33, G250, pro state-specific membrane antigen (PSMA), ferritin, CA-125, CA19-9, CD44v6, epidermal growth factor, p185, IL-2 receptor, interleukin 1 receptor accessory protein (IL1RAP), EGFRvIII (de2-7), fibroblast activation protein, tenascin, a metalloproteinase, endosialin, vascular endothelial growth factor, $\alpha v\beta 3$, WT1, LMP2, HPV E6, HPV E7, Her-2/neu, p53 nonmutant, NY-ESO-1, MelanA/MART 1, Ras mutant, gp100, FGFR1, FGFR2, FGFR3, FGFR4, GPC1, GPC2, GPC3, p53 mutant, PR1, bcr-abl, tyrosinase, survivin, PSA, hTERT, a Sarcoma translocation breakpoint fusion protein, EphA2, PAP, ML-IAP, AFP, ERG, NA17, PAX3, ALK, androgen receptor, cyclin B 1, MYCN, RhoC, TRP-2, mesothelin, PSCA, MAGE A1, MAGE A3, CYP1B 1, PLAV1, BORIS, ETV6-AML, NY-BR-1, RGS5, SART3, Carbonic anhydrase IX, PAX5, OY-TES 1, Sperm protein 17, LCK, HMWMAA, AKAP-4, SSX2, XAGE 1, B7H3, Legumain, Tie 3, PAGE4, VEGFR2, MAD-CT-1, PDGFR-B, MAD-CT-2, TRAIL 1, MUC1, MUC16/CA125, MAGE A4, MAGE C2, GAGE, EGFR, EGFR1, EGFR2/Her2, CMET, HER3, CA6, NAPI2B, TROP2, TEM1, TEM7, TEM8, FAP, LAP, CLDN3, CLDN6, CLDN8, CLDN16, CLDN18.2, RON, LY6E, DLL3, PTK7, UPK1B, STRA6, TMPRSS3, TMRRSS4, TMEM238, Clorfl86, LIV1, ROR1, ROR2, Fos-related antigen 1, VEGFR1, endoglin, CD90, CD326, CD70, SSEA4, CD318, CLA, TSPAN8, GPRC5D, EpCAM, Thy1, IL13Ra2, BDCA1, BDCA2, BDCA3, GD2, PSMA, FAP, CLL1, SLAMF7/CS1, CD147, DPPA5, GRP78, CD66c, VISTA, LRRC5, LRRC15, or any combinations thereof or a fragment thereof is provided, wherein the antibody or a fragment thereof comprises a fragment selected from the group consisting of an Fab fragment, an F(ab')2 fragment, an Fv fragment, a nanobody, a VHH, a ligand peptide, and a single chain Fv (ScFv), or a fragment of any of the preceding, or a molecule that is at least 80%, 85%, 90%, 95%, 96%, 97%, 98% or 99% homologous to any of the preceding, or any combination thereof. In yet another embodiment, a single, tandem, DuoCAR, or multiple-targeting CAR (with or without one or more boosting elements) is provided herein comprising a Tag or anti-Tag binding domain.

Depending on the desired antigen to be targeted, the single, tandem, DuoCAR, or multiple-targeting CAR (with or without one or more boosting elements) can be engineered to include the appropriate antigen binding domain that is specific to the desired antigen target. For example, if CD19 is the desired antigen that is to be targeted, an antibody or the scFv subfragment thereof specific for CD19 can be used as the antigen bind domain incorporated into the single, tandem, DuoCAR, or multiple-targeting CAR (with or without one or more boosting elements).

In one exemplary embodiment, the antigen binding domain portion of the single, tandem, DuoCAR, or multiple-targeting CAR (with or without one or more boosting elements) targets CD19. Preferably, the antigen binding domain in the single, tandem, DuoCAR, or multiple-targeting CAR (with or without one or more boosting elements) is anti-CD19 scFV, wherein the nucleic acid sequence of the anti-CD19 scFV comprises the sequence set forth in SEQ ID NO: 27. In one embodiment, the anti-CD19 scFV comprises the nucleic acid sequence that encodes the amino acid sequence of SEQ ID NO: 28. In another embodiment, the anti-CD19 scFV portion of the single, tandem, DuoCAR, or multiple-targeting CAR (with or without one or more boosting elements) comprises the amino acid sequence set forth in SEQ ID NO: 28. In a second exemplary embodiment, the antigen binding domain of the single, tandem, DuoCAR, or multiple-targeting CAR (with or without one or more boosting elements) targets CD20. Preferably, the antigen binding domains in the single, tandem, DuoCAR, or multiple-targeting CAR (with or without one or more boosting elements) is anti-CD20 scFv, wherein the nucleic acid sequence of the anti-CD20 scFv comprises the sequence set forth in SEQ ID NO: 1. In another embodiment, the anti-CD20 scFV portion of the single, tandem, DuoCAR, or multiple-targeting CAR (with or without one or more boosting elements) comprises the amino acid sequence set forth in SEQ ID NO: 2. In a third exemplary embodiment, the antigen binding domain of the single, tandem, DuoCAR, or multiple-targeting CAR (with or without one or more boosting elements) targets CD22. Preferably, the antigen binding domains in the single, tandem, DuoCAR, or multiple-targeting CAR (with or without one or more boosting elements) is anti-CD22 scFv, wherein the nucleic acid sequence of the anti-CD22 scFv comprises the sequence set forth in SEQ ID NO: 7. In another embodiment, the anti-CD22 scFV portion of the single, tandem, DuoCAR, or multiple-targeting CAR (with or without one or more boosting elements) comprises the amino acid sequence set forth in SEQ ID NO: 8.

In one aspect of the present invention, there is provided a single, tandem, DuoCAR, or multiple-targeting CAR (with or without one or more boosting elements) capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a single, tandem, DuoCAR, or multiple-targeting CAR (with or without one or more boosting elements) capable of binding to an antigen derived from a bacterial strain of Staphylococci, *Streptococcus, Escherichia coli, Pseudomonas*, or *Salmonella*. Particularly, there is provided a single, tandem, DuoCAR, or multiple-targeting CAR (with or without one or more boosting elements) capable of binding to an antigen derived from an infectious bacterium, for example, *Helicobacter pyloris, Legionella* pneumophilia, a bacterial strain of Mycobacteria sps. (e.g. *M. tuberculosis, M. avium, M. intracellulare, M. kansaii*, or *M. gordonea*), *Staphylococcus aureus, Neisseria gonorrhoeae, Neisseria meningitides, Listeria monocytogenes, Streptococcus pyogenes*, Group A *Streptococcus*, Group B *Streptococcus* (*Streptococcus agalactiae*), *Streptococcus pneumoniae*, or *Clostridium tetani*, or a combination thereof.

2. Transmembrane Domain

In the single, tandem, DuoCAR, multiple-targeting CAR (with or without one or more boosting elements) used in the patient-specific autologous anti-tumor lymphocyte cell population(s) as disclosed herein, the single, tandem, DuoCAR, or multiple-targeting CAR (with or without one or more boosting elements) comprises one or more transmembrane domains fused to the extracellular domain of the single, tandem, DuoCAR, or multiple-targeting CAR (with or without one or more boosting elements).

In one embodiment, an isolated nucleic acid molecule is provided wherein the encoded linker domain is derived from the extracellular domain of IgG1, IgG2, IgG3 or IgG4, CD8, TNFRSF19, or CD28, and is linked to the transmembrane domain.

In one embodiment, an isolated nucleic acid molecule is provided wherein the encoded linker domain is derived from the extracellular domain of the transmembrane domain and is linked to the transmembrane domain.

In some instances, the transmembrane domain can be selected or by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, CD271, TNFRSF19, Fc epsilon R, or any combination thereof. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the single, tandem, DuoCAR, or multiple-targeting CAR (with or without one or more boosting elements). A glycine-serine doublet or a triple alanine motif provides a particularly suitable linker.

In one embodiment, the transmembrane domain in the single, tandem, DuoCAR, or multiple-targeting CAR (with or without one or more boosting elements) of the invention is the CD8 transmembrane domain. In one embodiment, the CD8 transmembrane domain comprises the nucleic acid sequence of SEQ ID NO: 11. In one embodiment, the CD8 transmembrane domain comprises the nucleic acid sequence that encodes the amino acid sequence of SEQ ID NO: 12. In another embodiment, the CD8 transmembrane domain comprises the amino acid sequence of SEQ ID NO: 12.

In some instances, the transmembrane domain of the single, tandem, DuoCAR, or multiple-targeting CAR (with or without one or more boosting elements) comprises the CD8.alpha.hinge domain. In one embodiment, the CD8 hinge domain comprises the nucleic acid sequence of SEQ ID NO: 13. In one embodiment, the CD8 hinge domain comprises the nucleic acid sequence that encodes the amino acid sequence of SEQ ID NO: 14. In another embodiment, the CD8 hinge domain comprises the amino acid sequence of SEQ ID NO: 14.

Without being intended to limit to any particular mechanism of action, it is believed that possible reasons for the enhanced therapeutic function associated with the exemplary single, tandem, DuoCAR, multiple-targeting CAR (with or without one or more boosting elements) used in the patient-specific autologous anti-tumor lymphocyte cell population(s) as disclosed herein of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

In one embodiment of the patient-specific autologous anti-tumor lymphocyte cell population(s) as disclosed herein, non-limiting exemplary transmembrane domains for use in the single, tandem, DuoCAR, multiple-targeting CARs (with or without one or more boosting elements) disclosed herein include the TNFRSF16 and TNFRSF19 transmembrane domains may be used to derive the TNFRSF transmembrane domains and/or linker or spacer domains as disclosed in Applicant's issued U.S. Pat. No. 10,421,810, entitled CHIMERIC ANTIGEN RECEPTORS AND METHODS OF USE, as filed on Oct. 9, 2015, and assigned Lentigen Technology, Inc. matter number LEN_015PRO, including, in particular, those other TNFRSF members listed within the tumor necrosis factor receptor superfamily as listed in Table 1 therein.

3. Spacer Domain

In the single, tandem, DuoCAR, multiple-targeting CAR (with or without one or more boosting elements) used in the patient-specific autologous anti-tumor lymphocyte cell population(s) as disclosed herein, a spacer domain can be arranged between the extracellular domain and the TNFRSF transmembrane domain, or between the intracellular domain and the TNFRSF transmembrane domain. The spacer domain means any oligopeptide or polypeptide that serves to link the TNFRSF transmembrane domain with the extracellular domain and/or the TNFRSF transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a single, tandem, DuoCAR, or multiple-targeting CAR (with or without one or more boosting elements) with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 137 to 206 (SEQ ID NO: 15) which includes the hinge region of CD8.alpha. (NCBI RefSeq: NP.sub.—001759.3), amino acid numbers 135 to 195 of CD8.beta. (GenBank: AAA35664.1), amino acid numbers 315 to 396 of CD4 (NCBI RefSeq: NP.sub.—000607.1), or amino acid numbers 137 to 152 of CD28 (NCBI RefSeq: NP.sub.—006130.1) can be used. Also, as the spacer domain, a part of a constant region of an antibody H chain or L chain (CHI region or CL region, for example, a peptide having an amino acid sequence shown in SEQ ID NO: 16) can be used. Further, the spacer domain may be an artificially synthesized sequence.

Further, in the single, tandem, DuoCAR, or multiple-targeting CAR (with or without one or more boosting elements), a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the single, tandem, DuoCAR, or multiple-targeting CAR (with or without one or more boosting elements). In one embodiment, the signal peptide comprises the nucleotide sequence of the leader (signal peptide) sequence shown in SEQ ID NO: 5. In one embodiment, the signal peptide comprises the amino acid sequence shown in SEQ ID NO: 6.

4. Intracellular Domain

The cytoplasmic domain or otherwise the intracellular signaling domain of the single, tandem, DuoCAR, or multiple-targeting CAR (with or without one or more boosting elements) is responsible for activation of at least one of the normal effector functions of the immune cell in which the single, tandem, DuoCAR, or multiple-targeting CAR (with or without one or more boosting elements) has been placed in. The term "effector function" refers to a specialized function of a cell. Effector function of a T cell, for example, may be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the single, tandem, DuoCAR, or multiple-targeting CAR (with or without one or more boosting elements) include the cytoplasmic sequences of the T cell receptor (TCR) and co-receptors that act in concert to initiate signal transduction following antigen receptor engagement, as well as any derivative or variant of these sequences and any synthetic sequence that has the same functional capacity.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the single, tandem, DuoCAR, multiple-targeting CARs (with or without one or more boosting elements) disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.—932170.1), amino acid numbers 45 to 86 of Fc.epsilon.RI.gamma. (NCBI RefSeq: NP.sub.—004097.1), amino acid numbers 201 to 244 of Fc.epsilon.RI.beta. (NCBI RefSeq. NP.sub.—000130.1), amino acid numbers 139 to 182 of CD3.gamma. (NCBI RefSeq: NP.sub.—000064.1), amino acid numbers 128 to 171 of CD3.delta. (NCBI RefSeq: NP.sub.—000723.1), amino acid numbers 153 to 207 of CD3.epsilon. (NCBI RefSeq: NP.sub.—000724.1), amino acid numbers 402 to 495 of CD5 (NCBI RefSeq: NP.sub.—055022.2), amino acid numbers 707 to 847 of 0022 (NCBI RefSeq: NP.sub.—001762.2), amino acid numbers 166 to 226 of CD79a (NCBI RefSeq: NP.sub.—001774.1), amino acid numbers 182 to 229 of CD79b (NCBI RefSeq: NP.sub.—000617.1), and amino acid numbers 177 to 252 of CD66d (NCBI RefSeq: NP.sub.—001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the single, tandem, DuoCAR, or multiple-targeting CAR (with or without one or more boosting elements) comprises a cytoplasmic signaling sequence derived from CD3 zeta. In another embodiment one, two, or three of the ITAM motifs in CD3 zeta are attenuated by mutation or substitution of the tyrosine residue by another amino acid.

In a preferred embodiment, the intracellular domain of the single, tandem, DuoCAR, or multiple-targeting CAR (with or without one or more boosting elements) can be designed to comprise the CD3-zeta signaling domain by itself or combined with any other desired cytoplasmic domain(s) useful in the context of the single, tandem, DuoCAR, or multiple-targeting CAR (with or without one or more boosting elements). For example, the intracellular domain of the single, tandem, DuoCAR, or multiple-targeting CAR (with or without one or more boosting elements) can comprise a CD3 zeta chain portion and a costimulatory signaling region. The costimulatory signaling region refers to a portion of the single, tandem, DuoCAR, or multiple-targeting CAR (with or without one or more boosting elements) comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, 276/B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.—001758.2), amino acid numbers 421 to 458 of CD4 (NCBI RefSeq: NP.sub.—000607.1), amino acid numbers 402 to 495 of CD5 (NCBI RefSeq: NP.sub.—055022.2), amino acid numbers 207 to 235 of CD8.alpha. (NCBI RefSeq: NP.sub.—001759.3), amino acid numbers 196 to 210 of CD83 (GenBank: AAA35664.1), amino acid numbers 181 to 220 of CD28 (NCBI RefSeq: NP.sub.—006130.1), amino acid numbers 214 to 255 of CD137 (4-1BB, NCBI RefSeq: NP.sub.—001552.2), amino acid numbers 241 to 277 of CD134 (OX40, NCBI RefSeq: NP.sub.—003318.1), and amino acid numbers 166 to 199 of ICOS (NCBI RefSeq: NP.sub.—036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the single, tandem, DuoCAR, or multiple-targeting CAR (with or without one or more boosting elements) may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the single, tandem, DuoCAR, or multiple-targeting CAR (with or without one or more boosting elements) is designed to comprise the signaling domain of 4-1BB and the signaling domain of CD3-zeta, wherein the signaling domain of 4-1BB comprises the nucleic acid sequence set forth in SEQ ID NO: 17 and the signaling domain of CD3-zeta comprises the nucleic acid sequence set forth in SEQ ID NO: 19.

In one embodiment, the intracellular domain in the single, tandem, DuoCAR, or multiple-targeting CAR (with or without one or more boosting elements) is designed to comprise the signaling domain of 4-1BB and the signaling domain of CD3-zeta, wherein the signaling domain of 4-1BB comprises the nucleic acid sequence that encodes the amino acid sequence of SEQ ID NO: 18 and the signaling domain of CD3-zeta comprises the nucleic acid sequence that encodes the amino acid sequence of SEQ ID NO: 20.

In one embodiment, the intracellular domain in the single, tandem, DuoCAR, or multiple-targeting CAR (with or without one or more boosting elements) is designed to comprise the signaling domain of 4-1BB and the signaling domain of CD3-zeta, wherein the signaling domain of 4-1BB comprises the amino acid sequence set forth in SEQ ID NO: 18 and the signaling domain of CD3-zeta comprises the amino acid sequence set forth in SEQ ID NO: 20.

5. Additional Description of Single, Tandem, DuoCARs, Multiple-Targeting CARs (With or Without One or More Boosting Elements)

Also expressly included within the scope of the invention are functional portions of the single, tandem, DuoCARs, multiple-targeting CARs (with or without one or more boosting elements) used in the patient-specific autologous anti-tumor lymphocyte cell population(s) as disclosed herein. The term "functional portion" when used in reference to a single, tandem, DuoCAR, or multiple-targeting CAR (with or without one or more boosting elements) refers to any part or fragment of one or more of the single, tandem, DuoCARs, multiple-targeting CARs (with or without one or more boosting elements) disclosed herein, which part or fragment retains the biological activity of the single, tandem, DuoCAR, or multiple-targeting CAR (with or without one or more boosting elements) of which it is a part (the parent single, tandem, DuoCAR, multiple-targeting CAR (with or without one or more boosting elements)). Functional portions encompass, for example, those parts of a single, tandem, DuoCAR, or multiple-targeting CAR (with or without one or more boosting elements) that retain the ability to recognize target cells, or detect, treat, or prevent a disease, to a similar extent, the same extent, or to a higher extent, as the parent single, tandem, DuoCAR, multiple-targeting CAR (with or without one or more boosting elements). In reference to the parent single, tandem, DuoCAR, or multiple-targeting CAR (with or without one or more boosting elements), the functional portion can comprise, for instance, about 10%, 25%, 30%, 50%, 68%, 80%, 90%, 95%, or more, of the parent single, tandem, DuoCAR, or multiple-targeting CAR (with or without one or more boosting elements).

The functional portion can comprise additional amino acids at the amino or carboxy terminus of the portion, or at both termini, which additional amino acids are not found in the amino acid sequence of the parent single, tandem, DuoCAR, or multiple-targeting CAR (with or without one or more boosting elements). Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent single, tandem, DuoCAR, or multiple-targeting CAR (with or without one or more boosting elements).

Included in the scope of the disclosure are functional variants of the single, tandem, DuoCARs, multiple-targeting CARs (with or without one or more boosting elements) disclosed herein. The term "functional variant" as used herein refers to a single, tandem, DuoCAR, or multiple-targeting CAR (with or without one or more boosting elements), polypeptide, or protein having substantial or significant sequence identity or similarity to a parent single, tandem, DuoCAR, or multiple-targeting CAR (with or without one or more boosting elements), which functional variant retains the biological activity of the single, tandem, DuoCAR, or multiple-targeting CAR (with or without one or more boosting elements) of which it is a variant. Functional variants encompass, for example, those variants of the single, tandem, DuoCAR, or multiple-targeting CAR (with or without one or more boosting elements) described herein (the parent single, tandem, DuoCAR, or multiple-targeting CAR (with or without one or more boosting elements)) that retain the ability to recognize target cells to a similar extent, the same extent, or to a higher extent, as the parent single, tandem, DuoCAR, or multiple-targeting CAR (with or without one or more boosting elements). In reference to the parent single, tandem, DuoCAR, or multiple-targeting CAR (with or without one or more boosting elements), the functional variant can, for instance, be at least about 30%, 50%, 75%, 80%, 90%, 98% or more identical in amino acid sequence to the parent single, tandem, DuoCAR, or multiple-targeting CAR (with or without one or more boosting elements).

A functional variant can, for example, comprise the amino acid sequence of the parent single, tandem, DuoCAR, or multiple-targeting CAR (with or without one or more boosting elements) with at least one conservative amino acid substitution. Alternatively, or additionally, the functional variants can comprise the amino acid sequence of the parent single, tandem, DuoCAR, or multiple-targeting CAR (with or without one or more boosting elements) with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent single, tandem, DuoCAR, or multiple-targeting CAR (with or without one or more boosting elements).

Amino acid substitutions of the single, tandem, DuoCARs, multiple-targeting CARs (with or without one or more boosting elements) are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The single, tandem, DuoCAR, or multiple-targeting CAR (with or without one or more boosting elements) can consist essentially of the specified amino acid sequence or sequences described herein, such that other components, e.g., other amino acids, do not materially change the biological activity of the functional variant.

The single, tandem, DuoCARs, multiple-targeting CARs (with or without one or more boosting elements) (including functional portions and functional variants) can be of any length, i.e., can comprise any number of amino acids, provided that the single, tandem, DuoCARs, multiple-targeting CARs (with or without one or more boosting elements) (or functional portions or functional variants thereof) retain their biological activity, e.g., the ability to specifically bind to antigen, detect diseased cells in a mammal, or treat or prevent disease in a mammal, etc. For example, the single, tandem, DuoCAR, or multiple-targeting CAR (with or without one or more boosting elements) can be about 50 to about 5000 amino acids long, such as 50, 70, 75, 100, 125, 150, 175, 200, 300, 400, 500, 600, 700, 800, 900, 1000 or more amino acids in length.

The single, tandem, DuoCARs, multiple-targeting CARs (with or without one or more boosting elements) (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, a-aminocyclohexane carboxylic acid, a-aminocycloheptane carboxylic acid, a-(2-amino-2-norbornane)-carboxylic acid, γ-diaminobutyric acid, β-diaminopropionic acid, homophenylalanine, and a-tert-butylglycine.

The single, tandem, DuoCARs, multiple-targeting CARs (with or without one or more boosting elements) (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The single, tandem, DuoCARs, multiple-targeting CARs (with or without one or more boosting elements) (including functional portions and functional variants thereof) can be obtained by methods known in the art. The single, tandem, DuoCARs, multiple-targeting CARs (with or without one or more boosting elements) may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Methods of generating chimeric antigen receptors, T cells including such receptors, and their use (e.g., for treatment of cancer) are known in the art and further described herein (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., Trends Biotechnol., 29:550-557, 2011; Grupp et al., N Engl J Med., 368:1509-1518, 2013; Han et al., J. Hematol Oncol., 6:47, 2013; Tumaini et al., Cytotherapy, 15, 1406-1417, 2013; Haso et al., (2013) Blood, 121, 1165-1174; PCT Pubs. WO2012/079000, WO2013/126726; and U.S. Pub. 2012/0213783, each of which is incorporated by reference herein in its entirety). For example, a nucleic acid molecule encoding a disclosed chimeric antigen binding receptor can be included in an expression vector (such as a lentiviral vector) used to transduce a host cell, such as a T cell, to make the disclosed single, tandem, DuoCAR, or multiple-targeting CAR (with or without one or more boosting elements). In some embodiments, methods of using the chimeric antigen receptor include isolating T cells from a subject, transducing the T cells with an expression vector (such as a lentiviral vector) encoding the chimeric antigen receptor, and administering the single, tandem, DuoCAR, or multiple-targeting CAR (with or without one or more boosting elements)-expressing T cells to the subject for treatment, for example for treatment of a tumor in the subject.

6. Description of Boosting Elements (Boosters)

In addition to the aforementioned description provided supra, the booster elements of the single, tandem, DuoCARs, multiple-targeting CARs that may be used in the patient-specific autologous or allogeneic anti-tumor, anti-autoimmune, anti-alloimmune, or anti-autoaggressive-lymphocyte cell population(s) may additionally comprise functional percent identity variants thereof, as set forth below.

In one specific embodiment, also expressly included within the scope of the invention are functional boosting element portions of the single, tandem, DuoCARs, multiple-targeting CARs (with or without one or more boosting elements) used in the patient-specific autologous or allogeneic anti-tumor lymphocyte cell population(s) as disclosed herein. Boosting elements encompass, for example, additional therapeutic proteins or peptides expressed or secreted by the engineered T cell populations such as: i) one or more A-beta DPs (amyloid beta degrading proteases), ii) one or more matrix proteases (such as MMP-9 and MMP9), iii) one or more peptides or soluble antibody-like binders that interfere with plaque formation, iv) one or more cytokines (such as TGF-beta, IL-2, IL-4, IL-6, IL-7, IL-8, IL-9, IL-10, IL-11, IL-12, IL-15, IL-18, IL-21), v) one or more armor elements so as to overcome immunosuppression in TME, vi) one or more digestive enzymes to overcome the physical barrier of tumor stroma/extracellular matrix (ECM) and enable CAR T tumor penetration, vii) one or more pro-inflammatory immune activators, and viii) one or more on-switches or off-switches, or any combination thereof, to control the expression of the CAR, wherein the boosted CARs achieve a high surface expression on transduced T cells, a multi-targeting activity to overcome antigen escape, a high degree of cytolysis and transduced T cell in vivo expansion and persistence to promote in vivo expansion, persistence of patient-specific anti-tumor T-cells resulting in tumor stabilization, reduction, elimination, remission of cancer or autoimmune, alloimmune, or autoaggressive disease, or prevention or amelioration of relapse of cancer or autoimmune, alloimmune, or autoaggressive disease, or a combination thereof, in a patient-specific manner. In reference to the parent one or more boosting elements of the single, tandem, DuoCARs, or multiple-targeting CARs, the functional boosting element portion can comprise, for instance, about 10%, 25%, 30%, 50%, 68%, 80%, 90%, 95%, or more, of the parent one or more boosting elements of the single, tandem, DuoCARs, or multiple-targeting CARs.

The functional parent one or more boosting elements of the single, tandem, DuoCARs, or multiple-targeting CARs can comprise additional amino acids at the amino or carboxy terminus of the portion, or at both termini, which additional amino acids are not found in the amino acid sequence of the parent one or more boosting elements of the single, tandem, DuoCARs, or multiple-targeting CARs. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent one or more boosting elements of the single, tandem, DuoCARs, or multiple-targeting CARs.

Included in the scope of the disclosure are functional variants of the single, tandem, DuoCARs, multiple-targeting CARs (with or without one or more boosting elements) disclosed herein. The term "functional variant" as used herein refers to a single, tandem, DuoCAR, or multiple-targeting CAR (with or without one or more boosting elements), polypeptide, or protein having substantial or significant sequence identity or similarity to a parent one or more boosting elements of the single, tandem, DuoCARs, or multiple-targeting CARs which functional variant retains the biological activity of the single, tandem, DuoCAR, or multiple-targeting CAR (with or without one or more boosting elements) of which it is a variant. Functional variants encompass, for example, those variants of the single, tandem, DuoCAR, or multiple-targeting CAR (with or without one or more boosting elements) described herein (the parent one or more boosting elements of the single, tandem, DuoCARs, or multiple-targeting CARs) that retain the ability to recognize target cells to a similar extent, the same extent, or to a higher extent, as the parent one or more boosting elements of the single, tandem, DuoCARs, or multiple-targeting CARs. In reference to the parent one or more boosting elements of the single, tandem, DuoCARs, or multiple-targeting CARs, the functional variant can, for instance, be at least about 30%, 50%, 75%, 80%, 90%, 98% or more identical in amino acid sequence to the parent one or more boosting elements of the single, tandem, DuoCARs, or multiple-targeting CARs.

A functional variant can, for example, comprise the amino acid sequence of the parent one or more boosting elements of the single, tandem, DuoCARs, or multiple-targeting CARs with at least one conservative amino acid substitution. Alternatively, or additionally, the functional variants can comprise the amino acid sequence of the parent one or more boosting elements of the single, tandem, DuoCARs, or multiple-targeting CARs with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent one or more boosting elements of the single, tandem, DuoCARs, or multiple-targeting CARs.

Amino acid substitutions of the parent one or more boosting elements of the single, tandem, DuoCARs, or multiple-targeting CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The parent one or more boosting elements of the single, tandem, DuoCARs, or multiple-targeting CARs can consist essentially of the specified amino acid sequence or sequences described herein, such that other components, e.g., other amino acids, do not materially change the biological activity of the functional variant.

The parent one or more boosting elements of the single, tandem, DuoCARs, or multiple-targeting CARs (including functional portions and functional variants) can be of any length, i.e., can comprise any number of amino acids, provided that the parent one or more boosting elements of the single, tandem, DuoCARs, or multiple-targeting CARs (or functional portions or functional variants thereof) retain their biological activity, e.g., the ability to specifically bind to antigen, detect diseased cells in a mammal, or treat or prevent disease in a mammal, etc. For example, the parent one or more boosting elements of the single, tandem, DuoCARs, or multiple-targeting CARs can be about 50 to about 5000 amino acids long, such as 50, 70, 75, 100, 125, 150, 175, 200, 300, 400, 500, 600, 700, 800, 900, 1000 or more amino acids in length.

The parent one or more boosting elements of the single, tandem, DuoCARs, or multiple-targeting CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, a-aminocyclohexane carboxylic acid, a-aminocycloheptane carboxylic acid, a-(2-amino-2-norbornane)-carboxylic acid, γ-diaminobutyric acid, β-diaminopropionic acid, homophenylalanine, and a-tert-butylglycine.

The parent one or more boosting elements of the single, tandem, DuoCARs, or multiple-targeting CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The parent one or more boosting elements of the single, tandem, DuoCARs, or multiple-targeting CARs (including functional portions and functional variants thereof) can be obtained by methods known in the art. The parent one or more boosting elements of the single, tandem, DuoCARs, or multiple-targeting CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Methods of generating chimeric antigen receptors, T cells including such receptors, and their use (e.g., for treatment of cancer) are known in the art and further described herein (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., Trends Biotechnol., 29:550-557, 2011; Grupp et al., N Engl J Med., 368:1509-1518, 2013; Han et al., J. Hematol Oncol., 6:47, 2013; Tumaini et al., Cytotherapy, 15, 1406-1417, 2013; Haso et al., (2013) Blood, 121, 1165-1174; PCT Pubs. WO2012/079000, WO2013/126726; and U.S. Pub. 2012/0213783, each of which is incorporated by reference herein in its entirety). For example, a nucleic acid molecule encoding a disclosed chimeric antigen binding receptor can be included in an expression vector (such as a lentiviral vector) used to transduce a host cell, such as a T cell, to make the disclosed parent one or more boosting elements of the single, tandem, DuoCARs, or multiple-targeting CARs. In some embodiments, methods of using the chimeric antigen receptor include isolating T cells from a subject, transducing the T cells with an expression vector (such as a lentiviral vector) encoding the chimeric antigen receptor, and administering the parent one or more boosting elements of the single, tandem, DuoCARs, or multiple-targeting CARs-expressing T cells to the subject for treatment, for example for treatment of a tumor in the subject.

B. Antibodies and Antigen Binding Fragments

One embodiment further provides a single, tandem, DuoCAR, multiple-targeting CAR (with or without one or more boosting elements) used in the patient-specific autologous anti-tumor lymphocyte cell population(s) disclosed herein, a T cell expressing a single, tandem, DuoCAR, multiple-targeting CAR (with or without one or more boosting elements), an antibody, or antigen binding domain or portion thereof, which specifically binds to one or more of the antigens disclosed herein. As used herein, a "T cell expressing a single, tandem, DuoCARs, multiple-targeting CARs (with or without one or more boosting elements)," or a "single, tandem, DuoCARs, multiple-targeting CARs (with or without one or more boosting elements) T cell" means a T cell expressing a single, tandem, DuoCARs, multiple-targeting CARs (with or without one or more boosting elements), and has antigen specificity determined by, for example, the antibody-derived targeting domain of the single, tandem, DuoCARs, multiple-targeting CARs (with or without one or more boosting elements).

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6.sup.th ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, scFv, dsFv or Fab. References to "VL" or "VL" refer to the variable domain of an antibody light chain, including that of an Fv, scFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, M D, 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. scFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (scFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a scFv, is typically not decisive for scFvs. Thus, scFvs with both possible arrangements (VH-domain-linker domain-VL-domain; VL-domain-linker domain-VH-domain) may be used.

In a dsFv the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2.1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, IL); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the single, tandem, DuoCARs, multiple-targeting CARs (with or without one or more boosting elements) are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338,929).

Also, a single, tandem, DuoCARs, multiple-targeting CARs (with or without one or more boosting elements), a T cell expressing a single, tandem, DuoCARs, multiple-targeting CARs (with or without one or more boosting elements), an antibody, or antigen binding portion thereof, can be to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

The single, tandem, DuoCARs, multiple-targeting CARs (with or without one or more boosting elements) used in the patient-specific autologous anti-tumor lymphocyte cell population(s) disclosed herein, a T cell expressing a single, tandem, DuoCAR, multiple-targeting CAR (with or without one or more boosting elements), or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}I$, $^{32}P$, $^{14}C$, $^{3}H$ and $^{35}S$ and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups, such as carboxylic acid (COOH), free amine (—$NH_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, IL. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable, and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931: Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a single, tandem, DuoCAR, multiple-targeting CAR (with or without one or more boosting elements), a T cell expressing a single, tandem, DuoCAR, multiple-targeting CAR (with or without one or more boosting elements), an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a single, tandem, DuoCAR, multiple-targeting CAR (with or without one or more boosting elements), a T cell expressing a single, tandem, DuoCAR, multiple-targeting CAR (with or without one or more boosting elements), an antibody, or antigen binding portion thereof. Exemplary toxins include Pseudomonas exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, MO). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

The single, tandem, DuoCAR, multiple-targeting CAR (with or without one or more boosting elements) used in the patient-specific autologous anti-tumor lymphocyte cell population(s), a T cell expressing a single, tandem, DuoCAR, multiple-targeting CAR (with or without one or more boosting elements), monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A single, tandem, DuoCAR, multiple-targeting CAR (with or without one or more boosting elements), a T cell expressing a single, tandem, DuoCAR, multiple-targeting CAR (with or without one or more boosting elements), an antibody, or antigen binding portion thereof, can also be conjugated with enzymes that are useful for detection, such as horseradish peroxidase, D-galactosidase, luciferase, alkaline phosphatase, glucose oxidase and the like. When a single, tandem, DuoCAR, multiple-targeting CAR (with or without one or more boosting elements), a T cell expressing a single, tandem, DuoCAR, multiple-targeting CAR (with or without one or more boosting elements), an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A single, tandem, DuoCAR, multiple-targeting CAR (with or without one or more boosting elements), a T cell expressing a single, tandem, DuoCAR, multiple-targeting CAR (with or without one or more boosting elements), an antibody, or antigen binding portion thereof, may also be conjugated with biotin, and detected through indirect measurement of avidin or streptavidin binding. It should be noted that the avidin itself can be conjugated with an enzyme or a fluorescent label.

A single, tandem, DuoCAR, multiple-targeting CAR (with or without one or more boosting elements), a T cell expressing a single, tandem, DuoCAR, multiple-targeting CAR (with or without one or more boosting elements), an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A single, tandem, DuoCAR, multiple-targeting CAR (with or without one or more boosting elements), a T cell expressing a single, tandem, DuoCAR, multiple-targeting CAR (with or without one or more boosting elements), an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the single, tandem, DuoCARs, multiple-targeting CARs (with or without one or more boosting elements), an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In one embodiment, an isolated nucleic acid molecule encoding a chimeric antigen receptor (single, tandem, DuoCARs, multiple-targeting CARs (with or without one or more boosting elements)) is provided comprising, from N-terminus to C-terminus, at least one extracellular antigen binding domain, at least one transmembrane domain, and at least one intracellular signaling domain.

In one embodiment of the single, tandem, DuoCAR, multiple-targeting CAR (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the encoded extracellular antigen binding domain comprises at least one single chain variable fragment of an antibody that binds to the antigen.

In another embodiment of the single, tandem, DuoCAR, multiple-targeting CAR (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the encoded extracellular antigen binding domain comprises at least one heavy chain variable region of an antibody that binds to the antigen.

In yet another embodiment of the single, tandem, DuoCAR, multiple-targeting CAR (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the encoded single, tandem, DuoCAR, multiple-targeting CAR (with or without one or more boosting elements) extracellular antigen binding domain comprises at least one lipocalin-based antigen binding antigen (anticalins) that binds to the antigen.

In one embodiment of the single, tandem, DuoCAR, multiple-targeting CAR (with or without one or more boosting elements) used in the patient-specific autologous anti-tumor lymphocyte cell population(s), an isolated nucleic acid molecule is provided wherein the encoded extracellular antigen binding domain is connected to the transmembrane domain by a linker domain.

In another embodiment of the single, tandem, DuoCARs, multiple-targeting CARs (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the encoded extracellular antigen binding domain is preceded by a sequence encoding a leader or signal peptide.

In yet another embodiment of the single, tandem, DuoCARs, multiple-targeting CARs (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the encoded extracellular antigen binding domain targets an antigen that includes, but is not limited to, CD19, CD20, CD22, ROR1, mesothelin, CD33/IL3Ra, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, GD2, GD3, GM2, Ley, polysialic acid, fucosyl GM1, GM3, Tn, STn, sLe(animal), GloboH, CD5, CD7, CD19, CD20, CD22, CD25, CD37, CD30, CD33, CD38, CD123, CD45, CAMPATH-1, BCMA, CS-1, PD-L1, CD276/B7-H3, B7-H4, B7-DC, HLA-DR carcinoembryonic antigen (CEA), TAG-72, EpCAM, folate-binding protein, folate receptor alpha (FOLR1), folate receptor beta (FOLR2), A33, G250, pro state-specific membrane antigen (PSMA), ferritin, CA-125, CA19-9, CD44v6, epidermal growth factor, p185, IL-2 receptor, interleukin 1 receptor accessory protein (IL1RAP), EGFRvIII (de2-7), fibroblast activation protein, tenascin, a metalloproteinase, endosialin, vascular endothelial growth factor, αvβ3, WT1, LMP2, HPV E6, HPV E7, Her-2/neu, p53 nonmutant, NY-ESO-1, MelanA/MART 1, Ras mutant, gp100, FGFR1, FGFR2, FGFR3, FGFR4, GPC1, GPC2, GPC3, p53 mutant, PR1, bcr-abl, tyrosinase, survivin, PSA, hTERT, a Sarcoma translocation breakpoint fusion protein, EphA2, PAP, ML-IAP, AFP, ERG, NA17, PAX3, ALK, androgen receptor, cyclin B 1, MYCN, RhoC, TRP-2, mesothelin, PSCA, MAGE A1, MAGE A3, CYP1B 1, PLAV1, BORIS, ETV6-AML, NY-BR-1, RGS5, SART3, Carbonic anhydrase IX, PAX5, OY-TES 1, Sperm protein 17, LCK, HMWMAA, AKAP-4, SSX2, XAGE 1, B7H3, Legumain, Tie 3, PAGE4, VEGFR2, MAD-CT-1, PDGFR-B, MAD-CT-2, TRAIL 1, MUC1, MUC16/CA125, MAGE A4, MAGE C2, GAGE, EGFR, EGFR1, EGFR2/Her2, CMET, HER3, CA6, NAPI2B, TROP2, TEM1, TEM7, TEM8, FAP, LAP, CLDN3, CLDN6, CLDN8, CLDN16, CLDN18.2, RON, LY6E, DLL3, PTK7, UPK1B, STRA6, TMPRSS3, TMRRSS4, TMEM238, Clorfl86, LIV1, ROR1, ROR2, Fos-related antigen 1, VEGFR1, endoglin, CD90, CD326, CD70, SSEA4, CD318, CLA, TSPAN8, GPRC5D, EpCAM, Thy1, IL13Ra2, BDCA1, BDCA2, BDCA3, GD2, PSMA, FAP, CLL1, SLAMF7/CS1, CD147, DPPA5, GRP78, CD66c, VISTA, LRRC5, LRRC15, or any combinations thereof or a fragment thereof is provided, wherein the antibody or a fragment thereof comprises a fragment selected from the group consisting of an Fab fragment, an $F(ab')_2$ fragment, an Fv fragment, a nanobody, a VHH, a ligand peptide, and a single chain Fv (ScFv), or a fragment of any of the preceding, or a molecule that is at least 80%, 85%, 90%, 95%, 96%, 97%, 98% or 99% homologous to any of the preceding, or any combination thereof.

In certain embodiments of the single, tandem, DuoCARs, multiple-targeting CARs (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the encoded extracellular antigen binding domain comprises an anti-CD19 scFV antigen binding domain, an anti-CD20 scFV antigen binding domain, an anti-CD22 scFV antigen binding domain, an anti-ROR1 scFV antigen binding domain, an anti-TSLPR scFV antigen binding domain, an anti-mesothelin scFV antigen binding domain, an anti-CD33/IL3Ra scFV antigen binding domain, an anti-CD38 scFV antigen binding domain, an anti-CD123 (IL3RA) scFV antigen binding domain, an anti-CD138 scFV antigen binding domain, an anti-BCMA (CD269) scFV antigen binding domain, an anti-GPC2 scFV antigen binding domain, an anti-GPC3 scFV antigen binding domain, an anti-FGFR4 scFV antigen binding domain, an anti-c-Met scFV antigen binding domain, an anti-PMSA scFV antigen binding domain, an anti-glycolipid F77 scFV antigen binding domain, an anti-EGFRvIII scFV antigen binding domain, an anti-GD-2 scFV antigen binding domain, an anti-NY-ESo-1 TCR scFV antigen binding domain, an anti-MAGE A3 TCR scFV antigen binding domain, or an amino acid sequence with 85%, 90%, 95%, 96%, 97%, 98% or 99% identity thereof, or any combination thereof.

In one aspect of the single, tandem, DuoCARs, multiple-targeting CARs (with or without one or more boosting elements) used in the patient-specific autologous anti-tumor lymphocyte cell population(s), the single, tandem, DuoCARs, multiple-targeting CARs (with or without one or more boosting elements) provided herein further comprise a linker domain.

In one embodiment of the single, tandem, DuoCARs, multiple-targeting CARs (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the extracellular antigen binding domain, the intracellular signaling domain, or both are connected to the transmembrane domain by a linker domain.

In one embodiment of the single, tandem, DuoCARs, multiple-targeting CARs (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the encoded linker domain is derived from the extracellular domain of CD8, and is linked to the transmembrane domain.

In yet another embodiment of the single, tandem, DuoCARs, multiple-targeting CARs (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the nucleic acid sequence encoding the transmembrane domain comprises a nucleotide sequence with 85%, 90%, 95%, 96%, 97%, 98% or 99% identity thereof.

In one embodiment of the single, tandem, DuoCARs, multiple-targeting CARs (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the encoded transmembrane domain comprises an amino acid sequence comprising at least one but not more than 10 modifications, or a sequence with 85%, 90%, 95%, 96%, 97%, 98% or 99% identity thereof.

In another embodiment of the single, tandem, DuoCARs, multiple-targeting CARs (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the encoded single, tandem, DuoCAR, multiple-targeting CAR (with or without one or more boosting elements) further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In yet another embodiment of the single, tandem, DuoCARs, multiple-targeting CARs (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the encoded intracellular signaling domain further comprises a CD3 zeta intracellular domain.

In one embodiment of the single, tandem, DuoCAR, multiple-targeting CAR (with or without one or more boosting elements) disclosed herein, an isolated nucleic acid molecule encoding the single, tandem, DuoCAR, multiple-targeting CAR (with or without one or more boosting elements) is provided wherein the encoded intracellular signaling domain is arranged on a C-terminal side relative to the CD3 zeta intracellular domain.

In another embodiment of the single, tandem, DuoCARs, multiple-targeting CARs (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the encoded at least one intracellular signaling domain comprises a costimulatory domain, a primary signaling domain, or a combination thereof.

In further embodiments of the single, tandem, DuoCARs, multiple-targeting CARs (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), CD2, OX40, or a combination thereof.

In one embodiment of the single, tandem, DuoCARs, multiple-targeting CARs (with or without one or more boosting elements) used in the patient-specific autologous anti-tumor lymphocyte cell population(s), an isolated nucleic acid molecule encoding the single, tandem, DuoCAR, multiple-targeting CAR (with or without one or more boosting elements) is provided that further contains a leader sequence or signal peptide sequence.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive single, tandem, DuoCAR, multiple-targeting CAR (with or without one or more boosting elements). In another embodiment of the invention, the nucleic acid may comprise a codon-modified nucleotide sequence that encodes any of the single, tandem, DuoCARs, multiple-targeting CARs (with or without one or more boosting elements) described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, IA, USA).

The nucleic acid can comprise any isolated or purified nucleotide sequence which encodes any of the single, tandem, DuoCARs, multiple-targeting CARs (with or without one or more boosting elements) or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive single, tandem, DuoCARs, multiple-targeting CARs (with or without one or more boosting elements). It is generally appreciated that conditions can be rendered more stringent by the addition of increasing amounts of formamide.

Also provided is a nucleic acid comprising a nucleotide sequence that is at least about 70% or more, e.g., about 80%, about 90°/%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA).

Bacteriophage vectors, such as λϋTIO, λϋTI 1, λZapII (Stratagene), EMBL4, and λNMI 149, also can be used. Examples of plant expression vectors include pBIO1, pBI101.2, pBHO1.3, pBI121 and pBIN19 (Clontech). Examples of animal expression vectors include pEUK-C1, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR.R™. gene delivery technology from Oxford BioMedica plc, the LENTIMAX.™. vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al., Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751(1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al., Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the single, tandem, DuoCAR, multiple-targeting CAR (with or without one or more boosting elements) (including functional portions and functional variants thereof), or to the nucleotide sequence which is complementary to or which hybridizes to the nucleotide sequence encoding the single, tandem, DuoCAR, multiple-targeting CAR (with or without one or more boosting elements). The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant single, tandem, DuoCAR, multiple-targeting CAR (with or without one or more boosting elements), the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4+/CD8+ double positive T cells, CD4+ helper T cells, e.g., Th1 and Th2 cells, CD8+ T cells (e.g., cytotoxic T cells), tumor infiltrating cells, memory T cells, naive T cells, and the like. The T cell may be a CD8+ T cell or a CD4+ T cell.

In an embodiment, the single, tandem, DuoCARs, multiple-targeting CARs (with or without one or more boosting elements) as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

Single, tandem, DuoCARs, multiple-targeting CARs (with or without one or more boosting elements) (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the single, tandem, DuoCARs, multiple-targeting CARs (with or without one or more boosting elements) used in the patient-specific autologous anti-tumor lymphocyte cell population(s) can be used in methods of treating or preventing a disease in a mammal. In this regard, an embodiment provides a method of treating or preventing cancer in a mammal, comprising administering to the mammal the single, tandem, DuoCARs, multiple-targeting CARs (with or without one or more boosting elements), the nucleic acids, the recombinant expression vectors, the host cells, the population of cells, the antibodies and/or the antigen binding portions thereof, and/or the pharmaceutical compositions in an amount effective to treat or prevent cancer in the mammal. Additional methods of use of the aforementioned single, tandem, DuoCARs, multiple-targeting CARs (with or without one or more boosting elements) have been disclosed supra.

An embodiment further comprises lymphodepleting the mammal prior to administering the single, tandem, DuoCARs, multiple-targeting CARs (with or without one or more boosting elements) disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia (CLL), hairy cell leukemia, acute lymphocytic leukemia (ALL), acute myeloid leukemia (AML), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the single, tandem, DuoCARs, multiple-targeting CARs (with or without one or more boosting elements), the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the single, tandem, DuoCARs, multiple-targeting CARs (with or without one or more boosting elements) disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a single, tandem, DuoCAR, multiple-targeting CAR (with or without one or more boosting elements) for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, single, tandem, DuoCAR, multiple-targeting CAR (with or without one or more boosting elements) function can be evaluated by measurement of cellular cytotoxicity, as described in Zhao et al., J. Immunol. 174: 4415-4423 (2005).

Another embodiment provides for the use of the single, tandem, DuoCARs, multiple-targeting CARs (with or without one or more boosting elements), nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example, topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the single, tandem, DuoCAR, multiple-targeting CAR (with or without one or more boosting elements), single, tandem, DuoCAR, multiple-targeting CAR (with or without one or more boosting elements) T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, single, tandem, DuoCARs, multiple-targeting CARs (with or without one or more boosting elements), single, tandem, DuoCAR, multiple-targeting CAR (with or without one or more boosting elements) T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, single, tandem, DuoCAR, multiple-targeting CAR (with or without one or more boosting elements) or T cell expressing a single, tandem, DuoCAR, multiple-targeting CAR (with or without one or more boosting elements) (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the single, tandem, DuoCARs, multiple-targeting CARs (with or without one or more boosting elements), single, tandem, DuoCAR, multiple-targeting CAR (with or without one or more boosting elements)—T cells, antibodies, antigen binding fragment, or conjugates disclosed herein. Methods and therapeutic dosages of such agents are known to those skilled in the art, and can be determined by a skilled clinician.

Additional chemotherapeutic agents for combination immunotherapy include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as *podophyllum* (for example, etoposide, and teniposide), taxane (for example, docetaxel and paclitaxel), *vinca* (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin)(Liu et al., Cell 66:807-815, 1991; Henderson et al., Immun 73:316-321, 1991; Bierer et al., Curr. Opin. Immun 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy, adoptive immunotherapy, and/or cell therapy that include one or more of the disclosed single, tandem, DuoCARs, multiple-targeting CARs (with or without one or more boosting elements), or T cells expressing a single, tandem, DuoCAR, multiple-targeting CAR (with or without one or more boosting elements), antibodies, antigen binding fragments, conjugates, single, tandem, DuoCARs, multiple-targeting CARs (with or without one or more boosting elements), or T cells expressing a single, tandem, DuoCAR, multiple-targeting CAR (with or without one or more boosting elements) that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, a disclosed single, tandem, DuoCARs, multiple-targeting CARs (with or without one or more boosting elements), or T cells expressing a single, tandem, DuoCAR, multiple-targeting CAR (with or without one or more boosting elements), antibody, antigen binding fragment, conjugate, is formulated for parenteral administration, such as intravenous administration. Compositions including a single, tandem, DuoCAR, multiple-targeting CAR (with or without one or more boosting elements), or T cell expressing a single, tandem, DuoCAR, multiple-targeting CAR (with or without one or more boosting elements), a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a single, tandem, DuoCAR, multiple-targeting CAR (with or without one or more boosting elements), or T cell expressing a single, tandem, DuoCAR, multiple-targeting CAR (with or without one or more boosting elements), a conjugate, antibody or antigen binding fragment as disclosed herein are also of use, for example, for the detection of pathological angiogenesis.

The compositions for administration can include a solution of the single, tandem, DuoCAR, multiple-targeting CAR (with or without one or more boosting elements), or T cell expressing a single, tandem, DuoCAR, multiple-targeting CAR (with or without one or more boosting elements), conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a single, tandem, DuoCAR, multiple-targeting CAR (with or without one or more boosting elements), or T cell expressing a single, tandem, DuoCAR, multiple-targeting CAR (with or without one or more boosting elements), antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a single, tandem, DuoCAR, multiple-targeting CAR (with or without one or more boosting elements), or T cell expressing a single, tandem, DuoCAR, multiple-targeting CAR (with or without one or more boosting elements), conjugate including the antibody or antigen binding fragment). Actual methods for preparing administrable compositions will be known or apparent to those skilled in the art and are described in more detail in such publications as *Remington's Pharmaceutical Science, 19th ed.*, Mack Publishing Company, Easton, PA (1995).

A single, tandem, DuoCAR, multiple-targeting CAR (with or without one or more boosting elements), or T cell expressing a single, tandem, DuoCAR, multiple-targeting CAR (with or without one or more boosting elements), antibodies, antigen binding fragments, or conjugates may be provided in lyophilized form and rehydrated with sterile water before administration, although they are also provided in sterile solutions of known concentration. The single, tandem, DuoCARs, multiple-targeting CARs (with or without one or more boosting elements), or T cells expressing a single, tandem, DuoCAR, multiple-targeting CAR (with or without one or more boosting elements), antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A single, tandem, DuoCAR, multiple-targeting CAR (with or without one or more boosting elements), or T cell expressing a single, tandem, DuoCAR, multiple-targeting CAR (with or without one or more boosting elements), antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, *Treatise on Controlled Drug Delivery*, A. Kydonieus, ed., Marcel Dekker, Inc. New York, NY, pp. 315-339, (1992).

Polymers can be used for ion-controlled release of the single, tandem, DuoCARs, multiple-targeting CARs (with or without one or more boosting elements), or T cells expressing a single, tandem, DuoCAR, multiple-targeting CAR (with or without one or more boosting elements), antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, Kits employing the single, tandem, DuoCARs, multiple-targeting CARs (with or without one or more boosting elements) disclosed herein are also provided. For example, kits for treating a tumor in a subject, or making a single, tandem, DuoCAR, multiple-targeting CAR (with or without one or more boosting elements) T cell that expresses one or more of the single, tandem, DuoCARs, multiple-targeting CARs (with or without one or more boosting elements) disclosed herein. The kits will typically include a disclosed antibody, antigen binding fragment, conjugate, nucleic acid molecule, single, tandem, DuoCAR, multiple-targeting CAR (with or without one or more boosting elements) or T cell expressing a single, tandem, DuoCAR, multiple-targeting CAR (with or without one or more boosting elements) as disclosed herein. More than one of the disclosed antibodies, antigen binding fragments, conjugates, nucleic acid molecules, single, tandem, DuoCARs, multiple-targeting CARs (with or without one or more boosting elements) or T cells expressing a single, tandem, DuoCAR, multiple-targeting CAR (with or without one or more boosting elements) can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, single, tandem, DuoCARs, multiple-targeting CARs (with or without one or more boosting elements) or T cells expressing a single, tandem, DuoCAR, multiple-targeting CAR (with or without one or more boosting elements). In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, single, tandem, DuoCARs, multiple-targeting CARs (with or without one or more boosting elements) or T cells expressing a single, tandem, DuoCAR, multiple-targeting CAR (with or without one or more boosting elements), for example, in a method of treating or preventing a tumor or of making a single, tandem, DuoCAR, multiple-targeting CAR (with or without one or more boosting elements) T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the examples of the CARs depicted within the accompanying Figures infra and the disclosure at pages 14-19, inclusive supra, which examples are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

Description of Examples

Two examples are provided whereby CAR T cells in a single, tandem or multi-cistronic DuoCAR format with or without boosting elements are described. Example 1 describes the generation and in vitro evaluation of boosted CAR T cells targeting MSLN and/or ROR1 antigen for the treatment solid tumors. Example 2 describes the evaluation of the anti-tumor function of the ROR1 and MSLN-targeting CAR T cells in a mouse tumor xenograft model.

Example 1

Development of ROR1 and/or MSLN Targeting CAR Constructs with Boosting Elements

Materials and Methods

Cell Lines

The ovarian cancer cell line OVCAR3, lung squamous cell carcinoma cell line NCI-H226, pancreatic cancer cell lines CAPAN-2 and AsPC-1, and leukemia cell line HL-60 were purchased from American Tissue Culture Collection (ATCC, Manassas, VA). The MEC-1 leukemia line was purchased from DSMZ (Leibniz Institute DSMZ, Braunschweig, Germany). NCI-H226 and AsPC-1 were cultivated in RPMI-1640 medium (Corning, NY) supplemented with 10% heat-inactivated fetal bovine serum (FBS, Hyclone, Logan, UT). OVCAR-3 was cultured in RPMI-1640 medium(Corning, NY) supplemented with 20% heat-inactivated FBS and 10 μg/ml bovine insulin (Sigma, St Louis, MO). CAPAN-2 were propagated in McCoy-5a (ATCC, VA) supplemented with 10% heat-inactivated FBS. HL-60 was maintained in IMDM (Hyclone, Logan, UT) with 20% FBS. MEC-1 cell line and its derivatives were maintained in IMDM supplemented with 10% FBS. OVCAR-3, NCI-H226 and HL60 luciferase expressing cell lines were generated by stably transducing wild-type tumor lines with lentiviral vector encoding firefly luciferase, followed by limiting dilution and selection of luciferase-positive clones. Capan-2 single clone of luciferase and GFP expressing cell line was generated by stably transducing wild-type tumor lines with lentiviral vector encoding firefly luciferase and GFP connected with 2A peptide (Lentigen Technology, Inc., Gaithersburg, MD), followed by selection of luciferase-positive clones. MEC-1 ROR1$^{hi}$ MSLN$^{hi}$ cells were generated by stable transduction with lentivirus encoding ROR1 or MLSN gene, followed by microbeads selection and Tyto sorting (Miltenyi Biotec) for ROR1 or MSLN positivity.

Generation of CAR Constructs and Lentiviral Vector Production

The constructs of fully human anti-ROR1 and/or MSLN chimeric antigen receptor (CAR) with boosting elements were designed as CAR molecule and a booster molecule connected with P2A ribosomal skipping element sequence. CAR molecules included mono- and multi-targeting CAR. The various single chain variable fragment (ScFv) sequences targeting the extracellular domain of human ROR1 or MSLN were identified in house, the R12 ScFv targeting ROR1 was used as CAR ROR1 control. Mono CAR comprised of an antiROR1 or anti MSLN scFv, a IgG4 short hinge for ROR1 scFv, a CD8 hinge for MSLN scFv, connected to CD8 or OX40 transmembrane domain, costimulatory domain(s) derived from human ICOS, CD28, OX40 and 4-1BB, followed by CD3-ζ activating domain sequences. Multi-targeting CARs denoted tandem CARs and DuoCARs. Tandem CARs comprised of a MSLN targeting scFv connected with ROR1scFv9 via G4S linker, followed by IgG4 hinge, CD8 or CD28 transmembrane, 4-1BB or CD28_4-1BBcostimulatory domain(s), and CD3-ζ activating domain sequences. Bicistronic CARs contained a ROR1-targeting mono CAR, and a MSLN-targeting mono CAR, connected with P2A sequence. Boosting elements various from cytokines (membrane bound IL7), armors (TGFβRIIdn), suicide tag (tEGFR), extracellular matrix enzymes, chemokine receptors (CXCL8, CCL2), stroma targeting molecules (FAP), et al. ROR1 or MSLN mono CARs and MSLN_ROR1 tandem CARs without boosters were included as comparison.

CAR sequences were cloned into a Lentiviral Vector (LV) expression cassette under the control of the human EF-1α promoter or MND promoter (Lentigen Technology Inc., Gaithersburg, MD). Lentiviral particles were generated by transient transfection of HEK 293T cells, pelleted by centrifugation and stored at −80° C. until transduction.

Primary T Cell Preparation and Transduction

Healthy donor primary T cells were isolated from leukapheresis collections (AllCells, Alameda, CA) or from processed buffy coats (Oklahoma Blood Institute, Tulsa, OK), with donors' written consent. The CD4-positive and CD8-positive human T cells were purified via positive selection using a 1:1 mixture of CD4 and CD8 Microbeads (Miltenyi Biotec, Bergisch Gladbach, Germany) according to manufacturer's protocol. Purified T cells were activated with CD3/CD28 MACS® GMP T Cell TransAct reagent (Miltenyi Biotec), and cultured in serum free TexMACS medium supplemented with 30 IU/ml IL-2 at a density of $1\times10^6$ cells/mi. Further, activated T cells were transduced on day 1 with lentiviral vector particles encoding CAR constructs. On day 3, the transduced T cells were washed and resuspended to $0.5\times10^6$/ml to continue expansion. Every 2-3 days thereafter, cultures were supplemented with fresh TexMACS medium containing 30 IU/ml IL-2, until harvesting time on day 8-10.

Flow Cytometric Analysis of CAR Surface Expression

Half million CAR T cells were washed in cold AutoMACS buffer supplemented with 0.5% bovine serum albumin (Miltenyi Biotec, Bergisch Gladbach, Germany) and stained with CAR detection reagents. For ROR CAR, cells were stained with ROR1-Fc peptide (R&D System, Minneapolis, MN), followed by anti Fc-AF647 conjugate (Jackson ImmunoResearch, West Grove, PA). For MSLN CAR, cells were stained with MSLN-His (R&D System, Minneapolis, MN) or anti-His-APC (Miltenyi Biotec). The 7-Aminoactinomycin D staining (7-AAD, BD Biosciences, San Jose, CA) was added to exclude dead cells. CD4 antibody labeled with VioBlue fluorochrome or CD8 antibody labeled with VioGreen fluorochrome was used to separate CD4 and CD8 population. Non-transduced cells (UTD) were used as a negative control. Cells were washed twice, resuspended in 200 μl running buffer, and acquired by flow cytometry. Flow cytometric analysis was performed on a MACSQuant® 10 Analyzer (Miltenyi Biotec), and data plots were generated using FlowJo software (Ashland, OR).

CAR T Cell Cytotoxicity and Cytokine Assay

To assess CAR T cell mediated cytotoxicity, $5\times10^3$ tumor target cells stably transduced with firefly luciferase were combined with CAR T cells at the indicated effector to target ratios and incubated overnight at 37° C. with 5% $CO_2$. SteadyGlo reagent (Promega, Madison WI) was added to each well and the resulting luminescence quantified as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)). For cytokine release analysis, supernatants from overnight co-cultures were collected and analyzed by ELISA (eBioscience, San Diego, CA) for IFNγ, TNFα and IL-2 concentration. Two technical replicates were performed for each condition, and each experiment was repeated using CAR T cells generated from different healthy donors as indicated.

CAR T cell mediated cytotoxicity were evaluated using xCelligence RTCA instrument (Agilent, Santa Clara, CA) following manufactory instruction. Briefly, $4\times10^4$ AsPC-1 tumor target cells were seeded in a 96/E-Plate, incubated in the cradle of xCelligence RTCA instrument at 37° C. with 5% $CO_2$ for overnight. Effector CAR T cells were added into the plate at E T ratio 2:1 when target cells index reached or exceeded 1. Cell index was continuously monitored for desired assay time. Percentage of cytolysis was calculated by RTCA software as Cytolysis (sample) %=(1-normalized sample index/reference average normalized index)×100. The time required to reach 50% of the maximal killing of tumor cells was reported as KT50. In select experiments, TGF0 was spiked into the co-incubated cultures at the onset of experiment, at the concentrations indicated.

IL-2 Withdrawal Assay

Transduced CAR T cells were washed and seeded at density of 1e6 cells/ml in TexMACS medium without IL-2 supplement. Cell growth, viability and diameters were assessed weekly by Vicell counter, and fresh medium supplied as needed. Cell density was adjusted to 1e6/ml or as is. The end point of each construct was determined as no cell expansion detected and cell counts dropped continuously over 2-3 weeks.

Western Blotting

Ten million CAR T cells were washed with cold PBS (Lonza, Walkersville, MD), then lysed in 100 μl cold RIPA buffer containing a protease inhibitor cocktail (Thermo-Fisher Scientific, Grand Island, NY). The lysate was incubated at 4° C. for 1 hr, pelleted at 21000 g in a table top centrifuge at 4° C. for 15 min. Supernatants were collected and protein concentration was quantified using SBS standard following the Quick Start Bradford Protein Assay (Bio-Rad). Cell lysate were aliquoted and frozen at −80° C. Samples were denatured at 90° C. in Laemmli sample buffer (Bio-Rad) with 50 mM DTT for 5 min and resolved on 4-12% gradient SDS-PAGE gel under reducing conditions in SDS running buffer Proteins were transferred to 0.45 μm nitrocellulose transfer membrane (BioRad, Hercules, CA) and blocked in the washing buffer containing 5% nonfat milk at room temperature for 1 hr. After blocking, membrane was probed with antibody against IL7 (Thermo-Fisher Scientific), and followed by goat anti mouse IgG HRP conjugated second antibody(Abcam, Cambridge, UK). Bands were developed using West Femto detection kit (ThermoFisher Scientific) according to manufacturer's protocol and bands were visualized and quantified on an Odyssey imaging system with Image Studio lite software (LI-COR, Lincoln, Nebraska). The blot with GAPDH antibody and goat anti rabbit IgG HRP conjugated second antibody (Abcam) was included as loading control.

HPSE ELISA

To confirm HPSE expression, CAR-T cells were seeded in the absence of IL-2 and supernatant was collected after 2 days and analyzed by ELISA (Abcam, Cambridge, UK). Two technical replicates were performed for each dilution.

Trans-Well Assay

To assess ECM degradation in vitro, CAR-T cells were seeded in Cultrex™ BME-coated transwell inserts (Corning Life Sciences), and migration into the reciprocal chamber was measured. Corning® BioCoat® control inserts (8.0 μm PET membrane) in 24-well plate formats were uncoated or coated with 100 μL Cultrex™ BME (R&D Systems, Minneapolis, MN) at 5 mg/mL diluted in 0.01M Tris-HCl pH 8.0, 0.7% NaCl. Coated transwell inserts were allowed to solidify for 2 h at 37 C. CAR-T cells were thawed and resuspended in TexMACS medium. 0.5E6 cells were seeded in each transwell insert (500 μL volume). TexMACS medium with 5% FBS was used as a chemoattractant in the bottom chamber (750 μL volume). Cells that had migrated into the bottom chamber after 24 h were collected, washed and processed for flow cytometry. Cell counts were normalized to Absolute counting beads (Invitrogen, Waltham, MA).

Results

Example 1 describes the generation and in vitro evaluation of boosted CAR T cells targeting MSLN and/or ROR1 antigen for the treatment solid tumors.

Boosted CAR was designed to enhance the functionality of ROR1 and/or MSLN CAR. Schematic representations of the boosted CAR constructs are shown in FIG. 1. Boosted CAR comprised of a CAR molecule, in frame to a boosting element linked by P2A ribosomal skipping element sequence. CAR molecule denoted to mono CAR, tandem CAR and DuoCAR structure. Fully human binders scFv4, scFv9 targeting ROR1 and anti MSLN scFv were developed in house, ROR1 R12 scFv was included as well. Mono CAR configured with a scFv targeting ROR1 or MSLN, in frame to IgG4 or CD8 hinge, CD8 or OX40 transmembrane, 41-BB, OX40, CD28, ICOS, costimulatory and a CD3ζ activation domain. Tandem CARs designed as a MSLN scFv connected with ROR1 scFv 9 through G4S linker, followed by IgG4 hinge, CD8 or CD28 transmembrane region, 4-1BB or CD28_4-1BB co-stimulatory domain and CD3' activation domain. DuoCAR constructs comprised of a mono ROR1 CAR and a mono MSLN CAR separated by P2A sequence. Booster elements in this example include a cytokine (membrane bound IL7), an armor (TGFβRIIdn), a suicide tag (tEGFR), and extracellular matrix enzymes.

Table 1 listed designated MSLN CAR and ROR1 CAR and booster CAR constructs.

TABLE 1

| ROR1 and/or MSLN CAR constructs | | | |
|---|---|---|---|
| | Construct Number | Construct designation | Promoter |
| Single CAR | LTG2527 | ROR1 R12 -IgG4 hinge-CD8TM-41BB-CD3ζ | EF1α |
| | LTG2528 | ROR1 scFv 4-IgG4 hinge-CD8TM-41BB-CD3ζ | EF1α |
| | LTG2529 | ROR1 scFv9-IgG4 hinge-CD8TM-41BB-CD3ζ | EF1α |
| | D0181 | MSLN-CD8H&TM-41BB-CD3ζ | EF1α |
| Single CAR with booster(s) | D0229 | ROR1 scFv9-IgG4 hinge-CD8TM-41BB-CD3ζ_2A_mIL7 | EF1α |
| | D0245 | MSLN-CD8H&TM-41BB-CD3ζ_2A_mIl7 | EF1α |
| | D0284 | MSLN-CD8H&TM-CD28-CD3ζ_2A_mIL7 | EF1α |
| | D0228 | ROR1 scFv9-IgG4 hinge-CD8TM-41BB-CD3ζ_2A_TGFβRII dn | EF1α |
| | D0211 | MSLN-CD8H&TM-41BB-CD3ζ_2A_TGFβRII dn | EF1α |
| | D0231 | ROR1 scFv9-IgG4 hinge-CD8TM-41BB-CD3ζ_2A_tEGFR | EF1α |
| | D0246 | MSLN-CD8H&TM-41BB-CD3ζ_2A_mIL7_2A_tEGFR | EF1α |
| | D0347 | ROR1 scFv9-IgG4 hinge-CD8TM-41BB-CD3ζ_2A_HPSE | EF1α |
| | D0348 | ROR1 scFv9-IgG4 hinge-CD8TM-41BB-CD3ζ_2A_MMP2 | EF1α |
| | D0349 | ROR1 scFv9-IgG4 hinge-CD8TM-41BB-CD3ζ_2A_PH20 | EF1α |
| | D0344 | MSLN-CD8H&TM-41BB-CD3ζ_2A_HPSE | EF1α |
| | D0345 | MSLN-CD8H&TM-41BB-CD3ζ_2A_MMP2 | EF1α |
| | D0346 | MSLN-CD8H&TM-41BB-CD3ζ_2A_PH20 | EF1α |
| Tandem CAR | D0233 | MSLN-ROR1 scFv9-IgG4 hinge-CD8TM-41BB-CD3ζ | EF1α |
| Tandem CAR | D0358 | MSLN-ROR1 scFv9-IgG4 hinge-CD28TM-CD28-41BB-CD3ζ | MND |
| Tandem CAR with booster(s) | D0279 | MSLN-ROR1 scFv9-IgG4 hinge-CD8TM-41BB-CD3ζ_2A_mIL7 | EF1α |
| | D0280 | MSLN-ROR1 scFv9-IgG4 hinge-CD28TM-CD28-CD3ζ_2A_mIL7 | EF1α |
| | D0281 | MSLN-ROR1 scFv9-IgG4 hinge-CD8TM-CD28-41BB-CD3ζ_2A_mIL7 | EF1α |
| DuoCAR with booster(s) | D0282 | ROR1scFv9-IgG4H-OX40TM-OX40-CD3ζ_2A_MSLN-CD8H& TM-ICOS-CD3ζ_2A_mIL7 | EF1α |
| | D0283 | ROR1scFv9-IgG4H-CD8TM-41BB-CD3ζ_2A_MSLN-CD8H& TM-CD28-CD3ζ_2A_mIL7 | EF1α |
| Tandem CAR with booster(s) | D0355 | MSLN-ROR1 scFv9-IgG4 hinge-CD28TM-CD28-41BB-CD3ζ_2A_mIL7 | MND |
| DuoCAR with booster(s) | D0356 | ROR1scFv9-IgG4H-OX40TM-OX40-CD3ζ_2A_MSLN-CD8H& TM-ICOS-CD3ζ_2A_mIL7 | MND |
| | D0357 | ROR1scFv9-IgG4H-CD8TM-41BB-CD3ζ_2A_MSLN-CD8H& TM-CD28-CD3ζ_2A_mIL7 | MND |

Figures 2A, 2B, 2C:
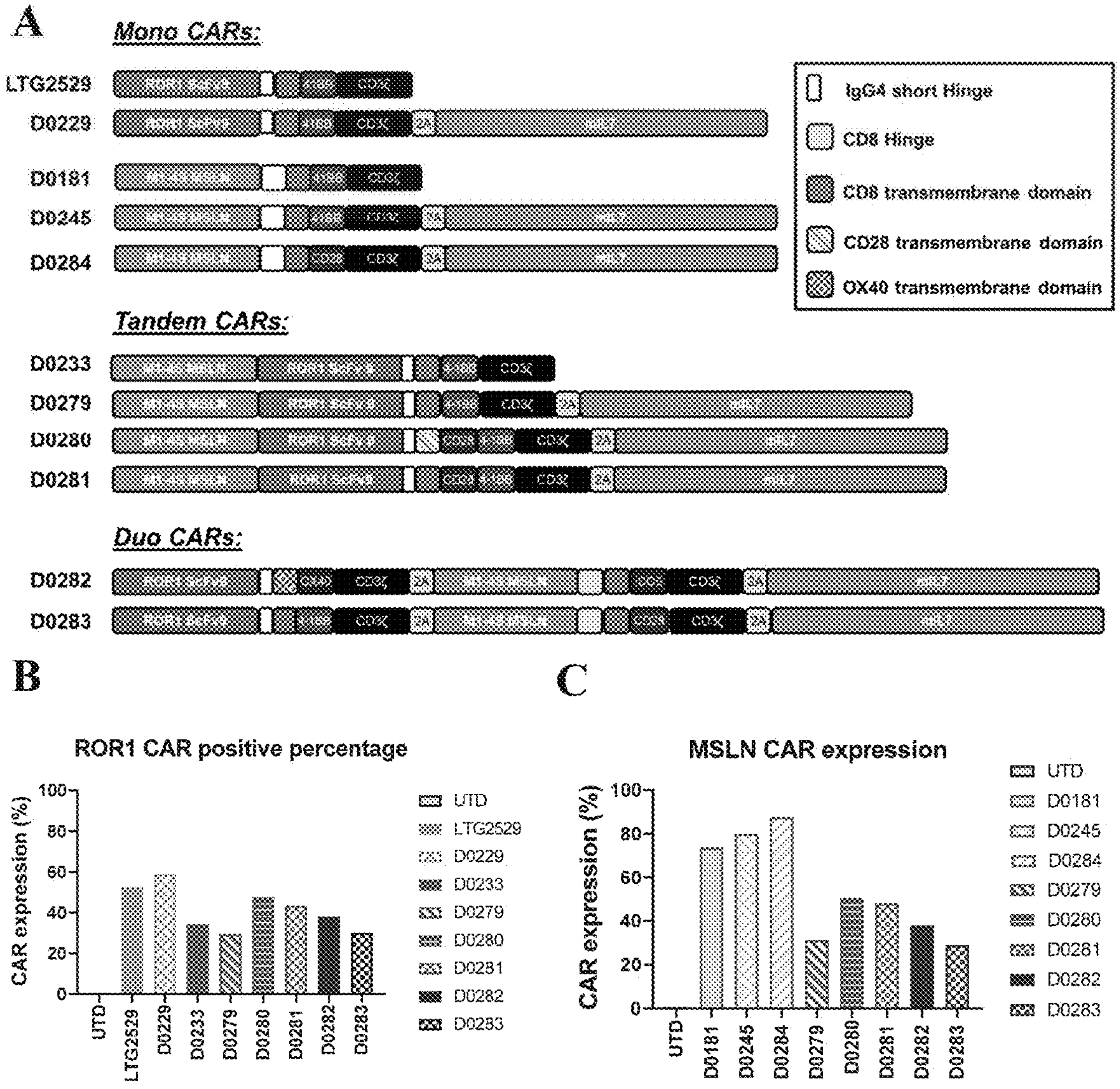
FIGS. 2A-2E depict the mIL7 armed ROR1 and/or MSLN CAR structure and surface expression on transduced primary T cell.
Figures 2D, 2E:
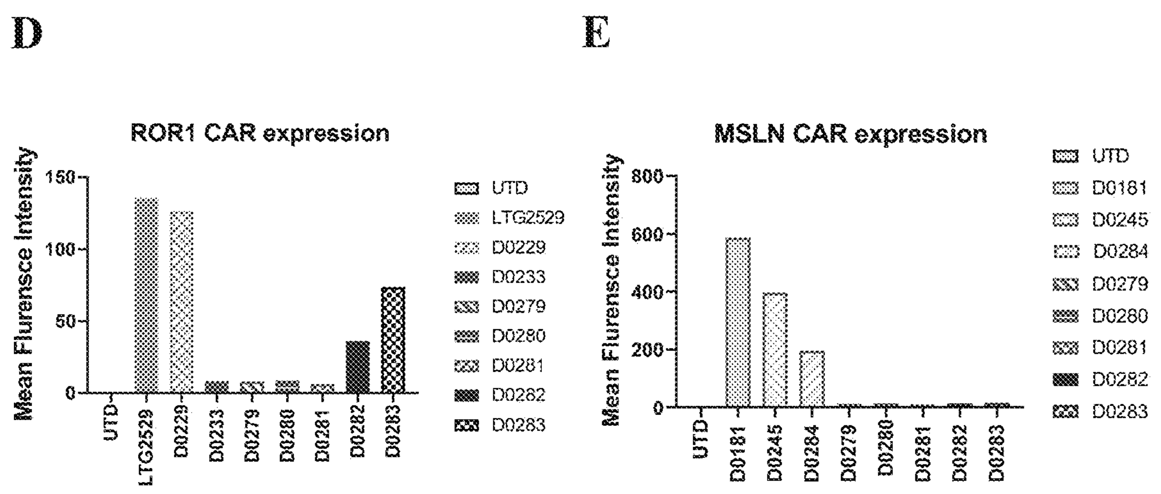

To prove the concept of boosted CAR functionality, ROR1 or MSLN mono CARs, MSLN_ROR1 tandem CARs and MSLN/ROR1 DuoCARs with membrane bound IL7 (mIL7) as booster element were characterized in vitro. ROR1 and MSLN mono CARs and tandem CARs without mIL7 were included as control (FIG. 2A). CAR sequences were further incorporated into a third-generation lentiviral vectors and transduced into human primary T cells at MOI 40, to generate the ROR1 and/or MSLN CAR T cells under the control of the mammalian EF-1α promoter. Un-transduced T cells derived from same donor (UTD) were used as negative control. Surface expression of CARs with ROR1 binder on transduced T cells was measured by flow cytometry using ROR1-Fc, followed by staining with anti-Fc Alexa Flour 647. CARs with MSLN scFv surface expression was detected by MSLN-His followed by anti-His APC. Different CAR constructs exhibited reasonable surface expression than un-transduced T cells (n=2). Quantified CAR positive percentage and mean fluorescence intensity (MFI) of ROR1 binders (FIG. 2B, 2D) and MSLN binders (FIG. 2C, 2E) were plotted as bar figure. For this donor, ROR1 CAR LTG2529 and IL7 boosted ROR1 CAR D0229, MSLN CAR D0181 and booster MSLNCAR D0245 showed similar percentage of CAR positivity and MFI, suggested mIL7 has negative impact on CAR expression. Tandem CARs with and without booster and DuoCARs with booster exhibited robust expression (30% to 50%). These results demonstrate high transduction efficiency and CAR expression.

Figures 3A, 3B, 3C:
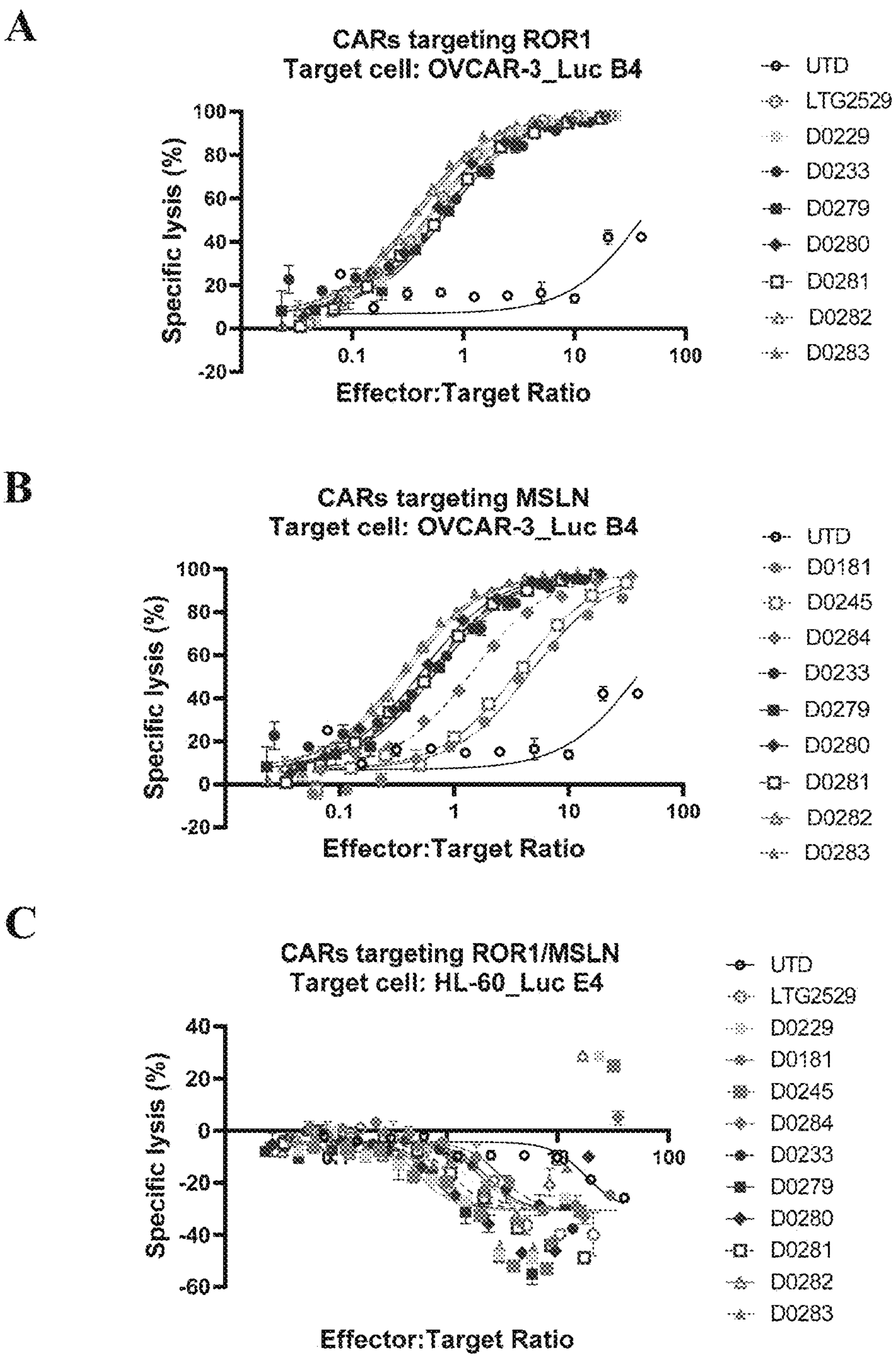
FIGS. 3A-3C depict the cytotoxicity of ROR1 and/or MSLN CAR constructs in vitro. Luciferase-based cytotoxicity assays were performed using $ROR1^{+}$ $MSLN^{+}$ tumor line OVCAR3 with (FIG. 3A) CARs containing ROR1 scFv, (FIG. 3B) CARs containing MSLN scFv, and $ROR1^{+}$ $MSLN^{+}$ tumor line (FIG. 3C) HL-60. All target lines were stably transduced with firefly luciferase. CAR T cells and tumor cells were co-cultured overnight at the 10 series effector to target (E:T) ratios. Percentage specific target lysis was assessed by luminometry and normalized to percentage of CAR expression. Non-linear EC50 shift, x is log concentration was used for curve fit. Data represented one independent experiment from two different donors.

To evaluate the target-specific cytotoxicity of ROR1 and/or MSLN CARs in vitro, $ROR1^+MSLN^+$ ovarian cancer line OVCAR-3, lung cancer line NCI-H226, pancreatic cancer line Capan-2, and $ROR1^-MSLN^-$ leukemic lines HL-60 were selected as target lines. CAR-T cells were co-incubated with target tumor cell lines at 10 different effector to target (ET) ratios. After overnight co-incubation, cytotoxicity of CARs was analyzed in a luminescence based in vitro killing assays. Percentage of specific lysis was plotted with ET ratio using non-linear curve fit. Complete killing curve of OVCAR-3 and HL60 were shown in FIG. 3. CARs with ROR scFv showed similar or higher killing capacity, compared to mono ROR1 CAR LTG2529, at all ET ratio tested (FIG. 3A). In contrast, tandem or DuoCARs with MSLN scFv outperformed mono MSLN CAR D0181 and mono MSLN booster CAR D0245 (FIG. 3B). UTD non-specific killing was noticed at high ET, due to a greater sensitivity of these tumor lines toward human T cells. Furthermore, no killing or limited background killing of HL-60 cell line, which is negative for the expression of ROR1 and MSLN, was observed in CAR T or UTD control groups (FIG. 3C), confirming that the cytotoxicity of ROR1 and MSLN CARs is target-specific.

Figure 4A:
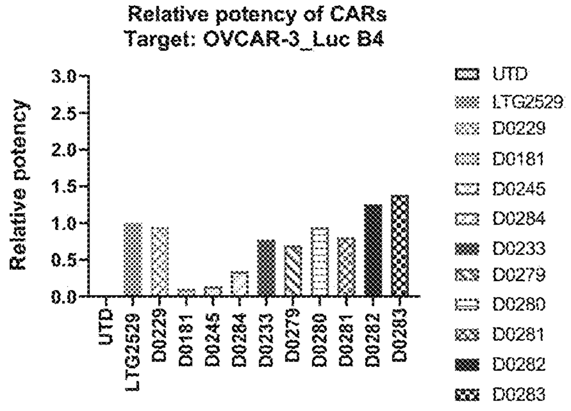
FIGS. 4A-4C depict the relative potency of ROR1 and/or MSLN CAR constructs in vitro. Luciferase-based cytotoxicity assays were performed using $ROR1^{+}$ $MSLN^{+}$ tumor lines. CAR T cells and tumor cells were co-cultured overnight at the 10 different effector to target (E:T) ratios. Percentage specific target lysis was assessed by luminometry and normalized to percentage of CAR expression. Relative potency comparing to ROR1 CAR LTG2529 was calculated using non-linear EC50 shift, x is log concentration function in GraphPad Prism. Relative potency of each constructs targeting $ROR1^{+}$ $MSLN^{+}$ tumor lines.
Figure 4B:
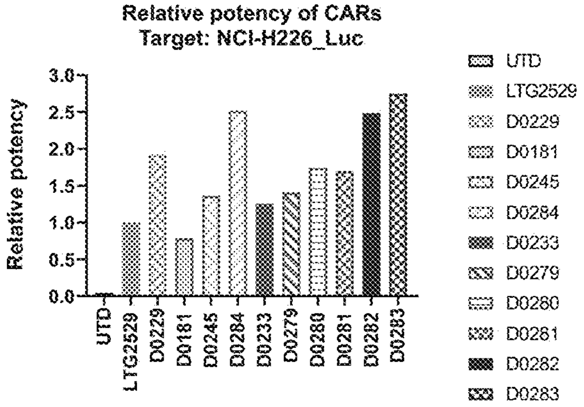
Figure 4C:
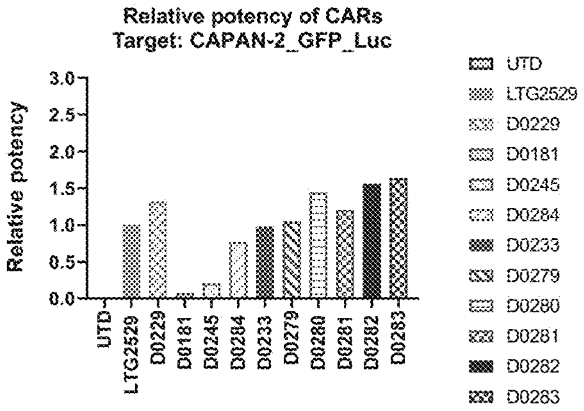

Relative potency was calculated using EC50 function in GraphPad Prism. As normalized to ROR1 CAR LTG2529, the relative potencies of all tested constructs targeting OVCAR-3 (FIG. 4A), NCI-H226 (FIG. 4B), and Capan-2 (FIG. 4C) are shown. All boosted CARs revealed similar or higher potency in vitro as compared to their non-boosted CAR counterparts, including ROR1 CAR LTG2529 vs boosted CAR D0229, MSLN CAR D0181 vs boosted CARs D0245, or D0284; non-boosted tandem CAR D0233 vs boosted CARs D0279, D0280 and D0281.

Figures 5A, 5B, 5C:
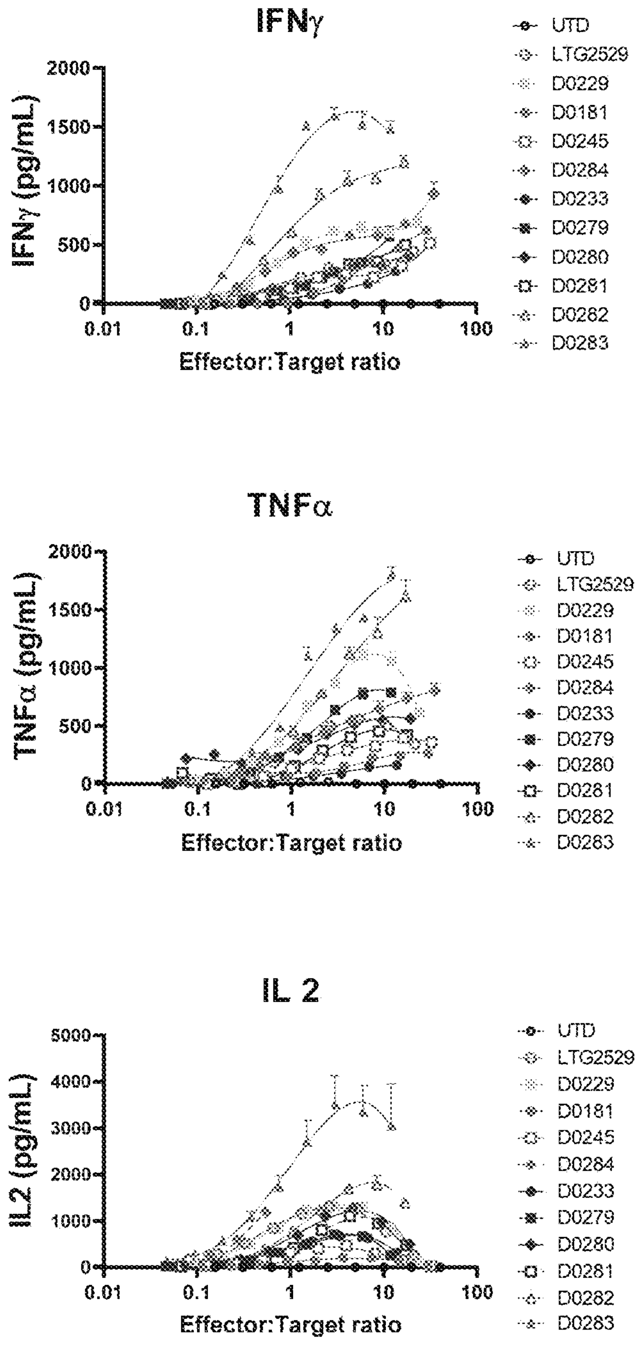
FIGS. 5A-5C depict CAR T cytokine release in response to NCI-H226 lung carcinoma cell lines. Culture supernatants of CAR T cells was evaluated after overnight incubation alone or with $ROR1^{+}$ $MSLN^{+}$ NCI-H226 target cells at 10 different E:T ratios. Cytokine production of (FIG. 5A) IFNγ, and (FIG. 5B) TNFα, (FIG. 5C) IL-2, were analyzed by ELISA. Mean±SEM of two technical replicates. Data show one experiment performed with technical triplicates from one donor, representing results from three independent experiments in separate donors.

Production of the T cell homeostatic and pro-inflammatory cytokines IL-2, IFN-γ, and TNF-α by the fully human ROR1 and/or MSLN CARs, was examined by ELISA. Culture supernatants after overnight co-incubation of CAR T cells with NCI-H226 target line (FIG. 5A-AC), were harvested for the measurement of cytokines elaboration by CAR T cells. Fully human ROR1 and/or MSLN CAR with or without boosting element exhibited CAR T cell dose dependent cytokine response when compared to UTD, indicating robust, target-specific CAR T cell cytokine responses. The intensity of cytokine release of duo ROR1/MSLN booster CAR constructs tend to be the highest for all three cytokines.

Figures 6A, 6B, 6C:
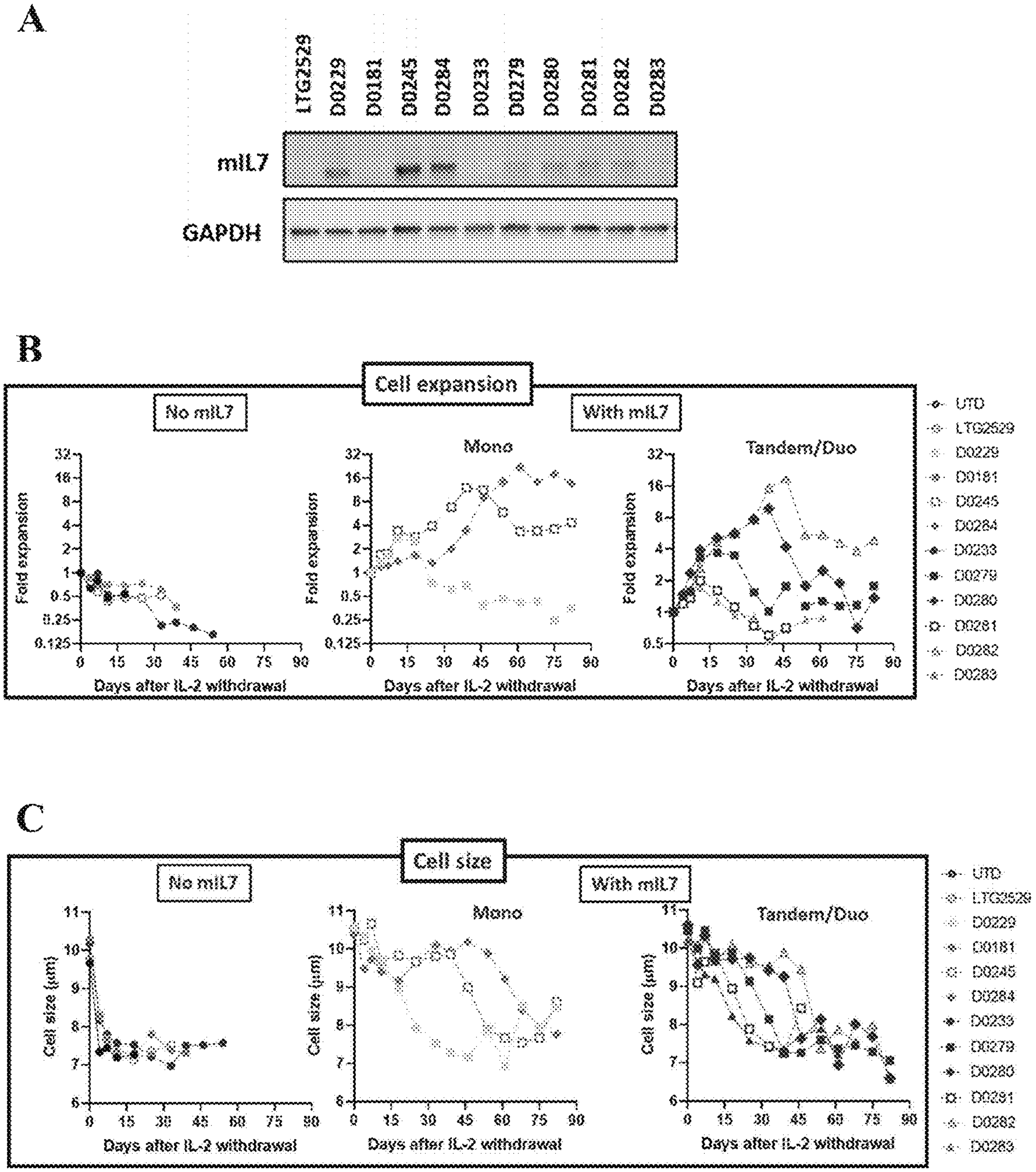
FIGS. 6A-6C depict the membrane bound IL7 expression and its functionality of sustaining CAR T-cell growth after IL-2 withdrawal.
Figure 7A:
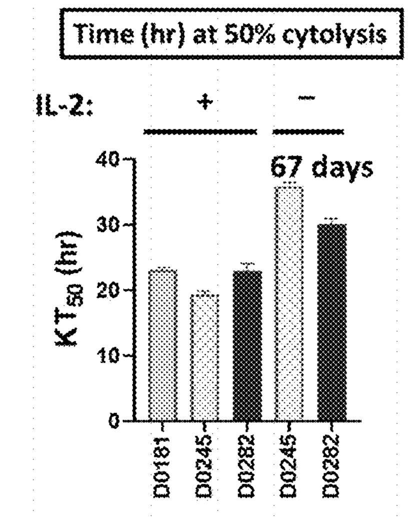
FIGS. 7A and 7B depict the time to 50% target cell killing (KT50) (FIG. 7A) and the relative potency of MLSN CAR T cells before and after IL-2 withdrawal (FIG. 7B). MSLN CAR with mIL7 D0245 and ROR2/MSLN DuoCAR with mIL7 D0282 were cultivated with TexMACS medium without IL-2 supplement for 69 days. Cytotoxicity of CAR D0245 and D0282 were measured by xCELLigence RTCA instrument using ROR1$^+$MSLN$^+$ pancreatic cancer cell line AsPC-1. MSLN CAR D0181, CAR D0245 and D0282 without IL-2 withdraw were included as controls. CAR T cells and target cells were cocultured at ET ratio 2:1. Percentage specific target lysis was assessed by impeded electron flow. KT50 represents the coincubation time necessary to achieve 50% of the target cells cytolysis. Relative potency calculated based on KT50 of MSLN CAR D0181 without IL-2 withdrawal. Data represented one independent experiment from two separate donors.
Figure 7B:
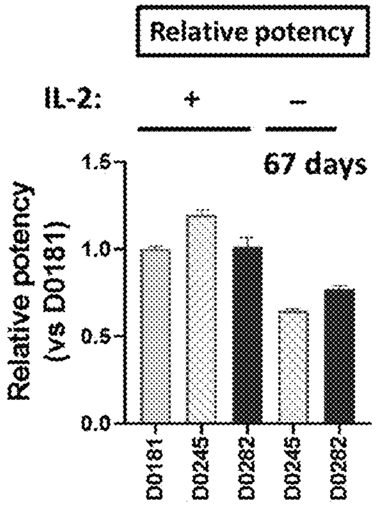

Western blotting was performed to further verify the expression of mIL7 in booster CARs. Human primary T cells were transduced with CAR constructs at MOI 10. Five million transduced T cells were harvested and lysed for western blot using IL7 antibody. GAPDH was included as loading control. Boosted CARs demonstrated mIL7 overexpression as compared to controls (FIG. 6A). Boosted MSLN mono CARs D0245 and D0284 showed the strongest expression among the boosted CAR constructs. To further assess the functionality of mIL7 to support T cells growth, transduced T cells were cultured with TexMACS medium without IL-2 supplement at density of 1e6/ml. Cell expansion (FIG. 6B) and cell size (FIG. 6C) were monitored periodically. CAR T cells without mIL7, shown on the left in FIGS. 6B and 6C, did not expand and cell size dropped immediately. As contrast, mIL7 boosted CAR T cells, shown in the middle and right panels, remained in activated state and continued proliferating. At the last time point on day 82 after IL-2 withdrawal, all boosted CAR T cells populations contracted from the peak expansion and returned to quiescent state. To evaluate the boosted CAR T cell cytotoxicity after IL-2 withdrawal, the boosted MSLN CAR with D0245 and boosted Duo CAR D0282 were maintained in IL-2-depleted TexMACS medium for 67 days, then cocultured with pancreatic cancer cell line AsPC1. MSLN CAR DO181, booster CAR D0245 and D0282 without IL-2 withdrawal were included as comparison. Target cell killing was monitored for 3 days. The killing time reached 50% target cell lysis (KT50) and relative potency based on CAR DO181 was calculated (FIGS. 7A and 7B). Despite 67 days of IL-2 withdrawal, the boosted CARs D0245 and D0282 maintained their cytotoxic potency. Therefore, mIL7 in boosted CARs supported CAR T cell homeostasis and functionality in the absence of IL-2. Transforming growth factor beta (TGF-β) is a multifunction cytokine, which may play important role in the immunosuppressive tumor microenvironment (TME).

Figures 8A, 8B:
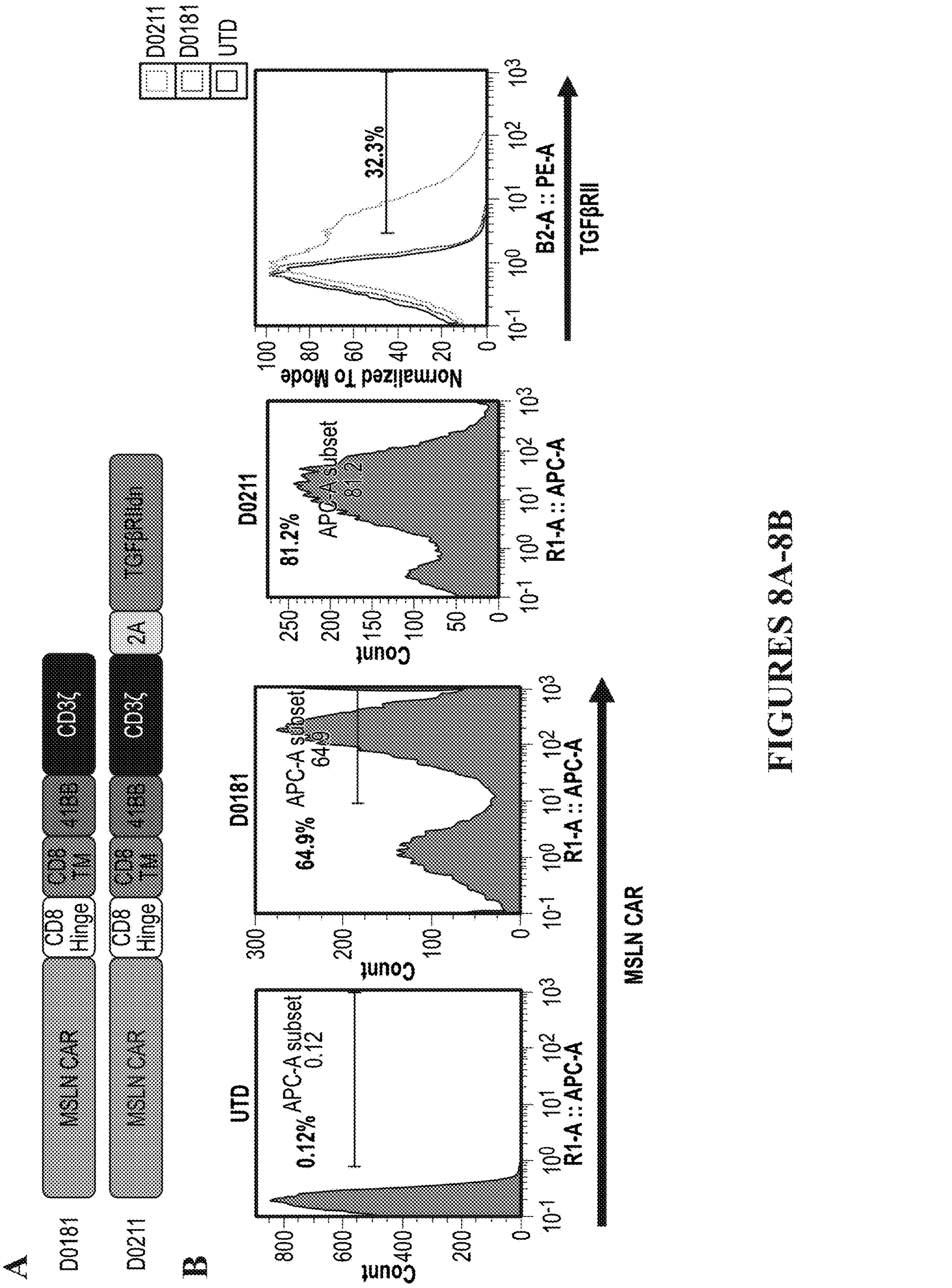
FIGS. 8A-8E depict in vitro characterization of TGFβRIIdn boosted MSLN CARs.
Figure 8C:
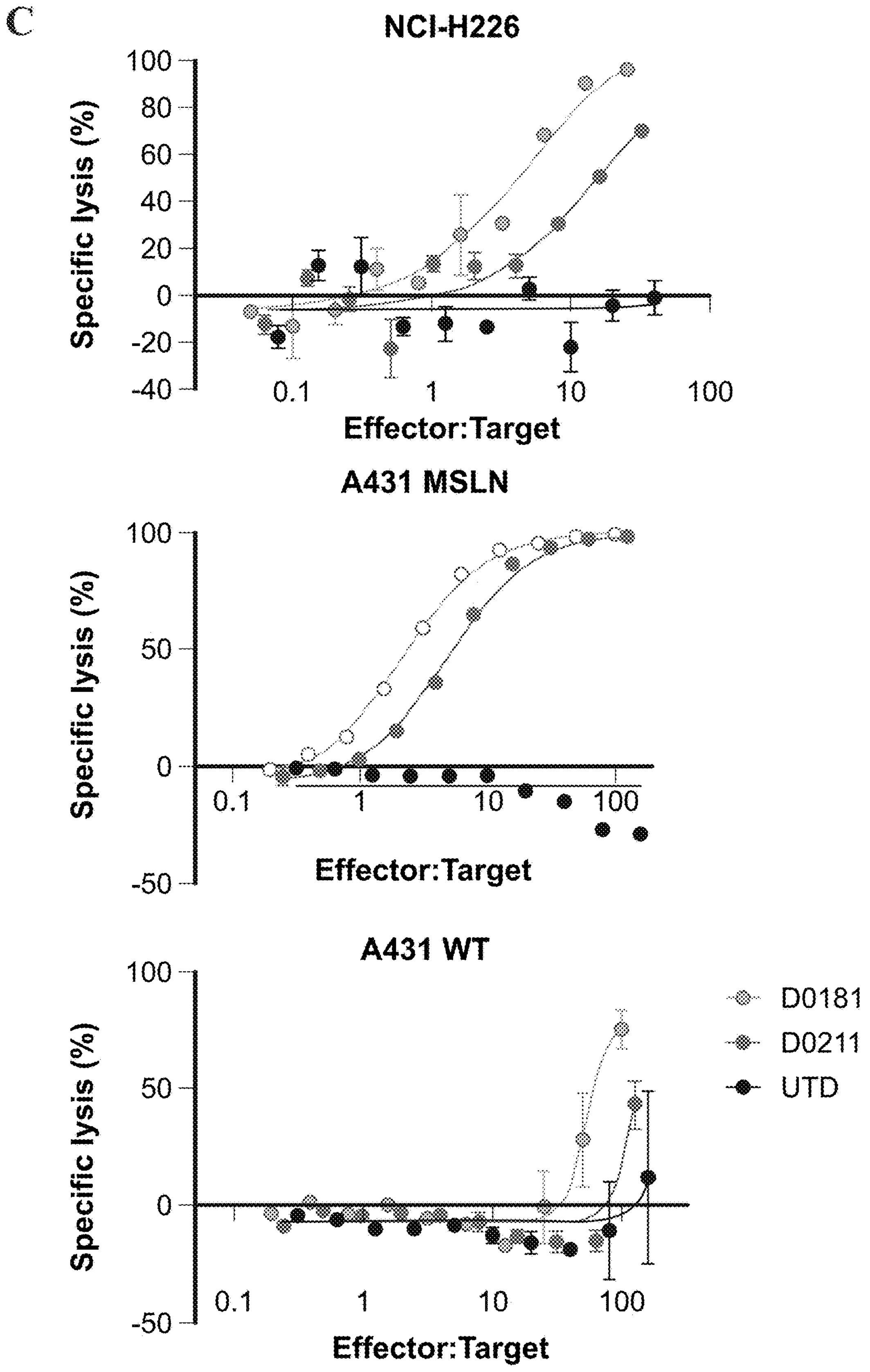
Figures 8D, 8E:
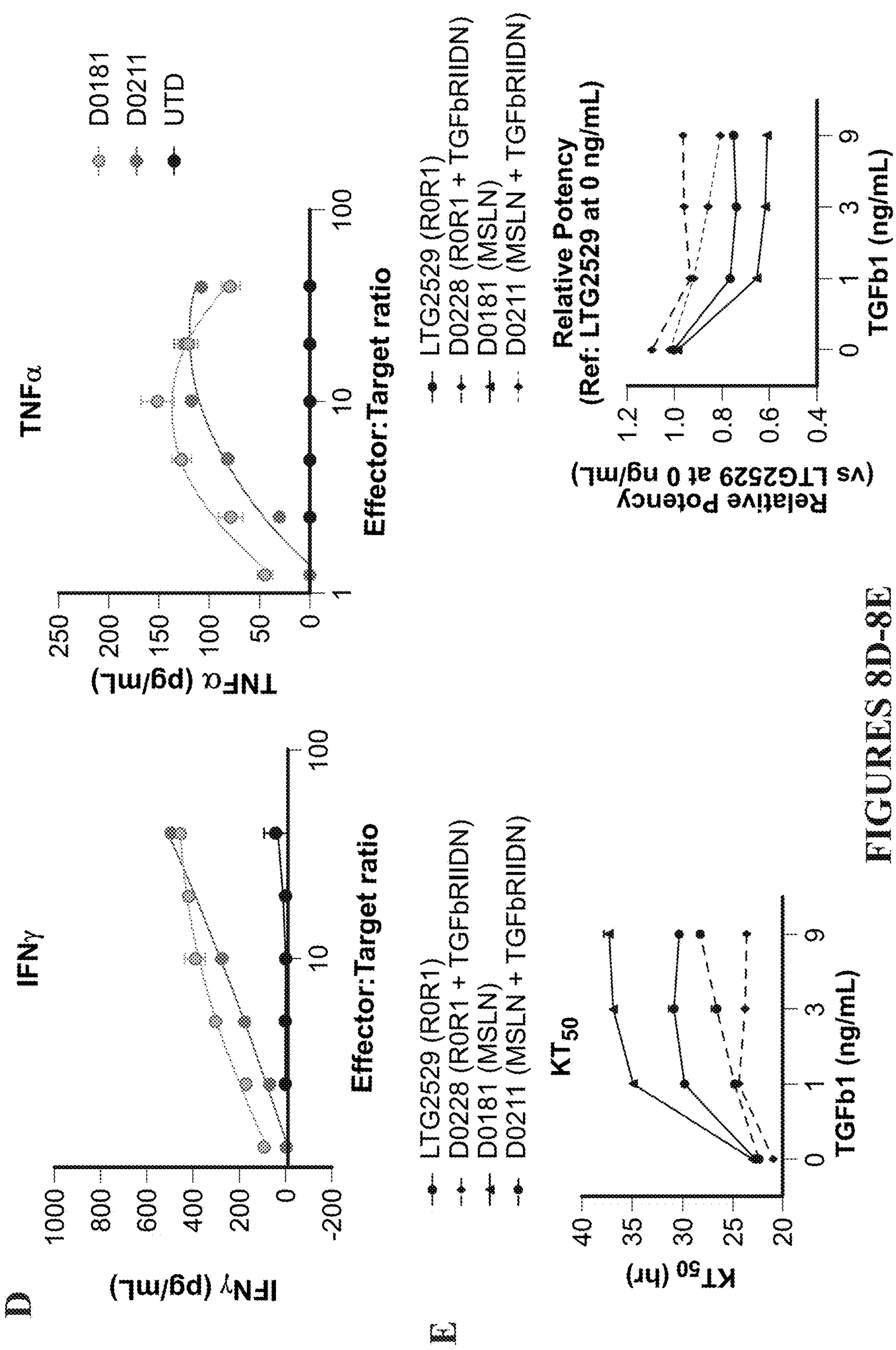
Figure 8E:
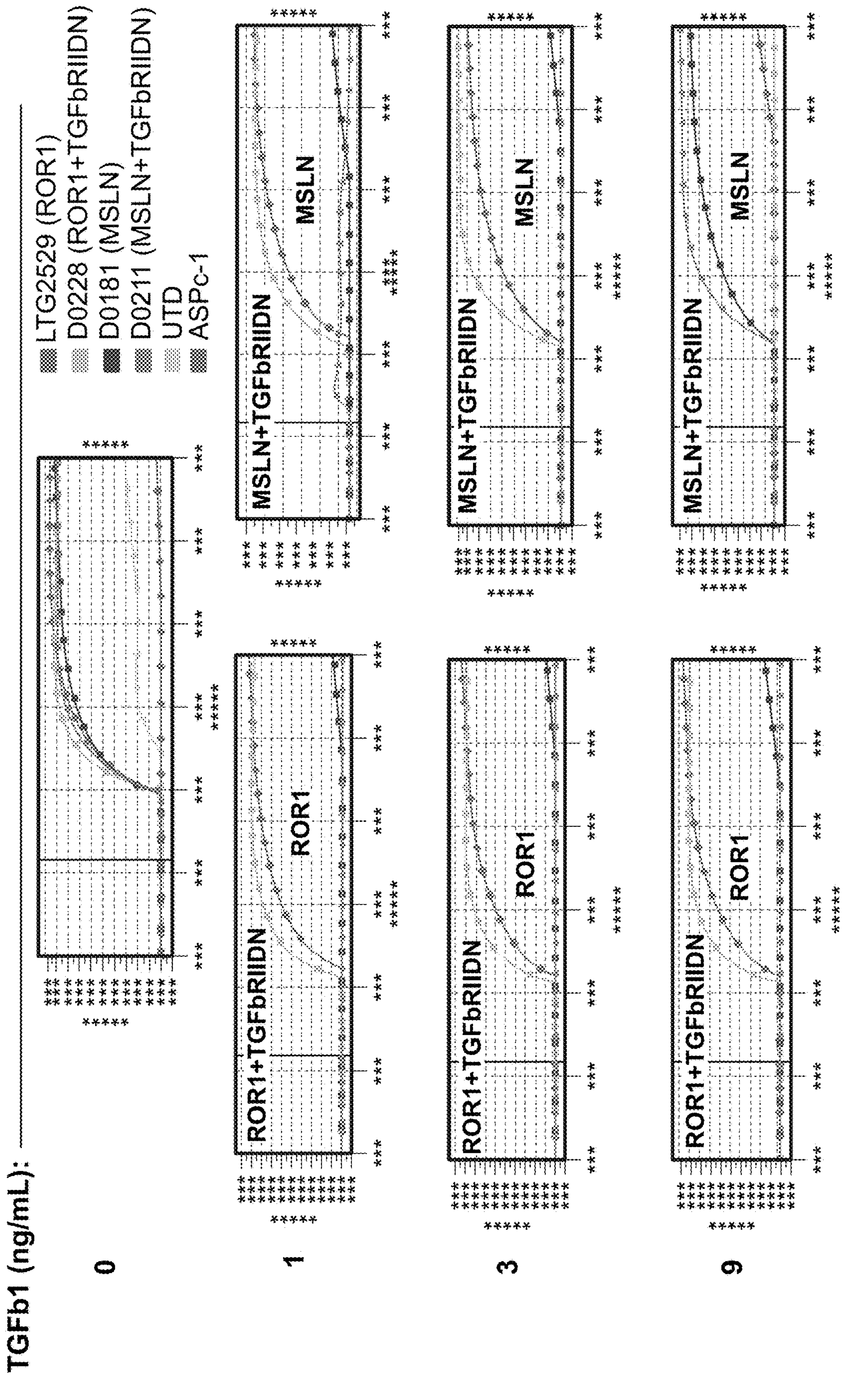

The dominant negative TGFβ receptor II (TGFβRIIdn) was designed as booster element to enhance CAR T cell functionality to against inhibitory TME. To evaluate the in vitro function of TGFβRIIdn, CAR MSLN D0181 and TGFβRIIdn armored CAR MSLN D0211 (FIG. 8A) were transduced with primary human T cells, surface expression of CAR MSLN and TGFβRIIdn were examined by flow cytometry. Armored CAR D0211 effectively transduced and expressed on the primary T cell surface with 81.2% MSLN CAR positivity, and TGFβRII showed robust but weaker (32.3%) compared to CAR expression (FIG. 8B). Target specific cytotoxicity of MSLN CAR without TGFβRIIdn was assessed with MSLN cell lines NCI-H226, A431-MSLN, $MSLN^-$ cell line A431 was included as control. Both MSLN CAR D0181 and armed CAR D0211 exhibited effective killing potency during coculture with NCI-H226 and A431-MSLN (FIG. 8C). Non-specific killing towards MSLN-A431 lines was noticed at very high E T ratios, possibly due to allo-reactivity, for both MSLN CAR constructs, while CAR D0211 showed less non-specific killing. The supernatant of overnight coculture of NCH-H226 and CAR T cells were used to exam T cell homeostatic and pro-inflammatory cytokines IFNγ, and TNFα. Armed CAR D0211 demonstrated target specific cytokine release at a similar level as CAR D0181 (FIG. 8D). The protective activity of the TGFBRIIdn element was investigated in the context of MLSLN and ROR1 CAR T cell constructs. For each target, a CAR alone (ROR1 LTG2529 and MSLN DO181), or the TGFBRIIdn armored CAR (ROR1 D0228, MSLN D0211) were included. CAR T cells were combined with AsPC-1 pancreatic tumor cells, which are MSLN-positive and ROR1-positive, for a kinetic co-culture assay (xCELLigence RTCA) either in the absence of TGFβ, or in the presence of TGFβ 1 at concentration of 1 ng/ml, 3 ng/ml, or 9 ng/ml (FIG. 8E). While the cytotoxic activity of the non-armored CARs was impeded by TGFβ in concentration-dependent manner, as indicated by KT50 (time to kill 50% of all tumor cells) and reduced relative potency, the armored CAR T cells sustained their cytotoxic function in the presence of TGFβ. These results underscore the functionality of the TGFβRIIdn boosting element in CAR T cells.

Figures 9A, 9B, 9C, 9D:
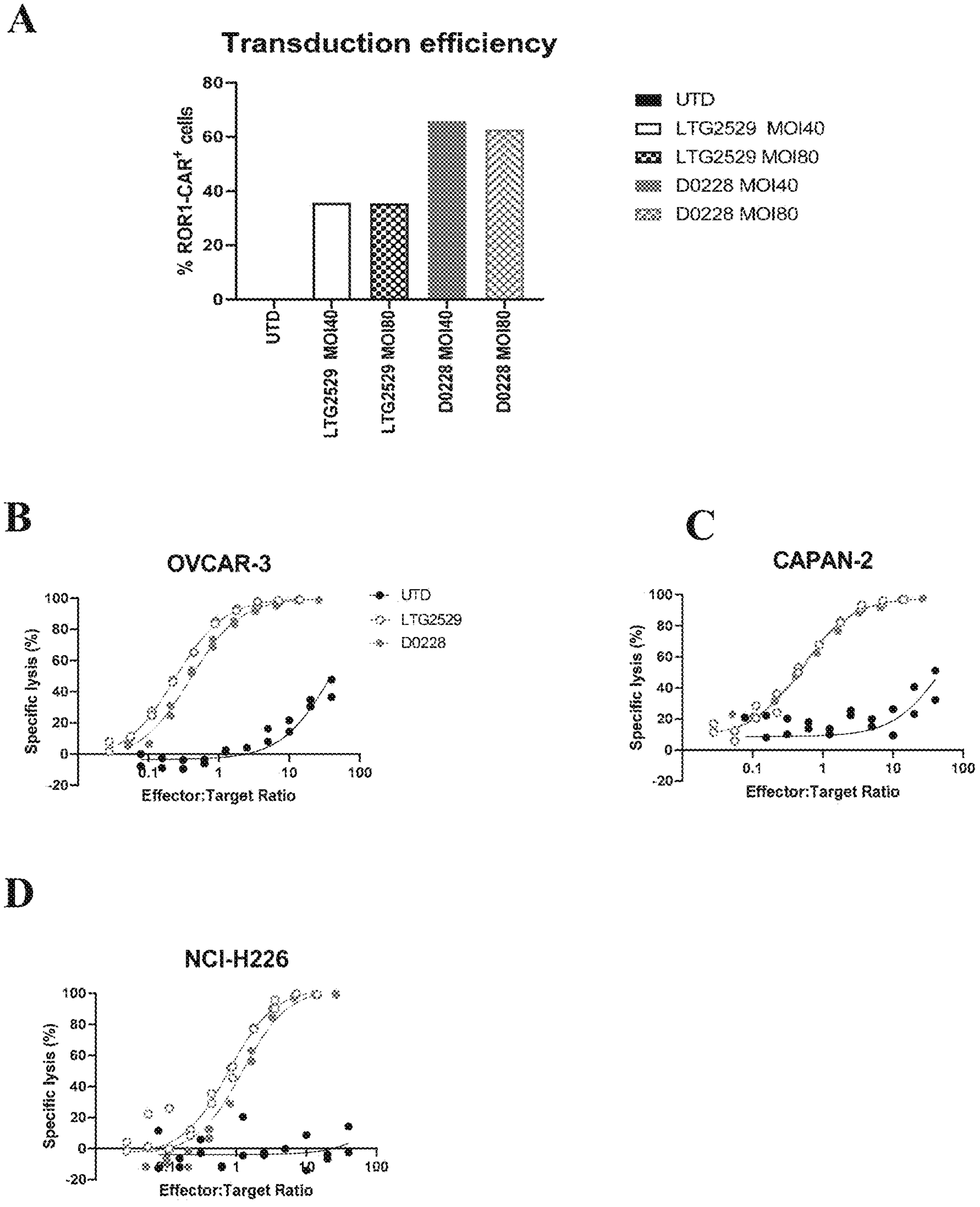
FIGS. 9A-9D depicts in expression and cytotoxicity of ROR1 CARs with TGFβRIIdn on an overnight endpoint killing assay at a range of effector to target cell ratios. Primary T cells from a healthy donor were activated with TransAct in the presence of IL-2, and transduced with lentiviral vectors encoding ROR1 CAR LTG2529 and boosted, TGFβRIIdn-armored ROR1CAR D0228 constructs. CAR surface expression was assessed by flow cytometry using ROR1 Fc followed by anti-Fc-AF647 staining. Percentage of CAR expression was plotted in panel (FIG. 9A). ROR1+ target lines, OVAR3 (FIG. 9B), CAPAN-2(FIG. 9C) and NCI-H226 (FIG. 9D) were stably transduced with firefly luciferase. CAR T cells and tumor cells were co-cultured overnight at the various effector to target (E:T) ratios. Percentage specific target lysis was assessed by luminometry and normalized to percentage of CAR expression. Non-linear EC50 shift, x is log concentration function in Prism was used for curve fit. Data represented one independent experiment from 1 different donor.

In an additional experiment, ROR CAR LTG2529 and TGFβRIIdn armed ROR CAR D0228 were also used for evaluating TGFβRIIdn effect in vitro. Primary human T cells were transduced by M0140 and MOI 80, ROR1 scFv positivity was detected by flow. At both MOI, TGFβRIIdn armed ROR1 CAR D0228 demonstrated higher transduction efficiency compared to ROR1 CAR LTG2529 (FIG. 9A). When co incubation with $ROR1^+$ target lines OVCAR3 (FIG. 9B), CAPAN-2 (FIG. 9C), NCI H226 (FIG. 9D), boosted CAR D0228 exhibited comparable target specific cytolysis as ROR1 CAR LTG2529. The results suggested co-expression of TGFβRIIdn has no negative impact to CAR functionality.

Figure 10A:
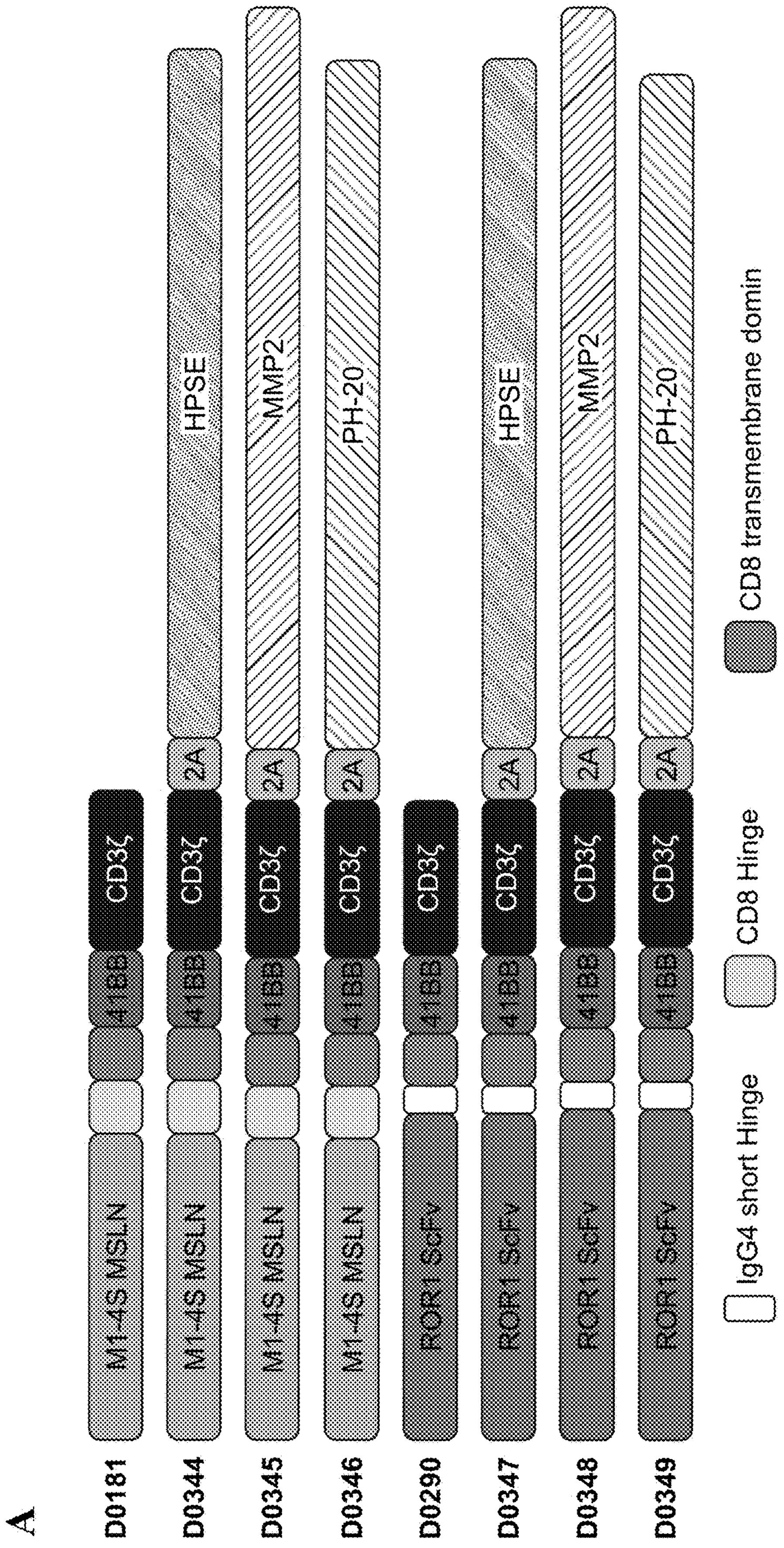
FIGS. 10A and 10B depict the structure of MSLN and ROR1 CAR with ECM booster and surface expression in human primary T cells.

One alternative approach to boost CAR-T therapy is by targeting the ECM components in solid tumors via co-expression of ECM enzymes. Schematic representations of the boosted CAR constructs are shown in FIG. 10A. CAR+ ECM enzymes comprised of MSLN/ROR1 CAR molecule, in frame to an extracellular matrix enzyme linked by P2A ribosomal skipping element sequence. Fully human binders scFv9 targeting ROR1 and anti MSLN scFv were developed in house. Mono CAR configured with a scFv targeting ROR1 or MSLN, in frame to IgG4 or CD8 hinge, CD8 transmembrane, 41-BB, costimulatory and a CD3ζ activation domain. ECM enzymes included in this set are heparanase (HPSE), matrix metalloproteinase-2 (MMP-2), or secreted hyaluronan (sPH-20 IgG1 Fc).

To test CAR-T functionality in vitro, ROR1 or MSLN mono CARs with HPSE, MMP-2 or sPH-20 as booster elements were characterized. ROR1 and MSLN CAR+/− ECM enzymes were further incorporated into a third-generation lentiviral vectors and transduced into human primary T cells at MOI 40, to generate the ROR1 and/or MSLN CAR T cells under the control of the mammalian EF-1α promoter. Un-transduced T cells derived from same donor (UTD) were used as negative control. Surface expression of CARs with ROR1 binder on transduced T cells was measured by flow cytometry using ROR1-Fc, followed by staining with anti-Fc Alexa Flour 647. CARs with MSLN scFv surface expression was detected by MSLN-His followed by anti-His APC. Different CAR constructs exhibited reasonable surface expression than un-transduced T cells. Quantified CAR positive percentage of ROR1 binders and MSLN binders (FIG. 10B) were plotted as a quadratic plot of CD4 vs. CAR. For this donor, CARs co-expressing HPSE or MMP-2 had similar CAR expression to that of CARs alone (62.5-84.3%). CARs co-expressing sPH-20 had reduced expression compared to that of CAR alone (39-44%). This could be due to the large payload size of the sPH-20. These results demonstrate effective transduction efficiency and CAR expression.

Figures 11A, 11B, 11C, 11D:
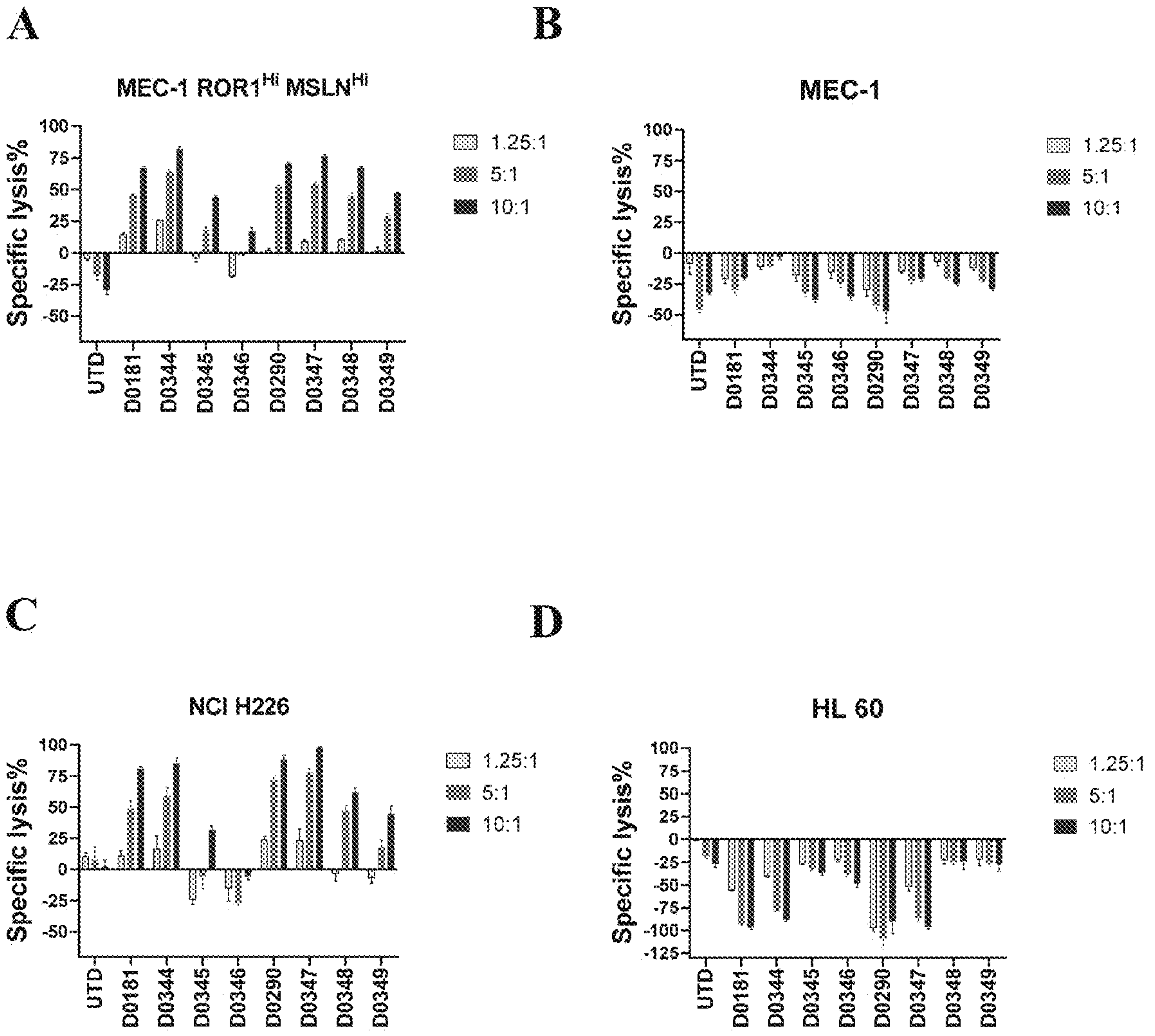
FIGS. 11A-11D depicts the cytotoxicity of MSLN and ROR1 CAR constructs in vitro. Luciferase-based cytotoxicity assays were performed using ROR1$^+$ MSLN$^+$ tumor lines.

To evaluate the target specific cytotoxicity of ROR1 and/or MSLN CARs in vitro, MEC-1 overexpressing $ROR1^{+}MSLN^{+}$ B cell line, lung cancer line NCI-H226, and $ROR1^{-}MSLN^{-}$ leukemic lines HL-60 and MEC-1 were selected as target lines. CAR-T cells were co-incubated with target tumor cell lines at effector to target ratios 10, 5, 1.25:1. After overnight co-incubation, cytotoxicity of CARs was analyzed in a luminescence based in vitro killing assays. Percentage of specific lysis was plotted with E:T ratio using bar graphs (FIG. 11A-D). CARs with HPSE (D0344, D0347) showed similar killing capacity, compared to mono ROR1 or MSLN CAR, at all E:T ratio tested, suggesting that HPSE addition does not reduce CAR potency (FIG. 11A,C). In contrast, CAR+MMP-2 (D0345, D0348) had slightly less killing and CAR+sPH-20 (D0346, D0349) killing was marginal compared to CAR alone (FIG. 11A, C). Furthermore, no killing of ROR1 and MSLN negative HL-60 and MEC-1 cell lines by CAR T cells, as compared to the negative control UTD, was observed (FIG. 11B, D), demonstrating the robust target-specific cytotoxic function of all ROR1 and/or MLSN CAR constructs designed.

Figure 10B:
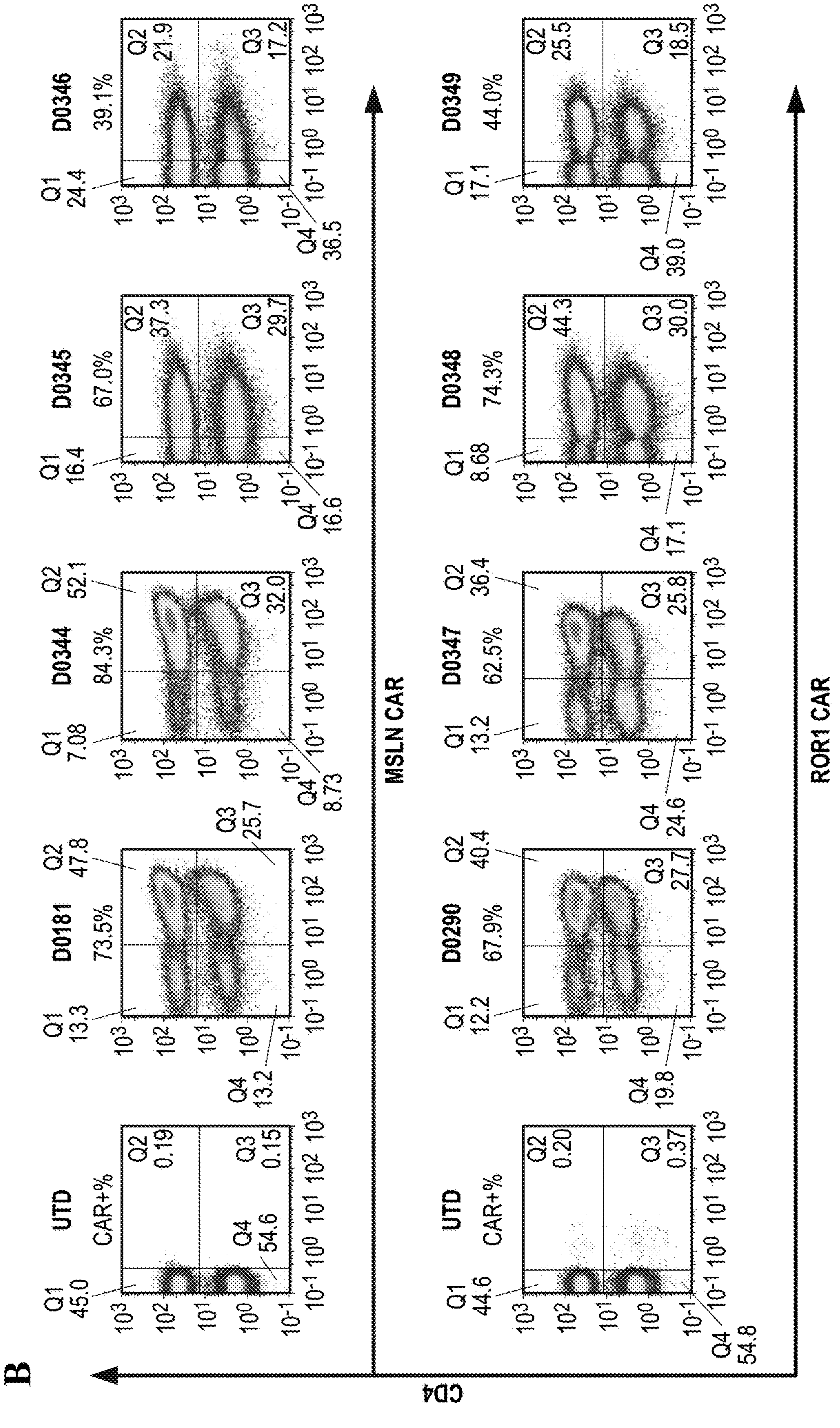
Figure 12A:
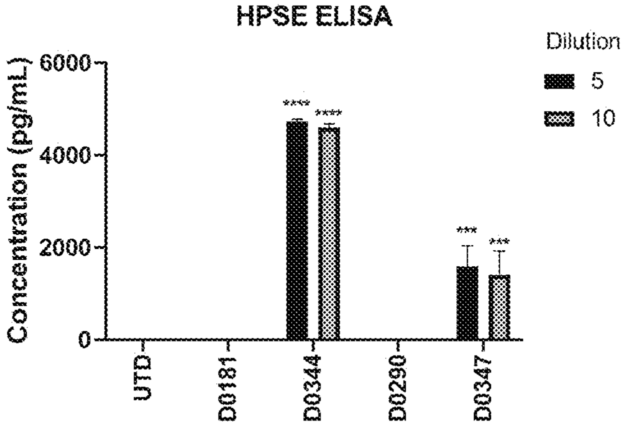
FIGS. 12A and 12B depict the expression of HPSE in booster CARs and its capacity to facilitate CAR T cell migration in vitro.

Production of the HPSE enzyme by the fully human ROR1 and/or MSLN CARs (D0347, D0344), was examined by ELISA. CAR-T supernatants after 2d in culture without IL-2 was harvested for the measurement of specific cytokine release. Fully human ROR1 and/or MSLN CAR with HPSE was observed when supernatants were diluted 5 or 10 fold (FIG. 12A). In comparison, no HPSE was observed in UTD or mono CAR-T cells alone (D0181, D0290). These results suggest that CARs co-expressing HPSE have robust CAR and enzyme expression (FIGS. 10B and 12A).

Figure 12B:
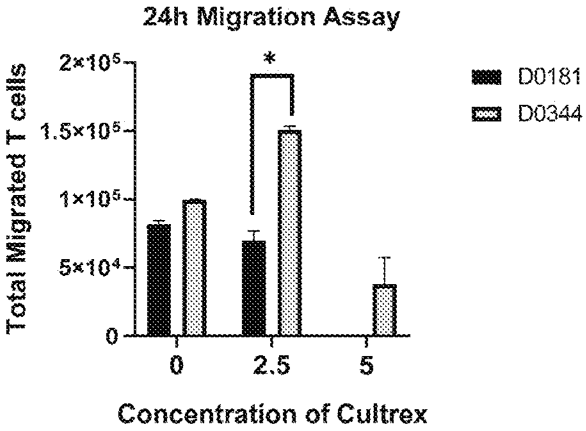
Figure 13A:
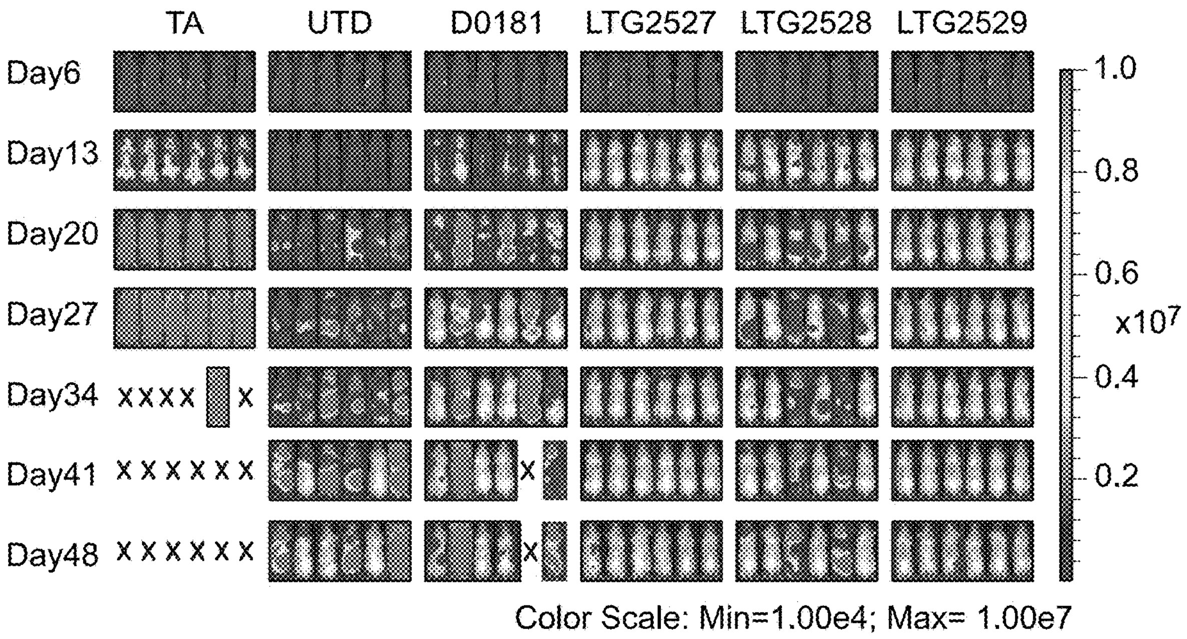
FIGS. 13A and 13B depict the in vivo activity of CAR T constructs in JeKo-1 xenograft model. NSG mice were implanted with $5\times10^5$ JeKo-1 cells stably transduced with luciferase, via tail vein on Day 0. Tumor burden was determined using bioluminescent imaging. Mice with comparable mean tumor burden were randomly distributed into each group and injected with $5\times10^6$/mouse CAR+ T cells or UTD on day 7. Tumor kinetics were measured at day 13, 20, 27, 34, 41, and 48.
Figure 13B:
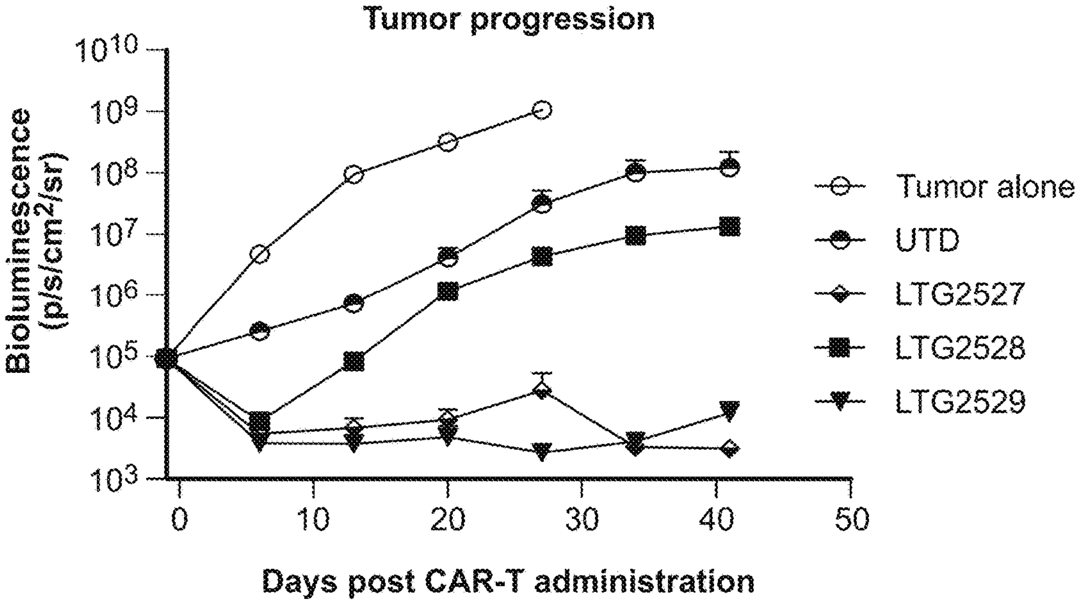

As a measure of CAR-T migration through an ECM-rich environment in vitro, CAR-T were subjected to an invasion assay in transwell inserts coated with Cultrex™ BME. UTD, CAR alone, or CARs bicistronically expressing HPSE were thawed, counted, and seeded into uncoated or Cultrex™-coated transwell inserts for 24 h (in the absence of IL-2). Medium in the bottom chamber was then collected, washed and processed via flow cytometry and normalized to Absolute counting beads. As shown in FIG. 12B, ROR1 or MSLN CARs co-expressing HPSE (D0347 or D0344) had greater migration in 5 mg/mL Cultrex™-coated transwell inserts than that of CARs alone (D0290, D0181). The results discussed here illustrate that CARs co-expressing HPSE can functionally by-pass an ECM better than CARs alone.

In summary, ROR1 and/or MSLN CARs constructs with mIL7 booster demonstrated reproducible and robust transduction efficiency, comparable cytotoxic function as their non-boosted CAR counterparts, and specific cytokine induction in vitro during coculture with target cells. In the absence of IL-2, the expression of mIL7 from boosted CARs extended CAR T cell survival and preserved cytotoxic function.

Example 2

Evaluation of the Anti-Tumor Function of ROR1 or MSLN Targeting CAR T Cells in an Ovarian Mouse Tumor Xenograft Model

Materials and Methods

In Vivo Analysis of CAR T Function in JeKo-1 and OVCAR3 Xenograft Model

Animal experiments were performed in compliance with the applicable laws, regulations and guidelines of the National Institutes of Health (NIH) and with the approval of MI Bioresearch (Ann Arbor, MI) Animal Care and Use Committee.

In JeKo-1 xenograft model, the function of ROR1 or MSLN targeting CAR T cells was evaluated in NSG (NOD.Cg-Prkdcs$^{cid}$IL-2rg$^{tm1\,Wjl}$/SzJ) mice in vivo using OVCAR-3 ovarian cancer cells. Six to eight week old female NSG mice, 5 per group, were injected intraperitoneally with $5\times10^{5}$ Jeko-1 $ROR1^{+}$ $MSLN^{-}$ mantel cell lymphoma cancer cells on day 0. Tumor burden was measured using IVIS bioluminescent imaging by IVIS-S5 instrument (Perkin Elmer, Waltham, MA). On day 7, mice were randomized into groups to achieve equal or similar overall mean tumor burden, and $5.0\times10^{6}$ CAR T cells/mouse (normalized for transduction efficiency) were administered via tail vain at same day. Tumor regression was determined by bioluminescent imaging (BLI) at day 13, 20, 27, 34, 41, and 48. Mouse weights were monitored three times/week.

In OVCAR-3 ovarian cancer model, six to eight week old female NSG mice, 5 per group, were injected intraperitoneally with $1\times10^{7}$ OVCAR-3 ROR1+MSLN+ ovarian cancer cells on day 0. Tumor burden was determined by IVIS bioluminescent imaging. On day 7, mice were randomized to groups based on equal or similar overall mean tumor burden, and $5.0\times10^{6}$ CAR $T^{+}$ cells/mouse (normalized for transduction efficiency) were administered via tail vain. Tumor regression was determined by bioluminescent imaging on days 10, 17, 24, 31, 38, 45, 52 using IVIS-S5. Animal body weights were recorded three times per week. Bioluminescent images were analyzed using Living Image, version 4.3, software (Perkin Elmer) and the bioluminescent signal flux for each mouse was expressed as average radiance.

Results

Figure 14:
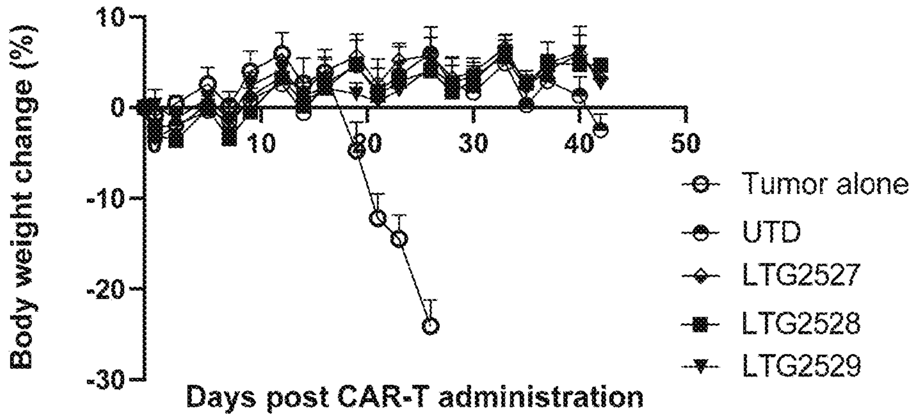
FIG. 14 depicts the body weight changes of mice during JeKo-1 xenograft study. NSG mice bearing JeKo-1 mantle cell lymphoma were treated with $5\times10^6$ CART+ cells per mouse and mouse weights were recorded three times/week. Body weight change was calculated as the percentage of change from study initiation. Mean±SEM. TA-tumor alone, UTD—non-transduced T cell control. N=6 mice/group.

JeKo-1 mantle cell lymphoma NSG xenograft model was used to evaluate the in vivo tumor rejection functionality of the CAR ROR1 candidates LTG2527, LTG2528, and LTG2529. $ROR1^{+}$ MSLN. JeKo-1 cells were stably transduced with lentiviral vector encoding luciferase. Half a million JeKo-1 tumor cells were injected intravenously (i.v.) into each NSG mouse. At day 6, tumor burden was measured by IVIS imaging and mice were randomized into each group to achieve similar mean tumor burden. ROR1 CAR constructs, LTG2527, LTG2528, LTG2529, as well as non-related CAR MSLN D0181 were included in the study. Mice inoculated with un-transduced T cells (UTD) from same donor, and untreated mice groups served as controls. At day 7, $5\times10^{6}$ human CAR+ T cells or UTD cells were administered by i.v. injection. Tumor growth was measured and quantified by in vivo imaging system (IVIS) at the denoted time points (FIGS. 14A and 14B). ROR1 CAR constructs LTG2527 and LTG2529 showed robust tumor rejection starting at day 13, and the remission was maintained until the study termination. ROR1 CAR LTG2528 controlled tumor progression at day 13. However, two mice relapsed on day 27. In contrast, tumors progressed rapidly in tumor alone (TA), UTD and MSLN CAR D0181 control groups. All mice in the ROR1 CAR T treated group survived until day 50 without significant body weight loss (FIG. 15), thus no ROR1 CAR-related toxicity was detected in this model.

Figure 15A:
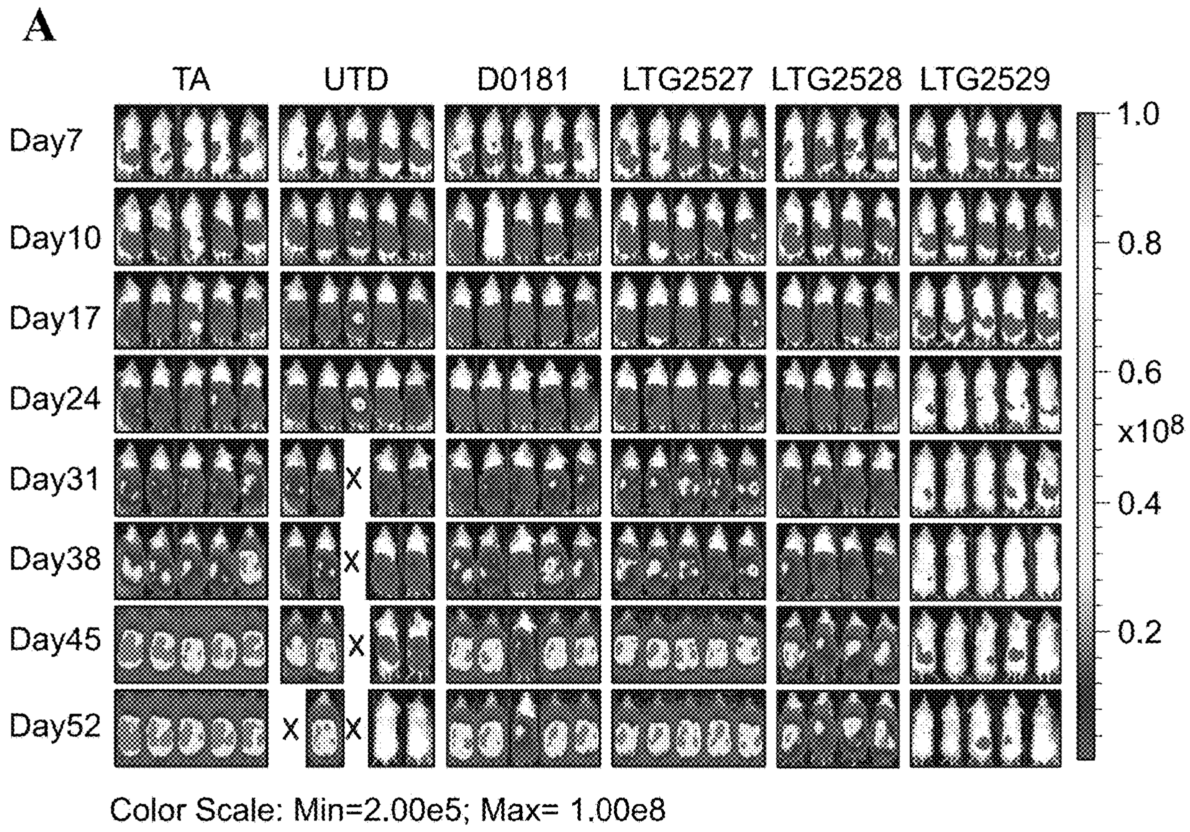
FIGS. 15A and 15B depict the in vivo activity of CAR T constructs in OVCAR-3 xenograft model. NSG mice were injected intraperitoneally with $1\times10^7$ OVCAR-3-luciferase cells on Day 0. Tumor burden was measured using bioluminescent imaging by IVIS-S5 instrument. Mice with comparable tumor burden were randomly distributed into each group, and treated with $5\times10^6$/mouse CAR+ T cells or UTD on day 7. Kinetics of tumor development were measured at day 10, 17, 24, 31, 38, 45, and 52.
Figure 15B:
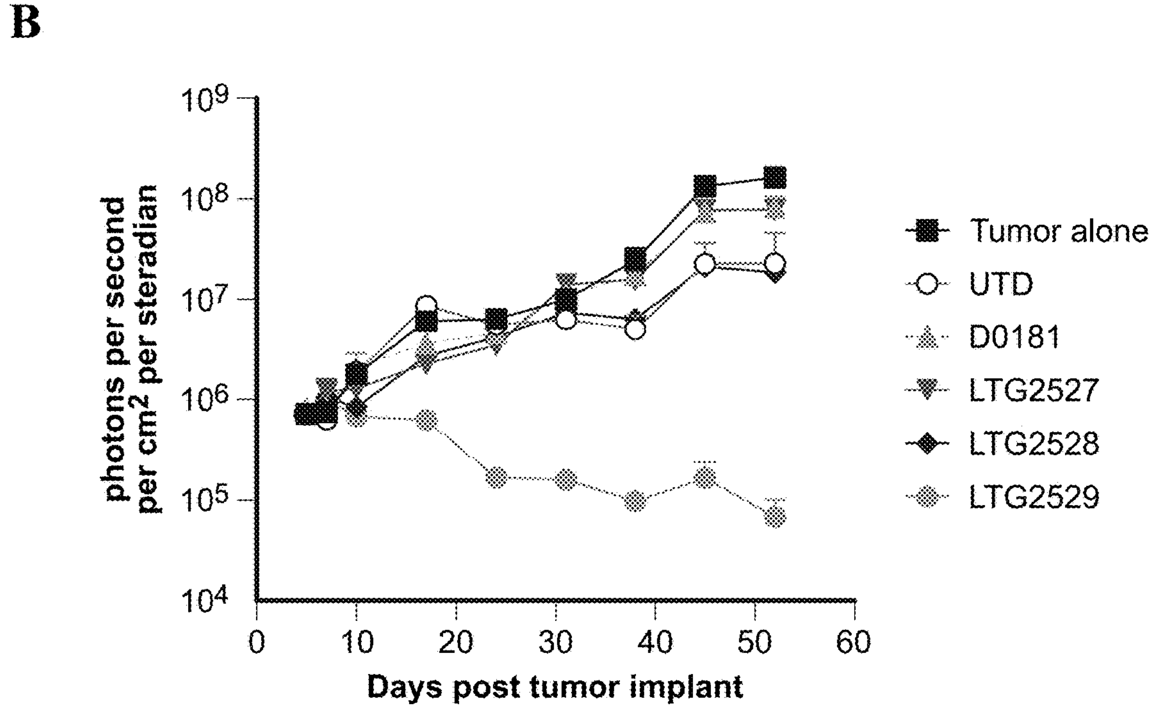
Figure 16:
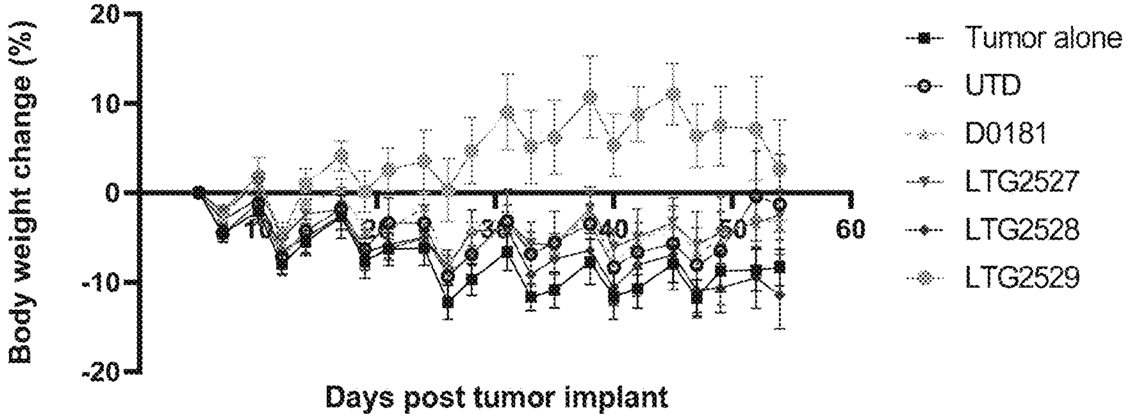
FIG. 16 depicts the body weight changes of mice during OVCAR-3 study. NSG mice bearing disseminated OVCAR-3 tumors were treated with $5\times10^5$ CAR T-positive (CAR T+) cells per mouse and mouse weights were recorded three times/week. Body weight change was calculated as the percentage of change from study initiation. Mean±SEM. TA-tumor alone, UTD—non-transduced T cell control. N=4~5 mice/group.

To further assess the tumor rejection functionality of CAR constructs in solid tumor xenograft models, the ROR1-positive MSLN-positive OVCAR-3 ovarian cancer cell line was stably transduced with luciferase gene and intraperitoneally implanted into female NSG mice to establish the OVCAR-3 xenograft model. CAR MSLN D0181 and ROR1 CARs LTG2527, LTG2528, and LTG2529, were included in the study, whereas mice dosed with donor-matched UTD cells, and untreated mice served as control groups. Ten million OVCAR-3 tumor cells were injected into each NSG mouse. Mice were distributed into experimental groups based on similar tumor burden measured by IVIS imaging on day 6. Five million human CAR+ T cells or UTD cells were administrated by i.v. injection at day 7. Tumor growth kinetics was recorded weekly (FIGS. 15A and 15B). Only in ROR1 CAR LTG2529 treated group, tumor cells were strongly rejected, and this effect was maintained until the study termination on day 52. All other CAR constructs, including ROR1 CAR LTG2527, LTG2528 and MSLN CAR D0181, failed to control the OVCAR3 tumor growth, similarly to the untreated TA group. Two mice in UTD treated group showed tumor regression after study day 45, which may due to grafts vs tumor effect of donor T cells. Body weights of enrolled animals were monitored three times a week. As shown in FIG. 17, ROR1 CAR LTG2529 treated group did not lose weight throughout the study, while other groups showed lower body weight compared to the body weight of the study initiation. This results effective tumor rejection and lack of demonstrates overt toxicity of the ROR1 CAR LTG2529.

In summary, ROR1 CAR LTG2529 efficiently eliminated tumors in JeKo-1 and OVCAR-3 NSG xenografts, representing the hematologic (MCL) and solid (ovarian) tumors, respectively. In contrast, ROR1 CAR LTG2527 was only effective in the hematologic tumor JeKo-1 model, while ROR1 CAR LTG2528 failed to clear tumors in both the hematologic and the solid tumor xenograft models in vivo. Therefore, CAR LTG2529 was identified as the leading candidate for CAR T therapy targeting ROR1$^{+}$ tumor types.

Example 3

ROR1 or FolR1 CARs Boosted with HPSE, MMP-2, MMP-9, or PH-20

Introduction

Another approach for boosting CAR-T therapy for solid tumors is by targeting the ECM via co-expression of ECM degrading/remodeling enzymes. The development and characterization of mono CARs against FolR1 and ROR1 co-expressing ECM enzymes heparanase (HPSE), matrix metalloproteinase-2 (MMP-2), matrix metalloproteinase-9 (MMP-9), or membrane-anchored or secreted hyaluronan (PH-20+/−GPI) is hereby described.

Materials and Methods

Cell Lines

The ovarian cancer cell line OVCAR3, lung squamous cell carcinoma cell line NCI-H226, and leukemia cell line HL-60 were purchased from American Tissue Culture Collection (ATCC, Manassas, VA). The MEC-1 leukemia line was purchased from DSMZ (Leibniz Institute DSMZ, Braunschweig, Germany). NCI-H226 were cultivated in RPMI-1640 medium (Corning, NY) supplemented with 10% heat-inactivated fetal bovine serum (FBS, Hyclone, Logan, UT). OVCAR-3 was cultured in RPMI-1640 medium (Corning, NY) supplemented with 20% heat-inactivated FBS and 10 μg/ml bovine insulin (Sigma, St Louis, MO). HL-60 was maintained in IMDM (Hyclone, Logan, UT) with 20% FBS. MEC-1 cell line and its derivatives were maintained in IMDM supplemented with 10% FBS. OVCAR-3, NCI-H226 and HL-60 luciferase expressing cell lines were generated by stably transducing wild-type tumor lines with lentiviral vector encoding firefly luciferase, followed by limiting dilution and selection of luciferase-positive clones. MEC-1 ROR1hi cells were generated by stable transduction with lentivirus encoding ROR1 gene, followed by microbeads selection for ROR1.

Generation of CAR Constructs and Lentiviral Vector Production

The constructs of fully human anti-ROR1 and FolR1 chimeric antigen receptor (CAR) with boosting elements were designed as CAR molecule and a booster molecule connected with P2A ribosomal skipping element sequence. CAR molecules included mono-targeting CAR. The various single chain variable fragment (ScFv) sequences targeting the extracellular domain of human ROR1 or FolR1 were identified in house. Mono CAR comprised of an anti-ROR1 or anti FolR1 scFv, a IgG4 short hinge for ROR1 scFv, a CD8 hinge for FolR1 scFv, connected to CD8 transmembrane domain, costimulatory domain derived from human 4-1BB, followed by CD3-ζ activating domain sequences. Bicistronic CARs contained a ROR1-targeting mono CAR, and a FolR1-targeting mono CAR, connected with P2A sequence. Boosting elements contained extracellular matrix enzymes heparanase (HPSE), matrix metalloproteinase-2 (MMP-2), matrix metalloproteinase-9 (MMP-9), or membrane-anchored or secreted hyaluronan (PH-20+/−GPI). PH-20 was followed by a native or tPA signaling peptide in the presence, absence or retains 7 amino acids of the GPI anchor. ROR1 or FolR1 mono CARs without boosters were included as comparison.

CAR sequences were cloned into a Lentiviral Vector (LV) expression cassette under the control of the human EF-1α promoter (anti-ROR1 and some anti-FolR1 CARs) or PGK (some anti-FolR1 CARs) promoter (Lentigen Technology Inc., Gaithersburg, MD). Lentiviral particles were generated by transient transfection of HEK 293T cells, pelleted by centrifugation and stored at −80° C. until transduction.

Primary T Cell Preparation and Transduction

Healthy donor primary T cells were isolated from leukapheresis collections (AllCells, Alameda, CA) or from processed buffy coats (Oklahoma Blood Institute, Tulsa, OK), with donors' written consent. The CD4-positive and CD8-positive human T cells were purified via positive selection using a 1:1 mixture of CD4 and CD8 Microbeads (Miltenyi Biotec, Bergisch Gladbach, Germany) according to manufacturer's protocol. Purified T cells were activated with CD3/CD28 MACS® GMP T Cell TransAct reagent (Miltenyi Biotec), and cultured in serum free TexMACS medium supplemented with 30 IU/mi IL-2 at a density of $1\times10^{6}$ cells/ml. Furthermore, activated T cells were transduced on day 1 with lentiviral vector particles encoding CAR constructs. On day 3, the transduced T cells were washed and resuspended to $0.5\times10^{6}$/ml to continue expansion. Every 2-3 days thereafter, cultures were supplemented with fresh TexMACS medium containing 30 IU/ml IL-2, until harvesting time on day 8-10.

Flow Cytometric Analysis of CAR Surface Expression 0.32E6 CAR-T cells were washed in cold AutoMACS buffer supplemented with 0.5% bovine serum albumin (Miltenyi Biotec, Bergisch Gladbach, Germany) and stained with CAR detection reagents. For ROR CAR, cells were stained with ROR1-Fc peptide (R&D Systems, Minneapolis, MN) and FolR1 CAR were stained with FolR1-Fc peptide (Acro Biosystems, Newark, DE) followed by anti Fc-AF647 conjugate (Jackson ImmunoResearch, West Grove, PA). The 7-Aminoactinomycin D staining (7-AAD, BD Biosciences, San Jose, CA) was added to exclude dead cells. CD4 antibody labeled with VioBlue fluorochrome was used to separate CD4 and CD8 population. Processed mouse bone marrow and spleen were stained with human CD3 VioBlue and human CD45 FITC (Miltenyi Biotec) to determine the presence of CAR-T. To assess for memory phenotype, cells were stained with CD62L PE and CD45RA APC-Vio700 (Miltenyi Biotec). Non-transduced cells (UTD) were used as a negative control. Cells were washed twice, resuspended in 200 μl running buffer, and acquired by flow cytometry. Flow cytometric analysis was performed on a MACSQuant® 10 Analyzer (Miltenyi Biotec), and data plots were generated using FlowJo software (Ashland, OR).

MMP-9/HPSE ELISA

To confirm MMP-9 or HPSE expression, supernatant from CAR-T cells on day 10 of production was collected and analyzed by ELISA (MMP-9 ELISA-Invitrogen, Waltham, MA; HPSE ELISA-Abcam, Cambridge, UK). Supernatants were diluted 10-fold and two technical replicates were performed for each sample.

CAR-T Cell Cytotoxicity and Cytokine Assay

To assess CAR-T cell mediated cytotoxicity, $5\times10^3$ tumor target cells stably transduced with firefly luciferase were combined with CAR-T cells at the indicated effector to target ratios and incubated overnight at 37° C. with 5% CO2. SteadyGlo reagent (Promega, Madison WI) was added to each well and the resulting luminescence quantified as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)). For cytokine release analysis, supernatants from overnight co-cultures were collected and analyzed by ELISA (eBioscience, San Diego, CA) for IFNγ, TNFα and IL-2 concentration. Two technical replicates were performed for each condition, and each experiment was repeated using CAR-T cells generated from different healthy donors as indicated.

Transwell Migration

To assess ECM degradation in vitro, CAR-T cells were seeded in either Cultrex™ BME-coated transwell inserts (Corning Life Sciences) to test functionality of MMP-2, MMP-9 or HPSE or in hyaluronan-coated (Lifecore Biomedical LLC) transwell inserts to test functionality of PH-20 and migration into the reciprocal chamber was measured. Corning® BioCoat® control inserts (8.0 μm PET membrane) in 24-well plate formats were uncoated or coated with 100 μL Cultrex™ BME (R&D Systems, Minneapolis, MN) at 5 mg/mL diluted in 0.01M Tris-HCl pH 8.0, 0.7% NaCl or 500 μL 5 mg/mL hyaluronan in TexMACS medium (Miltenyi Biotec). Cultrex™ coated transwell inserts were allowed to solidify for 2 h at 37 C and hyaluronan coated insets were used immediately upon coating. CAR-T cells were thawed and resuspended in TexMACS medium. 0.5E6 cells were seeded in each transwell insert (500 μL volume for Cultrex™ coated inserts and 100 μL volume for hyaluronan coated inserts). TexMACS medium+5% FBS was used as a chemoattractant in the bottom chamber (750 μL volume). Cells that had migrated into the bottom chamber after 24 h were collected, washed and processed for flow cytometry. Cell counts were normalized to Absolute counting beads (Invitrogen, Waltham, MA).

In Vivo Analysis of CAR-T Function OVCAR3 Xenograft Model

Animal experiments were performed in compliance with the applicable laws, regulations and guidelines of the National Institutes of Health (NIH) and with the approval of MI Bioresearch (Ann Arbor, MI) Animal Care and Use Committee.

In OVCAR-3 ovarian cancer model, six to eight week old female NSG mice, 4 per group, were injected intraperitoneally with $1\times10^7$ OVCAR-3 $ROR1^+FolR1^+$ ovarian cancer cells. Tumor burden was determined by IVIS bioluminescent imaging. On day 7, mice were randomized to groups based on equal or similar overall mean tumor burden, and $5.0\times10^6$ CAR-T+ cells/mouse (normalized for transduction efficiency) were administered via tail vain on day 8. Tumor regression was determined by bioluminescent imaging on days 11, 18, 25, 32, and 39 using IVIS-S5. Animal body weight was recorded three times weekly. All BLI Images were analyzed using Living Image, version 4.3, software (Perkin Elmer) and the bioluminescent signal flux for each mouse was expressed as average radiance. At the study termination day 41, ovary, pancreas, Peritoneal cavity wall, were harvested and fixed in 4% paraformaldehyde.

Results

Figure 17A:
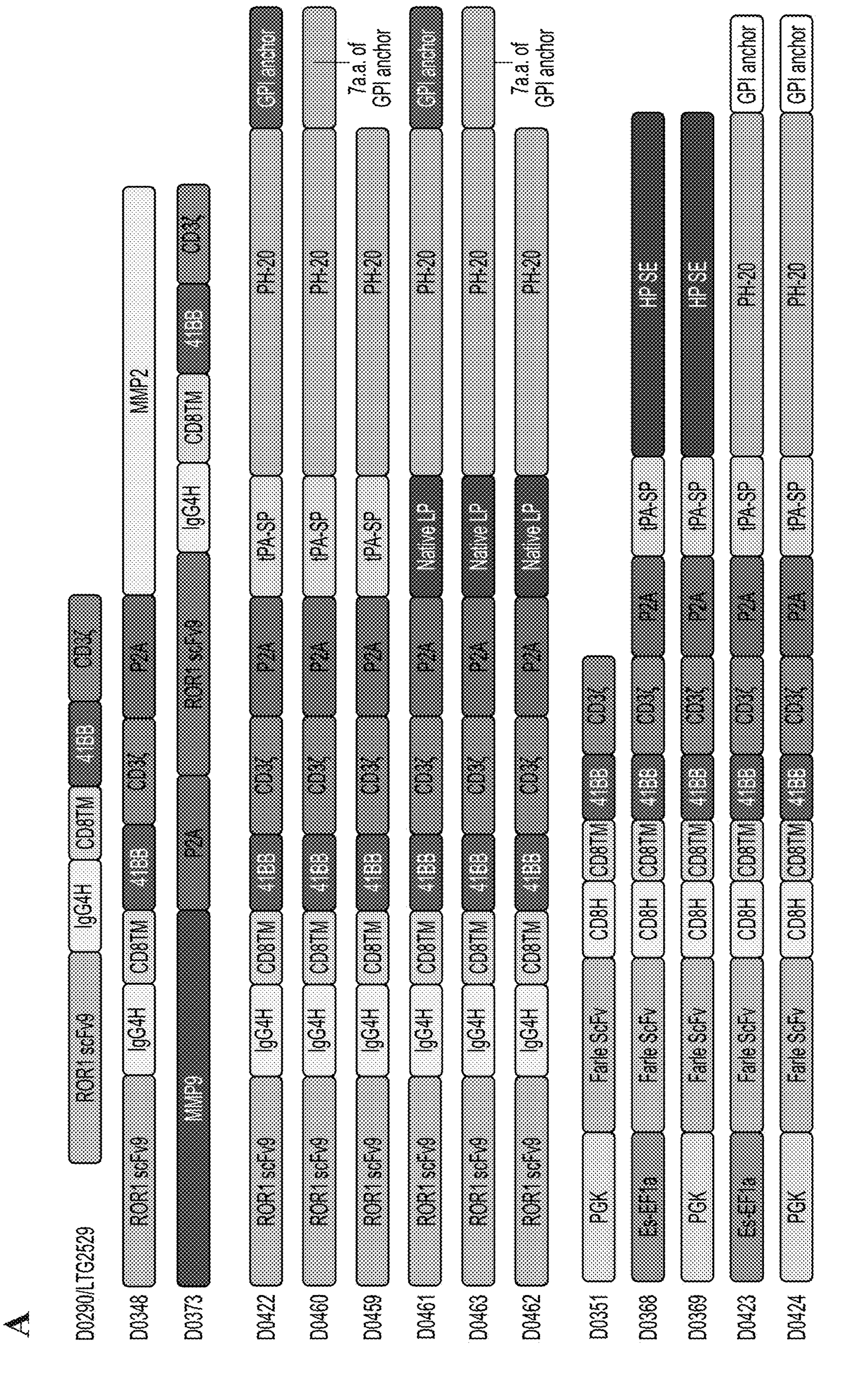
FIGS. 17A and 17B depict the structure of ROR1 and FolR1 CAR with ECM booster and surface expression in human primary T cells.

Schematic representations of CAR-T co-expressing ECM enzymes are shown in FIG. 17A. CAR+ECM enzymes are comprised of FolR1/ROR1 CAR in frame to an extracellular matrix enzyme linked by P2A ribosomal skipping element sequence. Fully human binders Farletuzumab (Farle) targeting FolR1 and ScFv9 targeting ROR1 hereby were developed in house. Mono CAR configured with a scFv targeting FolR1 or MSLN, in frame to CD8 or IgG4 hinge, CD8 transmembrane, 4-1BB, costimulatory and a CD3ζ activation domain. ECM enzymes included in this set are heparanase (HPSE), matrix metalloproteinase-2 (MMP-2), matrix metalloproteinase-9 (MMP-9), or membrane-anchored or secreted hyaluronan (PH-20+/−GPI, or 7 amino acids of the GPI). ROR1 CARs are under the control of the EF1α promoter and the Farle CARs are under the control of either the EF1α or PGK promoter. Table 2 summarizes ROR1 CAR and FolR1 CAR constructs with boosters.

TABLE 2

| | Construct Number | Construct designation | Promoter |
|---|---|---|---|
| Single CAR | D0290 | ROR1 scFv9-IgG4 hinge-CD8TM-41BB-CD3ζ | EF1α |
| | LTG2529 | ROR1 scFv9-IgG4 hinge-CD8TM-41BB-CD3ζ | EF1α |
| | D0351 | Farle-CD8H&TM-41BB-CD3ζ | PGK |
| Single CAR with booster(s) | D0348 | ROR1 scFv9-IgG4 hinge-CD8TM-41BB-CD3ζ_2A_MMP-2 | EF1α |
| | D0368 | Farle-CD8H&TM-41BB-CD3ζ_2A_HPSE | EF1α |
| | D0369 | Farle-CD8H&TM-41BB-CD3ζ_2A_HPSE | PGK |
| | D0373 | MMP-9 2A ROR1 scFv9-IgG4 hinge-CD8TM-41BB-CD3ζ | EF1α |
| | D0422 | ROR1 scFv9-IgG4 hinge-CD8TM-41BB-CD3ζ_2A_tPA-SP PH-20 GPI | EF1α |
| | D0423 | Farle-CD8H&TM-41BB-CD3ζ_2A_tPA-SP PH-20 GPI | EF1α |
| | D0424 | Farle-CD8H&TM-41BB-CD3ζ_2A_tPA-SP PH-20 GPI | PGK |

TABLE 2-continued

| Construct Number | Construct designation | Promoter |
|---|---|---|
| D0459 | ROR1 scFv9-IgG4 hinge-CD8TM-41BB-CD3ζ_2A_PH-20 | EF1α |
| D0460 | ROR1 scFv9-IgG4 hinge-CD8TM-41BB-CD3ζ_2A_tPA-SP PH-20 7 a.a. GPI | EF1α |
| D0461 | ROR1 scFv9-IgG4 hinge-CD8TM-41BB-CD3ζ_2A_NSP PH-20 GPI | EF1α |
| D0462 | ROR1 scFv9-IgG4 hinge-CD8TM-41BB-CD3ζ_2A_PH-20 | EF1α |
| D0463 | ROR1 scFv9-IgG4 hinge-CD8TM-41BB-CD3ζ_2A_NSP PH-20 7 a.a. GPI | EF1α |

To test CAR-T functionality in vitro, ROR1 or FolR1 mono CARs with MMP-2, MMP-9, HPSE or PH-20 as booster elements were characterized. ROR1 and FolR1 CAR+/−ECM enzymes were further incorporated into a third-generation lentiviral vectors and transduced into human primary T cells at MOI 10 for the ROR1 CARs and MOI 20 for the FolR1 CARs, to generate the ROR1 or FolR1 CAR-T cells under the control of the mammalian EF1α or PGK promoter. Un-transduced T cells derived from same donor (UTD) were used as a negative control. Surface expression of CARs with ROR1 or FolR1 binder on transduced T cells was measured by flow cytometry using ROR1-Fc or FolR1-Fc respectively, followed by staining with anti-Fc Alexa Flour 647. CAR constructs exhibited sustained T cell surface expression as compared to un-transduced T cells. Percentage of CAR positive T cells, based on flow cytometric detection of ROR1 binders and FolR1 binders (FIG. 17B) were plotted as a quadratic plot of CD4 vs. CAR. For the donors shown in FIG. 17B, CARs co-expressing MMP-2, MMP-9, HPSE or PH-20 had similar CAR expression to that of CARs alone (41-65% for the MMP-2, MMP-9 set; 40-70% for the ROR-1 CARs co-expressing PH-20; 80-93% for the Farle CARs co-expressing either HPSE or PH-20), with the exception of CAR construct D0424, which had ~45% expression, compared to 93.5% expression of the Farle CAR alone. These results overall demonstrate effective transduction efficiency and CAR expression of CARs combined with a digestive enzyme. However, the non-triviality of co-expressing CAR with a digestive element was exemplified by construct D0424.

Figures 18A, 18B:
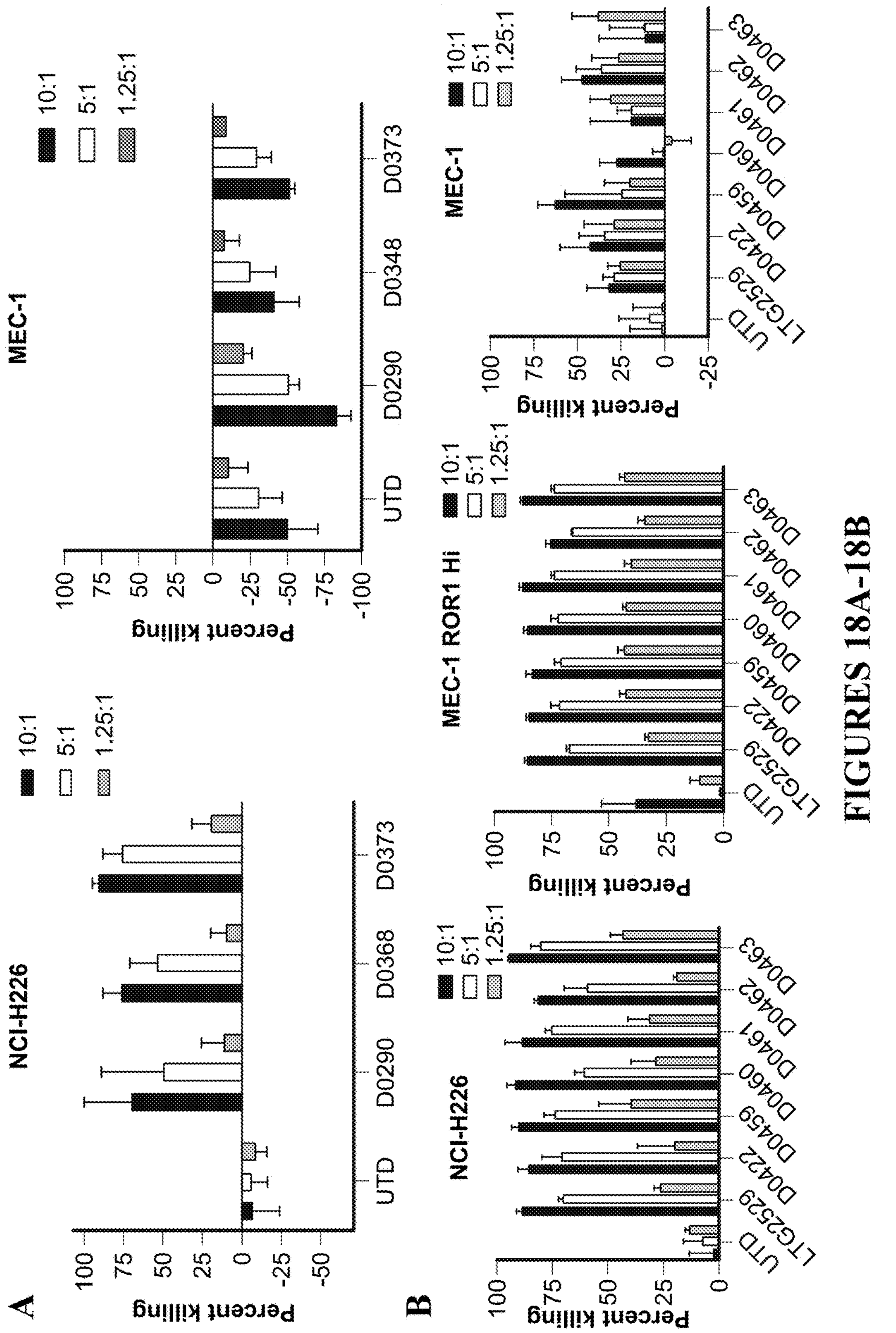
FIGS. 18A-18E depict the cytotoxicity and cytokine release of ROR1 and FolR1 CARs constructs in vitro. A, B) Luciferase-based cytotoxicity assays were performed using antigen-specific tumor lines. ROR1 CARs were tested against ROR1+ lines NCI-H226 and MEC-1 ROR1Hi, MEC-1 was used as a negative control line which expresses basal levels of ROR1. CAR-T cells and tumor cells were co-cultured overnight at the indicated effector to target (E:T) ratios: 10:1, 5:1, or 1.25:1. Percentage specific target lysis was assessed by luminometry.

To evaluate the target specific cytotoxicity of ROR1 CARs in vitro, MEC-1 overexpressing ROR1$^+$ B cell line, lung cancer line NCI-H226, and ROR1$^-$ leukemic line MEC-1 were selected as target lines. CAR-T cells were co-incubated with target tumor cell lines at effector to target ratios 10, 5, 1.25:1. After overnight co-incubation, cytotoxicity of CARs was analyzed in a luminescence based in vitro killing assays. Percentage of specific lysis was plotted with E:T ratio using bar graphs (FIG. 18A, 18B). CARs with MMP-2 and MMP-9 (D0348, D0373) showed similar killing capacity as compared to mono ROR1 CAR, at all E:T ratios tested (FIG. 18A). There was no background killing of ROR1 negative MEC-1 line, demonstrating the robust target-specific cytotoxic function of all ROR1 CAR constructs designed. Furthermore, ROR1 CAR with co-expression of PH-20 element (D0422, D0450-D0463) showed similar killing capacity, compared to mono ROR1 CAR, at all E:T ratios tested, demonstrating that addition of a PH-20 element does not interfere with CAR function.

Figure 18C:
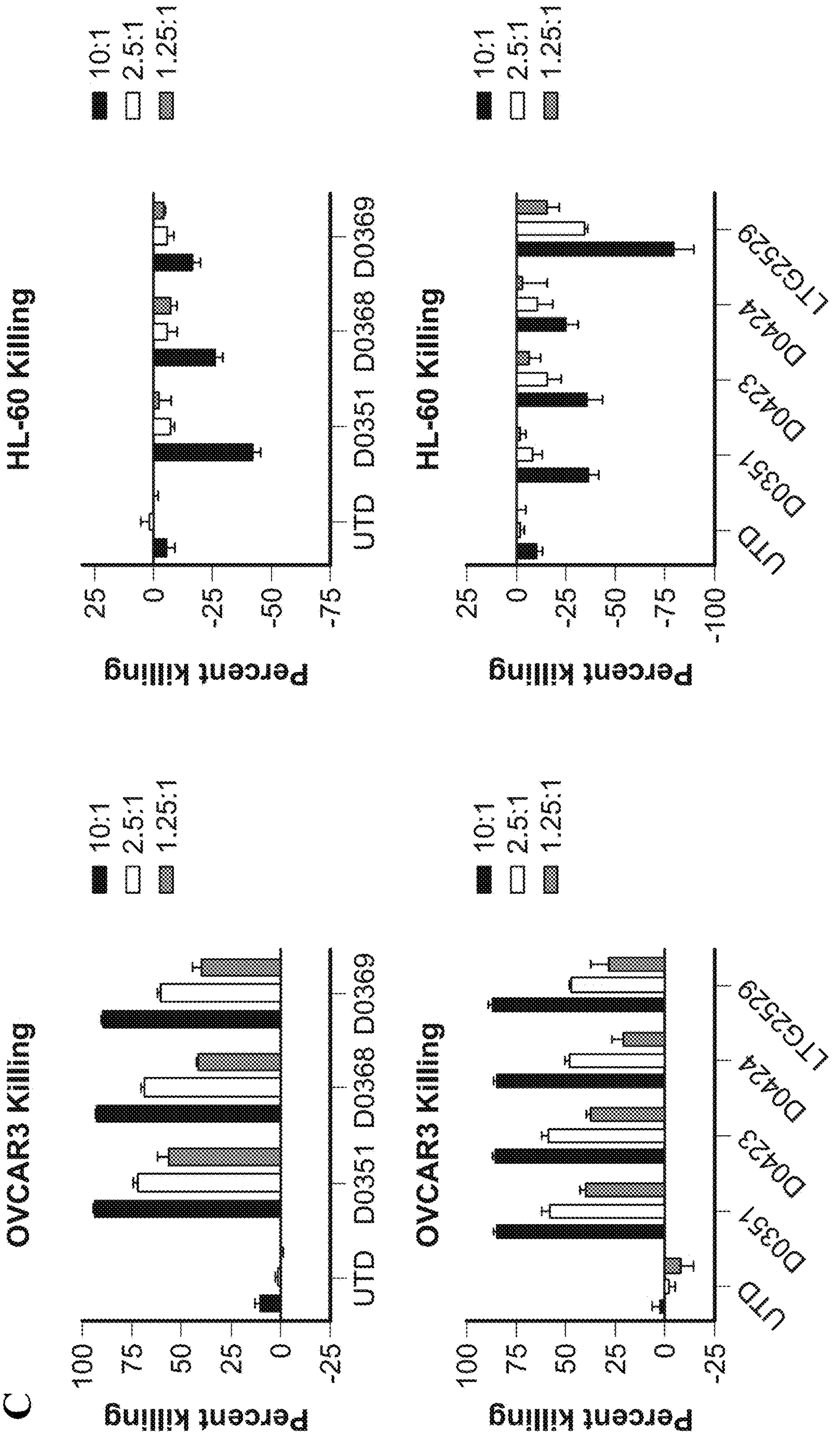

The specific cytotoxicity of FolR1 CARs was evaluated using OVCAR3 FolR1$^+$ ovarian cancer cell line and HL-60 FolR1$^-$ leukemia cell line as target lines. CAR-T cells were co-incubated with target tumor cell lines at effector to target ratios 10, 2.5, 1.25:1. After overnight co-incubation, cytotoxicity of CARs was analyzed in a luminescence based in vitro killing assays. Percentage of specific lysis was plotted with E:T ratio using bar graphs (FIG. 18C). All FolR1 CARs with HPSE or PH-20 (D0368, D0369, D0423, D0424) showed similar killing capacity, compared to mono FolR1, at all E:T ratios tested (FIG. 18C). There was no background killing of FolR1 negative HL-60 line, demonstrating the robust target-specific cytotoxic function of all FolR1 CAR constructs tested.

Figure 18D:
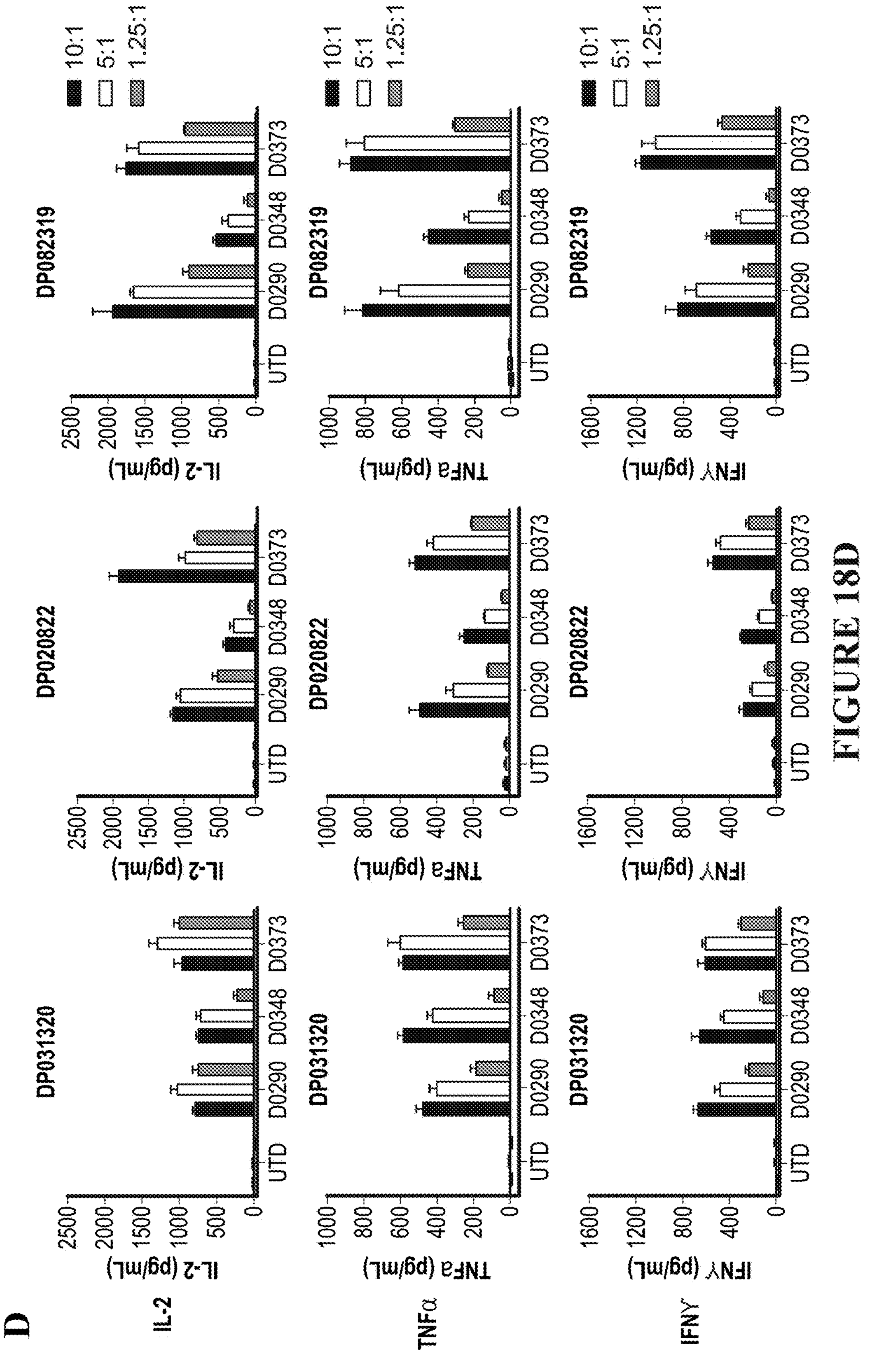
Figure 18E:
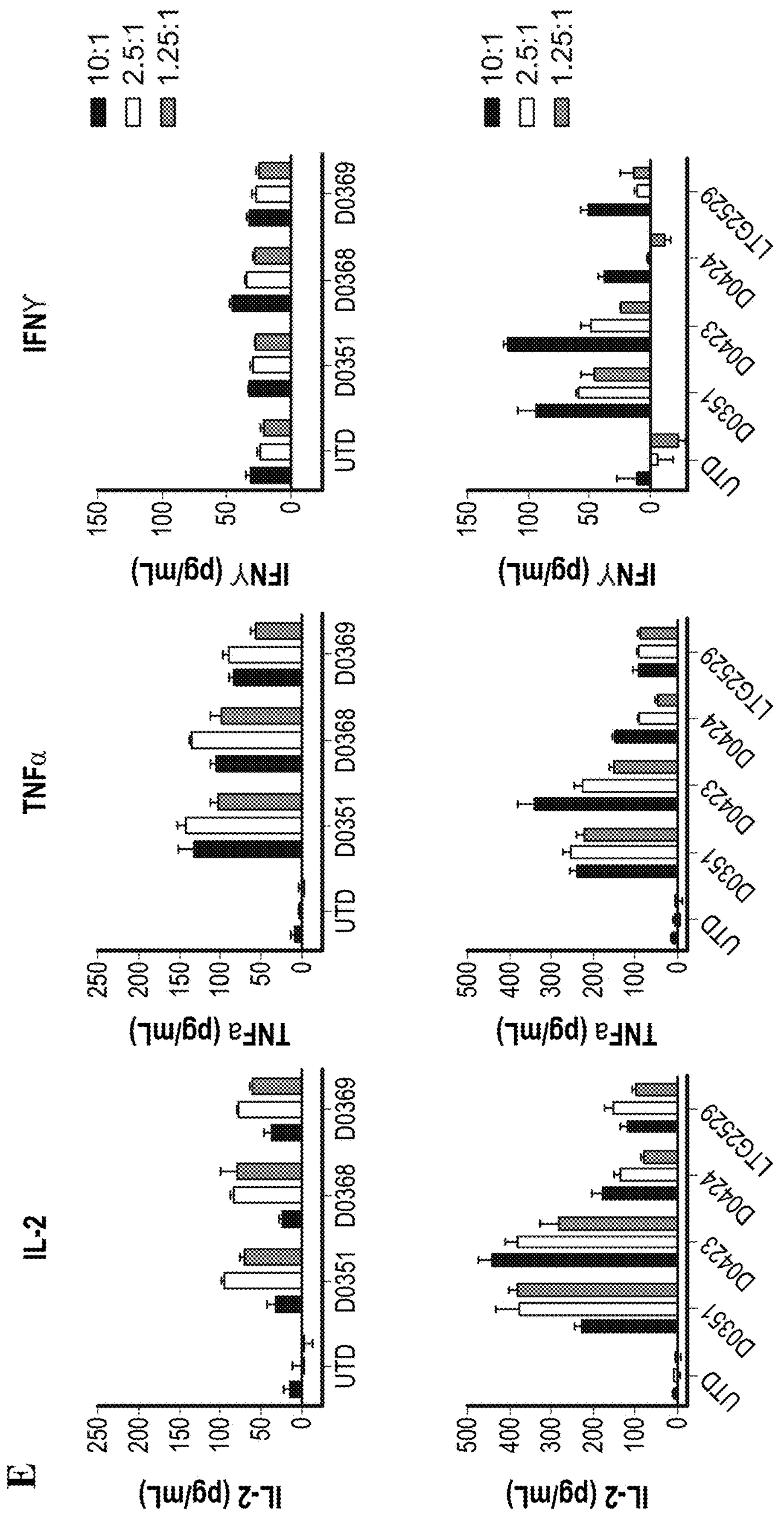

Production of T cell pro-inflammatory cytokines IL-2, IFNγ, and TNFα by the fully human ROR1 and FolR1 CARs were examined by ELISA. Culture supernatants after overnight co-incubation of CAR-T cells with NCI-H226 (FIG. 18D) and OVCAR3 (FIG. 18E) target lines at all tested E:T ratios were harvested for the measurement of specific cytokine release. For three donors tested, fully human ROR1 CAR with or without boosting elements MMP-2 or MMP-9 exhibited CAR-T cell dose dependent cytokine response when compared to UTD (FIG. 18D). Additionally, for three donors tested (one representative donor shown in FIG. 18E), fully human FolR1 CAR with or without boosting elements HPSE or PH-20 exhibited CAR-T cell dose dependent cytokine response similar to that of mono-CAR. These results indicate robust, target-specific CAR-T cell cytokine responses.

Figure 17B:
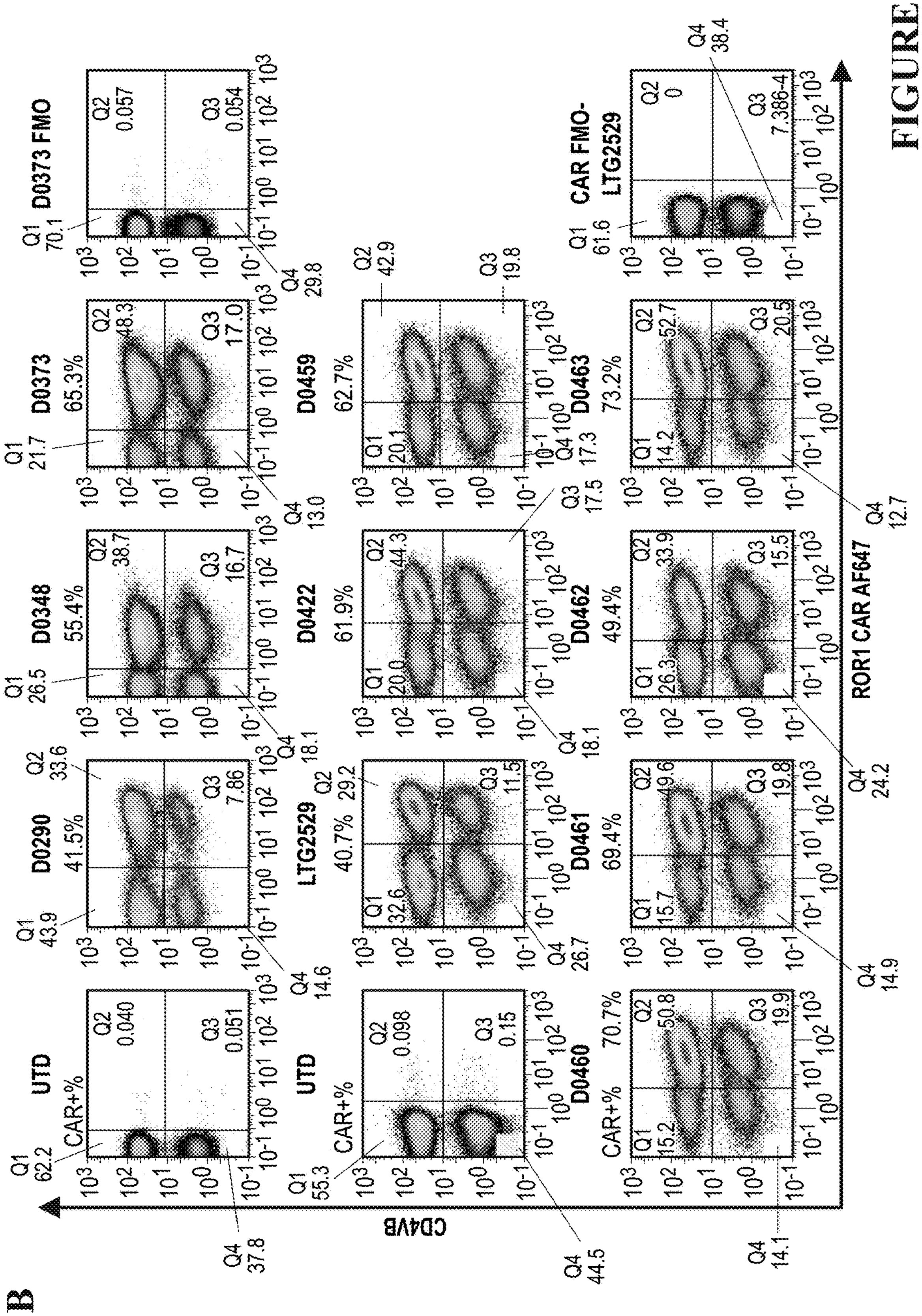
Figure 17B:
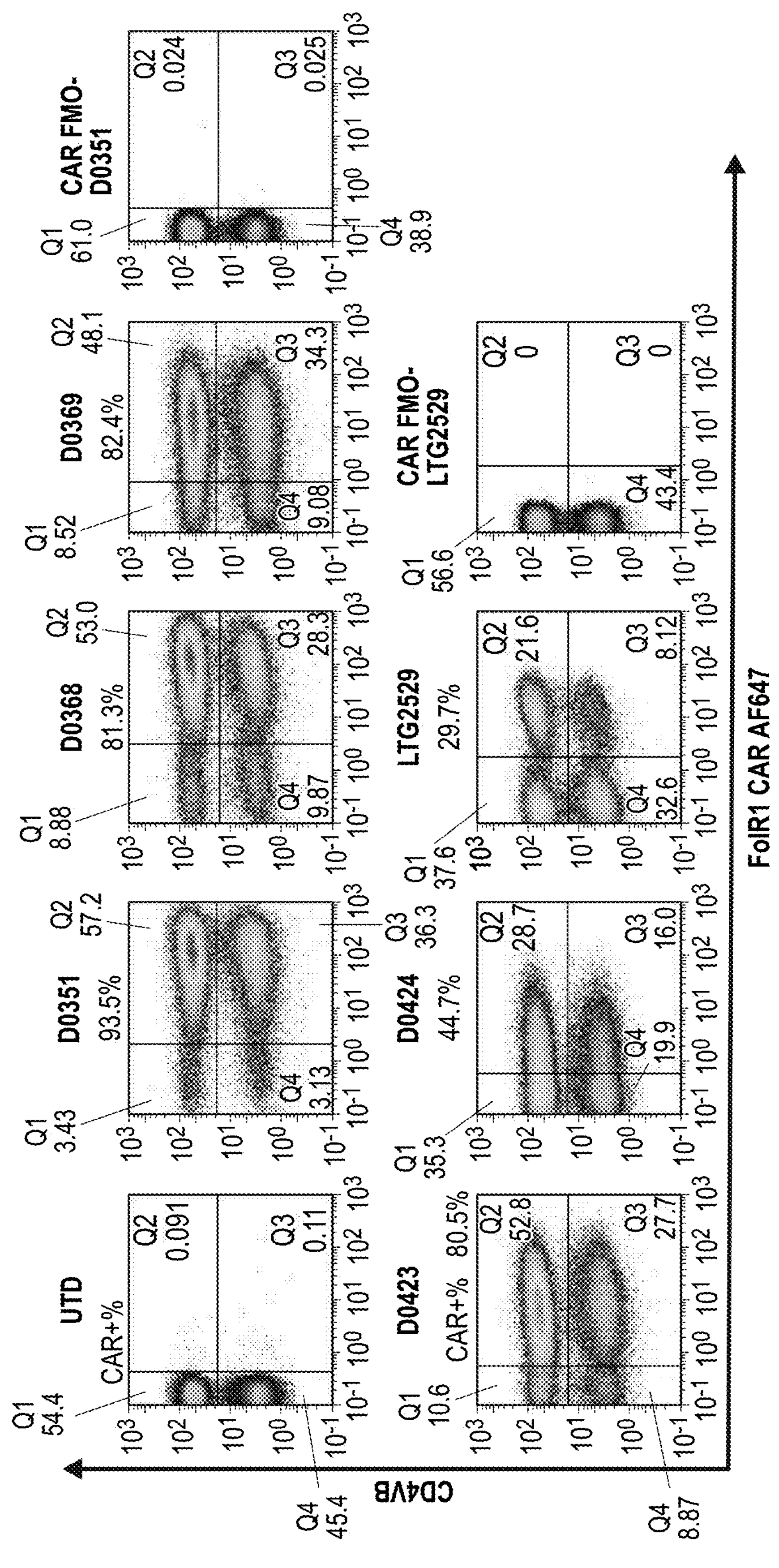
Figures 19A, 19B:
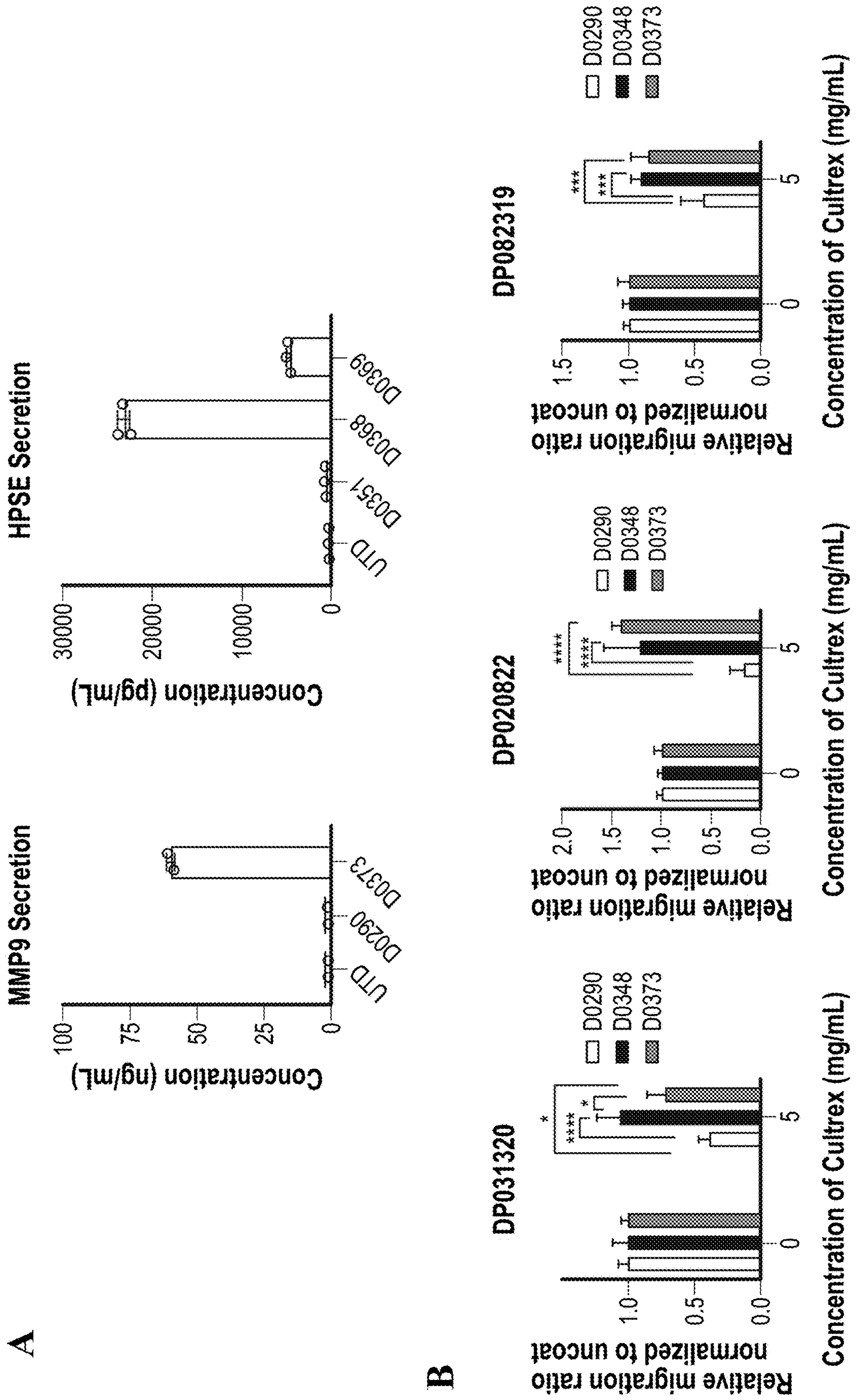
FIGS. 19A-19D depict the expression of enzymes in booster CARs and its capacity to facilitate CAR-T cell migration in vitro.

Production of MMP-9 by the ROR1 CAR (D0373) and the HPSE enzyme by the FolR1 CARs (D0368, D0369), was examined by ELISA. CAR-T supernatants were collected on day 10 of CAR-T production when CAR-T were grown in TexMACS+IL-2. All supernatants were measured upon dilution of 10-fold (FIG. 19A). There was a significant amount of MMP-9 secreted by ROR1 CAR co-expressing MMP-9 (D0373). In comparison, marginal MMP-9 expressed was measured for UTD or mono ROR1 CAR-T cells alone (D0290). Likewise, there was a substantial amount of HPSE secreted by FolR1 CARs D0368 and D0369 compared to negligible amounts by UTD or mono FolR1 CAR. CAR D0368 (EF1α promoter) secreted a considerable amount more HPSE than CAR D0369 (PGK promoter), demonstrating the non-obviousness of optimal promoter selection for CARs co-expressed with an ECM-digestive enzyme. These results suggest that CARs co-expressing MMP-9 or HPSE have robust CAR and enzyme expression (FIGS. 17B and 19A).

Figure 19C:
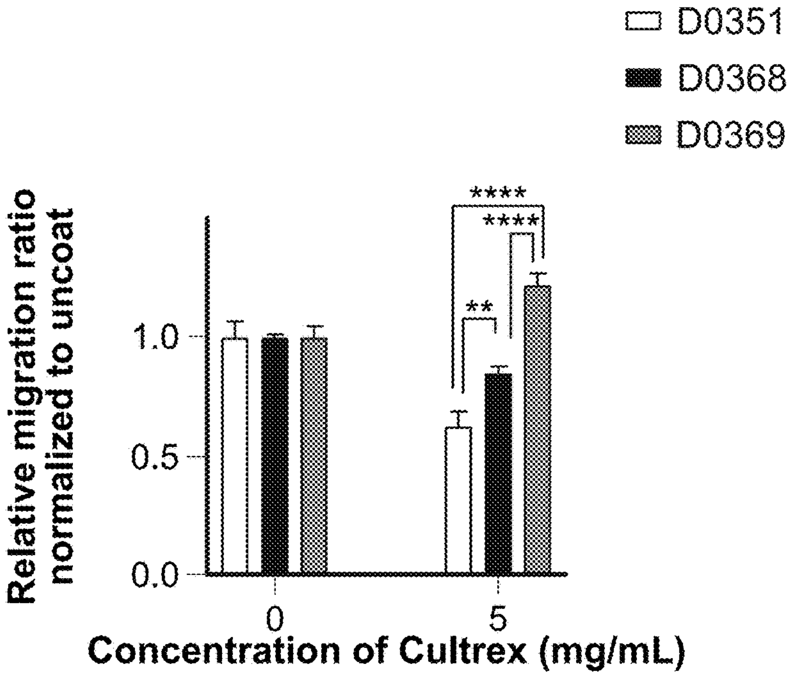
Figure 19D:
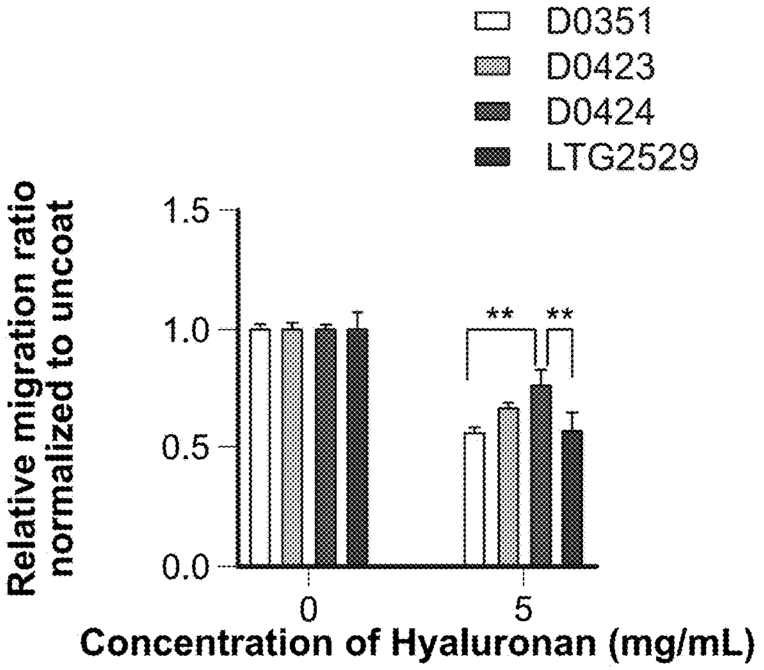

As a measure of CAR-T migration through an ECM-rich environment in vitro, CAR-T were subjected to an invasion assay in transwell inserts coated with Cultrex™ BME for MMP-2, MMP-9, and HPSE or hyaluronan for PH-20 activity. UTD, CAR alone, or CARs bicistronically expressing ECM enzymes were thawed, counted, and seeded into uncoated, Cultrex™-coated, or hyaluronan-coated transwell inserts for 24 h (in the absence of IL-2). Medium in the bottom chamber was then collected, washed and processed via flow cytometry and normalized to Absolute counting beads. As shown in FIG. 19B, ROR1 CARs co-expressing MMP-2 or MMP-9 (D0348 or D0373) had greater migration in 5 mg/mL Cultrex™-coated transwell inserts than that of CARs alone in 3 separate donors tested (D0290). Out of three distinct donors tested, FolR1 CARs co-expressing HPSE (D0368, D0369) had pronounced migration compared to mono-FolR1 CAR and UTD (FIG. 19C). In FIG. 19D, FolR1 CARs tested for migration through a hyaluronan coated insert shown greater migration when co-expressing PH-20 (D0423, D0424) The results discussed here illustrate that CARs co-expressing ECM enzymes can functionally by-pass an ECM better than CARs alone.

In conclusion, ROR1 and FolR1 CARs co-expressing various ECM enzymes were shown to have robust CAR-T cytolysis and ECM targeting functionality in vitro. The next direction is to test these top candidates in ECM-rich in vivo model(s).

Figure 20A:
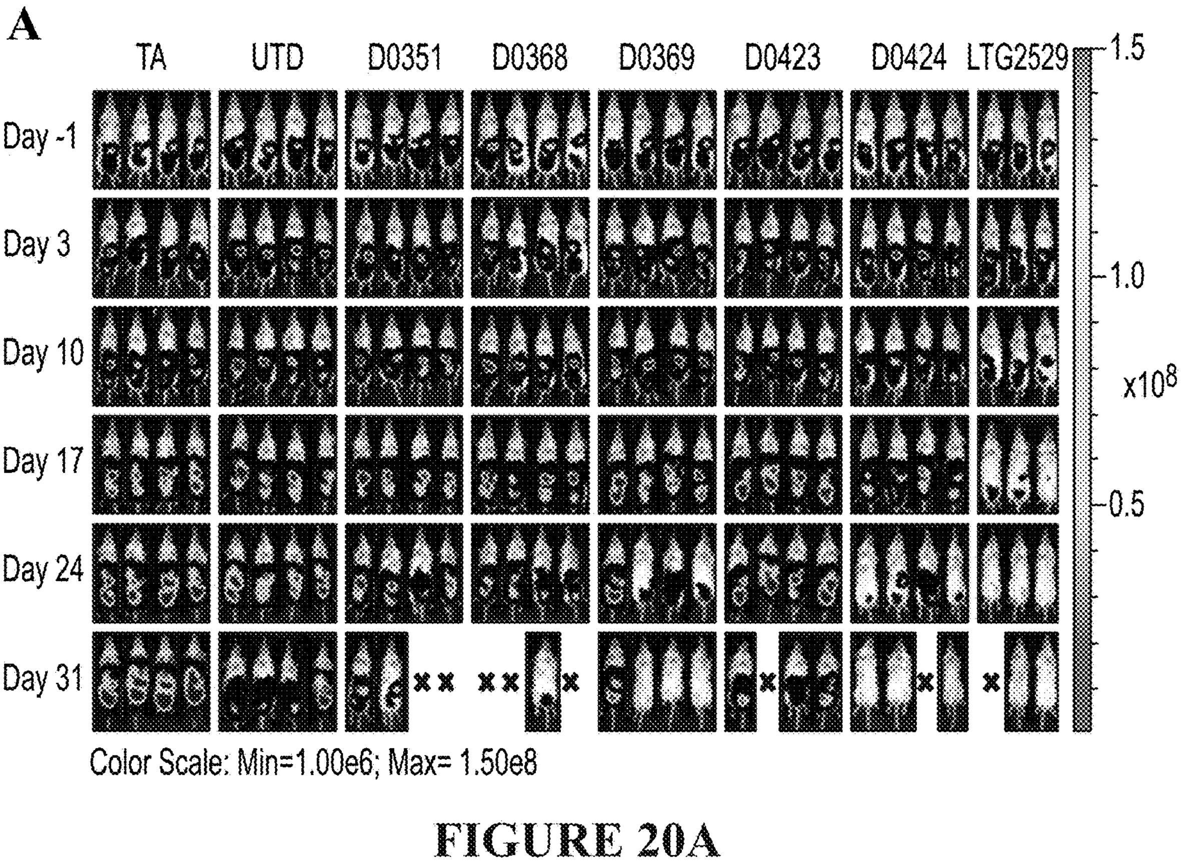
FIGS. 20A-20C depict the in vivo activity of FolR1 CAR-T co-expressing HPSE or PH-20 in an OVCAR3 xenograft model. NSG mice were implanted with $1\times10^7$ OVCAR3 cells stably transduced with luciferase, via intraperitoneal injection. Tumor burden was determined using bioluminescent imaging by IVIS-S5 instrument. Mice with comparable mean tumor burden were randomly distributed into each group and injected with $5\times10^6$/mouse CAR+ T cells or UTD on day 8. Tumor kinetics were measured at day 11, 18, 25, 32, and 39.
Figures 20B, 20C:
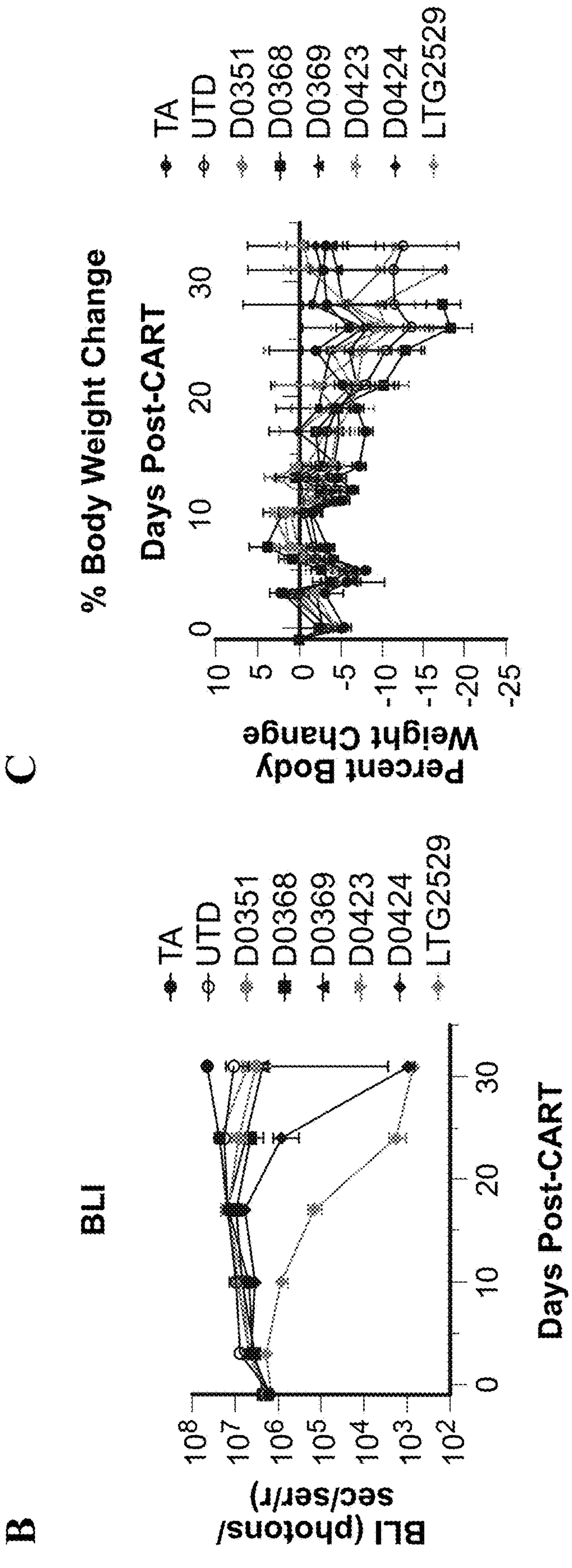

OVCAR3 ovarian cancer cell line stably transduced with luciferase with was used to evaluate the in vivo tumor rejection functionality of the FolR1 CAR candidates D0351, D0368, D0369, D0423, and D0424. CAR construct LTG2529, the fully human ROR1 CAR expressed alone, was previously characterized in same in vivo model, and was used as a positive control for OVCAR3 tumor regression. Mice cohorts Tumor Alone (TA) and UTD (tumor-bearing mice treated with same donor non-transduced T cells) were added as negative controls. $ROR1^+$ $FolR1^+$ OVCAR3 ovarian cancer cells were intraperitoneally implanted into NSG mice to establish OVCAR-3 xenograft model. Ten million OVCAR-3 tumor cells were injected into each NSG mouse. Mice were distributed into experimental groups based on similar tumor burden measured by IVIS imaging on day 7. Five million human $CAR^+$ T cells or UTD cells were administrated by i.v. injection at day 8. Tumor growth kinetics was recorded weekly (FIG. 20B). ROR1 CAR alone, LTG2529, mediated rapid tumor regression, followed by CAR D0424 (PGK Farle 2A PH-20) which achieved similar tumor regression to LTG2529 by the end of the study. CAR D0369 (PGK Farle 2A HPSE) mediated moderate tumor regression response. All other CAR constructs, including mono-FolR1 D0351, EF1α Farle+HPSE D0368 and EF1α Farle+PH-20 CARs, failed to control the OVCAR3 tumor cell growth, and tumor burden in these groups remained high, similarly to the negative controls UTD and TA (FIG. 20A, 20B). These results suggest that PH-20 and HPSE elements improved the function of FolR1 CAR in the disseminated OVCAR3 in vivo model, as compared to mono-FolR1 D0351 (FolR1-taregting CAR without ECM element). Body weights of enrolled animals were monitored three times a week. As shown in FIG. 20C, there were no specific FolR1 or ROR1 CAR treated groups that lost more weight over others throughout the study, however some mice needed to be euthanized near the end of the study due to significant body weight loss believed to be due to GVHD. These results suggested no CAR-mediated overall toxicity and effective tumor rejection of ROR1 CAR LTG2529, FolR1 CAR co-expressing PH-20 under the PGK promoter (D0424), and partial response by FolR1 CAR co-expressing HPSE under the PGK promoter (D0369). Therefore, optimal combinations of CAR and ECM enzymes, and selection of suitable promoter needs to be determined empirically and is not trivial.

Figure 21A:
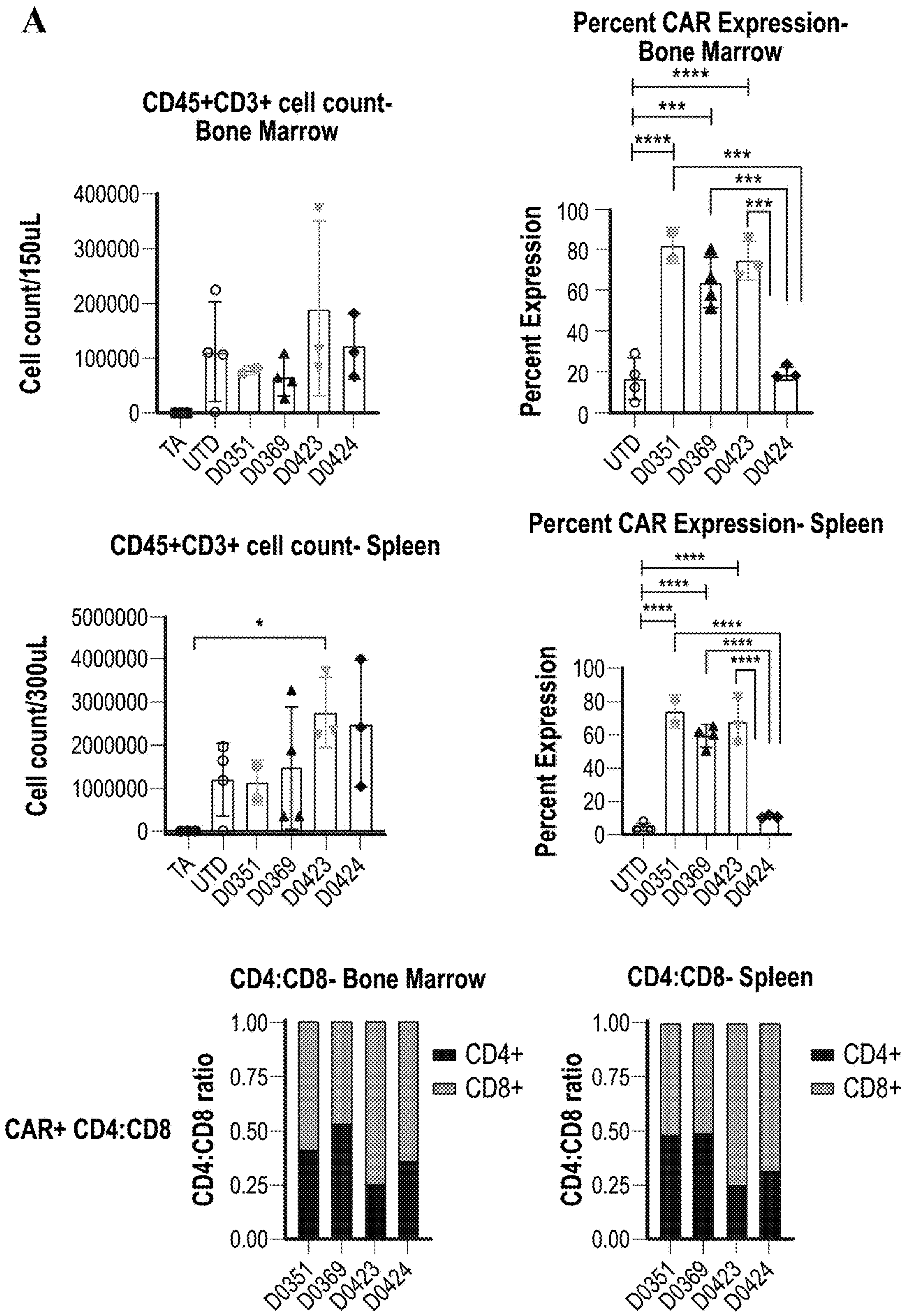
FIGS. 21A and 21B depict characterization of boosted Farle CAR-T with ECM enzymes HPSE or PH-20 in vivo.
Figure 21A:
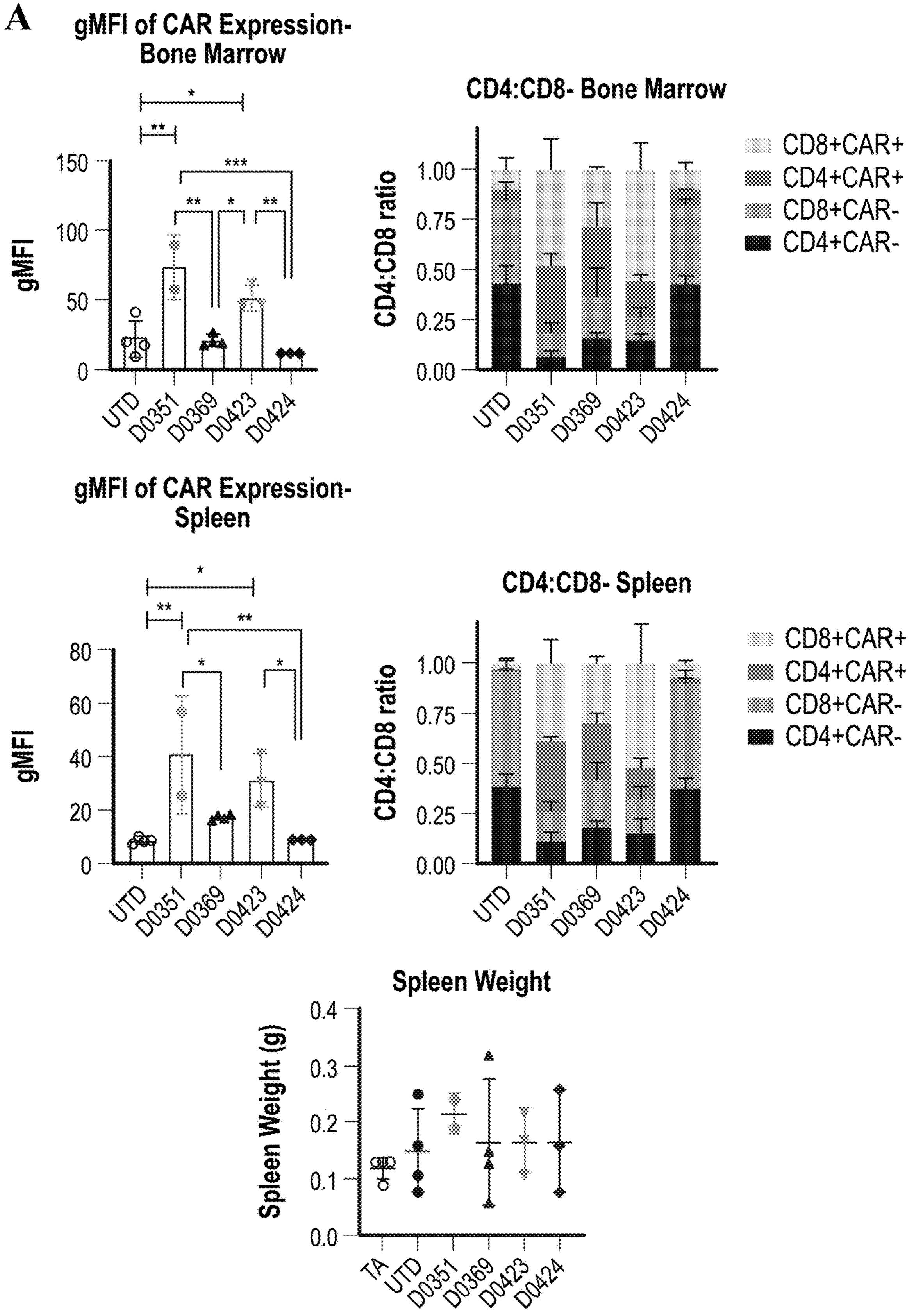

To assess the fitness and phenotype of CAR-T cells in vivo, bone marrow and spleens from mice were processed at the study end. These tissues were harvested, minced, filtered and processed for flow cytometry to evaluate the presence of human CAR-T cells (FIG. 21). Groups D0368 (EF1α Farle 2A HPSE) and LTG2529 (mono-ROR1 CAR) did not have enough mice per group to quantify end of life CAR-T cell phenotype, and were excluded from analysis. Notably, there was no significant difference in spleen weight amongst the different groups. All groups had significant amounts of CAR-T in both the bone marrow and spleen compared to tumor alone group. Percent CAR expression in the bone marrow and spleen were similar to CAR expression in T cell products prior to implant (FIG. 21A, 21B).

Figure 21B:
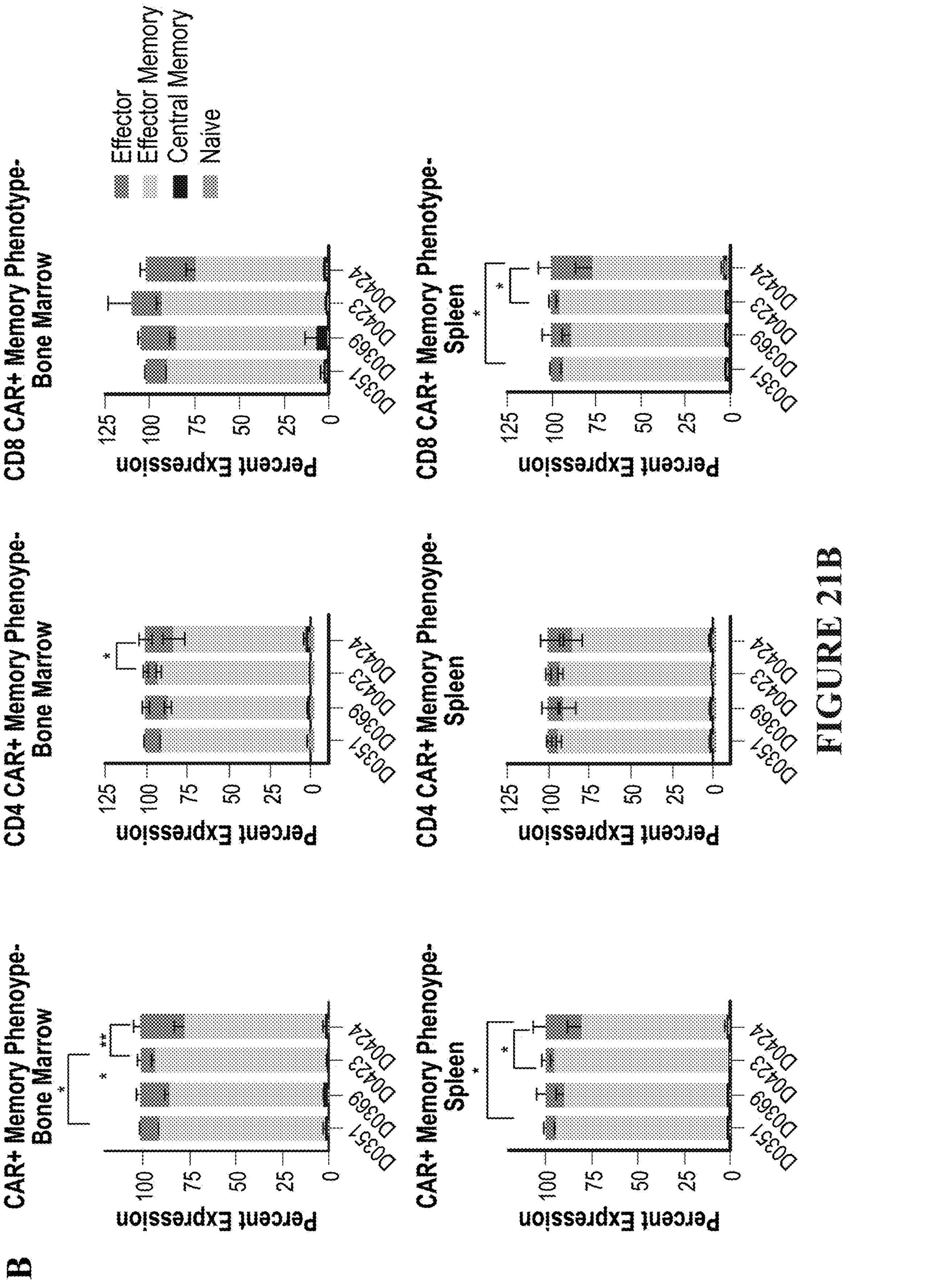

Next, CAR-T cells from bone marrow and spleen fractions were evaluated for memory phenotype (FIG. 21B). Samples were stained with CD62L and CD45RA to distinguish CAR-T cells' naïve, central memory, effector memory and effector phenotypes. In both bone marrow and spleen fractions, PGK Farle 2A PH-20 D0424 had a greater effector population than the other groups (significance is measured for the effector populations). This proportion was more distinct in the CD4 fraction in the bone marrow and the CD8 fraction in the spleen.

In summary, FolR1 CAR D0424 co-expressing PH-20 efficiently eliminated tumors in OVCAR3 NSG xenografts, similar to LTG2529 but with slower kinetics. FolR1 CAR D0369 co-expressing HPSE mediated slower, but detectable tumor regression. In contrast, D0351 mono-Farle CAR and D0369 and D0423 (under the EF1α promoter) failed to clear tumors in the OVCAR3 xenograft model. Therefore, CAR D0424 and D0369 were identified as leading candidates for CAR-T boosted therapy targeting $FolR1^+$ tumor types.

Example 4

Development of ROR1 Targeting CAR Constructs with Anti CD276 Chimeric Costimulatory Receptor (CCR) as a Boosting Element

Materials and Methods

Cell Lines

The ovarian cancer cell line OVCAR3, lung squamous cell carcinoma cell line NCI-H226, pancreatic cancer cell lines AsPC-1, and acute lymphoblastic leukemia ALL cell line RS4; 11 were purchased from the American Tissue Culture Collection (ATCC, Manassas, VA). OVCAR-3 was cultured in RPMI-1640 medium (Corning, NY) supplemented with 20% heat-inactivated fetal bovine serum (FBS, Hyclone, Logan, UT) and 10 μg/ml bovine insulin (Sigma, St Louis, MO). NCI-H226, AsPC-1 and RS4; 11 cells were cultivated in RPMI-1640 medium supplemented with 10% heat-inactivated FBS.

OVCAR-3 and NCI-H226 luciferase expressing cell lines were generated by stably transducing wild-type tumor lines with lentiviral vector encoding firefly luciferase, followed by limiting dilution and selection of luciferase-positive clones. AsPC-1 and RS4; 11 clones of luciferase and GFP expressing cell line was generated by stably transducing wild-type tumor lines with lentiviral vector encoding firefly luciferase and GFP connected with 2A peptide (Lentigen Technology, Inc., Gaithersburg, MD), followed by selection of luciferase-positive clones. RS4; 11 Luc GFP cell line was then transduced with lentiviral vectors encoding ROR1 or CD276 proteins, in order to create target overexpressing cell lines for testing the cognate CAR T cell killing function, named RS4:11-ROR1 and RS4; 11-CD276, respectively. Target-positive RS4; 11 cells were selected by ROR1 or CD276 magnetic microbeads, expanded, and utilized in luciferase-based overnight killing assays.

Generation of CAR Constructs and Production of Lentiviral Vectors

The constructs of fully human anti-ROR1 CAR with anti-CD276 CCR (Chimeric Co-stimulatory Receptor) were comprised of a ROR1-CAR molecule in frame to anti-CD276 CCR booster molecule connected with P2A ribosomal skip element. Mono ROR1 CAR and CD276 CARs were included as controls. Mono CARs were comprised of antiROR1 or anti CD276 scFv, a IgG4 short hinge for ROR1 scFv, a CD8 hinge for CD276 scFv, connected to CD8 transmembrane domain, 4-1BB costimulatory domain, followed by CD3-ζ activating domain. Anti-CD276 CCRs were comprised of CD276 targeting scFv followed with CD8 hinge and transmembrane, and CD28 costimulatory domain, without CD3-ζ activating domain sequence.

CAR sequences were cloned into a Lentiviral Vector (LV) expression cassette under the control of the human EF-1α promoter (Lentigen Technology Inc., Gaithersburg, MD). Lentiviral particles were generated by transient transfection of HEK 293T cells, pelleted by centrifugation and stored at −80° C. until transduction.

Flow Cytometric Analysis of CAR Surface Expression

Half million CAR T cells were washed in cold AutoMACS buffer supplemented with 0.5% bovine serum albumin (Miltenyi Biotec, Bergisch Gladbach, Germany) and stained with CAR detection reagents. For ROR1 CAR, cells were stained with ROR1-Fc peptide (R&D System, Minneapolis, MN), followed by anti Fc-AF647 conjugate (Jackson ImmunoResearch, West Grove, PA). For CD276 CAR or CCR, cells were stained with CD276-His (Acro biosystems, Newark, De), followed by anti-His PE (Miltenyi Biotech). The 7-Aminoactinomycin D staining (7-AAD, BD Biosciences, San Jose, CA) was added to exclude dead cells. CD4 antibody labeled with VioBlue was used to separate CD4 and CD8 population. Non-transduced cells (UTD) were used as a negative control. Cells were washed twice, resuspended in 200 μl running buffer, and acquired by flow cytometry. Flow cytometric analysis was performed on a MACSQuant® 10 Analyzer (Miltenyi Biotec), and data plots were generated using FlowJo software (Ashland, OR).

CAR T Cell Cytotoxicity and Cytokine Assay

To assess CAR T cell mediated cytotoxicity, $5\times10^3$ tumor target cells stably transduced with firefly luciferase were combined with CAR T cells at the indicated effector to target ratios and incubated overnight at 37° C. with 5% CO2. SteadyGlo reagent (Promega, Madison WI) was added to each well and the resulting luminescence quantified as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)). GraphPad Prism software, nonlinear EC50 shift, where x is log of concentration, was used for curve fit and relative potency calculation.

Results

In order to enhance ROR1 CAR functionality, ROR1 CAR was bicistronically co-expressed with a chimeric co-stimulatory receptor (CCR) targeting a second tumor associated antigen, CD276, providing an additional co-stimulatory signal to CAR. ROR1 CAR LTG 2529 and CD276-targeting CCR were co-expressed by lentiviral transduction in primary human T cells for functional evaluation. CAR LTG2529 is comprised of ROR1 targeting scFv9, in frame to IgG4 hinge, CD8 transmembrane, 41-BB costimulatory and a CD3ζ activation domain. The co-expressed CD276 CCR boosters comprised of in-house developed CD276 targeting binders, CD276-22 or CD276-30, followed CD8 hinge and transmembrane domain and CD 28 costimulatory domain, but without CD3ζ activation domain. Mono-targeting CD276 CARs based on different targeting scFv domains, CD8 hinge and transmembrane domain, a 4-4BB co-stimulatory domain and a CD3 activation domain were included for comparison. Previously published CD276-specific scFv 376.96 was included as positive control. Table 3 lists CD276 and ROR1 mono-targeting CARs constructs, and constructs co-expressing ROR1 CAR with CD276 CCR boosters.

TABLE 3

CD276 CAR and ROR1 CAR armored with CD276 CCR constructs

| | Construct Number | Construct designation | Promoter |
|---|---|---|---|
| Single CARs | D0426 | CD276 -22 CD8 hinge-CD8TM-41BB-CD3 | EF1α |
| | D0427 | CD276-30 CD8 hinge-CD8TM-41BB-CD3ζ | EF1α |
| | D0480 | CD276 376.96 CD8 hinge-CD8TM-41BB-CD3ζ | EF1α |
| | LTG2529 | ROR1 scFv9-IgG4 hinge-CD8TM-41BB-CD3ζ | EF1α |
| Single CAR with booster(s) | D0432 | ROR1 scFv9-IgG4 hinge-CD8TM-41BB-CD3ζ_2A_CD276 - 22 CD8 hinge-CD8TM-CD28 | EF1α |
| | D0433 | ROR1 scFv9-IgG4 hinge-CD8TM-41BB-CD3ζ_2A_CD276 - 30 CD8 hinge-CD8TM-CD28 | EF1α |
| | D0397 | ROR1 scFv9-IgG4 hinge-CD8TM-41BB-CD3ζ_2A_CD276 - 376.96 CD8 hinge-CD8TM-CD28 | EF1α |

Figures 22A, 22B:
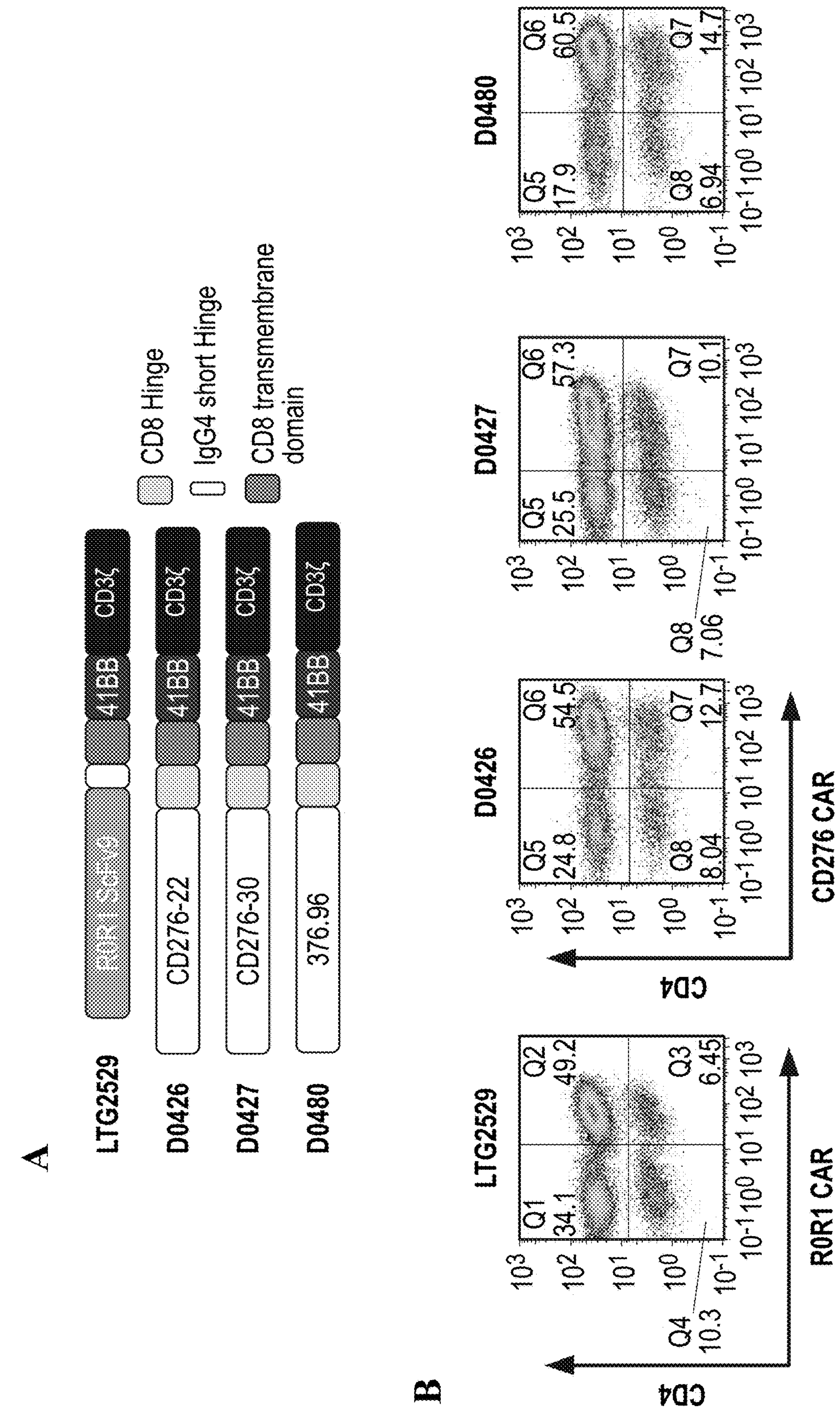
FIGS. 22A-22C depict ROR1 and CD276 CAR structure and surface expression on transduced primary T cells.
Figure 22C:
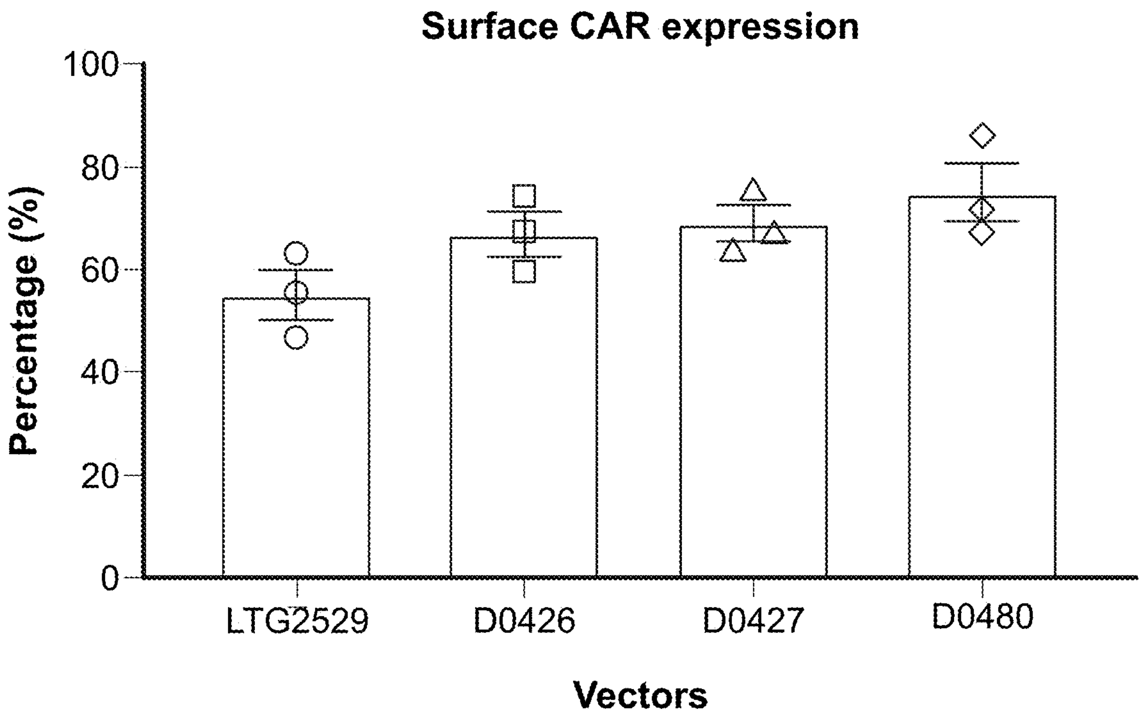

CD276 specific targeting-scFvs were first evaluated in CAR context in vitro, ROR1 CAR was included as control. The ROR1 and CD276 mono CARs (FIG. 22A) sequences were incorporated into third-generation lentiviral vectors and transduced into human primary T cells at MOI 20, to generate the ROR1 or CD276 CAR T cells under the control of the mammalian EF-1α promoter. Surface expression of CD276 CARs with ROR1 binder on transduced T cells was measured by flow cytometry using CD276-His, followed by staining with anti-His PE. ROR1 CAR expression was determined as previously described. Representative flow plots from one donor are shown in FIG. 22B. CAR surface expression, as measured by flow cytometry, was robust: CD276 CARs, 276-22 CAR D0426 and 276-30 CAR, as well as 276-96 CD276 CAR D0480, were expressed at 60%-80%, while ROR1 CAR LTG2529 transduction of T cells from same donors ranged 45%-65% (FIG. 22C). The target specific cytotoxicity of CD276 and/or ROR1 CARs was measured by luciferase based overnight killing assy. $ROR1^+CD276^+$ ovarian cancer line OVCAR3, pancreatic cancer line AsPC-1, lung cancer line NCI-H226 were used as target lines, and co-incubated with CAR T cells at 10 different effector to target (ET) ratios. Untransduced (UTD) T cells from same donors were included as negative control.

Figure 23A:
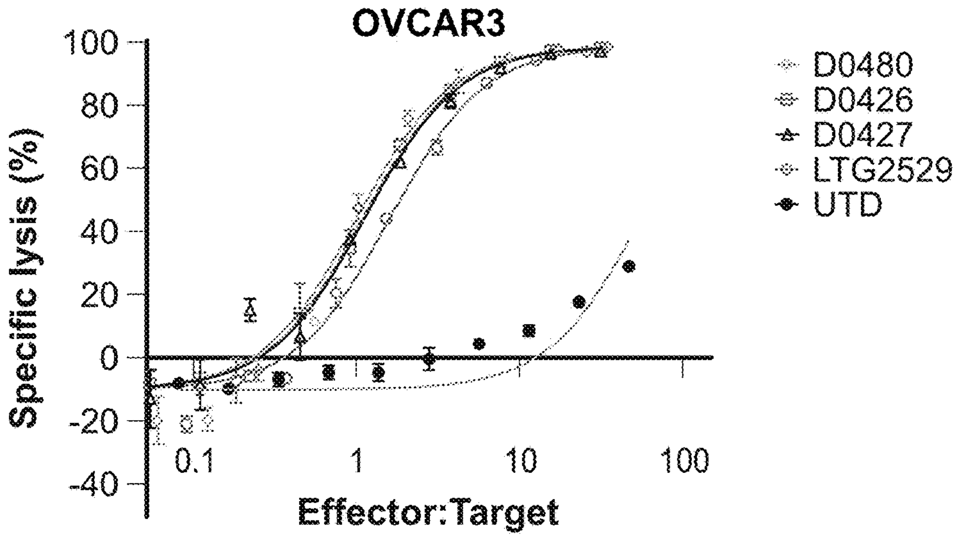
FIGS. 23A-23C depict the cytotoxicity of ROR1 or CD276 CAR constructs in vitro. Luciferase-based cytotoxicity assays were performed using ROR1+CD276+ tumor line (FIG. 23A) OVCAR3.
Figure 23B:
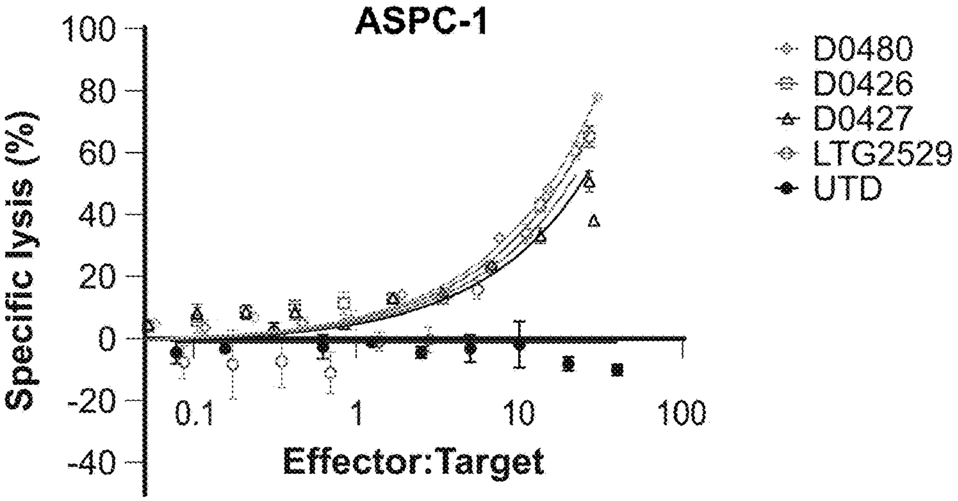
Figure 23C:
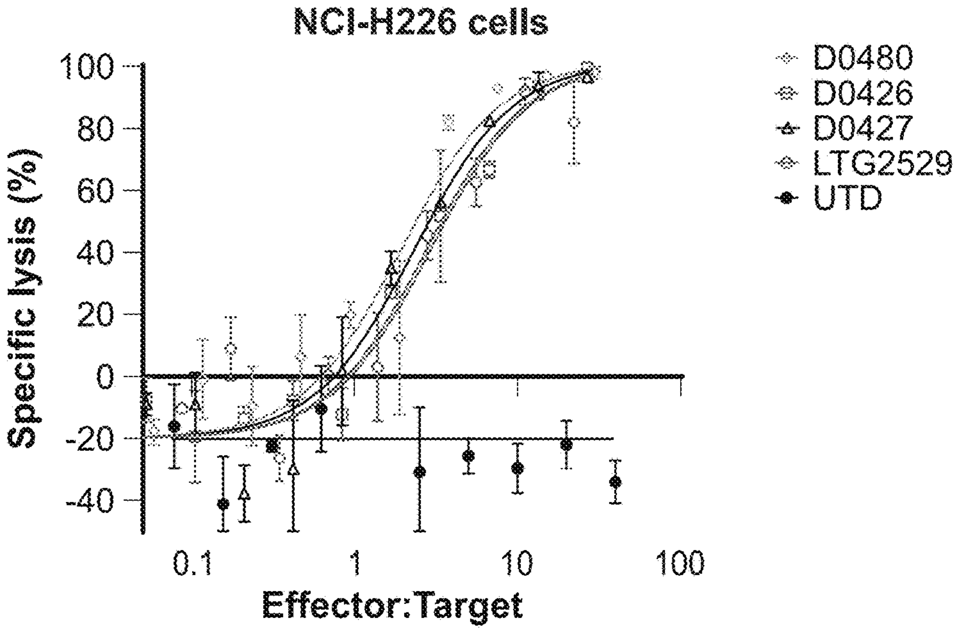

Percentage of specific lysis was plotted with ET ratio using non-linear curve fit, and is shown in FIG. 23. The CD276 CARs, D0426, D0427 and D0480 demonstrated comparable killing potency as compared to mono ROR1 CAR LTG2529, at all ET ratios tested (FIG. 23). UTD cells showed no appreciable target-specific killing, further demonstrating binder specificity of CD276 scFvs.

Figures 24A, 24B:
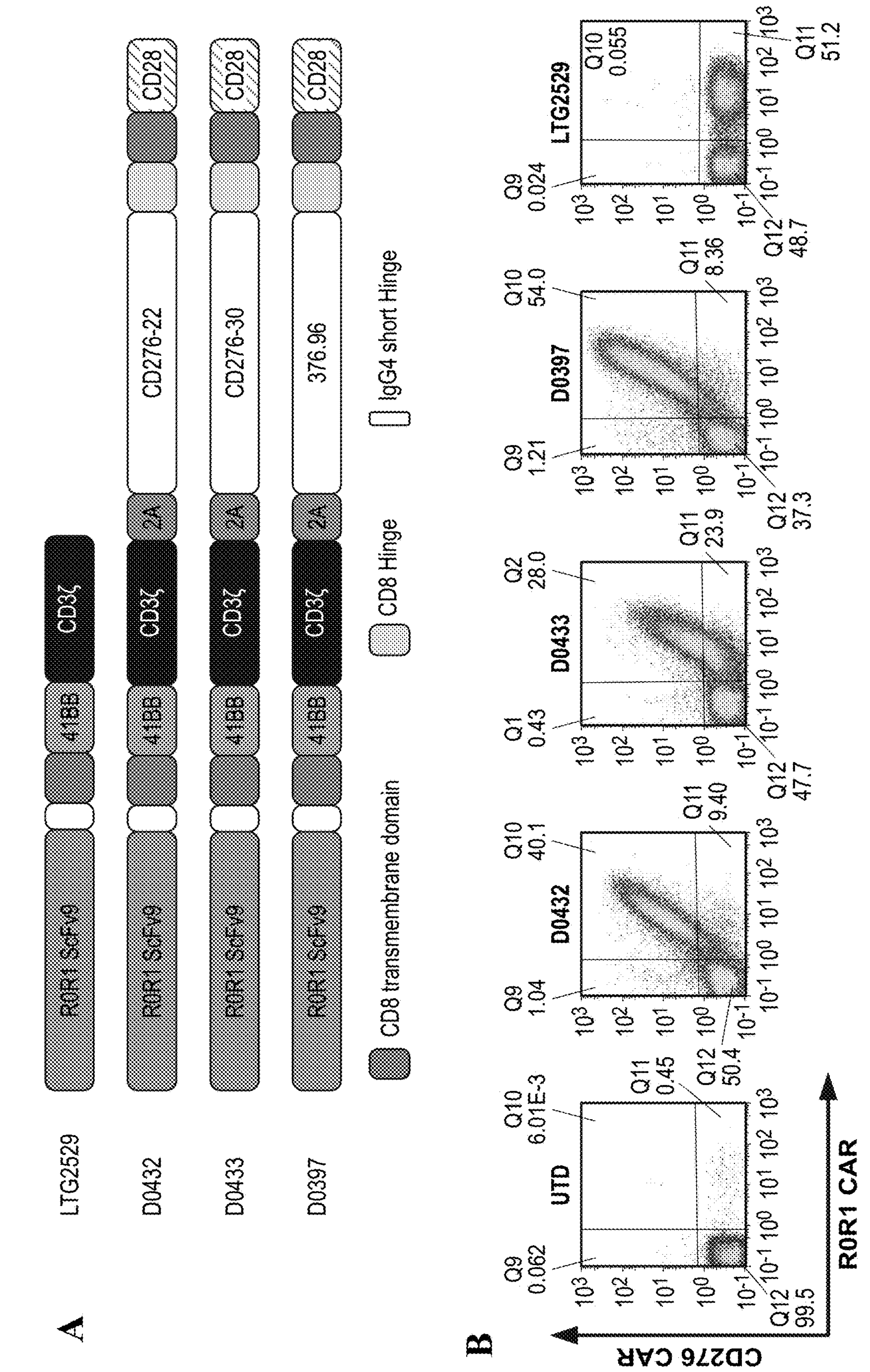
FIGS. 24A-24C depict the structure and primary human T cell surface expression of ROR1 CAR boosted with CD276 CCR.
Figure 24C:
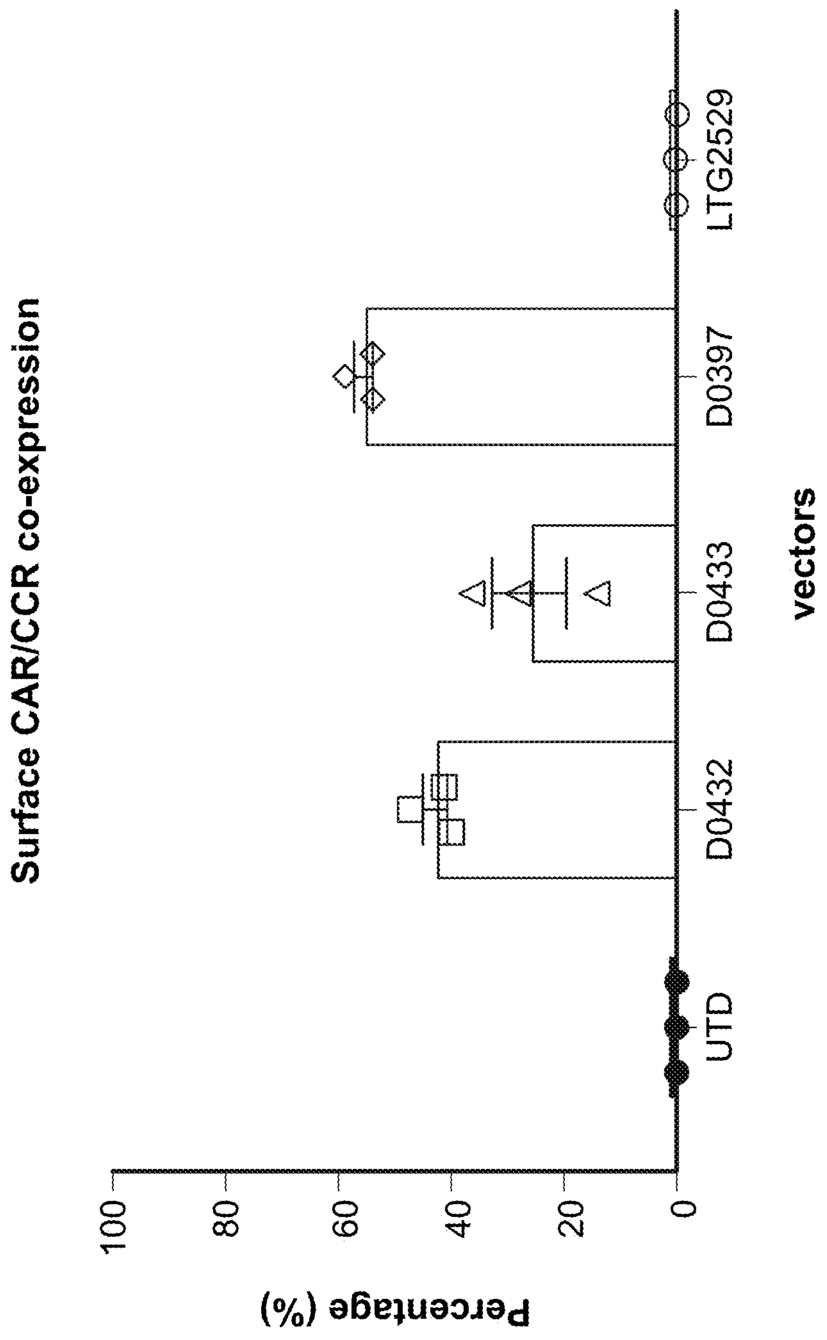
Figures 25A, 25B, 25C, 25D:
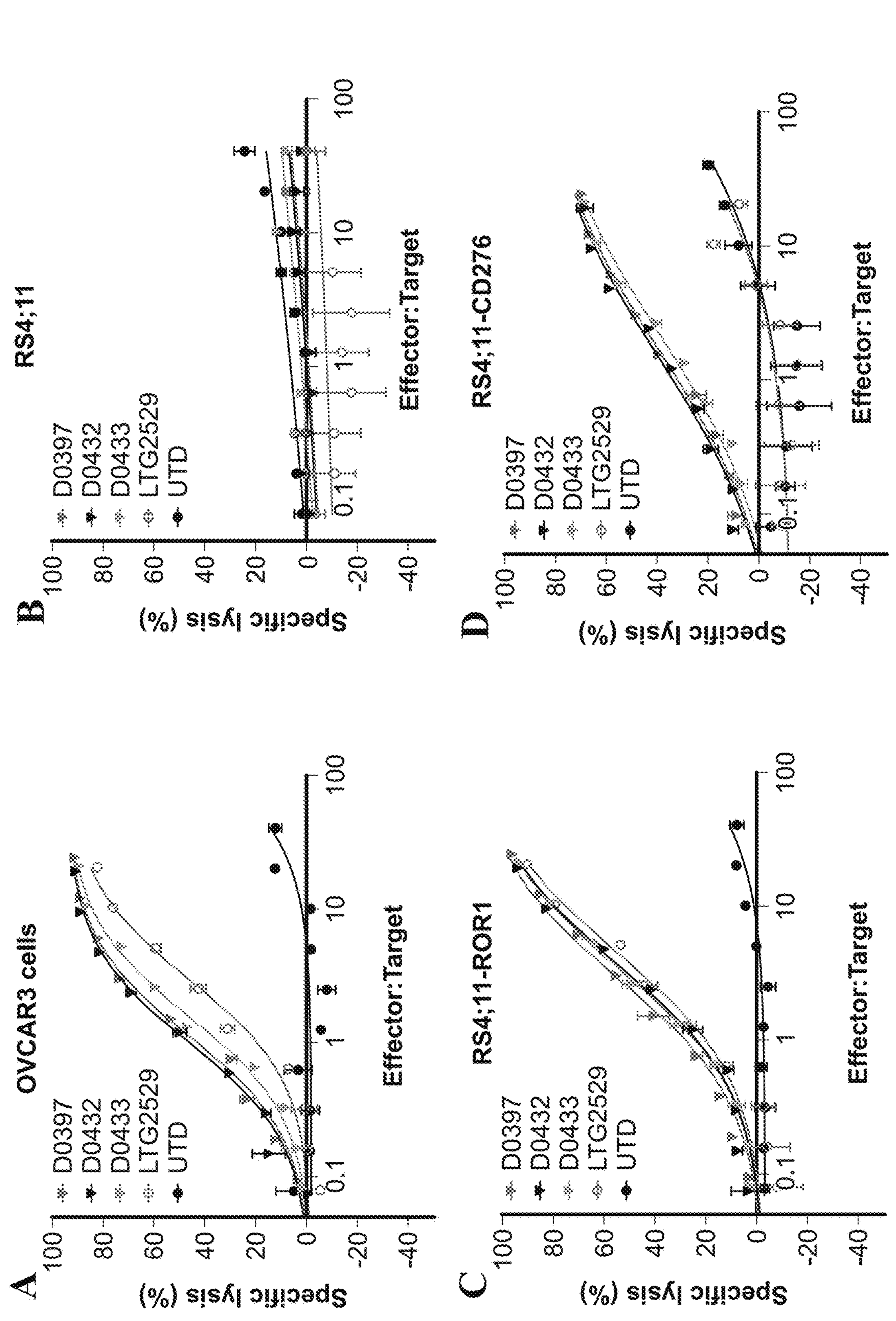
FIGS. 25A-25D depict the cytotoxicity of ROR1 CAR alone, without the CD276 CCR constructs in vitro. Luciferase-based cytotoxicity assays were performed using (FIG. 25A) ROR1+CD276+ tumor line OVCAR3.
Figure 26A:
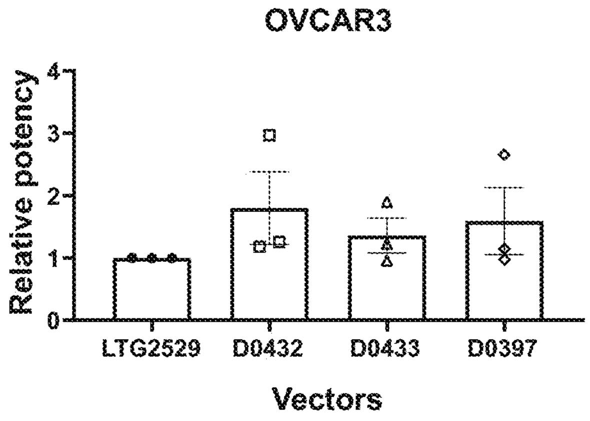
FIGS. 26A and 26B depict the relative potency of ROR1 CAR/CD276 CCR constructs in vitro. CAR T cells and ROR1+ tumor cells were co-cultured overnight at 10 different effector to target ratios. Percentage specific target lysis was assessed by luminometry and normalized to percentage of ROR1 CAR expression. Relative potency comparing to ROR1 CAR LTG2529 was calculated using nonlinear EC50 shift, function in GraphPad Prism, where x is log concentration. Relative potency of each constructs targeting ROR1+ in tumor lines.
Figure 26B:
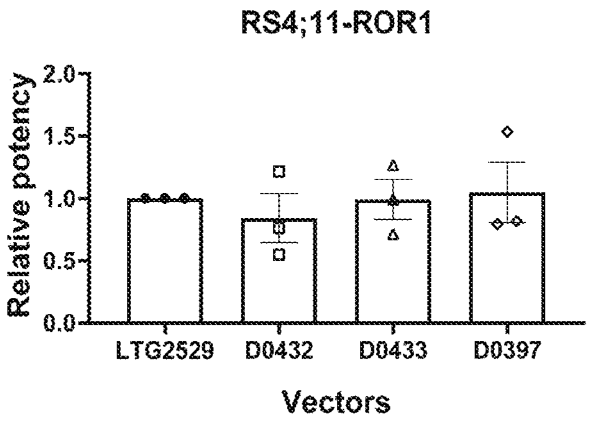

ROR1 CAR with CD276 CCR booster constructs (FIG. 24A) were evaluated for transduction efficiency and in vitro cytotoxicity. Human primary T cells were transduced with lentiviral vector bicistronically encoding ROR1CAR/CD276CCR constructs at MOI 20. As compared to UTD T cells from same donor, CAR/CCR construct D0432 with 276-22 CCR and D0397 with CD276 binder 376.96, showed effective ROR1 binder and CD276 binder co-expression (FIG. 24B), 50% of all T cells were double positive for the CAR and the CCR in three experiments using T cells from three unrelated donors (FIG. 24C). CAR/CCR construct D0433 with CD276 CCR comprising the 276-30 binder, had less CD276 binder expression as compared to ROR1 binder, with 30% of all T cells staining double positive for the ROR CAR and the CCR (FIG. 24B, 24C). As expected, the mono ROR1 CAR LTG 2529 transduced T cells showed no CD276 binder expression. The in vitro cytotoxicity of ROR1CAR/CD276 CCR constructs was measured at 10 different ET ratios with $ROR1^{+}CD276^{+}$ ovarian cancer line OVCAR3, $ROR1^{-}CD276^{-}$ ALL cell line RS4; 11, single antigen ROR1 overexpressing line RS4; 11-ROR1 and single antigen CD276 overexpressing cell line RS4; 11-CD276 (FIG. 25A-D). For ROR1+ target tumor cells, OVCAR3 or RS4; 11-ROR1, all CAR/CCR constructs demonstrated high killing efficiency (FIG. 25A, 25C). After normalization for percentage ROR1 CAR expression, the three ROR1CAR/CD276 CCR T constructs exhibited similar killing potency to that of the mono-targeting ROR1 CAR LTG2529 (FIG. 26A, 26B). Notably, when ROR1CAR/CD276 CCR transduced T cells were co-cultured with CD276+ target cell line RS4; 11-CD276, which is ROR1-negative, all constructs with CD276 CCRs revealed robust cytotoxicity (FIG. 25D). Therefore, the activation of the CCR by CD276 expressed on target cells triggered target cell killing, even though the CCR is lacking the CD3ζ activation domain. This effect is believed to be mediated by engagement of the CAR molecule via the CCR, which enables signaling through CD3ζ on the ROR CAR. No cytotoxicity was observed when ROR1CAR/CD276 CCR T cells were co-incubated with ROR1-CD276-RS4; 11 cells confirming the target specificity of ROR1 and CD276 binders.

In summary, ROR1 CARs with CD276 CCR boosters demonstrated high transduction efficiency, and had comparable cytotoxic function to the mono ROR CAR. Engagement of CD276 antigen alone mediated cytotoxicity, comparable to the engagement of ROR1 CAR via ROR1 antigen alone. Therefore, a logic [OR] CAR gate was created relying on one CD3ζ domain only for targeting both CD276 and ROR antigens.

Example 5

ROR1-CAR LTG2529 Cleared Both Hematologic and Solid Tumors, and Attenuated TGFβ-Rich Tumor Microenvironment when Armored with TGFβRIIdn Element

Introduction

Autologous chimeric antigen receptor (CAR) T cell therapy has revolutionized treatment for patients with B-cell leukemia, lymphoma and multiple myeloma. Over a third of all CAR T cell patients treated to date with commercial CAR T cells products targeting CD19 or BCMA, respectively, achieve complete and durable remissions (2). However, despite wide-scale efforts to tackle solid tumors, which account for 90% of all cancer types, they have yet to demonstrate high therapeutic efficacy, similar to that observed in hematologic malignancies. The immunosuppressive tumor microenvironment (TME) has been identified as one major challenge to the success of solid tumor CART cell therapies in solid tumors (3), and will need to be addressed.

Receptor tyrosine kinase-like orphan receptor 1 (ROR1) is an attractive target for immunotherapy of solid and hematologic tumors. ROR1 plays an important role during early embryonic development but remains absent from vital adult human tissues, except for expression in a subset of immature B-cell precursors in adult bone marrow, and low-level expression in adipocytes (4, 5). By contract, ROR is overexpressed on the surface of a large array of hematologic tumors, including B-ALL, B-CLL, MCL, FL, MZL, DLBCL, and a subset of solid tumors, including ovarian, pancreatic, lung, skin, breast, and colon cancers (6-8). Zilovertamab Vedotin, a novel antibody-drug conjugate comprising the humanized monoclonal antibody zilovertamam (or Cirtuzumab) and a linker-monomethyl auristatin E (Vedotin), is an antibody drug conjugate targeting ROR holds a promise for success in lymphoid cancers, and has demonstrated safety and anti-tumor effects in mantle cell lymphoma (MCL) and Diffuse large B cell lymphoma (DBLCL). However, Srivastava et al (1) faced the challenge in solid tumor as their ROR1 CAR-T cells with scFv-R12 binder infiltrated tumors poorly and became dysfunctional in patients with ROR1+TNBC and NSCLC.

Transforming growth factor beta (TGFβ) is a master regulator of TME, is known to be secreted by tumor cells, stromal fibroblasts, and other cells in many solid cancers, including pancreatic cancer, creating an immunosuppressive environment, inhibiting T cell effector function, cytokine response, proliferation, persistence and memory formation, promoting neoangiogenesis and metastasis (9). There are 3 isoforms of TGFβ1 in mammals, i.e. TGFβ 1, 2, and 3. TGFβ signals by binding to TGFβRI and II on cell surface, leading to phosphorylation and activation of transcription factor Smad2/3, which in turn activates responsive genes that inhibit T cell proliferation and differentiation into helper T cells and CTLs (10). Overcoming the immunosuppressive effects of TGFβ in TME may therefore offer a unique opportunity to simultaneously improve multiple CAR T cell attributes. Modulating the anti-tumor inhibitory effect of TGFβ has been studied by other groups and ours, including armoring CAR T with dominant-negative TGFβRII targeting PSMA in prostate cancer (11) and BCMA in Multiple Myeloma models (12), or knocking out TGFβRII in CAR T (13). Clinical trial employing PSMA-CAR T armored with a dominant negative form of TGFβRII showed promising results in patients with prostate cancer when administered at a safe dose (14).

Here, a novel, fully human ROR1-LTG2529 CAR employing scFv9 targeting domain is reported, which effectively eliminated hematologic tumors in Jeko-1 MCL xenografts, as well as solid tumors in OVCAR-3 ovarian cancer and AsPC-1 pancreatic cancer xenograft models. ROR1-LTG2529 elaborated greater cytokines and rejected solid tumors more effectively than a comparator LTG2527 based on the scFv-R12 binder, in agreement with the reported efficacy profile of R12-based CAR T cells in solid tumors (1). Furthermore, LTG2529 CAR T cells armored with TGFβRIIdn overcame the inhibitory effect of TGFβ in vivo in a pancreatic xenograft model AsPC1 overexpressing TGFβ 1. These findings support the application of TGFβRIIdn armor as a tool to ameliorate immunosuppressive TME for better treatment of patients with both hematologic and solid malignancies.

Methods

Generation of CAR Constructs, Lentiviral Vector Production and Titration

The constructs of fully human anti-ROR1 chimeric antigen receptor (CAR) either alone or with a booster element dominant negative (DN) TGFβRII were designed as CAR molecule and a booster molecule connected with P2A ribosomal skipping element sequence. The single chain variable fragment (ScFv) sequence scFv9 targeting the extracellular domain of human ROR1 was identified in house, the R12 ScFv targeting ROR1 was used as CAR ROR1 control. Mono CAR comprised of a anti-ROR1 scFv, a IgG4 short hinge for ROR1 scFv, a CD8 hinge, connected to CD8 transmembrane domain, costimulatory domain(s) derived from human 4-1BB, followed by CD3-ζ activating domain sequence.

CAR sequences were cloned into a Lentiviral Vector (LV) expression cassette under the control of the human EF-1α promoter (Lentigen Technology Inc., Gaithersburg, MD). Lentiviral particles were generated by transient transfection of HEK 293T cells, pelleted by centrifugation and stored at −80° C. until transduction. LV titers were determined by the serial transduction of SUP-T1 cell line and qPCR analysis of GAG and POL expression.

Preparation of Human T-Cells

Whole blood was collected from healthy volunteers at Oklahoma Blood Institute (OBI) with donors' written consent. Processed buffy coats were purchased from OBI (Oklahoma City, OK). The CD4-positive and CD8-positive human T cells were purified from buffy coats via positive selection using a 1:1 mixture of CD4- and CD8-MicroBeads (Miltenyi Biotec) according to manufacturer's protocol.

Preparation of Tumor Cell Lines

The mantle cell lymphoma (MCL) Jeko-1, Plasmacytoma B lymphocyte RPMI 822, Acute T cell Leukemia T lymphoblast, Chronic Myelogenous Leukemia line K562, Acute Lymphocytic Leukemia line Reh, Acute Promyelocytic Leukemia promyeloblast HL-60, Lymphoblastic Lymphoma T lymphoblast SUP-T1, Ovary Adenocarcinoma epithelial OVCAR-3, Pancreas Adenocarcinoma Capan-2 and AsPC-1, and Lung Squamous Cell Carcinoma NCI-H226 cell lines and culture reagents were purchased from American Tissue Culture Collection (ATCC; Manassas, VA, USA), unless otherwise noted. All cell lines were cultured following the manufacturer's instructions. Single-cell clones of luciferase-expressing cell lines were generated by stably transducing wild-type tumor lines with lentiviral vector encoding firefly luciferase (Lentigen Technology, Inc., Gaithersburg, MD), followed by cloning and selection of luciferase-positive clones. AsPC-1 cell line overexpressing human TGFβ1 was generated in-house.

Primary T Cell Transduction

Selected CD4+ and CD8+ human primary T cells from normal donors were cultivated in TexMACS medium (serum-free) supplemented with 40 IU/ml IL-2 at a density of 1e6 cells/ml, activated with CD3/CD28 MACS® GMP TransAct reagent (Miltenyi Biotec) on day 0 and transduced on day 1 with lentiviral vectors encoding CAR constructs, and media exchanged on day 3. Cultures were propagated on day 6 until harvest on days 9-10 for co-incubation analysis. Extra CAR-T cells were cryopreserved using 10% DMSO (Amresco), 70% FBS (HyClone, Logan, UT, USA), and 20% TexMACS in a controlled-rate freezer (Mr. Frosty; Nalgene) and then stored at Liquid nitrogen (−160° C.) until re-culture.

Luciferase-Based Cytotoxicity Assay & CAR T Potency Calculation

Cytotoxicity assay was performed as previously described (15). Briefly, 5,000 target cells stably transduced with firefly luciferase were combined with CAR T cells at various effector to target ratios and incubated for 18 hrs. SteadyGlo reagent (Promega, Madison, WI) was added to each well and the resulting luminescence was analyzed on an GloMax microplate reader (Promega, Madison, WI) and recorded as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)). Absolute potency ($EC_{50}$) and relative potency of effector T-cells were calculated using Prism software with 4-parameter parallel-line analysis approach.

Impedance-Based Cytotoxicity Assay

The assay was performed employing xCELLigence RTCA MP analyzer (Agilent Technologies, Santa Clara, CA, U.S.) following the manufacturer's instructions. Briefly, 40,000 AsPC-1 cells were co-cultured with 80,000 effector cells (i.e. E:T ratio=2:1) and the cytolysis was monitored for 3 days. The data was analyzed by RTCA Software Pro.

Quantification of Cytokine Release from the Co-Culture of Target Cells and Effector Cells Supernatant harvested from the co-culture of effector & target cells at the end of the assay was analyzed for IFN-γ, TNF-α, and IL-2 by ELISA (ThermoFisher Scientific, Inc., Waltham, MA) following manufacturer's instructions.

Quantification of TGFβ1 Produced by Tumor Cell Lines in Culture

Cell lines of interest were seeded in 6-well plates and cultured overnight in the appropriate medium, followed by exchange with fresh medium, and further cultured for 24 hrs. Then, 100 uL of supernatant was collected and subject to analysis for human TGFβ1 employing Duoset ELISA for human TGFβ1 (R&D Systems) following the manufacturer's instructions. Notes: No HCl treatment of samples was performed for detection of active TGFβ1 form.

Quantification of Human Cytokines in Mouse Serum

At the time points of interest during in vivo studies, 50 uL of blood from each mouse was collected and subject to analysis of human cytokines (GM-CSF, IFN-γ, TNF-α, IL-6, IL-2, TGF-01) employing MSD U-plex assays (Mesoscale Discovery). To detect active form of TGF-1, no HCL treatment of samples was performed.

Flow Cytometric Analysis

Flow cytometric analysis was performed as previously described (12, 15, 16). All cell staining reagents for flow cytometry were from Miltenyi Biotec, unless otherwise noted. These include anti-ROR1.AF647, mouse IgG1 control. APC, anti-CD45.PE, anti-CD8. Viogreen, anti-CD3.VioBlue, anti-CD45. VioBright FITC, anti-CD45RA. APC-Vio770, anti-CD62L.PE, anti-PD1.PE-Vio770, Streptavidin. PE (Miltenyi Biotec). Cell viability solution (7-AAD), BD Pharm Lysing buffer were purchased from BD Biosciences. Anti-ROR1.AF647 was from R&D systems. ROR1.Fc was from Sino Biologicals. Anti-human Fc.AF647 was from Jackson ImmunoResearch. Countbright absolute counting beads were from ThermoFisher Scientific. Anti- TGFβRII. Biotin was from Biolegend. Stained cells were analyzed using the MACSQuant Analyzer 10 flow cytometer (Miltenyi Biotec).

Antigen Density Quantification Assay

Target cells of interest were stained with Anti-ROR1.PE or mouse IgG2b control.PE, and Cell viability solution (7-AAD). Antigen density was calculated based on BD QuantiBrite beads. All reagents were purchased from BD Biosciences, and the assay was performed following the manufacturer's instructions.

In Vivo Analysis of CAR-T Activity

All animal studies were approved by Jackson Laboratory Animal Care and Use Committee (Sacramento, CA). Female 7 to 8-week old NSG mice (NOD.Cg-Prkd$^{scid}$Il2g$^{tm1Wjl}$/SzJ), Jackson Laboratory (Bar Harbor, ME) were utilized.

Mantle Cell Lymphoma (MCL) Jeko-J xenograft model: Mice (6 mice/group) were intravenously (i.v.) implanted with Jeko-1 cells (0.5e6 cells/mouse). On day 6 following Jeko-1 injection, tumor engraftment was measured by i.p. injection of 150 mg/kg luciferin and imaging 10 min later for 40 s on a Xenogen IVIS-200 instrument (Caliper Biosciences, now Perkin Elmer, Shelton, Connecticut). Images were analyzed using Living Image, version 4.1, software (Perkin Elmer) and the bioluminescent signal flux for each mouse was expressed as average radiance (photons per second per cm2 per steradian). Mice were distributed equally to study groups (staging) on day 6 based on tumor burden. CAR T cells were administered to mice via tail vein injection on Day 7 at the dose of 3e6 total CAR$^+$T cells/mouse. Un-transduced T cells from the same donor (UTD) and Tumor alone group served as controls. The amount of injected UTD T cells was adjusted to the number of total T cells in the CAR groups with the highest total cell count. Imaging was performed on days 6, 13, 20, 27, 34, and 41 following injection to establish the kinetics of tumor growth and eradication by CAR T cells. Body weight was monitored 3 times/week.

Ovarian Adenocarcinoma OVCAR-3 xenograft model: the study was perform as described in the MCL Jeko-1 model above with some modifications as following: Mice (5 mice/group) were intraperitoneally (i.p.) implanted with OVCAR-3 cells (10e6 cells/mouse). CAR T cells were administered to mice via tail vein injection on Day 7 at the dose of 5e6 total CAR$^+$T cells/mouse. Imaging was performed on days 3, 10, 17, 24, 31, 38, and 47 following injection.

Pancreas Adenocarcinoma AsPC-1 xenograft model: Mice (5 mice/group) were subcutaneously (s.c.) implanted with AsPC-1 cells (1e6 cells/mouse) in the right flank. Once tumors reached approx. 100 mm; as measured with a caliper, mice were stagged and CAR T cells were administered to mice via tail vein injection on Day 17 at the dose of 5e6 total CAR$^+$T cells/mouse. Tumor volume was measured by caliper 5 times per week for the first 2 weeks, followed by 3 times per week until study termination time point; the same schedule was applied to body weight monitoring. All mice untreated or treated with UTD T cells were sacrificed at day 52 post T cell infusion. Mice treated with either armored or non-armored CAR Ts and showed complete tumor clearance (i.e. tumor volume=0 mm$^3$) were re-challenged with AsPC-1 (1e6 cells/mouse) by s.c. injecting the tumor cells in the left flank at day 73 post T cell dosing (or 90 days after the first tumor implantation). Notably, 13 days before the re-challenge, one mouse from the armored CAR T treated group was sacrificed due to body weight dropped beyond 20%, therefore, there were 4 mice in the non-armored CAR and 3 mice in the armored one entered the re-challenge study; 4 age-matched mice were used as controls. Tumor volume on both flanks were measured by caliper 5 times per week for the first 2 weeks, and 3 times per week for the following weeks; body weight was monitored in the same schedule.

Pancreas Adenocarcinoma AsPC-1/TGFβ xenograft model: The study was performed as described in the AsPC-1 xenograft model above except that CAR T cells were injected after 15 days of tumor implantation and the study was ended at day 49 post T-cell infusion.

Histology & Immunohistochemistry Staining of Tumor Tissues

After 7 days of CAR T infusion, tumor tissues from 1 mouse per group (in AsPC-1 or AsPC-1/TGF0 xenograft model) were collected, fixed with 4% PFA buffer for 24 hrs, then stored in 70% EtOH before embedded in Paraffin. The sectioned tissues were then subject to H&E, Masson Trichrome staining, and immunohistochemistry staining with anti-CD3 antibody (Cell Signaling), anti-TGF-β antibody (abcam), or rabbit isotype control (Cell Signaling).

Graphs and Statistical Analysis

All statistical analyses were performed using Prism 9.3.1 software (GraphPad, San Diego, CA, USA). Technical replicates represent repeated measurements of same donor-derived population of cells, and biological replicates indicated 2 or more donor-derived cellular populations or separate mice. Bioluminescence, cytotoxicity of target cells, and expansion of T cells data were log transformed prior to analysis using parametric tests. Statistical significance was determined by one- or two-way ANOVA, followed by Tukey's multiple comparison test. Survival was evaluated by Kaplan-Meier test. p values were reported as the following: ns (non-significant), p>0.05, *p<0.05, p<0.01, *p<0.001, and ****p<0.0001. Error bars represent standard error of the mean.

Results

Figures 27A, 27B:
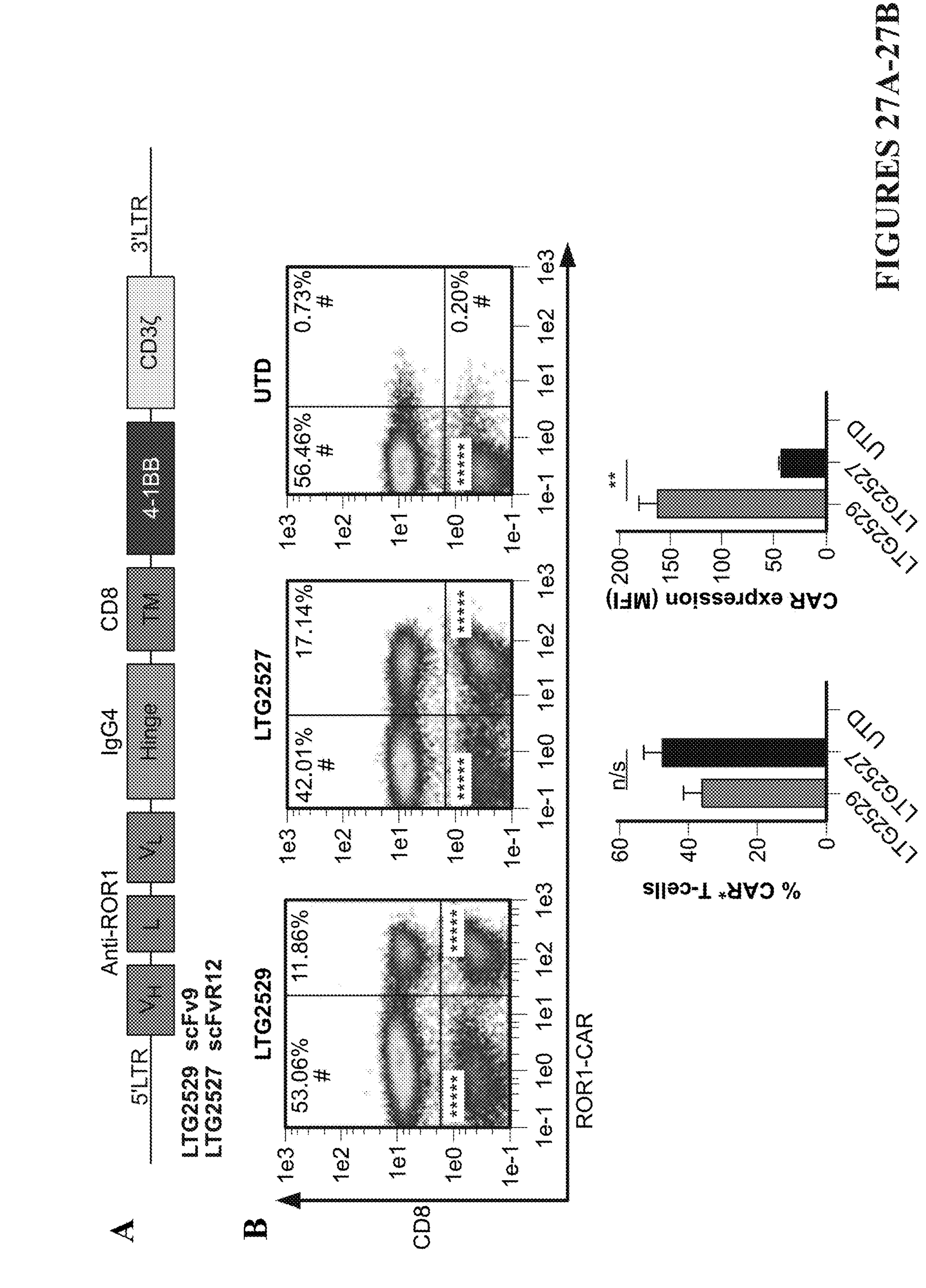
FIGS. 27A-27K depict that the novel anti-ROR1 LTG2529 (with scFV9 binder) demonstrated higher expression & cytokine secretion vs LTG2527 (with the control R12 binder) whereas exhibiting comparable cytotoxic potency in vitro and efficacy in vivo against hematologic tumors.

The Novel Fully-Human ROR1-LTG2529 Exerted Comparable Cytotoxic Activity Against Hematologic Tumor Cell Lines Positive for ROR1 vs Comparator CAR R12-ROR1 LTG2527 In Vitro, but Elaborated Greater Levels of Cytokines ROR1 is a 12-kDa protein containing extracellular immunoglobulin-like, Frizzled, and Kringle domains. Hudecek M et al (17) developed a second generation CAR specific to ROR1 with rabbit R12-scFv binder, short Hinge IgG4-Fc spacer, 4-1BB co-stimulating domain, and CD3z signaling domain which has recently been reported to poorly perform in phase 1 clinical trial on patients with ROR1+TNBC and NSCLC (1). In this study, similar CAR constructs were generated with either a new fully-human scFv binder (namely scFv9) specific to ROR1 and named it LTG2529, or the control R12-scFv binder (namely scFvR12) and named it LTG2527, a schematic diagram of which is shown in FIG. 27A. Lentiviral transduction of human primary T cells with LTG2529 or LTG2527 revealed higher cell surface density for LTG2529 compared to LTG2527 (i.e. approx. 4 fold), although transduction efficiency (% CAR$^+$T-cells/total T-cells) were comparable for LTG2529 vs LTG2527 (FIG. 27B). Next, cytotoxicity of ROR1 CARs was evaluated in vitro in MCL Jeko-1 cells.

Figures 27C, 27D, 27E:
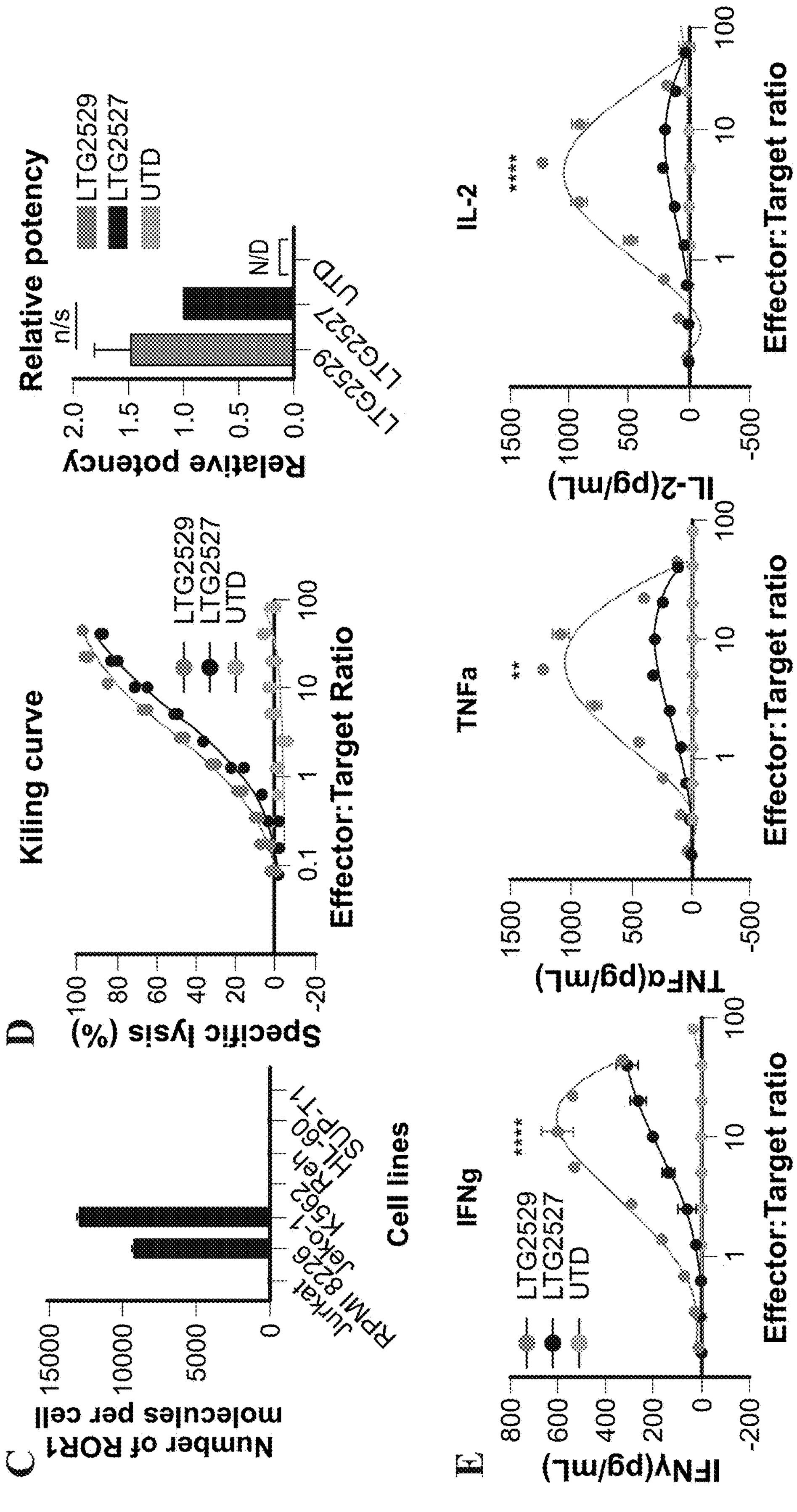

Overnight co-culture of LTG2529-transduced T cells with Jeko-1 cell line, exhibiting high ROR1 density (FIG. 27C), showed comparable cytotoxic potency between LTG2529 and LTG2527 (FIG. 27D). Further, Jeko-1 cells elicited significantly higher cytokine production from LTG2529 as compared to LTG2527 (FIG. 27E) suggesting that LTG2529 CAR mediated greater activation of T cells.

Figure 27F:
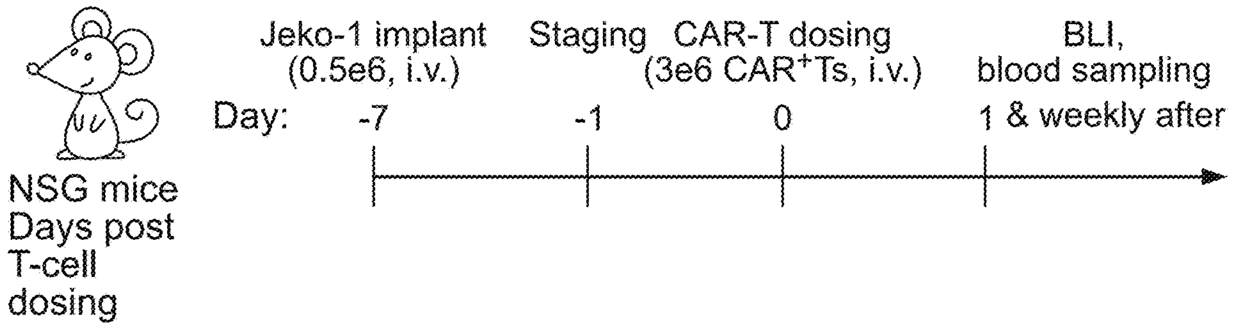
Figure 27G:
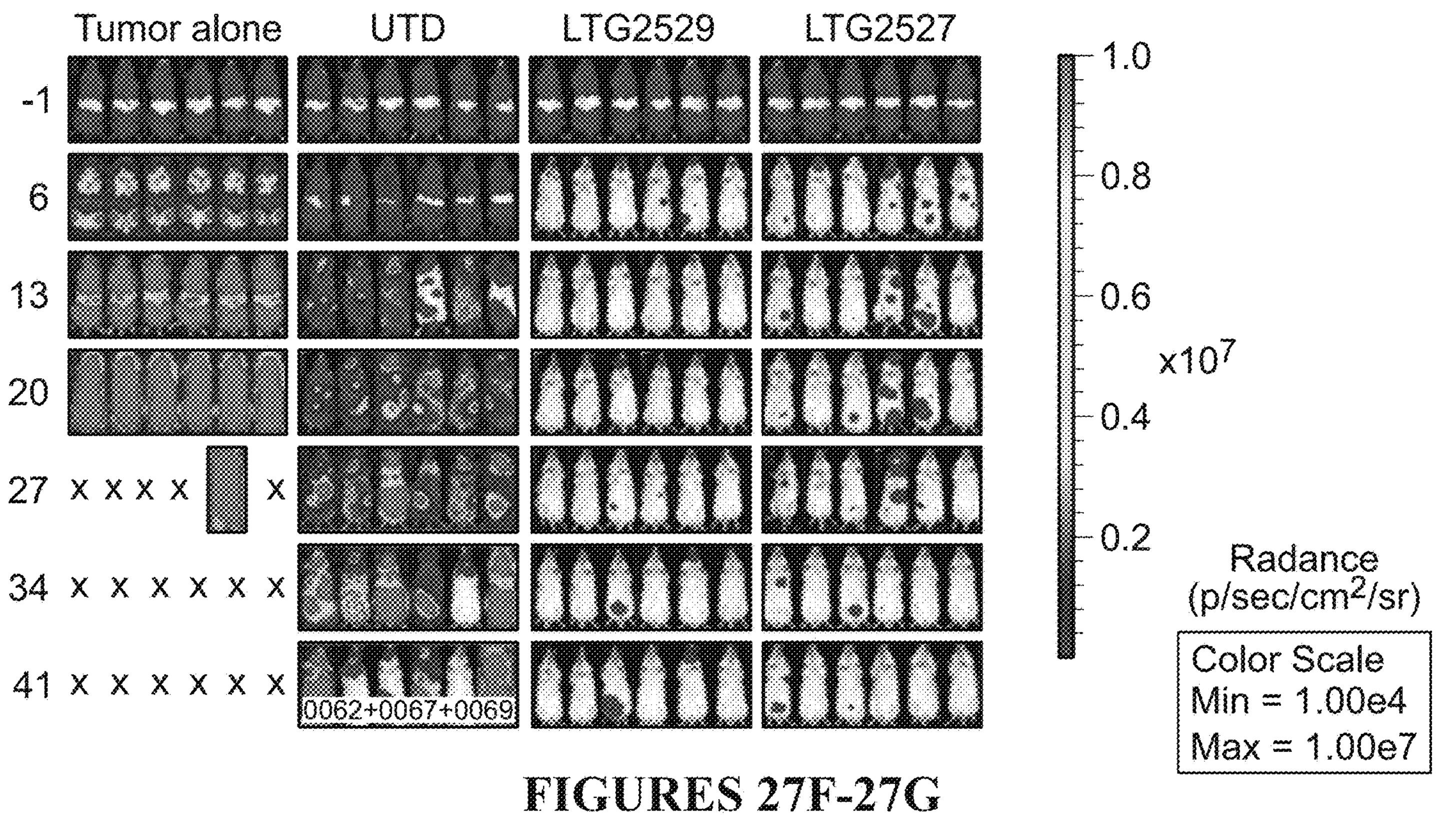
Figure 27H:
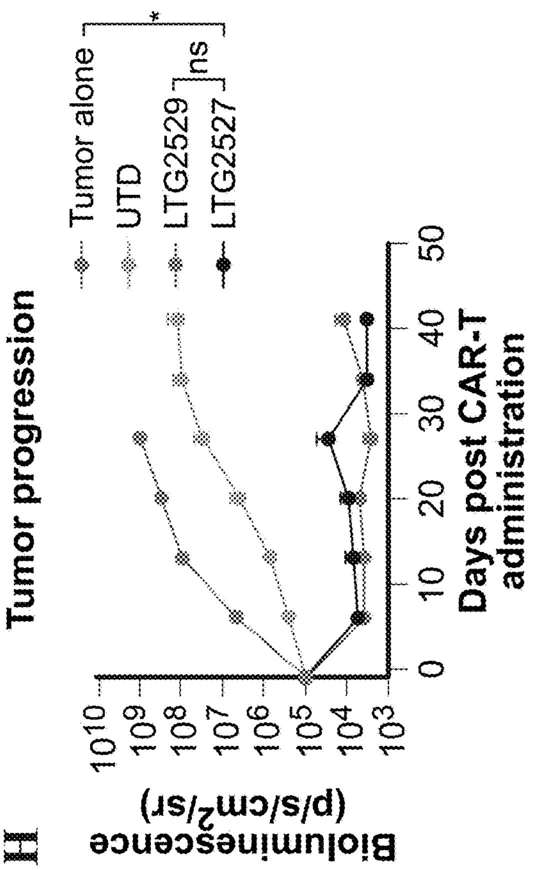
Figure 27I:
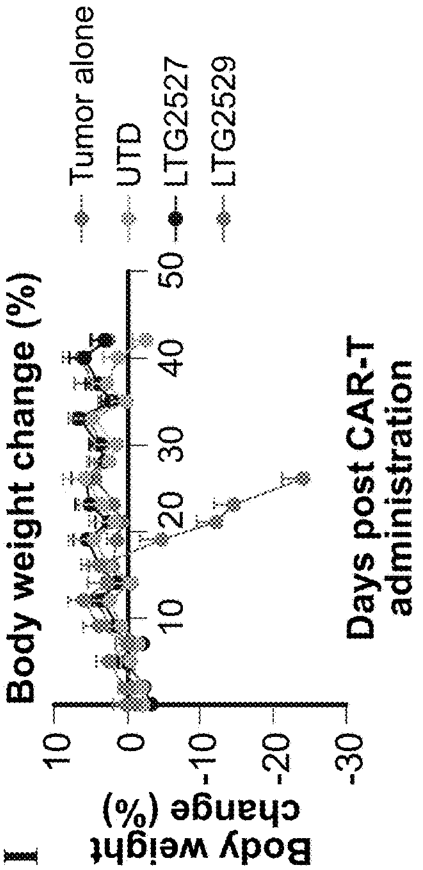

LTG2529 and LTG2527 were Equally Effective in Eradicating Hematologic Jeko-1 MCL Xenograft In Vivo Next whether the similar anti-tumor activity of the 2 CARs in vitro would translate to in vivo was examined. To address this question, Jeko-1 MCL xenograft model was used (FIG. 27F). Comparable tumor regression and improved survival were observed in Jeko-1-implanted immunodeficient NSG mice treated with LTG2529 or LTG2527, whereas 5 out of 6 untreated mice reached euthanasia criteria after 34 days of inoculation with Jeko-1 tumor (FIGS. 27G and 27H). No significant weight loss was observed in mice treated with either CAR during this study (FIG. 27I).

Figure 27J:
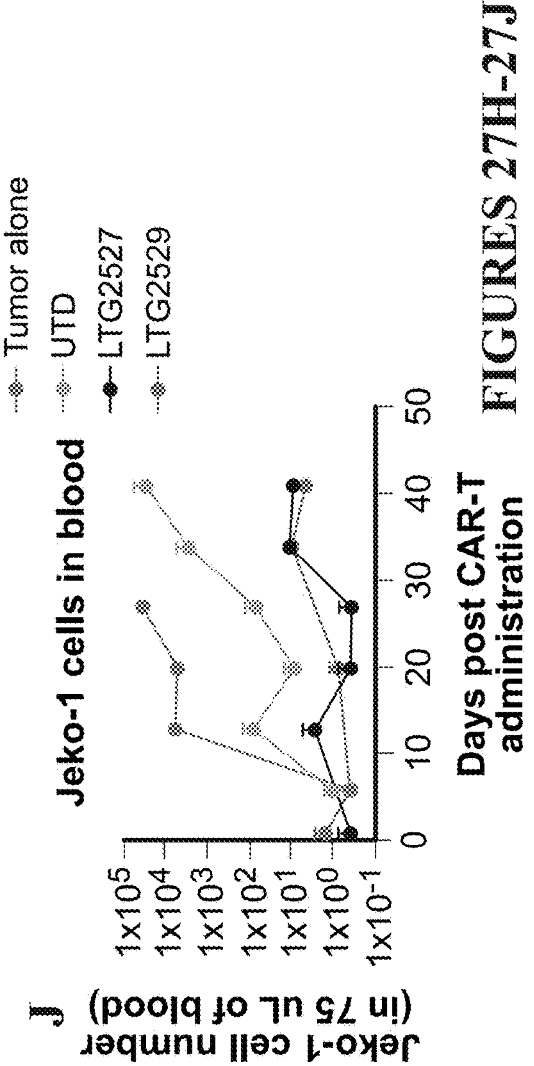
Figure 27K:
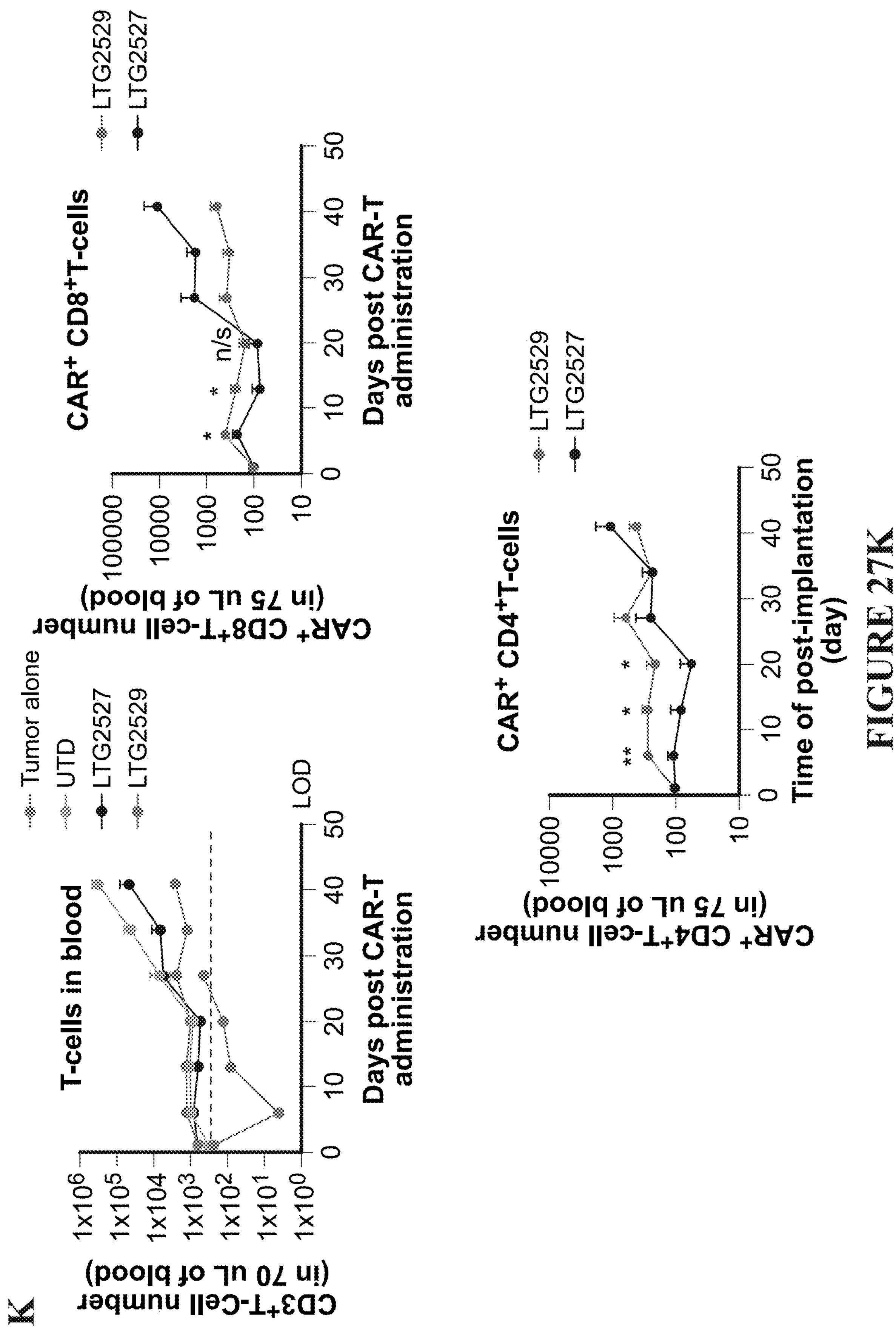

Blood from the mice was sampled and observe only a few Jeko-1 cells were observed in mice treated with either CAR, whereas the number of Jeko-1 cell was elevated 1000-fold in untreated mice after 20 days of tumor inoculation (FIG. 27J), which correlated with tumor progression, as measured by luciferase activity (BLI) (FIGS. 27G and 27H). Furthermore, LTG2529 exerted a faster expansion of total CAR-positive T cells as compared to LTG2527 CAR within 6 days after administration, due to higher expansion of both CD8' and CD4 T-cell populations (FIG. 27K).

LTG2529 Showed Enhanced Cytokine Response and Comparable or Greater Cytotoxicity Against OVCAR-3, Capan-2 and NCI-H226 $ROR1^+$ Solid Tumor Cell Lines In Vitro as Compared to LTG2527

Figures 28A, 28B:
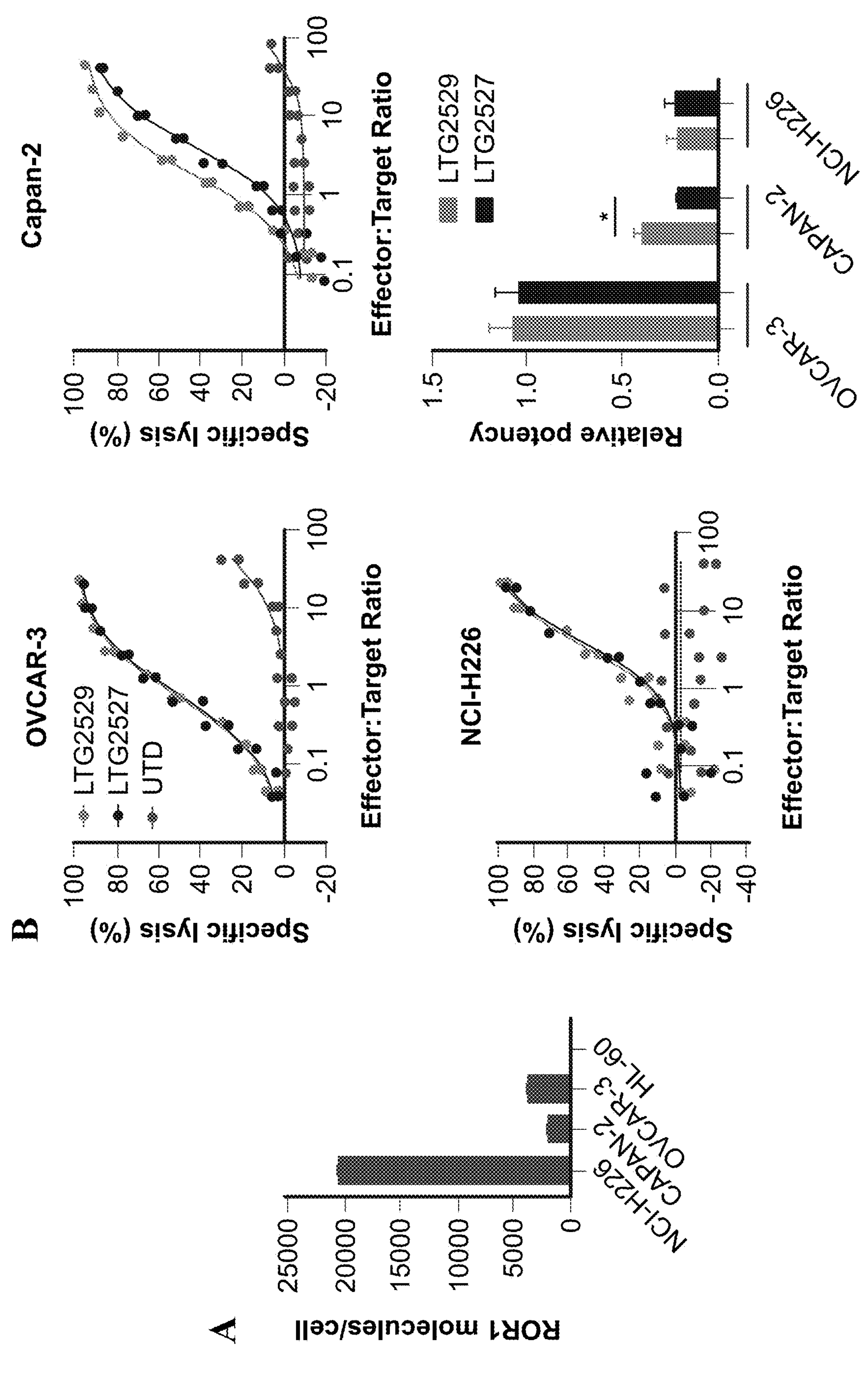
FIGS. 28A-28I depict that LTG2529, not LTG2527, was effective in suppressing solid tumor progression in in vivo ovarian cancer OVCAR-3 xenograft model despite exhibiting comparable in vitro cytotoxic activity (with higher cytokine production). (A) Quantification of ROR1 expression on surface of various solid tumor cancer cell lines; the experiment was performed in duplicates employing anti-ROR1 Ab from BD Biociences; a separate experiment was also performed in duplicates using anti-ROR-1 Abs from Miltenyi Biotec and R&D systems with similar results. (B) A representative Killing curve of CAR-Ts against various solid cancer cell lines in an 18-hr co-culture with relative cytotoxic potency of LTG2529 vs LTG2527 (n=3 donors) on the right. (C) Quantification of cytokines secreted in 18-hr co-culture of CAR Ts with OVCAR-3 cell line by ELISA, a representative data was shown, 3 independent experiments were performed employing 3 donors with similar results. (D-I): Efficacy of CAR-Ts in in vivo ovarian cancer OVCAR-3 xenograft model: NSG mice (5 mice/group) were implanted (i.p.) with OVCAR-3 cell line (10e6 cells/mouse)
Figures 28C, 28D:
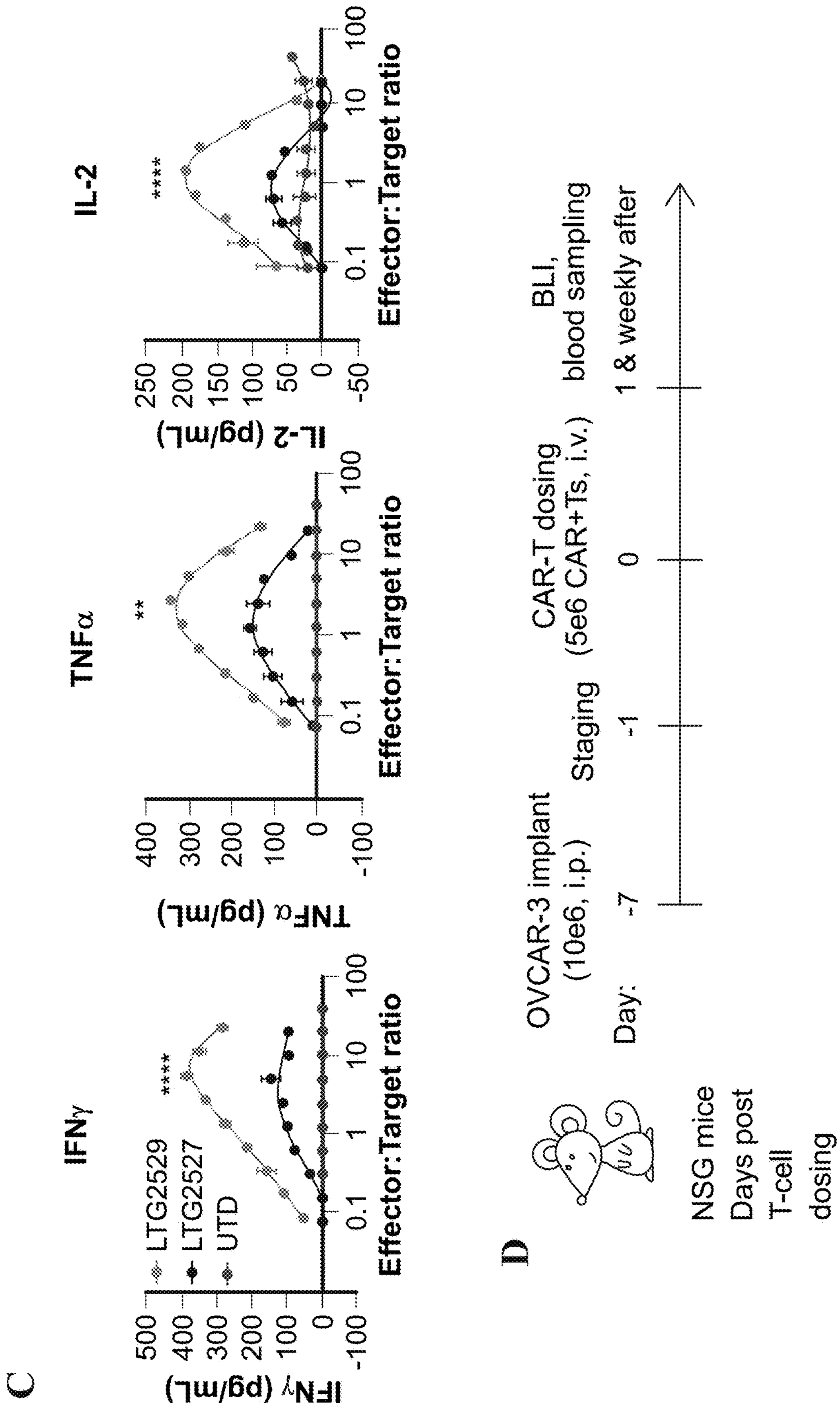
Figure 28E:
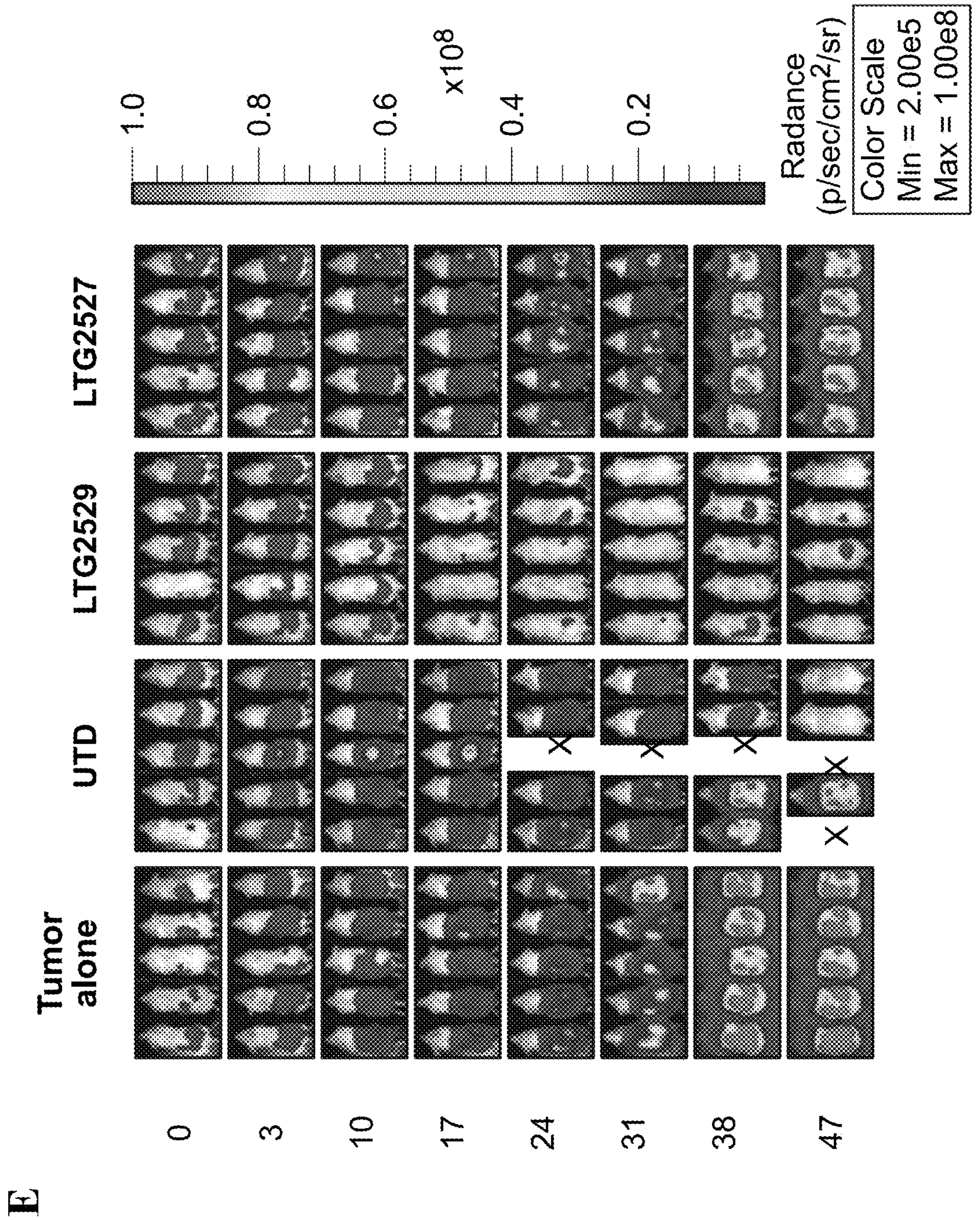

Furthermore, anti-tumor reactivity of LTG2529 vs LTG2527-transduced T cells against solid cancer cell lines in vitro was investigated. Quantification of ROR surface density on solid tumor cell lines, including NCI-H226, Capan-2, and OVCAR-3 (lung, pancreatic, ovarian, respectively) revealed broad range of ROR1 expression (FIG. 28A). T cells were transduced with either LTG2529 or LTG2527, and co-cultured with the target cells overnight. LTG2529-transduced T cells, as compared to LTG2527, exhibited comparable cytotoxic potency against OVCAR-3 and NCI-226 tumor lines, but higher potency against Capan-2, which may reflect overcoming the intrinsic resistance of pancreatic tumors to T cell therapy by LTG2529, but not LTG2527 (FIG. 28B). Additionally, greater amounts of IFNγ, TNFα, and IL2 were produced by LTG2529 vs LTG2527 T cells in OVCAR-3 (FIG. 28C), consistently with greater elaboration of cytokines by LTG2529 in response to hematologic tumor lines (FIG. 27E), suggesting a universal heightened cytokine response of LTG2529, irrespective of tumor type.

Only LTG2529, but not LTG2527, Mediated Tumor Regression in In Vivo Ovarian Cancer Model.

Figures 28F, 28G, 28H, 28I:
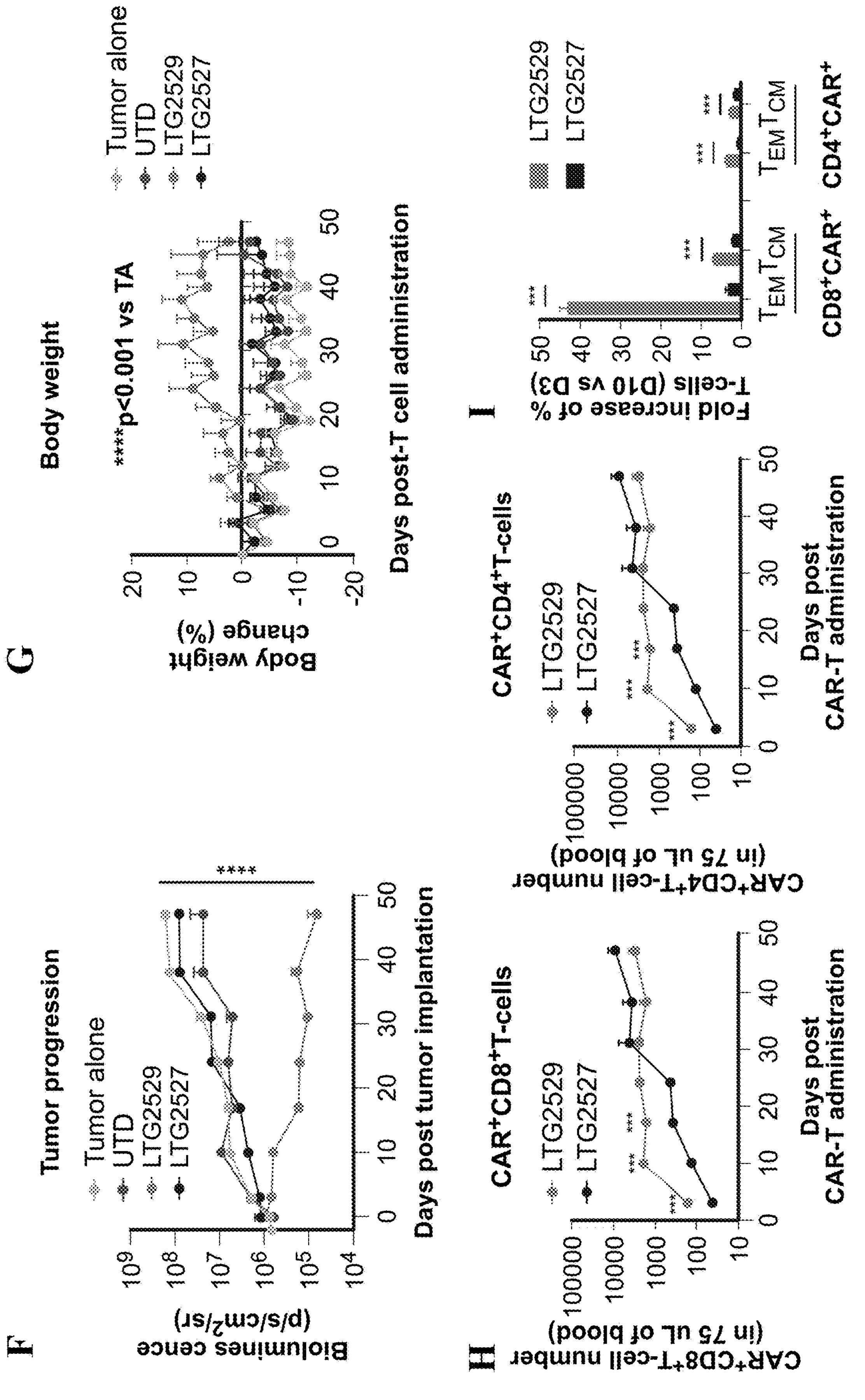

In order to investigate the anti-tumor response of CARs against solid tumor in in vivo, OVCAR-3 ovarian cancer model was chosen. Although both CARs showed similar cytotoxic activity against OVCAR-3 in vitro as shown in the above data, only LTG2529 mediated tumor regression in vivo (FIGS. 28D-29F). Additionally, mice administered LTG2529 T cells did not show significant weight loss as compared to mice administered either LTG2527, un-transduced T-cells, or untreated mice (FIG. 28G). Rapid expansion of $CD8^+$T and memory T cells after CAR T cell administration predicts positive clinical outcomes. Analysis of blood samples from mice treated with either LTG2529 or LTG2527 T cells revealed rapid expansion of LTG2529 group's $CD8^+$ and $CD4^+$ T-cells within the first 10 days after T cell administration as compared to LTG2527 (FIG. 28H). Additionally, from day 3 to day 10 post administration, LTG2529-transduced T cells showed a rapid expansion of $T_{EM}$ cells in both CD8 (43 fold, from 0.53% to 23%) and CD4 (4 fold, from 4.2% to 17.6%), indicative of prompt effector CAR T cell activity, as compared to LTG2527 (3.4 fold, from 5% to 17% for CD8, and no increase in % of CD4 $T_{EM}$ cells); a similar increase was observed in the fraction of $T_{EM}$ cells transduced with LTG2529, with faster expansion in CD8 (7 folds; i.e. from 6.6% to 46%) and CD4 (about 3 folds; i.e. from 17% to 49.7%) as compared to LTG2527 (2 folds for CD8 and 1.8 fold for CD4) (FIG. 28I), suggesting effective formation of immune memory and reserve for durable LTG2529 T cell function. In summary, our data demonstrate that LTG2529 exhibited anti-tumor efficacy in in vivo xenograft model of solid tumor, particularly ovarian cancer, which is attributed to timely expansion of CAR T cells, and enrichment for $T_{EM}$ and $T_{CM}$ phenotypes in both CD8 and CD4 T cell populations; whereas the suboptimal anti-tumor response of LTG2527 T cells was reflected in delayed CAR T cell expansion and emergence of the effector and central memory phenotypes.

Figures 29A, 29B:
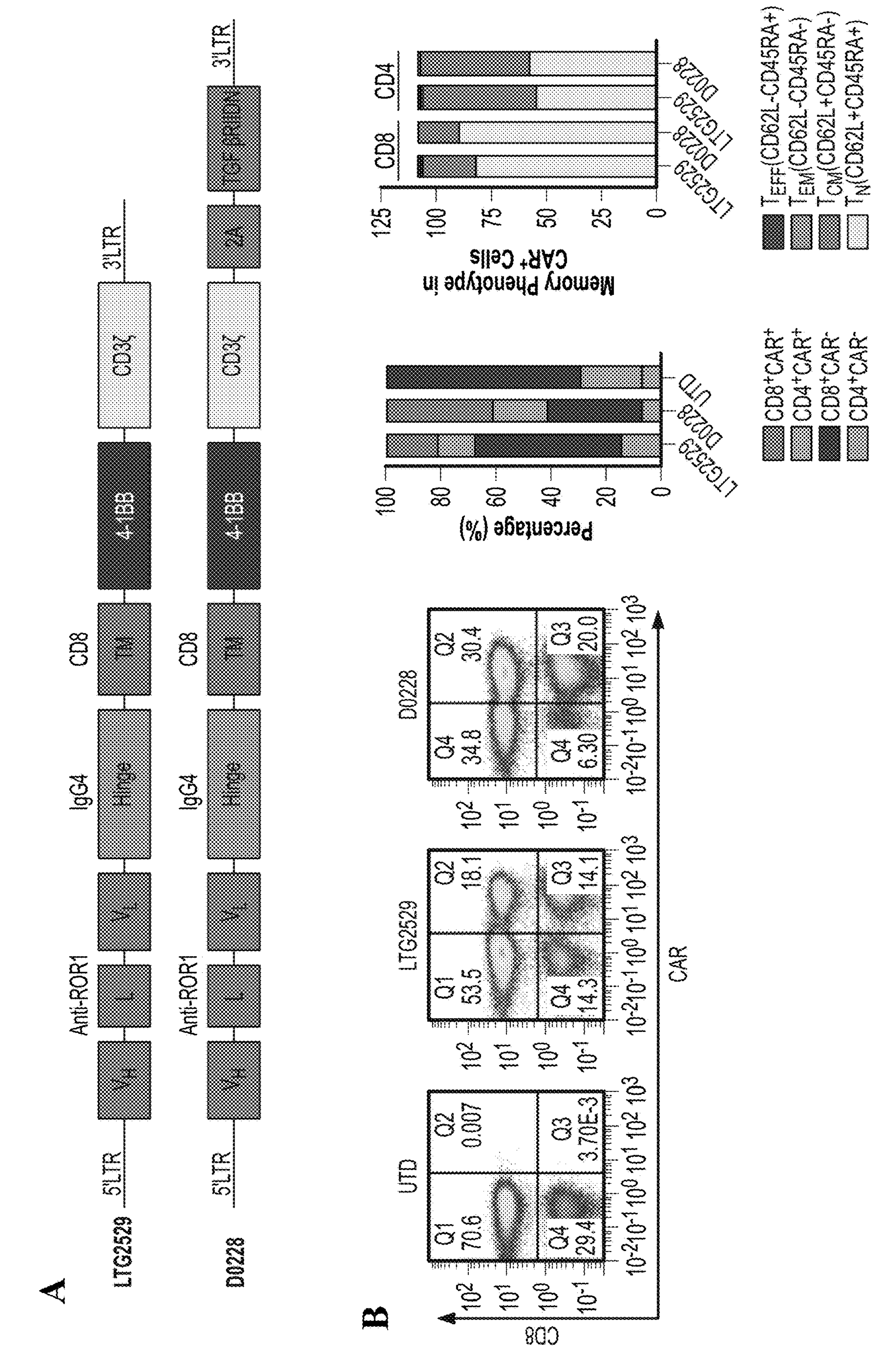
Figure 29C:
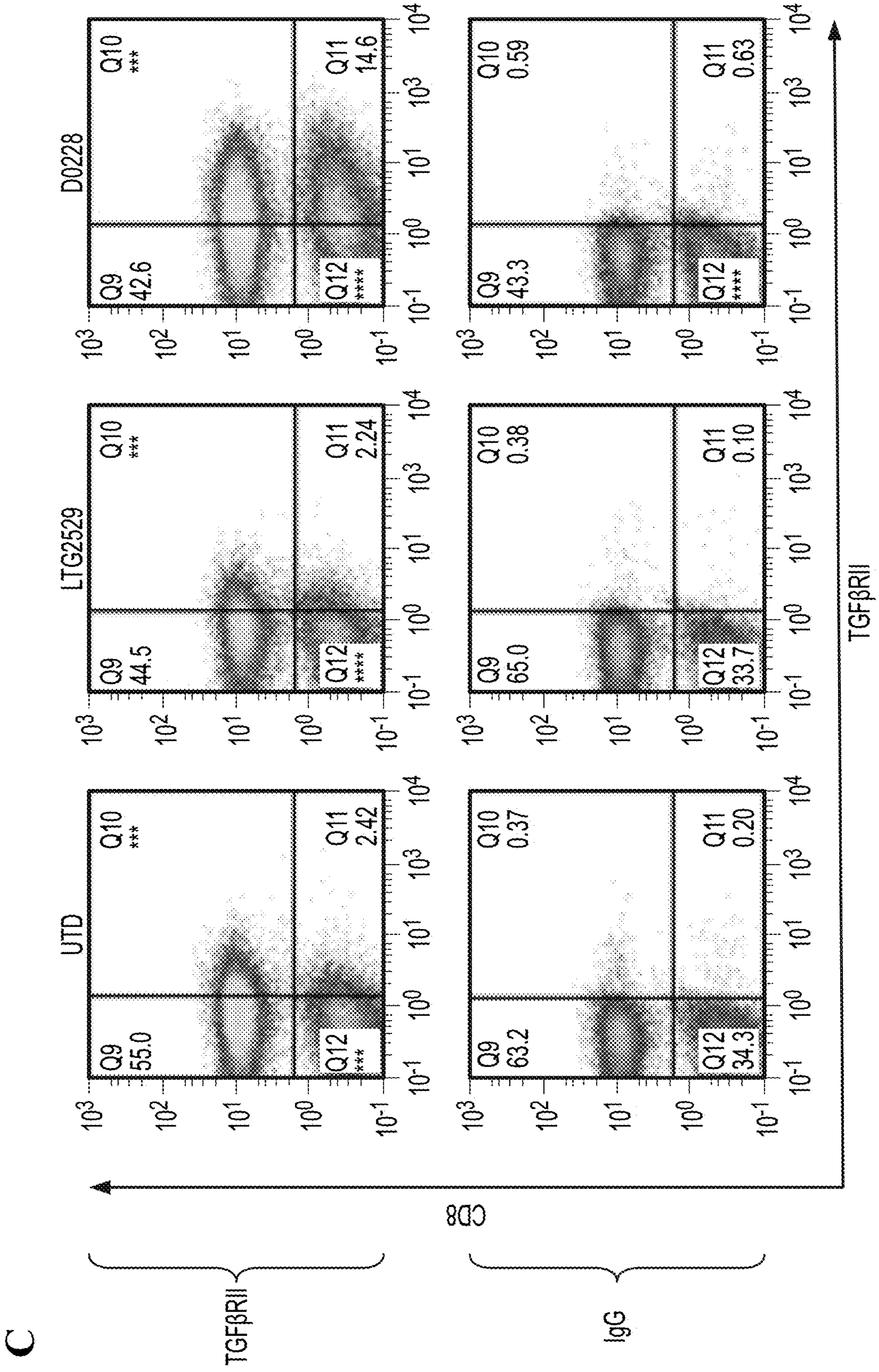
Figures 29D, 29E:
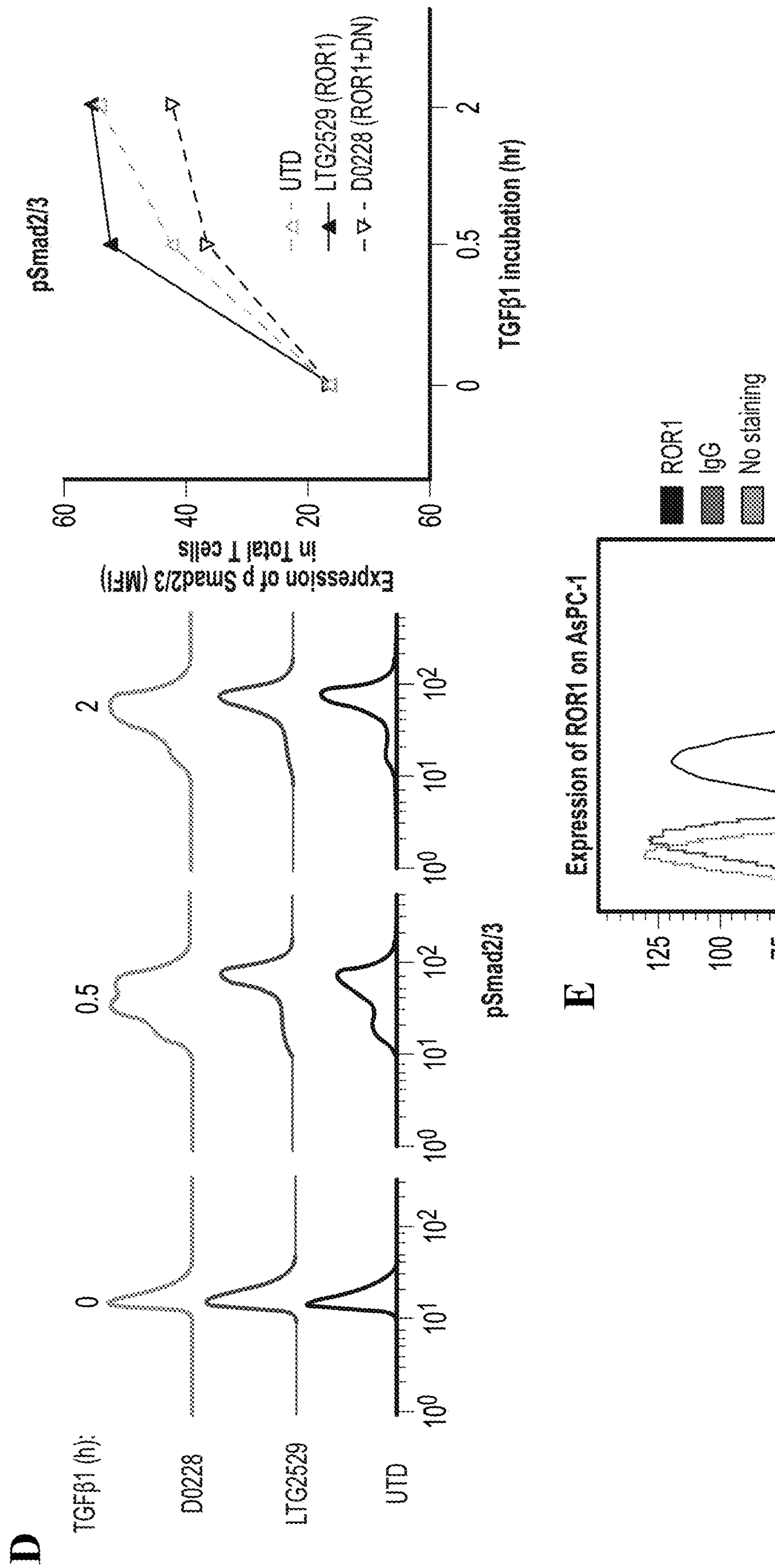

TGFβRIIdn-Armored LTG2529 Attenuated the Inhibitory Effect of TGF-β1 on CAR T-Cell Cytotoxic Activity In Vitro Having demonstrated high in vitro and in vivo potency of ROR-1 CAR T cells, protecting LTG2529 T cells from the inhibitory effects of TGFβ was proceeded. Lentiviral vector co-expressing ROR1 CAR and the TGFβRIIDN armor element was constructed, separated by ribosomal skip site, to facilitate co-expression of the two polypeptides, namely D0228 (FIG. 29A). TGFβRIIDN is a truncated form of TGFβ receptor II, capable of TGFβ binding, but devoid of intracellular signaling activity (12), thus attenuating the TGFβ-induced suppression of T cells. The armored ROR1 CAR was expressed robustly on healthy donor T cells with comparable enriched $CAR^+T_N$ and $T_{CM}$ phenotypes in both the CD8 and CD4 T cell fraction, similarly ROR-1 CAR alone (FIG. 29B). The overexpression of TGFβRIIdn element on the surface of armored LTG2529 T cells was visualized by flow cytometry using an anti-TGFβRII antibody (FIG. 29C). TGFβ signals through TGFβRII on cell surface, leading to phosphorylation of transcription factor Smad2/3. A reduction of pSmad2/3 in TGFβRIIdn-armored LTG2529 T cells treated with TGF-β1 compared to non-armored LTG2529 Ts was observed (FIG. 29D), which indicates the functional effect of the dominant negative TGFβRII on TGF-β01 signal transduction.

Figure 29F:
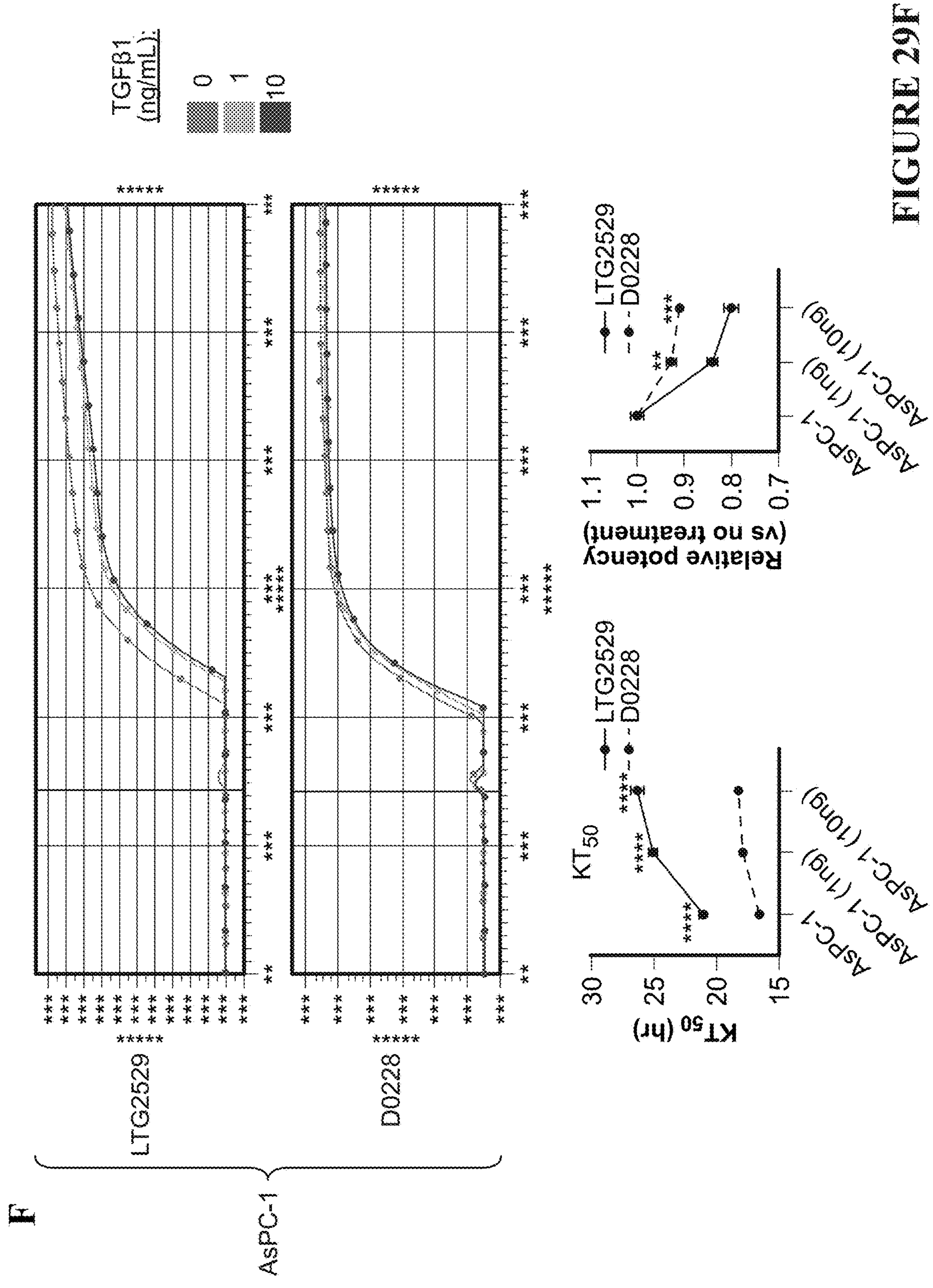
Figures 29G, 29H, 29I:
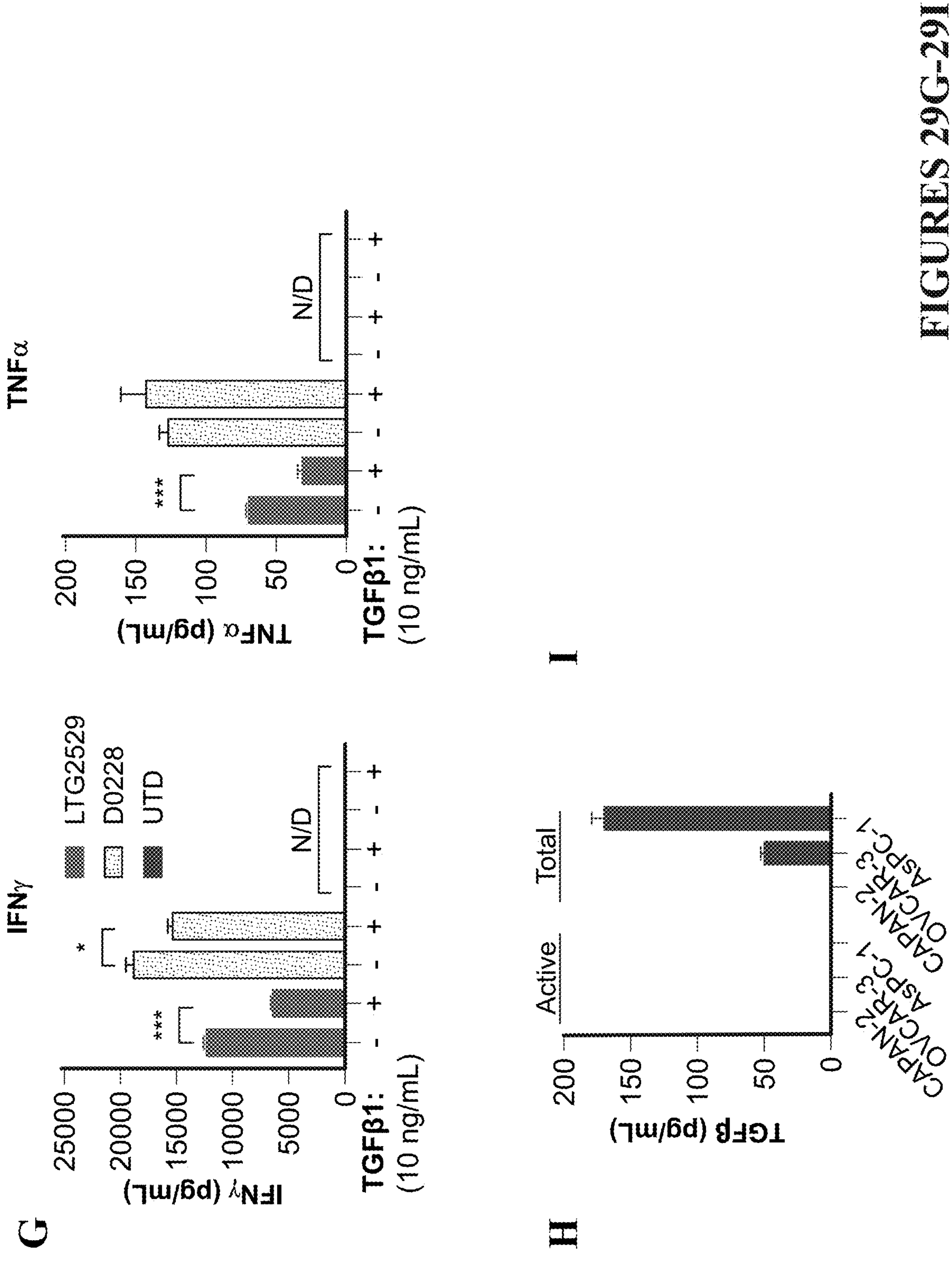
Figures 29J, 29K:
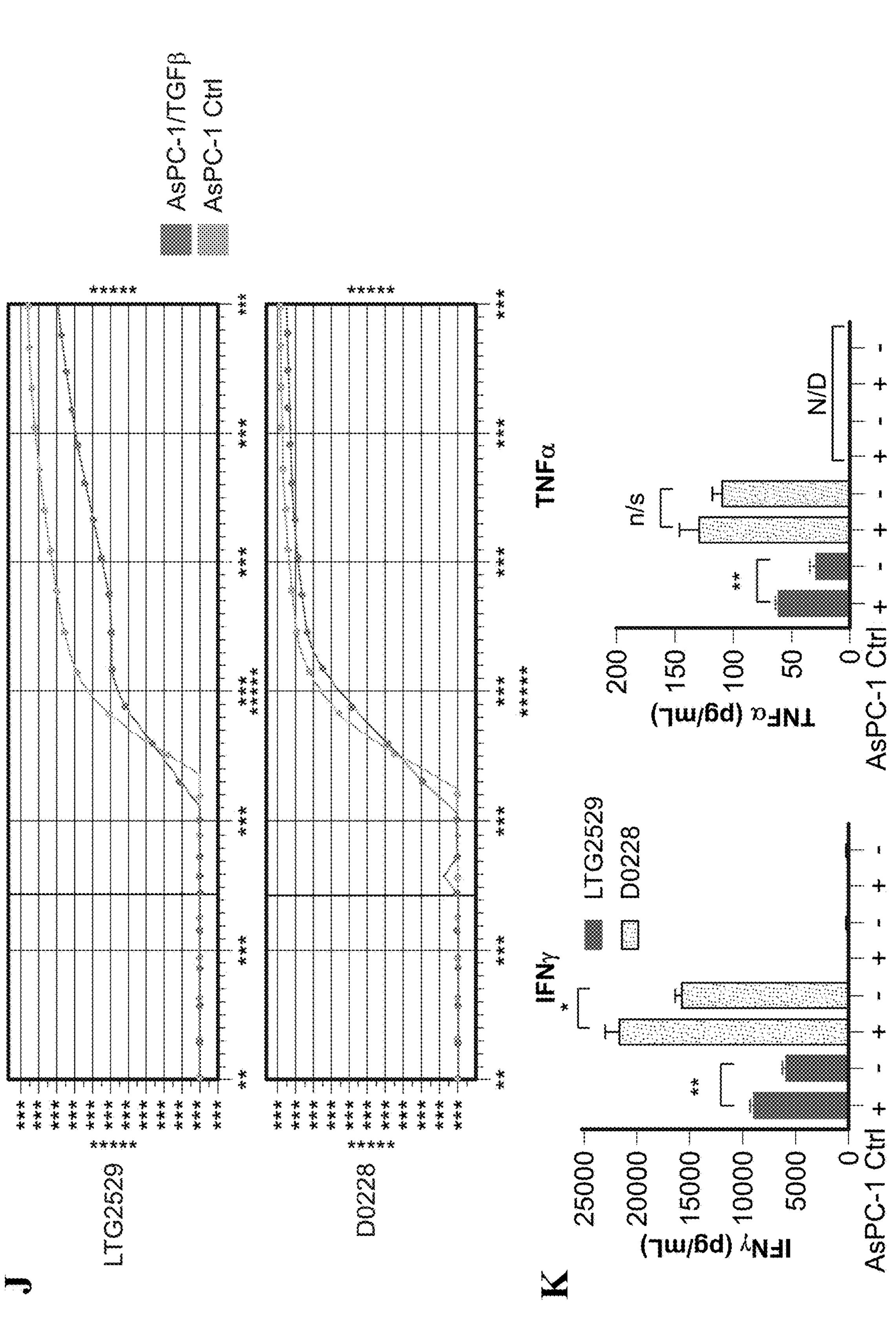

TGFβ is known for its negative effect cytotoxic T cells, including inhibiting the expression of multiple effector molecules (granzyme A, granzyme B, perforin, IFNγ and TNFα) (18). To demonstrate the functional effect of TGFβRIIdn on anti-tumor activity of CAR-transduced T cells in vitro, CAR T cells were co-cultured with pancreatic adenocarcinoma AsPC-1 cells (which highly expresses ROR1 (FIG. 29E) in the presence of TGF-β1. TGF-β1 reduced cytotoxic activity of LTG2529 T cells, decreased production of IFNγ and TNFα in the co-culture supernatant, which were restored in the armored LTG2529 T cells (FIGS. 29F and 29G). AsPC-1 cells express low level of latent (i.e. inactive) form of TGF-β1 in cell culture, which was detected upon activation by acidic treatment (FIG. 29H). AsPC-1 cell overexpressing TGF-β1 (namely AsPC-1/TGFβ) were then generated to investigate the effect of the armor in vitro and in vivo; as shown in FIG. 29I, this cell line produced high amount of both active (approx. 16,000 μg/mL) and latent (approx. 90,000 μg/mL) forms of TGF-β1 when cultured overnight. Cytotoxicity of LTG2529 T as well as its' production of cytokines (i.e. IFN-γ, TNF-α) were dramatically reduced when co-cultured with AsPC-1/TGFβ in comparison to AsPC-1 control cell; however, this effect was attenuated for LTG2529 T armored with TGFβRIIdn (FIGS. 29J and 29K).

Thus, our data demonstrated that the dominant negative TGFbRII lessened the inhibitory effect of TGFβ1 on cytotoxicity of CAR T cells in vitro.

TGFβRIIdn-Armored LTG2529 (D0228) Showed an Increase in CAR+ T-Cell Population in Pancreatic Cancer AsPC-1 Xenograft Model with Low TGFβ1 Expression.

TGFβ is known to be produced by various cell types (i.e. tumor, stomal, and immune cells) and exists as latent or inactive form in tumor microenvironment (TME), which is then activated by various enzymes in the extracellular matrix, including matrix metalloproteinases (MMPs) and acidic condition in TME in various cancers, including PDAC, providing a tumor protective environment. Whether the dominant negative TGFβRII would help T cell overcome this effect is to be determined. As mentioned above, pancreatic cancer AsPC-1 cell produces low amount of latent TGF-β1, mice were implanted with these cells subcutaneously (FIG. 30A). As shown in FIG. 30B, both LTG2529 with our without armor caused tumor volume reduction within 10 days after administration; interestingly, the one with armor started to show beneficial effect on day 17 post T cell dosing and the tumor was cleared in all mice started at day 24 whereas all mice with the non-armored CAR were cleared from tumor started at day 33. None of the CARs caused significant drop of body weight during the study course (FIG. 30C). Analysis of T cells in blood from these mice revealed a high frequency CD8'CAR+ T cell population in D0228 vs LTG2529 across all tested time points (FIG. 30D).

To determine if the CAR T cells were still functional at the end of in vivo time course, same mice were re-challenged with AsPC-1 cells on the left flank (please note that the first implantation was on the right flank)(FIG. 30E). As shown in FIG. 30F, no tumor was observed in mice treated with CAR T cells with or without armor whereas the tumor freely progressed in age-matching control mice; besides, no tumor was observed on the right flank in mice treated with both CAR constructs suggesting complete remission from the first tumor implantation. It's also worthy to note that 1 mouse from the armored CAR treated group was dead at day 60 post T cell dosing in the challenge study before rechallenge study which started at day 73 post T-cell dosing, which were most probably due to GvHD. Additionally, there was a benefit in survival for mice treated with the armored CAR (FIG. 30G). Analysis of T cells from bloods revealed predominant effector memory and terminal effector T cells in both groups of mice (FIG. 30H). CAR staining at day 23 and 42 post re-challenge revealed an increase in T cells positive for CAR which was much higher in the armored one (FIG. 30I). T cells isolated from spleen and bone marrow harvested at the end of life shared the same features of CAR positivity as observed in blood (FIG. 30J).

The Dominant Negative (Dn) TGFβ Receptor II Overcame the Inhibitory Effect of TGFβ on T Cells in the AsPC-1 Overexpressing TGF-β1 Xenograft Model.

To better investigate the effect of the dn element on anti-tumor activity of ROR1-CAR T-cells in the TGFβ-rich tumor microenvironment, NSG mice were implanted subcutaneously with AsPC-1/TGFβ cells (FIG. 31A). The armored CAR cleared tumor after 33 days of T-cell infusion, whereas the non-armored CAR showed partial tumor regression only (FIG. 31B). Importantly, analysis of cytokines in serum of these mice showed a significant reduction of TGFβ1 active form for both armored and non-armored CARs at day 5 post infusion compared to non-treated or UTD treated mice; this was probably due cytotoxic activity of CAR Ts against AsPC-1/TGFβ (FIG. 31C, left panel); however, this effect didn't last long for non-armored CAR as the TGFβ1 amount from this group of mice reached the same level as of non-treated and UTD treated mice at day 15 post infusion, whereas the ones treated with the armored CAR remained low. Quantification of other cytokines (IFNγ, GM-CSF) suggesting the onset of activity of CAR-Ts around day 5 and reduced by day 15 post T cell infusion (FIG. 31C, center & right panel).

Analysis of T-cells from blood of the mice revealed a 6-fold increase on day 12 vs day 2 post T cell infusion in the group treated with armored CAR whereas less than 2 fold increase was observed in the non-armored CAR groups (FIG. 31D). The number of $CAR^+$T-cells in both CD8 and CD4 populations declined after 12 day post infusion (FIG. 31E) which correlated with tumor volume reduction as shown in FIG. 31B. An increase in T-cells after day 29 post infusion was also observed (FIG. 31D), which is possibly due to GvHD. Analysis of T-cells isolated from spleen and bone marrow at the end of the study showed higher frequency of CAR+ T cells for the armored CAR (FIG. 31F), and similar pattern of memory phenotype for both armored and non-armored CARs (FIG. 31G).

Taken together, these results demonstrate the advantages of the TGFβRIIdn-armored ROR1 CAR in the treatment of solid tumors.

REFERENCES

1. S. Srivastava, S. N. Furlan, C. A. Jaeger-Ruckstuhl, M. Sarvothama, C. Berger, K. S. Smythe, S. M. Garrison, J. M. Specht, S. M. Lee, R. A. Amezquita, V. Voillet, V. Muhunthan, S. Yechan-Gunja, S. P. S. Pillai, C. Rader, A. M. Houghton, R. H. Pierce, R. Gottardo, D. G. Maloney, S. R. Riddell, Immunogenic Chemotherapy Enhances Recruitment of CAR-T Cells to Lung Tumors and Improves Antitumor Efficacy when Combined with Checkpoint Blockade. *Cancer cell* 39, 193-208e110 (2021); published online EpubFeb 8 (10.1016/j.ccell.2020.11.005).
2. R. C. Sterner, R. M. Sterner, CAR-T cell therapy: current limitations and potential strategies. *Blood cancer journal* 11, 69 (2021); published online EpubApr 6 (10.1038/s41408-021-00459-7).
3. N. M. Anderson, M. C. Simon, The tumor microenvironment. *Current biology: CB* 30, R921-R925 (2020); published online EpubAug 17 (10.1016/j.cub.2020.06.081).
4. T. J. Kipps, ROR1: an orphan becomes apparent. *Blood* 140, 1583-1591 (2022); published online EpubOct 6 (10.1182/blood.2021014760).
5. S. Baskar, K. Y. Kwong, T. Hofer, J. M. Levy, M. G. Kennedy, E. Lee, L. M. Staudt, W. H. Wilson, A. Wiestner, C. Rader, Unique cell surface expression of receptor tyrosine kinase ROR1 in human B-cell chronic lymphocytic leukemia. *Clinical cancer research: an official journal of the American Association for Cancer Research* 14, 396-404 (2008); published online EpubJan 15 (10.1158/1078-0432.ccr-07-1823).
6. S. Zhang, L. Chen, J. Wang-Rodriguez, L. Zhang, B. Cui, W. Frankel, R. Wu, T. J. Kipps, The onco-embryonic antigen ROR1 is expressed by a variety of human cancers. *The American journal of pathology* 181, 1903-1910 (2012); published online EpubDec (10.1016/j.ajpath.2012.08.024).
7. A. H. Daneshmanesh, A. Porwit, M. Hojjat-Farsangi, M. Jeddi-Tehrani, K. P. Tamm, D. Grandér, S. Lehmann, S. Norin, F. Shokri, H. Rabbani, H. Mellstedt, A. Österborg, Orphan receptor tyrosine kinases ROR1 and ROR2 in hematological malignancies. *Leukemia & lymphoma* 54, 843-850 (2013); published online EpubApr (10.3109/10428194.2012.731599).

8. S. Zhang, L. Chen, B. Cui, H. Y. Chuang, J. Yu, J. Wang-Rodriguez, L. Tang, G. Chen, G. W. Basak, T. J. Kipps, ROR1 is expressed in human breast cancer and associated with enhanced tumor-cell growth. *PloS one* 7, e31127 (2012)10.1371/journal.pone.0031127).
9. R. Derynck, S. J. Turley, R. J. Akhurst, TGFbeta biology in cancer progression and immunotherapy. *Nature reviews. Clinical oncology* 18, 9-34 (2021); published online EpubJan (10.1038/s41571-020-0403-1).
10. K. Tzavlaki, A. Moustakas, TGF-beta Signaling. *Biomolecules* 10, (2020); published online EpubMar 23 (10.3390/biom10030487).
11. C. C. Kloss, J. Lee, A. Zhang, F. Chen, J. J. Melenhorst, S. F. Lacey, M. V. Maus, J. A. Fraietta, Y. Zhao, C. H. June, Dominant-Negative TGF-beta Receptor Enhances PSMA-Targeted Human CAR T Cell Proliferation And Augments Prostate Cancer Eradication. *Molecular therapy: the journal of the American Society of Gene Therapy* 26, 1855-1866 (2018); published online EpubJul 5 (10.1016/j.ymthe.2018.05.003).
12. L. M. Alabanza, Y. Xiong, B. Vu, B. Webster, D. Wu, P. Hu, Z. Zhu, B. Dropulic, P. Dash, D. Schneider, Armored BCMA CAR T Cells Eliminate Multiple Myeloma and Are Resistant to the Suppressive Effects of TGF-beta. *Frontiers in immunology* 13, 832645 (2022)10.3389/fimmu.2022.832645).
13. N. Tang, C. Cheng, X. Zhang, M. Qiao, N. Li, W. Mu, X. F. Wei, W. Han, H. Wang, TGF-beta inhibition via CRISPR promotes the long-term efficacy of CAR T cells against solid tumors. *JCI insight* 5, (2020); published online EpubFeb 27 (10.1172/jci.insight.133977).
14. V. Narayan, J. S. Barber-Rotenberg, I. Y. Jung, S. F. Lacey, A. J. Rech, M. M. Davis, W. T. Hwang, P. Lal, E. L. Carpenter, S. L. Maude, G. Plesa, N. Vapiwala, A. Chew, M. Moniak, R. A. Sebro, M. D. Farwell, A. Marshall, J. Gilmore, L. Lledo, K. Dengel, S. E. Church, T. D. Hether, J. Xu, M. Gohil, T. H. Buckingham, S. S. Yee, V. E. Gonzalez, I. Kulikovskaya, F. Chen, L. Tian, K. Tien, W. Gladney, C. L. Nobles, H. E. Raymond, I. Prostate Cancer Cellular Therapy Program, E. O. Hexner, D. L. Siegel, F. D. Bushman, C. H. June, J. A. Fraietta, N. B. Haas, PSMA-targeting TGFbeta-insensitive armored CAR T cells in metastatic castration-resistant prostate cancer: a phase 1 trial. *Nature medicine* 28, 724-734 (2022); published online EpubApr (10.1038/s41591-022-01726-1).
15. D. Schneider, Y. Xiong, D. Wu, V. Nölle, S. Schmitz, W. Haso, A. Kaiser, B. Dropulic, R. J. Orentas, A tandem CD19/CD20 CAR lentiviral vector drives on-target and off-target antigen modulation in leukemia cell lines. *Journal for immunotherapy of cancer* 5, 42 (2017)10.1186/s40425-017-0246-1).
16. D. Schneider, Y. Xiong, D. Wu, P. Hu, L. Alabanza, B. Steimle, H. Mahmud, K. Anthony-Gonda, W. Krueger, Z. Zhu, D. S. Dimitrov, R. J. Orentas, B. Dropulic, Trispecific CD19-CD20-CD22-targeting duoCAR-T cells eliminate antigen-heterogeneous B cell tumors in preclinical models. *Science translational medicine* 13, (2021); published online EpubMar 24 (10.1126/scitranslmed-.abc6401).
17. M. Hudecek, M. T. Lupo-Stanghellini, P. L. Kosasih, D. Sommermeyer, M. C. Jensen, C. Rader, S. R. Riddell, Receptor affinity and extracellular domain modifications affect tumor recognition by ROR1-specific chimeric antigen receptor T cells. *Clinical cancer research: an official journal of the American Association for Cancer Research* 19, 3153-3164 (2013); published online EpubJun 15 (10.1158/1078-0432.ccr-13-0330).
18. E. Batlle, J. Massague, Transforming Growth Factor-beta Signaling in Immunity and Cancer. *Immunity* 50, 924-940 (2019); published online EpubApr 16 (10.1016/j.immuni.2019.03.024).

REFERENCE TO THE SEQUENCE LISTING

This application contains a Sequence Listing electronically to be submitted to the United States Patent and Trademark Receiving Office via a PDF file entitled "Sequence Listing". The Sequence Listing is incorporated by reference.

SEQUENCES OF THE DISCLOSURE

The nucleic and amino acid sequences listed below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

```
SEQ ID NO: 1 nucleotide sequence of CD20-reactive scFv binding domain (LTG1495):
GAGGTGCAGTTGCAACAGTCAGGAGCTGAACTGGTCAAGCCAGGAGCCAGCGTGAA
GATGAGCTGCAAGGCCTCCGGTTACACCTTCACCTCCTACAACATGCACTGGGTGAA
ACAGACCCCGGGACAAGGGCTCGAATGGATTGGCGCCATCTACCCCGGGAATGGCG
ATACTTCGTACAACCAGAAGTTCAAGGGAAAGGCCACCCTGACCGCCGACAAGAGC
TCCTCCACCGCGTATATGCAGTTGAGCTCCCTGACCTCCGAGGACTCCGCCGACTAC
TACTGCGCACGGTCCAACTACTATGGAAGCTCGTACTGGTTCTTCGATGTCTGGGGG
GCCGGCACCACTGTGACCGTCAGCTCCGGGGGGGGAGGATCCGGTGGAGGCGGAAG
CGGGGGTGGAGGATCCGACATTGTGCTGACTCAGTCCCCGGCAATCCTGTCGGCCTC
ACCGGGCGAAAAGGTCACGATGACTTGTAGAGCGTCGTCCAGCGTGAACTACATGG
ATTGGTACCAAAAGAAGCCTGGATCGTCACCCAAGCCTTGGATCTACGCTACATCTA
ACCTGGCCTCCGGCGTGCCAGCGCGGTTCAGCGGGTCCGGCTCGGGCACCTCATACT
CGCTGACCATCTCCCGCGTGGAGGCTGAGGACGCCGCGACCTACTACTGCCAGCAG
TGGTCCTTCAACCCGCCGACTTTTGGAGGCGGTACTAAGCTGGAGATCAAA
```

```
SEQ ID NO: 2 amino acid sequence of CD20-reactive scFv binding domain (LTG1495):
EVQLQQSGAELVKPGASVKMSCKASGYTFTSYNMHWVKQTPGQGLEWIGAIYPGNGD
TSYNQKFKGKATLTADKSSSTAYMQLSSLTSEDSADYYCARSNYYGSSYWFFDVWGA
GTTVTVSSGGGGSGGGGSGGGGSDIVLTQSPAILSASPGEKVTMTCRASSSVNYMDWY
QKKPGSSPKPWIYATSNLASGVPARFSGSGSGTSYSLTISRVEAEDAATYYCQQWSFNPP
TFGGGTKLEIK
```

-continued

SEQ ID NO: 3 nucleotide sequence of CAR LTG1495 (LP-1495-CD8 TM-41BB-CD3zeta):
ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG
GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG
CCGACTACTACTGCGCACGGTCCAACTACTATGGAAGCTCGTACTGGTTCTTCGATG
TCTGGGGGGCCGGCACCACTGTGACCGTCAGCTCCGGGGGGGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT
GCCAGCAGTGGTCCTTCAACCCGCCGACTTTTGGAGGCGGTACTAAGCTGGAGATCA
AAGCGGCCGCAACTACCACCCCTGCCCCTCGGCCGCCGACTCCGGCCCCAACCATCG
CAAGCCAACCCCTCTCCTTGCGCCCCGAAGCTTGCCGCCCGGCCGCGGGTGGAGCCG
TGCATACCCGGGGGCTGGACTTTGCCTGCGATATCTACATTTGGGCCCCGCTGGCCG
GCACTTGCGGCGTGCTCCTGCTGTCGCTGGTCATCACCCTTTACTGCAAGAGGGGCC
GGAAGAAGCTGCTTTACATCTTCAAGCAGCCGTTCATGCGGCCCGTGCAGACGACTC
AGGAAGAGGACGGATGCTCGTGCAGATTCCCTGAGGAGGAAGAGGGGGGATGCGA
ACTGCGCGTCAAGTTCTCACGGTCCGCCGACGCCCCCGCATATCAACAGGGCCAGA
ATCAGCTCTACAACGAGCTGAACCTGGGAAGGAGAGAGGAGTACGACGTGCTGGAC
AAGCGACGCGGACGCGACCCGGAGATGGGGGGGAAACCACGGCGGAAAAACCCTC
AGGAAGGACTGTACAACGAACTCCAGAAAGACAAGATGGCGGAAGCCTACTCAGA
AATCGGGATGAAGGGAGAGCGGAGGAGGGGAAAGGGTCACGACGGGCTGTACCAG
GGACTGAGCACCGCCACTAAGGATACCTACGATGCCTTGCATATGCAAGCACTCCC
ACCCCGG SEQ ID NO: 4 amino acid sequence of CAR LTG1495 (LP-1495-CD8 TM-41BB-CD3zeta):
MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE
KVTMTCRASSSVNYMDWYQKKPGSSPKPWIYATSNLASGVPARFSGSGSGTSYSLTISR
VEAEDAATYYCQQWSFNPPTFGGGTKLEIKAAATTTPAPRPPTPAPTIASQPLSLRPEAC
RPAAGGAVHTRGLDFACDIYIWAPLAGTCGVLLLSLVITLYCKRGRKKLLYIFKQPFMR
PVQTTQEEDGCSCRFPEEEEGGCELRVKFSRSADAPAYQQGQNQLYNELNLGRREEYD
VLDKRRGRDPEMGGKPRRKNPQEGLYNELQKDKMAEAYSEIGMKGERRRGKGHDGL
YQGLSTATKDTYDALHMQALPPR SEQ ID NO: 5 nucleotide sequence of leader/signal peptide sequence:
ATGCTGCTGCTGGTGACCAGCCTGCTGCTGTGCGAACTGCCGCATCCGGCGTTTCTG
CTGATTCCG SEQ ID NO: 6 amino acid sequence of leader/signal peptide sequence:
MLLLVTSLLLCELPHPAFLLIP SEQ ID NO: 7 nucleotide sequence of CD22-reactive scFv binding domain LTG2200):
CAGGTACAGCTCCAGCAGAGTGGCCCAGGGCTCGTGAAGCCAAGCCAGACGCTGTC
CCTGACTTGTGCAATTTCAGGGGATTCAGTTTCATCAAATAGCGCGGCGTGGAATTG
GATTCGACAATCTCCTTCCCGAGGGTTGGAATGGCTTGGACGAACATATTACAGATC
CAAATGGTATAACGACTATGCGGTATCAGTAAAGTCAAGAATAACCATTAACCCCG
ACACAAGCAAGAACCAATTCTCTTTGCAGCTTAACTCTGTCACGCCAGAAGACACG
GCAGTCTATTATTGCGCTCGCGAGGTAACGGGTGACCTGGAAGACGCTTTTGACATT
TGGGGGCAGGGTACGATGGTGACAGTCAGTTCAGGGGGCGGTGGGAGTGGGGGAG
GGGGTAGCGGGGGGGGAGGGTCAGACATTCAGATGACCCAGTCCCCTTCATCCTTG
TCTGCCTCCGTCGGTGACAGGGTGACAATAACATGCAGAGCAAGCCAAACAATCTG
GAGCTATCTCAACTGGTACCAGCAGCGACCAGGAAAAGCGCCAAACCTGCTGATTT
ACGCTGCTTCCTCCCTCCAATCAGGCGTGCCTAGTAGATTTAGCGGTAGGGGCTCCG
GCACCGATTTTACGCTCACTATAAGCTCTCTTCAAGCAGAAGATTTTGCGACTTATTA
CTGCCAGCAGTCCTATAGTATACCTCAGACTTTCGGACAGGGTACCAAGTTGGAGAT
TAAGGCGGCCGCA SEQ ID NO: 8 amino acid sequence of CD22-reactive scFv binding domain (LTG2200):
QVQLQQSGPGLVKPSQTLSLTCAISGDSVSSNSAAWNWIRQSPSRGLEWLGRTYYRSK
WYNDYAVSVKSRITINPDTSKNQFSLQLNSVTPEDTAVYYCAREVTGDLEDAFDIWGQG
TMVTVSSGGGGSGGGGSGGGGSDIQMTQSPSSLSASVGDRVTITCRASQTIWSYLNWY
QQRPGKAPNLLIYAASSLQSGVPSRFSGRGSGTDFTLTISSLQAEDFATYYCQQSYSIPQT
FGQGTKLEIKAAA SEQ ID NO: 9 nucleotide sequence of the CAR LTG2200 (LP-2200-CD8 TM-41BB-CD3zeta):
ATGCTTCTTTTGGTGACTTCCCTTTTGCTGTGCGAGTTGCCACACCCCGCCTTCCTGC
TTATTCCCCAGGTACAGCTCCAGCAGAGTGGCCCAGGGCTCGTGAAGCCAAGCCAG
ACGCTGTCCCTGACTTGTGCAATTTCAGGGGATTCAGTTTCATCAAATAGCGCGGCG
TGGAATTGGATTCGACAATCTCCTTCCCGAGGGTTGGAATGGCTTGGACGAACATAT
TACAGATCCAAATGGTATAACGACTATGCGGTATCAGTAAAGTCAAGAATAACCAT
TAACCCCGACACAAGCAAGAACCAATTCTCTTTGCAGCTTAACTCTGTCACGCCAGA
AGACACGGCAGTCTATTATTGCGCTCGCGAGGTAACGGGTGACCTGGAAGACGCTTT
TGACATTTGGGGGCAGGGTACGATGGTGACAGTCAGTTCAGGGGGCGGTGGGAGTG
GGGGAGGGGGTAGCGGGGGGGGAGGGTCAGACATTCAGATGACCCAGTCCCCTTCA
TCCTTGTCTGCCTCCGTCGGTGACAGGGTGACAATAACATGCAGAGCAAGCCAAAC -continued AATCTGGAGCTATCTCAACTGGTACCAGCAGCGACCAGGAAAAGCGCCAAACCTGC
TGATTTACGCTGCTTCCTCCCTCCAATCAGGCGTGCCTAGTAGATTTAGCGGTAGGG
GCTCCGGCACCGATTTTACGCTCACTATAAGCTCTCTTCAAGCAGAAGATTTTGCGA
CTTATTACTGCCAGCAGTCCTATAGTATACCTCAGACTTTCGGACAGGGTACCAAGT
TGGAGATTAAGGCGGCCGCAACTACCACCCCTGCCCCTCGGCCGCCGACTCCGGCCC
CAACCATCGCAAGCCAACCCCTCTCCTTGCGCCCCGAAGCTTGCCCGCCGGCCGCGG
GTGGAGCCGTGCATACCCGGGGGCTGGACTTTGCCTGCGATATCTACATTTGGGCCC
CGCTGGCCGGCACTTGCGGCGTGCTCCTGCTGTCGCTGGTCATCACCCTTTACTGCA
AGAGGGGCCGGAAGAAGCTGCTTTACATCTTCAAGCAGCCGTTCATGCGGCCCGTG
CAGACGACTCAGGAAGAGGACGGATGCTCGTGCAGATTCCCTGAGGAGGAAGAGG
GGGGATGCGAACTGCGCGTCAAGTTCTCACGGTCCGCCGACGCCCCCGCATATCAA
CAGGGCCAGAATCAGCTCTACAACGAGCTGAACCTGGGAAGGAGAGAGGAGTACG
ACGTGCTGGACAAGCGACGCGGACGCGACCCGGAGATGGGGGGGAAACCACGGCG
GAAAAACCCTCAGGAAGGACTGTACAACGAACTCCAGAAAGACAAGATGGCGGAA
GCCTACTCAGAAATCGGGATGAAGGGAGAGCGGAGGAGGGGAAAGGGTCACGACG
GGCTGTACCAGGGACTGAGCACCGCCACTAAGGATACCTACGATGCCTTGCATATG
CAAGCACTCCCACCCCGG SEQ ID NO: 10 amino acid sequence of CAR LTG2200(LP-2200-CD8 TM-41BB-CD3zeta):
MLLLVTSLLLCELPHPAFLLIPQVQLQQSGPGLVKPSQTLSLTCAISGDSVSSNSAAWNW
IRQSPSRGLEWLGRTYYRSKWYNDYAVSVKSRITINPDTSKNQFSLQLNSVTPEDTAVY
YCAREVTGDLEDAFDIWGQGTMVTVSSGGGGSGGGGSGGGGSDIQMTQSPSSLSASVG
DRVTITCRASQTIWSYLNWYQQRPGKAPNLLIYAASSLQSGVPSRFSGRGSGTDFTLTISS
LQAEDFATYYCQQSYSIPQTFGQGTKLEIKAAATTTPAPRPPTPAPTIASQPLSLRPEACR
PAAGGAVHTRGLDFACDIYIWAPLAGTCGVLLLSLVITLYCKRGRKKLLYIFKQPFMRP
VQTTQEEDGCSCRFPEEEEGGCELRVKFSRSADAPAYQQGQNQLYNELNLGRREEYDV
LDKRRGRDPEMGGKPRRKNPQEGLYNELQKDKMAEAYSEIGMKGERRRGKGHDGLY
QGLSTATKDTYDALHMQALPPR SEQ ID NO: 11 nucleotide sequence of DNA CD8 transmembrane domain:
ATCTACATCTGGGCGCCCTTGGCCGGGACTTGTGGGGTCCTTCTCCTGTCACTGGTTA
TCACCCTTTACTGC SEQ ID NO: 12 amino acid sequence of CD8 transmembrane domain:
IWAPLAGTCGVLLLSLVITLYC SEQ ID NO: 13 nucleotide sequence of DNA CD8 hinge domain:
ACCACGACGCCAGCGCCGCGACCACCAACACCGGCGCCCACCATCGCGTCGCAGCC
CCTGTCCCTGCGCCCAGAGGCGTGCCGGCCAGCGGGGGGGGCGCAGTGCACACGA
GGGGGCTGGACTTTGCCTGCGATATCTAC SEQ ID NO: 14 amino acid sequence of CD8 hinge domain:
TTTPAPRPPTPAPTIASQPLSLRPEACRPAAGGAVHTRGLDFACDIY SEQ ID NO: 15 amino acid sequence of amino acid numbers 137 to 206 of the hinge and transmembrane region of CD8.alpha. (NCBI RefSeq: NP.sub .--001759.3):
TTTPAPRPPTPAPTIASQPLSLRPEACRPAAGGAVHTRGLDFACDIYIWAPLAGTCGVLLL
SLVITLYC SEQ ID NO: 16 amino acid sequence of Human IgG CL sequence:
GQPKAAPSVTLFPPSSEELQANKATLVCLISDFYPGAVTVAWKADSSPVKAGVETTTPS
KQSNNKYAASSYLSLTPEQWKSHRSYSCQVTHEGSTVEKTVAPTECS SEQ ID NO: 17 nucleotide sequence of DNA signaling domain of 4-1BB:
AAACGGGGCAGAAAGAAACTCCTGTATATATTCAAACAACCATTTATGAGACCAGT
ACAAACTACTCAAGAGGAAGATGGCTGTAGCTGCCGATTTCCAGAAGAAGAAGAAG
GAGGATGTGAACTG SEQ ID NO: 18 amino acid sequence of signaling domain of 4-1BB:
KRGRKKLLYIFKQPFMRPVQTTQEEDGCSCRFPEEEEGGCEL SEQ ID NO: 19 nucleotide sequence of DNA signaling domain of CD3-zeta:
AGAGTGAAGTTCAGCAGGAGCGCAGACGCCCCCGCGTACAAGCAGGGCCAGAACC
AGCTCTATAACGAGCTCAATCTAGGACGAAGAGAGGAGTACGATGTTTTGGACAAG
AGACGTGGCCGGGACCCTGAGATGGGGGGAAAGCCGAGAAGGAAGAACCCTCAGG
AAGGCCTGTACAATGAACTGCAGAAAGATAAGATGGCGGAGGCCTACAGTGAGATT
GGGATGAAAGGCGAGCGCCGGAGGGGCAAGGGGCACGATGGCCTTTACCAGGGTCT
CAGTACAGCCACCAAGGACACCTACGACGCCCTTCACATGCAGGCCCTGCCCCCTCG
C SEQ ID NO: 20 amino acid sequence of CD3zeta:
RVKFSRSADAPAYKQGQNQLYNELNLGRREEYDVLDKRRGRDPEMGGKPRRKNPQEG
LYNELQKDKMAEAYSEIGMKGERRRGKGHDGLYQGLSTATKDTYDALHMQALPPR SEQ ID NO: 21 nucleotide sequence of CAR LTG1562 (LP-CD19binder-CD8linker-CD4tm-4-1BB-CD3-zeta):
ATGCTGCTGCTGGTGACCAGCCTGCTGCTGTGCGAACTGCCGCATCCGGCGTTTCTG
CTGATTCCGGATATTCAGATGACCCAGACCACCAGCAGCCTGAGCGCGAGCCTGGG
CGATCGCGTGACCATTAGCTGCCGCGCGAGCCAGGATATTAGCAAATATCTGAACTG
GTATCAGCAGAAACCGGATGGCACCGTGAAACTGCTGATTTATCATACCAGCCGCCT
GCATAGCGGCGTGCCGAGCCGCTTTAGCGGCAGCGGCAGCGGCACCGATTATAGCC -continued TGACCATTAGCAACCTGGAACAGGAAGATATTGCGACCTATTTTTGCCAGCAGGGCA
ACACCCTGCCGTATACCTTTGGCGGCGGCACCAAACTGGAAATTACCGGCGGCGGC
GGCAGCGGCGGCGGCGGCAGCGGCGGCGGCGGCAGCGAAGTGAAACTGCAGGAAA
GCGGCCCGGGCCTGGTGGCGCCGAGCCAGAGCCTGAGCGTGACCTGCACCGTGAGC
GGCGTGAGCCTGCCGGATTATGGCGTGAGCTGGATTCGCCAGCCGCCGCGCAAAGG
CCTGGAATGGCTGGGCGTGATTTGGGGCAGCGAAACCACCTATTATAACAGCGCGC
TGAAAAGCCGCCTGACCATTATTAAAGATAACAGCAAAAGCCAGGTGTTTCTGAAA
ATGAACAGCCTGCAGACCGATGATACCGCGATTTATTATTGCGCGAAACATTATTAT
TATGGCGGCAGCTATGCGATGGATTATTGGGGCCAGGGCACCAGCGTGACCGTGAG
CAGCGCGGCGGCGCCGGCGCCGCGCCCGCCGACCCCGGCGCCGACCATTGCGAGCC
AGCCGCTGAGCCTGCGCCCGGAAGCGTGCCGCCCGGCGGCGGGCGGCGCGGTGCAT
ACCCGCGGCCTGGATTTTGTGCAGCCGATGGCGCTGATTGTGCTGGGCGGCGTGGCG
GGCCTGCTGCTGTTTATTGGCCTGGGCATTTTTTTTTGCGTGCGCTGCCGCCCGCGCC
GCAAAAAACTGCTGTATATTTTTAAACAGCCGTTTATGCGCCCGGTGCAGACCACCC
AGGAAGAAGATGGCTGCAGCTGCCGCTTTCCGGAAGAAGAAGAAGGCGGCTGCGA
ACTGCGCGTGAAATTTAGCCGCAGCGCGGATGCGCCGGCGTATCAGCAGGGCCAGA
ACCAGCTGTATAACGAACTGAACCTGGGCCGCCGCGAAGAATATGATGTGCTGGAT
AAACGCCGCGGCCGCGATCCGGAAATGGGCGGCAAACCGCGCCGCAAAAACCCGC
AGGAAGGCCTGTATAACGAACTGCAGAAAGATAAAATGGCGGAAGCGTATAGCGA
AATTGGCATGAAAGGCGAACGCCGCCGCGGCAAAGGCCATGATGGCCTGTATCAGG
GCCTGAGCACCGCGACCAAAGATACCTATGATGCGCTGCATATGCAGGCGCTGCCG
CCGCGC SEQ ID NO: 22 amino acid sequence of CAR LTG1562 (LP-CD19binder-CD8link-CD4tm-41BB-CD3zeta):
MLLLVTSLLLCELPHPAFLLIPDIQMTQTTSSLSASLGDRVTISCRASQDISKYLNWYQQK
PDGTVKLLIYHTSRLHSGVPSRFSGSGSGTDYSLTISNLEQEDIATYFCQQGNTLPYTFGG
GTKLEITGGGGSGGGGSGGGGSEVKLQESGPGLVAPSQSLSVTCTVSGVSLPDYGVSWI
RQPPRKGLEWLGVIWGSETTYYNSALKSRLTIIKDNSKSQVFLKMNSLQTDDTAIYYCA
KHYYYGGSYAMDYWGQGTSVTVSSAAAPAPRPPTPAPTIASQPLSLRPEACRPAAGGA
VHTRGLDFVQPMALIVLGGVAGLLLFIGLGIFFCVRCRPRRKKLLYIFKQPFMRPVQTTQ
EEDGCSCRFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGLYQGLSTA
TKDTYDALHMQALPPR SEQ ID NO: 23 nucleotide sequence of CD20_19-reactive scFv binding domain (LTG1497 dual specific binder):
GAGGTGCAGTTGCAACAGTCAGGAGCTGAACTGGTCAAGCCAGGAGCCAGCGTGAA
GATGAGCTGCAAGGCCTCCGGTTACACCTTCACCTCCTACAACATGCACTGGGTGAA
ACAGACCCCGGGACAAGGGCTCGAATGGATTGGCGCCATCTACCCCGGGAATGGCG
ATACTTCGTACAACCAGAAGTTCAAGGGAAAGGCCACCCTGACCGCCGACAAGAGC
TCCTCCACCGCGTATATGCAGTTGAGCTCCCTGACCTCCGAGGACTCCGCCGACTAC
TACTGCGCACGGTCCAACTACTATGGAAGCTCGTACTGGTTCTTCGATGTCTGGGGG
GCCGGCACCACTGTGACCGTCAGCTCCGGGGGGGGAGGATCCGGTGGAGGCGGAAG
CGGGGGTGGAGGATCCGACATTGTGCTGACTCAGTCCCCGGCAATCCTGTCGGCCTC
ACCGGGCGAAAAGGTCACGATGACTTGTAGAGCGTCGTCCAGCGTGAACTACATGG
ATTGGTACCAAAAGAAGCCTGGATCGTCACCCAAGCCTTGGATCTACGCTACATCTA
ACCTGGCCTCCGGCGTGCCAGCGCGGTTCAGCGGGTCCGGCTCGGGCACCTCATACT
CGCTGACCATCTCCCGCGTGGAGGCTGAGGACGCCGCGACCTACTACTGCCAGCAG
TGGTCCTTCAACCCGCCGACTTTTGGAGGCGGTACTAAGCTGGAGATCAAAGGAGG
CGGCGGCAGCGGCGGGGGAGGGTCCGGAGGGGGTGGTTCTGGTGGAGGAGGATCG
GGAGGCGGTGGCAGCGACATTCAGATGACTCAGACCACCTCCTCCCTGTCCGCCTCC
CTGGGCGACCGCGTGACCATCTCATGCCGCGCCAGCCAGGACATCTCGAAGTACCTC
AACTGGTACCAGCAGAAGCCCGACGGAACCGTGAAGCTCCTGATCTACCACACCTC
CCGGCTGCACAGCGGAGTGCCGTCTAGATTCTCGGGTTCGGGGTCGGGAACTGACTA
CTCCCTTACTATTTCCAACCTGGAGCAGGAGGATATTGCCACCTACTTCTGCCAACA
AGGAAACACCCTGCCGTACACTTTTGGCGGGGGAACCAAGCTGGAAATCACTGGCA
GCACATCCGGTTCCGGGAAGCCCGGCTCCGGAGAGGGCAGCACCAAGGGGGAAGTC
AAGCTGCAGGAATCAGGACCTGGCCTGGTGGCCCCGAGCCAGTCACTGTCCGTGAC
TTGTACTGTGTCCGGAGTGTCGCTCCCGGATTACGGAGTGTCCTGGATCAGGCAGCC
ACCTCGGAAAGGATTGGAATGGCTCGGAGTCATCTGGGGTTCCGAAACCACCTATTA
CAACTCGGCACTGAAATCCAGGCTCACCATTATCAAGGATAACTCCAAGTCACAAG
TGTTCCTGAAGATGAATAGCCTGCAGACTGACGACACGGCGATCTACTATTGCGCCA
AGCACTACTACTACGGCGGATCCTACGCTATGGACTACTGGGGCCAGGGGACCAGC
GTGACCGTGTCATCCGCGGCCGCA SEQ ID NO: 24 amino acid sequence of CD20_19-reactive scFv binding domain (LTG1497 dual specific binder):
EVQLQQSGAELVKPGASVKMSCKASGYTFTSYNMHWVKQTPGQGLEWIGAIYPGNGD
TSYNQKFKGKATLTADKSSSTAYMQLSSLTSEDSADYYCARSNYYGSSYWFFDVWGA
GTTVTVSSGGGGSGGGGSGGGGSDIVLTQSPAILSASPGEKVTMTCRASSSVNYMDWY
QKKPGSSPKPWIYATSNLASGVPARFSGSGSGTSYSLTISRVEAEDAATYYCQQWSFNPP
TFGGGTKLEIKGGGGSGGGGSGGGGSGGGGSGGGGSDIQMTQTTSSLSASLGDRVTISC
RASQDISKYLNWYQQKPDGTVKLLIYHTSRLHSGVPSRFSGSGSGTDYSLTISNLEQEDI
ATYFCQQGNTLPYTFGGGTKLEITGSTSGSGKPGSGEGSTKGEVKLQESGPGLVAPSQSL
SVTCTVSGVSLPDYGVSWIRQPPRKGLEWLGVIWGSETTYYNSALKSRLTIIKDNSKSQV
FLKMNSLQTDDTAIYYCAKHYYYGGSYAMDYWGQGTSVTVSSAAA -continued SEQ ID NO: 25 nucleotide sequence of CAR LTG1497 (LP-LTG1497-CD8 TM-41BB-CD3zeta) or (LP-CD20 VH-(GGGGS)$_3$-CD20 VL-(GGGGS)$_5$-CD19VL-Whitlow linker-CD19 VH-CD8 hinge + TM-41BB-CD3zeta):
ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG
GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG
CCGACTACTACTGCGCACGGTCCAACTACTATGGAAGCTCGTACTGGTTCTTCGATG
TCTGGGGGGCCGGCACCACTGTGACCGTCAGCTCCGGGGGGGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT
GCCAGCAGTGGTCCTTCAACCCGCCGACTTTTGGAGGCGGTACTAAGCTGGAGATCA
AAGGAGGCGGCGGCAGCGGCGGGGGGGGTCCGGAGGGGGTGGTTCTGGTGGAGG
AGGATCGGGAGGCGGTGGCAGCGACATTCAGATGACTCAGACCACCTCCTCCCTGT
CCGCCTCCCTGGGCGACCGCGTGACCATCTCATGCCGCGCCAGCCAGGACATCTCGA
AGTACCTCAACTGGTACCAGCAGAAGCCCGACGGAACCGTGAAGCTCCTGATCTAC
CACACCTCCCGGCTGCACAGCGGAGTGCCGTCTAGATTCTCGGGTTCGGGGTCGGGA
ACTGACTACTCCCTTACTATTTCCAACCTGGAGCAGGAGGATATTGCCACCTACTTCT
GCCAACAAGGAAACACCCTGCCGTACACTTTTGGCGGGGGAACCAAGCTGGAAATC
ACTGGCAGCACATCCGGTTCCGGGAAGCCCGGCTCCGGAGAGGGCAGCACCAAGGG
GGAAGTCAAGCTGCAG
GAATCAGGACCTGGCCTGGTGGCCCCGAGCCAGTCACTGTCCGTGACTTGTACTGTG
TCCGGAGTGTCGCTCCCGGATTACGGAGTGTCCTGGATCAGGCAGCCACCTCGGAA
AGGATTGGAATGGCTCGGAGTCATCTGGGGTTCCGAAACCACCTATTACAACTCGGC
ACTGAAATCCAGGCTCACCATTATCAAGGATAACTCCAAGTCACAAGTGTTCCTGAA
GATGAATAGCCTGCAGACTGACGACACGGCGATCTACTATTGCGCCAAGCACTACT
ACTACGGCGGATCCTACGCTATGGACTACTGGGGCCAGGGGACCAGCGTGACCGTG
TCATCCGCGGCCGCAACTACCACCCCTGCCCCTCGGCCGCCGACTCCGGCCCCAACC
ATCGCAAGCCAACCCCTCTCCTTGCGCCCCGAAGCTTGCCGCCCGGCCGCGGGTGGA
GCCGTGCATACCCGGGGGCTGGACTTTGCCTGCGATATCTACATTTGGGCCCCGCTG
GCCGGCACTTGCGGCGTGCTCCTGCTGTCGCTGGTCATCACCCTTTACTGCAAGAGG
GGCCGGAAGAAGCTGCTTTACATCTTCAAGCAGCCGTTCATGCGGCCCGTGCAGAC
GACTCAGGAAGAGGACGGATGCTCGTGCAGATTCCCT
GAGGAGGAAGAGGGGGGATGCGAACTGCGCGTCAAGTTCTCACGGTCCGCCGACGC
CCCCGCATATCAACAGGGCCAGAATCAGCTCTACAACGAGCTGAACCTGGGAAGGA
GAGAGGAGTACGACGTGCTGGACAAGCGACGCGGACGCGACCCGGAGATGGGGGG
GAAACCACGGCGGAAAAACCCTCAGGAAGGACTGTACAACGAACTCCAGAAAGAC
AAGATGGCGGAAGCCTACTCAGAAATCGGGATGAAGGGAGAGCGGAGGAGGGGAA
AGGGTCACGACGGGCTGTACCAGGGACTGAGCACCGCCACTAAGGATACCTACGAT
GCCTTGCATATGCAAGCACTCCCACCCCGG SEQ ID NO: 26 amino acid sequence of CAR LTG1497 (LP-LTG1497-CD8 TM-41BB-CD3zeta) or (LP-CD20 VH(GGGGS)$_3$-CD20 VL-(GGGGS)$_5$-CD19 VL-Whitlow linker-CD19 VH-CD8 hinge + TM-41BB-CD3zeta):
MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE
KVTMTCRASSSVNYMDWYQKKPGSSPKPWIYATSNLASGVPARFSGSGSGTSYSLTISR
VEAEDAATYYCQQWSFNPPTFGGGTKLEIKGGGGSGGGGSGGGGSGGGGSGGGGSDIQ
MTQTTSSLSASLGDRVTISCRASQDISKYLNWYQQKPDGTVKLLIYHTSRLHSGVPSRFS
GSGSGTDYSLTISNLEQEDIATYFCQQGNTLPYTFGGGTKLEITGSTSGSGKPGSGEGSTK
GEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSV
TVSSAAATTTPAPRPPTPAPTIASQPLSLRPEACRPAAGGAVHTRGLDFACDIYIWAPLAG
TCGVLLLSLVITLYCKRGRKKLLYIFKQPFMRPVQTTQEEDGCCRFPEEEEGGCELRVK
FSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR SEQ ID NO: 27 nucleotide sequence of scFV for CD19:
GACATCCAGATGACACAGACTACATCCTCCCTGTCTGCCTCTCTGGGAGACAGAGTC
ACCATCAGTTGCAGGGCAAGTCAGGACATTAGTAAATATTTAAATTGGTATCAGCAG
AAACCAGATGGAACTGTTAAACTCCTGATCTACCATACATCAAGATTACACTCAGGA
GTCCCATCAAGGTTCAGTGGCAGTGGGTCTGGAACAGATTATTCTCTCACCATTAGC
AACCTGGAGCAAGAAGATATTGCCACTTACTTTTGCCAACAGGGTAATACGCTTCCG
TACACGTTCGGAGGGGGGACCAAGCTGGAGATCACAGGTGGCGGTGGCTCGGGCGG
TGGTGGGTCGGGTGGCGGCGGATCTGAGGTGAAACTGCAGGAGTCAGGACCTGGCC
TGGTGGCGCCCTCACAGAGCCTGTCCGTCACATGCACTGTCTCAGGGGTCTCATTAC
CCGACTATGGTGTAAGCTGGATTCGCCAGCCTCCACGAAAGGGTCTGGAGTGGCTG
GGAGTAATATGGGGTAGTGAAACCACATACTATAATTCAGCTCTCAAATCCAGACTG
ACCATCATCAAGGACAACTCCAAGAGCCAAGTTTTCTTAAAAATGAACAGTCTGCA
AACTGATGACACAGCCATTTACTACTGTGCCAAACATTATTACTACGGTGGTAGCTA
TGCTATGGACTACTGGGGCCAAGGAACCTCAGTCACCGTCTCCTCA SEQ ID NO: 28 amino acid sequence of scFV for CD19:
DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGGGGSGGGGSGGG -continued GSEVKLQESGPGLVAPSQSLSVTCTVSGVSLPDYGVSWIRQPPRKGLEWLGVIWGSETT
YYNSALKSRLTIIKDNSKSQVFLKMNSLQTDDTAIYYCAKHYYYGGSYAMDYWGQGTS
VTVSS SEQ ID NO: 29 nucleotide sequence of CAR LTG 1494 (LP-CD19binder-CD8link-CD8tm-41BB-CD3zeta):
ATGCTTCTCCTGGTCACCTCCCTGCTCCTCTGCGAACTGCCTCACCCTGCCTTCCTTC
TGATTCCTGACACTGACATTCAGATGACTCAGACCACCTCTTCCTTGTCCGCGTCACT
GGGAGACAGAGTGACCATCTCGTGTCGCGCAAGCCAGGATATCTCCAAGTACCTGA
ACTGGTACCAACAGAAGCCCGACGGGACTGTGAAGCTGCTGATCTACCACACCTCA
CGCCTGCACAGCGGAGTGCCAAGCAGATTCTCCGGCTCCGGCTCGGGAACCGATTA
CTCGCTTACCATTAGCAACCTCGAGCAGGAGGACATCGCTACCTACTTCTGCCAGCA
AGGAAATACCCTGCCCTACACCTTCGGCGGAGGAACCAAATTGGAAATCACCGGCT
CCACGAGCGGCTCCGGGAAGCCTGGTTCCGGGGAAGGCTCCACTAAGGGTGAAGTG
AAGCTCCAGGAGTCCGGCCCCGGCCTGGTGGCGCCGTCGCAATCACTCTCTGTGACC
TGTACCGTGTCGGGAGTGTCCCTGCCTGATTACGGCGTGAGCTGGATTCGGCAGCCG
CCGCGGAAGGGCCTGGAATGGCTGGGTGTCATCTGGGGATCCGAGACTACCTACTA
CAACTCGGCCCTGAAGTCCCGCCTGACTATCATCAAAGACAACTCGAAGTCCCAGGT
CTTTCTGAAGATGAACTCCCTGCAAACTGACGACACCGCCATCTATTACTGTGCTAA
GCACTACTACTACGGTGGAAGCTATGCTATGGACTACTGGGGCCAGGGGACATCCG
TGACAGTCAGCTCCGCGGCCGCAACTACCACCCCTGCCCCTCGGCCGCCGACTCCGG
CCCCAACCATCGCAAGCCAACCCCTCTCCTTGCGCCCCGAAGCTTGCCGCCCGGCCG
CGGGTGGAGCCGTGCATACCCGGGGGCTGGACTTTGCCTGCGATATCTACATTTGGG
CCCCGCTGGCCGGCACTTGCGGCGTGCTCCTGCTGTCGCTGGTCATCACCCTTTACTG
CAAGAGGGGCCGGAAGAAGCTGCTTTACATCTTCAAGCAGCCGTTCATGCGGCCCG
TGCAGACGACTCAGGAAGAGGACGGATGCTCGTGCAGATTCCCTGAGGAGGAAGAG
GGGGGATGCGAACTGCGCGTCAAGTTCTCACGGTCCGCCGACGCCCCCGCATATCA
ACAGGGCCAGAATCAGCTCTACAACGAGCTGAACCTGGGAAGGAGAGAGGAGTAC
GACGTGCTGGACAAGCGACGCGGACGCGACCCGGAGATGGGGGGGAAACCACGGC
GGAAAAACCCTCAGGAAGGACTGTACAACGAACTCCAGAAAGACAAGATGGCGGA
AGCCTACTCAGAAATCGGGATGAAGGGAGAGCGGAGGAGGGGAAAGGGTCACGAC
GGGCTGTACCAGGGACTGAGCACCGCCACTAAGGATACCTACGATGCCTTGCATAT
GCAAGCACTCCCACCCCGG SEQ ID NO: 30 amino acid sequence of CAR LTG1494 (LP-CD19binder-CD8link-CD8tm-41BB-CD3zeta):
MLLLVTSLLLCELPHPAFLLIPDTDIQMTQTTSSLSASLGDRVTISCRASQDISKYLNWYQ
QKPDGTVKLLIYHTSRLHSGVPSRFSGSGSGTDYSLTISNLEQEDIATYFCQQGNTLPYTF
GGGTKLEITGSTSGSGKPGSGEGSTKGEVKLQESGPGLVAPSQSLSVTCTVSGVSLPDYG
VSWIRQPPRKGLEWLGVIWGSETTYYNSALKSRLTIIKDNSKSQVFLKMNSLQTDDTAIY
YCAKHYYYGGSYAMDYWGQGTSVTVSSAAATTTPAPRPPTPAPTIASQPLSLRPEACRP
AAGGAVHTRGLDFACDIYIWAPLAGTCGVLLLSLVITLYCKRGRKKLLYIFKQPFMRPV
QTTQEEDGCSCRFPEEEEGGCELRVKFSRSADAPAYQQGQNQLYNELNLGRREEYDVL
DKRRGRDPEMGGKPRRKNPQEGLYNELQKDKMAEAYSEIGMKGERRRGKGHDGLYQ
GLSTATKDTYDALHMQALPPR SEQ ID NO: 31 nucleotide sequence of CAR LTG1538 (LP-CD19binder-CD8link-CD8tm-signals (LTI re-engineered CD19 CAR):
ATGCTTCTCCTGGTCACCTCCCTGCTCCTCTGCGAACTGCCTCACCCTGCCTTCCTTC
TGATTCCTGACATTCAGATGACTCAGACCACCTCTTCCTTGTCCGCGTCACTGGGAG
ACAGAGTGACCATCTCGTGTCGCGCAAGCCAGGATATCTCCAAGTACCTGAACTGGT
ACCAACAGAAGCCCGACGGGACTGTGAAGCTGCTGATCTACCACACCTCACGCCTG
CACAGCGGAGTGCCAAGCAGATTCTCCGGCTCCGGCTCGGGAACCGATTACTCGCTT
ACCATTAGCAACCTCGAGCAGGAGGACATCGCTACCTACTTCTGCCAGCAAGGAAA
TACCCTGCCCTACACCTTCGGCGGAGGAACCAAATTGGAAATCACCGGCGGAGGAG
GCTCCGGGGGAGGAGGTTCCGGGGGCGGGGGTTCCGAAGTGAAGCTCCAGGAGTCC
GGCCCCGGCCTGGTGGCGCCGTCGCAATCACTCTCTGTGACCTGTACCGTGTCGGGA
GTGTCCCTGCCTGATTACGGCGTGAGCTGGATTCGGCAGCCGCCGCGGAAGGGCCT
GGAATGGCTGGGTGTCATCTGGGGATCCGAGACTACCTACTACAACTCGGCCCTGAA
GTCCCGCCTGACTATCATCAAAGACAACTCGAAGTCC
CAGGTCTTTCTGAAGATGAACTCCCTGCAAACTGACGACACCGCCATCTATTACTGT
GCTAAGCACTACTACTACGGTGGAAGCTATGCTATGGACTACTGGGGGCAAGGCAC
TTCGGTGACTGTGTCAAGCGCGGCCGCAACTACCACCCCTGCCCCTCGGCCGCCGAC
TCCGGCCCCAACCATCGCAAGCCAACCCCTCTCCTTGCGCCCCGAAGCTTGCCGCCC
GGCCGCGGGTGGAGCCGTGCATACCCGGGGGCTGGACTTTGCCTGCGATATCTACAT
TTGGGCCCCGCTGGCCGGCACTTGCGGCGTGCTCCTGCTGTCGCTGGTCATCACCCT
TTACTGCAAGAGGGGCCGGAAGAAGCTGCTTTACATCTTCAAGCAGCCGTTCATGCG
GCCCGTGCAGACGACTCAGGAAGAGGACGGATGCTCGTGCAGATTCCCTGAGGAGG
AAGAGGGGGGATGCGAACTGCGCGTCAAGTTCTCACGGTCCGCCGACGCCCCCGCA
TATCAACAGGGCCAGAATCAGCTCTACAACGAGCTGAACCTGGGAAGGAGAGAGGA
GTACGACGTGCTGGACAAGCGACGCGGACGCGACCCGGAGATGGGGGGGAAACCA
CGGCGGAAAAACCCTCAGGAAGGACTGTACAACGAACTCCAGAAAGACAAGATGG
CGGAAGCCTACTCAGAAATCGGGATGAAGGGAGAGCGGAGGAGGGGAAAGGGTCA
CGACGGGCTGTACCAGGGACTGAGCACCGCCACTAAGGATACCTACGATGCCTTGC
ATATGCAAGCACTCCCACCCCGG SEQ ID NO: 32 amino acid sequence of CAR LTG1538 (LP-CD19binder-CD8link-CD8tm-signals (LTI re-engineered CD19 CAR):
MLLLVTSLLLCELPHPAFLLIPDIQMTQTTSSLSASLGDRVTISCRASQDISKYLNWYQQK
PDGTVKLLIYHTSRLHSGVPSRFSGSGSGTDYSLTISNLEQEDIATYFCQQGNTLPYTFGG
GTKLEITGGGGSGGGGSGGGGSEVKLQESGPGLVAPSQSLSVTCTVSGVSLPDYGVSWI -continued RQPPRKGLEWLGVIWGSETTYYNSALKSRLTIIKDNSKSQVFLKMNSLQTDDTAIYYCA
KHYYYGGSYAMDYWGQGTSVTVSSAAATTTPAPRPPTPAPTIASQPLSLRPEACRPAAG
GAVHTRGLDFACDIYIWAPLAGTCGVLLLSLVITLYCKRGRKKLLYIFKQPFMRPVQTT
QEEDGCSCRFPEEEEGGCELRVKFSRSADAPAYQQGQNQLYNELNLGRREEYDVLDKR
RGRDPEMGGKPRRKNPQEGLYNELQKDKMAEAYSEIGMKGERRRGKGHDGLYQGLST
ATKDTYDALHMQALPPR SEQ ID NO: 33 nucleotide sequence of CD19_20-reactive scFv binding domain (LTG1496):
GACATTCAGATGACTCAGACCACCTCCTCCCTGTCCGCCTCCCTGGGCGACCGCGTG
ACCATCTCATGCCGCGCCAGCCAGGACATCTCGAAGTACCTCAACTGGTACCAGCA
GAAGCCCGACGGAACCGTGAAGCTCCTGATCTACCACACCTCCCGGCTGCACAGCG
GAGTGCCGTCTAGATTCTCGGGTTCGGGGTCGGGAACTGACTACTCCCTTACTATTT
CCAACCTGGAGCAGGAGGATATTGCCACCTACTTCTGCCAACAAGGAAACACCCTG
CCGTACACTTTTGGCGGGGGAACCAAGCTGGAAATCACTGGCAGCACATCCGGTTC
CGGGAAGCCCGGCTCCGGAGAGGGCAGCACCAAGGGGGAAGTCAAGCTGCAGGAA
TCAGGACCTGGCCTGGTGGCCCCGAGCCAGTCACTGTCCGTGACTTGTACTGTGTCC
GGAGTGTCGCTCCCGGATTACGGAGTGTCCTGGATCAGGCAGCCACCTCGGAAAGG
ATTGGAATGGCTCGGAGTCATCTGGGGTTCCGAAACCACCTATTACAACTCGGCACT
GAAATCCAGGCTCACCATTATCAAGGATAACTCCAAGTCACAAGTGTTCCTGAAGAT
GAATAGCCTGCAGACTGACGACACGGCGATCTACTATTGCGCCAAGCACTACTACT
ACGGCGGATCCTACGCTATGGACTACTGGGGCCAGGGGACCAGCGTGACCGTGTCA
TCCGGAGGCGGCGGCAGCGGCGGGGGAGGGTCCGGAGGGGGTGGTTCTGGTGGAG
GAGGATCGGGAGGCGGTGGCAGCGAGGTGCAGTTGCAACAGTCAGGAGCTGAACTG
GTCAAGCCAGGAGCCAGCGTGAAGATGAGCTGCAAGGCCTCCGGTTACACCTTCAC
CTCCTACAACATGCACTGGGTGAAACAGACCCCGGGACAAGGGCTCGAATGGATTG
GCGCCATCTACCCCGGGAATGGCGATACTTCGTACAACCAGAAGTTCAAGGGAAAG
GCCACCCTGACCGCCGACAAGAGCTCCTCCACCGCGTATATGCAGTTGAGCTCCCTG
ACCTCCGAGGACTCCGCCGACTACTACTGCGCACGGTCCAACTACTATGGAAGCTCG
TACTGGTTCTTCGATGTCTGGGGGGCCGGCACCACTGTGACCGTCAGCTCCGGGGGC
GGAGGATCCGGTGGAGGCGGAAGCGGGGGTGGAGGATCCGACATTGTGCTGACTCA
GTCCCCGGCAATCCTGTCGGCCTCACCGGGCGAAAAGGTCACGATGACTTGTAGAG
CGTCGTCCAGCGTGAACTACATGGATTGGTACCAAAAGAAGCCTGGATCGTCACCC
AAGCCTTGGATCTACGCTACATCTAACCTGGCCTCCGGCGTGCCAGCGCGGTTCAGC
GGGTCCGGCTCGGGCACCTCATACTCGCTGACCATCTCCCGCGTGGAGGCTGAGGAC
GCCGCGACCTACTACTGCCAGCAGTGGTCCTTCAACCCGCCGACTTTTGGAGGCGGT
ACTAAGCTGGAGATCAAAGCGGCCGCA SEQ ID NO: 34 amino acid sequence of CD 19_20-reactive scFv binding domain (LTG1496):
DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGSTSGSGKPGSGEG
STKGEVKLQESGPGLVAPSQSLSVTCTVSGVSLPDYGVSWIRQPPRKGLEWLGVIWGSE
TTYYNSALKSRLTIIKDNSKSQVFLKMNSLQTDDTAIYYCAKHYYYGGSYAMDYWGQG
TSVTVSSGGGGSGGGGSGGGGSGGGGSGGGGSEVQLQQSGAELVKPGASVKMSCKAS
GYTFTSYNMHWVKQTPGQGLEWIGAIYPGNGDTSYNQKFKGKATLTADKSSSTAYMQ
LSSLTSEDSADYYCARSNYYGSSYWFFDVWGAGTTVTVSSGGGGSGGGGSGGGGSDIV
LTQSPAILSASPGEKVTMTCRASSSVNYMDWYQKKPGSSPKPWIYATSNLASGVPARFS
GSGSGTSYSLTISRVEAEDAATYYCQQWSFNPPTFGGGTKLEIKAAA SEQ ID NO: 35 nucleotide sequence of CAR LTG1496 (LP-LTG1496-CD8 TM-41BB-CD3zeta) or (LP-CD19 VL-Whitlow linker-CD19 VH $(GGGGS)_5$ CD20 VH $(GGGGS)_3$-CD20 VL CD8 hinge + TM-41BB-CD3zeta):
ATGCTCCTTCTCGTGACCTCCCTGCTTCTCTGCGAACTGCCCCATCCTGCCTTCCTGC
TGATTCCCGACATTCAGATGACTCAGACCACCTCCTCCCTGTCCGCCTCCCTGGGCG
ACCGCGTGACCATCTCATGCCGCGCCAGCCAGGACATCTCGAAGTACCTCAACTGGT
ACCAGCAGAAGCCCGACGGAACCGTGAAGCTCCTGATCTACCACACCTCCCGGCTG
CACAGCGGAGTGCCGTCTAGATTCTCGGGTTCGGGGTCGGGAACTGACTACTCCCTT
ACTATTTCCAACCTGGAGCAGGAGGATATTGCCACCTACTTCTGCCAACAAGGAAAC
ACCCTGCCGTACACTTTTGGCGGGGGAACCAAGCTGGAAATCACTGGCAGCACATC
CGGTTCCGGGAAGCCCGGCTCCGGAGAGGGCAGCACCAAGGGGGAAGTCAAGCTG
CAGGAATCAGGACCTGGCCTGGTGGCCCCGAGCCAGTCACTGTCCGTGACTTGTACT
GTGTCCGGAGTGTCGCTCCCGGATTACGGAGTGTCCTGGATCAGGCAGCCACCTCGG
AAAGGATTGGAATGGCTCGGAGTCATCTGGGGTTCCGAAACCACCTATTACAACTCG
GCACTGAAATCCAGGCTCACCATTATCAAGGATAACTCCAAGTCACAAGTGTTCCTG
AAGATGAATAGCCTGCAGACTGACGACACGGCGATCTACTATTGCGCCAAGCACTA
CTACTACGGCGGATCCTACGCTATGGACTACTGGGGCCAGGGGACCAGCGTGACCG
TGTCATCCGGAGGCGGCGGCAGCGGCGGGGGAGGGTCCGGAGGGGGTGGTTCTGGT
GGAGGAGGATCGGGAGGCGGTGGCAGCGAGGTGCAGTTGCAACAGTCAGGAGCTG
AACTGGTCAAGCCAGGAGCCAGCGTGAAGATGAGCTGCAAGGCCTCCGGTTACACC
TTCACCTCCTACAACATGCACTGGGTGAAACAGACCCCGGGACAAGGGCTCGAATG
GATTGGCGCCATCTACCCCGGGAATGGCGATACTTCGTACAACCAGAAGTTCAAGG
GAAAGGCCACCCTGACCGCCGACAAGAGCTCCTCCACCGCGTATATGCAGTTGAGC
TCCCTGACCTCCGAGGACTCCGCCGACTACTACTGCGCACGGTCCAACTACTATGGA
AGCTCGTACTGGTTCTTCGATGTCTGGGGGGCCGGCACCACTGTGACCGTCAGCTCC
GGGGGCGGAGGATCCGGT
GGAGGCGGAAGCGGGGGTGGAGGATCCGACATTGTGCTGACTCAGTCCCCGGCAAT
CCTGTCGGCCTCACCGGGCGAAAAGGTCACGATGACTTGTAGAGCGTCGTCCAGCG
TGAACTACATGGATTGGTACCAAAAGAAGCCTGGATCGTCACCCAAGCCTTGGATCT
ACGCTACATCTAACCTGGCCTCCGGCGTGCCAGCGCGGTTCAGCGGGTCCGGCTCGG
GCACCTCATACTCGCTGACCATCTCCCGCGTGGAGGCTGAGGACGCCGCGACCTACT
ACTGCCAGCAGTGGTCCTTCAACCCGCCGACTTTTGGAGGCGGTACTAAGCTGGAGA
TCAAAGCGGCCGCAACTACCACCCCTGCCCCTCGGCCGCCGACTCCGGCCCCAACCA -continued TCGCAAGCCAACCCCTCTCCTTGCGCCCCGAAGCTTGCCGCCCGGCCGCGGGTGGAG
CCGTGCATACCCGGGGGCTGGACTTTGCCTGCGATATCTACATTTGGGCCCCGCTGG
CCGGCACTTGCGGCGTGCTCCTGCTGTCGCTGGTCATCACCCTTTACTGCAAGAGGG
GCCGGAAGAAGCTGCTTTACATCTTCAAGCAGCCGTTCATGCGGCCCGTGCAGACG
ACTCAGGAAGAGGACGGATGCTCGTGCAGATTCCCT
GAGGAGGAAGAGGGGGGATGCGAACTGCGCGTCAAGTTCTCACGGTCCGCCGACGC
CCCCGCATATCAACAGGGCCAGAATCAGCTCTACAACGAGCTGAACCTGGGAAGGA
GAGAGGAGTACGACGTGCTGGACAAGCGACGCGGACGCGACCCGGAGATGGGGGG
GAAACCACGGCGGAAAAACCCTCAGGAAGGACTGTACAACGAACTCCAGAAAGAC
AAGATGGCGGAAGCCTACTCAGAAATCGGGATGAAGGGAGAGCGGAGGAGGGGAA
AGGGTCACGACGGGCTGTACCAGGGACTGAGCACCGCCACTAAGGATACCTACGAT
GCCTTGCATATGCAAGCACTCCCACCCCGG SEQ ID NO: 36 amino acid sequence of CAR LTG1496 (LP-LTG1496-CD8 TM-41BB-CD3zeta) or (LP-CD19 VL-Whitlow linker-CD19 VH-$(GGGGS)_5$-CD20 VH $(GGGGS)_3$-CD20 VL-CD8 hinge + TM-41BB-CD3zeta):
MLLLVTSLLLCELPHPAFLLIPDIQMTQTTSSLSASLGDRVTISCRASQDISKYLNWYQQK
PDGTVKLLIYHTSRLHSGVPSRFSGSGSGTDYSLTISNLEQEDIATYFCQQGNTLPYTFGG
GTKLEITGSTSGSGKPGSGEGSTKGEVKLQESGPGLVAPSQSLSVTCTVSGVSLPDYGVS
WIRQPPRKGLEWLGVIWGSETTYYNSALKSRLTIIKDNSKSQVFLKMNSLQTDDTAIYY
CAKHYYYGGSYAMDYWGQGTSVTVSSGGGGSGGGGSGGGGSGGGGSGGGGSEVQLQ
QSGAELVKPGASVKMSCKASGYTFTSYNMHWVKQTPGQGLEWIGAIYPGNGDTSYNQ
KFKGKATLTADKSSSTAYMQLSSLTSEDSADYYCARSNYYGSSYWFFDVWGAGTTVT
VSSGGGGSGGGGSGGGGSDIVLTQSPAILSASPGEKVTMTCRASSSVNYMDWYQKKPG
SSPKPWIYATSNLASGVPARFSGSGSGTSYSLTISRVEAEDAATYYCQQWSFNPPTFGGG
TKLEIKAAATTTPAPRPPTPAPTIASQPLSLRPEACRPAAGGAVHTRGLDFACDIYIWAPL
AGTCGVLLLSLVITLYCKRGRKKLLYIFKQPFMRPVQTTQEEDGCSCRFPEEEEGGCELR
VKFSRSADAPAYQQGQNQLYNELNLGRREEYDVLDKRRGRDPEMGGKPRRKNPQEGL
YNELQKDKMAEAYSEIGMKGERRRGKGHDGLYQGLSTATKDTYDALHMQALPPR SEQ ID NO: 37 nucleotide sequence of mesothelin-reactive scFv binding domain (LTG1904):
GAGGTCCAGCTGGTACAGTCTGGGGGAGGCTTGGTACAGCCTGGGGGGTCCCTGAG
ACTCTCCTGTGCAGCCTCTGGATTCACCTTTGATGATTATGCCATGCACTGGGTCCGG
CAAGCTCCAGGGAAGGGCCTGGAGTGGGTCTCAGGTATTAGTTGGAATAGTGGTAG
CATAGGCTATGCGGACTCTGTGAAGGGCCGATTCACCATCTCCAGAGACAACGCCA
AGAACTCCCTGTATCTGCAAATGAACAGTCTGAGAGCTGAGGACACGGCCTTGTATT
ACTGTGCAAAAGATTTATCGTCAGTGGCTGGACCCTTTAACTACTGGGGCCAGGGCA
CCCTGGTCACCGTCTCCTCAGGAGGTGGCGGGTCTGGTGGAGGCGGTAGCGGCGGT
GGCGGATCCTCTTCTGAGCTGACTCAGGACCCTGCTGTGTCTGTGGCCTTGGGACAG
ACAGTCAGGATCACATGCCAAGGAGACAGCCTCAGAAGCTATTATGCAAGCTGGTA
CCAGCAGAAGCCAGGACAGGCCCCTGTACTTGTCATCTATGGTAAAAACAACCGGC
CCTCAGGGATCCCAGACCGATTCTCTGGCTCCAGCTCAGGAAACACAGCTTCCTTGA
CCATCACTGGGGCTCAGGCGGAGGATGAGGCTGACTATTACTGTAACTCCCGGGAC
AGCAGTGGTAACCATCTGGTATTCGGCGGAGGCACCCAGCTGACCGTCCTCGGT SEQ ID NO: 38 amino acid sequence of mesothelin-reactive scFv binding domain (LTG1904):
EVQLVQSGGGLVQPGGSLRLSCAASGFTFDDYAMHWVRQAPGKGLEWVSGISWNSGSI
GYADSVKGRFTISRDNAKNSLYLQMNSLRAEDTALYYCAKDLSSVAGPFNYWGQGTL
VTVSSGGGGSGGGGSGGGGSSSELTQDPAVSVALGQTVRITCQGDSLRSYYASWYQQK
PGQAPVLVIYGKNNRPSGIPDRFSGSSSGNTASLTITGAQAEDEADYYCNSRDSSGNHLV
FGGGTQLTVLG SEQ ID NO: 39 nucleotide sequence of CAR LTG1904 (LP-LTG1904-CD8 TM-41BB-CD3zeta):
ATGCTGCTGCTGGTGACCAGCCTGCTGCTGTGCGAACTGCCGCATCCGGCGTTTCTG
CTGATTCCGGAGGTCCAGCTGGTACAGTCTGGGGGAGGCTTGGTACAGCCTGGGGG
GTCCCTGAGACTCTCCTGTGCAGCCTCTGGATTCACCTTTGATGATTATGCCATGCAC
TGGGTCCGGCAAGCTCCAGGGAAGGGCCTGGAGTGGGTCTCAGGTATTAGTTGGAA
TAGTGGTAGCATAGGCTATGCGGACTCTGTGAAGGGCCGATTCACCATCTCCAGAGA
CAACGCCAAGAACTCCCTGTATCTGCAAATGAACAGTCTGAGAGCTGAGGACACGG
CCTTGTATTACTGTGCAAAAGATTTATCGTCAGTGGCTGGACCCTTTAACTACTGGG
GCCAGGGCACCCTGGTCACCGTCTCCTCAGGAGGTGGCGGGTCTGGTGGAGGCGGT
AGCGGCGGTGGCGGATCCTCTTCTGAGCTGACTCAGGACCCTGCTGTGTCTGTGGCC
TTGGGACAGACAGTCAGGATCACATGCCAAGGAGACAGCCTCAGAAGCTATTATGC
AAGCTGGTACCAGCAGAAGCCAGGACAGGCCCCTGTACTTGTCATCTATGGTAAAA
ACAACCGGCCCTCAGGGATCCCAGACCGATTCTCTGGCTCCAGCTCAGGAAACACA
GCTTCCTTGACCATCACTGGGGCTCAGGCGGAGGATGAGGCTGACTATTACTGTAAC
TCCCGGGACAGCAGTGGTAACCATCTGGTATTCGGCGGAGGCACCCAGCTGACCGT
CCTCGGTGCGGCCGCAACTACCACCCCTGCCCCTCGGCCGCCGACTCCGGCCCCAAC
CATCGCAAGCCAACCCCTCTCCTTGCGCCCCGAAGCTTGCCGCCCGGCCGCGGGTGG
AGCCGTGCATACCCGGGGGCTGGACTTTGCCTGCGATATCTACATTTGGGCCCCGCT
GGCCGGCACTTGCGGCGTGCTCCTGCTGTCGCTGGTCATCACCCTTTACTGCAAGAG
GGGCCGGAAGAAGCTGCTTTACATCTTCAAGCAGCCGTTCATGCGGCCCGTGCAGA
CGACTCAGGAAGAGGACGGATGCTCGTGCAGATTCCCTGAGGAGGAAGAGGGGGG
ATGCGAACTGCGCGTCAAGTTCTCACGGTCCGCCGACGCCCCCGCATATCAACAGG
GCCAGAATCAGCTCTACAACGAGCTGAACCTGGGAAGGAGAGAGGAGTACGACGTG
CTGGACAAGCGACGCGGACGCGACCCGGAGATGGGGGGGAAACCACGGCGGAAAA
ACCCTCAGGAAGGACTGTACAACGAACTCCAGAAAGACAAGATGGCGGAAGCCTAC
TCAGAAATCGGGATGAAGGGAGAGCGGAGGAGGGGAAAGGGTCACGACGGGCTGT -continued
ACCAGGGACTGAGCACCGCCACTAAGGATACCTACGATGCCTTGCATATGCAAGCA
CTCCCACCCCGG SEQ ID NO: 40 amino acid sequence of CAR LTG1904 (LP-LTG1904-CD8 TM-41BB-CD3zeta):
MLLLVTSLLLCELPHPAFLLIPEVQLVQSGGGLVQPGGSLRLSCAASGFTFDDYAMHW
VRQAPGKGLEWVSGISWNSGSIGYADSVKGRFTISRDNAKNSLYLQMNSLRAEDTALY
YCAKDLSSVAGPFNYWGQGTLVTVSSGGGGSGGGGSGGGGSSSELTQDPAVSVALGQ
TVRITCQGDSLRSYYASWYQQKPGQAPVLVIYGKNNRPSGIPDRFSGSSSGNTASLTITG
AQAEDEADYYCNSRDSSGNHLVFGGGTQLTVLGAAATTTPAPRPPTPAPTIASQPLSLR
PEACRPAAGGAVHTRGLDFACDIYIWAPLAGTCGVLLLSLVITLYCKRGRKKLLYIFKQ
PFMRPVQTTQEEDGCSCRFPEEEEGGCELRVKFSRSADAPAYQQGQNQLYNELNLGRR
EEYDVLDKRRGRDPEMGGKPRRKNPQEGLYNELQKDKMAEAYSEIGMKGERRRGKG
HDGLYQGLSTATKDTYDALHMQALPPR SEQ ID NO: 41 nucleotide sequence of CD33-reactive single chain binding domain VH-4 (LTG1906):
GAGGTGCAGCTGGTGGAGTCTGGGGGAGGCTTGGTACAGCCTGGAGGGTCCCTGAG
ACTCTCCTGTGCAGCCTCTGGATTCACCTTCAGTAGCTATGGCATGAGCTGGGTCCG
CCAGGCTCCAAGACAAGGGCTTGAGTGGGTGGCCAACATAAAGCAAGATGGAAGTG
AGAAATACTATGCGGACTCAGTGAAGGGCCGATTCACCATCTCCAGAGACAATTCC
AAGAACACGCTGTATCTGCAAATGAACAGCCTGAGAGCCGAGGACACAGCCACGTA
TTACTGTGCGAAAGAAAATGTGGACTGGGGCCAGGGCACCCTGGTCACCGTCTCCTC
A SEQ ID NO: 42 amino acid sequence of CD33-reactive single chain binding domain VH-4 (LTG1906):
EVQLVESGGGLVQPGGSLRLSCAASGFTFSSYGMSWVRQAPRQGLEWVANIKQDGSEK
YYADSVKGRFTISRDNSKNTLYLQMNSLRAEDTATYYCAKENVDWGQGTLVTVSS SEQ ID NO: 43 nucleotide sequence of CAR LTG1906 (LP-VH4-CD8 TM-41BB-CD3zeta):
ATGCTGCTGCTGGTGACCAGCCTGCTGCTGTGCGAACTGCCGCATCCGGCGTTTCTG
CTGATTCCGGAGGTGCAGCTGGTGGAGTCTGGGGGAGGCTTGGTACAGCCTGGAGG
GTCCCTGAGACTCTCCTGTGCAGCCTCTGGATTCACCTTCAGTAGCTATGGCATGAG
CTGGGTCCGCCAGGCTCCAAGACAAGGGCTTGAGTGGGTGGCCAACATAAAGCAAG
ATGGAAGTGAGAAATACTATGCGGACTCAGTGAAGGGCCGATTCACCATCTCCAGA
GACAATTCCAAGAACACGCTGTATCTGCAAATGAACAGCCTGAGAGCCGAGGACAC
AGCCACGTATTACTGTGCGAAAGAAAATGTGGACTGGGGCCAGGGCACCCTGGTCA
CCGTCTCCTCAGCGGCCGCAACTACCACCCCTGCCCCTCGGCCGCCGACTCCGGCCC
CAACCATCGCAAGCCAACCCCTCTCCTTGCGCCCCGAAGCTTGCCGCCCGGCCGCGG
GTGGAGCCGTGCATACCCGGGGGCTGGACTTTGCCTGCGATATCTACATTTGGGCCC
CGCTGGCCGGCACTTGCGGCGTGCTCCTGCTGTCGCTGGTCATCACCCTTTACTGCA
AGAGGGGCCGGAAGAAGCTGCTTTACATCTTCAAGCAGCCGTTCATGCGGCCCGTG
CAGACGACTCAGGAAGAGGACGGATGCTCGTGCAGATTCCCTGAGGAGGAAGAGG
GGGGATGCGAACTGCGCGTCAAGTTCTCACGGTCCGCCGACGCCCCCGCATATCAA
CAGGGCCAGAATCAGCTCTACAACGAGCTGAACCTGGGAAGGAGAGAGGAGTACG
ACGTGCTGGACAAGCGACGCGGACGCGACCCGGAGATGGGGGGGAAACCACGGCG
GAAAAACCCTCAGGAAGGACTGTACAACGAACTCCAGAAAGACAAGATGGCGGAA
GCCTACTCAGAAATCGGGATGAAGGGAGAGCGGAGGAGGGGAAAGGGTCACGACG
GGCTGTACCAGGGACTGAGCACCGCCACTAAGGATACCTACGATGCCTTGCATATG
CAAGCACTCCCACCCCGG SEQ ID NO: 44 amino acid sequence of CAR LTG1906 (LP-VH4-CD8 TM-41BB-CD3zeta):
MLLLVTSLLLCELPHPAFLLIPEVQLVESGGGLVQPGGSLRLSCAASGFTFSSYGMSWVR
QAPRQGLEWVANIKQDGSEKYYADSVKGRFTISRDNSKNTLYLQMNSLRAEDTATYYC
AKENVDWGQGTLVTVSSAAATTTPAPRPPTPAPTIASQPLSLRPEACRPAAGGAVHTRG
LDFACDIYIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRRGRDPEMG
GKPRRKNPQEGLYNELQKDKMAEAYSEIGMKGERRRGKGHDGLYQGLSTATKDTYDA
LHMQALPPR SEQ ID NO: 45 nucleotide sequence of TSLPR-reactive scFv binding domain (LTG1789):
ATGGCACTGCCCGTGACCGCCCTGCTTCTGCCGCTTGCACTTCTGCTGCACGCCGCT
AGGCCCCAAGTCACCCTCAAAGAGTCAGGGCCAGGAATCCTCAAGCCCTCACAGAC
TCTGTCTCTTACTTGCTCATTCAGCGGATTCAGCCTTTCCACCTCTGGTATGGGCGTG
GGGTGGATTAGGCAACCTAGCGGAAAGGGGCTTGAATGGCTGGCCCACATCTGGTG
GGACGACGACAAGTACTACAACCCCTCACTGAAGTCCCAGCTCACTATTTCCAAAG
ATACTTCCCGGAATCAGGTGTTCCTCAAGATTACCTCTGTCGACACCGCTGATACCG
CCACTTACTATTGTTCACGCAGACCGAGAGGTACCATGGACGCAATGGACTACTGGG
GACAGGGCACCAGCGTGACCGTGTCATCTGGCGGTGGAGGGTCAGGAGGTGGAGGT
AGCGGAGGCGGTGGGTCCGACATTGTCATGACCCAGGCCGCCAGCAGCCTGAGCGC
TTCACTGGGCGACAGGGTGACCATCAGCTGTCGCGCATCACAAGATATCTCTAAGTA
TCTTAATTGGTACCAGCAAAAGCCGGATGGAACCGTGAAGCTGCTGATCTACTACAC
CTCACGGCTGCATTCTGGAGTGCCTAGCCGCTTTAGCGGATCTGGGTCCGGTACTGA
CTACAGCCTCACCATTAGAAACCTTGAACAGGAGGACATCGCAACTTATTTCTGCCA
ACAGGTCTATACTCTGCCGTGGACCTTCGGCGGAGGTACCAAACTGGAGATTAAGTC
CGG SEQ ID NO: 46 amino acid sequence of TSLPR-reactive scFv binding domain (LTG1789):
MALPVTALLLPLALLLHAARPQVTLKESGPGILKPSQTLSLTCSFSGFSLSTSGMGVGWI
RQPSGKGLEWLAHIWWDDDKYYNPSLKSQLTISKDTSRNQVFLKITSVDTADTATYYCS -continued RRPRGTMDAMDYWGQGTSVTVSSGGGGSGGGGSGGGGSDIVMTQAASSLSASLGDRV
TISCRASQDISKYLNWYQQKPDGTVKLLIYYTSRLHSGVPSRFSGSGSGTDYSLTIRNLEQ
EDIATYFCQQVYTLPWTFGGGTKLEIKS SEQ ID NO: 47 nucleotide sequence of CAR LTG1789 (LP-3G11-CD8 TM-41BB-CD3zeta):
ATGGCACTGCCCGTGACCGCCCTGCTTCTGCCGCTTGCACTTCTGCTGCACGCCGCT
AGGCCCCAAGTCACCCTCAAAGAGTCAGGGCCAGGAATCCTCAAGCCCTCACAGAC
TCTGTCTCTTACTTGCTCATTCAGCGGATTCAGCCTTTCCACCTCTGGTATGGGCGTG
GGGTGGATTAGGCAACCTAGCGGAAAGGGGCTTGAATGGCTGGCCCACATCTGGTG
GGACGACGACAAGTACTACAACCCCTCACTGAAGTCCCAGCTCACTATTTCCAAAG
ATACTTCCCGGAATCAGGTGTTCCTCAAGATTACCTCTGTCGACACCGCTGATACCG
CCACTTACTATTGTTCACGCAGACCGAGAGGTACCATGGACGCAATGGACTACTGGG
GACAGGGCACCAGCGTGACCGTGTCATCTGGCGGTGGAGGGTCAGGAGGTGGAGGT
AGCGGAGGCGGTGGGTCCGACATTGTCATGACCCAGGCCGCCAGCAGCCTGAGCGC
TTCACTGGGCGACAGGGTGACCATCAGCTGTCGCGCATCACAAGATATCTCTAAGTA
TCTTAATTGGTACCAGCAAAAGCCGGATGGAACCGTGAAGCTGCTGATCTACTACAC
CTCACGGCTGCATTCTGGAGTGCCTAGCCGCTTTAGC
GGCACTTGCGGCGTGCTCCTGCTGTCGCTGGTCATCACCCTTTACTGCAAGAGGGGC
CGGAAGAAGCTGCTTTACATCTTCAAGCAGCCGTTCATGCGGCCCGTGCAGACGACT
CAGGAAGAGGACGGATGCTCGTGCAGATTCCCTGAGGAGGAAGAGGGGGGATGCG
AACTGCGCGTCAAGTTCTCACGGTCCGCCGACGCCCCCGCATATCAACAGGGCCAG
AATCAGCTCTACAACGAGCTGAACCTGGGAAGGAGAGAGGAGTACGACGTGCTGGA
CAAGCGACGCGGACGCGACCCGGAGATGGGGGGGAAACCACGGCGGAAAAACCCT
CAGGAAGGACTGTACAACGAACTCCAGAAAGACAAGATGGCGGAAGCCTACTCAG
AAATCGGGATGAAGGGAGAGCGGAGGAGGGGAAAGGGTCACGACGGGCTGTACCA
GGGACTGAGCACCGCCACTAAGGATACCTACGATGCCTTGCATATGCAAGCACTCC
CACCCCGG SEQ ID NO: 48 amino acid sequence of CAR LTG1789 (LP-3G11-CD8 TM-41BB-CD3zeta):
MALPVTALLLPLALLLHAARPQVTLKESGPGILKPSQTLSLTCSFSGFSLSTSGMGVGWI
RQPSGKGLEWLAHIWWDDDKYYNPSLKSQLTISKDTSRNQVFLKITSVDTADTATYYCS
RRPRGTMDAMDYWGQGTSVTVSSGGGGSGGGGSGGGGSDIVMTQAASSLSASLGDRV
TISCRASQDISKYLNWYQQKPDGTVKLLIYYTSRLHSGVPSRFSGSGSGTDYSLTIRNLEQ
EDIATYFCQQVYTLPWTFGGGTKLEIKAAATTTPAPRPPTPAPTIASQPLSLRPEACRPAA
GGAVHTRGLDFACDIYIWAPLAGTCGVLLLSLVITLYCKRGRKKLLYIFKQPFMRPVQT
TQEEDGCSCRFPEEEEGGCELRVKFSRSADAPAYQQGQNQLYNELNLGRREEYDVLDK
RRGRDPEMGGKPRRKNPQEGLYNELQKDKMAEAYSEIGMKGERRRGKGHDGLYQGLS
TATKDTYDALHMQALPPR SEQ ID NO: 49 nucleotide sequence of CAR LTG1563 (LP-CD19-TNFRSF19TM-41BB-CD3zeta):
ATGCTGCTGCTGGTCACCAGCCTGCTGCTGTGCGAGCTCCCTCACCCCGCCTTTCTGC
TTATCCCGGACATTCAGATGACACAGACCACCTCGAGCTTGTCCGCGTCGCTGGGCG
ATCGCGTGACCATCTCCTGCCGGGCCTCCCAAGACATTTCAAAGTATCTCAACTGGT
ACCAGCAGAAGCCGGACGGAACCGTGAAACTGCTGATCTACCATACCAGCCGCCTG
CACTCCGGCGTGCCGTCCCGCTTCTCCGGATCGGGTTCCGGAACTGACTACTCACTG
ACTATCTCCAACTTGGAACAAGAGGACATCGCCACTTACTTCTGTCAACAAGGAAAT
ACCCTTCCCTACACCTTCGGGGGGGGTACCAAGCTGGAGATCACTGGGGGGGGAGG
CTCCGGTGGAGGCGGATCCGGCGGTGGAGGGAGCGAAGTCAAGCTGCAGGAATCAG
GACCAGGACTCGTGGCGCCATCCCAGTCCCTGTCGGTGACCTGTACTGTCTCCGGAG
TCAGCCTCCCCGATTACGGAGTGTCATGGATTAGGCAACCCCCAAGAAAAGGGCTG
GAATGGCTCGGAGTGATCTGGGGCTCCGAAACCACCTACTACAACTCGGCGCTGAA
GTCCCGGCTGACCATCATCAAGGACAACTCCAAGAGCCAAGTGTTCTTGAAGATGA
ACAGCTTGCAGACCGACGATACCGCAATCTACTACTGTGCCAAGCACTATTACTACG
GGGGGTCTTACGCCATGGACTACTGGGGACAGGGCACCTCCGTGACTGTGTCGTCCG
CGGCCGCGCCCGCCCCTCGGCCCCCGACTCCTGCCCCGACGATCGCTTCCCAACCTC
TCTCGCTGCGCCCGGAAGCATGCCGGCCCGCCGCCGGTGGCGCTGTCCACACTCGCG
GACTGGACTTTGATACCGCACTGGCGGCCGTGATCTGTAGCGCCCTGGCCACCGTGC
TGCTGGCGCTGCTCATCCTTTGCGTGATCTACTGCAAGCGGCAGCCTAGGCGAAAGA
AGCTCCTCTACATTTTCAAGCAACCCTTCATGCGCCCCGTGCAAACCACCCAGGAGG
AGGATGGATGCTCATGCCGGTTCCCTGAGGAAGAAGAGGGCGGTTGCGAGCTCAGA
GTGAAATTCAGCCGGTCGGCTGACGCCCCGGCGTACCAGCAGGGCCAGAACCAGCT
GTACAATGAGCTCAACCTGGGGCGCCGCGAAGAGTACGACGTGCTGGACAAGAGGA
GAGGCAGAGATCCGGAAATGGGCGGAAAGCCAAGGCGGAAGAACCCGCAGGAAGG
TCTTTACAACGAACTGCAGAAGGACAAGATGGCCGAGGCCTACTCCGAGATTGGGA
TGAAGGGAGAAAGACGGAGGGGAAAGGGACATGACGGACTTTACCAGGGCCTGAG
CACTGCCACGAAGGACACCTATGATGCCCTGCACATGCAGGCGCTGCCGCCTCGG SEQ ID NO: 50 amino acid sequence of CAR LTG1563 (LP-CD19-TNFRSF19TM-41BB-CD3zeta):
MLLLVTSLLLCELPHPAFLLIPDIQMTQTTSSLSASLGDRVTISCRASQDISKYLNWYQQK
PDGTVKLLIYHTSRLHSGVPSRFSGSGSGTDYSLTISNLEQEDIATYFCQQGNTLPYTFGG
GTKLEITGGGGSGGGGSGGGGSEVKLQESGPGLVAPSQSLSVTCTVSGVSLPDYGVSWI
RQPPRKGLEWLGVIWGSETTYYNSALKSRLTIIKDNSKSQVFLKMNSLQTDDTAIYYCA
KHYYYGGSYAMDYWGQGTSVTVSSAAAPAPRPPTPAPTIASQPLSLRPEACRPAAGGA
VHTRGLDFDTALAAVICSALATVLLALLILCVIYCKRQPRRKKLLYIFKQPFMRPVQTTQ
EEDGCSCRFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGLYQGLSTA
TKDTYDALHMQALPPR -continued SEQ ID NO: 51 nucleotide acid sequence of CAR LTG2228 (LP-CD20_CD19-CD8TM-CD28-CD3zeta):
ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG
GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG
CCGACTACTACTGCGCACGGTCCAACTACTATGGAAGCTCGTACTGGTTCTTCGATG
TCTGGGGGGCCGGCACCACTGTGACCGTCAGCTCCGGGGGCGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT
GCCAGCAGTGGTCCTTCAACCCGCCGACTTTTGGAGGCGGTACTAAGCTGGAGATCA
AAGGAGGCGGCGGCAGCGGCGGGGGAGGGTCCGGAGGGGGTGGTTCTGGTGGAGG
AGGATCGGGAGGCGGTGGCAGCGACATTCAGATGACTCAGACCACCTCCTCCCTGT
CCGCCTCCCTGGGCGACCGCGTGACCATCTCATGCCGCGCCAGCCAGGACATCTCGA
AGTACCTCAACTGGTACCAGCAGAAGCCCGACGGAACCGTGAAGCTCCTGATCTAC
CACACCTCCCGGCTGCACAGCGGAGTGCCGTCTAGATTCTCGGGTTCGGGGTCGGGA
ACTGACTACTCCCTTACTATTTCCAACCTGGAGCAGGAGGATATTGCCACCTACTTCT
GCCAACAAGGAAACACCCTGCCGTACACTTTTGGCGGGGGAACCAAGCTGGAAATC
ACTGGCAGCACATCCGGTTCCGGGAAGCCCGGCTCCGGAGAGGGCAGCACCAAGGG
GGAAGTCAAGCTGCAGGAATCAGGACCTGGCCTGGTGGCCCCGAGCCAGTCACTGT
CCGTGACTTGTACTGTGTCCGGAGTGTCGCTCCCGGATTACGGAGTGTCCTGGATCA
GGCAGCCACCTCGGAAAGGATTGGAATGGCTCGGAGTCATCTGGGGTTCCGAAACC
ACCTATTACAACTCGGCACTGAAATCCAGGCTCACCATTATCAAGGATAACTCCAAG
TCACAAGTGTTCCTGAAGATGAATAGCCTGCAGACTGACGACACGGCGATCTACTAT
TGCGCCAAGCACTACTACTACGGCGGATCCTACGCTATGGACTACTGGGGCCAGGG
GACCAGCGTGACCGTGTCATCCGCGGCCGCGACTACCACTCCTGCACCACGGCCACC
TACCCCAGCCCCCACCATTGCAAGCCAGCCACTTTCACTGCGCCCCGAAGCGTGTAG
ACCAGCTGCTGGAGGAGCCGTGCATACCCGAGGGCTGGACTTCGCCTGTGACATCT
ACATCTGGGCCCCATTGGCTGGAACTTGCGGCGTGCTGCTCTTGTCTCTGGTCATTAC
CCTGTACTGCCGGTCGAAGAGGTCCAGACTCTTGCACTCCGACTACATGAACATGAC
TCCTAGAAGGCCCGGACCCACTAGAAAGCACTACCAGCCGTACGCCCCTCCTCGGG
ATTTCGCCGCATACCGGTCCAGAGTGAAGTTCAGCCGCTCAGCCGATGCACCGGCCT
ACCAGCAGGGACAGAACCAGCTCTACAACGAGCTCAACCTGGGTCGGCGGGAAGA
ATATGACGTGCTGGACAAACGGCGCGGCAGAGATCCGGAGATGGGGGGAAAGCCG
AGGAGGAAGAACCCTCAAGAGGGCCTGTACAACGAACTGCAGAAGGACAAGATGG
CGGAAGCCTACTCCGAGATCGGCATGAAGGGAGAACGCCGGAGAGGGAAGGGTCA
TGACGGACTGTACCAGGGCCTGTCAACTGCCACTAAGGACACTTACGATGCGCTCCA
TATGCAAGCTTTGCCCCCGCGG SEQ ID NO: 52 amino acid sequence of CAR LTG2228 (LP-CD20_CD19-CD8TM-CD28-CD3zeta):
MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE
KVTMTCRASSSVNYMDWYQKKPGSSPKPWIYATSNLASGVPARFSGSGSGTSYSLTISR
VEAEDAATYYCQQWSFNPPTFGGGTKLEIKGGGGSGGGGSGGGGSGGGGSGGGGSDIQ
MTQTTSSLSASLGDRVTISCRASQDISKYLNWYQQKPDGTVKLLIYHTSRLHSGVPSRFS
GSGSGTDYSLTISNLEQEDIATYFCQQGNTLPYTFGGGTKLEITGSTSGSGKPGSGEGSTK
GEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSV
TVSSAAATTTPAPRPPTPAPTIASQPLSLRPEACRPAAGGAVHTRGLDFACDIYIWAPLAG
TCGVLLLSLVITLYCRSKRSRLLHSDYMNMTPRRPGPTRKHYQPYAPPRDFAAYRSRVK
FSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR SEQ ID NO: 53 nucleotide sequence of D0043:
ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG
GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG
CCGACTACTACTGCGCACGGTCCAACTACTATGGAAGCTCGTACTGGTTCTTCGATG
TCTGGGGGGCCGGCACCACTGTGACCGTCAGCTCCGGGGGCGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT
GCCAGCAGTGGTCCTTCAACCCGCCGACTTTTGGAGGCGGTACTAAGCTGGAGATCA
AAGGAGGCGGCGGCAGCGGCGGGGGAGGGTCCGGAGGGGGGTGGTTCTGGTGGAGG
AGGATCGGGAGGCGGTGGCAGCGACATTCAGATGACTCAGACCACCTCCTCCCTGT
CCGCCTCCCTGGGCGACCGCGTGACCATCTCATGCCGCGCCAGCCAGGACATCTCGA
AGTACCTCAACTGGTACCAGCAGAAGCCCGACGGAACCGTGAAGCTCCTGATCTAC
CACACCTCCCGGCTGCACAGCGGAGTGCCGTCTAGATTCTCGGGTTCGGGGTCGGGA
ACTGACTACTCCCTTACTATTTCCAACCTGGAGCAGGAGGATATTGCCACCTACTTCT -continued GCCAACAAGGAAACACCCTGCCGTACACTTTTGGCGGGGGAACCAAGCTGGAAATC
ACTGGCAGCACATCCGGTTCCGGGAAGCCCGGCTCCGGAGAGGGCAGCACCAAGGG
GGAAGTCAAGCTGCAGGAATCAGGACCTGGCCTGGTGGCCCCGAGCCAGTCACTGT
CCGTGACTTGTACTGTGTCCGGAGTGTCGCTCCCGGATTACGGAGTGTCCTGGATCA
GGCAGCCACCTCGGAAAGGATTGGAATGGCTCGGAGTCATCTGGGGTTCCGAAACC
ACCTATTACAACTCGGCACTGAAATCCAGGCTCACCATTATCAAGGATAACTCCAAG
TCACAAGTGTTCCTGAAGATGAATAGCCTGCAGACTGACGACACGGCGATCTACTAT
TGCGCCAAGCACTACTACTACGGCGGATCCTACGCTATGGACTACTGGGGCCAGGG
GACCAGCGTGACCGTGTCATCCGCGGCCGCGACTACCACTCCTGCACCACGGCCACC
TACCCCAGCCCCCACCATTGCAAGCCAGCCACTTTCACTGCGCCCCGAAGCGTGTAG
ACCAGCTGCTGGAGGAGCCGTGCATACCCGAGGGCTGGACTTCGCCTGTGACATCT
ACATCTGGGCCCCATTGGCTGGAACTTGCGGCGTGCTGCTCTTGTCTCTGGTCATTAC
CCTGTACTGCCGGTCGAAGAGGTCCAGACTCTTGCACTCCGACTACATGAACATGAC
TCCTAGAAGGCCCGGACCCACTAGAAAGCACTACCAGCCGTACGCCCCTCCTCGGG
ATTTCGCCGCATACCGGTCCAGAGTGAAGTTCAGCCGCTCAGCCGATGCACCGGCCT
ACCAGCAGGGACAGAACCAGCTCTACAACGAGCTCAACCTGGGTCGGCGGGAAGA
ATATGACGTGCTGGACAAACGGCGCGGCAGAGATCCGGAGATGGGGGGAAAGCCG
AGGAGGAAGAACCCTCAAGAGGGCCTGTACAACGAACTGCAGAAGGACAAGATGG
CGGAAGCCTACTCCGAGATCGGCATGAAGGGAGAACGCCGGAGAGGGAAGGGTCA
TGACGGACTGTACCAGGGCCTGTCAACTGCCACTAAGGACACTTACGATGCGCTCCA
TATGCAAGCTTTGCCCCCGCGGCGCGCGAAACGCGGCAGCGGCGCGACCAACTTTA
GCCTGCTGAAACAGGCGGGCGATGTGGAAGAAAACCCGGGCCCGCGAGCAAAGAG
GAATATTATGCTTCTATTAGTGACTTCCCTTTTGCTGTGCGAGTTGCCACACCCCGCC
TTCCTGCTTATTCCCCAGGTACAGCTCCAGCAGAGTGGCCCAGGGCTCGTGAAGCCA
AGCCAGACGCTGTCCCTGACTTGTGCAATTTCAGGGGATTCAGTTTCATCAAATAGC
GCGGCGTGGAATTGGATTCGACAATCTCCTTCCCGAGGGTTGGAATGGCTTGGACGA
ACATATTACAGATCCAAATGGTATAACGACTATGCGGTATCAGTAAAGTCAAGAAT
AACCATTAACCCCGACACAAGCAAGAACCAATTCTCTTTGCAGCTTAACTCTGTCAC
GCCAGAAGACACGGCAGTCTATTATTGCGCTCGCGAGGTAACGGGTGACCTGGAAG
ACGCTTTTGACATTTGGGGGCAGGGTACGATGGTGACAGTCAGTTCAGGGGGCGGT
GGGAGTGGGGGAGGGGGTAGCGGGGGGGGAGGGTCAGACATTCAGATGACCCAGT
CCCCTTCATCCTTGTCTGCCTCCGTCGGTGACAGGGTGACAATAACATGCAGAGCAA
GCCAAACAATCTGGAGCTATCTCAACTGGTACCAGCAGCGACCAGGAAAAGCGCCA
AACCTGCTGATTTACGCTGCTTCCTCCCTCCAATCAGGCGTGCCTAGTAGATTTAGCG
GTAGGGGCTCCGGCACCGATTTTACGCTCACTATAAGCTCTCTTCAAGCAGAAGATT
TTGCGACTTATTACTGCCAGCAGTCCTATAGTATACCTCAGACTTTCGGACAGGGTA
CCAAGTTGGAGATTAAGGCTAGCGCAACCACTACGCCTGCTCCGCGGCCTCCAACG
CCCGCGCCCACGATAGCTAGTCAGCCGTTGTCTCTCCGACCAGAGGCGTGTAGACCG
GCCGCTGGCGGAGCCGTACATACTCGCGGACTCGACTTCGCTTGCGACATCTACATT
TGGGCACCCTTGGCTGGGACCTGTGGGGTGCTGTTGCTGTCCTTGGTTATTACGTTGT
ACTGCAAGAGGGGCCGGAAGAAGCTGCTTTACATCTTCAAGCAGCCGTTCATGCGG
CCCGTGCAGACGACTCAGGAAGAGGACGGATGCTCGTGCAGATTCCCTGAGGAGGA
AGAGGGGGGATGCGAACTGAGAGTCAAATTTTCCAGGTCCGCAGATGCCCCCGCGT
ACCAGCAAGGCCAGAACCAACTTTACAACGAACTGAACCTGGGTCGCCGGGAGGAA
TATGATGTGCTGGATAAACGAAGGGGGAGGGACCCTGAGATGGGAGGGAAACCTCG
CAGGAAAAACCCGCAGGAAGGTTTGTACAACGAGTTGCAGAAGGATAAGATGGCTG
AGGCTTACTCTGAAATAGGGATGAAGGGAGAGAGACGGAGAGGAAAAGGCCATGA
TGGCCTTTACCAGGGCTTGAGCACAGCAACAAAGGATACTTACGACGCTCTTCACAT
GCAAGCTCTGCCACCACGG SEQ ID NO: 54 amino acid sequence of D0043:
MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE
KVTMTCRASSSVNYMDWYQKKPGSSPKPWIYATSNLASGVPARFSGSGSGTSYSLTISR
VEAEDAATYYCQQWSFNPPTFGGGTKLEIKGGGGSGGGGSGGGGSGGGGSGGGGSDIQ
MTQTTSSLSASLGDRVTISCRASQDISKYLNWYQQKPDGTVKLLIYHTSRLHSGVPSRFS
GSGSGTDYSLTISNLEQEDIATYFCQQGNTLPYTFGGGTKLEITGSTSGSGKPGSGEGSTK
GEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSV
TVSSAAATTTPAPRPPTPAPTIASQPLSLRPEACRPAAGGAVHTRGLDFACDIYIWAPLAG
TCGVLLLSLVITLYCRSKRSRLLHSDYMNMTPRRPGPTRKHYQPYAPPRDFAAYRSRVK
FSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPRRAKRG
SGATNFSLLKQAGDVEENPGPRAKRNIMLLLVTSLLLCELPHPAFLLIPQVQLQQSGPGL
VKPSQTLSLTCAISGDSVSSNSAAWNWIRQSPSRGLEWLGRTYYRSKWYNDYAVSVKS
RITINPDTSKNQFSLQLNSVTPEDTAVYYCAREVTGDLEDAFDIWGQGTMVTVSSGGGG
SGGGGSGGGGSDIQMTQSPSSLSASVGDRVTITCRASQTIWSYLNWYQQRPGKAPNLLI
YAASSLQSGVPSRFSGRGSGTDFTLTISSLQAEDFATYYCQQSYSIPQTFGQGTKLEIKAS
ATTTPAPRPPTPAPTIASQPLSLRPEACRPAAGGAVHTRGLDFACDIYIWAPLAGTCGVL
LLSLVITLYCKRGRKKLLYIFKQPFMRPVQTTQEEDGCSCRFPEEEEGGCELRVKFSRSA
DAPAYQQGQNQLYNELNLGRREEYDVLDKRRGRDPEMGGKPRRKNPQEGLYNELQKD
KMAEAYSEIGMKGERRRGKGHDGLYQGLSTATKDTYDALHMQALPPR SEQ ID NO: 55 nucleotide sequence of D0044:
ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG
GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG -continued CCGACTACTACTGCGCACGGTCCAACTACTATGGAAGCTCGTACTGGTTCTTCGATG
TCTGGGGGGCCGGCACCACTGTGACCGTCAGCTCCGGGGGGGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT
GCCAGCAGTGGTCCTTCAACCCGCCGACTTTTGGAGGCGGTACTAAGCTGGAGATCA
AAGGAGGCGGCGGCAGCGGCGGGGGAGGGTCCGGAGGGGGTGGTTCTGGTGGAGG
AGGATCGGGAGGCGGTGGCAGCGACATTCAGATGACTCAGACCACCTCCTCCCTGT
CCGCCTCCCTGGGCGACCGCGTGACCATCTCATGCCGCGCCAGCCAGGACATCTCGA
AGTACCTCAACTGGTACCAGCAGAAGCCCGACGGAACCGTGAAGCTCCTGATCTAC
CACACCTCCCGGCTGCACAGCGGAGTGCCGTCTAGATTCTCGGGTTCGGGGTCGGGA
ACTGACTACTCCCTTACTATTTCCAACCTGGAGCAGGAGGATATTGCCACCTACTTCT
GCCAACAAGGAAACACCCTGCCGTACACTTTTGGCGGGGGAACCAAGCTGGAAATC
ACTGGCAGCACATCCGGTTCCGGGAAGCCCGGCTCCGGAGAGGGCAGCACCAAGGG
GGAAGTCAAGCTGCAGGAATCAGGACCTGGCCTGGTGGCCCCGAGCCAGTCACTGT
CCGTGACTTGTACTGTGTCCGGAGTGTCGCTCCCGGATTACGGAGTGTCCTGGATCA
GGCAGCCACCTCGGAAAGGATTGGAATGGCTCGGAGTCATCTGGGGTTCCGAAACC
ACCTATTACAACTCGGCACTGAAATCCAGGCTCACCATTATCAAGGATAACTCCAAG
TCACAAGTGTTCCTGAAGATGAATAGCCTGCAGACTGACGACACGGCGATCTACTAT
TGCGCCAAGCACTACTACTACGGCGGATCCTACGCTATGGACTACTGGGGCCAGGG
GACCAGCGTGACCGTGTCATCCGCGGCCGCGACTACCACTCCTGCACCACGGCCACC
TACCCCAGCCCCCACCATTGCAAGCCAGCCACTTTCACTGCGCCCCGAAGCGTGTAG
ACCAGCTGCTGGAGGAGCCGTGCATACCCGAGGGCTGGACTTCGCCTGTGACATCT
ACATCTGGGCCCCATTGGCTGGAACTTGCGGCGTGCTGCTCTTGTCTCTGGTCATTAC
CCTGTACTGCCGGTCGAAGAGGTCCAGACTCTTGCACTCCGACTACATGAACATGAC
TCCTAGAAGGCCCGGACCCACTAGAAAGCACTACCAGCCGTACGCCCCTCCTCGGG
ATTTCGCCGCATACCGGTCCAGAGTGAAGTTCAGCCGCTCAGCCGATGCACCGGCCT
ACCAGCAGGGACAGAACCAGCTCTACAACGAGCTCAACCTGGGTCGGCGGGAAGA
ATATGACGTGCTGGACAAACGGCGCGGCAGAGATCCGGAGATGGGGGGAAAGCCG
AGGAGGAAGAACCCTCAAGAGGGCCTGTACAACGAACTGCAGAAGGACAAGATGG
CGGAAGCCTACTCCGAGATCGGCATGAAGGGAGAACGCCGGAGAGGGAAGGGTCA
TGACGGACTGTACCAGGGCCTGTCAACTGCCACTAAGGACACTTACGATGCGCTCCA
TATGCAAGCTTTGCCCCCGCGGCGCGCGAAACGCGGCAGCGGCGCGACCAACTTTA
GCCTGCTGAAACAGGCGGGCGATGTGGAAGAAAACCCGGGCCCGCGAGCAAAGAG
GAATATTATGTTGCTGCTCGTGACCTCGCTCCTTCTGTGCGAGCTGCCCCATCCGGCT
TTTCTGCTCATCCCTCAAGTGCAGCTGCAGCAGTCCGGTCCTGGACTGGTCAAGCCG
TCCCAGACTCTGAGCCTGACTTGCGCAATTAGCGGGGACTCAGTCTCGTCCAATTCG
GCGGCCTGGAACTGGATCCGGCAGTCACCATCAAGGGGCCTGGAATGGCTCGGGCG
CACTTACTACCGGTCCAAATGGTATACCGACTACGCCGTGTCCGTGAAGAATCGGAT
CACCATTAACCCCGACACCTCGAAGAACCAGTTCTCACTCCAACTGAACAGCGTGAC
CCCCGAGGATACCGCGGTGTACTACTGCGCACAAGAAGTGGAACCGCAGGACGCCT
TCGACATTTGGGGACAGGGAACGATGGTCACAGTGTCGTCCGGTGGAGGAGGTTCC
GGAGGCGGTGGATCTGGAGGCGGAGGTTCGGATATCCAGATGACCCAGAGCCCCTC
CTCGGTGTCCGCATCCGTGGGCGATAAGGTCACCATTACCTGTAGAGCGTCCCAGGA
CGTGTCCGGATGGCTGGCCTGGTACCAGCAGAAGCCAGGCTTGGCTCCTCAACTGCT
GATCTTCGGCGCCAGCACTCTTCAGGGGGAAGTGCCATCACGCTTCTCCGGATCCGG
TTCCGGCACCGACTTCACCCTGACCATCAGCAGCCTCCAGCCTGAGGACTTCGCCAC
TTACTACTGCCAACAGGCCAAGTACTTCCCCTATACCTTCGGAAGAGGCACTAAGCT
GGAAATCAAGGCTAGCGCAACCACTACGCCTGCTCCGCGGCCTCCAACGCCCGCGC
CCACGATAGCTAGTCAGCCGTTGTCTCTCCGACCAGAGGCGTGTAGACCGGCCGCTG
GCGGAGCCGTACATACTCGCGGACTCGACTTCGCTTGCGACATCTACATTTGGGCAC
CCTTGGCTGGGACCTGTGGGGTGCTGTTGCTGTCCTTGGTTATTACGTTGTACTGCAA
GAGGGGCCGGAAGAAGCTGCTTTACATCTTCAAGCAGCCGTTCATGCGGCCCGTGC
AGACGACTCAGGAAGAGGACGGATGCTCGTGCAGATTCCCTGAGGAGGAAGAGGG
GGGATGCGAACTGAGAGTCAAATTTTCCAGGTCCGCAGATGCCCCCGCGTACCAGC
AAGGCCAGAACCAACTTTACAACGAACTGAACCTGGGTCGCCGGGAGGAATATGAT
GTGCTGGATAAACGAAGGGGGAGGGACCCTGAGATGGGAGGGAAACCTCGCAGGA
AAAACCCGCAGGAAGGTTTGTACAACGAGTTGCAGAAGGATAAGATGGCTGAGGCT
TACTCTGAAATAGGGATGAAGGGAGAGAGACGGAGAGGAAAAGGCCATGATGGCC
TTTACCAGGGCTTGAGCACAGCAACAAAGGATACTTACGACGCTCTTCACATGCAAG
CTCTGCCACCACGG SEQ ID NO: 56 amino acid sequence of D0044:
MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE
KVTMTCRASSSVNYMDWYQKKPGSSPKPWIYATSNLASGVPARFSGSGSGTSYSLTISR
VEAEDAATYYCQQWSFNPPTFGGGTKLEIKGGGGSGGGGSGGGGSGGGGSGGGGSDIQ
MTQTTSSLSASLGDRVTISCRASQDISKYLNWYQQKPDGTVKLLIYHTSRLHSGVPSRFS
GSGSGTDYSLTISNLEQEDIATYFCQQGNTLPYTFGGGTKLEITGSTSGSGKPGSGEGSTK
GEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSV
TVSSAAATTTPAPRPPTPAPTIASQPLSLRPEACRPAAGGAVHTRGLDFACDIYIWAPLAG
TCGVLLLSLVITLYCRSKRSRLLHSDYMNMTPRRPGPTRKHYQPYAPPRDFAAYRSRVK
FSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPRRAKRG
SGATNFSLLKQAGDVEENPGPRAKRNIMLLLVTSLLLCELPHPAFLLIPQVQLQQSGPGL
VKPSQTLSLTCAISGDSVSSNSAAWNWIRQSPSRGLEWLGRTYYRSKWYTDYAVSVKN
RITINPDTSKNQFSLQLNSVTPEDTAVYYCAQEVEPQDAFDIWGQGTMVTVSSGGGGSG -continued GGGSGGGGSDIQMTQSPSSVSASVGDKVTITCRASQDVSGWLAWYQQKPGLAPQLLIF
GASTLQGEVPSRFSGSGSGTDFTLTISSLQPEDFATYYCQQAKYFPYTFGRGTKLEIKASA
TTTPAPRPPTPAPTIASQPLSLRPEACRPAAGGAVHTRGLDFACDIYIWAPLAGTCGVLLL
SLVITLYCKRGRKKLLYIFKQPFMRPVQTTQEEDGCSCRFPEEEEGGCELRVKFSRSADA
PAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPR SEQ ID NO: 59 nucleotide sequence of D0046
ATGCTTCTTTTGGTGACTTCCCTTTTGCTGTGCGAGTTGCCACACCCCGCCTTCCTGC
TTATTCCCCAGGTACAGCTCCAGCAGAGTGGCCCAGGGCTCGTGAAGCCAAGCCAG
ACGCTGTCCCTGACTTGTGCAATTTCAGGGGATTCAGTTTCATCAAATAGCGCGGCG
TGGAATTGGATTCGACAATCTCCTTCCCGAGGGTTGGAATGGCTTGGACGAACATAT
TACAGATCCAAATGGTATAACGACTATGCGGTATCAGTAAAGTCAAGAATAACCAT
TAACCCCGACACAAGCAAGAACCAATTCTCTTTGCAGCTTAACTCTGTCACGCCAGA
AGACACGGCAGTCTATTATTGCGCTCGCGAGGTAACGGGTGACCTGGAAGACGCTTT
TGACATTTGGGGGCAGGGTACGATGGTGACAGTCAGTTCAGGGGGCGGTGGGAGTG
GGGGAGGGGGTAGCGGGGGGGGAGGGTCAGACATTCAGATGACCCAGTCCCCTTCA
TCCTTGTCTGCCTCCGTCGGTGACAGGGTGACAATAACATGCAGAGCAAGCCAAAC
AATCTGGAGCTATCTCAACTGGTACCAGCAGCGACCAGGAAAAGCGCCAAACCTGC
TGATTTACGCTGCTTCCTCCCTCCAATCAGGCGTGCCTAGTAGATTTAGCGGTAGGG
GCTCCGGCACCGATTTTACGCTCACTATAAGCTCTCTTCAAGCAGAAGATTTTGCGA
CTTATTACTGCCAGCAGTCCTATAGTATACCTCAGACTTTCGGACAGGGTACCAAGT
TGGAGATTAAGGCGGCCGCTACCACAACCCCTGCGCCCCGGCCTCCTACCCCCGCAC
CCACGATTGCTTCTCAACCTCTTTCACTCCGACCTGAGGCTTGTAGACCTGCAGCCG
GGGGTGCCGTCCACACACGGGGACTCGACTTCGCTTGTGATATATATATTTGGGCGC
CCCTGGCCGGCACTTGTGGAGTTCTTTTGCTCTCTCTTGTTATCACATTGTACTGCAA
GCGAGGTAGGAAGAAATTGCTTTACATTTTTAAGCAGCCGTTCATGCGACCAGTACA
GACTACTCAAGAAGAAGATGGGTGCTCTTGTCGGTTCCCGGAAGAAGAAGAGGGTG
GTTGCGAGTTGAGGGTGAAGTTCTCCCGCTCTGCCGACGCACCGGCATATCAGCAGG
GACAAAACCAGCTCTACAACGAATTGAACCTGGGTCGGCGGGAAGAATATGACGTG
CTCGATAAGCGGCGGGGTCGCGACCCAGAAATGGGAGGCAAACCGCGCAGGAAAA
ATCCACAGGAGGGACTTTATAACGAACTTCAAAAGGATAAGATGGCAGAGGCATAC
AGCGAAATCGGGATGAAAGGCGAGAGAAGAAGGGGGAAAGGGCACGATGGTCTTT
ACCAGGGGCTTTCTACCGCGACGAAGGATACCTACGATGCTCTCCATATGCAAGCAC
TTCCTCCTAGACGGGCAAAGCGGGGCTCAGGGGCGACTAACTTTTCACTGTTGAAGC
AGGCCGGGGATGTGGAGGAGAATCCTGGTCCTAGAGCTAAGCGAGTAGACATGGCC
CTGCCCGTCACTGCGCTGCTTCTTCCACTTGCGCTTCTGCTGCACGCAGCGCGCCCGG
AAGTCCAGCTCCAGCAAAGCGGAGCCGAACTCGTGAAGCCGGGGGCCTCCGTGAAG
ATGAGCTGCAAGGCATCCGGCTACACCTTCACTAGCTACAACATGCACTGGGTGAA
GCAGACTCCGGGTCAAGGGCTGGAGTGGATTGGGGCGATCTACCCGGGCAACGGCG
ACACCTCCTACAACCAAAAGTTCAAGGGGAAGGCTACTCTTACGGCGGACAAGTCG
TCCAGCACCGCATACATGCAACTCTCCTCCCTGACCTCCGAGGACTCGGCGGACTAC
TACTGCGCCCGGAGCAACTACTACGGTTCCTCCTACTGGTTCTTCGACGTGTGGGGT
GCCGGAACTACTGTGACTGTGTCCTCCGGTGGTGGCGGATCAGGCGGCGGGGGATC
CGGCGGTGGAGGATCCGACATTGTGCTGACTCAGTCCCCCGCAATCCTTTCGGCCTC
CCCCGGAGAGAAGGTCACGATGACTTGCAGGGCTTCGTCCTCCGTGAACTACATGG
ATTGGTACCAAAAGAAGCCCGGGTCGTCGCCTAAGCCGTGGATCTACGCTACCTCA
AACCTGGCTTCCGGCGTCCCTGCGCGGTTCAGCGGCTCGGGGAGCGGTACCTCATAC
TCACTCACCATCTCCCGGGTGGAGGCCGAAGATGCGGCCACCTATTATTGCCAACAG
TGGTCCTTCAATCCGCCCACCTTCGGGGGGGGAACCAAGCTCGAGATCAAGGGGGG
TGGCGGCTCAGGGGGAGGCGGAAGCGGAGGGGGTGGCTCGGGCGGCGGCGGTTCC
GGCGGCGGAGGGTCCGATATCCAAATGACCCAGACTACTAGCTCGTTGAGCGCCTC
GCTCGGCGACAGAGTGACCATTAGCTGCAGGGCATCCCAGGACATTTCAAAGTACC
TGAACTGGTACCAACAGAAGCCCGACGGAACTGTGAAGCTCCTGATCTACCACACC
TCCCGGCTGCACTCCGGAGTCCCGTCGAGATTTTCCGGCTCCGGAAGCGGAACCGAT
TATTCGCTCACCATTTCTAACCTGGAACAGGAGGACATTGCCACTTACTTCTGTCAA
CAAGGAAACACTCTGCCTTACACCTTTGGTGGCGGAACCAAGTTGGAAATTACCGGC
TCCACCTCCGGATCCGGAAAGCCTGGATCCGGAGAGGGATCAACCAAGGGAGAAGT
GAAGCTGCAGGAGAGCGGGCCCGGCCTTGTCGCCCCGAGCCAGTCCTTGTCCGTGA
CCTGTACTGTCTCCGGAGTCAGCCTGCCGGACTACGGGGTGTCCTGGATCCGCCAGC
CGCCTCGCAAGGGCCTGGAGTGGCTCGGCGTGATCTGGGGATCCGAAACGACTTAC
TACAACTCGGCCCTCAAGTCGAGGCTCACTATTATCAAGGACAACTCGAAGTCCCAG
GTGTTCCTCAAGATGAACTCGCTGCAAACCGACGACACAGCGATCTACTACTGTGCA
AAGCATTACTACTACGGAGGCAGCTACGCAATGGACTACTGGGGACAGGGAACCTC
CGTGACTGTCTCTAGCGCTAGCGCGACCACTACGCCCGCCCCCCGCCCACCTACCCC
CGCCCCGACCATTGCGAGCCAACCGTTGTCACTCCGCCCGGAAGCCTGCCGCCCCGC
CGCTGGCGGAGCCGTGCACACCCGGGGACTGGACTTCGCATGCGACATCTACATTTG
GGCCCCGCTGGCTGGAACCTGTGGAGTCCTGCTGCTCTCCCTCGTGATCACTCTGTA
CTGCCGGTCGAAGCGCTCAAGACTGCTGCACTCAGACTACATGAACATGACTCCTCG
GCGGCCGGGGCCGACTCGGAAGCACTACCAGCCTTACGCACCCCCGAGAGATTTCG
CGGCCTACCGCTCCCGGGTCAAGTTTTCCCGGTCTGCCGACGCTCCGGCGTACCAGC
AGGGGCAGAACCAGCTCTACAATGAGCTGAATCTGGGTCGGAGAGAAGAGTACGAT
GTGCTGGATAAGCGGAGAGGCAGAGATCCAGAAATGGGAGGAAAGCCTCGGAGAA
AGAACCCACAGGAGGGACTGTATAATGAGCTGCAGAAGGACAAAATGGCCGAAGC
CTACAGCGAGATCGGCATGAAGGGAGAGCGGCGCAGAGGGAAGGGACATGACGGC
CTGTACCAGGGTCTGAGCACCGCGACTAAGGACACCTACGATGCCCTTCATATGCAA
GCACTCCCTCCGCGC SEQ ID NO: 60 amino acid sequence of D0046:
MLLLVTSLLLCELPHPAFLLIPQVQLQQSGPGLVKPSQTLSLTCAISGDSVSSNSAAWNW
IRQSPSRGLEWLGRTYYRSKWYNDYAVSVKSRITINPDTSKNQFSLQLNSVTPEDTAVY -continued YCAREVTGDLEDAFDIWGQGTMVTVSSGGGGSGGGGSGGGGSDIQMTQSPSSLSASVG
DRVTITCRASQTIWSYLNWYQQRPGKAPNLLIYAASSLQSGVPSRFSGRGSGTDFTLTISS
LQAEDFATYYCQQSYSIPQTFGQGTKLEIKAAATTTPAPRPPTPAPTIASQPLSLRPEACR
PAAGGAVHTRGLDFACDIYIWAPLAGTCGVLLLSLVITLYCKRGRKKLLYIFKQPFMRP
VQTTQEEDGCSCRFPEEEEGGCELRVKFSRSADAPAYQQGQNQLYNELNLGRREEYDV
LDKRRGRDPEMGGKPRRKNPQEGLYNELQKDKMAEAYSEIGMKGERRRGKGHDGLY
QGLSTATKDTYDALHMQALPPRRAKRGSGATNFSLLKQAGDVEENPGPRAKRVDMAL
PVTALLLPLALLLHAARPEVQLQQSGAELVKPGASVKMSCKASGYTFTSYNMHWVKQ
TPGQGLEWIGAIYPGNGDTSYNQKFKGKATLTADKSSSTAYMQLSSLTSEDSADYYCAR
SNYYGSSYWFFDVWGAGTTVTVSSGGGGSGGGGSGGGGSDIVLTQSPAILSASPGEKVT
MTCRASSSVNYMDWYQKKPGSSPKPWIYATSNLASGVPARFSGSGSGTSYSLTISRVEA
EDAATYYCQQWSFNPPTFGGGTKLEIKGGGGSGGGGSGGGGSGGGGSGGGGSDIQMT
QTTSSLSASLGDRVTISCRASQDISKYLNWYQQKPDGTVKLLIYHTSRLHSGVPSRFSGS
GSGTDYSLTISNLEQEDIATYFCQQGNTLPYTFGGGTKLEITGSTSGSGKPGSGEGSTKGE
VKLQESGPGLVAPSQSLSVTCTVSGVSLPDYGVSWIRQPPRKGLEWLGVIWGSETTYYN
SALKSRLTIIKDNSKSQVFLKMNSLQTDDTAIYYCAKHYYYGGSYAMDYWGQGTSVTV
SSASATTTPAPRPPTPAPTIASQPLSLRPEACRPAAGGAVHTRGLDFACDIYIWAPLAGTC
GVLLLSLVITLYCRSKRSRLLHSDYMNMTPRRPGPTRKHYQPYAPPRDFAAYRSRVKFS
RSADAPAYQQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR SEQ ID NO: 61 nucleotide sequence of D0047:
ATGTTGCTGCTCGTGACCTCGCTCCTTCTGTGCGAGCTGCCCCATCCGGCTTTTCTGC
TCATCCCTCAAGTGCAGCTGCAGCAGTCCGGTCCTGGACTGGTCAAGCCGTCCCAGA
CTCTGAGCCTGACTTGCGCAATTAGCGGGGACTCAGTCTCGTCCAATTCGGCGGCCT
GGAACTGGATCCGGCAGTCACCATCAAGGGGCCTGGAATGGCTCGGGCGCACTTAC
TACCGGTCCAAATGGTATACCGACTACGCCGTGTCCGTGAAGAATCGGATCACCATT
AACCCCGACACCTCGAAGAACCAGTTCTCACTCCAACTGAACAGCGTGACCCCCGA
GGATACCGCGGTGTACTACTGCGCACAAGAAGTGGAACCGCAGGACGCCTTCGACA
TTTGGGGACAGGGAACGATGGTCACAGTGTCGTCCGGTGGAGGAGGTTCCGGAGGC
GGTGGATCTGGAGGCGGAGGTTCGGATATCCAGATGACCCAGAGCCCCTCCTCGGT
GTCCGCATCCGTGGGCGATAAGGTCACCATTACCTGTAGAGCGTCCCAGGACGTGTC
CGGATGGCTGGCCTGGTACCAGCAGAAGCCAGGCTTGGCTCCTCAACTGCTGATCTT
CGGCGCCAGCACTCTTCAGGGGGAAGTGCCATCACGCTTCTCCGGATCCGGTTCCGG
CACCGACTTCACCCTGACCATCAGCAGCCTCCAGCCTGAGGACTTCGCCACTTACTA
CTGCCAACAGGCCAAGTACTTCCCCTATACCTTCGGAAGAGGCACTAAGCTGGAAA
TCAAGGCGGCCGCTACCACAACCCCTGCGCCCCGGCCTCCTACCCCCGCACCCACGA
TTGCTTCTCAACCTCTTTCACTCCGACCTGAGGCTTGTAGACCTGCAGCCGGGGGTG
CCGTCCACACACGGGGACTCGACTTCGCTTGTGATATATATATTTGGGCGCCCCTGG
CCGGCACTTGTGGAGTTCTTTTGCTCTCTCTTGTTATCACATTGTACTGCAAGCGAGG
TAGGAAGAAATTGCTTTACATTTTTAAGCAGCCGTTCATGCGACCAGTACAGACTAC
TCAAGAAGAAGATGGGTGCTCTTGTCGGTTCCCGGAAGAAGAAGAGGGTGGTTGCG
AGTTGAGGGTGAAGTTCTCCCGCTCTGCCGACGCACCGGCATATCAGCAGGGACAA
AACCAGCTCTACAACGAATTGAACCTGGGTCGGCGGGAAGAATATGACGTGCTCGA
TAAGCGGCGGGGTCGCGACCCAGAAATGGGAGGCAAACCGCGCAGGAAAAATCCA
CAGGAGGGACTTTATAACGAACTTCAAAAGGATAAGATGGCAGAGGCATACAGCGA
AATCGGGATGAAAGGCGAGAGAAGAAGGGGGAAAGGGCACGATGGTCTTTACCAG
GGGCTTTCTACCGCGACGAAGGATACCTACGATGCTCTCCATATGCAAGCACTTCCT
CCTAGACGGGCAAAGCGGGGCTCAGGGGCGACTAACTTTTCACTGTTGAAGCAGGC
CGGGGATGTGGAGGAGAATCCTGGTCCTAGAGCTAAGCGAGTAGACATGGCCCTGC
CCGTCACTGCGCTGCTTCTTCCACTTGCGCTTCTGCTGCACGCAGCGCGCCCGGAAG
TCCAGCTCCAGCAAAGCGGAGCCGAACTCGTGAAGCCGGGGGCCTCCGTGAAGATG
AGCTGCAAGGCATCCGGCTACACCTTCACTAGCTACAACATGCACTGGGTGAAGCA
GACTCCGGGTCAAGGGCTGGAGTGGATTGGGGCGATCTACCCGGGCAACGGCGACA
CCTCCTACAACCAAAAGTTCAAGGGGAAGGCTACTCTTACGGCGGACAAGTCGTCC
AGCACCGCATACATGCAACTCTCCTCCCTGACCTCCGAGGACTCGGCGGACTACTAC
TGCGCCCGGAGCAACTACTACGGTTCCTCCTACTGGTTCTTCGACGTGTGGGGTGCC
GGAACTACTGTGACTGTGTCCTCCGGTGGTGGCGGATCAGGCGGCGGGGGATCCGG
CGGTGGAGGATCCGACATTGTGCTGACTCAGTCCCCCGCAATCCTTTCGGCCTCCCC
CGGAGAGAAGGTCACGATGACTTGCAGGGCTTCGTCCTCCGTGAACTACATGGATTG
GTACCAAAAGAAGCCCGGGTCGTCGCCTAAGCCGTGGATCTACGCTACCTCAAACC
TGGCTTCCGGCGTCCCTGCGCGGTTCAGCGGCTCGGGGAGCGGTACCTCATACTCAC
TCACCATCTCCCGGGTGGAGGCCGAAGATGCGGCCACCTATTATTGCCAACAGTGGT
CCTTCAATCCGCCCACCTTCGGGGGGGGAACCAAGCTCGAGATCAAGGGGGGTGGC
GGCTCAGGGGGAGGCGGAAGCGGAGGGGGTGGCTCGGGCGGCGGCGGTTCCGGCG
GCGGAGGGTCCGATATCCAAATGACCCAGACTACTAGCTCGTTGAGCGCCTCGCTCG
GCGACAGAGTGACCATTAGCTGCAGGGCATCCCAGGACATTTCAAAGTACCTGAAC
TGGTACCAACAGAAGCCCGACGGAACTGTGAAGCTCCTGATCTACCACACCTCCCG
GCTGCACTCCGGAGTCCCGTCGAGATTTTCCGGCTCCGGAAGCGGAACCGATTATTC
GCTCACCATTTCTAACCTGGAACAGGAGGACATTGCCACTTACTTCTGTCAACAAGG
AAACACTCTGCCTTACACCTTTGGTGGCGGAACCAAGTTGGAAATTACCGGCTCCAC
CTCCGGATCCGGAAAGCCTGGATCCGGAGAGGGATCAACCAAGGGAGAAGTGAAG
CTGCAGGAGAGCGGGCCCGGCCTTGTCGCCCCGAGCCAGTCCTTGTCCGTGACCTGT
ACTGTCTCCGGAGTCAGCCTGCCGGACTACGGGGTGTCCTGGATCCGCCAGCCGCCT
CGCAAGGGCCTGGAGTGGCTCGGCGTGATCTGGGGATCCGAAACGACTTACTACAA
CTCGGCCCTCAAGTCGAGGCTCACTATTATCAAGGACAACTCGAAGTCCCAGGTGTT
CCTCAAGATGAACTCGCTGCAAACCGACGACACAGCGATCTACTACTGTGCAAAGC
ATTACTACTACGGAGGCAGCTACGCAATGGACTACTGGGGACAGGGAACCTCCGTG
ACTGTCTCTAGCGCTAGCGCGACCACTACGCCCGCCCCCCGCCCACCTACCCCCGCC
CCGACCATTGCGAGCCAACCGTTGTCACTCCGCCCGGAAGCCTGCCGCCCCGCCGCT
GGCGGAGCCGTGCACACCCGGGGACTGGACTTCGCATGCGACATCTACATTTGGGC -continued CCCGCTGGCTGGAACCTGTGGAGTCCTGCTGCTCTCCCTCGTGATCACTCTGTACTGC
CGGTCGAAGCGCTCAAGACTGCTGCACTCAGACTACATGAACATGACTCCTCGGCG
GCCGGGGCCGACTCGGAAGCACTACCAGCCTTACGCACCCCCGAGAGATTTCGCGG
CCTACCGCTCCCGGGTCAAGTTTTCCCGGTCTGCCGACGCTCCGGCGTACCAGCAGG
GGCAGAACCAGCTCTACAATGAGCTGAATCTGGGTCGGAGAGAAGAGTACGATGTG
CTGGATAAGCGGAGAGGCAGAGATCCAGAAATGGGAGGAAAGCCTCGGAGAAAGA
ACCCACAGGAGGGACTGTATAATGAGCTGCAGAAGGACAAAATGGCCGAAGCCTAC
AGCGAGATCGGCATGAAGGGAGAGCGGCGCAGAGGGAAGGGACATGACGGCCTGT
ACCAGGGTCTGAGCACCGCGACTAAGGACACCTACGATGCCCTTCATATGCAAGCA
CTCCCTCCGCGC SEQ ID NO: 62 amino acid sequence of D0047:
MLLLVTSLLLCELPHPAFLLIPQVQLQQSGPGLVKPSQTLSLTCAISGDSVSSNSAAWNW
IRQSPSRGLEWLGRTYYRSKWYTDYAVSVKNRITINPDTSKNQFSLQLNSVTPEDTAVY
YCAQEVEPQDAFDIWGQGTMVTVSSGGGGSGGGGSGGGGSDIQMTQSPSSVSASVGDK
VTITCRASQDVSGWLAWYQQKPGLAPQLLIFGASTLQGEVPSRFSGSGSGTDFTLTISSL
QPEDFATYYCQQAKYFPYTFGRGTKLEIKAAATTTPAPRPPTPAPTIASQPLSLRPEACRP
AAGGAVHTRGLDFACDIYIWAPLAGTCGVLLLSLVITLYCKRGRKKLLYIFKQPFMRPV
QTTQEEDGCSCRFPEEEEGGCELRVKFSRSADAPAYQQGQNQLYNELNLGRREEYDVL
DKRRGRDPEMGGKPRRKNPQEGLYNELQKDKMAEAYSEIGMKGERRRGKGHDGLYQ
GLSTATKDTYDALHMQALPPRRAKRGSGATNFSLLKQAGDVEENPGPRAKRVDMALP
VTALLLPLALLLHAARPEVQLQQSGAELVKPGASVKMSCKASGYTFTSYNMHWVKQT
PGQGLEWIGAIYPGNGDTSYNQKFKGKATLTADKSSSTAYMQLSSLTSEDSADYYCARS
NYYGSSYWFFDVWGAGTTVTVSSGGGGSGGGGSGGGGSDIVLTQSPAILSASPGEKVT
MTCRASSSVNYMDWYQKKPGSSPKPWIYATSNLASGVPARFSGSGSGTSYSLTISRVEA
EDAATYYCQQWSFNPPTFGGGTKLEIKGGGGSGGGGSGGGGSGGGGSGGGGSDIQMT
QTTSSLSASLGDRVTISCRASQDISKYLNWYQQKPDGTVKLLIYHTSRLHSGVPSRFSGS
GSGTDYSLTISNLEQEDIATYFCQQGNTLPYTFGGGTKLEITGSTSGSGKPGSGEGSTKGE
VKLQESGPGLVAPSQSLSVTCTVSGVSLPDYGVSWIRQPPRKGLEWLGVIWGSETTYYN
SALKSRLTIIKDNSKSQVFLKMNSLQTDDTAIYYCAKHYYYGGSYAMDYWGQGTSVTV
SSASATTTPAPRPPTPAPTIASQPLSLRPEACRPAAGGAVHTRGLDFACDIYIWAPLAGTC
GVLLLSLVITLYCRSKRSRLLHSDYMNMTPRRPGPTRKHYQPYAPPRDFAAYRSRVKFS
RSADAPAYQQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR SEQ ID NO: 65 nucleotide sequence of D0001:
ATGCTTCTTTTGGTGACTTCCCTTTTGCTGTGCGAGTTGCCACACCCCGCCTTCCTGC
TTATTCCCCAGGTACAGCTTCAACAGAGTGGGCCGGGACTGGTGAAACACTCCCAA
ACACTTTCTCTGACGTGCGCTATATCAGGTGACTCTGTTTCATCTAATTCTGCTGCGT
GGAACTGGATTCGACAATCTCCCAGTCGCGGGTTGGAATGGCTGGGACGAACATAT
TATCGGTCTAAGTGGTATAACGATTATGCTGTATCTGTTAAATCTCGAATTACGATTA
ATCCTGACACCTCCAAGAACCAGTTCTCCCTCCAGTTGAACTCAGTCACACCGGAAG
ACACTGCGGTCTACTATTGCGCTCAAGAAGTCGAGCCACATGATGCATTCGACATCT
GGGGCCAGGGAACGATGGTCACCGTCAGCAGTGGCGGCGGCGGATCTGGGGGTGGC
GGTTCTGGCGGTGGAGGATCAGACATACAAATGACGCAGAGTCCCTCAAGTGTGTA
CGCGAGTGTGGGGGATAAGGTAACTATTACGTGCAGAGCGTCACAGGATGTTAGTG
GATGGCTTGCCTGGTATCAGCAGAAGCCAGGCCTTGCTCCACAGCTCCTTATCAGTG
GTGCTTCTACACTTCAGGGCGAGGTTCCGAGTAGATTCTCTGGTTCTGGATCTGGTA
CTGACTTCACTCTTACAATTTCTTCTTTGCAACCAGAAGACTTTGCGACTTATTACTG
CCAACAGGCCAAATACTTCCCTTATACATTTGGCCAAGGTACCAAGTTGGAGATAAA
GGCGGCCGCAACTACCACCCCTGCCCCTCGGCCGCCGACTCCGGCCCCAACCATCGC
AAGCCAACCCCTCTCCTTGCGCCCCGAAGCTTGCCGCCCGGCCGCGGGTGGAGCCGT
GCATACCCGGGGGCTGGACTTTGCCTGCGATATCTACATTTGGGCCCCGCTGGCCGG
CACTTGCGGCGTGCTCCTGCTGTCGCTGGTCATCACCCTTTACTGCAAGAGGGGCCG
GAAGAAGCTGCTTTACATCTTCAAGCAGCCGTTCATGCGGCCCGTGCAGACGACTCA
GGAAGAGGACGGATGCTCGTGCAGATTCCCTGAGGAGGAAGAGGGGGGATGCGAA
CTGCGCGTCAAGTTCTCACGGTCCGCCGACGCCCCCGCATATCAACAGGGCCAGAAT
CAGCTCTACAACGAGCTGAACCTGGGAAGGAGAGAGGAGTACGACGTGCTGGACAA
GCGACGCGGACGCGACCCGGAGATGGGGGGGAAACCACGGCGGAAAAACCCTCAG
GAAGGACTGTACAACGAACTCCAGAAAGACAAGATGGCGGAAGCCTACTCAGAAAT
CGGGATGAAGGGAGAGCGGAGGAGGGGAAAGGGTCACGACGGGCTGTACCAGGGA
CTGAGCACCGCCACTAAGGATACCTACGATGCCTTGCATATGCAAGCACTCCCACCC
CGG SEQ ID NO: 66 amino acid sequence of D0001:
MLLLVTSLLLCELPHPAFLLIPQVQLQQSGPGLVKHSQTLSLTCAISGDSVSSNSAAWNW
IRQSPSRGLEWLGRTYYRSKWYNDYAVSVKSRITINPDTSKNQFSLQLNSVTPEDTAVY
YCAQEVEPHDAFDIWGQGTMVTVSSGGGGSGGGGSGGGGSDIQMTQSPSSVYASVGD
KVTITCRASQDVSGWLAWYQQKPGLAPQLLISGASTLQGEVPSRFSGSGSGTDFTLTISS
LQPEDFATYYCQQAKYFPYTFGQGTKLEIKAAATTTPAPRPPTPAPTIASQPLSLRPEACR
PAAGGAVHTRGLDFACDIYIWAPLAGTCGVLLLSLVITLYCKRGRKKLLYIFKQPFMRP
VQTTQEEDGCSCRFPEEEEGGCELRVKFSRSADAPAYQQGQNQLYNELNLGRREEYDV
LDKRRGRDPEMGGKPRRKNPQEGLYNELQKDKMAEAYSEIGMKGERRRGKGHDGLY
QGLSTATKDTYDALHMQALPPR SEQ ID NO: 67 nucleotide sequence of D0002:
ATGTTGCTGCTCGTGACCTCGCTCCTTCTGTGCGAGCTGCCCCATCCGGCTTTTCTGC
TCATCCCTCAAGTGCAGCTGCAGCAGTCCGGTCCTGGACTGGTCAAGCCGTCCCAGA
CTCTGAGCCTGACTTGCGCAATTAGCGGGGACTCAGTCTCGTCCAATTCGGCGGCCT
GGAACTGGATCCGGCAGTCACCATCAAGGGGCCTGGAATGGCTCGGGCGCACTTAC
TACCGGTCCAAATGGTATACCGACTACGCCGTGTCCGTGAAGAATCGGATCACCATT -continued AACCCCGACACCTCGAAGAACCAGTTCTCACTCCAACTGAACAGCGTGACCCCCGA
GGATACCGCGGTGTACTACTGCGCACAAGAAGTGGAACCGCAGGACGCCTTCGACA
TTTGGGGACAGGGAACGATGGTCACAGTGTCGTCCGGTGGAGGAGGTTCCGGAGGC
GGTGGATCTGGAGGCGGAGGTTCGGATATCCAGATGACCCAGAGCCCCTCCTCGGT
GTCCGCATCCGTGGGCGATAAGGTCACCATTACCTGTAGAGCGTCCCAGGACGTGTC
CGGATGGCTGGCCTGGTACCAGCAGAAGCCAGGCTTGGCTCCTCAACTGCTGATCTT
CGGCGCCAGCACTCTTCAGGGGGAAGTGCCATCACGCTTCTCCGGATCCGGTTCCGG
CACCGACTTCACCCTGACCATCAGCAGCCTCCAGCCTGAGGACTTCGCCACTTACTA
CTGCCAACAGGCCAAGTACTTCCCCTATACCTTCGGAAGAGGCACTAAGCTGGAAA
TCAAGGCGGCCGCAACTACCACCCCTGCCCCTCGGCCGCCGACTCCGGCCCCAACCA
TCGCAAGCCAACCCCTCTCCTTGCGCCCCGAAGCTTGCCGCCCGGCCGCGGGTGGAG
CCGTGCATACCCGGGGGCTGGACTTTGCCTGCGATATCTACATTTGGGCCCCGCTGG
CCGGCACTTGCGGCGTGCTCCTGCTGTCGCTGGTCATCACCCTTTACTGCAAGAGGG
GCCGGAAGAAGCTGCTTTACATCTTCAAGCAGCCGTTCATGCGGCCCGTGCAGACG
ACTCAGGAAGAGGACGGATGCTCGTGCAGATTCCCTGAGGAGGAAGAGGGGGGAT
GCGAACTGCGCGTCAAGTTCTCACGGTCCGCCGACGCCCCCGCATATCAACAGGGC
CAGAATCAGCTCTACAACGAGCTGAACCTGGGAAGGAGAGAGGAGTACGACGTGCT
GGACAAGCGACGCGGACGCGACCCGGAGATGGGGGGGAAACCACGGCGGAAAAAC
CCTCAGGAAGGACTGTACAACGAACTCCAGAAAGACAAGATGGCGGAAGCCTACTC
AGAAATCGGGATGAAGGGAGAGCGGAGGAGGGGAAAGGGTCACGACGGGCTGTAC
CAGGGACTGAGCACCGCCACTAAGGATACCTACGATGCCTTGCATATGCAAGCACT
CCCACCCCGG SEQ ID NO: 68 amino acid sequence of D0002:
MLLLVTSLLLCELPHPAFLLIPQVQLQQSGPGLVKPSQTLSLTCAISGDSVSSNSAAWNW
IRQSPSRGLEWLGRTYYRSKWYTDYAVSVKNRITINPDTSKNQFSLQLNSVTPEDTAVY
YCAQEVEPQDAFDIWGQGTMVTVSSGGGGSGGGGSGGGGSDIQMTQSPSSVSASVGDK
VTITCRASQDVSGWLAWYQQKPGLAPQLLIFGASTLQGEVPSRFSGSGSGTDFTLTISSL
QPEDFATYYCQQAKYFPYTFGRGTKLEIKAAATTTPAPRPPTPAPTIASQPLSLRPEACRP
AAGGAVHTRGLDFACDIYIWAPLAGTCGVLLLSLVITLYCKRGRKKLLYIFKQPFMRPV
QTTQEEDGCSCRFPEEEEGGCELRVKFSRSADAPAYQQGQNQLYNELNLGRREEYDVL
DKRRGRDPEMGGKPRRKNPQEGLYNELQKDKMAEAYSEIGMKGERRRGKGHDGLYQ
GLSTATKDTYDALHMQALPPR SEQ ID NO: 69 nucleotide sequence of D0003:
ATGTTGCTGCTCGTGACCTCGCTCCTTCTGTGCGAGCTGCCCCATCCGGCTTTTCTGC
TCATCCCTCAAGTGCAGCTGCAGCAGTCCGGTCCTGGACTGGTCAAGCCGTCCCAGA
CTCTGAGCCTGACTTGCGCCATTAGCGGGAACTCAGTCTCGTCCAATTCGGCGGCCT
GGAACTGGATCCGGCAGTCACCATCAAGGGGCCTGGAATGGCTCGGGCGCACTTAC
TACCGGTCCAAATGGTATAACGACTACGCCGTGTCCGTGAAGTCCCGGATCACCATT
AACCCCGACACCTCGAAGAACCAGTTCTCACTCCAACTGAACAGCGTGACCCCCGA
GGATACCGCGGTGTACTACTGCGCACAAGAAGTGGAACCGCAGGACGCCTTCGACA
TTTGGGGACAGGGAACGATGGTCACAGTGTCGTCCGGTGGAGGAGGTTCCGGAGGC
GGTGGATCTGGAGGCGGAGGTTCGGATATCCAGATGACCCAGAGCCCCTCCTCGGT
GTCCGCATCCGTGGGCGATAAGGTCACCATTACCTGTAGAGCGTCCCAGGACGTGTC
CGGATGGCTGGCCTGGTACCAGCAGAAGCCAGGCTTGGCTCCTCAACTGCTGATCTT
TGGCGCCAGCACTCTTCAGGGGGAGGTGCCATCACGCTTCTCCGGAGGTGGTTCCGG
CACCGACTTCACCCTGACCATCAGCAGCCTCCAGCCTGAGGACTTCGCCACTTACTA
CTGCCAACAGGCCAAGTACTTCCCCTATACCTTCGGACAAGGCACTAAGCTGGAAAT
CAAGGCGGCCGCAACTACCACCCCTGCCCCTCGGCCGCCGACTCCGGCCCCAACCAT
CGCAAGCCAACCCCTCTCCTTGCGCCCCGAAGCTTGCCGCCCGGCCGCGGGTGGAGC
CGTGCATACCCGGGGGCTGGACTTTGCCTGCGATATCTACATTTGGGCCCCGCTGGC
CGGCACTTGCGGCGTGCTCCTGCTGTCGCTGGTCATCACCCTTTACTGCAAGAGGGG
CCGGAAGAAGCTGCTTTACATCTTCAAGCAGCCGTTCATGCGGCCCGTGCAGACGAC
TCAGGAAGAGGACGGATGCTCGTGCAGATTCCCTGAGGAGGAAGAGGGGGGATGC
GAACTGCGCGTCAAGTTCTCACGGTCCGCCGACGCCCCCGCATATCAACAGGGCCA
GAATCAGCTCTACAACGAGCTGAACCTGGGAAGGAGAGAGGAGTACGACGTGCTGG
ACAAGCGACGCGGACGCGACCCGGAGATGGGGGGGAAACCACGGCGGAAAAACCC
TCAGGAAGGACTGTACAACGAACTCCAGAAAGACAAGATGGCGGAAGCCTACTCAG
AAATCGGGATGAAGGGAGAGCGGAGGAGGGGAAAGGGTCACGACGGGCTGTACCA
GGGACTGAGCACCGCCACTAAGGATACCTACGATGCCTTGCATATGCAAGCACTCC
CACCCCGG SEQ ID NO: 70 amino acid sequence of D0003:
MLLLVTSLLLCELPHPAFLLIPQVQLQQSGPGLVKPSQTLSLTCAISGNSVSSNSAAWNW
IRQSPSRGLEWLGRTYYRSKWYNDYAVSVKSRITINPDTSKNQFSLQLNSVTPEDTAVY
YCAQEVEPQDAFDIWGQGTMVTVSSGGGGSGGGGSGGGGSDIQMTQSPSSVSASVGDK
VTITCRASQDVSGWLAWYQQKPGLAPQLLIFGASTLQGEVPSRFSGGGSGTDFTLTISSL
QPEDFATYYCQQAKYFPYTFGQGTKLEIKAAATTTPAPRPPTPAPTIASQPLSLRPEACRP
AAGGAVHTRGLDFACDIYIWAPLAGTCGVLLLSLVITLYCKRGRKKLLYIFKQPFMRPV
QTTQEEDGCSCRFPEEEEGGCELRVKFSRSADAPAYQQGQNQLYNELNLGRREEYDVL
DKRRGRDPEMGGKPRRKNPQEGLYNELQKDKMAEAYSEIGMKGERRRGKGHDGLYQ
GLSTATKDTYDALHMQALPPR SEQ ID NO: 73 nucleotide sequence of LTG2273:
ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG
GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG -continued CCGACTACTACTGCGCACGGTCCAACTACTATGGAAGCTCGTACTGGTTCTTCGATG
TCTGGGGGGCCGGCACCACTGTGACCGTCAGCTCCGGGGGCGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT
GCCAGCAGTGGTCCTTCAACCCGCCGACTTTTGGAGGCGGTACTAAGCTGGAGATCA
AAGGAGGCGGCGGCAGCGGCGGGGGAGGGTCCGGAGGGGGTGGTTCTGGTGGAGG
AGGATCGGGAGGCGGTGGCAGCGACATTCAGATGACTCAGACCACCTCCTCCCTGT
CCGCCTCCCTGGGCGACCGCGTGACCATCTCATGCCGCGCCAGCCAGGACATCTCGA
AGTACCTCAACTGGTACCAGCAGAAGCCCGACGGAACCGTGAAGCTCCTGATCTAC
CACACCTCCCGGCTGCACAGCGGAGTGCCGTCTAGATTCTCGGGTTCGGGGTCGGGA
ACTGACTACTCCCTTACTATTTCCAACCTGGAGCAGGAGGATATTGCCACCTACTTCT
GCCAACAAGGAAACACCCTGCCGTACACTTTTGGCGGGGGAACCAAGCTGGAAATC
ACTGGCAGCACATCCGGTTCCGGGAAGCCCGGCTCCGGAGAGGGCAGCACCAAGGG
GGAAGTCAAGCTGCAGGAATCAGGACCTGGCCTGGTGGCCCCGAGCCAGTCACTGT
CCGTGACTTGTACTGTGTCCGGAGTGTCGCTCCCGGATTACGGAGTGTCCTGGATCA
GGCAGCCACCTCGGAAAGGATTGGAATGGCTCGGAGTCATCTGGGGTTCCGAAACC
ACCTATTACAACTCGGCACTGAAATCCAGGCTCACCATTATCAAGGATAACTCCAAG
TCACAAGTGTTCCTGAAGATGAATAGCCTGCAGACTGACGACACGGCGATCTACTAT
TGCGCCAAGCACTACTACTACGGCGGATCCTACGCTATGGACTACTGGGGCCAGGG
GACCAGCGTGACCGTGTCATCCGCGGCCGCGACTACCACTCCTGCACCACGGCCACC
TACCCCAGCCCCCACCATTGCAAGCCAGCCACTTTCACTGCGCCCCGAAGCGTGTAG
ACCAGCTGCTGGAGGAGCCGTGCATACCCGAGGGCTGGACTTCGCCTGTGACATCT
ACATCTGGGCCCCATTGGCTGGAACTTGCGGCGTGCTGCTCTTGTCTCTGGTCATTAC
CCTGTACTGCCGGTCGAAGAGGTCCAGACTCTTGCACTCCGACTACATGAACATGAC
TCCTAGAAGGCCCGGACCCACTAGAAAGCACTACCAGCCGTACGCCCCTCCTCGGG
ATTTCGCCGCATACCGGTCCAGAGTGAAGTTCAGCCGCTCAGCCGATGCACCGGCCT
ACCAGCAGGGACAGAACCAGCTCTACAACGAGCTCAACCTGGGTCGGCGGGAAGA
ATATGACGTGCTGGACAAACGGCGCGGCAGAGATCCGGAGATGGGGGGAAAGCCG
AGGAGGAAGAACCCTCAAGAGGGCCTGTACAACGAACTGCAGAAGGACAAGATGG
CGGAAGCCTACTCCGAGATCGGCATGAAGGGAGAACGCCGGAGAGGGAAGGGTCA
TGACGGACTGTACCAGGGCCTGTCAACTGCCACTAAGGACACTTACGATGCGCTCCA
TATGCAAGCTTTGCCCCCGCGG SEQ ID NO: 74 amino acid sequence of LTG2273:
MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE
KVTMTCRASSSVNYMDWYQKKPGSSPKPWIYATSNLASGVPARFSGSGSGTSYSLTISR
VEAEDAATYYCQQWSFNPPTFGGGTKLEIKGGGGSGGGGSGGGGSGGGGSGGGGSDIQ
MTQTTSSLSASLGDRVTISCRASQDISKYLNWYQQKPDGTVKLLIYHTSRLHSGVPSRFS
GSGSGTDYSLTISNLEQEDIATYFCQQGNTLPYTFGGGTKLEITGSTSGSGKPGSGEGSTK
GEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSV
TVSSAAATTTPAPRPPTPAPTIASQPLSLRPEACRPAAGGAVHTRGLDFACDIYIWAPLAG
TCGVLLLSLVITLYCRSKRSRLLHSDYMNMTPRRPGPTRKHYQPYAPPRDFAAYRSRVK
FSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR SEQ ID NO: 75 nucleotide sequence of LTG2200:
ATGCTTCTTTTGGTGACTTCCCTTTTGCTGTGCGAGTTGCCACACCCCGCCTTCCTGC
TTATTCCCCAGGTACAGCTCCAGCAGAGTGGCCCAGGGCTCGTGAAGCCAAGCCAG
ACGCTGTCCCTGACTTGTGCAATTTCAGGGGATTCAGTTTCATCAAATAGCGCGGCG
TGGAATTGGATTCGACAATCTCCTTCCCGAGGGTTGGAATGGCTTGGACGAACATAT
TACAGATCCAAATGGTATAACGACTATGCGGTATCAGTAAAGTCAAGAATAACCAT
TAACCCCGACACAAGCAAGAACCAATTCTCTTTGCAGCTTAACTCTGTCACGCCAGA
AGACACGGCAGTCTATTATTGCGCTCGCGAGGTAACGGGTGACCTGGAAGACGCTTT
TGACATTTGGGGGCAGGGTACGATGGTGACAGTCAGTTCAGGGGGCGGTGGGAGTG
GGGGAGGGGGTAGCGGGGGGGGAGGGTCAGACATTCAGATGACCCAGTCCCCTTCA
TCCTTGTCTGCCTCCGTCGGTGACAGGGTGACAATAACATGCAGAGCAAGCCAAAC
AATCTGGAGCTATCTCAACTGGTACCAGCAGCGACCAGGAAAAGCGCCAAACCTGC
TGATTTACGCTGCTTCCTCCCTCCAATCAGGCGTGCCTAGTAGATTTAGCGGTAGGG
GCTCCGGCACCGATTTTACGCTCACTATAAGCTCTCTTCAAGCAGAAGATTTTGCGA
CTTATTACTGCCAGCAGTCCTATAGTATACCTCAGACTTTCGGACAGGGTACCAAGT
TGGAGATTAAGGCGGCCGCAACTACCACCCCTGCCCCTCGGCCGCCGACTCCGGCCC
CAACCATCGCAAGCCAACCCCTCTCCTTGCGCCCCGAAGCTTGCCGCCCGGCCGCGG
GTGGAGCCGTGCATACCCGGGGGCTGGACTTTGCCTGCGATATCTACATTTGGGCCC
CGCTGGCCGGCACTTGCGGCGTGCTCCTGCTGTCGCTGGTCATCACCCTTTACTGCA
AGAGGGGCCGGAAGAAGCTGCTTTACATCTTCAAGCAGCCGTTCATGCGGCCCGTG
CAGACGACTCAGGAAGAGGACGGATGCTCGTGCAGATTCCCTGAGGAGGAAGAGG
GGGGATGCGAACTGCGCGTCAAGTTCTCACGGTCCGCCGACGCCCCCGCATATCAA
CAGGGCCAGAATCAGCTCTACAACGAGCTGAACCTGGGAAGGAGAGAGGAGTACG
ACGTGCTGGACAAGCGACGCGGACGCGACCCGGAGATGGGGGGGAAACCACGGCG
GAAAAACCCTCAGGAAGGACTGTACAACGAACTCCAGAAAGACAAGATGGCGGAA
GCCTACTCAGAAATCGGGATGAAGGGAGAGCGGAGGAGGGGAAAGGGTCACGACG
GGCTGTACCAGGGACTGAGCACCGCCACTAAGGATACCTACGATGCCTTGCATATG
CAAGCACTCCCACCCCGG -continued SEQ ID NO: 76 amino acid sequence of LTG2200:
MLLLVTSLLLCELPHPAFLLIPQVQLQQSGPGLVKPSQTLSLTCAISGDSVSSNSAAWNW
IRQSPSRGLEWLGRTYYRSKWYNDYAVSVKSRITINPDTSKNQFSLQLNSVTPEDTAVY
YCAREVTGDLEDAFDIWGQGTMVTVSSGGGGSGGGGSGGGGSDIQMTQSPSSLSASVG
DRVTITCRASQTIWSYLNWYQQRPGKAPNLLIYAASSLQSGVPSRFSGRGSGTDFTLTISS
LQAEDFATYYCQQSYSIPQTFGQGTKLEIKAAATTTPAPRPPTPAPTIASQPLSLRPEACR
PAAGGAVHTRGLDFACDIYIWAPLAGTCGVLLLSLVITLYCKRGRKKLLYIFKQPFMRP
VQTTQEEDGCSCRFPEEEEGGCELRVKFSRSADAPAYQQGQNQLYNELNLGRREEYDV
LDKRRGRDPEMGGKPRRKNPQEGLYNELQKDKMAEAYSEIGMKGERRRGKGHDGLY
QGLSTATKDTYDALHMQALPPR SEQ ID NO: 77 nucleotide sequence of GMCSF leader peptide
ATGCTTCTTTTGGTGACTTCCCTTTTGCTGTGCGAGTTGCCACACCCCGCCTTCCTGC
TTATTCCC SEQ ID NO: 78 amino acid sequence of GMCSF leader peptide
MLLLVTSLLLCELPHPAFLLIP SEQ ID NO: 79 nucleotide sequence of CD8a leader peptide
ATGGCCCTGCCCGTCACTGCGCTGCTTCTTCCACTTGCGCTTCTGCTGCACGCAGCGC
GCCCG SEQ ID NO: 80 amino acid sequence of CD8a leader peptide
MALPVTALLLPLALLLHAARP SEQ ID NO: 81 nucleotide sequence of CD8 hinge and transmembrane domain
GCGGCCGCTACCACAACCCCTGCGCCCCGGCCTCCTACCCCCGCACCCACGATTGCT
TCTCAACCTCTTTCACTCCGACCTGAGGCTTGTAGACCTGCAGCCGGGGGTGCCGTC
CACACACGGGGACTCGACTTCGCTTGTGATATATATATTTGGGCGCCCCTGGCCGGC
ACTTGTGGAGTTCTTTTGCTCTCTCTTGTTATCACATTGTACTGC SEQ ID NO: 82 amino acid sequence of CD8 hinge and transmembrane domain
AAATTTPAPRPPTPAPTIASQPLSLRPEACRPAAGGAVHTRGLDFACDIYIWAPLAGTCG
VLLLSLVITLYC SEQ ID NO: 83 nucleotide sequence of 4-1BB/CD137 costimulatory domain
AAGCGAGGTAGGAAGAAATTGCTTTACATTTTTAAGCAGCCGTTCATGCGACCAGTA
CAGACTACTCAAGAAGAAGATGGGTGCTCTTGTCGGTTCCCGGAAGAAGAAGAGGG
TGGTTGCGAGTTG SEQ ID NO: 84 amino acid sequence of 4-1BB/CD137 costimulatory domain
KRGRKKLLYIFKQPFMRPVQTTQEEDGCSCRFPEEEEGGCEL SEQ ID NO: 85 nucleotide sequence of CD28 costimulatory domain nucleotide sequence
CGGTCGAAGCGCTCAAGACTGCTGCACTCAGACTACATGAACATGACTCCTCGGCG
GCCGGGGCCGACTCGGAAGCACTACCAGCCTTACGCACCCCCGAGAGATTTCGCGG
CCTACCGCTCC SEQ ID NO: 86 amino acid sequence of CD28 costimulatory domain
RSKRSRLLHSDYMNMTPRRPGPTRKHYQPYAPPRDFAAYRS SEQ ID NO: 87 nucleotide sequence of CD3 zeta
AGGGTGAAGTTCTCCCGCTCTGCCGACGCACCGGCATATCAGCAGGGACAAAACCA
GCTCTACAACGAATTGAACCTGGGTCGGCGGGAAGAATATGACGTGCTCGATAAGC
GGCGGGGTCGCGACCCAGAAATGGGAGGCAAACCGCGCAGGAAAAATCCACAGGA
GGGACTTTATAACGAACTTCAAAAGGATAAGATGGCAGAGGCATACAGCGAAATCG
GGATGAAAGGCGAGAGAAGAAGGGGGAAAGGGCACGATGGTCTTTACCAGGGGCT
TTCTACCGCGACGAAGGATACCTACGATGCTCTCCATATGCAAGCACTTCCTCCTAG
A SEQ ID NO: 88 amino acid sequence of CD3 zeta
RVKFSRSADAPAYQQGQNQLYNELNLGRREEYDVLDKRRGRDPEMGGKPRRKNPQEG
LYNELQKDKMAEAYSEIGMKGERRRGKGHDGLYQGLSTATKDTYDALHMQALPPR SEQ ID NO: 89 nucleotide sequence of Furin P2A furin
CGGGCAAAGCGGGGCTCAGGGGCGACTAACTTTTCACTGTTGAAGCAGGCCGGGGA
TGTGGAGGAGAATCCTGGTCCTAGAGCTAAGCGAG SEQ ID NO: 90 amino acid sequence Furin P2A furin
RAKRGSGATNFSLLKQAGDVEENPGPRAKR SEQ ID NO: 95 nucleotide sequence of 16P17 CD22 scFv VH
CAGGTACAGCTTCAACAGAGTGGGCCGGGACTGGTGAAACACTCCCAAACACTTTC
TCTGACGTGCGCTATATCAGGTGACTCTGTTTCATCTAATTCTGCTGCGTGGAACTGG
ATTCGACAATCTCCCAGTCGCGGGTTGGAATGGCTGGGACGAACATATTATCGGTCT
AAGTGGTATAACGATTATGCTGTATCTGTTAAATCTCGAATTACGATTAATCCTGAC
ACCTCCAAGAACCAGTTCTCCCTCCAGTTGAACTCAGTCACACCGGAAGACACTGCG
GTCTACTATTGCGCTCAAGAAGTCGAGCCACATGATGCATTCGACATCTGGGGCCAG
GGAACGATGGTCACCGTCAGCAGT -continued SEQ ID NO: 96 amino acid sequence of 16P17 CD22 scFv VH
QVQLQQSGPGLVKHSQTLSLTCAISGDSVSSNSAAWNWIRQSPSRGLEWLGRTYYRSK
WYNDYAVSVKSRITINPDTSKNQFSLQLNSVTPEDTAVYYCAQEVEPHDAFDIWGQGT
MVTVSS SEQ ID NO: 97 nucleotide sequence of 16P17 CD22 scFv VL
GACATACAAATGACGCAGAGTCCCTCAAGTGTGTACGCGAGTGTGGGGGATAAGGT
AACTATTACGTGCAGAGCGTCACAGGATGTTAGTGGATGGCTTGCCTGGTATCAGCA
GAAGCCAGGCCTTGCTCCACAGCTCCTTATCAGTGGTGCTTCTACACTTCAGGGCGA
GGTTCCGAGTAGATTCTCTGGTTCTGGATCTGGTACTGACTTCACTCTTACAATTTCT
TCTTTGCAACCAGAAGACTTTGCGACTTATTACTGCCAACAGGCCAAATACTTCCCT
TATACATTTGGCCAAGGTACCAAGTTGGAGATAAAG SEQ ID NO: 98 amino acid sequence of 16P17 CD22 scFv VL
DIQMTQSPSSVYASVGDKVTITCRASQDVSGWLAWYQQKPGLAPQLLISGASTLQGEVP
SRFSGSGSGTDFTLTISSLQPEDFATYYCQQAKYFPYTFGQGTKLEIK SEQ ID NO: 99 nucleotide sequence of 16P8 CD22 scFv VH
CAAGTGCAGCTGCAGCAGTCCGGTCCTGGACTGGTCAAGCCGTCCCAGACTCTGAG
CCTGACTTGCGCAATTAGCGGGGACTCAGTCTCGTCCAATTCGGCGGCCTGGAACTG
GATCCGGCAGTCACCATCAAGGGGCCTGGAATGGCTCGGGCGCACTTACTACCGGT
CCAAATGGTATACCGACTACGCCGTGTCCGTGAAGAATCGGATCACCATTAACCCCG
ACACCTCGAAGAACCAGTTCTCACTCCAACTGAACAGCGTGACCCCCGAGGATACC
GCGGTGTACTACTGCGCACAAGAAGTGGAACCGCAGGACGCCTTCGACATTTGGGG
ACAGGGAACGATGGTCACAGTGTCGTCC SEQ ID NO: 100 amino acid sequence of 16P8 CD22 scFv VH
QVQLQQSGPGLVKPSQTLSLTCAISGDSVSSNSAAWNWIRQSPSRGLEWLGRTYYRSK
WYTDYAVSVKNRITINPDTSKNQFSLQLNSVTPEDTAVYYCAQEVEPQDAFDIWGQGT
MVTVSS SEQ ID NO: 101 nucleotide sequence of 16P8 CD22 scFv VL
GATATCCAGATGACCCAGAGCCCCTCCTCGGTGTCCGCATCCGTGGGCGATAAGGTC
ACCATTACCTGTAGAGCGTCCCAGGACGTGTCCGGATGGCTGGCCTGGTACCAGCA
GAAGCCAGGCTTGGCTCCTCAACTGCTGATCTTCGGCGCCAGCACTCTTCAGGGGGA
AGTGCCATCACGCTTCTCCGGATCCGGTTCCGGCACCGACTTCACCCTGACCATCAG
CAGCCTCCAGCCTGAGGACTTCGCCACTTACTACTGCCAACAGGCCAAGTACTTCCC
CTATACCTTCGGAAGAGGCACTAAGCTGGAAATCAAG SEQ ID NO: 102 amino acid sequence of 16P8 CD22 scFv VL
DIQMTQSPSSVSASVGDKVTITCRASQDVSGWLAWYQQKPGLAPQLLIFGASTLQGEVP
SRFSGSGSGTDFTLTISSLQPEDFATYYCQQAKYFPYTFGRGTKLEIK SEQ ID NO: 103 nucleotide sequence of 16P13 CD22 scFv VH
CAAGTGCAGCTGCAGCAGTCCGGTCCTGGACTGGTCAAGCCGTCCCAGACTCTGAG
CCTGACTTGCGCCATTAGCGGGAACTCAGTCTCGTCCAATTCGGCGGCCTGGAACTG
GATCCGGCAGTCACCATCAAGGGGCCTGGAATGGCTCGGGCGCACTTACTACCGGT
CCAAATGGTATAACGACTACGCCGTGTCCGTGAAGTCCCGGATCACCATTAACCCCG
ACACCTCGAAGAACCAGTTCTCACTCCAACTGAACAGCGTGACCCCCGAGGATACC
GCGGTGTACTACTGCGCACAAGAAGTGGAACCGCAGGACGCCTTCGACATTTGGGG
ACAGGGAACGATGGTCACAGTGTCGTCC SEQ ID NO: 104 amino acid sequence of 16P13 CD22 scFv VH
QVQLQQSGPGLVKPSQTLSLTCAISGNSVSSNSAAWNWIRQSPSRGLEWLGRTYYRSK
WYNDYAVSVKSRITINPDTSKNQFSLQLNSVTPEDTAVYYCAQEVEPQDAFDIWGQGT
MVTVSS SEQ ID NO: 105 nucleotide sequence of 16P13 CD22 scFv VL
GATATCCAGATGACCCAGAGCCCCTCCTCGGTGTCCGCATCCGTGGGCGATAAGGTC
ACCATTACCTGTAGAGCGTCCCAGGACGTGTCCGGATGGCTGGCCTGGTACCAGCA
GAAGCCAGGCTTGGCTCCTCAACTGCTGATCTTTGGCGCCAGCACTCTTCAGGGGGA
GGTGCCATCACGCTTCTCCGGAGGTGGTTCCGGCACCGACTTCACCCTGACCATCAG
CAGCCTCCAGCCTGAGGACTTCGCCACTTACTACTGCCAACAGGCCAAGTACTTCCC
CTATACCTTCGGACAAGGCACTAAGCTGGAAATCAAG SEQ ID NO: 106 amino acid sequence of 16P13 CD22 scFv VL
DIQMTQSPSSVSASVGDKVTITCRASQDVSGWLAWYQQKPGLAPQLLIFGASTLQGEVP
SRFSGGGSGTDFTLTISSLQPEDFATYYCQQAKYFPYTFGQGTKLEIK SEQ ID NO: 107 amino acid sequence of Whitlow linker
GSTSGSGKPGSGEGSTKG SEQ ID NO: 108 amino acid sequence of flexible interchain linker
GGGGSGGGGSGGGGSGGGGSGGGGS SEQ ID NO: 109 nucleotide sequence of LTG 2948 DuoCAR D93 CAR2019 ICOZz 2A
CAR22z
ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG -continued GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG
CCGACTACTACTGCGCACGGTCCAACTACTATGGAAGCTCGTACTGGTTCTTCGATG
TCTGGGGGGCCGGCACCACTGTGACCGTCAGCTCCGGGGGGGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT
GCCAGCAGTGGTCCTTCAACCCGCCGACTTTTGGAGGCGGTACTAAGCTGGAGATCA
AAGGAGGCGGCGGCAGCGGCGGGGGAGGGTCCGGAGGGGGTGGTTCTGGTGGAGG
AGGATCGGGAGGCGGTGGCAGCGACATTCAGATGACTCAGACCACCTCCTCCCTGT
CCGCCTCCCTGGGCGACCGCGTGACCATCTCATGCCGCGCCAGCCAGGACATCTCGA
AGTACCTCAACTGGTACCAGCAGAAGCCCGACGGAACCGTGAAGCTCCTGATCTAC
CACACCTCCCGGCTGCACAGCGGAGTGCCGTCTAGATTCTCGGGTTCGGGGTCGGGA
ACTGACTACTCCCTTACTATTTCCAACCTGGAGCAGGAGGATATTGCCACCTACTTCT
GCCAACAAGGAAACACCCTGCCGTACACTTTTGGCGGGGGAACCAAGCTGGAAATC
ACTGGCAGCACATCCGGTTCCGGGAAGCCCGGCTCCGGAGAGGGCAGCACCAAGGG
GGAAGTCAAGCTGCAGGAATCAGGACCTGGCCTGGTGGCCCCGAGCCAGTCACTGT
CCGTGACTTGTACTGTGTCCGGAGTGTCGCTCCCGGATTACGGAGTGTCCTGGATCA
GGCAGCCACCTCGGAAAGGATTGGAATGGCTCGGAGTCATCTGGGGTTCCGAAACC
ACCTATTACAACTCGGCACTGAAATCCAGGCTCACCATTATCAAGGATAACTCCAAG
TCACAAGTGTTCCTGAAGATGAATAGCCTGCAGACTGACGACACGGCGATCTACTAT
TGCGCCAAGCACTACTACTACGGCGGATCCTACGCTATGGACTACTGGGGCCAGGG
GACCAGCGTGACCGTGTCATCCGCGGCCGCAACGACCACTCCTGCACCACGGCCAC
CTACCCCAGCCCCCACCATTGCAAGCCAGCCACTTTCACTGCGCCCCGAAGCGTGTA
GACCAGCTGCTGGAGGAGCCGTGCATACCCGAGGGCTGGACTTCGCCTGTGACATC
TACATCTGGGCCCCATTGGCTGGAACTTGCGGCGTGCTGCTCTTGTCTCTGGTCATTA
CCCTGTACTGCTGGCTGACAAAAAAGAAGTATTCATCTAGTGTACATGATCCGAACG
GTGAATACATGTTCATGCGCGCGGTGAACACGGCCAAGAAGAGCAGACTGACCGAC
GTAACCCTTAGAGTGAAGTTTAGCCGCTCAGCCGATGCACCGGCCTACCAGCAGGG
ACAGAACCAGCTCTACAACGAGCTCAACCTGGGTCGGCGGGAAGAATATGACGTGC
TGGACAAACGGCGCGGCAGAGATCCGGAGATGGGGGGAAAGCCGAGGAGGAAGAA
CCCTCAAGAGGGCCTGTACAACGAACTGCAGAAGGACAAGATGGCGGAAGCCTACT
CCGAGATCGGCATGAAGGGAGAACGCCGGAGAGGGAAGGGTCATGACGGACTGTA
CCAGGGCCTGTCAACTGCCACTAAGGACACTTACGATGCGCTCCATATGCAAGCTTT
GCCCCCGCGGCGCGCGAAACGCGGCAGCGGCGCGACCAACTTTAGCCTGCTGAAAC
AGGCGGGCGATGTGGAAGAAAACCCGGGCCCGCGAGCAAAGAGGAATATTATGGC
TCTGCCTGTTACGGCACTGCTCCTTCCGCTTGCATTGTTGTTGCACGCAGCGCGGCCC
CAAGTGCAGCTGCAGCAGTCCGGTCCTGGACTGGTCAAGCCGTCCCAGACTCTGAG
CCTGACTTGCGCAATTAGCGGGGACTCAGTCTCGTCCAATTCGGCGGCCTGGAACTG
GATCCGGCAGTCACCATCAAGGGGCCTGGAATGGCTCGGGCGCACTTACTACCGGT
CCAAATGGTATACCGACTACGCCGTGTCCGTGAAGAATCGGATCACCATTAACCCCG
ACACCTCGAAGAACCAGTTCTCACTCCAACTGAACAGCGTGACCCCCGAGGATACC
GCGGTGTACTACTGCGCACAAGAAGTGGAACCGCAGGACGCCTTCGACATTTGGGG
ACAGGGAACGATGGTCACAGTGTCGTCCGGTGGAGGAGGTTCCGGAGGCGGTGGAT
CTGGAGGCGGAGGTTCGGATATCCAGATGACCCAGAGCCCCTCCTCGGTGTCCGCAT
CCGTGGGCGATAAGGTCACCATTACCTGTAGAGCGTCCCAGGACGTGTCCGGATGG
CTGGCCTGGTACCAGCAGAAGCCAGGCTTGGCTCCTCAACTGCTGATCTTCGGCGCC
AGCACTCTTCAGGGGGAAGTGCCATCACGCTTCTCCGGATCCGGTTCCGGCACCGAC
TTCACCCTGACCATCAGCAGCCTCCAGCCTGAGGACTTCGCCACTTACTACTGCCAA
CAGGCCAAGTACTTCCCCTATACCTTCGGAAGAGGCACTAAGCTGGAAATCAAGGC
TAGCGCAACCACTACGCCTGCTCCGCGGCCTCCAACGCCCGCGCCCACGATAGCTAG
TCAGCCGTTGTCTCTCCGACCAGAGGCGTGTAGACCGGCCGCTGGCGGAGCCGTAC
ATACTCGCGGACTCGACTTCGCTTGCGACATCTACATTTGGGCACCCTTGGCTGGGA
CCTGTGGGGTGCTGTTGCTGTCCTTGGTTATTACGTTGTACTGCAGAGTCAAATTTTC
CAGGTCCGCAGATGCCCCCGCGTACCAGCAAGGCCAGAACCAACTTTACAACGAAC
TGAACCTGGGTCGCCGGGAGGAATATGATGTGCTGGATAAACGAAGGGGGAGGGAC
CCTGAGATGGGAGGGAAACCTCGCAGGAAAAACCCGCAGGAAGGTTTGTACAACGA
GTTGCAGAAGGATAAGATGGCTGAGGCTTACTCTGAAATAGGGATGAAGGGAGAGA
GACGGAGAGGAAAAGGCCATGATGGCCTTTACCAGGGCTTAAGCACAGCAACAAAG
GATACTTACGACGCTCTTCACATGCAAGCTCTGCCACCACGG SEQ ID NO: 110 amino acid sequence of LTG 2948 DuoCAR D93 CAR2019 ICOZz 2A CAR22z MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE
KVTMTCRASSSVNYMDWYQKKPGSSPKPWIYATSNLASGVPARFSGSGSGTSYSLTISR
VEAEDAATYYCQQWSFNPPTFGGGTKLEIKGGGGSGGGGSGGGGSGGGGSGGGGSDIQ
MTQTTSSLSASLGDRVTISCRASQDISKYLNWYQQKPDGTVKLLIYHTSRLHSGVPSRFS
GSGSGTDYSLTISNLEQEDIATYFCQQGNTLPYTFGGGTKLEITGSTSGSGKPGSGEGSTK
GEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSV
TVSSAAATTTPAPRPPTPAPTIASQPLSLRPEACRPAAGGAVHTRGLDFACDIYIWAPLAG
TCGVLLLSLVITLYCWLTKKKYSSSVHDPNGEYMFMRAVNTAKKSRLTDVTLRVKFSR
SADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPRRAKRGSG
ATNFSLLKQAGDVEENPGPRAKRNIMALPVTALLLPLALLLHAARPQVQLQQSGPGLVK
PSQTLSLTCAISGDSVSSNSAAWNWIRQSPSRGLEWLGRTYYRSKWYTDYAVSVKNRIT
INPDTSKNQFSLQLNSVTPEDTAVYYCAQEVEPQDAFDIWGQGTMVTVSSGGGGSGGG -continued GSGGGGSDIQMTQSPSSVSASVGDKVTITCRASQDVSGWLAWYQQKPGLAPQLLIFGAS
TLQGEVPSRFSGSGSGTDFTLTISSLQPEDFATYYCQQAKYFPYTFGRGTKLEIKASATTT
PAPRPPTPAPTIASQPLSLRPEACRPAAGGAVHTRGLDFACDIYIWAPLAGTCGVLLLSLV
ITLYCRVKFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYDALHMQA
LPPR SEQ ID NO: 111 nucleotide sequence of LTG 2949 DuoCAR D94 CAR2019 OX40z 2A
CAR22z
ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG
GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG
CCGACTACTACTGCGCACGGTCCAACTACTATGGAAGCTCGTACTGGTTCTTCGATG
TCTGGGGGGCCGGCACCACTGTGACCGTCAGCTCCGGGGGGGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT
GCCAGCAGTGGTCCTTCAACCCGCCGACTTTTGGAGGCGGTACTAAGCTGGAGATCA
AAGGAGGCGGCGGCAGCGGCGGGGGAGGGTCCGGAGGGGGTGGTTCTGGTGGAGG
AGGATCGGGAGGCGGTGGCAGCGACATTCAGATGACTCAGACCACCTCCTCCCTGT
CCGCCTCCCTGGGCGACCGCGTGACCATCTCATGCCGCGCCAGCCAGGACATCTCGA
AGTACCTCAACTGGTACCAGCAGAAGCCCGACGGAACCGTGAAGCTCCTGATCTAC
CACACCTCCCGGCTGCACAGCGGAGTGCCGTCTAGATTCTCGGGTTCGGGGTCGGGA
ACTGACTACTCCCTTACTATTTCCAACCTGGAGCAGGAGGATATTGCCACCTACTTCT
GCCAACAAGGAAACACCCTGCCGTACACTTTTGGCGGGGGAACCAAGCTGGAAATC
ACTGGCAGCACATCCGGTTCCGGGAAGCCCGGCTCCGGAGAGGGCAGCACCAAGGG
GGAAGTCAAGCTGCAGGAATCAGGACCTGGCCTGGTGGCCCCGAGCCAGTCACTGT
CCGTGACTTGTACTGTGTCCGGAGTGTCGCTCCCGGATTACGGAGTGTCCTGGATCA
GGCAGCCACCTCGGAAAGGATTGGAATGGCTCGGAGTCATCTGGGGTTCCGAAACC
ACCTATTACAACTCGGCACTGAAATCCAGGCTCACCATTATCAAGGATAACTCCAAG
TCACAAGTGTTCCTGAAGATGAATAGCCTGCAGACTGACGACACGGCGATCTACTAT
TGCGCCAAGCACTACTACTACGGCGGATCCTACGCTATGGACTACTGGGGCCAGGG
GACCAGCGTGACCGTGTCATCCGCGGCCGCAACGACCACTCCAGCACCGAGACCGC
CAACCCCCGCGCCTACCATCGCAAGTCAACCACTTTCTCTCAGGCCTGAAGCGTGCC
GACCTGCAGCTGGTGGGGCAGTACATACCAGGGGTTTGGACTTCGCATGTGACGTG
GCGGCAATTCTCGGCCTGGGACTTGTCCTTGGTCTGCTTGGTCCGCTCGCAATACTTC
TGGCCTTGTACCTGCTCCGCAGAGACCAAAGACTTCCGCCCGACGCCCACAAGCCCC
CAGGAGGAGGTTCCTTCAGAACGCCTATACAAGAAGAACAAGCAGATGCCCACTCT
ACCCTGGCTAAAATCAGGGTGAAGTTTAGCCGCTCAGCCGATGCACCGGCCTACCA
GCAGGGACAGAACCAGCTCTACAACGAGCTCAACCTGGGTCGGCGGGAAGAATATG
ACGTGCTGGACAAACGGCGCGGCAGAGATCCGGAGATGGGGGGAAAGCCGAGGAG
GAAGAACCCTCAAGAGGGCCTGTACAACGAACTGCAGAAGGACAAGATGGCGGAA
GCCTACTCCGAGATCGGCATGAAGGGAGAACGCCGGAGAGGGAAGGGTCATGACG
GACTGTACCAGGGCCTGTCAACTGCCACTAAGGACACTTACGATGCGCTCCATATGC
AAGCTTTGCCCCCGCGGCGCGCGAAACGCGGCAGCGGCGCGACCAACTTTAGCCTG
CTGAAACAGGGGGCGATGTGGAAGAAAACCCGGGCCCGCGAGCAAAGAGGAATA
TTATGGCTCTGCCTGTTACGGCACTGCTCCTTCCGCTTGCATTGTTGTTGCACGCAGC
GCGGCCCCAAGTGCAGCTGCAGCAGTCCGGTCCTGGACTGGTCAAGCCGTCCCAGA
CTCTGAGCCTGACTTGCGCAATTAGCGGGGACTCAGTCTCGTCCAATTCGGCGGCCT
GGAACTGGATCCGGCAGTCACCATCAAGGGGCCTGGAATGGCTCGGGCGCACTTAC
TACCGGTCCAAATGGTATACCGACTACGCCGTGTCCGTGAAGAATCGGATCACCATT
AACCCCGACACCTCGAAGAACCAGTTCTCACTCCAACTGAACAGCGTGACCCCCGA
GGATACCGCGGTGTACTACTGCGCACAAGAAGTGGAACCGCAGGACGCCTTCGACA
TTTGGGGACAGGGAACGATGGTCACAGTGTCGTCCGGTGGAGGAGGTTCCGGAGGC
GGTGGATCTGGAGGCGGAGGTTCGGATATCCAGATGACCCAGAGCCCCTCCTCGGT
GTCCGCATCCGTGGGCGATAAGGTCACCATTACCTGTAGAGCGTCCCAGGACGTGTC
CGGATGGCTGGCCTGGTACCAGCAGAAGCCAGGCTTGGCTCCTCAACTGCTGATCTT
CGGCGCCAGCACTCTTCAGGGGGAAGTGCCATCACGCTTCTCCGGATCCGGTTCCGG
CACCGACTTCACCCTGACCATCAGCAGCCTCCAGCCTGAGGACTTCGCCACTTACTA
CTGCCAACAGGCCAAGTACTTCCCCTATACCTTCGGAAGAGGCACTAAGCTGGAAA
TCAAGGCTAGCGCAACCACTACGCCTGCTCCGCGGCCTCCAACGCCCGCGCCCACG
ATAGCTAGTCAGCCGTTGTCTCTCCGACCAGAGGCGTGTAGACCGGCCGCTGGCGG
AGCCGTACATACTCGCGGACTCGACTTCGCTTGCGACATCTACATTTGGGCACCCTT
GGCTGGGACCTGTGGGGTGCTGTTGCTGTCCTTGGTTATTACGTTGTACTGCAGAGT
CAAATTTTCCAGGTCCGCAGATGCCCCCGCGTACCAGCAAGGCCAGAACCAACTTTA
CAACGAACTGAACCTGGGTCGCCGGGAGGAATATGATGTGCTGGATAAACGAAGGG
GGAGGGACCCTGAGATGGGAGGGAAACCTCGCAGGAAAAACCCGCAGGAAGGTTT
GTACAACGAGTTGCAGAAGGATAAGATGGCTGAGGCTTACTCTGAAATAGGGATGA
AGGGAGAGAGACGGAGAGGAAAAGGCCATGATGGCCTTTACCAGGGCTTAAGCAC
AGCAACAAAGGATACTTACGACGCTCTTCACATGCAAGCTCTGCCACCACGG SEQ ID NO: 112 amino acid sequence of LTG 2949 DuoCAR D94 CAR2019 OX40z 2A
CAR22z
MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE -continued KVTMTCRASSSVNYMDWYQKKPGSSPKPWIYATSNLASGVPARFSGSGSGTSYSLTISR
VEAEDAATYYCQQWSFNPPTFGGGTKLEIKGGGGSGGGGSGGGGSGGGGSGGGGSDIQ
MTQTTSSLSASLGDRVTISCRASQDISKYLNWYQQKPDGTVKLLIYHTSRLHSGVPSRFS
GSGSGTDYSLTISNLEQEDIATYFCQQGNTLPYTFGGGTKLEITGSTSGSGKPGSGEGSTK
GEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSV
TVSSAAATTTPAPRPPTPAPTIASQPLSLRPEACRPAAGGAVHTRGLDFACDVAAILGLG
LVLGLLGPLAILLALYLLRRDQRLPPDAHKPPGGGSFRTPIQEEQADAHSTLAKIRVKFSR
SADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPRRAKRGSG
ATNFSLLKQAGDVEENPGPRAKRNIMALPVTALLLPLALLLHAARPQVQLQQSGPGLVK
PSQTLSLTCAISGDSVSSNSAAWNWIRQSPSRGLEWLGRTYYRSKWYTDYAVSVKNRIT
INPDTSKNQFSLQLNSVTPEDTAVYYCAQEVEPQDAFDIWGQGTMVTVSSGGGGSGGG
GSGGGGSDIQMTQSPSSVSASVGDKVTITCRASQDVSGWLAWYQQKPGLAPQLLIFGAS
TLQGEVPSRFSGSGSGTDFTLTISSLQPEDFATYYCQQAKYFPYTFGRGTKLEIKASATTT
PAPRPPTPAPTIASQPLSLRPEACRPAAGGAVHTRGLDFACDIYIWAPLAGTCGVLLLSLV
ITLYCRVKFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYDALHMQA
LPPR SEQ ID NO: 113 nucleotide sequence of LTG 2950 DuoCAR D95 CAR2019 OX40z 2A
CAR22 ICOSz
ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG
GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG
CCGACTACTACTGCGCACGGTCCAACTACTATGGAAGCTCGTACTGGTTCTTCGATG
TCTGGGGGGCCGGCACCACTGTGACCGTCAGCTCCGGGGGCGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT
GCCAGCAGTGGTCCTTCAACCCGCCGACTTTTGGAGGCGGTACTAAGCTGGAGATCA
AAGGAGGCGGCGGCAGCGGCGGGGGAGGGTCCGGAGGGGGTGGTTCTGGTGGAGG
AGGATCGGGAGGCGGTGGCAGCGACATTCAGATGACTCAGACCACCTCCTCCCTGT
CCGCCTCCCTGGGCGACCGCGTGACCATCTCATGCCGCGCCAGCCAGGACATCTCGA
AGTACCTCAACTGGTACCAGCAGAAGCCCGACGGAACCGTGAAGCTCCTGATCTAC
CACACCTCCCGGCTGCACAGCGGAGTGCCGTCTAGATTCTCGGGTTCGGGGTCGGGA
ACTGACTACTCCCTTACTATTTCCAACCTGGAGCAGGAGGATATTGCCACCTACTTCT
GCCAACAAGGAAACACCCTGCCGTACACTTTTGGCGGGGGAACCAAGCTGGAAATC
ACTGGCAGCACATCCGGTTCCGGGAAGCCCGGCTCCGGAGAGGGCAGCACCAAGGG
GGAAGTCAAGCTGCAGGAATCAGGACCTGGCCTGGTGGCCCCGAGCCAGTCACTGT
CCGTGACTTGTACTGTGTCCGGAGTGTCGCTCCCGGATTACGGAGTGTCCTGGATCA
GGCAGCCACCTCGGAAAGGATTGGAATGGCTCGGAGTCATCTGGGGTTCCGAAACC
ACCTATTACAACTCGGCACTGAAATCCAGGCTCACCATTATCAAGGATAACTCCAAG
TCACAAGTGTTCCTGAAGATGAATAGCCTGCAGACTGACGACACGGCGATCTACTAT
TGCGCCAAGCACTACTACTACGGCGGATCCTACGCTATGGACTACTGGGGCCAGGG
GACCAGCGTGACCGTGTCATCCGCGGCCGCAACGACCACTCCAGCACCGAGACCGC
CAACCCCCGCGCCTACCATCGCAAGTCAACCACTTTCTCTCAGGCCTGAAGCGTGCC
GACCTGCAGCTGGTGGGGCAGTACATACCAGGGGTTTGGACTTCGCATGTGACGTG
GCGGCAATTCTCGGCCTGGGACTTGTCCTTGGTCTGCTTGGTCCGCTCGCAATACTTC
TGGCCTTGTACCTGCTCCGCAGAGACCAAAGACTTCCGCCCGACGCCCACAAGCCCC
CAGGAGGAGGTTCCTTCAGAACGCCTATACAAGAAGAACAAGCAGATGCCCACTCT
ACCCTGGCTAAAATCAGGGTGAAGTTTAGCCGCTCAGCCGATGCACCGGCCTACCA
GCAGGGACAGAACCAGCTCTACAACGAGCTCAACCTGGGTCGGCGGGAAGAATATG
ACGTGCTGGACAAACGGCGCGGCAGAGATCCGGAGATGGGGGGAAAGCCGAGGAG
GAAGAACCCTCAAGAGGGCCTGTACAACGAACTGCAGAAGGACAAGATGGCGGAA
GCCTACTCCGAGATCGGCATGAAGGGAGAACGCCGGAGAGGGAAGGGTCATGACG
GACTGTACCAGGGCCTGTCAACTGCCACTAAGGACACTTACGATGCGCTCCATATGC
AAGCTTTGCCCCCGCGGCGCGCGAAACGCGGCAGCGGCGCGACCAACTTTAGCCTG
CTGAAACAGGCGGGCGATGTGGAAGAAAACCCGGGCCCGCGAGCAAAGAGGAATA
TTATGGCTCTGCCTGTTACGGCACTGCTCCTTCCGCTTGCATTGTTGTTGCACGCAGC
GCGGCCCCAAGTGCAGCTGCAGCAGTCCGGTCCTGGACTGGTCAAGCCGTCCCAGA
CTCTGAGCCTGACTTGCGCAATTAGCGGGGACTCAGTCTCGTCCAATTCGGCGGCCT
GGAACTGGATCCGGCAGTCACCATCAAGGGGCCTGGAATGGCTCGGGCGCACTTAC
TACCGGTCCAAATGGTATACCGACTACGCCGTGTCCGTGAAGAATCGGATCACCATT
AACCCCGACACCTCGAAGAACCAGTTCTCACTCCAACTGAACAGCGTGACCCCCGA
GGATACCGCGGTGTACTACTGCGCACAAGAAGTGGAACCGCAGGACGCCTTCGACA
TTTGGGGACAGGGAACGATGGTCACAGTGTCGTCCGGTGGAGGAGGTTCCGGAGGC
GGTGGATCTGGAGGCGGAGGTTCGGATATCCAGATGACCCAGAGCCCCTCCTCGGT
GTCCGCATCCGTGGGCGATAAGGTCACCATTACCTGTAGAGCGTCCCAGGACGTGTC
CGGATGGCTGGCCTGGTACCAGCAGAAGCCAGGCTTGGCTCCTCAACTGCTGATCTT
CGGCGCCAGCACTCTTCAGGGGGAAGTGCCATCACGCTTCTCCGGATCCGGTTCCGG
CACCGACTTCACCCTGACCATCAGCAGCCTCCAGCCTGAGGACTTCGCCACTTACTA
CTGCCAACAGGCCAAGTACTTCCCCTATACCTTCGGAAGAGGCACTAAGCTGGAAA
TCAAGGCTAGCGCAACCACTACGCCTGCTCCGCGGCCTCCAACGCCCGCGCCCACG
ATAGCTAGTCAGCCGTTGTCTCTCCGACCAGAGGCGTGTAGACCGGCCGCTGGCGG
AGCCGTACATACTCGCGGACTCGACTTCGCTTGCGACATCTACATTTGGGCACCCTT -continued GGCTGGGACCTGTGGGGTGCTGTTGCTGTCCTTGGTTATTACGTTGTACTGCTGGCTG
ACAAAAAAGAAGTATTCATCTAGTGTACATGATCCGAACGGTGAATACATGTTCATG
CGCGCGGTGAACACGGCCAAGAAGAGCAGACTGACCGACGTAACCCTTAGAGTCAA
ATTTTCCAGGTCCGCAGATGCCCCCGCGTACCAGCAAGGCCAGAACCAACTTTACAA
CGAACTGAACCTGGGTCGCCGGGAGGAATATGATGTGCTGGATAAACGAAGGGGGA
GGGACCCTGAGATGGGAGGGAAACCTCGCAGGAAAAACCCGCAGGAAGGTTTGTAC
AACGAGTTGCAGAAGGATAAGATGGCTGAGGCTTACTCTGAAATAGGGATGAAGGG
AGAGAGACGGAGAGGAAAAGGCCATGATGGCCTTTACCAGGGCTTGAGCACAGCA
ACAAAGGATACTTACGACGCTCTTCACATGCAAGCTCTGCCACCACGG SEQ ID NO: 114 amino acid sequence of LTG 2950 DuoCAR D95 CAR2019 OX40z 2A CAR22 ICOSz MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE
KVTMTCRASSSVNYMDWYQKKPGSSPKPWIYATSNLASGVPARFSGSGSGTSYSLTISR
VEAEDAATYYCQQWSFNPPTFGGGTKLEIKGGGGSGGGGSGGGGSGGGGSGGGGSDIQ
MTQTTSSLSASLGDRVTISCRASQDISKYLNWYQQKPDGTVKLLIYHTSRLHSGVPSRFS
GSGSGTDYSLTISNLEQEDIATYFCQQGNTLPYTFGGGTKLEITGSTSGSGKPGSGEGSTK
GEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSV
TVSSAAATTTPAPRPPTPAPTIASQPLSLRPEACRPAAGGAVHTRGLDFACDVAAILGLG
LVLGLLGPLAILLALYLLRRDQRLPPDAHKPPGGGSFRTPIQEEQADAHSTLAKIRVKFSR
SADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPRRAKRGSG
ATNFSLLKQAGDVEENPGPRAKRNIMALPVTALLLPLALLLHAARPQVQLQQSGPGLVK
PSQTLSLTCAISGDSVSSNSAAWNWIRQSPSRGLEWLGRTYYRSKWYTDYAVSVKNRIT
INPDTSKNQFSLQLNSVTPEDTAVYYCAQEVEPQDAFDIWGQGTMVTVSSGGGGSGGG
GSGGGGSDIQMTQSPSSVSASVGDKVTITCRASQDVSGWLAWYQQKPGLAPQLLIFGAS
TLQGEVPSRFSGSGSGTDFTLTISSLQPEDFATYYCQQAKYFPYTFGRGTKLEIKASATTT
PAPRPPTPAPTIASQPLSLRPEACRPAAGGAVHTRGLDFACDIYIWAPLAGTCGVLLLSLV
ITLYCWLTKKKYSSSVHDPNGEYMFMRAVNTAKKSRLTDVTLRVKFSRSADAPAYQQ
GQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR SEQ ID NO: 115 nucleotide sequence of LTG 2951 DuoCAR D96 CAR2019 27z 2A CAR22 ICOSz ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG
GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG
CCGACTACTACTGCGCACGGTCCAACTACTATGGAAGCTCGTACTGGTTCTTCGATG
TCTGGGGGGCCGGCACCACTGTGACCGTCAGCTCCGGGGGGGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT
GCCAGCAGTGGTCCTTCAACCCGCCGACTTTTGGAGGCGGTACTAAGCTGGAGATCA
AAGGAGGCGGCGGCAGCGGCGGGGGAGGGTCCGGAGGGGGTGGTTCTGGTGGAGG
AGGATCGGGAGGCGGTGGCAGCGACATTCAGATGACTCAGACCACCTCCTCCCTGT
CCGCCTCCCTGGGCGACCGCGTGACCATCTCATGCCGCGCCAGCCAGGACATCTCGA
AGTACCTCAACTGGTACCAGCAGAAGCCCGACGGAACCGTGAAGCTCCTGATCTAC
CACACCTCCCGGCTGCACAGCGGAGTGCCGTCTAGATTCTCGGGTTCGGGGTCGGGA
ACTGACTACTCCCTTACTATTTCCAACCTGGAGCAGGAGGATATTGCCACCTACTTCT
GCCAACAAGGAAACACCCTGCCGTACACTTTTGGCGGGGGAACCAAGCTGGAAATC
ACTGGCAGCACATCCGGTTCCGGGAAGCCCGGCTCCGGAGAGGGCAGCACCAAGGG
GGAAGTCAAGCTGCAGGAATCAGGACCTGGCCTGGTGGCCCCGAGCCAGTCACTGT
CCGTGACTTGTACTGTGTCCGGAGTGTCGCTCCCGGATTACGGAGTGTCCTGGATCA
GGCAGCCACCTCGGAAAGGATTGGAATGGCTCGGAGTCATCTGGGGTTCCGAAACC
ACCTATTACAACTCGGCACTGAAATCCAGGCTCACCATTATCAAGGATAACTCCAAG
TCACAAGTGTTCCTGAAGATGAATAGCCTGCAGACTGACGACACGGCGATCTACTAT
TGCGCCAAGCACTACTACTACGGCGGATCCTACGCTATGGACTACTGGGGCCAGGG
GACCAGCGTGACCGTGTCATCCGCGGCCGCGACTACCACTCCTGCACCACGGCCACC
TACCCCAGCCCCCACCATTGCAAGCCAGCCACTTTCACTGCGCCCCGAAGCGTGTAG
ACCAGCTGCTGGAGGAGCCGTGCATACCCGAGGGCTGGACTTCGCCTGTGACATCT
ACATCTGGGCCCCATTGGCTGGAACTTGCGGCGTGCTGCTCTTGTCTCTGGTCATTAC
CCTGTACTGCCAACGGCGCAAATACCGCTCCAATAAAGGCGAAAGTCCGGTAGAAC
CCGCAGAACCTTGCCACTACAGTTGTCCCAGAGAAGAAGAGGGTTCTACAATACCT
ATTCAAGAGGACTATAGGAAACCAGAGCCCGCATGTAGTCCCAGAGTGAAGTTCAG
CCGCTCAGCCGATGCACCGGCCTACCAGCAGGGACAGAACCAGCTCTACAACGAGC
TCAACCTGGGTCGGCGGGAAGAATATGACGTGCTGGACAAACGGCGCGGCAGAGAT
CCGGAGATGGGGGGAAAGCCGAGGAGGAAGAACCCTCAAGAGGGCCTGTACAACG
AACTGCAGAAGGACAAGATGGCGGAAGCCTACTCCGAGATCGGCATGAAGGGAGA
ACGCCGGAGAGGGAAGGGTCATGACGGACTGTACCAGGGCCTGTCAACTGCCACTA
AGGACACTTACGATGCGCTCCATATGCAAGCTTTGCCCCCGCGGCGCGCGAAACGC
GGCAGCGGCGCGACCAACTTTAGCCTGCTGAAACAGGCGGGCGATGTGGAAGAAAA
CCCGGGCCCGCGAGCAAAGAGGAATATTATGGCTCTGCCTGTTACGGCACTGCTCCT
TCCGCTTGCATTGTTGTTGCACGCAGCGCGGCCCCAAGTGCAGCTGCAGCAGTCCGG -continued TCCTGGACTGGTCAAGCCGTCCCAGACTCTGAGCCTGACTTGCGCAATTAGCGGGGA
CTCAGTCTCGTCCAATTCGGCGGCCTGGAACTGGATCCGGCAGTCACCATCAAGGGG
CCTGGAATGGCTCGGGCGCACTTACTACCGGTCCAAATGGTATACCGACTACGCCGT
GTCCGTGAAGAATCGGATCACCATTAACCCCGACACCTCGAAGAACCAGTTCTCACT
CCAACTGAACAGCGTGACCCCCGAGGATACCGCGGTGTACTACTGCGCACAAGAAG
TGGAACCGCAGGACGCCTTCGACATTTGGGGACAGGGAACGATGGTCACAGTGTCG
TCCGGTGGAGGAGGTTCCGGAGGCGGTGGATCTGGAGGCGGAGGTTCGGATATCCA
GATGACCCAGAGCCCCTCCTCGGTGTCCGCATCCGTGGGCGATAAGGTCACCATTAC
CTGTAGAGCGTCCCAGGACGTGTCCGGATGGCTGGCCTGGTACCAGCAGAAGCCAG
GCTTGGCTCCTCAACTGCTGATCTTCGGCGCCAGCACTCTTCAGGGGGAAGTGCCAT
CACGCTTCTCCGGATCCGGTTCCGGCACCGACTTCACCCTGACCATCAGCAGCCTCC
AGCCTGAGGACTTCGCCACTTACTACTGCCAACAGGCCAAGTACTTCCCCTATACCT
TCGGAAGAGGCACTAAGCTGGAAATCAAGGCTAGCGCAACCACTACGCCTGCTCCG
CGGCCTCCAACGCCCGCGCCCACGATAGCTAGTCAGCCGTTGTCTCTCCGACCAGAG
GCGTGTAGACCGGCCGCTGGCGGAGCCGTACATACTCGCGGACTCGACTTCGCTTGC
GACATCTACATTTGGGCACCCTTGGCTGGGACCTGTGGGGTGCTGTTGCTGTCCTTG
GTTATTACGTTGTACTGCTGGCTGACAAAAAAGAAGTATTCATCTAGTGTACATGAT
CCGAACGGTGAATACATGTTCATGCGCGCGGTGAACACGGCCAAGAAGAGCAGACT
GACCGACGTAACCCTTAGAGTCAAATTTTCCAGGTCCGCAGATGCCCCCGCGTACCA
GCAAGGCCAGAACCAACTTTACAACGAACTGAACCTGGGTCGCCGGGAGGAATATG
ATGTGCTGGATAAACGAAGGGGGAGGGACCCTGAGATGGGAGGGAAACCTCGCAG
GAAAAACCCGCAGGAAGGTTTGTACAACGAGTTGCAGAAGGATAAGATGGCTGAGG
CTTACTCTGAAATAGGGATGAAGGGAGAGAGACGGAGAGGAAAAGGCCATGATGG
CCTTTACCAGGGCTTGAGCACAGCAACAAAGGATACTTACGACGCTCTTCACATGCA
AGCTCTGCCACCACGG SEQ ID NO: 116 amino acid sequence of LTG2951 DuoCAR D96 CAR2019 27z 2A CAR22 ICOSz MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE
KVTMTCRASSSVNYMDWYQKKPGSSPKPWIYATSNLASGVPARFSGSGSGTSYSLTISR
VEAEDAATYYCQQWSFNPPTFGGGTKLEIKGGGGSGGGGSGGGGSGGGGSGGGGSDIQ
MTQTTSSLSASLGDRVTISCRASQDISKYLNWYQQKPDGTVKLLIYHTSRLHSGVPSRFS
GSGSGTDYSLTISNLEQEDIATYFCQQGNTLPYTFGGGTKLEITGSTSGSGKPGSGEGSTK
GEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSV
TVSSAAATTTPAPRPPTPAPTIASQPLSLRPEACRPAAGGAVHTRGLDFACDIYIWAPLAG
TCGVLLLSLVITLYCQRRKYRSNKGESPVEPAEPCHYSCPREEEGSTIPIQEDYRKPEPAC
SPRVKFSRSADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDALHMQALPPR
RAKRGSGATNFSLLKQAGDVEENPGPRAKRNIMALPVTALLLPLALLLHAARPQVQLQ
QSGPGLVKPSQTLSLTCAISGDSVSSNSAAWNWIRQSPSRGLEWLGRTYYRSKWYTDY
AVSVKNRITINPDTSKNQFSLQLNSVTPEDTAVYYCAQEVEPQDAFDIWGQGTMVTVSS
GGGGSGGGGSGGGGSDIQMTQSPSSVSASVGDKVTITCRASQDVSGWLAWYQQKPGL
APQLLIFGASTLQGEVPSRFSGSGSGTDFTLTISSLQPEDFATYYCQQAKYFPYTFGRGTK
LEIKASATTTPAPRPPTPAPTIASQPLSLRPEACRPAAGGAVHTRGLDFACDIYIWAPLAG
TCGVLLLSLVITLYCWLTKKKYSSSVHDPNGEYMFMRAVNTAKKSRLTDVTLRVKFSR
SADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR SEQ ID NO: 117 nucleotide sequence of D088 CAR2019 ICOSz ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG
GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG
CCGACTACTACTGCGCACGGTCCAACTACTATGGAAGCTCGTACTGGTTCTTCGATG
TCTGGGGGGCCGGCACCACTGTGACCGTCAGCTCCGGGGGCGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT
GCCAGCAGTGGTCCTTCAACCCGCCGACTTTTGGAGGCGGTACTAAGCTGGAGATCA
AAGGAGGCGGCGGCAGCGGCGGGGGAGGGTCCGGAGGGGGTGGTTCTGGTGGAGG
AGGATCGGGAGGCGGTGGCAGCGACATTCAGATGACTCAGACCACCTCCTCCCTGT
CCGCCTCCCTGGGCGACCGCGTGACCATCTCATGCCGCGCCAGCCAGGACATCTCGA
AGTACCTCAACTGGTACCAGCAGAAGCCCGACGGAACCGTGAAGCTCCTGATCTAC
CACACCTCCCGGCTGCACAGCGGAGTGCCGTCTAGATTCTCGGGTTCGGGGTCGGGA
ACTGACTACTCCCTTACTATTTCCAACCTGGAGCAGGAGGATATTGCCACCTACTTCT
GCCAACAAGGAAACACCCTGCCGTACACTTTTGGCGGGGGAACCAAGCTGGAAATC
ACTGGCAGCACATCCGGTTCCGGGAAGCCCGGCTCCGGAGAGGGCAGCACCAAGGG
GGAAGTCAAGCTGCAGGAATCAGGACCTGGCCTGGTGGCCCCGAGCCAGTCACTGT
CCGTGACTTGTACTGTGTCCGGAGTGTCGCTCCCGGATTACGGAGTGTCCTGGATCA
GGCAGCCACCTCGGAAAGGATTGGAATGGCTCGGAGTCATCTGGGGTTCCGAAACC
ACCTATTACAACTCGGCACTGAAATCCAGGCTCACCATTATCAAGGATAACTCCAAG
TCACAAGTGTTCCTGAAGATGAATAGCCTGCAGACTGACGACACGGCGATCTACTAT
TGCGCCAAGCACTACTACTACGGCGGATCCTACGCTATGGACTACTGGGGCCAGGG
GACCAGCGTGACCGTGTCATCCGCGGCCGCGACTACCACTCCTGCACCACGGCCACC -continued TACCCCAGCCCCCACCATTGCAAGCCAGCCACTTTCACTGCGCCCCGAAGCGTGTAG
ACCAGCTGCTGGAGGAGCCGTGCATACCCGAGGGCTGGACTTCGCCTGTGACATCT
ACATCTGGGCCCCATTGGCTGGAACTTGCGGCGTGCTGCTCTTGTCTCTGGTCATTAC
CCTGTACTGCTGGCTGACAAAAAAGAAGTATTCATCTAGTGTACATGATCCGAACGG
TGAATACATGTTCATGCGCGCGGTGAACACGGCCAAGAAGAGCAGACTGACCGACG
TAACCCTTAGAGTGAAGTTCAGCCGCTCAGCCGATGCACCGGCCTACCAGCAGGGA
CAGAACCAGCTCTACAACGAGCTCAACCTGGGTCGGCGGGAAGAATATGACGTGCT
GGACAAACGGCGCGGCAGAGATCCGGAGATGGGGGGAAAGCCGAGGAGGAAGAAC
CCTCAAGAGGGCCTGTACAACGAACTGCAGAAGGACAAGATGGCGGAAGCCTACTC
CGAGATCGGCATGAAGGGAGAACGCCGGAGAGGGAAGGGTCATGACGGACTGTAC
CAGGGCCTGTCAACTGCCACTAAGGACACTTACGATGCGCTCCATATGCAAGCTTTG
CCCCCGCGG SEQ ID NO: 118 amino acid sequence of D088 CAR2019 ICOSz
MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE
KVTMTCRASSSVNYMDWYQKKPGSSPKPWIYATSNLASGVPARFSGSGSGTSYSLTISR
VEAEDAATYYCQQWSENPPTFGGGTKLEIKGGGGSGGGGSGGGGSGGGGSGGGGSDIQ
MTQTTSSLSASLGDRVTISCRASQDISKYLNWYQQKPDGTVKLLIYHTSRLHSGVPSRFS
GSGSGTDYSLTISNLEQEDIATYFCQQGNTLPYTFGGGTKLEITGSTSGSGKPGSGEGSTK
GEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSV
TVSSAAATTTPAPRPPTPAPTIASQPLSLRPEACRPAAGGAVHTRGLDFACDIYIWAPLAG
TCGVLLLSLVITLYCWLTKKKYSSSVHDPNGEYMFMRAVNTAKKSRLTDVTLRVKFSR
SADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR SEQ ID NO: 119 nucleotide sequence of D089 CAR22 ICOSz
ATGTTGCTGCTCGTGACCTCGCTCCTTCTGTGCGAGCTGCCCCATCCGGCTTTTCTGC
TCATCCCTCAAGTGCAGCTGCAGCAGTCCGGTCCTGGACTGGTCAAGCCGTCCCAGA
CTCTGAGCCTGACTTGCGCAATTAGCGGGGACTCAGTCTCGTCCAATTCGGCGGCCT
GGAACTGGATCCGGCAGTCACCATCAAGGGGCCTGGAATGGCTCGGGCGCACTTAC
TACCGGTCCAAATGGTATACCGACTACGCCGTGTCCGTGAAGAATCGGATCACCATT
AACCCCGACACCTCGAAGAACCAGTTCTCACTCCAACTGAACAGCGTGACCCCCGA
GGATACCGCGGTGTACTACTGCGCACAAGAAGTGGAACCGCAGGACGCCTTCGACA
TTTGGGGACAGGGAACGATGGTCACAGTGTCGTCCGGTGGAGGAGGTTCCGGAGGC
GGTGGATCTGGAGGCGGAGGTTCGGATATCCAGATGACCCAGAGCCCCTCCTCGGT
GTCCGCATCCGTGGGCGATAAGGTCACCATTACCTGTAGAGCGTCCCAGGACGTGTC
CGGATGGCTGGCCTGGTACCAGCAGAAGCCAGGCTTGGCTCCTCAACTGCTGATCTT
CGGCGCCAGCACTCTTCAGGGGGAAGTGCCATCACGCTTCTCCGGATCCGGTTCCGG
CACCGACTTCACCCTGACCATCAGCAGCCTCCAGCCTGAGGACTTCGCCACTTACTA
CTGCCAACAGGCCAAGTACTTCCCCTATACCTTCGGAAGAGGCACTAAGCTGGAAA
TCAAGGCGGCCGCGACTACCACTCCTGCACCACGGCCACCTACCCCAGCCCCCACCA
TTGCAAGCCAGCCACTTTCACTGCGCCCCGAAGCGTGTAGACCAGCTGCTGGAGGA
GCCGTGCATACCCGAGGGCTGGACTTCGCCTGTGACATCTACATCTGGGCCCCATTG
GCTGGAACTTGCGGCGTGCTGCTCTTGTCTCTGGTCATTACCCTGTACTGCTGGCTGA
CAAAAAAGAAGTATTCATCTAGTGTACATGATCCGAACGGTGAATACATGTTCATGC
GCGCGGTGAACACGGCCAAGAAGAGCAGACTGACCGACGTAACCCTTAGAGTGAA
GTTCAGCCGCTCAGCCGATGCACCGGCCTACCAGCAGGGACAGAACCAGCTCTACA
ACGAGCTCAACCTGGGTCGGCGGGAAGAATATGACGTGCTGGACAAACGGCGCGGC
AGAGATCCGGAGATGGGGGGAAAGCCGAGGAGGAAGAACCCTCAAGAGGGCCTGT
ACAACGAACTGCAGAAGGACAAGATGGCGGAAGCCTACTCCGAGATCGGCATGAA
GGGAGAACGCCGGAGAGGGAAGGGTCATGACGGACTGTACCAGGGCCTGTCAACTG
CCACTAAGGACACTTACGATGCGCTCCATATGCAAGCTTTGCCCCCGCGG SEQ ID NO: 120 amino acid sequence of D089 CAR22 ICOSz
MLLLVTSLLLCELPHPAFLLIPQVQLQQSGPGLVKPSQTLSLTCAISGDSVSSNSAAWNW
IRQSPSRGLEWLGRTYYRSKWYTDYAVSVKNRITINPDTSKNQFSLQLNSVTPEDTAVY
YCAQEVEPQDAFDIWGQGTMVTVSSGGGGSGGGGSGGGGSDIQMTQSPSSVSASVGDK
VTITCRASQDVSGWLAWYQQKPGLAPQLLIFGASTLQGEVPSRFSGSGSGTDFTLTISSL
QPEDFATYYCQQAKYFPYTFGRGTKLEIKAAATTTPAPRPPTPAPTIASQPLSLRPEACRP
AAGGAVHTRGLDFACDIYIWAPLAGTCGVLLLSLVITLYCWLTKKKYSSSVHDPNGEY
MFMRAVNTAKKSRLTDVTLRVKFSRSADAPAYQQGQNQLYNELNLGRREEYDVLDKR
RGRDPEMGGKPRRKNPQEGLYNELQKDKMAEAYSEIGMKGERRRGKGHDGLYQGLST
ATKDTYDALHMQALPPR SEQ ID NO: 121 nucleotide sequence of D090 CAR2019 OX40z
ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG
GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG
CCGACTACTACTGCGCACGGTCCAACTACTATGGAAGCTCGTACTGGTTCTTCGATG
TCTGGGGGGCCGGCACCACTGTGACCGTCAGCTCCGGGGGGGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT -continued GCCAGCAGTGGTCCTTCAACCCGCCGACTTTTGGAGGCGGTACTAAGCTGGAGATCA
AAGGAGGCGGCGGCAGCGGCGGGGGAGGGTCCGGAGGGGGTGGTTCTGGTGGAGG
AGGATCGGGAGGCGGTGGCAGCGACATTCAGATGACTCAGACCACCTCCTCCCTGT
CCGCCTCCCTGGGCGACCGCGTGACCATCTCATGCCGCGCCAGCCAGGACATCTCGA
AGTACCTCAACTGGTACCAGCAGAAGCCCGACGGAACCGTGAAGCTCCTGATCTAC
CACACCTCCCGGCTGCACAGCGGAGTGCCGTCTAGATTCTCGGGTTCGGGGTCGGGA
ACTGACTACTCCCTTACTATTTCCAACCTGGAGCAGGAGGATATTGCCACCTACTTCT
GCCAACAAGGAAACACCCTGCCGTACACTTTTGGCGGGGGAACCAAGCTGGAAATC
ACTGGCAGCACATCCGGTTCCGGGAAGCCCGGCTCCGGAGAGGGCAGCACCAAGGG
GGAAGTCAAGCTGCAGGAATCAGGACCTGGCCTGGTGGCCCCGAGCCAGTCACTGT
CCGTGACTTGTACTGTGTCCGGAGTGTCGCTCCCGGATTACGGAGTGTCCTGGATCA
GGCAGCCACCTCGGAAAGGATTGGAATGGCTCGGAGTCATCTGGGGTTCCGAAACC
ACCTATTACAACTCGGCACTGAAATCCAGGCTCACCATTATCAAGGATAACTCCAAG
TCACAAGTGTTCCTGAAGATGAATAGCCTGCAGACTGACGACACGGCGATCTACTAT
TGCGCCAAGCACTACTACTACGGCGGATCCTACGCTATGGACTACTGGGGCCAGGG
GACCAGCGTGACCGTGTCATCCGCGGCCGCAACGACCACTCCAGCACCGAGACCGC
CAACCCCCGCGCCTACCATCGCAAGTCAACCACTTTCTCTCAGGCCTGAAGCGTGCC
GACCTGCAGCTGGTGGGGCAGTACATACCAGGGGTTTGGACTTCGCATGTGACGTG
GCGGCAATTCTCGGCCTGGGACTTGTCCTTGGTCTGCTTGGTCCGCTCGCAATACTTC
TGGCCTTGTACCTGCTCCGCAGAGACCAAAGACTTCCGCCCGACGCCCACAAGCCCC
CAGGAGGAGGTTCCTTCAGAACGCCTATACAAGAAGAACAAGCAGATGCCCACTCT
ACCCTGGCTAAAATCAGGGTGAAGTTTAGCCGGTCAGCTGATGCACCTGCATATCAG
CAGGGACAGAACCAGCTGTACAATGAGCTGAACCTCGGACGAAGAGAGGAGTACG
ACGTGTTGGACAAAAGACGAGGTAGAGACCCCGAGATGGGCGGCAAGCCGAGAAG
AAAAAACCCACAAGAAGGGCTTTATAATGAGCTTCAGAAAGATAAGATGGCAGAGG
CCTACAGTGAGATTGGCATGAAGGGCGAAAGAAGGAGGGGCAAAGGACACGACGG
TCTCTACCAAGGCCTCAGCACGGCTACCAAAGATACGTATGACGCATTGCATATGCA
GGCATTGCCGCCCCGC SEQ ID NO: 122 amino acid sequence of D090 CAR2019 OX40z
MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE
KVTMTCRASSSVNYMDWYQKKPGSSPKPWIYATSNLASGVPARFSGSGSGTSYSLTISR
VEAEDAATYYCQQWSFNPPTFGGGTKLEIKGGGGSGGGGSGGGGSGGGGSGGGGSDIQ
MTQTTSSLSASLGDRVTISCRASQDISKYLNWYQQKPDGTVKLLIYHTSRLHSGVPSRFS
GSGSGTDYSLTISNLEQEDIATYFCQQGNTLPYTFGGGTKLEITGSTSGSGKPGSGEGSTK
GEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSV
TVSSAAATTTPAPRPPTPAPTIASQPLSLRPEACRPAAGGAVHTRGLDFACDVAAILGLG
LVLGLLGPLAILLALYLLRRDQRLPPDAHKPPGGGSFRTPIQEEQADAHSTLAKIRVKFSR
SADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR SEQ ID NO: 123 nucleotide sequence of D091 CAR2019 CD27z
ATGCTCCTTCTCGTGACCTCCCTGCTTCTCTGCGAACTGCCCCATCCTGCCTTCCTGC
TGATTCCCGAGGTGCAGTTGCAACAGTCAGGAGCTGAACTGGTCAAGCCAGGAGCC
AGCGTGAAGATGAGCTGCAAGGCCTCCGGTTACACCTTCACCTCCTACAACATGCAC
TGGGTGAAACAGACCCCGGGACAAGGGCTCGAATGGATTGGCGCCATCTACCCCGG
GAATGGCGATACTTCGTACAACCAGAAGTTCAAGGGAAAGGCCACCCTGACCGCCG
ACAAGAGCTCCTCCACCGCGTATATGCAGTTGAGCTCCCTGACCTCCGAGGACTCCG
CCGACTACTACTGCGCACGGTCCAACTACTATGGAAGCTCGTACTGGTTCTTCGATG
TCTGGGGGGCCGGCACCACTGTGACCGTCAGCTCCGGGGGCGGAGGATCCGGTGGA
GGCGGAAGCGGGGGTGGAGGATCCGACATTGTGCTGACTCAGTCCCCGGCAATCCT
GTCGGCCTCACCGGGCGAAAAGGTCACGATGACTTGTAGAGCGTCGTCCAGCGTGA
ACTACATGGATTGGTACCAAAAGAAGCCTGGATCGTCACCCAAGCCTTGGATCTACG
CTACATCTAACCTGGCCTCCGGCGTGCCAGCGCGGTTCAGCGGGTCCGGCTCGGGCA
CCTCATACTCGCTGACCATCTCCCGCGTGGAGGCTGAGGACGCCGCGACCTACTACT
GCCAGCAGTGGTCCTTCAACCCGCCGACTTTTGGAGGCGGTACTAAGCTGGAGATCA
AAGGAGGCGGCGGCAGCGGCGGGGGAGGGTCCGGAGGGGGTGGTTCTGGTGGAGG
AGGATCGGGAGGCGGTGGCAGCGACATTCAGATGACTCAGACCACCTCCTCCCTGT
CCGCCTCCCTGGGCGACCGCGTGACCATCTCATGCCGCGCCAGCCAGGACATCTCGA
AGTACCTCAACTGGTACCAGCAGAAGCCCGACGGAACCGTGAAGCTCCTGATCTAC
CACACCTCCCGGCTGCACAGCGGAGTGCCGTCTAGATTCTCGGGTTCGGGGTCGGGA
ACTGACTACTCCCTTACTATTTCCAACCTGGAGCAGGAGGATATTGCCACCTACTTCT
GCCAACAAGGAAACACCCTGCCGTACACTTTTGGCGGGGGAACCAAGCTGGAAATC
ACTGGCAGCACATCCGGTTCCGGGAAGCCCGGCTCCGGAGAGGGCAGCACCAAGGG
GGAAGTCAAGCTGCAGGAATCAGGACCTGGCCTGGTGGCCCCGAGCCAGTCACTGT
CCGTGACTTGTACTGTGTCCGGAGTGTCGCTCCCGGATTACGGAGTGTCCTGGATCA
GGCAGCCACCTCGGAAAGGATTGGAATGGCTCGGAGTCATCTGGGGTTCCGAAACC
ACCTATTACAACTCGGCACTGAAATCCAGGCTCACCATTATCAAGGATAACTCCAAG
TCACAAGTGTTCCTGAAGATGAATAGCCTGCAGACTGACGACACGGCGATCTACTAT
TGCGCCAAGCACTACTACTACGGCGGATCCTACGCTATGGACTACTGGGGCCAGGG
GACCAGCGTGACCGTGTCATCCGCGGCCGCGACTACCACTCCTGCACCACGGCCACC
TACCCCAGCCCCCACCATTGCAAGCCAGCCACTTTCACTGCGCCCCGAAGCGTGTAG
ACCAGCTGCTGGAGGAGCCGTGCATACCCGAGGGCTGGACTTCGCCTGTGACATCT
ACATCTGGGCCCCATTGGCTGGAACTTGCGGCGTGCTGCTCTTGTCTCTGGTCATTAC
CCTGTACTGCCAACGGCGCAAATACCGCTCCAATAAAGGCGAAAGTCCGGTAGAAC
CCGCAGAACCTTGCCACTACAGTTGTCCCAGAGAAGAAGAGGGTTCTACAATACCT
ATTCAAGAGGACTATAGGAAACCAGAGCCCGCATGTAGTCCCAGAGTGAAGTTCAG
CCGCTCAGCCGATGCACCGGCCTACCAGCAGGGACAGAACCAGCTCTACAACGAGC -continued TCAACCTGGGTCGGCGGGAAGAATATGACGTGCTGGACAAACGGCGCGGCAGAGAT
CCGGAGATGGGGGGAAAGCCGAGGAGGAAGAACCCTCAAGAGGGCCTGTACAACG
AACTGCAGAAGGACAAGATGGCGGAAGCCTACTCCGAGATCGGCATGAAGGGAGA
ACGCCGGAGAGGGAAGGGTCATGACGGACTGTACCAGGGCCTGTCAACTGCCACTA
AGGACACTTACGATGCGCTCCATATGCAAGCTTTGCCCCCGCGG SEQ ID NO: 124 amino acid sequence D091 CAR2019 CD27z
MLLLVTSLLLCELPHPAFLLIPEVQLQQSGAELVKPGASVKMSCKASGYTFTSYNMHWV
KQTPGQGLEWIGAIYPGNGDTSYNQKFKGKATLTADKSSSTAYMQLSSLTSEDSADYY
CARSNYYGSSYWFFDVWGAGTTVTVSSGGGGSGGGGSGGGGSDIVLTQSPAILSASPGE
KVTMTCRASSSVNYMDWYQKKPGSSPKPWIYATSNLASGVPARFSGSGSGTSYSLTISR
VEAEDAATYYCQQWSFNPPTFGGGTKLEIKGGGGSGGGGSGGGGSGGGGSGGGGSDIQ
MTQTTSSLSASLGDRVTISCRASQDISKYLNWYQQKPDGTVKLLIYHTSRLHSGVPSRFS
GSGSGTDYSLTISNLEQEDIATYFCQQGNTLPYTFGGGTKLEITGSTSGSGKPGSGEGSTK
GEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSV
TVSSAAATTTPAPRPPTPAPTIASQPLSLRPEACRPAAGGAVHTRGLDFACDIYIWAPLAG
TCGVLLLSLVITLYCQRRKYRSNKGESPVEPAEPCHYSCPREEEGSTIPIQEDYRKPEPAC
SPRVKFSRSADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDALHMQALPPR SEQ ID NO: 125 nucleotide sequence of D92 CAR22z
ATGTTGCTGCTCGTGACCTCGCTCCTTCTGTGCGAGCTGCCCCATCCGGCTTTTCTGC
TCATCCCTCAAGTGCAGCTGCAGCAGTCCGGTCCTGGACTGGTCAAGCCGTCCCAGA
CTCTGAGCCTGACTTGCGCAATTAGCGGGGACTCAGTCTCGTCCAATTCGGCGGCCT
GGAACTGGATCCGGCAGTCACCATCAAGGGGCCTGGAATGGCTCGGGCGCACTTAC
TACCGGTCCAAATGGTATACCGACTACGCCGTGTCCGTGAAGAATCGGATCACCATT
AACCCCGACACCTCGAAGAACCAGTTCTCACTCCAACTGAACAGCGTGACCCCCGA
GGATACCGCGGTGTACTACTGCGCACAAGAAGTGGAACCGCAGGACGCCTTCGACA
TTTGGGGACAGGGAACGATGGTCACAGTGTCGTCCGGTGGAGGAGGTTCCGGAGGC
GGTGGATCTGGAGGCGGAGGTTCGGATATCCAGATGACCCAGAGCCCCTCCTCGGT
GTCCGCATCCGTGGGCGATAAGGTCACCATTACCTGTAGAGCGTCCCAGGACGTGTC
CGGATGGCTGGCCTGGTACCAGCAGAAGCCAGGCTTGGCTCCTCAACTGCTGATCTT
CGGCGCCAGCACTCTTCAGGGGGAAGTGCCATCACGCTTCTCCGGATCCGGTTCCGG
CACCGACTTCACCCTGACCATCAGCAGCCTCCAGCCTGAGGACTTCGCCACTTACTA
CTGCCAACAGGCCAAGTACTTCCCCTATACCTTCGGAAGAGGCACTAAGCTGGAAA
TCAAGGCGGCCGCAACCACTACACCAGCTCCGCGGCCACCCACCCCAGCACCAACA
ATAGCCAGTCAGCCTTTGTCTCTGAGACCTGAGGCTTGTCGACCCGCTGCAGGTGGG
GCAGTTCATACTCGGGGTCTTGATTTCGCCTGCGATATATATATTTGGGCCCCCCTGG
CGGGCACGTGTGGGGTGCTCCTTCTTTCACTCGTAATTACTCTTTACTGTAGGGTTAA
GTTCTCACGATCCGCCGATGCGCCAGCATACCAACAGGGACAGAACCAACTTTATA
ATGAGCTGAATCTTGGTCGCAGGGAAGAATATGATGTACTTGATAAACGCAGAGGC
CGGGATCCCGAGATGGGAGGGAAACCTCGGAGAAAGAACCCCCAGGAGGGCCTGT
ATAATGAATTGCAAAAAGATAAAATGGCTGAAGCTTATTCAGAGATTGGAATGAAA
GGCGAGCGGAGAAGAGGAAAAGGGCACGACGGGCTTTACCAAGGACTGTCCACCG
CGACAAAGGACACGTACGACGCCCTTCATATGCAGGCGCTTCCTCCACGA SEQ ID NO: 126 amino acid sequence of D92 CAR22z
MLLLVTSLLLCELPHPAFLLIPQVQLQQSGPGLVKPSQTLSLTCAISGDSVSSNSAAWNW
IRQSPSRGLEWLGRTYYRSKWYTDYAVSVKNRITINPDTSKNQFSLQLNSVTPEDTAVY
YCAQEVEPQDAFDIWGQGTMVTVSSGGGGSGGGGSGGGGSDIQMTQSPSSVSASVGDK
VTITCRASQDVSGWLAWYQQKPGLAPQLLIFGASTLQGEVPSRFSGSGSGTDFTLTISSL
QPEDFATYYCQQAKYFPYTFGRGTKLEIKAAATTTPAPRPPTPAPTIASQPLSLRPEACRP
AAGGAVHTRGLDFACDIYIWAPLAGTCGVLLLSLVITLYCRVKFSRSADAPAYQQGQN
QLYNELNLGRREEYDVLDKRRGRDPEMGGKPRRKNPQEGLYNELQKDKMAEAYSEIG
MKGERRRGKGHDGLYQGLSTATKDTYDALHMQALPPR SEQ ID NO: 127 nucleotide sequence of HER2 scFv
GAAGTGCAGCTGGTGGAAAGCGGCGGCGGCCTGGTGCAGCCGGGCGGCAGCCTGCGCCTGA
GCTGCGCGGCGAGCGGCTTTAACATTAAAGATACCTATATTCATTGGGTGCGCCAGGCGCCG
GGCAAAGGCCTGGAATGGGTGGCGCGCATTTATCCGACCAACGGCTATACCCGCTATGCGG
ATAGCGTGAAAGGCCGCTTTACCATTAGCGCGGATACCAGCAAAAACACCGCGTATCTGCA
GATGAACAGCCTGCGCGCGGAAGATACCGCGGTGTATTATTGCAGCCGCTGGGGCGGCGAT
GGCTTTTATGCGATGGATTATTGGGGCCAGGGCACCCTGGTGACCGTGAGCAGCGGCGGCG
GCGGCAGCGGCGGCGGCGGCAGCGGCGGCGGCGGCAGCGATATTCAGATGACCCAGAGCCC
GAGCAGCCTGAGCGCGAGCGTGGGCGATCGCGTGACCATTACCTGCCGCGCGAGCCAGGAT
GTGAACACCGCGGTGGCGTGGTATCAGCAGAAACCGGGCAAAGCGCCGAAACTGCTGATTT
ATAGCGCGAGCTTTCTGTATAGCGGCGTGCCGAGCCGCTTTAGCGGCAGCCGCAGCGGCACC
GATTTTACCCTGACCATTAGCAGCCTGCAGCCGGAAGATTTTGCGACCTATTATTGCCAGCA
GCATTATACCACCCCGCCGACCTTTGGCCAGGGCACCAAAGTGGAAATTAAA SEQ ID NO: 128 amino acid sequence of HER2 scFv
EVQLVESGGG LVQPGGSLRL SCAASGFNIK DTYIHWVRQA PGKGLEWVAR IYPTNGYTRY
ADSVKGRFTI SADTSKNTAY LQMNSLRAED TAVYYCSRWG GDGFYAMDYW GQGTLVTVSS
GGGGSGGGGSGGGGS
DIQMTQSPSS LSASVGDRVT ITCRASQDVN TAVAWYQQKP GKAPKLLIYS ASFLYSGVPS
RFSGSRSGTD FTLTISSLQP EDFATYYCQQ HYTTPPTFGQ GTKVEIK SEQ ID NO: 129 nucleotide sequence of Folate receptor alpha (FolR1) scFv
ATGGAAGTGCAGCTCGTGGAGTCCGGAGGCGGAGTCGTGCAGCCGGGCAGATCCCT
GCGCCTTTCCTGCTCGGCATCCGGGTTTACCTTCTCTGGCTACGGTCTGTCGTGGGTC -continued AGACAGGCTCCAGGGAAGGGCCTGGAATGGGTGGCCATGATCTCCTCGGGGGGTTC
GTACACCTACTACGCCGACTCAGTGAAGGGCCGGTTCGCCATCTCCCGCGACAACGC
CAAGAACACCCTGTTCCTGCAAATGGACTCGCTCCGGCCTGAGGACACTGGGGTGT
ACTTCTGCGCGAGACACGGAGATGACCCAGCTTGGTTCGCCTACTGGGGACAAGGC
ACCCCTGTGACCGTGTCCTCCGCGAGCACCAAGGGAGGCGGAGGAGGTTCCGGTGG
AGGGGGATCAGGGGGTGGAGGATCGGACATTCAGCTGACCCAGAGCCCCTCAAGCC
TGTCCGCGAGCGTTGGGGACCGCGTGACCATCACCTGTTCGGTGTCCTCCTCCATCT
CCTCCAACAATCTCCATTGGTACCAGCAGAAACCGGGGAAAGCCCCCAAGCCGTGG
ATCTACGGAACCTCCAACCTGGCTAGCGGAGTGCCGTCGAGGTTCTCGGGCTCCGGA
TCAGGGACTGACTACACTTTCACTATTTCCTCCCTGCAACCGGAGGACATTGCCACC
TACTACTGTCAGCAGTGGTCGTCCTACCCCTACATGTATACCTTCGGTCAAGGAACC
AAGGTCGAGATCAAG SEQ ID NO: 130 amino acid sequence of FolR1 scFv
MEVQLVESGGGVVQPGRSLRLSCSASGFTFSGYGLSWVRQAPGKGLEWVAMISSGGSY
TYYADSVKGRFAISRDNAKNTLFLQMDSLRPEDTGVYFCARHGDDPAWFAYWGQGTP
VTVSSGGGGGSGGGGSGGGGSDIQLTQSPSSLSASVGDRVTITCSVSSSISSNNLHWYQQ
KPGKAPKPWIYGTSNLASGVPSRFSGSGSGTDYTFTISSLQPEDIATYYCQQWSSYPYMY
TFGQGTKVEIK SEQ ID NO: 131 nucleotide sequence of CA125/MUC16
GAAGTACAGCTCGTAGAGTCTGGGGGTGGTCTCGTTCAACCAGGTGGCTCTTTGAGA
CTGTCATGCGCCGCGTCTGGGTACAGCATTACAAACGATTACGCATGGAATTGGGTG
AGACAGGCTCCCGGAAAGGGCCTCGAATGGGTAGGATACATCTCATATAGCGGTTA
TACAACGTACAATCCTAGCTTGAAATCAAGGTTTACAATCTCCAGGGACACGTCAAA
AAATACGCTTTACCTTCAGATGAACTCCCTGCGAGCAGAAGACACGGCTGTGTACTA
CTGTGCCCGATGGACAAGTGGCCTCGATTACTGGGGTCAAGGTACACTGGTGACAGT
ATCCTCTGGAGGTGGCGGATCAGGGGGGGGCGGCAGTGGTGGAGGTGGTTCAGATA
TCCAGATGACTCAGTCCCCCTCTTCCCTCAGTGCCTCCGTTGGTGACCGAGTTACTAT
CACGTGCAAAGCCAGTGACTTGATCCATAATTGGCTGGCGTGGTATCAGCAAAAAC
CTGGCAAAGCACCCAAGCTTCTGATATATGGTGCAACATCCCTGGAAACGGGCGTTC
CCAGTCGCTTTTCAGGGTCAGGGTCAGGAACTGATTTTACGCTCACCATTTCCAGCC
TGCAGCCTGAAGATTTCGCTACATACTACTGTCAGCAATATTGGACTACTCCATTTA
CCTTCGGGCAAGGCACGAAGGTTGAGATAAAG SEQ ID NO: 132 amino acid sequence of CA125/MUC16
EVQLVESGGG LVQPGGSLRL SCAASGYSIT NDYAWNWVRQ APGKGLEWVG YISYSGYTTY
NPSLKSRFTI SRDTSKNTLY LQMNSLRAED TAVYYCARWT SGLDYWGQGT LVTVSS
GGGGSGGGGSGGGGS
DIQMTQSPSS LSASVGDRVT ITCKASDLIH NWLAWYQQKP GKAPKLLIYG ATSLETGVPS
RFSGSGSGTD FTLTISSLQP EDFATYYCQQ YWTTPFTFGQ GTKVEIK SEQ ID NO: 133 nucleotide sequence of CD276/B7-H3 scFv
GAAGTCCAGTTGGTTGAGTCAGGAGGGGGACTCGTGCAACCTGGTGGTAGCTTGCGCTTGTC
ATGTGCTGCCTCCGGGTTTACATTCTCATCTTTCGGTATGCACTGGGTTAGACAAGCACCTGG
GAAGGGCTTGGAATGGGTTGCTTACATTAGCAGTGATTCTAGCGCGATCTACTACGCTGACA
CCGTAAAGGGCAGATTTACCATCAGCAGAGATAACGCTAAGAACTCCCTCTACCTCCAGATG
AACAGCCTCAGGGATGAAGACACTGCTGTTTATTACTGTGGGAGGGGCCGCGAAAATATTTA
CTACGGGAGCCGATTGGATTATTGGGGTCAGGGGACAACAGTGACTGTTTCAAGCGGTGGT
GGGGGGTCCGGCGGTGGGGGAAGCGGCGGTGGGGGGTCAGATATACAACTGACACAGAGC
CCTAGCTTTTTGAGTGCGTCTGTCGGGGATAGAGTTACGATTACTTGTAAGGCGAGCCAGAA
CGTTGATACGAACGTGGCATGGTACCAGCAGAAGCCAGGGAAAGCTCCGAAAGCCCTTATC
TATTCTGCTAGTTACCGATACAGCGGCGTCCCCTCTCGGTTCAGTGGGAGTGGAAGTGGAAC
GGACTTTACCCTTACGATCAGTTCCTTGCAACCGGAGGATTTCGCCACCTACTACTGCCAGC
AATACAATAACTATCCCTTTACTTTTGGCCAGGGCACAAAGCTTGAAATCAAA SEQ ID NO: 134 amino acid sequence of CD276/B7-H3 scFv
EVQLVESGGG LVQPGGSLRL SCAASGFTFS SFGMHWVRQA PGKGLEWVAY ISSDSSAIYY
ADTVKGRFTI SRDNAKNSLY LQMNSLRDED TAVYYCGRGR ENIYYGSRLD YWGQGTTVTV
SS
GGGGSGGGGSGGGGS
DIQLTQSPSF LSASVGDRVT ITCKASQNVD TNVAWYQQKP GKAPKALIYS ASYRYSGVPS
RFSGSGSGTD FTLTISSLQP EDFATYYCQQ YNNYPFTFGQ GTKLEIK SEQ ID NO: 135 nucleotide sequence of CD276/B7-H3 scFv
CAAGTTCAGTTGCAGCAGTCAGGCGCGGAGCTGGTGAAACCAGGTGCTTCAGTCAAGTTGTC
TTGTAAAGCAAGTGGCTATACATTCACAAATTATGATATCAACTGGGTGCGGCAGAGGCCCG
AACAGGGACTGGAATGGATCGGGTGGATCTTTCCTGGCGACGGTAGTACTCAATACAACGA
GAAATTCAAGGGAAAGGCTACTCTTACAACCGACACGTCATCATCTACAGCTTATATGCAAC
TTAGTAGACTCACATCAGAAGACTCCGCTGTATACTTTTGTGCTCGACAGACGACGGCAACA
TGGTTCGCCTACTGGGGGCAAGGAACACTCGTAACCGTATCTGCAGGCGGTGGTGGATCTGG
AGGAGGTGGAAGCGGTGGTGGAGGGTCCGACATCGTTATGACGCAAAGCCCCGCGACCCTC
AGTGTGACCCCCGGTGACAGAGTTTCACTCAGTTGCAGAGCCTCTCAGAGTATCTCAGATTA
CCTTCACTGGTATCAACAAAAAAGCCACGAAAGCCCCAGATTGCTCATAAAGTACGCGAGT
CAATCAATCTCTGGTATTCCCTCTAGGTTCTCAGGCTCAGGCAGCGGTAGCGATTTCACATTG
TCTATAAATAGTGTGGAACCTGAGGATGTTGGCGTATATTACTGTCAGAACGGTCACTCCTT
CCCGCTTACGTTTGGGGGGGGGACAAAATTGGAACTCAAG -continued SEQ ID NO: 136 amino acid sequence of CD276/B7-H3 scFv
QVQLQQSGAE LVKPGASVKL SCKASGYTFT NYDINWVRQR PEQGLEWIGW IFPGDGSTQY
NEKFKGKATL TTDTSSSTAY MQLSRLTSED SAVYFCARQT TATWFAYWGQ GTLVTVSA
GGGGSGGGGSGGGGS
DIVMTQSPAT LSVTPGDRVS LSCRASQSIS DYLHWYQQKS HESPRLLIKY ASQSISGIPS
RFSGSGSGSD FTLSINSVEP EDVGVYYCQN GHSFPLTFGA GTKLELK SEQ ID NO: 137 nucleotide sequence of EGFR scFv
CAAGTTCAATTGAAACAGAGTGGTCCGGGTCTTGTTCAGCCAAGTCAGAGTTTGAGCATCAC
CTGTACTGTCTCCGGATTTAGTCTTACAAATTACGGCGTACATTGGGTCAGACAATCCCCTGG
GAAGGGTTTGGAATGGCTGGGGGTGATTTGGTCAGGTGGAAACACGGACTACAATACTCCC
TTTACATCCCGATTGTCCATAAACAAAGATAATAGTAAATCTCAAGTATTTTTTAAGATGAA
CAGTCTTCAATCTAACGATACAGCGATCTATTACTGCGCTCGCGCATTGACGTACTATGACT
ATGAGTTTGCCTATTGGGGTCAAGGCACACTTGTCACAGTAAGCGCAGGGGGAGGCGGGTC
TGGAGGGGGCGGATCTGGCGGTGGCGGAAGCGATATCCTGTTGACTCAGTCCCCAGTGATA
CTTTCAGTATCACCGGGCGAACGGGTGAGTTTCAGTTGCCGCGCCTCTCAAAGTATCGGAAC
GAATATACACTGGTACCAGCAGCGGACAAACGGGAGCCCGCGCTTGCTTATTAAGTACGCTT
CCGAGTCTATATCAGGTATTCCATCCCGGTTTTCTGGTAGTGGAAGTGGGACAGATTTCACA
CTGTCTATTAATTCAGTTGAGTCTGAAGACATCGCGGATTATTACTGCCAACAAAACAATAA
TTGGCCGACGACCTTCGGCGCTGGGACCAAGCTTGAGCTTAAG SEQ ID NO: 138 amino acid sequence of EGFR scFv
QVQLKQSGPG LVQPSQSLSI TCTVSGFSLT NYGVHWVRQS PGKGLEWLGV IWSGGNTDYN
TPFTSRLSIN KDNSKSQVFF KMNSLQSNDT AIYYCARALT YYDYEFAYWG QGTLVTVSA
GGGGSGGGGSGGGGS
DILLTQSPVI LSVSPGERVS FSCRASQSIG TNIHWYQQRT NGSPRLLIKY ASESISGIPS
RFSGSGSGTD FTLSINSVES EDIADYYCQQ NNNWPTTFGA GTKLELK SEQ ID NO: 139 nucleotide sequence of GD2 scFv
GAGGTTCAGTTGCTCCAGTCTGGACCTGAGTTGGAGAAACCCGGTGCTAGTGTAATGATCAG
CTGCAAGGCATCAGGTTCCAGTTTCACCGGCTATAATATGAATTGGGTTCGGCAGAACATAG
GCAAAAGTCTCGAGTGGATAGGTGCGATTGACCCGTACTATGGCGGCACTTCATATAACCAA
AAGTTCAAGGGTCGAGCTACACTCACTGTCGATAAAAGCAGCTCCACAGCCTATATGCACCT
TAAGTCACTTACTAGCGAAGATTCTGCCGTATATTACTGCGTATCAGGTATGGAGTACTGGG
GGCAGGGCACGTCCGTCACAGTATCATCCGGCGGCGGTGGTAGCGGGGGAGGAGGTTCTGG
TGGTGGGGGGAGTGAAATAGTCATGACTCAATCCCCTGCGACCCTGTCCGTATCCCCGGGAG
AACGCGCAACTTTGTCCTGTCGCAGCTCTCAGTCTTTGGTTCATCGGAATGGTAATACATACC
TGCACTGGTATTTGCAAAAACCCGGCCAGAGTCCGAAGCTGCTCATCCATAAGGTCTCCAAT
CGCTTCTCTGGGGTACCTGATCGGTTTAGCGGGTCTGGATCAGGGACGGATTTTACACTGAA
AATAAGTAGAGTTGAGGCAGAGGACCTTGGAGTCTACTTCTGCAGTCAGTCCACGCACGTAC
CTCCACTCACATTTGGGGCTGGGACCAAGTTGGAACTCAAA SEQ ID NO: 140 amino acid sequence of GD2 scFv
EVQLLQSGPE LEKPGASVMI SCKASGSSFT GYNMNWVRQN IGKSLEWIGA IDPYYGGTSY
NQKFKGRATL TVDKSSSTAY MHLKSLTSED SAVYYCVSGM EYWGQGTSVT VSS
GGGGSGGGGSGGGGS
EIVMTQSPAT LSVSPGERAT LSCRSSQSLV HRNGNTYLHW YLQKPGQSPK LLIHKVSNRF
SGVPDRFSGS GSGTDFTLKI SRVEAEDLGV YFCSQSTHVP PLTFGAGTKL ELK SEQ ID NO: 141 nucleotide sequence of NKGD2 scFv
CAAGTTCATTTGCAAGAGTCAGGCCCTGGCCTCGTTAAGCCCTCCGAGACGCTCTCTTTGAC
CTGCACAGTTTCAGATGATTCCATTTCATCATACTACTGGTCATGGATTCGGCAGCCGCCAG
GGAAGGGCCTCGAATGGATTGGACATATCAGCTACTCCGGAAGTGCTAACTATAACCCATCC
TTGAAATCCAGAGTCACAATTTCCGTAGACACATCTAAGAACCAATTCAGCCTGAAACTTAG
TTCTGTTACTGCGGCGGATACTGCAGTGTATTATTGCGCTAATTGGGATGACGCCTTCAACAT
CTGGGGTCAAGGTACAATGGTGACCGTGAGTAGCGGGGGAGGAGGCTCAGGCGGGGGTGGT
TCAGGTGGTGGAGGCTCAGAAATCGTCTTGACGCAAAGTCCAGGAACTTTGAGTTTGTCTCC
AGGAGAACGCGCGACGCTTTCTTGCCGAGCTTCACAATCCGTCTCCAGCTCTTATTTGGCTTG
GTATCAGCAGAAACCAGGTCAAGCTCCCAGGCTTCTGATCTACGGTGCGTCTTCCCGAGCCA
CTGGGATTCCCGATCGGTTCAGCGGGTCCGGCAGCGGAACAGATTTCACTCTCACCATATCT
AGACTTGAACCGGAGGACTTCGCAGTGTATTACTGTCAGCAGTACGGCAGTTCACCCTGGAC
GTTTGGTCAGGGTACGAAAGTTGAGATCAAG SEQ ID NO: 142 amino acid sequence of NKGD2 scFv
QVHLQESGPG LVKPSETLSL TCTVSDDSIS SYYWSWIRQP PGKGLEWIGH ISYSGSANYN
PSLKSRVTIS VDTSKNQFSL KLSSVTAADT AVYYCANWDD AFNIWGQGTM VTVSS
GGGGSGGGGSGGGGS
EIVLTQSPGT LSLSPGERAT LSCRASQSVS SSYLAWYQQK PGQAPRLLIY GASSRATGIP
DRFSGSGSGT DFTLTISRLE PEDFAVYYCQ QYGSSPWTFG QGTKVEIK SEQ ID NO: 143 nucleotide sequence of ROR1 scFv4
CAAGTTCAGCTGCAAGAATCAGGACCTGGGCTTGTCAAACCATCTGAAACCCTCAG
CTTGACTTGTACCGTATCAGGAGGGTCAATTTCAAGCTCATCCTACTATTGGGGATG
GATCAGACAACCACCCGGGAAAGGGCTCGAGTGGATAGGGTCCATATATTACAGCG
GATCTACATACTACAACCCGTCATTGAAGTCCAGGGTAACGATTCCGGTGGACACTA
GCAAGAATCAGTTTAGCCTCAAGTTGAGCAGTGTAACTGCTGCGGACACGGCGGTA
TATTATTGTGCTCGACACCTCGGTGGAGATGCTTTTGACATATGGGGTCAAGGGACA
ACAGTCACCGTTAGCTCAGGTGGAGGGGGTAGCGGGGGGGGCGGATCTGGGGGAG
GCGGTTCATTGCCCGTACTTACACAGCCACCCTCTGTCAGCGTCGCACCTGGACAAA
CCGCTCGCATCACCTGTGGCGGAAATAATATAGGTTCCAAGTCTGTTCATTGGTATC
AGCAGAAACCGGGACAGGCCCCCGTCCTTGTGGTGTATGATGATTCTGATAGGCCAT -continued CTGGTATCCCAGAACGGTTTTCAGGTAGCAATTCAGGGAATACTGCCACTCTCACTA
TTAGCGGTACTCAAGCTATGGATGAGGCCGACTATTTTTGCCAGAGCTACGACTCTA
GTAACCCAGTCGTGTTCGGGGGAGGGACCCAGTTGACCGTGCTG SEQ ID NO: 144 amino acid sequence of ROR1 scFv4
QVQLQESGPGLVKPSETLSLTCTVSGGSISSSSYYWGWIRQPPGKGLEWIGSIYYSGSTY
YNPSLKSRVTIPVDTSKNQFSLKLSSVTAADTAVYYCARHLGGDAFDIWGQGTTVTVSS
GGGGSGGGGSGGGGSLPVLTQPPSVSVAPGQTARITCGGNNIGSKSVHWYQQKPGQAP
VLVVYDDSDRPSGIPERFSGSNSGNTATLTISGTQAMDEADYFCQSYDSSNPVVFGGGT
QLTVL SEQ ID NO: 145 nucleotide sequence of ROR1 scFv9
CAGGCGGCCCAGGTACAGCTGCAGCAGTCAGGGGCTGAGGTGAAGAAGCCTGGGTC
CTCGGTGAAGGTCTCCTGCAAGGCTTCTGGAGGCACCTTCAGCAGCTATGCTATCAG
CTGGGTGCGACAGGCCCCTGGACAAGGGCTTGAGTGGATGGGATGGATCAACCCTA
ACAGTGGTGGCACAAACTATGCACAGAGGTTTCAGGGCAGGGTCACCATGACCAGG
GACACGTCCATCAGCACAGCCTACATGGAGCTGAGCAGGCTGAGATCTGACGACAC
GGCCGTGTATTACTGTGCGAGTTATAATGATGCTTTTGATATCTGGGGCCAAGGCAC
CCTGGTCACCGTCTCCTCAGGAGGTGGCGGGTCTGGTGGTGGCGGTAGCGGTGGTGG
CGGATCCAATTTTATGCTGACTCAGCCCCACTCTGTGTCGGAGTCTCCGGGGAAGAC
GGTAACCATCTCCTGCACCCGCAGCAGTGGCAGCATTGCCAGCAACTATGTGCAGTG
GTACCAGCAGCGCCCGGGCAGTGCCCCCACCATTGTGATCTATGAGGATGATCAAA
GACCCTCTGGGGTCCCTGATCGGTTCTCTGGCTCCATCGACACCTCCTCCAACTCTGC
CTCCCTCACCATCTCTGGACTGCAGAGTGAGGACGAGGCTGACTACTACTGTCAGTC
TTATGAGCCCGGCAATGGGGTATTCGGCGGAGGGACCAAGGTCACCGTCCTA SEQ ID NO: 146 amino acid sequence of ROR1 scFv9
QAAQVQLQQSGAEVKKPGSSVKVSCKASGGTFSSYAISWVRQAPGQGLEWMGWINPN
SGGTNYAQRFQGRVTMTRDTSISTAYMELSRLRSDDTAVYYCASYNDAFDIWGQGTLV
TVSSGGGGSGGGGSGGGGSNFMLTQPHSVSESPGKTVTISCTRSSGSIASNYVQWYQQR
PGSAPTIVIYEDDQRPSGVPDRFSGSIDTSSNSASLTISGLQSEDEADYYCQSYEPGNGVF
GGGTKVTVL SEQ ID NO: 147 nucleotide sequence of ROR1 R12
CAAGAACAGCTTGTAGAGTCCGGCGGTAGATTGGTGACACCGGGGGGGAGCCTTAC
CCTGTCTTGTAAGGCATCTGGGTTCGATTTCAGTGCGTATTATATGAGCTGGGTTCGG
CAGGCGCCCGGGAAGGGGCTGGAATGGATAGCCACTATATACCCGTCATCCGGCAA
GACTTACTACGCGACTTGGGTAAACGGGAGGTTTACGATAAGCTCAGATAACGCCC
AAAACACGGTTGATCTCCAAATGAATAGCTTGACCGCCGCTGATAGGGCGACCTATT
TCTGTGCGCGGGACTCTTACGCTGATGACGGGGCCCTCTTCAATATATGGGGACCGG
GAACGCTCGTAACCATATCATCTGGAGGAGGTGGGAGCGGAGGCGGAGGGTCAGGT
GGGGGGGGAGCGAACTCGTACTTACACAATCTCCAAGCGTAAGCGCAGCGTTGGG
GAGTCCAGCAAAGATCACCTGCACTTTGTCAAGCGCCCACAAAACGGATACGATAG
ATTGGTATCAGCAACTCCAAGGTGAAGCGCCACGATATCTCATGCAGGTACAGAGC
GACGGGAGTTATACTAAGAGGCCCGGGGTCCCAGACAGATTCAGTGGCAGCAGTTC
AGGTGCCGACAGATACCTGATAATACCCTCAGTTCAAGCCGATGATGAAGCCGATT
ACTACTGTGGGGCTGACTACATAGGTGGGTATGTTTTCGGGGGGGGCACTCAATTGA
CAGTTACAGGG SEQ ID NO: 148 amino acid sequence of ROR1 R12
QEQLVESGGRLVTPGGSLTLSCKASGFDFSAYYMSWVRQAPGKGLEWIATIYPSSGKTY
YATWVNGRFTISSDNAQNTVDLQMNSLTAADRATYFCARDSYADDGALFNIWGPGTL
VTISSGGGGSGGGGSGGGGSELVLTQSPSVSAALGSPAKITCTLSSAHKTDTIDWYQQLQ
GEAPRYLMQVQSDGSYTKRPGVPDRFSGSSSGADRYLIIPSVQADDEADYYCGADYIGG
YVFGGGTQLTVTG SEQ ID NO: 149 nucleotide sequence of MSLN M1-4S
GAGGTCCAGCTGGTACAGTCTGGGGGAGGCTTGGTACAGCCTGGGGGGTCCCTGAG
ACTCTCCTGTGCAGCCTCTGGATTCACCTTTGATGATTATGCCATGCACTGGGTCCGG
CAAGCTCCAGGGAAGGGCCTGGAGTGGGTCTCAGGTATTAGTTGGAATAGTGGTAG
CATAGGCTATGCGGACTCTGTGAAGGGCCGATTCACCATCTCCAGAGACAACGCCA
AGAACTCCCTGTATCTGCAAATGAACAGTCTGAGAGCTGAGGACACGGCCTTGTATT
ACTGTGCAAAAGATTTATCGTCAGTGGCTGGACCCTTTAACTACTGGGGCCAGGGCA
CCCTGGTCACCGTCTCCTCAGGAGGTGGCGGGTCTGGTGGAGGCGGTAGCGGCGGT
GGCGGATCCTCTTCTGAGCTGACTCAGGACCCTGCTGTGTCTGTGGCCTTGGGACAG
ACAGTCAGGATCACATGCCAAGGAGACAGCCTCAGAAGCTATTATGCAAGCTGGTA
CCAGCAGAAGCCAGGACAGGCCCCTGTACTTGTCATCTATGGTAAAAACAACCGGC
CCTCAGGGATCCCAGACCGATTCTCTGGCTCCAGCTCAGGAAACACAGCTTCCTTGA
CCATCACTGGGGCTCAGGCGGAGGATGAGGCTGACTATTACTGTAACTCCCGGGAC
AGCAGTGGTAACCATCTGGTATTCGGCGGAGGCACCCAGCTGACCGTCCTCGGT SEQ ID NO: 150 amino acid sequence of MSLN M1-4S
EVQLVQSGGGLVQPGGSLRLSCAASGFTFDDYAMHWVRQAPGKGLEWVSGISWNSGSI
GYADSVKGRFTISRDNAKNSLYLQMNSLRAEDTALYYCAKDLSSVAGPFNYWGQGTL
VTVSSGGGGSGGGGSGGGGSSSELTQDPAVSVALGQTVRITCQGDSLRSYYASWYQQK
PGQAPVLVIYGKNNRPSGIPDRFSGSSSGNTASLTITGAQAEDEADYYCNSRDSSGNHLV
FGGGTQLTVLG SEQ ID NO: 151 nucleotide sequence of CAR LTG2527 ROR1 IgG4 CD8 BBz
ATGCTGCTGCTGGTGACCAGCCTGCTGCTGTGCGAACTGCCGCATCCGGCGTTTCTG
CTGATTCCGCAAGAACAGCTTGTAGAGTCCGGCGGTAGATTGGTGACACCGGGGGG -continued GAGCCTTACCCTGTCTTGTAAGGCATCTGGGTTCGATTTCAGTGCGTATTATATGAGC
TGGGTTCGGCAGGCGCCCGGGAAGGGGCTGGAATGGATAGCCACTATATACCCGTC
ATCCGGCAAGACTTACTACGCGACTTGGGTAAACGGGAGGTTTACGATAAGCTCAG
ATAACGCCCAAAACACGGTTGATCTCCAAATGAATAGCTTGACCGCCGCTGATAGG
GCGACCTATTTCTGTGCGCGGGACTCTTACGCTGATGACGGGGCCCTCTTCAATATA
TGGGGACCGGGAACGCTCGTAACCATATCATCTGGAGGAGGTGGGAGCGGAGGCGG
AGGGTCAGGTGGGGGGGGGAGCGAACTCGTACTTACACAATCTCCAAGCGTAAGCG
CAGCGTTGGGGAGTCCAGCAAAGATCACCTGCACTTTGTCAAGCGCCCACAAAACG
GATACGATAGATTGGTATCAGCAACTCCAAGGTGAAGCGCCACGATATCTCATGCA
GGTACAGAGCGACGGGAGTTATACTAAGAGGCCCGGGGTCCCAGACAGATTCAGTG
GCAGCAGTTCAGGTGCCGACAGATACCTGATAATACCCTCAGTTCAAGCCGATGATG
AAGCCGATTACTACTGTGGGGCTGACTACATAGGTGGGTATGTTTTCGGGGGCGGCA
CTCAATTGACAGTTACAGGGGCGGCCGCAGAGTCAAAATACGGTCCTCCGTGCCCTC
CGTGTCCGATCTACATTTGGGCCCCGCTGGCCGGCACTTGCGGCGTGCTCCTGCTGT
CGCTGGTCATCACCCTTTACTGCAAGAGGGGCCGGAAGAAGCTGCTTTACATCTTCA
AGCAGCCGTTCATGCGGCCCGTGCAGACGACTCAGGAAGAGGACGGATGCTCGTGC
AGATTCCCTGAGGAGGAAGAGGGGGGATGCGAACTGCGCGTCAAGTTCTCACGGTC
CGCCGACGCCCCCGCATATCAACAGGGCCAGAATCAGCTCTACAACGAGCTGAACC
TGGGAAGGAGAGAGGAGTACGACGTGCTGGACAAGCGACGCGGACGCGACCCGGA
GATGGGGGGGAAACCACGGCGGAAAAACCCTCAGGAAGGACTGTACAACGAACTC
CAGAAAGACAAGATGGCGGAAGCCTACTCAGAAATCGGGATGAAGGGAGAGCGGA
GGAGGGGAAAGGGTCACGACGGGCTGTACCAGGGACTGAGCACCGCCACTAAGGA
TACCTACGATGCCTTGCATATGCAAGCACTCCCACCCCGGTAG SEQ ID NO: 152 amino acid sequence of CAR LTG2527 ROR1 IgG4 CD8 BBz
MLLLVTSLLLCELPHPAFLLIPQEQLVESGGRLVTPGGSLILSCKASGFDFSAYYMSWVR
QAPGKGLEWIATIYPSSGKTYYATWVNGRFTISSDNAQNTVDLQMNSLTAADRATYFC
ARDSYADDGALFNIWGPGTLVTISSGGGGSGGGGSGGGGSELVLTQSPSVSAALGSPAK
ITCTLSSAHKTDTIDWYQQLQGEAPRYLMQVQSDGSYTKRPGVPDRFSGSSSGADRYLII
PSVQADDEADYYCGADYIGGYVFGGGTQLTVTGAAAESKYGPPCPPCPIYIWAPLAGTC
GVLLLSLVITLYCKRGRKKLLYIFKQPFMRPVQTTQEEDGCSCRFPEEEEGGCELRVKFS
RSADAPAYQQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR SEQ ID NO: 153 nucleotide sequence of CAR LTG2528 ROR1scFv4 IgG4 CD8 BBz
ATGCTGCTGCTGGTGACCAGCCTGCTGCTGTGCGAACTGCCGCATCCGGCGTTTCTG
CTGATTCCGCAAGTTCAGCTGCAAGAATCAGGACCTGGGCTTGTCAAACCATCTGAA
ACCCTCAGCTTGACTTGTACCGTATCAGGAGGGTCAATTTCAAGCTCATCCTACTATT
GGGGATGGATCAGACAACCACCCGGGAAAGGGCTCGAGTGGATAGGGTCCATATAT
TACAGCGGATCTACATACTACAACCCGTCATTGAAGTCCAGGGTAACGATTCCGGTG
GACACTAGCAAGAATCAGTTTAGCCTCAAGTTGAGCAGTGTAACTGCTGCGGACAC
GGCGGTATATTATTGTGCTCGACACCTCGGTGGAGATGCTTTTGACATATGGGGTCA
AGGGACAACAGTCACCGTTAGCTCAGGTGGAGGGGGTAGCGGGGGGGGCGGATCTG
GGGGAGGCGGTTCATTGCCCGTACTTACACAGCCACCCTCTGTCAGCGTCGCACCTG
GACAAACCGCTCGCATCACCTGTGGCGGAAATAATATAGGTTCCAAGTCTGTTCATT
GGTATCAGCAGAAACCGGGACAGGCCCCCGTCCTTGTGGTGTATGATGATTCTGATA
GGCCATCTGGTATCCCAGAACGGTTTTCAGGTAGCAATTCAGGGAATACTGCCACTC
TCACTATTAGCGGTACTCAAGCTATGGATGAGGCCGACTATTTTTGCCAGAGCTACG
ACTCTAGTAACCCAGTCGTGTTCGGGGGAGGGACCCAGTTGACCGTGCTGGCGGCC
GCAGAGTCAAAATACGGTCCTCCGTGCCCTCCGTGTCCGATCTACATTTGGGCCCCG
CTGGCCGGCACTTGCGGCGTGCTCCTGCTGTCGCTGGTCATCACCCTTTACTGCAAG
AGGGGCCGGAAGAAGCTGCTTTACATCTTCAAGCAGCCGTTCATGCGGCCCGTGCA
GACGACTCAGGAAGAGGACGGATGCTCGTGCAGATTCCCTGAGGAGGAAGAGGGG
GGATGCGAACTGCGCGTCAAGTTCTCACGGTCCGCCGACGCCCCCGCATATCAACA
GGGCCAGAATCAGCTCTACAACGAGCTGAACCTGGGAAGGAGAGAGGAGTACGAC
GTGCTGGACAAGCGACGCGGACGCGACCCGGAGATGGGGGGGAAACCACGGCGGA
AAAACCCTCAGGAAGGACTGTACAACGAACTCCAGAAAGACAAGATGGCGGAAGC
CTACTCAGAAATCGGGATGAAGGGAGAGCGGAGGAGGGGAAAGGGTCACGACGGG
CTGTACCAGGGACTGAGCACCGCCACTAAGGATACCTACGATGCCTTGCATATGCA
AGCACTCCCACCCCGGTAG SEQ ID NO: 154 amino acid sequence of CAR LTG2528 ROR1scFv4 IgG4 CD8 BBz
MLLLVTSLLLCELPHPAFLLIPQVQLQESGPGLVKPSETLSLTCTVSGGSISSSSYYWGWI
RQPPGKGLEWIGSIYYSGSTYYNPSLKSRVTIPVDTSKNQFSLKLSSVTAADTAVYYCAR
HLGGDAFDIWGQGTTVTVSSGGGGSGGGGSGGGGSLPVLTQPPSVSVAPGQTARITCGG
NNIGSKSVHWYQQKPGQAPVLVVYDDSDRPSGIPERFSGSNSGNTATLTISGTQAMDEA
DYFCQSYDSSNPVVFGGGTQLTVLAAAESKYGPPCPPCPIYIWAPLAGTCGVLLLSLVIT
LYCKRGRKKLLYIFKQPFMRPVQTTQEEDGCSCRFPEEEEGGCELRVKFSRSADAPAYQ
QGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR SEQ ID NO: 155 nucleotide sequence of CAR LTG2529 ROR1scFv9 IgG4 CD8 BBz
ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGCTGAGCAGGCTGAGATC
TGACGACACGGCCGTGTATTACTGTGCGAGTTATAATGATGCTTTTGATATCTGGGG
CCAAGGCACCCTGGTCACCGTCTCCTCAGGAGGTGGCGGGTCTGGTGGTGGCGGTA
GCGGTGGTGGCGGATCCAATTTTATGCTGACTCAGCCCCACTCTGTGTCGGAGTCTC -continued
CGGGGAAGACGGTAACCATCTCCTGCACCCGCAGCAGTGGCAGCATTGCCAGCAAC
TATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCCCTGAGG
AGGAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAGAGA
GGAGTACGACGTGCTGGACAAGCGACGCGGACGCGACCCGGAGATGGGGGGGAAA
CCACGGCGGAAAAACCCTCAGGAAGGACTGTACAACGAACTCCAGAAAGACAAGA
TGGCGGAAGCCTACTCAGAAATCGGGATGAAGGGAGAGCGGAGGAGGGGAAAGGG
TCACGACGGGCTGTACCAGGGACTGAGCACCGCCACTAAGGATACCTACGATGCCT
TGCATATGCAAGCACTCCCACCCCGGTAG SEQ ID NO: 156 amino acid sequence of CAR LTG2529 ROR1scFv9 IgG4 CD8 BBz
MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPR SEQ ID NO: 157 nucleotide sequence of CAR D0181 MSLN M1-4S CD8 BBz
ATGCTGCTGCTGGTGACCAGCCTGCTGCTGTGCGAACTGCCGCATCCGGCGTTTCTG
CTGATTCCGGAGGTCCAGCTGGTACAGTCTGGGGGAGGCTTGGTACAGCCTGGGGG
GTCCCTGAGACTCTCCTGTGCAGCCTCTGGATTCACCTTTGATGATTATGCCATGCAC
TGGGTCCGGCAAGCTCCAGGGAAGGGCCTGGAGTGGGTCTCAGGTATTAGTTGGAA
TAGTGGTAGCATAGGCTATGCGGACTCTGTGAAGGGCCGATTCACCATCTCCAGAGA
CAACGCCAAGAACTCCCTGTATCTGCAAATGAACAGTCTGAGAGCTGAGGACACGG
CCTTGTATTACTGTGCAAAAGATTTATCGTCAGTGGCTGGACCCTTTAACTACTGGG
GCCAGGGCACCCTGGTCACCGTCTCCTCAGGAGGTGGCGGGTCTGGTGGAGGCGGT
AGCGGCGGTGGCGGATCCTCTTCTGAGCTGACTCAGGACCCTGCTGTGTCTGTGGCC
TTGGGACAGACAGTCAGGATCACATGCCAAGGAGACAGCCTCAGAAGCTATTATGC
AAGCTGGTACCAGCAGAAGCCAGGACAGGCCCCTGTACTTGTCATCTATGGTAAAA
ACAACCGGCCCTCAGGGATCCCAGACCGATTCTCTGGCTCCAGCTCAGGAAACACA
GCTTCCTTGACCATCACTGGGGCTCAGGCGGAGGATGAGGCTGACTATTACTGTAAC
TCCCGGGACAGCAGTGGTAACCATCTGGTATTCGGCGGAGGCACCCAGCTGACCGT
CCTCGGTGCGGCCGCAACTACCACCCCTGCCCCTCGGCCGCCGACTCCGGCCCCAAC
CATCGCAAGCCAACCCCTCTCCTTGCGCCCCGAAGCTTGCCGCCCGGCCGCGGGTGG
AGCCGTGCATACCCGGGGGCTGGACTTTGCCTGCGATATCTACATTTGGGCCCCGCT
GGCCGGCACTTGCGGCGTGCTCCTGCTGTCGCTGGTCATCACCCTTTACTGCAAGAG
GGGCCGGAAGAAGCTGCTTTACATCTTCAAGCAGCCGTTCATGCGGCCCGTGCAGA
CGACTCAGGAAGAGGACGGATGCTCGTGCAGATTCCCTGAGGAGGAAGAGGGGGG
ATGCGAACTGCGCGTCAAGTTCTCACGGTCCGCCGACGCCCCCGCATATCAACAGG
GCCAGAATCAGCTCTACAACGAGCTGAACCTGGGAAGGAGAGAGGAGTACGACGTG
CTGGACAAGCGACGCGGACGCGACCCGGAGATGGGGGGGAAACCACGGCGGAAAA
ACCCTCAGGAAGGACTGTACAACGAACTCCAGAAAGACAAGATGGCGGAAGCCTAC
TCAGAAATCGGGATGAAGGGAGAGCGGAGGAGGGGAAAGGGTCACGACGGGCTGT
ACCAGGGACTGAGCACCGCCACTAAGGATACCTACGATGCCTTGCATATGCAAGCA
CTCCCACCCCGGTAG SEQ ID NO: 158 amino acid sequence of CAR D0181 MSLN M1-4S CD8 BBz
MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQTV
RITCQGDSLRSYYASWYQQKPGQAPVLVIYGKNNRPSGIPDRFSGSSSGNTASLTITGAQ
AEDEADYYCNSRDSSGNHLVFGGGTQLTVLGAAATTTPAPRPPTPAPTIASQPLSLRPEA
CRPAAGGAVHTRGLDFACDIYIWAPLAGTCGVLLLSLVITLYCKRGRKKLLYIFKQPFM
RPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDG
LYQGLSTATKDTYDALHMQALPPR SEQ ID NO: 159 nucleotide sequence of CAR D0229 ROR1 scFv9 IgG4 CD8 BBz 2A mIL7
ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGITGAGCAGGCTGAGATCT
GACGACACGGCCGTGTATTACTGTGCGAGTTATAATGATGCTTTTGATATCTGGGGC
CAAGGCACCCTGGTCACCGTCTCCTCAGGAGGTGGCGGGTCTGGTGGTGGCGGTAG
CGGTGGTGGCGGATCCAATTTTATGCTGACTCAGCCCCACTCTGTGTCGGAGTCTCC
GGGGAAGACGGTAACCATCTCCTGCACCCGCAGCAGTGGCAGCATTGCCAGCAACT
ATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC -continued TACTGTCAGTCTTATGAGCCCGGCAATGGGGTATTCGGCGGAGGGACCAAGGTCAC
CGTCCTAGCIGCCGCAGAGTCAAAATACGGTCCTCCGTGCCCTCCGTGTCCGATCTAC
ATTTGGGCCCCGCTGGCCGGCACTTGCGGCGTGCTCCTGCTGTCGCTGGTCATCACC
CTTTACTGCAAGCGcGGccGcAAGAAATTGCTTTACATTTTTAAGCAGCCGTTCATGCG
ACCAGTACAGACTACTCAAGAAGAAGATGGGTGCTCTTGTCGGTTCCCGGAAGAAG
AAGAGGGTGGTTGCGAGTTGAGGGTGAAGTTCTCCCGCTCTGCCGACGCACCGGCA
TATCAGCAGGGACAAAACCAGCTCTACAACGAATTGAACCTGGGTCGGCGGGAAGA
ATATGACGTGCTCGATAAGCGGGGGGTCGCGACCCAGAAATGGGAGGCAAACCGC
GCAGGAAAAATCCACAGGAGGGACTTTATAACGAACTTCAAAAGGATAAGATGGCA
GAGGCATACAGCGAAATCGGGATGAAAGGCGAGAGAAGAAGGGGGAAAGGGCACG
ATGGTCTTTACCAGGGGCTTTCTACCGCGACGAAGGATACCTACGATGCTCTCCATA
TGCAAGCACTTCCTCCTAGACGGGCAAAGCGGGGCTCAGGGGCGACTAACTTTTCA
CTGTTGAAGCAGGCCGGGGATGTGGAGGAGAATCCTGGTCCTAGAGCTAAGCGAGT
AATGCTCTTGCTCGTGACTTCTTTGCTTTTGTGCGAACTTCCGCACCCAGCCTTCCTTT
TGATACCTATGGATTGTGATATTGAAGGTAAAGATGGCAAACAATATGAGAGTGTTC
TAATGGTCAGCATCGATCAATTATTGGACAGCATGAAAGAAATTGGTAGCAATTGCC
TGAATAATGAATTTAACTTTTTTAAAAGACATATCTGTGATGCTAATAAGGAAGGTA
TGTTTTTATTCCGTGCTGCTCGCAAGTTGAGGCAATTTCTTAAAATGAATAGCACTGG
TGATTTTGATCTCCACTTATTAAAAGTTTCAGAAGGCACAACAATACTGTTGAACTG
CACTGGCCAGGTTAAAGGAAGAAAACCAGCTGCCCTGGGTGAAGCCCAACCAACAA
AGAGTTTGGAAGAAAATAAATCTTTAAAGGAACAGAAAAAACTGAATGACTTGTGT
TTCCTAAAGAGACTATTACAAGAGATAAAAACTTGTTGGAATAAAATTTTGATGGGC
ACTAAAGAACACTCCGGAGGTTCCGGTGGTGGCTCAGGTGGTGGCTCAGGTGAAAG
TGGCTATGCTCAAAATGGAGACTTGGAAGATGCAGAACTGGATGACTACTCATTCTC
ATGCTATAGCCAGTTGGAAGTGAATGGATCGCAGCACTCACTGACCTGTGCTTTTGA
GGACCCAGATGTCAACATCACCAATCTGGAATTTGAAATATGTGGGGCCCTCGTGGA
GGTAAAGTGCCTGAATTTCAGGAAACTACAAGAGATATATTTCATCGAGACAAAGA
AATTCTTACTGATTGGAAAGAGCAATATATGTGTGAAGGTTGGAGAAAAGAGTCTA
ACCTGCAAAAAAATAGACCTAACCACTATAGTTAAACCTGAGGCTCCTTTTGACCTG
AGTGTCGTCTATCGGGAAGGAGCCAATGACTTTGTGGTGACATTTAATACATCACAC
TTGCAAAAGAAGTATGTAAAAGTTTTAATGCACGATGTAGCTTACCGCCAGGAAAA
GGATGAAAACAAATGGACGCATGTGAATTTATCCAGCACAAAGCTGACACTCCTGC
AGAGAAAGCTCCAACCGGCAGCAATGTATGAGATTAAAGTTCGATCCATCCCTGAT
CACTATTTTAAAGGCTTCTGGAGTGAATGGAGTCCAAGTTATTACTTCAGAACTCCA
GAGATCAATAATAGCTCAGGGGAGATGGATCCTATCTTACTAACCATCAGCATTTTG
AGTTTTTTCTCTGTCGCTCTGTTGGTCATCTTGGCCTGTGTGTTATGGAAAAAAAGGA
TTAAGCCTATCGTATGGCCCAGTCTCCCCGATCATAAGAAGACTCTGGAACATCTTT
GTAAGAAACCAAGAAAAAATTTAAATGTGAGTTTCAATCCTGAAAGTTTCCTGGACT
GCCAGATTCATAGGGTGGATGACATTCAAGCTAGAGATGAAGTGGAAGGTTTTCTG
CAAGATACGTTTCCTCAGCAACTAGAAGAATCTGAGAAGCAGAGGCTTGGAGGGGA
TGTGCAGAGCCCCAACTGCCCATCTGAGGATGTAGTCATCACTCCAGAAAGCTTTGG
AAGAGATTCATCCCTCACATGCCTGGCTGGGAATGTCAGTGCATGTGACGCCCCTAT
TCTCTCCTCTTCCAGGTCCCTAGACTGCAGGGAGAGTGGCAAGAATGGGCCTCATGT
GTACCAGGACCTCCTTCTTAGCCTTGGGACTACAAACAGCACGCTGCCCCCTCCATT
TTCTCTCCAATCTGGAATCCTGACATTGAACCCAGTTGCTCAGGGTCAGCCCATTCTT
ACTTCCCTGGGATCAAATCAAGAAGAAGCATATGTCACCATGTCCAGCTTCTACCAA
AACCAGCCCTAG SEQ ID NO: 160 amino acid sequence of CAR D0229 ROR1 scFv9 IgG4 CD8 BBz 2A mIL7
MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRVMLLLVTSLLLCELPHPAFLLIPMDCDIEGKDGKQYESVL
MVSIDQLLDSMKEIGSNCLNNEFNFFKRHICDANKEGMFLFRAARKLRQFLKMNSTGDF
DLHLLKVSEGTTILLNCTGQVKGRKPAALGEAQPTKSLEENKSLKEQKKLNDLCFLKRL
LQEIKTCWNKILMGTKEHSGGSGGGSGGGSGESGYAQNGDLEDAELDDYSFSCYSQLE
VNGSQHSLTCAFEDPDVNITNLEFEICGALVEVKCLNFRKLQEIYFIETKKFLLIGKSNICV
KVGEKSLTCKKIDLTTIVKPEAPFDLSVVYREGANDFVVTFNTSHLQKKYVKVLMHDV
AYRQEKDENKWTHVNLSSTKLTLLQRKLQPAAMYEIKVRSIPDHYFKGFWSEWSPSYY
FRTPEINNSSGEMDPILLTISILSFFSVALLVILACVLWKKRIKPIVWPSLPDHKKTLEHLC
KKPRKNLNVSFNPESFLDCQIHRVDDIQARDEVEGFLQDTFPQQLEESEKQRLGGDVQSP
NCPSEDVVITPESFGRDSSLTCLAGNVSACDAPILSSSRSLDCRESGKNGPHVYQDLLLSL
GTTNSTLPPPFSLQSGILTLNPVAQGQPILTSLGSNQEEAYVTMSSFYQNQP SEQ ID NO: 161 nucleotide sequence of CAR D0228 ROR1 scFv9 IgG4 CD8 BBz 2A TGFbRIIdn
ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGITGAGCAGGCTGAGATCT
GACGACACGGCCGTGTATTACTGTGCGAGTTATAATGATGCTTTTGATATCTGGGGC
CAAGGCACCCTGGTCACCGTCTCCTCAGGAGGTGGCGGGTCTGGTGGTGGCGGTAG
CGGTGGTGGCGGATCCAATTTTATGCTGACTCAGCCCCACTCTGTGTCGGAGTCTCC
GGGGAAGACGGTAACCATCTCCTGCACCCGCAGCAGTGGCAGCATTGCCAGCAACT -continued ATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCIGCCGCAGAGTCAAAATACGGTCCTCCGTGCCCTCCGTGTCCGATCTAC
ATTTGGGCCCCGCTGGCCGGCACTTGCGGCGTGCTCCTGCTGTCGCTGGTCATCACC
CTTTACTGCAAGCGcGGccGcAAGAAATTGCTTTACATTTTTAAGCAGCCGTTCATGCG
ACCAGTACAGACTACTCAAGAAGAAGATGGGTGCTCTTGTCGGTTCCCGGAAGAAG
AAGAGGGTGGTTGCGAGTTGAGGGTGAAGTTCTCCCGCTCTGCCGACGCACCGGCA
TATCAGCAGGGACAAAACCAGCTCTACAACGAATTGAACCTGGGTCGGCGGGAAGA
ATATGACGTGCTCGATAAGCGGCGGGGTCGCGACCCAGAAATGGGAGGCAAACCGC
GCAGGAAAAATCCACAGGAGGGACTTTATAACGAACTTCAAAAGGATAAGATGGCA
GAGGCATACAGCGAAATCGGGATGAAAGGCGAGAGAAGAAGGGGGAAAGGGCACG
ATGGTCTTTACCAGGGGCTTTCTACCGCGACGAAGGATACCTACGATGCTCTCCATA
TGCAAGCACTTCCTCCTAGACGGGCAAAGCGGGGCTCAGGGGCGACTAACTTTTCA
CTGTTGAAGCAGGCCGGGGATGTGGAGGAGAATCCTGGTCCTAGAGCTAAGCGAGT
AGACATGGGAAGAGGGCTGCTCCGAGGCTTGTGGCCGTTGCATATTGTATTGTGGAC
GCGGATAGCGAGTACAATCCCGCCTCACGTGCAAAAATCAGTTAATAACGACATGA
TCGTTACTGACAACAATGGCGCAGTTAAATTTCCGCAGCTTTGTAAATTCTGTGATG
TAAGATTTTCAACGTGCGATAACCAGAAAAGCTGTATGTCCAACTGCAGCATCACAT
CAATCTGTGAAAAACCCCAAGAGGTATGTGTGGCCGTCTGGCGAAAGAATGACGAA
AATATCACACTGGAGACCGTTTGTCACGATCCTAAACTCCCTTATCATGACTTTATTC
TGGAAGACGCAGCGTCACCGAAGTGTATAATGAAAGAGAAGAAGAAGCCTGGAGA
GACGTTTTTCATGTGCAGTTGCTCCTCAGATGAGTGTAATGACAACATCATTTTTTCC
GAGGAGTACAATACGAGTAACCCAGACCTCCTGCTGGTTATTTTCCAGGTAACCGGC
ATCAGTTTGTTGCCCCCACTGGGTGTTGCAATCAGTGTAATAATCATATTTTATTGTT
ACCGGGTGTGA SEQ ID NO: 162 amino acid sequence of CAR D0228 ROR1 scFv9 IgG4 CD8 BBz 2A TGFbRIIdn
MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRVDMGRGLLRGLWPLHIVLWTRIASTIPPHVQKSVNNDMIV
TDNNGAVKFPQLCKFCDVRFSTCDNQKSCMSNCSITSICEKPQEVCVAVWRKNDENITL
ETVCHDPKLPYHDFILEDAASPKCIMKEKKKPGETFFMCSCSSDECNDNIIFSEEYNTSNP
DLLLVIFQVTGISLLPPLGVAISVIIIFYCYRV SEQ ID NO: 163 nucleotide sequence of CAR D0231 ROR1 scFv9 IgG4 CD8 BBz 2A tEGFR
ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGITGAGCAGGCTGAGATCT
GACGACACGGCCGTGTATTACTGTGCGAGTTATAATGATGCTTTTGATATCTGGGGC
CAAGGCACCCTGGTCACCGTCTCCTCAGGAGGTGGCGGGTCTGGTGGTGGCGGTAG
CGGTGGTGGCGGATCCAATTTTATGCTGACTCAGCCCCACTCTGTGTCGGAGTCTCC
GGGGAAGACGGTAACCATCTCCTGCACCCGCAGCAGTGGCAGCATTGCCAGCAACT
ATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCtGCCGCAGAGTCAAAATACGGTCCTCCGTGCCCTCCGTGTCCGATCTAC
ATTTGGGCCCCGCTGGCCGGCACTTGCGGCGTGCTCCTGCTGTCGCTGGTCATCACC
CTTTACTGCAAGCGcGGccGcAAGAAATTGCTTTACATTTTTAAGCAGCCGTTCATGCG
ACCAGTACAGACTACTCAAGAAGAAGATGGGTGCTCTTGTCGGTTCCCGGAAGAAG
AAGAGGGTGGTTGCGAGTTGAGGGTGAAGTTCTCCCGCTCTGCCGACGCACCGGCA
TATCAGCAGGGACAAAACCAGCTCTACAACGAATTGAACCTGGGTCGGCGGGAAGA
ATATGACGTGCTCGATAAGCGGCGGGGTCGCGACCCAGAAATGGGAGGCAAACCGC
GCAGGAAAAATCCACAGGAGGGACTTTATAACGAACTTCAAAAGGATAAGATGGCA
GAGGCATACAGCGAAATCGGGATGAAAGGCGAGAGAAGAAGGGGGAAAGGGCACG
ATGGTCTTTACCAGGGGCTTTCTACCGCGACGAAGGATACCTACGATGCTCTCCATA
TGCAAGCACTTCCTCCTAGACGGGCAAAGCGGGGCTCAGGGGCGACTAACTTTTCA
CTGTTGAAGCAGGCCGGGGATGTGGAGGAGAATCCTGGTCCTAGAGCTAAGCGAgcta
gcgtgtacATGGCACTGCCCGTGACCGCCCTGCTTCTGCCGCTTGCACTTCTGCTGCACG
CCGCTAGGCCCAGGAAGGTTTGCAATGGAATCGGTATAGGGGAGTTTAAGGATTCA
CTTAGCATAAACGCTACTAAcATTAAACACTTCAAAAACTGTACGAGTATAAGTGGA
GATCTTCACATTTTGCCGGTTGCATTCCGAGGCGATTCATTCACCCACACGCCACCG
CTTGACCCACAAGAATTGGATATTCTTAAAACCGTTAAAGAAATAACGGGGTTTTTG
CTCATTCAAGCGTGGCCAGAAAATCGCACTGACCTCCATGCTTTCGAGAACCTGGAG
ATTATAAGAGGACGAACTAAGCAGCATGGTCAATTCTCCCTTGCTGTGGTCAGCCTG
AACATCACCAGTCTTGGTTTGCGGTCCCTCAAGGAAATTTCAGATGGAGATGTCATC
ATAAGCGGCAACAAGAATTTGTGCTATGCAAATACCATAAACTGGAAAAAACTGTT
TGGCACTTCCGGCCAGAAAACCAAGATTATTTCAAATCGGGGTGAGAACAGCTGCA
AAGCCACCGGCCAGGTTTGTCATGCCTTGTGCTCTCCGGAAGGCTGTTGGGGGCCAG -continued AACCCAGGGACTGCGTCAGTTGCAGAAACGTCTCAAGAGGCCGCGAATGCGTTGAC
AAGTGTAACCTCCTTGAGGGTGAGCCACGAGAGTTTGTTGAGAACAGCGAGTGTAT
ACAATGTCACCCTGAATGTTTGCCCCAGGCTATGAATATAACCTGCACAGGCCGCGG
GCCTGATAACTGCATCCAGTGTGCTCATTACATAGATGGACCTCACTGTGTGAAAAC
CTGCCCGGCCGGAGTTATGGGAGAAAACAACACTCTGGTGTGGAAATACGCTGATG
CAGGCCACGTGTGCCACCTTTGTCACCCGAATTGcACATATGGGTGTACCGGTCCTG
GACTTGAAGGTTGCCCTACCAATGGCCCTAAAATACCCAGTATCGCAACTGGCATGG
TAGGCGCTCTTCTCTTGCTCTTGGTAGTTGCTCTCGGCATAGGTCTTTTTATGTGA SEQ ID NO: 164 amino acid sequence of CAR D0231 ROR1 scFv9 IgG4 CD8 BBz 2A tEGFR
MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRASVYMALPVTALLLPLALLLHAARPRKVCNGIGIGEFKDS
LSINATNIKHFKNCTSISGDLHILPVAFRGDSFTHTPPLDPQELDILKTVKEITGFLLIQAWP
ENRTDLHAFENLEIIRGRTKQHGQFSLAVVSLNITSLGLRSLKEISDGDVIISGNKNLCYA
NTINWKKLFGTSGQKTKIISNRGENSCKATGQVCHALCSPEGCWGPEPRDCVSCRNVSR
GRECVDKCNLLEGEPREFVENSECIQCHPECLPQAMNITCTGRGPDNCIQCAHYIDGPHC
VKTCPAGVMGENNTLVWKYADAGHVCHLCHPNCTYGCTGPGLEGCPTNGPKIPSIATG
MVGALLLLLVVALGIGLFM SEQ ID NO: 165 nucleotide sequence of CAR D0245 MSLN M1-4S CD8 BBz 2A mIL7
ATGCTGCTGCTGGTGACCAGCCTGCTGCTGTGCGAACTGCCGCATCCGGCGTTTCTG
CTGATTCCGGAGGTCCAGCTGGTACAGTCTGGGGGAGGCTTGGTACAGCCTGGGGG
GTCCCTGAGACTCTCCTGTGCAGCCTCTGGATTCACCTTTGATGATTATGCCATGCAC
TGGGTCCGGCAAGCTCCAGGGAAGGGCCTGGAGTGGGTCTCAGGTATTAGTTGGAA
TAGTGGTAGCATAGGCTATGCGGACTCTGTGAAGGGCCGATTCACCATCTCCAGAGA
CAACGCCAAGAACTCCCTGTATCTGCAAATGAACAGTCTGAGAGCTGAGGACACGG
CCTTGTATTACTGTGCAAAAGATTTATCGTCAGTGGCTGGACCCTTTAACTACTGGG
GCCAGGGCACCCTGGTCACCGTCTCCTCAGGAGGTGGCGGGTCTGGTGGAGGCGGT
AGCGGCGGTGGCGGATCCTCTTCTGAGCTGACTCAGGACCCTGCTGTGTCTGTGGCC
TTGGGACAGACAGTCAGGATCACATGCCAAGGAGACAGCCTCAGAAGCTATTATGC
AAGCTGGTACCAGCAGAAGCCAGGACAGGCCCCTGTACTTGTCATCTATGGTAAAA
ACAACCGGCCCTCAGGGATCCCAGACCGATTCTCTGGCTCCAGCTCAGGAAACACA
GCTTCCTTGACCATCACTGGGGCTCAGGCGGAGGATGAGGCTGACTATTACTGTAAC
TCCCGGGACAGCAGTGGTAACCATCTGGTATTCGGCGGAGGCACCCAGCTGACCGT
CCTCGGTGCGGCCGCTACCACAACCCCTGCGCCCCGGCCTCCTACCCCCGCACCCAC
GATTGCTTCTCAACCTCTTTCACTCCGACCTGAGGCTTGTAGACCTGCAGCCGGGGG
TGCCGTCCACACACGGGGACTCGACTTCGCTTGTGATATATATATTTGGGCGCCCCT
GGCCGGCACTTGTGGAGTTCTTTTGCTCTCTCTTGTTATCACATTGTACTGCAAGCGA
GGTAGGAAGAAATTGCTTTACATTTTTAAGCAGCCGTTCATGCGACCAGTACAGACT
ACTCAAGAAGAAGATGGGTGCTCTTGTCGGTTCCCGGAAGAAGAAGAGGGTGGTTG
CGAGTTGAGGGTGAAGTTCTCCCGCTCTGCCGACGCACCGGCATATCAGCAGGGAC
AAAACCAGCTCTACAACGAATTGAACCTGGGTCGGCGGGAAGAATATGACGTGCTC
GATAAGCGGCGGGGTCGCGACCCAGAAATGGGAGGCAAACCGCGCAGGAAAAATC
CACAGGAGGGACTTTATAACGAACTTCAAAAGGATAAGATGGCAGAGGCATACAGC
GAAATCGGGATGAAAGGCGAGAGAAGAAGGGGGAAAGGGCACGATGGTCTTTACC
AGGGGCTTTCTACCGCGACGAAGGATACCTACGATGCTCTCCATATGCAAGCACTTC
CTCCTAGACGGGCAAAGCGGGGCTCAGGGGCGACTAACTTTTCACTGTTGAAGCAG
GCCGGGGATGTGGAGGAGAATCCTGGTCCTAGAGCTAAGCGAGTAATGCTCTTGCT
CGTGACTTCTTTGCTTTTGTGCGAACTTCCGCACCCAGCCTTCCTTTTGATACCTATG
GATTGTGATATTGAAGGTAAAGATGGCAAACAATATGAGAGTGTTCTAATGGTCAG
CATCGATCAATTATTGGACAGCATGAAAGAAATTGGTAGCAATTGCCTGAATAATG
AATTTAACTTTTTTAAAAGACATATCTGTGATGCTAATAAGGAAGGTATGTTTTTATT
CCGTGCTGCTCGCAAGTTGAGGCAATTTCTTAAAATGAATAGCACTGGTGATTTTGA
TCTCCACTTATTAAAAGTTTCAGAAGGCACAACAATACTGTTGAACTGCACTGGCCA
GGTTAAAGGAAGAAAACCAGCTGCCCTGGGTGAAGCCCAACCAACAAAGAGTTTGG
AAGAAAATAAATCTTTAAAGGAACAGAAAAAACTGAATGACTTGTGTTTCCTAAAG
AGACTATTACAAGAGATAAAAACTTGTTGGAATAAAATTTTGATGGGCACTAAAGA
ACACTCCGGAGGTTCCGGTGGTGGCTCAGGTGGTGGCTCAGGTGAAAGTGGCTATG
CTCAAAATGGAGACTTGGAAGATGCAGAACTGGATGACTACTCATTCTCATGCTATA
GCCAGTTGGAAGTGAATGGATCGCAGCACTCACTGACCTGTGCTTTTGAGGACCCAG
ATGTCAACATCACCAATCTGGAATTTGAAATATGTGGGGCCCTCGTGGAGGTAAAGT
GCCTGAATTTCAGGAAACTACAAGAGATATATTTCATCGAGACAAAGAAATTCTTAC
TGATTGGAAAGAGCAATATATGTGTGAAGGTTGGAGAAAAGAGTCTAACCTGCAAA
AAAATAGACCTAACCACTATAGTTAAACCTGAGGCTCCTTTTGACCTGAGTGTCGTC
TATCGGGAAGGAGCCAATGACTTTGTGGTGACATTTAATACATCACACTTGCAAAAG
AAGTATGTAAAAGTTTTAATGCACGATGTAGCTTACCGCCAGGAAAAGGATGAAAA
CAAATGGACGCATGTGAATTTATCCAGCACAAAGCTGACACTCCTGCAGAGAAAGC
TCCAACCGGCAGCAATGTATGAGATTAAAGTTCGATCCATCCCTGATCACTATTTTA
AAGGCTTCTGGAGTGAATGGAGTCCAAGTTATTACTTCAGAACTCCAGAGATCAATA
ATAGCTCAGGGGAGATGGATCCTATCTTACTAACCATCAGCATTTTGAGTTTTTTCTC
TGTCGCTCTGTTGGTCATCTTGGCCTGTGTGTTATGGAAAAAAAGGATTAAGCCTAT
CGTATGGCCCAGTCTCCCCGATCATAAGAAGACTCTGGAACATCTTTGTAAGAAACC
AAGAAAAAATTTgAATGTGAGTTTCAATCCTGAAAGTTTCCTGGACTGCCAGATTCA
TAGGGTGGATGACATTCAAGCTAGAGATGAAGTGGAAGGTTTTCTGCAAGATACGT -continued TTCCTCAGCAACTAGAAGAATCTGAGAAGCAGAGGCTTGGAGGGGATGTGCAGAGC
CCCAACTGCCCATCTGAGGATGTAGTCATCACTCCAGAAAGCTTTGGAAGAGATTCA
TCCCTCACATGCCTGGCTGGGAATGTCAGTGCATGTGACGCCCCTATTCTCTCCTCTT
CCAGGTCCCTAGACTGCAGGGAGAGTGGCAAGAATGGGCCTCATGTGTACCAGGAC
CTCCTTCTTAGCCTTGGGACTACAAACAGCACGCTGCCCCCTCCATTTTCTCTCCAAT
CTGGAATCCTGACATTGAACCCAGTTGCTCAGGGTCAGCCCATTCTTACTTCCCTGG
GATCAAATCAAGAAGAAGCATATGTCACCATGTCCAGCTTCTACCAAAACCAGCCT
AGGTAA SEQ ID NO: 166 amino acid sequence of CAR D0245 MSLN M1-4S CD8 BBz 2A mIL7
MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQTV
RITCQGDSLRSYYASWYQQKPGQAPVLVIYGKNNRPSGIPDRFSGSSSGNTASLTITGAQ
AEDEADYYCNSRDSSGNHLVFGGGTQLTVLGAAATTTPAPRPPTPAPTIASQPLSLRPEA
CRPAAGGAVHTRGLDFACDIYIWAPLAGTCGVLLLSLVITLYCKRGRKKLLYIFKQPFM
RPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDG
LYQGLSTATKDTYDALHMQALPPRRAKRGSGATNFSLLKQAGDVEENPGPRAKRVML
LLVTSLLLCELPHPAFLLIPMDCDIEGKDGKQYESVLMVSIDQLLDSMKEIGSNCLNNEF
NFFKRHICDANKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILMGTKEHSGGSG
GGSGGGSGESGYAQNGDLEDAELDDYSFSCYSQLEVNGSQHSLTCAFEDPDVNITNLEF
EICGALVEVKCLNFRKLQEIYFIETKKFLLIGKSNICVKVGEKSLTCKKIDLTTIVKPEAPF
DLSVVYREGANDFVVTFNTSHLQKKYVKVLMHDVAYRQEKDENKWTHVNLSSTKLTL
LQRKLQPAAMYEIKVRSIPDHYFKGFWSEWSPSYYFRTPEINNSSGEMDPILLTISILSFFS
VALLVILACVLWKKRIKPIVWPSLPDHKKTLEHLCKKPRKNLNVSFNPESFLDCQIHRVD
DIQARDEVEGFLQDTFPQQLEESEKQRLGGDVQSPNCPSEDVVITPESFGRDSSLTCLAG
NVSACDAPILSSSRSLDCRESGKNGPHVYQDLLLSLGTTNSTLPPPFSLQSGILTLNPVAQ
GQPILTSLGSNQEEAYVTMSSFYQNQPR SEQ ID NO: 167 nucleotide sequence of CAR D0284 MSLN M1-4S CD8 28z 2A mIL7
ATGCTGCTGCTGGTGACCAGCCTGCTGCTGTGCGAACTGCCGCATCCGGCGTTTCTG
CTGATTCCGGAGGTCCAGCTGGTACAGTCTGGGGGAGGCTTGGTACAGCCTGGGGG
GTCCCTGAGACTCTCCTGTGCAGCCTCTGGATTCACCTTTGATGATTATGCCATGCAC
TGGGTCCGGCAAGCTCCAGGGAAGGGCCTGGAGTGGGTCTCAGGTATTAGTTGGAA
TAGTGGTAGCATAGGCTATGCGGACTCTGTGAAGGGCCGATTCACCATCTCCAGAGA
CAACGCCAAGAACTCCCTGTATCTGCAAATGAACAGTCTGAGAGCTGAGGACACGG
CCTTGTATTACTGTGCAAAAGATTTATCGTCAGTGGCTGGACCCTTTAACTACTGGG
GCCAGGGCACCCTGGTCACCGTCTCCTCAGGAGGTGGCGGGTCTGGTGGAGGCGGT
AGCGGCGGTGGCGGATCCTCTTCTGAGCTGACTCAGGACCCTGCTGTGTCTGTGGCC
TTGGGACAGACAGTCAGGATCACATGCCAAGGAGACAGCCTCAGAAGCTATTATGC
AAGCTGGTACCAGCAGAAGCCAGGACAGGCCCCTGTACTTGTCATCTATGGTAAAA
ACAACCGGCCCTCAGGGATCCCAGACCGATTCTCTGGCTCCAGCTCAGGAAACACA
GCTTCCTTGACCATCACTGGGGCTCAGGCGGAGGATGAGGCTGACTATTACTGTAAC
TCCCGGGACAGCAGTGGTAACCATCTGGTATTCGGCGGAGGCACCCAGCTGACCGT
CCTCGGTGCGGCCGCAACCACTACGCCTGCTCCGCGGCCTCCAACGCCCGCGCCCAC
GATAGCTAGTCAGCCGTTGTCTCTCCGACCAGAGGCGTGTAGACCGGCCGCTGGCG
GAGCCGTACATACTCGCGGACTCGACTTCGCTTGCGACATCTACATTTGGGCACCCT
TGGCTGGGACCTGTGGGGTGCTGTTGCTGTCCTTGGTTATTACGTTGTACTGCCGGTC
GAAGAGGTCCAGACTCTTGCACTCCGACTACATGAACATGACTCCTAGAAGGCCCG
GACCCACTAGAAAGCACTACCAGCCGTACGCCCCTCCTCGGGATTTCGCCGCATACC
GGTCCAGAGTCAAATTTTCCAGGTCCGCAGATGCCCCCGCGTACCAGCAAGGCCAG
AACCAACTTTACAACGAACTGAACCTGGGTCGCCGGGAGGAATATGATGTGCTGGA
TAAACGAAGGGGGAGGGACCCTGAGATGGGAGGGAAACCTCGCAGGAAAAACCCG
CAGGAAGGTTTGTACAACGAGTTGCAGAAGGATAAGATGGCTGAGGCTTACTCTGA
AATAGGGATGAAGGGAGAGAGACGGAGAGGAAAAGGCCATGATGGCCTTTACCAG
GGCTTAAGCACAGCAACAAAGGATACTTACGACGCTCTTCACATGCAAGCTCTGCC
ACCACGGCGGGCAAAGCGGGGCTCAGGGGCGACTAACTTTTCACTGTTGAAGCAGG
CCGGGGATGTGGAGGAGAATCCTGGTCCTAGAGCTAAGCGAGTAATGCTCTTGCTC
GTGACTTCTTTGCTTTTGTGCGAACTTCCGCACCCAGCCTTCCTTTTGATACCTATGG
ATTGTGATATTGAAGGTAAAGATGGCAAACAATATGAGAGTGTTCTAATGGTCAGC
ATCGATCAATTATTGGACAGCATGAAAGAAATTGGTAGCAATTGCCTGAATAATGA
ATTTAACTTTTTTAAAAGACATATCTGTGATGCTAATAAGGAAGGTATGTTTTTATTC
CGTGCTGCTCGCAAGTTGAGGCAATTTCTTAAAATGAATAGCACTGGTGATTTTGAT
CTCCACTTATTAAAAGTTTCAGAAGGCACAACAATACTGTTGAACTGCACTGGCCAG
GTTAAAGGAAGAAAACCAGCTGCCCTGGGTGAAGCCCAACCAACAAAGAGTTTGGA
AGAAAATAAATCTTTAAAGGAACAGAAAAAACTGAATGACTTGTGTTTCCTAAAGA
GACTATTACAAGAGATAAAAACTTGTTGGAATAAAATTTTGATGGGCACTAAAGAA
CACTCCGGAGGTTCCGGTGGTGGCTCAGGTGGTGGCTCAGGTGAAAGTGGCTATGCT
CAAAATGGAGACTTGGAAGATGCAGAACTGGATGACTACTCATTCTCATGCTATAGC
CAGTTGGAAGTGAATGGATCGCAGCACTCACTGACCTGTGCTTTTGAGGACCCAGAT
GTCAACATCACCAATCTGGAATTTGAAATATGTGGGGCCCTCGTGGAGGTAAAGTGC
CTGAATTTCAGGAAACTACAAGAGATATATTTCATCGAGACAAAGAAATTCTTACTG
ATTGGAAAGAGCAATATATGTGTGAAGGTTGGAGAAAAGAGTCTAACCTGCAAAAA
AATAGACCTAACCACTATAGTTAAACCTGAGGCTCCTTTTGACCTGAGTGTCGTCTA
TCGGGAAGGAGCCAATGACTTTGTGGTGACATTTAATACATCACACTTGCAAAAGA
AGTATGTAAAAGTTTTAATGCACGATGTAGCTTACCGCCAGGAAAAGGATGAAAAC
AAATGGACGCATGTGAATTTATCCAGCACAAAGCTGACACTCCTGCAGAGAAAGCT
CCAACCGGCAGCAATGTATGAGATTAAAGTTCGATCCATCCCTGATCACTATTTTAA
AGGCTTCTGGAGTGAATGGAGTCCAAGTTATTACTTCAGAACTCCAGAGATCAATAA -continued TAGCTCAGGGGAGATGGATCCTATCTTACTAACCATCAGCATTTTGAGTTTTTTCTCT
GTCGCTCTGTTGGTCATCTTGGCCTGTGTGTTATGGAAAAAAAGGATTAAGCCTATC
GTATGGCCCAGTCTCCCCGATCATAAGAAGACTCTGGAACATCTTTGTAAGAAACCA
AGAAAAAATTTAAATGTGAGTTTCAATCCTGAAAGTTTCCTGGACTGCCAGATTCAT
AGGGTGGATGACATTCAAGCTAGAGATGAAGTGGAAGGTTTTCTGCAAGATACGTT
TCCTCAGCAACTAGAAGAATCTGAGAAGCAGAGGCTTGGAGGGGATGTGCAGAGCC
CCAACTGCCCATCTGAGGATGTAGTCATCACTCCAGAAAGCTTTGGAAGAGATTCAT
CCCTCACATGCCTGGCTGGGAATGTCAGTGCATGTGACGCCCCTATTCTCTCCTCTTC
CAGGTCCCTAGACTGCAGGGAGAGTGGCAAGAATGGGCCTCATGTGTACCAGGACC
TCCTTCTTAGCCTTGGGACTACAAACAGCACGCTGCCCCCTCCATTTTCTCTCCAATC
TGGAATCCTGACATTGAACCCAGTTGCTCAGGGTCAGCCCATTCTTACTTCCCTGGG
ATCAAATCAAGAAGAAGCATATGTCACCATGTCCAGCTTCTACCAAAACCAGCCCT
AG SEQ ID NO: 168 amino acid sequence of CAR D0284 MSLN M1-4S CD8 28z 2A mIL7
MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQTV
RITCQGDSLRSYYASWYQQKPGQAPVLVIYGKNNRPSGIPDRFSGSSSGNTASLTITGAQ
AEDEADYYCNSRDSSGNHLVFGGGTQLTVLGAAATTTPAPRPPTPAPTIASQPLSLRPEA
CRPAAGGAVHTRGLDFACDIYIWAPLAGTCGVLLLSLVITLYCRSKRSRLLHSDYMNMT
PRRPGPTRKHYQPYAPPRDFAAYRSRVKFSRSADAPAYQQGQNQLYNELNLGRREEYD
VLDKRRGRDPEMGGKPRRKNPQEGLYNELQKDKMAEAYSEIGMKGERRRGKGHDGL
YQGLSTATKDTYDALHMQALPPRRAKRGSGATNFSLLKQAGDVEENPGPRAKRVMLL
LVTSLLLCELPHPAFLLIPMDCDIEGKDGKQYESVLMVSIDQLLDSMKEIGSNCLNNEFN
FFKRHICDANKEGMFLFRAARKLRQFLKMNSTGDFDLHLLKVSEGTTILLNCTGQVKGR
KPAALGEAQPTKSLEENKSLKEQKKLNDLCFLKRLLQEIKTCWNKILMGTKEHSGGSGG
GSGGGSGESGYAQNGDLEDAELDDYSFSCYSQLEVNGSQHSLTCAFEDPDVNITNLEFEI
CGALVEVKCLNFRKLQEIYFIETKKFLLIGKSNICVKVGEKSLTCKKIDLTTIVKPEAPFDL
SVVYREGANDFVVTFNTSHLQKKYVKVLMHDVAYRQEKDENKWTHVNLSSTKLTLLQ
RKLQPAAMYEIKVRSIPDHYFKGFWSEWSPSYYFRTPEINNSSGEMDPILLTISILSFFSVA
LLVILACVLWKKRIKPIVWPSLPDHKKTLEHLCKKPRKNLNVSFNPESFLDCQIHRVDDI
QARDEVEGFLQDTFPQQLEESEKQRLGGDVQSPNCPSEDVVITPESFGRDSSLTCLAGNV
SACDAPILSSSRSLDCRESGKNGPHVYQDLLLSLGTTNSTLPPPFSLQSGILTLNPVAQGQ
PILTSLGSNQEEAYVTMSSFYQNQP SEQ ID NO: 169 nucleotide sequence of CAR D0211 MSLN MI-4S CD8 BBz 2A TGFbRIIdn
ATGCTGCTGCTGGTGACCAGCCTGCTGCTGTGCGAACTGCCGCATCCGGCGTTTCTG
CTGATTCCGGAGGTCCAGCTGGTACAGTCTGGGGGAGGCTTGGTACAGCCTGGGGG
GTCCCTGAGACTCTCCTGTGCAGCCTCTGGATTCACCTTTGATGATTATGCCATGCAC
TGGGTCCGGCAAGCTCCAGGGAAGGGCCTGGAGTGGGTCTCAGGTATTAGTTGGAA
TAGTGGTAGCATAGGCTATGCGGACTCTGTGAAGGGCCGATTCACCATCTCCAGAGA
CAACGCCAAGAACTCCCTGTATCTGCAAATGAACAGTCTGAGAGCTGAGGACACGG
CCTTGTATTACTGTGCAAAAGATTTATCGTCAGTGGCTGGACCCTTTAACTACTGGG
GCCAGGGCACCCTGGTCACCGTCTCCTCAGGAGGTGGCGGGTCTGGTGGAGGCGGT
AGCGGCGGTGGCGGATCCTCTTCTGAGCTGACTCAGGACCCTGCTGTGTCTGTGGCC
TTGGGACAGACAGTCAGGATCACATGCCAAGGAGACAGCCTCAGAAGCTATTATGC
AAGCTGGTACCAGCAGAAGCCAGGACAGGCCCCTGTACTTGTCATCTATGGTAAAA
ACAACCGGCCCTCAGGGATCCCAGACCGATTCTCTGGCTCCAGCTCAGGAAACACA
GCTTCCTTGACCATCACTGGGGCTCAGGCGGAGGATGAGGCTGACTATTACTGTAAC
TCCCGGGACAGCAGTGGTAACCATCTGGTATTCGGCGGAGGCACCCAGCTGACCGT
CCTCGGTGCGGCCGCTACCACAACCCCTGCGCCCCGGCCTCCTACCCCCGCACCCAC
GATTGCTTCTCAACCTCTTTCACTCCGACCTGAGGCTTGTAGACCTGCAGCCGGGGG
TGCCGTCCACACACGGGGACTCGACTTCGCTTGTGATATATATATTTGGGCGCCCCT
GGCCGGCACTTGTGGAGTTCTTTTGCTCTCTCTTGTTATCACATTGTACTGCAAGCGA
GGTAGGAAGAAATTGCTTTACATTTTTAAGCAGCCGTTCATGCGACCAGTACAGACT
ACTCAAGAAGAAGATGGGTGCTCTTGTCGGTTCCCGGAAGAAGAAGAGGGTGGTTG
CGAGTTGAGGGTGAAGTTCTCCCGCTCTGCCGACGCACCGGCATATCAGCAGGGAC
AAAACCAGCTCTACAACGAATTGAACCTGGGTCGGCGGGAAGAATATGACGTGCTC
GATAAGCGGGGGGTCGCGACCCAGAAATGGGAGGCAAACCGCGCAGGAAAAATC
CACAGGAGGGACTTTATAACGAACTTCAAAAGGATAAGATGGCAGAGGCATACAGC
GAAATCGGGATGAAAGGCGAGAGAAGAAGGGGGAAAGGGCACGATGGTCTTTACC
AGGGGCTTTCTACCGCGACGAAGGATACCTACGATGCTCTCCATATGCAAGCACTTC
CTCCTAGACGGGCAAAGCGGGGCTCAGGGGCGACTAACTTTTCACTGTTGAAGCAG
GCCGGGGATGTGGAGGAGAATCCTGGTCCTAGAGCTAAGCGAGTAGACATGGGAAG
AGGGCTGCTCCGAGGCTTGTGGCCGTTGCATATTGTATTGTGGACGCGGATAGCGAG
TACAATCCCGCCTCACGTGCAAAAATCAGTTAATAACGACATGATCGTTACTGACAA
CAATGGCGCAGTTAAATTTCCGCAGCTTTGTAAATTCTGTGATGTAAGATTTTCAAC
GTGCGATAACCAGAAAAGCTGTATGTCCAACTGCAGCATCACATCAATCTGTGAAA
AACCCCAAGAGGTATGTGTGGCCGTCTGGCGAAAGAATGACGAAAATATCACACTG
GAGACCGTTTGTCACGATCCTAAACTCCCTTATCATGACTTTATTCTGGAAGACGCA
GCGTCACCGAAGTGTATAATGAAAGAGAAGAAGAAGCCTGGAGAGACGTTTTTCAT
GTGCAGTTGCTCCTCAGATGAGTGTAATGACAACATCATTTTTTCCGAGGAGTACAA
TACGAGTAACCCAGACCTCCTGCTGGTTATTTTCCAGGTAACCGGCATCAGTTTGTT
GCCCCCACTGGGTGTTGCAATCAGTGTAATAATCATATTTTATTGTTACCGGGTGTG
A SEQ ID NO: 170 amino acid sequence of CAR D0211 MSLN MI-4S CD8 BBz 2A TGFbRIIdn
MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQTV -continued RITCQGDSLRSYYASWYQQKPGQAPVLVIYGKNNRPSGIPDRFSGSSSGNTASLTITGAQ
AEDEADYYCNSRDSSGNHLVFGGGTQLTVLGAAATTTPAPRPPTPAPTIASQPLSLRPEA
CRPAAGGAVHTRGLDFACDIYIWAPLAGTCGVLLLSLVITLYCKRGRKKLLYIFKQPFM
RPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDG
LYQGLSTATKDTYDALHMQALPPRRAKRGSGATNFSLLKQAGDVEENPGPRAKRVDM
GRGLLRGLWPLHIVLWTRIASTIPPHVQKSVNNDMIVTDNNGAVKFPQLCKFCDVRFST
CDNQKSCMSNCSITSICEKPQEVCVAVWRKNDENITLETVCHDPKLPYHDFILEDAASPK
CIMKEKKKPGETFFMCSCSSDECNDNIIFSEEYNTSNPDLLLVIFQVTGISLLPPLGVAISVI
IIFYCYRV SEQ ID NO: 171 nucleotide sequence of CAR D0246 MSLN M1-4S CD8 BBz 2A mIL7 2A tEGFR ATGCTGCTGCTGGTGACCAGCCTGCTGCTGTGCGAACTGCCGCATCCGGCGTTTCTG
CTGATTCCGGAGGTCCAGCTGGTACAGTCTGGGGGAGGCTTGGTACAGCCTGGGGG
GTCCCTGAGACTCTCCTGTGCAGCCTCTGGATTCACCTTTGATGATTATGCCATGCAC
TGGGTCCGGCAAGCTCCAGGGAAGGGCCTGGAGTGGGTCTCAGGTATTAGTTGGAA
TAGTGGTAGCATAGGCTATGCGGACTCTGTGAAGGGCCGATTCACCATCTCCAGAGA
CAACGCCAAGAACTCCCTGTATCTGCAAATGAACAGTCTGAGAGCTGAGGACACGG
CCTTGTATTACTGTGCAAAAGATTTATCGTCAGTGGCTGGACCCTTTAACTACTGGG
GCCAGGGCACCCTGGTCACCGTCTCCTCAGGAGGTGGCGGGTCTGGTGGAGGCGGT
AGCGGCGGTGGCGGATCCTCTTCTGAGCTGACTCAGGACCCTGCTGTGTCTGTGGCC
TTGGGACAGACAGTCAGGATCACATGCCAAGGAGACAGCCTCAGAAGCTATTATGC
AAGCTGGTACCAGCAGAAGCCAGGACAGGCCCCTGTACTTGTCATCTATGGTAAAA
ACAACCGGCCCTCAGGGATCCCAGACCGATTCTCTGGCTCCAGCTCAGGAAACACA
GCTTCCTTGACCATCACTGGGGCTCAGGCGGAGGATGAGGCTGACTATTACTGTAAC
TCCCGGGACAGCAGTGGTAACCATCTGGTATTCGGCGGAGGCACCCAGCTGACCGT
CCTCGGTGCGGCCGCTACCACAACCCCTGCGCCCCGGCCTCCTACCCCCGCACCCAC
GATTGCTTCTCAACCTCTTTCACTCCGACCTGAGGCTTGTAGACCTGCAGCCGGGGG
TGCCGTCCACACACGGGGACTCGACTTCGCTTGTGATATATATATTTGGGCGCCCCT
GGCCGGCACTTGTGGAGTTCTTTTGCTCTCTCTTGTTATCACATTGTACTGCAAGCGA
GGTAGGAAGAAATTGCTTTACATTTTTAAGCAGCCGTTCATGCGACCAGTACAGACT
ACTCAAGAAGAAGATGGGTGCTCTTGTCGGTTCCCGGAAGAAGAAGAGGGTGGTTG
CGAGTTGAGGGTGAAGTTCTCCCGCTCTGCCGACGCACCGGCATATCAGCAGGGAC
AAAACCAGCTCTACAACGAATTGAACCTGGGTCGGCGGGAAGAATATGACGTGCTC
GATAAGCGGGGGGTCGCGACCCAGAAATGGGAGGCAAACCGCGCAGGAAAAATC
CACAGGAGGGACTTTATAACGAACTTCAAAAGGATAAGATGGCAGAGGCATACAGC
GAAATCGGGATGAAAGGCGAGAGAAGAAGGGGGAAAGGGCACGATGGTCTTTACC
AGGGGCTTTCTACCGCGACGAAGGATACCTACGATGCTCTCCATATGCAAGCACTTC
CTCCTAGACGGGCAAAGCGGGGCTCAGGGGCGACTAACTTTTCACTGTTGAAGCAG
GCCGGGGATGTGGAGGAGAATCCTGGTCCTAGAGCTAAGCGAGTAATGCTCTTGCT
CGTGACTTCTTTGCTTTTGTGCGAACTTCCGCACCCAGCCTTCCTTTTGATACCTATG
GATTGTGATATTGAAGGTAAAGATGGCAAACAATATGAGAGTGTTCTAATGGTCAG
CATCGATCAATTATTGGACAGCATGAAAGAAATTGGTAGCAATTGCCTGAATAATG
AATTTAACTTTTTTAAAAGACATATCTGTGATGCTAATAAGGAAGGTATGTTTTTATT
CCGTGCTGCTCGCAAGTTGAGGCAATTTCTTAAAATGAATAGCACTGGTGATTTTGA
TCTCCACTTATTAAAAGTTTCAGAAGGCACAACAATACTGTTGAACTGCACTGGCCA
GGTTAAAGGAAGAAAACCAGCTGCCCTGGGTGAAGCCCAACCAACAAAGAGTTTGG
AAGAAAATAAATCTTTAAAGGAACAGAAAAAACTGAATGACTTGTGTTTCCTAAAG
AGACTATTACAAGAGATAAAAACTTGTTGGAATAAAATTTTGATGGGCACTAAAGA
ACACTCCGGAGGTTCCGGTGGTGGCTCAGGTGGTGGCTCAGGTGAAAGTGGCTATG
CTCAAAATGGAGACTTGGAAGATGCAGAACTGGATGACTACTCATTCTCATGCTATA
GCCAGTTGGAAGTGAATGGATCGCAGCACTCACTGACCTGTGCTTTTGAGGACCCAG
ATGTCAACATCACCAATCTGGAATTTGAAATATGTGGGGCCCTCGTGGAGGTAAAGT
GCCTGAATTTCAGGAAACTACAAGAGATATATTTCATCGAGACAAAGAAATTCTTAC
TGATTGGAAAGAGCAATATATGTGTGAAGGTTGGAGAAAAGAGTCTAACCTGCAAA
AAAATAGACCTAACCACTATAGTTAAACCTGAGGCTCCTTTTGACCTGAGTGTCGTC
TATCGGGAAGGAGCCAATGACTTTGTGGTGACATTTAATACATCACACTTGCAAAAG
AAGTATGTAAAAGTTTTAATGCACGATGTAGCTTACCGCCAGGAAAAGGATGAAAA
CAAATGGACGCATGTGAATTTATCCAGCACAAAGCTGACACTCCTGCAGAGAAAGC
TCCAACCGGCAGCAATGTATGAGATTAAAGTTCGATCCATCCCTGATCACTATTTTA
AAGGCTTCTGGAGTGAATGGAGTCCAAGTTATTACTTCAGAACTCCAGAGATCAATA
ATAGCTCAGGGGAGATGGATCCTATCTTACTAACCATCAGCATTTTGAGTTTTTTCTC
TGTCGCTCTGTTGGTCATCTTGGCCTGTGTGTTATGGAAAAAAAGGATTAAGCCTAT
CGTATGGCCCAGTCTCCCCGATCATAAGAAGACTCTGGAACATCTTTGTAAGAAACC
AAGAAAAAATTTgAATGTGAGTTTCAATCCTGAAAGTTTCCTGGACTGCCAGATTCA
TAGGGTGGATGACATTCAAGCTAGAGATGAAGTGGAAGGTTTTCTGCAAGATACGT
TTCCTCAGCAACTAGAAGAATCTGAGAAGCAGAGGCTTGGAGGGGATGTGCAGAGC
CCCAACTGCCCATCTGAGGATGTAGTCATCACTCCAGAAAGCTTTGGAAGAGATTCA
TCCCTCACATGCCTGGCTGGGAATGTCAGTGCATGTGACGCCCCTATTCTCTCCTCTT
CCAGGTCCCTAGACTGCAGGGAGAGTGGCAAGAATGGGCCTCATGTGTACCAGGAC
CTCCTTCTTAGCCTTGGGACTACAAACAGCACGCTGCCCCCTCCATTTTCTCTCCAAT
CTGGAATCCTGACATTGAACCCAGTTGCTCAGGGTCAGCCCATTCTTACTTCCCTGG
GATCAAATCAAGAAGAAGCATATGTCACCATGTCCAGCTTCTACCAAAACCAGCCT
AGGCGCGCGAAACGCGGCAGCGGCGAAGGCCGCGGCAGCCTGCTGACCTGCGGCG
ATGTGGAAGAAAACCCAGGCCCGATGATGGCACTGCCCGTGACCGCCCTGCTTCTG
CCGCTTGCACTTCTGCTGCACGCCGCTAGGCCCAGGAAGGTTTGCAATGGAATCGGT
ATAGGGGAGTTTAAGGATTCACTTAGCATAAACGCTACTAACATTAAACACTTCAAA
AACTGTACGAGTATAAGTGGAGATCTTCACATTTTGCCGGTTGCATTCCGAGGCGAT
TCATTCACCCACACGCCACCGCTTGACCCACAAGAATTGGATATTCTTAAAACCGTT
AAAGAAATAACGGGGTTTTTGCTCATTCAAGCGTGGCCAGAAAATCGCACTGACCTC -continued CATGCTTTCGAGAACCTGGAGATTATAAGAGGACGAACTAAGCAGCATGGTCAATT
CTCCCTTGCTGTGGTCAGCCTGAACATCACCAGTCTTGGTTTGCGGTCCCTCAAGGA
AATTTCAGATGGAGATGTCATCATAAGCGGCAACAAGAATTTGTGCTATGCAAATAC
CATAAACTGGAAAAAACTGTTTGGCACTTCCGGCCAGAAAACCAAGATTATTTCAA
ATCGGGGTGAGAACAGCTGCAAAGCCACCGGCCAGGTTTGTCATGCCTTGTGCTCTC
CGGAAGGCTGTTGGGGGCCAGAACCCAGGGACTGCGTCAGTTGCAGAAACGTCTCA
AGAGGCCGCGAATGCGTTGACAAGTGTAACCTCCTTGAGGGTGAGCCACGAGAGTT
TGTTGAGAACAGCGAGTGTATACAATGTCACCCTGAATGTTTGCCCCAGGCTATGAA
TATAACCTGCACAGGCCGCGGGCCTGATAACTGCATCCAGTGTGCTCATTACATAGA
TGGACCTCACTGTGTGAAAACCTGCCCGGCCGGAGTTATGGGAGAAAACAACACTC
TGGTGTGGAAATACGCTGATGCAGGCCACGTGTGCCACCTTTGTCACCCGAATTGCA
CATATGGGTGTACCGGTCCTGGACTTGAAGGTTGCCCTACCAATGGCCCTAAAATAC
CCAGTATCGCAACTGGCATGGTAGGCGCTCTTCTCTTGCTCTTGGTAGTTGCTCTCGG
CATAGGTCTTTTTATGTGA SEQ ID NO: 172 amino acid sequence of CAR D0246 MSLN M1-4S CD8 BBz 2A mIL7 2A tEGFR MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGGGGGSSSELTQDPAVSVALGQTV
RITCQGDSLRSYYASWYQQKPGQAPVLVIYGKNNRPSGIPDRFSGSSSGNTASLTITGAQ
AEDEADYYCNSRDSSGNHLVFGGGTQLTVLGAAATTTPAPRPPTPAPTIASQPLSLRPEA
CRPAAGGAVHTRGLDFACDIYIWAPLAGTCGVLLLSLVITLYCKRGRKKLLYIFKQPFM
RPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDG
LYQGLSTATKDTYDALHMQALPPRRAKRGSGATNFSLLKQAGDVEENPGPRAKRVML
LLVTSLLLCELPHPAFLLIPMDCDIEGKDGKQYESVLMVSIDQLLDSMKEIGSNCLNNEF
NFFKRHICDANKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILMGTKEHSGGSG
GGSGGGSGESGYAQNGDLEDAELDDYSFSCYSQLEVNGSQHSLTCAFEDPDVNITNLEF
EICGALVEVKCLNFRKLQEIYFIETKKFLLIGKSNICVKVGEKSLTCKKIDLTTIVKPEAPF
DLSVVYREGANDFVVTFNTSHLQKKYVKVLMHDVAYRQEKDENKWTHVNLSSTKLTL
LQRKLQPAAMYEIKVRSIPDHYFKGFWSEWSPSYYFRTPEINNSSGEMDPILLTISILSFFS
VALLVILACVLWKKRIKPIVWPSLPDHKKTLEHLCKKPRKNLNVSFNPESFLDCQIHRVD
DIQARDEVEGFLQDTFPQQLEESEKQRLGGDVQSPNCPSEDVVITPESFGRDSSLTCLAG
NVSACDAPILSSSRSLDCRESGKNGPHVYQDLLLSLGTTNSTLPPPFSLQSGILTLNPVAQ
GQPILTSLGSNQEEAYVTMSSFYQNQPRRAKRGSGEGRGSLLTCGDVEENPGPMMALP
VTALLLPLALLLHAARPRKVCNGIGIGEFKDSLSINATNIKHFKNCTSISGDLHILPVAFRG
DSFTHTPPLDPQELDILKTVKEITGFLLIQAWPENRTDLHAFENLEIIRGRTKQHGQFSLA
VVSLNITSLGLRSLKEISDGDVIISGNKNLCYANTINWKKLFGTSGQKTKIISNRGENSCK
ATGQVCHALCSPEGCWGPEPRDCVSCRNVSRGRECVDKCNLLEGEPREFVENSECIQCH
PECLPQAMNITCTGRGPDNCIQCAHYIDGPHCVKTCPAGVMGENNTLVWKYADAGHV
CHLCHPNCTYGCTGPGLEGCPTNGPKIPSIATGMVGALLLLLVVALGIGLFM SEQ ID NO: 173 nucleotide sequence of CAR D0233 MSLN M1-4S ROR1 scFv9 IgG4 CD8 BBz ATGCTGTTACTTGTGACAAGCTTGCTTCTATGTGAACTGCCGCATCCGGCGTTTCTGC
TGATTCCGGAAGTACAGCTGGTACAGTCTGGAGGGGGATTGGTTCAGCCGGGGGG
TCTTTGCGCCTGTCCTGCGCAGCTAGTGGCTTCACTTTTGATGACTATGCTATGCACT
GGGTCAGACAAGCGCCTGGCAAAGGCCTTGAATGGGTGTCCGGAATTAGCTGGAAT
AGTGGATCCATCGGCTATGCCGATAGTGTAAAGGGCAGGTTCACGATCAGCCGGGA
TAATGCAAAGAACTCTCTCTATTTGCAAATGAACAGTCTGCGGGCTGAAGATACTGC
TCTTTACTATTGTGCTAAAGATTTGTCAAGCGTCGCCGGACCCTTCAACTACTGGGGT
CAAGGGACACTGGTGACAGTTAGCAGCGGTGGTGGAGGCTCCGGTGGAGGTGGTAG
TGGTGGAGGAGGTAGTTCTTCTGAGCTTACGCAAGATCCGGCGGTTAGTGTTGCTCT
GGGGCAGACTGTACGAATCACGTGCCAGGGTGACTCTTTGCGCTCTTACTACGCTAG
TTGGTATCAACAAAAACCCGGACAAGCGCCCGTCCTCGTCATCTATGGCAAGAACA
ATCGCCCAAGCGGCATCCCTGATAGGTTCTCCGGATCATCTTCAGGGAACACAGCCT
CCCTGACTATTACAGGTGCTCAAGCTGAGGACGAGGCTGACTATTATTGCAACAGCC
GGGACTCTAGCGGTAACCACTTGGTCTTTGGTGGGGGTACCCAGCTGACGGTACTTG
GAGGTGGTGGAGGTTCAGGTGGTGGCGGATCAGGTGGAGGTGGTTCTGGAGGGGGT
GGAAGTGGCGGAGGTGGTTCACAGGCGGCCCAGGTACAGCTGCAGCAGTCAGGGGC
TGAGGTGAAGAAGCCTGGGTCCTCGGTGAAGGTCTCCTGCAAGGCTTCTGGAGGCA
CCTTCAGCAGCTATGCTATCAGCTGGGTGCGACAGGCCCCTGGACAAGGGCTTGAGT
GGATGGGATGGATCAACCCTAACAGTGGTGGCACAAACTATGCACAGAGGTTTCAG
GGCAGGGTCACCATGACCAGGGACACGTCCATCAGCACAGCCTACATGGAGTTGAG
CAGGCTGAGATCTGACGACACGGCCGTGTATTACTGTGCGAGTTATAATGATGCTTT
TGATATCTGGGGCCAAGGCACCCTGGTCACCGTCTCCTCAGGAGGTGGCGGGTCTGG
TGGTGGCGGTAGCGGAGGTGGTGGATCTAATTTTATGCTGACTCAGCCCCACTCTGT
GTCGGAGTCTCCGGGGAAGACGGTAACCATCTCCTGCACCCGCAGCAGTGGCAGCA
TTGCCAGCAACTATGTGCAGTGGTACCAGCAGCGACCGGGCAGTGCCCCCACCATT
GTGATCTATGAGGATGATCAAAGACCCTCTGGGGTCCCTGATCGGTTCTCTGGCTCC
ATCGACACCTCCTCCAACTCTGCCTCCCTCACCATCTCTGGACTGCAGAGTGAGGAC
GAGGCTGACTACTACTGTCAGTCTTATGAGCCCGGCAATGGGGTATTCGGCGGAGG
GACCAAGGTCACCGTCCTAGCGGCCGCAGAGTCAAAATACGGTCCTCCGTGCCCTCC
GTGTCCGATCTACATTTGGGCCCCGCTGGCCGGCACTTGCGGCGTGCTCCTGCTGTC
GCTGGTCATCACCCTTTACTGCAAGAGGGGCCGGAAGAAGCTGCTTTACATCTTCAA
GCAGCCGTTCATGCGGCCCGTGCAGACGACTCAGGAAGAGGACGGATGCTCGTGCA
GATTCCCTGAGGAGGAAGAGGGGGGATGCGAACTGCGCGTCAAGTTCTCACGGTCC
GCCGACGCCCCCGCATATCAACAGGGCCAGAATCAGCTCTACAACGAGCTGAACCT
GGGAAGGAGAGAGGAGTACGACGTGCTGGACAAGCGACGCGGACGCGACCCGGAG -continued ATGGGGGGGAAACCACGGCGGAAAAACCCTCAGGAAGGACTGTACAACGAACTCC
AGAAAGACAAGATGGCGGAAGCCTACTCAGAAATCGGGATGAAGGGAGAGCGGAG
GAGGGGAAAGGGTCACGACGGGCTGTACCAGGGACTGAGCACCGCCACTAAGGAT
ACCTACGATGCCTTGCATATGCAAGCACTCCCACCCCGGTAG SEQ ID NO: 174 amino acid sequence of CAR D0233 MSLN M1-4S ROR1 scFv9 IgG4 CD8 BBz
MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQTV
RITCQGDSLRSYYASWYQQKPGQAPVLVIYGKNNRPSGIPDRFSGSSSGNTASLTITGAQ
AEDEADYYCNSRDSSGNHLVFGGGTQLTVLGGGGGSGGGGSGGGGSGGGGSGGGGSQ
AAQVQLQQSGAEVKKPGSSVKVSCKASGGTFSSYAISWVRQAPGQGLEWMGWINPNS
GGTNYAQRFQGRVTMTRDTSISTAYMELSRLRSDDTAVYYCASYNDAFDIWGQGTLVT
VSSGGGGSGGGGSGGGGSNFMLTQPHSVSESPGKTVTISCTRSSGSIASNYVQWYQQRP
GSAPTIVIYEDDQRPSGVPDRFSGSIDTSSNSASLTISGLQSEDEADYYCQSYEPGNGVFG
GGTKVTVLAAAESKYGPPCPPCPIYIWAPLAGTCGVLLLSLVITLYCKRGRKKLLYIFKQ
PFMRPVQTTQEEDGCSCRFPEEEEGGCELRVKFSRSADAPAYQQGQNQLYNELNLGRRE
EYDVLDKRRGRDPEMGGKPRRKNPQEGLYNELQKDKMAEAYSEIGMKGERRRGKGH
DGLYQGLSTATKDTYDALHMQALPPR SEQ ID NO: 175 nucleotide sequence of CAR D0279 MSLN M1-4S ROR1 scFv9 IgG4 CD8 BBz 2A mIL7
ATGCTGTTACTTGTGACAAGCTTGCTTCTATGTGAACTGCCGCATCCGGCGTTTCTGC
TGATTCCGGAAGTACAGCTGGTACAGTCTGGAGGGGGATTGGTTCAGCCGGGCGGG
TCTTTGCGCCTGTCCTGCGCAGCTAGTGGCTTCACTTTTGATGACTATGCTATGCACT
GGGTCAGACAAGCGCCTGGCAAAGGCCTTGAATGGGTGTCCGGAATTAGCTGGAAT
AGTGGATCCATCGGCTATGCCGATAGTGTAAAGGGCAGGTTCACGATCAGCCGGGA
TAATGCAAAGAACTCTCTCTATTTGCAAATGAACAGTCTGCGGGCTGAAGATACTGC
TCTTTACTATTGTGCTAAAGATTTGTCAAGCGTCGCCGGACCCTTCAACTACTGGGGT
CAAGGGACACTGGTGACAGTTAGCAGCGGTGGTGGAGGCTCCGGTGGAGGTGGTAG
TGGTGGAGGAGGTAGTTCTTCTGAGCTTACGCAAGATCCGGCGGTTAGTGTTGCTCT
GGGGCAGACTGTACGAATCACGTGCCAGGGTGACTCTTTGCGCTCTTACTACGCTAG
TTGGTATCAACAAAAACCCGGACAAGCGCCCGTCCTCGTCATCTATGGCAAGAACA
ATCGCCCAAGCGGCATCCCTGATAGGTTCTCCGGATCATCTTCAGGGAACACAGCCT
CCCTGACTATTACAGGTGCTCAAGCTGAGGACGAGGCTGACTATTATTGCAACAGCC
GGGACTCTAGCGGTAACCACTTGGTCTTTGGTGGGGGTACCCAGCTGACGGTACTTG
GAGGTGGTGGAGGTTCAGGTGGTGGCGGATCAGGTGGAGGTGGTTCTGGAGGGGGT
GGAAGTGGCGGAGGTGGTTCACAGGCGGCCCAGGTACAGCTGCAGCAGTCAGGGGC
TGAGGTGAAGAAGCCTGGGTCCTCGGTGAAGGTCTCCTGCAAGGCTTCTGGAGGCA
CCTTCAGCAGCTATGCTATCAGCTGGGTGCGACAGGCCCCTGGACAAGGGCTTGAGT
GGATGGGATGGATCAACCCTAACAGTGGTGGCACAAACTATGCACAGAGGTTTCAG
GGCAGGGTCACCATGACCAGGGACACGTCCATCAGCACAGCCTACATGGAGTTGAG
CAGGCTGAGATCTGACGACACGGCCGTGTATTACTGTGCGAGTTATAATGATGCTTT
TGATATCTGGGGCCAAGGCACCCTGGTCACCGTCTCCTCAGGAGGTGGCGGGTCTGG
TGGTGGCGGTAGCGGTGGTGGCGGATCCAATTTTATGCTGACTCAGCCCCACTCTGT
GTCGGAGTCTCCGGGGAAGACGGTAACCATCTCCTGCACCCGCAGCAGTGGCAGCA
TTGCCAGCAACTATGTGCAGTGGTACCAGCAGCGCCCGGGCAGTGCCCCCACCATTG
TGATCTATGAGGATGATCAAAGACCCTCTGGGGTCCCTGATCGGTTCTCTGGCTCCA
TCGACACCTCCTCCAACTCTGCCTCCCTCACCATCTCTGGACTGCAGAGTGAGGACG
AGGCTGACTACTACTGTCAGTCTTATGAGCCCGGCAATGGGGTATTCGGCGGAGGG
ACCAAGGTCACCGTCCTAGCIGCCGCAGAGTCAAAATACGGTCCTCCGTGCCCTCCG
TGTCCGATCTACATTTGGGCCCCGCTGGCCGGCACTTGCGGCGTGCTCCTGCTGTCG
CTGGTCATCACCCTTTACTGCAAGCGCGGCCGCAAGAAATTGCTTTACATTTTTAAG
CAGCCGTTCATGCGACCAGTACAGACTACTCAAGAAGAAGATGGGTGCTCTTGTCG
GTTCCCGGAAGAAGAAGAGGGTGGTTGCGAGTTGAGGGTGAAGTTCTCCCGCTCTG
CCGACGCACCGGCATATCAGCAGGGACAAAACCAGCTCTACAACGAATTGAACCTG
GGTCGGCGGGAAGAATATGACGTGCTCGATAAGCGGCGGGGTCGCGACCCAGAAAT
GGGAGGCAAACCGCGCAGGAAAAATCCACAGGAGGGACTTTATAACGAACTTCAAA
AGGATAAGATGGCAGAGGCATACAGCGAAATCGGGATGAAAGGCGAGAGAAGAAG
GGGGAAAGGGCACGATGGTCTTTACCAGGGGCTTTCTACCGCGACGAAGGATACCT
ACGATGCTCTCCATATGCAAGCACTTCCTCCTAGACGGGCAAAGCGGGGCTCAGGG
GCGACTAACTTTTCACTGTTGAAGCAGGCCGGGGATGTGGAGGAGAATCCTGGTCCT
AGAGCTAAGCGAGTAATGCTCTTGCTCGTGACTTCTTTGCTTTTGTGCGAACTTCCGC
ACCCAGCCTTCCTTTTGATACCTATGGATTGTGATATTGAAGGTAAAGATGGCAAAC
AATATGAGAGTGTTCTAATGGTCAGCATCGATCAATTATTGGACAGCATGAAAGAA
ATTGGTAGCAATTGCCTGAATAATGAATTTAACTTTTTTAAAAGACATATCTGTGAT
GCTAATAAGGAAGGTATGTTTTTATTCCGTGCTGCTCGCAAGTTGAGGCAATTTCTT
AAAATGAATAGCACTGGTGATTTTGATCTCCACTTATTAAAAGTTTCAGAAGGCACA
ACAATACTGTTGAACTGCACTGGCCAGGTTAAAGGAAGAAAACCAGCTGCCCTGGG
TGAAGCCCAACCAACAAAGAGTTTGGAAGAAAATAAATCTTTAAAGGAACAGAAAA
AACTGAATGACTTGTGTTTCCTAAAGAGACTATTACAAGAGATAAAAACTTGTTGGA
ATAAAATTTTGATGGGCACTAAAGAACACTCCGGAGGTTCCGGTGGTGGCTCAGGT
GGTGGCTCAGGTGAAAGTGGCTATGCTCAAAATGGAGACTTGGAAGATGCAGAACT
GGATGACTACTCATTCTCATGCTATAGCCAGTTGGAAGTGAATGGATCGCAGCACTC
ACTGACCTGTGCTTTTGAGGACCCAGATGTCAACATCACCAATCTGGAATTTGAAAT
ATGTGGGGCCCTCGTGGAGGTAAAGTGCCTGAATTTCAGGAAACTACAAGAGATAT
ATTTCATCGAGACAAAGAAATTCTTACTGATTGGAAAGAGCAATATATGTGTGAAG
GTTGGAGAAAAGAGTCTAACCTGCAAAAAAATAGACCTAACCACTATAGTTAAACC
TGAGGCTCCTTTTGACCTGAGTGTCGTCTATCGGGAAGGAGCCAATGACTTTGTGGT
GACATTTAATACATCACACTTGCAAAAGAAGTATGTAAAAGTTTTAATGCACGATGT -continued AGCTTACCGCCAGGAAAAGGATGAAAACAAATGGACGCATGTGAATTTATCCAGCA
CAAAGCTGACACTCCTGCAGAGAAAGCTCCAACCGGCAGCAATGTATGAGATTAAA
GTTCGATCCATCCCTGATCACTATTTTAAAGGCTTCTGGAGTGAATGGAGTCCAAGT
TATTACTTCAGAACTCCAGAGATCAATAATAGCTCAGGGGAGATGGATCCTATCTTA
CTAACCATCAGCATTTTGAGTTTTTTCTCTGTCGCTCTGTTGGTCATCTTGGCCTGTGT
GTTATGGAAAAAAAGGATTAAGCCTATCGTATGGCCCAGTCTCCCCGATCATAAGA
AGACTCTGGAACATCTTTGTAAGAAACCAAGAAAAAATTTAAATGTGAGTTTCAATC
CTGAAAGTTTCCTGGACTGCCAGATTCATAGGGTGGATGACATTCAAGCTAGAGATG
AAGTGGAAGGTTTTCTGCAAGATACGTTTCCTCAGCAACTAGAAGAATCTGAGAAG
CAGAGGCTTGGAGGGGATGTGCAGAGCCCCAACTGCCCATCTGAGGATGTAGTCAT
CACTCCAGAAAGCTTTGGAAGAGATTCATCCCTCACATGCCTGGCTGGGAATGTCAG
TGCATGTGACGCCCCTATTCTCTCCTCTTCCAGGTCCCTAGACTGCAGGGAGAGTGG
CAAGAATGGGCCTCATGTGTACCAGGACCTCCTTCTTAGCCTTGGGACTACAAACAG
CACGCTGCCCCCTCCATTTTCTCTCCAATCTGGAATCCTGACATTGAACCCAGTTGCT
CAGGGTCAGCCCATTCTTACTTCCCTGGGATCAAATCAAGAAGAAGCATATGTCACC
ATGTCCAGCTTCTACCAAAACCAGCCCTAG SEQ ID NO: 176 amino acid sequence of CAR D0279 MSLN M1-4S ROR1 scFv9 IgG4 CD8 BBz 2A mIL7

MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQTV
RITCQGDSLRSYYASWYQQKPGQAPVLVIYGKNNRPSGIPDRFSGSSSGNTASLTITGAQ
AEDEADYYCNSRDSSGNHLVFGGGTQLTVLGGGGGSGGGGSGGGGSGGGGSGGGGSQ
AAQVQLQQSGAEVKKPGSSVKVSCKASGGTFSSYAISWVRQAPGQGLEWMGWINPNS
GGTNYAQRFQGRVTMTRDTSISTAYMELSRLRSDDTAVYYCASYNDAFDIWGQGTLVT
VSSGGGGSGGGGSGGGGSNFMLTQPHSVSESPGKTVTISCTRSSGSIASNYVQWYQQRP
GSAPTIVIYEDDQRPSGVPDRFSGSIDTSSNSASLTISGLQSEDEADYYCQSYEPGNGVFG
GGTKVTVLAAAESKYGPPCPPCPIYIWAPLAGTCGVLLLSLVITLYCKRGRKKLLYIFKQ
PFMRPVQTTQEEDGCSCRFPEEEEGGCELRVKFSRSADAPAYQQGQNQLYNELNLGRRE
EYDVLDKRRGRDPEMGGKPRRKNPQEGLYNELQKDKMAEAYSEIGMKGERRRGKGH
DGLYQGLSTATKDTYDALHMQALPPRRAKRGSGATNFSLLKQAGDVEENPGPRAKRV
MLLLVTSLLLCELPHPAFLLIPMDCDIEGKDGKQYESVLMVSIDQLLDSMKEIGSNCLNN
EFNFFKRHICDANKEGMFLFRAARKLRQFLKMNSTGDFDLHLLKVSEGTTILLNCTGQV
KGRKPAALGEAQPTKSLEENKSLKEQKKLNDLCFLKRLLQEIKTCWNKILMGTKEHSGG
SGGGSGGGSGESGYAQNGDLEDAELDDYSFSCYSQLEVNGSQHSLTCAFEDPDVNITNL
EFEICGALVEVKCLNFRKLQEIYFIETKKFLLIGKSNICVKVGEKSLTCKKIDLTTIVKPEA
PFDLSVVYREGANDFVVTFNTSHLQKKYVKVLMHDVAYRQEKDENKWTHVNLSSTKL
TLLQRKLQPAAMYEIKVRSIPDHYFKGFWSEWSPSYYFRTPEINNSSGEMDPILLTISILSF
FSVALLVILACVLWKKRIKPIVWPSLPDHKKTLEHLCKKPRKNLNVSFNPESFLDCQIHR
VDDIQARDEVEGFLQDTFPQQLEESEKQRLGGDVQSPNCPSEDVVITPESFGRDSSLTCL
AGNVSACDAPILSSSRSLDCRESGKNGPHVYQDLLLSLGTTNSTLPPPFSLQSGILTLNPV
AQGQPILTSLGSNQEEAYVTMSSFYQNQP

SEQ ID NO: 177 nucleotide sequence of CAR D0280 MSLN M1-4S ROR1 scFv9 IgG4 CD28 28BBz 2A mIL7

ATGCTGTTACTTGTGACAAGCTTGCTTCTATGTGAACTGCCGCATCCGGCGTTTCTGC
TGATTCCGGAAGTACAGCTGGTACAGTCTGGAGGGGGATTGGTTCAGCCGGGCGGG
TCTTTGCGCCTGTCCTGCGCAGCTAGTGGCTTCACTTTTGATGACTATGCTATGCACT
GGGTCAGACAAGCGCCTGGCAAAGGCCTTGAATGGGTGTCCGGAATTAGCTGGAAT
AGTGGATCCATCGGCTATGCCGATAGTGTAAAGGGCAGGTTCACGATCAGCCGGGA
TAATGCAAAGAACTCTCTCTATTTGCAAATGAACAGTCTGCGGGCTGAAGATACTGC
TCTTTACTATTGTGCTAAAGATTTGTCAAGCGTCGCCGGACCCTTCAACTACTGGGGT
CAAGGGACACTGGTGACAGTTAGCAGCGGTGGTGGAGGCTCCGGTGGAGGTGGTAG
TGGTGGAGGAGGTAGTTCTTCTGAGCTTACGCAAGATCCGGCGGTTAGTGTTGCTCT
GGGGCAGACTGTACGAATCACGTGCCAGGGTGACTCTTTGCGCTCTTACTACGCTAG
TTGGTATCAACAAAAACCCGGACAAGCGCCCGTCCTCGTCATCTATGGCAAGAACA
ATCGCCCAAGCGGCATCCCTGATAGGTTCTCCGGATCATCTTCAGGGAACACAGCCT
CCCTGACTATTACAGGTGCTCAAGCTGAGGACGAGGCTGACTATTATTGCAACAGCC
GGGACTCTAGCGGTAACCACTTGGTCTTTGGTGGGGGTACCCAGCTGACGGTACTTG
GAGGTGGTGGAGGTTCAGGTGGTGGCGGATCAGGTGGAGGTGGTTCTGGAGGGGGT
GGAAGTGGCGGAGGTGGTTCACAGGCGGCCCAGGTACAGCTGCAGCAGTCAGGGGC
TGAGGTGAAGAAGCCTGGGTCCTCGGTGAAGGTCTCCTGCAAGGCTTCTGGAGGCA
CCTTCAGCAGCTATGCTATCAGCTGGGTGCGACAGGCCCCTGGACAAGGGCTTGAGT
GGATGGGATGGATCAACCCTAACAGTGGTGGCACAAACTATGCACAGAGGTTTCAG
GGCAGGGTCACCATGACCAGGGACACGTCCATCAGCACAGCCTACATGGAGTTGAG
CAGGCTGAGATCTGACGACACGGCCGTGTATTACTGTGCGAGTTATAATGATGCTTT
TGATATCTGGGGCCAAGGCACCCTGGTCACCGTCTCCTCAGGAGGTGGCGGGTCTGG
TGGTGGCGGTAGCGGTGGTGGCGGATCCAATTTTATGCTGACTCAGCCCCACTCTGT
GTCGGAGTCTCCGGGGAAGACGGTAACCATCTCCTGCACCCGCAGCAGTGGCAGCA
TTGCCAGCAACTATGTGCAGTGGTACCAGCAGCGCCCGGGCAGTGCCCCCACCATTG
TGATCTATGAGGATGATCAAAGACCCTCTGGGGTCCCTGATCGGTTCTCTGGCTCCA
TCGACACCTCCTCCAACTCTGCCTCCCTCACCATCTCTGGACTGCAGAGTGAGGACG
AGGCTGACTACTACTGTCAGTCTTATGAGCCCGGCAATGGGGTATTCGGCGGAGGG
ACCAAGGTCACCGTCCTAGCGGCCGCAGAGTCAAAATACGGTCCTCCGTGCCCTCCG
TGTCCGTTCTGGGTGCTTGTCGTTGTTGGGGGTGTACTCGCATGTTATTCTTTGCTGG
TGACTGTGGCGTTTATCATCTTCTGGGTAAGGAGTAAACGCAGCCGCCTGCTGCATT
CAGACTACATGAACATGACCCCACGGCGGCCCGGCCCAACGCGCAAACACTACCAA
CCTTACGCCCCACCGCGAGACTTTGCCGCCTACAGATCCAAGCGCGGACGGAAGAA
ACTCTTGTACATCTTCAAGCAGCCGTTCATGCGCCCTGTGCAAACCACCCAAGAAGA
GGACGGGTGCTCCTGCCGGTTCCCGGAAGAGGAAGAGGGCGGCTGCGAACTGCGCG

-continued

TGAAGTTTTCCCGGTCCGCCGACGCTCCGGCGTACCAGCAGGGGCAAAACCAGCTG
TACAACGAACTTAACCTCGGTCGCCGGGAAGAATATGACGTGCTGGACAAGCGGCG
GGGAAGAGATCCCGAGATGGGTGGAAAGCCGCGGCGGAAGAACCCTCAGGAGGGC
TTGTACAACGAGCTGCAAAAGGACAAAATGGCCGAAGCCTACTCCGAGATTGGCAT
GAAGGGAGAGCGCAGACGCGGGAAGGGACACGATGGACTGTACCAGGGACTGTCA
ACCGCGACTAAGGACACTTACGACGCCCTGCACATGCAGGCCCTGCCCCCGCGCCG
GGCAAAGCGGGGCTCAGGGGCGACTAACTTTTCACTGTTGAAGCAGGCCGGGGATG
TGGAGGAGAATCCTGGTCCTAGAGCTAAGCGAGTAATGCTCTTGCTCGTGACTTCTT
TGCTTTTGTGCGAACTTCCGCACCCAGCCTTCCTTTTGATACCTATGGATTGTGATAT
TGAAGGTAAAGATGGCAAACAATATGAGAGTGTTCTAATGGTCAGCATCGATCAAT
TATTGGACAGCATGAAAGAAATTGGTAGCAATTGCCTGAATAATGAATTTAACTTTT
TTAAAAGACATATCTGTGATGCTAATAAGGAAGGTATGTTTTTATTCCGTGCTGCTC
GCAAGTTGAGGCAATTTCTTAAAATGAATAGCACTGGTGATTTTGATCTCCACTTAT
TAAAAGTTTCAGAAGGCACAACAATACTGTTGAACTGCACTGGCCAGGTTAAAGGA
AGAAAACCAGCTGCCCTGGGTGAAGCCCAACCAACAAAGAGTTTGGAAGAAAATAA
ATCTTTAAAGGAACAGAAAAAACTGAATGACTTGTGTTTCCTAAAGAGACTATTACA
AGAGATAAAAACTTGTTGGAATAAAATTTTGATGGGCACTAAAGAACACTCCGGAG
GTTCCGGTGGTGGCTCAGGTGGTGGCTCAGGTGAAAGTGGCTATGCTCAAAATGGA
GACTTGGAAGATGCAGAACTGGATGACTACTCATTCTCATGCTATAGCCAGTTGGAA
GTGAATGGATCGCAGCACTCACTGACCTGTGCTTTTGAGGACCCAGATGTCAACATC
ACCAATCTGGAATTTGAAATATGTGGGGCCCTCGTGGAGGTAAAGTGCCTGAATTTC
AGGAAACTACAAGAGATATATTTCATCGAGACAAAGAAATTCTTACTGATTGGAAA
GAGCAATATATGTGTGAAGGTTGGAGAAAAGAGTCTAACCTGCAAAAAAATAGACC
TAACCACTATAGTTAAACCTGAGGCTCCTTTTGACCTGAGTGTCGTCTATCGGGAAG
GAGCCAATGACTTTGTGGTGACATTTAATACATCACACTTGCAAAAGAAGTATGTAA
AAGTTTTAATGCACGATGTAGCTTACCGCCAGGAAAAGGATGAAAACAAATGGACG
CATGTGAATTTATCCAGCACAAAGCTGACACTCCTGCAGAGAAAGCTCCAACCGGC
AGCAATGTATGAGATTAAAGTTCGATCCATCCCTGATCACTATTTTAAAGGCTTCTG
GAGTGAATGGAGTCCAAGTTATTACTTCAGAACTCCAGAGATCAATAATAGCTCAG
GGGAGATGGATCCTATCTTACTAACCATCAGCATTTTGAGTTTTTTCTCTGTCGCTCT
GTTGGTCATCTTGGCCTGTGTGTTATGGAAAAAAAGGATTAAGCCTATCGTATGGCC
CAGTCTCCCCGATCATAAGAAGACTCTGGAACATCTTTGTAAGAAACCAAGAAAAA
ATTTAAATGTGAGTTTCAATCCTGAAAGTTTCCTGGACTGCCAGATTCATAGGGTGG
ATGACATTCAAGCTAGAGATGAAGTGGAAGGTTTTCTGCAAGATACGTTTCCTCAGC
AACTAGAAGAATCTGAGAAGCAGAGGCTTGGAGGGGATGTGCAGAGCCCCAACTGC
CCATCTGAGGATGTAGTCATCACTCCAGAAAGCTTTGGAAGAGATTCATCCCTCACA
TGCCTGGCTGGGAATGTCAGTGCATGTGACGCCCCTATTCTCTCCTCTTCCAGGTCCC
TAGACTGCAGGGAGAGTGGCAAGAATGGGCCTCATGTGTACCAGGACCTCCTTCTTA
GCCTTGGGACTACAAACAGCACGCTGCCCCCTCCATTTTCTCTCCAATCTGGAATCC
TGACATTGAACCCAGTTGCTCAGGGTCAGCCCATTCTTACTTCCCTGGGATCAAATC
AAGAAGAAGCATATGTCACCATGTCCAGCTTCTACCAAAACCAGCCCTAG

SEQ ID NO: 178 amino acid sequence of CAR D0280 MSLN M1-4S ROR1 scFv9 IgG4 CD28 28BBz 2A mIL7

MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQTV
RITCQGDSLRSYYASWYQQKPGQAPVLVIYGKNNRPSGIPDRFSGSSSGNTASLTITGAQ
AEDEADYYCNSRDSSGNHLVFGGGTQLTVLGGGGGSGGGGSGGGGSGGGGSGGGGSQ
AAQVQLQQSGAEVKKPGSSVKVSCKASGGTFSSYAISWVRQAPGQGLEWMGWINPNS
GGTNYAQRFQGRVTMTRDTSISTAYMELSRLRSDDTAVYYCASYNDAFDIWGQGTLVT
VSSGGGGSGGGGSGGGGSNFMLTQPHSVSESPGKTVTISCTRSSGSIASNYVQWYQQRP
GSAPTIVIYEDDQRPSGVPDRFSGSIDTSSNSASLTISGLQSEDEADYYCQSYEPGNGVFG
GGTKVTVLAAAESKYGPPCPPCPFWVLVVVGGVLACYSLLVTVAFIIFWVRSKRSRLLH
SDYMNMTPRRPGPTRKHYQPYAPPRDFAAYRSKRGRKKLLYIFKQPFMRPVQTTQEED
GCSCRFPEEEEGGCELRVKFSRSADAPAYQQGQNQLYNELNLGRREEYDVLDKRRGRD
PEMGGKPRRKNPQEGLYNELQKDKMAEAYSEIGMKGERRRGKGHDGLYQGLSTATKD
TYDALHMQALPPRRAKRGSGATNFSLLKQAGDVEENPGPRAKRVMLLLVTSLLLCELP
HPAFLLIPMDCDIEGKDGKQYESVLMVSIDQLLDSMKEIGSNCLNNEFNFFKRHICDANK
EGMFLFRAARKLRQFLKMNSTGDFDLHLLKVSEGTTILLNCTGQVKGRKPAALGEAQP
TKSLEENKSLKEQKKLNDLCFLKRLLQEIKTCWNKILMGTKEHSGGSGGGSGGGSGESG
YAQNGDLEDAELDDYSFSCYSQLEVNGSQHSLTCAFEDPDVNITNLEFEICGALVEVKC
LNFRKLQEIYFIETKKFLLIGKSNICVKVGEKSLTCKKIDLTTIVKPEAPFDLSVVYREGAN
DFVVTFNTSHLQKKYVKVLMHDVAYRQEKDENKWTHVNLSSTKLTLLQRKLQPAAM
YEIKVRSIPDHYFKGFWSEWSPSYYFRTPEINNSSGEMDPILLTISILSFFSVALLVILACVL
WKKRIKPIVWPSLPDHKKTLEHLCKKPRKNLNVSFNPESFLDCQIHRVDDIQARDEVEGF
LQDTFPQQLEESEKQRLGGDVQSPNCPSEDVVITPESFGRDSSLTCLAGNVSACDAPILSS
SRSLDCRESGKNGPHVYQDLLLSLGTTNSTLPPPFSLQSGILTLNPVAQGQPILTSLGSNQ
EEAYVTMSSFYQNQP

SEQ ID NO: 179 nucleotide sequence of CAR D0281 MSLN M1-4S ROR1 scFv9 IgG4 CD8 28BBz 2A mIL7

ATGCTGTTACTTGTGACAAGCTTGCTTCTATGTGAACTGCCGCATCCGGCGTTTCTGC
TGATTCCGGAAGTACAGCTGGTACAGTCTGGAGGGGGATTGGTTCAGCCGGGCGGG
TCTTTGCGCCTGTCCTGCGCAGCTAGTGGCTTCACTTTTGATGACTATGCTATGCACT
GGGTCAGACAAGCGCCTGGCAAAGGCCTTGAATGGGTGTCCGGAATTAGCTGGAAT
AGTGGATCCATCGGCTATGCCGATAGTGTAAAGGGCAGGTTCACGATCAGCCGGGA
TAATGCAAAGAACTCTCTCTATTTGCAAATGAACAGTCTGCGGGCTGAAGATACTGC
TCTTTACTATTGTGCTAAAGATTTGTCAAGCGTCGCCGGACCCTTCAACTACTGGGGT
CAAGGGACACTGGTGACAGTTAGCAGCGGTGGTGGAGGCTCCGGTGGAGGTGGTAG
TGGTGGAGGAGGTAGTTCTTCTGAGCTTACGCAAGATCCGGCGGTTAGTGTTGCTCT

-continued

GGGGCAGACTGTACGAATCACGTGCCAGGGTGACTCTTTGCGCTCTTACTACGCTAG
TTGGTATCAACAAAAACCCGGACAAGCGCCCGTCCTCGTCATCTATGGCAAGAACA
ATCGCCCAAGCGGCATCCCTGATAGGTTCTCCGGATCATCTTCAGGGAACACAGCCT
CCCTGACTATTACAGGTGCTCAAGCTGAGGACGAGGCTGACTATTATTGCAACAGCC
GGGACTCTAGCGGTAACCACTTGGTCTTTGGTGGGGTACCCAGCTGACGGTACTTG
GAGGTGGTGGAGGTTCAGGTGGTGGCGGATCAGGTGGAGGTGGTTCTGGAGGGGGT
GGAAGTGGCGGAGGTGGTTCACAGGCGGCCCAGGTACAGCTGCAGCAGTCAGGGGC
TGAGGTGAAGAAGCCTGGGTCCTCGGTGAAGGTCTCCTGCAAGGCTTCTGGAGGCA
CCTTCAGCAGCTATGCTATCAGCTGGGTGCGACAGGCCCCTGGACAAGGGCTTGAGT
GGATGGGATGGATCAACCCTAACAGTGGTGGCACAAACTATGCACAGAGGTTTCAG
GGCAGGGTCACCATGACCAGGGACACGTCCATCAGCACAGCCTACATGGAGTTGAG
CAGGCTGAGATCTGACGACACGGCCGTGTATTACTGTGCGAGTTATAATGATGCTTT
TGATATCTGGGGCCAAGGCACCCTGGTCACCGTCTCCTCAGGAGGTGGCGGGTCTGG
TGGTGGCGGTAGCGGTGGTGGCGGATCCAATTTTATGCTGACTCAGCCCCACTCTGT
GTCGGAGTCTCCGGGGAAGACGGTAACCATCTCCTGCACCCGCAGCAGTGGCAGCA
TTGCCAGCAACTATGTGCAGTGGTACCAGCAGCGCCCGGGCAGTGCCCCCACCATTG
TGATCTATGAGGATGATCAAAGACCCTCTGGGGTCCCTGATCGGTTCTCTGGCTCCA
TCGACACCTCCTCCAACTCTGCCTCCCTCACCATCTCTGGACTGCAGAGTGAGGACG
AGGCTGACTACTACTGTCAGTCTTATGAGCCCGGCAATGGGGTATTCGGCGGAGGG
ACCAAGGTCACCGTCCTAGCGGCCGCAGAGTCAAAATACGGTCCTCCGTGCCCTCCG
TGTCCGATCTACATCTGGGCCCCATTGGCTGGAACTTGCGGCGTGCTGCTCTTGTCTC
TGGTCATTACCCTGTACTGCAGGAGTAAACGCAGCCGCCTGCTGCATTCAGACTACA
TGAACATGACCCCACGGCGGCCCGGCCCAACGCGCAAACACTACCAACCTTACGCC
CCACCGCGAGACTTTGCCGCCTACAGATCCAAGCGCGGACGGAAGAAACTCTTGTA
CATCTTCAAGCAGCCGTTCATGCGCCCTGTGCAAACCACCCAAGAAGAGGACGGGT
GCTCCTGCCGGTTCCCGGAAGAGGAAGAGGGCGGCTGCGAACTGCGCGTGAAGTTT
TCCCGGTCCGCCGACGCTCCGGCGTACCAGCAGGGGCAAAACCAGCTGTACAACGA
ACTTAACCTCGGTCGCCGGGAAGAATATGACGTGCTGGACAAGCGGGGGGAAGAG
ATCCCGAGATGGGTGGAAAGCCGCGGCGGAAGAACCCTCAGGAGGGCTTGTACAAC
GAGCTGCAAAAGGACAAAATGGCCGAAGCCTACTCCGAGATTGGCATGAAGGGAG
AGCGCAGACGCGGGAAGGGACACGATGGACTGTACCAGGGACTGTCAACCGCGACT
AAGGACACTTACGACGCCCTGCACATGCAGGCCCTGCCCCCGCGCCGGGCAAAGCG
GGGCTCAGGGGCGACTAACTTTTCACTGTTGAAGCAGGCCGGGGATGTGGAGGAGA
ATCCTGGTCCTAGAGCTAAGCGAGTAATGCTCTTGCTCGTGACTTCTTTGCTTTTGTG
CGAACTTCCGCACCCAGCCTTCCTTTTGATACCTATGGATTGTGATATTGAAGGTAA
AGATGGCAAACAATATGAGAGTGTTCTAATGGTCAGCATCGATCAATTATTGGACA
GCATGAAAGAAATTGGTAGCAATTGCCTGAATAATGAATTTAACTTTTTTAAAAGAC
ATATCTGTGATGCTAATAAGGAAGGTATGTTTTTATTCCGTGCTGCTCGCAAGTTGA
GGCAATTTCTTAAAATGAATAGCACTGGTGATTTTGATCTCCACTTATTAAAAGTTTC
AGAAGGCACAACAATACTGTTGAACTGCACTGGCCAGGTTAAAGGAAGAAAACCAG
CTGCCCTGGGTGAAGCCCAACCAACAAAGAGTTTGGAAGAAAATAAATCTTTAAAG
GAACAGAAAAAACTGAATGACTTGTGTTTCCTAAAGAGACTATTACAAGAGATAAA
AACTTGTTGGAATAAAATTTTGATGGGCACTAAAGAACACTCCGGAGGTTCCGGTGG
TGGCTCAGGTGGTGGCTCAGGTGAAAGTGGCTATGCTCAAAATGGAGACTTGGAAG
ATGCAGAACTGGATGACTACTCATTCTCATGCTATAGCCAGTTGGAAGTGAATGGAT
CGCAGCACTCACTGACCTGTGCTTTTGAGGACCCAGATGTCAACATCACCAATCTGG
AATTTGAAATATGTGGGGCCCTCGTGGAGGTAAAGTGCCTGAATTTCAGGAAACTAC
AAGAGATATATTTCATCGAGACAAAGAAATTCTTACTGATTGGAAAGAGCAATATA
TGTGTGAAGGTTGGAGAAAAGAGTCTAACCTGCAAAAAAATAGACCTAACCACTAT
AGTTAAACCTGAGGCTCCTTTTGACCTGAGTGTCGTCTATCGGGAAGGAGCCAATGA
CTTTGTGGTGACATTTAATACATCACACTTGCAAAAGAAGTATGTAAAAGTTTTAAT
GCACGATGTAGCTTACCGCCAGGAAAAGGATGAAAACAAATGGACGCATGTGAATT
TATCCAGCACAAAGCTGACACTCCTGCAGAGAAAGCTCCAACCGGCAGCAATGTAT
GAGATTAAAGTTCGATCCATCCCTGATCACTATTTTAAAGGCTTCTGGAGTGAATGG
AGTCCAAGTTATTACTTCAGAACTCCAGAGATCAATAATAGCTCAGGGGAGATGGA
TCCTATCTTACTAACCATCAGCATTTTGAGTTTTTTCTCTGTCGCTCTGTTGGTCATCT
TGGCCTGTGTGTTATGGAAAAAAAGGATTAAGCCTATCGTATGGCCCAGTCTCCCCG
ATCATAAGAAGACTCTGGAACATCTTTGTAAGAAACCAAGAAAAAATTTAAATGTG
AGTTTCAATCCTGAAAGTTTCCTGGACTGCCAGATTCATAGGGTGGATGACATTCAA
GCTAGAGATGAAGTGGAAGGTTTTCTGCAAGATACGTTTCCTCAGCAACTAGAAGA
ATCTGAGAAGCAGAGGCTTGGAGGGGATGTGCAGAGCCCCAACTGCCCATCTGAGG
ATGTAGTCATCACTCCAGAAAGCTTTGGAAGAGATTCATCCCTCACATGCCTGGCTG
GGAATGTCAGTGCATGTGACGCCCCTATTCTCTCCTCTTCCAGGTCCCTAGACTGCA
GGGAGAGTGGCAAGAATGGGCCTCATGTGTACCAGGACCTCCTTCTTAGCCTTGGGA
CTACAAACAGCACGCTGCCCCCTCCATTTTCTCTCCAATCTGGAATCCTGACATTGA
ACCCAGTTGCTCAGGGTCAGCCCATTCTTACTTCCCTGGGATCAAATCAAGAAGAAG
CATATGTCACCATGTCCAGCTTCTACCAAAACCAGCCCTAG

SEQ ID NO: 180 amino acid sequence of CAR D0281 MSLN M1-4S ROR1 scFv9 IgG4 CD8 28BBz 2A mIL7

MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQTV
RITCQGDSLRSYYASWYQQKPGQAPVLVIYGKNNRPSGIPDRFSGSSSGNTASLTITGAQ
AEDEADYYCNSRDSSGNHLVFGGGTQLTVLGGGGGSGGGGSGGGGSGGGGSGGGGSQ
AAQVQLQQSGAEVKKPGSSVKVSCKASGGTFSSYAISWVRQAPGQGLEWMGWINPNS
GGTNYAQRFQGRVTMTRDTSISTAYMELSRLRSDDTAVYYCASYNDAFDIWGQGTLVT
VSSGGGGSGGGGSGGGGSNFMLTQPHSVSESPGKTVTISCTRSSGSIASNYVQWYQQRP
GSAPTIVIYEDDQRPSGVPDRFSGSIDTSSNSASLTISGLQSEDEADYYCQSYEPGNGVFG
GGTKVTVLAAAESKYGPPCPPCPIYIWAPLAGTCGVLLLSLVITLYCRSKRSRLLHSDYM
NMTPRRPGPTRKHYQPYAPPRDFAAYRSKRGRKKLLYIFKQPFMRPVQTTQEEDGCSCR

-continued

FPEEEEGGCELRVKFSRSADAPAYQQGQNQLYNELNLGRREEYDVLDKRRGRDPEMGG
KPRRKNPQEGLYNELQKDKMAEAYSEIGMKGERRRGKGHDGLYQGLSTATKDTYDAL
HMQALPPRRAKRGSGATNFSLLKQAGDVEENPGPRAKRVMLLLVTSLLLCELPHPAFLL
IPMDCDIEGKDGKQYESVLMVSIDQLLDSMKEIGSNCLNNEFNFFKRHICDANKEGMFL
FRAARKLRQFLKMNSTGDFDLHLLKVSEGTTILLNCTGQVKGRKPAALGEAQPTKSLEE
NKSLKEQKKLNDLCFLKRLLQEIKTCWNKILMGTKEHSGGSGGGSGGGSGESGYAQNG
DLEDAELDDYSFSCYSQLEVNGSQHSLTCAFEDPDVNITNLEFEICGALVEVKCLNFRKL
QEIYFIETKKFLLIGKSNICVKVGEKSLTCKKIDLTTIVKPEAPFDLSVVYREGANDFVVTF
NTSHLQKKYVKVLMHDVAYRQEKDENKWTHVNLSSTKLTLLQRKLQPAAMYEIKVRS
IPDHYFKGFWSEWSPSYYFRTPEINNSSGEMDPILLTISILSFFSVALLVILACVLWKKRIK
PIVWPSLPDHKKTLEHLCKKPRKNLNVSFNPESFLDCQIHRVDDIQARDEVEGFLQDTFP
QQLEESEKQRLGGDVQSPNCPSEDVVITPESFGRDSSLTCLAGNVSACDAPILSSSRSLDC
RESGKNGPHVYQDLLLSLGTTNSTLPPPFSLQSGILTLNPVAQGQPILTSLGSNQEBAYVT
MSSFYQNQP

SEQ ID NO: 181 nucleotide sequence of CAR D0282 ROR1 scFv9 IgG4 OX40 OX40BBz 2A MSLN M1-4S CD8 ICOSz2A mIL7

ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGITGAGCAGGCTGAGATCT
GACGACACGGCCGTGTATTACTGTGCGAGTTATAATGATGCTTTTGATATCTGGGGC
CAAGGCACCCTGGTCACCGTCTCCTCAGGAGGTGGCGGGTCTGGTGGTGGCGGTAG
CGGTGGTGGCGGATCCAATTTTATGCTGACTCAGCCCCACTCTGTGTCGGAGTCTCC
GGGGAAGACGGTAACCATCTCCTGCACCCGCAGCAGTGGCAGCATTGCCAGCAACT
ATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGGTGGC
GGCAATTCTCGGCCTGGGACTTGTCCTTGGTCTGCTTGGTCCGCTCGCAATACTTCTG
GCCTTGTACCTGCTCCGCAGAGACCAAAGACTTCCGCCCGACGCCCACAAGCCCCCA
GGAGGAGGTTCCTTCAGAACGCCTATACAAGAAGAACAAGCAGATGCCCACTCTAC
CCTGGCTAAAATCAGGGTGAAGTTTAGCCGCTCAGCCGATGCACCGGCCTACCAGC
AGGGACAGAACCAGCTCTACAACGAGCTCAACCTGGGTCGGCGGGAAGAATATGAC
GTGCTGGACAAACGGCGCGGCAGAGATCCGGAGATGGGGGGAAAGCCGAGGAGGA
AGAACCCTCAAGAGGGCCTGTACAACGAACTGCAGAAGGACAAGATGGCGGAAGC
CTACTCCGAGATCGGCATGAAGGGAGAACGCCGGAGAGGGAAGGGTCATGACGGA
CTGTACCAGGGCCTGTCAACTGCCACTAAGGACACTTACGATGCGCTCCATATGCAA
GCTTTGCCCCCGCGGCGCGCGAAACGCGGCAGCGGCGCGACCAACTTTAGCCTGCT
GAAACAGGCGGGCGATGTGGAAGAAAACCCGGGCCCGCGAGCAAAGAGGAATATT
ATGGCTCTGCCTGTTACGGCACTGCTCCTTCCGCTTGCATTGTTGTTGCACGCAGCGC
GGCCCGAGGTCCAGCTGGTACAGTCTGGGGGAGGCTTGGTACAGCCTGGGGGGTCC
CTGAGACTCTCCTGTGCAGCCTCTGGATTCACCTTTGATGATTATGCCATGCACTGGG
TCCGGCAAGCTCCAGGGAAGGGCCTGGAGTGGGTCTCAGGTATTAGTTGGAATAGT
GGTAGCATAGGCTATGCGGACTCTGTGAAGGGCCGATTCACCATCTCCAGAGACAA
CGCCAAGAACTCCCTGTATCTGCAAATGAACAGTCTGAGAGCTGAGGACACGGCCT
TGTATTACTGTGCAAAAGATTTATCGTCAGTGGCTGGACCCTTTAACTACTGGGGCC
AGGGCACCCTGGTCACCGTCTCCTCAGGAGGTGGCGGGTCTGGTGGAGGCGGTAGC
GGCGGTGGCGGATCCTCTTCTGAGCTGACTCAGGACCCTGCTGTGTCTGTGGCCTTG
GGACAGACAGTCAGGATCACATGCCAAGGAGACAGCCTCAGAAGCTATTATGCAAG
CTGGTACCAGCAGAAGCCAGGACAGGCCCCTGTACTTGTCATCTATGGTAAAAACA
ACCGGCCCTCAGGGATCCCAGACCGATTCTCTGGCTCCAGCTCAGGAAACACAGCTT
CCTTGACCATCACTGGGGCTCAGGCGGAGGATGAGGCTGACTATTACTGTAACTCCC
GGGACAGCAGTGGTAACCATCTGGTATTCGGCGGAGGCACCCAGCTGACCGTCCTC
GGTGCTAGCGCAACCACTACGCCTGCTCCGCGGCCTCCAACGCCCGCGCCCACGATA
GCTAGTCAGCCGTTGTCTCTCCGACCAGAGGCGTGTAGACCGGCCGCTGGCGGAGC
CGTACATACTCGCGGACTCGACTTCGCTTGCGACATCTACATTTGGGCACCCTTGGC
TGGGACCTGTGGGGTGCTGTTGCTGTCCTTGGTTATTACGTTGTACTGCTGGCTGACA
AAAAAGAAGTATTCATCTAGTGTACATGATCCGAACGGTGAATACATGTTCATGCGC
GCGGTGAACACGGCCAAGAAGAGCAGACTGACCGACGTAACCCTTAGAGTCAAATT
TTCCAGGTCCGCAGATGCCCCCGCGTACCAGCAAGGCCAGAACCAACTTTACAACG
AACTGAACCTGGGTCGCCGGGAGGAATATGATGTGCTGGATAAACGAAGGGGGAGG
GACCCTGAGATGGGAGGGAAACCTCGCAGGAAAAACCCGCAGGAAGGTTTGTACAA
CGAGTTGCAGAAGGATAAGATGGCTGAGGCTTACTCTGAAATAGGGATGAAGGGAG
AGAGACGGAGAGGAAAAGGCCATGATGGCCTTTACCAGGGCTTGAGCACAGCAACA
AAGGATACTTACGACGCTCTTCACATGCAAGCTCTGCCACCACGGCGGGCAAAGCG
GGGCTCAGGGGCGACTAACTTTTCACTGTTGAAGCAGGCCGGGGATGTGGAGGAGA
ATCCTGGTCCTAGAGCTAAGCGAGTAATGCTCTTGCTCGTGACTTCTTTGCTTTTGTG
CGAACTTCCGCACCCAGCCTTCCTTTTGATACCTATGGATTGTGATATTGAAGGTAA
AGATGGCAAACAATATGAGAGTGTTCTAATGGTCAGCATCGATCAATTATTGGACA
GCATGAAAGAAATTGGTAGCAATTGCCTGAATAATGAATTTAACTTTTTTAAAAGAC
ATATCTGTGATGCTAATAAGGAAGGTATGTTTTTATTCCGTGCTGCTCGCAAGTTGA
GGCAATTTCTTAAAATGAATAGCACTGGTGATTTTGATCTCCACTTATTAAAAGTTTC
AGAAGGCACAACAATACTGTTGAACTGCACTGGCCAGGTTAAAGGAAGAAAACCAG
CTGCCCTGGGTGAAGCCCAACCAACAAAGAGTTTGGAAGAAAATAAATCTTTAAAG
GAACAGAAAAAACTGAATGACTTGTGTTTCCTAAAGAGACTATTACAAGAGATAAA
AACTTGTTGGAATAAAATTTTGATGGGCACTAAAGAACACTCCGGAGGTTCCGGTGG
TGGCTCAGGTGGTGGCTCAGGTGAAAGTGGCTATGCTCAAAATGGAGACTTGGAAG

-continued

ATGCAGAACTGGATGACTACTCATTCTCATGCTATAGCCAGTTGGAAGTGAATGGAT
CGCAGCACTCACTGACCTGTGCTTTTGAGGACCCAGATGTCAACATCACCAATCTGG
AATTTGAAATATGTGGGGCCCTCGTGGAGGTAAAGTGCCTGAATTTCAGGAAACTAC
AAGAGATATATTTCATCGAGACAAAGAAATTCTTACTGATTGGAAAGAGCAATATA
TGTGTGAAGGTTGGAGAAAAGAGTCTAACCTGCAAAAAAATAGACCTAACCACTAT
AGTTAAACCTGAGGCTCCTTTTGACCTGAGTGTCGTCTATCGGGAAGGAGCCAATGA
CTTTGTGGTGACATTTAATACATCACACTTGCAAAAGAAGTATGTAAAAGTTTTAAT
GCACGATGTAGCTTACCGCCAGGAAAAGGATGAAAACAAATGGACGCATGTGAATT
TATCCAGCACAAAGCTGACACTCCTGCAGAGAAAGCTCCAACCGGCAGCAATGTAT
GAGATTAAAGTTCGATCCATCCCTGATCACTATTTTAAAGGCTTCTGGAGTGAATGG
AGTCCAAGTTATTACTTCAGAACTCCAGAGATCAATAATAGCTCAGGGGAGATGGA
TCCTATCTTACTAACCATCAGCATTTTGAGTTTTTTCTCTGTCGCTCTGTTGGTCATCT
TGGCCTGTGTGTTATGGAAAAAAAGGATTAAGCCTATCGTATGGCCCAGTCTCCCCG
ATCATAAGAAGACTCTGGAACATCTTTGTAAGAAACCAAGAAAAAATTTAAATGTG
AGTTTCAATCCTGAAAGTTTCCTGGACTGCCAGATTCATAGGGTGGATGACATTCAA
GCTAGAGATGAAGTGGAAGGTTTTCTGCAAGATACGTTTCCTCAGCAACTAGAAGA
ATCTGAGAAGCAGAGGCTTGGAGGGGATGTGCAGAGCCCCAACTGCCCATCTGAGG
ATGTAGTCATCACTCCAGAAAGCTTTGGAAGAGATTCATCCCTCACATGCCTGGCTG
GGAATGTCAGTGCATGTGACGCCCCTATTCTCTCCTCTTCCAGGTCCCTAGACTGCA
GGGAGAGTGGCAAGAATGGGCCTCATGTGTACCAGGACCTCCTTCTTAGCCTTGGGA
CTACAAACAGCACGCTGCCCCCTCCATTTTCTCTCCAATCTGGAATCCTGACATTGA
ACCCAGTTGCTCAGGGTCAGCCCATTCTTACTTCCCTGGGATCAAATCAAGAAGAAG
CATATGTCACCATGTCCAGCTTCTACCAAAACCAGCCCTAG

SEQ ID NO: 182 amino acid sequence of CAR D0282 ROR1 scFv9 IgG4 OX40 OX40BBz 2A MSLN M1-4S CD8 ICOSz2A mIL7

MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRQTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPVAAILGLGLVLGLLG
PLAILLALYLLRRDQRLPPDAHKPPGGGSFRTPIQEEQADAHSTLAKIRVKFSRSADAPA
YQQGQNQLYNELNLGRREEYDVLDKRRGRDPEMGGKPRRKNPQEGLYNELQKDKMA
EAYSEIGMKGERRRGKGHDGLYQGLSTATKDTYDALHMQALPPRRAKRGSGATNFSLL
KQAGDVEENPGPRAKRNIMALPVTALLLPLALLLHAARPEVQLVQSGGGLVQPGGSLR
LSCAASGFTFDDYAMHWVRQAPGKGLEWVSGISWNSGSIGYADSVKGRFTISRDNAKN
SLYLQMNSLRAEDTALYYCAKDLSSVAGPFNYWGQGTLVTVSSGGGGSGGGGSGGGG
SSSELTQDPAVSVALGQTVRITCQGDSLRSYYASWYQQKPGQAPVLVIYGKNNRPSGIP
DRFSGSSSGNTASLTITGAQAEDEADYYCNSRDSSGNHLVFGGGTQLTVLGASATTTPA
PRPPTPAPTIASQPLSLRPEACRPAAGGAVHTRGLDFACDIYIWAPLAGTCGVLLLSLVIT
LYCWLTKKKYSSSVHDPNGEYMFMRAVNTAKKSRLTDVTLRVKFSRSADAPAYQQGQ
NQLYNELNLGRREEYDVLDKRRGRDPEMGGKPRRKNPQEGLYNELQKDKMAEAYSEI
GMKGERRRGKGHDGLYQGLSTATKDTYDALHMQALPPRRAKRGSGATNFSLLKQAGD
VEENPGPRAKRVMLLLVTSLLLCELPHPAFLLIPMDCDIEGKDGKQYESVLMVSIDQLLD
SMKEIGSNCLNNEFNFFKRHICDANKEGMFLFRAARKLRQFLKMNSTGDFDLHLLKVSE
GTTILLNCTGQVKGRKPAALGEAQPTKSLEENKSLKEQKKLNDLCFLKRLLQEIKTCWN
KILMGTKEHSGGSGGGSGGGSGESGYAQNGDLEDAELDDYSFSCYSQLEVNGSQHSLT
CAFEDPDVNITNLEFEICGALVEVKCLNFRKLQEIYFIETKKFLLIGKSNICVKVGEKSLTC
KKIDLTTIVKPEAPFDLSVVYREGANDFVVTFNTSHLQKKYVKVLMHDVAYRQEKDEN
KWTHVNLSSTKLTLLQRKLQPAAMYEIKVRSIPDHYFKGFWSEWSPSYYFRTPEINNSS
GEMDPILLTISILSFFSVALLVILACVLWKKRIKPIVWPSLPDHKKTLEHLCKKPRKNLNV
SFNPESFLDCQIHRVDDIQARDEVEGFLQDTFPQQLEESEKQRLGGDVQSPNCPSEDVVI
TPESFGRDSSLTCLAGNVSACDAPILSSSRSLDCRESGKNGPHVYQDLLLSLGTTNSTLPP
PFSLQSGILTLNPVAQGQPILTSLGSNQEEAYVTMSSFYQNQP

SEQ ID NO: 183 nucleotide sequence of CAR D0283 ROR1 scFv9 IgG4 CD8 BBz 2A MSLN M1-4S CD8 28z 2A mIL7

ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGITGAGCAGGCTGAGATCT
GACGACACGGCCGTGTATTACTGTGCGAGTTATAATGATGCTTTTGATATCTGGGGC
CAAGGCACCCTGGTCACCGTCTCCTCAGGAGGTGGCGGGTCTGGTGGTGGCGGTAG
CGGTGGTGGCGGATCCAATTTTATGCTGACTCAGCCCCACTCTGTGTCGGAGTCTCC
GGGGAAGACGGTAACCATCTCCTGCACCCGCAGCAGTGGCAGCATTGCCAGCAACT
ATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATCTGGGCCCCATTGGCTGGAACTTGCGGCGTGCTGCTCTTGTCTCTGGTCATTACC
CTGTACTGCAAGCGCGGACGGAAGAAACTCTTGTACATCTTCAAGCAGCCGTTCATG
CGCCCTGTGCAAACCACCCAAGAAGAGGACGGGTGCTCCTGCCGGTTCCCGGAAGA
GGAAGAGGGCGGCTGCGAACTGAGAGTGAAGTTTAGCCGCTCAGCCGATGCACCGG
CCTACCAGCAGGGACAGAACCAGCTCTACAACGAGCTCAACCTGGGTCGGCGGGAA
GAATATGACGTGCTGGACAAACGGCGCGGCAGAGATCCGGAGATGGGGGGAAAGC
CGAGGAGGAAGAACCCTCAAGAGGGCCTGTACAACGAACTGCAGAAGGACAAGAT
GGCGGAAGCCTACTCCGAGATCGGCATGAAGGGAGAACGCCGGAGAGGGAAGGGT
CATGACGGACTGTACCAGGGCCTGTCAACTGCCACTAAGGACACTTACGATGCGCTC

-continued

CATATGCAAGCTTTGCCCCCGCGGCGCGCGAAACGCGGCAGCGGCGCGACCAACTT
TAGCCTGCTGAAACAGGCGGGCGATGTGGAAGAAAACCCGGGCCCGCGAGCAAAG
AGGAATATTATGGCTCTGCCTGTTACGGCACTGCTCCTTCCGCTTGCATTGTTGTTGC
ACGCAGCGCGGCCCGAGGTCCAGCTGGTACAGTCTGGGGGAGGCTTGGTACAGCCT
GGGGGGTCCCTGAGACTCTCCTGTGCAGCCTCTGGATTCACCTTTGATGATTATGCC
ATGCACTGGGTCCGGCAAGCTCCAGGGAAGGGCCTGGAGTGGGTCTCAGGTATTAG
TTGGAATAGTGGTAGCATAGGCTATGCGGACTCTGTGAAGGGCCGATTCACCATCTC
CAGAGACAACGCCAAGAACTCCCTGTATCTGCAAATGAACAGTCTGAGAGCTGAGG
ACACGGCCTTGTATTACTGTGCAAAAGATTTATCGTCAGTGGCTGGACCCTTTAACT
ACTGGGGCCAGGGCACCCTGGTCACCGTCTCCTCAGGAGGTGGCGGGTCTGGTGGA
GGCGGTAGCGGCGGTGGCGGATCCTCTTCTGAGCTGACTCAGGACCCTGCTGTGTCT
GTGGCCTTGGGACAGACAGTCAGGATCACATGCCAAGGAGACAGCCTCAGAAGCTA
TTATGCAAGCTGGTACCAGCAGAAGCCAGGACAGGCCCCTGTACTTGTCATCTATGG
TAAAAACAACCGGCCCTCAGGGATCCCAGACCGATTCTCTGGCTCCAGCTCAGGAA
ACACAGCTTCCTTGACCATCACTGGGGCTCAGGCGGAGGATGAGGCTGACTATTACT
GTAACTCCCGGGACAGCAGTGGTAACCATCTGGTATTCGGCGGAGGCACCCAGCTG
ACCGTCCTCGGTGCTAGCGCAACCACTACGCCTGCTCCGCGGCCTCCAACGCCCGCG
CCCACGATAGCTAGTCAGCCGTTGTCTCTCCGACCAGAGGCGTGTAGACCGGCCGCT
GGCGGAGCCGTACATACTCGCGGACTCGACTTCGCTTGCGACATCTACATTTGGGCA
CCCTTGGCTGGGACCTGTGGGGTGCTGTTGCTGTCCTTGGTTATTACGTTGTACTGCC
GGTCGAAGAGGTCCAGACTCTTGCACTCCGACTACATGAACATGACTCCTAGAAGG
CCCGGACCCACTAGAAAGCACTACCAGCCGTACGCCCCTCCTCGGGATTTCGCCGCA
TACCGGTCCAGAGTCAAATTTTCCAGGTCCGCAGATGCCCCCGCGTACCAGCAAGGC
CAGAACCAACTTTACAACGAACTGAACCTGGGTCGCCGGGAGGAATATGATGTGCT
GGATAAACGAAGGGGGAGGGACCCTGAGATGGGAGGGAAACCTCGCAGGAAAAAC
CCGCAGGAAGGTTTGTACAACGAGTTGCAGAAGGATAAGATGGCTGAGGCTTACTC
TGAAATAGGGATGAAGGGAGAGAGACGGAGAGGAAAAGGCCATGATGGCCTTTAC
CAGGGCTTAAGCACAGCAACAAAGGATACTTACGACGCTCTTCACATGCAAGCTCT
GCCACCACGGCGGGCAAAGCGGGGCTCAGGGGCGACTAACTTTTCACTGTTGAAGC
AGGCCGGGGATGTGGAGGAGAATCCTGGTCCTAGAGCTAAGCGAGTAATGCTCTTG
CTCGTGACTTCTTTGCTTTTGTGCGAACTTCCGCACCCAGCCTTCCTTTTGATACCTAT
GGATTGTGATATTGAAGGTAAAGATGGCAAACAATATGAGAGTGTTCTAATGGTCA
GCATCGATCAATTATTGGACAGCATGAAAGAAATTGGTAGCAATTGCCTGAATAAT
GAATTTAACTTTTTTAAAAGACATATCTGTGATGCTAATAAGGAAGGTATGTTTTTAT
TCCGTGCTGCTCGCAAGTTGAGGCAATTTCTTAAAATGAATAGCACTGGTGATTTTG
ATCTCCACTTATTAAAAGTTTCAGAAGGCACAACAATACTGTTGAACTGCACTGGCC
AGGTTAAAGGAAGAAAACCAGCTGCCCTGGGTGAAGCCCAACCAACAAAGAGTTTG
GAAGAAAATAAATCTTTAAAGGAACAGAAAAAACTGAATGACTTGTGTTTCCTAAA
GAGACTATTACAAGAGATAAAAACTTGTTGGAATAAAATTTTGATGGGCACTAAAG
AACACTCCGGAGGTTCCGGTGGTGGCTCAGGTGGTGGCTCAGGTGAAAGTGGCTAT
GCTCAAAATGGAGACTTGGAAGATGCAGAACTGGATGACTACTCATTCTCATGCTAT
AGCCAGTTGGAAGTGAATGGATCGCAGCACTCACTGACCTGTGCTTTTGAGGACCCA
GATGTCAACATCACCAATCTGGAATTTGAAATATGTGGGGCCCTCGTGGAGGTAAA
GTGCCTGAATTTCAGGAAACTACAAGAGATATATTTCATCGAGACAAAGAAATTCTT
ACTGATTGGAAAGAGCAATATATGTGTGAAGGTTGGAGAAAAGAGTCTAACCTGCA
AAAAAATAGACCTAACCACTATAGTTAAACCTGAGGCTCCTTTTGACCTGAGTGTCG
TCTATCGGGAAGGAGCCAATGACTTTGTGGTGACATTTAATACATCACACTTGCAAA
AGAAGTATGTAAAAGTTTTAATGCACGATGTAGCTTACCGCCAGGAAAAGGATGAA
AACAAATGGACGCATGTGAATTTATCCAGCACAAAGCTGACACTCCTGCAGAGAAA
GCTCCAACCGGCAGCAATGTATGAGATTAAAGTTCGATCCATCCCTGATCACTATTT
TAAAGGCTTCTGGAGTGAATGGAGTCCAAGTTATTACTTCAGAACTCCAGAGATCAA
TAATAGCTCAGGGGAGATGGATCCTATCTTACTAACCATCAGCATTTTGAGTTTTTTC
TCTGTCGCTCTGTTGGTCATCTTGGCCTGTGTGTTATGGAAAAAAAGGATTAAGCCT
ATCGTATGGCCCAGTCTCCCCGATCATAAGAAGACTCTGGAACATCTTTGTAAGAAA
CCAAGAAAAAATTTAAATGTGAGTTTCAATCCTGAAAGTTTCCTGGACTGCCAGATT
CATAGGGTGGATGACATTCAAGCTAGAGATGAAGTGGAAGGTTTTCTGCAAGATAC
GTTTCCTCAGCAACTAGAAGAATCTGAGAAGCAGAGGCTTGGAGGGGATGTGCAGA
GCCCCAACTGCCCATCTGAGGATGTAGTCATCACTCCAGAAAGCTTTGGAAGAGATT
CATCCCTCACATGCCTGGCTGGGAATGTCAGTGCATGTGACGCCCCTATTCTCTCCTC
TTCCAGGTCCCTAGACTGCAGGGAGAGTGGCAAGAATGGGCCTCATGTGTACCAGG
ACCTCCTTCTTAGCCTTGGGACTACAAACAGCACGCTGCCCCCTCCATTTTCTCTCCA
ATCTGGAATCCTGACATTGAACCCAGTTGCTCAGGGTCAGCCCATTCTTACTTCCCTG
GGATCAAATCAAGAAGAAGCATATGTCACCATGTCCAGCTTCTACCAAAACCAGCC
CTAG

SEQ ID NO: 184 amino acid sequence of CAR D0283 ROR1 scFv9 IgG4 CD8 BBz 2A MSLN M1-4S CD8 28z 2A mIL7

MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRNIMALPVTALLLPLALLLHAARPEVQLVQSGGGLVQPGGS
LRLSCAASGFTFDDYAMHWVRQAPGKGLEWVSGISWNSGSIGYADSVKGRFTISRDNA
KNSLYLQMNSLRAEDTALYYCAKDLSSVAGPFNYWGQGTLVTVSSGGGGSGGGGSGG
GGSSSELTQDPAVSVALGQTVRITCQGDSLRSYYASWYQQKPGQAPVLVIYGKNNRPSG
IPDRFSGSSSGNTASLTITGAQAEDEADYYCNSRDSSGNHLVFGGGTQLTVLGASATTTP
APRPPTPAPTIASQPLSLRPEACRPAAGGAVHTRGLDFACDIYIWAPLAGTCGVLLLSLVI

-continued

TLYCRSKRSRLLHSDYMNMTPRRPGPTRKHYQPYAPPRDFAAYRSRVKFSRSADAPAY
QQGQNQLYNELNLGRREEYDVLDKRRGRDPEMGGKPRRKNPQEGLYNELQKDKMAE
AYSEIGMKGERRRGKGHDGLYQGLSTATKDTYDALHMQALPPRRAKRGSGATNFSLL
KQAGDVEENPGPRAKRVMLLLVTSLLLCELPHPAFLLIPMDCDIEGKDGKQYESVLMVS
IDQLLDSMKEIGSNCLNNEFNFFKRHICDANKEGMFLFRAARKLRQFLKMNSTGDFDLH
LLKVSEGTTILLNCTGQVKGRKPAALGEAQPTKSLEENKSLKEQKKLNDLCFLKRLLQEI
KTCWNKILMGTKEHSGGSGGGSGGGSGESGYAQNGDLEDAELDDYSFSCYSQLEVNGS
QHSLTCAFEDPDVNITNLEFEICGALVEVKCLNFRKLQEIYFIETKKFLLIGKSNICVKVGE
KSLTCKKIDLTTIVKPEAPFDLSVVYREGANDFVVTFNTSHLQKKYVKVLMHDVAYRQ
EKDENKWTHVNLSSTKLILLQRKLQPAAMYEIKVRSIPDHYFKGFWSEWSPSYYFRTPE
INNSSGEMDPILLTISILSFFSVALLVILACVLWKKRIKPIVWPSLPDHKKTLEHLCKKPRK
NLNVSFNPESFLDCQIHRVDDIQARDEVEGFLQDTFPQQLEESEKQRLGGDVQSPNCPSE
DVVITPESFGRDSSLTCLAGNVSACDAPILSSSRSLDCRESGKNGPHVYQDLLLSLGTTNS
TLPPPFSLQSGILTLNPVAQGQPILTSLGSNQEEAYVTMSSFYQNQP

SEQ ID NO: 185 nucleotide sequence of CAR D0344 MSLN M1-4S CD8 BBz 2A HPSE
ATGCTGCTGCTGGTGACCAGCCTGCTGCTGTGCGAACTGCCGCATCCGGCGTTTCTG
CTGATTCCGGAGGTCCAGCTGGTACAGTCTGGGGGAGGCTTGGTACAGCCTGGGGG
GTCCCTGAGACTCTCCTGTGCAGCCTCTGGATTCACCTTTGATGATTATGCCATGCAC
TGGGTCCGGCAAGCTCCAGGGAAGGGCCTGGAGTGGGTCTCAGGTATTAGTTGGAA
TAGTGGTAGCATAGGCTATGCGGACTCTGTGAAGGGCCGATTCACCATCTCCAGAGA
CAACGCCAAGAACTCCCTGTATCTGCAAATGAACAGTCTGAGAGCTGAGGACACGG
CCTTGTATTACTGTGCAAAAGATTTATCGTCAGTGGCTGGACCCTTTAACTACTGGG
GCCAGGGCACCCTGGTCACCGTCTCCTCAGGAGGTGGCGGGTCTGGTGGAGGCGGT
AGCGGCGGTGGCGGATCCTCTTCTGAGCTGACTCAGGACCCTGCTGTGTCTGTGGCC
TTGGGACAGACAGTCAGGATCACATGCCAAGGAGACAGCCTCAGAAGCTATTATGC
AAGCTGGTACCAGCAGAAGCCAGGACAGGCCCCTGTACTTGTCATCTATGGTAAAA
ACAACCGGCCCTCAGGGATCCCAGACCGATTCTCTGGCTCCAGCTCAGGAAACACA
GCTTCCTTGACCATCACTGGGGCTCAGGCGGAGGATGAGGCTGACTATTACTGTAAC
TCCCGGGACAGCAGTGGTAACCATCTGGTATTCGGCGGAGGCACCCAGCTGACCGT
CCTCGGTGCGGCCGCAACTACCACCCCTGCCCCTCGGCCGCCGACTCCGGCCCCAAC
CATCGCAAGCCAACCCCTCTCCTTGCGCCCCGAAGCTTGCCGCCCGGCCGCGGGTGG
AGCCGTGCATACCCGGGGGCTGGACTTTGCCTGCGATATCTACATTTGGGCCCCGCT
GGCCGGCACTTGCGGCGTGCTCCTGCTGTCGCTGGTCATCACCCTTTACTGCAAGAG
GGGCCGGAAGAAGCTGCTTTACATCTTCAAGCAGCCGTTCATGCGGCCCGTGCAGA
CGACTCAGGAAGAGGACGGATGCTCGTGCAGATTCCCTGAGGAGGAAGAGGGGGG
ATGCGAACTGCGCGTCAAGTTCTCACGGTCCGCCGACGCCCCCGCATATCAACAGG
GCCAGAATCAGCTCTACAACGAGCTGAACCTGGGAAGGAGAGAGGAGTACGACGTG
CTGGACAAGCGACGCGGACGCGACCCGGAGATGGGGGGGAAACCACGGCGGAAAA
ACCCTCAGGAAGGACTGTACAACGAACTCCAGAAAGACAAGATGGCGGAAGCCTAC
TCAGAAATCGGGATGAAGGGAGAGCGGAGGAGGGGAAAGGGTCACGACGGGCTGT
ACCAGGGACTGAGCACCGCCACTAAGGATACCTACGATGCCTTGCATATGCAAGCA
CTCCCACCCCGGCGGGCAAAGCGGGGCTCAGGGGCGACTAACTTTTCACTGTTGAA
GCAGGCCGGGGATGTGGAGGAGAATCCTGGTCCTAGAGCAAAGCGAATGCTTCTAC
GTTCTAAACCTGCACTTCCTCCACCACTTATGCTACTTCTTCTAGGACCTCTTGGTCC
TCTATCACCTGGAGCTCTACCTCGACCTGCACAAGCACAGGACGTCGTGGACCTGGA
CTTCTTCACCCAGGAGCCGCTGCACCTGGTGAGCCCCTCGTTCCTGTCCGTCACCATT
GACGCCAACCTGGCCACGGACCCGCGGTTCCTCATCCTCCTGGGTTCTCCAAAGCTT
CGTACCTTGGCCAGAGGCTTGTCTCCTGCGTACCTGAGGTTTGGTGGCACCAAGACA
GACTTCCTAATTTTCGATCCCAAGAAGGAATCAACCTTTGAAGAGAGAAGTTACTGG
CAATCTCAAGTCAACCAGGATATTTGCAAATATGGATCCATCCCTCCTGATGTGGAG
GAGAAGTTACGGTTGGAATGGCCCTACCAGGAGCAATTGCTACTCCGAGAACACTA
CCAGAAAAAGTTCAAGAACAGCACCTACTCAAGAAGCTCTGTAGATGTGCTATACA
CTTTTGCAAACTGCTCAGGACTGGACTTGATCTTTGGCCTAAATGCGTTATTAAGAA
CAGCAGATTTGCAGTGGAACAGTTCTAATGCTCAGTTGCTCCTGGACTACTGCTCTT
CCAAGGGGTATAACATTTCTTGGGAACTAGGCAATGAACCTAACAGTTTCCTTAAGA
AGGCTGATATTTTCATCAATGGGTCGCAGTTAGGAGAAGATTTTATTCAATTGCATA
AACTTCTAAGAAAGTCCACCTTCAAAAATGCAAAACTCTATGGTCCTGATGTTGGTC
AGCCTCGAAGAAAGACGGCTAAGATGCTGAAGAGCTTCCTGAAGGCTGGTGGAGAA
GTGATTGATTCAGTTACATGGCATCACTACTATTTGAATGGACGGACTGCTACCAAG
GAAGATTTTCTAAACCCTGATGTATTGGACATTTTTATTTCATCTGTGCAAAAAGTTT
TCCAGGTGGTTGAGAGCACCAGGCCTGGCAAGAAGGTCTGGTTAGGAGAAACAAGC
TCTGCATATGGAGGCGGAGCGCCCTTGCTATCCGACACCTTTGCAGCTGGCTTTATG
TGGCTGGATAAATTGGGCCTGTCAGCCCGAATGGGAATAGAAGTGGTGATGAGGCA
AGTATTCTTTGGAGCAGGAAACTACCATTTAGTGGATGAAAACTTCGATCCTTTACC
TGATTATTGGCTATCTCTTCTGTTCAAGAAATTGGTGGGCACCAAGGTGTTAATGGC
AAGCGTGCAAGGTTCAAAGAGAAGGAAGCTTCGAGTATACCTTCATTGCACAAACA
CTGACAATCCAAGGTATAAAGAAGGAGATTTAACTCTGTATGCCATAAACCTCCATA
ATGTCACCAAGTACTTGCGGTTACCCTATCCTTTTTCTAACAAGCAAGTGGATAAAT
ACCTTCTAAGACCTTTGGGACCTCATGGATTACTTTCCAAATCTGTCCAACTCAATGG
TCTAACTCTAAAGATGGTGGATGATCAAACCTTGCCACCTTTAATGGAAAAACCTCT
CCGGCCAGGAAGTTCACTGGGCTTGCCAGCTTTCTCATATAGTTTTTTTGTGATAAGA
AATGCCAAAGTTGCTGCTTGCATCTAA SEQ ID NO: 186 amino acid sequence of CAR D0344 MSLN M1-4S CD8 BBz 2A HPSE
MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQTV
RITCQGDSLRSYYASWYQQKPGQAPVLVIYGKNNRPSGIPDRFSGSSSGNTASLTITGAQ
AEDEADYYCNSRDSSGNHLVFGGGTQLTVLGAAATTTPAPRPPTPAPTIASQPLSLRPEA
CRPAAGGAVHTRGLDFACDIYIWAPLAGTCGVLLLSLVITLYCKRGRKKLLYIFKQPFM -continued RPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDG
LYQGLSTATKDTYDALHMQALPPRRAKRGSGATNFSLLKQAGDVEENPGPRAKRMLL
RSKPALPPPLMLLLLGPLGPLSPGALPRPAQAQDVVDLDFFTQEPLHLVSPSFLSVTIDAN
LATDPRFLILLGSPKLRTLARGLSPAYLRFGGTKTDFLIFDPKKESTFEERSYWQSQVNQ
DICKYGSIPPDVEEKLRLEWPYQEQLLLREHYQKKFKNSTYSRSSVDVLYTFANCSGLD
LIFGLNALLRTADLQWNSSNAQLLLDYCSSKGYNISWELGNEPNSFLKKADIFINGSQLG
EDFIQLHKLLRKSTFKNAKLYGPDVGQPRRKTAKMLKSFLKAGGEVIDSVTWHHYYLN
GRTATKEDFLNPDVLDIFISSVQKVFQVVESTRPGKKVWLGETSSAYGGGAPLLSDTFA
AGFMWLDKLGLSARMGIEVVMRQVFFGAGNYHLVDENFDPLPDYWLSLLFKKLVGTK
VLMASVQGSKRRKLRVYLHCTNTDNPRYKEGDLTLYAINLHNVTKYLRLPYPFSNKQV
DKYLLRPLGPHGLLSKSVQLNGLTLKMVDDQTLPPLMEKPLRPGSSLGLPAFSYSFFVIR
NAKVAACI SEQ ID NO: 187 nucleotide sequence of CAR D0345 MSLN M1-4S CD8 BBz 2A MMP2
ATGCTGCTGCTGGTGACCAGCCTGCTGCTGTGCGAACTGCCGCATCCGGCGTTTCTG
CTGATTCCGGAGGTCCAGCTGGTACAGTCTGGGGGAGGCTTGGTACAGCCTGGGGG
GTCCCTGAGACTCTCCTGTGCAGCCTCTGGATTCACCTTTGATGATTATGCCATGCAC
TGGGTCCGGCAAGCTCCAGGGAAGGGCCTGGAGTGGGTCTCAGGTATTAGTTGGAA
TAGTGGTAGCATAGGCTATGCGGACTCTGTGAAGGGCCGATTCACCATCTCCAGAGA
CAACGCCAAGAACTCCCTGTATCTGCAAATGAACAGTCTGAGAGCTGAGGACACGG
CCTTGTATTACTGTGCAAAAGATTTATCGTCAGTGGCTGGACCCTTTAACTACTGGG
GCCAGGGCACCCTGGTCACCGTCTCCTCAGGAGGTGGCGGGTCTGGTGGAGGCGGT
AGCGGCGGTGGCGGATCCTCTTCTGAGCTGACTCAGGACCCTGCTGTGTCTGTGGCC
TTGGGACAGACAGTCAGGATCACATGCCAAGGAGACAGCCTCAGAAGCTATTATGC
AAGCTGGTACCAGCAGAAGCCAGGACAGGCCCCTGTACTTGTCATCTATGGTAAAA
ACAACCGGCCCTCAGGGATCCCAGACCGATTCTCTGGCTCCAGCTCAGGAAACACA
GCTTCCTTGACCATCACTGGGGCTCAGGCGGAGGATGAGGCTGACTATTACTGTAAC
TCCCGGGACAGCAGTGGTAACCATCTGGTATTCGGCGGAGGCACCCAGCTGACCGT
CCTCGGTGCGGCCGCAACTACCACCCCTGCCCCTCGGCCGCCGACTCCGGCCCCAAC
CATCGCAAGCCAACCCCTCTCCTTGCGCCCCGAAGCTTGCCGCCCGGCCGCGGGTGG
AGCCGTGCATACCCGGGGGCTGGACTTTGCCTGCGATATCTACATTTGGGCCCCGCT
GGCCGGCACTTGCGGCGTGCTCCTGCTGTCGCTGGTCATCACCCTTTACTGCAAGAG
GGGCCGGAAGAAGCTGCTTTACATCTTCAAGCAGCCGTTCATGCGGCCCGTGCAGA
CGACTCAGGAAGAGGACGGATGCTCGTGCAGATTCCCTGAGGAGGAAGAGGGGGG
ATGCGAACTGCGCGTCAAGTTCTCACGGTCCGCCGACGCCCCCGCATATCAACAGG
GCCAGAATCAGCTCTACAACGAGCTGAACCTGGGAAGGAGAGAGGAGTACGACGTG
CTGGACAAGCGACGCGGACGCGACCCGGAGATGGGGGGGAAACCACGGCGGAAAA
ACCCTCAGGAAGGACTGTACAACGAACTCCAGAAAGACAAGATGGCGGAAGCCTAC
TCAGAAATCGGGATGAAGGGAGAGCGGAGGAGGGGAAAGGGTCACGACGGGCTGT
ACCAGGGACTGAGCACCGCCACTAAGGATACCTACGATGCCTTGCATATGCAAGCA
CTCCCACCCCGGCGGGCAAAGCGGGGCTCAGGGGCGACTAACTTTTCACTGTTGAA
GCAGGCCGGGGATGTGGAGGAGAATCCTGGTCCTAGAGCaAAGCGAATGGAAGCTC
TTATGGCTAGGGGAGCGCTCACAGGTCCATTGCGGGCACTGTGCCTGTTGGGGTGCC
TGTTGTCTCATGCGGCTGCGGCTCCGTCACCAATTATCAAATTTCCTGGCGACGTTGC
CCCGAAGACAGACAAGGAACTTGCCGTGCAGTACCTCAATACGTTCTATGGATGTCC
TAAAGAATCATGCAATCTGTTCGTTTTGAAAGATACCCTTAAGAAGATGCAAAAGTT
CTTTGGCTTGCCACAGACTGGGGACCTTGACCAGAATACaATTGAAACTATGAGAAA
ACCGAGATGCGGCAACCCCGATGTGGCTAACTACAACTTTTTTCCCAGAAAGCCTAA
ATGGGATAAGAACCAGATTACATACCGGATAATAGGATATACACCCGACCTGGACC
CGGAGACAGTTGACGACGCATTTGCGCGCGCCTTTCAGGTTTGGTCAGATGTAACTC
CGCTTCGCTTTTCACGAATACATGACGGAGAAGCTGACATCATGATTAATTTCGGTC
GGTGGGAGCATGGGGATGGTTATCCTTTCGACGGCAAAGACGGGCTGCTCGCCCAT
GCCTTTGCGCCTGGGACCGGCGTCGGTGGTGATAGCCACTTCGATGACGATGAACTC
TGGACCCTCGGAGAGGGACAAGTGGTGAGAGTAAAATACGGAAACGCCGACGGAG
AATATTGCAAGTTCCCCTTTCTATTCAATGGTAAGGAATATAATAGCTGTACTGATA
CAGGTAGATCAGACGGCTTCCTTTGGTGCTCAACCACCTACAATTTCGAAAAAGATG
GTAAGTACGGCTTCTGCCCTCATGAGGCCCTGTTCACTATGGGAGGCAATGCAGAGG
GACAGCCGTGCAAATTTCCATTTCGCTTTCAAGGTACGAGCTACGATTCTTGTACGA
CGGAGGGGAGAACGGATGGGTATAGATGGTGTGGCACAACAGAGGATTACGATAG
AGACAAGAAATATGGGTTCTGTCCCGAGACCGCTATGAGTACAGTTGGGGGTAATT
CCGAGGGAGCTCCCTGCGTGTTCCCGTTCACATTCTTGGGTAACAAGTACGAGTCCT
GTACCAGCGCTGGGCGGTCTGATGGTAAAATGTGGTGTGCAACGACGGCAAATTAC
GACGACGATCGGAAGTGGGGTTTTTGTCCTGACCAGGGTTACTCTCTGTTTCTCGTTG
CAGCGCATGAATTIGGACAcGCAATGGGTCTTGAGCACTCACAGGACCCCGGCGCAC
TTATGGCGCCAATATACACTTACACCAAGAACTTTAGATTGAGTCAGGACGATATTA
AGGGCATCCAGGAGCTTTATGGAGCCTCACCAGACATCGATCTGGGGACTGGTCCC
ACTCCCACTCTTGGTCCTGTCACACCAGAAATTTGTAAACAGGATATAGTCTTTGAT
GGTATAGCCCAGATTCGCGGAGAGATCTTTTTCTTTAAGGACAGGTTCATCTGGAGG
ACAGTGACGCCAAGAGATAAACCCATGGGTCCTCTGTTGGTAGCAACCTTCTGGCCC
GAGCTCCCAGAGAAGATAGATGCAGTGTATGAGGCCCCACAAGAGGAGAAAGCGG
TCTTTTTCGCGGGGAATGAGTATTGGATCTACTCAGCCTCCACTCTGGAAAGAGGGT
ACCCAAAACCACTGACTTCTCTGGGTTTGCCCCCAGATGTACAGCGAGTAGATGCTG
CATTTAATTGGAGCAAGAATAAGAAGACCTACATTTTCGCGGGGGATAAGTTCTGG
AGGTACAATGAAGTCAAGAAGAAAATGGATCCCGGATTTCCAAAGCTCATAGCCGA
CGCATGGAATGCCATCCCGGACAACCTGGATGCCGTCGTAGACTTGCAGGGTGGGG
GACACTCCTATTTTTTCAAAGGAGCGTATTATTTGAAATTGGAGAATCAAAGTCTTA
AGTCAGTTAAGTTTGGATCAATCAAGAGCGACTGGCTCGGGTGTTAG -continued SEQ ID NO: 188 amino acid sequence of CAR D0345 MSLN M1-4S CD8 BBz 2A MMP2
MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQTV
RITCQGDSLRSYYASWYQQKPGQAPVLVIYGKNNRPSGIPDRFSGSSSGNTASLTITGAQ
AEDEADYYCNSRDSSGNHLVFGGGTQLTVLGAAATTTPAPRPPTPAPTIASQPLSLRPEA
CRPAAGGAVHTRGLDFACDIYIWAPLAGTCGVLLLSLVITLYCKRGRKKLLYIFKQPFM
RPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDG
LYQGLSTATKDTYDALHMQALPPRRAKRGSGATNFSLLKQAGDVEENPGPRAKRMEA
LMARGALTGPLRALCLLGCLLSHAAAAPSPIIKFPGDVAPKTDKELAVQYLNTFYGCPK
ESCNLFVLKDTLKKMQKFFGLPQTGDLDQNTIETMRKPRCGNPDVANYNFFPRKPKWD
KNQITYRIIGYTPDLDPETVDDAFARAFQVWSDVTPLRFSRIHDGEADIMINFGRWEHGD
GYPFDGKDGLLAHAFAPGTGVGGDSHFDDDELWTLGEGQVVRVKYGNADGEYCKFPF
LFNGKEYNSCTDTGRSDGFLWCSTTYNFEKDGKYGFCPHEALFTMGGNAEGQPCKFPF
RFQGTSYDSCTTEGRTDGYRWCGTTEDYDRDKKYGFCPETAMSTVGGNSEGAPCVFPF
TFLGNKYESCTSAGRSDGKMWCATTANYDDDRKWGFCPDQGYSLFLVAAHEFGHAM
GLEHSQDPGALMAPIYTYTKNFRLSQDDIKGIQELYGASPDIDLGTGPTPTLGPVTPEICK
QDIVFDGIAQIRGEIFFFKDRFIWRTVTPRDKPMGPLLVATFWPELPEKIDAVYEAPQEEK
AVFFAGNEYWIYSASTLERGYPKPLTSLGLPPDVQRVDAAFNWSKNKKTYIFAGDKFW
RYNEVKKKMDPGFPKLIADAWNAIPDNLDAVVDLQGGGHSYFFKGAYYLKLENQSLK
SVKFGSIKSDWLGC SEQ ID NO: 189 nucleotide sequence of CAR D0346 MSLN M1-4S CD8 BBz 2A SP PH20 IgG1 Fc
ATGCTGCTGCTGGTGACCAGCCTGCTGCTGTGCGAACTGCCGCATCCGGCGTTTCTG
CTGATTCCGGAGGTCCAGCTGGTACAGTCTGGGGGAGGCTTGGTACAGCCTGGGGG
GTCCCTGAGACTCTCCTGTGCAGCCTCTGGATTCACCTTTGATGATTATGCCATGCAC
TGGGTCCGGCAAGCTCCAGGGAAGGGCCTGGAGTGGGTCTCAGGTATTAGTTGGAA
TAGTGGTAGCATAGGCTATGCGGACTCTGTGAAGGGCCGATTCACCATCTCCAGAGA
CAACGCCAAGAACTCCCTGTATCTGCAAATGAACAGTCTGAGAGCTGAGGACACGG
CCTTGTATTACTGTGCAAAAGATTTATCGTCAGTGGCTGGACCCTTTAACTACTGGG
GCCAGGGCACCCTGGTCACCGTCTCCTCAGGAGGTGGCGGGTCTGGTGGAGGCGGT
AGCGGCGGTGGCGGATCCTCTTCTGAGCTGACTCAGGACCCTGCTGTGTCTGTGGCC
TTGGGACAGACAGTCAGGATCACATGCCAAGGAGACAGCCTCAGAAGCTATTATGC
AAGCTGGTACCAGCAGAAGCCAGGACAGGCCCCTGTACTTGTCATCTATGGTAAAA
ACAACCGGCCCTCAGGGATCCCAGACCGATTCTCTGGCTCCAGCTCAGGAAACACA
GCTTCCTTGACCATCACTGGGGCTCAGGCGGAGGATGAGGCTGACTATTACTGTAAC
TCCCGGGACAGCAGTGGTAACCATCTGGTATTCGGCGGAGGCACCCAGCTGACCGT
CCTCGGTGCGGCCGCAACTACCACCCCTGCCCCTCGGCCGCCGACTCCGGCCCCAAC
CATCGCAAGCCAACCCCTCTCCTTGCGCCCCGAAGCTTGCCGCCCGGCCGCGGGTGG
AGCCGTGCATACCCGGGGGCTGGACTTTGCCTGCGATATCTACATTTGGGCCCCGCT
GGCCGGCACTTGCGGCGTGCTCCTGCTGTCGCTGGTCATCACCCTTTACTGCAAGAG
GGGCCGGAAGAAGCTGCTTTACATCTTCAAGCAGCCGTTCATGCGGCCCGTGCAGA
CGACTCAGGAAGAGGACGGATGCTCGTGCAGATTCCCTGAGGAGGAAGAGGGGGG
ATGCGAACTGCGCGTCAAGTTCTCACGGTCCGCCGACGCCCCCGCATATCAACAGG
GCCAGAATCAGCTCTACAACGAGCTGAACCTGGGAAGGAGAGAGGAGTACGACGTG
CTGGACAAGCGACGCGGACGCGACCCGGAGATGGGGGGGAAACCACGGCGGAAAA
ACCCTCAGGAAGGACTGTACAACGAACTCCAGAAAGACAAGATGGCGGAAGCCTAC
TCAGAAATCGGGATGAAGGGAGAGCGGAGGAGGGGAAAGGGTCACGACGGGCTGT
ACCAGGGACTGAGCACCGCCACTAAGGATACCTACGATGCCTTGCATATGCAAGCA
CTCCCACCCCGGCGGGCAAAGCGGGGCTCAGGGGCGACTAACTTTTCACTGTTGAA
GCAGGCCGGGGATGTGGAGGAGAATCCTGGTCCTAGAGCaAAGCGAATGGATGCAA
TGAAGAGAGGGCTCTGCTGTGTGCTGCTGCTGTGTGGAGCAGTCTTCGTTTCGCCCA
GCCTGAACTTTCGCGCCCCACCAGTGATCCCTAATGTGCCATTCCTTTGGGCTTGGA
ATGCGCCTTCTGAATTCTGCTTGGGAAAATTTGATGAGCCTCTGGATATGTCTCTTTT
CAGTTTTATTGGGTCACCAAGGATTAACGCGACTGGACAAGGAGTGACGATATTTTA
TGTCGATAGGCTCGGCTACTACCCCTACATAGATTCCATTACCGGCGTAACCGTGAA
TGGTGGTATCCCTCAAAAGATCTCTCTTCAAGACCACTTGGACAAAGCAAAAAAAG
ACATTACATTCTACATGCCGGTGGATAACCTGGGGATGGCCGTTATCGATTGGGAGG
AGTGGAGACCCACGTGGGCTAGAAACTGGAAGCCGAAGGACGTCTATAAAAACAG
GTCTATCGAATTGGTTCAGCAGCAGAACGTGCAATTGTCCTTGACTGAGGCGACAGA
GAAGGCCAAGCAAGAGTTTGAGAAGGCGGGAAAGGACTTTTTGGTTGAGACCATTA
AGCTCGGTAAACTGCTGCGACCTAATCATCTGTGGGGTTACTACCTCTTCCCTGACT
GCTACAATCACCATTACAAGAAACCGGGCTACAATGGCTCTTGTTTTAATGTCGAAA
TCAAACGAAACGACGACCTGAGCTGGCTTTGGAACGAATCCACCGCACTCTACCCC
AGCATCTATCTGAACACCCAGCAGAGTCCTGTAGCAGCAACGCTGTACGTCCGGAA
CCGGGTACGAGAGGCAATCAGAGTATCTAAGATCCCGGATGCTAAATCCCCACTGC
CGGTATTTGCGTACACCCGAATCGTGTTCACTGACCAGGTTCTGAAGTTTCTCTCCCA
GGACGAACTTGTCTATACGTTTGGAGAGACAGTAGCACTCGGCGCATCAGGCATTGT
TATATGGGGAACCCTTAGCATCATGCGGTCAATGAAGTCCTGCTTGCTTCTTGATAA
CTATATGGAGACAATCTTGAACCCCTATATCATCAATGTAACACTTGCAGCAAAAAT
GTGCTCCCAAGTACTCTGTCAAGAGCAGGGAGTATGCATACGAAAAAATTGGAACA
GTTCCGACTACCTGCACCTTAACCCCGATAATTTTGCTATACAGCTTGAAAAGGGCG
GAAAATTTACAGTCCGAGGGAAGCCGACATTGGAGGATCTCGAGCAATTCTCTGAA
AAGTTTTATTGCTCATGCTACAGTACCCTTAGCTGTAAAGAAAAGGCGGACGTCAAG
GATACTGACGCCGTGGACGTCTGCATCGCCGACGGAGTTTGCATCGACGCATTTCTT
AAACCTCCCATGGAAACCGAAGAGCCACAAATCTTCTATAACGCTTCTCCCTCAACA
CTTAGTGCTACTATGTTTATAGTTTCTATTTTGTTCCTTATTATTTCAAGTGTAGCTAG
TCTTGCTAGCGACAAAACTCACACATGCCCACCGTGCCCAGCACCTGAAGCTGCGG
GGGGACCGTCAGTCTTCCTCTTCCCCCCAAAACCCAAGGACACCCTCATGATCTCCC -continued GGACCCCTGAGGTCACATGCGTGGTGGTGGACGTGAGCCACGAAGACCCTGAGGTC
AAGTTCAACTGGTACGTGGACGGCGTGGAGGTGCATAATGCCAAGACAAAGCCGCG
GGAGGAGCAGTACAACAGCACGTACCGTGTGGTCAGCGTCCTCACCGTCCTGCACC
AGGACTGGCTGAATGGCAAGGAGTACAAGTGCAAGGTCTCCAACAAGGCACTTGGG
GCCCCTATCGAGAAAACCATCTCCAAAGCCAAAGGGCAGCCCCGAGAACCACAGGT
GTACACCCTGCCCCCATCTCGGGAGGAGATGACCAAGAACCAGGTCAGCCTGACCT
GCCTGGTCAAAGGCTTCTATCCCAGCGACATCGCCGTGGAGTGGGAGAGCAATGGG
CAGCCGGAGAACAACTACAAGACCACGCCTCCCGTGCTGGACTCCGACGGCTCCTT
CTTCCTCTACAGCAAGCTCACCGTGGACAAGAGCAGGTGGCAGCAGGGGAACGTCT
TCTCATGCTCCGTGATGCACGAGGCTCTGCACAACCACTACACGCAGAAGAGCCTCT
CCCTGTCTCCGGGTAAATAA SEQ ID NO: 190 amino acid sequence of CAR D0346 MSLN M1-4S CD8 BBz 2A SP PH20 IgG1 Fc
MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQTV
RITCQGDSLRSYYASWYQQKPGQAPVLVIYGKNNRPSGIPDRFSGSSSGNTASLTITGAQ
AEDEADYYCNSRDSSGNHLVFGGGTQLTVLGAAATTTPAPRPPTPAPTIASQPLSLRPEA
CRPAAGGAVHTRGLDFACDIYIWAPLAGTCGVLLLSLVITLYCKRGRKKLLYIFKQPFM
RPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDG
LYQGLSTATKDTYDALHMQALPPRRAKRGSGATNFSLLKQAGDVEENPGPRAKRMDA
MKRGLCCVLLLCGAVFVSPSLNFRAPPVIPNVPFLWAWNAPSEFCLGKFDEPLDMSLFS
FIGSPRINATGQGVTIFYVDRLGYYPYIDSITGVTVNGGIPQKISLQDHLDKAKKDITFYM
PVDNLGMAVIDWEEWRPTWARNWKPKDVYKNRSIELVQQQNVQLSLTEATEKAKQEF
EKAGKDFLVETIKLGKLLRPNHLWGYYLFPDCYNHHYKKPGYNGSCFNVEIKRNDDLS
WLWNESTALYPSIYLNTQQSPVAATLYVRNRVREAIRVSKIPDAKSPLPVFAYTRIVFTD
QVLKFLSQDELVYTFGETVALGASGIVIWGTLSIMRSMKSCLLLDNYMETILNPYIINVTL
AAKMCSQVLCQEQGVCIRKNWNSSDYLHLNPDNFAIQLEKGGKFTVRGKPTLEDLEQF
SEKFYCSCYSTLSCKEKADVKDTDAVDVCIADGVCIDAFLKPPMETEEPQIFYNASPSTL
SATMFIVSILFLIISSVASLASDKTHTCPPCPAPEAAGGPSVFLFPPKPKDTLMISRTPEVTC
VVVDVSHEDPEVKFNWYVDGVEVHNAKTKPREEQYNSTYRVVSVLTVLHQDWLNGK
EYKCKVSNKALGAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHN
HYTQKSLSLSPGK SEQ ID NO: 191 nucleotide sequence of CAR D0347 ROR1 scFv9 IgG4 CD8 BBz 2A HPSE
ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGCTGAGCAGGCTGAGATC
TGACGACACGGCCGTGTATTACTGTGCGAGTTATAATGATGCTTTTGATATCTGGGG
CCAAGGCACCCTGGTCACCGTCTCCTCAGGAGGTGGCGGGTCTGGTGGTGGCGGTA
GCGGTGGTGGCGGATCCAATTTTATGCTGACTCAGCCCCACTCTGTGTCGGAGTCTC
CGGGGAAGACGGTAACCATCTCCTGCACCCGCAGCAGTGGCAGCATTGCCAGCAAC
TATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCCCTGAGG
AGGAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAGAGA
GGAGTACGACGTGCTGGACAAGCGACGCGGACGCGACCCGGAGATGGGGGGGAAA
CCACGGCGGAAAAACCCTCAGGAAGGACTGTACAACGAACTCCAGAAAGACAAGA
TGGCGGAAGCCTACTCAGAAATCGGGATGAAGGGAGAGCGGAGGAGGGGAAAGGG
TCACGACGGGCTGTACCAGGGACTGAGCACCGCCACTAAGGATACCTACGATGCCT
TGCATATGCAAGCACTCCCACCCCGGCGGGCAAAGCGGGGCTCAGGGGCGACTAAC
TTTTCACTGTTGAAGCAGGCCGGGGATGTGGAGGAGAATCCTGGTCCTAGAGCaAAG
CGAATGCTtCTaCGtTCtAAaCCTGCaCTtCCtCCaCCaCTtATGCTaCTtCTtCTaGGaCCtCTtG
GTCCtCTaTCaCCTGGaGCtCTaCCtCGACCTGCaCAAGCACAGGACGTCGTGGACCTGG
ACTTCTTCACCCAGGAGCCGCTGCACCTGGTGAGCCCCTCGTTCCTGTCCGTCACCA
TTGACGCCAACCTGGCCACGGACCCGCGGTTCCTCATCCTCCTGGGTTCTCCAAAGC
TTCGTACCTTGGCCAGAGGCTTGTCTCCTGCGTACCTGAGGTTTGGTGGCACCAAGA
CAGACTTCCTAATTTTCGATCCCAAGAAGGAATCAACCTTTGAAGAGAGAAGTTACT
GGCAATCTCAAGTCAACCAGGATATTTGCAAATATGGATCCATCCCTCCTGATGTGG
AGGAGAAGTTACGGTTGGAATGGCCCTACCAGGAGCAATTGCTACTCCGAGAACAC
TACCAGAAAAAGTTCAAGAACAGCACCTACTCAAGAAGCTCTGTAGATGTGCTATA
CACTTTTGCAAACTGCTCAGGACTGGACTTGATCTTTGGCCTAAATGCGTTATTAAG
AACAGCAGATTTGCAGTGGAACAGTTCTAATGCTCAGTTGCTCCTGGACTACTGCTC
TTCCAAGGGGTATAACATTTCTTGGGAACTAGGCAATGAACCTAACAGTTTCCTTAA
GAAGGCTGATATTTTCATCAATGGGTCGCAGTTAGGAGAAGATTTTATTCAATTGCA
TAAACTTCTAAGAAAGTCCACCTTCAAAAATGCAAAACTCTATGGTCCTGATGTTGG
TCAGCCTCGAAGAAAGACGGCTAAGATGCTGAAGAGCTTCCTGAAGGCTGGTGGAG
AAGTGATTGATTCAGTTACATGGCATCACTACTATTTGAATGGACGGACTGCTACCA
AGGAAGATTTTCTAAACCCTGATGTATTGGACATTTTTATTTCATCTGTGCAAAAAGT -continued TTTCCAGGTGGTTGAGAGCACCAGGCCTGGCAAGAAGGTCTGGTTAGGAGAAACAA
GCTCTGCATATGGAGGCGGAGCGCCCTTGCTATCCGACACCTTTGCAGCTGGCTTTA
TGTGGCTGGATAAATTGGGCCTGTCAGCCCGAATGGGAATAGAAGTGGTGATGAGG
CAAGTATTCTTTGGAGCAGGAAACTACCATTTAGTGGATGAAAACTTCGATCCTTTA
CCTGATTATTGGCTATCTCTTCTGTTCAAGAAATTGGTGGGCACCAAGGTGTTAATG
GCAAGCGTGCAAGGTTCAAAGAGAAGGAAGCTTCGAGTATACCTTCATTGCACAAA
CACTGACAATCCAAGGTATAAAGAAGGAGATTTAACTCTGTATGCCATAAACCTCCA
TAATGTCACCAAGTACTTGCGGTTACCCTATCCTTTTTCTAACAAGCAAGTGGATAA
ATACCTTCTAAGACCTTTGGGACCTCATGGATTACTTTCCAAATCTGTCCAACTCAAT
GGTCTAACTCTAAAGATGGTGGATGATCAAACCTTGCCACCTTTAATGGAAAAACCT
CTCCGGCCAGGAAGTTCACTGGGCTTGCCAGCTTTCTCATATAGTTTTTTTGTGATAA
GAAATGCCAAAGTTGCTGCTTGCATCTAA SEQ ID NO: 192 amino acid sequence of CAR D0347 ROR1 scFv9 IgG4 CD8 BBz 2A HPSE
MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRMLLRSKPALPPPLMLLLLGPLGPLSPGALPRPAQAQDVVD
LDFFTQEPLHLVSPSFLSVTIDANLATDPRFLILLGSPKLRTLARGLSPAYLRFGGTKTDFL
IFDPKKESTFEERSYWQSQVNQDICKYGSIPPDVEEKLRLEWPYQEQLLLREHYQKKFK
NSTYSRSSVDVLYTFANCSGLDLIFGLNALLRTADLQWNSSNAQLLLDYCSSKGYNISW
ELGNEPNSFLKKADIFINGSQLGEDFIQLHKLLRKSTFKNAKLYGPDVGQPRRKTAKML
KSFLKAGGEVIDSVTWHHYYLNGRTATKEDFLNPDVLDIFISSVQKVFQVVESTRPGKK
VWLGETSSAYGGGAPLLSDTFAAGFMWLDKLGLSARMGIEVVMRQVFFGAGNYHLVD
ENFDPLPDYWLSLLFKKLVGTKVLMASVQGSKRRKLRVYLHCTNTDNPRYKEGDLTLY
AINLHNVTKYLRLPYPFSNKQVDKYLLRPLGPHGLLSKSVQLNGLTLKMVDDQTLPPL
MEKPLRPGSSLGLPAFSYSFFVIRNAKVAACI SEQ ID NO: 193 nucleotide sequence of CAR D0348 ROR1 scFv9 IgG4 CD8 BBz 2A MMP2
ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGCTGAGCAGGCTGAGATC
TGACGACACGGCCGTGTATTACTGTGCGAGTTATAATGATGCTTTTGATATCTGGGG
CCAAGGCACCCTGGTCACCGTCTCCTCAGGAGGTGGCGGGTCTGGTGGTGGCGGTA
GCGGTGGTGGCGGATCCAATTTTATGCTGACTCAGCCCCACTCTGTGTCGGAGTCTC
CGGGGAAGACGGTAACCATCTCCTGCACCCGCAGCAGTGGCAGCATTGCCAGCAAC
TATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCCCTGAGG
AGGAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAGAGA
GGAGTACGACGTGCTGGACAAGCGACGCGGACGCGACCCGGAGATGGGGGGGAAA
CCACGGCGGAAAAACCCTCAGGAAGGACTGTACAACGAACTCCAGAAAGACAAGA
TGGCGGAAGCCTACTCAGAAATCGGGATGAAGGGAGAGCGGAGGAGGGGAAAGGG
TCACGACGGGCTGTACCAGGGACTGAGCACCGCCACTAAGGATACCTACGATGCCT
TGCATATGCAAGCACTCCCACCCCGGCGGGCAAAGCGGGGCTCAGGGGCGACTAAC
TTTTCACTGTTGAAGCAGGCCGGGGATGTGGAGGAGAATCCTGGTCCTAGAGCaAAG
CGAATGGAAGCTCTTATGGCTAGGGGAGCGCTCACAGGTCCATTGCGGGCACTGTG
CCTGTTGGGGTGCCTGTTGTCTCATGCGGCTGCGGCTCCGTCACCAATTATCAAATTT
CCTGGCGACGTTGCCCCGAAGACAGACAAGGAACTTGCCGTGCAGTACCTCAATAC
GTTCTATGGATGTCCTAAAGAATCATGCAATCTGTTCGTTTTGAAAGATACCCTTAA
GAAGATGCAAAAGTTCTTTGGCTTGCCACAGACTGGGGACCTTGACCAGAATACaAT
TGAAACTATGAGAAAACCGAGATGCGGCAACCCCGATGTGGCTAACTACAACTTTTT
TCCCAGAAAGCCTAAATGGGATAAGAACCAGATTACATACCGGATAATAGGATATA
CACCCGACCTGGACCCGGAGACAGTTGACGACGCATTTGCGCGCGCCTTTCAGGTTT
GGTCAGATGTAACTCCGCTTCGCTTTTCaCGAATaCATGACGGAGAAGCTGACATCAT
GATTAATTTCGGTCGGTGGGAGCATGGGGATGGTTATCCTTTCGACGGCAAAGACGG
GCTGCTCGCCCATGCCTTTGCGCCTGGGACCGGCGTCGGTGGTGATAGCCACTTCGA
TGACGATGAACTCTGGACCCTCGGAGAGGGACAAGTGGTGAGAGTAAAATACGGAA
ACGCCGACGGAGAATATTGCAAGTTCCCCTTTCTaTTCAATGGTAAGGAATATAATA
GCTGTACTGATACAGGTAGATCAGACGGCTTCCTTTGGTGCTCAACCACCTACAATT
TCGAAAAAGATGGTAAGTACGGCTTCTGCCCTCATGAGGCCCTGTTCACTATGGGAG
GCAATGCAGAGGGACAGCCGTGCAAATTTCCATTTCGCTTTCAAGGTACGAGCTACG
ATTCTTGTACGACGGAGGGGAGAACGGATGGGTATAGATGGTGTGGCACAACAGAG
GATTACGATAGAGACAAGAAATATGGGTTCTGTCCCGAGACCGCTATGAGTACAGT
TGGGGGTAATTCCGAGGGAGCTCCCTGCGTGTTCCCGTTCACATTCTTGGGTAACAA
GTACGAGTCCTGTACCAGCGCTGGGCGGTCTGATGGTAAAATGTGGTGTGCAACGA
CGGCAAATTACGACGACGATCGGAAGTGGGGTTTTTGTCCTGACCAGGGTTACTCTC -continued TGTTTCTCGTTGCAGCGCATGAATTtGGACAcGCAATGGGTCTTGAGCACTCACAGGA
CCCCGGCGCACTTATGGCGCCAATATACACTTACACCAAGAACTTTAGATTGAGTCA
GGACGATATTAAGGGCATCCAGGAGCTTTATGGAGCCTCACCAGACATCGATCTGG
GGACTGGTCCCACTCCCACTCTTGGTCCTGTCACACCAGAAATTTGTAAACAGGATA
TAGTCTTTGATGGTATAGCCCAGATTCGCGGAGAGATCTTTTTCTTTAAGGACAGGT
TCATCTGGAGGACAGTGACGCCAAGAGATAAACCCATGGGTCCTCTGTTGGTAGCA
ACCTTCTGGCCCGAGCTCCCAGAGAAGATAGATGCAGTGTATGAGGCCCCACAAGA
GGAGAAAGCGGTCTTTTTCGCGGGGAATGAGTATTGGATCTACTCAGCCTCCACTCT
GGAAAGAGGGTACCCAAAACCACTGACTTCTCTGGGTTTGCCCCCAGATGTACAGC
GAGTAGATGCTGCATTTAATTGGAGCAAGAATAAGAAGACCTACATTTTCGCGGGG
GATAAGTTCTGGAGGTACAATGAAGTCAAGAAGAAAATGGATCCCGGATTTCCAAA
GCTCATAGCCGACGCATGGAATGCCATCCCGGACAACCTGGATGCCGTCGTAGACTT
GCAGGGTGGGGGACACTCCTATTTTTTCAAAGGAGCGTATTATTTGAAATTGGAGAA
TCAAAGTCTTAAGTCAGTTAAGTTTGGATCAATCAAGAGCGACTGGCTCGGGTGTTA
G SEQ ID NO: 194 amino acid sequence of CAR D0348 ROR1 scFv9 IgG4 CD8 BBz 2A MMP2
MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRMEALMARGALTGPLRALCLLGCLLSHAAAAPSPIIKFPGD
VAPKTDKELAVQYLNTFYGCPKESCNLFVLKDTLKKMQKFFGLPQTGDLDQNTIETMR
KPRCGNPDVANYNFFPRKPKWDKNQITYRIIGYTPDLDPETVDDAFARAFQVWSDVTPL
RFSRIHDGEADIMINFGRWEHGDGYPFDGKDGLLAHAFAPGTGVGGDSHFDDDELWTL
GEGQVVRVKYGNADGEYCKFPFLFNGKEYNSCTDTGRSDGFLWCSTTYNFEKDGKYG
FCPHEALFTMGGNAEGQPCKFPFRFQGTSYDSCTTEGRTDGYRWCGTTEDYDRDKKYG
FCPETAMSTVGGNSEGAPCVFPFTFLGNKYESCTSAGRSDGKMWCATTANYDDDRKW
GFCPDQGYSLFLVAAHEFGHAMGLEHSQDPGALMAPIYTYTKNFRLSQDDIKGIQELYG
ASPDIDLGTGPTPTLGPVTPEICKQDIVFDGIAQIRGEIFFFKDRFIWRTVTPRDKPMGPLL
VATFWPELPEKIDAVYEAPQEEKAVFFAGNEYWIYSASTLERGYPKPLTSLGLPPDVQR
VDAAFNWSKNKKTYIFAGDKFWRYNEVKKKMDPGFPKLIADAWNAIPDNLDAVVDLQ
GGGHSYFFKGAYYLKLENQSLKSVKFGSIKSDWLGC SEQ ID NO: 195 nucleotide sequence of CAR D0349 ROR1 scFv9 IgG4 CD8 BBz 2A SP PH20 IgG1 Fc
ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGCTGAGCAGGCTGAGATC
TGACGACACGGCCGTGTATTACTGTGCGAGTTATAATGATGCTTTTGATATCTGGGG
CCAAGGCACCCTGGTCACCGTCTCCTCAGGAGGTGGGGGTCTGGTGGTGGCGGTA
GCGGTGGTGGCGGATCCAATTTTATGCTGACTCAGCCCCACTCTGTGTCGGAGTCTC
CGGGGAAGACGGTAACCATCTCCTGCACCCGCAGCAGTGGCAGCATTGCCAGCAAC
TATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCCCTGAGG
AGGAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAGAGA
GGAGTACGACGTGCTGGACAAGCGACGCGGACGCGACCCGGAGATGGGGGGGAAA
CCACGGCGGAAAAACCCTCAGGAAGGACTGTACAACGAACTCCAGAAAGACAAGA
TGGCGGAAGCCTACTCAGAAATCGGGATGAAGGGAGAGCGGAGGAGGGGAAAGGG
TCACGACGGGCTGTACCAGGGACTGAGCACCGCCACTAAGGATACCTACGATGCCT
TGCATATGCAAGCACTCCCACCCCGGCGGGCAAAGCGGGGCTCAGGGGCGACTAAC
TTTTCACTGTTGAAGCAGGCCGGGGATGTGGAGGAGAATCCTGGTCCTAGAGCAAA
GCGAATGGATGCAATGAAGAGAGGGCTCTGCTGTGTGCTGCTGCTGTGTGGAGCAG
TCTTCGTTTCGCCCAGCCTGAACTTTCGCGCCCCACCAGTGATCCCTAATGTGCCATT
CCTTTGGGCTTGGAATGCGCCTTCTGAATTCTGCTTGGGAAAATTTGATGAGCCTCTG
GATATGTCTCTTTTCAGTTTTATTGGGTCACCAAGGATTAACGCGACTGGACAAGGA
GTGACGATATTTTATGTCGATAGGCTCGGCTACTACCCCTACATAGATTCCATTACC
GGCGTAACCGTGAATGGTGGTATCCCTCAAAAGATCTCTCTTCAAGACCACTTGGAC
AAAGCAAAAAAAGACATTACATTCTACATGCCGGTGGATAACCTGGGGATGGCCGT
TATCGATTGGGAGGAGTGGAGACCCACGTGGGCTAGAAACTGGAAGCCGAAGGACG
TCTATAAAAACAGGTCTATCGAATTGGTTCAGCAGCAGAACGTGCAATTGTCCTTGA
CTGAGGCGACAGAGAAGGCCAAGCAAGAGTTTGAGAAGGCGGGAAAGGACTTTTTG
GTTGAGACCATTAAGCTCGGTAAACTGCTGCGACCTAATCATCTGTGGGGTTACTAC
CTCTTCCCTGACTGCTACAATCACCATTACAAGAAACCGGGCTACAATGGCTCTTGT
TTTAATGTCGAAATCAAACGAAACGACGACCTGAGCTGGCTTTGGAACGAATCCAC
CGCACTCTACCCCAGCATCTATCTGAACACCCAGCAGAGTCCTGTAGCAGCAACGCT
GTACGTCCGGAACCGGGTACGAGAGGCAATCAGAGTATCTAAGATCCCGGATGCTA -continued AATCCCCACTGCCGGTATTTGCGTACACCCGAATCGTGTTCACTGACCAGGTTCTGA
AGTTTCTCTCCCAGGACGAACTTGTCTATACGTTTGGAGAGACAGTAGCACTCGGCG
CATCAGGCATTGTTATATGGGGAACCCTTAGCATCATGCGGTCAATGAAGTCCTGCT
TGCTTCTTGATAACTATATGGAGACAATCTTGAACCCCTATATCATCAATGTAACAC
TTGCAGCAAAAATGTGCTCCCAAGTACTCTGTCAAGAGCAGGGAGTATGCATACGA
AAAAATTGGAACAGTTCCGACTACCTGCACCTTAACCCCGATAATTTTGCTATACAG
CTTGAAAAGGGCGGAAAATTTACAGTCCGAGGGAAGCCGACATTGGAGGATCTCGA
GCAATTCTCTGAAAAGTTTTATTGCTCATGCTACAGTACCCTTAGCTGTAAAGAAAA
GGCGGACGTCAAGGATACTGACGCCGTGGACGTCTGCATCGCCGACGGAGTTTGCA
TCGACGCATTTCTTAAACCTCCCATGGAAACCGAAGAGCCACAAATCTTCTATAACG
CTTCTCCCTCAACACTTAGTGCTACTATGTTTATAGTTTCTATTTTGTTCCTTATTATT
TCAAGTGTAGCTAGTCTTGCTAGCGACAAAACTCACACATGCCCACCGTGCCCAGCA
CCTGAAGCTGCGGGGGGACCGTCAGTCTTCCTCTTCCCCCCAAAACCCAAGGACACC
CTCATGATCTCCCGGACCCCTGAGGTCACATGCGTGGTGGTGGACGTGAGCCACGA
AGACCCTGAGGTCAAGTTCAACTGGTACGTGGACGGCGTGGAGGTGCATAATGCCA
AGACAAAGCCGCGGGAGGAGCAGTACAACAGCACGTACCGTGTGGTCAGCGTCCTC
ACCGTCCTGCACCAGGACTGGCTGAATGGCAAGGAGTACAAGTGCAAGGTCTCCAA
CAAGGCACTTGGGGCCCCTATCGAGAAAACCATCTCCAAAGCCAAAGGGCAGCCCC
GAGAACCACAGGTGTACACCCTGCCCCCATCTCGGGAGGAGATGACCAAGAACCAG
GTCAGCCTGACCTGCCTGGTCAAAGGCTTCTATCCCAGCGACATCGCCGTGGAGTGG
GAGAGCAATGGGCAGCCGGAGAACAACTACAAGACCACGCCTCCCGTGCTGGACTC
CGACGGCTCCTTCTTCCTCTACAGCAAGCTCACCGTGGACAAGAGCAGGTGGCAGC
AGGGGAACGTCTTCTCATGCTCCGTGATGCACGAGGCTCTGCACAACCACTACACGC
AGAAGAGCCTCTCCCTGTCTCCGGGTAAATAA SEQ ID NO: 196 amino acid sequence of CAR D0349 ROR1 scFv9 IgG4 CD8 BBz 2A SP PH20 IgG1 Fc MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRMDAMKRGLCCVLLLCGAVFVSPSLNFRAPPVIPNVPFLW
AWNAPSEFCLGKFDEPLDMSLFSFIGSPRINATGQGVTIFYVDRLGYYPYIDSITGVTVNG
GIPQKISLQDHLDKAKKDITFYMPVDNLGMAVIDWEEWRPTWARNWKPKDVYKNRSIE
LVQQQNVQLSLTEATEKAKQEFEKAGKDFLVETIKLGKLLRPNHLWGYYLFPDCYNHH
YKKPGYNGSCFNVEIKRNDDLSWLWNESTALYPSIYLNTQQSPVAATLYVRNRVREAIR
VSKIPDAKSPLPVFAYTRIVFTDQVLKFLSQDELVYTFGETVALGASGIVIWGTLSIMRSM
KSCLLLDNYMETILNPYIINVTLAAKMCSQVLCQEQGVCIRKNWNSSDYLHLNPDNFAI
QLEKGGKFTVRGKPTLEDLEQFSEKFYCSCYSTLSCKEKADVKDTDAVDVCIADGVCID
AFLKPPMETEEPQIFYNASPSTLSATMFIVSILFLIISSVASLASDKTHTCPPCPAPEAAGGP
SVFLFPPKPKDTLMISRTPEVTCVVVDVSHEDPEVKFNWYVDGVEVHNAKTKPREEQY
NSTYRVVSVLTVLHQDWLNGKEYKCKVSNKALGAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPGK SEQ ID NO: 197 nucleotide sequence of CAR D0358 MSLN ROR1 scFv9 IgG4 CD28 TM CD28 BB2

ATGCTGTTACTTGTGACAAGCTTGCTTCTATGTGAACTGCCGCATCCGGCGTTTCTGC
TGATTCCGGAAGTACAGCTGGTACAGTCTGGAGGGGGATTGGTTCAGCCGGGCGGG
TCTTTGCGCCTGTCCTGCGCAGCTAGTGGCTTCACTTTTGATGACTATGCTATGCACT
GGGTCAGACAAGCGCCTGGCAAAGGCCTTGAATGGGTGTCCGGAATTAGCTGGAAT
AGTGGATCCATCGGCTATGCCGATAGTGTAAAGGGCAGGTTCACGATCAGCCGGGA
TAATGCAAAGAACTCTCTCTATTTGCAAATGAACAGTCTGCGGGCTGAAGATACTGC
TCTTTACTATTGTGCTAAAGATTTGTCAAGCGTCGCCGGACCCTTCAACTACTGGGGT
CAAGGGACACTGGTGACAGTTAGCAGCGGTGGTGGAGGCTCCGGTGGAGGTGGTAG
TGGTGGAGGAGGTAGTTCTTCTGAGCTTACGCAAGATCCGGCGGTTAGTGTTGCTCT
GGGGCAGACTGTACGAATCACGTGCCAGGGTGACTCTTTGCGCTCTTACTACGCTAG
TTGGTATCAACAAAAACCCGGACAAGCGCCCGTCCTCGTCATCTATGGCAAGAACA
ATCGCCCAAGCGGCATCCCTGATAGGTTCTCCGGATCATCTTCAGGGAACACAGCCT
CCCTGACTATTACAGGTGCTCAAGCTGAGGACGAGGCTGACTATTATTGCAACAGCC
GGGACTCTAGCGGTAACCACTTGGTCTTTGGTGGGGGTACCCAGCTGACGGTACTTG
GAGGTGGTGGAGGTTCAGGTGGTGGCGGATCAGGTGGAGGTGGTTCTGGAGGGGGT
GGAAGTGGCGGAGGTGGTTCACAGGCGGCCCAGGTACAGCTGCAGCAGTCAGGGGC
TGAGGTGAAGAAGCCTGGGTCCTCGGTGAAGGTCTCCTGCAAGGCTTCTGGAGGCA
CCTTCAGCAGCTATGCTATCAGCTGGGTGCGACAGGCCCCTGGACAAGGGCTTGAGT
GGATGGGATGGATCAACCCTAACAGTGGTGGCACAAACTATGCACAGAGGTTTCAG
GGCAGGGTCACCATGACCAGGGACACGTCCATCAGCACAGCCTACATGGAGTTGAG
CAGGCTGAGATCTGACGACACGGCCGTGTATTACTGTGCGAGTTATAATGATGCTTT
TGATATCTGGGGCCAAGGCACCCTGGTCACCGTCTCCTCAGGAGGTGGCGGGTCTGG
TGGTGGCGGTAGCGGTGGTGGCGGATCCAATTTTATGCTGACTCAGCCCCACTCTGT
GTCGGAGTCTCCGGGGAAGACGGTAACCATCTCCTGCACCCGCAGCAGTGGCAGCA
TTGCCAGCAACTATGTGCAGTGGTACCAGCAGCGCCCGGGCAGTGCCCCCACCATTG
TGATCTATGAGGATGATCAAAGACCCTCTGGGGTCCCTGATCGGTTCTCTGGCTCCA
TCGACACCTCCTCCAACTCTGCCTCCCTCACCATCTCTGGACTGCAGAGTGAGGACG
AGGCTGACTACTACTGTCAGTCTTATGAGCCCGGCAATGGGGTATTCGGCGGAGGG
ACCAAGGTCACCGTCCTAGCGGCCGCAGAGTCAAAATACGGTCCTCCGTGCCCTCCG
TGTCCGTTCTGGGTGCTTGTCGTTGTTGGGGGTGTACTCGCATGTTATTCTTTGCTGG

-continued

TGACTGTGGCGTTTATCATCTTCTGGGTAAGGAGTAAACGCAGCCGCCTGCTGCATT
CAGACTACATGAACATGACCCCACGGCGGCCCGGCCCAACGCGCAAACACTACCAA
CCTTACGCCCCACCGCGAGACTTTGCCGCCTACAGATCCAAGCGCGGACGGAAGAA
ACTCTTGTACATCTTCAAGCAGCCGTTCATGCGCCCTGTGCAAACCACCCAAGAAGA
GGACGGGTGCTCCTGCCGGTTCCCGGAAGAGGAAGAGGGCGGCTGCGAACTGCGCG
TGAAGTTTTCCCGGTCCGCCGACGCTCCGGCGTACCAGCAGGGGCAAAACCAGCTG
TACAACGAACTTAACCTCGGTCGCCGGGAAGAATATGACGTGCTGGACAAGCGGCG
GGGAAGAGATCCCGAGATGGGTGGAAAGCCGCGGCGGAAGAACCCTCAGGAGGGC
TTGTACAACGAGCTGCAAAAGGACAAAATGGCCGAAGCCTACTCCGAGATTGGCAT
GAAGGGAGAGCGCAGACGCGGGAAGGGACACGATGGACTGTACCAGGGACTGTCA
ACCGCGACTAAGGACACTTACGACGCCCTGCACATGCAGGCCCTGCCCCCGCGCTA
A

SEQ ID NO: 198 amino acid sequence of CAR D0358 MSLN ROR1 scFv9 IgG4 CD28 TM CD28 BBZ
MLLLVTSLLLCELPHPAFLLIPEVQLVQSGGGLVQPGGSLRLSCAASGFTFDDYAMHWV
RQAPGKGLEWVSGISWNSGSIGYADSVKGRFTISRDNAKNSLYLQMNSLRAEDTALYY
CAKDLSSVAGPFNYWGQGTLVTVSSGGGGSGGGGSGGGGSSSELTQDPAVSVALGQTV
RITCQGDSLRSYYASWYQQKPGQAPVLVIYGKNNRPSGIPDRFSGSSSGNTASLTITGAQ
AEDEADYYCNSRDSSGNHLVFGGGTQLTVLGGGGGSGGGGSGGGGSGGGGSGGGGSQ
AAQVQLQQSGAEVKKPGSSVKVSCKASGGTFSSYAISWVRQAPGQGLEWMGWINPNS
GGTNYAQRFQGRVTMTRDTSISTAYMELSRLRSDDTAVYYCASYNDAFDIWGQGTLVT
VSSGGGGSGGGGSGGGGSNFMLTQPHSVSESPGKTVTISCTRSSGSIASNYVQWYQQRP
GSAPTIVIYEDDQRPSGVPDRFSGSIDTSSNSASLTISGLQSEDEADYYCQSYEPGNGVFG
GGTKVTVLAAAESKYGPPCPPCPFWVLVVVGGVLACYSLLVTVAFIIFWVRSKRSRLLH
SDYMNMTPRRPGPTRKHYQPYAPPRDFAAYRSKRGRKKLLYIFKQPFMRPVQTTQEED
GCSCRFPEEEEGGCELRVKFSRSADAPAYQQGQNQLYNELNLGRREEYDVLDKRRGRD
PEMGGKPRRKNPQEGLYNELQKDKMAEAYSEIGMKGERRRGKGHDGLYQGLSTATKD
TYDALHMQALPPR SEQ ID NO: 199 nucleotide sequence of EF1a Promoter
CGTGAGGCTCCGGTGCCCGTCAGTGGGCAGAGCGCACATCGCCCACAGTCCCCGAG
AAGTTGGGGGGAGGGGTCGGCAATTGAACCGGTGCCTAGAGAAGGTGGCGCGGGGT
AAACTGGGAAAGTGATGTCGTGTACTGGCTCCGCCTTTTTCCCGAGGGTGGGGGAGA
ACCGTATATAAGTGCAGTAGTCGCCGTGAACGTTCTTTTTCGCAACGGGTTTGCCGC
CAGAACACAGGTAAGTGCCGTGTGTGGTTCCCGCGGGCCTGGCCTCTTTACGGGTTA
TGGCCCTTGCGTGCCTTGAATTACTTCCACCTGGCTGCAGTACGTGATTCTTGATCCC
GAGCTTCGGGTTGGAAGTGGGTGGGAGAGTTCGAGGCCTTGCGCTTAAGGAGCCCC
TTCGCCTCGTGCTTGAGTTGAGGCCTGGCCTGGGCGCTGGGGCCGCCGCGTGCGAAT
CTGGTGGCACCTTCGCGCCTGTCTCGCTGCTTTCGATAAGTCTCTAGCCATTTAAAAT
TTTTGATGACCTGCTGCGACGCTTTTTTTCTGGCAAGATAGTCTTGTAAATGCGGGCC
AAGATCTGCACACTGGTATTTCGGTTTTTGGGGCCGCGGGCGGCGACGGGGCCCGTG
CGTCCCAGCGCACATGTTCGGCGAGGCGGGGCCTGCGAGCGCGGCCACCGAGAATC
GGACGGGGGTAGTCTCAAGCTGGCCGGCCTGCTCTGGTGCCTGGCCTCGCGCCGCCG
TGTATCGCCCCGCCCTGGGCGGCAAGGCTGGCCCGGTCGGCACCAGTTGCGTGAGC
GGAAAGATGGCCGCTTCCCGGCCCTGCTGCAGGGAGCTCAAAATGGAGGACGCGGC
GCTCGGGAGAGCGGGCGGGTGAGTCACCCACACAAAGGAAAAGGGCCTTTCCGTCC
TCAGCCGTCGCTTCATGTGACTCCACGGAGTACCGGGCGCCGTCCAGGCACCTCGAT
TAGTTCTCGAGCTTTTGGAGTACGTCGTCTTTAGGTTGGGGGGAGGGGTTTTATGCG
ATGGAGTTTCCCCACACTGAGTGGGTGGAGACTGAAGTTAGGCCAGCTTGGCACTTG
ATGTAATTCTCCTTGGAATTTGCCCTTTTTGAGTTTGGATCTTGGTTCATTCTCAAGC
CTCAGACAGTGGTTCAAAGTTTTTTTCTTCCATTTCAGGTGTCGTG SEQ ID NO: 200 nucleotide sequence of MND Promoter
AGTGGTCCAGGCTCTAGTTTTGACTCAACAATATCACCAGCTGAAGCCTATAGAGTA
CGAGCCATAGATAGAATAAAAGATTTTATTTAGTCTCCAGAAAAAGGGGGGAATGA
AAGACCCCACCTGTAGGTTTGGCAAGCTAGGATCAAGGTTAGGAACAGAGAGACAG
CAGAATATGGGCCAAACAGGATATCTGTGGTAAGCAGTTCCTGCCCCGGCTCAGGG
CCAAGAACAGTTGGAACAGCAGAATATGGGCCAAACAGGATATCTGTGGTAAGCAG
TTCCTGCCCCGGCTCAGGGCCAAGAACAGATGGTCCCCAGATGCGGTCCCGCCCTCA
GCAGTTTCTAGAGAACCATCAGATGTTTCCAGGGTGCCCCAAGGACCTGAAATGACC
CTGTGCCTTATTTGAACTAACCAATCAGTTCGCTTCTCGCTTCTGTTCGCGCGCTTCT
GCTCCCCGAGCTCAATAAAAGAGCCCACAACCCCTCACTCGGCG SEQ ID NO: 201 nucleotide sequence of MSCV Promoter
TGAAAGACCCCACCTGTAGGTTTGGCAAGCTAGCTTAAGTAACGCCATTTTGCAAGG
CATGGAAAATACATAACTGAGAATAGAGAAGTTCAGATCAAGGTTAGGAACAGAGA
GACAGCAGAATATGGGCCAAACAGGATATCTGTGGTAAGCAGTTCCTGCCCCGGCT
CAGGGCCAAGAACAGATGGTCCCCAGATGCGGTCCCGCCCTCAGCAGTTTCTAGAG
AACCATCAGATGTTTCCAGGGTGCCCCAAGGACCTGAAAATGACCCTGTGCCTTATT
TGAACTAACCAATCAGTTCGCTTCTCGCTTCTGTTCGCGCGTTTCTGCTCCCCGAGCT
CAATAAAAGAGCCCACAACCCCTCACT SEQ ID NO: 202 nucleotide sequence of PGK Promoter
TCCACGGGGTTGGGGTTGCGCCTTTTCCAAGGCAGCCCTGGGTTTGCGCAGGGACGC
GGCTGCTCTGGGCGTGGTTCCGGGAAACGCAGCGGCGCCGACCCTGGGTCTCGCAC
ATTCTTCACGTCCGTTCGCAGCGTCACCCGGATCTTCGCCGCTACCCTTGTGGGCCCC
CCGGCGACGCTTCCTGCTCCGCCCCTAAGTCGGGAAGGTTCCTTGCGGTTCGCGGCG
TGCCGGACGTGACAAACGGAAGCCGCACGTCTCACTAGTACCCTCGCAGACGGACA
GCGCCAGGGAGCAATGGCAGCGCGCCGACCGCGATGGGCTGTGGCCAATAGCGGCT
GCTCAGCGGGGCGCGCCGAGAGCAGCGGCCGGGAAGGGGCGGTGCGGGAGGCGGG -continued GTGTGGGGCGGTAGTGTGGGCCCTGTTCCTGCCCGCGCGGTGTTCCGCATTCTGCAA
GCCTCCGGAGCGCACGTCGGCAGTCGGCTCCCTCGTTGACCGAATCACCGACCTCTC
TCCCCG SEQ ID NO: 203 nucleotide sequence of NFAT Promoter
TGGAGGAAAAACTGTTTCATACAGAAGGCGTGGAGGAAAAACTGTTTCATACAGAA
GGCGTGGAGGAAAAACTGTTTCATACAGAAGGCGTGGAGGAAAAACTGTTTCATAC
AGAAGGCGTGGAGGAAAAACTGTTTCATACAGAAGGCGTGGAGGAAAAACTGTTTC
ATACAGAAGGCGTCTGCAGGAGACTCTAGAGGGTATATAATGGTTTAAACTTAAGC
TTGGTACCGGGCCCCCGAAG SEQ ID NO: 204 nucleotide sequence of AP1/NFKb Promoter
TGAGTCAGTGACTCAGTGAGTCAGTGACTCAGTGAGTCAGTGACTCAGCTCGAGGAT
CTCGCTAGCGGGAATTTCCGGGGACTTTCCGGGAATTTCCGGGGACTTTCCGGGAAT
TTCC SEQ ID NO 205: nucleotide sequence of NAP (Helicobacter pylori neutrophil-activating protein A)
ATGAAAACGTTTGAGATACTTAAACATCTCCAGGCCGACGCCATTGTCCTGTTCATG
AAGGTTCATAATTTTCATTGGAACGTGAAAGGAACTGATTTCTTTAATGTCCACAAA
GCCACCGAGGAAATTTATGAGGAGTTTGCGGATATGTTTGACGATTTGGCTGAACGA
ATAGTGCAGTTGGGTCATCATCCGTTGGTAACTCTGTCCGAGGCAATCAAGCTTACG
AGGGTGAAAGAGGAGACAAAGACATCATTCCACTCTAAGGACATTTTCAAAGAAAT
TTTGGAAGATTATAAATACCTGGAAAAGGAGTTCAAGGAGCTTTCCAACACGGCCG
AAAAGGAGGGAGACAAAGTTACAGTCACATATGCGGACGATCAACTGGCCAAGCTC
CAGAAGAGTATCTGGATGCTCCAAGCCCATTTGGCC SEQ ID NO 206: amino acid sequence of NAP
MKTFEILKHLQADAIVLFMKVHNFHWNVKGTDFFNVHKATEEIYEEFADMFDDLAERI
VQLGHHPLVTLSEAIKLTRVKEETKTSFHSKDIFKEILEDYKYLEKEFKELSNTAEKEGD
KVTVTYADDQLAKLQKSIWMLQAHLA SEQ ID NO 207: amino acid sequence of MMP-2
MEALMARGALTGPLRALCLLGCLLSHAAAAPSPIIKFPGDVAPKTDKELAVQYLNTFYG
CPKESCNLFVLKDTLKKMQKFFGLPQTGDLDQNTIETMRKPRCGNPDVANYNFFPRKP
KWDKNQITYRIIGYTPDLDPETVDDAFARAFQVWSDVTPLRFSRIHDGEADIMINFGRW
EHGDGYPFDGKDGLLAHAFAPGTGVGGDSHFDDDELWTLGEGQVVRVKYGNADGEY
CKFPFLFNGKEYNSCTDTGRSDGFLWCSTTYNFEKDGKYGFCPHEALFTMGGNAEGQP
CKFPFRFQGTSYDSCTTEGRTDGYRWCGTTEDYDRDKKYGFCPETAMSTVGGNSEGAP
CVFPFTFLGNKYESCTSAGRSDGKMWCATTANYDDDRKWGFCPDQGYSLFLVAAHEF
GHAMGLEHSQDPGALMAPIYTYTKNFRLSQDDIKGIQELYGASPDIDLGTGPTPTLGPVT
PEICKQDIVFDGIAQIRGEIFFFKDRFIWRTVTPRDKPMGPLLVATFWPELPEKIDAVYEA
PQEEKAVFFAGNEYWIYSASTLERGYPKPLTSLGLPPDVQRVDAAFNWSKNKKTYIFAG
DKFWRYNEVKKKMDPGFPKLIADAWNAIPDNLDAVVDLQGGGHSYFFKGAYYLKLEN
QSLKSVKFGSIKSDWLGC SEQ ID NO 208: nucleotide sequence of MMP-2
ATGGAAGCTCTTATGGCTAGGGGAGCGCTCACAGGTCCATTGCGGGCACTGTGCCTG
TTGGGGTGCCTGTTGTCTCATGCGGCTGCGGCTCCGTCACCAATTATCAAATTTCCTG
GCGACGTTGCCCCGAAGACAGACAAGGAACTTGCCGTGCAGTACCTCAATACGTTC
TATGGATGTCCTAAAGAATCATGCAATCTGTTCGTTTTGAAAGATACCCTTAAGAAG
ATGCAAAAGTTCTTTGGCTTGCCACAGACTGGGGACCTTGACCAGAATACaATTGAA
ACTATGAGAAAACCGAGATGCGGCAACCCCGATGTGGCTAACTACAACTTTTTTCCC
AGAAAGCCTAAATGGGATAAGAACCAGATTACATACCGGATAATAGGATATACACC
CGACCTGGACCCGGAGACAGTTGACGACGCATTTGCGCGCGCCTTTCAGGTTTGGTC
AGATGTAACTCCGCTTCGCTTTTCaCGAATaCATGACGGAGAAGCTGACATCATGATT
AATTTCGGTCGGTGGGAGCATGGGGATGGTTATCCTTTCGACGGCAAAGACGGGCT
GCTCGCCCATGCCTTTGCGCCTGGGACCGGCGTCGGTGGTGATAGCCACTTCGATGA
CGATGAACTCTGGACCCTCGGAGAGGGACAAGTGGTGAGAGTAAAATACGGAAACG
CCGACGGAGAATATTGCAAGTTCCCCTTTCTaTTCAATGGTAAGGAATATAATAGCT
GTACTGATACAGGTAGATCAGACGGCTTCCTTTGGTGCTCAACCACCTACAATTTCG
AAAAAGATGGTAAGTACGGCTTCTGCCCTCATGAGGCCCTGTTCACTATGGGAGGCA
ATGCAGAGGGACAGCCGTGCAAATTTCCATTTCGCTTTCAAGGTACGAGCTACGATT
CTTGTACGACGGAGGGGAGAACGGATGGGTATAGATGGTGTGGCACAACAGAGGAT
TACGATAGAGACAAGAAATATGGGTTCTGTCCCGAGACCGCTATGAGTACAGTTGG
GGGTAATTCCGAGGGAGCTCCCTGCGTGTTCCCGTTCACATTCTTGGGTAACAAGTA
CGAGTCCTGTACCAGCGCTGGGCGGTCTGATGGTAAAATGTGGTGTGCAACGACGG
CAAATTACGACGACGATCGGAAGTGGGGTTTTTGTCCTGACCAGGGTTACTCTCTGT
TTCTCGTTGCAGCGCATGAATTIGGACAcGCAATGGGTCTTGAGCACTCACAGGACCC
CGGCGCACTTATGGCGCCAATATACACTTACACCAAGAACTTTAGATTGAGTCAGGA
CGATATTAAGGGCATCCAGGAGCTTTATGGAGCCTCACCAGACATCGATCTGGGGA
CTGGTCCCACTCCCACTCTTGGTCCTGTCACACCAGAAATTTGTAAACAGGATATAG
TCTTTGATGGTATAGCCCAGATTCGCGGAGAGATCTTTTTCTTTAAGGACAGGTTCAT
CTGGAGGACAGTGACGCCAAGAGATAAACCCATGGGTCCTCTGTTGGTAGCAACCT
TCTGGCCCGAGCTCCCAGAGAAGATAGATGCAGTGTATGAGGCCCCACAAGAGGAG
AAAGCGGTCTTTTTCGCGGGGAATGAGTATTGGATCTACTCAGCCTCCACTCTGGAA
AGAGGGTACCCAAAACCACTGACTTCTCTGGGTTTGCCCCCAGATGTACAGCGAGTA -continued GATGCTGCATTTAATTGGAGCAAGAATAAGAAGACCTACATTTTCGCGGGGATAA
GTTCTGGAGGTACAATGAAGTCAAGAAGAAAATGGATCCCGGATTTCCAAAGCTCA
TAGCCGACGCATGGAATGCCATCCCGGACAACCTGGATGCCGTCGTAGACTTGCAG
GGTGGGGGACACTCCTATTTTTTCAAAGGAGCGTATTATTTGAAATTGGAGAATCAA
AGTCTTAAGTCAGTTAAGTTTGGATCAATCAAGAGCGACTGGCTCGGGTGT SEQ ID NO 209: amino acid sequence of MMP-9
MSLWQPLVLVLLVLGCCFAAPRQRQSTLVLFPGDLRTNLTDRQLAEEYLYRYGYTRVA
EMRGESKSLGPALLLLQKQLSLPETGELDSATLKAMRTPRCGVPDLGRFQTFEGDLKW
HHHNITYWIQNYSEDLPRAVIDDAFARAFALWSAVTPLTFTRVYSRDADIVIQFGVAEH
GDGYPFDGKDGLLAHAFPPGPGIQGDAHFDDDELWSLGKGVVVPTRFGNADGAACHFP
FIFEGRSYSACTTDGRSDGLPWCSTTANYDTDDRFGFCPSERLYTQDGNADGKPCQFPFI
FQGQSYSACTTDGRSDGYRWCATTANYDRDKLFGFCPTRADSTVMGGNSAGELCVFPF
TFLGKEYSTCTSEGRGDGRLWCATTSNFDSDKKWGFCPDQGYSLFLVAAHEFGHALGL
DHSSVPEALMYPMYRFTEGPPLHKDDVNGIRHLYGPRPEPEPRPPTTTTPQPTAPPTVCP
TGPPTVHPSERPTAGPTGPPSAGPTGPPTAGPSTATTVPLSPVDDACNVNIFDAIAEIGNQ
LYLFKDGKYWRFSEGRGSRPQGPFLIADKWPALPRKLDSVFEERLSKKLFFFSGRQVWV
YTGASVLGPRRLDKLGLGADVAQVTGALRSGRGKMLLFSGRRLWRFDVKAQMVDPRS
ASEVDRMFPGVPLDTHDVFQYREKAYFCQDRFYWRVSSRSELNQVDQVGYVTYDILQC
PED SEQ ID NO 210: nucleotide sequence of MMP-9
ATGAGCCTCTGGCAGCCCCTGGTCCTGGTGCTCCTGGTGCTGGGCTGCTGCTTTGCTG
CCCCCAGACAGCGCCAGTCCACCCTTGTGCTCTTCCCTGGAGACCTGAGAACCAATC
TCACCGACAGGCAGCTGGCAGAGGAATACCTGTACCGCTATGGTTACACTCGGGTG
GCAGAGATGCGTGGAGAGTCGAAATCTCTGGGGCCTGCGCTGCTGCTTCTCCAGAA
GCAACTGTCCCTGCCCGAGACCGGTGAGCTGGATAGCGCCACGCTGAAGGCCATGC
GAACCCCACGGTGCGGGGTCCCAGACCTGGGCAGATTCCAAACCTTTGAGGGCGAC
CTCAAGTGGCACCACCACAACATCACCTATTGGATCCAAAACTACTCGGAAGACTTG
CCGCGGGCGGTGATTGACGACGCCTTTGCCCGCGCCTTCGCACTGTGGAGCGCGGTG
ACGCCGCTCACCTTCACTCGCGTGTACAGCCGGGACGCAGACATCGTCATCCAGTTT
GGTGTCGCGGAGCACGGAGACGGGTATCCCTTCGACGGGAAGGACGGGCTCCTGGC
ACACGCCTTTCCTCCTGGCCCCGGCATTCAGGGAGACGCCCATTTCGACGATGACGA
GTTGTGGTCCCTGGGCAAGGGCGTCGTGGTTCCAACTCGGTTTGGAAACGCAGATGG
CGCGGCCTGCCACTTCCCCTTCATCTTCGAGGGCCGCTCCTACTCTGCCTGCACCACC
GATGGACGGTCCGACGGCTTGCCCTGGTGCAGTACCACGGCCAACTACGACACCGA
CGACCGGTTTGGCTTCTGCCCCAGCGAGAGACTCTACACCCAGGACGGCAATGCTG
ATGGGAAACCCTGCCAGTTTCCATTCATCTTCCAAGGCCAATCCTACTCCGCCTGCA
CCACGGACGGTCGCTCCGACGGGTACCGCTGGTGCGCCACCACCGCCAACTACGAC
CGGGACAAGCTCTTCGGCTTCTGCCCGACCCGAGCTGACTCGACGGTGATGGGGGG
CAACTCGGCGGGGGAGCTGTGCGTCTTCCCCTTCACTTTCCTGGGTAAGGAGTACTC
GACCTGTACCAGCGAGGGCCGCGGAGATGGGCGCCTCTGGTGCGCTACCACCTCGA
ACTTTGACAGCGACAAGAAGTGGGGCTTCTGCCCGGACCAAGGATACAGTTTGTTCC
TCGTGGCGGCGCATGAGTTCGGCCACGCGCTGGGCTTAGATCATTCCTCAGTGCCGG
AGGCGCTCATGTACCCTATGTACCGCTTCACTGAGGGGCCCCCCTTGCATAAGGACG
ACGTGAATGGCATCCGGCACCTCTATGGTCCTCGCCCTGAACCTGAGCCACGACCTC
CAACAACCACCACACCGCAGCCCACGGCTCCACCGACGGTCTGCCCCACCGGACCC
CCCACTGTCCACCCCTCAGAGCGCCCCACTGCTGGCCCAACAGGACCTCCCTCAGCT
GGCCCCACAGGTCCCCCAACTGCTGGCCCTTCTACGGCCACTACTGTGCCTTTGAGT
CCGGTGGACGATGCCTGCAACGTGAACATCTTCGACGCCATCGCGGAGATTGGGAA
CCAGCTGTATTTGTTCAAGGATGGGAAGTACTGGCGATTCTCTGAGGGCAGGGGGA
GCCGGCCGCAGGGCCCCTTCCTTATCGCCGACAAGTGGCCCGCGCTGCCCCGCAAGC
TGGACTCGGTCTTTGAGGAGCGGCTCTCCAAGAAGCTTTTCTTCTTCTCTGGTCGCCA
GGTGTGGGTGTACACAGGTGCGTCGGTGCTGGGACCGAGGCGTCTAGACAAGCTAG
GCCTGGGAGCAGACGTGGCCCAGGTGACCGGGGCCCTCCGGAGTGGCAGGGGGAA
GATGCTGCTGTTCAGCGGGCGGCGCCTCTGGAGGTTCGACGTGAAGGCGCAGATGG
TGGATCCCCGGAGCGCCAGCGAGGTGGACCGGATGTTCCCCGGGGTGCCTTTGGAC
ACGCACGACGTCTTCCAGTACCGAGAGAAAGCCTATTTCTGCCAGGACCGCTTCTAC
TGGCGCGTGAGTTCCCGGAGTGAGTTGAACCAGGTGGACCAAGTGGGCTACGTGAC
CTATGACATCCTGCAGTGCCCTGAGGAC SEQ ID NO 211: amino acid sequence of HPSE
MLLRSKPALPPPLMLLLLGPLGPLSPGALPRPAQAQDVVDLDFFTQEPLHLVSPSFLSVTI
DANLATDPRFLILLGSPKLRTLARGLSPAYLRFGGTKTDFLIFDPKKESTFEERSYWQSQ
VNQDICKYGSIPPDVEEKLRLEWPYQEQLLLREHYQKKFKNSTYSRSSVDVLYTFANCS
GLDLIFGLNALLRTADLQWNSSNAQLLLDYCSSKGYNISWELGNEPNSFLKKADIFINGS
QLGEDFIQLHKLLRKSTFKNAKLYGPDVGQPRRKTAKMLKSFLKAGGEVIDSVTWHHY
YLNGRTATKEDFLNPDVLDIFISSVQKVFQVVESTRPGKKVWLGETSSAYGGGAPLLSD
TFAAGFMWLDKLGLSARMGIEVVMRQVFFGAGNYHLVDENFDPLPDYWLSLLFKKLV
GTKVLMASVQGSKRRKLRVYLHCTNTDNPRYKEGDLTLYAINLHNVTKYLRLPYPFSN
KQVDKYLLRPLGPHGLLSKSVQLNGLTLKMVDDQTLPPLMEKPLRPGSSLGLPAFSYSF
FVIRNAKVAACI SEQ ID NO 212: nucleotide sequence of HPSE
ATGCTTCTACGTTCTAAACCTGCACTTCCTCCACCACTTATGCTACTTCTTCTAGGAC
CTCTTGGTCCTCTATCACCTGGAGCTCTACCTCGACCTGCACAAGCACAGGACGTCG
TGGACCTGGACTTCTTCACCCAGGAGCCGCTGCACCTGGTGAGCCCCTCGTTCCTGT
CCGTCACCATTGACGCCAACCTGGCCACGGACCCGCGGTTCCTCATCCTCCTGGGTT
CTCCAAAGCTTCGTACCTTGGCCAGAGGCTTGTCTCCTGCGTACCTGAGGTTTGGTG
GCACCAAGACAGACTTCCTAATTTTCGATCCCAAGAAGGAATCAACCTTTGAAGAG
AGAAGTTACTGGCAATCTCAAGTCAACCAGGATATTTGCAAATATGGATCCATCCCT -continued CCTGATGTGGAGGAGAAGTTACGGTTGGAATGGCCCTACCAGGAGCAATTGCTACT
CCGAGAACACTACCAGAAAAAGTTCAAGAACAGCACCTACTCAAGAAGCTCTGTAG
ATGTGCTATACACTTTTGCAAACTGCTCAGGACTGGACTTGATCTTTGGCCTAAATG
CGTTATTAAGAACAGCAGATTTGCAGTGGAACAGTTCTAATGCTCAGTTGCTCCTGG
ACTACTGCTCTTCCAAGGGGTATAACATTTCTTGGGAACTAGGCAATGAACCTAACA
GTTTCCTTAAGAAGGCTGATATTTTCATCAATGGGTCGCAGTTAGGAGAAGATTTTA
TTCAATTGCATAAACTTCTAAGAAAGTCCACCTTCAAAAATGCAAAACTCTATGGTC
CTGATGTTGGTCAGCCTCGAAGAAAGACGGCTAAGATGCTGAAGAGCTTCCTGAAG
GCTGGTGGAGAAGTGATTGATTCAGTTACATGGCATCACTACTATTTGAATGGACGG
ACTGCTACCAAGGAAGATTTTCTAAACCCTGATGTATTGGACATTTTTATTTCATCTG
TGCAAAAAGTTTTCCAGGTGGTTGAGAGCACCAGGCCTGGCAAGAAGGTCTGGTTA
GGAGAAACAAGCTCTGCATATGGAGGCGGAGCGCCCTTGCTATCCGACACCTTTGC
AGCTGGCTTTATGTGGCTGGATAAATTGGGCCTGTCAGCCCGAATGGGAATAGAAGT
GGTGATGAGGCAAGTATTCTTTGGAGCAGGAAACTACCATTTAGTGGATGAAAACTT
CGATCCTTTACCTGATTATTGGCTATCTCTTCTGTTCAAGAAATTGGTGGGCACCAAG
GTGTTAATGGCAAGCGTGCAAGGTTCAAAGAGAAGGAAGCTTCGAGTATACCTTCA
TTGCACAAACACTGACAATCCAAGGTATAAAGAAGGAGATTTAACTCTGTATGCCAT
AAACCTCCATAATGTCACCAAGTACTTGCGGTTACCCTATCCTTTTTCTAACAAGCA
AGTGGATAAATACCTTCTAAGACCTTTGGGACCTCATGGATTACTTTCCAAATCTGT
CCAACTCAATGGTCTAACTCTAAAGATGGTGGATGATCAAACCTTGCCACCTTTAAT
GGAAAAACCTCTCCGGCCAGGAAGTTCACTGGGCTTGCCAGCTTTCTCATATAGTTT
TTTTGTGATAAGAAATGCCAAAGTTGCTGCTTGCATC SEQ ID NO 213: amino acid sequence of tPA-SP PH-20 GPI
MDAMKRGLCCVLLLCGAVFVSPSLNFRAPPVIPNVPFLWAWNAPSEFCLGKFDEPLDM
SLFSFIGSPRINATGQGVTIFYVDRLGYYPYIDSITGVTVNGGIPQKISLQDHLDKAKKDIT
FYMPVDNLGMAVIDWEEWRPTWARNWKPKDVYKNRSIELVQQQNVQLSLTEATEKA
KQEFEKAGKDFLVETIKLGKLLRPNHLWGYYLFPDCYNHHYKKPGYNGSCENVEIKRN
DDLSWLWNESTALYPSIYLNTQQSPVAATLYVRNRVREAIRVSKIPDAKSPLPVFAYTRI
VFTDQVLKFLSQDELVYTFGETVALGASGIVIWGTLSIMRSMKSCLLLDNYMETILNPYII
NVTLAAKMCSQVLCQEQGVCIRKNWNSSDYLHLNPDNFAIQLEKGGKFTVRGKPTLED
LEQFSEKFYCSCYSTLSCKEKADVKDTDAVDVCIADGVCIDAFLKPPMETEEPQIFYNAS
PSTLSATMFIVSILFLIISSVASL SEQ ID NO 214: nucleotide sequence of tPA-SP PH-20 GPI
ATGGATGCAATGAAGAGAGGGCTCTGCTGTGTGCTGCTGCTGTGTGGAGCAGTCTTC
GTTTCGCCCAGCCTGAACTTTCGCGCCCCACCAGTGATCCCTAATGTGCCATTCCTTT
GGGCTTGGAATGCGCCTTCTGAATTCTGCTTGGGAAAATTTGATGAGCCTCTGGATA
TGTCTCTTTTCAGTTTTATTGGGTCACCAAGGATTAACGCGACTGGACAAGGAGTGA
CGATATTTTATGTCGATAGGCTCGGCTACTACCCCTACATAGATTCCATTACCGGCGT
AACCGTGAATGGTGGTATCCCTCAAAAGATCTCTCTTCAAGACCACTTGGACAAAGC
AAAAAAAGACATTACATTCTACATGCCGGTGGATAACCTGGGGATGGCCGTTATCG
ATTGGGAGGAGTGGAGACCCACGTGGGCTAGAAACTGGAAGCCGAAGGACGTCTAT
AAAAACAGGTCTATCGAATTGGTTCAGCAGCAGAACGTGCAATTGTCCTTGACTGAG
GCGACAGAGAAGGCCAAGCAAGAGTTTGAGAAGGCGGGAAAGGACTTTTTGGTTGA
GACCATTAAGCTCGGTAAACTGCTGCGACCTAATCATCTGTGGGGTTACTACCTCTT
CCCTGACTGCTACAATCACCATTACAAGAAACCGGGCTACAATGGCTCTTGTTTTAA
TGTCGAAATCAAACGAAACGACGACCTGAGCTGGCTTTGGAACGAATCCACCGCAC
TCTACCCCAGCATCTATCTGAACACCCAGCAGAGTCCTGTAGCAGCAACGCTGTACG
TCCGGAACCGGGTACGAGAGGCAATCAGAGTATCTAAGATCCCGGATGCTAAATCC
CCACTGCCGGTATTTGCGTACACCCGAATCGTGTTCACTGACCAGGTTCTGAAGTTT
CTCTCCCAGGACGAACTTGTCTATACGTTTGGAGAGACAGTAGCACTCGGCGCATCA
GGCATTGTTATATGGGGAACCCTTAGCATCATGCGGTCAATGAAGTCCTGCTTGCTT
CTTGATAACTATATGGAGACAATCTTGAACCCCTATATCATCAATGTAACACTTGCA
GCAAAAATGTGCTCCCAAGTACTCTGTCAAGAGCAGGGAGTATGCATACGAAAAAA
TTGGAACAGTTCCGACTACCTGCACCTTAACCCCGATAATTTTGCTATACAGCTTGA
AAAGGGCGGAAAATTTACAGTCCGAGGGAAGCCGACATTGGAGGATCTCGAGCAAT
TCTCTGAAAAGTTTTATTGCTCATGCTACAGTACCCTTAGCTGTAAAGAAAAGGCGG
ACGTCAAGGATACTGACGCCGTGGACGTCTGCATCGCCGACGGAGTTTGCATCGAC
GCATTTCTTAAACCTCCCATGGAAACCGAAGAGCCACAAATCTTCTATAACGCTTCT
CCCTCAACACTTAGTGCTACTATGTTTATAGTTTCTATTTTGTTCCTTATTATTTCAAG
TGTAGCTAGTCTT SEQ ID NO 215: amino acid sequence of tPA-SP PH-20 7 A.A. of GPI
MDAMKRGLCCVLLLCGAVFVSPSLNFRAPPVIPNVPFLWAWNAPSEFCLGKFDEPLDM
SLFSFIGSPRINATGQGVTIFYVDRLGYYPYIDSITGVTVNGGIPQKISLQDHLDKAKKDIT
FYMPVDNLGMAVIDWEEWRPTWARNWKPKDVYKNRSIELVQQQNVQLSLTEATEKA
KQEFEKAGKDFLVETIKLGKLLRPNHLWGYYLFPDCYNHHYKKPGYNGSCFNVEIKRN
DDLSWLWNESTALYPSIYLNTQQSPVAATLYVRNRVREAIRVSKIPDAKSPLPVFAYTRI
VFTDQVLKFLSQDELVYTFGETVALGASGIVIWGTLSIMRSMKSCLLLDNYMETILNPYII
NVTLAAKMCSQVLCQEQGVCIRKNWNSSDYLHLNPDNFAIQLEKGGKFTVRGKPTLED
LEQFSEKFYCSCYSTLSCKEKADVKDTDAVDVCIADGVCIDAFLKPPMETEEPQIFYNAS
PSTLS SEQ ID NO 216: nucleotide sequence of tPA-SP PH-20 7 A.A. of GPI
ATGGATGCAATGAAGAGAGGGCTCTGCTGTGTGCTGCTGCTGTGTGGAGCAGTCTTC
GTTTCGCCCAGCCTGAACTTTCGCGCCCCACCAGTGATCCCTAATGTGCCATTCCTTT
GGGCTTGGAATGCGCCTTCTGAATTCTGCTTGGGAAAATTTGATGAGCCTCTGGATA
TGTCTCTTTTCAGTTTTATTGGGTCACCAAGGATTAACGCGACTGGACAAGGAGTGA
CGATATTTTATGTCGATAGGCTCGGCTACTACCCCTACATAGATTCCATTACCGGCGT
AACCGTGAATGGTGGTATCCCTCAAAAGATCTCTCTTCAAGACCACTTGGACAAAGC -continued
AAAAAAAGACATTACATTCTACATGCCGGTGGATAACCTGGGGATGGCCGTTATCG
ATTGGGAGGAGTGGAGACCCACGTGGGCTAGAAACTGGAAGCCGAAGGACGTCTAT
AAAAACAGGTCTATCGAATTGGTTCAGCAGCAGAACGTGCAATTGTCCTTGACTGAG
GCGACAGAGAAGGCCAAGCAAGAGTTTGAGAAGGCGGGAAAGGACTTTTTGGTTGA
GACCATTAAGCTCGGTAAACTGCTGCGACCTAATCATCTGTGGGGTTACTACCTCTT
CCCTGACTGCTACAATCACCATTACAAGAAACCGGGCTACAATGGCTCTTGTTTTAA
TGTCGAAATCAAACGAAACGACGACCTGAGCTGGCTTTGGAACGAATCCACCGCAC
TCTACCCCAGCATCTATCTGAACACCCAGCAGAGTCCTGTAGCAGCAACGCTGTACG
TCCGGAACCGGGTACGAGAGGCAATCAGAGTATCTAAGATCCCGGATGCTAAATCC
CCACTGCCGGTATTTGCGTACACCCGAATCGTGTTCACTGACCAGGTTCTGAAGTTT
CTCTCCCAGGACGAACTTGTCTATACGTTTGGAGAGACAGTAGCACTCGGCGCATCA
GGCATTGTTATATGGGGAACCCTTAGCATCATGCGGTCAATGAAGTCCTGCTTGCTT
CTTGATAACTATATGGAGACAATCTTGAACCCCTATATCATCAATGTAACACTTGCA
GCAAAAATGTGCTCCCAAGTACTCTGTCAAGAGCAGGGAGTATGCATACGAAAAAA
TTGGAACAGTTCCGACTACCTGCACCTTAACCCCGATAATTTTGCTATACAGCTTGA
AAAGGGCGGAAAATTTACAGTCCGAGGGAAGCCGACATTGGAGGATCTCGAGCAAT
TCTCTGAAAAGTTTTATTGCTCATGCTACAGTACCCTTAGCTGTAAAGAAAAGGCGG
ACGTCAAGGATACTGACGCCGTGGACGTCTGCATCGCCGACGGAGTTTGCATCGAC
GCATTTCTTAAACCTCCCATGGAAACCGAAGAGCCACAAATCTTCTATAACGCTTCT
CCCTCAACACTTAGT SEQ ID NO 217: amino acid sequence of tPA-SP PH-20
MDAMKRGLCCVLLLCGAVFVSPSLNFRAPPVIPNVPFLWAWNAPSEFCLGKFDEPLDM
SLFSFIGSPRINATGQGVTIFYVDRLGYYPYIDSITGVTVNGGIPQKISLQDHLDKAKKDIT
FYMPVDNLGMAVIDWEEWRPTWARNWKPKDVYKNRSIELVQQQNVQLSLTEATEKA
KQEFEKAGKDFLVETIKLGKLLRPNHLWGYYLFPDCYNHHYKKPGYNGSCFNVEIKRN
DDLSWLWNESTALYPSIYLNTQQSPVAATLYVRNRVREAIRVSKIPDAKSPLPVFAYTRI
VFTDQVLKFLSQDELVYTFGETVALGASGIVIWGTLSIMRSMKSCLLLDNYMETILNPYII
NVTLAAKMCSQVLCQEQGVCIRKNWNSSDYLHLNPDNFAIQLEKGGKFTVRGKPTLED
LEQFSEKFYCSCYSTLSCKEKADVKDTDAVDVCIADGVCIDAFLKPPMETEEPQIFYN SEQ ID NO 218: nucleotide sequence of tPA-SP PH-20
ATGGATGCAATGAAGAGAGGGCTCTGCTGTGTGCTGCTGCTGTGTGGAGCAGTCTTC
GTTTCGCCCAGCCTGAACTTTCGCGCCCCACCAGTGATCCCTAATGTGCCATTCCTTT
GGGCTTGGAATGCGCCTTCTGAATTCTGCTTGGGAAAATTTGATGAGCCTCTGGATA
TGTCTCTTTTCAGTTTTATTGGGTCACCAAGGATTAACGCGACTGGACAAGGAGTGA
CGATATTTTATGTCGATAGGCTCGGCTACTACCCCTACATAGATTCCATTACCGGCGT
AACCGTGAATGGTGGTATCCCTCAAAAGATCTCTCTTCAAGACCACTTGGACAAAGC
AAAAAAAGACATTACATTCTACATGCCGGTGGATAACCTGGGGATGGCCGTTATCG
ATTGGGAGGAGTGGAGACCCACGTGGGCTAGAAACTGGAAGCCGAAGGACGTCTAT
AAAAACAGGTCTATCGAATTGGTTCAGCAGCAGAACGTGCAATTGTCCTTGACTGAG
GCGACAGAGAAGGCCAAGCAAGAGTTTGAGAAGGCGGGAAAGGACTTTTTGGTTGA
GACCATTAAGCTCGGTAAACTGCTGCGACCTAATCATCTGTGGGGTTACTACCTCTT
CCCTGACTGCTACAATCACCATTACAAGAAACCGGGCTACAATGGCTCTTGTTTTAA
TGTCGAAATCAAACGAAACGACGACCTGAGCTGGCTTTGGAACGAATCCACCGCAC
TCTACCCCAGCATCTATCTGAACACCCAGCAGAGTCCTGTAGCAGCAACGCTGTACG
TCCGGAACCGGGTACGAGAGGCAATCAGAGTATCTAAGATCCCGGATGCTAAATCC
CCACTGCCGGTATTTGCGTACACCCGAATCGTGTTCACTGACCAGGTTCTGAAGTTT
CTCTCCCAGGACGAACTTGTCTATACGTTTGGAGAGACAGTAGCACTCGGCGCATCA
GGCATTGTTATATGGGGAACCCTTAGCATCATGCGGTCAATGAAGTCCTGCTTGCTT
CTTGATAACTATATGGAGACAATCTTGAACCCCTATATCATCAATGTAACACTTGCA
GCAAAAATGTGCTCCCAAGTACTCTGTCAAGAGCAGGGAGTATGCATACGAAAAAA
TTGGAACAGTTCCGACTACCTGCACCTTAACCCCGATAATTTTGCTATACAGCTTGA
AAAGGGCGGAAAATTTACAGTCCGAGGGAAGCCGACATTGGAGGATCTCGAGCAAT
TCTCTGAAAAGTTTTATTGCTCATGCTACAGTACCCTTAGCTGTAAAGAAAAGGCGG
ACGTCAAGGATACTGACGCCGTGGACGTCTGCATCGCCGACGGAGTTTGCATCGAC
GCATTTCTTAAACCTCCCATGGAAACCGAAGAGCCACAAATCTTCTATAAC SEQ ID NO 219: amino acid sequence of NSP PH-20 GPI
MGVLKFKHIFFRSFVKSSGVSQIVFTFLLIPCCLTLNFRAPPVIPNVPFLWAWNAPSEFCL
GKFDEPLDMSLFSFIGSPRINATGQGVTIFYVDRLGYYPYIDSITGVTVNGGIPQKISLQDH
LDKAKKDITFYMPVDNLGMAVIDWEEWRPTWARNWKPKDVYKNRSIELVQQQNVQL
SLTEATEKAKQEFEKAGKDFLVETIKLGKLLRPNHLWGYYLFPDCYNHHYKKPGYNGS
CFNVEIKRNDDLSWLWNESTALYPSIYLNTQQSPVAATLYVRNRVREAIRVSKIPDAKSP
LPVFAYTRIVFTDQVLKFLSQDELVYTFGETVALGASGIVIWGTLSIMRSMKSCLLLDNY
METILNPYIINVTLAAKMCSQVLCQEQGVCIRKNWNSSDYLHLNPDNFAIQLEKGGKFT
VRGKPTLEDLEQFSEKFYCSCYSTLSCKEKADVKDTDAVDVCIADGVCIDAFLKPPMET
EEPQIFYNASPSTLSATMFIVSILFLIISSVASL SEQ ID NO 220: nucleotide sequence of NSP PH-20 GPI
ATGGGAGTGCTAAAATTCAAGCACATCTTTTTCAGAAGCTTTGTTAAATCAAGTGGA
GTATCCCAGATAGTTTTCACCTTCCTTCTGATTCCATGTTGCTTGACTCTGAACTTTC
GCGCCCCACCAGTGATCCCTAATGTGCCATTCCTTTGGGCTTGGAATGCGCCTTCTG
AATTCTGCTTGGGAAAATTTGATGAGCCTCTGGATATGTCTCTTTTCAGTTTTATTGG
GTCACCAAGGATTAACGCGACTGGACAAGGAGTGACGATATTTTATGTCGATAGGC
TCGGCTACTACCCCTACATAGATTCCATTACCGGCGTAACCGTGAATGGTGGTATCC
CTCAAAAGATCTCTCTTCAAGACCACTTGGACAAAGCAAAAAAAGACATTACATTCT
ACATGCCGGTGGATAACCTGGGGATGGCCGTTATCGATTGGGAGGAGTGGAGACCC
ACGTGGGCTAGAAACTGGAAGCCGAAGGACGTCTATAAAAACAGGTCTATCGAATT
GGTTCAGCAGCAGAACGTGCAATTGTCCTTGACTGAGGCGACAGAGAAGGCCAAGC
AAGAGTTTGAGAAGGCGGGAAAGGACTTTTTGGTTGAGACCATTAAGCTCGGTAAA -continued CTGCTGCGACCTAATCATCTGTGGGGTTACTACCTCTTCCCTGACTGCTACAATCACC
ATTACAAGAAACCGGGCTACAATGGCTCTTGTTTTAATGTCGAAATCAAACGAAACG
ACGACCTGAGCTGGCTTTGGAACGAATCCACCGCACTCTACCCCAGCATCTATCTGA
ACACCCAGCAGAGTCCTGTAGCAGCAACGCTGTACGTCCGGAACCGGGTACGAGAG
GCAATCAGAGTATCTAAGATCCCGGATGCTAAATCCCCACTGCCGGTATTTGCGTAC
ACCCGAATCGTGTTCACTGACCAGGTTCTGAAGTTTCTCTCCCAGGACGAACTTGTC
TATACGTTTGGAGAGACAGTAGCACTCGGCGCATCAGGCATTGTTATATGGGGAACC
CTTAGCATCATGCGGTCAATGAAGTCCTGCTTGCTTCTTGATAACTATATGGAGACA
ATCTTGAACCCCTATATCATCAATGTAACACTTGCAGCAAAAATGTGCTCCCAAGTA
CTCTGTCAAGAGCAGGGAGTATGCATACGAAAAAATTGGAACAGTTCCGACTACCT
GCACCTTAACCCCGATAATTTTGCTATACAGCTTGAAAAGGGCGGAAAATTTACAGT
CCGAGGGAAGCCGACATTGGAGGATCTCGAGCAATTCTCTGAAAAGTTTTATTGCTC
ATGCTACAGTACCCTTAGCTGTAAAGAAAAGGCGGACGTCAAGGATACTGACGCCG
TGGACGTCTGCATCGCCGACGGAGTTTGCATCGACGCATTTCTTAAACCTCCCATGG
AAACCGAAGAGCCACAAATCTTCTATAACGCTTCTCCCTCAACACTTAGTGCTACTA
TGTTTATAGTTTCTATTTTGTTCCTTATTATTTCAAGTGTAGCTAGTCTT SEQ ID NO 221: amino acid sequence of NSP PH-20 7 A.A. of GPI
MGVLKFKHIFFRSFVKSSGVSQIVFTFLLIPCCLTLNFRAPPVIPNVPFLWAWNAPSEFCL
GKFDEPLDMSLFSFIGSPRINATGQGVTIFYVDRLGYYPYIDSITGVTVNGGIPQKISLQDH
LDKAKKDITFYMPVDNLGMAVIDWEEWRPTWARNWKPKDVYKNRSIELVQQQNVQL
SLTEATEKAKQEFEKAGKDFLVETIKLGKLLRPNHLWGYYLFPDCYNHHYKKPGYNGS
CFNVEIKRNDDLSWLWNESTALYPSIYLNTQQSPVAATLYVRNRVREAIRVSKIPDAKSP
LPVFAYTRIVFTDQVLKFLSQDELVYTFGETVALGASGIVIWGTLSIMRSMKSCLLLDNY
METILNPYIINVTLAAKMCSQVLCQEQGVCIRKNWNSSDYLHLNPDNFAIQLEKGGKFT
VRGKPTLEDLEQFSEKFYCSCYSTLSCKEKADVKDTDAVDVCIADGVCIDAFLKPPMET
EEPQIFYNASPSTLS SEQ ID NO 222: nucleotide sequence of NSP PH-20 7 A.A. of GPI
ATGGGAGTGCTAAAATTCAAGCACATCTTTTTCAGAAGCTTTGTTAAATCAAGTGGA
GTATCCCAGATAGTTTTCACCTTCCTTCTGATTCCATGTTGCTTGACTCTGAACTTTC
GCGCCCCACCAGTGATCCCTAATGTGCCATTCCTTTGGGCTTGGAATGCGCCTTCTG
AATTCTGCTTGGGAAAATTTGATGAGCCTCTGGATATGTCTCTTTTCAGTTTTATTGG
GTCACCAAGGATTAACGCGACTGGACAAGGAGTGACGATATTTTATGTCGATAGGC
TCGGCTACTACCCCTACATAGATTCCATTACCGGCGTAACCGTGAATGGTGGTATCC
CTCAAAAGATCTCTCTTCAAGACCACTTGGACAAAGCAAAAAAAGACATTACATTCT
ACATGCCGGTGGATAACCTGGGGATGGCCGTTATCGATTGGGAGGAGTGGAGACCC
ACGTGGGCTAGAAACTGGAAGCCGAAGGACGTCTATAAAAACAGGTCTATCGAATT
GGTTCAGCAGCAGAACGTGCAATTGTCCTTGACTGAGGCGACAGAGAAGGCCAAGC
AAGAGTTTGAGAAGGCGGGAAAGGACTTTTTGGTTGAGACCATTAAGCTCGGTAAA
CTGCTGCGACCTAATCATCTGTGGGGTTACTACCTCTTCCCTGACTGCTACAATCACC
ATTACAAGAAACCGGGCTACAATGGCTCTTGTTTTAATGTCGAAATCAAACGAAACG
ACGACCTGAGCTGGCTTTGGAACGAATCCACCGCACTCTACCCCAGCATCTATCTGA
ACACCCAGCAGAGTCCTGTAGCAGCAACGCTGTACGTCCGGAACCGGGTACGAGAG
GCAATCAGAGTATCTAAGATCCCGGATGCTAAATCCCCACTGCCGGTATTTGCGTAC
ACCCGAATCGTGTTCACTGACCAGGTTCTGAAGTTTCTCTCCCAGGACGAACTTGTC
TATACGTTTGGAGAGACAGTAGCACTCGGCGCATCAGGCATTGTTATATGGGGAACC
CTTAGCATCATGCGGTCAATGAAGTCCTGCTTGCTTCTTGATAACTATATGGAGACA
ATCTTGAACCCCTATATCATCAATGTAACACTTGCAGCAAAAATGTGCTCCCAAGTA
CTCTGTCAAGAGCAGGGAGTATGCATACGAAAAAATTGGAACAGTTCCGACTACCT
GCACCTTAACCCCGATAATTTTGCTATACAGCTTGAAAAGGGCGGAAAATTTACAGT
CCGAGGGAAGCCGACATTGGAGGATCTCGAGCAATTCTCTGAAAAGTTTTATTGCTC
ATGCTACAGTACCCTTAGCTGTAAAGAAAAGGCGGACGTCAAGGATACTGACGCCG
TGGACGTCTGCATCGCCGACGGAGTTTGCATCGACGCATTTCTTAAACCTCCCATGG
AAACCGAAGAGCCACAAATCTTCTATAACGCTTCTCCCTCAACACTTAGT SEQ ID NO 223: amino acid sequence of NSP PH-20
MGVLKFKHIFFRSFVKSSGVSQIVFTFLLIPCCLTLNFRAPPVIPNVPFLWAWNAPSEFCL
GKFDEPLDMSLFSFIGSPRINATGQGVTIFYVDRLGYYPYIDSITGVTVNGGIPQKISLQDH
LDKAKKDITFYMPVDNLGMAVIDWEEWRPTWARNWKPKDVYKNRSIELVQQQNVQL
SLTEATEKAKQEFEKAGKDFLVETIKLGKLLRPNHLWGYYLFPDCYNHHYKKPGYNGS
CFNVEIKRNDDLSWLWNESTALYPSIYLNTQQSPVAATLYVRNRVREAIRVSKIPDAKSP
LPVFAYTRIVFTDQVLKFLSQDELVYTFGETVALGASGIVIWGTLSIMRSMKSCLLLDNY
METILNPYIINVTLAAKMCSQVLCQEQGVCIRKNWNSSDYLHLNPDNFAIQLEKGGKFT
VRGKPTLEDLEQFSEKFYCSCYSTLSCKEKADVKDTDAVDVCIADGVCIDAFLKPPMET
EEPQIFYN SEQ ID NO 224: nucleotide sequence of NSP PH-20
ATGGGAGTGCTAAAATTCAAGCACATCTTTTTCAGAAGCTTTGTTAAATCAAGTGGA
GTATCCCAGATAGTTTTCACCTTCCTTCTGATTCCATGTTGCTTGACTCTGAACTTTC
GCGCCCCACCAGTGATCCCTAATGTGCCATTCCTTTGGGCTTGGAATGCGCCTTCTG
AATTCTGCTTGGGAAAATTTGATGAGCCTCTGGATATGTCTCTTTTCAGTTTTATTGG
GTCACCAAGGATTAACGCGACTGGACAAGGAGTGACGATATTTTATGTCGATAGGC
TCGGCTACTACCCCTACATAGATTCCATTACCGGCGTAACCGTGAATGGTGGTATCC
CTCAAAAGATCTCTCTTCAAGACCACTTGGACAAAGCAAAAAAAGACATTACATTCT
ACATGCCGGTGGATAACCTGGGGATGGCCGTTATCGATTGGGAGGAGTGGAGACCC
ACGTGGGCTAGAAACTGGAAGCCGAAGGACGTCTATAAAAACAGGTCTATCGAATT
GGTTCAGCAGCAGAACGTGCAATTGTCCTTGACTGAGGCGACAGAGAAGGCCAAGC
AAGAGTTTGAGAAGGCGGGAAAGGACTTTTTGGTTGAGACCATTAAGCTCGGTAAA
CTGCTGCGACCTAATCATCTGTGGGGTTACTACCTCTTCCCTGACTGCTACAATCACC
ATTACAAGAAACCGGGCTACAATGGCTCTTGTTTTAATGTCGAAATCAAACGAAACG -continued ACGACCTGAGCTGGCTTTGGAACGAATCCACCGCACTCTACCCCAGCATCTATCTGA
ACACCCAGCAGAGTCCTGTAGCAGCAACGCTGTACGTCCGGAACCGGGTACGAGAG
GCAATCAGAGTATCTAAGATCCCGGATGCTAAATCCCCACTGCCGGTATTTGCGTAC
ACCCGAATCGTGTTCACTGACCAGGTTCTGAAGTTTCTCTCCCAGGACGAACTTGTC
TATACGTTTGGAGAGACAGTAGCACTCGGCGCATCAGGCATTGTTATATGGGGAACC
CTTAGCATCATGCGGTCAATGAAGTCCTGCTTGCTTCTTGATAACTATATGGAGACA
ATCTTGAACCCCTATATCATCAATGTAACACTTGCAGCAAAAATGTGCTCCCAAGTA
CTCTGTCAAGAGCAGGGAGTATGCATACGAAAAAATTGGAACAGTTCCGACTACCT
GCACCTTAACCCCGATAATTTTGCTATACAGCTTGAAAAGGGCGGAAAATTTACAGT
CCGAGGGAAGCCGACATTGGAGGATCTCGAGCAATTCTCTGAAAAGTTTTATTGCTC
ATGCTACAGTACCCTTAGCTGTAAAGAAAAGGCGGACGTCAAGGATACTGACGCCG
TGGACGTCTGCATCGCCGACGGAGTTTGCATCGACGCATTTCTTAAACCTCCCATGG
AAACCGAAGAGCCACAAATCTTCTATAAC SEQ ID NO: 225 amino acid sequence of CAR CAR D0351 Farle CD8 BBz
MLLLVTSLLLCELPHPAFLLIPMEVQLVESGGGVVQPGRSLRLSCSASGFTFSGYGLSWV
RQAPGKGLEWVAMISSGGSYTYYADSVKGRFAISRDNAKNTLFLQMDSLRPEDTGVYF
CARHGDDPAWFAYWGQGTPVTVSSASTKGGGGGSGGGGSGGGGSDIQLTQSPSSLSAS
VGDRVTITCSVSSSISSNNLHWYQQKPGKAPKPWIYGTSNLASGVPSRFSGSGSGTDYTF
TISSLQPEDIATYYCQQWSSYPYMYTFGQGTKVEIKRTAAATTTPAPRPPTPAPTIASQPL
SLRPEACRPAAGGAVHTRGLDFACDIYIWAPLAGTCGVLLLSLVITLYCKRGRKKLLYIF
KQPFMRPVQTTQEEDGCSCRFPEEEEGGCELRVKFSRSADAPAYQQGQNQLYNELNLG
RREEYDVLDKRRGRDPEMGGKPRRKNPQEGLYNELQKDKMAEAYSEIGMKGERRRGK
GHDGLYQGLSTATKDTYDALHMQALPPR SEQ ID NO: 226 nucleotide sequence of CAR D0351 Farle CD8 BBz
ATGTTGCTGCTCGTGACCAGCCTCCTTCTGTGCGAACTTCCCCACCCCGCATTCCTGC
TGATTCCTATGGAAGTGCAGCTCGTGGAGTCCGGAGGCGGAGTCGTGCAGCCGGGC
AGATCCCTGCGCCTTTCCTGCTCGGCATCCGGGTTTACCTTCTCTGGCTACGGTCTGT
CGTGGGTCAGACAGGCTCCAGGGAAGGGCCTGGAATGGGTGGCCATGATCTCCTCG
GGGGGTTCGTACACCTACTACGCCGACTCAGTGAAGGGCCGGTTCGCCATCTCCCGC
GACAACGCCAAGAACACCCTGTTCCTGCAAATGGACTCGCTCCGGCCTGAGGACAC
TGGGGTGTACTTCTGCGCGAGACACGGAGATGACCCAGCTTGGTTCGCCTACTGGGG
ACAAGGCACCCCTGTGACCGTGTCCTCCGCGAGCACCAAGGGAGGCGGAGGAGGTT
CCGGTGGAGGGGGATCAGGGGGTGGAGGATCGGACATTCAGCTGACCCAGAGCCCC
TCAAGCCTGTCCGCGAGCGTTGGGGACCGCGTGACCATCACCTGTTCGGTGTCCTCC
TCCATCTCCTCCAACAATCTCCATTGGTACCAGCAGAAACCGGGGAAAGCCCCCAA
GCCGTGGATCTACGGAACCTCCAACCTGGCTAGCGGAGTGCCGTCGAGGTTCTCGG
GCTCCGGATCAGGGACTGACTACACTTTCACTATTTCCTCCCTGCAACCGGAGGACA
TTGCCACCTACTACTGTCAGCAGTGGTCGTCCTACCCCTACATGTATACCTTCGGTCA
AGGAACCAAGGTCGAGATCAAGAGGACAGCGGCCGCAACGACCACTCCTGCACCCC
GCCCTCCGACTCCGGCCCCAACCATTGCCAGCCAGCCCCTGTCCCTGCGGCCGGAAG
CCTGCAGACCGGCTGCCGGCGGAGCCGTCCATACCCGGGGACTGGATTTCGCCTGC
GATATCTATATCTGGGCACCACTCGCCGGAACCTGTGGAGTGCTGCTGCTGTCCCTT
GTGATCACCCTGTACTGCAAGCGCGGACGGAAGAAACTCTTGTACATCTTCAAGCAG
CCGTTCATGCGCCCTGTGCAAACCACCCAAGAAGAGGACGGGTGCTCCTGCCGGTTC
CCGGAAGAGGAAGAGGGCGGCTGCGAACTGCGCGTGAAGTTTTCCCGGTCCGCCGA
CGCTCCGGCGTACCAGCAGGGGCAAAACCAGCTGTACAACGAACTTAACCTCGGTC
GCCGGGAAGAATATGACGTGCTGGACAAGCGGCGGGGAAGAGATCCCGAGATGGG
TGGAAAGCCGCGGCGGAAGAACCCTCAGGAGGGCTTGTACAACGAGCTGCAAAAG
GACAAAATGGCCGAAGCCTACTCCGAGATTGGCATGAAGGGAGAGCGCAGACGCG
GGAAGGGACACGATGGACTGTACCAGGGACTGTCAACCGCGACTAAGGACACTTAC
GACGCCCTGCACATGCAGGCCCTGCCCCCGCGC SEQ ID NO: 227 amino acid sequence of CAR D0373 MMP-9 2A ROR1 ScFv9 IgG4H CD8TM BBz
MSLWQPLVLVLLVLGCCFAAPRQRQSTLVLFPGDLRTNLTDRQLAEEYLYRYGYTRVA
EMRGESKSLGPALLLLQKQLSLPETGELDSATLKAMRTPRCGVPDLGRFQTFEGDLKW
HHHNITYWIQNYSEDLPRAVIDDAFARAFALWSAVTPLTFTRVYSRDADIVIQFGVAEH
GDGYPFDGKDGLLAHAFPPGPGIQGDAHFDDDELWSLGKGVVVPTRFGNADGAACHFP
FIFEGRSYSACTTDGRSDGLPWCSTTANYDTDDRFGFCPSERLYTQDGNADGKPCQFPFI
FQGQSYSACTTDGRSDGYRWCATTANYDRDKLFGFCPTRADSTVMGGNSAGELCVFPF
TFLGKEYSTCTSEGRGDGRLWCATTSNFDSDKKWGFCPDQGYSLFLVAAHEFGHALGL
DHSSVPEALMYPMYRFTEGPPLHKDDVNGIRHLYGPRPEPEPRPPTTTTPQPTAPPTVCP
TGPPTVHPSERPTAGPTGPPSAGPTGPPTAGPSTATTVPLSPVDDACNVNIFDAIAEIGNQ
LYLFKDGKYWRFSEGRGSRPQGPFLIADKWPALPRKLDSVFEERLSKKLFFFSGRQVWV
YTGASVLGPRRLDKLGLGADVAQVTGALRSGRGKMLLFSGRRLWRFDVKAQMVDPRS
ASEVDRMFPGVPLDTHDVFQYREKAYFCQDRFYWRVSSRSELNQVDQVGYVTYDILQC
PEDRAKRGSGATNFSLLKQAGDVEENPGPRAKRMLLLVTSLLLCELPHPAFLLIPQAAQ
VQLQQSGAEVKKPGSSVKVSCKASGGTFSSYAISWVRQAPGQGLEWMGWINPNSGGT
NYAQRFQGRVTMTRDTSISTAYMELSRLRSDDTAVYYCASYNDAFDIWGQGTLVTVSS
GGGGSGGGGSGGGGSNFMLTQPHSVSESPGKTVTISCTRSSGSIASNYVQWYQQRPGSA
PTIVIYEDDQRPSGVPDRFSGSIDTSSNSASLTISGLQSEDEADYYCQSYEPGNGVFGGGT
KVTVLAAAESKYGPPCPPCPIYIWAPLAGTCGVLLLSLVITLYCKRGRKKLLYIFKQPFM
RPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDG
LYQGLSTATKDTYDALHMQALPPR -continued SEQ ID NO: 228 nucleotide sequence of CAR D0373 MMP-9 2A ROR1 ScFv9 IgG4H CD8TM BBz
ATGAGCCTCTGGCAGCCCCTGGTCCTGGTGCTCCTGGTGCTGGGCTGCTGCTTTGCTG
CCCCCAGACAGCGCCAGTCCACCCTTGTGCTCTTCCCTGGAGACCTGAGAACCAATC
TCACCGACAGGCAGCTGGCAGAGGAATACCTGTACCGCTATGGTTACACTCGGGTG
GCAGAGATGCGTGGAGAGTCGAAATCTCTGGGGCCTGCGCTGCTGCTTCTCCAGAA
GCAACTGTCCCTGCCCGAGACCGGTGAGCTGGATAGCGCCACGCTGAAGGCCATGC
GAACCCCACGGTGCGGGGTCCCAGACCTGGGCAGATTCCAAACCTTTGAGGGCGAC
CTCAAGTGGCACCACCACAACATCACCTATTGGATCCAAAACTACTCGGAAGACTTG
CCGCGGGCGGTGATTGACGACGCCTTTGCCCGCGCCTTCGCACTGTGGAGCGCGGTG
ACGCCGCTCACCTTCACTCGCGTGTACAGCCGGGACGCAGACATCGTCATCCAGTTT
GGTGTCGCGGAGCACGGAGACGGGTATCCCTTCGACGGGAAGGACGGGCTCCTGGC
ACACGCCTTTCCTCCTGGCCCCGGCATTCAGGGAGACGCCCATTTCGACGATGACGA
GTTGTGGTCCCTGGGCAAGGGCGTCGTGGTTCCAACTCGGTTTGGAAACGCAGATGG
CGCGGCCTGCCACTTCCCCTTCATCTTCGAGGGCCGCTCCTACTCTGCCTGCACCACC
GATGGACGGTCCGACGGCTTGCCCTGGTGCAGTACCACGGCCAACTACGACACCGA
CGACCGGTTTGGCTTCTGCCCCAGCGAGAGACTCTACACCCAGGACGGCAATGCTG
ATGGGAAACCCTGCCAGTTTCCATTCATCTTCCAAGGCCAATCCTACTCCGCCTGCA
CCACGGACGGTCGCTCCGACGGGTACCGCTGGTGCGCCACCACCGCCAACTACGAC
CGGGACAAGCTCTTCGGCTTCTGCCCGACCCGAGCTGACTCGACGGTGATGGGGGG
CAACTCGGCGGGGGAGCTGTGCGTCTTCCCCTTCACTTTCCTGGGTAAGGAGTACTC
GACCTGTACCAGCGAGGGCCGCGGAGATGGGCGCCTCTGGTGCGCTACCACCTCGA
ACTTTGACAGCGACAAGAAGTGGGGCTTCTGCCCGGACCAAGGATACAGTTTGTTCC
TCGTGGCGGCGCATGAGTTCGGCCACGCGCTGGGCTTAGATCATTCCTCAGTGCCGG
AGGCGCTCATGTACCCTATGTACCGCTTCACTGAGGGGCCCCCCTTGCATAAGGACG
ACGTGAATGGCATCCGGCACCTCTATGGTCCTCGCCCTGAACCTGAGCCACGACCTC
CAACAACCACCACACCGCAGCCCACGGCTCCACCGACGGTCTGCCCCACCGGACCC
CCCACTGTCCACCCCTCAGAGCGCCCCACTGCTGGCCCAACAGGACCTCCCTCAGCT
GGCCCCACAGGTCCCCCAACTGCTGGCCCTTCTACGGCCACTACTGTGCCTTTGAGT
CCGGTGGACGATGCCTGCAACGTGAACATCTTCGACGCCATCGCGGAGATTGGGAA
CCAGCTGTATTTGTTCAAGGATGGGAAGTACTGGCGATTCTCTGAGGGCAGGGGGA
GCCGGCCGCAGGGCCCCTTCCTTATCGCCGACAAGTGGCCCGCGCTGCCCCGCAAGC
TGGACTCGGTCTTTGAGGAGCGGCTCTCCAAGAAGCTTTTCTTCTTCTCTGGTCGCCA
GGTGTGGGTGTACACAGGTGCGTCGGTGCTGGGACCGAGGCGTCTAGACAAGCTAG
GCCTGGGAGCAGACGTGGCCCAGGTGACCGGGGCCCTCCGGAGTGGCAGGGGGAA
GATGCTGCTGTTCAGCGGGCGGCGCCTCTGGAGGTTCGACGTGAAGGCGCAGATGG
TGGATCCCCGGAGCGCCAGCGAGGTGGACCGGATGTTCCCCGGGGTGCCTTTGGAC
ACGCACGACGTCTTCCAGTACCGAGAGAAAGCCTATTTCTGCCAGGACCGCTTCTAC
TGGCGCGTGAGTTCCCGGAGTGAGTTGAACCAGGTGGACCAAGTGGGCTACGTGAC
CTATGACATCCTGCAGTGCCCTGAGGACCGGGCAAAGCGGGGCTCAGGGGCGACTA
ACTTTTCACTGTTGAAGCAGGCCGGGGATGTGGAGGAGAATCCTGGTCCTAGAGCA
AAGCGAATGCTGCTGCTGGTGACCAGCCTGCTGCTGTGCGAACTGCCGCATCCGGCG
TTTCTGCTGATTCCGCAGGCGGCCCAGGTACAGCTGCAGCAGTCAGGGGCTGAGGTG
AAGAAGCCTGGGTCCTCGGTGAAGGTCTCCTGCAAGGCTTCTGGAGGCACCTTCAGC
AGCTATGCTATCAGCTGGGTGCGACAGGCCCCTGGACAAGGGCTTGAGTGGATGGG
ATGGATCAACCCTAACAGTGGTGGCACAAACTATGCACAGAGGTTTCAGGGCAGGG
TCACCATGACCAGGGACACGTCCATCAGCACAGCCTACATGGAGCTGAGCAGGCTG
AGATCTGACGACACGGCCGTGTATTACTGTGCGAGTTATAATGATGCTTTTGATATC
TGGGGCCAAGGCACCCTGGTCACCGTCTCCTCAGGAGGTGGGGGTCTGGTGGTGG
CGGTAGCGGTGGTGGCGGATCCAATTTTATGCTGACTCAGCCCCACTCTGTGTCGGA
GTCTCCGGGGAAGACGGTAACCATCTCCTGCACCCGCAGCAGTGGCAGCATTGCCA
GCAACTATGTGCAGTGGTACCAGCAGCGCCCGGGCAGTGCCCCCACCATTGTGATCT
ATGAGGATGATCAAAGACCCTCTGGGGTCCCTGATCGGTTCTCTGGCTCCATCGACA
CCTCCTCCAACTCTGCCTCCCTCACCATCTCTGGACTGCAGAGTGAGGACGAGGCTG
ACTACTACTGTCAGTCTTATGAGCCCGGCAATGGGGTATTCGGCGGAGGGACCAAG
GTCACCGTCCTAGCGGCCGCAGAGTCAAAATACGGTCCTCCGTGCCCTCCGTGTCCG
ATCTACATTTGGGCCCCGCTGGCCGGCACTTGCGGCGTGCTCCTGCTGTCGCTGGTC
ATCACCCTTTACTGCAAGAGGGGCCGGAAGAAGCTGCTTTACATCTTCAAGCAGCCG
TTCATGCGGCCCGTGCAGACGACTCAGGAAGAGGACGGATGCTCGTGCAGATTCCC
TGAGGAGGAAGAGGGGGGATGCGAACTGCGCGTCAAGTTCTCACGGTCCGCCGACG
CCCCCGCATATCAACAGGGCCAGAATCAGCTCTACAACGAGCTGAACCTGGGAAGG
AGAGAGGAGTACGACGTGCTGGACAAGCGACGCGGACGCGACCCGGAGATGGGGG
GGAAACCACGGCGGAAAAACCCTCAGGAAGGACTGTACAACGAACTCCAGAAAGA
CAAGATGGCGGAAGCCTACTCAGAAATCGGGATGAAGGGAGAGCGGAGGAGGGGA
AAGGGTCACGACGGGCTGTACCAGGGACTGAGCACCGCCACTAAGGATACCTACGA
TGCCTTGCATATGCAAGCACTCCCACCCCGG SEQ ID NO: 229 amino acid sequence of CAR D0368, D0369 Farle CD8 BBz 2A HPSE
MLLLVTSLLLCELPHPAFLLIPMEVQLVESGGGVVQPGRSLRLSCSASGFTFSGYGLSWV
RQAPGKGLEWVAMISSGGSYTYYADSVKGRFAISRDNAKNTLFLQMDSLRPEDTGVYF
CARHGDDPAWFAYWGQGTPVTVSSASTKGGGGGSGGGGSGGGGSDIQLTQSPSSLSAS
VGDRVTITCSVSSSISSNNLHWYQQKPGKAPKPWIYGTSNLASGVPSRFSGSGSGTDYTF
TISSLQPEDIATYYCQQWSSYPYMYTFGQGTKVEIKRTAAATTTPAPRPPTPAPTIASQPL
SLRPEACRPAAGGAVHTRGLDFACDIYIWAPLAGTCGVLLLSLVITLYCKRGRKKLLYIF
KQPFMRPVQTTQEEDGCSCRFPEEEEGGCELRVKFSRSADAPAYQQGQNQLYNELNLG
RREEYDVLDKRRGRDPEMGGKPRRKNPQEGLYNELQKDKMAEAYSEIGMKGERRRGK
GHDGLYQGLSTATKDTYDALHMQALPPRRAKRGSGATNFSLLKQAGDVEENPGPRAK
RMLLRSKPALPPPLMLLLLGPLGPLSPGALPRPAQAQDVVDLDFFTQEPLHLVSPSFLSV
TIDANLATDPRFLILLGSPKLRTLARGLSPAYLRFGGTKTDFLIFDPKKESTFEERSYWQS
QVNQDICKYGSIPPDVEEKLRLEWPYQEQLLLREHYQKFKNSTYSRSSVDVLYTFANC
SGLDLIFGLNALLRTADLQWNSSNAQLLLDYCSSKGYNISWELGNEPNSFLKKADIFING -continued SQLGEDFIQLHKLLRKSTFKNAKLYGPDVGQPRRKTAKMLKSFLKAGGEVIDSVTWHH
YYLNGRTATKEDFLNPDVLDIFISSVQKVFQVVESTRPGKKVWLGETSSAYGGGAPLLS
DTFAAGFMWLDKLGLSARMGIEVVMRQVFFGAGNYHLVDENFDPLPDYWLSLLFKKL
VGTKVLMASVQGSKRRKLRVYLHCTNTDNPRYKEGDLTLYAINLHNVTKYLRLPYPFS
NKQVDKYLLRPLGPHGLLSKSVQLNGLTLKMVDDQTLPPLMEKPLRPGSSLGLPAFSYS
FFVIRNAKVAACI SEQ ID NO: 230 nucleotide sequence of CAR D0368, D0369 Farle CD8 BBz 2A HPSE
ATGTTGCTGCTCGTGACCAGCCTCCTTCTGTGCGAACTTCCCCACCCCGCATTCCTGC
TGATTCCTATGGAAGTGCAGCTCGTGGAGTCCGGAGGCGGAGTCGTGCAGCCGGGC
AGATCCCTGCGCCTTTCCTGCTCGGCATCCGGGTTTACCTTCTCTGGCTACGGTCTGT
CGTGGGTCAGACAGGCTCCAGGGAAGGGCCTGGAATGGGTGGCCATGATCTCCTCG
GGGGGTTCGTACACCTACTACGCCGACTCAGTGAAGGGCCGGTTCGCCATCTCCCGC
GACAACGCCAAGAACACCCTGTTCCTGCAAATGGACTCGCTCCGGCCTGAGGACAC
TGGGGTGTACTTCTGCGCGAGACACGGAGATGACCCAGCTTGGTTCGCCTACTGGGG
ACAAGGCACCCCTGTGACCGTGTCCTCCGCGAGCACCAAGGGAGGCGGAGGAGGTT
CCGGTGGAGGGGGATCAGGGGGTGGAGGATCGGACATTCAGCTGACCCAGAGCCCC
TCAAGCCTGTCCGCGAGCGTTGGGGACCGCGTGACCATCACCTGTTCGGTGTCCTCC
TCCATCTCCTCCAACAATCTCCATTGGTACCAGCAGAAACCGGGGAAAGCCCCCAA
GCCGTGGATCTACGGAACCTCCAACCTGGCTAGCGGAGTGCCGTCGAGGTTCTCGG
GCTCCGGATCAGGGACTGACTACACTTTCACTATTTCCTCCCTGCAACCGGAGGACA
TTGCCACCTACTACTGTCAGCAGTGGTCGTCCTACCCCTACATGTATACCTTCGGTCA
AGGAACCAAGGTCGAGATCAAGAGGACAGCGGCCGCAACTACCACCCCTGCCCCTC
GGCCGCCGACTCCGGCCCCAACCATCGCAAGCCAACCCCTCTCCTTGCGCCCCGAAG
CTTGCCGCCCGGCCGCGGGTGGAGCCGTGCATACCCGGGGGCTGGACTTTGCCTGCG
ATATCTACATTTGGGCCCCGCTGGCCGGCACTTGCGGCGTGCTCCTGCTGTCGCTGG
TCATCACCCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGCAGATTC
CCTGAGGAGGAAGAGGGGGGATGCGAACTGCGCGTCAAGTTCTCACGGTCCGCCGA
CGCCCCCGCATATCAACAGGGCCAGAATCAGCTCTACAACGAGCTGAACCTGGGAA
GGAGAGAGGAGTACGACGTGCTGGACAAGCGACGCGGACGCGACCCGGAGATGGG
GGGGAAACCACGGCGGAAAAACCCTCAGGAAGGACTGTACAACGAACTCCAGAAA
GACAAGATGGCGGAAGCCTACTCAGAAATCGGGATGAAGGGAGAGCGGAGGAGGG
GAAAGGGTCACGACGGGCTGTACCAGGGACTGAGCACCGCCACTAAGGATACCTAC
GATGCCTTGCATATGCAAGCACTCCCACCCCGGGGGCAAAGCGGGGCTCAGGGGC
GACTAACTTTTCACTGTTGAAGCAGGCCGGGGATGTGGAGGAGAATCCTGGTCCTAG
AGCaAAGCGAATGCTtCTaCGtTCtAAaCCTGCaCTtCCtCCaCCaCTtATGCTaCTtCTtCTaG
GaCCtCTtGGTCCtCTaTCaCCTGGaGCtCTaCCtCGACCTGCaCAAGCACAGGACGTCGTG
GACCTGGACTTCTTCACCCAGGAGCCGCTGCACCTGGTGAGCCCCTCGTTCCTGTCC
GTCACCATTGACGCCAACCTGGCCACGGACCCGCGGTTCCTCATCCTCCTGGGTTCT
CCAAAGCTTCGTACCTTGGCCAGAGGCTTGTCTCCTGCGTACCTGAGGTTTGGTGGC
ACCAAGACAGACTTCCTAATTTTCGATCCCAAGAAGGAATCAACCTTTGAAGAGAG
AAGTTACTGGCAATCTCAAGTCAACCAGGATATTTGCAAATATGGATCCATCCCTCC
TGATGTGGAGGAGAAGTTACGGTTGGAATGGCCCTACCAGGAGCAATTGCTACTCC
GAGAACACTACCAGAAAAAGTTCAAGAACAGCACCTACTCAAGAAGCTCTGTAGAT
GTGCTATACACTTTTGCAAACTGCTCAGGACTGGACTTGATCTTTGGCCTAAATGCG
TTATTAAGAACAGCAGATTTGCAGTGGAACAGTTCTAATGCTCAGTTGCTCCTGGAC
TACTGCTCTTCCAAGGGGTATAACATTTCTTGGGAACTAGGCAATGAACCTAACAGT
TTCCTTAAGAAGGCTGATATTTTCATCAATGGGTCGCAGTTAGGAGAAGATTTTATT
CAATTGCATAAACTTCTAAGAAAGTCCACCTTCAAAAATGCAAAACTCTATGGTCCT
GATGTTGGTCAGCCTCGAAGAAAGACGGCTAAGATGCTGAAGAGCTTCCTGAAGGC
TGGTGGAGAAGTGATTGATTCAGTTACATGGCATCACTACTATTTGAATGGACGGAC
TGCTACCAAGGAAGATTTTCTAAACCCTGATGTATTGGACATTTTTATTTCATCTGTG
CAAAAAGTTTTCCAGGTGGTTGAGAGCACCAGGCCTGGCAAGAAGGTCTGGTTAGG
AGAAACAAGCTCTGCATATGGAGGCGGAGCGCCCTTGCTATCCGACACCTTTGCAG
CTGGCTTTATGTGGCTGGATAAATTGGGCCTGTCAGCCCGAATGGGAATAGAAGTGG
TGATGAGGCAAGTATTCTTTGGAGCAGGAAACTACCATTTAGTGGATGAAAACTTCG
ATCCTTTACCTGATTATTGGCTATCTCTTCTGTTCAAGAAATTGGTGGGCACCAAGGT
GTTAATGGCAAGCGTGCAAGGTTCAAAGAGAAGGAAGCTTCGAGTATACCTTCATT
GCACAAACACTGACAATCCAAGGTATAAAGAAGGAGATTTAACTCTGTATGCCATA
AACCTCCATAATGTCACCAAGTACTTGCGGTTACCCTATCCTTTTTCTAACAAGCAA
GTGGATAAATACCTTCTAAGACCTTTGGGACCTCATGGATTACTTTCCAAATCTGTCC
AACTCAATGGTCTAACTCTAAAGATGGTGGATGATCAAACCTTGCCACCTTTAATGG
AAAAACCTCTCCGGCCAGGAAGTTCACTGGGCTTGCCAGCTTTCTCATATAGTTTTTT
TGTGATAAGAAATGCCAAAGTTGCTGCTTGCATC SEQ ID NO: 231 amino acid sequence of CAR D0423, D0424 Farle CD8 BBz 2A tPA-SP PH-20 GPI
MLLLVTSLLLCELPHPAFLLIPMEVQLVESGGGVVQPGRSLRLSCSASGFTFSGYGLSWV
RQAPGKGLEWVAMISSGGSYTYYADSVKGRFAISRDNAKNTLFLQMDSLRPEDTGVYF
CARHGDDPAWFAYWGQGTPVTVSSASTKGGGGGSGGGGSGGGGSDIQLTQSPSSLSAS
VGDRVTITCSVSSSISSNNLHWYQQKPGKAPKPWIYGTSNLASGVPSRFSGSGSGTDYTF
TISSLQPEDIATYYCQQWSSYPYMYTFGQGTKVEIKRTAAATTTPAPRPPTPAPTIASQPL
SLRPEACRPAAGGAVHTRGLDFACDIYIWAPLAGTCGVLLLSLVITLYCKRGRKKLLYIF
KQPFMRPVQTTQEEDGCSCRFPEEEEGGCELRVKFSRSADAPAYQQGQNQLYNELNLG
RREEYDVLDKRRGRDPEMGGKPRRKNPQEGLYNELQKDKMAEAYSEIGMKGERRRGK
GHDGLYQGLSTATKDTYDALHMQALPPRRAKRGSGATNFSLLKQAGDVEENPGPRAK
RMDAMKRGLCCVLLLCGAVFVSPSLNFRAPPVIPNVPFLWAWNAPSEFCLGKFDEPLD
MSLFSFIGSPRINATGQGVTIFYVDRLGYYPYIDSITGVTVNGGIPQKISLQDHLDKAKKD
ITFYMPVDNLGMAVIDWEEWRPTWARNWKPKDVYKNRSIELVQQQNVQLSLTEATEK
AKQEFEKAGKDFLVETIKLGKLLRPNHLWGYYLFPDCYNHHYKKPGYNGSCFNVEIKR -continued NDDLSWLWNESTALYPSIYLNTQQSPVAATLYVRNRVREAIRVSKIPDAKSPLPVFAYT
RIVFTDQVLKFLSQDELVYTFGETVALGASGIVIWGTLSIMRSMKSCLLLDNYMETILNP
YIINVTLAAKMCSQVLCQEQGVCIRKNWNSSDYLHLNPDNFAIQLEKGGKFTVRGKPTL
EDLEQFSEKFYCSCYSTLSCKEKADVKDTDAVDVCIADGVCIDAFLKPPMETEEPQIFYN
ASPSTLSATMFIVSILFLIISSVASL SEQ ID NO: 232 nucleotide sequence of CAR D0423, D0424 Farle CD8 BBz 2A tPA-SP PH-20 GPI ATGTTGCTGCTCGTGACCAGCCTCCTTCTGTGCGAACTTCCCCACCCCGCATTCCTGC
TGATTCCTATGGAAGTGCAGCTCGTGGAGTCCGGAGGCGGAGTCGTGCAGCCGGGC
AGATCCCTGCGCCTTTCCTGCTCGGCATCCGGGTTTACCTTCTCTGGCTACGGTCTGT
CGTGGGTCAGACAGGCTCCAGGGAAGGGCCTGGAATGGGTGGCCATGATCTCCTCG
GGGGGTTCGTACACCTACTACGCCGACTCAGTGAAGGGCCGGTTCGCCATCTCCCGC
GACAACGCCAAGAACACCCTGTTCCTGCAAATGGACTCGCTCCGGCCTGAGGACAC
TGGGGTGTACTTCTGCGCGAGACACGGAGATGACCCAGCTTGGTTCGCCTACTGGGG
ACAAGGCACCCCTGTGACCGTGTCCTCCGCGAGCACCAAGGGAGGCGGAGGAGGTT
CCGGTGGAGGGGGATCAGGGGGTGGAGGATCGGACATTCAGCTGACCCAGAGCCCC
TCAAGCCTGTCCGCGAGCGTTGGGGACCGCGTGACCATCACCTGTTCGGTGTCCTCC
TCCATCTCCTCCAACAATCTCCATTGGTACCAGCAGAAACCGGGGAAAGCCCCCAA
GCCGTGGATCTACGGAACCTCCAACCTGGCTAGCGGAGTGCCGTCGAGGTTCTCGG
GCTCCGGATCAGGGACTGACTACACTTTCACTATTTCCTCCCTGCAACCGGAGGACA
TTGCCACCTACTACTGTCAGCAGTGGTCGTCCTACCCCTACATGTATACCTTCGGTCA
AGGAACCAAGGTCGAGATCAAGAGGACAGCGGCCGCAACTACCACCCCTGCCCCTC
GGCCGCCGACTCCGGCCCCAACCATCGCAAGCCAACCCCTCTCCTTGCGCCCCGAAG
CTTGCCGCCCGGCCGCGGGTGGAGCCGTGCATACCCGGGGGCTGGACTTTGCCTGCG
ATATCTACATTTGGGCCCCGCTGGCCGGCACTTGCGGCGTGCTCCTGCTGTCGCTGG
TCATCACCCTTTACTGCAAGAGGGGCCGGAAGAAGCTGCTTTACATCTTCAAGCAGC
CGTTCATGCGGCCCGTGCAGACGACTCAGGAAGAGGACGGATGCTCGTGCAGATTC
CCTGAGGAGGAAGAGGGGGGATGCGAACTGCGCGTCAAGTTCTCACGGTCCGCCGA
CGCCCCCGCATATCAACAGGGCCAGAATCAGCTCTACAACGAGCTGAACCTGGGAA
GGAGAGAGGAGTACGACGTGCTGGACAAGCGACGCGGACGCGACCCGGAGATGGG
GGGGAAACCACGGCGGAAAAACCCTCAGGAAGGACTGTACAACGAACTCCAGAAA
GACAAGATGGCGGAAGCCTACTCAGAAATCGGGATGAAGGGAGAGCGGAGGAGGG
GAAAGGGTCACGACGGGCTGTACCAGGGACTGAGCACCGCCACTAAGGATACCTAC
GATGCCTTGCATATGCAAGCACTCCCACCCCGGGGGCAAAGCGGGGCTCAGGGGC
GACTAACTTTTCACTGTTGAAGCAGGCCGGGGATGTGGAGGAGAATCCTGGTCCTAG
AGCaAAGCGAATGGATGCAATGAAGAGAGGGCTCTGCTGTGTGCTGCTGCTGTGTGG
AGCAGTCTTCGTTTCGCCCAGCCTGAACTTTCGCGCCCCACCAGTGATCCCTAATGT
GCCATTCCTTTGGGCTTGGAATGCGCCTTCTGAATTCTGCTTGGGAAAATTTGATGA
GCCTCTGGATATGTCTCTTTTCAGTTTTATTGGGTCACCAAGGATTAACGCGACTGGA
CAAGGAGTGACGATATTTTATGTCGATAGGCTCGGCTACTACCCCTACATAGATTCC
ATTACCGGCGTAACCGTGAATGGTGGTATCCCTCAAAAGATCTCTCTTCAAGACCAC
TTGGACAAAGCAAAAAAAGACATTACATTCTACATGCCGGTGGATAACCTGGGGAT
GGCCGTTATCGATTGGGAGGAGTGGAGACCCACGTGGGCTAGAAACTGGAAGCCGA
AGGACGTCTATAAAAACAGGTCTATCGAATTGGTTCAGCAGCAGAACGTGCAATTG
TCCTTGACTGAGGCGACAGAGAAGGCCAAGCAAGAGTTTGAGAAGGCGGGAAAGG
ACTTTTTGGTTGAGACCATTAAGCTCGGTAAACTGCTGCGACCTAATCATCTGTGGG
GTTACTACCTCTTCCCTGACTGCTACAATCACCATTACAAGAAACCGGGCTACAATG
GCTCTTGTTTTAATGTCGAAATCAAACGAAACGACGACCTGAGCTGGCTTTGGAACG
AATCCACCGCACTCTACCCCAGCATCTATCTGAACACCCAGCAGAGTCCTGTAGCAG
CAACGCTGTACGTCCGGAACCGGGTACGAGAGGCAATCAGAGTATCTAAGATCCCG
GATGCTAAATCCCCACTGCCGGTATTTGCGTACACCCGAATCGTGTTCACTGACCAG
GTTCTGAAGTTTCTCTCCCAGGACGAACTTGTCTATACGTTTGGAGAGACAGTAGCA
CTCGGCGCATCAGGCATTGTTATATGGGGAACCCTTAGCATCATGCGGTCAATGAAG
TCCTGCTTGCTTCTTGATAACTATATGGAGACAATCTTGAACCCCTATATCATCAATG
TAACACTTGCAGCAAAAATGTGCTCCCAAGTACTCTGTCAAGAGCAGGGAGTATGC
ATACGAAAAAATTGGAACAGTTCCGACTACCTGCACCTTAACCCCGATAATTTTGCT
ATACAGCTTGAAAAGGGCGGAAAATTTACAGTCCGAGGGAAGCCGACATTGGAGGA
TCTCGAGCAATTCTCTGAAAAGTTTTATTGCTCATGCTACAGTACCCTTAGCTGTAAA
GAAAAGGCGGACGTCAAGGATACTGACGCCGTGGACGTCTGCATCGCCGACGGAGT
TTGCATCGACGCATTTCTTAAACCTCCCATGGAAACCGAAGAGCCACAAATCTTCTA
TAACGCTTCTCCCTCAACACTTAGTGCTACTATGTTTATAGTTTCTATTTTGTTCCTTA
TTATTTCAAGTGTAGCTAGTCTT SEQ ID NO: 233 amino acid sequence of CAR D0422 ROR1 ScFv9 IgG4H CD8TM BBz 2A tPA-SP PH20 GPI MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRAKRGSGATNF
SLLKQAGDVEENPGPRAKRMDAMKRGLCCVLLLCGAVFVSPSLNFRAPPVIPNVPFLW -continued AWNAPSEFCLGKFDEPLDMSLFSFIGSPRINATGQGVTIFYVDRLGYYPYIDSITGVTVNG
GIPQKISLQDHLDKAKKDITFYMPVDNLGMAVIDWEEWRPTWARNWKPKDVYKNRSIE
LVQQQNVQLSLTEATEKAKQEFEKAGKDFLVETIKLGKLLRPNHLWGYYLFPDCYNHH
YKKPGYNGSCFNVEIKRNDDLSWLWNESTALYPSIYLNTQQSPVAATLYVRNRVREAIR
VSKIPDAKSPLPVFAYTRIVFTDQVLKFLSQDELVYTFGETVALGASGIVIWGTLSIMRSM
KSCLLLDNYMETILNPYIINVTLAAKMCSQVLCQEQGVCIRKNWNSSDYLHLNPDNFAI
QLEKGGKFTVRGKPTLEDLEQFSEKFYCSCYSTLSCKEKADVKDTDAVDVCIADGVCID
AFLKPPMETEEPQIFYNASPSTLSATMFIVSILFLIISSVASL SEQ ID NO: 234 nucleotide sequence of CAR D0422 ROR1 ScFv9 IgG4H CD8TM BBz 2A tPA-SP PH20 GPI ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGCTGAGCAGGCTGAGATC
TGACGACACGGCCGTGTATTACTGTGCGAGTTATAATGATGCTTTTGATATCTGGGG
CCAAGGCACCCTGGTCACCGTCTCCTCAGGAGGTGGCGGGTCTGGTGGTGGCGGTA
GCGGTGGTGGCGGATCCAATTTTATGCTGACTCAGCCCCACTCTGTGTCGGAGTCTC
CGGGGAAGACGGTAACCATCTCCTGCACCCGCAGCAGTGGCAGCATTGCCAGCAAC
TATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCCCTGAGG
AGGAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAGAGA
GGAGTACGACGTGCTGGACAAGCGACGCGGACGCGACCCGGAGATGGGGGGGAAA
CCACGGCGGAAAAACCCTCAGGAAGGACTGTACAACGAACTCCAGAAAGACAAGA
TGGCGGAAGCCTACTCAGAAATCGGGATGAAGGGAGAGCGGAGGAGGGGAAAGGG
TCACGACGGGCTGTACCAGGGACTGAGCACCGCCACTAAGGATACCTACGATGCCT
TGCATATGCAAGCACTCCCACCCCGGCGGGCAAAGCGGGGCTCAGGGGCGACTAAC
TTTTCACTGTTGAAGCAGGCCGGGGATGTGGAGGAGAATCCTGGTCCTAGAGCaAAG
CGAATGGATGCAATGAAGAGAGGGCTCTGCTGTGTGCTGCTGCTGTGTGGAGCAGT
CTTCGTTTCGCCCAGCCTGAACTTTCGCGCCCCACCAGTGATCCCTAATGTGCCATTC
CTTTGGGCTTGGAATGCGCCTTCTGAATTCTGCTTGGGAAAATTTGATGAGCCTCTG
GATATGTCTCTTTTCAGTTTTATTGGGTCACCAAGGATTAACGCGACTGGACAAGGA
GTGACGATATTTTATGTCGATAGGCTCGGCTACTACCCCTACATAGATTCCATTACC
GGCGTAACCGTGAATGGTGGTATCCCTCAAAAGATCTCTCTTCAAGACCACTTGGAC
AAAGCAAAAAAAGACATTACATTCTACATGCCGGTGGATAACCTGGGGATGGCCGT
TATCGATTGGGAGGAGTGGAGACCCACGTGGGCTAGAAACTGGAAGCCGAAGGACG
TCTATAAAAACAGGTCTATCGAATTGGTTCAGCAGCAGAACGTGCAATTGTCCTTGA
CTGAGGCGACAGAGAAGGCCAAGCAAGAGTTTGAGAAGGCGGGAAAGGACTTTTTG
GTTGAGACCATTAAGCTCGGTAAACTGCTGCGACCTAATCATCTGTGGGGTTACTAC
CTCTTCCCTGACTGCTACAATCACCATTACAAGAAACCGGGCTACAATGGCTCTTGT
TTTAATGTCGAAATCAAACGAAACGACGACCTGAGCTGGCTTTGGAACGAATCCAC
CGCACTCTACCCCAGCATCTATCTGAACACCCAGCAGAGTCCTGTAGCAGCAACGCT
GTACGTCCGGAACCGGGTACGAGAGGCAATCAGAGTATCTAAGATCCCGGATGCTA
AATCCCCACTGCCGGTATTTGCGTACACCCGAATCGTGTTCACTGACCAGGTTCTGA
AGTTTCTCTCCCAGGACGAACTTGTCTATACGTTTGGAGAGACAGTAGCACTCGGCG
CATCAGGCATTGTTATATGGGGAACCCTTAGCATCATGCGGTCAATGAAGTCCTGCT
TGCTTCTTGATAACTATATGGAGACAATCTTGAACCCCTATATCATCAATGTAACAC
TTGCAGCAAAAATGTGCTCCCAAGTACTCTGTCAAGAGCAGGGAGTATGCATACGA
AAAAATTGGAACAGTTCCGACTACCTGCACCTTAACCCCGATAATTTTGCTATACAG
CTTGAAAAGGGCGGAAAATTTACAGTCCGAGGGAAGCCGACATTGGAGGATCTCGA
GCAATTCTCTGAAAAGTTTTATTGCTCATGCTACAGTACCCTTAGCTGTAAAGAAAA
GGCGGACGTCAAGGATACTGACGCCGTGGACGTCTGCATCGCCGACGGAGTTTGCA
TCGACGCATTTCTTAAACCTCCCATGGAAACCGAAGAGCCACAAATCTTCTATAACG
CTTCTCCCTCAACACTTAGTGCTACTATGTTTATAGTTTCTATTTTGTTCCTTATTATT
TCAAGTGTAGCTAGTCTT SEQ ID NO: 235 amino acid sequence of CAR D0460 ROR1 ScFv9 IgG4H CD8TM BBz 2A tPA-SP PH20 7 A.A. of GPI MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRMDAMKRGLCCVLLLCGAVFVSPSLNFRAPPVIPNVPFLW
AWNAPSEFCLGKFDEPLDMSLFSFIGSPRINATGQGVTIFYVDRLGYYPYIDSITGVTVNG
GIPQKISLQDHLDKAKKDITFYMPVDNLGMAVIDWEEWRPTWARNWKPKDVYKNRSIE
LVQQQNVQLSLTEATEKAKQEFEKAGKDFLVETIKLGKLLRPNHLWGYYLFPDCYNHH
YKKPGYNGSCFNVEIKRNDDLSWLWNESTALYPSIYLNTQQSPVAATLYVRNRVREAIR
VSKIPDAKSPLPVFAYTRIVFTDQVLKFLSQDELVYTFGETVALGASGIVIWGTLSIMRSM -continued KSCLLLDNYMETILNPYIINVTLAAKMCSQVLCQEQGVCIRKNWNSSDYLHLNPDNFAI
QLEKGGKFTVRGKPTLEDLEQFSEKFYCSCYSTLSCKEKADVKDTDAVDVCIADGVCID
AFLKPPMETEEPQIFYNASPSTLS SEQ ID NO: 236 nucleotide sequence of CAR D0460 ROR1 ScFv9 IgG4H CD8TM BBz 2A tPA-SP PH20 7 A.A. of GPI ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGCTGAGCAGGCTGAGATC
TGACGACACGGCCGTGTATTACTGTGCGAGTTATAATGATGCTTTTGATATCTGGGG
CCAAGGCACCCTGGTCACCGTCTCCTCAGGAGGTGGCGGGTCTGGTGGTGGCGGTA
GCGGTGGTGGCGGATCCAATTTTATGCTGACTCAGCCCCACTCTGTGTCGGAGTCTC
CGGGGAAGACGGTAACCATCTCCTGCACCCGCAGCAGTGGCAGCATTGCCAGCAAC
TATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCCCTGAGG
AGGAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAGAGA
GGAGTACGACGTGCTGGACAAGCGACGCGGACGCGACCCGGAGATGGGGGGGAAA
CCACGGCGGAAAAACCCTCAGGAAGGACTGTACAACGAACTCCAGAAAGACAAGA
TGGCGGAAGCCTACTCAGAAATCGGGATGAAGGGAGAGCGGAGGAGGGGAAAGGG
TCACGACGGGCTGTACCAGGGACTGAGCACCGCCACTAAGGATACCTACGATGCCT
TGCATATGCAAGCACTCCCACCCCGGCGGGCAAAGCGGGGCTCAGGGGCGACTAAC
TTTTCACTGTTGAAGCAGGCCGGGGATGTGGAGGAGAATCCTGGTCCTAGAGCaAAG
CGAATGGATGCAATGAAGAGAGGGCTCTGCTGTGTGCTGCTGCTGTGTGGAGCAGT
CTTCGTTTCGCCCAGCCTGAACTTTCGCGCCCCACCAGTGATCCCTAATGTGCCATTC
CTTTGGGCTTGGAATGCGCCTTCTGAATTCTGCTTGGGAAAATTTGATGAGCCTCTG
GATATGTCTCTTTTCAGTTTTATTGGGTCACCAAGGATTAACGCGACTGGACAAGGA
GTGACGATATTTTATGTCGATAGGCTCGGCTACTACCCCTACATAGATTCCATTACC
GGCGTAACCGTGAATGGTGGTATCCCTCAAAAGATCTCTCTTCAAGACCACTTGGAC
AAAGCAAAAAAAGACATTACATTCTACATGCCGGTGGATAACCTGGGGATGGCCGT
TATCGATTGGGAGGAGTGGAGACCCACGTGGGCTAGAAACTGGAAGCCGAAGGACG
TCTATAAAAACAGGTCTATCGAATTGGTTCAGCAGCAGAACGTGCAATTGTCCTTGA
CTGAGGCGACAGAGAAGGCCAAGCAAGAGTTTGAGAAGGCGGGAAAGGACTTTTTG
GTTGAGACCATTAAGCTCGGTAAACTGCTGCGACCTAATCATCTGTGGGGTTACTAC
CTCTTCCCTGACTGCTACAATCACCATTACAAGAAACCGGGCTACAATGGCTCTTGT
TTTAATGTCGAAATCAAACGAAACGACGACCTGAGCTGGCTTTGGAACGAATCCAC
CGCACTCTACCCCAGCATCTATCTGAACACCCAGCAGAGTCCTGTAGCAGCAACGCT
GTACGTCCGGAACCGGGTACGAGAGGCAATCAGAGTATCTAAGATCCCGGATGCTA
AATCCCCACTGCCGGTATTTGCGTACACCCGAATCGTGTTCACTGACCAGGTTCTGA
AGTTTCTCTCCCAGGACGAACTTGTCTATACGTTTGGAGAGACAGTAGCACTCGGCG
CATCAGGCATTGTTATATGGGGAACCCTTAGCATCATGCGGTCAATGAAGTCCTGCT
TGCTTCTTGATAACTATATGGAGACAATCTTGAACCCCTATATCATCAATGTAACAC
TTGCAGCAAAAATGTGCTCCCAAGTACTCTGTCAAGAGCAGGGAGTATGCATACGA
AAAAATTGGAACAGTTCCGACTACCTGCACCTTAACCCCGATAATTTTGCTATACAG
CTTGAAAAGGGCGGAAAATTTACAGTCCGAGGGAAGCCGACATTGGAGGATCTCGA
GCAATTCTCTGAAAAGTTTTATTGCTCATGCTACAGTACCCTTAGCTGTAAAGAAAA
GGCGGACGTCAAGGATACTGACGCCGTGGACGTCTGCATCGCCGACGGAGTTTGCA
TCGACGCATTTCTTAAACCTCCCATGGAAACCGAAGAGCCACAAATCTTCTATAACG
CTTCTCCCTCAACACTTAGT SEQ ID NO: 237 amino acid sequence of CAR D0459 ROR1 ScFv9 IgG4H CD8TM BBz 2A tPA-SP PH20

MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRMDAMKRGLCCVLLLCGAVFVSPSLNFRAPPVIPNVPFLW
AWNAPSEFCLGKFDEPLDMSLFSFIGSPRINATGQGVTIFYVDRLGYYPYIDSITGVTVNG
GIPQKISLQDHLDKAKKDITFYMPVDNLGMAVIDWEEWRPTWARNWKPKDVYKNRSIE
LVQQQNVQLSLTEATEKAKQEFEKAGKDFLVETIKLGKLLRPNHLWGYYLFPDCYNHH

-continued

YKKPGYNGSCFNVEIKRNDDLSWLWNESTALYPSIYLNTQQSPVAATLYVRNRVREAIR
VSKIPDAKSPLPVFAYTRIVFTDQVLKFLSQDELVYTFGETVALGASGIVIWGTLSIMRSM
KSCLLLDNYMETILNPYIINVTLAAKMCSQVLCQEQGVCIRKNWNSSDYLHLNPDNFAI
QLEKGGKFTVRGKPTLEDLEQFSEKFYCSCYSTLSCKEKADVKDTDAVDVCIADGVCID
AFLKPPMETEEPQIFYN

SEQ ID NO: 238 nucleotide sequence of CAR D0459 ROR1 ScFv9 IgG4H CD8TM BBz 2A tPA-SP PH20

ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGCTGAGCAGGCTGAGATC
TGACGACACGGCCGTGTATTACTGTGCGAGTTATAATGATGCTTTTGATATCTGGGG
CCAAGGCACCCTGGTCACCGTCTCCTCAGGAGGTGGCGGGTCTGGTGGTGGCGGTA
GCGGTGGTGGCGGATCCAATTTTATGCTGACTCAGCCCCACTCTGTGTCGGAGTCTC
CGGGGAAGACGGTAACCATCTCCTGCACCCGCAGCAGTGGCAGCATTGCCAGCAAC
TATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCCCTGAGG
AGGAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAGAGA
GGAGTACGACGTGCTGGACAAGCGACGCGGACGCGACCCGGAGATGGGGGGGAAA
CCACGGCGGAAAAACCCTCAGGAAGGACTGTACAACGAACTCCAGAAAGACAAGA
TGGCGGAAGCCTACTCAGAAATCGGGATGAAGGGAGAGCGGAGGAGGGGAAAGGG
TCACGACGGGCTGTACCAGGGACTGAGCACCGCCACTAAGGATACCTACGATGCCT
TGCATATGCAAGCACTCCCACCCCGGCGGGCAAAGCGGGGCTCAGGGGCGACTAAC
TTTTCACTGTTGAAGCAGGCCGGGGATGTGGAGGAGAATCCTGGTCCTAGAGCaAAG
CGAATGGATGCAATGAAGAGAGGGCTCTGCTGTGTGCTGCTGCTGTGTGGAGCAGT
CTTCGTTTCGCCCAGCCTGAACTTTCGCGCCCCACCAGTGATCCCTAATGTGCCATTC
CTTTGGGCTTGGAATGCGCCTTCTGAATTCTGCTTGGGAAAATTTGATGAGCCTCTG
GATATGTCTCTTTTCAGTTTTATTGGGTCACCAAGGATTAACGCGACTGGACAAGGA
GTGACGATATTTTATGTCGATAGGCTCGGCTACTACCCCTACATAGATTCCATTACC
GGCGTAACCGTGAATGGTGGTATCCCTCAAAAGATCTCTCTTCAAGACCACTTGGAC
AAAGCAAAAAAAGACATTACATTCTACATGCCGGTGGATAACCTGGGGATGGCCGT
TATCGATTGGGAGGAGTGGAGACCCACGTGGGCTAGAAACTGGAAGCCGAAGGACG
TCTATAAAAACAGGTCTATCGAATTGGTTCAGCAGCAGAACGTGCAATTGTCCTTGA
CTGAGGCGACAGAGAAGGCCAAGCAAGAGTTTGAGAAGGCGGGAAAGGACTTTTTG
GTTGAGACCATTAAGCTCGGTAAACTGCTGCGACCTAATCATCTGTGGGGTTACTAC
CTCTTCCCTGACTGCTACAATCACCATTACAAGAAACCGGGCTACAATGGCTCTTGT
TTTAATGTCGAAATCAAACGAAACGACGACCTGAGCTGGCTTTGGAACGAATCCAC
CGCACTCTACCCCAGCATCTATCTGAACACCCAGCAGAGTCCTGTAGCAGCAACGCT
GTACGTCCGGAACCGGGTACGAGAGGCAATCAGAGTATCTAAGATCCCGGATGCTA
AATCCCCACTGCCGGTATTTGCGTACACCCGAATCGTGTTCACTGACCAGGTTCTGA
AGTTTCTCTCCCAGGACGAACTTGTCTATACGTTTGGAGAGACAGTAGCACTCGGCG
CATCAGGCATTGTTATATGGGGAACCCTTAGCATCATGCGGTCAATGAAGTCCTGCT
TGCTTCTTGATAACTATATGGAGACAATCTTGAACCCCTATATCATCAATGTAACAC
TTGCAGCAAAAATGTGCTCCCAAGTACTCTGTCAAGAGCAGGGAGTATGCATACGA
AAAAATTGGAACAGTTCCGACTACCTGCACCTTAACCCCGATAATTTTGCTATACAG
CTTGAAAAGGGCGGAAAATTTACAGTCCGAGGGAAGCCGACATTGGAGGATCTCGA
GCAATTCTCTGAAAAGTTTTATTGCTCATGCTACAGTACCCTTAGCTGTAAAGAAAA
GGCGGACGTCAAGGATACTGACGCCGTGGACGTCTGCATCGCCGACGGAGTTTGCA
TCGACGCATTTCTTAAACCTCCCATGGAAACCGAAGAGCCACAAATCTTCTATAAC

SEQ ID NO: 239 amino acid sequence of CAR D0461 ROR1 ScFv9 IgG4H CD8TM BBz 2A NSP PH20 GPI MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRMGVLKFKHIFFRSFVKSSGVSQIVFTFLLIPCCLTLNFRAPP
VIPNVPFLWAWNAPSEFCLGKFDEPLDMSLFSFIGSPRINATGQGVTIFYVDRLGYYPYID
SITGVTVNGGIPQKISLQDHLDKAKKDITFYMPVDNLGMAVIDWEEWRPTWARNWKPK
DVYKNRSIELVQQQNVQLSLTEATEKAKQEFEKAGKDFLVETIKLGKLLRPNHLWGYY -continued LFPDCYNHHYKKPGYNGSCFNVEIKRNDDLSWLWNESTALYPSIYLNTQQSPVAATLY
VRNRVREAIRVSKIPDAKSPLPVFAYTRIVFTDQVLKFLSQDELVYTFGETVALGASGIVI
WGTLSIMRSMKSCLLLDNYMETILNPYIINVTLAAKMCSQVLCQEQGVCIRKNWNSSDY
LHLNPDNFAIQLEKGGKFTVRGKPTLEDLEQFSEKFYCSCYSTLSCKEKADVKDTDAVD
VCIADGVCIDAFLKPPMETEEPQIFYNASPSTLSATMFIVSILFLIISSVASL SEQ ID NO: 240 nucleotide sequence of CAR D0461 ROR1 ScFv9 IgG4H CD8TM BBz 2A NSP PH20 GPI ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGCTGAGCAGGCTGAGATC
TGACGACACGGCCGTGTATTACTGTGCGAGTTATAATGATGCTTTTGATATCTGGGG
CCAAGGCACCCTGGTCACCGTCTCCTCAGGAGGTGGCGGGTCTGGTGGTGGCGGTA
GCGGTGGTGGCGGATCCAATTTTATGCTGACTCAGCCCCACTCTGTGTCGGAGTCTC
CGGGGAAGACGGTAACCATCTCCTGCACCCGCAGCAGTGGCAGCATTGCCAGCAAC
TATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCCCTGAGG
AGGAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAGAGA
GGAGTACGACGTGCTGGACAAGCGACGCGGACGCGACCCGGAGATGGGGGGGAAA
CCACGGCGGAAAAACCCTCAGGAAGGACTGTACAACGAACTCCAGAAAGACAAGA
TGGCGGAAGCCTACTCAGAAATCGGGATGAAGGGAGAGCGGAGGAGGGGAAAGGG
TCACGACGGGCTGTACCAGGGACTGAGCACCGCCACTAAGGATACCTACGATGCCT
TGCATATGCAAGCACTCCCACCCCGGCGGGCAAAGCGGGGCTCAGGGGCGACTAAC
TTTTCACTGTTGAAGCAGGCCGGGGATGTGGAGGAGAATCCTGGTCCTAGAGCaAAG
CGAATGGGAGTGCTAAAATTCAAGCACATCTTTTTCAGAAGCTTTGTTAAATCAAGT
GGAGTATCCCAGATAGTTTTCACCTTCCTTCTGATTCCATGTTGCTTGACTCTGAACT
TTCGCGCCCCACCAGTGATCCCTAATGTGCCATTCCTTTGGGCTTGGAATGCGCCTTC
TGAATTCTGCTTGGGAAAATTTGATGAGCCTCTGGATATGTCTCTTTTCAGTTTTATT
GGGTCACCAAGGATTAACGCGACTGGACAAGGAGTGACGATATTTTATGTCGATAG
GCTCGGCTACTACCCCTACATAGATTCCATTACCGGCGTAACCGTGAATGGTGGTAT
CCCTCAAAAGATCTCTCTTCAAGACCACTTGGACAAAGCAAAAAAAGACATTACATT
CTACATGCCGGTGGATAACCTGGGGATGGCCGTTATCGATTGGGAGGAGTGGAGAC
CCACGTGGGCTAGAAACTGGAAGCCGAAGGACGTCTATAAAAACAGGTCTATCGAA
TTGGTTCAGCAGCAGAACGTGCAATTGTCCTTGACTGAGGCGACAGAGAAGGCCAA
GCAAGAGTTTGAGAAGGCGGGAAAGGACTTTTTGGTTGAGACCATTAAGCTCGGTA
AACTGCTGCGACCTAATCATCTGTGGGGTTACTACCTCTTCCCTGACTGCTACAATCA
CCATTACAAGAAACCGGGCTACAATGGCTCTTGTTTTAATGTCGAAATCAAACGAAA
CGACGACCTGAGCTGGCTTTGGAACGAATCCACCGCACTCTACCCCAGCATCTATCT
GAACACCCAGCAGAGTCCTGTAGCAGCAACGCTGTACGTCCGGAACCGGGTACGAG
AGGCAATCAGAGTATCTAAGATCCCGGATGCTAAATCCCCACTGCCGGTATTTGCGT
ACACCCGAATCGTGTTCACTGACCAGGTTCTGAAGTTTCTCTCCCAGGACGAACTTG
TCTATACGTTTGGAGAGACAGTAGCACTCGGCGCATCAGGCATTGTTATATGGGGAA
CCCTTAGCATCATGCGGTCAATGAAGTCCTGCTTGCTTCTTGATAACTATATGGAGA
CAATCTTGAACCCCTATATCATCAATGTAACACTTGCAGCAAAAATGTGCTCCCAAG
TACTCTGTCAAGAGCAGGGAGTATGCATACGAAAAAATTGGAACAGTTCCGACTAC
CTGCACCTTAACCCCGATAATTTTGCTATACAGCTTGAAAAGGGCGGAAAATTTACA
GTCCGAGGGAAGCCGACATTGGAGGATCTCGAGCAATTCTCTGAAAAGTTTTATTGC
TCATGCTACAGTACCCTTAGCTGTAAAGAAAAGGCGGACGTCAAGGATACTGACGC
CGTGGACGTCTGCATCGCCGACGGAGTTTGCATCGACGCATTTCTTAAACCTCCCAT
GGAAACCGAAGAGCCACAAATCTTCTATAACGCTTCTCCCTCAACACTTAGTGCTAC
TATGTTTATAGTTTCTATTTTGTTCCTTATTATTTCAAGTGTAGCTAGTCTT SEQ ID NO: 241 amino acid sequence of CAR D0463 ROR1 ScFv9 IgG4H CD8TM BBz 2A NSP PH20 7 A.A. of GPI MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRMGVLKFKHIFFRSFVKSSGVSQIVFTFLLIPCCLTLNFRAPP
VIPNVPFLWAWNAPSEFCLGKFDEPLDMSLFSFIGSPRINATGQGVTIFYVDRLGYYPYID
SITGVTVNGGIPQKISLQDHLDKAKKDITFYMPVDNLGMAVIDWEEWRPTWARNWKPK
DVYKNRSIELVQQQNVQLSLTEATEKAKQEFEKAGKDFLVETIKLGKLLRPNHLWGYY
LFPDCYNHHYKKPGYNGSCFNVEIKRNDDLSWLWNESTALYPSIYLNTQQSPVAATLY
VRNRVREAIRVSKIPDAKSPLPVFAYTRIVFTDQVLKFLSQDELVYTFGETVALGASGIVI
WGTLSIMRSMKSCLLLDNYMETILNPYIINVTLAAKMCSQVLCQEQGVCIRKNWNSSDY
LHLNPDNFAIQLEKGGKFTVRGKPTLEDLEQFSEKFYCSCYSTLSCKEKADVKDTDAVD
VCIADGVCIDAFLKPPMETEEPQIFYNASPSTLS SEQ ID NO: 242 nucleotide sequence of CAR D0463 ROR1 ScFv9 lgG4H CD8TM BBz 2A NSP PH20 7 A.A. of GPI
ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGCTGAGCAGGCTGAGATC
TGACGACACGGCCGTGTATTACTGTGCGAGTTATAATGATGCTTTTGATATCTGGGG
CCAAGGCACCCTGGTCACCGTCTCCTCAGGAGGTGGCGGGTCTGGTGGTGGCGGTA
GCGGTGGTGGCGGATCCAATTTTATGCTGACTCAGCCCCACTCTGTGTCGGAGTCTC
CGGGGAAGACGGTAACCATCTCCTGCACCCGCAGCAGTGGCAGCATTGCCAGCAAC
TATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCCCTGAGG
AGGAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAGAGA
GGAGTACGACGTGCTGGACAAGCGACGCGGACGCGACCCGGAGATGGGGGGGAAA
CCACGGCGGAAAAACCCTCAGGAAGGACTGTACAACGAACTCCAGAAAGACAAGA
TGGCGGAAGCCTACTCAGAAATCGGGATGAAGGGAGAGCGGAGGAGGGGAAAGGG
TCACGACGGGCTGTACCAGGGACTGAGCACCGCCACTAAGGATACCTACGATGCCT
TGCATATGCAAGCACTCCCACCCCGGCGGGCAAAGCGGGGCTCAGGGGCGACTAAC
TTTTCACTGTTGAAGCAGGCCGGGGATGTGGAGGAGAATCCTGGTCCTAGAGCaAAG
CGAATGGGAGTGCTAAAATTCAAGCACATCTTTTTCAGAAGCTTTGTTAAATCAAGT
GGAGTATCCCAGATAGTTTTCACCTTCCTTCTGATTCCATGTTGCTTGACTCTGAACT
TTCGCGCCCCACCAGTGATCCCTAATGTGCCATTCCTTTGGGCTTGGAATGCGCCTTC
TGAATTCTGCTTGGGAAAATTTGATGAGCCTCTGGATATGTCTCTTTTCAGTTTTATT
GGGTCACCAAGGATTAACGCGACTGGACAAGGAGTGACGATATTTTATGTCGATAG
GCTCGGCTACTACCCCTACATAGATTCCATTACCGGCGTAACCGTGAATGGTGGTAT
CCCTCAAAAGATCTCTCTTCAAGACCACTTGGACAAAGCAAAAAAAGACATTACATT
CTACATGCCGGTGGATAACCTGGGGATGGCCGTTATCGATTGGGAGGAGTGGAGAC
CCACGTGGGCTAGAAACTGGAAGCCGAAGGACGTCTATAAAAACAGGTCTATCGAA
TTGGTTCAGCAGCAGAACGTGCAATTGTCCTTGACTGAGGCGACAGAGAAGGCCAA
GCAAGAGTTTGAGAAGGCGGGAAAGGACTTTTTGGTTGAGACCATTAAGCTCGGTA
AACTGCTGCGACCTAATCATCTGTGGGGTTACTACCTCTTCCCTGACTGCTACAATCA
CCATTACAAGAAACCGGGCTACAATGGCTCTTGTTTTAATGTCGAAATCAAACGAAA
CGACGACCTGAGCTGGCTTTGGAACGAATCCACCGCACTCTACCCCAGCATCTATCT
GAACACCCAGCAGAGTCCTGTAGCAGCAACGCTGTACGTCCGGAACCGGGTACGAG
AGGCAATCAGAGTATCTAAGATCCCGGATGCTAAATCCCCACTGCCGGTATTTGCGT
ACACCCGAATCGTGTTCACTGACCAGGTTCTGAAGTTTCTCTCCCAGGACGAACTTG
TCTATACGTTTGGAGAGACAGTAGCACTCGGCGCATCAGGCATTGTTATATGGGGAA
CCCTTAGCATCATGCGGTCAATGAAGTCCTGCTTGCTTCTTGATAACTATATGGAGA
CAATCTTGAACCCCTATATCATCAATGTAACACTTGCAGCAAAAATGTGCTCCCAAG
TACTCTGTCAAGAGCAGGGAGTATGCATACGAAAAAATTGGAACAGTTCCGACTAC
CTGCACCTTAACCCCGATAATTTTGCTATACAGCTTGAAAAGGGCGGAAAATTTACA
GTCCGAGGGAAGCCGACATTGGAGGATCTCGAGCAATTCTCTGAAAAGTTTTATTGC
TCATGCTACAGTACCCTTAGCTGTAAAGAAAAGGCGGACGTCAAGGATACTGACGC
CGTGGACGTCTGCATCGCCGACGGAGTTTGCATCGACGCATTTCTTAAACCTCCCAT
GGAAACCGAAGAGCCACAAATCTTCTATAACGCTTCTCCCTCAACACTTAGT SEQ ID NO: 243 amino acid sequence of CAR D0462 ROR1 ScFv9 IgG4H CD8TM BBz 2A NSP PH20
MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRMGVLKFKHIFFRSFVKSSGVSQIVFTFLLIPCCLTLNFRAPP
VIPNVPFLWAWNAPSEFCLGKFDEPLDMSLFSFIGSPRINATGQGVTIFYVDRLGYYPYID
SITGVTVNGGIPQKISLQDHLDKAKKDITFYMPVDNLGMAVIDWEEWRPTWARNWKPK
DVYKNRSIELVQQQNVQLSLTEATEKAKQEFEKAGKDFLVETIKLGKLLRPNHLWGYY
LFPDCYNHHYKKPGYNGSCFNVEIKRNDDLSWLWNESTALYPSIYLNTQQSPVAATLY
VRNRVREAIRVSKIPDAKSPLPVFAYTRIVFTDQVLKFLSQDELVYTFGETVALGASGIVI
WGTLSIMRSMKSCLLLDNYMETILNPYIINVTLAAKMCSQVLCQEQGVCIRKNWNSSDY
LHLNPDNFAIQLEKGGKFTVRGKPTLEDLEQFSEKFYCSCYSTLSCKEKADVKDTDAVD
VCIADGVCIDAFLKPPMETEEPQIFYN SEQ ID NO: 244 nucleotide sequence of CAR D0462 ROR1 ScFv9 IgG4H CD8TM BBz 2A PH20
ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA -continued TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGCTGAGCAGGCTGAGATC
TGACGACACGGCCGTGTATTACTGTGCGAGTTATAATGATGCTTTTGATATCTGGGG
CCAAGGCACCCTGGTCACCGTCTCCTCAGGAGGTGGCGGGTCTGGTGGTGGCGGTA
GCGGTGGTGGCGGATCCAATTTTATGCTGACTCAGCCCCACTCTGTGTCGGAGTCTC
CGGGGAAGACGGTAACCATCTCCTGCACCCGCAGCAGTGGCAGCATTGCCAGCAAC
TATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTCAT
GCGGCCCGTGCAGACGACTCAGGAAGAGGACGGATGCTCGTGCAGATTCCCTGAGG
AGGAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAGAGA
GGAGTACGACGTGCTGGACAAGCGACGCGGACGCGACCCGGAGATGGGGGGGAAA
CCACGGCGGAAAAACCCTCAGGAAGGACTGTACAACGAACTCCAGAAAGACAAGA
TGGCGGAAGCCTACTCAGAAATCGGGATGAAGGGAGAGCGGAGGAGGGGAAAGGG
TCACGACGGGCTGTACCAGGGACTGAGCACCGCCACTAAGGATACCTACGATGCCT
TGCATATGCAAGCACTCCCACCCCGGCGGGCAAAGCGGGGCTCAGGGGCGACTAAC
TTTTCACTGTTGAAGCAGGCCGGGGATGTGGAGGAGAATCCTGGTCCTAGAGCaAAG
CGAATGGGAGTGCTAAAATTCAAGCACATCTTTTTCAGAAGCTTTGTTAAATCAAGT
GGAGTATCCCAGATAGTTTTCACCTTCCTTCTGATTCCATGTTGCTTGACTCTGAACT
TTCGCGCCCCACCAGTGATCCCTAATGTGCCATTCCTTTGGGCTTGGAATGCGCCTTC
TGAATTCTGCTTGGGAAAATTTGATGAGCCTCTGGATATGTCTCTTTTCAGTTTTATT
GGGTCACCAAGGATTAACGCGACTGGACAAGGAGTGACGATATTTTATGTCGATAG
GCTCGGCTACTACCCCTACATAGATTCCATTACCGGCGTAACCGTGAATGGTGGTAT
CCCTCAAAAGATCTCTCTTCAAGACCACTTGGACAAAGCAAAAAAAGACATTACATT
CTACATGCCGGTGGATAACCTGGGGATGGCCGTTATCGATTGGGAGGAGTGGAGAC
CCACGTGGGCTAGAAACTGGAAGCCGAAGGACGTCTATAAAAACAGGTCTATCGAA
TTGGTTCAGCAGCAGAACGTGCAATTGTCCTTGACTGAGGCGACAGAGAAGGCCAA
GCAAGAGTTTGAGAAGGCGGGAAAGGACTTTTTGGTTGAGACCATTAAGCTCGGTA
AACTGCTGCGACCTAATCATCTGTGGGGTTACTACCTCTTCCCTGACTGCTACAATCA
CCATTACAAGAAACCGGGCTACAATGGCTCTTGTTTTAATGTCGAAATCAAACGAAA
CGACGACCTGAGCTGGCTTTGGAACGAATCCACCGCACTCTACCCCAGCATCTATCT
GAACACCCAGCAGAGTCCTGTAGCAGCAACGCTGTACGTCCGGAACCGGGTACGAG
AGGCAATCAGAGTATCTAAGATCCCGGATGCTAAATCCCCACTGCCGGTATTTGCGT
ACACCCGAATCGTGTTCACTGACCAGGTTCTGAAGTTTCTCTCCCAGGACGAACTTG
TCTATACGTTTGGAGAGACAGTAGCACTCGGCGCATCAGGCATTGTTATATGGGGAA
CCCTTAGCATCATGCGGTCAATGAAGTCCTGCTTGCTTCTTGATAACTATATGGAGA
CAATCTTGAACCCCTATATCATCAATGTAACACTTGCAGCAAAAATGTGCTCCCAAG
TACTCTGTCAAGAGCAGGGAGTATGCATACGAAAAAATTGGAACAGTTCCGACTAC
CTGCACCTTAACCCCGATAATTTTGCTATACAGCTTGAAAAGGGCGGAAAATTTACA
GTCCGAGGGAAGCCGACATTGGAGGATCTCGAGCAATTCTCTGAAAAGTTTTATTGC
TCATGCTACAGTACCCTTAGCTGTAAAGAAAAGGCGGACGTCAAGGATACTGACGC
CGTGGACGTCTGCATCGCCGACGGAGTTTGCATCGACGCATTTCTTAAACCTCCCAT
GGAAACCGAAGAGCCACAAATCTTCTATAAC SEQ ID NO: 245 nucleotide sequence of CAR D0426 CD276-22 CD8 BBz
ATGCTCTTGCTCGTGACTTCTTTGCTTTTGTGCGAACTTCCGCACCCAGCCTTCCTTTT
GATACCTCAGGTACAGCTGCAGCAGTCAGGGGCTGAGGTGAAGAAGCCTGGAAGCT
CAGTGAAGGTCTCCTGCAAGGATTCTGGAGGCACCCTCAGCAGCCATGCTATCAGCT
GGGTGCGACAGGCCCCTGGACAAGGGCTTGAGTGGATGGGAGGAATCATCCCTATC
CTTGGTATAGCAAACTACGCACAGAAGTTCCAGGGCAGAGTCACGATTACAGCGGA
CGAATCCACGAGCACAGCCTACATGGAGCTGAGCAGCCTGAGATCTGAGGACACGG
CCGTGTATTACTGTGCGAGAGGGGGTCCAGGGAGTTACCATATGGACGTCTGGGGC
AAAGGCACCCTGGTCACCGTCTCCTCAGGAGGTGGCGGGTCTGGTGGAGGCGGCAG
CGGTGGTGGCGGATCCGAAATTGTGCTGACTCAGTCTCCAGCCACCCTGTCTTTGTC
TCCAGGGGAAAGAGCCACCCTCTCCTGCAGGGCCAGTCAGAGTGTTGGCAGCTCCTT
AGGCTGGTACCAACAGAAACCTGGCCAGGCTCCCAGGCTCCTCATCTATGATGTATC
CAACAGGGCCTCTGGCATCCCAGCCAGGTTCAGTGGCAGTGGGTCTGGGATAGACTT
CACTCTCACCATCAGCAGCCTAGAGCCTGAAGATTTTGCAGTTTATTACTGTCAGCA
GCGTAGCAACTGGCCCCCCATGTACACTTTTGGCCAGGGGACCAAGCTGGAGATCA
AAGCGGCCGCAACGACCACTCCTGCACCCCGCCCTCCGACTCCGGCCCCAACCATTG
CCAGCCAGCCCCTGTCCCTGCGGCCGGAAGCCTGCAGACCGGCTGCCGGCGGAGCC
GTCCATACCCGGGGACTGGATTTCGCCTGCGATATCTATATCTGGGCACCACTCGCC
GGAACCTGTGGAGTGCTGCTGCTGTCCCTTGTGATCACCCTGTACTGCAAGCGCGGA
CGGAAGAAACTCTTGTACATCTTCAAGCAGCCGTTCATGCGCCCTGTGCAAACCACC
CAAGAAGAGGACGGGTGCTCCTGCCGGTTCCCGGAAGAGGAAGAGGGCGGCTGCG
AACTGCGCGTGAAGTTTTCCCGGTCCGCCGACGCTCCGGCGTACCAGCAGGGGCAA
AACCAGCTGTACAACGAACTTAACCTCGGTCGCCGGGAAGAATATGACGTGCTGGA
CAAGCGGCGGGGAAGAGATCCCGAGATGGGTGGAAAGCCGCGGCGGAAGAACCCT
CAGGAGGGCTTGTACAACGAGCTGCAAAAGGACAAAATGGCCGAAGCCTACTCCGA
GATTGGCATGAAGGGAGAGCGCAGACGCGGGAAGGGACACGATGGACTGTACCAG
GGACTGTCAACCGCGACTAAGGACACTTACGACGCCCTGCACATGCAGGCCCTGCC
CCCGCGCTAA -continued SEQ ID NO: 246 amino acid sequence of CAR D0426 CD276-22 CD8 BBz
MLLLVTSLLLCELPHPAFLLIPQVQLQQSGAEVKKPGSSVKVSCKDSGGTLSSHAISWVR
QAPGQGLEWMGGIIPILGIANYAQKFQGRVTITADESTSTAYMELSSLRSEDTAVYYCAR
GGPGSYHMDVWGKGTLVTVSSGGGGSGGGGSGGGGSEIVLTQSPATLSLSPGERATLS
CRASQSVGSSLGWYQQKPGQAPRLLIYDVSNRASGIPARFSGSGSGIDFTLTISSLEPEDF
AVYYCQQRSNWPPMYTFGQGTKLEIKAAATTTPAPRPPTPAPTIASQPLSLRPEACRPAA
GGAVHTRGLDFACDIYIWAPLAGTCGVLLLSLVITLYCKRGRKKLLYIFKQPFMRPVQT
TQEEDGCSCRFPEEEEGGCELRVKFSRSADAPAYQQGQNQLYNELNLGRREEYDVLDK
RRGRDPEMGGKPRRKNPQEGLYNELQKDKMAEAYSEIGMKGERRRGKGHDGLYQGLS
TATKDTYDALHMQALPPR SEQ ID NO: 247 nucleotide sequence of CAR D0427 CD276-30 CD8 BBz
ATGCTCTTGCTCGTGACTTCTTTGCTTTTGTGCGAACTTCCGCACCCAGCCTTCCTTTT
GATACCTCAGCTGCAGCTGCAGGAGTCCGGCCCAGGACTGGTGAAGCCTTCGGAGA
CCCTGTCCCTCACCTGCGCTGTCTCTGGTGGCTCCGTCAGCAGTAGTAACTGGTGGA
GTTGGGTCCGCCAGCCCCCAGGGAAGGGGCTGGAGTGGATTGGGGAAATCTATCAT
AGTGGGAGCACCAACTACAACCCGTCCCTCAAGAGTCGAGTCACCATATCAGTAGA
CAAGTCCAAGAATCAATTCTCCCTGCACCTGAACTCTGTGACTCCCGAGGACACGGC
TGTGTACTACTGTGCGAGAGAGGTGGCTGGTTCTGCGGCTTTTGACATCTGGGGCCA
AGGGACAATGGTCACCGTCTCCTCAGGAGGTGGCGGGTCTGGTGGAGGCGGCAGCG
GTGGTGGCGGATCCCAGTCTGTCGTGACGCAGCCGCCCTCAGTGTCTGCGGCCCCAG
GACAGAAGGTCACCATCTCCTGCTCTGGAAGCAGCTCCAACATTGGGAATAATTATG
TATCCTGGTACCAGCAGCTCCCAGGAACAGCCCCCAAACTCCTCATCTATGGAAATA
ATAAGCGACCCTCAGGGATTCCTGACCGATTCTCTGGCTCCAAGTCTGGCACGTCAG
CCACCCTGGGCATCACCGGACTCCAGACTGGGGACGAGGCCGATTATTACTGCGGA
ACATGGGATAGCAGCCTGAGTGCGGTATTCGGCGGAGGCACCCAGCTGACCGTCCT
CGCGGCCGCAACGACCACTCCTGCACCCCGCCCTCCGACTCCGGCCCCAACCATTGC
CAGCCAGCCCCTGTCCCTGCGGCCGGAAGCCTGCAGACCGGCTGCCGGCGGAGCCG
TCCATACCCGGGGACTGGATTTCGCCTGCGATATCTATATCTGGGCACCACTCGCCG
GAACCTGTGGAGTGCTGCTGCTGTCCCTTGTGATCACCCTGTACTGCAAGCGCGGAC
GGAAGAAACTCTTGTACATCTTCAAGCAGCCGTTCATGCGCCCTGTGCAAACCACCC
AAGAAGAGGACGGGTGCTCCTGCCGGTTCCCGGAAGAGGAAGAGGGCGGCTGCGA
ACTGCGCGTGAAGTTTTCCCGGTCCGCCGACGCTCCGGCGTACCAGCAGGGGCAAA
ACCAGCTGTACAACGAACTTAACCTCGGTCGCCGGGAAGAATATGACGTGCTGGAC
AAGCGGCGGGGAAGAGATCCCGAGATGGGTGGAAAGCCGCGGCGGAAGAACCCTC
AGGAGGGCTTGTACAACGAGCTGCAAAAGGACAAAATGGCCGAAGCCTACTCCGAG
ATTGGCATGAAGGGAGAGCGCAGACGCGGGAAGGGACACGATGGACTGTACCAGG
GACTGTCAACCGCGACTAAGGACACTTACGACGCCCTGCACATGCAGGCCCTGCCC
CCGCGCTAA SEQ ID NO: 248 amino acid sequence of CAR D0427 CD276-30 CD8 BBz
MLLLVTSLLLCELPHPAFLLIPQLQLQESGPGLVKPSETLSLTCAVSGGSVSSSNWWSWV
RQPPGKGLEWIGEIYHSGSTNYNPSLKSRVTISVDKSKNQFSLHLNSVTPEDTAVYYCAR
EVAGSAAFDIWGQGTMVTVSSGGGGSGGGGSGGGGSQSVVTQPPSVSAAPGQKVTISC
SGSSSNIGNNYVSWYQQLPGTAPKLLIYGNNKRPSGIPDRFSGSKSGTSATLGITGLQTG
DEADYYCGTWDSSLSAVFGGGTQLTVLAAATTTPAPRPPTPAPTIASQPLSLRPEACRPA
AGGAVHTRGLDFACDIYIWAPLAGTCGVLLLSLVITLYCKRGRKKLLYIFKQPFMRPVQ
TTQEEDGCSCRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKGHDGLYQG
LSTATKDTYDALHMQALPPR SEQ ID NO: 249 nucleotide sequence of CAR D0480 CD276 376.96 CD8 BBz
ATGCTCTTGCTCGTGACTTCTTTGCTTTTGTGCGAACTTCCGCACCCAGCCTTCCTTTT
GATACCTGACATTGTGATGACCCAGTCTCACAAATTCATGTCCACATCAATTGGAGC
CAGGGTCAGCATCACCTGCAAGGCCAGTCAGGATGTGAGAACTGCTGTAGCCTGGT
ATCAACAGAAACCAGGCCAGTCTCCTAAACTTCTTATTTACTCAGCATCCTACCGGT
ACACTGGAGTCCCTGATCGCTTCACTGGCAGTGGATCTGGGACGGATTTCACTTTCA
CCATCAGCAGTGTGCAGGCTGAAGACCTGGCAGTTTATTACTGTCAGCAACATTATG
GTACTCCTCCGTGGACGTTCGGTGGAGGCACCAAGCTGGAAATCAAAGGCGGCGGA
GGATCTGGCGGAGGCGGAAGTGGCGGAGGGGGCTCTGAAGTGCAGCTGGTGGAGTC
TGGGGGAGGCTTGGTGAAGCCTGGAGGGTCCCTGAAACTCTCCTGTGAAGCCTCCA
GATTCACTTTCAGTAGCTATGCCATGTCTTGGGTTCGCCAGACTCCGGAGAAGAGGC
TGGAGTGGGTCGCAGCCATTAGTGGAGGTGGTAGGTACACCTACTATCCAGACAGT
ATGAAGGGTCGATTCACCATCTCCAGAGACAATGCCAAGAATTTCCTGTACCTGCAA
ATGAGCAGTCTGAGGTCTGAGGACACGGCCATGTATTACTGTGCAAGACACTATGAT
GGTTATCTTGACTACTGGGGCCAAGGCACCACTCTCACAGTCTCCTCAGCGGCCGCA
ACGACCACTCCTGCACCCCGCCCTCCGACTCCGGCCCCAACCATTGCCAGCCAGCCC
CTGTCCCTGCGGCCGGAAGCCTGCAGACCGGCTGCCGGCGGAGCCGTCCATACCCG
GGGACTGGATTTCGCCTGCGATATCTATATCTGGGCACCACTCGCCGGAACCTGTGG
AGTGCTGCTGCTGTCCCTTGTGATCACCCTGTACTGCAAGCGCGGACGGAAGAAACT
CTTGTACATCTTCAAGCAGCCGTTCATGCGCCCTGTGCAAACCACCCAAGAAGAGGA
CGGGTGCTCCTGCCGGTTCCCGGAAGAGGAAGAGGGCGGCTGCGAACTGCGCGTGA
AGTTTTCCCGGTCCGCCGACGCTCCGGCGTACCAGCAGGGGCAAAACCAGCTGTAC
AACGAACTTAACCTCGGTCGCCGGGAAGAATATGACGTGCTGGACAAGCGGCGGGG
AAGAGATCCCGAGATGGGTGGAAAGCCGCGGCGGAAGAACCCTCAGGAGGGCTTGT
ACAACGAGCTGCAAAAGGACAAAATGGCCGAAGCCTACTCCGAGATTGGCATGAAG
GGAGAGCGCAGACGCGGGAAGGGACACGATGGACTGTACCAGGGACTGTCAACCG
CGACTAAGGACACTTACGACGCCCTGCACATGCAGGCCCTGCCCCCGCGCTAA -continued SEQ ID NO: 250 amino acid sequence of CAR D0480 CD276 376.96 CD8 BBz
MLLLVTSLLLCELPHPAFLLIPDIVMTQSHKFMSTSIGARVSITCKASQDVRTAVAWYQQ
KPGQSPKLLIYSASYRYTGVPDRFTGSGSGTDFTFTISSVQAEDLAVYYCQQHYGTPPWT
FGGGTKLEIKGGGGSGGGGSGGGGSEVQLVESGGGLVKPGGSLKLSCEASRFTFSSYAM
SWVRQTPEKRLEWVAAISGGGRYTYYPDSMKGRFTISRDNAKNFLYLQMSSLRSEDTA
MYYCARHYDGYLDYWGQGTTLTVSSAAATTTPAPRPPTPAPTIASQPLSLRPEACRPAA
GGAVHTRGLDFACDIYIWAPLAGTCGVLLLSLVITLYCKRGRKKLLYIFKQPFMRPVQT
TQEEDGCSCRFPEEEEGGCELRVKFSRSADAPAYQQGQNQLYNELNLGRREEYDVLDK
RRGRDPEMGGKPRRKNPQEGLYNELQKDKMAEAYSEIGMKGERRRGKGHDGLYQGLS
TATKDTYDALHMQALPPR SEQ ID NO: 251 nucleotide sequence of CAR D0432 ROR1scFv9 IgG4 CD8 BBz 2A CD276-22 CD8 CD28 CCR
ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGITGAGCAGGCTGAGATCT
GACGACACGGCCGTGTATTACTGTGCGAGTTATAATGATGCTTTTGATATCTGGGGC
CAAGGCACCCTGGTCACCGTCTCCTCAGGAGGTGGCGGGTCTGGTGGTGGCGGTAG
CGGTGGTGGCGGATCCAATTTTATGCTGACTCAGCCCCACTCTGTGTCGGAGTCTCC
GGGGAAGACGGTAACCATCTCCTGCACCCGCAGCAGTGGCAGCATTGCCAGCAACT
ATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATCTGGGCCCCATTGGCTGGAACTTGCGGCGTGCTGCTCTTGTCTCTGGTCATTACC
CTGTACTGCAAGCGCGGACGGAAGAAACTCTTGTACATCTTCAAGCAGCCGTTCATG
CGCCCTGTGCAAACCACCCAAGAAGAGGACGGGTGCTCCTGCCGGTTCCCGGAAGA
GGAAGAGGGCGGCTGCGAACTGAGAGTGAAGTTTAGCCGCTCAGCCGATGCACCGG
CCTACCAGCAGGGACAGAACCAGCTCTACAACGAGCTCAACCTGGGTCGGCGGGAA
GAATATGACGTGCTGGACAAACGGCGCGGCAGAGATCCGGAGATGGGGGGAAAGC
CGAGGAGGAAGAACCCTCAAGAGGGCCTGTACAACGAACTGCAGAAGGACAAGAT
GGCGGAAGCCTACTCCGAGATCGGCATGAAGGGAGAACGCCGGAGAGGGAAGGGT
CATGACGGACTGTACCAGGGCCTGTCAACTGCCACTAAGGACACTTACGATGCGCTC
CATATGCAAGCTTTGCCCCCGCGGCGCGCGAAACGCGGCAGCGGCGCGACCAACTT
TAGCCTGCTGAAACAGGCGGGCGATGTGGAAGAAAACCCGGGCCCGCGAGCAAAG
AGGAATATTATGGCTCTGCCTGTTACGGCACTGCTCCTTCCGCTTGCATTGTTGTTGC
ACGCAGCGCGGCCCCAAGTGCAACTGCAACAATCCGGTGCTGAAGTGAAGAAACCG
GGTAGCTCCGTCAAGGTGTCTTGTAAAGATTCAGGCGGAACTTTGTCTTCTCATGCG
ATTTCATGGGTACGCCAAGCCCCAGGGCAGGGACTTGAATGGATGGGAGGAATCAT
CCCTATCCTTGGTATAGCAAACTACGCACAGAAGTTCCAGGGCAGAGTCACGATTAC
AGCGGACGAATCCACGAGCACTGCGTATATGGAGCTGAGTTCTCTGAGGAGCGAAG
ATACTGCTGTCTACTACTGTGCGAGAGGGGGTCCAGGGAGTTACCATATGGACGTCT
GGGGAAAGGGCACTTTGGTCACTGTTTCTAGCGGTGGTGGAGGCAGTGGTGGCGGA
GGATCAGGGGGGGGGGGGTCCGAAATTGTGCTGACTCAGTCTCCAGCCACCCTGTCT
TTGTCTCCAGGGGAAAGAGCCACCCTCTCCTGCAGGGCCAGTCAGAGTGTTGGCAG
CTCCTTAGGCTGGTACCAACAGAAACCTGGCCAGGCTCCCAGGCTCCTCATCTATGA
TGTATCCAACAGGGCCTCTGGCATCCCAGCCAGGTTCAGTGGCAGTGGGTCTGGGAT
AGACTTCACTCTCACCATCAGCAGCCTAGAGCCTGAAGATTTTGCAGTTTATTACTG
TCAGCAGCGTAGCAACTGGCCCCCCATGTACACTTTTGGCCAGGGGACCAAGCTGG
AGATCAAAGCTAGCGCAACTACCACTCCTGCACCACGGCCACCTACCCCAGCCCCC
ACCATTGCAAGCCAGCCACTTTCACTGCGCCCCGAAGCGTGTAGACCAGCTGCTGGA
GGAGCCGTGCATACCCGAGGGCTGGACTTCGCCTGTGACATCTACATTTGGGCACCC
TTGGCTGGGACCTGTGGGGTGCTGTTGCTGTCCTTGGTTATTACGTTGTACTGCCGGT
CGAAGAGGTCCAGACTCTTGCACTCCGACTACATGAACATGACTCCTAGAAGGCCC
GGACCCACTAGAAAGCACTACCAGCCGTACGCCCCTCCTCGGGATTTCGCCGCATAC
CGGTCCTGA SEQ ID NO: 252 amino acid sequence of CAR D0432 ROR1scFv9 IgG4 CD8 BBz 2A CD276-22 CD8 CD28 CCR
MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRNIMALPVTALLLPLALLLHAARPQVQLQQSGAEVKKPGSS
VKVSCKDSGGTLSSHAISWVRQAPGQGLEWMGGIIPILGIANYAQKFQGRVTITADESTS
TAYMELSSLRSEDTAVYYCARGGPGSYHMDVWGKGTLVTVSSGGGGSGGGGSGGGGS
EIVLTQSPATLSLSPGERATLSCRASQSVGSSLGWYQQKPGQAPRLLIYDVSNRASGIPAR
FSGSGSGIDFTLTISSLEPEDFAVYYCQQRSNWPPMYTFGQGTKLEIKASATTTPAPRPPT
PAPTIASQPLSLRPEACRPAAGGAVHTRGLDFACDIYIWAPLAGTCGVLLLSLVITLYCRS
KRSRLLHSDYMNMTPRRPGPTRKHYQPYAPPRDFAAYRS -continued SEQ ID NO: 253 nucleotide sequence of CAR D0433 ROR1scFv9 IgG4 CD8 BBz 2A CD276-30 CD8 CD28 CCR
ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGITGAGCAGGCTGAGATCT
GACGACACGGCCGTGTATTACTGTGCGAGTTATAATGATGCTTTTGATATCTGGGGC
CAAGGCACCCTGGTCACCGTCTCCTCAGGAGGTGGCGGGTCTGGTGGTGGCGGTAG
CGGTGGTGGCGGATCCAATTTTATGCTGACTCAGCCCCACTCTGTGTCGGAGTCTCC
GGGGAAGACGGTAACCATCTCCTGCACCCGCAGCAGTGGCAGCATTGCCAGCAACT
ATGTGCAGTGGTACCAGCAGCGCCCGGGCAGTGCCCCCACCATTGTGATCTATGAG
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATCTGGGCCCCATTGGCTGGAACTTGCGGCGTGCTGCTCTTGTCTCTGGTCATTACC
CTGTACTGCAAGCGCGGACGGAAGAAACTCTTGTACATCTTCAAGCAGCCGTTCATG
CGCCCTGTGCAAACCACCCAAGAAGAGGACGGGTGCTCCTGCCGGTTCCCGGAAGA
GGAAGAGGGCGGCTGCGAACTGAGAGTGAAGTTTAGCCGCTCAGCCGATGCACCGG
CCTACCAGCAGGGACAGAACCAGCTCTACAACGAGCTCAACCTGGGTCGGCGGGAA
GAATATGACGTGCTGGACAAACGGCGCGGCAGAGATCCGGAGATGGGGGGAAAGC
CGAGGAGGAAGAACCCTCAAGAGGGCCTGTACAACGAACTGCAGAAGGACAAGAT
GGCGGAAGCCTACTCCGAGATCGGCATGAAGGGAGAACGCCGGAGAGGGAAGGGT
CATGACGGACTGTACCAGGGCCTGTCAACTGCCACTAAGGACACTTACGATGCGCTC
CATATGCAAGCTTTGCCCCCGCGGCGCGCGAAACGCGGCAGCGGCGCGACCAACTT
TAGCCTGCTGAAACAGGCGGGCGATGTGGAAGAAAACCCGGGCCCGCGAGCAAAG
AGGAATATTATGGCTCTGCCTGTTACGGCACTGCTCCTTCCGCTTGCATTGTTGTTGC
ACGCAGCGCGGCCCCAGCTGCAGCTGCAGGAGTCCGGCCCAGGACTGGTGAAGCCT
TCGGAGACCCTGTCCCTCACCTGCGCTGTCTCTGGTGGCTCCGTCAGCAGTAGTAAC
TGGTGGAGTTGGGTCCGCCAGCCCCCAGGGAAGGGGCTGGAGTGGATTGGGGAAAT
CTATCATAGTGGGAGCACCAACTACAACCCGTCCCTCAAGAGTCGAGTCACCATATC
AGTAGACAAGTCCAAGAATCAATTCTCCCTGCACCTGAACTCTGTGACTCCCGAGGA
CACGGCTGTGTACTACTGTGCGAGAGAGGTGGCTGGTTCTGCGGCTTTCGACATCTG
GGGTCAGGGAACGATGGTGACTGTCTCTTCTGGAGGCGGAGGGTCTGGTGGCGGAG
GCTCAGGTGGGGGCGGAAGCCAAAGTGTAGTGACGCAGCCGCCCTCAGTGTCTGCG
GCCCCAGGACAGAAGGTCACCATCTCCTGCTCTGGAAGCAGCTCCAACATTGGGAA
TAATTATGTATCCTGGTACCAGCAGCTCCCAGGAACAGCCCCCAAACTCCTCATCTA
TGGAAATAATAAGCGACCCTCAGGGATTCCTGACCGATTCTCTGGCTCCAAGTCTGG
CACGTCAGCCACCCTGGGCATCACCGGACTCCAGACTGGGGACGAGGCCGATTATT
ACTGCGGAACATGGGATAGCAGCCTGAGTGCGGTATTCGGCGGAGGCACCCAGCTG
ACCGTCCTCGCTAGCGCAACTACCACTCCTGCACCACGGCCACCTACCCCAGCCCCC
ACCATTGCAAGCCAGCCACTTTCACTGCGCCCCGAAGCGTGTAGACCAGCTGCTGGA
GGAGCCGTGCATACCCGAGGGCTGGACTTCGCCTGTGACATCTACATTTGGGCACCC
TTGGCTGGGACCTGTGGGGTGCTGTTGCTGTCCTTGGTTATTACGTTGTACTGCCGGT
CGAAGAGGTCCAGACTCTTGCACTCCGACTACATGAACATGACTCCTAGAAGGCCC
GGACCCACTAGAAAGCACTACCAGCCGTACGCCCCTCCTCGGGATTTCGCCGCATAC
CGGTCCTGA SEQ ID NO: 254 amino acid sequence of CAR D0433 ROR1scFv9 IgG4 CD8 BBz 2A CD276-30 CD8 CD28 CCR
MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRNIMALPVTALLLPLALLLHAARPQLQLQESGPGLVKPSET
LSLTCAVSGGSVSSSNWWSWVRQPPGKGLEWIGEIYHSGSTNYNPSLKSRVTISVDKSK
NQFSLHLNSVTPEDTAVYYCAREVAGSAAFDIWGQGTMVTVSSGGGGSGGGGSGGGG
SQSVVTQPPSVSAAPGQKVTISCSGSSSNIGNNYVSWYQQLPGTAPKLLIYGNNKRPSGIP
DRFSGSKSGTSATLGITGLQTGDEADYYCGTWDSSLSAVFGGGTQLTVLASATTTPAPR
PPTPAPTIASQPLSLRPEACRPAAGGAVHTRGLDFACDIYIWAPLAGTCGVLLLSLVITLY
CRSKRSRLLHSDYMNMTPRRPGPTRKHYQPYAPPRDFAAYRS SEQ ID NO: 255 nucleotide sequence of CAR D0397 ROR1scFv9 IgG4 CD8 BBz 2A CD276-376.96 CD8 CD28 CCR
ATGCTGCTGCTGGTGACCAGCCTGCTGCTGTGCGAACTGCCGCATCCGGCGTTTCTG
CTGATTCCGCAGGCGGCCCAGGTACAGCTGCAGCAGTCAGGGGCTGAGGTGAAGAA
GCCTGGGTCCTCGGTGAAGGTCTCCTGCAAGGCTTCTGGAGGCACCTTCAGCAGCTA
TGCTATCAGCTGGGTGCGACAGGCCCCTGGACAAGGGCTTGAGTGGATGGGATGGA
TCAACCCTAACAGTGGTGGCACAAACTATGCACAGAGGTTTCAGGGCAGGGTCACC
ATGACCAGGGACACGTCCATCAGCACAGCCTACATGGAGITGAGCAGGCTGAGATCT
GACGACACGGCCGTGTATTACTGTGCGAGTTATAATGATGCTTTTGATATCTGGGGC
CAAGGCACCCTGGTCACCGTCTCCTCAGGAGGTGGCGGGTCTGGTGGTGGCGGTAG
CGGTGGTGGCGGATCCAATTTTATGCTGACTCAGCCCCACTCTGTGTCGGAGTCTCC
GGGGAAGACGGTAACCATCTCCTGCACCCGCAGCAGTGGCAGCATTGCCAGCAACT
ATGTGCAGTGGTACCAGCAGCGCCCGGGCAGTGCCCCCACCATTGTGATCTATGAG -continued
GATGATCAAAGACCCTCTGGGGTCCCTGATCGGTTCTCTGGCTCCATCGACACCTCC
TCCAACTCTGCCTCCCTCACCATCTCTGGACTGCAGAGTGAGGACGAGGCTGACTAC
TACTGTCAGTCTTATGAGCCCGGCAATGGGGTATTCGGCGGAGGGACCAAGGTCAC
CGTCCTAGCGGCCGCAGAGTCAAAATACGGTCCTCCGTGCCCTCCGTGTCCGATCTA
CATCTGGGCCCCATTGGCTGGAACTTGCGGCGTGCTGCTCTTGTCTCTGGTCATTACC
CTGTACTGCAAGCGCGGACGGAAGAAACTCTTGTACATCTTCAAGCAGCCGTTCATG
CGCCCTGTGCAAACCACCCAAGAAGAGGACGGGTGCTCCTGCCGGTTCCCGGAAGA
GGAAGAGGGCGGCTGCGAACTGAGAGTGAAGTTTAGCCGCTCAGCCGATGCACCGG
CCTACCAGCAGGGACAGAACCAGCTCTACAACGAGCTCAACCTGGGTCGGCGGGAA
GAATATGACGTGCTGGACAAACGGCGCGGCAGAGATCCGGAGATGGGGGGAAAGC
CGAGGAGGAAGAACCCTCAAGAGGGCCTGTACAACGAACTGCAGAAGGACAAGAT
GGCGGAAGCCTACTCCGAGATCGGCATGAAGGGAGAACGCCGGAGAGGGAAGGGT
CATGACGGACTGTACCAGGGCCTGTCAACTGCCACTAAGGACACTTACGATGCGCTC
CATATGCAAGCTTTGCCCCCGCGGCGCGCGAAACGCGGCAGCGGCGCGACCAACTT
TAGCCTGCTGAAACAGGCGGGCGATGTGGAAGAAAACCCGGGCCCGCGAGCAAAG
AGGAATATTATGGCTCTGCCTGTTACGGCACTGCTCCTTCCGCTTGCATTGTTGTTGC
ACGCAGCGCGGCCCGACATTGTGATGACCCAGTCTCACAAATTCATGTCCACATCAA
TTGGAGCCAGGGTCAGCATCACCTGCAAGGCCAGTCAGGATGTGAGAACTGCTGTA
GCCTGGTATCAACAGAAACCAGGCCAGTCTCCTAAACTTCTTATTTACTCAGCATCC
TACCGGTACACTGGAGTCCCTGATCGCTTCACTGGCAGTGGATCTGGGACGGATTTC
ACTTTCACCATCAGCAGTGTGCAGGCTGAAGACCTGGCAGTTTATTACTGTCAGCAA
CATTATGGTACTCCTCCGTGGACGTTCGGTGGAGGCACCAAGCTGGAAATCAAAGG
CGGCGGAGGATCTGGCGGAGGCGGAAGTGGCGGAGGGGGCTCTGAAGTGCAGCTG
GTGGAGTCTGGGGGAGGCTTGGTGAAGCCTGGAGGGTCCCTGAAACTCTCCTGTGA
AGCCTCCAGATTCACTTTCAGTAGCTATGCCATGTCTTGGGTTCGCCAGACTCCGGA
GAAGAGGCTGGAGTGGGTCGCAGCCATTAGTGGAGGTGGTAGGTACACCTACTATC
CAGACAGTATGAAGGGTCGATTCACCATCTCCAGAGACAATGCCAAGAATTTCCTGT
ACCTGCAAATGAGCAGTCTGAGGTCTGAGGACACGGCCATGTATTACTGTGCAAGA
CACTATGATGGTTATCTTGACTACTGGGGCCAAGGCACCACTCTCACAGTCTCCTCA
GCTAGCGCAACTACCACTCCTGCACCACGGCCACCTACCCCAGCCCCCACCATTGCA
AGCCAGCCACTTTCACTGCGCCCCGAAGCGTGTAGACCAGCTGCTGGAGGAGCCGT
GCATACCCGAGGGCTGGACTTCGCCTGTGACATCTACATTTGGGCACCCTTGGCTGG
GACCTGTGGGGTGCTGTTGCTGTCCTTGGTTATTACGTTGTACTGCCGGTCGAAGAG
GTCCAGACTCTTGCACTCCGACTACATGAACATGACTCCTAGAAGGCCCGGACCCAC
TAGAAAGCACTACCAGCCGTACGCCCCTCCTCGGGATTTCGCCGCATACCGGTCCTG
A SEQ ID NO: 256 amino acid sequence of CAR D0397 ROR1scFv9 IgG4 CD8 BBz 2A CD276-376.96 CD8 CD28 CCR
MLLLVTSLLLCELPHPAFLLIPQAAQVQLQQSGAEVKKPGSSVKVSCKASGGTFSSYAIS
WVRQAPGQGLEWMGWINPNSGGTNYAQRFQGRVTMTRDTSISTAYMELSRLRSDDTA
VYYCASYNDAFDIWGQGTLVTVSSGGGGSGGGGSGGGGSNFMLTQPHSVSESPGKTVT
ISCTRSSGSIASNYVQWYQQRPGSAPTIVIYEDDQRPSGVPDRFSGSIDTSSNSASLTISGL
QSEDEADYYCQSYEPGNGVFGGGTKVTVLAAAESKYGPPCPPCPIYIWAPLAGTCGVLL
LSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPRRAKRGSGATNF
SLLKQAGDVEENPGPRAKRNIMALPVTALLLPLALLLHAARPDIVMTQSHKFMSTSIGA
RVSITCKASQDVRTAVAWYQQKPGQSPKLLIYSASYRYTGVPDRFTGSGSGTDFTFTISS
VQAEDLAVYYCQQHYGTPPWTFGGGTKLEIKGGGGSGGGGSGGGGSEVQLVESGGGL
VKPGGSLKLSCEASRFTFSSYAMSWVRQTPEKRLEWVAAISGGGRYTYYPDSMKGRFTI
SRDNAKNFLYLQMSSLRSEDTAMYYCARHYDGYLDYWGQGTTLTVSSASATTTPAPRP
PTPAPTIASQPLSLRPEACRPAAGGAVHTRGLDFACDIYIWAPLAGTCGVLLLSLVITLYC
RSKRSRLLHSDYMNMTPRRPGPTRKHYQPYAPPRDFAAYRS

---

What is claimed is:

1. A method of treating a ROR1$^+$-cancer in a subject in need thereof, the method comprising administering to the subject having the ROR1$^+$-cancer a pharmaceutical composition comprising an anti-tumor effective amount of a population of T cells, wherein the T cells comprise a constitutive promoter operably linked to a nucleic acid sequence that encodes a single chimeric antigen receptor (CAR) with one or more booster elements, a tandem CAR with one or more booster elements, a multi-targeting CAR with one or more booster elements, or a DuoCAR with one or more booster elements, wherein the CAR of the single CAR with one or more booster elements, the tandem CAR with one or more booster elements, the multi-targeting CAR with one or more booster elements, or the DuoCAR with one or more booster elements comprises the amino acid sequence of SEQ ID NO: 152, 154, 156, 160, 162, 164, 174, 176, 178, 180, 182, 184, 192, 194, 196, 198, 227, 233, 235, 237, 239, 241, 243, 252, 254, or 256, wherein the T cells are T cells of the subject having the ROR$^+$-cancer.

2. The method of claim 1, wherein the T cells are T cells of a human having a hematological ROR1$^+$-cancer.

3. The method of claim 2, wherein the hematological ROR1$^+$-cancer is leukemia or lymphoma.

4. The method of claim 3, wherein the leukemia is acute myeloid leukemia (AML), blastic plasmacytoid dendritic cell neoplasm (BPDCN), chronic myelogenous leukemia (CML), chronic lymphocytic leukemia (CLL), acute lymphoblastic T cell leukemia (T-ALL), or acute lymphoblastic B cell leukemia (B-ALL).

5. The method of claim 3, wherein the lymphoma is mantle cell lymphoma, non-Hodgkin's lymphoma or Hodgkin's lymphoma.

6. The method of claim 2, wherein the hematological ROR1$^+$-cancer is multiple myeloma.

7. The method of claim 1, wherein the ROR1$^+$-cancer is an adult carcinoma, wherein the adult carcinoma is an oral and pharynx cancer, a digestive system cancer, a respiratory system cancer, a bone and joint cancer, a soft tissue cancer, a skin cancer, a tumor of the central nervous system, a cancer of the breast, a cancer of the genital system, a cancer of the urinary system, a cancer of the eye and orbit, a cancer of the endocrine system, a cancer of the brain and other nervous system, or any combination thereof.

8. The method of claim 1, wherein the T cells comprise a nucleic acid sequence that encodes a single ROR1 CAR with one or more booster elements, wherein the CAR of the single ROR1 CAR with one or more booster elements comprises the amino acid sequence of SEQ ID NO: 160, SEQ ID NO: 162, SEQ ID NO: 164, SEQ ID NO: 192, SEQ ID NO: 194, SEQ ID NO: 196, SEQ ID NO: 233, SEQ ID NO: 235, SEQ ID NO: 237, SEQ ID NO: 239, SEQ ID NO: 241, or SEQ ID NO: 243.

9. The method of claim 1, wherein the T cells comprise a nucleic acid sequence that encodes a tandem ROR1-MSLN CAR with one or more booster elements, wherein the CAR of the tandem ROR1-MLSN CAR with one or more booster elements comprises the amino acid sequence of SEQ ID NO: 176, SEQ ID NO: 178, or SEQ ID NO: 180.

10. The method of claim 1, wherein the T cells comprise a nucleic acid sequence that encodes a ROR1-MSLN DuoCAR with one or more booster elements, wherein the CAR of the ROR1-MSLN DuoCAR with one or more booster elements comprises the amino acid sequence of SEQ ID NO: 182 or SEQ ID NO: 184.

* * * * *